US011851716B2

(12) United States Patent
Kurtz et al.

(10) Patent No.: US 11,851,716 B2
(45) **Date of Patent: *Dec. 26, 2023**

(54) METHODS AND SYSTEMS FOR ANALYZING NUCLEIC ACID MOLECULES

(71) Applicant: The Board of Trustees of the Leland Stanford Junior University, Stanford, CA (US)

(72) Inventors: David M. Kurtz, San Carlos, CA (US); Maximilian Diehn, San Carlos, CA (US); Arash Ash Alizadeh, San Mateo, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/056,652

(22) Filed: Nov. 17, 2022

(65) Prior Publication Data

US 2023/0203597 A1 Jun. 29, 2023

Related U.S. Application Data

(63) Continuation of application No. 17/646,473, filed on Dec. 29, 2021, now Pat. No. 11,613,787, which is a continuation of application No. PCT/US2020/059526, filed on Nov. 6, 2020.

(60) Provisional application No. 62/931,688, filed on Nov. 6, 2019.

(51) Int. Cl.

| | |
|---|---|
| ***G16B 30/10*** | (2019.01) |
| ***G16B 20/20*** | (2019.01) |
| ***G16B 35/20*** | (2019.01) |
| ***G16B 30/00*** | (2019.01) |
| ***C12Q 1/6874*** | (2018.01) |
| ***G16H 70/60*** | (2018.01) |
| ***G16H 10/40*** | (2018.01) |
| ***G16H 50/30*** | (2018.01) |
| ***G16H 50/70*** | (2018.01) |
| ***G16H 20/10*** | (2018.01) |
| ***G16B 40/00*** | (2019.01) |
| ***G16B 20/10*** | (2019.01) |
| ***G16H 50/20*** | (2018.01) |
| ***G16B 20/00*** | (2019.01) |
| ***G16H 10/60*** | (2018.01) |
| ***C12Q 1/6886*** | (2018.01) |
| ***C12N 15/10*** | (2006.01) |
| ***C12Q 1/6869*** | (2018.01) |

(52) U.S. Cl.

CPC ....... *C12Q 1/6886* (2013.01); *C12N 15/1089* (2013.01); *C12Q 1/6869* (2013.01); *C12Q 1/6874* (2013.01); *G16B 20/00* (2019.02); *G16B 20/10* (2019.02); *G16B 20/20* (2019.02); *G16B 30/00* (2019.02); *G16B 30/10* (2019.02); *G16B 35/20* (2019.02); *G16B 40/00* (2019.02); *G16H 10/40* (2018.01); *G16H 20/10* (2018.01); *G16H 50/20* (2018.01); *G16H 50/30* (2018.01); *G16H 50/70* (2018.01); *G16H 70/60* (2018.01); *C12Q 2600/112* (2013.01); *C12Q 2600/156* (2013.01); *C12Q 2600/158* (2013.01); *G01N 2800/7028* (2013.01); *G16H 10/60* (2018.01)

(58) Field of Classification Search

None

See application file for complete search history.

(56) References Cited

U.S. PATENT DOCUMENTS

| | | | |
|---|---|---|---|
| 5,804,396 | A | 9/1998 | Plowman |
| 6,171,856 | B1 | 1/2001 | Thigpen et al. |
| 8,105,769 | B2 | 1/2012 | Bell et al. |
| 8,318,433 | B2 | 11/2012 | Brenner |
| 8,580,497 | B2 | 11/2013 | Stratton et al. |
| 8,722,368 | B2 | 5/2014 | Casbon et al. |
| 8,741,606 | B2 | 6/2014 | Casbon et al. |
| 8,835,358 | B2 | 9/2014 | Fodor et al. |
| 9,035,036 | B2 | 5/2015 | Bell et al. |
| 9,340,830 | B2 | 5/2016 | Lipson et al. |
| 9,598,731 | B2 | 3/2017 | Talasaz |
| 9,752,188 | B2 | 9/2017 | Schmitt et al. |
| 9,834,822 | B2 | 12/2017 | Talasaz |
| 9,840,743 | B2 | 12/2017 | Talasaz |
| 9,850,523 | B1 | 12/2017 | Chudova et al. |
| 9,902,992 | B2 | 2/2018 | Talasaz et al. |

(Continued)

FOREIGN PATENT DOCUMENTS

| | | | |
|---|---|---|---|
| BR | 112022008752 | A2 | 8/2022 |
| CN | 109337983 | A | 2/2019 |

(Continued)

OTHER PUBLICATIONS

Spindler et al.Quantitative Cell-Free DNA, KRAS, and BRAF Mutations in Plasma from Patients with Metastatic Colorectal Cancer during Treatment with Cetuximab and Irinotecan, Clin Cancer Res; 18(4); 1177-85.*

(Continued)

*Primary Examiner* — Joseph Woitach

(74) *Attorney, Agent, or Firm* — KPPB LLP

(57) ABSTRACT

Processes and materials to detect cancer from a biopsy are described. In some cases, cell-free nucleic acids can be sequenced, and the sequencing result can be utilized to detect sequences derived from a neoplasm. Detection of somatic variants occurring in phase can indicate the presence of cancer in a diagnostic scan and a clinical intervention can be performed.

23 Claims, 86 Drawing Sheets

Specification includes a Sequence Listing.

(56) References Cited

U.S. PATENT DOCUMENTS

| | | | |
|---|---|---|---|
| 9,920,366 | B2 | 3/2018 | Eltoukhy et al. |
| 10,041,127 | B2 | 8/2018 | Talasaz |
| 10,450,611 | B2 | 10/2019 | West et al. |
| 10,457,955 | B2 | 10/2019 | Kumar et al. |
| 10,494,678 | B2 | 12/2019 | Talasaz |
| 10,501,808 | B2 | 12/2019 | Talasaz |
| 10,501,810 | B2 | 12/2019 | Talasaz |
| 10,704,085 | B2 | 7/2020 | Talasaz et al. |
| 10,704,086 | B2 | 7/2020 | Talasaz et al. |
| 10,738,364 | B2 | 8/2020 | Talasaz |
| 11,299,783 | B2 | 4/2022 | West et al. |
| 11,384,394 | B2 | 7/2022 | Bartha et al. |
| 11,447,833 | B2 | 9/2022 | Kurtz et al. |
| 11,613,787 | B2 | 3/2023 | Kurtz et al. |
| 11,634,779 | B2 | 4/2023 | Kurtz et al. |
| 2002/0015718 | A1 | 2/2002 | Kruse et al. |
| 2013/0210645 | A1 | 8/2013 | Volgelstein et al. |
| 2014/0227705 | A1 | 8/2014 | Vogelstein et al. |
| 2014/0296081 | A1 | 10/2014 | Diehn et al. |
| 2015/0024950 | A1 | 1/2015 | Bielas et al. |
| 2015/0376700 | A1 | 12/2015 | Schnall-Levin et al. |
| 2016/0032396 | A1 | 2/2016 | Diehn et al. |
| 2017/0107576 | A1 | 4/2017 | Babiarz et al. |
| 2018/0251848 | A1 | 9/2018 | Diehn et al. |
| 2019/0264257 | A1 | 8/2019 | Desharnais et al. |
| 2020/0131505 | A1 | 4/2020 | Green et al. |
| 2021/0025005 | A1 | 1/2021 | Babiarz et al. |
| 2021/0172022 | A1 | 6/2021 | Kurtz et al. |
| 2021/0366571 | A1 | 11/2021 | Kurtz et al. |
| 2022/0251664 | A1 | 8/2022 | Kurtz et al. |
| 2022/0375540 | A1 | 11/2022 | Chabon et al. |
| 2022/0389518 | A1 | 12/2022 | Kurtz et al. |
| 2023/0124070 | A1 | 4/2023 | Kurtz et al. |
| 2023/0183816 | A1 | 6/2023 | Kurtz et al. |

FOREIGN PATENT DOCUMENTS

| | | | |
|---|---|---|---|
| CN | 113383085 | A | 9/2021 |
| CN | 115443341 | A | 12/2022 |
| DE | 112020005433 | T5 | 10/2022 |
| EP | 3561075 | A1 | 10/2019 |
| EP | 4055187 | A1 | 9/2022 |
| EP | 4110397 | A1 | 1/2023 |
| EP | 4110957 | A2 | 1/2023 |
| GB | 2595193 | A | 11/2021 |
| GB | 2595193 | B | 10/2022 |
| HK | 40060652 | A | 5/2022 |
| HK | 40064341 | | 6/2022 |
| IN | 202217026392 | | 4/2022 |
| JP | 2023501376 | A | 1/2023 |
| KR | 20220094218 | A | 7/2022 |
| KR | 20220145891 | A | 10/2022 |
| KR | 20220157976 | A | 11/2022 |
| WO | WO-2014151117 | A1 | 9/2014 |
| WO | WO-2015188192 | A2 | 12/2015 |
| WO | WO-2016040901 | A1 | 3/2016 |
| WO | WO-2017100441 | A1 | 6/2017 |
| WO | WO-2017161175 | A1 | 9/2017 |
| WO | WO-2018231818 | A1 | 12/2018 |
| WO | WO-2020154682 | A2 | 7/2020 |
| WO | WO-2020204674 | A2 | 10/2020 |
| WO | WO-2021003485 | A1 | 1/2021 |
| WO | WO-2021092476 | A1 | 5/2021 |
| WO | WO-2021173722 | A2 | 9/2021 |
| WO | WO-2021173724 | A1 | 9/2021 |
| WO | WO-2021173722 | A3 | 10/2021 |
| WO | WO-2022236221 | A1 | 11/2022 |

OTHER PUBLICATIONS

Ardila et al., "End-to-end lung cancer screening with three-dimensional deep learning on low-dose chest computed tomography", Nat. Med., Jun. 2019, vol. 25, No. pp. 954-961, published online May 20, 2019, doi: 10.1038/s41591-019-0447-x.

Bailey, et al. Comprehensive characterization of cancer driver genes and mutations. Cell 173.2 (2018): 371-385.

Ballenghien et al., "Patterns of cross-contamination in a multispecies population genomic project: detection, quantification, impact, and solutions", BMC Biology, vol. 15, No. 25, Mar. 29, 2017, 16 pgs.

Bandelt et al., "Contamination and sample mix-up can best explain some patterns of mtDNA instabilities in buccal cells and oral squamous cell carcinoma", BMC Cancer, vol. 9, No. 113 Apr. 16, 2009, 8 pgs.

Bentley et al., "Accurate Whole Human Genome Sequencing using Reversible Terminator Chemistry," Nature, 456(7218): 53-59 (2008).

Cancer Genome Atlas Research Network, "Comprehensive genomic characterization of squamous cell lung cancers," Nature, 489, 519-525 (2012).

"Carter et al., "Absolute quantification of somatic DNA alterations in human cancer," Nat Biotechnol, 30:413-21 (2012).".

Chan, et al. Cancer genome scanning in plasma: detection of tumor-associated copy No. aberrations, single-nucleotide variants, and tumoral heterogeneity by massively parallel sequencing. Clin Chem. Jan. 2013;59(1):211-24. doi: 10.1373/clinchem.2012.196014. Epub Oct. 11, 2012.

Chaudhuri et al. Early Detection of Molecular Residual Disease in Localized Lung Cancer by Circulating Tumor DnA Profiling. Cancer Discov; 7(12); 1394-403 (2017). With Supplemental Tables Table of Contents and Table S6.

Chen et al., "AfterQC: automatic filtering, trimming, error removing and quality control for fastq data", BMC Bioinformatics, vol. 18, Suppl. 3, Mar. 14, 2017,10 pgs.

Church et al., "Results of Initial Low-Dose Computed Tomographic Screening for Lung Cancer", The National Lung Screening Trial Research Team, The New England Journal of Medicine, vol. 368, No. 21, May 23, 2013, pp. 1980-1991.

Cohen, et al., Detection and localization of surgically resectable cancers with a multi-analyte blood test. Science Feb. 23, 2018: vol. 359, Issue 6378, pp. 926-930. DOI: 10.1126/science.aar3247.

"Comprehensive molecular profiling of lung adenocarcinoma", The Cancer Genome Atlas Research Network, Nature, vol. 511, Jul. 31, 2014, pp. 543-550.

Co-pending U.S. Appl. No. 18/167,803, inventors Kurtz; David M et al., filed Feb. 10, 2023.

Co-pending U.S. Appl. No. 18/167,804, inventors Kurtz; David M et al., filed Feb. 10, 2023.

Costello, et al. Discovery and characterization of artifactual mutations in deep coverage targeted capture sequencing data due to oxidative DNA damage during sample preparation. Nucleic Acids Res. Apr. 1, 2013;41(6):e67. doi: 10.1093/nar/gks1443. Epub Jan. 8, 2013.

Cristiano et al. Genome-Wide Cell-Free DNA Fragmentation in Patients with Cancer. Nature 570 (7761):385-389. (Jun. 2019).

Dai et al. Identification of risk loci and a polygenic risk score for lung cancer: a large-scale prospective cohort study in Chinese populations. The Lancet, vol. 7, Issue 10, pp. 881-891 (Oct. 2019).

De Koning et al., "PL02.05 Effects of vol. CT Lung Cancer Screening: Mortality Results of the NELSON Randomised-Controlled Population Based Trial", Journal of Thoracic Oncology, vol. 13, No. 10, Supplement, Oct. 2018, pp. S185.

Denissenko et al., "Preferential Formation of Benzo[a]pyrene Adducts at Lung Cancer Mutational Hotspots in P53", Science, vol. 274, No. 5286, Oct. 18, 1996, pp. 430-432.

Diaconis et al., "Methods for Studying Coincidences", Journal of the American Statistical Association, vol. 84, No. 408, Dec. 1989, pp. 853-861.

Dissertations and theses, Stanford Libraries, Special Collections & University Archives website, accessed on Jun. 21, 2021, available online at: https://library.stanford.edu/spc/university-archives/dissertations-and-theses.

Doria-Rose et al., "Use of Lung Cancer Screening Tests in the United States: Results from the 2010 National Health Interview Survey", Cancer Epidemiology, Biomarkers & Prevention, vol. 21, No. 7, Jul. 1, 2012, pp. 1049-1059.

(56) References Cited

OTHER PUBLICATIONS

Ersek et al., "Knowledge of, Attitudes Toward, and Use of Low-Dose Computed Tomography for Lung Cancer Screening Among Family Physicians", Cancer, vol. 122, No. 15, Aug. 1, 2016, pp. 2324-2331.
Forshew, et al. Noninvasive identification and monitoring of cancer mutations by targeted deep sequencing of plasma DNA. Sci Transl Med. May 30, 2012;4(136):136ra68.
Genovese et al., "Clonal Hematopoiesis and Blood-Cancer Risk Inferred from Blood DNA Sequence", The New England Journal of Medicine, vol. 371, Dec. 25, 2014, pp. 2477-2487.
Goldstraw et al., "The IASLC Lung Cancer Staging Project: Proposals for Revision of the TNM Stage Groupings in the Forthcoming (Eighth) Edition of the TNM Classification for Lung Cancer", Journal of Thoracic Oncology, vol. 11, No. 1, Jan. 2016, pp. 39-51.
Gregory et al. Targeted single molecule mutation detection with massively parallel sequencing. Nucleic Acids Research, 2016, vol. 44, No. 3 e22. Published online Sep. 17, 2015. 11 pages.
Hainaut et al., "Somatic TP53 Mutations in the Era of Genome Sequencing", Cold Spring Harbor Perspectives in Medicine, vol. 6, No. 11, Nov. 2016, 22 pgs.
Han, et al. The Biology of Cell-free DNA Fragmentation and the Roles of DNASE1, DNASE1L3, and DFFB. Am J Hum Genet. Feb. 6, 2020;106(2):202-214. doi: 10.1016/j.ajhg.2020.01.008. Epub Jan. 30, 2020.
Hawkins et al. Indel-correcting DNA barcodes for high-throughput sequencing. PNAS, vol. 115, No. 27 (E6217-E6226) (Published online Jun. 20, 2018).
Hu et al., "False-Positive Plasma Genotyping Due to Clonal Hematopoiesis", Clinical Cancer Research, vol. 24, No. 18, Sep. 15, 2018, pp. 4437-4443.
Imperiale, et al., Multitarget stool DNA testing for colorectal-cancer screening. N Engl J Med. Apr. 2014; 370:1287-1297.
Jaiswal et al., "Age-Related Clonal Hematopoiesis Associated with Adverse Outcomes", The New England Journal of Medicine, vol. 371, No. 26, Dec. 25, 2014, pp. 2488-2498.
Jemal et al., Lung cancer screening with low-dose computed tomography in the United States- 2010 to 2015. JAMA Oncol. 3(9):1278-1281 (2017).
Jensen et al., "Decision Memo for Screening for Lung Cancer with Low Dose Computed Tomography (LDCT)", Centers for Medicare & Medicaid Services, CAG-00439N, Retrieved from: https://www.cms.gov/medicare-coverage-database/view/ncacal-decision-memo.aspx?proposed=N&NCAId=274, Feb. 5, 2015, 71 pgs.
Kandoth et al., "Mutational landscape and significance across 12 major cancer types," Nature, 502:333-339 (2013).
Abbosh et al. Abstract CT023: Phylogenetic tracking and minimal residual disease detection using ctDNA in early-stage NSCLC: A lung TRACERx study. Cancer Research, Proceedings: AACR Annual Meeting 2020; Apr. 27-28, 2020 and Jun. 22-24, 2020; Philadelphia, PA. Published Aug. 2020. Accessed Sep. 14, 2021 at: https://cancerres.aacrjournals.org/content/80/16_Supplement/CT023 . 4 pages.
Abbosh et al., "Early stage NSCLC—challenges to implementing ctDNA-based screening and MRD detection", Nature Reviews Clinical Oncology, vol. 15, Jul. 3, 2018, pp. 577-586.
Abbosh et al., "Phylogenetic ctDNA analysis depicts early-stage lung cancer evolution", Nature, vol. 545, Apr. 26, 2017, pp. 446-451.
Alexandrov et al., "Clock-like mutational processes in human somatic cells", Nature Genetics, vol. 47, Nov. 9, 2015, pp. 1402-1407.
Alexandrov, et al. Signatures of mutational processes in human cancer. Nature. Aug. 22, 2013;500(7463):415-421. doi: 10.1038/nature12477. Epub Aug. 14, 2013.
Alexandrov, et al. The repertoire of mutational signatures in human cancer. Nature. Feb. 2020;578(7793):94-101. doi: 10.1038/s41586-020-1943-3. Epub Feb. 5, 2020.
Alizadeh, et al. Distinct types of diffuse large B-cell lymphoma identified by gene expression profiling. Nature. Feb. 3, 2000;403(6769):503-11.
Alkodsi et al., "Distinct subtypes of diffuse large B-cell lymphoma defined by hypermutated genes", Leukemia, vol. 33, Jun. 11, 2019, pp. 2662-2672.
Bell et al., "Chromosome-scale mega-haplotypes enable digitalkaryotyping of cancer aneuploidy", Nucleic Acids Research, vol. 45, No. 19, Nov. 2, 2017, 13 pgs.
Bettegowda et al. Detection of Circulating Tumor DNA in Early- and Late-Stage Human Malignancies. Sci. Transl. Med. 6(224):224ra24 (2014).
Bianconi et al., "An estimation of the number of cells in the human body", Annals of Human Biology, vol. 40, No. 6, Jul. 5, 2013, pp. 463-471.
Bozdech et al., "Expression profiling of the schizont and trophozoite stages of Plasmodium falciparum with a long-oligonucleotide microarray", Genome Biology, vol. 4, No. R9, Jan. 31, 2003, 15 pgs.
Brenner, et al. Next-generation sequencing diagnostics of bacteremia in sepsis (Next GeneSiS-Trial): Study protocol of a prospective, observational, noninterventional, multicenter, clinical trial. Medicine (Baltimore). Feb. 2018;97(6):e9868. doi: 10.1097/MD.0000000000009868.
Burns, et al. Evidence for APOBEC3B mutagenesis in multiple human cancers. Nat Genet. Sep. 2013; 45(9): 977-983. Published online Jul. 14, 2013. doi: 10.1038/ng.2701.
Chabon, et al. Circulating tumour DNA profiling reveals heterogeneity of EGFR inhibitor resistance mechanisms in lung cancer patients. Nat Commun. Jun. 10, 2016;7:11815. doi: 10.1038/ncomms11815.
Chaudhuri, et al. Early Detection of Molecular Residual Disease in Localized Lung Cancer by Circulating Tumor DNA Profiling. Cancer Discov. Dec. 2017;7(12):1394-1403. doi: 10.1158/2159-8290.CD-17-0716. Epub Sep. 24, 2017.
Cibulskis et al. Sensitive detection of somatic point mutations in impure and heterogenous cancer samples. Nat Biotechnol 31:213-219 (2013).
Copyright Reminder: Dissertations, Stanford Libraries website, accessed on Aug. 18, 2021; Available online at: https://library.stanford.edu/using/copyright-reminder/common-situations/dissertations .
Corcoran et al., "Application of Cell-free DNA Analysis to Cancer Treatment", The New England Journal of Medicine, vol. 379, pp. 1754-1765 (2018).
De Vlaminck, et al. Circulating cell-free DNA enables noninvasive diagnosis of heart transplant rejection. Sci Transl Med. Jun. 18, 2014;6(241):241ra77. doi: 10.1126/scitranslmed.3007803.
De Vlaminck, et al. Noninvasive monitoring of infection and rejection after lung transplantation. Proc Natl Acad Sci USA. Oct. 27, 2015;112(43):13336-13341. doi: 10.1073/pnas.1517494112. Epub Oct. 12, 2015.
De Yébenes, et al. Activation-induced deaminase: light and dark sides. Trends Mol Med. Sep. 2006; 12(9):432-439. doi: 10.1016/j.molmed.2006.07.001. Epub Jul. 24, 2006.
Deng et al., "TNER: a novel background error suppression method for mutation detection in circulating tumor DNA", BMC Bioinformatics, vol. 19, No. 387, Oct. 20, 2018, 7 pgs.
Dewey et al. Phased whole-genome genetic risk in a family quartet using a major allele reference sequence. PLOS Genetics 7(9):e1002280 (2011).
Diaz, et al. Performance of Streck cfDNA Blood Collection Tubes for Liquid Biopsy Testing. PLOS One. Nov. 10, 2016;11(11):e0166354. doi: 10.1371/journal.pone.0166354. eCollection 2016.
Diehl et al. Circulating mutant DNA to assess tumor dynamics. Nat Med 14(9):985-990 (2008).
Dissertations and Theses. Stanford Libraries, Robin Li and Melissa M Science Library. (Website.) Accessed Sep. 11, 2021 at: https://library.stanford.edu/science/collections/chemistry-and-chemical-engineering-collection/dissertations-and-theses . 4 pages.
"Dissertations and theses", Stanford Libraries, Special Collections & University Archives, Retrieved from https://library.stanford.edu/using/copyright-reminder/ common-situations/dissertations on Jun. 21, 2021, 3 pgs.
Dou et al., "Detecting Somatic Mutations in Normal Cells", Trends Genet. Jul. 2018, 34(7):545-557. doi:10.1016/j.tig.2018.04.003.

(56) References Cited

OTHER PUBLICATIONS

EDissertation Requirements for Submission, Stanford University Registrar's office: Student affairs website, accessedJun. 24, 2021 at https://registrar.stanford.edu/students/dissertation-and-thesis-submission/preparing-dissertations-electronic-submission.
"Embargo and Restriction Options", ProQuest, Retrieved from https://support.proquest.com/articledetail?id=kA0400000004JJCCA2 on Sep. 15, 2021, 4 pgs.
Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.
Format Requirements for eDissertation, Stanford University, Registrar's office: Student affairs website, accessed Aug. 19, 2021 at https://registrar.stanford.edu/students/dissertation-and-thesis-submission/preparing-dissertations-electronic-submission/format.
Garcia-Murillas, et al. Mutation tracking in circulating tumor DNA predicts relapse in early breast cancer. Sci Transl Med. Aug. 26, 2015;7(302):302ra133. doi: 10.1126/scitranslmed.aab0021.
Jaeger et al., "Improved predictions of secondary structures for RNA", Proceedings of the National Academy of Sciences, vol. 86, No. 20, Oct. 1, 1989, pp. 7706-7710.
Jiang, P. et al. Lengthening and shortening of plasma DNA in hepatocellular carcinoma patients. Proc Natl Acad Sci U S A 2015;112:E1317-25.
Kalinich, et al. Cancer detection: Seeking signals in blood. Science. Feb. 23, 2018;359(6378):866-867. doi: 10.1126/science.aas9102.
Kennedy et al. Detecting ultralow-frequency mutations by Duplex Sequencing. Nature Protocols 9(11):2586-2606 (2014).
Khodabakhshi, et al. Recurrent targets of aberrant somatic hypermutation in lymphoma. Oncotarget. Nov. 2012;3(11):1308-1319. doi: 10.18632/oncotarget.653.
Kim, S. et al. Strelka2: fast and accurate calling of germline and somatic variants. Nat. Methods 15; 591-594, Jul. 16, 2018.
Koboldt, et al. VarScan 2: somatic mutation and copy number alteration discovery in cancer by exome sequencing. Genome Res. Mar. 2012;22(3):568-76. doi: 10.1101/gr.129684.111. Epub Feb. 2, 2012.
Kurtz et al., "Circulating Tumor DNA Measurements As Early OutcomePredictors in Diffuse Large B-Cell Lymphoma", Journal of ClinicalOncology: Official Journal of the American Society of Clinical Oncology, vol. 36, No. 28, Oct. 1, 2018, pp. 2845-2853.
Kurtz et al., "Noninvasive monitoring of diffuse large B-cell lymphoma by immunoglobulin high-throughput sequencing", Blood, vol. 125, No. 24, Jun. 11, 2015, pp. 3679-3687.
Kurtz et al., "Phased Variant Enrichment for Enhanced Minimal Residual Disease Detection from Cell-Free DNA", Blood, vol. 134, Supp. 1, Nov. 13, 2019, pp. 552.
Kurtz et al., "Reply to J. Wang et al.", Journal of Clinical Oncology: Official Journal of the American Society of Clinical Oncology, vol. 37, No. 9, Mar. 20, 2019, pp. 755-757.
Kurtz, Personalized Risk Assessment and Disease Monitoring in Non-Hodgkin Lymphoma from Circulating Tumor DNA, 2017, Stanford University, ProQuest, p. 1-242.
Lenz, et al. Aberrant immunoglobulin class switch recombination and switch translocations in activated B cell-like diffuse large B cell lymphoma. J Exp Med. Mar. 19, 2007;204(3):633-643. doi: 10.1084/jem.20062041. Epub Mar. 12, 2007.
Li, et al. Fast and accurate short read alignment with Burrows-Wheeler transform. Bioinformatics. Jul. 15, 2009;25(14):1754-1760. doi: 10.1093/bioinformatics/btp324. Epub May 18, 2009.
Librarian view of catalog entry for:"Personalized risk assessment and disease monitoring in non-Hodgkinlymphoma from circulating tumor DNA, David Kurtz"; datecatalogued: Dec. 11, 2017. Accessed Aug. 19, 2021.
Lieber, "Mechanisms of human lymphoid chromosomal translocations", Nature Reviews Cancer, vol. 16, May 25, 2016, pp. 387-398.
Lo, et al. Prenatal Diagnosis of Fetal RhD Status by Molecular Analysis of Maternal Plasma. New England Journal of Medicine, 339:1734-1738 (Dec. 10, 1998).
Lo, et al. Presence of fetal DNA in maternal plasma and serum. The Lancet, Aug. 16, 1997, vol. 350, 485-487.
Lu et al., "BCL6 breaks occur at different AID sequence motifs in Ig-BCL6 and non-Ig-BCL6 rearrangements", Blood, vol. 121, No. 22, May 30, 2013, pp. 4551-4554.
Morin, et al. Mutational and structural analysis of diffuse large B-cell lymphoma using whole-genome sequencing. Blood. Aug. 15, 2013;122(7):1256-1265. doi: 10.1182/blood-2013-02-483727. Epub May 22, 2013.
Nakamura, et al. Analysis of the immunoglobulin heavy chain gene variable region of CD5-positive and -negative diffuse large B cell lymphoma. Leukemia. Mar. 2001;15(3):452-457. doi: 10.1038/sj.leu.2402031.
Neelapu et al., "Axicabtagene Ciloleucel CAR T-Cell Therapy in Refractory Large B-Cell Lymphoma", The New England Journal of Medicine, vol. 377, No. 26, Dec. 28, 2017, pp. 2531-2544.
Newman et al. An ultrasensitive method for quantitating circulating tumor DNA with broad patient coverage. Nat Med. May 2014 ; 20(5): 548-554. With Supplementary Text and Figures (Supplementary Figures 1-8 and (Supplementary Methods) and Supplementary Table 1 (NSCLC selector design and coordinates).
Newman, et al. An ultrasensitive method for quantitating circulating tumor DNA with broad patient coverage. Nat Med. May 2014;20(5):548-54. Epub Apr. 6, 2014.
Newman, et al. Integrated digital error suppression for improved detection of circulating tumor DNA. Nat Biotechnol. May 2016;34(5):547-555. doi: 10.1038/nbt.3520. Epub Mar. 28, 2016.
Notice of Allowance for U.S. Appl. No. 17/455,209, dated Apr. 18, 2022, 10 pgs.
Office Action for U.S. Appl. No. 17/107,668, dated Jun. 17, 2021, 27 pgs.
Office Action for U.S. Appl. No. 17/107,668, dated Oct. 21, 2021, 40 pgs.
"Pan-cancer analysis of whole genomes", The ICGC/TCGA Pan-Cancer Analysis of Whole Genomes Consortium, Nature, vol. 578, Feb. 5, 2020, pp. 82-93.
Papageorgiou et al. Fetal-specific DNA methylation ratio permits noninvasive prenatal diagnosis of trisomy 21. Nat Med. Apr. 2011;17(4):510-3. doi: 10.1038/nm.2312. Epub Mar. 6, 2011.
Pasqualucci et al. Analysis of the coding genome of diffuse large B-cell lymphoma. Nature Genet. 43(9):830-837 (2011).
Pasqualucci, et al. Hypermutation of multiple proto-oncogenes in B-cell diffuse large-cell lymphomas. Nature. Jul. 19, 2001;412(6844):341-346. doi: 10.1038/35085588.
Permission to Publish, Stanford Libraries Special Collections & University Archives website, accessed on Aug. 30, 2021 ; available online at: https://library.stanford.edu/spc/using-our-collections/permission-publish.
Personalized risk assessment and disease monitoring in non-Hodgkin lymphoma from circulating tumor DNA [electronic resource], Stanford University Library Searchworks Catalog entry accessed Jul. 21, 2021, available online at: https://searchworks.stanford.edu/view/12266090.
Phallen, et al. Direct detection of early-stage cancers using circulating tumor DNA. Science translational medicine 9.403 (2017): eaan2415.
Puente, et al. Non-coding recurrent mutations in chronic lymphocytic leukaemia. Nature. Oct. 22, 2015;526(7574):519-524. doi: 10.1038/nature14666. Epub Jul. 22, 2015.
Qian, et al. B cell super-enhancers and regulatory clusters recruit AID tumorigenic activity. Cell. Dec. 18, 2014;159(7):1524-1537.
Reading room policies & procedures, Stanford Libraries, Special Collections and University Archives website, accessed on Jul. 30, 2021, available online at: https://library.stanford.edu/spc/using-our-collections/reading-room-policies-procedures .
Reinert et al., "Analysis of Plasma Cell-Free DNA by Ultradeep Sequencing in Patients With Stages I to III Colorectal Cancer", JAMA Oncology, vol. 5, No. 8, May 9, 2019, pp. 1124-1131.
Response to Jun. 17, 2021 Office Action for U.S. Appl. No. 17/107,668, filed Sep. 17, 2021, 79 pgs.
Response to Oct. 21, 2021 Office Action for U.S. Appl. No. 17/107,668, filed Apr. 21, 2022, 101 pgs.

(56) References Cited

OTHER PUBLICATIONS

Restriction Requirement for U.S. Appl. No. 17/107,668, dated Apr. 26, 2021, 9 pgs.
Richter, et al. Recurrent mutation of the ID3 gene in Burkitt lymphoma identified by integrated genome, exome and transcriptome sequencing. Nat Genet. Dec. 2012;44(12):1316-1320. doi: 10.1038/ng.2469. Epub Nov. 11, 2012.
Robbiani et al., "AID Is Required for the Chromosomal Breaks in c-myc that Lead to c-myc/IgH Translocations", Cell, vol. 135, No. 6, Dec. 12, 2008, pp. 1028-1038.
Roschewski et al., "Circulating tumour DNA and CT monitoring in patients with untreated diffuse large B-cell lymphoma: a correlative biomarker study", The Lancet Oncology, vol. 16, No. 5, May 1, 2015, pp. 541-549.
Rosenthal, et al. DeconstructSigs: delineating mutational processes in single tumors distinguishes DNA repair deficiencies and patterns of carcinoma evolution. Genome Biol. Feb. 22, 2016;17:31. doi: 10.1186/s13059-016-0893-4.
Rowley, "Chromosome studies in the non-Hodgkin's lymphomas: the role of the 14;18 translocation", Journal of Clinical Oncology: Official Journal of the American Society of Clinical Oncology, vol. 6, No. 5, May 1988, pp. 919-925.
Scherer, et al. Distinct biological subtypes and patterns of genome evolution in lymphoma revealed by circulating tumor DNA. Sci Transl Med. Nov. 9, 2016;8(364):364ra155. doi: 10.1126/scitranslmed.aai8545.
Scherer et al., "High-throughput sequencing for noninvasive disease detection in hematologic malignancies", Blood, vol. 130, No. 4, Jul. 27, 2017, pp. 440-452.
Schmitt et al., "Detection of ultra-rare mutations by next-generation sequencing", Proceedings of the National Academy of Sciences, vol. 109, No. 36, Sep. 4, 2012, pp. 14508-14513.
Schmitz et al., "Burkitt lymphoma pathogenesis and therapeutic targets from structural and functional genomics", Nature, vol. 490, Aug. 12, 2012, pp. 116-120.
Schmitz, et al. Genetics and Pathogenesis of Diffuse Large B-Cell Lymphoma. N Engl J Med. Apr. 12, 2018;378(15):1396-1407. doi: 10.1056/NEJMoa1801445.
Sozzi, et al. Analysis of circulating tumor DNA in plasma at diagnosis and during follow-up of lung cancer patients. Cancer Res. Jun. 15, 2001;61(12):4675-4678.
Special Policies: Guidelines to counsel & researchers seeking discovery from Stanford Libraries, Stanford Libraries, accessed on Jun. 25, 2021; available online at: https://library.stanford.edu/using/special-policies/guidelines-counsel-researchers-seeking-discovery-stanford-libraries .
Steidl et al., "MHC class II transactivator CIITA is a recurrent gene fusion partner in lymphoid cancers", Nature, vol. 471, Mar. 2, 2011, pp. 377-381.
Sugimoto et al., "Improved Thermodynamic Parameters and Helix Initiation Factor to Predict Stability of DNA Duplexes", Nucleic Acids Research, vol. 24, No. 22, Nov. 1, 1996, pp. 4501-4505.
Thierry, et al. Clinical validation of the detection of KRAS and BRAF mutations from circulating tumor DNA. Nat Med. Apr. 2014;20(4):430-5. doi: 10.1038/nm.3511. Epub Mar. 23, 2014.
Tie, et al. Circulating tumor DNA analysis detects minimal residual disease and predicts recurrence in patients with stage II colon cancer. Sci Transl Med. Jul. 6, 2016;8(346):346ra92. doi: 10.1126/scitranslmed.aaf6219.
U.S. Appl. No. 17/455,209 Notice of Allowance dated Aug. 2, 2022.
U.S. Appl. No. 17/455,209 Notice of Allowance dated Jun. 13, 2022.
U.S. Appl. No. 17/646,472 Office Action dated Aug. 29, 2022.
U.S. Appl. No. 17/661,730 Office Action dated Aug. 22, 2022.
"Using our collections", Stanford Libraries, Special Collections & University Archives, Retrieved from https://library.stanford.edu/spc/using-our-collections on Aug. 19, 2021, 3 pgs.
Van der Auwera, G. A. et al. From FastQ data to high-confidence variant calls: the Genome Analysis Toolkit best practices pipeline. Curr. Protoc. Bioinformatics 43, Published online Oct. 15, 2013.
Vaqué, et al. B-cell lymphoma mutations: improving diagnostics and enabling targeted therapies. Haematologica. Feb. 2014;99(2):222-231. doi: 10.3324/haematol.2013.096248.
Wang, et al. Diagnosis of Pneumocystis jirovecii pneumonia with serum cell-free DNA in non-HIV-infected immunocompromised patients. Oncotarget. May 20, 2017;8(42):71946-71953. doi: 10.18632/oncotarget.18037. eCollection Sep. 22, 2017.
Karczewski et al., "Variation across 141,456 human exomes and genomes reveals the spectrum of loss-of-function intolerance across human protein-coding genes", bioRxiv, doi: 10.1101/531210, Aug. 13, 2019, 44 pgs.
Kinde et al. Detection and quantification of rare mutations with massively parallel sequencing. PNAS, vol. 108, No. 23, pp. 9530-9535 (Jun. 7, 2011). With Supporting Information (10 pages).
Kircher et al., Double indexing overcomes inaccuracies in multiplex sequencing on the Illumina platform, Nucleic Acids Res., 40(1): e3 (8 pages) (2012).
Kucab et al., "A Compendium of Mutational Signatures of Environmental Agents", Cell, vol. 177, No. 4, May 2, 2019, pp. 821-836.e16.
Kurtz et al., "Dynamic Risk Profiling Using Serial Tumor Biomarkers for Personalized Outcome Prediction", Cell, vol. 178, No. 3, Jul. 25, 2019, pp. 699-713.
Lawrence, MS et al. Mutational heterogeneity in cancer and the search for new cancer genes. Nature 499(7457):214-218 (Jul. 11, 2013) Epub Jun. 16, 2013.
Leary, et al. Development of personalized tumor biomarkers using massively parallel sequencing. Sci Transl Med. Feb. 24, 2010;2(20):20ra14. .
Lewis et al., "Low-Dose CT Lung Cancer Screening Practices and Attitudes among Primary Care Providers at an Academic Medical Center", Cancer Epidemiology, Biomarkers & Prevention, vol. 24, No. 4, Apr. 1, 2015, pp. 664-670.
Ley, et al. DNA sequencing of a cytogenetically normal acute myeloid leukaemia genome. Nature. Nov. 6, 2008;456(7218):66-72.
Liao, G.J.W. et al., "Targeted massively parallel sequencing of maternal plasma DNA permits efficient and unbiased detection of fetal alleles," Clin. Chem. 2011, 57(1), 92-101.
Liu et al., "Biological background of the genomic variations of cf-DNA in healthy individuals", Annals of Oncology, vol. 30, No. 3, Mar. 1, 2019, pp. 464-470.
Lui, et al. Predominant hematopoietic origin of cell-free DNA in plasma and serum after sex-mismatched bone marrow transplantation. Clin Chem. Mar. 2002;48(3):421-427.
Ma et al., "Annual Number of Lung Cancer Deaths Potentially Avertable by Screening in the United States", Cancer, vol. 119, No. 7, Apr. 1, 2013, pp. 1381-1385.
Martincorena et al. Universal Patterns of Selection in Cancer and Somatic Tissues. Cell 171, 1029-1041 (Nov. 16, 2017). With Erratum.
Mermel et al., GISTIC2.0 facilitates sensitive and confident localization of the targets of focal somatic copy-number alteration in human cancers, Genome Biol, 12:R41 (2011).
Mir et al., "Short Barcodes for Next Generation Sequencing", PLOS One, vol. 8, No. 12, Dec. 2013, e82933, 8 pgs.
Moss et al. Comprehensive Human Cell-Type Methylation Atlas Reveals Origins of Circulating Cell-Free DNA in Health and Disease. Nature Communications 9(1):5068 (2018).
Mouliere et al. Enhanced Detection of Circulating Tumor DNA by Fragment Size Analysis. Science Translational Medicine 10(466):eaat4921 (2018).
Pfeifer et al., "Tobacco smoke carcinogens, DNA damage and p53 mutations in smoking-associated cancers", Oncogene, vol. 21, No. 48, Oct. 15, 2002, pp. 7435-7451.
Pinsky et al., "Performance of Lung-RADS in the National Lung Screening Trial: A Retrospective Assessment", Annals of Internal Medicine, vol. 162, No. 7, Apr. 7, 2015, pp. 485-491.
Pinsky et al., "The National Lung Screening Trial: Results stratified by demographics, smoking history, and lung cancer histology", Cancer, vol. 119, No. 22, Nov. 15, 2013, pp. 3976-3983.
Ptashkin et al., "Prevalence of Clonal Hematopoiesis Mutations in Tumor-Only Clinical Genomic Profiling of Solid Tumors", JAMA Oncology, vol. 4, No. 11, Nov. 1, 2018, pp. 1589-1593.

(56) References Cited

OTHER PUBLICATIONS

Qian et al. A novel pathway-based approach improves lung cancer risk prediction using germline genetic variations. Cancer Epidemiol Biomarkers Prev. Aug. 2016 ; 25(8): 1208-1215.
Roberts et al. Hypermutation in human cancer genomes: footprints and mechanisms. Nature Reviews Cancer, vol. 14, pp. 786-800 (2014).
Saunders et al. Strelka: accurate somatic small-variant calling from sequenced tumor-normal sample pairs. Bioinformatic, 28(14):1811-1817 (2012).
Serpas et al. Dnase1l3 deletion causes aberrations in length and end-motif frequencies in plasma DNA. PNAS, vol. 116, No. 2, pp. 641-649 (Jan. 8, 2019). Published online Dec. 28, 2018.
Shen et al. Sensitive tumour detection and classification using plasma cell-free DNA methylomes. Nature. 2018;563:579-83.
Siegel et al. Cancer statistics, 2019. A Cancer Journal For Clinicians 69(1):7-34 (2019).
Snyder et al., Cell-free DNA comprises an in vivo nucleosome footprint that informs its tissues-of-origin. Cell. 164(1-2):57-68 (2016).
Steensma et al., "Clonal hematopoiesis of indeterminate potential and its distinction from myelodysplastic syndromes", Blood, vol. 126, No. 1, Jul. 2, 2015, pp. 9-16.
Supplementary Information for CHABON et al. Integrating genomic features for non-invasive early lung cancer detection. Nature. https://doi.org/10.1038/s41586-020-2140-0 . Published online Mar. 25, 2020. 27 pages.
Supplementary Note for CHABON et al. Integrating genomic features for non-invasive early lung cancer detection. Nature. https://doi.org/10.1038/s41586-020-2140-0 . Published online Mar. 25, 2020. 4 pages.
Swanton et al., "Prevalence of clonal hematopoiesis of indeterminate potential (CHIP) measured by an ultra-sensitive sequencing assay: Exploratory analysis of the Circulating Cancer Genome Atlas (CCGA) study", Journal of Clinical Oncology, vol. 36, No. 15, Supplement, May 20, 2018, pp. 12003.
Travis et al., "International Association for the Study of Lung Cancer/American Thoracic Society/European Respiratory Society International Multidisciplinary Classification of Lung Adenocarcinoma", Journal of Thoracic Oncology, vol. 6, No. 2, Feb. 2011, pp. 244-285.
Underhill et al. Fragment Length of Circulating Tumor DNA. Edited by David J. Kwiatkowski. PLOS Genetics 12(7):e1006162 (2016).
U.S. Appl. No. 17/646,473 Notice of Allowance dated Jan. 13, 2023.
U.S. Appl. No. 17/646,473 Notice of Allowance dated Nov. 9, 2022.
U.S. Appl. No. 17/646,473 Office Action dated Jun. 22, 2022.
U.S. Appl. No. 17/646,473 Office Action dated Oct. 17, 2022.
U.S. Appl. No. 17/661,034 Notice of Allowance dated Jun. 2, 2023.
U.S. Appl. No. 17/661,034 Office Action dated Feb. 2, 2023.
U.S. Appl. No. 17/661,730 Notice of Allowance dated Jan. 12, 2023.
U.S. Appl. No. 17/661,730 Office Action dated Dec. 1, 2022.
U.S. Appl. No. 17/820,200 Office Action dated Apr. 26, 2023.
U.S. Appl. No. 18/056,656 Office Action dated Jul. 3, 2023.
U.S. Appl. No. 18/172,957 Office Action dated Apr. 26, 2023.
Vendrell et al. Circulating Cell Free Tumor DNA Detection as a Routine Tool for Lung Cancer Patient Management. Int. J. Mol. Sci. 2017, 18, 264. 19 pages.
Vodak et al., "Sample-Index Misassignment Impacts Tumour Exome Sequencing", Scientific Reports, vol. 8, No. 5307, Mar. 28, 2018, 6 pgs.
Wagle et al. High-Throughput Detection of Actionable Genomic Alterations in Clinical Tumor Samples by Targeted, Massively Parallel Sequencing. Cancer Discov. Jan. 2012 ; 2(1): 82-93.
Weissfeld et al. Lung cancer risk prediction using common SNPs located in GWAS-identified susceptibility regions. J Thorac Oncol. Nov. 2015 ; 10(11): 1538-1545.
Wender et al., "American Cancer Society lung cancer screening guidelines", Ca: A Cancer Journal for Clinicians, vol. 63, No. 2, March/Apr. 2013, pp. 106-117.
Xie et al., "Age-related mutations associated with clonal hematopoietic expansion and malignancies", Nature Medicine, vol. 20, No. 12, Oct. 19, 2014, pp. 1472-1478.
Young et al., "Clonal haematopoiesis harbouring AML-associated mutations is ubiquitous in healthy adults", Nature Communications, vol. 7, 12484, Aug. 22, 2016, 7 pgs.
U.S. Appl. No. 17/820,200 Office Action dated Aug. 17, 2023.
U.S. Appl. No. 18/172,957 Office Action dated Aug. 17, 2023.

* cited by examiner

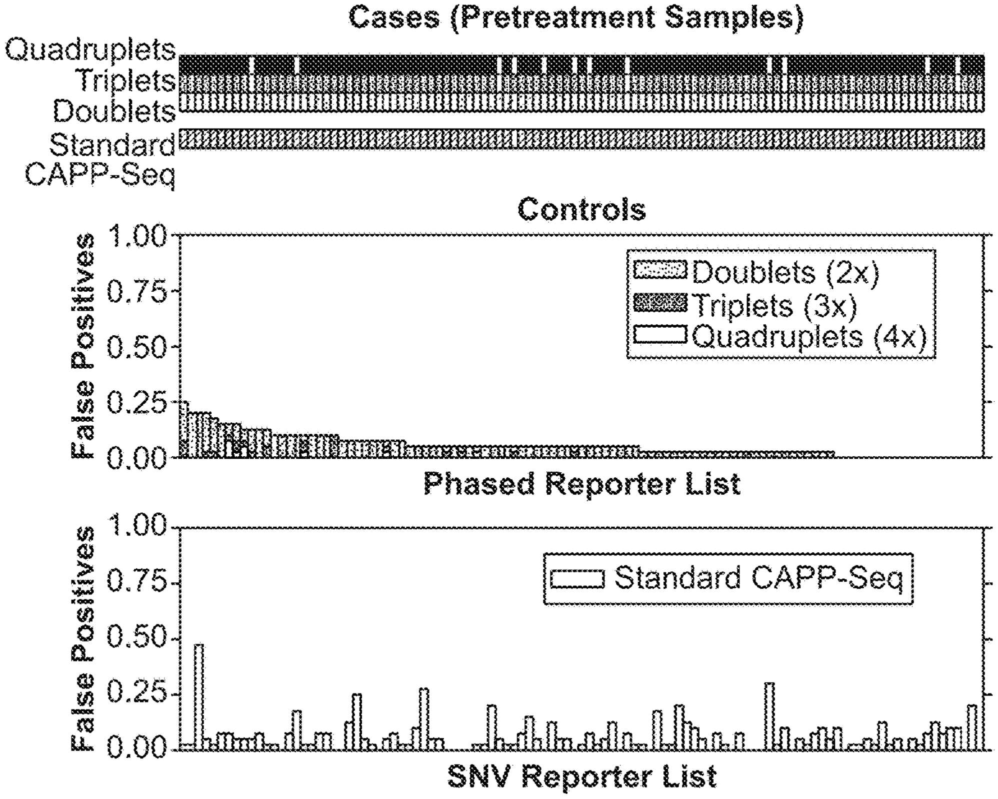
FIG. 15
| | Sensitivity | Specificity |
|---|---|---|
| CAPP-Seq | 0.98 | 0.94 |
| Doublets | 0.98 | 0.95 |
| Triplets | 0.95 | 0.99 |
| Quadruplets | 0.89 | 1.00 |
FIG. 16A
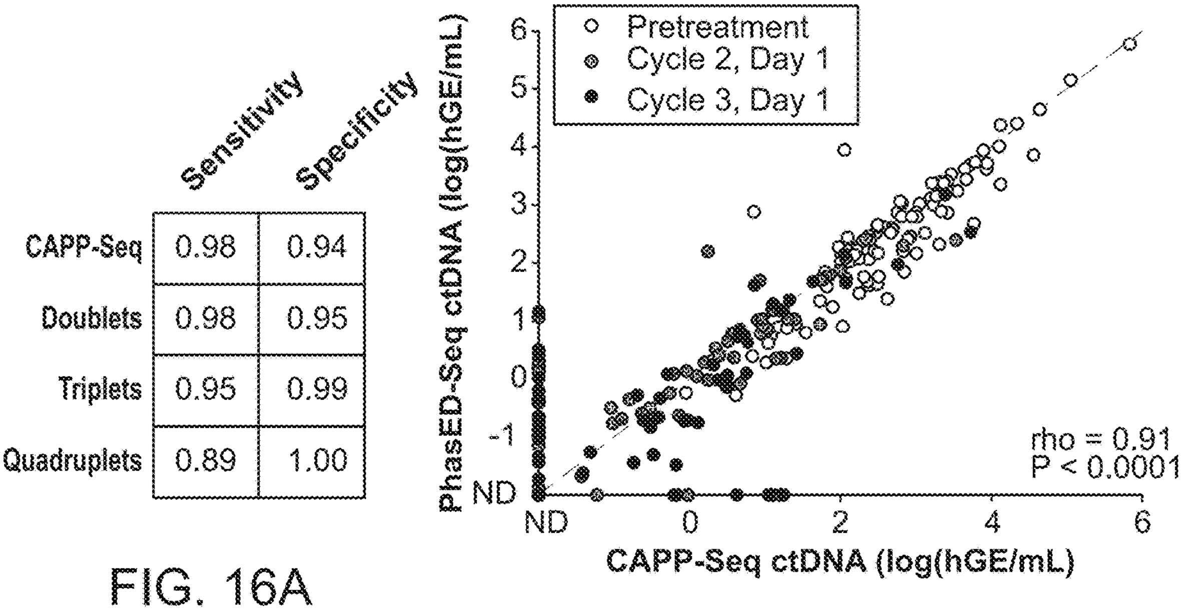
FIG. 16B

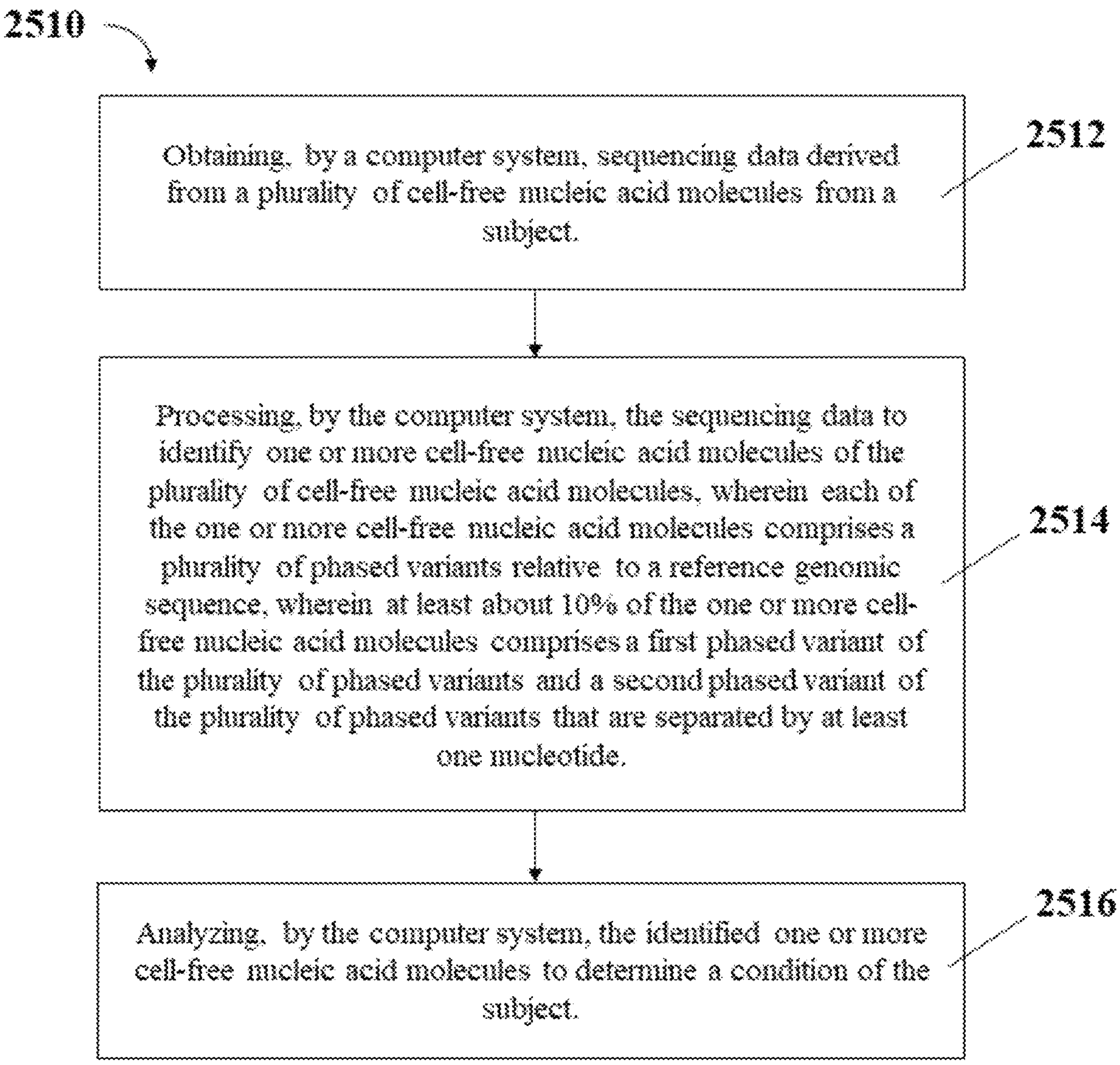

2512 — Obtaining, by a computer system, sequencing data derived from a plurality of cell-free nucleic acid molecules from a subject.

2514 — Processing, by the computer system, the sequencing data to identify one or more cell-free nucleic acid molecules of the plurality of cell-free nucleic acid molecules, wherein each of the one or more cell-free nucleic acid molecules comprises a plurality of phased variants relative to a reference genomic sequence, wherein at least about 10% of the one or more cell-free nucleic acid molecules comprises a first phased variant of the plurality of phased variants and a second phased variant of the plurality of phased variants that are separated by at least one nucleotide.

2516 — Analyzing, by the computer system, the identified one or more cell-free nucleic acid molecules to determine a condition of the subject.

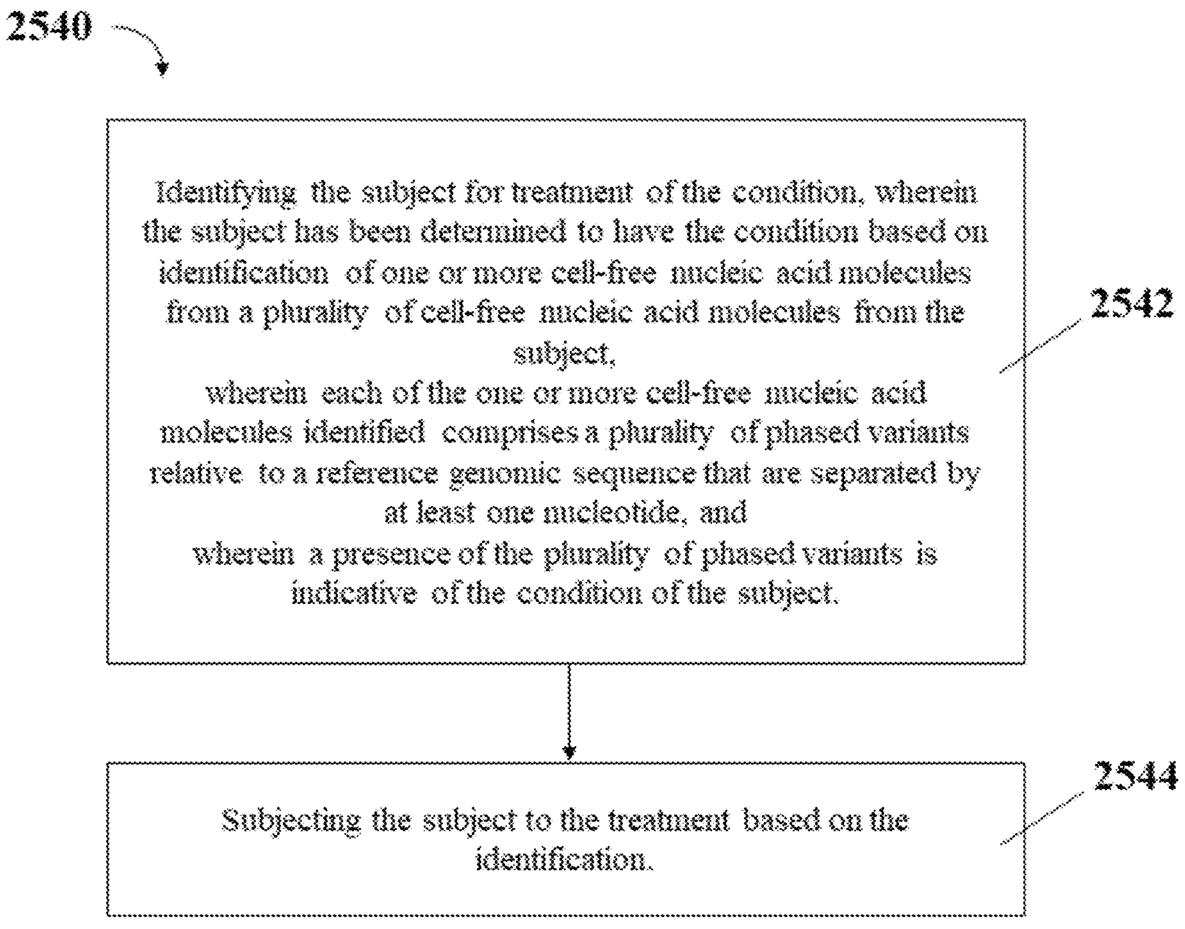

2542 — Identifying the subject for treatment of the condition, wherein the subject has been determined to have the condition based on identification of one or more cell-free nucleic acid molecules from a plurality of cell-free nucleic acid molecules from the subject,
wherein each of the one or more cell-free nucleic acid molecules identified comprises a plurality of phased variants relative to a reference genomic sequence that are separated by at least one nucleotide, and
wherein a presence of the plurality of phased variants is indicative of the condition of the subject.

2544 — Subjecting the subject to the treatment based on the identification.

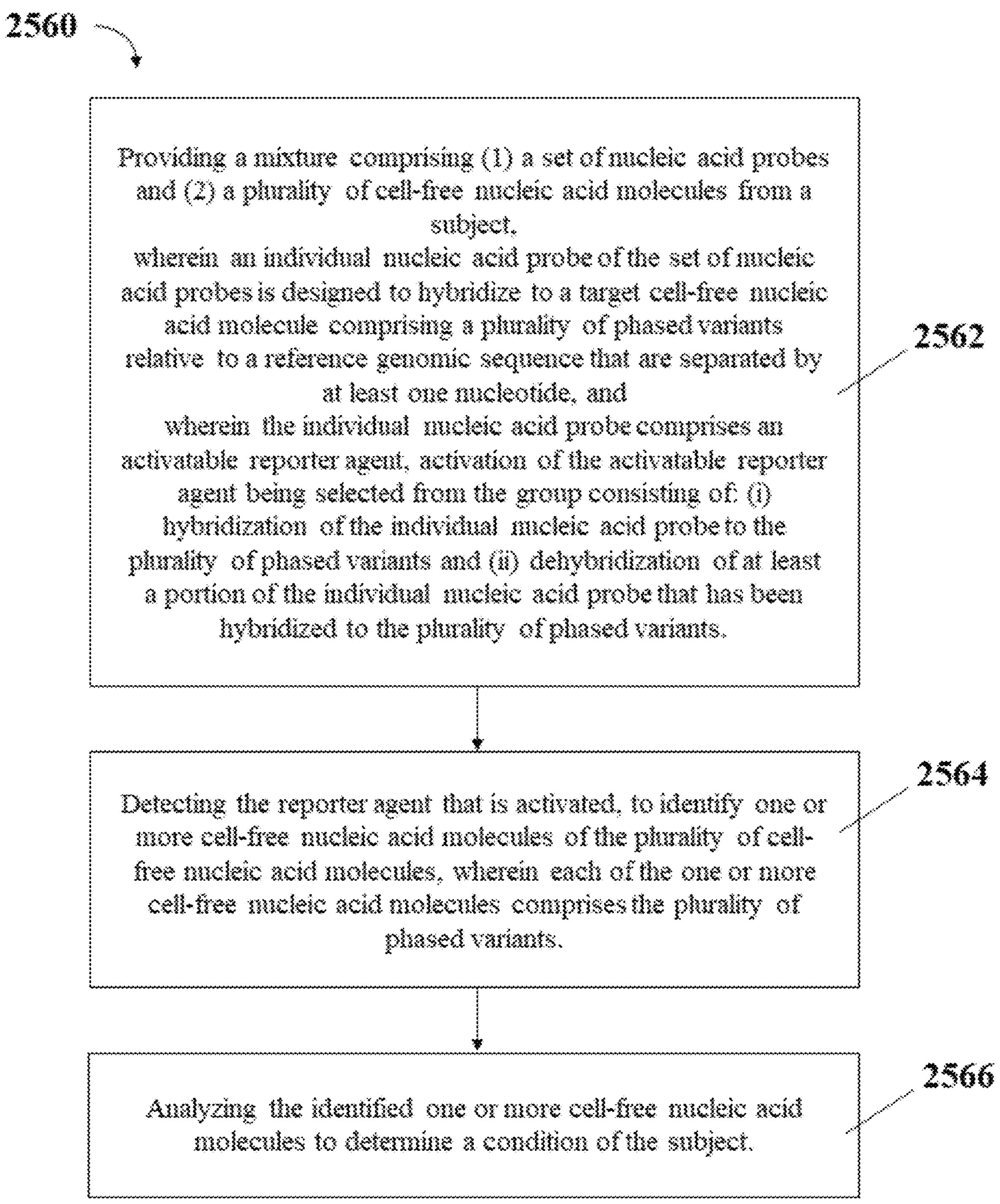

2562 — Providing a mixture comprising (1) a set of nucleic acid probes and (2) a plurality of cell-free nucleic acid molecules from a subject,
wherein an individual nucleic acid probe of the set of nucleic acid probes is designed to hybridize to a target cell-free nucleic acid molecule comprising a plurality of phased variants relative to a reference genomic sequence that are separated by at least one nucleotide, and
wherein the individual nucleic acid probe comprises an activatable reporter agent, activation of the activatable reporter agent being selected from the group consisting of: (i) hybridization of the individual nucleic acid probe to the plurality of phased variants and (ii) dehybridization of at least a portion of the individual nucleic acid probe that has been hybridized to the plurality of phased variants.

2564 — Detecting the reporter agent that is activated, to identify one or more cell-free nucleic acid molecules of the plurality of cell-free nucleic acid molecules, wherein each of the one or more cell-free nucleic acid molecules comprises the plurality of phased variants.

2566 — Analyzing the identified one or more cell-free nucleic acid molecules to determine a condition of the subject.

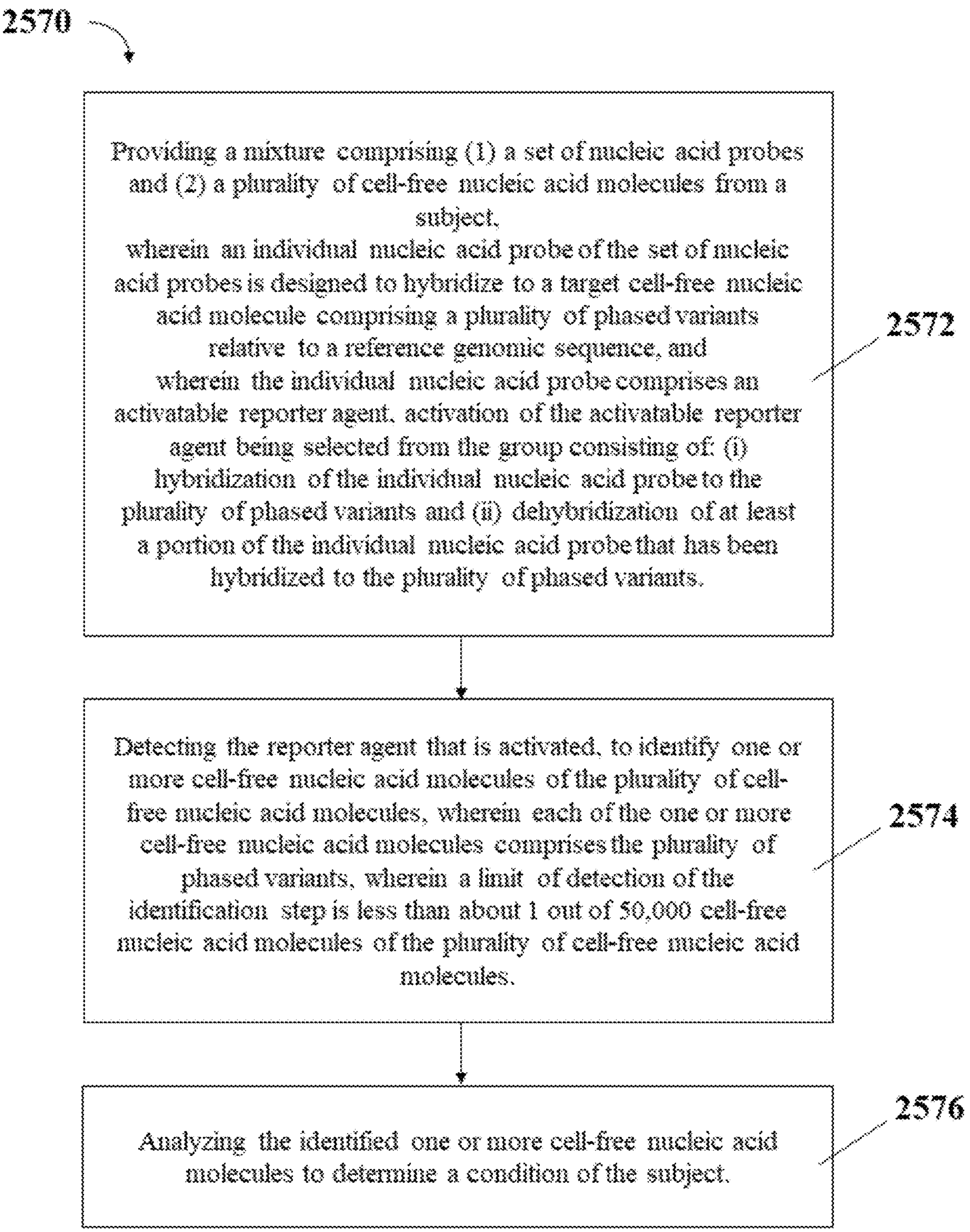

2572 — Providing a mixture comprising (1) a set of nucleic acid probes and (2) a plurality of cell-free nucleic acid molecules from a subject,
wherein an individual nucleic acid probe of the set of nucleic acid probes is designed to hybridize to a target cell-free nucleic acid molecule comprising a plurality of phased variants relative to a reference genomic sequence, and
wherein the individual nucleic acid probe comprises an activatable reporter agent, activation of the activatable reporter agent being selected from the group consisting of: (i) hybridization of the individual nucleic acid probe to the plurality of phased variants and (ii) dehybridization of at least a portion of the individual nucleic acid probe that has been hybridized to the plurality of phased variants.

2574 — Detecting the reporter agent that is activated, to identify one or more cell-free nucleic acid molecules of the plurality of cell-free nucleic acid molecules, wherein each of the one or more cell-free nucleic acid molecules comprises the plurality of phased variants, wherein a limit of detection of the identification step is less than about 1 out of 50,000 cell-free nucleic acid molecules of the plurality of cell-free nucleic acid molecules.

2576 — Analyzing the identified one or more cell-free nucleic acid molecules to determine a condition of the subject.

SEQUENCE LISTING

```
Sequence total quantity: 1358
SEQ ID NO: 1           moltype = DNA  length = 100
FEATURE                Location/Qualifiers
source                 1..100
                       mol_type = genomic DNA
                       organism = Homo sapiens
SEQUENCE: 1
tctcttctgg cccacagccg cagcaatggc gctgagttcc tctgctggag ttcatcctgc  60
tagctgggtt cccgagctgc cggtctgagc ctgaggcatg                        100

SEQ ID NO: 2           moltype = DNA  length = 100
FEATURE                Location/Qualifiers
source                 1..100
                       mol_type = genomic DNA
                       organism = Homo sapiens
SEQUENCE: 2
gagcctcctg gagactgggg gcctcctccc tggagatcca cccccaaaac cgacgtcttg  60
aggctggtga gcccccgagc ctcctctccg tctgctcgca                        100

SEQ ID NO: 3           moltype = DNA  length = 100
FEATURE                Location/Qualifiers
source                 1..100
                       mol_type = genomic DNA
                       organism = Homo sapiens
SEQUENCE: 3
gatcccagtt ctgaccccag ggcctcccac agatctcttc cccatgcccc tgtcctggcc  60
gttgctggct ccggcgtcca gcccgtcccc tgctgcctgg                        100

SEQ ID NO: 4           moltype = DNA  length = 100
FEATURE                Location/Qualifiers
source                 1..100
                       mol_type = genomic DNA
                       organism = Homo sapiens
SEQUENCE: 4
ccatgttgct ggcttacttg gcatttccca tgatctcaca ctgctggctt atttggcatt  60
tcccatgatc ccctgctgct ggtttacttg gcattcccta                        100

SEQ ID NO: 5           moltype = DNA  length = 100
FEATURE                Location/Qualifiers
source                 1..100
                       mol_type = genomic DNA
                       organism = Homo sapiens
SEQUENCE: 5
tgatcccatg ttgctggttt acttagcatt tcccatgatc ccatgttgct ggcttacttg  60
gcatttccca tgataccatg ttgctggctt acttggcatt                        100

SEQ ID NO: 6           moltype = DNA  length = 100
FEATURE                Location/Qualifiers
source                 1..100
                       mol_type = genomic DNA
                       organism = Homo sapiens
SEQUENCE: 6
atagattaga ggaaggaatt ctagatgaaa ttaagtaaat gagttattta agtcaactaa  60
tacaagtcct caaaactttg attatataga gagctaaact                        100

SEQ ID NO: 7           moltype = DNA  length = 100
FEATURE                Location/Qualifiers
source                 1..100
                       mol_type = genomic DNA
                       organism = Homo sapiens
SEQUENCE: 7
gataaatata gacaaatata gtgagcctat aaattaaagc tatactatga tgaaaaaata  60
aatgaataat tgtgaaatag ccaaaaatac taaaatacag                        100

SEQ ID NO: 8           moltype = DNA  length = 100
FEATURE                Location/Qualifiers
source                 1..100
                       mol_type = genomic DNA
                       organism = Homo sapiens
SEQUENCE: 8
aatgaataat tgtgaaatag ccaaaaatac taaaatacag ctataaggtt aaaaataaat  60
ctgaataaaa aatgtaggag ggaaaagtga ttaccttacc                        100

SEQ ID NO: 9           moltype = DNA  length = 100
FEATURE                Location/Qualifiers
source                 1..100
                       mol_type = genomic DNA
                       organism = Homo sapiens
```

```
SEQUENCE: 9
gacatgcatc aaatgtaaac aaatgattac agccatttta taaaaagtca tattctttaa  60
aacatttttt gtcatcatta aaaattaaaa ggcaataaag                       100

SEQ ID NO: 10          moltype = DNA  length = 100
FEATURE                Location/Qualifiers
source                 1..100
                       mol_type = genomic DNA
                       organism = Homo sapiens
SEQUENCE: 10
tgtcattgtc gtgaaacagt acgtgatctt aagggaagaa acatctcact agagtttgca  60
caagttcctt cttcttctaa ctgtagatct ggtggcaaag                       100

SEQ ID NO: 11          moltype = DNA  length = 100
FEATURE                Location/Qualifiers
source                 1..100
                       mol_type = genomic DNA
                       organism = Homo sapiens
SEQUENCE: 11
gaggagcccc tgggtcccca ggtctgggaa gtgtagttga agagaagatg gtattttcag  60
ttctgcctac ttctagaaca ggcaaattca gagaagaatt                       100

SEQ ID NO: 12          moltype = DNA  length = 100
FEATURE                Location/Qualifiers
source                 1..100
                       mol_type = genomic DNA
                       organism = Homo sapiens
SEQUENCE: 12
agtagaaaaa aagggcgtcg tgctggattc tccttctgga tggtacatga cagtggatgc  60
cctcagtttt tcagagaaat tactctcatc tgaatttgat                       100

SEQ ID NO: 13          moltype = DNA  length = 100
FEATURE                Location/Qualifiers
source                 1..100
                       mol_type = genomic DNA
                       organism = Homo sapiens
SEQUENCE: 13
ctggagaggt tgttcgtggc tccatctgga aaaggttcac aactgctaca ttttagtcct  60
acaataaaat tattcagatg taaatgaaaa agtaactaaa                       100

SEQ ID NO: 14          moltype = DNA  length = 100
FEATURE                Location/Qualifiers
source                 1..100
                       mol_type = genomic DNA
                       organism = Homo sapiens
SEQUENCE: 14
acccgagacc tctcactgag cccgagccgc gcgcgacatg agccacggga agggaaccga  60
catgctcccg gagatcgccg ccgccgtggg cttcctctcc                       100

SEQ ID NO: 15          moltype = DNA  length = 100
FEATURE                Location/Qualifiers
source                 1..100
                       mol_type = genomic DNA
                       organism = Homo sapiens
SEQUENCE: 15
agcctcctga ggacccgggg ctgcgtgagc gagcagaggc ttaaggtctt cagcggggcg  60
ctccaggagg cactcacagg tgagcgcatg ccgaggggcc                       100

SEQ ID NO: 16          moltype = DNA  length = 100
FEATURE                Location/Qualifiers
source                 1..100
                       mol_type = genomic DNA
                       organism = Homo sapiens
SEQUENCE: 16
tggcgccacc gggggtcggc cccatccctg ccagggccgt ctttcttcta ctcctgcggc  60
agggtgaccc acgggagcag ctttgggact cggtggccct                       100

SEQ ID NO: 17          moltype = DNA  length = 100
FEATURE                Location/Qualifiers
source                 1..100
                       mol_type = genomic DNA
                       organism = Homo sapiens
SEQUENCE: 17
cctccgaccc ccggggcggc ccgcagtccc cagtttcctg ggtcctcctc cccagccctg  60
tgctcgggtc tcggccgtgg cggttctgat ggggcgcgcc                       100

SEQ ID NO: 18          moltype = DNA  length = 100
FEATURE                Location/Qualifiers
source                 1..100
```

```
                         mol_type = genomic DNA
                         organism = Homo sapiens
SEQUENCE: 18
cctctacgct ctcggaggcg cagaccctgg tcctggagtg ccagcccgag tccccagctt  60
atgcccctgt ctcattacgg gctcgtctcc ctcgctggac                        100

SEQ ID NO: 19            moltype = DNA  length = 100
FEATURE                  Location/Qualifiers
source                   1..100
                         mol_type = genomic DNA
                         organism = Homo sapiens
SEQUENCE: 19
cctcgagatc ttaagaccct cgatggatgt tgttgcgggc cgcccggtcg gccgaggggt  60
cccgatgagg gaagaaggtg cagtcgagcc ttttcaacaa                        100

SEQ ID NO: 20            moltype = DNA  length = 100
FEATURE                  Location/Qualifiers
source                   1..100
                         mol_type = genomic DNA
                         organism = Homo sapiens
SEQUENCE: 20
tttggagtcc cagtgcggtt cttcctgccg gtcggggtgc gctgtgcctg gggtagtcca  60
ctggttgctg actggcttca agttggaatt tgggccccct                        100

SEQ ID NO: 21            moltype = DNA  length = 100
FEATURE                  Location/Qualifiers
source                   1..100
                         mol_type = genomic DNA
                         organism = Homo sapiens
SEQUENCE: 21
ttgtgttatc tttggttccc cttagccatc tgccacctat tgtggtaggg aggagagcct  60
cgtagctcgt gaccctgccg tgcgggcctt caagttggga                        100

SEQ ID NO: 22            moltype = DNA  length = 100
FEATURE                  Location/Qualifiers
source                   1..100
                         mol_type = genomic DNA
                         organism = Homo sapiens
SEQUENCE: 22
ggtgaagaga taagcagccc gctcgctggc tggggagaga cctctctccc agctgtttct  60
agctggttac tgtcagtttt gggaagcgat agccatctcg                        100

SEQ ID NO: 23            moltype = DNA  length = 100
FEATURE                  Location/Qualifiers
source                   1..100
                         mol_type = genomic DNA
                         organism = Homo sapiens
SEQUENCE: 23
gaacgcaccc acacagaccc tgccttctga ggaaaacaga tgtttcatca aaacaaccca  60
gttttcactc ccttaggcac tgctaaggaa ggttctctga                        100

SEQ ID NO: 24            moltype = DNA  length = 100
FEATURE                  Location/Qualifiers
source                   1..100
                         mol_type = genomic DNA
                         organism = Homo sapiens
SEQUENCE: 24
ctcttctgaa ggaagcagag ggaacacagg gtgggaggtc cagtgacttg ctgtggaccc  60
aacaatgttg gcagccttcc tggccctgaa acttcagctc                        100

SEQ ID NO: 25            moltype = DNA  length = 100
FEATURE                  Location/Qualifiers
source                   1..100
                         mol_type = genomic DNA
                         organism = Homo sapiens
SEQUENCE: 25
acaggtctcc agaggccctg cctggacatg ccagtcccag tcacaccctt cccttgcttt  60
gggggtgtgc caaaagcaat acactggcca ctagagagta                        100

SEQ ID NO: 26            moltype = DNA  length = 100
FEATURE                  Location/Qualifiers
source                   1..100
                         mol_type = genomic DNA
                         organism = Homo sapiens
SEQUENCE: 26
ccctagagct ctagaatccc ctcccaacac gcacacacac acacacacac actctctctc  60
tcacacacac acactcagtc acacacacac acacacacac                        100

SEQ ID NO: 27            moltype = DNA  length = 100
```

```
FEATURE                Location/Qualifiers
source                 1..100
                       mol_type = genomic DNA
                       organism = Homo sapiens
SEQUENCE: 27
ctttcagatc tttcgcagcg tcccaacagg gcaaaggctc cagcattctg ccagaaggaa  60
ttcccgcctc cacattcccg gtccccggct gtgctgaggg                       100

SEQ ID NO: 28          moltype = DNA  length = 100
FEATURE                Location/Qualifiers
source                 1..100
                       mol_type = genomic DNA
                       organism = Homo sapiens
SEQUENCE: 28
gctgccccca agcaagccca gcgttgggga ccctccctcc actctgtcgg agagctgcca  60
acgccccccg cccacggggg ccccacttcg ggcctcctca                       100

SEQ ID NO: 29          moltype = DNA  length = 100
FEATURE                Location/Qualifiers
source                 1..100
                       mol_type = genomic DNA
                       organism = Homo sapiens
SEQUENCE: 29
gggcctacgg aggccagggc cctgggcagc ctggaccagc tcagggaatc agaggactct  60
gcgctttgca cgctcacagt cgtctcctct ggccttttgc                       100

SEQ ID NO: 30          moltype = DNA  length = 100
FEATURE                Location/Qualifiers
source                 1..100
                       mol_type = genomic DNA
                       organism = Homo sapiens
SEQUENCE: 30
ccacttcagg ctccccagag cccggcatgc cacagggcag atatcctttc cccatcttcc  60
cagggggttc tccatcgcgg ggcccgcccc tttctggggc                       100

SEQ ID NO: 31          moltype = DNA  length = 100
FEATURE                Location/Qualifiers
source                 1..100
                       mol_type = genomic DNA
                       organism = Homo sapiens
SEQUENCE: 31
tgggcttgtc tcactgccca gaaactgccc ctgcctctcc accagggcct ctgggggctg  60
caggtcctca agctcacggg ctctcccaga cggctcagtg                       100

SEQ ID NO: 32          moltype = DNA  length = 100
FEATURE                Location/Qualifiers
source                 1..100
                       mol_type = genomic DNA
                       organism = Homo sapiens
SEQUENCE: 32
agggcaagat cctgtggacg gtgtggccca gtggatgtaa ctctcgctgc cacttccgtg  60
gccatcgtta agctagctcc gaacagcccc aatgagggag                       100

SEQ ID NO: 33          moltype = DNA  length = 100
FEATURE                Location/Qualifiers
source                 1..100
                       mol_type = genomic DNA
                       organism = Homo sapiens
SEQUENCE: 33
ctaggcagct ccgagttccc ggggtaggag agcccctttt gtcaatttcc atagctgtgg  60
gtgagccaca gcggggactg gcagggatac ccttctccat                       100

SEQ ID NO: 34          moltype = DNA  length = 100
FEATURE                Location/Qualifiers
source                 1..100
                       mol_type = genomic DNA
                       organism = Homo sapiens
SEQUENCE: 34
ccttacaaaa gcggatggac cctgagcctc tgatcctgta ggggcagccc ggccgggaag  60
aggtggcatt cctttcttca cctgcgagga gcataggctg                       100

SEQ ID NO: 35          moltype = DNA  length = 100
FEATURE                Location/Qualifiers
source                 1..100
                       mol_type = genomic DNA
                       organism = Homo sapiens
SEQUENCE: 35
ggccctcctt tcctcccgga gtcggttcct gaagtctctg gacattgctc cccccaggac  60
tttgtcctcc gttcctcgct ccgggcgccc tgaaccagga                       100
```

```
SEQ ID NO: 36          moltype = DNA  length = 100
FEATURE                Location/Qualifiers
source                 1..100
                       mol_type = genomic DNA
                       organism = Homo sapiens
SEQUENCE: 36
cccttccagg gggctgactg ctgctgcgga aggggcacgg ggagggcgag cgagccctgc  60
ccaaacgcgg gctgcggggc gcttgaatgg cggagctctg                        100

SEQ ID NO: 37          moltype = DNA  length = 100
FEATURE                Location/Qualifiers
source                 1..100
                       mol_type = genomic DNA
                       organism = Homo sapiens
SEQUENCE: 37
tgcctggatg tgcgcctcaa acatgcccac tttctggttc acctgcacgt tctgcaactc  60
gcgctgcaag atccgcagct tcctcttggc ctcctccggc                        100

SEQ ID NO: 38          moltype = DNA  length = 100
FEATURE                Location/Qualifiers
source                 1..100
                       mol_type = genomic DNA
                       organism = Homo sapiens
SEQUENCE: 38
cctggcgggg agagggtacc ggctgccacc acctgctgcc ggtcccctcg caggcgacca  60
gcccaacttg ggctgctcac gctactgccg ctgctgccgc                        100

SEQ ID NO: 39          moltype = DNA  length = 100
FEATURE                Location/Qualifiers
source                 1..100
                       mol_type = genomic DNA
                       organism = Homo sapiens
SEQUENCE: 39
tgccactgcc gctgctacta ttcagcctgc gccggccgct ccgccagccc ccggggctcc  60
ggggctcctc gggggacagc gactcggctg gggggaagag                        100

SEQ ID NO: 40          moltype = DNA  length = 100
FEATURE                Location/Qualifiers
source                 1..100
                       mol_type = genomic DNA
                       organism = Homo sapiens
SEQUENCE: 40
gaaagaggcg cctctcccgg ggctgaaaac gctgccgggg ctcagcactg ccctcctcgg  60
gggcgggggc gtctcgctgc cactgggccc cgggccgccg                        100

SEQ ID NO: 41          moltype = DNA  length = 100
FEATURE                Location/Qualifiers
source                 1..100
                       mol_type = genomic DNA
                       organism = Homo sapiens
SEQUENCE: 41
ccgctcttca tctcgttggc gctattcatg atcaccaggc tattgagcgc atagcagtac  60
acagccatag tactgggtcc cgcgctgccc gccgccgcgg                        100

SEQ ID NO: 42          moltype = DNA  length = 100
FEATURE                Location/Qualifiers
source                 1..100
                       mol_type = genomic DNA
                       organism = Homo sapiens
SEQUENCE: 42
ctcccgctcc tgctccgccg ccggcgcctc ctcctcccgg cgctcccggc tcagccccgg  60
aggcccggca gccgcggctc cgcgcgcaga tggggcggca                        100

SEQ ID NO: 43          moltype = DNA  length = 100
FEATURE                Location/Qualifiers
source                 1..100
                       mol_type = genomic DNA
                       organism = Homo sapiens
SEQUENCE: 43
aagtgcgaag gaagtgtcag gctggatgtc aaaatgaaca ccttggagaa ctggatgatg  60
gaacagacgg taaaaatcag ctaaacatca gagaaaatgg                        100

SEQ ID NO: 44          moltype = DNA  length = 100
FEATURE                Location/Qualifiers
source                 1..100
                       mol_type = genomic DNA
                       organism = Homo sapiens
SEQUENCE: 44
```

```
aggaagaggt caaaactgtg aacaggaact agaagaaagt gtagcagaaa aagacttgtc  60
acaaacttcg agagatttgg agaaaatgat gtcaaaacac                        100

SEQ ID NO: 45          moltype = DNA  length = 100
FEATURE                Location/Qualifiers
source                 1..100
                       mol_type = genomic DNA
                       organism = Homo sapiens
SEQUENCE: 45
atcttcctca agcccatgct gagtatctct gatttggtta atttcttggt aagtgttcca  60
agtacagaca acaaagcaga aaagcactga ttacagggaa                        100

SEQ ID NO: 46          moltype = DNA  length = 100
FEATURE                Location/Qualifiers
source                 1..100
                       mol_type = genomic DNA
                       organism = Homo sapiens
SEQUENCE: 46
tatgcagaat gatccttcag atcatgtgaa cgctataatt aaatgttgct accaaatccc  60
cactaccctt tctcccacct agaaaaagtt aatgcatgaa                        100

SEQ ID NO: 47          moltype = DNA  length = 100
FEATURE                Location/Qualifiers
source                 1..100
                       mol_type = genomic DNA
                       organism = Homo sapiens
SEQUENCE: 47
ttcagtatga gcaaattgtg atttataaaa acaaacaaac aaacaaacaa acaaaaccca  60
ccctattcac tccgtagggg aataaagctt tcttgcatta                        100

SEQ ID NO: 48          moltype = DNA  length = 100
FEATURE                Location/Qualifiers
source                 1..100
                       mol_type = genomic DNA
                       organism = Homo sapiens
SEQUENCE: 48
aacaaacaaa acccacccta ttcactccgt aggggaataa agctttcttg cattaagtca  60
cgcatcatgg gggtaggaaa aaagcacagt actgaaagaa                        100

SEQ ID NO: 49          moltype = DNA  length = 100
FEATURE                Location/Qualifiers
source                 1..100
                       mol_type = genomic DNA
                       organism = Homo sapiens
SEQUENCE: 49
gtgaagtgat ccaaatgtag cccagagatc ctaaagaaaa aacgatgctc atgtgttaca  60
aaacaaaatt ttaaggcaat cagtgaggaa tcacagacaa                        100

SEQ ID NO: 50          moltype = DNA  length = 100
FEATURE                Location/Qualifiers
source                 1..100
                       mol_type = genomic DNA
                       organism = Homo sapiens
SEQUENCE: 50
atttccttag tgcttttatc aaggttgaat ctgaatataa attactagag gaaagcaaat  60
cagatttcac atctgaaaat taaaaacaaa attcttagct                        100

SEQ ID NO: 51          moltype = DNA  length = 100
FEATURE                Location/Qualifiers
source                 1..100
                       mol_type = genomic DNA
                       organism = Homo sapiens
SEQUENCE: 51
aggcaacaaa atgagatcct gtccctagaa aacatttcaa aaaattaaca gcatggtgac  60
gcacacttgt agccctagct acttgggagg ctgagtggga                        100

SEQ ID NO: 52          moltype = DNA  length = 100
FEATURE                Location/Qualifiers
source                 1..100
                       mol_type = genomic DNA
                       organism = Homo sapiens
SEQUENCE: 52
aagaacttaa gcagactagg atataaagta taggagcgta ttgtgtacag gaacgggaaa  60
tactgtttcc tggatctttt gtttcactta cgcacacacc                        100

SEQ ID NO: 53          moltype = DNA  length = 100
FEATURE                Location/Qualifiers
source                 1..100
                       mol_type = genomic DNA
```

```
                         organism = Homo sapiens
SEQUENCE: 53
cacacccgcc agtagtgtac caggttgcga tggaaatctc tctctttctg tggatgagtt  60
tgtggaagcc cttgctccag catgccctcc ttcctgccca                        100

SEQ ID NO: 54            moltype = DNA  length = 100
FEATURE                  Location/Qualifiers
source                   1..100
                         mol_type = genomic DNA
                         organism = Homo sapiens
SEQUENCE: 54
cccctggacc attccttccc ttcacagcac tgtcccatgg gtaggccaca gcccagcaca  60
ggccccagcc tggcggctgc agcaggagcc ccatcccagg                        100

SEQ ID NO: 55            moltype = DNA  length = 100
FEATURE                  Location/Qualifiers
source                   1..100
                         mol_type = genomic DNA
                         organism = Homo sapiens
SEQUENCE: 55
gcctgagggg ccatgcgggg gtctgggtgg gagtgggaac cgctgaggaa ggtgaaggga  60
aatatggtga gatgacaggc ccgctgtcag ggagagtggg                        100

SEQ ID NO: 56            moltype = DNA  length = 100
FEATURE                  Location/Qualifiers
source                   1..100
                         mol_type = genomic DNA
                         organism = Homo sapiens
SEQUENCE: 56
aggagccctg gagtgcccta cctctgtggg gctggaactc cctgtatccg agctagggtc  60
ttccacacgc atgctactac cccaagtgcc acagctggag                        100

SEQ ID NO: 57            moltype = DNA  length = 100
FEATURE                  Location/Qualifiers
source                   1..100
                         mol_type = genomic DNA
                         organism = Homo sapiens
SEQUENCE: 57
tcatctccca ctggataaca gtgttgtcgg gaacttccat ccagcactgg cggacactcc  60
cgtcgcagct gctcctgact gagcaagtca tttaaggggg                        100

SEQ ID NO: 58            moltype = DNA  length = 100
FEATURE                  Location/Qualifiers
source                   1..100
                         mol_type = genomic DNA
                         organism = Homo sapiens
SEQUENCE: 58
tccttggcac tcataagcac tcacagaatg gggctggcag tgcgcccggc ctccctggga  60
tgggtccaga atggtaggaa gcgcagtccg ggagggaccc                        100

SEQ ID NO: 59            moltype = DNA  length = 100
FEATURE                  Location/Qualifiers
source                   1..100
                         mol_type = genomic DNA
                         organism = Homo sapiens
SEQUENCE: 59
actgcttaga gctctcagcc ctagatggcg tatcacagtt aatgctctat aaaacccatc  60
atggcttttc cctagtaagc ctcaaatcgc tgcaagcaag                        100

SEQ ID NO: 60            moltype = DNA  length = 100
FEATURE                  Location/Qualifiers
source                   1..100
                         mol_type = genomic DNA
                         organism = Homo sapiens
SEQUENCE: 60
gcttcatata tgagagtttc tgctgtctcc tggagccatc tcacccaaag ccactgactc  60
tgggagacca gcccaggcca caaaccagca aagcaccagt                        100

SEQ ID NO: 61            moltype = DNA  length = 100
FEATURE                  Location/Qualifiers
source                   1..100
                         mol_type = genomic DNA
                         organism = Homo sapiens
SEQUENCE: 61
tatagttaga gctgcattat aaagtggcca gaggacattt ctttgcagtg agatgtgtat  60
cgtgaacgtt tggggcctgt gctcgcctag tcctcatctt                        100

SEQ ID NO: 62            moltype = DNA  length = 100
FEATURE                  Location/Qualifiers
```

```
source                 1..100
                       mol_type = genomic DNA
                       organism = Homo sapiens
SEQUENCE: 62
tgcttttcta ggtacacaaa gccatcccat ggctgcaaat gttagctggg ctgggctccc  60
tacttgcctc aagccccttc atagaccctt caggcacatg                        100

SEQ ID NO: 63          moltype = DNA  length = 100
FEATURE                Location/Qualifiers
source                 1..100
                       mol_type = genomic DNA
                       organism = Homo sapiens
SEQUENCE: 63
cttttctctg gacgtttaca gacaggtcct cagaggtcag agcaggttgt cctagggagc  60
agggaggctt cctagggagg tcagactcca aatagtggat                        100

SEQ ID NO: 64          moltype = DNA  length = 100
FEATURE                Location/Qualifiers
source                 1..100
                       mol_type = genomic DNA
                       organism = Homo sapiens
SEQUENCE: 64
atggcaaaaa tgcagctgca gactcatgag gagtcgccct gggctgccac tagggctccc  60
acagtgtgcg ctgccaacct gctgcccgtg cagaaactct                        100

SEQ ID NO: 65          moltype = DNA  length = 100
FEATURE                Location/Qualifiers
source                 1..100
                       mol_type = genomic DNA
                       organism = Homo sapiens
SEQUENCE: 65
caactgtgcc ctgcactgtt agggcccttg tcaaaacaac acatttctca gtgattctga  60
gactctttct cttatctata gaagtcataa ctcaagagta                        100

SEQ ID NO: 66          moltype = DNA  length = 100
FEATURE                Location/Qualifiers
source                 1..100
                       mol_type = genomic DNA
                       organism = Homo sapiens
SEQUENCE: 66
aaatcatacc aatattttac ataaacccta gaatttttat agatctatta tttcttttta  60
gagtacatat tggaagtaac ttcacaagga acattttctt                        100

SEQ ID NO: 67          moltype = DNA  length = 100
FEATURE                Location/Qualifiers
source                 1..100
                       mol_type = genomic DNA
                       organism = Homo sapiens
SEQUENCE: 67
tctggtcaaa ccactccaca aataaagtgg actgatcctc ttgactctat gtgtaagtgc  60
ccattgtgtg tgcacagagc tggtgagaac ggccatggtg                        100

SEQ ID NO: 68          moltype = DNA  length = 100
FEATURE                Location/Qualifiers
source                 1..100
                       mol_type = genomic DNA
                       organism = Homo sapiens
SEQUENCE: 68
ctaggtgggg gtggtgttgg tggagttgga ctagattatc tgggatcatg cgaaatggaa  60
attcatttct agctggctgg cttcagaagg tgccatctcc                        100

SEQ ID NO: 69          moltype = DNA  length = 100
FEATURE                Location/Qualifiers
source                 1..100
                       mol_type = genomic DNA
                       organism = Homo sapiens
SEQUENCE: 69
tatttttata tgaagcgtgc tttggaactc agggcaacga agggtgggtg tgctgcacaa  60
ggacagcaga agagtgagct gactggtccc tgaaatcgca                        100

SEQ ID NO: 70          moltype = DNA  length = 100
FEATURE                Location/Qualifiers
source                 1..100
                       mol_type = genomic DNA
                       organism = Homo sapiens
SEQUENCE: 70
gttggaaagt ggattaccag tgcagtagaa ctcttcacgg aggcctggac catcaggtct  60
aatggtgttg ttccaggtgg gtggtcatgt ggagcaaaaa                        100
```

```
SEQ ID NO: 71          moltype = DNA  length = 100
FEATURE                Location/Qualifiers
source                 1..100
                       mol_type = genomic DNA
                       organism = Homo sapiens
SEQUENCE: 71
tatttgaaat cagcgagcac gtacctgaga gatgactttt ccacttgggc tagtctcttg  60
atatttctgg tcctgtttct tcatctgtaa actgggttag                        100

SEQ ID NO: 72          moltype = DNA  length = 100
FEATURE                Location/Qualifiers
source                 1..100
                       mol_type = genomic DNA
                       organism = Homo sapiens
SEQUENCE: 72
aaggagacca agaagcgtat ttaaaatctt gatgttttga gtttcttcct agcttccccc  60
tattccttaa taaagttcta aattgttttg ttggagctct                        100

SEQ ID NO: 73          moltype = DNA  length = 100
FEATURE                Location/Qualifiers
source                 1..100
                       mol_type = genomic DNA
                       organism = Homo sapiens
SEQUENCE: 73
ttgcagccat tctgagggct ttgcatgctt ttctgacctt gcagtaaact caatgcttta  60
ggcaaagaat ggccacgtca tccgaccccc tcagagttta                        100

SEQ ID NO: 74          moltype = DNA  length = 100
FEATURE                Location/Qualifiers
source                 1..100
                       mol_type = genomic DNA
                       organism = Homo sapiens
SEQUENCE: 74
gaattcagaa caggtctgaa gaagaccagg cagcggctga gtcaaggaaa gcctccgtcc  60
gcttttattt cccctgtgcc tcttccagga ctgtgctggg                        100

SEQ ID NO: 75          moltype = DNA  length = 100
FEATURE                Location/Qualifiers
source                 1..100
                       mol_type = genomic DNA
                       organism = Homo sapiens
SEQUENCE: 75
ataacaggct cccgggggtt actttggctg ggctgggcta aaacctccct gcagagcagg  60
ccctgagccc tgcctctgcg cctgggtggt gtcagcccct                        100

SEQ ID NO: 76          moltype = DNA  length = 100
FEATURE                Location/Qualifiers
source                 1..100
                       mol_type = genomic DNA
                       organism = Homo sapiens
SEQUENCE: 76
ccaccttctg actgttccag caactctcta agccctccca aaggcctcaa ggcctgtaac  60
catatgcagc aattttcagc cataccagga gaggtcaact                        100

SEQ ID NO: 77          moltype = DNA  length = 100
FEATURE                Location/Qualifiers
source                 1..100
                       mol_type = genomic DNA
                       organism = Homo sapiens
SEQUENCE: 77
gtaatcttgg ccacctgcct aagaggaagt ggctagcttc acttctgacc ctcagcaact  60
gccaggtggc ctcttggaaa tccccctctg ggggattcca                        100

SEQ ID NO: 78          moltype = DNA  length = 100
FEATURE                Location/Qualifiers
source                 1..100
                       mol_type = genomic DNA
                       organism = Homo sapiens
SEQUENCE: 78
cccgttgggt gggagagcag tagttaaaat gtaaaataag aatcttttgc tgggagaagt  60
caacagatag ggagaagtca gctgataaca gaaatagttt                        100

SEQ ID NO: 79          moltype = DNA  length = 100
FEATURE                Location/Qualifiers
source                 1..100
                       mol_type = genomic DNA
                       organism = Homo sapiens
SEQUENCE: 79
taaaactaac ttcactgtta accaagcagt tcaacatgaa agactgaatc tcttatgttt  60
```

```
aatattttct tctcttttaa tcttcataac taattttttt                       100

SEQ ID NO: 80          moltype = DNA  length = 100
FEATURE                Location/Qualifiers
source                 1..100
                       mol_type = genomic DNA
                       organism = Homo sapiens
SEQUENCE: 80
cagataattg tataaaataa ccatggtagc aaaataatgt gatcactgga aaataagcag  60
ggaaaaacat gctatgaaga tactcctatc tgggtgaatt                       100

SEQ ID NO: 81          moltype = DNA  length = 100
FEATURE                Location/Qualifiers
source                 1..100
                       mol_type = genomic DNA
                       organism = Homo sapiens
SEQUENCE: 81
cttgatagct ttacattttt catctggcat ttaaacatta aacagttaat gtatttgaca  60
tgaaaattat ttcaagttat cttattagtt ttaatagagt                       100

SEQ ID NO: 82          moltype = DNA  length = 100
FEATURE                Location/Qualifiers
source                 1..100
                       mol_type = genomic DNA
                       organism = Homo sapiens
SEQUENCE: 82
ttaaaaagtg tttaaaagag ttttcaaaag gctctaaaat cattttgaaa tagtttaaaa  60
cagttttgaa tcgttgtaag ttagttttaa tagagcttta                       100

SEQ ID NO: 83          moltype = DNA  length = 100
FEATURE                Location/Qualifiers
source                 1..100
                       mol_type = genomic DNA
                       organism = Homo sapiens
SEQUENCE: 83
aaaaggccct aaaatagtcc tatcaagttg ttgcagacca aaataatctc cttaaatatc  60
acttttgaga tcagctgggg taaacgacag caacacaatg                       100

SEQ ID NO: 84          moltype = DNA  length = 100
FEATURE                Location/Qualifiers
source                 1..100
                       mol_type = genomic DNA
                       organism = Homo sapiens
SEQUENCE: 84
acaaatcatt aaactatttt agagattatg aaattaaaat actcagatta aaattttcct  60
atcacagaat taaggtactg gaaaatatgt ttaagttttt                       100

SEQ ID NO: 85          moltype = DNA  length = 100
FEATURE                Location/Qualifiers
source                 1..100
                       mol_type = genomic DNA
                       organism = Homo sapiens
SEQUENCE: 85
attaatcaca ttgctatagg tttagatatt ttgtacaact gaaataaaat cacacactgg  60
cagctacatt tttgaaagtt aaaaacatgg tcacgaatat                       100

SEQ ID NO: 86          moltype = DNA  length = 100
FEATURE                Location/Qualifiers
source                 1..100
                       mol_type = genomic DNA
                       organism = Homo sapiens
SEQUENCE: 86
atcttatttt aaaatcagtt aatatacctt aatggtattt aatgccaaat tcaaagtgaa  60
ttgatcaagc cctcagtggc caggtcatgg gtgtgatttt                       100

SEQ ID NO: 87          moltype = DNA  length = 100
FEATURE                Location/Qualifiers
source                 1..100
                       mol_type = genomic DNA
                       organism = Homo sapiens
SEQUENCE: 87
tactctgaaa gaattacata tttctttctt tttggttgag cttttgttat ttaaatacat  60
ttgatgagag gatattgaaa taattaaata gcactgaaaa                       100

SEQ ID NO: 88          moltype = DNA  length = 100
FEATURE                Location/Qualifiers
source                 1..100
                       mol_type = genomic DNA
                       organism = Homo sapiens
```

```
SEQUENCE: 88
aaaaaaagct ttaaattatt tacaatcccc taatggaaat tttcactaat gagatatcat  60
aatgaatgtg aattttattt ctgaaatctc taataaatca                        100

SEQ ID NO: 89          moltype = DNA  length = 100
FEATURE                Location/Qualifiers
source                 1..100
                       mol_type = genomic DNA
                       organism = Homo sapiens
SEQUENCE: 89
aagctttaaa ttatttacaa tcccctaatg gaaattttca ctaatgagat atcataatga  60
atgtgaattt tatttctgaa atctctaata aatcagtctt                        100

SEQ ID NO: 90          moltype = DNA  length = 100
FEATURE                Location/Qualifiers
source                 1..100
                       mol_type = genomic DNA
                       organism = Homo sapiens
SEQUENCE: 90
ctccctggtt ttcccagctc agcgcccatt acgtttctgt tctctttccc ttagtggcat  60
tatttgtatc actgtgcatc aggaaagctg gctacggcag                        100

SEQ ID NO: 91          moltype = DNA  length = 100
FEATURE                Location/Qualifiers
source                 1..100
                       mol_type = genomic DNA
                       organism = Homo sapiens
SEQUENCE: 91
catcaatcgg gcagacacag ggtggccacg gccactagcg gcaaggcggc tgccccaaga  60
gcgcggtggc atggccacca aagccactca atcgagaaag                        100

SEQ ID NO: 92          moltype = DNA  length = 100
FEATURE                Location/Qualifiers
source                 1..100
                       mol_type = genomic DNA
                       organism = Homo sapiens
SEQUENCE: 92
accgcggctc tgtctacagc tcgcggtgcc acggccttct tggcagaata aaaatgtaga  60
caagtaataa cagaggataa tgaaagaaca tactctttaa                        100

SEQ ID NO: 93          moltype = DNA  length = 100
FEATURE                Location/Qualifiers
source                 1..100
                       mol_type = genomic DNA
                       organism = Homo sapiens
SEQUENCE: 93
aatatttcct attttttca cagacccacg gtcattaaaa aatgcaatta tttacttttt  60
ttcatttaaa cacatttctt tgagattgag cttttgggaa                        100

SEQ ID NO: 94          moltype = DNA  length = 100
FEATURE                Location/Qualifiers
source                 1..100
                       mol_type = genomic DNA
                       organism = Homo sapiens
SEQUENCE: 94
taaccacctt tccaccatta caataagaga taatttcacg tttagtctaa tgtacaaatt  60
ggatttttaa aaaatgagct ctatctgtga agcccttatt                        100

SEQ ID NO: 95          moltype = DNA  length = 100
FEATURE                Location/Qualifiers
source                 1..100
                       mol_type = genomic DNA
                       organism = Homo sapiens
SEQUENCE: 95
aaaatgagct ctatctgtga agcccttatt cctatagaat gtgtcttttt gagtttatta  60
cttattacag actctaaaaa caacattgct gctgattttc                        100

SEQ ID NO: 96          moltype = DNA  length = 100
FEATURE                Location/Qualifiers
source                 1..100
                       mol_type = genomic DNA
                       organism = Homo sapiens
SEQUENCE: 96
aagtaagctg cctcttctac atagcaaata ggtacacttc acttttccct gatttttctt  60
agggcgtgct attgattttt attgttgtct gacaaaataa                        100

SEQ ID NO: 97          moltype = DNA  length = 100
FEATURE                Location/Qualifiers
source                 1..100
```

```
                         mol_type = genomic DNA
                         organism = Homo sapiens
SEQUENCE: 97
tttatcaaac aaaagggaga aagactaaaa aatgtatttt tccacttttc tgtatcatgc  60
ataatcagca acaaccaata caatatttgg caagagtgaa                        100

SEQ ID NO: 98            moltype = DNA  length = 100
FEATURE                  Location/Qualifiers
source                   1..100
                         mol_type = genomic DNA
                         organism = Homo sapiens
SEQUENCE: 98
caaaaataaa tttacttttg ctccttagaa atacaagggt tcctttttag ttacactttt  60
ttttttact ttgtgtcatt cagtttagag caatttaatc                         100

SEQ ID NO: 99            moltype = DNA  length = 100
FEATURE                  Location/Qualifiers
source                   1..100
                         mol_type = genomic DNA
                         organism = Homo sapiens
SEQUENCE: 99
ttttttctc caaatccatt tttgaagctg agtttaactt ttgcaaccca tggcaaatct   60
taaatgccct catttaccaa tctttaccaa actcctattt                        100

SEQ ID NO: 100           moltype = DNA  length = 100
FEATURE                  Location/Qualifiers
source                   1..100
                         mol_type = genomic DNA
                         organism = Homo sapiens
SEQUENCE: 100
aagcctctaa aagtcaatac tggccatcag acccaaattt cagaagacaa tagtgaaaaa  60
ttacttacgt ttaatctcca gtcgtgtccc ttggccgaag                        100

SEQ ID NO: 101           moltype = DNA  length = 100
FEATURE                  Location/Qualifiers
source                   1..100
                         mol_type = genomic DNA
                         organism = Homo sapiens
SEQUENCE: 101
gtgatccaca gtgttaactt aattactttc cccttaacaa aaatctcttt tcgctgttaa  60
tatcactaac ctgaccgatg cagagaaaat cttgcaattg                        100

SEQ ID NO: 102           moltype = DNA  length = 100
FEATURE                  Location/Qualifiers
source                   1..100
                         mol_type = genomic DNA
                         organism = Homo sapiens
SEQUENCE: 102
agatgcctca cttaactggc tagcgcttgg ctgttcctta agatgaacta attttctatc  60
ccttactcat ctgacttttt gaaagaatct ggtactcttt                        100

SEQ ID NO: 103           moltype = DNA  length = 100
FEATURE                  Location/Qualifiers
source                   1..100
                         mol_type = genomic DNA
                         organism = Homo sapiens
SEQUENCE: 103
ggaattgacc tgagctaata tctcaaacac aaaaacgctc caaatttaaa accttataag  60
aaaaagcatt aggaaagtgc acttacgttt gatctccacc                        100

SEQ ID NO: 104           moltype = DNA  length = 100
FEATURE                  Location/Qualifiers
source                   1..100
                         mol_type = genomic DNA
                         organism = Homo sapiens
SEQUENCE: 104
ttggtccctc cgccgaaagt gagccacagt gagggatctc accctttccc ctcaacaaaa  60
acctctcttg aagccaatca tatgagatag gctgcttgtt                        100

SEQ ID NO: 105           moltype = DNA  length = 100
FEATURE                  Location/Qualifiers
source                   1..100
                         mol_type = genomic DNA
                         organism = Homo sapiens
SEQUENCE: 105
cagagaaaaa tctagctatt tcttccccat ttcccccatg aatcctattc tcctctcaaa  60
cccaatgatt cgtctatttg ctcagctttt taagttcatt                        100

SEQ ID NO: 106           moltype = DNA  length = 100
```

```
FEATURE                Location/Qualifiers
source                 1..100
                       mol_type = genomic DNA
                       organism = Homo sapiens
SEQUENCE: 106
ttctggtgtc ctgctattta cttctgggtc accaggttta ttcaaccaaa atatcacaaa  60
acttgcacaa atgatacaat ggcactaaaa tctcacgaat                        100

SEQ ID NO: 107         moltype = DNA  length = 100
FEATURE                Location/Qualifiers
source                 1..100
                       mol_type = genomic DNA
                       organism = Homo sapiens
SEQUENCE: 107
aattgagaca gatgtactta cgtttgatat ccactttggt cccagggccg aaagtgaatc  60
acagtgattc gtcttaactt ttccctttac aaaaacctcc                        100

SEQ ID NO: 108         moltype = DNA  length = 100
FEATURE                Location/Qualifiers
source                 1..100
                       mol_type = genomic DNA
                       organism = Homo sapiens
SEQUENCE: 108
ctgaaagctc agcaagcctc tttcccccaa tgaagttatt ttgatttaga aatcttaaaa  60
attagccaca agctagcgtc ctgtggaaca atttcccctc                        100

SEQ ID NO: 109         moltype = DNA  length = 100
FEATURE                Location/Qualifiers
source                 1..100
                       mol_type = genomic DNA
                       organism = Homo sapiens
SEQUENCE: 109
ctctgtacct aacctgggaa tgaagtttgt tagatccctg gcatccgact aatgaaaatc  60
cacacaaagg aacacaaagt aaactaatta gcaacagtga                        100

SEQ ID NO: 110         moltype = DNA  length = 100
FEATURE                Location/Qualifiers
source                 1..100
                       mol_type = genomic DNA
                       organism = Homo sapiens
SEQUENCE: 110
agaatcagtg gaaaaaagta cttacgtttg atctccagct tggtcccctg gccaaaagtg  60
tacacacaat ggttcctctt aacttccctc ctatacaaaa                        100

SEQ ID NO: 111         moltype = DNA  length = 100
FEATURE                Location/Qualifiers
source                 1..100
                       mol_type = genomic DNA
                       organism = Homo sapiens
SEQUENCE: 111
actccctttc tgacaattga ccaaggctct gtccagaaca tgttatgttc cccaggacat  60
ttctgaagct attacttaga caagttattc tcacccaatg                        100

SEQ ID NO: 112         moltype = DNA  length = 100
FEATURE                Location/Qualifiers
source                 1..100
                       mol_type = genomic DNA
                       organism = Homo sapiens
SEQUENCE: 112
actgaatctt gcttgctctt caaagaaaat gtgcaatcaa ttctcgagtt tgactacaga  60
cttatcttta tcttttccct gaaggatatc agaggctgat                        100

SEQ ID NO: 113         moltype = DNA  length = 100
FEATURE                Location/Qualifiers
source                 1..100
                       mol_type = genomic DNA
                       organism = Homo sapiens
SEQUENCE: 113
tgcagagtca ccttatagat cacttcatag acacagggaa cagaagacac agacaactga  60
ggaagcaaag tttaaattct actcacgttt gatttccacc                        100

SEQ ID NO: 114         moltype = DNA  length = 100
FEATURE                Location/Qualifiers
source                 1..100
                       mol_type = genomic DNA
                       organism = Homo sapiens
SEQUENCE: 114
ttggtccctt ggccgaacgt ccaccacagt gagagctctc cattgtcttg ctgaacaaaa  60
acccttctca ccaaagggga acagagtcct gggtcagctg                        100
```

```
SEQ ID NO: 115          moltype = DNA  length = 100
FEATURE                 Location/Qualifiers
source                  1..100
                        mol_type = genomic DNA
                        organism = Homo sapiens
SEQUENCE: 115
atcaacttaa ggctcataac tttgaaatgc attttgaaat gtagctccag atggtatacg  60
aaaccaaagt gaagactaat agagtagaaa agtagacttt                        100

SEQ ID NO: 116          moltype = DNA  length = 100
FEATURE                 Location/Qualifiers
source                  1..100
                        mol_type = genomic DNA
                        organism = Homo sapiens
SEQUENCE: 116
acttggttgg tttgtctgtt ttcacagcac aggaagagct cagctcttac tgagctggac  60
caggcgcatg ccatctttgg agctgccatg gagtcccagt                        100

SEQ ID NO: 117          moltype = DNA  length = 100
FEATURE                 Location/Qualifiers
source                  1..100
                        mol_type = genomic DNA
                        organism = Homo sapiens
SEQUENCE: 117
gttccatagt gtttccatag taatctcatc aacaacactg aagacctttt cagtattttc  60
ttttgagtcc agctccattt ttgcagcctt gtatctctct                        100

SEQ ID NO: 118          moltype = DNA  length = 100
FEATURE                 Location/Qualifiers
source                  1..100
                        mol_type = genomic DNA
                        organism = Homo sapiens
SEQUENCE: 118
ccgcgcccag ccgagtgcct gtttattttt acctgctttc agattctctt ctacccttct  60
aaattataag ctgtttgatg ttttatttgc cctgtatttg                        100

SEQ ID NO: 119          moltype = DNA  length = 100
FEATURE                 Location/Qualifiers
source                  1..100
                        mol_type = genomic DNA
                        organism = Homo sapiens
SEQUENCE: 119
ggaggctccg tccagtatct ttacttagca aatgcttaac aaacattttc agaataaata  60
aaaaaaaata cctaattgaa agtcaataat agatcagaga                        100

SEQ ID NO: 120          moltype = DNA  length = 100
FEATURE                 Location/Qualifiers
source                  1..100
                        mol_type = genomic DNA
                        organism = Homo sapiens
SEQUENCE: 120
tgctatcata gaccaaagac taatactgac tgccacaaca gtaactttta caacagaaat  60
cataactaca attctaaaga ttaggggtag gtttatttga                        100

SEQ ID NO: 121          moltype = DNA  length = 100
FEATURE                 Location/Qualifiers
source                  1..100
                        mol_type = genomic DNA
                        organism = Homo sapiens
SEQUENCE: 121
ttctgtcact ggcagctttg ctagttgcct tgaatagcag aattagcatt tggtctcacc  60
agaagatgag gaaggagagg gatcaagtta gaggtggaga                        100

SEQ ID NO: 122          moltype = DNA  length = 100
FEATURE                 Location/Qualifiers
source                  1..100
                        mol_type = genomic DNA
                        organism = Homo sapiens
SEQUENCE: 122
gttaacattg gcaagtgaaa tttaatgtgc aaaatagctg accaagggca tagtcctttt  60
ttaaagggga cacaaagtga ttttctctgc agacatacac                        100

SEQ ID NO: 123          moltype = DNA  length = 100
FEATURE                 Location/Qualifiers
source                  1..100
                        mol_type = genomic DNA
                        organism = Homo sapiens
SEQUENCE: 123
```

```
gcaataccaa tcataaaggg tgacatttat tgagcactta ctaagtgcca gacattgtac  60
atggatcatc acatttaatt attcccaaga ctctatgaac                        100

SEQ ID NO: 124         moltype = DNA  length = 100
FEATURE                Location/Qualifiers
source                 1..100
                       mol_type = genomic DNA
                       organism = Homo sapiens
SEQUENCE: 124
tgagcactta ctaagtgcca gacattgtac atggatcatc acatttaatt attcccaaga  60
ctctatgaac taggaactaa tattatcccc tactttgtag                        100

SEQ ID NO: 125         moltype = DNA  length = 100
FEATURE                Location/Qualifiers
source                 1..100
                       mol_type = genomic DNA
                       organism = Homo sapiens
SEQUENCE: 125
gtgcaaaaac ttgagggcag agaggtcaag gaactggctt atggcagtaa gtggcagagc  60
tgtgacctaa actcagatcc catgttttta actgaactat                        100

SEQ ID NO: 126         moltype = DNA  length = 100
FEATURE                Location/Qualifiers
source                 1..100
                       mol_type = genomic DNA
                       organism = Homo sapiens
SEQUENCE: 126
atgcagatta tactccagga gtaaagtcac tcaacggaag caacaagcgt gacagggaat  60
gctgggatgg gggaaggtaa aaggaactcc ttagactggg                        100

SEQ ID NO: 127         moltype = DNA  length = 100
FEATURE                Location/Qualifiers
source                 1..100
                       mol_type = genomic DNA
                       organism = Homo sapiens
SEQUENCE: 127
ataagtgtgt acagacgtat gtataagact acacatggaa atattgttta aagagtgaaa  60
aataactaaa atcctcatta ataggagttt ggttaaactg                        100

SEQ ID NO: 128         moltype = DNA  length = 100
FEATURE                Location/Qualifiers
source                 1..100
                       mol_type = genomic DNA
                       organism = Homo sapiens
SEQUENCE: 128
tgctagagct ttacaatgta gcacaaagca gacattaagg ggaagacgta gacttctata  60
tagttacgtg gaaggtgttt gtgaaaatgc aggtcactga                        100

SEQ ID NO: 129         moltype = DNA  length = 100
FEATURE                Location/Qualifiers
source                 1..100
                       mol_type = genomic DNA
                       organism = Homo sapiens
SEQUENCE: 129
agagtatgtg tggtgagata tcatgatccc atctacattg aatatatatg tatataaata  60
cgggctgaat tttaaaagac ataaattgtg cttggtagtt                        100

SEQ ID NO: 130         moltype = DNA  length = 100
FEATURE                Location/Qualifiers
source                 1..100
                       mol_type = genomic DNA
                       organism = Homo sapiens
SEQUENCE: 130
aaatacgggc tgaattttaa aagacataaa ttgtgcttgg tagttatctc ctgggattgc  60
agaggaggaa caatgacact ttatgccatc tcctcctact                        100

SEQ ID NO: 131         moltype = DNA  length = 100
FEATURE                Location/Qualifiers
source                 1..100
                       mol_type = genomic DNA
                       organism = Homo sapiens
SEQUENCE: 131
cttctgtatg gtgatgtgaa tatattcatt ttatagtttt tagaaataat aaaactgtac  60
taattttgaa aaacagtaaa ctctgacatt gcctattagc                        100

SEQ ID NO: 132         moltype = DNA  length = 100
FEATURE                Location/Qualifiers
source                 1..100
                       mol_type = genomic DNA
```

```
                       organism = Homo sapiens
SEQUENCE: 132
attctcgata ttcctgtgca atgcataaac ataacttttt aaaagatatg tacacacatg  60
tgtgagtttt ctttgtcaaa tacttttcta taatctttaa                        100

SEQ ID NO: 133         moltype = DNA  length = 100
FEATURE                Location/Qualifiers
source                 1..100
                       mol_type = genomic DNA
                       organism = Homo sapiens
SEQUENCE: 133
atcaagcatg ccaaaaaggt aaaagctttc ctgtttcagt gtaggagata gtcgtctgca  60
aaggaaagag atgtagggga tagaaacagg aatgaaaaag                        100

SEQ ID NO: 134         moltype = DNA  length = 100
FEATURE                Location/Qualifiers
source                 1..100
                       mol_type = genomic DNA
                       organism = Homo sapiens
SEQUENCE: 134
atgactgagc tgttcgaggg acttatgttc ctaagtgagc taattggaaa tctaatatga  60
acagtgcaac cgaataacta ttgtaaagca gtatttgtaa                        100

SEQ ID NO: 135         moltype = DNA  length = 100
FEATURE                Location/Qualifiers
source                 1..100
                       mol_type = genomic DNA
                       organism = Homo sapiens
SEQUENCE: 135
acaataaaag atgattatca taagtaccat tgttgcaaaa actattttat tgatcacatg  60
cagtggtgat ctgtaggaat gattgttgtg atgtttgctg                        100

SEQ ID NO: 136         moltype = DNA  length = 100
FEATURE                Location/Qualifiers
source                 1..100
                       mol_type = genomic DNA
                       organism = Homo sapiens
SEQUENCE: 136
taacataaaa tgaaacatgg gaagtggctg agatctttag gatgtgtgtg gttcattttt  60
tgaaagcaaa tgttgtctca gaagcatctg tgagactctg                        100

SEQ ID NO: 137         moltype = DNA  length = 100
FEATURE                Location/Qualifiers
source                 1..100
                       mol_type = genomic DNA
                       organism = Homo sapiens
SEQUENCE: 137
ccaggatcca ccgttctaca aaatatctgt gatggacatt gataagattg atctgttgag  60
gaaaggcaag gtgtcagtaa gatagtctga gagcttcttg                        100

SEQ ID NO: 138         moltype = DNA  length = 100
FEATURE                Location/Qualifiers
source                 1..100
                       mol_type = genomic DNA
                       organism = Homo sapiens
SEQUENCE: 138
gatttcatgt aaaagagtgc tggaaataga atttcttggg gaacattcca actaactcat  60
cactgaaggt gctttacatt gaaccctcag caaagttaga                        100

SEQ ID NO: 139         moltype = DNA  length = 100
FEATURE                Location/Qualifiers
source                 1..100
                       mol_type = genomic DNA
                       organism = Homo sapiens
SEQUENCE: 139
ttatcagaaa aaaaatataa actgctgtgg aggggacagg aaggaaagtc agggagggag  60
gggggcaagg agagaaagag cgagagagag gagagaaaga                        100

SEQ ID NO: 140         moltype = DNA  length = 100
FEATURE                Location/Qualifiers
source                 1..100
                       mol_type = genomic DNA
                       organism = Homo sapiens
SEQUENCE: 140
agagaggaga gagagagcac aagtacacac ttcaatgcac atctataaat catcctgaaa  60
actactgata aattatttta gcaatgttcc tcagatgtaa                        100

SEQ ID NO: 141         moltype = DNA  length = 100
FEATURE                Location/Qualifiers
```

```
source                  1..100
                        mol_type = genomic DNA
                        organism = Homo sapiens
SEQUENCE: 141
catttcaaga aatatcattt ttgcttttta tttggcataa tttactagcc aatttaggaa  60
gttcccctca catcagtaac atacagtaca tcacccagta                        100

SEQ ID NO: 142          moltype = DNA  length = 100
FEATURE                 Location/Qualifiers
source                  1..100
                        mol_type = genomic DNA
                        organism = Homo sapiens
SEQUENCE: 142
tgtcagagga cacaatggca taagtttgcc ttttgcaagg tttgagggat ggccatttcc  60
ctacctgact caggaaagtc tgtagctgat atccatcttc                        100

SEQ ID NO: 143          moltype = DNA  length = 100
FEATURE                 Location/Qualifiers
source                  1..100
                        mol_type = genomic DNA
                        organism = Homo sapiens
SEQUENCE: 143
aagtttgtgg ttctttctct ctatatatat atttgagctc agcagtcatg ctggagtcca  60
gagtaggtga ttctttctgc tttagcttga ctcctcctta                        100

SEQ ID NO: 144          moltype = DNA  length = 100
FEATURE                 Location/Qualifiers
source                  1..100
                        mol_type = genomic DNA
                        organism = Homo sapiens
SEQUENCE: 144
tatatatttg agctcagcag tcatgctgga gtccagagta ggtgattctt tctgctttag  60
cttgactcct ccttaagatt gtaactctct cagttttaca                        100

SEQ ID NO: 145          moltype = DNA  length = 100
FEATURE                 Location/Qualifiers
source                  1..100
                        mol_type = genomic DNA
                        organism = Homo sapiens
SEQUENCE: 145
ttttttgtca gacgtaagct gacattccac aaggagagga ggaaattctg tggttcacat  60
ccagtggtgc ttggaacctg attggttgtc attcttccag                        100

SEQ ID NO: 146          moltype = DNA  length = 100
FEATURE                 Location/Qualifiers
source                  1..100
                        mol_type = genomic DNA
                        organism = Homo sapiens
SEQUENCE: 146
ctagtttgtc acgagtggat atctgtcctg gattcccaag gatcaaggct gccccattag  60
ccaggaagta gggagataga ggaggtcact tgagaaagag                        100

SEQ ID NO: 147          moltype = DNA  length = 100
FEATURE                 Location/Qualifiers
source                  1..100
                        mol_type = genomic DNA
                        organism = Homo sapiens
SEQUENCE: 147
ctgcttcttt gccgcctcca ggttgtgtct gtttcctctc atatctgaag acagatgtgc  60
tggcagaagc aaagtccttt gtccggccac gtgcaaatgc                        100

SEQ ID NO: 148          moltype = DNA  length = 100
FEATURE                 Location/Qualifiers
source                  1..100
                        mol_type = genomic DNA
                        organism = Homo sapiens
SEQUENCE: 148
atgggacata aatatgaaca gagattcttg tcccactcta gaaaatgtag atgttcatct  60
tgtttccaag gggacagtaa ggctgcaggt gttttttgac                        100

SEQ ID NO: 149          moltype = DNA  length = 100
FEATURE                 Location/Qualifiers
source                  1..100
                        mol_type = genomic DNA
                        organism = Homo sapiens
SEQUENCE: 149
cttttgtact cactggttgt ttttgcatag gcccctccag gccacgacca gctgtttgga  60
ttttataaac gggccgtttg cattgtgaac tgagctacaa                        100
```

```
SEQ ID NO: 150         moltype = DNA  length = 100
FEATURE                Location/Qualifiers
source                 1..100
                       mol_type = genomic DNA
                       organism = Homo sapiens
SEQUENCE: 150
caggcaggca ggggcagcaa gatggtgttg cagacccagg tcttcatttc tctgttgctc  60
tggatctctg gtgaggaatt aaaaagtgcc acagtctttt                       100

SEQ ID NO: 151         moltype = DNA  length = 100
FEATURE                Location/Qualifiers
source                 1..100
                       mol_type = genomic DNA
                       organism = Homo sapiens
SEQUENCE: 151
cagagtaata tctgtgtaga aataaaaaaa attaagatat agttggaaat aatgactatt  60
tccaatatgg atccaattat ctgctgactt ataatactac                       100

SEQ ID NO: 152         moltype = DNA  length = 100
FEATURE                Location/Qualifiers
source                 1..100
                       mol_type = genomic DNA
                       organism = Homo sapiens
SEQUENCE: 152
attaagatat agttggaaat aatgactatt tccaatatgg atccaattat ctgctgactt  60
ataatactac tagaaagcaa atttaaatga catatttcaa                       100

SEQ ID NO: 153         moltype = DNA  length = 100
FEATURE                Location/Qualifiers
source                 1..100
                       mol_type = genomic DNA
                       organism = Homo sapiens
SEQUENCE: 153
ttatatctga gacagcgtgt ataagtttat gtataatcat tgtccattac tgactacagg  60
tgcctacggg gacatcgtga tgacccagtc tccagactcc                       100

SEQ ID NO: 154         moltype = DNA  length = 100
FEATURE                Location/Qualifiers
source                 1..100
                       mol_type = genomic DNA
                       organism = Homo sapiens
SEQUENCE: 154
ctggctgtgt ctctgggcga gagggccacc atcaactgca agtccagcca gagtgtttta  60
tacagctcca acaataagaa ctacttagct tggtaccagc                       100

SEQ ID NO: 155         moltype = DNA  length = 100
FEATURE                Location/Qualifiers
source                 1..100
                       mol_type = genomic DNA
                       organism = Homo sapiens
SEQUENCE: 155
agaaaccagg acagcctcct aagctgctca tttactgggc atctacccgg gaatccgggg  60
tccctgaccg attcagtggc agcgggtctg ggacagattt                       100

SEQ ID NO: 156         moltype = DNA  length = 100
FEATURE                Location/Qualifiers
source                 1..100
                       mol_type = genomic DNA
                       organism = Homo sapiens
SEQUENCE: 156
cactctcacc atcagcagcc tgcaggctga agatgtggca gtttattact gtcagcaata  60
ttatagtact cctcccacag tgcttcagcc tcgaacacaa                       100

SEQ ID NO: 157         moltype = DNA  length = 100
FEATURE                Location/Qualifiers
source                 1..100
                       mol_type = genomic DNA
                       organism = Homo sapiens
SEQUENCE: 157
acctcctccc catacgctgg gccagtaggt ctttgctgca gcagctgctt cctctgcaca  60
cagcccccaa catgcatgct tcctctgtgt gttggggagg                       100

SEQ ID NO: 158         moltype = DNA  length = 100
FEATURE                Location/Qualifiers
source                 1..100
                       mol_type = genomic DNA
                       organism = Homo sapiens
SEQUENCE: 158
aatacatgaa aacaactacc gaaatgttat gaaattatag tttagtagaa ctaacaagtg  60
```

```
cattaatgca aaagaaaagt agggctcagt aatcagggaa                        100

SEQ ID NO: 159         moltype = DNA  length = 100
FEATURE                Location/Qualifiers
source                 1..100
                       mol_type = genomic DNA
                       organism = Homo sapiens
SEQUENCE: 159
ccaagtgtgc attgtaaaag tgcagcctct ctaacactgg gtttcatcac aagtaacaga  60
acaggatgcc tgatgcaggg aaaaaagaaa ggcaattgtt                        100

SEQ ID NO: 160         moltype = DNA  length = 100
FEATURE                Location/Qualifiers
source                 1..100
                       mol_type = genomic DNA
                       organism = Homo sapiens
SEQUENCE: 160
gatctctggt aagagaaaca cttcctctcc tctgtgccac caagtcccct gcatatccac  60
aaaaataata tattttcata aggaattgat tttcctcatt                        100

SEQ ID NO: 161         moltype = DNA  length = 100
FEATURE                Location/Qualifiers
source                 1..100
                       mol_type = genomic DNA
                       organism = Homo sapiens
SEQUENCE: 161
ctctgcaaat atgatgcatt tgatttatgt tttttacttt gctccataat cagataccag  60
ggcagaaacg acactcacgc agtctccagc attcatgtca                        100

SEQ ID NO: 162         moltype = DNA  length = 100
FEATURE                Location/Qualifiers
source                 1..100
                       mol_type = genomic DNA
                       organism = Homo sapiens
SEQUENCE: 162
gcgactccag gagacaaagt caacatctcc tgcaaagcca gccaagacat tgatgatgat  60
atgaactggt accaacagaa accaggagaa gctgctattt                        100

SEQ ID NO: 163         moltype = DNA  length = 100
FEATURE                Location/Qualifiers
source                 1..100
                       mol_type = genomic DNA
                       organism = Homo sapiens
SEQUENCE: 163
tcattattca agaagctact actctcgttc ctggaatccc acctcgattc agtggcagcg  60
ggtatggaac agattttacc ctcacaatta ataacataga                        100

SEQ ID NO: 164         moltype = DNA  length = 100
FEATURE                Location/Qualifiers
source                 1..100
                       mol_type = genomic DNA
                       organism = Homo sapiens
SEQUENCE: 164
atctgaggat gctgcatatt acttctgtct acaacatgat aatttccctc tcacagtgat  60
acaccctgtt acaaaaacct ccaagttctc tcagtgggat                        100

SEQ ID NO: 165         moltype = DNA  length = 100
FEATURE                Location/Qualifiers
source                 1..100
                       mol_type = genomic DNA
                       organism = Homo sapiens
SEQUENCE: 165
gccctctgtc ctggagacac ggccaaggag gctggagact gggtcagcac aatgtcccca  60
ttgcagcctg aaatgataaa gacagataaa ttatatcaga                        100

SEQ ID NO: 166         moltype = DNA  length = 100
FEATURE                Location/Qualifiers
source                 1..100
                       mol_type = genomic DNA
                       organism = Homo sapiens
SEQUENCE: 166
tatactgaga ctgtccccat gtaggccatg cattggtgac acttgtaacc acagtcatat  60
gcaacatctt gagtaaccag aaaacaaaag ataactgggg                        100

SEQ ID NO: 167         moltype = DNA  length = 100
FEATURE                Location/Qualifiers
source                 1..100
                       mol_type = genomic DNA
                       organism = Homo sapiens
```

```
SEQUENCE: 167
aacttacaac ctacaatgag tgccctaaat ccaacaacca agaatccaga gacacaaaaa  60
acaatgatgg ccacatgagt ttgcccgatg tttccctata                        100

SEQ ID NO: 168         moltype = DNA  length = 100
FEATURE                Location/Qualifiers
source                 1..100
                       mol_type = genomic DNA
                       organism = Homo sapiens
SEQUENCE: 168
taccaacacc atcagagtgt ggctgcatct gaggaccact ctcagctgat agaggcatca  60
ggaggagcag ctggggcagc cctgcctcac acatctgctt                        100

SEQ ID NO: 169         moltype = DNA  length = 100
FEATURE                Location/Qualifiers
source                 1..100
                       mol_type = genomic DNA
                       organism = Homo sapiens
SEQUENCE: 169
ggggtttatg ttcgggtgtg taacactgtg ggagaataac tattatactg ttggcagtaa  60
taagttgcaa aatcatcagg ctgcaggctg ctgatggtga                        100

SEQ ID NO: 170         moltype = DNA  length = 100
FEATURE                Location/Qualifiers
source                 1..100
                       mol_type = genomic DNA
                       organism = Homo sapiens
SEQUENCE: 170
gccgctgaac cttgatggga ccccactttc taaactagac gccttataga tcaggagctt  60
aggggctttc cctggtttct gctgatacca ggccaaccag                        100

SEQ ID NO: 171         moltype = DNA  length = 100
FEATURE                Location/Qualifiers
source                 1..100
                       mol_type = genomic DNA
                       organism = Homo sapiens
SEQUENCE: 171
ctactaatac tctgactggc ccggcaagtg atggtgactc tgtctcctac agatgcagac  60
agggtggaag gagactgggt catctggatg tcacatttgg                        100

SEQ ID NO: 172         moltype = DNA  length = 100
FEATURE                Location/Qualifiers
source                 1..100
                       mol_type = genomic DNA
                       organism = Homo sapiens
SEQUENCE: 172
ggatgtcaca tttggcacct gagattggaa atagaaacac aaatattcat actattgatc  60
atattatagg aagacttccc tgaataacca ggcagtactg                        100

SEQ ID NO: 173         moltype = DNA  length = 100
FEATURE                Location/Qualifiers
source                 1..100
                       mol_type = genomic DNA
                       organism = Homo sapiens
SEQUENCE: 173
agcacactgg gctgagtaaa ttcctagtgt tctccttcct tacctgggag ccagagcagc  60
aggagcccca ggagctgagc ggggaccctc atgtccatgc                        100

SEQ ID NO: 174         moltype = DNA  length = 100
FEATURE                Location/Qualifiers
source                 1..100
                       mol_type = genomic DNA
                       organism = Homo sapiens
SEQUENCE: 174
gggactattt tattatgaga aacaattttt aggtattttt ttgagaattt taaatattcc  60
tcaggagccg atagagtaat gtatttcatt ggtgtatcag                        100

SEQ ID NO: 175         moltype = DNA  length = 100
FEATURE                Location/Qualifiers
source                 1..100
                       mol_type = genomic DNA
                       organism = Homo sapiens
SEQUENCE: 175
gattatttag gagaatattc ttgtttgtag gaaacacata gtaaaatgtt agatggtagg  60
attctcaagt cttcaaaaga ctctcataag attccgggta                        100

SEQ ID NO: 176         moltype = DNA  length = 100
FEATURE                Location/Qualifiers
source                 1..100
```

```
                        mol_type = genomic DNA
                        organism = Homo sapiens
SEQUENCE: 176
tattcttgtt tgtaggaaac acatagtaaa atgttagatg gtaggattct caagtcttca  60
aaagactctc ataagattcc gggtagggaa gggggtaatt                        100

SEQ ID NO: 177          moltype = DNA  length = 100
FEATURE                 Location/Qualifiers
source                  1..100
                        mol_type = genomic DNA
                        organism = Homo sapiens
SEQUENCE: 177
tgtaagtatt aggtaatggt gttatgcctt tgttcttact agtattagat caagcaattt  60
attacagata tacaaagatg ataccgtgtt gtctccatgc                        100

SEQ ID NO: 178          moltype = DNA  length = 100
FEATURE                 Location/Qualifiers
source                  1..100
                        mol_type = genomic DNA
                        organism = Homo sapiens
SEQUENCE: 178
atgcagcact cacagatcca ccactatcaa gaactgcagg tctctttaat acccagagac  60
taaatgaggt gcaccttatt cttgttttgg gtaccttcat                        100

SEQ ID NO: 179          moltype = DNA  length = 100
FEATURE                 Location/Qualifiers
source                  1..100
                        mol_type = genomic DNA
                        organism = Homo sapiens
SEQUENCE: 179
ttgggtgtgt aacactgtgg gagggtaact ataatactgt tgacagtaat aagttgcaaa  60
atcttcagac tgcaggcagc tgatggtgag agtgaaatct                        100

SEQ ID NO: 180          moltype = DNA  length = 100
FEATURE                 Location/Qualifiers
source                  1..100
                        mol_type = genomic DNA
                        organism = Homo sapiens
SEQUENCE: 180
ctgactcgcc cgacaagtga tggtgactct gtctcctgta gatgcagaga atgaggatgg  60
agactgggtc atccggatgg cacatctggc acctgagatt                        100

SEQ ID NO: 181          moltype = DNA  length = 100
FEATURE                 Location/Qualifiers
source                  1..100
                        mol_type = genomic DNA
                        organism = Homo sapiens
SEQUENCE: 181
ctttcccctg gagacaaaga cagggtgcct ggagactgcg tcaacacaat ttctccggtg  60
gtatctgaga ttggaaataa aacagaaaag tcacccatgt                        100

SEQ ID NO: 182          moltype = DNA  length = 100
FEATURE                 Location/Qualifiers
source                  1..100
                        mol_type = genomic DNA
                        organism = Homo sapiens
SEQUENCE: 182
aatctaaatc aaacccattg tcttcccaga agagccagaa ttattgcttt atattgagct  60
ttaattattg tattgactga gcagagttgc caggtaacag                        100

SEQ ID NO: 183          moltype = DNA  length = 100
FEATURE                 Location/Qualifiers
source                  1..100
                        mol_type = genomic DNA
                        organism = Homo sapiens
SEQUENCE: 183
gacttgagag ggttttcact gacatgcaaa accatcccat gttcccctca cctgggagcc  60
agagtagcag gaggaagaga agctgcgctg gggtttccat                        100

SEQ ID NO: 184          moltype = DNA  length = 100
FEATURE                 Location/Qualifiers
source                  1..100
                        mol_type = genomic DNA
                        organism = Homo sapiens
SEQUENCE: 184
agctcttctc cagagctctg acccaggcat tgatatgggc tctggactgc agggcggctg  60
ggagggacat gcaaagcagc tggggcgggt gctgggcttg                        100

SEQ ID NO: 185          moltype = DNA  length = 100
```

```
FEATURE                Location/Qualifiers
source                 1..100
                       mol_type = genomic DNA
                       organism = Homo sapiens
SEQUENCE: 185
cagctgcaga gacaatctgc ctccccttc tgctctcagc agcccatgcc caggtgatca  60
ggccagaaaa ggccgttggc tcagtctgag ggtagaactt                       100

SEQ ID NO: 186         moltype = DNA  length = 100
FEATURE                Location/Qualifiers
source                 1..100
                       mol_type = genomic DNA
                       organism = Homo sapiens
SEQUENCE: 186
ctcccctgcg gccacagaat ttaaccccctg tgtcctcttg tctcaccatc acctagattg  60
agccacagaa tgtttggtac aagtctgtta gaaacaaaat                       100

SEQ ID NO: 187         moltype = DNA  length = 100
FEATURE                Location/Qualifiers
source                 1..100
                       mol_type = genomic DNA
                       organism = Homo sapiens
SEQUENCE: 187
agaaggctgt ggtttcattt ttctctttct gctccaactt gtgcccagtc agctccctaa  60
atgcatgatg gatcaggttg aaaggaagag tctattacaa                       100

SEQ ID NO: 188         moltype = DNA  length = 100
FEATURE                Location/Qualifiers
source                 1..100
                       mol_type = genomic DNA
                       organism = Homo sapiens
SEQUENCE: 188
ctttatcttc cggatatact tgtatttact tgttagtgat ctttcctgag ggtccagaag  60
ctgtctcatt ctttgcagaa attaaaagag taacattcaa                       100

SEQ ID NO: 189         moltype = DNA  length = 100
FEATURE                Location/Qualifiers
source                 1..100
                       mol_type = genomic DNA
                       organism = Homo sapiens
SEQUENCE: 189
ttaacctcag cactgtgggt gtgaggactt tcacaactgc acagataagt gagacctggg  60
ctccaaatcc tcagggtagt gataccattt ccctaaagac                       100

SEQ ID NO: 190         moltype = DNA  length = 100
FEATURE                Location/Qualifiers
source                 1..100
                       mol_type = genomic DNA
                       organism = Homo sapiens
SEQUENCE: 190
agaagatggt tttgtccatg caggcaaaga actatttctt gggtgatcct ctaaactatc  60
cagtcttttt attctgtata gctggtatag tttaccctta                       100

SEQ ID NO: 191         moltype = DNA  length = 100
FEATURE                Location/Qualifiers
source                 1..100
                       mol_type = genomic DNA
                       organism = Homo sapiens
SEQUENCE: 191
ggctatatat gtatttgttc atatttcaaa aatacacagt ttcaaaatgg aactcaaggg  60
atccaaggct caaaggggtc tccagaagac cccacaccat                       100

SEQ ID NO: 192         moltype = DNA  length = 100
FEATURE                Location/Qualifiers
source                 1..100
                       mol_type = genomic DNA
                       organism = Homo sapiens
SEQUENCE: 192
cccctttctg tgtcagtctt ccccagagca cagatccttg tttctgcttg aatcttcctc  60
actctcacag atctgatcat cacatgcccc actctggagg                       100

SEQ ID NO: 193         moltype = DNA  length = 100
FEATURE                Location/Qualifiers
source                 1..100
                       mol_type = genomic DNA
                       organism = Homo sapiens
SEQUENCE: 193
acaacatgtg catgtccaat acaggaaagg aacacacata ggagtgtagt gagaccccca  60
gagatcactg ttgttagagg cagtggggcc ccagaactca                       100
```

```
SEQ ID NO: 194          moltype = DNA  length = 100
FEATURE                 Location/Qualifiers
source                  1..100
                        mol_type = genomic DNA
                        organism = Homo sapiens
SEQUENCE: 194
ggagcagcag cgggtggaga ccccatgggc tggccgagac aagaggactc ctcagccagt  60
cctcctgacc tgagacaggt ctcaggaatg tgcggaggac                        100

SEQ ID NO: 195          moltype = DNA  length = 100
FEATURE                 Location/Qualifiers
source                  1..100
                        mol_type = genomic DNA
                        organism = Homo sapiens
SEQUENCE: 195
acaccgggac atacatttcc cttcatgctc ccaacataca catgcaaaca tacacagacc  60
catacaggca cgcgcgagca gccatgcccc accccctccc                        100

SEQ ID NO: 196          moltype = DNA  length = 100
FEATURE                 Location/Qualifiers
source                  1..100
                        mol_type = genomic DNA
                        organism = Homo sapiens
SEQUENCE: 196
ccaacacaca cacgtataaa agtgtgtgta tatgggcaaa ctgctcgcat ccccaaatgg  60
caggctcttt ccctagaggc gcccagtccg cggcggggag                        100

SEQ ID NO: 197          moltype = DNA  length = 100
FEATURE                 Location/Qualifiers
source                  1..100
                        mol_type = genomic DNA
                        organism = Homo sapiens
SEQUENCE: 197
aagctcactc actggggcca ttgactggga tccagtctgt ggccatgtca tggtttctat  60
ttttgaggtt atagctaatg agcaacatga ggttaagaca                        100

SEQ ID NO: 198          moltype = DNA  length = 100
FEATURE                 Location/Qualifiers
source                  1..100
                        mol_type = genomic DNA
                        organism = Homo sapiens
SEQUENCE: 198
cacttttcat aaggccccag ccagcatcat aaatatgtgt gtgagcatgt tcacactcag  60
gttatgtctt ctttatgtgc accctctacc acacacacac                        100

SEQ ID NO: 199          moltype = DNA  length = 100
FEATURE                 Location/Qualifiers
source                  1..100
                        mol_type = genomic DNA
                        organism = Homo sapiens
SEQUENCE: 199
gccaagaacc acgactctct aattttactt cccagcaggt attcagtgca taatagttcc  60
tacttagaag tatcatattt gcccaaacac aaggtgatac                        100

SEQ ID NO: 200          moltype = DNA  length = 100
FEATURE                 Location/Qualifiers
source                  1..100
                        mol_type = genomic DNA
                        organism = Homo sapiens
SEQUENCE: 200
ccaaaatgag gtaagtttcc tgttttctca gtgagatctt ttgttgttgt tgttgttgtt  60
gttgttttgt tgtcgatgtt gttgtttttg gttttggtct                        100

SEQ ID NO: 201          moltype = DNA  length = 100
FEATURE                 Location/Qualifiers
source                  1..100
                        mol_type = genomic DNA
                        organism = Homo sapiens
SEQUENCE: 201
ccgggtcgtc cagccccggg ccgccgcggc tgcccactac acccacgcca accgcccgca  60
agcagcgctg caggggctcc gctgggcgac acgccaggct                        100

SEQ ID NO: 202          moltype = DNA  length = 100
FEATURE                 Location/Qualifiers
source                  1..100
                        mol_type = genomic DNA
                        organism = Homo sapiens
SEQUENCE: 202
```

```
ctgtcccaca gggtgctggg gagcgactgg gcggctccgc cgcgagcgtc tttgaattgc  60
gcgccgctgc aggaaaccaa aaactcccta gcaagagggt                        100

SEQ ID NO: 203         moltype = DNA  length = 100
FEATURE                Location/Qualifiers
source                 1..100
                       mol_type = genomic DNA
                       organism = Homo sapiens
SEQUENCE: 203
ttcaaaaggt ttctggaaac caccgacggt taaacatcac aactggactc ggagagagcc  60
aaacggtttc cccacttgca cctgccagtc ttcgcggcgg                        100

SEQ ID NO: 204         moltype = DNA  length = 100
FEATURE                Location/Qualifiers
source                 1..100
                       mol_type = genomic DNA
                       organism = Homo sapiens
SEQUENCE: 204
cgacctggca gcccaggtgc ggtcttaacc gcccccgccc ctcaccccgt acccgctcct  60
atccccggag cgcaaatctc agggctggca gctgcgcggt                        100

SEQ ID NO: 205         moltype = DNA  length = 100
FEATURE                Location/Qualifiers
source                 1..100
                       mol_type = genomic DNA
                       organism = Homo sapiens
SEQUENCE: 205
ggaaggtttt ccccctcaaa cccaaagcgc gcgggcggat caactcctag ctgctgccac  60
cactcgatcc cctcagagga tcggcgcggt gggtccaccc                        100

SEQ ID NO: 206         moltype = DNA  length = 100
FEATURE                Location/Qualifiers
source                 1..100
                       mol_type = genomic DNA
                       organism = Homo sapiens
SEQUENCE: 206
gcctctcccg ccctctgcct actgtgctgg gagactggca cagctccgtc ggccgcacag  60
agtttaacaa acacgcaccc agtgtcaaga acagtcacca                        100

SEQ ID NO: 207         moltype = DNA  length = 100
FEATURE                Location/Qualifiers
source                 1..100
                       mol_type = genomic DNA
                       organism = Homo sapiens
SEQUENCE: 207
ggcgcttaac cccgaagtta aagcgggcgc aatctcctcc tgggaactca gcccaggcac  60
gccgccctcc gcctctaaat tcagacaatg taactcgctc                        100

SEQ ID NO: 208         moltype = DNA  length = 100
FEATURE                Location/Qualifiers
source                 1..100
                       mol_type = genomic DNA
                       organism = Homo sapiens
SEQUENCE: 208
caagacatcc ccgcttcccc aaggaagaga ccggtggtct gagtcccgag gcagcgcgca  60
cgccttctct gcacttgtgc acagaatgtt cttacgtttg                        100

SEQ ID NO: 209         moltype = DNA  length = 100
FEATURE                Location/Qualifiers
source                 1..100
                       mol_type = genomic DNA
                       organism = Homo sapiens
SEQUENCE: 209
caaacagcgt gcaagccgcc gcgcgcggcg ggactcaagg gggagacaca tgcagccact  60
ggaacgctct ttccagtcgt ttctcctcga ctcacagaga                        100

SEQ ID NO: 210         moltype = DNA  length = 100
FEATURE                Location/Qualifiers
source                 1..100
                       mol_type = genomic DNA
                       organism = Homo sapiens
SEQUENCE: 210
aaaagattcc aatcctgctc cccccccacc cacccgcact atataggcat ggtcaagaaa  60
actcctttcg gtgacccttt tttggagtac gggtacctcc                        100

SEQ ID NO: 211         moltype = DNA  length = 100
FEATURE                Location/Qualifiers
source                 1..100
                       mol_type = genomic DNA
```

```
                        organism = Homo sapiens
SEQUENCE: 211
aatgtcctgg ccgcttctgc ccgctcggag aggggctgcg ctctaagttc aaacgtttgt  60
acatttatga caaagcaggt tgaaactgga cttacactga                        100

SEQ ID NO: 212          moltype = DNA  length = 100
FEATURE                 Location/Qualifiers
source                  1..100
                        mol_type = genomic DNA
                        organism = Homo sapiens
SEQUENCE: 212
tcccctccat ggtaaccgct ggttctccag atgcggtggc tactggagca ctcaggccct  60
cggcgtcact ttgctacctg ctgccgcagc caacaaactg                        100

SEQ ID NO: 213          moltype = DNA  length = 100
FEATURE                 Location/Qualifiers
source                  1..100
                        mol_type = genomic DNA
                        organism = Homo sapiens
SEQUENCE: 213
cccattgctg acatacttac tccctgagag tggctcttca tgcacctcca aggggttgct  60
ctccggtcca tccagtgtct tgctcacccc ctgtggtgaa                        100

SEQ ID NO: 214          moltype = DNA  length = 100
FEATURE                 Location/Qualifiers
source                  1..100
                        mol_type = genomic DNA
                        organism = Homo sapiens
SEQUENCE: 214
agttctccac catctccctc tccggagggt gagctgggct gcttggcgag gggcacctcc  60
cctctggggc ctgagctggg ctctgggctt tggtttctcc                        100

SEQ ID NO: 215          moltype = DNA  length = 100
FEATURE                 Location/Qualifiers
source                  1..100
                        mol_type = genomic DNA
                        organism = Homo sapiens
SEQUENCE: 215
cagccggagc actgcacaca tccccagtcc ccggtttctc attctccagt gacgcgtgat  60
ccccacgtgc gttttttgca tctctggcat cctcggtgct                        100

SEQ ID NO: 216          moltype = DNA  length = 100
FEATURE                 Location/Qualifiers
source                  1..100
                        mol_type = genomic DNA
                        organism = Homo sapiens
SEQUENCE: 216
atttgcaggt tatatcctgg atggtggcac gacagcgcct ggaacacaga aggttgggag  60
gcgtgacgct catcaggaag gctcttttgg ggagccagga                        100

SEQ ID NO: 217          moltype = DNA  length = 100
FEATURE                 Location/Qualifiers
source                  1..100
                        mol_type = genomic DNA
                        organism = Homo sapiens
SEQUENCE: 217
agagtccccc agaagcccac ttggcaccct atctataaca agttgctctt taagaatcat  60
gggaactcca gaatcatttt cacaaatacc ttccactcat                        100

SEQ ID NO: 218          moltype = DNA  length = 100
FEATURE                 Location/Qualifiers
source                  1..100
                        mol_type = genomic DNA
                        organism = Homo sapiens
SEQUENCE: 218
gattcaatta aatggcagaa aacacaaacc ttccgttccc actggcaaac tgggtctagc  60
taactgagca cagctagcac aaggcaggcc ccctgctagc                        100

SEQ ID NO: 219          moltype = DNA  length = 100
FEATURE                 Location/Qualifiers
source                  1..100
                        mol_type = genomic DNA
                        organism = Homo sapiens
SEQUENCE: 219
agggcaagtg gcggcccggt ccccaaggcc caggggagcc tctgcagctc cctggaagga  60
cggtcaagtg aacagagagc tggctgccat ctgggttctt                        100

SEQ ID NO: 220          moltype = DNA  length = 100
FEATURE                 Location/Qualifiers
```

```
source                  1..100
                        mol_type = genomic DNA
                        organism = Homo sapiens
SEQUENCE: 220
atgagatcac cagtttatcg taactagagg cctctcccat ctaaagcatc tttgtaactg  60
ctttcccttt ccccacactg cctacacata aagaagcccc                        100

SEQ ID NO: 221          moltype = DNA  length = 100
FEATURE                 Location/Qualifiers
source                  1..100
                        mol_type = genomic DNA
                        organism = Homo sapiens
SEQUENCE: 221
taatttgtaa caagtcattt gacaactcca gaagaggggc cacatccttt ttctctatgt  60
ctgttgatta acaaagacaa cattatgttt ccaacaccag                        100

SEQ ID NO: 222          moltype = DNA  length = 100
FEATURE                 Location/Qualifiers
source                  1..100
                        mol_type = genomic DNA
                        organism = Homo sapiens
SEQUENCE: 222
tcagaccaag ggggaaaaaa gtccccatga cttcagtaat tttccatcct ttggaacaag  60
gaaatataca caaaaggttt actatagaat gtaagcattg                        100

SEQ ID NO: 223          moltype = DNA  length = 100
FEATURE                 Location/Qualifiers
source                  1..100
                        mol_type = genomic DNA
                        organism = Homo sapiens
SEQUENCE: 223
aactgttcaa gattgggctc tcacactaac acacctcttc cttgcaactt gcacccaatt  60
tgactctggt cctaggcatg ctgacctgaa atagttgctg                        100

SEQ ID NO: 224          moltype = DNA  length = 100
FEATURE                 Location/Qualifiers
source                  1..100
                        mol_type = genomic DNA
                        organism = Homo sapiens
SEQUENCE: 224
gctgcggcaa gcaccacgcg gtggcaggag aattcctgaa tgtccacaca caagatgaca  60
tctgtcagag cgttttccat tcgcagggtt tccaggccat                        100

SEQ ID NO: 225          moltype = DNA  length = 100
FEATURE                 Location/Qualifiers
source                  1..100
                        mol_type = genomic DNA
                        organism = Homo sapiens
SEQUENCE: 225
tctgaagaat taaggagagt cccgcgtcgt caaatttgac cttttcccca tttaagatct  60
cgaccaagtc tcctgttttc tgggagggct catctgtaga                        100

SEQ ID NO: 226          moltype = DNA  length = 100
FEATURE                 Location/Qualifiers
source                  1..100
                        mol_type = genomic DNA
                        organism = Homo sapiens
SEQUENCE: 226
aggtgccagg ggcccttcca aactcttctc gaccacatca cccatggtcc aggcgcccct  60
ttgtcctgcc atcaacatcg agactgaagg agcgcccaag                        100

SEQ ID NO: 227          moltype = DNA  length = 100
FEATURE                 Location/Qualifiers
source                  1..100
                        mol_type = genomic DNA
                        organism = Homo sapiens
SEQUENCE: 227
ccttcctgtt ggccactaca tacgtgtccc ccgcttcttg cccctctctg cttgggtccc  60
tgctacactg gtatcctgca ctttccacct tgtattgcca                        100

SEQ ID NO: 228          moltype = DNA  length = 100
FEATURE                 Location/Qualifiers
source                  1..100
                        mol_type = genomic DNA
                        organism = Homo sapiens
SEQUENCE: 228
gtttgtttcc aaggccatct ccactttgag cttgttcatg accacctcac acagcacact  60
tggtctgtgt ggtggtttga ggggttctgt ctgtacactg                        100
```

```
SEQ ID NO: 229         moltype = DNA  length = 100
FEATURE                Location/Qualifiers
source                 1..100
                       mol_type = genomic DNA
                       organism = Homo sapiens
SEQUENCE: 229
tgctttggct gtgttggagg cgggcaggtg ggaaggaaga aatgtattct tggggagatt  60
tgtttttaga gacatgagac atggaaaata gttaagtaat                        100

SEQ ID NO: 230         moltype = DNA  length = 100
FEATURE                Location/Qualifiers
source                 1..100
                       mol_type = genomic DNA
                       organism = Homo sapiens
SEQUENCE: 230
aatataatat gggaggcatg gactatcaga ggaggcaggc aggactgccc aacctcctca  60
ctgggcacgt tacgctactt cctcctgacc tctatagtcc                        100

SEQ ID NO: 231         moltype = DNA  length = 100
FEATURE                Location/Qualifiers
source                 1..100
                       mol_type = genomic DNA
                       organism = Homo sapiens
SEQUENCE: 231
ctatcattgc cctttcttac cttgatatcc taaaaagctg gtggtctgtc ttctctatct  60
tttgtcctgg tcagttatcc taactatttt gtgtctgttt                        100

SEQ ID NO: 232         moltype = DNA  length = 100
FEATURE                Location/Qualifiers
source                 1..100
                       mol_type = genomic DNA
                       organism = Homo sapiens
SEQUENCE: 232
ctgtggatta gtaaacgggg tccccacccc cactccacaa ggagaacatc tggcacccag  60
aagtcactga gagaatagct gttgctttgg tagaattctg                        100

SEQ ID NO: 233         moltype = DNA  length = 100
FEATURE                Location/Qualifiers
source                 1..100
                       mol_type = genomic DNA
                       organism = Homo sapiens
SEQUENCE: 233
cctctgagtg gcttgttctt ttcccagacg gagaggtctc ctgacagcag ctctcttctt  60
tttctttttt tttttttttg agacagagtt ttgctcttgc                        100

SEQ ID NO: 234         moltype = DNA  length = 100
FEATURE                Location/Qualifiers
source                 1..100
                       mol_type = genomic DNA
                       organism = Homo sapiens
SEQUENCE: 234
ctcctgtacc ctgtgggcct gagagaggag acaatgggac aagaagaccc agtggcttcc  60
ttggaagctt ttgtgctagc tggagagaga agacctactt                        100

SEQ ID NO: 235         moltype = DNA  length = 100
FEATURE                Location/Qualifiers
source                 1..100
                       mol_type = genomic DNA
                       organism = Homo sapiens
SEQUENCE: 235
cctatatgcc tagcaacagt ccacactgac tggactgcaa ccaggacatt tccagattac  60
tcagtggggc ttatcttgaa ataatagttg atgccatttg                        100

SEQ ID NO: 236         moltype = DNA  length = 100
FEATURE                Location/Qualifiers
source                 1..100
                       mol_type = genomic DNA
                       organism = Homo sapiens
SEQUENCE: 236
ttaaatatat tatatatacc atctaagggt cttacatgcc ttctctcatt tgatcttcat  60
ggcaaaccct gtgaggtatg accaccaacc accattttac                        100

SEQ ID NO: 237         moltype = DNA  length = 100
FEATURE                Location/Qualifiers
source                 1..100
                       mol_type = genomic DNA
                       organism = Homo sapiens
SEQUENCE: 237
ctcagaactc aggctcccag agtttaagtt gctcacagga gcccagaaag taagcgacag  60
```

-continued

```
aggtgggatt tggttctagg tgtttgccac cagcacttta                         100

SEQ ID NO: 238         moltype = DNA  length = 100
FEATURE                Location/Qualifiers
source                 1..100
                       mol_type = genomic DNA
                       organism = Homo sapiens
SEQUENCE: 238
aatcaccaaa gctttctgga agctccaact tttcttctca agatactgaa agacaggtat  60
ctggatgggt tggcagggcg ggtgggaggt gggcgagatt                         100

SEQ ID NO: 239         moltype = DNA  length = 100
FEATURE                Location/Qualifiers
source                 1..100
                       mol_type = genomic DNA
                       organism = Homo sapiens
SEQUENCE: 239
tccatcaaca acgggtctaa aaccagcgat ggtgagctgg gtgattttga tggaacccct  60
gccatacagt ctattaatat cataattgga gctaaaattt                         100

SEQ ID NO: 240         moltype = DNA  length = 100
FEATURE                Location/Qualifiers
source                 1..100
                       mol_type = genomic DNA
                       organism = Homo sapiens
SEQUENCE: 240
aatcatgatg gcaatcatga gttctggggc ttcttgattt gggccagcag acacagtctc  60
agtcactagt tctccgaatc agagaaagga tgccttcagg                         100

SEQ ID NO: 241         moltype = DNA  length = 100
FEATURE                Location/Qualifiers
source                 1..100
                       mol_type = genomic DNA
                       organism = Homo sapiens
SEQUENCE: 241
ctgtgtcttc acatggcttt tcctctgtgc gtggtggaaa gagagagctc tgcgggtctc  60
ttcttgttgt aaggacactg gccccattgg attagggccc                         100

SEQ ID NO: 242         moltype = DNA  length = 100
FEATURE                Location/Qualifiers
source                 1..100
                       mol_type = genomic DNA
                       organism = Homo sapiens
SEQUENCE: 242
caccacatga cacatttaat cctaattacc tccctcacag ccctatttcc aaacagggta  60
ttagtcacat tagggattag ggcttcaaca taggaattct                         100

SEQ ID NO: 243         moltype = DNA  length = 100
FEATURE                Location/Qualifiers
source                 1..100
                       mol_type = genomic DNA
                       organism = Homo sapiens
SEQUENCE: 243
gggggcacac aattcagtct ataacagagg gaaaacagat ttgagaagaa aaaagtccaa  60
aatatgcaca gtggtaatat ctgaagatgt gcgtgcgtgc                         100

SEQ ID NO: 244         moltype = DNA  length = 100
FEATURE                Location/Qualifiers
source                 1..100
                       mol_type = genomic DNA
                       organism = Homo sapiens
SEQUENCE: 244
tcaagggctc agcaaacgac aacttaagca tttagagtcc catccctatc caccaaaccc  60
agaataagtt agtcttttca agaaagcatt ggtataaaac                         100

SEQ ID NO: 245         moltype = DNA  length = 100
FEATURE                Location/Qualifiers
source                 1..100
                       mol_type = genomic DNA
                       organism = Homo sapiens
SEQUENCE: 245
ccttcaaaac tgaaaagaag aaaggggcaa ttggagaatt cccacttttt ctggctgtct  60
ccttcaagtc gcccagtttt tatgaacagc atctagcctt                         100

SEQ ID NO: 246         moltype = DNA  length = 100
FEATURE                Location/Qualifiers
source                 1..100
                       mol_type = genomic DNA
                       organism = Homo sapiens
```

```
SEQUENCE: 246
actgtcacta tcaacaaccc ttaaaactag ccaatgcttc ggcctctagt attggaaagt  60
cttccaaata ggatactgga aacttctatt tataagcttg                        100

SEQ ID NO: 247          moltype = DNA  length = 100
FEATURE                 Location/Qualifiers
source                  1..100
                        mol_type = genomic DNA
                        organism = Homo sapiens
SEQUENCE: 247
gggtggcggg cggggcgggg aggtggagag agagttgcca tctacaggtt tctattttgg  60
cctgaagact caactgcagt cattagagta agggaatgcc                        100

SEQ ID NO: 248          moltype = DNA  length = 100
FEATURE                 Location/Qualifiers
source                  1..100
                        mol_type = genomic DNA
                        organism = Homo sapiens
SEQUENCE: 248
ttatttatta aaaccacaca caccttgcaa agaaaaaggg aaactggcag tctctgtaga  60
ggaagccggt ggcatcgctc agagccacaa actgtatttc                        100

SEQ ID NO: 249          moltype = DNA  length = 100
FEATURE                 Location/Qualifiers
source                  1..100
                        mol_type = genomic DNA
                        organism = Homo sapiens
SEQUENCE: 249
taaacagccc tttccctggt tccctctctc ctgccccact ttttttaaaa tccagactgt  60
aaaaaacaca tctactgaca ctcactttac tttaaaaaaa                        100

SEQ ID NO: 250          moltype = DNA  length = 100
FEATURE                 Location/Qualifiers
source                  1..100
                        mol_type = genomic DNA
                        organism = Homo sapiens
SEQUENCE: 250
gaagagaaaa agtaaagcgt tacaagactt tcctcctgga aactataaac tgaaaaaaaa  60
atccataaaa gattaaatcc tggcgggttg tggggtggcg                        100

SEQ ID NO: 251          moltype = DNA  length = 100
FEATURE                 Location/Qualifiers
source                  1..100
                        mol_type = genomic DNA
                        organism = Homo sapiens
SEQUENCE: 251
ggggccggcg gggagggggc gcggagtgga gattggctct ctgaggtggt caggggccct  60
gtgacagctt gggactttca gcacctggtt tggggtcatt                        100

SEQ ID NO: 252          moltype = DNA  length = 100
FEATURE                 Location/Qualifiers
source                  1..100
                        mol_type = genomic DNA
                        organism = Homo sapiens
SEQUENCE: 252
tatctgctca actgtcagga ccccccaccc ccaaacccca gccaccaaca caaccatcgt  60
agaagggaac acaacacaga gggtcttttt tcattttttt                        100

SEQ ID NO: 253          moltype = DNA  length = 100
FEATURE                 Location/Qualifiers
source                  1..100
                        mol_type = genomic DNA
                        organism = Homo sapiens
SEQUENCE: 253
tttttaaaaa atcggtttgg ttgtgttttt gttttccatg ggggagcttt aaaactcatt  60
attgcaacac tagttccatt tttcgccagg gttccaataa                        100

SEQ ID NO: 254          moltype = DNA  length = 100
FEATURE                 Location/Qualifiers
source                  1..100
                        mol_type = genomic DNA
                        organism = Homo sapiens
SEQUENCE: 254
caagacattt accacggtca ctacatccgg cagcggggtg gcccctagct cctgctgccc  60
ccccgccctt tctccccgcc cgcccccgga gctcagccga                        100

SEQ ID NO: 255          moltype = DNA  length = 100
FEATURE                 Location/Qualifiers
source                  1..100
```

```
                        mol_type = genomic DNA
                        organism = Homo sapiens
SEQUENCE: 255
tttctgaggc tccaactcta cccactccct ccccgggccg ccgccgccgc gccttccccc  60
attcttactc cctcgaggag agccacaggt tgcaaatcca                        100

SEQ ID NO: 256          moltype = DNA  length = 100
FEATURE                 Location/Qualifiers
source                  1..100
                        mol_type = genomic DNA
                        organism = Homo sapiens
SEQUENCE: 256
accaacctcg caatctattt ttgcaaaatc actcacaaag atctcccttt cgcgcccgcg  60
cccgctcctc ccgcgccggg tcccctcagc cacggccaca                        100

SEQ ID NO: 257          moltype = DNA  length = 100
FEATURE                 Location/Qualifiers
source                  1..100
                        mol_type = genomic DNA
                        organism = Homo sapiens
SEQUENCE: 257
aagtgccctt ctctcctcct gagtcttgca cataaggaac gcgggctggg gctctgttcg  60
tctttctcct cgcccaaggt aaggacctcg ggaatctgaa                        100

SEQ ID NO: 258          moltype = DNA  length = 100
FEATURE                 Location/Qualifiers
source                  1..100
                        mol_type = genomic DNA
                        organism = Homo sapiens
SEQUENCE: 258
gcctggcgtc cactacgctc aggcccgcag ttcccttttt acagagcttg caccatggga  60
aaaaataaaa taaaatttag gaaagggagg caacagccat                        100

SEQ ID NO: 259          moltype = DNA  length = 100
FEATURE                 Location/Qualifiers
source                  1..100
                        mol_type = genomic DNA
                        organism = Homo sapiens
SEQUENCE: 259
taaaatttag gaaagggagg caacagccat tgggagccaa cacagagtca cgcagcgccc  60
aaaatacaaa caccgcagcg gccagaaatc ccgccacctt                        100

SEQ ID NO: 260          moltype = DNA  length = 100
FEATURE                 Location/Qualifiers
source                  1..100
                        mol_type = genomic DNA
                        organism = Homo sapiens
SEQUENCE: 260
tctcgttctc ccaggctgtc ctgtcgaggt tccctgagtc cccccgcaca ctgaaaggca  60
tcgcaggtgc agtgcgcacc cctttcccac ccaccccaag                        100

SEQ ID NO: 261          moltype = DNA  length = 100
FEATURE                 Location/Qualifiers
source                  1..100
                        mol_type = genomic DNA
                        organism = Homo sapiens
SEQUENCE: 261
aagccctgtc ccgccatcag tctctctcct cgggatgagc agggagagcg cgcggaggtt  60
cccgactccc tcgactacaa ccaagaaaga ataattttca                        100

SEQ ID NO: 262          moltype = DNA  length = 100
FEATURE                 Location/Qualifiers
source                  1..100
                        mol_type = genomic DNA
                        organism = Homo sapiens
SEQUENCE: 262
aagtgttcaa catccccgcc cccaagctcc ccaaaacaca ggggcaggga acaccaaaac  60
actcggctct cattaggaag atcacggctc tgaaaggaaa                        100

SEQ ID NO: 263          moltype = DNA  length = 100
FEATURE                 Location/Qualifiers
source                  1..100
                        mol_type = genomic DNA
                        organism = Homo sapiens
SEQUENCE: 263
tagtagacac gatacttcat ctcatctgga tttatgacca aaaaaacaaa aacaaaaacc  60
caaagagttc gcttgcattt tttccttcca aatctcggtt                        100

SEQ ID NO: 264          moltype = DNA  length = 100
```

```
FEATURE                Location/Qualifiers
source                 1..100
                       mol_type = genomic DNA
                       organism = Homo sapiens
SEQUENCE: 264
aacaaaaacc caaagagttc gcttgcattt tttccttcca aatctcggtt cggctcgaag  60
gcagggaatc taaaagaccg aggccgatgg aagagagcca                        100

SEQ ID NO: 265         moltype = DNA  length = 100
FEATURE                Location/Qualifiers
source                 1..100
                       mol_type = genomic DNA
                       organism = Homo sapiens
SEQUENCE: 265
gcggggcgag cgagcgggca gcctcccttt ttgcctcccg gagttaccca gaaggacagg  60
ggaagggaag gaagaagagg cgaggaaaaa gaggagggag                        100

SEQ ID NO: 266         moltype = DNA  length = 100
FEATURE                Location/Qualifiers
source                 1..100
                       mol_type = genomic DNA
                       organism = Homo sapiens
SEQUENCE: 266
ggaagcggag gccaggagcg acggagcaag gaaagcagtt tgcaagcgag aaaagaggga  60
aaaaacacag ccgcacgaat ccagagagat cacaagccgt                        100

SEQ ID NO: 267         moltype = DNA  length = 100
FEATURE                Location/Qualifiers
source                 1..100
                       mol_type = genomic DNA
                       organism = Homo sapiens
SEQUENCE: 267
acgcaagcag cagcagaaag agcgagagcg cgagcgcgcg tcctctccgc ggtctggggc  60
cagacagccc ccagactagc ccgaatcacc ccccaagcac                        100

SEQ ID NO: 268         moltype = DNA  length = 100
FEATURE                Location/Qualifiers
source                 1..100
                       mol_type = genomic DNA
                       organism = Homo sapiens
SEQUENCE: 268
tgtctcgtcc tctctgctcc ggccgccccc taattcccct ccttcctctc ctccacctcc  60
tttccaaaaa ccaaaacaac acaagggagg gtggcaaaag                        100

SEQ ID NO: 269         moltype = DNA  length = 100
FEATURE                Location/Qualifiers
source                 1..100
                       mol_type = genomic DNA
                       organism = Homo sapiens
SEQUENCE: 269
cctccccaaa ccggccgatt cactcaaaga caacaataat aataataaat acataacaat  60
ctatatccta tggtgggaga gacgtgggac taatcttcgg                        100

SEQ ID NO: 270         moltype = DNA  length = 100
FEATURE                Location/Qualifiers
source                 1..100
                       mol_type = genomic DNA
                       organism = Homo sapiens
SEQUENCE: 270
acataacaat ctatatccta tggtgggaga gacgtgggac taatcttcgg catttatttt  60
aacacctgac agctagaata aataaatata tacatttata                        100

SEQ ID NO: 271         moltype = DNA  length = 100
FEATURE                Location/Qualifiers
source                 1..100
                       mol_type = genomic DNA
                       organism = Homo sapiens
SEQUENCE: 271
aataaatata tacatttata tcaatagata cacatagaaa acttggagcc aaagcatttg  60
gcaagagcgg aaaaaaaaag aattaaaagg taaaataatg                        100

SEQ ID NO: 272         moltype = DNA  length = 100
FEATURE                Location/Qualifiers
source                 1..100
                       mol_type = genomic DNA
                       organism = Homo sapiens
SEQUENCE: 272
atcatgagca gcggcggcgg cagcggcacc agcggcaaca gcggcggcgg cggcagtagc  60
agcagcagcg gcggcagcaa cagcaataat cacctggtgt                        100
```

```
SEQ ID NO: 273         moltype = DNA  length = 100
FEATURE                Location/Qualifiers
source                 1..100
                       mol_type = genomic DNA
                       organism = Homo sapiens
SEQUENCE: 273
ccggcctttc ctagaaactt cttgcatcac cacttctaag aaccccagtt ctaagaatca  60
acagagctca attctcggaa tttgagcttc ggactttacc                        100

SEQ ID NO: 274         moltype = DNA  length = 100
FEATURE                Location/Qualifiers
source                 1..100
                       mol_type = genomic DNA
                       organism = Homo sapiens
SEQUENCE: 274
actgctacgt ggcaggggag gacttggtgt cagctctccg agatttttac tgcccctggc  60
caaccaaaag ccctcaaagc cacaagattt tttcactggc                        100

SEQ ID NO: 275         moltype = DNA  length = 100
FEATURE                Location/Qualifiers
source                 1..100
                       mol_type = genomic DNA
                       organism = Homo sapiens
SEQUENCE: 275
cggcatattt cgaggtcctc ataagcagag cgtctcggat ttggaggttc cggttcgagg  60
ctcgaggggc ctgaaggtgg ctctccctcc ccgggcccaa                        100

SEQ ID NO: 276         moltype = DNA  length = 100
FEATURE                Location/Qualifiers
source                 1..100
                       mol_type = genomic DNA
                       organism = Homo sapiens
SEQUENCE: 276
gacgatggta tggcctgctc cgccaccatc acgtgggctc ctcctctgtg acgtcggcgc  60
cttcgctgta gcaaagctcg gcctctggaa ttctgagaac                        100

SEQ ID NO: 277         moltype = DNA  length = 100
FEATURE                Location/Qualifiers
source                 1..100
                       mol_type = genomic DNA
                       organism = Homo sapiens
SEQUENCE: 277
gcacaaaagg gagcgagagg tttgaaccac tgggaaaagt atgttatata tatagtaggg  60
ttagagaggc gagtaagaga aaaataaaat aaaataaaca                        100

SEQ ID NO: 278         moltype = DNA  length = 100
FEATURE                Location/Qualifiers
source                 1..100
                       mol_type = genomic DNA
                       organism = Homo sapiens
SEQUENCE: 278
aaaataaaat aaacatcaca gctctttcca actagaatat taggcaccac gagaaaaata  60
tttgccaagc agttttcggt gggttcattt gctttatttt                        100

SEQ ID NO: 279         moltype = DNA  length = 100
FEATURE                Location/Qualifiers
source                 1..100
                       mol_type = genomic DNA
                       organism = Homo sapiens
SEQUENCE: 279
tatttaggac aggggttttt gctgttgttc tgggtttttt tctttctggt gtggtggctt  60
gggatttttg gtttctgtat tttgatggtt tatggatttt                        100

SEQ ID NO: 280         moltype = DNA  length = 100
FEATURE                Location/Qualifiers
source                 1..100
                       mol_type = genomic DNA
                       organism = Homo sapiens
SEQUENCE: 280
tgcttctgat tttttgcctt ttgcaagttt gtggtgttac gtaaatcaca ggatcggcat  60
cggttggatt tttttgtacg tgccttttct ttccctatct                        100

SEQ ID NO: 281         moltype = DNA  length = 100
FEATURE                Location/Qualifiers
source                 1..100
                       mol_type = genomic DNA
                       organism = Homo sapiens
SEQUENCE: 281
```

```
aatccctcaa gcgttttaaa gatgtattat ttcaatacta atactattga aagaagctta  60
aatttttggc catatgtaac aatcccagcc cccacttttt                        100

SEQ ID NO: 282         moltype = DNA  length = 100
FEATURE                Location/Qualifiers
source                 1..100
                       mol_type = genomic DNA
                       organism = Homo sapiens
SEQUENCE: 282
attatcatca tcaccaccaa catcctctgc cctggagacc aagagaattc aaacaggtca  60
gcacctctaa ttgctgtata gaacattgac cctactgtct                        100

SEQ ID NO: 283         moltype = DNA  length = 100
FEATURE                Location/Qualifiers
source                 1..100
                       mol_type = genomic DNA
                       organism = Homo sapiens
SEQUENCE: 283
cccagttcct gaggatggtg tgataataat acatctcaga gttctgtagt ttcttcacca  60
ctgtgcaggt gtggttggtg ggagcaatgc cctggatgga                        100

SEQ ID NO: 284         moltype = DNA  length = 100
FEATURE                Location/Qualifiers
source                 1..100
                       mol_type = genomic DNA
                       organism = Homo sapiens
SEQUENCE: 284
taagccaagc tcttgtgtcc tggcagataa acaaggtgaa ccctcaatcc gtgtagcagg  60
agtttccaga caaactcact ttgcatggaa ggacactaac                        100

SEQ ID NO: 285         moltype = DNA  length = 100
FEATURE                Location/Qualifiers
source                 1..100
                       mol_type = genomic DNA
                       organism = Homo sapiens
SEQUENCE: 285
ccttccaggt gcatggaaat attttgtagt ttttactgtc tccccccttcc tccactgcct  60
catctttttt gtttttttccc ctgtgagact atttgctctg                        100

SEQ ID NO: 286         moltype = DNA  length = 100
FEATURE                Location/Qualifiers
source                 1..100
                       mol_type = genomic DNA
                       organism = Homo sapiens
SEQUENCE: 286
cctttccaac actggcctgc cttagggact caccgtctgc actccgcctg cacaggtgga  60
actgagttca gatgagggag aattgctttc cattgttcag                        100

SEQ ID NO: 287         moltype = DNA  length = 100
FEATURE                Location/Qualifiers
source                 1..100
                       mol_type = genomic DNA
                       organism = Homo sapiens
SEQUENCE: 287
taggcttttt gtaatttcta gttttgctta cctttcctac tcaccacaca cacaaaacag  60
tgtgagcttt ctcattctag tgcataaaca caggtcggtc                        100

SEQ ID NO: 288         moltype = DNA  length = 100
FEATURE                Location/Qualifiers
source                 1..100
                       mol_type = genomic DNA
                       organism = Homo sapiens
SEQUENCE: 288
aatacccaca agtgttccaa aaggtgagct ggcattgctg cccaactggg cattatagtc  60
ccttctgtcc ctgcccatca ggcttgcctt cctcggcaac                        100

SEQ ID NO: 289         moltype = DNA  length = 100
FEATURE                Location/Qualifiers
source                 1..100
                       mol_type = genomic DNA
                       organism = Homo sapiens
SEQUENCE: 289
ctttctagct tgaattgtac tgtgactcct tctcacggac cactcccgga gactggtgaa  60
agttgggccc attcttgaag cctctgcttc taaatcatgt                        100

SEQ ID NO: 290         moltype = DNA  length = 100
FEATURE                Location/Qualifiers
source                 1..100
                       mol_type = genomic DNA
```

```
                         organism = Homo sapiens
SEQUENCE: 290
tttccataaa gtctccctca tcgtgcttgc ttccaccttc tcctatttgg aattactggt  60
gggctcttcc actgtcccat agcaagtgtt ctatacattc                        100

SEQ ID NO: 291           moltype = DNA  length = 100
FEATURE                  Location/Qualifiers
source                   1..100
                         mol_type = genomic DNA
                         organism = Homo sapiens
SEQUENCE: 291
tgaaggcaca tttgaatata tactttgtca tggttgcttg gaaccatgtc gtcttttcca  60
agtaggctgt gaacattcag tggcatggat cataccgtgc                        100

SEQ ID NO: 292           moltype = DNA  length = 100
FEATURE                  Location/Qualifiers
source                   1..100
                         mol_type = genomic DNA
                         organism = Homo sapiens
SEQUENCE: 292
cccattgttc aaagaaaggc attatggagt ctccaaaagc cattggcagg tggtgtctgt  60
gacttcctta gcctggaaat aaacaaataa acaagcacaa                        100

SEQ ID NO: 293           moltype = DNA  length = 100
FEATURE                  Location/Qualifiers
source                   1..100
                         mol_type = genomic DNA
                         organism = Homo sapiens
SEQUENCE: 293
aaacaaataa acaagcacaa attagaagtc tttgccctat tactgcacta ttagtattga  60
ttgcgcaaca tcatgcaaaa agtcacttta atttatctgg                        100

SEQ ID NO: 294           moltype = DNA  length = 100
FEATURE                  Location/Qualifiers
source                   1..100
                         mol_type = genomic DNA
                         organism = Homo sapiens
SEQUENCE: 294
caggtcctat gtaaacacca atacagtcaa gagggcttgg atgggtattt gctttcattt  60
ctaatgaaat ttcaggcctc tagggtagga tatcaaaatt                        100

SEQ ID NO: 295           moltype = DNA  length = 100
FEATURE                  Location/Qualifiers
source                   1..100
                         mol_type = genomic DNA
                         organism = Homo sapiens
SEQUENCE: 295
ggtagatcat ttgcaattta ttttatccca aacacctcac tttacagtca gagaaactga  60
ggcccagaga agtaaaatga gttgctcaag gtctcagaga                        100

SEQ ID NO: 296           moltype = DNA  length = 100
FEATURE                  Location/Qualifiers
source                   1..100
                         mol_type = genomic DNA
                         organism = Homo sapiens
SEQUENCE: 296
actgaggccc agagaagtaa aatgagttgc tcaaggtctc agagagcaag aaatagagat  60
gggacttgag cacctagatc tctggtattg ctgtcctgta                        100

SEQ ID NO: 297           moltype = DNA  length = 100
FEATURE                  Location/Qualifiers
source                   1..100
                         mol_type = genomic DNA
                         organism = Homo sapiens
SEQUENCE: 297
gttcatggag ctggcagatg gatacatctg tgacctggga tgatggagag actgctggac  60
ccttcagagg atctcatctc aaggtggggt ttatgtgtaa                        100

SEQ ID NO: 298           moltype = DNA  length = 100
FEATURE                  Location/Qualifiers
source                   1..100
                         mol_type = genomic DNA
                         organism = Homo sapiens
SEQUENCE: 298
atgatatctg tgtgtttcat tttcctttca taaactaatt taaaaatcct tttggtatca  60
aattttaagc caaaaagtag tgagggggaa catgggtagg                        100

SEQ ID NO: 299           moltype = DNA  length = 100
FEATURE                  Location/Qualifiers
```

```
source                 1..100
                       mol_type = genomic DNA
                       organism = Homo sapiens
SEQUENCE: 299
aatagcttac agcttgccta acaaggttgt tgactgcata agagtcagga gttttgggta  60
agagtgtgtg tgtgtgtgtg tgtgtgtgtg tgtgtgtgag                        100

SEQ ID NO: 300         moltype = DNA  length = 100
FEATURE                Location/Qualifiers
source                 1..100
                       mol_type = genomic DNA
                       organism = Homo sapiens
SEQUENCE: 300
cgtactgaat ttgactgctt tattttgtag ggaaggaaac tgatgtgcct agagtagttg  60
agagctttat tcaaactcat tccactgtta ttgagtagtt                        100

SEQ ID NO: 301         moltype = DNA  length = 100
FEATURE                Location/Qualifiers
source                 1..100
                       mol_type = genomic DNA
                       organism = Homo sapiens
SEQUENCE: 301
aggatattag accagcaaca tatttgggta gaaactttca tataaaaaag cgtaatcata  60
actatccaat catgtcaact agtaaggctg ctcaggtggg                        100

SEQ ID NO: 302         moltype = DNA  length = 100
FEATURE                Location/Qualifiers
source                 1..100
                       mol_type = genomic DNA
                       organism = Homo sapiens
SEQUENCE: 302
ataacacatc aaccttcttt gggattcttc cctcagacat ggttttggtg ggaggagcat  60
ggcaagggag gggcgagctc caaatgcagg gctgctctgt                        100

SEQ ID NO: 303         moltype = DNA  length = 100
FEATURE                Location/Qualifiers
source                 1..100
                       mol_type = genomic DNA
                       organism = Homo sapiens
SEQUENCE: 303
cctcggcgac ctgagcagac acacgagcag agatcagaga cactcttagt gaatgaacct  60
ccctattggc tatattaaag taatgctctg aaaaagttcc                        100

SEQ ID NO: 304         moltype = DNA  length = 100
FEATURE                Location/Qualifiers
source                 1..100
                       mol_type = genomic DNA
                       organism = Homo sapiens
SEQUENCE: 304
tatgtatgca tagtctaaag tgatgatttt agaggtagca agacagtgag aatgtcccta  60
catgtgaaat gggcacagtt ttatcaggga agtgtcaata                        100

SEQ ID NO: 305         moltype = DNA  length = 100
FEATURE                Location/Qualifiers
source                 1..100
                       mol_type = genomic DNA
                       organism = Homo sapiens
SEQUENCE: 305
gagggttaat gttccacgta gtggctgcaa gaatgataag tggtcatggg gatagcctga  60
cactctagga gcagaaggtg gtgggtatgg atagaactac                        100

SEQ ID NO: 306         moltype = DNA  length = 100
FEATURE                Location/Qualifiers
source                 1..100
                       mol_type = genomic DNA
                       organism = Homo sapiens
SEQUENCE: 306
tgatatagca tgaatccaac ctgctgttat ctgcgcaggc ctctctgcag ctgtttgccc  60
tgaagtacat gctgtacgtt tctccagctg atcctgcatg                        100

SEQ ID NO: 307         moltype = DNA  length = 100
FEATURE                Location/Qualifiers
source                 1..100
                       mol_type = genomic DNA
                       organism = Homo sapiens
SEQUENCE: 307
actgggtata aacgcctgtc cgctgtgtgc tggacagccc cagacaccct cggcagcctg  60
ctgtgtttgt gtgagacatg ctgtgttagg gatttaagca                        100
```

```
SEQ ID NO: 308         moltype = DNA  length = 100
FEATURE                Location/Qualifiers
source                 1..100
                       mol_type = genomic DNA
                       organism = Homo sapiens
SEQUENCE: 308
acagctttct catctacatg gacaacctat ttttaaagaa tcttcagaga gtcgttgact  60
ttgttataac tactactata tacgtaattt cagatgatag                        100

SEQ ID NO: 309         moltype = DNA  length = 100
FEATURE                Location/Qualifiers
source                 1..100
                       mol_type = genomic DNA
                       organism = Homo sapiens
SEQUENCE: 309
aattgaaaat ttaacttgtt tttctagaaa gagtttattt tccctataac ttcaaagagt  60
aatggtgggg agtaggacat tctgaaaata agaagaaaca                        100

SEQ ID NO: 310         moltype = DNA  length = 100
FEATURE                Location/Qualifiers
source                 1..100
                       mol_type = genomic DNA
                       organism = Homo sapiens
SEQUENCE: 310
tgtcaaatga atttctgact tccagctagg catatggaat aaaggtcttt attccagtga  60
cctctgctca ttggaaaact ttgggctggt agatttcatg                        100

SEQ ID NO: 311         moltype = DNA  length = 100
FEATURE                Location/Qualifiers
source                 1..100
                       mol_type = genomic DNA
                       organism = Homo sapiens
SEQUENCE: 311
tctcttgcat tcttaacttg caatttagta ctgtttatat tctgcttgaa ggttagagac  60
attcgactaa atggtctttt ctccacattg ctgtcattca                        100

SEQ ID NO: 312         moltype = DNA  length = 100
FEATURE                Location/Qualifiers
source                 1..100
                       mol_type = genomic DNA
                       organism = Homo sapiens
SEQUENCE: 312
ttaatgtcct ggtcctggac tttactcatt gaccacagga caagtggctc aactctctcc  60
tgccactacc caggctgtta gtcctgttgg gaggctcagg                        100

SEQ ID NO: 313         moltype = DNA  length = 100
FEATURE                Location/Qualifiers
source                 1..100
                       mol_type = genomic DNA
                       organism = Homo sapiens
SEQUENCE: 313
gcccaactca ctcatctgta actctcatct ccattcagct gcagcctcta cagcccctgg  60
ttataccctg gatcttatca ttgcttcgct ctattttacc                        100

SEQ ID NO: 314         moltype = DNA  length = 100
FEATURE                Location/Qualifiers
source                 1..100
                       mol_type = genomic DNA
                       organism = Homo sapiens
SEQUENCE: 314
tcctaaatcg taaaaattaa aaccagcctc ggaacacaac ccctcattct tccagcactc  60
tctctcattc aggtaactcc tattctactt ttcttcagca                        100

SEQ ID NO: 315         moltype = DNA  length = 100
FEATURE                Location/Qualifiers
source                 1..100
                       mol_type = genomic DNA
                       organism = Homo sapiens
SEQUENCE: 315
ttgttttttt ttactttacc ttaatttctc tttttggact aagatgttaa aatgtttctt  60
aatgtgactg tctccgaaac tgttttgtgt ctaccactca                        100

SEQ ID NO: 316         moltype = DNA  length = 100
FEATURE                Location/Qualifiers
source                 1..100
                       mol_type = genomic DNA
                       organism = Homo sapiens
SEQUENCE: 316
tcctagtggc agtcattgat ccttttcttg ttgcgagtgt ttgagtgtgg gtgtgtgtga  60
```

```
gtgtgtatat gtatttgtag agggaaaaac aagagagagg                        100

SEQ ID NO: 317          moltype = DNA  length = 100
FEATURE                 Location/Qualifiers
source                  1..100
                        mol_type = genomic DNA
                        organism = Homo sapiens
SEQUENCE: 317
tgtgagtgtg tatatgtatt tgtagaggga aaaacaagag agagggaaac agacattgga  60
gccacctttc ccccactagc cacgtacctg ttgaaccttc                        100

SEQ ID NO: 318          moltype = DNA  length = 100
FEATURE                 Location/Qualifiers
source                  1..100
                        mol_type = genomic DNA
                        organism = Homo sapiens
SEQUENCE: 318
aagcctctct atagaatcag atatacacaa gcacagtgac agaactacat gtgtcctaca  60
gtccagcttt taagatatga taaaaactct tgtattcaca                        100

SEQ ID NO: 319          moltype = DNA  length = 100
FEATURE                 Location/Qualifiers
source                  1..100
                        mol_type = genomic DNA
                        organism = Homo sapiens
SEQUENCE: 319
gagctaaatg gcaataacca taggagattg catattgcta cattatgtaa agacagagtc  60
ccaagaaaat agtgagaact cagtttgatg tatgatgtga                        100

SEQ ID NO: 320          moltype = DNA  length = 100
FEATURE                 Location/Qualifiers
source                  1..100
                        mol_type = genomic DNA
                        organism = Homo sapiens
SEQUENCE: 320
tatgtgatat cttactttac atggctaaca gttgacattc tttgtggatt ctatattgtc  60
taaggctaca gaagagccat atgataaatt catcggcaac                        100

SEQ ID NO: 321          moltype = DNA  length = 100
FEATURE                 Location/Qualifiers
source                  1..100
                        mol_type = genomic DNA
                        organism = Homo sapiens
SEQUENCE: 321
cagtgaaaag gcttgggccg cttttgtttt cacctgcttt tgttgaacaa atttgatttc  60
cggagtcagt cattttactg tcaagacatt tcttcggcat                        100

SEQ ID NO: 322          moltype = DNA  length = 100
FEATURE                 Location/Qualifiers
source                  1..100
                        mol_type = genomic DNA
                        organism = Homo sapiens
SEQUENCE: 322
tctgcaacag gtaaggattt tgcttcctta aaagtatttc tttggtgtca aaagaaattt  60
ttctaatttt atttagcttt tactctaggc caaacatcgt                        100

SEQ ID NO: 323          moltype = DNA  length = 100
FEATURE                 Location/Qualifiers
source                  1..100
                        mol_type = genomic DNA
                        organism = Homo sapiens
SEQUENCE: 323
aatgactctg agctacctgc tgtaaggtgt agaatcaatt tacaggggga cgggggtcgg  60
gggggtgagt gttgctttga tattcactgc ccctcaccac                        100

SEQ ID NO: 324          moltype = DNA  length = 100
FEATURE                 Location/Qualifiers
source                  1..100
                        mol_type = genomic DNA
                        organism = Homo sapiens
SEQUENCE: 324
agtcctaaca agatttttga aacatgaaaa gttacaatag ttggcttttt ggttttccag  60
atattctaga gaatgcatat gcttgtgact gtggctgagc                        100

SEQ ID NO: 325          moltype = DNA  length = 100
FEATURE                 Location/Qualifiers
source                  1..100
                        mol_type = genomic DNA
                        organism = Homo sapiens
```

```
SEQUENCE: 325
tcaactgtat gggtagttta aatactaccc aaggtttgat gaagtaaatc taaagatgct  60
ctaagttgtg caaatatgaa ttttaaagtt gtctagttca                        100

SEQ ID NO: 326         moltype = DNA  length = 100
FEATURE                Location/Qualifiers
source                 1..100
                       mol_type = genomic DNA
                       organism = Homo sapiens
SEQUENCE: 326
gaaaagaaac agaaccgaag tctaaatgat gtagatttca atctggaatt tctagcttgt  60
gtttttcacc tattgccaat gttaatgacc atttcccaaa                        100

SEQ ID NO: 327         moltype = DNA  length = 100
FEATURE                Location/Qualifiers
source                 1..100
                       mol_type = genomic DNA
                       organism = Homo sapiens
SEQUENCE: 327
agtgctctat gatgtataac atgtattttt taattaaatt taatctttct tctgaggtgg  60
tttgatttgg agatatgcta cgaggtacca gtcagtagcc                        100

SEQ ID NO: 328         moltype = DNA  length = 100
FEATURE                Location/Qualifiers
source                 1..100
                       mol_type = genomic DNA
                       organism = Homo sapiens
SEQUENCE: 328
tgagttgtaa ctaaacaaag tttgggaaat caccggtttt aggtgcttta ctaaatgaaa  60
gttgccattg acgtattcaa gcaggcaaca agtagttggt                        100

SEQ ID NO: 329         moltype = DNA  length = 100
FEATURE                Location/Qualifiers
source                 1..100
                       mol_type = genomic DNA
                       organism = Homo sapiens
SEQUENCE: 329
gtccccttat tggttctaag ctggtgccgt ggaggatata agagaaatat tttaaaaatc  60
tctactttga aggaccctat aatctggtag ttgtgataag                        100

SEQ ID NO: 330         moltype = DNA  length = 100
FEATURE                Location/Qualifiers
source                 1..100
                       mol_type = genomic DNA
                       organism = Homo sapiens
SEQUENCE: 330
tttaaaaatc tctactttga aggaccctat aatctggtag ttgtgataag aagtaaaatt  60
taggaagcaa tgcaagatga gaattcagtg atgagtgggg                        100

SEQ ID NO: 331         moltype = DNA  length = 100
FEATURE                Location/Qualifiers
source                 1..100
                       mol_type = genomic DNA
                       organism = Homo sapiens
SEQUENCE: 331
cagcacaggc ttgaagagtt ctgtgaattc catggagggg gcctgggggc aaactggagt  60
tgtcaggaag atctgggctt tggaagaatg cgaagtgtcg                        100

SEQ ID NO: 332         moltype = DNA  length = 100
FEATURE                Location/Qualifiers
source                 1..100
                       mol_type = genomic DNA
                       organism = Homo sapiens
SEQUENCE: 332
gtagaaggag aaggggcagg tgatttcaga ctgggaggac cttgtgggca aaggcacaaa  60
ggcgagactg acctggagat gataaggcca gttgaagaga                        100

SEQ ID NO: 333         moltype = DNA  length = 100
FEATURE                Location/Qualifiers
source                 1..100
                       mol_type = genomic DNA
                       organism = Homo sapiens
SEQUENCE: 333
acattgcagg aaatcagatt agacagttag ggtgtggaca caaaagcgag gaccttgcag  60
gcactgggga gaagtgaccc cattcaatag tccttggtct                        100

SEQ ID NO: 334         moltype = DNA  length = 100
FEATURE                Location/Qualifiers
source                 1..100
```

```
                         mol_type = genomic DNA
                         organism = Homo sapiens
SEQUENCE: 334
ccttctgccc tgcggctgcg cttcctcggc tctcacggca ccagcagaat tccatgtgag  60
agggagcttg tcgagcgtgg cctcttccca cttggggctg                        100

SEQ ID NO: 335           moltype = DNA  length = 100
FEATURE                  Location/Qualifiers
source                   1..100
                         mol_type = genomic DNA
                         organism = Homo sapiens
SEQUENCE: 335
ctttctgcat ccctgtgcct ggctgtgggc ctccatttgc cctctactgt cttcccttag  60
gacatcattt atgcagagaa aggttcgtgt ggctcggggt                        100

SEQ ID NO: 336           moltype = DNA  length = 100
FEATURE                  Location/Qualifiers
source                   1..100
                         mol_type = genomic DNA
                         organism = Homo sapiens
SEQUENCE: 336
ggacgttgtt tagagagtca gtagatcata ataattcaga cacttttttt ctggaccata  60
aaatatctga acccatataa taacaaacat acagcacggt                        100

SEQ ID NO: 337           moltype = DNA  length = 100
FEATURE                  Location/Qualifiers
source                   1..100
                         mol_type = genomic DNA
                         organism = Homo sapiens
SEQUENCE: 337
gaataagaac ccaacttttg agccagatca ctttgcatgg aatccccatt ctatcattct  60
atcatttctg ggctgtggga acctcagaca agttacttaa                        100

SEQ ID NO: 338           moltype = DNA  length = 100
FEATURE                  Location/Qualifiers
source                   1..100
                         mol_type = genomic DNA
                         organism = Homo sapiens
SEQUENCE: 338
cttcttcaat gctcagatta aaaaaaaaat tcacaaaata tctctaataa cagtaataat  60
aactgaaaat acctacctca gagggttgtc gtagagatca                        100

SEQ ID NO: 339           moltype = DNA  length = 100
FEATURE                  Location/Qualifiers
source                   1..100
                         mol_type = genomic DNA
                         organism = Homo sapiens
SEQUENCE: 339
aaaattcaca aaatatctct aataacagta ataataactg aaaataccta cctcagaggg  60
ttgtcgtaga gatcaaatga gataaaaata tgtaaagcat                        100

SEQ ID NO: 340           moltype = DNA  length = 100
FEATURE                  Location/Qualifiers
source                   1..100
                         mol_type = genomic DNA
                         organism = Homo sapiens
SEQUENCE: 340
gtagcctagt gcctgactga aaaaaaaatc tctcaataga tgcaactctt atgattctta  60
ttaaggactt ggctattgcc acaaatgaag gtgttatgag                        100

SEQ ID NO: 341           moltype = DNA  length = 100
FEATURE                  Location/Qualifiers
source                   1..100
                         mol_type = genomic DNA
                         organism = Homo sapiens
SEQUENCE: 341
ccctggctta agagcaagaa gcctgcaaag ctaactctcc taatcccaac attcctttcc  60
agggaaagta gggtgacagg tggaggctgg gaattaacgt                        100

SEQ ID NO: 342           moltype = DNA  length = 100
FEATURE                  Location/Qualifiers
source                   1..100
                         mol_type = genomic DNA
                         organism = Homo sapiens
SEQUENCE: 342
tttttgagca ccaaatatgg acaaggcaca ggggttgggt gtttttctag tgagaataca  60
tatgaaagaa ggaaaacaaa cttggaaacc gctattttaa                        100

SEQ ID NO: 343           moltype = DNA  length = 100
```

```
FEATURE                Location/Qualifiers
source                 1..100
                       mol_type = genomic DNA
                       organism = Homo sapiens
SEQUENCE: 343
gccatttggt aacagtttct ctagcttatg agatgagaga ggtcctctca gtatccgctg  60
cattacttgt gggcctcctt ggttgacgtc gctctctgaa                        100

SEQ ID NO: 344         moltype = DNA  length = 100
FEATURE                Location/Qualifiers
source                 1..100
                       mol_type = genomic DNA
                       organism = Homo sapiens
SEQUENCE: 344
cgcttggggt ggaattctag aggtgctttt cattagaggc agagagcatg acctttcttc  60
cttgcccagt ttaaattaaa ttattttatc ttacaatgtg                        100

SEQ ID NO: 345         moltype = DNA  length = 100
FEATURE                Location/Qualifiers
source                 1..100
                       mol_type = genomic DNA
                       organism = Homo sapiens
SEQUENCE: 345
ttaattttag tgctagcaag gcacagctaa aattccattt ctacttagga gtggggatca  60
ttgtggcagt gagtgcttat ttgggtttgg gatgcttgga                        100

SEQ ID NO: 346         moltype = DNA  length = 100
FEATURE                Location/Qualifiers
source                 1..100
                       mol_type = genomic DNA
                       organism = Homo sapiens
SEQUENCE: 346
tctgggtgaa agccaggatt aaaaagcatc ctccttcccc attccactct ctaggttata  60
aatatttttt tggattaaaa gcctccttta aaaaaatgca                        100

SEQ ID NO: 347         moltype = DNA  length = 100
FEATURE                Location/Qualifiers
source                 1..100
                       mol_type = genomic DNA
                       organism = Homo sapiens
SEQUENCE: 347
aatccacctg gcatgttaat tgtgcagggg attcctaatt atgtgtgcag atgacgtgag  60
tcacacggtg atagtgttcc ttctagagtc ccactggtgt                        100

SEQ ID NO: 348         moltype = DNA  length = 100
FEATURE                Location/Qualifiers
source                 1..100
                       mol_type = genomic DNA
                       organism = Homo sapiens
SEQUENCE: 348
actaggcgtt catcctgtgt aatttgaaaa tatgtcacac gtggtgatga gaatctattt  60
gaggaacatg ggcagtttga aataatatat gcaatgtatg                        100

SEQ ID NO: 349         moltype = DNA  length = 100
FEATURE                Location/Qualifiers
source                 1..100
                       mol_type = genomic DNA
                       organism = Homo sapiens
SEQUENCE: 349
actagtttat ataatgaaag gaagtattta aaaagataga atgacataga ctaatctaat  60
tgagaaatat gaaagtctaa cagaaatgat tgcttgtgaa                        100

SEQ ID NO: 350         moltype = DNA  length = 100
FEATURE                Location/Qualifiers
source                 1..100
                       mol_type = genomic DNA
                       organism = Homo sapiens
SEQUENCE: 350
attttatgaa gaaatccaca gataaattct ccaccttgat ctatgtaatc cgaaatttag  60
atgttaaaaa tatgttgatt ctgaaaattt atatttattc                        100

SEQ ID NO: 351         moltype = DNA  length = 100
FEATURE                Location/Qualifiers
source                 1..100
                       mol_type = genomic DNA
                       organism = Homo sapiens
SEQUENCE: 351
tttggtatga ataggtcaaa acaagtcacc attaactgac aggaagcaca gaattctcaa  60
tttagttttg gcaaagacat tattttataa atatgagttt                        100
```

```
SEQ ID NO: 352          moltype = DNA  length = 100
FEATURE                 Location/Qualifiers
source                  1..100
                        mol_type = genomic DNA
                        organism = Homo sapiens
SEQUENCE: 352
ttaaatgatt cttatgaaga aactagcacc aaagtgaatg cactctgcaa ataactccca  60
gcttctctga atttcaaaag cagccactaa atattattag                         100

SEQ ID NO: 353          moltype = DNA  length = 100
FEATURE                 Location/Qualifiers
source                  1..100
                        mol_type = genomic DNA
                        organism = Homo sapiens
SEQUENCE: 353
caaatcaatt tagctgaaag cgatgaatta cagaagtaaa tctttaggta caaagtagac  60
agctgacaca catgtagcat atacacacta gtgatctgcc                         100

SEQ ID NO: 354          moltype = DNA  length = 100
FEATURE                 Location/Qualifiers
source                  1..100
                        mol_type = genomic DNA
                        organism = Homo sapiens
SEQUENCE: 354
ttccttcttt accaacatag agtttcccat gagccctgaa tccggggcac ttttgctaac  60
ttcccctgca gcggcgacgc tgccactccc agtgcccccg                         100

SEQ ID NO: 355          moltype = DNA  length = 100
FEATURE                 Location/Qualifiers
source                  1..100
                        mol_type = genomic DNA
                        organism = Homo sapiens
SEQUENCE: 355
cagtggaagg ggctcgcgcc acctccattg ctcttggccc caaagccata gaggtgcccc  60
ccggaagggg cctggctgcc actgccattc tggtggccct                         100

SEQ ID NO: 356          moltype = DNA  length = 100
FEATURE                 Location/Qualifiers
source                  1..100
                        mol_type = genomic DNA
                        organism = Homo sapiens
SEQUENCE: 356
gaagcaggtc gtgcttgtcc ttcctggatt tccccgcatc cttatcccgc ttggcgcctc  60
ggctgctctg gcttttacct ggcttctcct ctttgctttt                         100

SEQ ID NO: 357          moltype = DNA  length = 100
FEATURE                 Location/Qualifiers
source                  1..100
                        mol_type = genomic DNA
                        organism = Homo sapiens
SEQUENCE: 357
cccacaggag cctgcccccg cggtggcggc agaggtgctg gtgctggtac tattgctgtt  60
tgggttgccg ctgccgccgc tgctcacact ttgacccagc                         100

SEQ ID NO: 358          moltype = DNA  length = 100
FEATURE                 Location/Qualifiers
source                  1..100
                        mol_type = genomic DNA
                        organism = Homo sapiens
SEQUENCE: 358
gctgaattca tgccagttgc ctctccaggg cgcccttgga cttcctgcct cttgccagtg  60
ctgctgatct cgggaatccc atacaaggca gcagaaggca                         100

SEQ ID NO: 359          moltype = DNA  length = 100
FEATURE                 Location/Qualifiers
source                  1..100
                        mol_type = genomic DNA
                        organism = Homo sapiens
SEQUENCE: 359
gagatttatt agcatcctta gaagttttac tccttttcac ttttgatttg ctggtctctt  60
tgtgtgaatt cccctgggga gcagaggcct gaacagaagc                         100

SEQ ID NO: 360          moltype = DNA  length = 100
FEATURE                 Location/Qualifiers
source                  1..100
                        mol_type = genomic DNA
                        organism = Homo sapiens
SEQUENCE: 360
```

```
aaattttagg ccatcagcta aggctgcggt agcaccagcc ccactggagg ccggacctcc  60
acaatccttg gagttgctgc tactagtggt ggtggtggaa                        100

SEQ ID NO: 361         moltype = DNA  length = 100
FEATURE                Location/Qualifiers
source                 1..100
                       mol_type = genomic DNA
                       organism = Homo sapiens
SEQUENCE: 361
ttattcatct caaatttctg tctgtccttc tccaaatcag cgtccaaatc aattattaaa  60
tttccaaccc cgatttccca atcatcgcca ctgtcataag                        100

SEQ ID NO: 362         moltype = DNA  length = 100
FEATURE                Location/Qualifiers
source                 1..100
                       mol_type = genomic DNA
                       organism = Homo sapiens
SEQUENCE: 362
tatcaactgt atttggatcc acaccttttc ctgcagtaga aatgttcact gacatcctga  60
agatgagctc tctagaataa aaatccgatg aacttttctt                        100

SEQ ID NO: 363         moltype = DNA  length = 100
FEATURE                Location/Qualifiers
source                 1..100
                       mol_type = genomic DNA
                       organism = Homo sapiens
SEQUENCE: 363
ttcctcagga atttgagctg gggatctgca tcctggccat tgcagtcctt tagcatcctc  60
gccgcgccct gagcgcgctg gaggctcgca ggctgcgccc                        100

SEQ ID NO: 364         moltype = DNA  length = 100
FEATURE                Location/Qualifiers
source                 1..100
                       mol_type = genomic DNA
                       organism = Homo sapiens
SEQUENCE: 364
tcccagggct gatgccgcgt cctgctccgc cgttctggga cgtcggggac aaaagtggag  60
gagacgggag agcccgggca gaaaaagcag gacgcgcgtc                        100

SEQ ID NO: 365         moltype = DNA  length = 100
FEATURE                Location/Qualifiers
source                 1..100
                       mol_type = genomic DNA
                       organism = Homo sapiens
SEQUENCE: 365
ccaggtgccc acctcttcgc tttgaggcgg gggcggtggg atggaatatg ggtgcgcgag  60
gtcggggctg gtaactctcg gaggggcacg gcctccacgc                        100

SEQ ID NO: 366         moltype = DNA  length = 100
FEATURE                Location/Qualifiers
source                 1..100
                       mol_type = genomic DNA
                       organism = Homo sapiens
SEQUENCE: 366
tgggagggat gaatggacgc tgggccccgg caaatgaggc gctgtgggtc cccaggaagt  60
ggggtaccag gctctactcc caccccggcc tctgaaacgc                        100

SEQ ID NO: 367         moltype = DNA  length = 100
FEATURE                Location/Qualifiers
source                 1..100
                       mol_type = genomic DNA
                       organism = Homo sapiens
SEQUENCE: 367
ggccaggagg ggtggcggct gggtggggag agagggtgca agacgagcgg cgcgtgtcgg  60
gagcctttgg gctgcgggtg cgttacagga gagcaggcgg                        100

SEQ ID NO: 368         moltype = DNA  length = 100
FEATURE                Location/Qualifiers
source                 1..100
                       mol_type = genomic DNA
                       organism = Homo sapiens
SEQUENCE: 368
gtaggagcct tcgcgggggc cgagctcgga aggcggacgg ctgtgcccgc ccaggggatg  60
cgcccgggcc ggccgcgaag gtgccttctt ccgggggccc                        100

SEQ ID NO: 369         moltype = DNA  length = 100
FEATURE                Location/Qualifiers
source                 1..100
                       mol_type = genomic DNA
```

```
                        organism = Homo sapiens
SEQUENCE: 369
ggacgaccct gacacggcac gcgcgcgctt cgcagcctca aagactccgg ggcctcgtgg  60
tcactggcgc aggggatcgg ggcggggtgc ccggagtgcg                        100

SEQ ID NO: 370          moltype = DNA  length = 100
FEATURE                 Location/Qualifiers
source                  1..100
                        mol_type = genomic DNA
                        organism = Homo sapiens
SEQUENCE: 370
cccgcagtgc agagcagagc gggcggagga ccccgggcgc gggcgcggac ggcacgcggg  60
gcatgaacct ggagggcggc ggccgaggcg gagagttcgg                        100

SEQ ID NO: 371          moltype = DNA  length = 100
FEATURE                 Location/Qualifiers
source                  1..100
                        mol_type = genomic DNA
                        organism = Homo sapiens
SEQUENCE: 371
catgagcgcg gtgagctgcg gcaacgggaa gctccgccag tggctgatcg accagatcga  60
cagcggcaag taccccgggc tggtgtggga gaacgaggag                        100

SEQ ID NO: 372          moltype = DNA  length = 100
FEATURE                 Location/Qualifiers
source                  1..100
                        mol_type = genomic DNA
                        organism = Homo sapiens
SEQUENCE: 372
aagagcatct tccgcatccc ctggaagcac gcgggcaagc aggactacaa ccgcgaggag  60
gacgccgcgc tcttcaaggt ctccggcctc gggagccggc                        100

SEQ ID NO: 373          moltype = DNA  length = 100
FEATURE                 Location/Qualifiers
source                  1..100
                        mol_type = genomic DNA
                        organism = Homo sapiens
SEQUENCE: 373
cccgcgcgcc acagctctgc agctcgtggc agcggcgcag cgctccagcc atgtcgcgcg  60
gcctccagct tctgctcctg agctgcggta gggctcgcga                        100

SEQ ID NO: 374          moltype = DNA  length = 100
FEATURE                 Location/Qualifiers
source                  1..100
                        mol_type = genomic DNA
                        organism = Homo sapiens
SEQUENCE: 374
gcgcctgtct cgcctgtcgc cccccgcccc tccacgacac cccctcccgt cggtcgcttg  60
ctcacgacgc gctctctctt tcttgtagcc tacagcctgg                        100

SEQ ID NO: 375          moltype = DNA  length = 100
FEATURE                 Location/Qualifiers
source                  1..100
                        mol_type = genomic DNA
                        organism = Homo sapiens
SEQUENCE: 375
ctcccgcgac gccggaggtg aaggtggctt gctccgaaga tgtggacttg ccctgcaccg  60
ccccctggga tccgcaggtt ccctacacgg tctcctgggt                        100

SEQ ID NO: 376          moltype = DNA  length = 100
FEATURE                 Location/Qualifiers
source                  1..100
                        mol_type = genomic DNA
                        organism = Homo sapiens
SEQUENCE: 376
caaggtaggt gctgcgatac ccacgggctg gggtttggtg ggctcatttg aagacagcag  60
gaaccatctc ccctaggctg gcgaccctct gtggctgcca                        100

SEQ ID NO: 377          moltype = DNA  length = 100
FEATURE                 Location/Qualifiers
source                  1..100
                        mol_type = genomic DNA
                        organism = Homo sapiens
SEQUENCE: 377
ggtgggggcg aggggcgtct cccgcagctg aacttggagt acccagcctc ccgtcgcgcc  60
tcccccaccc catccgcatc caggtacagg gccgaattag                        100

SEQ ID NO: 378          moltype = DNA  length = 100
FEATURE                 Location/Qualifiers
```

```
source                  1..100
                        mol_type = genomic DNA
                        organism = Homo sapiens
SEQUENCE: 378
gttttgctct ccgcagacct caatcccctt cctgtcactg aaggtggcct gagatgaatg  60
atccacttaa gatgttttgg aagggcagag actctcattt                        100

SEQ ID NO: 379          moltype = DNA  length = 100
FEATURE                 Location/Qualifiers
source                  1..100
                        mol_type = genomic DNA
                        organism = Homo sapiens
SEQUENCE: 379
ggattaattc tggaggccac ctgtggttgt gggccagcag gtcaggaaga aagcaacagg  60
gacctagatt tgggcattgg acagggggaa tgtctccaga                        100

SEQ ID NO: 380          moltype = DNA  length = 100
FEATURE                 Location/Qualifiers
source                  1..100
                        mol_type = genomic DNA
                        organism = Homo sapiens
SEQUENCE: 380
ctctccagtt cctatattct aatacccctc cgccgccaaa taaaatttgg cgtctggcca  60
cagctctttt agtgggtatc tgggtggctc ttaaaagagc                        100

SEQ ID NO: 381          moltype = DNA  length = 100
FEATURE                 Location/Qualifiers
source                  1..100
                        mol_type = genomic DNA
                        organism = Homo sapiens
SEQUENCE: 381
ctttggggtt aggtgttaag acgcttactt ggaatgttta cttggagctg gtgtacttgg  60
tgacggcctt ggtgccctcc gacacggcgt gcttggccag                        100

SEQ ID NO: 382          moltype = DNA  length = 100
FEATURE                 Location/Qualifiers
source                  1..100
                        mol_type = genomic DNA
                        organism = Homo sapiens
SEQUENCE: 382
ctccggcccc tgccgagaag actcccgtga agaagaaggc ccgcaagtct gcaggtgcgg  60
ccaagcgcaa agcgtctggg cccccggtgt ccgagctcat                        100

SEQ ID NO: 383          moltype = DNA  length = 100
FEATURE                 Location/Qualifiers
source                  1..100
                        mol_type = genomic DNA
                        organism = Homo sapiens
SEQUENCE: 383
tactaaagct gttgccgcct ccaaggagcg cagcggcgta tctttggccg ctctcaagaa  60
agcgctggca gccgctggct atgacgtgga gaagaacaac                        100

SEQ ID NO: 384          moltype = DNA  length = 100
FEATURE                 Location/Qualifiers
source                  1..100
                        mol_type = genomic DNA
                        organism = Homo sapiens
SEQUENCE: 384
agccgcatca agctgggtct caagagcctg gtgagcaagg gcaccctggt gcagaccaag  60
ggcaccggcg cgtcgggttc cttcaaactc aacaagaagg                        100

SEQ ID NO: 385          moltype = DNA  length = 100
FEATURE                 Location/Qualifiers
source                  1..100
                        mol_type = genomic DNA
                        organism = Homo sapiens
SEQUENCE: 385
cggcctctgg ggaagccaag cctaaggcta aaaaggcagg cgcggccaag gccaagaagc  60
cagcaggagc ggcgaagaag cccaagaagg cgacgggggc                        100

SEQ ID NO: 386          moltype = DNA  length = 100
FEATURE                 Location/Qualifiers
source                  1..100
                        mol_type = genomic DNA
                        organism = Homo sapiens
SEQUENCE: 386
ggccaccccc aagaagagcg ccaagaagac cccaaagaag gcgaagaagc cggctgcagc  60
tgctggagcc aaaaaagcga aaagcccgaa aaaggcgaaa                        100
```

```
SEQ ID NO: 387         moltype = DNA  length = 100
FEATURE                Location/Qualifiers
source                 1..100
                       mol_type = genomic DNA
                       organism = Homo sapiens
SEQUENCE: 387
gcagccaagc caaaaaaggc gcccaagagc ccagcgaagg ccaaagcagt taaacccaag  60
gcggctaaac caaagaccgc caagcccaag gcagccaagc                        100

SEQ ID NO: 388         moltype = DNA  length = 100
FEATURE                Location/Qualifiers
source                 1..100
                       mol_type = genomic DNA
                       organism = Homo sapiens
SEQUENCE: 388
caaagaaggc ggcagccaag aaaaagtaga aagttccttt ggccaactgc ttagaagccc  60
aacacaaccc aaaggctctt ttcagagcca cccaccgctc                        100

SEQ ID NO: 389         moltype = DNA  length = 100
FEATURE                Location/Qualifiers
source                 1..100
                       mol_type = genomic DNA
                       organism = Homo sapiens
SEQUENCE: 389
tcagtaaaag agctgttgca ctattagggg gcgtggctcg ggaaaacgct gctaagcagg  60
ggcgggtctc ccgggaacaa agtcggggag aggagtggga                        100

SEQ ID NO: 390         moltype = DNA  length = 100
FEATURE                Location/Qualifiers
source                 1..100
                       mol_type = genomic DNA
                       organism = Homo sapiens
SEQUENCE: 390
ctccttagcc agactcgatt acaagcactg catgcattac tcagtgtgat aagatcatga  60
taatcccttt aaaaagatcg cccgaattta agcctggatt                        100

SEQ ID NO: 391         moltype = DNA  length = 100
FEATURE                Location/Qualifiers
source                 1..100
                       mol_type = genomic DNA
                       organism = Homo sapiens
SEQUENCE: 391
aggaacacgt gtttacagct ctaatatcga taatttaagt ggctcttaaa agagcctttg  60
gggttgggct ttaagacgct tacttggcaa gtttacttag                        100

SEQ ID NO: 392         moltype = DNA  length = 100
FEATURE                Location/Qualifiers
source                 1..100
                       mol_type = genomic DNA
                       organism = Homo sapiens
SEQUENCE: 392
cgctggtgta cttggtgacg gccttggtgc cctcggacac ggcgtgcttg gccaactccc  60
cgggcagcag caggcgcacg gccgtctgga tctccctgga                        100

SEQ ID NO: 393         moltype = DNA  length = 100
FEATURE                Location/Qualifiers
source                 1..100
                       mol_type = genomic DNA
                       organism = Homo sapiens
SEQUENCE: 393
ccccggctcc ggctcctgcg gcagctcctc tgggcaccgt ccctgcgccg acatcctgga  60
ggttgggatg ctcttgtcca aaatcaactc gcttgcccac                        100

SEQ ID NO: 394         moltype = DNA  length = 100
FEATURE                Location/Qualifiers
source                 1..100
                       mol_type = genomic DNA
                       organism = Homo sapiens
SEQUENCE: 394
ctgcgcgccg cgccctgcaa cgacctgcac gccaccaagc tggcgcccgg tgagagcacc  60
ccccgcctcc ggcccgggga tgcggggcgg cggcgggatc                        100

SEQ ID NO: 395         moltype = DNA  length = 100
FEATURE                Location/Qualifiers
source                 1..100
                       mol_type = genomic DNA
                       organism = Homo sapiens
SEQUENCE: 395
tcctgggtgg ggagctggcg gctcgcgggc cggcactgag tccccgtgct tccccctttc  60
```

```
ctaggcaagg agaaggagcc cctggagtcg cagtaccagg                        100

SEQ ID NO: 396         moltype = DNA  length = 100
FEATURE                Location/Qualifiers
source                 1..100
                       mol_type = genomic DNA
                       organism = Homo sapiens
SEQUENCE: 396
tgggcccgct actgggcagc ggcggcttcg gctcggtcta ctcaggcatc cgcgtctccg  60
acaacttgcc ggtgagtggg cgccccgcgg tggggagggc                        100

SEQ ID NO: 397         moltype = DNA  length = 100
FEATURE                Location/Qualifiers
source                 1..100
                       mol_type = genomic DNA
                       organism = Homo sapiens
SEQUENCE: 397
gcgccgggcg gggggcgcac gggcgtgctt tagcccggac gagggaacct gacggagacc  60
ctgggcttcc aggtggccat caaacacgtg gagaaggacc                        100

SEQ ID NO: 398         moltype = DNA  length = 100
FEATURE                Location/Qualifiers
source                 1..100
                       mol_type = genomic DNA
                       organism = Homo sapiens
SEQUENCE: 398
ggatttccga ctggggagag ctggtgagtg ccctgcagga gcgacccccca ggatgagtgg  60
gtggggtgag gggcgccccc gactcccgcc ctaacgcggc                        100

SEQ ID NO: 399         moltype = DNA  length = 100
FEATURE                Location/Qualifiers
source                 1..100
                       mol_type = genomic DNA
                       organism = Homo sapiens
SEQUENCE: 399
cccctcgccc ctgcagccta atggcactcg agtgcccatg gaagtggtcc tgctgaagaa  60
ggtgagctcg ggtttctccg gcgtcattag gctcctggac                        100

SEQ ID NO: 400         moltype = DNA  length = 100
FEATURE                Location/Qualifiers
source                 1..100
                       mol_type = genomic DNA
                       organism = Homo sapiens
SEQUENCE: 400
tggttcgaga ggcccgacag tttcgtcctg atcctggaga ggcccgagcc ggtgcaagat  60
ctcttcgact tcatcacgga aaggggagcc ctgcaagagg                        100

SEQ ID NO: 401         moltype = DNA  length = 100
FEATURE                Location/Qualifiers
source                 1..100
                       mol_type = genomic DNA
                       organism = Homo sapiens
SEQUENCE: 401
agctggcccg cagcttcttc tggcaggtgc tggaggccgt gcggcactgc cacaactgcg  60
gggtgctcca ccgcgacatc aaggacgaaa acatccttat                        100

SEQ ID NO: 402         moltype = DNA  length = 100
FEATURE                Location/Qualifiers
source                 1..100
                       mol_type = genomic DNA
                       organism = Homo sapiens
SEQUENCE: 402
cgacctcaat cgcggcgagc tcaagctcat cgacttcggg tcgggggcgc tgctcaagga  60
caccgtctac acggacttcg atggtgagcc aggcccggga                        100

SEQ ID NO: 403         moltype = DNA  length = 100
FEATURE                Location/Qualifiers
source                 1..100
                       mol_type = genomic DNA
                       organism = Homo sapiens
SEQUENCE: 403
gggagctgcc caggtgactc ggcccggccc ggcccagtcc ggaggcctcg gccagtctcc  60
cgcgccagcc ttttgtaaag gtcattgggc cgcctggctc                        100

SEQ ID NO: 404         moltype = DNA  length = 100
FEATURE                Location/Qualifiers
source                 1..100
                       mol_type = genomic DNA
                       organism = Homo sapiens
```

```
SEQUENCE: 404
gatgctagcc ggggtgggac gcaggagagc ctcccagcgt agtaaagccg gggattttca  60
gccagctgaa cctgtaatgt ttctggcatg attttattct                        100

SEQ ID NO: 405         moltype = DNA  length = 100
FEATURE                Location/Qualifiers
source                 1..100
                       mol_type = genomic DNA
                       organism = Homo sapiens
SEQUENCE: 405
tcaagtggaa ttcagttagt tccaggcttt cccgatgaat aagaggttgt gggcaaccgg  60
cggtagccca gatttttcta aagtctgacc cagtttcccc                        100

SEQ ID NO: 406         moltype = DNA  length = 100
FEATURE                Location/Qualifiers
source                 1..100
                       mol_type = genomic DNA
                       organism = Homo sapiens
SEQUENCE: 406
ctctaaacag acaaaagcaa aatatctcat taggcatcat ctccgccaag gttcccacta  60
ggcaggaaag gatttttatc taaagtaatt acccttttta                        100

SEQ ID NO: 407         moltype = DNA  length = 100
FEATURE                Location/Qualifiers
source                 1..100
                       mol_type = genomic DNA
                       organism = Homo sapiens
SEQUENCE: 407
gttaaataca ctcaacagat gaaatttaca gagagtgaga gactgcagca ctagacagcg  60
aaggtgaaaa ccaggaacgc cgcgtctcgc cgcccgcggg                        100

SEQ ID NO: 408         moltype = DNA  length = 100
FEATURE                Location/Qualifiers
source                 1..100
                       mol_type = genomic DNA
                       organism = Homo sapiens
SEQUENCE: 408
cccgccggga gactgcgggt ccgtctcgcg ggtggggcgc cccggtccct ctcgtttcct  60
ggaggccaca ggtcacggcg acggcggtga ccgggagagc                        100

SEQ ID NO: 409         moltype = DNA  length = 100
FEATURE                Location/Qualifiers
source                 1..100
                       mol_type = genomic DNA
                       organism = Homo sapiens
SEQUENCE: 409
cgggtctgac agctgctgcg gctcgcgcgg acgcgcgcct cctgcagccc gccctcccca  60
tgcctgactt attactctct gctcctcctc cctctgctgt                        100

SEQ ID NO: 410         moltype = DNA  length = 100
FEATURE                Location/Qualifiers
source                 1..100
                       mol_type = genomic DNA
                       organism = Homo sapiens
SEQUENCE: 410
tccaaaacac ccttcgacgc cagcaaaata caatgcgcct cggccgccgt aaacagccgg  60
gagggagagc acacattcgg cgcggcgcgg ccgccggctc                        100

SEQ ID NO: 411         moltype = DNA  length = 100
FEATURE                Location/Qualifiers
source                 1..100
                       mol_type = genomic DNA
                       organism = Homo sapiens
SEQUENCE: 411
ggctcccacc cccttcccgt tcctagaaaa tgccataaaa gcgggcaggg cgcggggagg  60
gcggctgcgc gcccggcggc cggggctccc ttcccgcgcc                        100

SEQ ID NO: 412         moltype = DNA  length = 100
FEATURE                Location/Qualifiers
source                 1..100
                       mol_type = genomic DNA
                       organism = Homo sapiens
SEQUENCE: 412
tatgaaacag ccagtgctac gtctccttta taccaaaact ggtagcctga agagctctca  60
ggcttaccta taaacgatgt tcagtgaatg caggtagccc                        100

SEQ ID NO: 413         moltype = DNA  length = 100
FEATURE                Location/Qualifiers
source                 1..100
```

```
                        mol_type = genomic DNA
                        organism = Homo sapiens
SEQUENCE: 413
aaggcactgg ctatttcagc agcatagaaa cgagcccgtg gttccaggaa gcagcgttcc  60
ctctggagat ggtagaacaa ctgcaggaga cagaacaaag                        100

SEQ ID NO: 414          moltype = DNA  length = 100
FEATURE                 Location/Qualifiers
source                  1..100
                        mol_type = genomic DNA
                        organism = Homo sapiens
SEQUENCE: 414
tcattctggg ttgcaaatga atttaattag ttttgacata cacagcaaaa gaacaactgc  60
aggaagtggc cccaagtaat ctattaacta taaacctgac                        100

SEQ ID NO: 415          moltype = DNA  length = 100
FEATURE                 Location/Qualifiers
source                  1..100
                        mol_type = genomic DNA
                        organism = Homo sapiens
SEQUENCE: 415
aggttgaagg aaatgctaat tctggtaaca ttctccccac caaaaatctt tgaaaacttt  60
tttctcaaac taaaacaaag caggctgtgc agagacacta                        100

SEQ ID NO: 416          moltype = DNA  length = 100
FEATURE                 Location/Qualifiers
source                  1..100
                        mol_type = genomic DNA
                        organism = Homo sapiens
SEQUENCE: 416
agagttgact tctatccccc ctgctcacct ctccaccatt aatgtagtct aggacaaagt  60
acaatttgtc agcagtctgg aaagagaagt gaaggcccac                        100

SEQ ID NO: 417          moltype = DNA  length = 100
FEATURE                 Location/Qualifiers
source                  1..100
                        mol_type = genomic DNA
                        organism = Homo sapiens
SEQUENCE: 417
caggaaaggg tgcttcacat tcttcaacag aacattccgc tccgacataa tatgcttctc  60
ctaggaaaat gacgattcag atttagtggc atgtttcaac                        100

SEQ ID NO: 418          moltype = DNA  length = 100
FEATURE                 Location/Qualifiers
source                  1..100
                        mol_type = genomic DNA
                        organism = Homo sapiens
SEQUENCE: 418
gaggacatga aggaagtgta ccaaaagatc ttcagatttg aaattacctt tccaaaactg  60
ccctttccga tcactttcaa gaagtgaaag tcagatggtt                        100

SEQ ID NO: 419          moltype = DNA  length = 100
FEATURE                 Location/Qualifiers
source                  1..100
                        mol_type = genomic DNA
                        organism = Homo sapiens
SEQUENCE: 419
tagcatgagg attggacgac gggccaaggt tgatttgctg agaaggactt ggctagaaaa  60
aaaaaaaaag aatttctttt aataccattg cttcaaagga                        100

SEQ ID NO: 420          moltype = DNA  length = 100
FEATURE                 Location/Qualifiers
source                  1..100
                        mol_type = genomic DNA
                        organism = Homo sapiens
SEQUENCE: 420
aatttctttt aataccattg cttcaaagga agacatctat aacataaacg atgtagaaaa  60
tgttacatct acaaatgact gatgcaaatg accatacatc                        100

SEQ ID NO: 421          moltype = DNA  length = 100
FEATURE                 Location/Qualifiers
source                  1..100
                        mol_type = genomic DNA
                        organism = Homo sapiens
SEQUENCE: 421
aataaaataa tactctgact caatacttaa atatttatat cacttgttat gccataatga  60
agcattcctg ccttgatact aatttctaga aatgctattt                        100

SEQ ID NO: 422          moltype = DNA  length = 100
```

```
FEATURE                Location/Qualifiers
source                 1..100
                       mol_type = genomic DNA
                       organism = Homo sapiens
SEQUENCE: 422
taatccatta atgtaggaat actaactgac tcccttacag ttctccacag atgcacggca  60
catacaaaaa cttactggag gagaagggtt ggcattcata                        100

SEQ ID NO: 423         moltype = DNA  length = 100
FEATURE                Location/Qualifiers
source                 1..100
                       mol_type = genomic DNA
                       organism = Homo sapiens
SEQUENCE: 423
agctcaggct cctgaggttg ggagatcttc aagatggact gaacttcagg gctgcaggga  60
ataaagggca cgatttagaa tccagctcgc cactaggggg                        100

SEQ ID NO: 424         moltype = DNA  length = 100
FEATURE                Location/Qualifiers
source                 1..100
                       mol_type = genomic DNA
                       organism = Homo sapiens
SEQUENCE: 424
cacaccaaca tcaaaagtga gtttctggct ctaccgactt ctacccggat aattcactgt  60
ttaaactgaa aataccccaa tacattagtc agttaaagaa                        100

SEQ ID NO: 425         moltype = DNA  length = 100
FEATURE                Location/Qualifiers
source                 1..100
                       mol_type = genomic DNA
                       organism = Homo sapiens
SEQUENCE: 425
aataataaac cccattaaat acagaaataa ggattgttgc tcatggagaa aggccgtgaa  60
ttcggccaac acgaaccatt tatcttacat ctccagttca                        100

SEQ ID NO: 426         moltype = DNA  length = 100
FEATURE                Location/Qualifiers
source                 1..100
                       mol_type = genomic DNA
                       organism = Homo sapiens
SEQUENCE: 426
agccaaatca gcaaattaac tttaatgttt aaaatgtgtc aaatatatta gaatttaagg  60
agaaatgaga tccccacccc agaagaagtc ttcgccttcc                        100

SEQ ID NO: 427         moltype = DNA  length = 100
FEATURE                Location/Qualifiers
source                 1..100
                       mol_type = genomic DNA
                       organism = Homo sapiens
SEQUENCE: 427
cgataaacgc cgtgatgaga atgtttaccg ctggcaaatt caaactatac tagttatttc  60
ctcaaatccg gtcaaactta ctgtttgcat gcataggagt                        100

SEQ ID NO: 428         moltype = DNA  length = 100
FEATURE                Location/Qualifiers
source                 1..100
                       mol_type = genomic DNA
                       organism = Homo sapiens
SEQUENCE: 428
tattggcaat cttctgaata aagtcgttca gacccatcct cctctgcttc atgaaagctg  60
tggatgaagg aggagaaata aagaaacgtt tagacggctt                        100

SEQ ID NO: 429         moltype = DNA  length = 100
FEATURE                Location/Qualifiers
source                 1..100
                       mol_type = genomic DNA
                       organism = Homo sapiens
SEQUENCE: 429
cataacgtcc ggcgccacac acactaatct gatccgggac tttcaaaaaa tttccacttt  60
gcgtctcctg gagcagaagt cccgcaagat tcctgcactc                        100

SEQ ID NO: 430         moltype = DNA  length = 100
FEATURE                Location/Qualifiers
source                 1..100
                       mol_type = genomic DNA
                       organism = Homo sapiens
SEQUENCE: 430
accgatgaga attgccacca tgcccctcat cctggagtaa gtgagggtgc ccttagcagc  60
ctcagttttc accgtcatca ccaccgcggg gagacagaaa                        100
```

```
SEQ ID NO: 431         moltype = DNA  length = 100
FEATURE                Location/Qualifiers
source                 1..100
                       mol_type = genomic DNA
                       organism = Homo sapiens
SEQUENCE: 431
gacgttagcg ctcaaagacc ggctcggcgt atgctgcgcc aggccgcgcg ctcggcctta  60
taaaaaaggc accgccgcgg gggcggggcc tgcgcgacag                        100

SEQ ID NO: 432         moltype = DNA  length = 100
FEATURE                Location/Qualifiers
source                 1..100
                       mol_type = genomic DNA
                       organism = Homo sapiens
SEQUENCE: 432
agggtgagag gagtcaccag gtaaagatgg gttggaagga cctggcaggc agagcaggga  60
gcaggacccc agtccagggc agcagggaag cgggagtctg                        100

SEQ ID NO: 433         moltype = DNA  length = 100
FEATURE                Location/Qualifiers
source                 1..100
                       mol_type = genomic DNA
                       organism = Homo sapiens
SEQUENCE: 433
ggcagagctg attccaggca gctcagtatt gctggcctgt gcatcctgag acttatccga  60
gtcgcaggtg aagctggtgg gaatcaggca gagtgcagag                        100

SEQ ID NO: 434         moltype = DNA  length = 100
FEATURE                Location/Qualifiers
source                 1..100
                       mol_type = genomic DNA
                       organism = Homo sapiens
SEQUENCE: 434
ctttagctgg ggcagggtta gccaagagcc tgtcatggag ctgctctctg ggcactggga  60
aacataagtc tggaggcttt ggctgcagct gcagataaag                        100

SEQ ID NO: 435         moltype = DNA  length = 100
FEATURE                Location/Qualifiers
source                 1..100
                       mol_type = genomic DNA
                       organism = Homo sapiens
SEQUENCE: 435
atgcaggggc ctctgacgat gggggcctta gtcatctcag aggtggtgca gagggtagaa  60
gcctgactgg ggtcagagat gaggaaggag agggtcagaa                        100

SEQ ID NO: 436         moltype = DNA  length = 100
FEATURE                Location/Qualifiers
source                 1..100
                       mol_type = genomic DNA
                       organism = Homo sapiens
SEQUENCE: 436
acagtgattc taaaccaatt tggttgaggc agaagatact aatggccgag gggaggagag  60
agggagcgta ggctctaaag gggaagcttg ttaggaatga                        100

SEQ ID NO: 437         moltype = DNA  length = 100
FEATURE                Location/Qualifiers
source                 1..100
                       mol_type = genomic DNA
                       organism = Homo sapiens
SEQUENCE: 437
agacagaggc gcaggcacag ccctttcatc agctgaccag gagtgctcgg cccggcctgc  60
caggaacctc ttatcaaact ccaccggctg cctgcatcta                        100

SEQ ID NO: 438         moltype = DNA  length = 100
FEATURE                Location/Qualifiers
source                 1..100
                       mol_type = genomic DNA
                       organism = Homo sapiens
SEQUENCE: 438
caattcaagt ccatggctaa ccttctgtta gagacagaaa ttctgctgca gccagcaagt  60
ttgctggtgt acagggcacc gcttcatggg cctagtagga                        100

SEQ ID NO: 439         moltype = DNA  length = 100
FEATURE                Location/Qualifiers
source                 1..100
                       mol_type = genomic DNA
                       organism = Homo sapiens
SEQUENCE: 439
```

```
agcgaagctg aaaggcaact tccgaaagcc agtctcctct cccaaacgcc ctttaatatc  60
tccccagttg gatctggggc gcctgtggtt tcggaccctt                        100

SEQ ID NO: 440         moltype = DNA  length = 100
FEATURE                Location/Qualifiers
source                 1..100
                       mol_type = genomic DNA
                       organism = Homo sapiens
SEQUENCE: 440
aggagctctg agaactggtg tgtgtggtcg gaagccatct gagtctccct gtgatttgga  60
ctttttaaga aacttctaag ttgtattact ataccettta                        100

SEQ ID NO: 441         moltype = DNA  length = 100
FEATURE                Location/Qualifiers
source                 1..100
                       mol_type = genomic DNA
                       organism = Homo sapiens
SEQUENCE: 441
ttcccttgtc atatgacttc catcctcagc actacaatat tatcattaat gtttaaatca  60
ttgtcaagtc tgtgattgcc ttagagattt attaagaata                        100

SEQ ID NO: 442         moltype = DNA  length = 100
FEATURE                Location/Qualifiers
source                 1..100
                       mol_type = genomic DNA
                       organism = Homo sapiens
SEQUENCE: 442
acatgctagg attaggaaag tttaactttt taccatcctt aaaattagat ttttgaaaac  60
tgtcttatcc ccattaaaga aaaaaataaa aaggatgaat                        100

SEQ ID NO: 443         moltype = DNA  length = 100
FEATURE                Location/Qualifiers
source                 1..100
                       mol_type = genomic DNA
                       organism = Homo sapiens
SEQUENCE: 443
tatacatacc tgcacatata tacagcatat gtatatgtgt ctgtattata tgtattaaat  60
gaaagattat ccacattttg ttctttagga tcttcagcag                        100

SEQ ID NO: 444         moltype = DNA  length = 100
FEATURE                Location/Qualifiers
source                 1..100
                       mol_type = genomic DNA
                       organism = Homo sapiens
SEQUENCE: 444
ctctcttccc atcacaatag aaaggcctga gctaacattt ccatttctgc aaaaggcaga  60
ttttgttcaa ttaaaaatta taatgcctta aatttccaca                        100

SEQ ID NO: 445         moltype = DNA  length = 100
FEATURE                Location/Qualifiers
source                 1..100
                       mol_type = genomic DNA
                       organism = Homo sapiens
SEQUENCE: 445
gacatttaag agacttcgtt ttcactgtga taaacaggtt tgatttggac ttataacttt  60
tttctaaaat tatcaaatta ataacgacta taatgaaata                        100

SEQ ID NO: 446         moltype = DNA  length = 100
FEATURE                Location/Qualifiers
source                 1..100
                       mol_type = genomic DNA
                       organism = Homo sapiens
SEQUENCE: 446
gaggcaaata ttttagagga ttcattcctt ggggtaacat ttgttctata atttatagtc  60
tcataatgtt gagagattaa agcatttaaa taacattgtc                        100

SEQ ID NO: 447         moltype = DNA  length = 100
FEATURE                Location/Qualifiers
source                 1..100
                       mol_type = genomic DNA
                       organism = Homo sapiens
SEQUENCE: 447
aactaacttt cagcttacct ttcttaagga aaaaaaacaa aaaaatgtta aaaatagaca  60
tgtatttttc aaacatacaa ttcatgtttt tatgtcatta                        100

SEQ ID NO: 448         moltype = DNA  length = 100
FEATURE                Location/Qualifiers
source                 1..100
                       mol_type = genomic DNA
```

```
                         organism = Homo sapiens
SEQUENCE: 448
aagagatgtg agggacttat aaataatatt aagataacag gaattaaagt ctcggtgtgt  60
gaaaatactg tatatctagg atgcacataa aaactgccct                        100

SEQ ID NO: 449           moltype = DNA  length = 100
FEATURE                  Location/Qualifiers
source                   1..100
                         mol_type = genomic DNA
                         organism = Homo sapiens
SEQUENCE: 449
tacagatctt gcagggaaaa gtacctgact atactgtata agacttctgc tgtaccattt  60
aatcatacca aaaaaaatgg aatcaacaca caaatagatt                        100

SEQ ID NO: 450           moltype = DNA  length = 100
FEATURE                  Location/Qualifiers
source                   1..100
                         mol_type = genomic DNA
                         organism = Homo sapiens
SEQUENCE: 450
tcttttccac tgttctcaat ttaaaaataa ttggagaaat gtgtgctttg tttagaagag  60
taaaggaaaa cattcattca atagtaccat gcagaatgat                        100

SEQ ID NO: 451           moltype = DNA  length = 100
FEATURE                  Location/Qualifiers
source                   1..100
                         mol_type = genomic DNA
                         organism = Homo sapiens
SEQUENCE: 451
cagaaaaata gaaagattat catcggattt gggaatcaaa gacagctcag caaaatacta  60
ggacatggct catataagat ggaataagcc tggaaataca                        100

SEQ ID NO: 452           moltype = DNA  length = 100
FEATURE                  Location/Qualifiers
source                   1..100
                         mol_type = genomic DNA
                         organism = Homo sapiens
SEQUENCE: 452
ctttagggga tagctctgca aggggagagg ttcgggactg tggcgcgcac tgcgcgctgc  60
gccaggtttc cgcaccaaga cccctttaac tcaagactgc                        100

SEQ ID NO: 453           moltype = DNA  length = 100
FEATURE                  Location/Qualifiers
source                   1..100
                         mol_type = genomic DNA
                         organism = Homo sapiens
SEQUENCE: 453
ctcccgcttt gtgtgccccg ctccagcagc ctcccgcgac gatgcccctc aacgttagct  60
tcaccaacag gaactatgac ctcgactacg actcggtgca                        100

SEQ ID NO: 454           moltype = DNA  length = 100
FEATURE                  Location/Qualifiers
source                   1..100
                         mol_type = genomic DNA
                         organism = Homo sapiens
SEQUENCE: 454
gccgtatttc tactgcgacg aggaggagaa cttctaccag cagcagcagc agagcgagct  60
gcagcccccg gcgcccagcg aggatatctg gaagaaattc                        100

SEQ ID NO: 455           moltype = DNA  length = 100
FEATURE                  Location/Qualifiers
source                   1..100
                         mol_type = genomic DNA
                         organism = Homo sapiens
SEQUENCE: 455
gagctgctgc ccaccccgcc cctgtcccct agccgccgct ccgggctctg ctcgccctcc  60
tacgttgcgg tcacaccctt ctcccttcgg ggagacaacg                        100

SEQ ID NO: 456           moltype = DNA  length = 100
FEATURE                  Location/Qualifiers
source                   1..100
                         mol_type = genomic DNA
                         organism = Homo sapiens
SEQUENCE: 456
acggcggtgg cgggagcttc tccacggccg accagctgga gatggtgacc gagctgctgg  60
gaggagacat ggtgaaccag agtttcatct gcgacccgga                        100

SEQ ID NO: 457           moltype = DNA  length = 100
FEATURE                  Location/Qualifiers
```

```
source                  1..100
                        mol_type = genomic DNA
                        organism = Homo sapiens
SEQUENCE: 457
cgacgagacc ttcatcaaaa acatcatcat ccaggactgt atgtggagcg gcttctcggc  60
cgccgccaag ctcgtctcag agaagctggc ctcctaccag                        100

SEQ ID NO: 458          moltype = DNA  length = 100
FEATURE                 Location/Qualifiers
source                  1..100
                        mol_type = genomic DNA
                        organism = Homo sapiens
SEQUENCE: 458
gctgcgcgca aagacagcgg cagcccgaac cccgcccgcg gccacagcgt ctgctccacc  60
tccagcttgt acctgcagga tctgagcgcc gccgcctcag                        100

SEQ ID NO: 459          moltype = DNA  length = 100
FEATURE                 Location/Qualifiers
source                  1..100
                        mol_type = genomic DNA
                        organism = Homo sapiens
SEQUENCE: 459
agtgcatcga cccctcggtg gtcttcccct accctctcaa cgacagcagc tcgcccaagt  60
cctgcgcctc gcaagactcc agcgccttct ctccgtcctc                        100

SEQ ID NO: 460          moltype = DNA  length = 100
FEATURE                 Location/Qualifiers
source                  1..100
                        mol_type = genomic DNA
                        organism = Homo sapiens
SEQUENCE: 460
ggattctctg ctctcctcga cggagtcctc cccgcagggc agccccgagc ccctggtgct  60
ccatgaggag acaccgccca ccaccagcag cgactctggt                        100

SEQ ID NO: 461          moltype = DNA  length = 100
FEATURE                 Location/Qualifiers
source                  1..100
                        mol_type = genomic DNA
                        organism = Homo sapiens
SEQUENCE: 461
gctccccatc tgtccccaca gttgctcctt ggctgagcca agggcttgct cacctctcag  60
agcattgccc taactggttt gttttgggct tacattgcaa                        100

SEQ ID NO: 462          moltype = DNA  length = 100
FEATURE                 Location/Qualifiers
source                  1..100
                        mol_type = genomic DNA
                        organism = Homo sapiens
SEQUENCE: 462
gatcaggtcc tccccagagc caggctggag tccgaggcag aaaaggctgt ggagggcact  60
ggggtcacca cagactggaa accggttggg cgcaggcccc                        100

SEQ ID NO: 463          moltype = DNA  length = 100
FEATURE                 Location/Qualifiers
source                  1..100
                        mol_type = genomic DNA
                        organism = Homo sapiens
SEQUENCE: 463
aaaccttgag gaatcgtttg ggctgggacc agaacagggg gctcctctgc acagagctcc  60
ccaccgcttt ggtggattac ttcagactca gaaaattgac                        100

SEQ ID NO: 464          moltype = DNA  length = 100
FEATURE                 Location/Qualifiers
source                  1..100
                        mol_type = genomic DNA
                        organism = Homo sapiens
SEQUENCE: 464
acaaagagaa actgacctgc ccgcagccag ccctggctgc ctacacaagc tttcccctgc  60
ttgccaggcc actcagcact gcgtggcaga cacggacatg                        100

SEQ ID NO: 465          moltype = DNA  length = 100
FEATURE                 Location/Qualifiers
source                  1..100
                        mol_type = genomic DNA
                        organism = Homo sapiens
SEQUENCE: 465
ctcgccccgg gaagctcacc ttcactccag ccgggtctct gctgcctttg ttaaataggg  60
gacctgcggc taggaaagct ggatcccagg ctgttgggat                        100
```

```
SEQ ID NO: 466         moltype = DNA  length = 100
FEATURE                Location/Qualifiers
source                 1..100
                       mol_type = genomic DNA
                       organism = Homo sapiens
SEQUENCE: 466
ggggggggagc ggggtgggag gaccaggcat ggggacggct cctagcccgg gagcaactcc  60
ctgacctgaa gcccgcagag accccgagcg gcacccgagc                        100

SEQ ID NO: 467         moltype = DNA  length = 100
FEATURE                Location/Qualifiers
source                 1..100
                       mol_type = genomic DNA
                       organism = Homo sapiens
SEQUENCE: 467
cgaggctgcc gaagcctgtc accttcctcc agcctggctc tgcagcaaac agaaaggaaa  60
cgcgattcgt tccacttgga atttccttga aatctccgaa                        100

SEQ ID NO: 468         moltype = DNA  length = 100
FEATURE                Location/Qualifiers
source                 1..100
                       mol_type = genomic DNA
                       organism = Homo sapiens
SEQUENCE: 468
tctaatccgg cgttaactca ccgtgagagg agcgctcatc tcacaggagg ctgtggtaat  60
gggtgaattg gcaggatccc tgcgggccag gcagccaggc                        100

SEQ ID NO: 469         moltype = DNA  length = 100
FEATURE                Location/Qualifiers
source                 1..100
                       mol_type = genomic DNA
                       organism = Homo sapiens
SEQUENCE: 469
ttttcgtttc ttatcctctt tttttaaagg ggagaagcca tgagaaaagg cgtcctgcag  60
agaaggaccc aatggggtct ttaagggtct ctgtatgaac                        100

SEQ ID NO: 470         moltype = DNA  length = 100
FEATURE                Location/Qualifiers
source                 1..100
                       mol_type = genomic DNA
                       organism = Homo sapiens
SEQUENCE: 470
tggccggctc ctaagcagaa gctgaactca gaaaccgcta cttccttgat ttttcaaagc  60
cccctcctca actccaggac gcctttggag ccctagcccc                        100

SEQ ID NO: 471         moltype = DNA  length = 100
FEATURE                Location/Qualifiers
source                 1..100
                       mol_type = genomic DNA
                       organism = Homo sapiens
SEQUENCE: 471
tgtcgccgcc ggagccttga aaggctgcag ctcgctgccc aagctacgcg ttgccggagg  60
cgggattccc aggtgcctca gcccgggcgg ccaagtgcgt                        100

SEQ ID NO: 472         moltype = DNA  length = 100
FEATURE                Location/Qualifiers
source                 1..100
                       mol_type = genomic DNA
                       organism = Homo sapiens
SEQUENCE: 472
tgtttcaggt cccctgcctg ggatccctgc actttgcaaa gttagctgcg cggctgcaga  60
ggtccgagat ccttccggcc ttagtacctg acccacggtc                        100

SEQ ID NO: 473         moltype = DNA  length = 100
FEATURE                Location/Qualifiers
source                 1..100
                       mol_type = genomic DNA
                       organism = Homo sapiens
SEQUENCE: 473
cggcaccccc aacccggtcc cggcgggaga gtgagagaag cgagctcgcc gcctacttac  60
tatgcatgga tgcaaacggg tcgtgcttac agtgtatttc                        100

SEQ ID NO: 474         moltype = DNA  length = 100
FEATURE                Location/Qualifiers
source                 1..100
                       mol_type = genomic DNA
                       organism = Homo sapiens
SEQUENCE: 474
catcggggcg ctccagactg caggccggcc cacgccgccg cctcccggcg ccaaggggct  60
```

```
gcccagggcg gatagggagc ctcgccacca ggccaggcac                         100

SEQ ID NO: 475          moltype = DNA  length = 100
FEATURE                 Location/Qualifiers
source                  1..100
                        mol_type = genomic DNA
                        organism = Homo sapiens
SEQUENCE: 475
tgtgcgagct gggctcagaa aacactgctg gagcttcggg gtctctctca gagcctccct  60
gctggagacc gcccggagct gcgcggagag gcgggaaatg                         100

SEQ ID NO: 476          moltype = DNA  length = 100
FEATURE                 Location/Qualifiers
source                  1..100
                        mol_type = genomic DNA
                        organism = Homo sapiens
SEQUENCE: 476
gtgctagcgc acccgggcta ggagcgggtg cccaactccg gctggcttcc ctccctggct  60
ggctcaagca gcagctccgg gcccagcccg gggtagctgc                         100

SEQ ID NO: 477          moltype = DNA  length = 100
FEATURE                 Location/Qualifiers
source                  1..100
                        mol_type = genomic DNA
                        organism = Homo sapiens
SEQUENCE: 477
ggccaaggcg cccgcggctt cgggggcata gcgtaggggc ccgcctccgg gacagccagc  60
agcccccggc cccaggaagg agcagctttg aggaggccgc                         100

SEQ ID NO: 478          moltype = DNA  length = 100
FEATURE                 Location/Qualifiers
source                  1..100
                        mol_type = genomic DNA
                        organism = Homo sapiens
SEQUENCE: 478
cggaacaatc ggcccttgac ttcactcagg gggcggagag acccgggggc tgccaggctg  60
gttccgcggc ctcgatgctt ctgaggtccc tcctcgaccc                         100

SEQ ID NO: 479          moltype = DNA  length = 100
FEATURE                 Location/Qualifiers
source                  1..100
                        mol_type = genomic DNA
                        organism = Homo sapiens
SEQUENCE: 479
cacacaggca aacaactttt ggacacaaac tcatatattt ttacatcttt taaaaataca  60
tatactgtaa tgaacacact gagtccctta tataaacaca                         100

SEQ ID NO: 480          moltype = DNA  length = 100
FEATURE                 Location/Qualifiers
source                  1..100
                        mol_type = genomic DNA
                        organism = Homo sapiens
SEQUENCE: 480
caggccctaa cttgcagacc cccggaagga cgccagcgtg aacattcaga aacagagaaa  60
aacacagaca aactcacaga tatttggact gatgcagaag                         100

SEQ ID NO: 481          moltype = DNA  length = 100
FEATURE                 Location/Qualifiers
source                  1..100
                        mol_type = genomic DNA
                        organism = Homo sapiens
SEQUENCE: 481
acagtttgaa gtgtgagcct gaacatgttt gatctaaggt ctggaggaag atgtgaagca  60
aatctgacct aaaaaaaatt ataggaaaaa agcaaattgt                         100

SEQ ID NO: 482          moltype = DNA  length = 100
FEATURE                 Location/Qualifiers
source                  1..100
                        mol_type = genomic DNA
                        organism = Homo sapiens
SEQUENCE: 482
tctggatttg tttcaccaag gaacaagtaa gcagagaacc agacactgga gaaaaaaagg  60
agtcaggaag tagacaagga aatgttaaaa gaaataatag                         100

SEQ ID NO: 483          moltype = DNA  length = 100
FEATURE                 Location/Qualifiers
source                  1..100
                        mol_type = genomic DNA
                        organism = Homo sapiens
```

```
SEQUENCE: 483
gataactgaa agaatgtagc ttccagattg ctagctatca gcagatagat agaaactttt  60
atacagcctt taaatcttcc ctagaaacct ttttaaaagt                        100

SEQ ID NO: 484         moltype = DNA  length = 100
FEATURE                Location/Qualifiers
source                 1..100
                       mol_type = genomic DNA
                       organism = Homo sapiens
SEQUENCE: 484
caagggcctg ccaggatgag aacgggcaaa cctggccaag gtgaccccat tagggactac  60
cctcctaggg acagcactca gggccgttcc caatcacccc                        100

SEQ ID NO: 485         moltype = DNA  length = 100
FEATURE                Location/Qualifiers
source                 1..100
                       mol_type = genomic DNA
                       organism = Homo sapiens
SEQUENCE: 485
ggatttcctg tcctgctcgt ctcctgccac acctcctttt gatctacccc caagacaccc  60
ctaccttttt attctgtgaa aatttactca tgctgtgggc                        100

SEQ ID NO: 486         moltype = DNA  length = 100
FEATURE                Location/Qualifiers
source                 1..100
                       mol_type = genomic DNA
                       organism = Homo sapiens
SEQUENCE: 486
cctgctggaa atgccctcct actgtttccc caaaccccgt cagaaattcc acggggaaac  60
tcccttccct tctgctgcag gcaccgtcac tgtgtctctc                        100

SEQ ID NO: 487         moltype = DNA  length = 100
FEATURE                Location/Qualifiers
source                 1..100
                       mol_type = genomic DNA
                       organism = Homo sapiens
SEQUENCE: 487
agctctgccc cccagcctct gagtaccacc ttatcctagc ccttagctac tggcttgtca  60
ttgtctcttt acgttctcag cctcccacag aagcctggga                        100

SEQ ID NO: 488         moltype = DNA  length = 100
FEATURE                Location/Qualifiers
source                 1..100
                       mol_type = genomic DNA
                       organism = Homo sapiens
SEQUENCE: 488
aggcacactc gcccctggtc tccaaggctc tgggtcctca gactggctga gtactgggga  60
ccaaggtcac ccaagaagcc ctgagtggcc ctcttgaggg                        100

SEQ ID NO: 489         moltype = DNA  length = 100
FEATURE                Location/Qualifiers
source                 1..100
                       mol_type = genomic DNA
                       organism = Homo sapiens
SEQUENCE: 489
ttagcagagc ttctctctgt ccaagacagg tcaggctctc tcccctggcc ccagctccac  60
cgtcactcag aggagtggcc taaacaaacg ctgcaggtga                        100

SEQ ID NO: 490         moltype = DNA  length = 100
FEATURE                Location/Qualifiers
source                 1..100
                       mol_type = genomic DNA
                       organism = Homo sapiens
SEQUENCE: 490
ggctcccgag cccctgacat ggatgtttat ggaagaggac tcttggcatc agcacctggg  60
caaggtgggt agaggcagga gtgggcaaat gggaaagtct                        100

SEQ ID NO: 491         moltype = DNA  length = 100
FEATURE                Location/Qualifiers
source                 1..100
                       mol_type = genomic DNA
                       organism = Homo sapiens
SEQUENCE: 491
ggagagccgt ttgagattca ccaggtgaat gaaccccggt ttttttctgg gtaacaggtc  60
gaatgtgaat tacttatttt cacaagctct tgacatgttc                        100

SEQ ID NO: 492         moltype = DNA  length = 100
FEATURE                Location/Qualifiers
source                 1..100
```

```
                        mol_type = genomic DNA
                        organism = Homo sapiens
SEQUENCE: 492
cgtcaaattg ctgttcccca aagagtggac tctggtgaca tataagtgtg tgggaccatt  60
gcatcttacc ccagagatcc actcctgatc tggcattatt                        100

SEQ ID NO: 493          moltype = DNA  length = 100
FEATURE                 Location/Qualifiers
source                  1..100
                        mol_type = genomic DNA
                        organism = Homo sapiens
SEQUENCE: 493
caaaatctgc tgaattcaaa acgatcctgt acttcctgct caccaggtct gaaaagaaaa  60
aagaaaaaag aagaaggaaa gactacacct gacaaaagac                        100

SEQ ID NO: 494          moltype = DNA  length = 100
FEATURE                 Location/Qualifiers
source                  1..100
                        mol_type = genomic DNA
                        organism = Homo sapiens
SEQUENCE: 494
ttcacggttt ctctttagtt ttatctgaaa tacatttgta agcttagggt gcaatttgga  60
ttaaaacagt tttctttagt gtcaataatg gcctttacta                        100

SEQ ID NO: 495          moltype = DNA  length = 100
FEATURE                 Location/Qualifiers
source                  1..100
                        mol_type = genomic DNA
                        organism = Homo sapiens
SEQUENCE: 495
gagtgaatgg atatttttcc attctggatt atcgtttaat cgaaactttg tttcctgtgg  60
aaatttttct ggtttaagtt atttgatttg ggagataaat                        100

SEQ ID NO: 496          moltype = DNA  length = 100
FEATURE                 Location/Qualifiers
source                  1..100
                        mol_type = genomic DNA
                        organism = Homo sapiens
SEQUENCE: 496
catgtaactt aataaacttt ggcatcctgg ttaactgaaa ttgcttcatt caatatttga  60
agactgaaat ctgtattgtt gcctgtacct aaattatggg                        100

SEQ ID NO: 497          moltype = DNA  length = 100
FEATURE                 Location/Qualifiers
source                  1..100
                        mol_type = genomic DNA
                        organism = Homo sapiens
SEQUENCE: 497
ggacagacag ggagagatga ctgagttaga tgagacgagg gggcgggctg ggggtgcgag  60
aaggaagctt ggcaaggaga ctaggtctag ggggaccaca                        100

SEQ ID NO: 498          moltype = DNA  length = 100
FEATURE                 Location/Qualifiers
source                  1..100
                        mol_type = genomic DNA
                        organism = Homo sapiens
SEQUENCE: 498
gtggggcagg ctgcatggaa aatatccgca gggtccccca ggcagaacag ccacgctcca  60
ggccaggctg tccctactgc ctggtggagg gggaacttga                        100

SEQ ID NO: 499          moltype = DNA  length = 100
FEATURE                 Location/Qualifiers
source                  1..100
                        mol_type = genomic DNA
                        organism = Homo sapiens
SEQUENCE: 499
cctctgggag ggcgccgctc ttgcatagct gagcgagccc gggtgcgctg gtctgtgtgg  60
aaggaggaag gcagggagag gtagaagggg tggaggagtc                        100

SEQ ID NO: 500          moltype = DNA  length = 100
FEATURE                 Location/Qualifiers
source                  1..100
                        mol_type = genomic DNA
                        organism = Homo sapiens
SEQUENCE: 500
ggggcaggcg gagcttgagg aaaccgcaga taagtttttt tctctttgaa agatagagat  60
taatacaact acttaaaaaa tatagtcaat aggttactaa                        100

SEQ ID NO: 501          moltype = DNA  length = 100
```

```
FEATURE                Location/Qualifiers
source                 1..100
                       mol_type = genomic DNA
                       organism = Homo sapiens
SEQUENCE: 501
gatattgctt agcgttaagt ttttaacgta attttaatag cttaagattt taagagaaaa  60
tatgaagact tagaagagta gcatgaggaa ggaaaagata                        100

SEQ ID NO: 502         moltype = DNA  length = 100
FEATURE                Location/Qualifiers
source                 1..100
                       mol_type = genomic DNA
                       organism = Homo sapiens
SEQUENCE: 502
aaaggtttct aaaacatgac ggaggttgag atgaagcttc ttcatggagt aaaaaatgta  60
tttaaaagaa aattgagaga aaggactaca gagccccgaa                        100

SEQ ID NO: 503         moltype = DNA  length = 100
FEATURE                Location/Qualifiers
source                 1..100
                       mol_type = genomic DNA
                       organism = Homo sapiens
SEQUENCE: 503
ttaataccaa tagaagggca atgcttttag attaaaatga aggtgactta aacagcttaa  60
agtttagttt aaaagttgta ggtgattaaa ataatttgaa                        100

SEQ ID NO: 504         moltype = DNA  length = 100
FEATURE                Location/Qualifiers
source                 1..100
                       mol_type = genomic DNA
                       organism = Homo sapiens
SEQUENCE: 504
ttggagaagt atagaagata gaaaaatata aagccaaaaa ttggataaaa tagcactgaa  60
aaaatgagga aattattggt aaccaattta ttttaaaagc                        100

SEQ ID NO: 505         moltype = DNA  length = 100
FEATURE                Location/Qualifiers
source                 1..100
                       mol_type = genomic DNA
                       organism = Homo sapiens
SEQUENCE: 505
ccatcaattt aatttctggt ggtgcagaag ttagaaggta aagcttgaga agatgagggt  60
gtttacgtag accagaacca atttagaaga atacttgaag                        100

SEQ ID NO: 506         moltype = DNA  length = 100
FEATURE                Location/Qualifiers
source                 1..100
                       mol_type = genomic DNA
                       organism = Homo sapiens
SEQUENCE: 506
ctagaagggg aagttggtta aaaatcacat caaaaagcta ctaaaaggac tggtgtaatt  60
taaaaaaaac taaggcagaa ggcttttgga agagttagaa                        100

SEQ ID NO: 507         moltype = DNA  length = 100
FEATURE                Location/Qualifiers
source                 1..100
                       mol_type = genomic DNA
                       organism = Homo sapiens
SEQUENCE: 507
tggtgtaaga gatgtgccag cggctggccg aggggcgctt agggctagag cccggggcgc  60
tgcagaggtt gagagtcagt gggtggggcg cagttatcaa                        100

SEQ ID NO: 508         moltype = DNA  length = 100
FEATURE                Location/Qualifiers
source                 1..100
                       mol_type = genomic DNA
                       organism = Homo sapiens
SEQUENCE: 508
acaccagggc ccaaaagcag gctctagata ggttccaggt gctcaatttc tatttcacgt  60
ttggagtgag ccagtggaat tgtgaagttg tggcattttg                        100

SEQ ID NO: 509         moltype = DNA  length = 100
FEATURE                Location/Qualifiers
source                 1..100
                       mol_type = genomic DNA
                       organism = Homo sapiens
SEQUENCE: 509
attcggttgc caagagttat cactgggcct ttgcaggtgc caaataaatt tcaggacaga  60
gcctaaggca gagctctggc acaggaagga agtaaaacgt                        100
```

```
SEQ ID NO: 510          moltype = DNA  length = 100
FEATURE                 Location/Qualifiers
source                  1..100
                        mol_type = genomic DNA
                        organism = Homo sapiens
SEQUENCE: 510
ttaatgagca aatggacgca tgtttccaag cggtggtagg aagacagcag tttttggttg  60
tcttcctggt gatcagcatg gaaacctagt agtgctctta                        100

SEQ ID NO: 511          moltype = DNA  length = 100
FEATURE                 Location/Qualifiers
source                  1..100
                        mol_type = genomic DNA
                        organism = Homo sapiens
SEQUENCE: 511
ctctgatcaa tacattgtcg aaggcatgta cctgatgcta acgtaacaat aatattaaat  60
attgacttta tttgctatta tttattgcta acattaagta                        100

SEQ ID NO: 512          moltype = DNA  length = 100
FEATURE                 Location/Qualifiers
source                  1..100
                        mol_type = genomic DNA
                        organism = Homo sapiens
SEQUENCE: 512
ctgctacctg ctatgtgcta ggtttgtctc tgaagacttt acatgtattt ttcacgttta  60
attatcataa tcttaagaag caggtaccat aattatctcc                        100

SEQ ID NO: 513          moltype = DNA  length = 100
FEATURE                 Location/Qualifiers
source                  1..100
                        mol_type = genomic DNA
                        organism = Homo sapiens
SEQUENCE: 513
gggaaaaaga atgacgaaag gcaagacagt ggagcaagtg aggacacgct tcaccgagcc  60
agatctccac tcctcccagg gtatccacag ggacaagtca                        100

SEQ ID NO: 514          moltype = DNA  length = 100
FEATURE                 Location/Qualifiers
source                  1..100
                        mol_type = genomic DNA
                        organism = Homo sapiens
SEQUENCE: 514
cacctggcag aaagctaagt cactcagcta gaaacaggcc cagggaattc aacagaaggc  60
tgaagagcca ctgcttatgg aaataaagcc cctcctgtaa                        100

SEQ ID NO: 515          moltype = DNA  length = 100
FEATURE                 Location/Qualifiers
source                  1..100
                        mol_type = genomic DNA
                        organism = Homo sapiens
SEQUENCE: 515
agaactgcat ggcttttccc tcccaacccc aaacccatcc cacatctggc ttttgttgtg  60
tgaatcataa actgcccttt cttcaccaca gtgattcatg                        100

SEQ ID NO: 516          moltype = DNA  length = 100
FEATURE                 Location/Qualifiers
source                  1..100
                        mol_type = genomic DNA
                        organism = Homo sapiens
SEQUENCE: 516
aatcctctcc cactgtggat ctgtaaaatc tagacaggtc agtcagctcc cgccctttaa  60
gagtttattt tccattctgt ggaagaagca gataaggaga                        100

SEQ ID NO: 517          moltype = DNA  length = 100
FEATURE                 Location/Qualifiers
source                  1..100
                        mol_type = genomic DNA
                        organism = Homo sapiens
SEQUENCE: 517
gctgctgtcc ttaggagaca tcctttagag gaagctggaa gacacgggtt caggccctgc  60
atcctcctct gagttgctat gtgactggga acaggatact                        100

SEQ ID NO: 518          moltype = DNA  length = 100
FEATURE                 Location/Qualifiers
source                  1..100
                        mol_type = genomic DNA
                        organism = Homo sapiens
SEQUENCE: 518
```

```
tcacctctcc attctttctc tccttttctc ttagggtcgg aatatggaac tagacaggaa  60
agtactttgg aggttttctt accgtaagga ggctggcatt                        100

SEQ ID NO: 519         moltype = DNA  length = 100
FEATURE                Location/Qualifiers
source                 1..100
                       mol_type = genomic DNA
                       organism = Homo sapiens
SEQUENCE: 519
gggccctcca cccagcctca gttctatggg ggacgtggag tcaggcgatg atgtcctctg  60
aggcagcgtc catctcccct taacattaag gaataaggcc                        100

SEQ ID NO: 520         moltype = DNA  length = 100
FEATURE                Location/Qualifiers
source                 1..100
                       mol_type = genomic DNA
                       organism = Homo sapiens
SEQUENCE: 520
agagggttct cgctcatttg ggaaaataaa aaaagcagga atggggcgct ggaaattcta  60
taagcttttc cccaccactc acaaaaacac agctgtgaaa                        100

SEQ ID NO: 521         moltype = DNA  length = 100
FEATURE                Location/Qualifiers
source                 1..100
                       mol_type = genomic DNA
                       organism = Homo sapiens
SEQUENCE: 521
ataaatacca ccccccaaac caagggtcta gggccaccaa cagtcctcct cctcctcctc  60
ctcctccttc tcctcctcgt cctccagatc cagctgccaa                        100

SEQ ID NO: 522         moltype = DNA  length = 100
FEATURE                Location/Qualifiers
source                 1..100
                       mol_type = genomic DNA
                       organism = Homo sapiens
SEQUENCE: 522
ccttctcctc ctcgtcctcc agatccagct gccaacagca tcccccgctc ctgaagaaat  60
gcaccgccca gaagggaacg gcgaaagggg gaagaagtcc                        100

SEQ ID NO: 523         moltype = DNA  length = 100
FEATURE                Location/Qualifiers
source                 1..100
                       mol_type = genomic DNA
                       organism = Homo sapiens
SEQUENCE: 523
aggggacccc cggcctctgg ccgagagctt gggtgggggc ctcggccgtc gccactcacc  60
cggggagggg aaaagctcca gatcgacttt ttccgtcttg                        100

SEQ ID NO: 524         moltype = DNA  length = 100
FEATURE                Location/Qualifiers
source                 1..100
                       mol_type = genomic DNA
                       organism = Homo sapiens
SEQUENCE: 524
atgatggtga gagtcggctt gagatcgacg gccgccttca tggtgccagg agtgggggac  60
gtacgggatg gtagcaagtt tgcagttact gttgtttttc                        100

SEQ ID NO: 525         moltype = DNA  length = 100
FEATURE                Location/Qualifiers
source                 1..100
                       mol_type = genomic DNA
                       organism = Homo sapiens
SEQUENCE: 525
tttttaatga ggattagtaa cagggggaag gggacggggg aaatccgact ttcttcccaa  60
aaatctcaaa ttcccgctgc ctttctttcc cccgcgcccg                        100

SEQ ID NO: 526         moltype = DNA  length = 100
FEATURE                Location/Qualifiers
source                 1..100
                       mol_type = genomic DNA
                       organism = Homo sapiens
SEQUENCE: 526
gacggtgcgc gcccggcact ccaggggaag ttggcacttt gcggcgaagt gagcgcgctc  60
gggtcccagc ctcgcccgcg ccgcgcccgc tcctcctgcc                        100

SEQ ID NO: 527         moltype = DNA  length = 100
FEATURE                Location/Qualifiers
source                 1..100
                       mol_type = genomic DNA
```

```
                         organism = Homo sapiens
SEQUENCE: 527
gagtgagtag caaatattca tttatgaccc agtttttgtc caccctcagg cggggcatag  60
gactacagac atttttctag attacagcta ggatattatt                        100

SEQ ID NO: 528           moltype = DNA  length = 100
FEATURE                  Location/Qualifiers
source                   1..100
                         mol_type = genomic DNA
                         organism = Homo sapiens
SEQUENCE: 528
cctgagttta tgacaatgaa atggtttgag aaggcaatat tgtggggctt tcagagaggt  60
ttgctgagtg gctaggtgca tgcatgggtt taaccattaa                        100

SEQ ID NO: 529           moltype = DNA  length = 100
FEATURE                  Location/Qualifiers
source                   1..100
                         mol_type = genomic DNA
                         organism = Homo sapiens
SEQUENCE: 529
cttccctttt tgccttttta ttataagctg gttttgtctg tggctgtttt tttcttttaa  60
aattaattaa aacttctcaa aatttctaaa agtaaacaag                        100

SEQ ID NO: 530           moltype = DNA  length = 100
FEATURE                  Location/Qualifiers
source                   1..100
                         mol_type = genomic DNA
                         organism = Homo sapiens
SEQUENCE: 530
gcattctcta catacatcta catacatatt ttgcatttta aaaattggaa tatttgtcat  60
ttttctgtat tacccaaaag tatataaaca gttaccagag                        100

SEQ ID NO: 531           moltype = DNA  length = 100
FEATURE                  Location/Qualifiers
source                   1..100
                         mol_type = genomic DNA
                         organism = Homo sapiens
SEQUENCE: 531
atttatgtga gaagacagtt gtcacattac agatgtcaga ttagctataa aattgtttca  60
ttctagaaac ctaatatggt aaaaataaac cttacttatt                        100

SEQ ID NO: 532           moltype = DNA  length = 100
FEATURE                  Location/Qualifiers
source                   1..100
                         mol_type = genomic DNA
                         organism = Homo sapiens
SEQUENCE: 532
tagccattta tcagacaatt gcttttgttc agccagtttc ttgttctagc agtataaata  60
ttctttttat agaaagttac ttggtttgag aaataaacat                        100

SEQ ID NO: 533           moltype = DNA  length = 100
FEATURE                  Location/Qualifiers
source                   1..100
                         mol_type = genomic DNA
                         organism = Homo sapiens
SEQUENCE: 533
ataagcttaa ggtaggctag agatgaaaaa tttcagactt gtgtttgttt tggatttatt  60
gtacccttc tactattatc tgagaaagct atttaggagt                         100

SEQ ID NO: 534           moltype = DNA  length = 100
FEATURE                  Location/Qualifiers
source                   1..100
                         mol_type = genomic DNA
                         organism = Homo sapiens
SEQUENCE: 534
ttaagaaata gtctagtttt aaaatagcaa tggtttgccg gacacagtgg ctcacccctg  60
taatcccagc attttgggag gccgaggtgg gcagattgct                        100

SEQ ID NO: 535           moltype = DNA  length = 100
FEATURE                  Location/Qualifiers
source                   1..100
                         mol_type = genomic DNA
                         organism = Homo sapiens
SEQUENCE: 535
gaatttgcca gttttcaata ttctgattca ctctgttaag ctagtaaggc agtctttaaa  60
ttacacagtc tgtgtgttat tttactactg ctcagagggc                        100

SEQ ID NO: 536           moltype = DNA  length = 100
FEATURE                  Location/Qualifiers
```

```
source                  1..100
                        mol_type = genomic DNA
                        organism = Homo sapiens
SEQUENCE: 536
attggagaag gttcccttgt gattagaact gttcatgttg agacatgaat cataaggcat  60
tccaaagttg gtttaaggtg tgtctgcttt agacactgtg                        100

SEQ ID NO: 537          moltype = DNA  length = 100
FEATURE                 Location/Qualifiers
source                  1..100
                        mol_type = genomic DNA
                        organism = Homo sapiens
SEQUENCE: 537
cccaggacta ttcttttgct ccagttttgc cttttgatta aatcaatatt atacctgagt  60
tttataaact actaagaatt tgttcccctt cctcactgtg                        100

SEQ ID NO: 538          moltype = DNA  length = 100
FEATURE                 Location/Qualifiers
source                  1..100
                        mol_type = genomic DNA
                        organism = Homo sapiens
SEQUENCE: 538
attttcttgc agtattttct tagaagagtc aactttaata acttacccca aagtgcacgt  60
tcttgatatt atgaacttgc tattgttgtc ttcccagttt                        100

SEQ ID NO: 539          moltype = DNA  length = 100
FEATURE                 Location/Qualifiers
source                  1..100
                        mol_type = genomic DNA
                        organism = Homo sapiens
SEQUENCE: 539
tattgtagtt tttggaaggg ctcgttctgc ccaagagaag ttcctcctta cagctgattc  60
ggctgtctac catttgcacg ttggtgctgt tttgagtgct                        100

SEQ ID NO: 540          moltype = DNA  length = 100
FEATURE                 Location/Qualifiers
source                  1..100
                        mol_type = genomic DNA
                        organism = Homo sapiens
SEQUENCE: 540
acctcctgct ggtgaggctt catacagcac acagatggag ccatcctctc caattctgta  60
ggacacttca taggggtcaa cccagagtgt gagttcactt                        100

SEQ ID NO: 541          moltype = DNA  length = 100
FEATURE                 Location/Qualifiers
source                  1..100
                        mol_type = genomic DNA
                        organism = Homo sapiens
SEQUENCE: 541
gggagaagcc tgaacagctc ctgactgctc agtccaatcc gctgtgctgc ctgtccaatc  60
agaggatcca ttttatggtt gatgcgaata caacggtaac                        100

SEQ ID NO: 542          moltype = DNA  length = 100
FEATURE                 Location/Qualifiers
source                  1..100
                        mol_type = genomic DNA
                        organism = Homo sapiens
SEQUENCE: 542
ccgatcccctt gcatggcttt tctgggaacc agtgatgttt ataatgttct atagaagaaa  60
agaagaacag agaaacaacg cttaggatcg ttagctccca                        100

SEQ ID NO: 543          moltype = DNA  length = 100
FEATURE                 Location/Qualifiers
source                  1..100
                        mol_type = genomic DNA
                        organism = Homo sapiens
SEQUENCE: 543
ctgcggattc ctcctacccc aggctccttt gaggagcgaa aatgaaaact atcaactttt  60
taaaatgtcc aggattgcat ccgttgttgt gcatgtgcgg                        100

SEQ ID NO: 544          moltype = DNA  length = 100
FEATURE                 Location/Qualifiers
source                  1..100
                        mol_type = genomic DNA
                        organism = Homo sapiens
SEQUENCE: 544
ggatggaaaa agcgggcagg gttttagaaa taacacagta gtaccggaca aaacaatctc  60
caggaaccaa ccggttgagc cgccaaaaca ggaatcaggc                        100
```

```
SEQ ID NO: 545          moltype = DNA  length = 100
FEATURE                 Location/Qualifiers
source                  1..100
                        mol_type = genomic DNA
                        organism = Homo sapiens
SEQUENCE: 545
gcgcagcctc ggccagtcgg gaagccactg gcacctatgg ccaggcgaga aactgtttac  60
tttctccacc ccaccccaga tgcacacaat ggagttgatg                        100

SEQ ID NO: 546          moltype = DNA  length = 100
FEATURE                 Location/Qualifiers
source                  1..100
                        mol_type = genomic DNA
                        organism = Homo sapiens
SEQUENCE: 546
gctttggaga tgagaagcgc caccggactg ttaaccccga agggaagaaa aacaagcaac  60
cctaaaccac gctctgggca gggctgttaa ttgtgccggt                        100

SEQ ID NO: 547          moltype = DNA  length = 100
FEATURE                 Location/Qualifiers
source                  1..100
                        mol_type = genomic DNA
                        organism = Homo sapiens
SEQUENCE: 547
acgcaacggt tggagggggc tgaggaaagg ggacgtcgaa cccaccccag ccccacggct  60
cctttgtccc caaatccgcc gacggtcctc ggaccgcagc                        100

SEQ ID NO: 548          moltype = DNA  length = 100
FEATURE                 Location/Qualifiers
source                  1..100
                        mol_type = genomic DNA
                        organism = Homo sapiens
SEQUENCE: 548
tcccgcctcg gtgggcttaa gtttctttgt tgtgcgtgtt gtcttctcct ctccgttttg  60
ccagctgggg ggaagggggc gccctccgtc cagcccctaa                        100

SEQ ID NO: 549          moltype = DNA  length = 100
FEATURE                 Location/Qualifiers
source                  1..100
                        mol_type = genomic DNA
                        organism = Homo sapiens
SEQUENCE: 549
agcctcgcgg ggaaccgctg ttagcggcca cccagcgcaa ccacaccggt cccgcggcgg  60
ggcccaagcg cgaccggccc cggggcgctg ccgaggttcc                        100

SEQ ID NO: 550          moltype = DNA  length = 100
FEATURE                 Location/Qualifiers
source                  1..100
                        mol_type = genomic DNA
                        organism = Homo sapiens
SEQUENCE: 550
cgcagccccg acggccggac tctgacccag ggatgtgggg cccgcgtccc tccgacgccc  60
tcgccctgct cacctgccag cagctcctgc aggctctggc                        100

SEQ ID NO: 551          moltype = DNA  length = 100
FEATURE                 Location/Qualifiers
source                  1..100
                        mol_type = genomic DNA
                        organism = Homo sapiens
SEQUENCE: 551
tgaaggtctg cagctgtcgc tcgctcgtga gccccttggt gcggagaaac ttggagatga  60
aggacacggc ggcggcgatc tcgcctatca tggtggcggc                        100

SEQ ID NO: 552          moltype = DNA  length = 100
FEATURE                 Location/Qualifiers
source                  1..100
                        mol_type = genomic DNA
                        organism = Homo sapiens
SEQUENCE: 552
ccgggtgtag aagggatgca tgggggcggc gtgcgggggc ggcccggggc ggctggggct  60
cggcggcgcg gccccgacgg cggagcagcc accccgggct                        100

SEQ ID NO: 553          moltype = DNA  length = 100
FEATURE                 Location/Qualifiers
source                  1..100
                        mol_type = genomic DNA
                        organism = Homo sapiens
SEQUENCE: 553
acgccgcacc cctcccccgt gcgttctgcg gccacccagg ccttccagga caccgtggag  60
```

agggaacaag ggggcaggga cgccccccttc ggcaggagcc 100

SEQ ID NO: 554 moltype = DNA length = 100
FEATURE Location/Qualifiers
source 1..100
mol_type = genomic DNA
organism = Homo sapiens
SEQUENCE: 554
gtcggagaag ggggcccaga ccggagggag gcgagaagcc ccactgaagc cgggcgcagg 60
gtctgggacg cagttgggag tgcaaagggc tggctgagag 100

SEQ ID NO: 555 moltype = DNA length = 100
FEATURE Location/Qualifiers
source 1..100
mol_type = genomic DNA
organism = Homo sapiens
SEQUENCE: 555
ccgcaggagc agcaggctgt ggcccaggcc tcctgggtga caggccctgt ctggcgggga 60
agagggacca agagacaaca cggaagaggc tggacctcga 100

SEQ ID NO: 556 moltype = DNA length = 100
FEATURE Location/Qualifiers
source 1..100
mol_type = genomic DNA
organism = Homo sapiens
SEQUENCE: 556
acaggggcgg ctgcctcact ccctacctga gccagccgag ggggccaagg actttagagc 60
tgtttcctcc ggcataagag agacacttgc tttccagggc 100

SEQ ID NO: 557 moltype = DNA length = 100
FEATURE Location/Qualifiers
source 1..100
mol_type = genomic DNA
organism = Homo sapiens
SEQUENCE: 557
agcacccttt atcggagaag gctctacagg gaaggggtct ttgcagcctg gatggccatc 60
ccacattcct ttaacggagg tctctaggcc tcagagagaa 100

SEQ ID NO: 558 moltype = DNA length = 100
FEATURE Location/Qualifiers
source 1..100
mol_type = genomic DNA
organism = Homo sapiens
SEQUENCE: 558
cccagagtta gaaaggaggc cagacggtcc ttgctgtccc cctggggaga gaggaagttg 60
ccgcctgctg ccaggcccag gaggagctgg gcctgcaata 100

SEQ ID NO: 559 moltype = DNA length = 100
FEATURE Location/Qualifiers
source 1..100
mol_type = genomic DNA
organism = Homo sapiens
SEQUENCE: 559
gtgggggacc tggcccctga ggcagtggcg gccatgtcac ggccaggcca cggtgggctg 60
atgcctgtga atggtctggg cttcccaccg cagaacgtgg 100

SEQ ID NO: 560 moltype = DNA length = 100
FEATURE Location/Qualifiers
source 1..100
mol_type = genomic DNA
organism = Homo sapiens
SEQUENCE: 560
cccgggtggt ggtgtgggag tggctgaatg agcacagccg ctggcggccc tacacggcca 60
ccgtgtgcca ccacattgag aacgtgctga aggaggacgc 100

SEQ ID NO: 561 moltype = DNA length = 100
FEATURE Location/Qualifiers
source 1..100
mol_type = genomic DNA
organism = Homo sapiens
SEQUENCE: 561
tcgcggttcc gtggtcctgg ggcaggtgga cgcccagctt gtgccctaca tcatcgacct 60
gcagtccatg caccagtttc gccaggacac aggtgagcag 100

SEQ ID NO: 562 moltype = DNA length = 100
FEATURE Location/Qualifiers
source 1..100
mol_type = genomic DNA
organism = Homo sapiens

```
SEQUENCE: 562
acacccaccc catgccaccc gccccgccga gccatcacta ccttgcagcg taggatgctg  60
aaaatcccag taaatctgct gatgccaaat cccttcccca                        100

SEQ ID NO: 563         moltype = DNA  length = 100
FEATURE                Location/Qualifiers
source                 1..100
                       mol_type = genomic DNA
                       organism = Homo sapiens
SEQUENCE: 563
tctccctgcc tcacctccag aaaaacaggg cagtctaacc ttgtccagtt taagacttgg  60
attccaatgc agcctctgag caagctgtag ggccttgagc                        100

SEQ ID NO: 564         moltype = DNA  length = 100
FEATURE                Location/Qualifiers
source                 1..100
                       mol_type = genomic DNA
                       organism = Homo sapiens
SEQUENCE: 564
gggtagatca atatctctca cagctgagtg aggattaaat aaaattgtgc tcactgagca  60
cagaacctag aacagcagta gcatgggatt gtagaataag                        100

SEQ ID NO: 565         moltype = DNA  length = 100
FEATURE                Location/Qualifiers
source                 1..100
                       mol_type = genomic DNA
                       organism = Homo sapiens
SEQUENCE: 565
ggctttacat gcacttcctc atttgatttt tcccaagaat cacaggcagt aagtctgtgt  60
attgttgtat tattatgagt cccattttat agatgaagaa                        100

SEQ ID NO: 566         moltype = DNA  length = 100
FEATURE                Location/Qualifiers
source                 1..100
                       mol_type = genomic DNA
                       organism = Homo sapiens
SEQUENCE: 566
tttatagatg aagaaaccga gtctcccaga agctgagtga tttaaactca gagctgggat  60
ttaaacccag gcggttgagt tccagaacca aagttcttaa                        100

SEQ ID NO: 567         moltype = DNA  length = 100
FEATURE                Location/Qualifiers
source                 1..100
                       mol_type = genomic DNA
                       organism = Homo sapiens
SEQUENCE: 567
ctggtatcct atactggctc caagtgttgg tttgtggggt ggagtcgtgc tggtggtaat  60
taattgggga tggggggcgt tggtggtgtt gatggtgggg                        100

SEQ ID NO: 568         moltype = DNA  length = 100
FEATURE                Location/Qualifiers
source                 1..100
                       mol_type = genomic DNA
                       organism = Homo sapiens
SEQUENCE: 568
tgaggtggca atgatggagg agacagtgtt agcggttgtg ttggtggtga ctcagtgata  60
gtattgatgg tggtggggtc ttggtgacaa tggagggatg                        100

SEQ ID NO: 569         moltype = DNA  length = 100
FEATURE                Location/Qualifiers
source                 1..100
                       mol_type = genomic DNA
                       organism = Homo sapiens
SEQUENCE: 569
tgttggtgac attgatagtt gtgttggtgg tggtgctgga agtggtgtga tggggtggtg  60
atgatggaga aaatgagaga atgatgttgg tggcagtctt                        100

SEQ ID NO: 570         moltype = DNA  length = 100
FEATURE                Location/Qualifiers
source                 1..100
                       mol_type = genomic DNA
                       organism = Homo sapiens
SEQUENCE: 570
cgtggccatg tggtgtggct ggtagccctg tgtgtggctg ttacttagtg gtattggtga  60
tcctgttgtg gttgtaatga tggtgatgtt gatggttgcg                        100

SEQ ID NO: 571         moltype = DNA  length = 100
FEATURE                Location/Qualifiers
source                 1..100
```

```
                         mol_type = genomic DNA
                         organism = Homo sapiens
SEQUENCE: 571
ttggtggtaa tgtgatggct gatgatggag ataaaatcga tgaggtccca ctctcaggcc  60
tactctcttt tgttctggag atttgtcatc gttggggaga                        100

SEQ ID NO: 572           moltype = DNA  length = 100
FEATURE                  Location/Qualifiers
source                   1..100
                         mol_type = genomic DNA
                         organism = Homo sapiens
SEQUENCE: 572
tgaaatggct gctgtcgggc tgtcatctcc aggcccgggg cgctgacatt tgggccactc  60
tcggtctccc tcttcattct gggcgcgcat tagctctggt                        100

SEQ ID NO: 573           moltype = DNA  length = 100
FEATURE                  Location/Qualifiers
source                   1..100
                         mol_type = genomic DNA
                         organism = Homo sapiens
SEQUENCE: 573
ccggccggtt ccgctgcagc tgaacagcaa gatgcggcac ccaggttacc ctgatcatcg  60
cagatttctc cccggggctc tgttctgagg cctcaaaagt                        100

SEQ ID NO: 574           moltype = DNA  length = 100
FEATURE                  Location/Qualifiers
source                   1..100
                         mol_type = genomic DNA
                         organism = Homo sapiens
SEQUENCE: 574
gctccttgta gatgggacca ggggtcattt gggcagtagc agcgcctggt ctcagtctgg  60
tactgaagtc aggaatggct taaggtgaaa tcgtggtcct                        100

SEQ ID NO: 575           moltype = DNA  length = 100
FEATURE                  Location/Qualifiers
source                   1..100
                         mol_type = genomic DNA
                         organism = Homo sapiens
SEQUENCE: 575
ctggtgaagc tcagcgaaga ccccctcgcc ttgtttatga caagagaact tctgggggcg  60
ggaggaagag tccctgttac gatgctgatc atcattgagc                        100

SEQ ID NO: 576           moltype = DNA  length = 100
FEATURE                  Location/Qualifiers
source                   1..100
                         mol_type = genomic DNA
                         organism = Homo sapiens
SEQUENCE: 576
ttttgctgag cagaaaactc tttagtactc aaggtcgaga gtctctggtg gtctgcctgg  60
caccaggcac cttcctacaa ccctagtttt ccaaaaggac                        100

SEQ ID NO: 577           moltype = DNA  length = 100
FEATURE                  Location/Qualifiers
source                   1..100
                         mol_type = genomic DNA
                         organism = Homo sapiens
SEQUENCE: 577
aaagcctggg gcaggcgacg tcctagctcg catttgaaca gggccgcggg ccagcagaga  60
tgcgcgatgc ccaactcttt ccaagagcac ctcgcgtccc                        100

SEQ ID NO: 578           moltype = DNA  length = 100
FEATURE                  Location/Qualifiers
source                   1..100
                         mol_type = genomic DNA
                         organism = Homo sapiens
SEQUENCE: 578
gaaccggtgc cttcaactcg gagaagtcaa gagacccgca agaaacttgc acgactgcac  60
ccgccgccgc gctctggggg ctgggcaggg gcagctgggc                        100

SEQ ID NO: 579           moltype = DNA  length = 100
FEATURE                  Location/Qualifiers
source                   1..100
                         mol_type = genomic DNA
                         organism = Homo sapiens
SEQUENCE: 579
tggctcccgg ggaacgcgac ccccccgcgc cccgcagacc ggctgtctcc catggacccc  60
tcggcacctg cagcctccga ggaagggtca gcgcgcgtgt                        100

SEQ ID NO: 580           moltype = DNA  length = 100
```

```
FEATURE                Location/Qualifiers
source                 1..100
                       mol_type = genomic DNA
                       organism = Homo sapiens
SEQUENCE: 580
ggggggctcg ggccagccga tgtttttggc cagaagccgt tcgtcctggg ccgcggctgc  60
ctctccacac cgggagctcg tgtttgtttt gcggagggag                        100

SEQ ID NO: 581         moltype = DNA  length = 100
FEATURE                Location/Qualifiers
source                 1..100
                       mol_type = genomic DNA
                       organism = Homo sapiens
SEQUENCE: 581
ctgttgtttt tgttctctgc accggggaga gggggacttg gtggcggccg cgcgtggttt  60
tcgggatcac attagcgtcc gcccggcgtg gcccggtcga                        100

SEQ ID NO: 582         moltype = DNA  length = 100
FEATURE                Location/Qualifiers
source                 1..100
                       mol_type = genomic DNA
                       organism = Homo sapiens
SEQUENCE: 582
cattaagggg atcgaacctt tccgcggcct cgtcggggtc tgctcggaat cggcccctgg  60
gccaggcccg aggcgcaagc agatcgccag gttgggtcag                        100

SEQ ID NO: 583         moltype = DNA  length = 100
FEATURE                Location/Qualifiers
source                 1..100
                       mol_type = genomic DNA
                       organism = Homo sapiens
SEQUENCE: 583
agttgttgaa aactccccgc tgcctgattt caactttatt atttttttcc cacgccttca  60
ctggggtccc ggagggagag gagccgccgc aacgctggct                        100

SEQ ID NO: 584         moltype = DNA  length = 100
FEATURE                Location/Qualifiers
source                 1..100
                       mol_type = genomic DNA
                       organism = Homo sapiens
SEQUENCE: 584
agtagcgcct cggtctctaa aagccactgg gggcgagcct ccggtgtggc ggtgtcacaa  60
gttagctgtc ctttctgagt caaacccaac aaaaaaggca                        100

SEQ ID NO: 585         moltype = DNA  length = 100
FEATURE                Location/Qualifiers
source                 1..100
                       mol_type = genomic DNA
                       organism = Homo sapiens
SEQUENCE: 585
agaggaaaat caataaagtc cacgtgctcc ccggcctcct atggaaaggg ctggctgcga  60
tggccggatg cccggccgtg ggctgggttt ggctccagtg                        100

SEQ ID NO: 586         moltype = DNA  length = 100
FEATURE                Location/Qualifiers
source                 1..100
                       mol_type = genomic DNA
                       organism = Homo sapiens
SEQUENCE: 586
ggacaaagaa ttttcagaac cgtgagaagg ggaggctttc caaagttgag atccaagtcg  60
tcggtgtctc gggagctccc ctggtacaca gggtgcccgg                        100

SEQ ID NO: 587         moltype = DNA  length = 100
FEATURE                Location/Qualifiers
source                 1..100
                       mol_type = genomic DNA
                       organism = Homo sapiens
SEQUENCE: 587
tgcccgactg gagccattta aaaatggcag aaacagctgc aggccaacac acacacgctg  60
gaaaacaacc cgcagccccc tctactgtgg gattccccgc                        100

SEQ ID NO: 588         moltype = DNA  length = 100
FEATURE                Location/Qualifiers
source                 1..100
                       mol_type = genomic DNA
                       organism = Homo sapiens
SEQUENCE: 588
gggaagcccg gagttgctcc cctccttgcc tcagcccctg tgcaaagaaa gaactggtgt  60
ctgtgcctgg gtcccttctg tcgccggcct ggaggttggg                        100
```

```
SEQ ID NO: 589          moltype = DNA  length = 100
FEATURE                 Location/Qualifiers
source                  1..100
                        mol_type = genomic DNA
                        organism = Homo sapiens
SEQUENCE: 589
aaacagccgg caagccgcct ttctctgctc gaggaggcgt ggtggggcct cctactccag  60
gttcccggct ggacagaggc tcctgcaccc tgacagctgc                        100

SEQ ID NO: 590          moltype = DNA  length = 100
FEATURE                 Location/Qualifiers
source                  1..100
                        mol_type = genomic DNA
                        organism = Homo sapiens
SEQUENCE: 590
ggaggccttc cagcccgctg accccgcggg gaccaggcct gtagttggag cttgaggggc  60
tgtacctctg cgcctccctg ggtttgggga aacaacacat                        100

SEQ ID NO: 591          moltype = DNA  length = 100
FEATURE                 Location/Qualifiers
source                  1..100
                        mol_type = genomic DNA
                        organism = Homo sapiens
SEQUENCE: 591
cgtgtcctct gaagacctca ggctttggga tctcatggtc cagcttccag ttcacttcgt  60
tgccgcgacc ttgggcatat cattgtcact tctctaacca                        100

SEQ ID NO: 592          moltype = DNA  length = 100
FEATURE                 Location/Qualifiers
source                  1..100
                        mol_type = genomic DNA
                        organism = Homo sapiens
SEQUENCE: 592
tggtgacccg gggttttgtg cttggcttcc aggtcccctc gggttattga ggacgattga  60
ggtcatgcct ccgagagcac cgcgccctgg gcgcaggagg                        100

SEQ ID NO: 593          moltype = DNA  length = 100
FEATURE                 Location/Qualifiers
source                  1..100
                        mol_type = genomic DNA
                        organism = Homo sapiens
SEQUENCE: 593
aatgcaaatt taacagggca ccctgtattt tacccagagg gaagccgaag tgtttggcag  60
atcatttggc cccatgagcc ttgggtgggt ttctcctcag                        100

SEQ ID NO: 594          moltype = DNA  length = 100
FEATURE                 Location/Qualifiers
source                  1..100
                        mol_type = genomic DNA
                        organism = Homo sapiens
SEQUENCE: 594
ccctagtgac ccctaaaatt accccccga cccacccact gtcccctgat gcttccccca  60
cccccggaaa aagctgtggc ctccctctca tttggggcag                        100

SEQ ID NO: 595          moltype = DNA  length = 100
FEATURE                 Location/Qualifiers
source                  1..100
                        mol_type = genomic DNA
                        organism = Homo sapiens
SEQUENCE: 595
gctgcctcct gttctctttt tctggtgttt cagcaaggca ggccagtgga ggtgaggtga  60
ccagaagatg gctaaaggga aaacaaaatg gtgggcctct                        100

SEQ ID NO: 596          moltype = DNA  length = 100
FEATURE                 Location/Qualifiers
source                  1..100
                        mol_type = genomic DNA
                        organism = Homo sapiens
SEQUENCE: 596
ccagggtttg ggggccctgt gctggtggag gagagaagac cccagggcga tggtaggaga  60
cgaaagcttg ggctgcagcg taagcttgga ggcccgctgc                        100

SEQ ID NO: 597          moltype = DNA  length = 100
FEATURE                 Location/Qualifiers
source                  1..100
                        mol_type = genomic DNA
                        organism = Homo sapiens
SEQUENCE: 597
```

```
ggtggctcac gcctgtaatc ccagagcttt gggaggctga gacaggagga ttgcttgagc  60
ccaggagttt gagaccagcc tgggtctcaa accaaaaaaa                        100

SEQ ID NO: 598          moltype = DNA  length = 100
FEATURE                 Location/Qualifiers
source                  1..100
                        mol_type = genomic DNA
                        organism = Homo sapiens
SEQUENCE: 598
taaatataat tttaacgcca atctgagaaa aatgacttat tagctgtgtg attttgagca  60
atgctcttaa cctcccccat gaaggatggt gtgagaacga                        100

SEQ ID NO: 599          moltype = DNA  length = 100
FEATURE                 Location/Qualifiers
source                  1..100
                        mol_type = genomic DNA
                        organism = Homo sapiens
SEQUENCE: 599
acagaattgt agcacgtgta tcagtctggt acacaatgtc ctatgaaggt tagctttatt  60
atcaccatca ttattattgc agaaagactt tcagttcaga                        100

SEQ ID NO: 600          moltype = DNA  length = 100
FEATURE                 Location/Qualifiers
source                  1..100
                        mol_type = genomic DNA
                        organism = Homo sapiens
SEQUENCE: 600
ataagacagc acagttacag agacctggtt ttattttcca gcttcttaac tgagtcatct  60
ttcagctcct tttaattaaa aagaaaaaac aatcagagat                        100

SEQ ID NO: 601          moltype = DNA  length = 100
FEATURE                 Location/Qualifiers
source                  1..100
                        mol_type = genomic DNA
                        organism = Homo sapiens
SEQUENCE: 601
tcaaagacct ggcagaaatg acttcccaac cccagatgcc cccagcagca gtatttagca  60
gtcatacaat tgcctgaaat gaagaatgag taatctggat                        100

SEQ ID NO: 602          moltype = DNA  length = 100
FEATURE                 Location/Qualifiers
source                  1..100
                        mol_type = genomic DNA
                        organism = Homo sapiens
SEQUENCE: 602
gagtcggccc tgaaatcgac ctgcaactta cccggaacgt gagctgtctc tctctgacct  60
ctgctggctg cttcacctgg agtctgagtc cgactcatgt                        100

SEQ ID NO: 603          moltype = DNA  length = 100
FEATURE                 Location/Qualifiers
source                  1..100
                        mol_type = genomic DNA
                        organism = Homo sapiens
SEQUENCE: 603
agcacttcac tgtccgcgtt agtttagcct tcactgtcag caactcgtca ccttgtcctc  60
ttgcagcgaa ggtttggaat cccatcacgg gtgtgcagtg                        100

SEQ ID NO: 604          moltype = DNA  length = 100
FEATURE                 Location/Qualifiers
source                  1..100
                        mol_type = genomic DNA
                        organism = Homo sapiens
SEQUENCE: 604
gttagtcctg agatcatggt ggtgctagga gaacctgcca accaatacag aaagttgtca  60
cgaatagaaa cctaagctct ggccgggtgc ggtggttcaa                        100

SEQ ID NO: 605          moltype = DNA  length = 100
FEATURE                 Location/Qualifiers
source                  1..100
                        mol_type = genomic DNA
                        organism = Homo sapiens
SEQUENCE: 605
agatatactg ttctagacat gtgtctgaaa ggaatcctgc aaattctgtc ttattgaaca  60
ggcataaggt gtcacgtcag gcgtaaggtg tcacagcagg                        100

SEQ ID NO: 606          moltype = DNA  length = 100
FEATURE                 Location/Qualifiers
source                  1..100
                        mol_type = genomic DNA
```

```
                         -continued

                         organism = Homo sapiens
SEQUENCE: 606
cgtaaggcgt cacgtcaggc gtaaggtgtc acagcaggcg taaggcatca cgtcaggcgt    60
aaggcgtcac gtcaggcgta aggtgtcaca agctcggtga                         100

SEQ ID NO: 607           moltype = DNA  length = 100
FEATURE                  Location/Qualifiers
source                   1..100
                         mol_type = genomic DNA
                         organism = Homo sapiens
SEQUENCE: 607
acgtcagggg tgtgccttgt gttctctgtt cgttgctttc agaagcagca gcatgtggca    60
gcatctctgt gcctatgacg atattgcagt gaatatgaga                         100

SEQ ID NO: 608           moltype = DNA  length = 100
FEATURE                  Location/Qualifiers
source                   1..100
                         mol_type = genomic DNA
                         organism = Homo sapiens
SEQUENCE: 608
aattgtacat ttcaacaaca taaataagct gttcaagact gtctcccatg cctccaaaac    60
aaataaaaac cccccacaac tcaaatgcat ataagctgtt                         100

SEQ ID NO: 609           moltype = DNA  length = 100
FEATURE                  Location/Qualifiers
source                   1..100
                         mol_type = genomic DNA
                         organism = Homo sapiens
SEQUENCE: 609
actatagtat aatggtgagt tatagccagt gtatgatggg attgttgata gaataatgca    60
tattagagct tttagttcaa aaatttgaga tagtgattca                         100

SEQ ID NO: 610           moltype = DNA  length = 100
FEATURE                  Location/Qualifiers
source                   1..100
                         mol_type = genomic DNA
                         organism = Homo sapiens
SEQUENCE: 610
gaaagaaaaa aaggaatgat tatcatgaat tctgtttatt agaattctgt ttattaaaga    60
gttaaagata tgttttattt ttttatcttt attatcatta                         100

SEQ ID NO: 611           moltype = DNA  length = 100
FEATURE                  Location/Qualifiers
source                   1..100
                         mol_type = genomic DNA
                         organism = Homo sapiens
SEQUENCE: 611
aattctaatg ttggtccctt aggatcagca gggggggacc gggaatctgt aactgcaacc    60
accccaccga gaggattaca ggaacccagt cgagagctgg                         100

SEQ ID NO: 612           moltype = DNA  length = 100
FEATURE                  Location/Qualifiers
source                   1..100
                         mol_type = genomic DNA
                         organism = Homo sapiens
SEQUENCE: 612
ttcccaacaa tgaggttcat ttaaaaagtc gtgaggggg aggggggcca aagaaagaaa     60
tagatcaaag agcgggagag tcgagaaaag aaggaagaaa                         100

SEQ ID NO: 613           moltype = DNA  length = 100
FEATURE                  Location/Qualifiers
source                   1..100
                         mol_type = genomic DNA
                         organism = Homo sapiens
SEQUENCE: 613
tgttggggag cgctggcagc cgggctggca agtggagttt gggaatgtgc agggagggaa    60
ggaagctgaa aaattcaaac tttttaaatg ctactcttca                         100

SEQ ID NO: 614           moltype = DNA  length = 100
FEATURE                  Location/Qualifiers
source                   1..100
                         mol_type = genomic DNA
                         organism = Homo sapiens
SEQUENCE: 614
gctcctcggc gtccctgcac cccaaccctg cagccctggg gcgttggcag ctgcaccaac    60
aggagcagca agctgggaaa acagagcaac atgacccgac                         100

SEQ ID NO: 615           moltype = DNA  length = 100
FEATURE                  Location/Qualifiers
```

```
source                  1..100
                        mol_type = genomic DNA
                        organism = Homo sapiens
SEQUENCE: 615
gtgttaagag aaggcaaaac acttcagcaa ttaaaaagta gcccagcagc ttcacccttt  60
caaattggga gggggaggtt ggaaagaaat ttaacaacat                        100

SEQ ID NO: 616          moltype = DNA  length = 100
FEATURE                 Location/Qualifiers
source                  1..100
                        mol_type = genomic DNA
                        organism = Homo sapiens
SEQUENCE: 616
ccatagactt ttgctatgta catttaaacc gcagtcctgg aacattccga gtttaaaact  60
tgctttttca acactggctg acaagcaaca tgttttaagg                        100

SEQ ID NO: 617          moltype = DNA  length = 100
FEATURE                 Location/Qualifiers
source                  1..100
                        mol_type = genomic DNA
                        organism = Homo sapiens
SEQUENCE: 617
agccccccat taaatcctta ctcgcgggac tctcgagttc aagccagcat tttgtcgcca  60
cctccccccc caaccccgcc cgcaatcgat gagccgcaat                        100

SEQ ID NO: 618          moltype = DNA  length = 100
FEATURE                 Location/Qualifiers
source                  1..100
                        mol_type = genomic DNA
                        organism = Homo sapiens
SEQUENCE: 618
gcctcggcaa cacaggtaag cgggtcaacc tgaatgcctc tttcacccca aagtttgctg  60
cacgatcggc tatcgcggga agaagcccaa cggagctagg                        100

SEQ ID NO: 619          moltype = DNA  length = 100
FEATURE                 Location/Qualifiers
source                  1..100
                        mol_type = genomic DNA
                        organism = Homo sapiens
SEQUENCE: 619
gcggactcaa gccccactgc aaacttgttc tgcaacatct ttttgaatca caacttggcc  60
tttcttcctc gcatatcccc agctcccccc aaagagtgga                        100

SEQ ID NO: 620          moltype = DNA  length = 100
FEATURE                 Location/Qualifiers
source                  1..100
                        mol_type = genomic DNA
                        organism = Homo sapiens
SEQUENCE: 620
ggaaaacatt gtcccgagac tcacttcccc gagggacctc ccactcccaa ccccacgggt  60
gggtaatgcc gctggacaga cctagggcgc agactgggaa                        100

SEQ ID NO: 621          moltype = DNA  length = 100
FEATURE                 Location/Qualifiers
source                  1..100
                        mol_type = genomic DNA
                        organism = Homo sapiens
SEQUENCE: 621
cccgatcaga ccagcaaacc tgggatccag cagcacgtta cgtaaaacag gatcgcccaa  60
aacttgtccc aatcccagcc ctccccccga agcccccggg                        100

SEQ ID NO: 622          moltype = DNA  length = 100
FEATURE                 Location/Qualifiers
source                  1..100
                        mol_type = genomic DNA
                        organism = Homo sapiens
SEQUENCE: 622
ctgccctgcc aggcaaactt cgcccctcaa aaccctggcc tccagattca catgtaatcc  60
ccgccagcaa ctgttgaaac tcaaagggtg ggaaggacgg                        100

SEQ ID NO: 623          moltype = DNA  length = 100
FEATURE                 Location/Qualifiers
source                  1..100
                        mol_type = genomic DNA
                        organism = Homo sapiens
SEQUENCE: 623
ggccaaattc cttcaaactt gggagaaatg ccggaggaga aaagaatcat ctcgctgcac  60
cactttcccc attgccttcc aagacccaaa cttttggggg                        100
```

```
SEQ ID NO: 624         moltype = DNA  length = 100
FEATURE                Location/Qualifiers
source                 1..100
                       mol_type = genomic DNA
                       organism = Homo sapiens
SEQUENCE: 624
ttctttctta aggcaaaaga aaaagacttt ttgaaaagca aatgctccgc ccccctttac  60
cttgcataaa acttcgctca agtcgaagat ggtggcagac                        100

SEQ ID NO: 625         moltype = DNA  length = 100
FEATURE                Location/Qualifiers
source                 1..100
                       mol_type = genomic DNA
                       organism = Homo sapiens
SEQUENCE: 625
acgagggtgg tggtcatcct gtgcgttcgc gcgagccagg ggcgaggatc tggtgtgtcg  60
cgaaggtccc ggtgcgggga aggcgcagcc tctcctgtct                        100

SEQ ID NO: 626         moltype = DNA  length = 100
FEATURE                Location/Qualifiers
source                 1..100
                       mol_type = genomic DNA
                       organism = Homo sapiens
SEQUENCE: 626
ttattttttt atattaagat ttattctaaa ttttgattct tctaaatata gtatatattt  60
agtatatata taatgcacct ctcttaccta atgatcattt                        100

SEQ ID NO: 627         moltype = DNA  length = 100
FEATURE                Location/Qualifiers
source                 1..100
                       mol_type = genomic DNA
                       organism = Homo sapiens
SEQUENCE: 627
ctaaataatc ataacaacat cgagtaaaac tatgtaataa cacatattat tattaagata  60
agtataagaa atataataat aaattgtccc tgttctaaaa                        100

SEQ ID NO: 628         moltype = DNA  length = 100
FEATURE                Location/Qualifiers
source                 1..100
                       mol_type = genomic DNA
                       organism = Homo sapiens
SEQUENCE: 628
ggtaattata taatgctgaa tgtgtcagag gcattcgaac cagagtgact ccattttgag  60
tgagggctag gaaaatgagg ctgagacttg ctgggatgca                        100

SEQ ID NO: 629         moltype = DNA  length = 100
FEATURE                Location/Qualifiers
source                 1..100
                       mol_type = genomic DNA
                       organism = Homo sapiens
SEQUENCE: 629
tttaattttt atgctttctt cagtgtatgt ttggagagag tttgaacatt ttttgactct  60
ttttcattga gtaaatccaa atacttgtaa aagacttatc                        100

SEQ ID NO: 630         moltype = DNA  length = 100
FEATURE                Location/Qualifiers
source                 1..100
                       mol_type = genomic DNA
                       organism = Homo sapiens
SEQUENCE: 630
tatttcttta acaaaaactt aacatggatt aaggacccat cttaaggcat cacacattaa  60
aaaagtcaat attgattcaa taccggcgct tatactacga                        100

SEQ ID NO: 631         moltype = DNA  length = 100
FEATURE                Location/Qualifiers
source                 1..100
                       mol_type = genomic DNA
                       organism = Homo sapiens
SEQUENCE: 631
catcacttgt taaatttgtt ttctaaataa agcccagagg tagtggaaaa tacttcacac  60
tctaggccag tgtttgctat gcctggttga ccctaaactg                        100

SEQ ID NO: 632         moltype = DNA  length = 100
FEATURE                Location/Qualifiers
source                 1..100
                       mol_type = genomic DNA
                       organism = Homo sapiens
SEQUENCE: 632
ttgagggttc tttttaaaaa tacagatttc tgggacccac ctgagatgat tccgataatc  60
```

```
ggccatatgg atgagtcact tagagatacc catttttaag                         100

SEQ ID NO: 633         moltype = DNA  length = 100
FEATURE                Location/Qualifiers
source                 1..100
                       mol_type = genomic DNA
                       organism = Homo sapiens
SEQUENCE: 633
gattaggacc ccgaagccca gaaaatgcct gctgtagtca acattatagt cacactccac  60
aggcactggg tccacccctt tgaccgacat tcctttgcgg                         100

SEQ ID NO: 634         moltype = DNA  length = 100
FEATURE                Location/Qualifiers
source                 1..100
                       mol_type = genomic DNA
                       organism = Homo sapiens
SEQUENCE: 634
ttttcccacc cttcttccct gcctggagaa ctcctattca tcctccagag cccggctcaa  60
agtggcttca tctgtgggga tcctccctgc cccatagtga                         100

SEQ ID NO: 635         moltype = DNA  length = 100
FEATURE                Location/Qualifiers
source                 1..100
                       mol_type = genomic DNA
                       organism = Homo sapiens
SEQUENCE: 635
gtgctccttg agtcctcgcc cttcctaggg catcccaagc tcccaggggc tgcccctgct  60
gcctcgccat ccgctccaaa gctggctgta cctcgatggt                         100

SEQ ID NO: 636         moltype = DNA  length = 100
FEATURE                Location/Qualifiers
source                 1..100
                       mol_type = genomic DNA
                       organism = Homo sapiens
SEQUENCE: 636
taagggcagc caggcgtgct gcttctcgtc caaatacacg aacttctccc aggcccacag  60
gcggtccggg tggtcggtga ctgcctcccc gagtgtcggg                         100

SEQ ID NO: 637         moltype = DNA  length = 100
FEATURE                Location/Qualifiers
source                 1..100
                       mol_type = genomic DNA
                       organism = Homo sapiens
SEQUENCE: 637
aggaatcaga tttcaaaatg aatatgtata agaaaagaac cggggatcag tgatcaggaa  60
cagggatcca tgatctggtc cagggctcag cggtcaggaa                         100

SEQ ID NO: 638         moltype = DNA  length = 100
FEATURE                Location/Qualifiers
source                 1..100
                       mol_type = genomic DNA
                       organism = Homo sapiens
SEQUENCE: 638
ccctggcctg gagtcccaag tccccagccc atcctgcccc tggagcccag tttagcttgg  60
tcttgaagtc tgctctaggt acccccaaaa tcacagtatc                         100

SEQ ID NO: 639         moltype = DNA  length = 100
FEATURE                Location/Qualifiers
source                 1..100
                       mol_type = genomic DNA
                       organism = Homo sapiens
SEQUENCE: 639
cagccccgct ctgcccaccg ggacagccaa gttcagctga gactggccta ccgggggagt  60
cgccctctga agttcactct aagccagcct ggttcagcct                         100

SEQ ID NO: 640         moltype = DNA  length = 100
FEATURE                Location/Qualifiers
source                 1..100
                       mol_type = genomic DNA
                       organism = Homo sapiens
SEQUENCE: 640
ggcccaggtc agcccaggac ctccccttgc aggcagcaaa ctcttatttc agtccagcca  60
gctcaaccag cttgcttctg actcagctcc tcttagccag                         100

SEQ ID NO: 641         moltype = DNA  length = 100
FEATURE                Location/Qualifiers
source                 1..100
                       mol_type = genomic DNA
                       organism = Homo sapiens
```

```
SEQUENCE: 641
ttagctcagc aaagctggac ctaaagtagc cacctcaccc cagcttcatc cagatgaata    60
cagtccagat cagcttagtc agttaagcct agcctagcta                         100

SEQ ID NO: 642           moltype = DNA   length = 100
FEATURE                  Location/Qualifiers
source                   1..100
                         mol_type = genomic DNA
                         organism = Homo sapiens
SEQUENCE: 642
gttaaatcca gttacgacca gctcaactaa tcctgctcag gcctgctcag cccagcccag    60
ctgaacccag tttagccgag gccaggccag cccagctgaa                         100

SEQ ID NO: 643           moltype = DNA   length = 100
FEATURE                  Location/Qualifiers
source                   1..100
                         mol_type = genomic DNA
                         organism = Homo sapiens
SEQUENCE: 643
tacagttgcc cagtctagct cagcccagtc cagcactgcc cagtttagct gagctcagcc    60
tggcccagcc cagctcatat cagcccatct cagctgaacc                         100

SEQ ID NO: 644           moltype = DNA   length = 100
FEATURE                  Location/Qualifiers
source                   1..100
                         mol_type = genomic DNA
                         organism = Homo sapiens
SEQUENCE: 644
agtttgaccc agtctaaccc aaccccgctc agctgaaccc agcccagccc agcccagccc    60
agccaaaccc agtttagcct agctcagctc agcccatttc                         100

SEQ ID NO: 645           moltype = DNA   length = 100
FEATURE                  Location/Qualifiers
source                   1..100
                         mol_type = genomic DNA
                         organism = Homo sapiens
SEQUENCE: 645
cctgtcctag gggtggcagg cagtctgcac ccagcctagc cctgcccagc gtggggtctc    60
tgaccttctt ggtcttgggc ccagccaaga ttcccagccc                         100

SEQ ID NO: 646           moltype = DNA   length = 100
FEATURE                  Location/Qualifiers
source                   1..100
                         mol_type = genomic DNA
                         organism = Homo sapiens
SEQUENCE: 646
ttctagcttt cctgtgtccc catgcaggga agggatgcct agagtccacg cagtgaccaa    60
gaagcttggt tgatgctgtg agggtggccc aggagtcccc                         100

SEQ ID NO: 647           moltype = DNA   length = 100
FEATURE                  Location/Qualifiers
source                   1..100
                         mol_type = genomic DNA
                         organism = Homo sapiens
SEQUENCE: 647
cacctgctgt ccttggtcct ggctgagagg agggccctac ggccagctct gctgaccctg    60
ccctgggctc tggtgatgct gccggcctgg acaagcccct                         100

SEQ ID NO: 648           moltype = DNA   length = 100
FEATURE                  Location/Qualifiers
source                   1..100
                         mol_type = genomic DNA
                         organism = Homo sapiens
SEQUENCE: 648
gagctcaggt cggtcgtgcc catcctggca tcaccccaca gccggttctg ccgcatcccg    60
tcatgttcct cgtgctccca gcccggtcgt cctggaggcc                         100

SEQ ID NO: 649           moltype = DNA   length = 100
FEATURE                  Location/Qualifiers
source                   1..100
                         mol_type = genomic DNA
                         organism = Homo sapiens
SEQUENCE: 649
tgagcatgag tggggcgggc agaggcctcc gggtgaggag acagatgggg cctgccttgc    60
tgccctgggc tggggctgca cagccggggt gcgtccaggc                         100

SEQ ID NO: 650           moltype = DNA   length = 100
FEATURE                  Location/Qualifiers
source                   1..100
```

```
                         mol_type = genomic DNA
                         organism = Homo sapiens
SEQUENCE: 650
aggagggctg agcctggctt ccagcagaca ccctccctcc ctgagctggc ctctcaccaa  60
ctgtcttgtc caccttggtg ttgctgggct tgtgatctac                        100

SEQ ID NO: 651           moltype = DNA  length = 100
FEATURE                  Location/Qualifiers
source                   1..100
                         mol_type = genomic DNA
                         organism = Homo sapiens
SEQUENCE: 651
accaactgtc ttgtccacct tggtgttgct gggcttgtga tctacgttgc aggtgtaggt  60
ctgggtgccg aagttgctgg agggcacggt caccacgctg                        100

SEQ ID NO: 652           moltype = DNA  length = 100
FEATURE                  Location/Qualifiers
source                   1..100
                         mol_type = genomic DNA
                         organism = Homo sapiens
SEQUENCE: 652
ggactgtagg acagccggga aggtgtgcac gccgctggtc agagcgcctg agttccacga  60
caccgtcacc ggttcgggga agtagtcctt gaccaggcag                        100

SEQ ID NO: 653           moltype = DNA  length = 100
FEATURE                  Location/Qualifiers
source                   1..100
                         mol_type = genomic DNA
                         organism = Homo sapiens
SEQUENCE: 653
tgctacactg ccctgcacca cctccactca gcttcattgt gctggtggcc ctggctcctg  60
gcagcccatc ttgctccttc tggggcgcca gcctcagagg                        100

SEQ ID NO: 654           moltype = DNA  length = 100
FEATURE                  Location/Qualifiers
source                   1..100
                         mol_type = genomic DNA
                         organism = Homo sapiens
SEQUENCE: 654
ccttcctgcc tagggtccgc tggggccagc cctgggaccc tcctggtctc aagcacacat  60
tccccctgca gccacacctg cccctgcctg agagctcagc                        100

SEQ ID NO: 655           moltype = DNA  length = 100
FEATURE                  Location/Qualifiers
source                   1..100
                         mol_type = genomic DNA
                         organism = Homo sapiens
SEQUENCE: 655
cccgagccct ggaatgcctt cccttctcca tcccagctca cccttgccaa ctgctcagtg  60
ggatgggctc acactccctt cctggcacca ggaggctgca                        100

SEQ ID NO: 656           moltype = DNA  length = 100
FEATURE                  Location/Qualifiers
source                   1..100
                         mol_type = genomic DNA
                         organism = Homo sapiens
SEQUENCE: 656
ctgcactttc accagccctc agctgtctgc tgccagcaac tacccagctc ctgccaaaat  60
ctaggagctg agtgatgcct cccaccggcc ctgctcacct                        100

SEQ ID NO: 657           moltype = DNA  length = 100
FEATURE                  Location/Qualifiers
source                   1..100
                         mol_type = genomic DNA
                         organism = Homo sapiens
SEQUENCE: 657
gtggttgcct tgccctgagc tctagtgcct gtcccctgct cgtcctgcct cccaccggcc  60
ctgctcacct gtggctgctc tgctctgatt ccctgaggct                        100

SEQ ID NO: 658           moltype = DNA  length = 100
FEATURE                  Location/Qualifiers
source                   1..100
                         mol_type = genomic DNA
                         organism = Homo sapiens
SEQUENCE: 658
aagcctcagt cctgctcacc ttctgatgct ctcctctgtc ccctgagctc caggggctgt  60
cccctgctcg tcctgcctcc tacctgcccc tgcttacctg                        100

SEQ ID NO: 659           moltype = DNA  length = 100
```

```
FEATURE                 Location/Qualifiers
source                  1..100
                        mol_type = genomic DNA
                        organism = Homo sapiens
SEQUENCE: 659
agggtgctct gccctggtgc tctgagctcc aggggctgtc ccctgctcct cctgcttcct  60
accagcccct gctcacctgt ggctgctctg ccctggtccc                        100

SEQ ID NO: 660          moltype = DNA  length = 100
FEATURE                 Location/Qualifiers
source                  1..100
                        mol_type = genomic DNA
                        organism = Homo sapiens
SEQUENCE: 660
ctctgccctg gtcccctgag ctccaggggc ttccccctgc tcttcctgcc cccaccagcc  60
cctgttcacc ttcagatgcc ctcccctggt cccctgaagt                        100

SEQ ID NO: 661          moltype = DNA  length = 100
FEATURE                 Location/Qualifiers
source                  1..100
                        mol_type = genomic DNA
                        organism = Homo sapiens
SEQUENCE: 661
cccagagctg ccccctgttc ctcctgcctc ccaccagccc gtgctcacct gccgctgctc  60
tgccctggtc ccgagttcca ggggctgcac cctgttcgcc                        100

SEQ ID NO: 662          moltype = DNA  length = 100
FEATURE                 Location/Qualifiers
source                  1..100
                        mol_type = genomic DNA
                        organism = Homo sapiens
SEQUENCE: 662
cacctcccac tagccatgct cagctcttga tgctctgtcc tggtcccctg agctccagga  60
gctgtcccct actcgtcctg ccacccacca gcccctgctc                        100

SEQ ID NO: 663          moltype = DNA  length = 100
FEATURE                 Location/Qualifiers
source                  1..100
                        mol_type = genomic DNA
                        organism = Homo sapiens
SEQUENCE: 663
acctgaggca cctgaggctg ctctgccctg gtcccctgag ctccagggtc ttccccctgc  60
tcatcctgcc tcccacctgc ccttgttcac cttcagttgc                        100

SEQ ID NO: 664          moltype = DNA  length = 100
FEATURE                 Location/Qualifiers
source                  1..100
                        mol_type = genomic DNA
                        organism = Homo sapiens
SEQUENCE: 664
tctgccctgg tctgctgagc tccaggaggt gccccctgct ccttctgccc ccacctgccc  60
tgctcacctg tggctgctcg gtcctggtac cctgaactcc                        100

SEQ ID NO: 665          moltype = DNA  length = 100
FEATURE                 Location/Qualifiers
source                  1..100
                        mol_type = genomic DNA
                        organism = Homo sapiens
SEQUENCE: 665
gccccctgct ccttctgccc ccacctgccc tgctcacctg tggctgctcg gtcctggtac  60
cctgaactcc aatgcctgcc ccctgctcac tctgccctcc                        100

SEQ ID NO: 666          moltype = DNA  length = 100
FEATURE                 Location/Qualifiers
source                  1..100
                        mol_type = genomic DNA
                        organism = Homo sapiens
SEQUENCE: 666
ctcaacccgg gcagcaatgt cactcaggtc actgttgccc ccctgcctgt cctggcaccc  60
tctgtccagg tttgggctgt ttttctggcc tcatttttgt                        100

SEQ ID NO: 667          moltype = DNA  length = 100
FEATURE                 Location/Qualifiers
source                  1..100
                        mol_type = genomic DNA
                        organism = Homo sapiens
SEQUENCE: 667
tgtccagtca ggtctcccca acagagcccc ttgcccttgc ccatgtgccc ctcctgggtg  60
agctcccaga tcctcccgtc cctgcactgc tcctgctctg                        100
```

```
SEQ ID NO: 668         moltype = DNA  length = 100
FEATURE                Location/Qualifiers
source                 1..100
                       mol_type = genomic DNA
                       organism = Homo sapiens
SEQUENCE: 668
gaagcctctc cagaacctca gctcctcagt ggcctctgct ctgctgggtc agctccctga  60
acgcacggag cctcacccct cccctcgccc caggcctgct                        100

SEQ ID NO: 669         moltype = DNA  length = 100
FEATURE                Location/Qualifiers
source                 1..100
                       mol_type = genomic DNA
                       organism = Homo sapiens
SEQUENCE: 669
gcactctggg cctttctggg cctccctgga ctcttccctc ctcccatctg tgcactcagc  60
acagctctcc cctccactcc gctgctgacc acagccctgc                        100

SEQ ID NO: 670         moltype = DNA  length = 100
FEATURE                Location/Qualifiers
source                 1..100
                       mol_type = genomic DNA
                       organism = Homo sapiens
SEQUENCE: 670
cctttctggg cctccctgga ctcttccctc ctcccatctg tgcactcagc acagctctcc  60
cctccactcc gctgctgacc acagccctgc tccccgccag                        100

SEQ ID NO: 671         moltype = DNA  length = 100
FEATURE                Location/Qualifiers
source                 1..100
                       mol_type = genomic DNA
                       organism = Homo sapiens
SEQUENCE: 671
cccacggcca gcactgctga ccctgccctg ggctccagtg atgctgctgg cctggacaag  60
cccctccgtt cacctggggc ctctcctcct ccctcgttct                        100

SEQ ID NO: 672         moltype = DNA  length = 100
FEATURE                Location/Qualifiers
source                 1..100
                       mol_type = genomic DNA
                       organism = Homo sapiens
SEQUENCE: 672
actgcctcct cagctcaggt gggtcctgcc catgctggca tcaccccacg gccggctctg  60
ccgcatcccg tcaggttcct cgtgctccca gcctggtcgt                        100

SEQ ID NO: 673         moltype = DNA  length = 100
FEATURE                Location/Qualifiers
source                 1..100
                       mol_type = genomic DNA
                       organism = Homo sapiens
SEQUENCE: 673
catggaggcc tcagtcagcc tctggtgtgt cctgccctgt tggcttggaa gcccctgccc  60
acggtccccg tcatcttgca ctgggtgggc gttggtgcct                        100

SEQ ID NO: 674         moltype = DNA  length = 100
FEATURE                Location/Qualifiers
source                 1..100
                       mol_type = genomic DNA
                       organism = Homo sapiens
SEQUENCE: 674
agctcagccc agcctagtcc agcccagccc agcacaggtc agcccagctt agcttagccc  60
aggtcagtcc agctcagctc agtccactta agctcaccca                        100

SEQ ID NO: 675         moltype = DNA  length = 100
FEATURE                Location/Qualifiers
source                 1..100
                       mol_type = genomic DNA
                       organism = Homo sapiens
SEQUENCE: 675
ggtcagctcc gtccagctca gcccagccta gcccagctta gcccagccca gcccaacaca  60
ggtcagccca gctcagccta gcccagccca gctcagcaca                        100

SEQ ID NO: 676         moltype = DNA  length = 100
FEATURE                Location/Qualifiers
source                 1..100
                       mol_type = genomic DNA
                       organism = Homo sapiens
SEQUENCE: 676
```

```
ggtcagacca gctcagtaca gctcaggtca gcccagacca gtccaaccca gcccagcgca  60
gtccaaccca gcccagctca gctcatccaa gcctagctca                        100

SEQ ID NO: 677          moltype = DNA  length = 100
FEATURE                 Location/Qualifiers
source                  1..100
                        mol_type = genomic DNA
                        organism = Homo sapiens
SEQUENCE: 677
gctcagccca gcccaggtca gcctagccca gccgaaccca gctcagccca ggtcaaccca  60
attcagctca gctcagccca ggtcaaccca accaagctca                        100

SEQ ID NO: 678          moltype = DNA  length = 100
FEATURE                 Location/Qualifiers
source                  1..100
                        mol_type = genomic DNA
                        organism = Homo sapiens
SEQUENCE: 678
gctcagccta gcccagtcca gctcagccca gctcagctca gcccagtcca gctcaatcca  60
cctaagctca cccagctcag cccagtctgg ctcagcttag                        100

SEQ ID NO: 679          moltype = DNA  length = 100
FEATURE                 Location/Qualifiers
source                  1..100
                        mol_type = genomic DNA
                        organism = Homo sapiens
SEQUENCE: 679
gtcagcccag cccagcctag cccagatcag tccagcttag cccagcccag gtcagcccag  60
cccaggtcag cccagctcag ctcagcccag cccagctcag                        100

SEQ ID NO: 680          moltype = DNA  length = 100
FEATURE                 Location/Qualifiers
source                  1..100
                        mol_type = genomic DNA
                        organism = Homo sapiens
SEQUENCE: 680
cccagcccag ctcagcgcag cccagcctag ctcaccccag ccaggtccag cttagcccag  60
ctcagcccag cccaactcag ctcagcccag ctcagcccaa                        100

SEQ ID NO: 681          moltype = DNA  length = 100
FEATURE                 Location/Qualifiers
source                  1..100
                        mol_type = genomic DNA
                        organism = Homo sapiens
SEQUENCE: 681
tctgagctcc aggggctgcc cacctgctcc tcctgcttcc caccggccct gctcacctgc  60
agctgctctg ccctggctcc ctgaggctga gcctcagtcc                        100

SEQ ID NO: 682          moltype = DNA  length = 100
FEATURE                 Location/Qualifiers
source                  1..100
                        mol_type = genomic DNA
                        organism = Homo sapiens
SEQUENCE: 682
tgctcacctt ctgatgctct ccccttgtcc cctgagctcc aggggctgac ccctgatctt  60
tctgcttcct acctgcccct gctcacctgt ggctgctctg                        100

SEQ ID NO: 683          moltype = DNA  length = 100
FEATURE                 Location/Qualifiers
source                  1..100
                        mol_type = genomic DNA
                        organism = Homo sapiens
SEQUENCE: 683
ccctgatccc ctgagctcca ggagctgcct cctgctcttc ctgcctccca cctgcccctg  60
ctcacctgca gatctgccct ggctctctga ggtccagggg                        100

SEQ ID NO: 684          moltype = DNA  length = 100
FEATURE                 Location/Qualifiers
source                  1..100
                        mol_type = genomic DNA
                        organism = Homo sapiens
SEQUENCE: 684
ctgcccccctg ctcgcccacc tcccaccagc catgctgacg ttgtgatgct ctgccctggt  60
ctcctgaggt ccaggggctg tcccctgctt attctgcctc                        100

SEQ ID NO: 685          moltype = DNA  length = 100
FEATURE                 Location/Qualifiers
source                  1..100
                        mol_type = genomic DNA
```

```
                         organism = Homo sapiens
SEQUENCE: 685
ccacctgccc cttctcacct gaggctcttc tgccctggtg ctctgagctc caaaagctgc  60
ccacttgctc ctcctgcttc ctaccagccc ctgctctcct                        100

SEQ ID NO: 686           moltype = DNA  length = 100
FEATURE                  Location/Qualifiers
source                   1..100
                         mol_type = genomic DNA
                         organism = Homo sapiens
SEQUENCE: 686
gtggatgatc tgccctggct ctctgagctc caggggctgc ccacctgctc cccatgcttc  60
ccacctgccc ctgctgacct gcggctgctc tgccttggct                        100

SEQ ID NO: 687           moltype = DNA  length = 100
FEATURE                  Location/Qualifiers
source                   1..100
                         mol_type = genomic DNA
                         organism = Homo sapiens
SEQUENCE: 687
ccctgagctc caggagcttc cccctgctca tcctgccccc cactggcccc tgttcacctt  60
cagatgccct ccctggtccc ctgaagtcca ggagctgccc                        100

SEQ ID NO: 688           moltype = DNA  length = 100
FEATURE                  Location/Qualifiers
source                   1..100
                         mol_type = genomic DNA
                         organism = Homo sapiens
SEQUENCE: 688
cctgttcctc ccgcctccca ccagcccgtg ctcacctgcg gctgctctgc cctggtcccc  60
tgagttccag gggctgcccc ctgctcgccc acctcccact                        100

SEQ ID NO: 689           moltype = DNA  length = 100
FEATURE                  Location/Qualifiers
source                   1..100
                         mol_type = genomic DNA
                         organism = Homo sapiens
SEQUENCE: 689
agccatgctc acctcctgat gctctgtcct ggtcccctga gctccagggg ctgccccctg  60
cttgcccatc tcccactagc catgctcacc ttctgatgct                        100

SEQ ID NO: 690           moltype = DNA  length = 100
FEATURE                  Location/Qualifiers
source                   1..100
                         mol_type = genomic DNA
                         organism = Homo sapiens
SEQUENCE: 690
ctgccctggt cccctgagct ccagggtctt ccccctgctc atcctgccgc ccaccagccc  60
ctgctcacct gaggctgctc tgccctggtc ccctgagctc                        100

SEQ ID NO: 691           moltype = DNA  length = 100
FEATURE                  Location/Qualifiers
source                   1..100
                         mol_type = genomic DNA
                         organism = Homo sapiens
SEQUENCE: 691
cccctgagct ccagggtctt ccccctgctc atcctgccgc ccaccagccc ctgctcacct  60
gaggctgctc tgccctggtc ccctgagctc caggaggtgc                        100

SEQ ID NO: 692           moltype = DNA  length = 100
FEATURE                  Location/Qualifiers
source                   1..100
                         mol_type = genomic DNA
                         organism = Homo sapiens
SEQUENCE: 692
ttctgccccc acctgccctg ctcacctgtg gctgcttggt cctggtccct gagctccaat  60
gcctgctccc tgctcactct gccctccctc aacccgggca                        100

SEQ ID NO: 693           moltype = DNA  length = 100
FEATURE                  Location/Qualifiers
source                   1..100
                         mol_type = genomic DNA
                         organism = Homo sapiens
SEQUENCE: 693
gcaatgtcac tcaggtcact gttgccccc tgcctgtcct ggcaccctct gtccaggttt  60
gggctgtttt tctgccctca tttttgattt tgcagcactt                        100

SEQ ID NO: 694           moltype = DNA  length = 100
FEATURE                  Location/Qualifiers
```

```
source                  1..100
                        mol_type = genomic DNA
                        organism = Homo sapiens
SEQUENCE: 694
cctctgtcca ggtttgggct gtttttctgc cctcattttt gattttgcag cacttggcgt  60
gttccctatg ctgtggagca gccccagtgt ccagtcaggt                        100

SEQ ID NO: 695          moltype = DNA  length = 100
FEATURE                 Location/Qualifiers
source                  1..100
                        mol_type = genomic DNA
                        organism = Homo sapiens
SEQUENCE: 695
agtgtccagt caggtctccc caacagagcc ccttgccctt gcccatgtgc ccctcctgaa  60
tgagctcccg gatcctcctg tccctgcact gctcctgctc                        100

SEQ ID NO: 696          moltype = DNA  length = 100
FEATURE                 Location/Qualifiers
source                  1..100
                        mol_type = genomic DNA
                        organism = Homo sapiens
SEQUENCE: 696
tggaagcctc tctggaacct cagctcctca gtggcctctg ctctgctggg tcagttccct  60
gaacgcacgg agcctcagcc cttcccctcg ccccaggcct                        100

SEQ ID NO: 697          moltype = DNA  length = 100
FEATURE                 Location/Qualifiers
source                  1..100
                        mol_type = genomic DNA
                        organism = Homo sapiens
SEQUENCE: 697
gctgcactct gggcctttct gggcctccct ggactcttcc cttctcccgc ccgtgcactc  60
agcacagctc tcccctcctc tccactgctg accacagccc                        100

SEQ ID NO: 698          moltype = DNA  length = 100
FEATURE                 Location/Qualifiers
source                  1..100
                        mol_type = genomic DNA
                        organism = Homo sapiens
SEQUENCE: 698
tgctccccgc cagcaggtgc cccaacccca tcagctggct ctgagcccag cccctgtgcc  60
tcccctgtcc ctgcctctgc ctctgggctc cttggcttcc                        100

SEQ ID NO: 699          moltype = DNA  length = 100
FEATURE                 Location/Qualifiers
source                  1..100
                        mol_type = genomic DNA
                        organism = Homo sapiens
SEQUENCE: 699
acctgctgtc cttggtcctg gctgagagga gggccccacg gccagcactg ctgaccctgc  60
cctgggctcc ggtgatgctg ccggcctgga caagcccctc                        100

SEQ ID NO: 700          moltype = DNA  length = 100
FEATURE                 Location/Qualifiers
source                  1..100
                        mol_type = genomic DNA
                        organism = Homo sapiens
SEQUENCE: 700
cgttcacctg gggcctctcc tcctccctcg ctctgctgcc tcctgagctc aggtcggtcg  60
tgcccatcct ggcatcaccc cacggccggc tctgccgcat                        100

SEQ ID NO: 701          moltype = DNA  length = 100
FEATURE                 Location/Qualifiers
source                  1..100
                        mol_type = genomic DNA
                        organism = Homo sapiens
SEQUENCE: 701
ccagtcatgt tcctcgtgct cccagcccgg tcgtcctgga ggcctcagtc agcctctggt  60
gtgtcctgcc ctgttggctt ggaagcccct gcccacggtc                        100

SEQ ID NO: 702          moltype = DNA  length = 100
FEATURE                 Location/Qualifiers
source                  1..100
                        mol_type = genomic DNA
                        organism = Homo sapiens
SEQUENCE: 702
cccgtcgtct cgcactgggt gggcatcggt gcctgaaggc tgcccacctc ccccgtgctg  60
gctccgcttg ggcctccatg tggggccggc ctcgacccca                        100
```

```
SEQ ID NO: 703         moltype = DNA  length = 100
FEATURE                Location/Qualifiers
source                 1..100
                       mol_type = genomic DNA
                       organism = Homo sapiens
SEQUENCE: 703
cactgcactt tcaccagccc tcagctgtct gctgccggca actacccagc tcctgccaaa  60
gtctaggagc tgcgtgctgc ctcccaccgt ccctgctcac                        100

SEQ ID NO: 704         moltype = DNA  length = 100
FEATURE                Location/Qualifiers
source                 1..100
                       mol_type = genomic DNA
                       organism = Homo sapiens
SEQUENCE: 704
ctgtggctgc tctgccctgg tgctctgagc tccaggagat gccccctgct cctcctgccc  60
cccacctgcc cctgctcacc tgcagcggct ctgccctggt                        100

SEQ ID NO: 705         moltype = DNA  length = 100
FEATURE                Location/Qualifiers
source                 1..100
                       mol_type = genomic DNA
                       organism = Homo sapiens
SEQUENCE: 705
gagctccaag agctgccccc tgctcctcct gtcccctgac cctgctcctg tttgcctatg  60
gctgctctgc ccttgtcccc tgagctccag gagctgcccc                        100

SEQ ID NO: 706         moltype = DNA  length = 100
FEATURE                Location/Qualifiers
source                 1..100
                       mol_type = genomic DNA
                       organism = Homo sapiens
SEQUENCE: 706
tgctcattct gccgcccacc tgcccctgtt cacctgtggc tgctcttccc tggtcctctg  60
agctccatga gctgcccctt gctcctcctg ctttccacca                        100

SEQ ID NO: 707         moltype = DNA  length = 100
FEATURE                Location/Qualifiers
source                 1..100
                       mol_type = genomic DNA
                       organism = Homo sapiens
SEQUENCE: 707
gcccctgctc acctaccgat gatcttcccc ggctctctga gctccagggg ctgcccacct  60
gctacccctg cttcccacca gccctgctta cctgcagctg                        100

SEQ ID NO: 708         moltype = DNA  length = 100
FEATURE                Location/Qualifiers
source                 1..100
                       mol_type = genomic DNA
                       organism = Homo sapiens
SEQUENCE: 708
ctctgccctg gctggcagag ctgcagaagc tgccccctgc tctgcaacct cccaccggcc  60
cttctcatct tctgatgttc tcccctgttc cctgagctcc                        100

SEQ ID NO: 709         moltype = DNA  length = 100
FEATURE                Location/Qualifiers
source                 1..100
                       mol_type = genomic DNA
                       organism = Homo sapiens
SEQUENCE: 709
aggagctgcc ccctactcgt tctacctccc accaacccgt gctcacctgc gactgctctg  60
ccctggtccc ctgagctcca ggggctgccc cctgctcgcc                        100

SEQ ID NO: 710         moltype = DNA  length = 100
FEATURE                Location/Qualifiers
source                 1..100
                       mol_type = genomic DNA
                       organism = Homo sapiens
SEQUENCE: 710
tgccctgatc ccctgagctc caggactgcc ccctgctcgt cctgcccctc acctgcccct  60
gctcacctga ggctgctctg ccctggtccc ctgagctaaa                        100

SEQ ID NO: 711         moltype = DNA  length = 100
FEATURE                Location/Qualifiers
source                 1..100
                       mol_type = genomic DNA
                       organism = Homo sapiens
SEQUENCE: 711
ggggctgccc cttactcatc ctgcctccca ccagcccctg ctcaccttct gatgccctcc  60
```

```
cctggtcccc tgagctccag gggctgcccc ctgctcgtcc                      100

SEQ ID NO: 712          moltype = DNA  length = 100
FEATURE                 Location/Qualifiers
source                  1..100
                        mol_type = genomic DNA
                        organism = Homo sapiens
SEQUENCE: 712
gggctgcccc ctgctcgtcc tgcctcccac cagcccctgc tcacctgcag ctacactgcc  60
ctggttccct gagctccagg agctgccacc tgcttgtcct                      100

SEQ ID NO: 713          moltype = DNA  length = 100
FEATURE                 Location/Qualifiers
source                  1..100
                        mol_type = genomic DNA
                        organism = Homo sapiens
SEQUENCE: 713
gccttccacc agcccctgct cacctgcagc tacactgccc tggttccctg agctccggga  60
gctgccgcct gcttgtcctg cctcccacca gcccctgctc                      100

SEQ ID NO: 714          moltype = DNA  length = 100
FEATURE                 Location/Qualifiers
source                  1..100
                        mol_type = genomic DNA
                        organism = Homo sapiens
SEQUENCE: 714
acctgtggct acactgccct ggtgccctga gctccaggag ctgccccctg cttgcccatc  60
ttccactgag ccctgctcac ctgcaactgc tctgccctgg                      100

SEQ ID NO: 715          moltype = DNA  length = 100
FEATURE                 Location/Qualifiers
source                  1..100
                        mol_type = genomic DNA
                        organism = Homo sapiens
SEQUENCE: 715
ctctatgagc tccaggggct gccccctgct ggtcctgcct cccacctgcc ctgcgcacct  60
gtggctgcct cctcacctgt ggctgctctg ccctggtccc                      100

SEQ ID NO: 716          moltype = DNA  length = 100
FEATURE                 Location/Qualifiers
source                  1..100
                        mol_type = genomic DNA
                        organism = Homo sapiens
SEQUENCE: 716
ctgagctcca gggtcttcct cctgctcatc ctgcccctcc accggctcct gttcaccttc  60
agatgctctc ccgtggtccc ctgagctcca ggagctgccc                      100

SEQ ID NO: 717          moltype = DNA  length = 100
FEATURE                 Location/Qualifiers
source                  1..100
                        mol_type = genomic DNA
                        organism = Homo sapiens
SEQUENCE: 717
cctgttcttc ctgcctccca cctgccctgt gcacctgtgg ctgcttggtc ctggtcccct  60
gaactccaat gcctgccccc tgctcactct gccctccctc                      100

SEQ ID NO: 718          moltype = DNA  length = 100
FEATURE                 Location/Qualifiers
source                  1..100
                        mol_type = genomic DNA
                        organism = Homo sapiens
SEQUENCE: 718
aacctggggc agcaacgtca ctcggtccac tgttgccccc ctgcctgtcc tggcaccctc  60
tgtccaggtt taggctgttt ttcttgcctc atttttgttt                      100

SEQ ID NO: 719          moltype = DNA  length = 100
FEATURE                 Location/Qualifiers
source                  1..100
                        mol_type = genomic DNA
                        organism = Homo sapiens
SEQUENCE: 719
tggcaccctc tgtccaggtt taggctgttt ttcttgcctc atttttgttt ttgcagcact  60
tggcgtgttc cctatgctgt ggagcagccc cagtgtccag                      100

SEQ ID NO: 720          moltype = DNA  length = 100
FEATURE                 Location/Qualifiers
source                  1..100
                        mol_type = genomic DNA
                        organism = Homo sapiens
```

```
SEQUENCE: 720
tccagtcagg tctccccaac agagcccctt gcccttgccc atgtgcccct cctggatgag  60
ctcccggatc ctcccgtccc tgcactgctc ctgctctgga                        100

SEQ ID NO: 721         moltype = DNA  length = 100
FEATURE                Location/Qualifiers
source                 1..100
                       mol_type = genomic DNA
                       organism = Homo sapiens
SEQUENCE: 721
agcctctcca gaacctcagc tcctcagtgg cctctgctct gctgggtcag ttccctgaac  60
gcacggagcc tcagcccctc ccctcgcccc aggcctgctg                        100

SEQ ID NO: 722         moltype = DNA  length = 100
FEATURE                Location/Qualifiers
source                 1..100
                       mol_type = genomic DNA
                       organism = Homo sapiens
SEQUENCE: 722
cactctgggc ctttctgggc ctccctggac tcttccctcc tcccgcccgt gcactcagca  60
cagctctccc ctcctctccg ctgctgacca cagccctgct                        100

SEQ ID NO: 723         moltype = DNA  length = 100
FEATURE                Location/Qualifiers
source                 1..100
                       mol_type = genomic DNA
                       organism = Homo sapiens
SEQUENCE: 723
gaccacagcc ctgctcccgg ccagcaggtg ccccaacccc atcagctggc tctgagccca  60
gcccctgtgc ctcccctgtc cctgcctctg cctctgggct                        100

SEQ ID NO: 724         moltype = DNA  length = 100
FEATURE                Location/Qualifiers
source                 1..100
                       mol_type = genomic DNA
                       organism = Homo sapiens
SEQUENCE: 724
gctctgctcc cagctcacct gctgtccttg gtcctggctg agaggagggc cctacggcca  60
gctctgctga ccctgccctg ggctccggtg atgctgccgg                        100

SEQ ID NO: 725         moltype = DNA  length = 100
FEATURE                Location/Qualifiers
source                 1..100
                       mol_type = genomic DNA
                       organism = Homo sapiens
SEQUENCE: 725
cctggacaag cccctcggtt cacctggggc ctctcctcct ccctctctct gctgcctcct  60
gagctcaggt cggtcatgcc catcctggca tcaccccatg                        100

SEQ ID NO: 726         moltype = DNA  length = 100
FEATURE                Location/Qualifiers
source                 1..100
                       mol_type = genomic DNA
                       organism = Homo sapiens
SEQUENCE: 726
gctggctctg ccccatcccg tcatgttcct cacactccca gcccggtcgt cctggaggcc  60
tcagtcagcc tctggtgtgt cctgccctgt tggcttggaa                        100

SEQ ID NO: 727         moltype = DNA  length = 100
FEATURE                Location/Qualifiers
source                 1..100
                       mol_type = genomic DNA
                       organism = Homo sapiens
SEQUENCE: 727
gggtagagcc cacctcgtgg cctgcaagcc agccagcccc tgccggtcga gaaggaagcc  60
tgtgtgagag cacacaactg gaggccgggc ggggaagaga                        100

SEQ ID NO: 728         moltype = DNA  length = 100
FEATURE                Location/Qualifiers
source                 1..100
                       mol_type = genomic DNA
                       organism = Homo sapiens
SEQUENCE: 728
aacacgtgcc aacaggccac gcaggccagg accccagacc cggaggcagc gccccttga   60
gttcctctct ctggtctccg atgttcttct gttgggatca                        100

SEQ ID NO: 729         moltype = DNA  length = 100
FEATURE                Location/Qualifiers
source                 1..100
```

```
                         mol_type = genomic DNA
                         organism = Homo sapiens
SEQUENCE: 729
tttcacctac aggcaacaga gacagtgtga aatgctttcc ctgtggtcgg gaagggagcc  60
ggggcagaga tgacccagtg gggtggtgtg ggggcctccg                        100

SEQ ID NO: 730           moltype = DNA  length = 100
FEATURE                  Location/Qualifiers
source                   1..100
                         mol_type = genomic DNA
                         organism = Homo sapiens
SEQUENCE: 730
ctttgcacac cacgtgttcg tctgtgccct gcatgacgtc cttggaaggc agcagcacct  60
gtgaggtggc tgcgtacttg ccccctctca ggactgatgg                        100

SEQ ID NO: 731           moltype = DNA  length = 100
FEATURE                  Location/Qualifiers
source                   1..100
                         mol_type = genomic DNA
                         organism = Homo sapiens
SEQUENCE: 731
gaagccccgg gtgctgctga tgtcagagtt gttcttgtat ttccaggaga aagtgatgga  60
gtcgggaagg aagtcctgtg cgaggcagcc aacggccacg                        100

SEQ ID NO: 732           moltype = DNA  length = 100
FEATURE                  Location/Qualifiers
source                   1..100
                         mol_type = genomic DNA
                         organism = Homo sapiens
SEQUENCE: 732
ctgctcgtat ccgacgggga attctcacag gagacgaggg ggaaaagggt tggggcggat  60
gcactccctg aggacccgca ggacaaaaga gaaagggagg                        100

SEQ ID NO: 733           moltype = DNA  length = 100
FEATURE                  Location/Qualifiers
source                   1..100
                         mol_type = genomic DNA
                         organism = Homo sapiens
SEQUENCE: 733
actccagcta ccctgaagtc tccccaggca gacaacccag gcctgggagt gagtataggg  60
agggtgggtg tgatggggaa cgcagtgtag actcagctga                        100

SEQ ID NO: 734           moltype = DNA  length = 100
FEATURE                  Location/Qualifiers
source                   1..100
                         mol_type = genomic DNA
                         organism = Homo sapiens
SEQUENCE: 734
ggctatccat ctatgtccaa caagatcatg aagattggcc cagtgccatg tcctccagtt  60
catcccagcc caggccagct caatccagtt catcccagcc                        100

SEQ ID NO: 735           moltype = DNA  length = 100
FEATURE                  Location/Qualifiers
source                   1..100
                         mol_type = genomic DNA
                         organism = Homo sapiens
SEQUENCE: 735
caggccagct caatccagcc cagcccaccc caccccagct cagcaaagcc aagctcagct  60
cagcccaact cagatgagct cagaccagct cagcccagcc                        100

SEQ ID NO: 736           moltype = DNA  length = 100
FEATURE                  Location/Qualifiers
source                   1..100
                         mol_type = genomic DNA
                         organism = Homo sapiens
SEQUENCE: 736
cagctcagct cagcccaacc cagcccagct cgctcaacct tgctcggctc agcttagccc  60
agcccagccc agctcaatcc agcctggctc agcccagccc                        100

SEQ ID NO: 737           moltype = DNA  length = 100
FEATURE                  Location/Qualifiers
source                   1..100
                         mol_type = genomic DNA
                         organism = Homo sapiens
SEQUENCE: 737
agcccagttt ggctcaaccc agcttggctc agcccaggtc agcctggctc aactcagccc  60
agcccagccc agctctgctc aacccagctc tgctcaactc                        100

SEQ ID NO: 738           moltype = DNA  length = 100
```

```
FEATURE                Location/Qualifiers
source                 1..100
                       mol_type = genomic DNA
                       organism = Homo sapiens
SEQUENCE: 738
agcccagctc atcccagctc agcccagccc agcctagctt agctcaaccc agctcagctc  60
agttcagctc agccctgctc agcacagcac agcagagccc                        100

SEQ ID NO: 739         moltype = DNA  length = 100
FEATURE                Location/Qualifiers
source                 1..100
                       mol_type = genomic DNA
                       organism = Homo sapiens
SEQUENCE: 739
agcccggatc ggctcaaccc agcttagctc agcccaggtc agcccagctt aactcagccc  60
aggtcagccc agcttaactc agcccagccc agcccagctc                        100

SEQ ID NO: 740         moltype = DNA  length = 100
FEATURE                Location/Qualifiers
source                 1..100
                       mol_type = genomic DNA
                       organism = Homo sapiens
SEQUENCE: 740
tcagcccagt tcagcccagc tcagcccagc ccagcctagc ttggctcaac acagctcagc  60
tcagccagcc cagaccagct cagctcagcc cagtccagct                        100

SEQ ID NO: 741         moltype = DNA  length = 100
FEATURE                Location/Qualifiers
source                 1..100
                       mol_type = genomic DNA
                       organism = Homo sapiens
SEQUENCE: 741
caacccagcc cagcccaacc cagctcggct taacccagct cggctcagcc cagatcagcc  60
tggctcaact cagcccagcc cagctcaacc cagcccagtt                        100

SEQ ID NO: 742         moltype = DNA  length = 100
FEATURE                Location/Qualifiers
source                 1..100
                       mol_type = genomic DNA
                       organism = Homo sapiens
SEQUENCE: 742
cagctcagct gagcccagcc cagcccagtc cggctcagct cagccccgcc ccactcagcc  60
cagctcagct cagcccagct cagcccagct cagcttagcc                        100

SEQ ID NO: 743         moltype = DNA  length = 100
FEATURE                Location/Qualifiers
source                 1..100
                       mol_type = genomic DNA
                       organism = Homo sapiens
SEQUENCE: 743
cagcccagat catcccagct cagctcagct cagctcggct tagcccagct caacctggcc  60
cagcctggtc caggtcagcc cagcctggac cacccagccc                        100

SEQ ID NO: 744         moltype = DNA  length = 100
FEATURE                Location/Qualifiers
source                 1..100
                       mol_type = genomic DNA
                       organism = Homo sapiens
SEQUENCE: 744
agctcagctc agcccagctc atcctggttc agctcagctc aacccggctc agcccaggtc  60
tgctcaaccc agcccaaatc agctcagccc agcccaggtc                        100

SEQ ID NO: 745         moltype = DNA  length = 100
FEATURE                Location/Qualifiers
source                 1..100
                       mol_type = genomic DNA
                       organism = Homo sapiens
SEQUENCE: 745
atcccagctc agcccagcac agcctacttc agctcagctc agctcagcct aggtcagctc  60
agttgaggtc agctcaactc agcccaatcc agcctggctc                        100

SEQ ID NO: 746         moltype = DNA  length = 100
FEATURE                Location/Qualifiers
source                 1..100
                       mol_type = genomic DNA
                       organism = Homo sapiens
SEQUENCE: 746
agcccagctc accctagctc agcttagctc agcccaactc aacccagccc agccttgccc  60
aacccagctc agctcagccc agcccaggtt agcccagccc                        100
```

```
SEQ ID NO: 747          moltype = DNA  length = 100
FEATURE                 Location/Qualifiers
source                  1..100
                        mol_type = genomic DNA
                        organism = Homo sapiens
SEQUENCE: 747
agcctcggct tagctctgct cagctcggcc ctgctcgcct cagcccgttc agcccagttc  60
agctcagctc agctcagccc agctcagccc agccctggtt                        100

SEQ ID NO: 748          moltype = DNA  length = 100
FEATURE                 Location/Qualifiers
source                  1..100
                        mol_type = genomic DNA
                        organism = Homo sapiens
SEQUENCE: 748
agctcagccc agctaagctc agctcggctt ggctctgctg agcttggccc agcttggctt  60
agcctgatac aacctgctca gcccagttca gctcggctca                        100

SEQ ID NO: 749          moltype = DNA  length = 100
FEATURE                 Location/Qualifiers
source                  1..100
                        mol_type = genomic DNA
                        organism = Homo sapiens
SEQUENCE: 749
gcccagcgta gctcagctca gctgagccca gcccaggtta gctcagcccc agtccaggtc  60
agctcaactc agcccaaacc agcctggctc ggcccagctc                        100

SEQ ID NO: 750          moltype = DNA  length = 100
FEATURE                 Location/Qualifiers
source                  1..100
                        mol_type = genomic DNA
                        organism = Homo sapiens
SEQUENCE: 750
accctagttc agcttagctc agcccagccc agccctgccc aacccagctc agctcagccc  60
agcccaggtt agcccagccc agcctcggct tagctctgct                        100

SEQ ID NO: 751          moltype = DNA  length = 100
FEATURE                 Location/Qualifiers
source                  1..100
                        mol_type = genomic DNA
                        organism = Homo sapiens
SEQUENCE: 751
agcccagccc aggttagccc agcccagcct cggcttagct ctgctcagct cggcccagcc  60
caggttagcc cagcccagcc tcggcttagc tctgctcagc                        100

SEQ ID NO: 752          moltype = DNA  length = 100
FEATURE                 Location/Qualifiers
source                  1..100
                        mol_type = genomic DNA
                        organism = Homo sapiens
SEQUENCE: 752
tcggccctgc tcgcctcagc ccgttcagcc cagttcagct cagctcagct cagcccagct  60
cagcccagcc ctggttagct cagcccagct aagctcagct                        100

SEQ ID NO: 753          moltype = DNA  length = 100
FEATURE                 Location/Qualifiers
source                  1..100
                        mol_type = genomic DNA
                        organism = Homo sapiens
SEQUENCE: 753
cggctcagct ctgctgagct cggcccagct tggctcagcc cgacacagcc tgctcagccc  60
agttcagctc ggctcagccc agcccagccc agcgtagctc                        100

SEQ ID NO: 754          moltype = DNA  length = 100
FEATURE                 Location/Qualifiers
source                  1..100
                        mol_type = genomic DNA
                        organism = Homo sapiens
SEQUENCE: 754
agctgagccc agcccaggtt agctcagccc cagcccaggt tagctcagcc cagctcagct  60
ctgcccaggt tagctcagcc ccagtccagg ttagctcagc                        100

SEQ ID NO: 755          moltype = DNA  length = 100
FEATURE                 Location/Qualifiers
source                  1..100
                        mol_type = genomic DNA
                        organism = Homo sapiens
SEQUENCE: 755
```

```
ccagctcagc tctgcccagg ttagctcagc cccagtccag gttagctcag cccagctcag  60
ccttgcccag gttagctcag cccagctaag ctcaacttgg                        100

SEQ ID NO: 756          moltype = DNA  length = 100
FEATURE                 Location/Qualifiers
source                  1..100
                        mol_type = genomic DNA
                        organism = Homo sapiens
SEQUENCE: 756
ctcagctcag cctagcttgg ctcagcccag cacagcacgc tcaacccggt tcagcttggc  60
tcagcccagc ccagcccagc ctagctcagc tcagccccgc                        100

SEQ ID NO: 757          moltype = DNA  length = 100
FEATURE                 Location/Qualifiers
source                  1..100
                        mol_type = genomic DNA
                        organism = Homo sapiens
SEQUENCE: 757
ccagctcagc gcagcccagc tcagctcagc tcagcctagc cttgctcggc ccagctcagc  60
tcagcccagc tcagcctagc cttgctcagc ccagctcagc                        100

SEQ ID NO: 758          moltype = DNA  length = 100
FEATURE                 Location/Qualifiers
source                  1..100
                        mol_type = genomic DNA
                        organism = Homo sapiens
SEQUENCE: 758
tcagcccagc cctgcccagc tcagcccagc ttagtgcagc caagcccagc tcagctcagc  60
tcacctggtg caacttagcc cagctcagct cagctcagct                        100

SEQ ID NO: 759          moltype = DNA  length = 100
FEATURE                 Location/Qualifiers
source                  1..100
                        mol_type = genomic DNA
                        organism = Homo sapiens
SEQUENCE: 759
caacccagtt caactcagcc cagttcagct cagctcagcc cagttcagcc ttgtttagtc  60
taggtcagct taggtcagtt ttgcccatct gagtccattt                        100

SEQ ID NO: 760          moltype = DNA  length = 100
FEATURE                 Location/Qualifiers
source                  1..100
                        mol_type = genomic DNA
                        organism = Homo sapiens
SEQUENCE: 760
ctgaaagctg gatggagttg tcatggccag aaatggtcag cccaccagac ctgcttgtct  60
cagctaaagc catctcattg ccaggttcct gcacagccag                        100

SEQ ID NO: 761          moltype = DNA  length = 100
FEATURE                 Location/Qualifiers
source                  1..100
                        mol_type = genomic DNA
                        organism = Homo sapiens
SEQUENCE: 761
gctggcttcc atcttttgtc tccctctact tgatacccca gttccctgca gtcctgcccc  60
agcgccacct gggttttggt tccaaagcat taccaatcat                        100

SEQ ID NO: 762          moltype = DNA  length = 100
FEATURE                 Location/Qualifiers
source                  1..100
                        mol_type = genomic DNA
                        organism = Homo sapiens
SEQUENCE: 762
taccaccctc cactacctgg gtggaatatt tctttgctgc tttaaagtca ttaaaacatc  60
ttgagaatga gaccaagaat ttaggagcct gtgctgtgat                        100

SEQ ID NO: 763          moltype = DNA  length = 100
FEATURE                 Location/Qualifiers
source                  1..100
                        mol_type = genomic DNA
                        organism = Homo sapiens
SEQUENCE: 763
aaaaatgagc aggtcccctt gctctagaag tggcagcata tcttctgcac caagaggagg  60
gtattgagat gctcagagcc tccaccttcc cggagcatcc                        100

SEQ ID NO: 764          moltype = DNA  length = 100
FEATURE                 Location/Qualifiers
source                  1..100
                        mol_type = genomic DNA
```

```
                        organism = Homo sapiens
SEQUENCE: 764
cctcccttct gagtctgcag taaaccccctg cctttaaatt ccctctagat aacagtcatc  60
attggaaaca accaagaaat gcattttatc tgaatttgcc                          100

SEQ ID NO: 765          moltype = DNA  length = 100
FEATURE                 Location/Qualifiers
source                  1..100
                        mol_type = genomic DNA
                        organism = Homo sapiens
SEQUENCE: 765
acttaaaatt ctgccattta ccataaatcg ctttggaagg catgggctac tttcaagggt  60
gcgatgatga cctacagtca atgacttaga caagggcgat                          100

SEQ ID NO: 766          moltype = DNA  length = 100
FEATURE                 Location/Qualifiers
source                  1..100
                        mol_type = genomic DNA
                        organism = Homo sapiens
SEQUENCE: 766
gccagtgggg cttggtatgt tctcaagcat cattacccat gccatcccca ttcagaggtt  60
gtggagcagc tcgtgcgacc tctccttcaa atgggcttta                          100

SEQ ID NO: 767          moltype = DNA  length = 100
FEATURE                 Location/Qualifiers
source                  1..100
                        mol_type = genomic DNA
                        organism = Homo sapiens
SEQUENCE: 767
gggaaagtta aatgggagtg acccagacaa tggtcactca aaagactcac ataaatgagt  60
ctcctgctct tcatcaagca attaagacca gttccccttc                          100

SEQ ID NO: 768          moltype = DNA  length = 100
FEATURE                 Location/Qualifiers
source                  1..100
                        mol_type = genomic DNA
                        organism = Homo sapiens
SEQUENCE: 768
tagtggaaat aagacgtcaa atacaaagtt ttaagagaag caaatgcagc agcggcggct  60
gcctgtctct taccatgtcg ggcgcctggt cactgcgagc                          100

SEQ ID NO: 769          moltype = DNA  length = 100
FEATURE                 Location/Qualifiers
source                  1..100
                        mol_type = genomic DNA
                        organism = Homo sapiens
SEQUENCE: 769
cttgcaaagc tttggcatgg aatcattcct ccaagtccat taacaagggc tggggcctga  60
gcagccagtc ggcccggcag cagaagccac gcatcccagc                          100

SEQ ID NO: 770          moltype = DNA  length = 100
FEATURE                 Location/Qualifiers
source                  1..100
                        mol_type = genomic DNA
                        organism = Homo sapiens
SEQUENCE: 770
tctgggtagt ccggggagac ccaaagccca ggccgggcct ggcagccacc ctcccagagc  60
ctccgctagg ccagtcctgc tgacgccgca tcggtgattc                          100

SEQ ID NO: 771          moltype = DNA  length = 100
FEATURE                 Location/Qualifiers
source                  1..100
                        mol_type = genomic DNA
                        organism = Homo sapiens
SEQUENCE: 771
ggaacagaat ctgtccttct aaggtgtctc cacagtcctg tcttcagcac tatctgattg  60
agttttctct tatgccacca actaacatgc ttaactgaaa                          100

SEQ ID NO: 772          moltype = DNA  length = 100
FEATURE                 Location/Qualifiers
source                  1..100
                        mol_type = genomic DNA
                        organism = Homo sapiens
SEQUENCE: 772
taattcagga taatgatgca cattttacct aaaacttatc ctaaagtgag tagttgaaaa  60
gtggtcttga aaaatactaa aatgaaggcc actctatcag                          100

SEQ ID NO: 773          moltype = DNA  length = 100
FEATURE                 Location/Qualifiers
```

-continued

```
source                  1..100
                        mol_type = genomic DNA
                        organism = Homo sapiens
SEQUENCE: 773
aatatcaaag tgtttctcct taatcacaaa gagaaaacga gttaacctaa aaagattgtg  60
aacacagtca ttatgaaaat aatgctctga ggtatcgaaa                        100

SEQ ID NO: 774          moltype = DNA  length = 100
FEATURE                 Location/Qualifiers
source                  1..100
                        mol_type = genomic DNA
                        organism = Homo sapiens
SEQUENCE: 774
aagtatttga gattagttat cacatgaagg gataacaagc taatttaaaa aactttttga  60
atacagtcat aaactctccc taagactgtt taatttctta                        100

SEQ ID NO: 775          moltype = DNA  length = 100
FEATURE                 Location/Qualifiers
source                  1..100
                        mol_type = genomic DNA
                        organism = Homo sapiens
SEQUENCE: 775
aacatcttac tttaaaaatg aatgcagttt agaagttgat atgctgtttg cacaaactag  60
cagttgataa gctaagattg gaaatgaaat tcagatagtt                        100

SEQ ID NO: 776          moltype = DNA  length = 100
FEATURE                 Location/Qualifiers
source                  1..100
                        mol_type = genomic DNA
                        organism = Homo sapiens
SEQUENCE: 776
aaaaaaagcc ttttcagttt cggtcagcct cgccttattt tagaaacgca aattgtccag  60
gtgttgtttt gctcagtaga gcactttcag atctgggcct                        100

SEQ ID NO: 777          moltype = DNA  length = 100
FEATURE                 Location/Qualifiers
source                  1..100
                        mol_type = genomic DNA
                        organism = Homo sapiens
SEQUENCE: 777
gggcaaaacc acctcttcac aaccagaagt gataaattta ccaattgtgt ttttttgctt  60
cctaaaatag actctcgcgg tgacctgctt cctgccacct                        100

SEQ ID NO: 778          moltype = DNA  length = 100
FEATURE                 Location/Qualifiers
source                  1..100
                        mol_type = genomic DNA
                        organism = Homo sapiens
SEQUENCE: 778
gctgtgggtg ccggagaccc ccatgcagcc atcttgactc taattcatca tctgcttcca  60
gcttcgctca attaattaaa aaaataaact tgatttatga                        100

SEQ ID NO: 779          moltype = DNA  length = 100
FEATURE                 Location/Qualifiers
source                  1..100
                        mol_type = genomic DNA
                        organism = Homo sapiens
SEQUENCE: 779
tggtcaaaac gcagtcccgc atcggggccg acagcactgt gctagtattt cttagctgag  60
cttgctttgg cctcaattcc agacacatat cactcatggg                        100

SEQ ID NO: 780          moltype = DNA  length = 100
FEATURE                 Location/Qualifiers
source                  1..100
                        mol_type = genomic DNA
                        organism = Homo sapiens
SEQUENCE: 780
tgttaatcaa atgataagaa tttcaaatac ttggacagtt aaaaaaatta atatacttga  60
aaatctctca catttttaag tcataatttt cttaaccatt                        100

SEQ ID NO: 781          moltype = DNA  length = 100
FEATURE                 Location/Qualifiers
source                  1..100
                        mol_type = genomic DNA
                        organism = Homo sapiens
SEQUENCE: 781
tttctcagaa gccacttcaa acatatcctg tcttttaaca gtaagcatgc ctcctaagat  60
aaacaatcct tttctcttgg aaaccagctt caaggcactg                        100
```

-continued

```
SEQ ID NO: 782         moltype = DNA  length = 100
FEATURE                Location/Qualifiers
source                 1..100
                       mol_type = genomic DNA
                       organism = Homo sapiens
SEQUENCE: 782
aggtcctgga gcctccctaa gcccctgtca ggacggcagc caccgtttct gggctacccc  60
tgcccccaac cctgctctca tcaagaccgg ggctacgcgt                        100

SEQ ID NO: 783         moltype = DNA  length = 100
FEATURE                Location/Qualifiers
source                 1..100
                       mol_type = genomic DNA
                       organism = Homo sapiens
SEQUENCE: 783
ccctcctggc tggattcacc cactccgaca gttctctttc cagccaataa agaatttaag  60
atgcaggttg acacacagcg cacctcataa ttctaaagaa                        100

SEQ ID NO: 784         moltype = DNA  length = 100
FEATURE                Location/Qualifiers
source                 1..100
                       mol_type = genomic DNA
                       organism = Homo sapiens
SEQUENCE: 784
aatatttcac gattcgctgc tgtgcagcga tcttgcagtc ctacagacac cgctcctgag  60
acacattcct cagccatcac taagacccct ggtttgttca                        100

SEQ ID NO: 785         moltype = DNA  length = 100
FEATURE                Location/Qualifiers
source                 1..100
                       mol_type = genomic DNA
                       organism = Homo sapiens
SEQUENCE: 785
ggcatctcgt ccaaatgtgg ctccccaagc ccccaggctc agttactcca tcagacgcac  60
ccaacctgag tcccattttc caaaggcatc ggaaaatcca                        100

SEQ ID NO: 786         moltype = DNA  length = 100
FEATURE                Location/Qualifiers
source                 1..100
                       mol_type = genomic DNA
                       organism = Homo sapiens
SEQUENCE: 786
cagaggctcc cagatcctca aggcacccca gtgcccgtcc cctcctggcc agtccgccca  60
ggtcccctcg gaacatgccc cgaggaccaa cctgcaatgc                        100

SEQ ID NO: 787         moltype = DNA  length = 100
FEATURE                Location/Qualifiers
source                 1..100
                       mol_type = genomic DNA
                       organism = Homo sapiens
SEQUENCE: 787
tcaggaaacc ccacaggcag tagcagaaaa caaaggccct agagtggcca ttcttacctg  60
aggagacggt gaccgtggtc cctttgcccc agacgtccat                        100

SEQ ID NO: 788         moltype = DNA  length = 100
FEATURE                Location/Qualifiers
source                 1..100
                       mol_type = genomic DNA
                       organism = Homo sapiens
SEQUENCE: 788
gtagtagtag tagtagtaat cacaatggca gaatgtccat cctcacccca caaaaaccca  60
gccacccaga gaccttctgt ctccgggcgt cacatggaag                        100

SEQ ID NO: 789         moltype = DNA  length = 100
FEATURE                Location/Qualifiers
source                 1..100
                       mol_type = genomic DNA
                       organism = Homo sapiens
SEQUENCE: 789
ctgactgtcc gtggccctgt cctgcccttc tcatggaacc ctctgctggc ctcccacgta  60
ccccacattc tggcctgacc cctcagaagc cagaccactg                        100

SEQ ID NO: 790         moltype = DNA  length = 100
FEATURE                Location/Qualifiers
source                 1..100
                       mol_type = genomic DNA
                       organism = Homo sapiens
SEQUENCE: 790
tcggcctggg aagtccaact gcaagcagac ggctgctaag tcacccccag gagtccaaaa  60
```

-continued

```
accccggggg gcacccgtcc cagagagcgg gtgccttgga                        100

SEQ ID NO: 791          moltype = DNA  length = 100
FEATURE                 Location/Qualifiers
source                  1..100
                        mol_type = genomic DNA
                        organism = Homo sapiens
SEQUENCE: 791
gcgggacaga gtcccaccac gcaatcatca cgacagcccc tgagaatgct ccaggtgaag  60
cggagagagg tcaccccaga ccagccgaag gagcccccca                        100

SEQ ID NO: 792          moltype = DNA  length = 100
FEATURE                 Location/Qualifiers
source                  1..100
                        mol_type = genomic DNA
                        organism = Homo sapiens
SEQUENCE: 792
gctgccgaca tctgtggccg gacttgggga ggacaggctg ggttcccatt cgaagggtcc  60
ctctccccgg ctttctttcc tgacctccaa aatgcctcca                        100

SEQ ID NO: 793          moltype = DNA  length = 100
FEATURE                 Location/Qualifiers
source                  1..100
                        mol_type = genomic DNA
                        organism = Homo sapiens
SEQUENCE: 793
agactctgac cctgagaccc tggcaagctg agtctcccta agtggactca gagagggggt  60
ggtgaggact cacctgagga gacggtgacc agggttccct                        100

SEQ ID NO: 794          moltype = DNA  length = 100
FEATURE                 Location/Qualifiers
source                  1..100
                        mol_type = genomic DNA
                        organism = Homo sapiens
SEQUENCE: 794
ggccccaggg gtcgaaccag ttgtcacatt gtgacaacaa tgccaggacc ccaggcaaga  60
actggcgccc cgctacgtcc ctgggaccct ctcagactga                        100

SEQ ID NO: 795          moltype = DNA  length = 100
FEATURE                 Location/Qualifiers
source                  1..100
                        mol_type = genomic DNA
                        organism = Homo sapiens
SEQUENCE: 795
gcccggggag ggcccggggg ttgttgggca ttggacccca gaggcctagg gtggccctgg  60
ccacagagag acccgtgctg ctgggctcag gaggaaggag                        100

SEQ ID NO: 796          moltype = DNA  length = 100
FEATURE                 Location/Qualifiers
source                  1..100
                        mol_type = genomic DNA
                        organism = Homo sapiens
SEQUENCE: 796
catctggagc ccttgcccct cgtctgtgtg gccgctgttg cctcagggca tcctcctgag  60
ccccccagga tgctccgggg ctctcttggc aggagaccca                        100

SEQ ID NO: 797          moltype = DNA  length = 100
FEATURE                 Location/Qualifiers
source                  1..100
                        mol_type = genomic DNA
                        organism = Homo sapiens
SEQUENCE: 797
gcacccttat ttccccccag aaatgcagca aaacccttca gagttaaagc aggagagagg  60
ttgtgaggac tcacctgagg agacggtgac cagggttccc                        100

SEQ ID NO: 798          moltype = DNA  length = 100
FEATURE                 Location/Qualifiers
source                  1..100
                        mol_type = genomic DNA
                        organism = Homo sapiens
SEQUENCE: 798
tggccccagt agtcaaagta gtcacattgt gggaggcccc attaaggggt gcacaaaaac  60
ctgactctcc gactgtcccg ggccggccgt ggcagccagc                        100

SEQ ID NO: 799          moltype = DNA  length = 100
FEATURE                 Location/Qualifiers
source                  1..100
                        mol_type = genomic DNA
                        organism = Homo sapiens
```

```
SEQUENCE: 799
cccgtgtccc aaggtcattt tgtccccagc acaagcatga ctctgcccac cctttgcccc  60
agcagcagag tcccagttcc caaagaaagg ccttctgctg                        100

SEQ ID NO: 800         moltype = DNA  length = 100
FEATURE                Location/Qualifiers
source                 1..100
                       mol_type = genomic DNA
                       organism = Homo sapiens
SEQUENCE: 800
aacgtggtcc caaacagccg gagaaggagc cccggagggc cccacatggc ccagcgcaga  60
ccaaggagcc cccggacatt atctcccagc tccaggacag                        100

SEQ ID NO: 801         moltype = DNA  length = 100
FEATURE                Location/Qualifiers
source                 1..100
                       mol_type = genomic DNA
                       organism = Homo sapiens
SEQUENCE: 801
aggacgctgg gcccagagaa aggaggcaga aggaaagcca tcttacctga agagacggtg  60
accattgtcc cttggcccca gatatcaaaa gcatcacaca                        100

SEQ ID NO: 802         moltype = DNA  length = 100
FEATURE                Location/Qualifiers
source                 1..100
                       mol_type = genomic DNA
                       organism = Homo sapiens
SEQUENCE: 802
gggacacagt ccctgttcct gcccagacac aaacctgtgc ccgtgcagga cactcgaatg  60
ggtcacatgg cccaagcaca gagcagaggc agccggcgtc                        100

SEQ ID NO: 803         moltype = DNA  length = 100
FEATURE                Location/Qualifiers
source                 1..100
                       mol_type = genomic DNA
                       organism = Homo sapiens
SEQUENCE: 803
cctgtcccca gccacacaga cccccgggct gagacccagg cagggagggg tgacgttccc  60
agggagacgg tggccgggct gccctggccc cagtgctcca                        100

SEQ ID NO: 804         moltype = DNA  length = 100
FEATURE                Location/Qualifiers
source                 1..100
                       mol_type = genomic DNA
                       organism = Homo sapiens
SEQUENCE: 804
agcacttgta gccacactaa agcgcaggcc tggtccccgg cacatgaaca gccagcgccc  60
agccccagcc caggctctgc ccacaacttc tccttcccgt                        100

SEQ ID NO: 805         moltype = DNA  length = 100
FEATURE                Location/Qualifiers
source                 1..100
                       mol_type = genomic DNA
                       organism = Homo sapiens
SEQUENCE: 805
ccctgccctc ggcctgcttg ctacctgtgg agggtccctg acggggctga agcccagcgg  60
ggtccctgcc tgtccttggg ggctccagct ggccccaggg                        100

SEQ ID NO: 806         moltype = DNA  length = 100
FEATURE                Location/Qualifiers
source                 1..100
                       mol_type = genomic DNA
                       organism = Homo sapiens
SEQUENCE: 806
ctaagtgaca gcagggctct ggcatgcagc ccatggcgga gaccccaggg atggcagctg  60
gtgtggcctc aggccagacc caggccggct gcagacccca                        100

SEQ ID NO: 807         moltype = DNA  length = 100
FEATURE                Location/Qualifiers
source                 1..100
                       mol_type = genomic DNA
                       organism = Homo sapiens
SEQUENCE: 807
gatacctggc ctggtgcctg gacagagaag actgggaggg ggctgcagtg ggactcacct  60
gaggagacag tgaccagggt gccacggccc cagagatcga                        100

SEQ ID NO: 808         moltype = DNA  length = 100
FEATURE                Location/Qualifiers
source                 1..100
```

```
                        mol_type = genomic DNA
                        organism = Homo sapiens
SEQUENCE: 808
agtaccagta gcacagcctc tgccctcctg cttctcccat acaaaaacac accctccgcc  60
ctcctgccga cctcctttgc tgagcacctg tccccaagtc                        100

SEQ ID NO: 809          moltype = DNA  length = 100
FEATURE                 Location/Qualifiers
source                  1..100
                        mol_type = genomic DNA
                        organism = Homo sapiens
SEQUENCE: 809
tgaagccaaa gcccttgcct ggcccagtac acctggctcc ccgctatccc cagacagcag  60
actcacctga ggagacggtg accagggtgc cctggcccca                        100

SEQ ID NO: 810          moltype = DNA  length = 100
FEATURE                 Location/Qualifiers
source                  1..100
                        mol_type = genomic DNA
                        organism = Homo sapiens
SEQUENCE: 810
gtgctggaag tattcagcca cggtgagtca gccctgagcc aggggctaca gaaacccaca  60
gcccggggtc ccgggggagc atggtttttg tagagctgcc                        100

SEQ ID NO: 811          moltype = DNA  length = 100
FEATURE                 Location/Qualifiers
source                  1..100
                        mol_type = genomic DNA
                        organism = Homo sapiens
SEQUENCE: 811
aatcactgtg tccccagtta gcacagtggt tctcagctca gccaaaaccc tgcggctggt  60
agggggcctg tggggctggg ggctgatgtg gctgcggtct                        100

SEQ ID NO: 812          moltype = DNA  length = 100
FEATURE                 Location/Qualifiers
source                  1..100
                        mol_type = genomic DNA
                        organism = Homo sapiens
SEQUENCE: 812
tgctgggtct gtcctctgtg ggaggggctg ctacccaggc ccaggactgc agtggagggc  60
tcactgaggg gcttttgggt ctggcctgag ccgctgtggg                        100

SEQ ID NO: 813          moltype = DNA  length = 100
FEATURE                 Location/Qualifiers
source                  1..100
                        mol_type = genomic DNA
                        organism = Homo sapiens
SEQUENCE: 813
gctctcaggt ctactgcggg gacactcggg tctgcccctg gcttaggtgg acagtgtccg  60
tgcccacctg tgccctgagg ctccatttca ggctgatatc                        100

SEQ ID NO: 814          moltype = DNA  length = 100
FEATURE                 Location/Qualifiers
source                  1..100
                        mol_type = genomic DNA
                        organism = Homo sapiens
SEQUENCE: 814
tgtctgtatt gtccctaccc gctgcatggc catgtccttt tgggtttata aattgccccc  60
aaatcacgca ggcatcattc aggcttttta tattccctgg                        100

SEQ ID NO: 815          moltype = DNA  length = 100
FEATURE                 Location/Qualifiers
source                  1..100
                        mol_type = genomic DNA
                        organism = Homo sapiens
SEQUENCE: 815
tattccctgg gccaccaggt gcctccaccc agaaagctga gatgtgggag gttctagagt  60
cattctgcaa ccctggatga gcccctgcag cctcagtgct                        100

SEQ ID NO: 816          moltype = DNA  length = 100
FEATURE                 Location/Qualifiers
source                  1..100
                        mol_type = genomic DNA
                        organism = Homo sapiens
SEQUENCE: 816
actgaggttc cagcaagacc tggagcaggt gcagatgagg cctgaggcca ggtgaagccc  60
aggccaggtg aggtccaggc cagtgaggcc caggtcagat                        100

SEQ ID NO: 817          moltype = DNA  length = 100
```

```
FEATURE                Location/Qualifiers
source                 1..100
                       mol_type = genomic DNA
                       organism = Homo sapiens
SEQUENCE: 817
gaggcccagg tcaggtgaag cccaggtcag gtgaaaccca ggtcaggtga ggcccagatc  60
atgtgagctc aggacaggca aggtccaagt caggtgaggc                        100

SEQ ID NO: 818         moltype = DNA  length = 100
FEATURE                Location/Qualifiers
source                 1..100
                       mol_type = genomic DNA
                       organism = Homo sapiens
SEQUENCE: 818
cgagctcagg tgaagcccag aggtgaggtc taggccaggt gaggtccagg ccaggtgagg  60
tccaggtcag gtgaggccca ggtcaggcaa ggctgaggta                        100

SEQ ID NO: 819         moltype = DNA  length = 100
FEATURE                Location/Qualifiers
source                 1..100
                       mol_type = genomic DNA
                       organism = Homo sapiens
SEQUENCE: 819
tccaggtcag gtgaggccca ggtcaggcaa ggctgaggta gatgtatgag acttctgtaa  60
ttttcagttg gtgccaaccc tgcctggtgt ccctgcccct                        100

SEQ ID NO: 820         moltype = DNA  length = 100
FEATURE                Location/Qualifiers
source                 1..100
                       mol_type = genomic DNA
                       organism = Homo sapiens
SEQUENCE: 820
cctcccagcc catgctctgt gcctgccaga tggcggcccc tgcacaggtg ctgctggctg  60
tggaggagct gggctctgcc tccctgtgca tgggcgtccc                        100

SEQ ID NO: 821         moltype = DNA  length = 100
FEATURE                Location/Qualifiers
source                 1..100
                       mol_type = genomic DNA
                       organism = Homo sapiens
SEQUENCE: 821
gcctgcagcc tgtccgggga tgcccaggga ggtgagtgcc accacatatc aggccttttc  60
tctttaaagt catttctttg gggatacatc atcaatgtct                        100

SEQ ID NO: 822         moltype = DNA  length = 100
FEATURE                Location/Qualifiers
source                 1..100
                       mol_type = genomic DNA
                       organism = Homo sapiens
SEQUENCE: 822
tctaaacaca gctgtgtgca ttttcctctt cttgcaattt agaattttaa ctgctgtttt  60
caaggtactg taatgtattt gttctcttct tgttaggaga                        100

SEQ ID NO: 823         moltype = DNA  length = 100
FEATURE                Location/Qualifiers
source                 1..100
                       mol_type = genomic DNA
                       organism = Homo sapiens
SEQUENCE: 823
cttgccaacc ctgtgtgtct cagttcatac cctcttcctt ccccagtaga agtaacgacc  60
actgtgttta tgtgatcatc cttttcttga ttttccttat                        100

SEQ ID NO: 824         moltype = DNA  length = 100
FEATURE                Location/Qualifiers
source                 1..100
                       mol_type = genomic DNA
                       organism = Homo sapiens
SEQUENCE: 824
tgtgatcatc cttttcttga ttttccttat agttttccta gtggaaagtt tatcccttaa  60
gaagatagtt cattttgccg gctgtaaatt ttatttagaa                        100

SEQ ID NO: 825         moltype = DNA  length = 100
FEATURE                Location/Qualifiers
source                 1..100
                       mol_type = genomic DNA
                       organism = Homo sapiens
SEQUENCE: 825
ctgccatcgt ttatttgcct gttttccttc agatggctgt ttgcttcatt ctcagtttgg  60
ggctatgaca aacatatgtt ctgcacatct ttgcccatga                        100
```

```
SEQ ID NO: 826         moltype = DNA  length = 100
FEATURE                Location/Qualifiers
source                 1..100
                       mol_type = genomic DNA
                       organism = Homo sapiens
SEQUENCE: 826
ggctctcagg gagggctctg gagctggcat tgcctgcagg gctctgcttt gttgcaggga  60
gttcctgcca aggcttttca gagtgtctgt gcccagcctg                        100

SEQ ID NO: 827         moltype = DNA  length = 100
FEATURE                Location/Qualifiers
source                 1..100
                       mol_type = genomic DNA
                       organism = Homo sapiens
SEQUENCE: 827
aaggtacaca ctgtactttg cccttgcatc aggcactttc cttgtgcttg cttctgtgtg  60
gctccacatt ctggagaatt tattcagatc tgtgctgcaa                        100

SEQ ID NO: 828         moltype = DNA  length = 100
FEATURE                Location/Qualifiers
source                 1..100
                       mol_type = genomic DNA
                       organism = Homo sapiens
SEQUENCE: 828
cttcccacac tgtcctcctg ggctcactcc cagccatcga tcttgaacac cagtttatgg  60
aactatctgc acaggaaagc agaaacagca aaaggccctg                        100

SEQ ID NO: 829         moltype = DNA  length = 100
FEATURE                Location/Qualifiers
source                 1..100
                       mol_type = genomic DNA
                       organism = Homo sapiens
SEQUENCE: 829
ttgcgtggac cctgtttttg gtcaagggaa gtacttgctg gtgaaggaga cctcccctcc  60
tttctttctc aggagccccc tctgatgccg ttgcctggtg                        100

SEQ ID NO: 830         moltype = DNA  length = 100
FEATURE                Location/Qualifiers
source                 1..100
                       mol_type = genomic DNA
                       organism = Homo sapiens
SEQUENCE: 830
tttctcaggg ctggtgctgg gggctcagca gtgtctgccc tgttccaggt gggaatgtgg  60
gtctgttctg tttccacgcg gtgttctggg gccgccagtg                        100

SEQ ID NO: 831         moltype = DNA  length = 100
FEATURE                Location/Qualifiers
source                 1..100
                       mol_type = genomic DNA
                       organism = Homo sapiens
SEQUENCE: 831
cagcagtgtc tgccctgttc caggtgggaa tgtgggtctg ttctgtttcc acgcggtgtt  60
ctggggccgc cagtgagggg ctcgggatgt cagcggctgg                        100

SEQ ID NO: 832         moltype = DNA  length = 100
FEATURE                Location/Qualifiers
source                 1..100
                       mol_type = genomic DNA
                       organism = Homo sapiens
SEQUENCE: 832
tctctgtccc tatggtctgg gctccggttc actgctcccc tgccctccag gtcggtcact  60
gactcagtta ctatccagcg ggctccgtgg ctgttcagtg                        100

SEQ ID NO: 833         moltype = DNA  length = 100
FEATURE                Location/Qualifiers
source                 1..100
                       mol_type = genomic DNA
                       organism = Homo sapiens
SEQUENCE: 833
gggagcaaat ggagagggaa gtggcagcgg cccgagtgcc aggcggtccc ggtttggggt  60
tgatctttgt ggaacagctc cctggcccgt gtgtaagtgg                        100

SEQ ID NO: 834         moltype = DNA  length = 100
FEATURE                Location/Qualifiers
source                 1..100
                       mol_type = genomic DNA
                       organism = Homo sapiens
SEQUENCE: 834
```

```
tcgggggagg cacggaggtc tggagctaca agcggtggca ggaaggcagg tcccagtctt  60
gggggtctgg agcttatctt cttcctgtga actgagtgtg                        100

SEQ ID NO: 835          moltype = DNA  length = 100
FEATURE                 Location/Qualifiers
source                  1..100
                        mol_type = genomic DNA
                        organism = Homo sapiens
SEQUENCE: 835
atggaggacc tgcctcggat gacacccta tcttaagaag gtcatggtgg gttccagctg  60
ggaggaaggg aagtgggcca cctcctgggg gtcttccacc                        100

SEQ ID NO: 836          moltype = DNA  length = 100
FEATURE                 Location/Qualifiers
source                  1..100
                        mol_type = genomic DNA
                        organism = Homo sapiens
SEQUENCE: 836
gtcttccacc cccaccacct cagcctgggg cctctgtgat tcctctctgc acagacccca  60
aagtctgtgc tgccgcaggg caggaaggaa gggcctgtgg                        100

SEQ ID NO: 837          moltype = DNA  length = 100
FEATURE                 Location/Qualifiers
source                  1..100
                        mol_type = genomic DNA
                        organism = Homo sapiens
SEQUENCE: 837
tcgaggttgg ggccacagtg gtgttcccta agcccgagtc tggtctcatg gcccgccccg  60
cagcaggtcc tgagtgaggg acagagaccg gggcggggtc                        100

SEQ ID NO: 838          moltype = DNA  length = 100
FEATURE                 Location/Qualifiers
source                  1..100
                        mol_type = genomic DNA
                        organism = Homo sapiens
SEQUENCE: 838
tttggtcctg gtggactctg gggtggattc cagtggggag tcatcagggt cggtgtcccc  60
cagggtactg gggtgtctct gctcctggag tcggctctgg                        100

SEQ ID NO: 839          moltype = DNA  length = 100
FEATURE                 Location/Qualifiers
source                  1..100
                        mol_type = genomic DNA
                        organism = Homo sapiens
SEQUENCE: 839
cctgggtttt tgtacaggag gtgccctggg ctgtgtcttt gtggtctgtg tgcacagtaa  60
tatgtggctg tgtccacagg gtccatgttg gtcattgtaa                        100

SEQ ID NO: 840          moltype = DNA  length = 100
FEATURE                 Location/Qualifiers
source                  1..100
                        mol_type = genomic DNA
                        organism = Homo sapiens
SEQUENCE: 840
gtgtccttgg tgatggtgag cctgctcttc agagatgggc tgtagcgctt atcatcattc  60
caataaatga gtgcaagcca ctccagggcc tttcctgggg                        100

SEQ ID NO: 841          moltype = DNA  length = 100
FEATURE                 Location/Qualifiers
source                  1..100
                        mol_type = genomic DNA
                        organism = Homo sapiens
SEQUENCE: 841
gctgacggat ccagcccaca cccactccac tagtgctgag tgagaaccca gagaaggtgc  60
aggtcagcgt gagggtctgt gtgggtttca ccagcgtagg                        100

SEQ ID NO: 842          moltype = DNA  length = 100
FEATURE                 Location/Qualifiers
source                  1..100
                        mol_type = genomic DNA
                        organism = Homo sapiens
SEQUENCE: 842
ctgtggagaa agcataagaa gatgaagccc acaaacaaga aaactgatgt ttcacccgtg  60
aaggagtccc tgaccacagc actcacatga agggatggtc                        100

SEQ ID NO: 843          moltype = DNA  length = 100
FEATURE                 Location/Qualifiers
source                  1..100
                        mol_type = genomic DNA
```

```
                         organism = Homo sapiens
SEQUENCE: 843
agcagcagga gcgtggagca aagtgtgtcc atggtggggc acaggagtca ctgagctggg  60
acctgtgctc ggctttttca acccagagga gggtggagct                        100

SEQ ID NO: 844           moltype = DNA  length = 100
FEATURE                  Location/Qualifiers
source                   1..100
                         mol_type = genomic DNA
                         organism = Homo sapiens
SEQUENCE: 844
aagtgtgtcc atggtggggc acaggagtca ctgagctggg acctgtgctc ggctttttca  60
acccagagga gggtggagct ggtggagatt tgcattcccc                        100

SEQ ID NO: 845           moltype = DNA  length = 100
FEATURE                  Location/Qualifiers
source                   1..100
                         mol_type = genomic DNA
                         organism = Homo sapiens
SEQUENCE: 845
agatttgcat tcccctcatc tgtgccctac tctatgggat ggagtcaggt ttcaggactc  60
aggagggtgt tgcatctgtg gtgaggacca gtgatagtaa                        100

SEQ ID NO: 846           moltype = DNA  length = 100
FEATURE                  Location/Qualifiers
source                   1..100
                         mol_type = genomic DNA
                         organism = Homo sapiens
SEQUENCE: 846
catgatcagt gtaattcaga tggcattaat ctaaggctgg gcaagtagat tctgagtaga  60
agtctttgca gaagtcatga ttatgaggtc atgttggtct                        100

SEQ ID NO: 847           moltype = DNA  length = 100
FEATURE                  Location/Qualifiers
source                   1..100
                         mol_type = genomic DNA
                         organism = Homo sapiens
SEQUENCE: 847
gcccttcaca gagtccacat agtatttctc acttccatct tgctttatgt tggccaccca  60
ctccagcccc ttccctggag cctggcggac ccagctcatc                        100

SEQ ID NO: 848           moltype = DNA  length = 100
FEATURE                  Location/Qualifiers
source                   1..100
                         mol_type = genomic DNA
                         organism = Homo sapiens
SEQUENCE: 848
tgagtcctct gtgctcagtg ctgatcacca agtggaaagg ccttggagtc cagggctaag  60
gctcctctct gagacctgca gggtcagggt tgggttggtt                        100

SEQ ID NO: 849           moltype = DNA  length = 100
FEATURE                  Location/Qualifiers
source                   1..100
                         mol_type = genomic DNA
                         organism = Homo sapiens
SEQUENCE: 849
ttcatcagta gagggagggc cctatttgca tgtctcctac tatataagaa gctctagtgg  60
gatgctggag gaataggctg tacccatata agaagacggt                        100

SEQ ID NO: 850           moltype = DNA  length = 100
FEATURE                  Location/Qualifiers
source                   1..100
                         mol_type = genomic DNA
                         organism = Homo sapiens
SEQUENCE: 850
agggccctat ttgcatgtct cctactatat aagaagctct agtgggatgc tggaggaata  60
ggctgtaccc atataagaag acggtgctct gcagaagttt                        100

SEQ ID NO: 851           moltype = DNA  length = 100
FEATURE                  Location/Qualifiers
source                   1..100
                         mol_type = genomic DNA
                         organism = Homo sapiens
SEQUENCE: 851
gctgacaatg atggtatttg gaaaatatgc tgtcttatga aattgtgctg tgataaacac  60
tttgccctga tcaccctatt acattttta aaaaatgtgt                         100

SEQ ID NO: 852           moltype = DNA  length = 100
FEATURE                  Location/Qualifiers
```

```
source                  1..100
                        mol_type = genomic DNA
                        organism = Homo sapiens
SEQUENCE: 852
caaacacaga gacaacctag tcagaaactg ccacatatat tcactgctta tctcactcac  60
gtccactcaa tgtctctagt tctccataaa tcacctttta                        100

SEQ ID NO: 853          moltype = DNA  length = 100
FEATURE                 Location/Qualifiers
source                  1..100
                        mol_type = genomic DNA
                        organism = Homo sapiens
SEQUENCE: 853
taatagcaac aaggaaaacc cagctcagcc caaactccat ggtgagtcct ctgtgttcag  60
tgctgatcac cgaatggaaa ctcctgggaa ttctggggct                        100

SEQ ID NO: 854          moltype = DNA  length = 100
FEATURE                 Location/Qualifiers
source                  1..100
                        mol_type = genomic DNA
                        organism = Homo sapiens
SEQUENCE: 854
gtcctctgtg ttcagtgctg atcaccgaat ggaaactcct gggaattctg gggctggggc  60
tcttctccca gagctgcagg gtctgggctc ggctggtttt                        100

SEQ ID NO: 855          moltype = DNA  length = 100
FEATURE                 Location/Qualifiers
source                  1..100
                        mol_type = genomic DNA
                        organism = Homo sapiens
SEQUENCE: 855
tatcagcaga gggagggccc tatttgcatg tctcctacta tatagcaagc tctagtggga  60
cgctggagga gagggcagtg cccagagcag atgagagggt                        100

SEQ ID NO: 856          moltype = DNA  length = 100
FEATURE                 Location/Qualifiers
source                  1..100
                        mol_type = genomic DNA
                        organism = Homo sapiens
SEQUENCE: 856
cccggaaaac actggaggta atcctatctc tcaggaaaat ataacttcag attatgtgat  60
tgtgacttga tgatcaatta gcagtcatca tcttatttaa                        100

SEQ ID NO: 857          moltype = DNA  length = 100
FEATURE                 Location/Qualifiers
source                  1..100
                        mol_type = genomic DNA
                        organism = Homo sapiens
SEQUENCE: 857
tgtttacata tttgcagaat atattcagtg caagtgtcaa tgttacattt ttagagaaga  60
tgaattacat acataacaga gcagttgtgc aatgtgtcca                        100

SEQ ID NO: 858          moltype = DNA  length = 100
FEATURE                 Location/Qualifiers
source                  1..100
                        mol_type = genomic DNA
                        organism = Homo sapiens
SEQUENCE: 858
actcacactt aatctctcta gttctccata aatcaccttt taaaatagca gcaaggaaaa  60
tccagctcag cccaaactcc atggtgagtc ctctgtgttc                        100

SEQ ID NO: 859          moltype = DNA  length = 100
FEATURE                 Location/Qualifiers
source                  1..100
                        mol_type = genomic DNA
                        organism = Homo sapiens
SEQUENCE: 859
gatgctattt aatagcccaa ttcctgaccc aggatgagaa agagcaaata catgacacat  60
ggacgacaca attgtagaag ctgagggttc aagccgtaat                        100

SEQ ID NO: 860          moltype = DNA  length = 100
FEATURE                 Location/Qualifiers
source                  1..100
                        mol_type = genomic DNA
                        organism = Homo sapiens
SEQUENCE: 860
cctgttagag gccacgcatc ccctacccat ccctgaactc tgtgttgaca gagcttcccc  60
cactggagaa caagctcccc caggacacgc acctcactta                        100
```

-continued

```
SEQ ID NO: 861         moltype = DNA  length = 100
FEATURE                Location/Qualifiers
source                 1..100
                       mol_type = genomic DNA
                       organism = Homo sapiens
SEQUENCE: 861
ggcccttcac ggagtctgcg tagtatgtgc taccaccact accactaata gctgagaccc  60
actccagccc cttccctgga gcctggcgga cccagctcat                        100

SEQ ID NO: 862         moltype = DNA  length = 100
FEATURE                Location/Qualifiers
source                 1..100
                       mol_type = genomic DNA
                       organism = Homo sapiens
SEQUENCE: 862
ggcatagctg ctaaaggtga atccagaggc tgcacaggag agtctcaggg accccccagg  60
ctgtaccaag cctcccccag actccaacag ctgcacctca                        100

SEQ ID NO: 863         moltype = DNA  length = 100
FEATURE                Location/Qualifiers
source                 1..100
                       mol_type = genomic DNA
                       organism = Homo sapiens
SEQUENCE: 863
actgtttctc tcactcttat ccattcacac tcaatttttc tatttctcca tgaattacct  60
tttaaaatag ccacaagaaa aagccagctc agcccaaact                        100

SEQ ID NO: 864         moltype = DNA  length = 100
FEATURE                Location/Qualifiers
source                 1..100
                       mol_type = genomic DNA
                       organism = Homo sapiens
SEQUENCE: 864
ccatggtgag ttctctctgt tcagtcctga tcaccaaatg aaaacacctg aaaatcccag  60
ggctgggctc ctctctcaga gctgcagggt cagggctggg                        100

SEQ ID NO: 865         moltype = DNA  length = 100
FEATURE                Location/Qualifiers
source                 1..100
                       mol_type = genomic DNA
                       organism = Homo sapiens
SEQUENCE: 865
tttgcatatc tcctactata tagtaagctc tggggtgaga ggcctttgga gatagtgggg  60
ctcagagcat gtcagaatgt cctcggggag atctgtgata                        100

SEQ ID NO: 866         moltype = DNA  length = 100
FEATURE                Location/Qualifiers
source                 1..100
                       mol_type = genomic DNA
                       organism = Homo sapiens
SEQUENCE: 866
ttgaaagcat tgggaaattg tgctttccta ttgtcagttt gttttgtgat aaacttaaac  60
cttaaaacct aaaaatctta taattttgta atttttattt                        100

SEQ ID NO: 867         moltype = DNA  length = 100
FEATURE                Location/Qualifiers
source                 1..100
                       mol_type = genomic DNA
                       organism = Homo sapiens
SEQUENCE: 867
gaggtaccat agatctacat aaactgcata tttttaaagt tagcaccaat catcttttat  60
ttttacatac gcagagaaac catggtatat agtatcaata                        100

SEQ ID NO: 868         moltype = DNA  length = 100
FEATURE                Location/Qualifiers
source                 1..100
                       mol_type = genomic DNA
                       organism = Homo sapiens
SEQUENCE: 868
ttatttccat gttaaagatg aaaaattatc agcaaaagca caggtgggtt ttacaatgtc  60
cccagtgctc acttttggtc agagtgagcc tgggcatctg                        100

SEQ ID NO: 869         moltype = DNA  length = 100
FEATURE                Location/Qualifiers
source                 1..100
                       mol_type = genomic DNA
                       organism = Homo sapiens
SEQUENCE: 869
tcctacataa tgacagtgta cacatctttc cattgctgtt ttactcaatt actcaaccca  60
```

```
ttttctaaac agatttaaac ttcataaatc ctgtcatctc                        100

SEQ ID NO: 870          moltype = DNA  length = 100
FEATURE                 Location/Qualifiers
source                  1..100
                        mol_type = genomic DNA
                        organism = Homo sapiens
SEQUENCE: 870
ctcagcctca gcacagctgc ctcattcctc agggtttctg acgctctcag gatgtgggtt  60
ttcacactgt gtctgttgca cagtaataca cggccgtgtc                        100

SEQ ID NO: 871          moltype = DNA  length = 100
FEATURE                 Location/Qualifiers
source                  1..100
                        mol_type = genomic DNA
                        organism = Homo sapiens
SEQUENCE: 871
gctcagctcc atgtaggctg tgtctgtaga tgtgtcctcg gtcatggtga ctctgccctg  60
gaacttctgt gcgtagattg tttcaccatc ttcaggatca                        100

SEQ ID NO: 872          moltype = DNA  length = 100
FEATURE                 Location/Qualifiers
source                  1..100
                        mol_type = genomic DNA
                        organism = Homo sapiens
SEQUENCE: 872
ttcaggatca aaacctccca tccactcaag ccctttttcca ggagcctgtc gcacccagtg  60
catggataat tcagtgaggg tgtatccgga aaccttgcag                        100

SEQ ID NO: 873          moltype = DNA  length = 100
FEATURE                 Location/Qualifiers
source                  1..100
                        mol_type = genomic DNA
                        organism = Homo sapiens
SEQUENCE: 873
gagaccttca ctgaggcccc aggcttcttc acctcagccc cagactgtac cagctggacc  60
tgggcgtggg tgcctgtgga gaggacagag gagtggatga                        100

SEQ ID NO: 874          moltype = DNA  length = 100
FEATURE                 Location/Qualifiers
source                  1..100
                        mol_type = genomic DNA
                        organism = Homo sapiens
SEQUENCE: 874
gacaccactt aactggaccc agtcccctca tcagccctgg aactcaggat tctcttgcct  60
gtagctgctg ccaccaagaa gaggatcctc caggtgcagt                        100

SEQ ID NO: 875          moltype = DNA  length = 100
FEATURE                 Location/Qualifiers
source                  1..100
                        mol_type = genomic DNA
                        organism = Homo sapiens
SEQUENCE: 875
gagggtggga atctgggaga gcaaggggct tcccataagt gttctgataa aaatcctctt  60
tgtttagggg gaaagtgatg attttttttga atgatagaga                        100

SEQ ID NO: 876          moltype = DNA  length = 100
FEATURE                 Location/Qualifiers
source                  1..100
                        mol_type = genomic DNA
                        organism = Homo sapiens
SEQUENCE: 876
atacatcacc caaacattta aaaatgtatt gtgtaaagaa gtgtaaatgg catctcagcc  60
atttacacac tgcaagacac acagcttatt agtgtgcctg                        100

SEQ ID NO: 877          moltype = DNA  length = 100
FEATURE                 Location/Qualifiers
source                  1..100
                        mol_type = genomic DNA
                        organism = Homo sapiens
SEQUENCE: 877
tggtgaatcg gcccttcacg gagtctgcat agtatttatt acttccatca tatgatataa  60
ctgccaccca ctccagcccc ttgcctggag cctggcggac                        100

SEQ ID NO: 878          moltype = DNA  length = 100
FEATURE                 Location/Qualifiers
source                  1..100
                        mol_type = genomic DNA
                        organism = Homo sapiens
```

```
SEQUENCE: 878
acaatcactt gagttcagac acaccaggat tcacttaatg ttatttttag ttcagaacct  60
ctatcaggtt tagagggaat cgctctgtcc cagggagtgg                        100

SEQ ID NO: 879         moltype = DNA  length = 100
FEATURE                Location/Qualifiers
source                 1..100
                       mol_type = genomic DNA
                       organism = Homo sapiens
SEQUENCE: 879
atcttacaat agcaaaacgg tcttagaaaa cccaacataa tctacagcga gacctcagca  60
tggcaagcaa ggaatcacta aagccaccag ggagatccgg                        100

SEQ ID NO: 880         moltype = DNA  length = 100
FEATURE                Location/Qualifiers
source                 1..100
                       mol_type = genomic DNA
                       organism = Homo sapiens
SEQUENCE: 880
cactaaagcc accagggaga tccggatgca ctgatacgat ccagaaacat agcgagtccg  60
ggaactgatg cggactttga ggcagcctct tttttttttt                        100

SEQ ID NO: 881         moltype = DNA  length = 100
FEATURE                Location/Qualifiers
source                 1..100
                       mol_type = genomic DNA
                       organism = Homo sapiens
SEQUENCE: 881
gatggtgaat cggcccttca cggagtctgc atagtattta ttacttccat cataccatat  60
aactgccacc cactccagcc ccttgcctgg agcctggcgg                        100

SEQ ID NO: 882         moltype = DNA  length = 100
FEATURE                Location/Qualifiers
source                 1..100
                       mol_type = genomic DNA
                       organism = Homo sapiens
SEQUENCE: 882
acccagtgca tgccatagct actgaaggtg aatccagacg ctgcacagga gagtctcagg  60
gacctcccag gctggaccac gcctccccca gactccacca                        100

SEQ ID NO: 883         moltype = DNA  length = 100
FEATURE                Location/Qualifiers
source                 1..100
                       mol_type = genomic DNA
                       organism = Homo sapiens
SEQUENCE: 883
ctcgactctt gagggacggg ttgtagttgg tgcttccact atgattgatt tccccaatcc  60
actccagccc cttccctggg ggctggcgga tccagctcca                        100

SEQ ID NO: 884         moltype = DNA  length = 100
FEATURE                Location/Qualifiers
source                 1..100
                       mol_type = genomic DNA
                       organism = Homo sapiens
SEQUENCE: 884
ggctggcgga tccagctcca gtagtaacca ctgaaggacc caccatagac agcgcaggtg  60
agggacaggg tctccgaagg cttcaacagt cctgcgcccc                        100

SEQ ID NO: 885         moltype = DNA  length = 100
FEATURE                Location/Qualifiers
source                 1..100
                       mol_type = genomic DNA
                       organism = Homo sapiens
SEQUENCE: 885
actgctgtag ctgcacctgg gacaggaccc ctgtgaacag agaaacccac agtgagccct  60
gggatcagag gcagcatctc atatcttcat atccgcattc                        100

SEQ ID NO: 886         moltype = DNA  length = 100
FEATURE                Location/Qualifiers
source                 1..100
                       mol_type = genomic DNA
                       organism = Homo sapiens
SEQUENCE: 886
ctgagacact cacatctggg agctgccacc aggaggagga agaaccacag gtgtttcatg  60
ttcttgtgca ggaggtccat gactctcaga aagcacttcc                        100

SEQ ID NO: 887         moltype = DNA  length = 100
FEATURE                Location/Qualifiers
source                 1..100
```

```
                         mol_type = genomic DNA
                         organism = Homo sapiens
SEQUENCE: 887
gaggatttgc atgtgggtgg tgcctttgta tggataggta aaaagggatg agggaggccc  60
cagtcttttg ggctcaccct gggaggtgta tgctggctgt                        100

SEQ ID NO: 888           moltype = DNA  length = 100
FEATURE                  Location/Qualifiers
source                   1..100
                         mol_type = genomic DNA
                         organism = Homo sapiens
SEQUENCE: 888
agttctcttc ctgtggcctc ccctcaccaa acccagagtc ctcttcttcc aggtaggaaa  60
tgtgctgaag gagctggtct gggagacaag tgtgatcatg                        100

SEQ ID NO: 889           moltype = DNA  length = 100
FEATURE                  Location/Qualifiers
source                   1..100
                         mol_type = genomic DNA
                         organism = Homo sapiens
SEQUENCE: 889
ggtctgggag acaagtgtga tcatggatca aagacagatt ttggaataca gttaatactg  60
ttctacattt aaagattcat ataacaccaa ccatacaccc                        100

SEQ ID NO: 890           moltype = DNA  length = 100
FEATURE                  Location/Qualifiers
source                   1..100
                         mol_type = genomic DNA
                         organism = Homo sapiens
SEQUENCE: 890
aggtcaccta aattgtcatt taccccttca gacatattga aacagctgct gagtgtaata  60
atcacagtga attgagacaa acctggatcc atgcaatgtg                        100

SEQ ID NO: 891           moltype = DNA  length = 100
FEATURE                  Location/Qualifiers
source                   1..100
                         mol_type = genomic DNA
                         organism = Homo sapiens
SEQUENCE: 891
tactgtagtt cagaacatcc atcatggtta gaaggatgct acctgtccca ggaagtgggt  60
tatttttaaa tagtacctga gagctgccct tctgagacct                        100

SEQ ID NO: 892           moltype = DNA  length = 100
FEATURE                  Location/Qualifiers
source                   1..100
                         mol_type = genomic DNA
                         organism = Homo sapiens
SEQUENCE: 892
tttgaaattt gagattgtgt gtgagatctc aggagaaggt agtagaatat atctccatcc  60
ttctcaatgt gtaaccctga gaatatggcc tgacctctaa                        100

SEQ ID NO: 893           moltype = DNA  length = 100
FEATURE                  Location/Qualifiers
source                   1..100
                         mol_type = genomic DNA
                         organism = Homo sapiens
SEQUENCE: 893
acatttctgt gtgaaaagat gtacattggg gatagcagtg acagcttcag atgaaaactc  60
tatagtacat cagcactgga ggatagtctc atcaccaaga                        100

SEQ ID NO: 894           moltype = DNA  length = 100
FEATURE                  Location/Qualifiers
source                   1..100
                         mol_type = genomic DNA
                         organism = Homo sapiens
SEQUENCE: 894
ttagtgaaat tacctttcct gggaaccaga gaggacctct gtgagctcta ccctctgaga  60
gaacaaggaa ctctggttct tccctgacag gtcacacctg                        100

SEQ ID NO: 895           moltype = DNA  length = 100
FEATURE                  Location/Qualifiers
source                   1..100
                         mol_type = genomic DNA
                         organism = Homo sapiens
SEQUENCE: 895
aacaagtggg ctggccttct atgagacgac agagggaaag agacagactc aatatccaga  60
gcgaggtgag ctccttacct acctaccagg tggtctctgg                        100

SEQ ID NO: 896           moltype = DNA  length = 100
```

```
FEATURE                Location/Qualifiers
source                 1..100
                       mol_type = genomic DNA
                       organism = Homo sapiens
SEQUENCE: 896
gccatttgtt tgagcagacc cagaagtacc ttcctcaccc tcaggagaat tatgaacatt  60
gagagaaact gagatacttt ttttatttac agggaatatt                        100

SEQ ID NO: 897         moltype = DNA  length = 100
FEATURE                Location/Qualifiers
source                 1..100
                       mol_type = genomic DNA
                       organism = Homo sapiens
SEQUENCE: 897
tcatcggcgt gtttacatct acctgggtgt gtacagggat gctaggatgt gctcatacac  60
agaagagcaa gaattatatt tcgtggaaag aaaaccaaag                        100

SEQ ID NO: 898         moltype = DNA  length = 100
FEATURE                Location/Qualifiers
source                 1..100
                       mol_type = genomic DNA
                       organism = Homo sapiens
SEQUENCE: 898
agcttctgaa tttgtaggta ttgtttgctg caaatgtgtc aggtcactag atcatgttat  60
gctgctagaa gaaaaacttc ccaacattgt catggagaca                        100

SEQ ID NO: 899         moltype = DNA  length = 100
FEATURE                Location/Qualifiers
source                 1..100
                       mol_type = genomic DNA
                       organism = Homo sapiens
SEQUENCE: 899
aaatgcaaaa cagtaaagat tcaactgaga ttcccttgaa aatcaccagt aatgaacagg  60
ccaaaagaaa tcaaccattg tggaaagagt ggtcattaag                        100

SEQ ID NO: 900         moltype = DNA  length = 100
FEATURE                Location/Qualifiers
source                 1..100
                       mol_type = genomic DNA
                       organism = Homo sapiens
SEQUENCE: 900
cccagtgtca ccttacacat cctgcaggtc acctcacaca tccaccaggt caccgcacat  60
ataccccaca tcacctcaga cacaccctgg tcacctcata                        100

SEQ ID NO: 901         moltype = DNA  length = 100
FEATURE                Location/Qualifiers
source                 1..100
                       mol_type = genomic DNA
                       organism = Homo sapiens
SEQUENCE: 901
catacgtcag gtcacctcac gctcacccaa ggtcacctca cacatcccgc aggtcacctc  60
gtaaatcccc caggtcacca catacatgca ccagttcacc                        100

SEQ ID NO: 902         moltype = DNA  length = 100
FEATURE                Location/Qualifiers
source                 1..100
                       mol_type = genomic DNA
                       organism = Homo sapiens
SEQUENCE: 902
ctcttgaggg acgggttgta gtaggtgctc ccactataat agatactccc aatccactcc  60
agccccttcc ctgggggctg gcggatccag ccccagtagt                        100

SEQ ID NO: 903         moltype = DNA  length = 100
FEATURE                Location/Qualifiers
source                 1..100
                       mol_type = genomic DNA
                       organism = Homo sapiens
SEQUENCE: 903
aactactact gctgatggag ccaccagaga cagtgcaggt gagggacagg gtctccgaag  60
gcttcaccag tcctgggccc gactcctgca gctgcagctg                        100

SEQ ID NO: 904         moltype = DNA  length = 100
FEATURE                Location/Qualifiers
source                 1..100
                       mol_type = genomic DNA
                       organism = Homo sapiens
SEQUENCE: 904
gaacagaaaa acccacagtg agccctggga tcagaggcag cctcccatat ctccatgtct  60
gcatcctaga aacactcaca tctgggagcc gccaccagca                        100
```

```
SEQ ID NO: 905         moltype = DNA  length = 100
FEATURE                Location/Qualifiers
source                 1..100
                       mol_type = genomic DNA
                       organism = Homo sapiens
SEQUENCE: 905
ggaggaagaa ccacaggtgc ttcattttct tgcacatgag atccatgact ctcagaaagc  60
atttccctta tgagttggac ctgaatttaa ggaaatgtgt                        100

SEQ ID NO: 906         moltype = DNA  length = 100
FEATURE                Location/Qualifiers
source                 1..100
                       mol_type = genomic DNA
                       organism = Homo sapiens
SEQUENCE: 906
ggtggcttcc tgtgggcgcc taagtgagga tttgcatggg ggtggtgcgt ttgtacggag  60
cagtgaaaag ggatgagaga ggcgccagtc ttttgagctc                        100

SEQ ID NO: 907         moltype = DNA  length = 100
FEATURE                Location/Qualifiers
source                 1..100
                       mol_type = genomic DNA
                       organism = Homo sapiens
SEQUENCE: 907
accctgggag gagaatgctg gctgtgccct ttgagaactc agttctcttc ttgggcctcc  60
cctctccaag cccagagtcc tcttcttcca ggtaaagaga                        100

SEQ ID NO: 908         moltype = DNA  length = 100
FEATURE                Location/Qualifiers
source                 1..100
                       mol_type = genomic DNA
                       organism = Homo sapiens
SEQUENCE: 908
tgtgctgaag gagctggtct gagagatgag tgtgatcctg gatcaaggac agattttgga  60
atagggtcag tactgttcaa cccttaaaga ttcatataaa                        100

SEQ ID NO: 909         moltype = DNA  length = 100
FEATURE                Location/Qualifiers
source                 1..100
                       mol_type = genomic DNA
                       organism = Homo sapiens
SEQUENCE: 909
acccaccaca cacccaggcc atctaaatag tcatttaccc tttcagacac attgaaacaa  60
cagctgaatg taataatgac agtgacttca aacaatactg                        100

SEQ ID NO: 910         moltype = DNA  length = 100
FEATURE                Location/Qualifiers
source                 1..100
                       mol_type = genomic DNA
                       organism = Homo sapiens
SEQUENCE: 910
atgtttattg tagttcagaa catccaccat ggttacaggg aagctcactg tccctggaag  60
tgggtcattt tttaaaagca cctgagagct gtccttctgt                        100

SEQ ID NO: 911         moltype = DNA  length = 100
FEATURE                Location/Qualifiers
source                 1..100
                       mol_type = genomic DNA
                       organism = Homo sapiens
SEQUENCE: 911
aaggtagtgg gacatatctc catacttctc aatgtgtgac cttgaagatg tgtcctgccc  60
tctaaacact tctgattgaa aatatgtaga ttggggatta                        100

SEQ ID NO: 912         moltype = DNA  length = 100
FEATURE                Location/Qualifiers
source                 1..100
                       mol_type = genomic DNA
                       organism = Homo sapiens
SEQUENCE: 912
gtggaaatgc cttggaatcc agggctaagg cacctctctg agagctgcag ggtcagggtt  60
gggttggttt tcatcagtag agggagggcc ctatttgcat                        100

SEQ ID NO: 913         moltype = DNA  length = 100
FEATURE                Location/Qualifiers
source                 1..100
                       mol_type = genomic DNA
                       organism = Homo sapiens
SEQUENCE: 913
```

```
ggacccttga ggagtaggct gtacccagat aagacgacgg tgccctgtag aagtttgctg    60
gcaatgattg catttggaaa atatgctgtc ttattatgaa                          100

SEQ ID NO: 914          moltype = DNA  length = 100
FEATURE                 Location/Qualifiers
source                  1..100
                        mol_type = genomic DNA
                        organism = Homo sapiens
SEQUENCE: 914
attgtgctgt gataaacact ttgcactaat caccctattt cattttaaat attcatgtaa    60
actatgttct gtaggagaca atattttctc catttacaga                          100

SEQ ID NO: 915          moltype = DNA  length = 100
FEATURE                 Location/Qualifiers
source                  1..100
                        mol_type = genomic DNA
                        organism = Homo sapiens
SEQUENCE: 915
acactttgca ctaatcaccc tatttcattt taaatattca tgtaaactat gttctgtagg    60
agacaatatt ttctccattt acagaagtgg aagtaaaccc                          100

SEQ ID NO: 916          moltype = DNA  length = 100
FEATURE                 Location/Qualifiers
source                  1..100
                        mol_type = genomic DNA
                        organism = Homo sapiens
SEQUENCE: 916
ctgtatgcat ctaggagctc atgtctggga tgagtgaacc ccggtatctg gccctgtgct    60
cttcatcact gtctctgaca tccccctaaa ccaactccag                          100

SEQ ID NO: 917          moltype = DNA  length = 100
FEATURE                 Location/Qualifiers
source                  1..100
                        mol_type = genomic DNA
                        organism = Homo sapiens
SEQUENCE: 917
gacaaagctg gatgtgtcta gtgtttttat cagaacccac tttccgtaat aagagcatgt    60
gtggttttgc tgccctccag cactcttctg aaaatatgga                          100

SEQ ID NO: 918          moltype = DNA  length = 100
FEATURE                 Location/Qualifiers
source                  1..100
                        mol_type = genomic DNA
                        organism = Homo sapiens
SEQUENCE: 918
gagaactagg atccaggcac attaattttc aggtacttct gacattgaac ttattttttc    60
tatctttcta ttactctttc cttgtctaag tttccatttg                          100

SEQ ID NO: 919          moltype = DNA  length = 100
FEATURE                 Location/Qualifiers
source                  1..100
                        mol_type = genomic DNA
                        organism = Homo sapiens
SEQUENCE: 919
agagagaccc acagtgagcc ctgggatcag aggcacctcc catatcccca tgtctggatc    60
cctgagatac tcacatctgg gagctgccac caggagaagg                          100

SEQ ID NO: 920          moltype = DNA  length = 100
FEATURE                 Location/Qualifiers
source                  1..100
                        mol_type = genomic DNA
                        organism = Homo sapiens
SEQUENCE: 920
aagaaccaca gatgtttcat gttcttgcac aggaggtcca ggactctcag aaagtatttc    60
ccatgtgagc tggaacctga atttaaggaa atgtgtggtg                          100

SEQ ID NO: 921          moltype = DNA  length = 100
FEATURE                 Location/Qualifiers
source                  1..100
                        mol_type = genomic DNA
                        organism = Homo sapiens
SEQUENCE: 921
atttgcatgt gggtggtgcc tttgtatgga gaggtgaaaa aggaggaggg aggccccagt    60
cttttgggct cgccctggga gtaggatgct ggctgtgccc                          100

SEQ ID NO: 922          moltype = DNA  length = 100
FEATURE                 Location/Qualifiers
source                  1..100
                        mol_type = genomic DNA
```

```
                        organism = Homo sapiens
SEQUENCE: 922
tttgagaact cagttgtctt cttggggtct cccctctcca agcccagagt cctcttcttt  60
caggtaaaga gacgtgctga aggacctggt ctgggagatg                        100

SEQ ID NO: 923          moltype = DNA  length = 100
FEATURE                 Location/Qualifiers
source                  1..100
                        mol_type = genomic DNA
                        organism = Homo sapiens
SEQUENCE: 923
ctgacagtgg tgaccatggt tgagaacttt tcatctcctc tgtgaggatc aatctgcatt  60
ttctgcatag gagaataggt tttcatatta aaacaatcat                        100

SEQ ID NO: 924          moltype = DNA  length = 100
FEATURE                 Location/Qualifiers
source                  1..100
                        mol_type = genomic DNA
                        organism = Homo sapiens
SEQUENCE: 924
tttaaaaata tgtagaaatg accctagtaa tcacagaatt ccgaacttag gttcagtaga  60
gaaactttaa gaagatgaag tcccacatcg tgacaggaaa                        100

SEQ ID NO: 925          moltype = DNA  length = 100
FEATURE                 Location/Qualifiers
source                  1..100
                        mol_type = genomic DNA
                        organism = Homo sapiens
SEQUENCE: 925
tggagatggt gaatctgccc ttcacagagt ctgcataata tgtgctaccc ccattactac  60
taatagctga aacatattcc agtcccttcc ctggagcctg                        100

SEQ ID NO: 926          moltype = DNA  length = 100
FEATURE                 Location/Qualifiers
source                  1..100
                        mol_type = genomic DNA
                        organism = Homo sapiens
SEQUENCE: 926
gcggacccag tgcatagcat agctactgaa ggtgaatcca gaggctgcac aggagagtct  60
cagggacccc ccaggctgga ccaagccttc cccagactcc                        100

SEQ ID NO: 927          moltype = DNA  length = 100
FEATURE                 Location/Qualifiers
source                  1..100
                        mol_type = genomic DNA
                        organism = Homo sapiens
SEQUENCE: 927
ttctctcact catgtccact cacactcaat atctctattt cctcatgaat cacctttaaa  60
aatagcaaca aggaaaaccc agctcagccc aaactccatc                        100

SEQ ID NO: 928          moltype = DNA  length = 100
FEATURE                 Location/Qualifiers
source                  1..100
                        mol_type = genomic DNA
                        organism = Homo sapiens
SEQUENCE: 928
atgactcttc tgtgttcagt gctgatcacc aaatgaaaac acctgggaat cccagggcgg  60
gggctcctct cccagagctg cggagtcagg gctgggctgg                        100

SEQ ID NO: 929          moltype = DNA  length = 100
FEATURE                 Location/Qualifiers
source                  1..100
                        mol_type = genomic DNA
                        organism = Homo sapiens
SEQUENCE: 929
tagggcacat ccttcccatc cactcaagcc cttgtgcatg ggcctggcgc acctagtgca  60
tagagtaact ggtgaaggta ggtgtatcca caagtcttgc                        100

SEQ ID NO: 930          moltype = DNA  length = 100
FEATURE                 Location/Qualifiers
source                  1..100
                        mol_type = genomic DNA
                        organism = Homo sapiens
SEQUENCE: 930
aggagacttt cactgatgcc ccagccttct tcatctcatc cccagactgc accagctgca  60
cctgggactg ggcacctgtg gagaggacac gggagtggat                        100

SEQ ID NO: 931          moltype = DNA  length = 100
FEATURE                 Location/Qualifiers
```

```
source                  1..100
                        mol_type = genomic DNA
                        organism = Homo sapiens
SEQUENCE: 931
gaaaacttgt tcacagtagc accttcatgg aatgtttgta tcaacgttat agagtgtggc  60
cttttccact ctgtgaattt ggcttatatt acgactcttg                        100

SEQ ID NO: 932          moltype = DNA  length = 100
FEATURE                 Location/Qualifiers
source                  1..100
                        mol_type = genomic DNA
                        organism = Homo sapiens
SEQUENCE: 932
aatggaatat ttatcttaaa attagagtat gtacttgttt ctactgttct ttttttctca  60
aatatataac ccattttgta aacagcctta aacctaataa                        100

SEQ ID NO: 933          moltype = DNA  length = 100
FEATURE                 Location/Qualifiers
source                  1..100
                        mol_type = genomic DNA
                        organism = Homo sapiens
SEQUENCE: 933
ctgctcagct ccatgtaggc tgtgctcgtg gatttgtccg cggtaatcgt gactctgccc  60
tggaacttct gtgcgtagtt tgctgtacca aagataggga                        100

SEQ ID NO: 934          moltype = DNA  length = 100
FEATURE                 Location/Qualifiers
source                  1..100
                        mol_type = genomic DNA
                        organism = Homo sapiens
SEQUENCE: 934
tgatccctcc catccactca agcccttgtc caggggcctg tcgcacccag ctgatagcat  60
agctgctgaa ggtgcctcca gaagccttgc aggagacctt                        100

SEQ ID NO: 935          moltype = DNA  length = 100
FEATURE                 Location/Qualifiers
source                  1..100
                        mol_type = genomic DNA
                        organism = Homo sapiens
SEQUENCE: 935
caccgaggac ccaggcttct tcacctcagc cccagactgc accagctgca cctgggactg  60
gacacctgtg gagaggacac aggggtgaat aaaatcctct                        100

SEQ ID NO: 936          moltype = DNA  length = 100
FEATURE                 Location/Qualifiers
source                  1..100
                        mol_type = genomic DNA
                        organism = Homo sapiens
SEQUENCE: 936
cctgggactg gacacctgtg gagaggacac aggggtgaat aaaatcctct ttaactaaac  60
caggatccct tcctcagcct taggactagg aagcccctta                        100

SEQ ID NO: 937          moltype = DNA  length = 100
FEATURE                 Location/Qualifiers
source                  1..100
                        mol_type = genomic DNA
                        organism = Homo sapiens
SEQUENCE: 937
cctgtagctg ctgccaccac aaagaggaac ctccaggtcc agtccatggt gatgagctgt  60
gctcccaggg gcttcttcag aggaggaatg tggttgttat                        100

SEQ ID NO: 938          moltype = DNA  length = 100
FEATURE                 Location/Qualifiers
source                  1..100
                        mol_type = genomic DNA
                        organism = Homo sapiens
SEQUENCE: 938
gtgatgctct cagggcacca atatatctat atttatctca gaagacctca ggttatttgc  60
atatgcatga ggcagggtat ttcacagctc aaagcctgat                        100

SEQ ID NO: 939          moltype = DNA  length = 100
FEATURE                 Location/Qualifiers
source                  1..100
                        mol_type = genomic DNA
                        organism = Homo sapiens
SEQUENCE: 939
tttgcatatg catgaggcag ggtatttcac agctcaaagc ctgatctagg atgagaaaga  60
aaacacagat gccacatcag ctgtacaagt gtgggatgct                        100
```

```
SEQ ID NO: 940         moltype = DNA  length = 100
FEATURE                Location/Qualifiers
source                 1..100
                       mol_type = genomic DNA
                       organism = Homo sapiens
SEQUENCE: 940
cagaacaaac cccaacccca ggatgcactc ctcactgtga acccacattt tattggccta  60
aagattacct gggttttttg tgggaccatt gctgtctctg                        100

SEQ ID NO: 941         moltype = DNA  length = 100
FEATURE                Location/Qualifiers
source                 1..100
                       mol_type = genomic DNA
                       organism = Homo sapiens
SEQUENCE: 941
acattgagca ggcacctaga cccatcctgg tcccattagg aacactcaga gctcactggt  60
aacactgaaa aggtggccac tcgttaccct acatgagtgt                        100

SEQ ID NO: 942         moltype = DNA  length = 100
FEATURE                Location/Qualifiers
source                 1..100
                       mol_type = genomic DNA
                       organism = Homo sapiens
SEQUENCE: 942
ccagcaggac ccatggagag ttctgagatc tgctgggcac tcccaagaca gggtccccag  60
cactttcctg agggtcctga cctcccaggt ccttcagtgg                        100

SEQ ID NO: 943         moltype = DNA  length = 100
FEATURE                Location/Qualifiers
source                 1..100
                       mol_type = genomic DNA
                       organism = Homo sapiens
SEQUENCE: 943
ttatccattt ctatgtgttc ttttgaaaat gtctactcat gtcctttgct cattttaacg  60
gagttatttg gttcttgttg ctgttgttgt tgtagagttg                        100

SEQ ID NO: 944         moltype = DNA  length = 100
FEATURE                Location/Qualifiers
source                 1..100
                       mol_type = genomic DNA
                       organism = Homo sapiens
SEQUENCE: 944
ttgcaaattc ttcatattag ttccctgtca caggcaaagt gtgcaaaagt tttctgtcat  60
tctgtaaatt gcgtattcac tctgttgttg tgaaaaaaat                        100

SEQ ID NO: 945         moltype = DNA  length = 100
FEATURE                Location/Qualifiers
source                 1..100
                       mol_type = genomic DNA
                       organism = Homo sapiens
SEQUENCE: 945
tatttaggtt aattaaatct catctgtcta ttttttttta ggtagcagga cctttcatgc  60
tgaatctttg tcaaacagga tacagcttct gcttgcatga                        100

SEQ ID NO: 946         moltype = DNA  length = 100
FEATURE                Location/Qualifiers
source                 1..100
                       mol_type = genomic DNA
                       organism = Homo sapiens
SEQUENCE: 946
accactaaca ggggacatgc catttattag taaagaaaaa ggaggaaaac aaggctctga  60
gtcagatggg gatgggaaac gcacgccctg ggcaggaaat                        100

SEQ ID NO: 947         moltype = DNA  length = 100
FEATURE                Location/Qualifiers
source                 1..100
                       mol_type = genomic DNA
                       organism = Homo sapiens
SEQUENCE: 947
ggcatctcag ccacactatc ctgttctgca gaagtgggga gggagcacca ctgaaaaaca  60
cctgggttct tgtacaggaa gcgccctggg ctgtgtctct                        100

SEQ ID NO: 948         moltype = DNA  length = 100
FEATURE                Location/Qualifiers
source                 1..100
                       mol_type = genomic DNA
                       organism = Homo sapiens
SEQUENCE: 948
gtggtatccg tgcacaataa tacgtggctg tgtccacagg gtccatgttg gtcattgtaa  60
```

-continued

```
ggaccacctg gtttttggag gtgtccttgg agatggtgag                          100

SEQ ID NO: 949          moltype = DNA  length = 100
FEATURE                 Location/Qualifiers
source                  1..100
                        mol_type = genomic DNA
                        organism = Homo sapiens
SEQUENCE: 949
acctggtttt tggaggtgtc cttggagatg gtgagcctgg tcttcagaga tgtgctgtag  60
tatttatcat catcccaatc aatgagtgca agccactcca                          100

SEQ ID NO: 950          moltype = DNA  length = 100
FEATURE                 Location/Qualifiers
source                  1..100
                        mol_type = genomic DNA
                        organism = Homo sapiens
SEQUENCE: 950
gggccttccc tgggggctga cggatccagc tcacacacat tccactagtg ctgagtgaga  60
acccagagaa ggtgcaggtc agtgtgaggg tctgtgtggg                          100

SEQ ID NO: 951          moltype = DNA  length = 100
FEATURE                 Location/Qualifiers
source                  1..100
                        mol_type = genomic DNA
                        organism = Homo sapiens
SEQUENCE: 951
tttcaccagc gcaggaccag actccctcaa ggtgacctgg gataagaccc ctgtggagaa  60
gacataagaa gatgaagccc acaaaggaga gaatagattt                          100

SEQ ID NO: 952          moltype = DNA  length = 100
FEATURE                 Location/Qualifiers
source                  1..100
                        mol_type = genomic DNA
                        organism = Homo sapiens
SEQUENCE: 952
ctgtggagaa gacataagaa gatgaagccc acaaaggaga gaatagattt tttgcttctg  60
aagtactacc tgaccacagc actcacagga cgggacagtc                          100

SEQ ID NO: 953          moltype = DNA  length = 100
FEATURE                 Location/Qualifiers
source                  1..100
                        mol_type = genomic DNA
                        organism = Homo sapiens
SEQUENCE: 953
agtagcagga gcgtggaaca aagtatgtcc atggtggaga gcaggattca ctgagcgagg  60
ccctgtcctc gtcttttgaa cccaggggag ggtggagctg                          100

SEQ ID NO: 954          moltype = DNA  length = 100
FEATURE                 Location/Qualifiers
source                  1..100
                        mol_type = genomic DNA
                        organism = Homo sapiens
SEQUENCE: 954
gtggagattt gcatcccctc atctgagccc tactctatgg ggtgcactca ggtctcagga  60
ctcagtaggg gagtgcatct gtggtgagga gcagtgagcc                          100

SEQ ID NO: 955          moltype = DNA  length = 100
FEATURE                 Location/Qualifiers
source                  1..100
                        mol_type = genomic DNA
                        organism = Homo sapiens
SEQUENCE: 955
tactctatgg ggtgcactca ggtctcagga ctcagtaggg gagtgcatct gtggtgagga  60
gcagtgagcc ctcaggtgtg ggggtccacg tgtgctctcc                          100

SEQ ID NO: 956          moltype = DNA  length = 100
FEATURE                 Location/Qualifiers
source                  1..100
                        mol_type = genomic DNA
                        organism = Homo sapiens
SEQUENCE: 956
atcagggaat ctatctcatt tcagcaccat ggctctcagt caagtcttga cgctcctgct  60
tctacagaca ggatcttctt cgatgctccc gcaccggaca                          100

SEQ ID NO: 957          moltype = DNA  length = 100
FEATURE                 Location/Qualifiers
source                  1..100
                        mol_type = genomic DNA
                        organism = Homo sapiens
```

```
SEQUENCE: 957
tgcaaccttc tggttttagt cctagaggat tagagtagaa atcaagagag ctgccgttcc  60
tcctcccttc aagaataatg atggtgggca tctgggggc                         100

SEQ ID NO: 958         moltype = DNA  length = 100
FEATURE                Location/Qualifiers
source                 1..100
                       mol_type = genomic DNA
                       organism = Homo sapiens
SEQUENCE: 958
aaggggctcc ccacaagcat tctgatcaaa atcctctttg attatgggga aaagtgatga  60
atttgtgtaa aaaaattgga gagaataaat aagaaaatac                        100

SEQ ID NO: 959         moltype = DNA  length = 100
FEATURE                Location/Qualifiers
source                 1..100
                       mol_type = genomic DNA
                       organism = Homo sapiens
SEQUENCE: 959
agttacaagt aattatgtaa agaagtgtgt gcttagcagt gtgtgtgcac acagctgcat  60
tcctagaggc atgttccatg aaaaatcgat gttgtccttg                        100

SEQ ID NO: 960         moltype = DNA  length = 100
FEATURE                Location/Qualifiers
source                 1..100
                       mol_type = genomic DNA
                       organism = Homo sapiens
SEQUENCE: 960
tgccccgtca gttctgtgga gagagtagac tgcatgaatg acttcccttt tctcagccca  60
tgaatgagcg gatgctttgg acaagggaat tggaagactc                        100

SEQ ID NO: 961         moltype = DNA  length = 100
FEATURE                Location/Qualifiers
source                 1..100
                       mol_type = genomic DNA
                       organism = Homo sapiens
SEQUENCE: 961
ctgagggagc agcaggctga ctgttgcagc cttgctctgc acctgcactg gatgtggtct  60
ctgtgctcat aaggccgtgg aaactcatca atccaggttc                        100

SEQ ID NO: 962         moltype = DNA  length = 100
FEATURE                Location/Qualifiers
source                 1..100
                       mol_type = genomic DNA
                       organism = Homo sapiens
SEQUENCE: 962
caaaaagggg ttaaatgatt ttggaaaagt aagtagaaaa taaaagaagg agggagtaag  60
agcggacaga agggaggaag gcaagcaagc aatgatgaac                        100

SEQ ID NO: 963         moltype = DNA  length = 100
FEATURE                Location/Qualifiers
source                 1..100
                       mol_type = genomic DNA
                       organism = Homo sapiens
SEQUENCE: 963
tgtgtaaaat tttcactaat taaaagacta ttatattgaa gaggtgccta ttaggcagcc  60
ttttgatgtt aaccatgtaa tatacaccat gaacaacctt                        100

SEQ ID NO: 964         moltype = DNA  length = 100
FEATURE                Location/Qualifiers
source                 1..100
                       mol_type = genomic DNA
                       organism = Homo sapiens
SEQUENCE: 964
gaacaacctt gtagaacaca caagagcccc ctcagagaac tggatgggtc aggtctccca  60
tccagttgcc ttaggggtta ggaacgctcc catgttgttc                        100

SEQ ID NO: 965         moltype = DNA  length = 100
FEATURE                Location/Qualifiers
source                 1..100
                       mol_type = genomic DNA
                       organism = Homo sapiens
SEQUENCE: 965
tctggttttt gctcctgagg acacaaacag ccagtgtttc ctccccggat gaatagagag  60
gcccctgggg agggtgtgtc tggcagctca ctctgcacct                        100

SEQ ID NO: 966         moltype = DNA  length = 100
FEATURE                Location/Qualifiers
source                 1..100
```

```
                         mol_type = genomic DNA
                         organism = Homo sapiens
SEQUENCE: 966
gtttcctccc cggatgaata gagaggcccc tggggagggt gtgtctggca gctcactctg  60
cacctgcacc gcggaaggtt ttagatggtc cctctcacac                        100

SEQ ID NO: 967           moltype = DNA  length = 100
FEATURE                  Location/Qualifiers
source                   1..100
                         mol_type = genomic DNA
                         organism = Homo sapiens
SEQUENCE: 967
aataatacat ggcggcgtcc gaggccttca ggctgctcca ctgcaggtag gcggtgctgc  60
tggagctgtc ggctgagatg gtgacgtggc cttggaagga                        100

SEQ ID NO: 968           moltype = DNA  length = 100
FEATURE                  Location/Qualifiers
source                   1..100
                         mol_type = genomic DNA
                         organism = Homo sapiens
SEQUENCE: 968
tgggctgtat ctggtatcag agttcccagg atagatgctc cccatccact ccagttcttt  60
cccgggcatc tggcgcaccc agtggatcca gtagctggta                        100

SEQ ID NO: 969           moltype = DNA  length = 100
FEATURE                  Location/Qualifiers
source                   1..100
                         mol_type = genomic DNA
                         organism = Homo sapiens
SEQUENCE: 969
acaggagatc ctcagagact ccccgggtct tttcacctct gctgcagact gcaacagctg  60
cacctcggca aagacacctg tgtgggagac acaaaatttg                        100

SEQ ID NO: 970           moltype = DNA  length = 100
FEATURE                  Location/Qualifiers
source                   1..100
                         mol_type = genomic DNA
                         organism = Homo sapiens
SEQUENCE: 970
gtgtctggag tatgaaccat gtatcagcac cgaaaggttc tagaagtcag actttcgggc  60
agtgtgtcac taactctcag catgctggcc tggctcggcc                        100

SEQ ID NO: 971           moltype = DNA  length = 100
FEATURE                  Location/Qualifiers
source                   1..100
                         mol_type = genomic DNA
                         organism = Homo sapiens
SEQUENCE: 971
cacagcaagg tcttctcgcc tccctttggg taaatactga ggggtgcctc tgcaggacgg  60
gacctctgcc agactccact ccatacccag agaagcaggg                        100

SEQ ID NO: 972           moltype = DNA  length = 100
FEATURE                  Location/Qualifiers
source                   1..100
                         mol_type = genomic DNA
                         organism = Homo sapiens
SEQUENCE: 972
aaaccaaaat tggagtcagc cttgaggtgt agctgttgag ccctcagcag ctggggagag  60
ctggcggatg ctgccctccc cccagtttcc taatggtgtt                        100

SEQ ID NO: 973           moltype = DNA  length = 100
FEATURE                  Location/Qualifiers
source                   1..100
                         mol_type = genomic DNA
                         organism = Homo sapiens
SEQUENCE: 973
gtttaaaaag ggtcagggga cgggggaaca gatggtggga agagcacagt gcagacacct  60
ggcaccggct ctgaaggcag catggcagct acaccgttgg                        100

SEQ ID NO: 974           moltype = DNA  length = 100
FEATURE                  Location/Qualifiers
source                   1..100
                         mol_type = genomic DNA
                         organism = Homo sapiens
SEQUENCE: 974
ctgggaaggg tgtgcccctg aagaagtcgt ttacattctc gagtcaattt tcctggagtg  60
tacaatggac ctgtgggaaa gcctgtatga aagggtaatg                        100

SEQ ID NO: 975           moltype = DNA  length = 100
```

```
FEATURE                 Location/Qualifiers
source                  1..100
                        mol_type = genomic DNA
                        organism = Homo sapiens
SEQUENCE: 975
atgagggacc tagcacagtg tccaatattt tataggaact ggaattgagc tcataggagc  60
tcaattttat tggcattgct gttgttggat ggttaaaggg                        100

SEQ ID NO: 976          moltype = DNA  length = 100
FEATURE                 Location/Qualifiers
source                  1..100
                        mol_type = genomic DNA
                        organism = Homo sapiens
SEQUENCE: 976
gtggtatccc ttttctcaga ctcccctgaa atgtatggtt tgctttgaac ccagagactg  60
atgacaggtc tgccggtgtg gttgggtgca gccttaagtt                        100

SEQ ID NO: 977          moltype = DNA  length = 100
FEATURE                 Location/Qualifiers
source                  1..100
                        mol_type = genomic DNA
                        organism = Homo sapiens
SEQUENCE: 977
gctacgggaa agtgttggag ggggagaagt cagaggtaac cttgccccct ccctcaattc  60
cagatgagga aattcaggcc tgaaaaggga aagtgaccac                        100

SEQ ID NO: 978          moltype = DNA  length = 100
FEATURE                 Location/Qualifiers
source                  1..100
                        mol_type = genomic DNA
                        organism = Homo sapiens
SEQUENCE: 978
ctcaaagtct catgccttgg aggacccagc aggaatccaa gacctctgaa aaggaccggc  60
agggctcttg ccacggctgg gggtgtggtc atggtaacac                        100

SEQ ID NO: 979          moltype = DNA  length = 100
FEATURE                 Location/Qualifiers
source                  1..100
                        mol_type = genomic DNA
                        organism = Homo sapiens
SEQUENCE: 979
aggttttcca tccatggaag gtacctgagg gattttctct tcctccctag ggccagcatc  60
agaggagtga atagctcagt tagctcatct caggggccat                        100

SEQ ID NO: 980          moltype = DNA  length = 100
FEATURE                 Location/Qualifiers
source                  1..100
                        mol_type = genomic DNA
                        organism = Homo sapiens
SEQUENCE: 980
gtgccctcgg aggtggtttg ccactttcac ggttggactg agttggagag aaacagagac  60
ccacccaggg gtggggacaa gctccctgca actcaggact                        100

SEQ ID NO: 981          moltype = DNA  length = 100
FEATURE                 Location/Qualifiers
source                  1..100
                        mol_type = genomic DNA
                        organism = Homo sapiens
SEQUENCE: 981
tgcagatcac ttgcccaagt ggctccctag ctcctggctc ctggcccggg gcctgggact  60
ctccccgaag tggggctggc cactgtgagg aaccgactgg                        100

SEQ ID NO: 982          moltype = DNA  length = 100
FEATURE                 Location/Qualifiers
source                  1..100
                        mol_type = genomic DNA
                        organism = Homo sapiens
SEQUENCE: 982
aggcagggac ctcttggatg ccccaggcag ttgggatgcc acttctgata aagcacgtgg  60
tggccacagt aggtgcttgg ttgctccaca gcctggcccg                        100

SEQ ID NO: 983          moltype = DNA  length = 100
FEATURE                 Location/Qualifiers
source                  1..100
                        mol_type = genomic DNA
                        organism = Homo sapiens
SEQUENCE: 983
agctcagcgc tgcagaaaga aagtgaaagg gaaaaagaac tgcggggagg cggggaggta  60
ggatgaccag cggacgagct gccacagact tgccgcggcc                        100
```

```
SEQ ID NO: 984          moltype = DNA  length = 100
FEATURE                 Location/Qualifiers
source                  1..100
                        mol_type = genomic DNA
                        organism = Homo sapiens
SEQUENCE: 984
ccagagctgg cgggagggag aggccaccag cagcgcgcgc gggagcccgg ggaacagcgg  60
taggtgacca aagtctcctc tgtaacccct aaggtcgggc                        100

SEQ ID NO: 985          moltype = DNA  length = 100
FEATURE                 Location/Qualifiers
source                  1..100
                        mol_type = genomic DNA
                        organism = Homo sapiens
SEQUENCE: 985
tgagaatcga ggctccgaga ctgtcagcta cttgctcaag gtcacacagc aagtctggga  60
ggatgggggg atggaatatg caaaatgtag ggccgggaaa                        100

SEQ ID NO: 986          moltype = DNA  length = 100
FEATURE                 Location/Qualifiers
source                  1..100
                        mol_type = genomic DNA
                        organism = Homo sapiens
SEQUENCE: 986
cacctcgttt ccagcatccc cgcaacgact ctgcgcggga accaggagcc gggaacccgg  60
agcttggctt gctgtgccca gagctccggg gccgtgggcg                        100

SEQ ID NO: 987          moltype = DNA  length = 100
FEATURE                 Location/Qualifiers
source                  1..100
                        mol_type = genomic DNA
                        organism = Homo sapiens
SEQUENCE: 987
ggtggcagga aagcctggcg gcagcttctg cagagaagcc ggagcgcaga ctgggagcgc  60
ggagcagaca cactccccg gccacccttg gccgactccg                         100

SEQ ID NO: 988          moltype = DNA  length = 100
FEATURE                 Location/Qualifiers
source                  1..100
                        mol_type = genomic DNA
                        organism = Homo sapiens
SEQUENCE: 988
cgcgcccggg atcctgcaga ggtgcgcgcc cttcttgtac gccagacttt ggaccagggc  60
cgccgttccc tgagcttcac tttccctgtt gggtcatatt                        100

SEQ ID NO: 989          moltype = DNA  length = 100
FEATURE                 Location/Qualifiers
source                  1..100
                        mol_type = genomic DNA
                        organism = Homo sapiens
SEQUENCE: 989
ccatctctaa ctctggaatc ttgggtattg ggctctccag gcggggggcc ctgctcaggg  60
aggcagtagg gagccaaacc tttaaccaga ggatgggata                        100

SEQ ID NO: 990          moltype = DNA  length = 100
FEATURE                 Location/Qualifiers
source                  1..100
                        mol_type = genomic DNA
                        organism = Homo sapiens
SEQUENCE: 990
agtcctcaac tctcgttgaa catcttggcg aaggtgtgtg ttgttgggag gggtggggga  60
gggatccccc cggactgaac cgatctcttg atctctcact                        100

SEQ ID NO: 991          moltype = DNA  length = 100
FEATURE                 Location/Qualifiers
source                  1..100
                        mol_type = genomic DNA
                        organism = Homo sapiens
SEQUENCE: 991
tctctacctc gctttggggc cctgagtcac accctctaag gagagaggct aaagcgcccc  60
ggaaagccag cgtgcgaatg ccggggtggg agtgggagat                        100

SEQ ID NO: 992          moltype = DNA  length = 100
FEATURE                 Location/Qualifiers
source                  1..100
                        mol_type = genomic DNA
                        organism = Homo sapiens
SEQUENCE: 992
```

```
tggatctccc tggggtccag gaaagccgga atcggagcca ccatgcttag cttagtctgg  60
aactcttaaa agccgcggtc ctcctgagtc ccacagcccc                        100

SEQ ID NO: 993         moltype = DNA  length = 100
FEATURE                Location/Qualifiers
source                 1..100
                       mol_type = genomic DNA
                       organism = Homo sapiens
SEQUENCE: 993
tctccaccct aggtggcaca ggagaggtgg caaaagccta gaagttcaag gcatggctcc  60
ctccccagcc gcagcctgga gtgtctaact ttggcaggaa                        100

SEQ ID NO: 994         moltype = DNA  length = 100
FEATURE                Location/Qualifiers
source                 1..100
                       mol_type = genomic DNA
                       organism = Homo sapiens
SEQUENCE: 994
gtcttccgtt tctgctcccc actccagaga aaaaataaat aaatacttct ccggagtgag  60
attaaggaaa caggtacttc ttcctcttgg agaaagagga                        100

SEQ ID NO: 995         moltype = DNA  length = 100
FEATURE                Location/Qualifiers
source                 1..100
                       mol_type = genomic DNA
                       organism = Homo sapiens
SEQUENCE: 995
cttctccgga gtgagattaa ggaaacaggt acttcttcct cttggagaaa gaggagccaa  60
aggaacttga ctccaacaaa tgatcacctt gcaaacccc                         100

SEQ ID NO: 996         moltype = DNA  length = 100
FEATURE                Location/Qualifiers
source                 1..100
                       mol_type = genomic DNA
                       organism = Homo sapiens
SEQUENCE: 996
ggctcccta ggggatgacc tggtctccaa caatctcaga gcgtttggag gcagggtctt   60
tggagatgac tgagtgggga atcccaggct ccccacacat                        100

SEQ ID NO: 997         moltype = DNA  length = 100
FEATURE                Location/Qualifiers
source                 1..100
                       mol_type = genomic DNA
                       organism = Homo sapiens
SEQUENCE: 997
gaacatcacc tgggatgatc aacctgttca ggatgtaggt tcccgggctc acccccaggc  60
ccggttggct aggcctgggg tgaggctgag atcctgcagg                        100

SEQ ID NO: 998         moltype = DNA  length = 100
FEATURE                Location/Qualifiers
source                 1..100
                       mol_type = genomic DNA
                       organism = Homo sapiens
SEQUENCE: 998
ttaaaccatc tatcccaggt gactccaatg ttcgtttgtg gggcaaaagt ccctcaagtc  60
agagacactg ggaggcgctg atgtggtctc atctctttac                        100

SEQ ID NO: 999         moltype = DNA  length = 100
FEATURE                Location/Qualifiers
source                 1..100
                       mol_type = genomic DNA
                       organism = Homo sapiens
SEQUENCE: 999
caagaggtga gaaggggtct gcggcctcgt ctccagccga gggcgggagg cgcctcgccc  60
ctacacccat ccgctccctc caacccaggc cggggagggt                        100

SEQ ID NO: 1000        moltype = DNA  length = 100
FEATURE                Location/Qualifiers
source                 1..100
                       mol_type = genomic DNA
                       organism = Homo sapiens
SEQUENCE: 1000
acccacatgg ttccaggcaa gtaataacaa aataacacgg catcccagtt aatgctgcgt  60
gcacggcggg cgctgccggt caaatctgga aggggaagga                        100

SEQ ID NO: 1001        moltype = DNA  length = 100
FEATURE                Location/Qualifiers
source                 1..100
                       mol_type = genomic DNA
```

```
                         organism = Homo sapiens
SEQUENCE: 1001
gctcaggtag tcgcggagga cggggttgag ggggatgcga gccaggttct cgcggcccac  60
ggtggccacg atgcgctggc ggcacagctc ctgcagcggc                        100

SEQ ID NO: 1002          moltype = DNA  length = 100
FEATURE                  Location/Qualifiers
source                   1..100
                         mol_type = genomic DNA
                         organism = Homo sapiens
SEQUENCE: 1002
cgcacgcggc gctggcgcag cggggccccc agcatgcggc gcggcgccgc cacgtagtgc  60
tccagcagct cgaagaggca gtcgaagctc tcgcggctgc                        100

SEQ ID NO: 1003          moltype = DNA  length = 100
FEATURE                  Location/Qualifiers
source                   1..100
                         mol_type = genomic DNA
                         organism = Homo sapiens
SEQUENCE: 1003
catccaggtg aaagcggccg gcctgaaagt gcacgcggat gctcgtgggt cccgaggcca  60
tcttcacgct aagggcgaaa aagcagttcc gctggcggct                        100

SEQ ID NO: 1004          moltype = DNA  length = 100
FEATURE                  Location/Qualifiers
source                   1..100
                         mol_type = genomic DNA
                         organism = Homo sapiens
SEQUENCE: 1004
gtcgcgcacc aggaaggtgc ccacgggctc ggcgcgcagc cgctcgtgcg ccccgtgcac  60
gctcaggggc ccccagtaga atccgcaggc gtccaggagc                        100

SEQ ID NO: 1005          moltype = DNA  length = 100
FEATURE                  Location/Qualifiers
source                   1..100
                         mol_type = genomic DNA
                         organism = Homo sapiens
SEQUENCE: 1005
gcgctggcgc gcgtgatgcg ccggtaatcg gcgtgcgaac ggaatgtgcg gaagtgcgtg  60
tcgccggggg ccggggccgg gaccgcgggg cacggccgcg                        100

SEQ ID NO: 1006          moltype = DNA  length = 100
FEATURE                  Location/Qualifiers
source                   1..100
                         mol_type = genomic DNA
                         organism = Homo sapiens
SEQUENCE: 1006
ggcgcgcggg ggccgcgggc gaggaggagg aagaggagga aggttctggc cgccgtcggg  60
gctctgctgc tgtggagact gcattgtcgg ctgccacctg                        100

SEQ ID NO: 1007          moltype = DNA  length = 100
FEATURE                  Location/Qualifiers
source                   1..100
                         mol_type = genomic DNA
                         organism = Homo sapiens
SEQUENCE: 1007
tttaaaatca cccaaatcaa aataatttta tcttcattaa taaataatca tcagaagttt  60
aactaatttt tactttataa tactaggttt aaaaattctt                        100

SEQ ID NO: 1008          moltype = DNA  length = 100
FEATURE                  Location/Qualifiers
source                   1..100
                         mol_type = genomic DNA
                         organism = Homo sapiens
SEQUENCE: 1008
aatctgaatg cccaagtcgt tgattgtcgt ttgcctgttt ccaaagattg gtagatagat  60
gcctttttaa aaatctcatt tttctttaaa tctggtttac                        100

SEQ ID NO: 1009          moltype = DNA  length = 100
FEATURE                  Location/Qualifiers
source                   1..100
                         mol_type = genomic DNA
                         organism = Homo sapiens
SEQUENCE: 1009
atggaaaacg ttaggagagc tcatataatg aacggcaata gcaacccccct atcttgaaac  60
gcgctctatc atcccactga aattctacca cgtggaataa                        100

SEQ ID NO: 1010          moltype = DNA  length = 100
FEATURE                  Location/Qualifiers
```

```
source                  1..100
                        mol_type = genomic DNA
                        organism = Homo sapiens
SEQUENCE: 1010
tgcttggagg gtcagagttg tggaactgcc caataaccag tcgttactga gggttagttt  60
gtgaaggagg ggacagactg cttctaaaat tctgtttaat                        100

SEQ ID NO: 1011         moltype = DNA  length = 100
FEATURE                 Location/Qualifiers
source                  1..100
                        mol_type = genomic DNA
                        organism = Homo sapiens
SEQUENCE: 1011
gacagtcaat taagatttct gagtctggct tgagggcctt tgcttccatc acagcccagt  60
cgtccttggc aagagagtct gtatatgggc cacagctcac                        100

SEQ ID NO: 1012         moltype = DNA  length = 100
FEATURE                 Location/Qualifiers
source                  1..100
                        mol_type = genomic DNA
                        organism = Homo sapiens
SEQUENCE: 1012
aaaagcattg tttgaaaaaa tttattgaaa gaacattgtt tgtaaaatga gtcccaatac  60
ataggacaga ctttcctaag gtgagatgtg ttacttaccc                        100

SEQ ID NO: 1013         moltype = DNA  length = 100
FEATURE                 Location/Qualifiers
source                  1..100
                        mol_type = genomic DNA
                        organism = Homo sapiens
SEQUENCE: 1013
agagctgtga aaggctttac ggatggaaac tagagactga attttccaga attttaagaa  60
gtctccccaa ccaatggccc cccactttct ttttttaaac                        100

SEQ ID NO: 1014         moltype = DNA  length = 100
FEATURE                 Location/Qualifiers
source                  1..100
                        mol_type = genomic DNA
                        organism = Homo sapiens
SEQUENCE: 1014
ggcgtgatct ccgaagccca cagtacactc atccataaag taggaaacac tacaccctcc  60
agtgctgtta gtagtgcttt ctactttatg ggtgactgca                        100

SEQ ID NO: 1015         moltype = DNA  length = 100
FEATURE                 Location/Qualifiers
source                  1..100
                        mol_type = genomic DNA
                        organism = Homo sapiens
SEQUENCE: 1015
ctgtctgtct gtccgtcggc gtgtactctt caggctgccc aggcctcctg actcctgctc  60
caagagcccc ccagccctcc ttgtggcttc ctaagatccc                        100

SEQ ID NO: 1016         moltype = DNA  length = 100
FEATURE                 Location/Qualifiers
source                  1..100
                        mol_type = genomic DNA
                        organism = Homo sapiens
SEQUENCE: 1016
ccctcttccc ttccccctaa aggctccacc ccatcccccc agtttcagag acactcaggt  60
agagactagg gcctctggag gcctcacctt cagttctgtg                        100

SEQ ID NO: 1017         moltype = DNA  length = 100
FEATURE                 Location/Qualifiers
source                  1..100
                        mol_type = genomic DNA
                        organism = Homo sapiens
SEQUENCE: 1017
aacccctggc tggccgcttc cagccacgct agccaccctc cagcgtccaa atgaggcagc  60
cacagctccc ctgccaaggt cttggtctcc agtccacccc                        100

SEQ ID NO: 1018         moltype = DNA  length = 100
FEATURE                 Location/Qualifiers
source                  1..100
                        mol_type = genomic DNA
                        organism = Homo sapiens
SEQUENCE: 1018
aaccgtgagg tcctgactgc ccagagcctc agtccccacc cttcagcctc cccaccagcc  60
caagatcctg accccccagg gcctaagtcc ccagcctccc                        100
```

```
SEQ ID NO: 1019        moltype = DNA  length = 100
FEATURE                Location/Qualifiers
source                 1..100
                       mol_type = genomic DNA
                       organism = Homo sapiens
SEQUENCE: 1019
caacagccca gggtcctgac cccccagggc ctcaggccct ggcctcccca ccagcccaag  60
gtcttgaaca caccagggcc tcaattccca gcctccccac                        100

SEQ ID NO: 1020        moltype = DNA  length = 100
FEATURE                Location/Qualifiers
source                 1..100
                       mol_type = genomic DNA
                       organism = Homo sapiens
SEQUENCE: 1020
cagctcaagg tcctgactcc cccagagcct cagtcccagc ctccatagca gcccaaggtc  60
ctgacccccc agggcctcag tccccagcca ctccaccagc                        100

SEQ ID NO: 1021        moltype = DNA  length = 100
FEATURE                Location/Qualifiers
source                 1..100
                       mol_type = genomic DNA
                       organism = Homo sapiens
SEQUENCE: 1021
cccaaagtcc tgactcccca gagccttgat tctcggcctc cccaccagcc caaagtcctg  60
actccctcac tgccctgctg ttcccctggc aggagcccaa                        100

SEQ ID NO: 1022        moltype = DNA  length = 100
FEATURE                Location/Qualifiers
source                 1..100
                       mol_type = genomic DNA
                       organism = Homo sapiens
SEQUENCE: 1022
ggctatccca acaaaaatgg tggccatgtt gggcggagga agaggctggc gccccttgag  60
acactggtcc cacttctcag cctctgcgta ccctctgcca                        100

SEQ ID NO: 1023        moltype = DNA  length = 100
FEATURE                Location/Qualifiers
source                 1..100
                       mol_type = genomic DNA
                       organism = Homo sapiens
SEQUENCE: 1023
tccccgcctt actctccagc cctcctcctt ggacacctct ttccccgcct ggggtcccgg  60
agccatttta ccttccttca ctagagaggg tttcaaggcg                        100

SEQ ID NO: 1024        moltype = DNA  length = 100
FEATURE                Location/Qualifiers
source                 1..100
                       mol_type = genomic DNA
                       organism = Homo sapiens
SEQUENCE: 1024
ctaagatttt caagaagtta aacgtagaat taagattgtt ctaattctgg ttgtaaactg  60
ctattttaaa aaacaaaaca aacagaaaac atcaaaaaca                        100

SEQ ID NO: 1025        moltype = DNA  length = 100
FEATURE                Location/Qualifiers
source                 1..100
                       mol_type = genomic DNA
                       organism = Homo sapiens
SEQUENCE: 1025
aaacaaacag aaaacatcaa aaacacaaaa agatattaaa acagcaagtc ttttgtacat  60
cactgtagca taagctgctt gaggttgtca tgcagaatag                        100

SEQ ID NO: 1026        moltype = DNA  length = 100
FEATURE                Location/Qualifiers
source                 1..100
                       mol_type = genomic DNA
                       organism = Homo sapiens
SEQUENCE: 1026
tatccttcac gtcacggaaa acaaggcgga tgttctccgt gttgatagca gtggtgaagt  60
ggtggtataa gggcttctgt tgctggtccc ggcgtttgtt                        100

SEQ ID NO: 1027        moltype = DNA  length = 100
FEATURE                Location/Qualifiers
source                 1..100
                       mol_type = genomic DNA
                       organism = Homo sapiens
SEQUENCE: 1027
ccggaaacat tccaccagga atttttggac gtctcttaag cagtggggat ccccttcaaa  60
```

```
ttctaggaaa tagtctttga tgctcacaat ttgcaccttc                        100

SEQ ID NO: 1028        moltype = DNA  length = 100
FEATURE                Location/Qualifiers
source                 1..100
                       mol_type = genomic DNA
                       organism = Homo sapiens
SEQUENCE: 1028
tcctcaagca agtctgtctt gtttaagaac agaattatgg agacattgct gaaaacccgg  60
ttattgacga ttgtttcaaa aatgttcaga gactctgtaa                        100

SEQ ID NO: 1029        moltype = DNA  length = 100
FEATURE                Location/Qualifiers
source                 1..100
                       mol_type = genomic DNA
                       organism = Homo sapiens
SEQUENCE: 1029
ggcgattggt cagtcgatct tccataagca cctggtcaaa ttcacttgag gaaacaagga  60
aaagtattga tgtcacactg tcgaaacatt caaaccaacg                        100

SEQ ID NO: 1030        moltype = DNA  length = 100
FEATURE                Location/Qualifiers
source                 1..100
                       mol_type = genomic DNA
                       organism = Homo sapiens
SEQUENCE: 1030
tttcctttct gatctctgac cacctacatc aaccattttg aaaggaacat tttttatttc  60
aaagtcgtat tcatggatgc ctttggtggg tcttctggca                        100

SEQ ID NO: 1031        moltype = DNA  length = 100
FEATURE                Location/Qualifiers
source                 1..100
                       mol_type = genomic DNA
                       organism = Homo sapiens
SEQUENCE: 1031
agcagaatat cttgttgtga tggaatataa tcctggaaaa gaaaaaactt gttttatacc  60
tattaatccc gaagtaatgc gaatttttaa tggactacta                        100

SEQ ID NO: 1032        moltype = DNA  length = 100
FEATURE                Location/Qualifiers
source                 1..100
                       mol_type = genomic DNA
                       organism = Homo sapiens
SEQUENCE: 1032
tgtaaatatt tggccaacta agctgagtgg ctaagttctc ctgctgcccg gagcttcttg  60
gaacatgttt ccttttcgca aggggtttcc ctggcttcca                        100

SEQ ID NO: 1033        moltype = DNA  length = 100
FEATURE                Location/Qualifiers
source                 1..100
                       mol_type = genomic DNA
                       organism = Homo sapiens
SEQUENCE: 1033
ggagggccag gaagaaattc gaattggcca ccgctttctc taaaatcact ccgctcaagt  60
tatcacccct ctgggctccc gaagaccggc tggctggagg                        100

SEQ ID NO: 1034        moltype = DNA  length = 100
FEATURE                Location/Qualifiers
source                 1..100
                       mol_type = genomic DNA
                       organism = Homo sapiens
SEQUENCE: 1034
ctggagatag tctcaatgct cgaaatgccg taaccgaagc tccccgcggc gccggcactg  60
ggatccaggg agctgctgct acagcgcagc tctggattcc                        100

SEQ ID NO: 1035        moltype = DNA  length = 100
FEATURE                Location/Qualifiers
source                 1..100
                       mol_type = genomic DNA
                       organism = Homo sapiens
SEQUENCE: 1035
tggatgtgtt ggatatgtgc agggcgttcc tgggaggagc ggggagggag ggtgctgctg  60
gcggggctgg tctgcgtgtg ctttgcttct ctacaatggc                        100

SEQ ID NO: 1036        moltype = DNA  length = 100
FEATURE                Location/Qualifiers
source                 1..100
                       mol_type = genomic DNA
                       organism = Homo sapiens
```

```
SEQUENCE: 1036
atgctgcgtg tcggccatgc agaggcatgt cagtgagcag gggctgaggg atctccctaa  60
cggacctgct ttcagagggt cttttcatgc tgggagaacc                        100

SEQ ID NO: 1037        moltype = DNA  length = 100
FEATURE                Location/Qualifiers
source                 1..100
                       mol_type = genomic DNA
                       organism = Homo sapiens
SEQUENCE: 1037
ccagagacta aatcatgcag ccaacggggt ggtccccggc ctcaaagcag ggaggggcga  60
ggagctttgt aggcaatgcc atctgctcct gaaacgccgt                        100

SEQ ID NO: 1038        moltype = DNA  length = 100
FEATURE                Location/Qualifiers
source                 1..100
                       mol_type = genomic DNA
                       organism = Homo sapiens
SEQUENCE: 1038
cagcctcctt agtagctacc gccttagtaa gtaccactta gtaagtaccg ccttagtaag  60
taccacttag tagctacctc cttagtaagt accacttagt                        100

SEQ ID NO: 1039        moltype = DNA  length = 100
FEATURE                Location/Qualifiers
source                 1..100
                       mol_type = genomic DNA
                       organism = Homo sapiens
SEQUENCE: 1039
aagtacctcc ttagtaagta ccacttagta ctaccaccac gcctggctaa tttcgtattt  60
tttttttttt agtagagacg gggtttctcc atattggtca                        100

SEQ ID NO: 1040        moltype = DNA  length = 100
FEATURE                Location/Qualifiers
source                 1..100
                       mol_type = genomic DNA
                       organism = Homo sapiens
SEQUENCE: 1040
aggtcaggcg catactgcat gcgggtctcg cggtcgtgct ccagccacag cacggacatc  60
tggaagagcg ccagctccga ctccacgggg ggcggcagcg                        100

SEQ ID NO: 1041        moltype = DNA  length = 100
FEATURE                Location/Qualifiers
source                 1..100
                       mol_type = genomic DNA
                       organism = Homo sapiens
SEQUENCE: 1041
agtccagcag ggcgcgcatc tcctcgaagt tgagcagcag cacatcctcc accaggtact  60
tgttggccag cttcttggtc tcctccaggc cgtgcagcgc                        100

SEQ ID NO: 1042        moltype = DNA  length = 100
FEATURE                Location/Qualifiers
source                 1..100
                       mol_type = genomic DNA
                       organism = Homo sapiens
SEQUENCE: 1042
ggcgatcttg cacacctgct tgtagttctg caccgagatc tggtcgttga ggaactgcac  60
gcagagcttg gtgacctggg ggatgtgcag gatcttgctg                        100

SEQ ID NO: 1043        moltype = DNA  length = 100
FEATURE                Location/Qualifiers
source                 1..100
                       mol_type = genomic DNA
                       organism = Homo sapiens
SEQUENCE: 1043
accgacagca cctcctccac cgtgtccagg gacagggtca cgttggccgt gtagaggtac  60
tcgagcacca ggcgcagccc gatggacgag cagccctgca                        100

SEQ ID NO: 1044        moltype = DNA  length = 100
FEATURE                Location/Qualifiers
source                 1..100
                       mol_type = genomic DNA
                       organism = Homo sapiens
SEQUENCE: 1044
gcaccaggtt gttgatggcc cgggggctgg tcagcagctt gtcgtcgggg gaggaagaag  60
gagtcccggg ctcctcctgc ggcggcggct gctgctgctg                        100

SEQ ID NO: 1045        moltype = DNA  length = 100
FEATURE                Location/Qualifiers
source                 1..100
```

```
                         mol_type = genomic DNA
                         organism = Homo sapiens
SEQUENCE: 1045
tgacggctgc tgctgcggcg gctgctgctg gtccttgggg gcccccaggc cgtcctggcc  60
gccgacccct cccccgagag gggggtggct ggagaagagc                        100

SEQ ID NO: 1046          moltype = DNA  length = 100
FEATURE                  Location/Qualifiers
source                   1..100
                         mol_type = genomic DNA
                         organism = Homo sapiens
SEQUENCE: 1046
gagacttcag ccggagctgg ctattccaga gatggacctc agaggattcc ttagtctaat  60
taccttctgg gctggggtag aagatggtgt ctggagggaa                        100

SEQ ID NO: 1047          moltype = DNA  length = 100
FEATURE                  Location/Qualifiers
source                   1..100
                         mol_type = genomic DNA
                         organism = Homo sapiens
SEQUENCE: 1047
gcacagaacc aagttcccta ctgccgcact agctatgcaa atactgcagg gcacctgtgg  60
gctcatgtcc ctcctgcaag aaggtgtggt cagtccagta                        100

SEQ ID NO: 1048          moltype = DNA  length = 100
FEATURE                  Location/Qualifiers
source                   1..100
                         mol_type = genomic DNA
                         organism = Homo sapiens
SEQUENCE: 1048
attcaaaaga cgtacttctg aaataggtgg agaaatgcat ttatagcaaa aagtgctaaa  60
aatatgttaa tagttatgct atttggttca ccaggttagt                        100

SEQ ID NO: 1049          moltype = DNA  length = 100
FEATURE                  Location/Qualifiers
source                   1..100
                         mol_type = genomic DNA
                         organism = Homo sapiens
SEQUENCE: 1049
gtaataaacc ataacaagag agactaaagg ccgtatctat atgaccttga aatctcatct  60
tcagcgggct tattcattca gtaaccaaac tatttttgta                        100

SEQ ID NO: 1050          moltype = DNA  length = 100
FEATURE                  Location/Qualifiers
source                   1..100
                         mol_type = genomic DNA
                         organism = Homo sapiens
SEQUENCE: 1050
aggtgctgag tatttagctt aaagctaaat aagacacatg ccctgcccta tagtaactgc  60
ttggtaatat tcccagtggc ttccatgggc ctgataattt                        100

SEQ ID NO: 1051          moltype = DNA  length = 100
FEATURE                  Location/Qualifiers
source                   1..100
                         mol_type = genomic DNA
                         organism = Homo sapiens
SEQUENCE: 1051
tcttagtact gaattcaaag cactttgtgt cttgtctgca ggcccatttg cccagcagtg  60
gccttgccag gagagaacag gcccatgctc ctgtcctcat                        100

SEQ ID NO: 1052          moltype = DNA  length = 100
FEATURE                  Location/Qualifiers
source                   1..100
                         mol_type = genomic DNA
                         organism = Homo sapiens
SEQUENCE: 1052
caaacaaaca attcaagaag aggatttaaa ttttagaaat ttaaattggg gcattttagt  60
taatcttact tttaaacacc aaacagtggc atcaatattt                        100

SEQ ID NO: 1053          moltype = DNA  length = 100
FEATURE                  Location/Qualifiers
source                   1..100
                         mol_type = genomic DNA
                         organism = Homo sapiens
SEQUENCE: 1053
tgtcaacttt ggtcaaataa gatcagatgt tcacatcaat catctacttt tcttggcctt  60
ttctctattt ggcctcctag tatgagcaca ctttgtaaaa                        100

SEQ ID NO: 1054          moltype = DNA  length = 100
```

```
FEATURE                Location/Qualifiers
source                 1..100
                       mol_type = genomic DNA
                       organism = Homo sapiens
SEQUENCE: 1054
tgtaataaaa acatgtggtg tgcttcttga catctaatcc acttgcagta atttctaggc  60
tttttgctcc tgttaggtcc tataaaataa tgacattagt                        100

SEQ ID NO: 1055        moltype = DNA  length = 100
FEATURE                Location/Qualifiers
source                 1..100
                       mol_type = genomic DNA
                       organism = Homo sapiens
SEQUENCE: 1055
atagatacct agatgcaaat ttttttcagc cgaccacaaa attaggtcca ctctgagtgg  60
tgaaaaacaa aagattctaa cattctagca aactggtaaa                        100

SEQ ID NO: 1056        moltype = DNA  length = 100
FEATURE                Location/Qualifiers
source                 1..100
                       mol_type = genomic DNA
                       organism = Homo sapiens
SEQUENCE: 1056
ccatacacaa attatagaat acaaagaatg cagccgatgc aaattctgtc actgacaagg  60
tagcaaagcc atagcctgat actcctcagg acacctcatc                        100

SEQ ID NO: 1057        moltype = DNA  length = 100
FEATURE                Location/Qualifiers
source                 1..100
                       mol_type = genomic DNA
                       organism = Homo sapiens
SEQUENCE: 1057
acgcccactg ggaacatggc acacactgga gattccagtc caaggacttt ggaatgtcaa  60
cttagctctt tacaaacaca actaagtttt tcagggaaaa                        100

SEQ ID NO: 1058        moltype = DNA  length = 100
FEATURE                Location/Qualifiers
source                 1..100
                       mol_type = genomic DNA
                       organism = Homo sapiens
SEQUENCE: 1058
agacttacat tggttttcct cttttggaaa attttaccga ttgatgatgc ccttggtctt  60
ctgtggagtc tattcttcta atcgggttgt tctccaattt                        100

SEQ ID NO: 1059        moltype = DNA  length = 100
FEATURE                Location/Qualifiers
source                 1..100
                       mol_type = genomic DNA
                       organism = Homo sapiens
SEQUENCE: 1059
tagtgtacaa cgggcttgtt tcaggggagc ttgtttggga tgcagactgt caagacccaa  60
cctggtatct ggttcataag cagtccctga aacctccctc                        100

SEQ ID NO: 1060        moltype = DNA  length = 100
FEATURE                Location/Qualifiers
source                 1..100
                       mol_type = genomic DNA
                       organism = Homo sapiens
SEQUENCE: 1060
cggttccaac aagctgctca agccaggaaa cggtggtcct ggggactcct ggaccttcag  60
cttgagaaac actgaagggg taccatttac caccacatcc                        100

SEQ ID NO: 1061        moltype = DNA  length = 100
FEATURE                Location/Qualifiers
source                 1..100
                       mol_type = genomic DNA
                       organism = Homo sapiens
SEQUENCE: 1061
tactggatta caaacgctag atctttggat ctccacgact agcaagcaag ttaaagactt  60
ttagatggca ggcgttatcg gtcaggttgg gagtgaacgc                        100

SEQ ID NO: 1062        moltype = DNA  length = 100
FEATURE                Location/Qualifiers
source                 1..100
                       mol_type = genomic DNA
                       organism = Homo sapiens
SEQUENCE: 1062
tttgtccaga ggaggaggta gggacgccgg gaagcaacaa ctctgatttt atttcgccgg  60
ctccacagcc tcccattgcc ccaggagccc acccgcactc                        100
```

```
SEQ ID NO: 1063        moltype = DNA  length = 100
FEATURE                Location/Qualifiers
source                 1..100
                       mol_type = genomic DNA
                       organism = Homo sapiens
SEQUENCE: 1063
caacccccgc atctcggacc tgtggcctca gcccagactc acatcaccaa gtgcacctac  60
ccagcctccg ttatcctgga tccaggtgtg caggtgccgg                        100

SEQ ID NO: 1064        moltype = DNA  length = 100
FEATURE                Location/Qualifiers
source                 1..100
                       mol_type = genomic DNA
                       organism = Homo sapiens
SEQUENCE: 1064
ttcaggtact cagtcatcca cagggcgatg ttgtccacca ggggcgacat ctcccggttg  60
acgctctcca cacacatgac cccaccgaac tcaaagaagg                        100

SEQ ID NO: 1065        moltype = DNA  length = 100
FEATURE                Location/Qualifiers
source                 1..100
                       mol_type = genomic DNA
                       organism = Homo sapiens
SEQUENCE: 1065
ccacaatcct cccccagttc accccgtccc tgaagagctc ctccaccacc gtggcaaagc  60
gtccccgcgc ggtgaagggc gtcaggtgca gctggctgga                        100

SEQ ID NO: 1066        moltype = DNA  length = 100
FEATURE                Location/Qualifiers
source                 1..100
                       mol_type = genomic DNA
                       organism = Homo sapiens
SEQUENCE: 1066
catctcggcg aagtcgcggc ggtagcggcg ggagaagtcg tcgccggcct ggcggagggt  60
caggtggacc acaggtggca ccgggctgag cgcaggcccc                        100

SEQ ID NO: 1067        moltype = DNA  length = 100
FEATURE                Location/Qualifiers
source                 1..100
                       mol_type = genomic DNA
                       organism = Homo sapiens
SEQUENCE: 1067
gcggcggcgc cgggggcagc cggggtctgc agcggcgagg tcctggcgac cgggtcccgg  60
gatgcggctg gatggggcgt gtgcccgggc tgggaggaga                        100

SEQ ID NO: 1068        moltype = DNA  length = 100
FEATURE                Location/Qualifiers
source                 1..100
                       mol_type = genomic DNA
                       organism = Homo sapiens
SEQUENCE: 1068
agatgcccgg tgcgggggcg gcccccgggg gcgcggcgcc cacatctccc gcatcccact  60
cgtagcccct ctgcgacagc ttataatgga tgtacttcat                        100

SEQ ID NO: 1069        moltype = DNA  length = 100
FEATURE                Location/Qualifiers
source                 1..100
                       mol_type = genomic DNA
                       organism = Homo sapiens
SEQUENCE: 1069
cactatctcc cggttatcgt accctgttct cccagcgtgc gccatccttc ccagaggaaa  60
agcaacgggg gccaacggca cctctcgccc cagctcccac                        100

SEQ ID NO: 1070        moltype = DNA  length = 100
FEATURE                Location/Qualifiers
source                 1..100
                       mol_type = genomic DNA
                       organism = Homo sapiens
SEQUENCE: 1070
cccacggccc ccagagaaag aagaggagtt ataatccagc tattttattg gatgtgcttt  60
gcattcttgg acgagggggt gtcttcaatc acgcggaaca                        100

SEQ ID NO: 1071        moltype = DNA  length = 100
FEATURE                Location/Qualifiers
source                 1..100
                       mol_type = genomic DNA
                       organism = Homo sapiens
SEQUENCE: 1071
```

```
cttgattctg gtgtttcccc cttggcatga gatgcaggaa atttttattc caattccttt  60
cggatcttta tttcatgagg cacgttatta ttagtaagta                        100

SEQ ID NO: 1072        moltype = DNA  length = 100
FEATURE                Location/Qualifiers
source                 1..100
                       mol_type = genomic DNA
                       organism = Homo sapiens
SEQUENCE: 1072
ttgttaatat cagtctactt cctctgtgat gctgaaaggt taaagaaaaa acaaactaat  60
aagtaaaaaa tcaggtgcgt ttccctgtac acactgagtg                        100

SEQ ID NO: 1073        moltype = DNA  length = 100
FEATURE                Location/Qualifiers
source                 1..100
                       mol_type = genomic DNA
                       organism = Homo sapiens
SEQUENCE: 1073
aaagcagggc atacacacta caagtaacac ggctaaaaag aatgtattaa gctgcctgga  60
aattaaattt actcgaatgc actttaagta aaaaatctca                        100

SEQ ID NO: 1074        moltype = DNA  length = 100
FEATURE                Location/Qualifiers
source                 1..100
                       mol_type = genomic DNA
                       organism = Homo sapiens
SEQUENCE: 1074
aaggtttcca ttgaaagtta cattaaacca atttcctgtg cagagaactt acttgtattt  60
tttaagtaca gcatgatcct ctgtcaagtt tcctttttgt                        100

SEQ ID NO: 1075        moltype = DNA  length = 100
FEATURE                Location/Qualifiers
source                 1..100
                       mol_type = genomic DNA
                       organism = Homo sapiens
SEQUENCE: 1075
aaaaccaaaa caaatgcata aggcaacgat cccatcaatc ttcagcactc tccagttata  60
gctgatttga aacttcccaa tgaatcagga gtcgcgggga                        100

SEQ ID NO: 1076        moltype = DNA  length = 100
FEATURE                Location/Qualifiers
source                 1..100
                       mol_type = genomic DNA
                       organism = Homo sapiens
SEQUENCE: 1076
gagggagtaa aaattaggag gatttccaga tcgattccca gacttctgct tcacagaaat  60
gtcaatccgc aggaatccca accggagatc tcaagagctc                        100

SEQ ID NO: 1077        moltype = DNA  length = 100
FEATURE                Location/Qualifiers
source                 1..100
                       mol_type = genomic DNA
                       organism = Homo sapiens
SEQUENCE: 1077
gagaaaaaaa aaaggcagcg gcggcggcag atgaattaca attttcagtc cggtattcgc  60
agaagtcctg tgatgttttc cccttctcgg caatttacac                        100

SEQ ID NO: 1078        moltype = DNA  length = 100
FEATURE                Location/Qualifiers
source                 1..100
                       mol_type = genomic DNA
                       organism = Homo sapiens
SEQUENCE: 1078
tgaaggagcc ggggacggag gcaggaatcc tcttctgatt aaactccgaa cagcaaatgc  60
attttccgaa aagctgctgg ataaatgaag gcaggacgcg                        100

SEQ ID NO: 1079        moltype = DNA  length = 100
FEATURE                Location/Qualifiers
source                 1..100
                       mol_type = genomic DNA
                       organism = Homo sapiens
SEQUENCE: 1079
cctggcccgc cggtgccgag cgctagaagc ccgcgctgtg tgtggtgcgg cgaggggtgg  60
ggagaaggag gtggtggggg agggttttat tttttccctc                        100

SEQ ID NO: 1080        moltype = DNA  length = 100
FEATURE                Location/Qualifiers
source                 1..100
                       mol_type = genomic DNA
```

```
                         organism = Homo sapiens
SEQUENCE: 1080
ttttcctaaa aaggatgact gctacgaagt tctccccccct ggaccccctc ttccgctgca  60
ccccaccggc gcaccccgcc tccgggctgc gcaccctttc                        100

SEQ ID NO: 1081          moltype = DNA  length = 100
FEATURE                  Location/Qualifiers
source                   1..100
                         mol_type = genomic DNA
                         organism = Homo sapiens
SEQUENCE: 1081
gtgtgtgtct cgcctggacc ttttctagcc gtgtatgtgg gagtgtgtgt gtcgcctgga  60
ccctttctag ccgtgtatga gagtgtgtac acgcgcctac                        100

SEQ ID NO: 1082          moltype = DNA  length = 100
FEATURE                  Location/Qualifiers
source                   1..100
                         mol_type = genomic DNA
                         organism = Homo sapiens
SEQUENCE: 1082
acacacacac gttgtgttac cggcgctcgg ccgccggggg aagacccagg ccaatgccgc  60
cccccaccgc ccccagcagt gggacctcag cgctgccctg                        100

SEQ ID NO: 1083          moltype = DNA  length = 100
FEATURE                  Location/Qualifiers
source                   1..100
                         mol_type = genomic DNA
                         organism = Homo sapiens
SEQUENCE: 1083
ctgtgaagac aggtgactct gcacgtttta agcaatgtct agggacgccc cgagcgtggt  60
gtttactttc aagtagcttc ctaggtgtcc gcgcactaca                        100

SEQ ID NO: 1084          moltype = DNA  length = 100
FEATURE                  Location/Qualifiers
source                   1..100
                         mol_type = genomic DNA
                         organism = Homo sapiens
SEQUENCE: 1084
cacgcacgcg catccccgcc cgtgtccacc tgaacaccta gtccgtggcc caggccatgc  60
agaactcagc gctccaggga aggggtttat caagggcttt                        100

SEQ ID NO: 1085          moltype = DNA  length = 100
FEATURE                  Location/Qualifiers
source                   1..100
                         mol_type = genomic DNA
                         organism = Homo sapiens
SEQUENCE: 1085
acgacagttt aagtcaatgt tttccctctg tccctaacac cttttacact ggtttagtgc  60
tacacgatga ggacttccat atagtaactt tcaggcccac                        100

SEQ ID NO: 1086          moltype = DNA  length = 100
FEATURE                  Location/Qualifiers
source                   1..100
                         mol_type = genomic DNA
                         organism = Homo sapiens
SEQUENCE: 1086
cgtcctaacg ctggggtggg tggctccta aaggtctcca cctttgcctc gtagccaatc  60
ctagttggcc gcactttctc aaatgaggta catagataca                        100

SEQ ID NO: 1087          moltype = DNA  length = 100
FEATURE                  Location/Qualifiers
source                   1..100
                         mol_type = genomic DNA
                         organism = Homo sapiens
SEQUENCE: 1087
gtgtctccat ggagatggca gcaggacccg accccgtgct ggcccgcact ctcggcctcc  60
ttatctggtt taggaatgcg cggtatccac gctcgctcgc                        100

SEQ ID NO: 1088          moltype = DNA  length = 100
FEATURE                  Location/Qualifiers
source                   1..100
                         mol_type = genomic DNA
                         organism = Homo sapiens
SEQUENCE: 1088
gcgggagcca cgcctcctct cccccccgcc cccgagaccg ccacacgcgc ggggccccca  60
cgtctccaag cggcactgga aggattcctc tccgtcccgc                        100

SEQ ID NO: 1089          moltype = DNA  length = 100
FEATURE                  Location/Qualifiers
```

```
source                  1..100
                        mol_type = genomic DNA
                        organism = Homo sapiens
SEQUENCE: 1089
caggggtccc gcctcgagat tctgggaaga ctgggggtgg gggaccagat cgcagcagca  60
gctgcaccgc gagttccgcg cctggccgtg tcgccccacg                        100

SEQ ID NO: 1090         moltype = DNA  length = 100
FEATURE                 Location/Qualifiers
source                  1..100
                        mol_type = genomic DNA
                        organism = Homo sapiens
SEQUENCE: 1090
agggggactg tgggctcagc gcgtggggcc cggagcatct gacaaggaca gagacagagg  60
agggggtgga aatccccggg tgagtcaacc cgtgcctgag                        100

SEQ ID NO: 1091         moltype = DNA  length = 100
FEATURE                 Location/Qualifiers
source                  1..100
                        mol_type = genomic DNA
                        organism = Homo sapiens
SEQUENCE: 1091
aagggggcga gttccgacgc tccgcccggc tcggggccac gcgaggtccg cgccacgcgc  60
gccttcaccc acgacccatc cctgagccgg agttgaaaga                        100

SEQ ID NO: 1092         moltype = DNA  length = 100
FEATURE                 Location/Qualifiers
source                  1..100
                        mol_type = genomic DNA
                        organism = Homo sapiens
SEQUENCE: 1092
ggaggcgtct gagccacgca gtcactttct ctttccttac aaaacaaagc cacgcccccc  60
gccgggggac cggaggaggc aaacaacttg gggaaaccga                        100

SEQ ID NO: 1093         moltype = DNA  length = 100
FEATURE                 Location/Qualifiers
source                  1..100
                        mol_type = genomic DNA
                        organism = Homo sapiens
SEQUENCE: 1093
cccactttcc ccttctgtcc ctaaagtttt ttcttcctct tgcctccccc agcccttttg  60
aaagctcccc gcgtcgtcct cctgctgccc cggctcctta                        100

SEQ ID NO: 1094         moltype = DNA  length = 100
FEATURE                 Location/Qualifiers
source                  1..100
                        mol_type = genomic DNA
                        organism = Homo sapiens
SEQUENCE: 1094
gcagcttctg ggacgcacgg gagggaaaag ccgcggggac cccccccacc ccagcctccc  60
agccgggtga gatttggttg ctgtgtttcc tcctcacttg                        100

SEQ ID NO: 1095         moltype = DNA  length = 100
FEATURE                 Location/Qualifiers
source                  1..100
                        mol_type = genomic DNA
                        organism = Homo sapiens
SEQUENCE: 1095
ccaccccagc ctcccagccg ggtgagattt ggttgctgtg tttcctcctc acttgggcat  60
ttaaaaaata ttttaacacg aattgtccgc ggaattttca                        100

SEQ ID NO: 1096         moltype = DNA  length = 100
FEATURE                 Location/Qualifiers
source                  1..100
                        mol_type = genomic DNA
                        organism = Homo sapiens
SEQUENCE: 1096
catggcctgg acccctctcc tcctccagct tctcaccctc tgctcaggtg actgcctgtg  60
gaatgccaaa gtgattattg gggacacatg ggatgacttt                        100

SEQ ID NO: 1097         moltype = DNA  length = 100
FEATURE                 Location/Qualifiers
source                  1..100
                        mol_type = genomic DNA
                        organism = Homo sapiens
SEQUENCE: 1097
tctcttatat tttaacattg tggggtgggt agtgaaccca gactcacctc tctgtgcctg  60
cctcctctgt tccagggtcc tgggcacagt ctgcgctgac                        100
```

```
SEQ ID NO: 1098        moltype = DNA  length = 100
FEATURE                Location/Qualifiers
source                 1..100
                       mol_type = genomic DNA
                       organism = Homo sapiens
SEQUENCE: 1098
ccaggaagcc tcggtgtcag ggaccgtggg acagaaggtc accctctcct gtactggaaa  60
cagcaacaac gttggaagtt atgctgtggg ctggtaccaa                        100

SEQ ID NO: 1099        moltype = DNA  length = 100
FEATURE                Location/Qualifiers
source                 1..100
                       mol_type = genomic DNA
                       organism = Homo sapiens
SEQUENCE: 1099
cagatttctc acggtgctcc caaaactgtg atgtttggaa attctctgcc ctcagggatc  60
cctgaccgct tctctggctc aaagtctggg accacagcct                        100

SEQ ID NO: 1100        moltype = DNA  length = 100
FEATURE                Location/Qualifiers
source                 1..100
                       mol_type = genomic DNA
                       organism = Homo sapiens
SEQUENCE: 1100
ccctgactat ctcgggcctc tagcctgagg acgaggctga ttattactgt tcaacatggg  60
actacagcct cagtgctcac acagtgctgc aggcacatgg                        100

SEQ ID NO: 1101        moltype = DNA  length = 100
FEATURE                Location/Qualifiers
source                 1..100
                       mol_type = genomic DNA
                       organism = Homo sapiens
SEQUENCE: 1101
ggaaccgaga caaaaacctg cccttggcct gtcccgaggc tgatcactcc atacttgcct  60
atgacaaaca aagagggtgc ctgtggctga tcgtacagtt                        100

SEQ ID NO: 1102        moltype = DNA  length = 100
FEATURE                Location/Qualifiers
source                 1..100
                       mol_type = genomic DNA
                       organism = Homo sapiens
SEQUENCE: 1102
gaaatgttgt ttgctcttgt ccttccttca ggccataatg agcgtctctg ttttcagggt  60
ctctctccca gcctgtgctg actcaatcat cctctgcctc                        100

SEQ ID NO: 1103        moltype = DNA  length = 100
FEATURE                Location/Qualifiers
source                 1..100
                       mol_type = genomic DNA
                       organism = Homo sapiens
SEQUENCE: 1103
tcaagctcac ctgcactctg agcagtgggc acagtagcta catcatcgca tggcatcagc  60
agcagccagg gaaggcccct cggtacttga tgaagcttga                        100

SEQ ID NO: 1104        moltype = DNA  length = 100
FEATURE                Location/Qualifiers
source                 1..100
                       mol_type = genomic DNA
                       organism = Homo sapiens
SEQUENCE: 1104
aggtagtgga agctacaaca aggggagcgg agttcctgat cgcttctcag gctccagctc  60
tggggctgac cgctacctca ccatctccaa cctccagttt                        100

SEQ ID NO: 1105        moltype = DNA  length = 100
FEATURE                Location/Qualifiers
source                 1..100
                       mol_type = genomic DNA
                       organism = Homo sapiens
SEQUENCE: 1105
gaggatgagg ctgattatta ctgtgagacc tgggacagta acactcacac agtgatacag  60
gcagatgagg aagtgggaca aaatcctcaa cctgctgagg                        100

SEQ ID NO: 1106        moltype = DNA  length = 100
FEATURE                Location/Qualifiers
source                 1..100
                       mol_type = genomic DNA
                       organism = Homo sapiens
SEQUENCE: 1106
aaggtcacca tctcctgctc tggaagcagc tccaacattg ggaataatta tgtatcctgg  60
```

```
taccagcagc tcccaggaac agcccccaaa ctcctcattt                        100

SEQ ID NO: 1107        moltype = DNA  length = 100
FEATURE                Location/Qualifiers
source                 1..100
                       mol_type = genomic DNA
                       organism = Homo sapiens
SEQUENCE: 1107
atgacaataa taagcgaccc tcagggattc ctgaccgatt ctctggctcc aagtctggca  60
cgtcagccac cctgggcatc accggactcc agactgggga                        100

SEQ ID NO: 1108        moltype = DNA  length = 100
FEATURE                Location/Qualifiers
source                 1..100
                       mol_type = genomic DNA
                       organism = Homo sapiens
SEQUENCE: 1108
tcagccagac tcacctgcac cttgcgcagt ggcatcaatc ttggtagcta caggatattc  60
tggtaccagc agaagccaga gagccctccc cggtatctcc                        100

SEQ ID NO: 1109        moltype = DNA  length = 100
FEATURE                Location/Qualifiers
source                 1..100
                       mol_type = genomic DNA
                       organism = Homo sapiens
SEQUENCE: 1109
tgagctacta ctcagactca agtaagcatc agggctctgg agtccccagc cgcttctctg  60
gatccaaaga tgcttcgagc aatgcaggga ttttagtcat                        100

SEQ ID NO: 1110        moltype = DNA  length = 100
FEATURE                Location/Qualifiers
source                 1..100
                       mol_type = genomic DNA
                       organism = Homo sapiens
SEQUENCE: 1110
agagatctgg gggaagctca gcttcagctg tggtagagaa gacaggattc aggacaatct  60
ccagcatggc cggcttccct ctcctcctca ccctcctcac                        100

SEQ ID NO: 1111        moltype = DNA  length = 100
FEATURE                Location/Qualifiers
source                 1..100
                       mol_type = genomic DNA
                       organism = Homo sapiens
SEQUENCE: 1111
tcactgtgca ggtgacagga tggggaccaa gagaggggcc ctgggaagcc catggggccc  60
tgctttctcc tcttgtctcc tttcgtctct tgtcaatcac                        100

SEQ ID NO: 1112        moltype = DNA  length = 100
FEATURE                Location/Qualifiers
source                 1..100
                       mol_type = genomic DNA
                       organism = Homo sapiens
SEQUENCE: 1112
catgtctgtg tctctctcac ttccagggtc ctgggcccag tctgtgctga ctcagccacc  60
ctcagcgtct gggacccccg ggcagagggt caccatctct                        100

SEQ ID NO: 1113        moltype = DNA  length = 100
FEATURE                Location/Qualifiers
source                 1..100
                       mol_type = genomic DNA
                       organism = Homo sapiens
SEQUENCE: 1113
tgttctggaa gcagctccaa catcggaagt aattatgtat actggtacca gcagctccca  60
ggaacggccc ccaaactcct catctatagt aataatcagc                        100

SEQ ID NO: 1114        moltype = DNA  length = 100
FEATURE                Location/Qualifiers
source                 1..100
                       mol_type = genomic DNA
                       organism = Homo sapiens
SEQUENCE: 1114
ggccctcagg ggtccctgac cgattctctg gctccaagtc tggcacctca gcctccctgg  60
ccatcagtgg gctccggtcc gaggatgagg ctgattatta                        100

SEQ ID NO: 1115        moltype = DNA  length = 100
FEATURE                Location/Qualifiers
source                 1..100
                       mol_type = genomic DNA
                       organism = Homo sapiens
```

```
SEQUENCE: 1115
atttgcataa agcagcacac agcacacccc ctccgtgcgg agagctcaat aggagataaa    60
gagccatcag aatccagccc cagctctggc accaggggtc                         100

SEQ ID NO: 1116         moltype = DNA  length = 100
FEATURE                 Location/Qualifiers
source                  1..100
                        mol_type = genomic DNA
                        organism = Homo sapiens
SEQUENCE: 1116
ccttccaata tcagcaccat ggcctggact cctctctttc tgttcctcct cacttgctgc    60
ccaggttaag agagatttca aataccagcc tttggaggga                         100

SEQ ID NO: 1117         moltype = DNA  length = 100
FEATURE                 Location/Qualifiers
source                  1..100
                        mol_type = genomic DNA
                        organism = Homo sapiens
SEQUENCE: 1117
tccctttttc tccctttcta attcctaata tatgtctgtt ttttttgttt cagggtccaa    60
ttcccaggct gtggtgactc aggagccctc actgactgtg                         100

SEQ ID NO: 1118         moltype = DNA  length = 100
FEATURE                 Location/Qualifiers
source                  1..100
                        mol_type = genomic DNA
                        organism = Homo sapiens
SEQUENCE: 1118
ggacagtcac tctcacctgt ggctccagca ctggagctgt caccagtggt cattatccct    60
actggttcca gcagaagcct ggccaagccc ccaggacact                         100

SEQ ID NO: 1119         moltype = DNA  length = 100
FEATURE                 Location/Qualifiers
source                  1..100
                        mol_type = genomic DNA
                        organism = Homo sapiens
SEQUENCE: 1119
gatttatgat acaagcaaca aacactcctg gacacctgcc cggttctcag gctccctcct    60
tgggggcaaa gctgccctga cccttttggg tgcgcagcct                         100

SEQ ID NO: 1120         moltype = DNA  length = 100
FEATURE                 Location/Qualifiers
source                  1..100
                        mol_type = genomic DNA
                        organism = Homo sapiens
SEQUENCE: 1120
gaggatgagg ctgagtatta ctgcttgctc tcctatagtg gtgctcggca cagtgacaga    60
cccatgagag gaaccaagac ataaacctcc ctcggccctt                         100

SEQ ID NO: 1121         moltype = DNA  length = 100
FEATURE                 Location/Qualifiers
source                  1..100
                        mol_type = genomic DNA
                        organism = Homo sapiens
SEQUENCE: 1121
ggtcagccac ccagcctgat tctgactctt ctggcaaaga tccctgaaaa actttaccct    60
ggtttctgcc ttagcaccca ttaatgtctg tgtttccagg                         100

SEQ ID NO: 1122         moltype = DNA  length = 100
FEATURE                 Location/Qualifiers
source                  1..100
                        mol_type = genomic DNA
                        organism = Homo sapiens
SEQUENCE: 1122
ttccctctcg caggctgtgc tgactcagcc gtcttccctc tctgcatctc ctggagcatc    60
agccagtctc acctgcacct tgcgcagtgg catcaatgtt                         100

SEQ ID NO: 1123         moltype = DNA  length = 100
FEATURE                 Location/Qualifiers
source                  1..100
                        mol_type = genomic DNA
                        organism = Homo sapiens
SEQUENCE: 1123
gcatcagcca gtctcacctg caccttgcgc agtggcatca atgttggtac ctacaggata    60
tactggtacc agcagaagcc agggagtcct ccccagtatc                         100

SEQ ID NO: 1124         moltype = DNA  length = 100
FEATURE                 Location/Qualifiers
source                  1..100
```

```
                         mol_type = genomic DNA
                         organism = Homo sapiens
SEQUENCE: 1124
tcctgaggta caaatcagac tcagataagc agcagggctc tggagtcccc agccgcttct  60
ctggatccaa agatgcttcg gccaatgcag ggattttact                        100

SEQ ID NO: 1125          moltype = DNA  length = 100
FEATURE                  Location/Qualifiers
source                   1..100
                         mol_type = genomic DNA
                         organism = Homo sapiens
SEQUENCE: 1125
acagatgggg aagtgggaca aaaacctcac cctgctctgg gtcttgctct gtaccaattt  60
ttaaatttta aaataactgg cctaggcaca aactatattt                        100

SEQ ID NO: 1126          moltype = DNA  length = 100
FEATURE                  Location/Qualifiers
source                   1..100
                         mol_type = genomic DNA
                         organism = Homo sapiens
SEQUENCE: 1126
gcccagtctg tgctgactca gccaccctca gcgtctggga cccccgggca gagggtcacc  60
atctcttgtt ctggaagcag ctccaacatc ggaagtaata                        100

SEQ ID NO: 1127          moltype = DNA  length = 100
FEATURE                  Location/Qualifiers
source                   1..100
                         mol_type = genomic DNA
                         organism = Homo sapiens
SEQUENCE: 1127
ctgtaaactg gtaccagcag ctcccaggaa cggcccccaa actcctcatc tatagtaata  60
atcagcggcc ctcaggggtc cctgaccgat tctctggctc                        100

SEQ ID NO: 1128          moltype = DNA  length = 100
FEATURE                  Location/Qualifiers
source                   1..100
                         mol_type = genomic DNA
                         organism = Homo sapiens
SEQUENCE: 1128
tgctgctcag gcctggcctg tggcttctgc tgctgcagct tccttcatgg gtccaggggc  60
atccagggcc ctgcctgaga gtggaggctc ctcctcccct                        100

SEQ ID NO: 1129          moltype = DNA  length = 100
FEATURE                  Location/Qualifiers
source                   1..100
                         mol_type = genomic DNA
                         organism = Homo sapiens
SEQUENCE: 1129
tccagcactg gagcagtcac cagtggttac tatccaaact ggttccagca gaaacctgga  60
caagcaccca gggcactgat ttatagtaca agcaacaaac                        100

SEQ ID NO: 1130          moltype = DNA  length = 100
FEATURE                  Location/Qualifiers
source                   1..100
                         mol_type = genomic DNA
                         organism = Homo sapiens
SEQUENCE: 1130
ccctccttgg gggcaaagct gccctgacac tgtcaggtgt gcagcctgag gacgaggctg  60
agtattactg cctgctctac tatggtggtg ctcagcacag                        100

SEQ ID NO: 1131          moltype = DNA  length = 100
FEATURE                  Location/Qualifiers
source                   1..100
                         mol_type = genomic DNA
                         organism = Homo sapiens
SEQUENCE: 1131
tgacagactc ataagaggaa ccaagacata aacctccctc ggcccttgtg atgtggagat  60
tgtgtgatca tacacaccag ctctcaagac agcctacatg                        100

SEQ ID NO: 1132          moltype = DNA  length = 100
FEATURE                  Location/Qualifiers
source                   1..100
                         mol_type = genomic DNA
                         organism = Homo sapiens
SEQUENCE: 1132
acataaacct ccctcggccc ttgtgatgtg gagattgtgt gatcatacac accagctctc  60
aagacagcct acatgtggac cagccataga aaggggaagg                        100

SEQ ID NO: 1133          moltype = DNA  length = 100
```

-continued

```
FEATURE                 Location/Qualifiers
source                  1..100
                        mol_type = genomic DNA
                        organism = Homo sapiens
SEQUENCE: 1133
atagaaaggg gaaggaaagg gtctgaattg atttctatcc ctccttgtgc cctgaagtgg  60
aggaaatgtg agagtgattt gcagtaattg aatgagacaa                        100

SEQ ID NO: 1134         moltype = DNA  length = 100
FEATURE                 Location/Qualifiers
source                  1..100
                        mol_type = genomic DNA
                        organism = Homo sapiens
SEQUENCE: 1134
agcaaaagtt atttgtttta tatgaaaaaa aaaaacagaa acagcaggat cagatctaaa  60
ggctgagtct aaatgcattt cctccagaca gaagcttctt                        100

SEQ ID NO: 1135         moltype = DNA  length = 100
FEATURE                 Location/Qualifiers
source                  1..100
                        mol_type = genomic DNA
                        organism = Homo sapiens
SEQUENCE: 1135
cagatctaaa ggctgagtct aaatgcattt cctccagaca gaagcttctt caaacgatgg  60
gctttctgag ctaagagcaa agaaaataaa ctctccacgg                        100

SEQ ID NO: 1136         moltype = DNA  length = 100
FEATURE                 Location/Qualifiers
source                  1..100
                        mol_type = genomic DNA
                        organism = Homo sapiens
SEQUENCE: 1136
gtatattatt aaagtttatt ttattgagtt actttcaaag caatccatga ctattatata  60
aagtcagaaa gtattaaaaa tcaccaagtt ctctgctaag                        100

SEQ ID NO: 1137         moltype = DNA  length = 100
FEATURE                 Location/Qualifiers
source                  1..100
                        mol_type = genomic DNA
                        organism = Homo sapiens
SEQUENCE: 1137
ctaccttatc ccatgcaatc aaaataagta cttttcttca tttggatgca ttttttattt  60
ctgtttttaa tatttccaca atggtgatta aacctggtgc                        100

SEQ ID NO: 1138         moltype = DNA  length = 100
FEATURE                 Location/Qualifiers
source                  1..100
                        mol_type = genomic DNA
                        organism = Homo sapiens
SEQUENCE: 1138
acagggtcag gggaggggtc caggaagccc atgaggccct gctttctcct tctctctcta  60
gaccaagaat caccgtgtct gtgtctctcc tgcttccacg                        100

SEQ ID NO: 1139         moltype = DNA  length = 100
FEATURE                 Location/Qualifiers
source                  1..100
                        mol_type = genomic DNA
                        organism = Homo sapiens
SEQUENCE: 1139
gtcctgggcc cagtctgtgt tgacgcagcc gccttcagtg tctgcggccc caggacagaa  60
ggtcaccatc tcctgctctg gaagcagctc cgacatgggg                        100

SEQ ID NO: 1140         moltype = DNA  length = 100
FEATURE                 Location/Qualifiers
source                  1..100
                        mol_type = genomic DNA
                        organism = Homo sapiens
SEQUENCE: 1140
aattatgcgg tatcctggta ccagcagctc ccaggaacag cccccaaact cctcatctat  60
gaaaataata agcgaccctc agggattcct gaccgattct                        100

SEQ ID NO: 1141         moltype = DNA  length = 100
FEATURE                 Location/Qualifiers
source                  1..100
                        mol_type = genomic DNA
                        organism = Homo sapiens
SEQUENCE: 1141
ctggctccaa gtctggcacc tcagccaccc tgggcatcac tggcctctgg cctgaggact  60
aggccgatta ttactgctta gcatgggata ccagcctgag                        100
```

```
SEQ ID NO: 1142        moltype = DNA  length = 100
FEATURE                Location/Qualifiers
source                 1..100
                       mol_type = genomic DNA
                       organism = Homo sapiens
SEQUENCE: 1142
agcttgcaca gtgctccagg ccaatgggga actgagacaa gaaccctctt cctcctccgc  60
caggagggtg agtgcctgca gctgctgctc acacctgacc                        100

SEQ ID NO: 1143        moltype = DNA  length = 100
FEATURE                Location/Qualifiers
source                 1..100
                       mol_type = genomic DNA
                       organism = Homo sapiens
SEQUENCE: 1143
tgtagcttct gctgctgtag cttcccccat gggcctcggg gcatccaggg ccttgcctag  60
gagtggaggc tccaccactt ttgtcctcag agtcaggaac                        100

SEQ ID NO: 1144        moltype = DNA  length = 100
FEATURE                Location/Qualifiers
source                 1..100
                       mol_type = genomic DNA
                       organism = Homo sapiens
SEQUENCE: 1144
agggacccca ggagacagaa tatcctgctc ctcagcttgg gacacagggt ctctgcactg  60
aaatcgtggg ctgaggtggc aggtccaact gtgtcttcac                        100

SEQ ID NO: 1145        moltype = DNA  length = 100
FEATURE                Location/Qualifiers
source                 1..100
                       mol_type = genomic DNA
                       organism = Homo sapiens
SEQUENCE: 1145
ctctgcactg aaatcgtggg ctgaggtggc aggtccaact gtgtcttcac agtccttcct  60
gtgcctgccc atggtgtggg gacggagtga ggaagtgtgg                        100

SEQ ID NO: 1146        moltype = DNA  length = 100
FEATURE                Location/Qualifiers
source                 1..100
                       mol_type = genomic DNA
                       organism = Homo sapiens
SEQUENCE: 1146
tcctcactct cctcgctcac tgcacaggtg actggataca ggtccagggg aggggccctg  60
ggaagcctat ggattcttgc tttctcctgt tgtctctaga                        100

SEQ ID NO: 1147        moltype = DNA  length = 100
FEATURE                Location/Qualifiers
source                 1..100
                       mol_type = genomic DNA
                       organism = Homo sapiens
SEQUENCE: 1147
agccgaataa tgatgcctgt gtctctccca cttccagggt cctgggccca gtctgtgctg  60
acgcagccgc cctcagtgtc tggggcccca gggcagaggg                        100

SEQ ID NO: 1148        moltype = DNA  length = 100
FEATURE                Location/Qualifiers
source                 1..100
                       mol_type = genomic DNA
                       organism = Homo sapiens
SEQUENCE: 1148
tcaccatctc ctgcactggg agcagctcca acatcggggc aggttatgat gtacactggt  60
accagcagct tccaggaaca gcccccaaac tcctcatcta                        100

SEQ ID NO: 1149        moltype = DNA  length = 100
FEATURE                Location/Qualifiers
source                 1..100
                       mol_type = genomic DNA
                       organism = Homo sapiens
SEQUENCE: 1149
ctccaggctg aggatgaggc tgattattac tgccagtcct atgacagcag cctgagtggt  60
tccacagtgc tccaggcccg gggggaactg agacaagaac                        100

SEQ ID NO: 1150        moltype = DNA  length = 100
FEATURE                Location/Qualifiers
source                 1..100
                       mol_type = genomic DNA
                       organism = Homo sapiens
SEQUENCE: 1150
```

-continued

```
gctcctcact ctcctcactc aggacacagg tgacgcctcc agggaagggg tcttggggac  60
ctctgggctg atccttggtc tcctgctcct caggctcacc                        100

SEQ ID NO: 1151        moltype = DNA  length = 100
FEATURE                Location/Qualifiers
source                 1..100
                       mol_type = genomic DNA
                       organism = Homo sapiens
SEQUENCE: 1151
ttccagggtc ctgggcccag tctgccctga ctcagcctgc ctccgtgtct gggtctcctg  60
gacagtcgat caccatctcc tgcactggaa ccagcagtga                        100

SEQ ID NO: 1152        moltype = DNA  length = 100
FEATURE                Location/Qualifiers
source                 1..100
                       mol_type = genomic DNA
                       organism = Homo sapiens
SEQUENCE: 1152
tgttgggagt tataaccttg tctcctggta ccaacagcac ccaggcaaag cccccaaact  60
catgatttat gagggcagta agcggccctc aggggtttct                        100

SEQ ID NO: 1153        moltype = DNA  length = 100
FEATURE                Location/Qualifiers
source                 1..100
                       mol_type = genomic DNA
                       organism = Homo sapiens
SEQUENCE: 1153
aatcgcttct ctggctccaa gtctggcaac acggcctccc tgacaatctc tgggctccag  60
gctgaggacg aggctgatta ttactgctgc tcatatgcag                        100

SEQ ID NO: 1154        moltype = DNA  length = 100
FEATURE                Location/Qualifiers
source                 1..100
                       mol_type = genomic DNA
                       organism = Homo sapiens
SEQUENCE: 1154
gctgaggacg aggctgatta ttactgctgc tcatatgcag gtagtagcac tttccacagt  60
ggtccaagtt catggggaac tgagaccaaa acctgcccag                        100

SEQ ID NO: 1155        moltype = DNA  length = 100
FEATURE                Location/Qualifiers
source                 1..100
                       mol_type = genomic DNA
                       organism = Homo sapiens
SEQUENCE: 1155
ggccttcaga cttcctcctt gctctgaaga tgcttcctca cccggtgcaa gaggcttgct  60
gcagcgcggc cttgagaatt cttctctctc agctccttcc                        100

SEQ ID NO: 1156        moltype = DNA  length = 100
FEATURE                Location/Qualifiers
source                 1..100
                       mol_type = genomic DNA
                       organism = Homo sapiens
SEQUENCE: 1156
ctttccacca tgaattccaa caggaaacct gccctgtggt ttcccatcca ggacagggac  60
agcttcctga tgcttgtgtg ctgtggtccc tgaatgtgca                        100

SEQ ID NO: 1157        moltype = DNA  length = 100
FEATURE                Location/Qualifiers
source                 1..100
                       mol_type = genomic DNA
                       organism = Homo sapiens
SEQUENCE: 1157
actcttccca gctcttcaaa tgcagggaca gtgacaagga gctgcctgat tggtgcagtc  60
actgcttttt tcagggatgt cttcacccta catgtatcat                        100

SEQ ID NO: 1158        moltype = DNA  length = 100
FEATURE                Location/Qualifiers
source                 1..100
                       mol_type = genomic DNA
                       organism = Homo sapiens
SEQUENCE: 1158
catcccctac actgtgggta gaattttagc aactacattc taatggttat cgccacaact  60
ttgatcttag aaataacagt gcagtgaaca tccctatgca                        100

SEQ ID NO: 1159        moltype = DNA  length = 100
FEATURE                Location/Qualifiers
source                 1..100
                       mol_type = genomic DNA
```

```
                         organism = Homo sapiens
SEQUENCE: 1159
ggctcctttg agttcctgtg tgaatacgac cataggattc atttctaaaa gtgaaattgc  60
gggtcagaaa gatgtgtgtt tgtgattttc acccaatgtt                        100

SEQ ID NO: 1160          moltype = DNA  length = 100
FEATURE                  Location/Qualifiers
source                   1..100
                         mol_type = genomic DNA
                         organism = Homo sapiens
SEQUENCE: 1160
accagcagaa gccaggccag gcccctgtgc tggtcgtcta tgatgatagc gaccggccct  60
cagggatccc tgagcgattc tctggctcca actctgggaa                        100

SEQ ID NO: 1161          moltype = DNA  length = 100
FEATURE                  Location/Qualifiers
source                   1..100
                         mol_type = genomic DNA
                         organism = Homo sapiens
SEQUENCE: 1161
cccagcctcg gtcaccctct tgctccagcc ccgggaagcc tgttgataaa gccatgagtg  60
aatctggccc agttcacctg gatctgagcc tttcaggttg                        100

SEQ ID NO: 1162          moltype = DNA  length = 100
FEATURE                  Location/Qualifiers
source                   1..100
                         mol_type = genomic DNA
                         organism = Homo sapiens
SEQUENCE: 1162
cccttccctc cagccccctc caggagtctc tacagaagat acatcaggca taaatatggc  60
ctggaagggc cagaatcatc tggtgacttg gggctgttgt                        100

SEQ ID NO: 1163          moltype = DNA  length = 100
FEATURE                  Location/Qualifiers
source                   1..100
                         mol_type = genomic DNA
                         organism = Homo sapiens
SEQUENCE: 1163
ggtcctgggc ccagtctgcc ctgactcagc ctgcctccgt gtctgggtct cctggacagt  60
cgatcaccat ctcctgcact ggaaccagca gtgacgttgg                        100

SEQ ID NO: 1164          moltype = DNA  length = 100
FEATURE                  Location/Qualifiers
source                   1..100
                         mol_type = genomic DNA
                         organism = Homo sapiens
SEQUENCE: 1164
aaagccccca aactcatgat ttatgaggtc agtaatcggc cctcaggggt ttctaatcgc  60
ttctctggct ccaagtctgg caacacggcc tccctgacca                        100

SEQ ID NO: 1165          moltype = DNA  length = 100
FEATURE                  Location/Qualifiers
source                   1..100
                         mol_type = genomic DNA
                         organism = Homo sapiens
SEQUENCE: 1165
aggctcagtg cccatagacc ccaagttggc cctgccctga accctgtgca aagcccagac  60
acagtcttag ggtaggaccc ctgggaatgg gctcttgatc                        100

SEQ ID NO: 1166          moltype = DNA  length = 100
FEATURE                  Location/Qualifiers
source                   1..100
                         mol_type = genomic DNA
                         organism = Homo sapiens
SEQUENCE: 1166
ttcaagcccc ctctcctgtt ttccttgcag tctctgaggc ctcctatgag ctgacacagc  60
caccctcggt gtcagtgtcc ccaggacaaa cggccaggat                        100

SEQ ID NO: 1167          moltype = DNA  length = 100
FEATURE                  Location/Qualifiers
source                   1..100
                         mol_type = genomic DNA
                         organism = Homo sapiens
SEQUENCE: 1167
agaagtcagg ccaggcccct gtgctggtca tctatgagga cagcaaacga ccctccggga  60
tccctgagag attctctggc tccagctcag ggacaatggc                        100

SEQ ID NO: 1168          moltype = DNA  length = 100
FEATURE                  Location/Qualifiers
```

```
source                  1..100
                        mol_type = genomic DNA
                        organism = Homo sapiens
SEQUENCE: 1168
caccttgact atcagtgggg cccaggtgga ggatgaagct gactactact gttactcaac  60
agacagcagt ggtaatcata gcacagtgac actggcagat                        100

SEQ ID NO: 1169         moltype = DNA  length = 100
FEATURE                 Location/Qualifiers
source                  1..100
                        mol_type = genomic DNA
                        organism = Homo sapiens
SEQUENCE: 1169
ggggaagtga gacacaaacc ccttcttcat ctattttacc ctctccctcc agccccagga  60
ccgctgtgga ccaacccata agcaggtctg gcagaattca                        100

SEQ ID NO: 1170         moltype = DNA  length = 100
FEATURE                 Location/Qualifiers
source                  1..100
                        mol_type = genomic DNA
                        organism = Homo sapiens
SEQUENCE: 1170
aggctcacct gggcccagca ctgactcact agactgtgtt tctccctttc cagggtcctg  60
ggcccagtct gccctgactc agcctccctc cgcgtccggg                        100

SEQ ID NO: 1171         moltype = DNA  length = 100
FEATURE                 Location/Qualifiers
source                  1..100
                        mol_type = genomic DNA
                        organism = Homo sapiens
SEQUENCE: 1171
catctcctgc actggaacca gcagtgacgt tggtggttat aactatgtct cctggtacca  60
acagcaccca ggcaaagccc ccaaactcat gatttatgag                        100

SEQ ID NO: 1172         moltype = DNA  length = 100
FEATURE                 Location/Qualifiers
source                  1..100
                        mol_type = genomic DNA
                        organism = Homo sapiens
SEQUENCE: 1172
gtcagtaagc ggccctcagg ggtccctgat cgcttctctg gctccaagtc tggcaacacg  60
gcctccctga ccgtctctgg gctccaggct gaggatgagg                        100

SEQ ID NO: 1173         moltype = DNA  length = 100
FEATURE                 Location/Qualifiers
source                  1..100
                        mol_type = genomic DNA
                        organism = Homo sapiens
SEQUENCE: 1173
aggctgagga tgaggctgat tattactgca gctcatatgc aggcagcaac aatttccaca  60
gtgttttaag tcaatgagga agtaagatca aaacctgccc                        100

SEQ ID NO: 1174         moltype = DNA  length = 100
FEATURE                 Location/Qualifiers
source                  1..100
                        mol_type = genomic DNA
                        organism = Homo sapiens
SEQUENCE: 1174
tcaggctcag aacccatagg atcctgagct gggcctgccc aaacatgagt tcatcccagg  60
cacaacctca gggtgggacc ccctgggaac agattcatca                        100

SEQ ID NO: 1175         moltype = DNA  length = 100
FEATURE                 Location/Qualifiers
source                  1..100
                        mol_type = genomic DNA
                        organism = Homo sapiens
SEQUENCE: 1175
tttacaagcc tcctctcctg tcctctcttg caagctccta tgagcttaca cagccaccct  60
cagtgtcagt gtcaccagga caggcagcca tgatcacctg                        100

SEQ ID NO: 1176         moltype = DNA  length = 100
FEATURE                 Location/Qualifiers
source                  1..100
                        mol_type = genomic DNA
                        organism = Homo sapiens
SEQUENCE: 1176
ctcttgagat aacctcaaag atgagtatgt ttactggttc tggcagaagc cagaccaggc  60
ccatactggt gatatatgaa ggcagcaagc ggccctcagg                        100
```

-continued

```
SEQ ID NO: 1177        moltype = DNA  length = 100
FEATURE                Location/Qualifiers
source                 1..100
                       mol_type = genomic DNA
                       organism = Homo sapiens
SEQUENCE: 1177
aatttctgat tttctgagtc cagctcaggg aacatggcca ccctgaccat cagcagggct  60
cagactgagg acgaggctga ctattactgt cacaggtaca                        100

SEQ ID NO: 1178        moltype = DNA  length = 100
FEATURE                Location/Qualifiers
source                 1..100
                       mol_type = genomic DNA
                       organism = Homo sapiens
SEQUENCE: 1178
atagaaacag tgatgagccc acagtgacac aggcagatta ggaagtgaga cacaaacccc  60
ttcccaatct gtgtcaccct ctttctccag ccccaggatg                        100

SEQ ID NO: 1179        moltype = DNA  length = 100
FEATURE                Location/Qualifiers
source                 1..100
                       mol_type = genomic DNA
                       organism = Homo sapiens
SEQUENCE: 1179
gggatgagaa gggaccaggg gcctgggatt gagctgtgaa gggaaccaaa aggcaggagg  60
gacagggcag gggctgtcag ctatgactca ggggaggttc                        100

SEQ ID NO: 1180        moltype = DNA  length = 100
FEATURE                Location/Qualifiers
source                 1..100
                       mol_type = genomic DNA
                       organism = Homo sapiens
SEQUENCE: 1180
ctgggcctca ggatcctccc tctgaggcca ccagggggcg ggggtggcac atgcctggac  60
ctgggaggtc cctgctgggc ttcaccctgg gtgggtccta                        100

SEQ ID NO: 1181        moltype = DNA  length = 100
FEATURE                Location/Qualifiers
source                 1..100
                       mol_type = genomic DNA
                       organism = Homo sapiens
SEQUENCE: 1181
atgcctggac ctgggaggtc cctgctgggc ttcaccctgg gtgggtccta ggagctcctt  60
cctcctaagt ccccctaaag agacagaggc attctggggt                        100

SEQ ID NO: 1182        moltype = DNA  length = 100
FEATURE                Location/Qualifiers
source                 1..100
                       mol_type = genomic DNA
                       organism = Homo sapiens
SEQUENCE: 1182
cctaaatctg tcatgccccc ataaatgcat ttctacgagg gccaataaat gaactccagg  60
tttatccaag cagcagcttc aggcgtctgc agacacagag                        100

SEQ ID NO: 1183        moltype = DNA  length = 100
FEATURE                Location/Qualifiers
source                 1..100
                       mol_type = genomic DNA
                       organism = Homo sapiens
SEQUENCE: 1183
cggggaggaa ttagccaacc tgaggcaccc tagaagggct gaagggggct gaaggggact  60
gaagggtccc tgtggggcct gtggtcctgg ggaggggaga                        100

SEQ ID NO: 1184        moltype = DNA  length = 100
FEATURE                Location/Qualifiers
source                 1..100
                       mol_type = genomic DNA
                       organism = Homo sapiens
SEQUENCE: 1184
gctggggtgt ctcccagcca ctctgggccc tgtcctgaca cttctcccac aaagaaggga  60
agggaaatcc tgggacccca cagccaggac caaccgtgaa                        100

SEQ ID NO: 1185        moltype = DNA  length = 100
FEATURE                Location/Qualifiers
source                 1..100
                       mol_type = genomic DNA
                       organism = Homo sapiens
SEQUENCE: 1185
ccacaggaca ggaaggacag ggacccccaa ggctggctcc atttcccagg cactgtcatg  60
```

```
ggctgagtct caggaaatcc aagtcaagga gtttcaatcc                       100

SEQ ID NO: 1186        moltype = DNA  length = 100
FEATURE                Location/Qualifiers
source                 1..100
                       mol_type = genomic DNA
                       organism = Homo sapiens
SEQUENCE: 1186
ccaaggaaac agaagtctac gggcccaggc ccaggtgagg gtggggtaag aagaggagct  60
taggatgcag atttgcatgg aggccccgcc ctcctctgag                       100

SEQ ID NO: 1187        moltype = DNA  length = 100
FEATURE                Location/Qualifiers
source                 1..100
                       mol_type = genomic DNA
                       organism = Homo sapiens
SEQUENCE: 1187
gcatcagggt aagacaaggc tgggggcagg cccagtgctg ggtctcagg aggcagcgct  60
ctggggacgt ctccaccatg gcctgggctc tgctcctcct                       100

SEQ ID NO: 1188        moltype = DNA  length = 100
FEATURE                Location/Qualifiers
source                 1..100
                       mol_type = genomic DNA
                       organism = Homo sapiens
SEQUENCE: 1188
ctcagggcac aggtgacgcc tccagggaag gggcctcggg gacccttggg ctgatccttg  60
gtctcctgct cctcaggctc acctgggccc agcactgact                       100

SEQ ID NO: 1189        moltype = DNA  length = 100
FEATURE                Location/Qualifiers
source                 1..100
                       mol_type = genomic DNA
                       organism = Homo sapiens
SEQUENCE: 1189
ttgggagtta tgactatgtc tcctggtacc aacagcaccc aggcacagtc cccaaaccca  60
tgatctacaa tgtcaatact cagccctcag gggtccctga                       100

SEQ ID NO: 1190        moltype = DNA  length = 100
FEATURE                Location/Qualifiers
source                 1..100
                       mol_type = genomic DNA
                       organism = Homo sapiens
SEQUENCE: 1190
tcgtttctct ggctccaagt ctggcaatac ggcctccatg accatctctg gactccaggc  60
tgaggacgag gctgattatt agtgctgctc atatacaagc                       100

SEQ ID NO: 1191        moltype = DNA  length = 100
FEATURE                Location/Qualifiers
source                 1..100
                       mol_type = genomic DNA
                       organism = Homo sapiens
SEQUENCE: 1191
tgaggacgag gctgattatt agtgctgctc atatacaagc agtgccactt aaccacagtg  60
gtccaagttc ttggggaact gagacgaaaa cctgccctgg                       100

SEQ ID NO: 1192        moltype = DNA  length = 100
FEATURE                Location/Qualifiers
source                 1..100
                       mol_type = genomic DNA
                       organism = Homo sapiens
SEQUENCE: 1192
cctgggctct caggctccct ttttgctctg aagatgtttc ctcacccagt gcaacgggct  60
tcctgaagca cagccttgag aattcttctc cctcagcaac                       100

SEQ ID NO: 1193        moltype = DNA  length = 100
FEATURE                Location/Qualifiers
source                 1..100
                       mol_type = genomic DNA
                       organism = Homo sapiens
SEQUENCE: 1193
tctcttttcc caccatgaaa tccaaaggaa acctgctctg tggtttctca tccaggacag  60
ggacagcttc cttttgcttg tgtgttgtgg tccctgagtg                       100

SEQ ID NO: 1194        moltype = DNA  length = 100
FEATURE                Location/Qualifiers
source                 1..100
                       mol_type = genomic DNA
                       organism = Homo sapiens
```

```
SEQUENCE: 1194
ggtgcaactc ttcctagctt tttaaattat gggagggtga caatgagctc cctgactggt  60
gcagtccctg ctgttttcag gaacatcctc atcctaaatg                        100

SEQ ID NO: 1195        moltype = DNA  length = 100
FEATURE                Location/Qualifiers
source                 1..100
                       mol_type = genomic DNA
                       organism = Homo sapiens
SEQUENCE: 1195
catctgaatc tcccactgtg tgcagaccaa tctggacaga tgttattagg gggagtttcc  60
agaagccaca tcttactcaa ctctgtatcc accacactct                        100

SEQ ID NO: 1196        moltype = DNA  length = 100
FEATURE                Location/Qualifiers
source                 1..100
                       mol_type = genomic DNA
                       organism = Homo sapiens
SEQUENCE: 1196
tgcctcagcc atggcatgga tccctctctt cctcggcgtc cttgcttact gcacaggtgc  60
tgcccctagg gtcctagcca ctggtccagt cccagggctc                        100

SEQ ID NO: 1197        moltype = DNA  length = 100
FEATURE                Location/Qualifiers
source                 1..100
                       mol_type = genomic DNA
                       organism = Homo sapiens
SEQUENCE: 1197
tgggtccagc ctggccctga ctctgagctc agcagggccc ccgcctgtgg tgggcaggat  60
gctcatgacc ctgctgcagg tggatgggct cggcggggct                        100

SEQ ID NO: 1198        moltype = DNA  length = 100
FEATURE                Location/Qualifiers
source                 1..100
                       mol_type = genomic DNA
                       organism = Homo sapiens
SEQUENCE: 1198
tgggcaggat gctcatgacc ctgctgcagg tggatgggct cggcggggct gaaatccccc  60
cacacagtgc tcatgtgctc acactgcctt agggctcttt                        100

SEQ ID NO: 1199        moltype = DNA  length = 100
FEATURE                Location/Qualifiers
source                 1..100
                       mol_type = genomic DNA
                       organism = Homo sapiens
SEQUENCE: 1199
catccctgga tctgtgtcca ggccaggcac gtgggaagat ttacttggag ttcagctcct  60
cagtttcaag ccttttctct cccgttttct ctcctgtagg                        100

SEQ ID NO: 1200        moltype = DNA  length = 100
FEATURE                Location/Qualifiers
source                 1..100
                       mol_type = genomic DNA
                       organism = Homo sapiens
SEQUENCE: 1200
atccgtggcc tcctatgagc tgactcagcc accctcagtg tccgtgtccc caggacagac  60
agccagcatc acctgctctg gagataaatt gggggataaa                        100

SEQ ID NO: 1201        moltype = DNA  length = 100
FEATURE                Location/Qualifiers
source                 1..100
                       mol_type = genomic DNA
                       organism = Homo sapiens
SEQUENCE: 1201
caggacagac agccagcatc acctgctctg gagataaatt gggggataaa tatgcttgct  60
ggtatcagca gaagccaggc cagtcccctg tgctggtcat                        100

SEQ ID NO: 1202        moltype = DNA  length = 100
FEATURE                Location/Qualifiers
source                 1..100
                       mol_type = genomic DNA
                       organism = Homo sapiens
SEQUENCE: 1202
ctatcaagat agcaagcggc cctcagggat ccctgagcga ttctctggct ccaactctgg  60
gaacacagcc actctgacca tcagcgggac ccaggctatg                        100

SEQ ID NO: 1203        moltype = DNA  length = 100
FEATURE                Location/Qualifiers
source                 1..100
```

```
                         mol_type = genomic DNA
                         organism = Homo sapiens
SEQUENCE: 1203
gatgaggctg actattactg tcaggcgtgg gacagcagca ctgcacacag tgacacaggc  60
agatgcggaa gtgagacaga aaccagccac ctcggcctgg                        100

SEQ ID NO: 1204          moltype = DNA  length = 100
FEATURE                  Location/Qualifiers
source                   1..100
                         mol_type = genomic DNA
                         organism = Homo sapiens
SEQUENCE: 1204
ctcacaagac ccttccctct ctcctgccct gtcacactga gcaggaggga gccttccatg  60
tggaatggaa gtttccagtc ctatccctgc ccttatgttc                        100

SEQ ID NO: 1205          moltype = DNA  length = 100
FEATURE                  Location/Qualifiers
source                   1..100
                         mol_type = genomic DNA
                         organism = Homo sapiens
SEQUENCE: 1205
ctgagagacg ggagcaagtt cctgcccacc tctaggctca gcttatccca gaataaactg  60
agctagtcat tttgatgatc aaatgccagc tcccaaaaga                        100

SEQ ID NO: 1206          moltype = DNA  length = 100
FEATURE                  Location/Qualifiers
source                   1..100
                         mol_type = genomic DNA
                         organism = Homo sapiens
SEQUENCE: 1206
ccccagaaac cctgatatct aagtagcacc gactctatta gtatcaaggg agactagccc  60
tagggtggaa tcattttagt gtctcagaag gcacagggca                        100

SEQ ID NO: 1207          moltype = DNA  length = 100
FEATURE                  Location/Qualifiers
source                   1..100
                         mol_type = genomic DNA
                         organism = Homo sapiens
SEQUENCE: 1207
atggaaagtg tttatgaggt ttcaggatat gcacgtgagc agttaaaggc aggtcttaca  60
aggaaggaac ctactagaat tggggcccat ctgtgacatc                        100

SEQ ID NO: 1208          moltype = DNA  length = 100
FEATURE                  Location/Qualifiers
source                   1..100
                         mol_type = genomic DNA
                         organism = Homo sapiens
SEQUENCE: 1208
acatccctct gctttgggag agaagggcca gggcgggacc cagagagctc tgcagaggca  60
ccacagaccc tcagcagggg gtctgccaaa caggacagct                        100

SEQ ID NO: 1209          moltype = DNA  length = 100
FEATURE                  Location/Qualifiers
source                   1..100
                         mol_type = genomic DNA
                         organism = Homo sapiens
SEQUENCE: 1209
ggacttggct gcttctgccc aggcctggat ccagcccttg cacatctcag ggcaggggat  60
aggcctgggt ggccagagct gcagctgcac ctgctgggga                        100

SEQ ID NO: 1210          moltype = DNA  length = 100
FEATURE                  Location/Qualifiers
source                   1..100
                         mol_type = genomic DNA
                         organism = Homo sapiens
SEQUENCE: 1210
ggcctagtcc agtcctccag ggtccccaga cagactcgga tttccgactg cagccaccat  60
ggaaggatgt ggtctgcggt gacgatgtct atccagaggc                        100

SEQ ID NO: 1211          moltype = DNA  length = 100
FEATURE                  Location/Qualifiers
source                   1..100
                         mol_type = genomic DNA
                         organism = Homo sapiens
SEQUENCE: 1211
ccgaatatcc aaggagccca agatcagagg caggaatagg ccaagctccc cagtggagaa  60
gctgtgctgg accaggggtt tcccagggcc ctcccttgtg                        100

SEQ ID NO: 1212          moltype = DNA  length = 100
```

-continued

```
FEATURE                Location/Qualifiers
source                 1..100
                       mol_type = genomic DNA
                       organism = Homo sapiens
SEQUENCE: 1212
ccctgaatga tgtctgttag ggcacctaca ccctgttact gctcagtgcc ttgcctattt  60
tgaaggacag ggatgtgtgg tgattatttg tataatccag                        100

SEQ ID NO: 1213        moltype = DNA  length = 100
FEATURE                Location/Qualifiers
source                 1..100
                       mol_type = genomic DNA
                       organism = Homo sapiens
SEQUENCE: 1213
cccccagcac ctggtcctca aaagttaccc aagcaatgtg tataaagatc cagcctggag  60
atctttgaaa accgattcga tgagtcgaac cattaagtca                        100

SEQ ID NO: 1214        moltype = DNA  length = 100
FEATURE                Location/Qualifiers
source                 1..100
                       mol_type = genomic DNA
                       organism = Homo sapiens
SEQUENCE: 1214
tgatcaccat cctcaacttc atctctttct tcctcctcct cctcattatc atcaccttca  60
agaactgtta agagtctgag acttcatcct atttgcagac                        100

SEQ ID NO: 1215        moltype = DNA  length = 100
FEATURE                Location/Qualifiers
source                 1..100
                       mol_type = genomic DNA
                       organism = Homo sapiens
SEQUENCE: 1215
tcctcctcct cctcattatc atcaccttca agaactgtta agagtctgag acttcatcct  60
atttgcagac taaaaagtaa gcctgccaca gtgccatgga                        100

SEQ ID NO: 1216        moltype = DNA  length = 100
FEATURE                Location/Qualifiers
source                 1..100
                       mol_type = genomic DNA
                       organism = Homo sapiens
SEQUENCE: 1216
tgctggcaga agatacaaga ctcctgggtc agagacaacg aataatctgt ttttcacagc  60
aatagcagtt gccaaggtat cagcattgtc ttgcaccagt                        100

SEQ ID NO: 1217        moltype = DNA  length = 100
FEATURE                Location/Qualifiers
source                 1..100
                       mol_type = genomic DNA
                       organism = Homo sapiens
SEQUENCE: 1217
tccacaaggt gatgcaaaga gggccaggtg acatctgcat gccagagctc agggatccca  60
aatatttcat acttgacagt aagcatatat ctgtgttttg                        100

SEQ ID NO: 1218        moltype = DNA  length = 100
FEATURE                Location/Qualifiers
source                 1..100
                       mol_type = genomic DNA
                       organism = Homo sapiens
SEQUENCE: 1218
ctccaaagag aggcattctc tgtaccttcc gaggttgttc actccacaaa cactcttgaa  60
aagataatcc acaatcagtg cctttgcccg agagacatgc                        100

SEQ ID NO: 1219        moltype = DNA  length = 100
FEATURE                Location/Qualifiers
source                 1..100
                       mol_type = genomic DNA
                       organism = Homo sapiens
SEQUENCE: 1219
agaaatgcag agatccatag tagaccactg tctcccaaca accatcaact ttatcaatga  60
aatgaagtct caggctattt gtctgttacc atagcccaca                        100

SEQ ID NO: 1220        moltype = DNA  length = 100
FEATURE                Location/Qualifiers
source                 1..100
                       mol_type = genomic DNA
                       organism = Homo sapiens
SEQUENCE: 1220
aaaatgtctg gcttgattgt caccaaatgt atcaaggaag ttaaggagta tctgacacaa  60
aatgtgaacc aagcaattct caaaggagcc tcccaggaaa                        100
```

SEQ ID NO: 1221 moltype = DNA length = 100
FEATURE Location/Qualifiers
source 1..100
mol_type = genomic DNA
organism = Homo sapiens
SEQUENCE: 1221
ttcactttag gaagtcctag gaggctcctc tgagagttgc taaaacaaaa cattgagagt 60
cctagagggc tgcagatctg aacttgagca gatattttta 100

SEQ ID NO: 1222 moltype = DNA length = 100
FEATURE Location/Qualifiers
source 1..100
mol_type = genomic DNA
organism = Homo sapiens
SEQUENCE: 1222
aagattttgt ggcagaaaaa gaaactggaa agcaagaggg cagaccctca ttgcagttct 60
gtaatgtaag ggggcagagc aggggccttt ctcaccagag 100

SEQ ID NO: 1223 moltype = DNA length = 100
FEATURE Location/Qualifiers
source 1..100
mol_type = genomic DNA
organism = Homo sapiens
SEQUENCE: 1223
gatattggac cctgcattca tcttctctgg atggtaattt tctcacctgt aaaacagaga 60
cactggcccc aaggacaccc cacaagtagt tgtgaatccc 100

SEQ ID NO: 1224 moltype = DNA length = 100
FEATURE Location/Qualifiers
source 1..100
mol_type = genomic DNA
organism = Homo sapiens
SEQUENCE: 1224
aaagtaagag aagaacaaaa aaagaaccag aatttattca acacccactg agtgcttagc 60
aaacacatgg tttctttaac tctcataagc ttcatgctgc 100

SEQ ID NO: 1225 moltype = DNA length = 100
FEATURE Location/Qualifiers
source 1..100
mol_type = genomic DNA
organism = Homo sapiens
SEQUENCE: 1225
agaggaactc tccccatttt acagataagg aaactgaggc ccagaggtaa cctaggtcta 60
gatagactcc acatttatga cttcaccact cttccttgcc 100

SEQ ID NO: 1226 moltype = DNA length = 100
FEATURE Location/Qualifiers
source 1..100
mol_type = genomic DNA
organism = Homo sapiens
SEQUENCE: 1226
aaactgaggc ccagaggtaa cctaggtcta gatagactcc acatttatga cttcaccact 60
cttccttgcc tgaaggatat agaatcactc cctgcagggc 100

SEQ ID NO: 1227 moltype = DNA length = 100
FEATURE Location/Qualifiers
source 1..100
mol_type = genomic DNA
organism = Homo sapiens
SEQUENCE: 1227
tcttgcctga ctcaggaaag ggccacagga tagccagcca ggcttaacca acccagccaa 60
gaaagggctg gtcccaactg gctggagtgc agtgtacagg 100

SEQ ID NO: 1228 moltype = DNA length = 100
FEATURE Location/Qualifiers
source 1..100
mol_type = genomic DNA
organism = Homo sapiens
SEQUENCE: 1228
gttggtagat gcccctctgg gagagatccc caggggtgac agccatggac cctggaaggg 60
cctgggctag ggacagggac cagagccagt ccagggagag 100

SEQ ID NO: 1229 moltype = DNA length = 100
FEATURE Location/Qualifiers
source 1..100
mol_type = genomic DNA
organism = Homo sapiens
SEQUENCE: 1229

```
gacagagcca atggactggg gtgtactgta acagccctgc tggcgagagg gaccagggca  60
ccgtcctcca gggagcccat gctgcaagtc gggccagagg                        100

SEQ ID NO: 1230        moltype = DNA  length = 100
FEATURE                Location/Qualifiers
source                 1..100
                       mol_type = genomic DNA
                       organism = Homo sapiens
SEQUENCE: 1230
tgcccctgaa cctgaaggcc aatgagaccc aagacaggcc aagtgggttg tgagacccct  60
gaggagctgg gccctggtcc caggcagcgc tggcccctgc                        100

SEQ ID NO: 1231        moltype = DNA  length = 100
FEATURE                Location/Qualifiers
source                 1..100
                       mol_type = genomic DNA
                       organism = Homo sapiens
SEQUENCE: 1231
tgctgctggg tctggccatg gtcgcccatg gcctgctgcg cccaatggtt gcaccgcaaa  60
gcggggaccc agaccctgga gcctcagttg gaagcagccg                        100

SEQ ID NO: 1232        moltype = DNA  length = 100
FEATURE                Location/Qualifiers
source                 1..100
                       mol_type = genomic DNA
                       organism = Homo sapiens
SEQUENCE: 1232
atccagcctg cggagcctgt ggggcaggta aggggcaaga gattccaggg gatgtggggg  60
tcctgcagca gagctgggaa agggtgacca aggggagaca                        100

SEQ ID NO: 1233        moltype = DNA  length = 100
FEATURE                Location/Qualifiers
source                 1..100
                       mol_type = genomic DNA
                       organism = Homo sapiens
SEQUENCE: 1233
agccagagga gtgaggagga aggttaaccc ctaagagggg cctgggctga cactggcttt  60
agtaatgggt tgatattttg tccatcacag atttgtttga                        100

SEQ ID NO: 1234        moltype = DNA  length = 100
FEATURE                Location/Qualifiers
source                 1..100
                       mol_type = genomic DNA
                       organism = Homo sapiens
SEQUENCE: 1234
attactgttt ttaatatcat attacgatat tatttttctt gatttctgag ttttctggcg  60
ccacttaaat tttcaccagg gtcagtgcct caatcaccta                        100

SEQ ID NO: 1235        moltype = DNA  length = 100
FEATURE                Location/Qualifiers
source                 1..100
                       mol_type = genomic DNA
                       organism = Homo sapiens
SEQUENCE: 1235
gtcctagtcc tctgggtagg gaaggaacag aggcagggac aggacatcca caggggggtgg  60
tggccactgt ccccacaggg tgcccaggcc tgttcctccc                        100

SEQ ID NO: 1236        moltype = DNA  length = 100
FEATURE                Location/Qualifiers
source                 1..100
                       mol_type = genomic DNA
                       organism = Homo sapiens
SEQUENCE: 1236
cctcctcctc tctgcccatg tgcctcctgc ccagtgaggg caggggccac tccctggaga  60
aggcagcaag ggcttggttt ggtctccccc aaggctgtct                        100

SEQ ID NO: 1237        moltype = DNA  length = 100
FEATURE                Location/Qualifiers
source                 1..100
                       mol_type = genomic DNA
                       organism = Homo sapiens
SEQUENCE: 1237
gttcaccaac ttgcacataa atgcttactg gggccaggct caaggacaca gggagggtgg  60
gatgaaccga ggggagctgt ccagtcattg gaacaggccc                        100

SEQ ID NO: 1238        moltype = DNA  length = 100
FEATURE                Location/Qualifiers
source                 1..100
                       mol_type = genomic DNA
```

```
                         organism = Homo sapiens
SEQUENCE: 1238
acggcccatg tttggagcaa taaagggaga ggggatctcc ctctgggatg atgcccaggc  60
tggtctcaca gatcgagggg cactggctgg tgatgggtgc                        100

SEQ ID NO: 1239          moltype = DNA  length = 100
FEATURE                  Location/Qualifiers
source                   1..100
                         mol_type = genomic DNA
                         organism = Homo sapiens
SEQUENCE: 1239
tggtctcaca gatcgagggg cactggctgg tgatgggtgc ccccaaaaga cagagcagcg  60
tcagaggaga ggagagcaca ggatgaggct gggagctcct                        100

SEQ ID NO: 1240          moltype = DNA  length = 100
FEATURE                  Location/Qualifiers
source                   1..100
                         mol_type = genomic DNA
                         organism = Homo sapiens
SEQUENCE: 1240
gggtgactgg gaaggggagg caagaagacc atagggtccg tgcaccattc ccagtccagg  60
acgagtcctt ggatggattt aggtagattg attatcagag                        100

SEQ ID NO: 1241          moltype = DNA  length = 100
FEATURE                  Location/Qualifiers
source                   1..100
                         mol_type = genomic DNA
                         organism = Homo sapiens
SEQUENCE: 1241
tcagatttgt gtttttggaa aaatcagcac cggattggag gctgatgcga cgcccgatta  60
gaggagggag gagagggggt gatggccaag tccagggtag                        100

SEQ ID NO: 1242          moltype = DNA  length = 100
FEATURE                  Location/Qualifiers
source                   1..100
                         mol_type = genomic DNA
                         organism = Homo sapiens
SEQUENCE: 1242
gtggggatcc tggaggaagc cgtgccttgg ggatggggag gacactcaga ttcagagcac  60
ccaggggccc agtttcctat gaaatgggag catgaagttg                        100

SEQ ID NO: 1243          moltype = DNA  length = 100
FEATURE                  Location/Qualifiers
source                   1..100
                         mol_type = genomic DNA
                         organism = Homo sapiens
SEQUENCE: 1243
aagtgagggc tgagcagagg ggagcagaca cgctcgggga ctgtctatgg gcattaaaaa  60
tgtataacca ttttagcaac aggcggcgag tcaaaaaaca                        100

SEQ ID NO: 1244          moltype = DNA  length = 100
FEATURE                  Location/Qualifiers
source                   1..100
                         mol_type = genomic DNA
                         organism = Homo sapiens
SEQUENCE: 1244
aagtgtgttt atctaaactg ggcaattcca cttctaggaa tttatcctaa gggttggttg  60
ggggaataat caaagctgta accaaatctt tataacaagg                        100

SEQ ID NO: 1245          moltype = DNA  length = 100
FEATURE                  Location/Qualifiers
source                   1..100
                         mol_type = genomic DNA
                         organism = Homo sapiens
SEQUENCE: 1245
gtggttagct cagcattatt agtgatggga gaaaactgga aaaaatccaa atatctacca  60
gaaagggtgt gaaaaaacac aattgtattt gggggactgt                        100

SEQ ID NO: 1246          moltype = DNA  length = 100
FEATURE                  Location/Qualifiers
source                   1..100
                         mol_type = genomic DNA
                         organism = Homo sapiens
SEQUENCE: 1246
tggctaattt tgattaggat tattattagt ttagagacag agcctcgcta tattgctcag  60
gcctgtctca aattcctaag ctcaagcaat ctttctgcct                        100

SEQ ID NO: 1247          moltype = DNA  length = 100
FEATURE                  Location/Qualifiers
```

```
source                  1..100
                        mol_type = genomic DNA
                        organism = Homo sapiens
SEQUENCE: 1247
actgcacctg acccaactgt gtttttaaag tatatatgca ttttcaaaaa cctgtcagaa  60
aatatagaaa aatgtcaatg gtgtgtctgg ctggctgatg                        100

SEQ ID NO: 1248         moltype = DNA  length = 100
FEATURE                 Location/Qualifiers
source                  1..100
                        mol_type = genomic DNA
                        organism = Homo sapiens
SEQUENCE: 1248
ggatttcacc taattttaat gtggctttat aattttctgg ttttgtgaag ttgttcacaa  60
aaagagacat ttcttctaat ataattttta atacaacagt                        100

SEQ ID NO: 1249         moltype = DNA  length = 100
FEATURE                 Location/Qualifiers
source                  1..100
                        mol_type = genomic DNA
                        organism = Homo sapiens
SEQUENCE: 1249
aatgtactca tgtgcattac tctttttgta atgagtatat tacaaaatgt aatgactttt  60
gtacattact ctttttttctt gccaaaaaaa aaaaagatta                       100

SEQ ID NO: 1250         moltype = DNA  length = 100
FEATURE                 Location/Qualifiers
source                  1..100
                        mol_type = genomic DNA
                        organism = Homo sapiens
SEQUENCE: 1250
agcagagaag tatataaagt aaaagcaagt gcttctgctt accatctctc acctcttccc  60
agagatagcc actgtcaggt tggtcaatat acttccagaa                        100

SEQ ID NO: 1251         moltype = DNA  length = 100
FEATURE                 Location/Qualifiers
source                  1..100
                        mol_type = genomic DNA
                        organism = Homo sapiens
SEQUENCE: 1251
cttttcctgt gtgtgtgtgt gtccctgaaa acacacacac acacacacac acacacacac  60
acagttggtg ctgggatttt attttgcaaa agtaagagcc                        100

SEQ ID NO: 1252         moltype = DNA  length = 100
FEATURE                 Location/Qualifiers
source                  1..100
                        mol_type = genomic DNA
                        organism = Homo sapiens
SEQUENCE: 1252
cacacacagt tggtgctggg attttatttt gcaaaagtaa gagccatatt ctgcatatta  60
ccaactttta atctattatt gacactttct gtatcagtcc                        100

SEQ ID NO: 1253         moltype = DNA  length = 100
FEATURE                 Location/Qualifiers
source                  1..100
                        mol_type = genomic DNA
                        organism = Homo sapiens
SEQUENCE: 1253
atatggatta accacattca ttgcttataa actttgtttt ataagcaaag tttagatgag  60
ccagaattta tttccactaa aaaatctaaa tgacaaatga                        100

SEQ ID NO: 1254         moltype = DNA  length = 100
FEATURE                 Location/Qualifiers
source                  1..100
                        mol_type = genomic DNA
                        organism = Homo sapiens
SEQUENCE: 1254
tgctgcagtg gaaatttgtg tgtgtgtgtg tgtgtgtgtg tgtgtgtgtg tgtgtgtgtg  60
tgtatgtgta caaagtgcac ttatatatct ccccaggata                        100

SEQ ID NO: 1255         moltype = DNA  length = 100
FEATURE                 Location/Qualifiers
source                  1..100
                        mol_type = genomic DNA
                        organism = Homo sapiens
SEQUENCE: 1255
tgacctgggt gtttttcttt ttctctgtag gatgttaata gtatcttgtg tcatgctagg  60
atgtctagga cagagggcaa tacaatgagg ggaaggcatt                        100
```

-continued

```
SEQ ID NO: 1256        moltype = DNA  length = 100
FEATURE                Location/Qualifiers
source                 1..100
                       mol_type = genomic DNA
                       organism = Homo sapiens
SEQUENCE: 1256
ctgcgatgtc cccaggcctc tggcttgaag agtaacttgc tgaagtgagg actctgtgga  60
ggagcaagtt atacagaaag aagtttagtt gtgatctgtt                        100

SEQ ID NO: 1257        moltype = DNA  length = 100
FEATURE                Location/Qualifiers
source                 1..100
                       mol_type = genomic DNA
                       organism = Homo sapiens
SEQUENCE: 1257
gagttggagg tgtctacagg gcatccaagc agacataggt tgaggaggca gaatatatgt  60
gaatctggag ccaagaagag aggtaagggc tggaaatagg                        100

SEQ ID NO: 1258        moltype = DNA  length = 100
FEATURE                Location/Qualifiers
source                 1..100
                       mol_type = genomic DNA
                       organism = Homo sapiens
SEQUENCE: 1258
gatctaagac ccctggacag ttgtgagtgt gcacaatgag ggtcagatgc agagaaaatt  60
aggagactac agagagcaga acccagggtg gggatctggg                        100

SEQ ID NO: 1259        moltype = DNA  length = 100
FEATURE                Location/Qualifiers
source                 1..100
                       mol_type = genomic DNA
                       organism = Homo sapiens
SEQUENCE: 1259
agtcagcagt tgggcatggg cctggtagaa agggaagcca aggaggagga gagggggcag  60
tctcagacac caaggagggg agagtgacta gaaagaaaac                        100

SEQ ID NO: 1260        moltype = DNA  length = 100
FEATURE                Location/Qualifiers
source                 1..100
                       mol_type = genomic DNA
                       organism = Homo sapiens
SEQUENCE: 1260
cttcttgcag agacataggg gatggggaag aactgcagac tgaactgggg caaaggactg  60
ttggccttaa ccagagagat ttgagggaga gatgaggctg                        100

SEQ ID NO: 1261        moltype = DNA  length = 100
FEATURE                Location/Qualifiers
source                 1..100
                       mol_type = genomic DNA
                       organism = Homo sapiens
SEQUENCE: 1261
agagccaggg gatcctgcca tgtcccagca taaaaacagt acctgacaca gatgggtgct  60
tgggagctgt tgtcggatga atgagtggac agatgcatgg                        100

SEQ ID NO: 1262        moltype = DNA  length = 100
FEATURE                Location/Qualifiers
source                 1..100
                       mol_type = genomic DNA
                       organism = Homo sapiens
SEQUENCE: 1262
atggacggat ggatggaagg atgatagatt gatggacaaa cagatgaaca gatgaatagc  60
tggatggaca actggatgga tgggtagaca gaatgatctc                        100

SEQ ID NO: 1263        moltype = DNA  length = 100
FEATURE                Location/Qualifiers
source                 1..100
                       mol_type = genomic DNA
                       organism = Homo sapiens
SEQUENCE: 1263
agagatcaga aaaagcttca tgcactaagt gggactgaac cgcgtctcca tgggtagaaa  60
gcagaggaat ctccacttga gtcaggaatg acccagtgct                        100

SEQ ID NO: 1264        moltype = DNA  length = 100
FEATURE                Location/Qualifiers
source                 1..100
                       mol_type = genomic DNA
                       organism = Homo sapiens
SEQUENCE: 1264
ctcaatccag ggagaaagcc agcctggctt cactggggac acttgtgtgg gggactcaga  60
```

```
ggccctttaa atgaggccag acgaggttgg acaggtccaa                        100

SEQ ID NO: 1265        moltype = DNA  length = 100
FEATURE                Location/Qualifiers
source                 1..100
                       mol_type = genomic DNA
                       organism = Homo sapiens
SEQUENCE: 1265
gccaactcag cactcctctg ccacactgca caggagggga tgtgtcactc agggagttgc  60
tgggacctat gggtcccagt gttgtcatca gcaccgacag                        100

SEQ ID NO: 1266        moltype = DNA  length = 100
FEATURE                Location/Qualifiers
source                 1..100
                       mol_type = genomic DNA
                       organism = Homo sapiens
SEQUENCE: 1266
cctcagagag gaaagacaca cactggggta actccaaggc tgtgtgtggc acttgccttg  60
gacagcagac aggcacaggg acacctctag ggggctggcc                        100

SEQ ID NO: 1267        moltype = DNA  length = 100
FEATURE                Location/Qualifiers
source                 1..100
                       mol_type = genomic DNA
                       organism = Homo sapiens
SEQUENCE: 1267
acccccctgc ctcatgtcta ggtcccagcc ccgcccactg caaccctgtg cccgtcatgc  60
ccagcaggct cctgctccag cccagccccc agagagcaga                        100

SEQ ID NO: 1268        moltype = DNA  length = 100
FEATURE                Location/Qualifiers
source                 1..100
                       mol_type = genomic DNA
                       organism = Homo sapiens
SEQUENCE: 1268
cactgcaacc ctgtgcccgt catgcccagc aggctcctgc tccagcccag cccccagaga  60
gcagacccca ggtgctggcc ccgggggttt tggtctgagc                        100

SEQ ID NO: 1269        moltype = DNA  length = 100
FEATURE                Location/Qualifiers
source                 1..100
                       mol_type = genomic DNA
                       organism = Homo sapiens
SEQUENCE: 1269
ctcagtcact gtgttatgtc ttcggaactg ggaccaaggt caccgtccta ggtaagtggc  60
tctcaacctt tcccagcctg tctcaccctc tgctgtccct                        100

SEQ ID NO: 1270        moltype = DNA  length = 100
FEATURE                Location/Qualifiers
source                 1..100
                       mol_type = genomic DNA
                       organism = Homo sapiens
SEQUENCE: 1270
ggaaaatctg ttttctctct ctggggcttc ctcccctctg tcctcccagc cttaagcact  60
gacccttacc tttctccatg gggcctggag gaggtgcatt                        100

SEQ ID NO: 1271        moltype = DNA  length = 100
FEATURE                Location/Qualifiers
source                 1..100
                       mol_type = genomic DNA
                       organism = Homo sapiens
SEQUENCE: 1271
agtctccggg taaccggcag gaagggcctc cacagtggga gcagccggat gcagcctggt  60
cccggggcct gagctgggat tgggcagggt cagggctcct                        100

SEQ ID NO: 1272        moltype = DNA  length = 100
FEATURE                Location/Qualifiers
source                 1..100
                       mol_type = genomic DNA
                       organism = Homo sapiens
SEQUENCE: 1272
cctctcttcc agggcagatg tctgagtgag ggacagaggc tggttctgat gaggggccct  60
gcagtgtcct tagggacatt gcccagtgac tcctggggtc                        100

SEQ ID NO: 1273        moltype = DNA  length = 100
FEATURE                Location/Qualifiers
source                 1..100
                       mol_type = genomic DNA
                       organism = Homo sapiens
```

```
SEQUENCE: 1273
ggacagaggc tggttctgat gaggggccct gcagtgtcct tagggacatt gcccagtgac  60
tcctggggtc aaggacagag gctgctgggg tgggcctggg                        100

SEQ ID NO: 1274        moltype = DNA  length = 100
FEATURE                Location/Qualifiers
source                 1..100
                       mol_type = genomic DNA
                       organism = Homo sapiens
SEQUENCE: 1274
agctgctgag tctcatagtc taggggagca gccccaagaa cagctgaggg tctaggctga  60
ggactggatg ccaatccagc ctgggagggc cacacggcct                        100

SEQ ID NO: 1275        moltype = DNA  length = 100
FEATURE                Location/Qualifiers
source                 1..100
                       mol_type = genomic DNA
                       organism = Homo sapiens
SEQUENCE: 1275
tctcatagtc taggggagca gccccaagaa cagctgaggg tctaggctga ggactggatg  60
ccaatccagc ctgggagggc cacacggcct ggtgacacag                        100

SEQ ID NO: 1276        moltype = DNA  length = 100
FEATURE                Location/Qualifiers
source                 1..100
                       mol_type = genomic DNA
                       organism = Homo sapiens
SEQUENCE: 1276
aggtcacccc aaggggagac caatggaggg cacagagagg gctctgggtc taggctgcag  60
ctctgtggcc tgtgctgggt catgaggaca tggggacaca                        100

SEQ ID NO: 1277        moltype = DNA  length = 100
FEATURE                Location/Qualifiers
source                 1..100
                       mol_type = genomic DNA
                       organism = Homo sapiens
SEQUENCE: 1277
tgtgctgggt catgaggaca tggggacaca gagggacggg tgagactggg tgaggtgcca  60
gaatccaacc ctcccaggac agtcaccaga aaggagacag                        100

SEQ ID NO: 1278        moltype = DNA  length = 100
FEATURE                Location/Qualifiers
source                 1..100
                       mol_type = genomic DNA
                       organism = Homo sapiens
SEQUENCE: 1278
tctcttaggg cagagatgtg tctgtccctg gagccccgtc acctctgggg cccagtgtct  60
ctctgttcac ggatcggcct cctgccttcc tcaaagggca                        100

SEQ ID NO: 1279        moltype = DNA  length = 100
FEATURE                Location/Qualifiers
source                 1..100
                       mol_type = genomic DNA
                       organism = Homo sapiens
SEQUENCE: 1279
tgttagactc aggaaatgac cagaggggag tgaatgaggg gtgcagagaa ctccatggct  60
accaggtgaa gtttggggtc atcacaggct gctggggtgg                        100

SEQ ID NO: 1280        moltype = DNA  length = 100
FEATURE                Location/Qualifiers
source                 1..100
                       mol_type = genomic DNA
                       organism = Homo sapiens
SEQUENCE: 1280
catagtctgt gggagcagcc ccaggaacag ctgaggtgaa gggttctgtg gtcgggcttg  60
tggagacagg aaacatctca gagcctcaga ggagccctga                        100

SEQ ID NO: 1281        moltype = DNA  length = 100
FEATURE                Location/Qualifiers
source                 1..100
                       mol_type = genomic DNA
                       organism = Homo sapiens
SEQUENCE: 1281
ggcttgtcta ggtggagccc actccttgcc aggagagcca agtgggctgg gctggggcag  60
agcccggtgc ctgtgaggga taggaagctc cagttcaaag                        100

SEQ ID NO: 1282        moltype = DNA  length = 100
FEATURE                Location/Qualifiers
source                 1..100
```

```
                        mol_type = genomic DNA
                        organism = Homo sapiens
SEQUENCE: 1282
caggcttggg tctccccaca cactgcctgc caggacagtc ctacaggatg agcaggggac  60
ccacagttca cggaggaggc tctaggtcct ggaagaataa                        100

SEQ ID NO: 1283         moltype = DNA  length = 100
FEATURE                 Location/Qualifiers
source                  1..100
                        mol_type = genomic DNA
                        organism = Homo sapiens
SEQUENCE: 1283
agtgggtgat ggaggggggt atagggatgg aaatgaggga tccaggggtc aaggccagat  60
tctaaactca gactccagag atcagagaag aaggaacaca                        100

SEQ ID NO: 1284         moltype = DNA  length = 100
FEATURE                 Location/Qualifiers
source                  1..100
                        mol_type = genomic DNA
                        organism = Homo sapiens
SEQUENCE: 1284
gcctgccctg ggtatatgga gaaattgagg ctgtagagga gaggggctgg gccaggacac  60
ctgtgaaagg tgacttggga gggctcctag gaaggcacag                        100

SEQ ID NO: 1285         moltype = DNA  length = 100
FEATURE                 Location/Qualifiers
source                  1..100
                        mol_type = genomic DNA
                        organism = Homo sapiens
SEQUENCE: 1285
tgaaagcccc actgctatga ccaggtagcc gggacgtggg gtggatgcca gaaaagactc  60
cacggaataa gagagagccc aggacagcag gcaggctctc                        100

SEQ ID NO: 1286         moltype = DNA  length = 100
FEATURE                 Location/Qualifiers
source                  1..100
                        mol_type = genomic DNA
                        organism = Homo sapiens
SEQUENCE: 1286
cgatcccccc aggcccttgc cccatacacg ggctccagaa cacacatttg gctggaacag  60
cctgagggac caaaaggccc cagtatccca cagagctgag                        100

SEQ ID NO: 1287         moltype = DNA  length = 100
FEATURE                 Location/Qualifiers
source                  1..100
                        mol_type = genomic DNA
                        organism = Homo sapiens
SEQUENCE: 1287
gagccaggcc agaaaagtaa ccccagagtt cgctgtgcag gggagacaca gagctctctt  60
tatctgtcag gatggcagga ggggacaggg tcagggcgct                        100

SEQ ID NO: 1288         moltype = DNA  length = 100
FEATURE                 Location/Qualifiers
source                  1..100
                        mol_type = genomic DNA
                        organism = Homo sapiens
SEQUENCE: 1288
gagggtcaga tgtcggtgtt gggggccaag gccccgagag atctcaggac aggtggtcag  60
gtgtctaagg taaaacagct ccccgtgcag atcagggcat                        100

SEQ ID NO: 1289         moltype = DNA  length = 100
FEATURE                 Location/Qualifiers
source                  1..100
                        mol_type = genomic DNA
                        organism = Homo sapiens
SEQUENCE: 1289
atgcaggaca gtccggagag ggaaatcagg agaagtgaag gggtctctgg ggagcccaga  60
tgtgggctag aggcagaagt aagggtgaag agcacctatg                        100

SEQ ID NO: 1290         moltype = DNA  length = 100
FEATURE                 Location/Qualifiers
source                  1..100
                        mol_type = genomic DNA
                        organism = Homo sapiens
SEQUENCE: 1290
agtcaatgtc atggtctcag caggaacaca gttgaaaatc cccattccac acaagaccgt  60
ttagcaggaa aggagtccat acttgtgctg ccaccaggat                        100

SEQ ID NO: 1291         moltype = DNA  length = 100
```

```
FEATURE                 Location/Qualifiers
source                  1..100
                        mol_type = genomic DNA
                        organism = Homo sapiens
SEQUENCE: 1291
gtcctgagaa gccttggaga atgaaacata caggtgcatt tcctagactt gacaatgcac  60
gttagccaag taaaggcaat gaaaagttct ctactaggga                        100

SEQ ID NO: 1292         moltype = DNA  length = 100
FEATURE                 Location/Qualifiers
source                  1..100
                        mol_type = genomic DNA
                        organism = Homo sapiens
SEQUENCE: 1292
tttgtttgtt tctgtatctt gtctcaactt gtggtcagcc tttctccctg catcccaggc  60
ctgagcaagg acctctgccc tccctgttca gacccttgct                        100

SEQ ID NO: 1293         moltype = DNA  length = 100
FEATURE                 Location/Qualifiers
source                  1..100
                        mol_type = genomic DNA
                        organism = Homo sapiens
SEQUENCE: 1293
tgcctcagca ggtcactaca accacttcac ctctgaccgc aggggcaggg gactagatag  60
aatgacctac tgagcctcgt ctgtctgtct gtctgtctgt                        100

SEQ ID NO: 1294         moltype = DNA  length = 100
FEATURE                 Location/Qualifiers
source                  1..100
                        mol_type = genomic DNA
                        organism = Homo sapiens
SEQUENCE: 1294
ctgtttgtct ctctgtctgt ctgacaggcg caggctgggt ctctaagcct tgttctgttc  60
tggcctcctc agtctgggtt cttgtcggaa cagctttgcc                        100

SEQ ID NO: 1295         moltype = DNA  length = 100
FEATURE                 Location/Qualifiers
source                  1..100
                        mol_type = genomic DNA
                        organism = Homo sapiens
SEQUENCE: 1295
cttgggttac ctgggttcca tctcctgggg aattgggaac aaggggtctg agggaggcac  60
ctcctgggag actttagaag gacccagtgc cctcggggct                        100

SEQ ID NO: 1296         moltype = DNA  length = 100
FEATURE                 Location/Qualifiers
source                  1..100
                        mol_type = genomic DNA
                        organism = Homo sapiens
SEQUENCE: 1296
agagttcgct gtgcagggga gacacagagc tctctttatc tgtcaggatg gcaggagggg  60
acagggtcag ggcgctgagg gtcagatgtc ggtgttgggg                        100

SEQ ID NO: 1297         moltype = DNA  length = 100
FEATURE                 Location/Qualifiers
source                  1..100
                        mol_type = genomic DNA
                        organism = Homo sapiens
SEQUENCE: 1297
gccaaggccc cgagagatct caggacaggt ggtcaggtgt ctaaggtaaa acagctcccc  60
gtgcagatca ggacatagtg gaaaacaccc tgacccctct                        100

SEQ ID NO: 1298         moltype = DNA  length = 100
FEATURE                 Location/Qualifiers
source                  1..100
                        mol_type = genomic DNA
                        organism = Homo sapiens
SEQUENCE: 1298
gcctggcata gaccttcaga cacagagccc ctgaacaagg gcaccccaac acctcatcat  60
atactgaggt caggggctcc ccaggtggac accaggactc                        100

SEQ ID NO: 1299         moltype = DNA  length = 100
FEATURE                 Location/Qualifiers
source                  1..100
                        mol_type = genomic DNA
                        organism = Homo sapiens
SEQUENCE: 1299
agaatattcc gtgagaaggt ggccccacag cgctgggtca cacgccatcc cccaagacag  60
gcaggacacc acagacaggg tggtgggtct cagaaaactc                        100
```

```
SEQ ID NO: 1300        moltype = DNA  length = 100
FEATURE                Location/Qualifiers
source                 1..100
                       mol_type = genomic DNA
                       organism = Homo sapiens
SEQUENCE: 1300
aggccctaaa cgtggatgct taccaattcc tccactggag gaagacctca gagcagatgc  60
ccaggacagg gacttctggt agggacggtg actgggacgg                        100

SEQ ID NO: 1301        moltype = DNA  length = 100
FEATURE                Location/Qualifiers
source                 1..100
                       mol_type = genomic DNA
                       organism = Homo sapiens
SEQUENCE: 1301
gtgcctgttt gtcagggaaa acccactgga gagtcagatc ccccagataa cttctcacga  60
catggagact ctttcgaaca gacaaagctc cacgttcagc                        100

SEQ ID NO: 1302        moltype = DNA  length = 100
FEATURE                Location/Qualifiers
source                 1..100
                       mol_type = genomic DNA
                       organism = Homo sapiens
SEQUENCE: 1302
tcagggagta aaaaaaaaat gcctcaaatg gaggcctttg atctactgga atccagcccc  60
caggactgac accctgtctc accaggcagc ccagaggggt                        100

SEQ ID NO: 1303        moltype = DNA  length = 100
FEATURE                Location/Qualifiers
source                 1..100
                       mol_type = genomic DNA
                       organism = Homo sapiens
SEQUENCE: 1303
cagggtccac cagaaggcat ctcagaacca gccagcagtg gccctgattg tcagcaggac  60
cccagggagg ggggtggcca ggacagggct ctgaagcccc                        100

SEQ ID NO: 1304        moltype = DNA  length = 100
FEATURE                Location/Qualifiers
source                 1..100
                       mol_type = genomic DNA
                       organism = Homo sapiens
SEQUENCE: 1304
caccccagga ccttccctgg gcagaacgag ttggtgaggg agtgatgagc aaccacaggc  60
ctcctaactt cccaagctgg cgattctgag aggcctcaag                        100

SEQ ID NO: 1305        moltype = DNA  length = 100
FEATURE                Location/Qualifiers
source                 1..100
                       mol_type = genomic DNA
                       organism = Homo sapiens
SEQUENCE: 1305
gctgagacac ggttcagcct tttaggccct cctgaacgtg tcccctgtct ccacagcctg  60
ggaatgcact ctcttttgac ccagaaatcc tgctcataag                        100

SEQ ID NO: 1306        moltype = DNA  length = 100
FEATURE                Location/Qualifiers
source                 1..100
                       mol_type = genomic DNA
                       organism = Homo sapiens
SEQUENCE: 1306
ctgtcattgt acaacacatc atttcacttt gtttttcaaa catagtgaat tctttcctaa  60
ttaaagaaga aaagagtata aagagaaagt ttccagtgca                        100

SEQ ID NO: 1307        moltype = DNA  length = 100
FEATURE                Location/Qualifiers
source                 1..100
                       mol_type = genomic DNA
                       organism = Homo sapiens
SEQUENCE: 1307
gtataaagag aaagtttcca gtgcagcctg gagatctgta ctggttgtat ctggaattcc  60
agactcagcc ttgcatttca catagcagat agatgatgat                        100

SEQ ID NO: 1308        moltype = DNA  length = 100
FEATURE                Location/Qualifiers
source                 1..100
                       mol_type = genomic DNA
                       organism = Homo sapiens
SEQUENCE: 1308
```

-continued

```
gatggagaag gagaagaaga aggaggagga ggaggaaaga aggaagaaga agaagaagag  60
gaggaggaag aagaagacga agggaagaag aagaaggatg                        100

SEQ ID NO: 1309        moltype = DNA  length = 100
FEATURE                Location/Qualifiers
source                 1..100
                       mol_type = genomic DNA
                       organism = Homo sapiens
SEQUENCE: 1309
tccaggtctg ccaggtgtag gggaggtgtg actggttcca tcatggaccg gttcctccat  60
ggaccggttc ctccgtggac cggttccgcc atggaccggt                        100

SEQ ID NO: 1310        moltype = DNA  length = 100
FEATURE                Location/Qualifiers
source                 1..100
                       mol_type = genomic DNA
                       organism = Homo sapiens
SEQUENCE: 1310
tccgccatgg accactcctg ccctggacca ctcctgccct ggaccggttc tgccgtggac  60
tggttcccgc cgtggaccag ttcccgctgt atactggttc                        100

SEQ ID NO: 1311        moltype = DNA  length = 100
FEATURE                Location/Qualifiers
source                 1..100
                       mol_type = genomic DNA
                       organism = Homo sapiens
SEQUENCE: 1311
tgccctggac tggttcccgc tgtggactgg ttccttgggg ctctaagtgc ggaagggccc  60
agagctggtc cctgcccagc gccctgctag ggctgtgtcc                        100

SEQ ID NO: 1312        moltype = DNA  length = 100
FEATURE                Location/Qualifiers
source                 1..100
                       mol_type = genomic DNA
                       organism = Homo sapiens
SEQUENCE: 1312
tcgtactcgt gcgcctcgct tcggtgagcc ccagggcccc tgcctccttc ctcctgccgt  60
cctgcctccg tccccgccct ttcatcatcc gcgtccctgt                        100

SEQ ID NO: 1313        moltype = DNA  length = 100
FEATURE                Location/Qualifiers
source                 1..100
                       mol_type = genomic DNA
                       organism = Homo sapiens
SEQUENCE: 1313
gaaggcattc cctaaatccg agcccgagtg gttctccccg ggaaggctac tttggggagc  60
tggggggatg cgaaacaccc tagatactgg ataatggggt                        100

SEQ ID NO: 1314        moltype = DNA  length = 100
FEATURE                Location/Qualifiers
source                 1..100
                       mol_type = genomic DNA
                       organism = Homo sapiens
SEQUENCE: 1314
ggggaaatcg atgatttaag aacaaaaccg aaaaactggc gttttgccgt gccgctcgga  60
ggggacatta aaaaatttct tagtgtttgc ccgcaaaggt                        100

SEQ ID NO: 1315        moltype = DNA  length = 100
FEATURE                Location/Qualifiers
source                 1..100
                       mol_type = genomic DNA
                       organism = Homo sapiens
SEQUENCE: 1315
tagtgtttgc ccgcaaaggt attgtgcgtt gccttggagg ctgagatatg gggggaataga  60
caagtccttt gttctgaggt tcatcttccg agccccgagc                        100

SEQ ID NO: 1316        moltype = DNA  length = 100
FEATURE                Location/Qualifiers
source                 1..100
                       mol_type = genomic DNA
                       organism = Homo sapiens
SEQUENCE: 1316
ctcctcccag cctcggacgg ctgcgcgggc tgcatctgtg cagcctggcg gcggcggggc  60
tgtgctatga catctttaca gtccttcttg cagagacatg                        100

SEQ ID NO: 1317        moltype = DNA  length = 100
FEATURE                Location/Qualifiers
source                 1..100
                       mol_type = genomic DNA
```

```
                        organism = Homo sapiens
SEQUENCE: 1317
tgtgccaggg atgccgaatt gccgggagag caggcaagac cggcttcggg gcgcgcggcg  60
gccgctttgt gtgcggggct gcattgtgac gcgggcgatg                        100

SEQ ID NO: 1318         moltype = DNA  length = 100
FEATURE                 Location/Qualifiers
source                  1..100
                        mol_type = genomic DNA
                        organism = Homo sapiens
SEQUENCE: 1318
aagccggtag ggcggtggtc ggaagctcca gccgcggccg ccgcctttgt gagaggacta  60
gaaagccgga tccggcccgc atccttgcgg agaggccgcg                        100

SEQ ID NO: 1319         moltype = DNA  length = 100
FEATURE                 Location/Qualifiers
source                  1..100
                        mol_type = genomic DNA
                        organism = Homo sapiens
SEQUENCE: 1319
gctaggaaat ggaaacgctt ttcctacctg ggctccattt taggaattct tgccgatttt  60
tcccacttga atttggaagt ggctttcctc ttctttcctt                        100

SEQ ID NO: 1320         moltype = DNA  length = 100
FEATURE                 Location/Qualifiers
source                  1..100
                        mol_type = genomic DNA
                        organism = Homo sapiens
SEQUENCE: 1320
gtcctagcca gcctttaatt ttaaacgctg taattaacaa ttcgcagtgg tcaatttcct  60
ttattctgca agattcggct ttgagaggca tccgccctct                        100

SEQ ID NO: 1321         moltype = DNA  length = 100
FEATURE                 Location/Qualifiers
source                  1..100
                        mol_type = genomic DNA
                        organism = Homo sapiens
SEQUENCE: 1321
ttggtccaca gcgttttgaa atatggggag gaggggcgcg gggggtgtcg cctctttttc  60
tgtagaaaga ggaagctcgt gagcgcggaa cggcagcagt                        100

SEQ ID NO: 1322         moltype = DNA  length = 100
FEATURE                 Location/Qualifiers
source                  1..100
                        mol_type = genomic DNA
                        organism = Homo sapiens
SEQUENCE: 1322
aagtgcagtt cccagcccag agacagcggg gcgggtggct cttcctcacg ctcgctcttg  60
gcttgctccc tgcagctttt cctccgcaac catgtctgac                        100

SEQ ID NO: 1323         moltype = DNA  length = 100
FEATURE                 Location/Qualifiers
source                  1..100
                        mol_type = genomic DNA
                        organism = Homo sapiens
SEQUENCE: 1323
aaacccgata tggctgagat cgagaaattc gataagtcga aactgaagaa gacagagacg  60
caagagaaaa atccactgcc ttccaaagaa agtgagctcc                        100

SEQ ID NO: 1324         moltype = DNA  length = 100
FEATURE                 Location/Qualifiers
source                  1..100
                        mol_type = genomic DNA
                        organism = Homo sapiens
SEQUENCE: 1324
agacgcaaga gaaaaatcca ctgccttcca aagaaagtga gctccgaccc acccccatct  60
ttagaaaggc tgggtgggag cggccggtgg gagggcggga                        100

SEQ ID NO: 1325         moltype = DNA  length = 100
FEATURE                 Location/Qualifiers
source                  1..100
                        mol_type = genomic DNA
                        organism = Homo sapiens
SEQUENCE: 1325
tttatagaaa ggcatatgga acaggagtca tccaaatata tcccaggggt tgcaaattga  60
ccaaaagagt cacctttagg gaagcctgct tctgaatgct                        100

SEQ ID NO: 1326         moltype = DNA  length = 100
FEATURE                 Location/Qualifiers
```

```
source                  1..100
                        mol_type = genomic DNA
                        organism = Homo sapiens
SEQUENCE: 1326
tgtggaattt atcattcttc tgaatggctg ttgcatttat ctgcagcttt tactcaccag  60
atgagacctc agacatttca aattctgcgg aggctggcta                        100

SEQ ID NO: 1327         moltype = DNA  length = 100
FEATURE                 Location/Qualifiers
source                  1..100
                        mol_type = genomic DNA
                        organism = Homo sapiens
SEQUENCE: 1327
cacaccttca taggaaagct ttttgctgat ttccctgttg gtacttttct cttacacatt  60
ctatggggta tggtaaacct ggaggtagag tcatagccaa                        100

SEQ ID NO: 1328         moltype = DNA  length = 100
FEATURE                 Location/Qualifiers
source                  1..100
                        mol_type = genomic DNA
                        organism = Homo sapiens
SEQUENCE: 1328
gcacagataa agcaggcaca gaatctctga ccagcctcac aaaagcagac aaacacacaa  60
tctttttgca cctgtttctt ccactccggt tgccgtgaat                        100

SEQ ID NO: 1329         moltype = DNA  length = 100
FEATURE                 Location/Qualifiers
source                  1..100
                        mol_type = genomic DNA
                        organism = Homo sapiens
SEQUENCE: 1329
tagaaatggt tcaaccagtc caatatcaat atagctgctt attactctat tcacttactt  60
caaagtggca tttgttttga gtaagacttt atttaattct                        100

SEQ ID NO: 1330         moltype = DNA  length = 100
FEATURE                 Location/Qualifiers
source                  1..100
                        mol_type = genomic DNA
                        organism = Homo sapiens
SEQUENCE: 1330
taccgttagc ttgaaaccat agagatcttc tctctatttg ccctacttcc ttcaaaagtc  60
aaatgacctc ctacaaataa aagacgttct tattttcatt                        100

SEQ ID NO: 1331         moltype = DNA  length = 150
FEATURE                 Location/Qualifiers
source                  1..150
                        mol_type = genomic DNA
                        organism = Homo sapiens
SEQUENCE: 1331
cgactacgac tcggtgcagc cgtatttcta ctgcgacgag gaggagaact tctaccagca  60
gcagcagcag agcgagctgc agcccccggc gcccagcgag gatatctgga agaaattcga  120
gctgctgccc accccgcccc tgtcccctag                                   150

SEQ ID NO: 1332         moltype = DNA  length = 150
FEATURE                 Location/Qualifiers
source                  1..150
                        mol_type = genomic DNA
                        organism = Homo sapiens
SEQUENCE: 1332
cgactacgac tcggtgcagc cgtagttcta ctgcgacgag gaggaaaact tctaccagca  60
gcagcagcag agcgagctgc agcccctggc gcccagcgag gatatctgga agaacttcga  120
gctgctgccc accccgcccc tgtcccctag                                   150

SEQ ID NO: 1333         moltype = DNA  length = 150
FEATURE                 Location/Qualifiers
source                  1..150
                        mol_type = genomic DNA
                        organism = Homo sapiens
SEQUENCE: 1333
cgactacgac tcggtgcagc cgtagttcta ctgcgacgag gaggaatact tctaccagca  60
gcagccgcag agcgagctgc agcccctggc gcccagcgag ggtatctgga agaacttcga  120
gctactgccc accccgcccc tgtcccctag                                   150

SEQ ID NO: 1334         moltype = DNA  length = 150
FEATURE                 Location/Qualifiers
source                  1..150
                        mol_type = genomic DNA
                        organism = Homo sapiens
SEQUENCE: 1334
```

-continued

```
cgactacgac tcgttgcagc cgtagttcta ctgcgacgag gaggaatact tctaccagca  60
gcagccgcag agcgagctgc agcgcctggc gcccagcgag ggtatctgga agaacttcga  120
gctacagccc accccgcccc tgtcccctag                                   150

SEQ ID NO: 1335        moltype = DNA  length = 150
FEATURE                Location/Qualifiers
source                 1..150
                       mol_type = genomic DNA
                       organism = Homo sapiens
SEQUENCE: 1335
cgactacgac tcgttgcagc cgtagatcta ctgcgacgag gaggaatact tctacctgca  60
gcagccgcag agcgagctgc agcgcctggc gcccagcgag cgtatctgga agaacttcga  120
gctacagccc accccgccct tgtcccctag                                   150

SEQ ID NO: 1336        moltype = DNA  length = 150
FEATURE                Location/Qualifiers
source                 1..150
                       mol_type = genomic DNA
                       organism = Homo sapiens
SEQUENCE: 1336
cgacaacgac tcgttgcacc cgtagatcta ctgcgacgag gaggaatact tctacctgca  60
gcagccgcag agcgagctgc agcgcctggc gcccagcgag cgtatctgaa agaacttcga  120
gctacagccc acgccgccct tgtcccctag                                   150

SEQ ID NO: 1337        moltype = DNA  length = 150
FEATURE                Location/Qualifiers
source                 1..150
                       mol_type = genomic DNA
                       organism = Homo sapiens
SEQUENCE: 1337
cgacaacgac tcgttgcacc cgtagatcta ctgcgacgag gaggaatact tctacctgca  60
gcagccgcag agcgagctgc agcgcctggc gcccagcgag cgtatctgaa agaacttcga  120
gctacagccc acgccgccct tgtcccctag                                   150

SEQ ID NO: 1338        moltype = DNA  length = 150
FEATURE                Location/Qualifiers
source                 1..150
                       mol_type = genomic DNA
                       organism = Homo sapiens
SEQUENCE: 1338
gctcacctgt acaaatctgg ctccgcaggt ttcgcatttg tagggcttct ctccagagtg  60
aattcgagtg tgggttttca ggttggctgg ccggttgaac tgggccccac agatgttgca  120
acgatagggt ttctcaccta ttaccaagaa                                   150

SEQ ID NO: 1339        moltype = DNA  length = 150
FEATURE                Location/Qualifiers
source                 1..150
                       mol_type = genomic DNA
                       organism = Homo sapiens
SEQUENCE: 1339
gctcacctgt acaaatctgc ctccgcaggt ttcgcatttg tagggctcct ctccagagtg  60
aattcgagtg tgggttttca ggttggctgg gcggttgaac tgggccccac agatgttgca  120
acgctagggt ttctcaccta ttaccaagaa                                   150

SEQ ID NO: 1340        moltype = DNA  length = 150
FEATURE                Location/Qualifiers
source                 1..150
                       mol_type = genomic DNA
                       organism = Homo sapiens
SEQUENCE: 1340
gctcacctgt acaaatctgc ctccgcaggt ttcgcctttg tagggctcct ctccagagtg  60
aattcgagtg taggttttca agttggctgg gcggttgaac tgggccccac ggatgttgca  120
acgctagggt ttctcaccta ttaccaagaa                                   150

SEQ ID NO: 1341        moltype = DNA  length = 150
FEATURE                Location/Qualifiers
source                 1..150
                       mol_type = genomic DNA
                       organism = Homo sapiens
SEQUENCE: 1341
gctcacctgt acaaatctgc ctccgccggt ttcgcctttt tagggctcct ctccagagtg  60
aattcgagtg taggttttca agttggctgg gcggttgaac tgggccccac ggatgttgca  120
acgctagggt ttctcaccta tttccaagaa                                   150

SEQ ID NO: 1342        moltype = DNA  length = 150
FEATURE                Location/Qualifiers
source                 1..150
                       mol_type = genomic DNA
                       organism = Homo sapiens
```

```
SEQUENCE: 1342
gctcacctgt acaagtctgc ctccgccggt tacgcctttt tagggctcct ctccagagtg  60
aattcgagtg taggttttca agttggctgg gcggttgaac tgggctccac ggatgttgca  120
acgctaggga ttctcaccta tttccaagaa                                   150

SEQ ID NO: 1343        moltype = DNA  length = 150
FEATURE                Location/Qualifiers
source                 1..150
                       mol_type = genomic DNA
                       organism = Homo sapiens
SEQUENCE: 1343
gctcacctgg acaagtctgc ctccgccggt tacgactttt tagggctcct ctccagagtg  60
aattcgagtg taggctttca agttggctgg gcggttgaac tgggctccac ggctgttgca  120
acgctaggga ttctcaccta tttccaagaa                                   150

SEQ ID NO: 1344        moltype = DNA  length = 150
FEATURE                Location/Qualifiers
source                 1..150
                       mol_type = genomic DNA
                       organism = Homo sapiens
SEQUENCE: 1344
gctcacctgg acaagtctgc ctccgccggt tacgactttt tagggcacct ctccagagtg  60
aattcgagtg taggctttca agttggctgg gagcttgaac tgggctgcac ggctgttgca  120
acgctaggga ttctcaccta tttccaagaa                                   150

SEQ ID NO: 1345        moltype = DNA  length = 150
FEATURE                Location/Qualifiers
source                 1..150
                       mol_type = genomic DNA
                       organism = Homo sapiens
SEQUENCE: 1345
ctaggggaca ggggcggggt gggcagcagc tcgaatttct tccagatatc ctcgctgggc  60
gccgggggct gcagctcgct ctgctgctgc tgctggtaga agttctcctc ctcgtcgcag  120
tagaaatacg gctgcaccga gtcgtagtcg                                   150

SEQ ID NO: 1346        moltype = DNA  length = 150
FEATURE                Location/Qualifiers
source                 1..150
                       mol_type = genomic DNA
                       organism = Homo sapiens
SEQUENCE: 1346
ctaggggaca ggggcggggt gggcagcagc tcgaagttct tccagatatc ctcgctgggc  60
gccaggggct gcagctcgct ctgctgctgc tgctggtaga agttttcctc ctcgtcgcag  120
tagaactacg gctgcaccga gtcgtagtcg                                   150

SEQ ID NO: 1347        moltype = DNA  length = 150
FEATURE                Location/Qualifiers
source                 1..150
                       mol_type = genomic DNA
                       organism = Homo sapiens
SEQUENCE: 1347
ctaggggaca ggggcggggt gggcagtagc tcgaagttct tccagatacc ctcgctgggc  60
gccaggggct gcagctcgct ctgcggctgc tgctggtaga agtattcctc ctcgtcgcag  120
tagaactacg gctgcaccga gtcgtagtcg                                   150

SEQ ID NO: 1348        moltype = DNA  length = 150
FEATURE                Location/Qualifiers
source                 1..150
                       mol_type = genomic DNA
                       organism = Homo sapiens
SEQUENCE: 1348
ctaggggaca ggggcggggt gggctgtagc tcgaagttct tccagatacc ctcgctgggc  60
gccaggcgct gcagctcgct ctgcggctgc tgctggtaga agtattcctc ctcgtcgcag  120
tagaactacg gctgcaacga gtcgtagtcg                                   150

SEQ ID NO: 1349        moltype = DNA  length = 150
FEATURE                Location/Qualifiers
source                 1..150
                       mol_type = genomic DNA
                       organism = Homo sapiens
SEQUENCE: 1349
ctaggggaca agggcggggt gggctgtagc tcgaagttct tccagatacg ctcgctgggc  60
gccaggcgct gcagctcgct ctgcggctgc tgcaggtaga agtattcctc ctcgtcgcag  120
tagatctacg gctgcaacga gtcgtagtcg                                   150

SEQ ID NO: 1350        moltype = DNA  length = 150
FEATURE                Location/Qualifiers
source                 1..150
                       mol_type = genomic DNA
```

```
                        organism = Homo sapiens
SEQUENCE: 1350
ctaggggaca agggcggcgt gggctgtagc tcgaagttct ttcagatacg ctcgctgggc  60
gccaggcgct gcagctcgct ctgcggctgc tgcaggtaga agtattcctc ctcgtcgcag  120
tagatctacg ggtgcaacga gtcgttgtcg                                   150

SEQ ID NO: 1351         moltype = DNA  length = 150
FEATURE                 Location/Qualifiers
source                  1..150
                        mol_type = genomic DNA
                        organism = Homo sapiens
SEQUENCE: 1351
ctaggcgaca agggcggcgt gggctgtagc tcgaagttct ttcagatacg ctcggtgggc  60
gccaggcgct gcagcacgct ctgcggctgc tgcaggtaga agtattcctc ctcgtcgcag  120
tagatctacg ggtgcaacga gtcgctgtcg                                   150

SEQ ID NO: 1352         moltype = DNA  length = 150
FEATURE                 Location/Qualifiers
source                  1..150
                        mol_type = genomic DNA
                        organism = Homo sapiens
SEQUENCE: 1352
ttcttggtaa taggtgagaa accctatcgt tgcaacatct gtggggccca gttcaaccgg  60
ccagccaacc tgaaaaccca cactcgaatt cactctggag agaagcccta caaatgcgaa  120
acctgcggag ccagatttgt acaggtgagc                                   150

SEQ ID NO: 1353         moltype = DNA  length = 150
FEATURE                 Location/Qualifiers
source                  1..150
                        mol_type = genomic DNA
                        organism = Homo sapiens
SEQUENCE: 1353
ttcttggtaa taggtgagaa accctagcgt tgcaacatct gtggggccca gttcaaccgc  60
ccagccaacc tgaaaaccca cactcgaatt cactctggag aggagcccta caaatgcgaa  120
acctgcggag gcagatttgt acaggtgagc                                   150

SEQ ID NO: 1354         moltype = DNA  length = 150
FEATURE                 Location/Qualifiers
source                  1..150
                        mol_type = genomic DNA
                        organism = Homo sapiens
SEQUENCE: 1354
ttcttggtaa taggtgagaa accctagcgt tgcaacatcc gtggggccca gttcaaccgc  60
ccagccaact tgaaaaccta cactcgaatt cactctggag aggagcccta caaaggcgaa  120
acctgcggag gcagatttgt acaggtgagc                                   150

SEQ ID NO: 1355         moltype = DNA  length = 150
FEATURE                 Location/Qualifiers
source                  1..150
                        mol_type = genomic DNA
                        organism = Homo sapiens
SEQUENCE: 1355
ttcttggaaa taggtgagaa accctagcgt tgcaacatcc gtggggccca gttcaaccgc  60
ccagccaact tgaaaaccta cactcgaatt cactctggag aggagcccta aaaaggcgaa  120
accggcggag gcagatttgt acaggtgagc                                   150

SEQ ID NO: 1356         moltype = DNA  length = 150
FEATURE                 Location/Qualifiers
source                  1..150
                        mol_type = genomic DNA
                        organism = Homo sapiens
SEQUENCE: 1356
ttcttggaaa taggtgagaa tccctagcgt tgcaacatcc gtggagccca gttcaaccgc  60
ccagccaact tgaaaaccta cactcgaatt cactctggag aggagcccta aaaaggcgta  120
accggcggag gcagacttgt acaggtgagc                                   150

SEQ ID NO: 1357         moltype = DNA  length = 150
FEATURE                 Location/Qualifiers
source                  1..150
                        mol_type = genomic DNA
                        organism = Homo sapiens
SEQUENCE: 1357
ttcttggaaa taggtgagaa tccctagcgt tgcaacagcc gtggagccca gttcaaccgc  60
ccagccaact tgaaagccta cactcgaatt cactctggag aggagcccta aaaagtcgta  120
accggcggag gcagacttgt ccaggtgagc                                   150

SEQ ID NO: 1358         moltype = DNA  length = 150
FEATURE                 Location/Qualifiers
source                  1..150
```

-continued

```
                      mol_type = genomic DNA
                      organism = Homo sapiens
SEQUENCE: 1358
ttcttggaaa taggtgagaa tccctagcgt tgcaacagcc gtgcagccca gttcaagctc  60
ccagccaact tgaaagccta cactcgaatt cactctggag aggtgcccta aaaagtcgta  120
accggcggag gcagacttgt ccaggtgagc                                   150
```

METHODS AND SYSTEMS FOR ANALYZING NUCLEIC ACID MOLECULES

CROSS-REFERENCE

This application is a continuation of U.S. patent application Ser. No. 17/646,473, filed Dec. 29, 2021, which is a continuation of PCT Patent Application No. PCT/US2020/059526, filed Nov. 6, 2020, which claims the benefit of U.S. Provisional Patent Application No. 62/931,688, filed Nov. 6, 2019, the disclosures of which are entirely incorporated herein by reference in their entirety.

GOVERNMENT RIGHTS

This invention was made with Government support under CA233975, CA241076, and CA188298 awarded by the National Institutes of Health. The Government has certain rights in the invention.

SEQUENCE LISTING

The instant application contains a Sequence Listing which has been submitted electronically in XML file format and is hereby incorporated by reference in its entirety. Said XML copy, created on Aug. 11, 2022, is named 58626-702_601_SL.xml and is 1,304,877 bytes in size.

BACKGROUND

Noninvasive blood tests that can detect somatic alterations (e.g., mutated nucleic acids) based on the analysis of cell-free nucleic acids (e.g., cell-free deoxyribonucleic acid (cfDNA) and cell-free ribonucleic acid (cfRNA)) are attractive candidates for cancer screening applications due to the relative ease of obtaining biological specimens (e.g., biological fluids). Circulating tumor nucleic acids (e.g., ctDNA or ctRNA; i.e., nucleic acids derived from cancerous cells) can be sensitive and specific biomarkers in numerous cancer subtypes. However, current methods for minimal residual disease (MRD) detection from ctDNA can be limited by one or more factors, such as low input DNA amounts and high background error rates.

Recent approaches have improved ctDNA MRD performance by tracking multiple somatic mutations with error-suppressed sequencing, resulting in detection limits as low as 4 parts in 100,000 from limited cfDNA input. Detection of residual disease during or after treatment is a powerful tool, with detectable MRD representing an adverse prognostic sign even during radiographic remission. However, current limits of detection may be insufficient to universally detect residual disease in patients destined for disease relapse or progression. This 'loss of detection' is exemplified in diffuse large B-cell lymphoma (DLBCL), where ctDNA detection after two cycles of curative-intent therapy is a strong prognostic marker. Despite this, almost one-third of patients experiencing disease progression do not have detectable ctDNA at this landmark, representing 'false-negative' tests. Similar false-negative rates in colon cancer and breast cancer have been observed.

SUMMARY

The present disclosure provides methods and systems for analyzing cell-free nucleic acids (e.g., cfDNA, cfRNA) from a subject. Methods and systems of the present disclosure can utilize sequencing results derived from the subject to detect cancer-derived nucleic acids (e.g., ctDNA, ctRNA) for, e.g., disease diagnosis, disease monitoring, or determining treatments for the subject. Methods and systems of the present disclosure can exhibit enhanced sensitivity, specificity and/or reliability of detection of cancer-derived nucleic acids.

In one aspect, the present disclosure provides a method comprising: (a) obtaining, by a computer system, sequencing data derived from a plurality of cell-free nucleic acid molecules that is obtained or derived from a subject; (b) processing, by the computer system, the sequencing data to identify one or more cell-free nucleic acid molecules of the plurality of cell-free nucleic acid molecules, wherein each of the one or more cell-free nucleic acid molecules comprises a plurality of phased variants relative to a reference genomic sequence, wherein at least about 10% of the one or more cell-free nucleic acid molecules comprises a first phased variant of the plurality of phased variants and a second phased variant of the plurality of phased variants that are separated by at least one nucleotide; and (c) analyzing, by the computer system, the identified one or more cell-free nucleic acid molecules to determine a condition of the subject.

In some embodiments of any one of the methods disclosed herein, the at least about 10% of the cell-free nucleic acid molecules comprise at least about 20%, at least about 30%, at least about 40%, at least about 50%, at least about 60%, at least about 70%, at least about 80%, at least about 90%, or about 100% of the one or more cell-free nucleic acid molecules.

In one aspect, the present disclosure provides a method comprising: (a) obtaining, by a computer system, sequencing data derived from a plurality of cell-free nucleic acid molecules that is obtained or derived from a subject; (b) processing, by the computer system, the sequencing data to identify one or more cell-free nucleic acid molecules of the plurality of cell-free nucleic acid molecules, wherein each of the one or more cell-free nucleic acid molecules comprises a plurality of phased variants relative to a reference genomic sequence that are separated by at least one nucleotide; and (c) analyzing, by the computer system, the identified one or more cell-free nucleic acid molecules to determine a condition of the subject.

In one aspect, the present disclosure provides a method comprising: (a) obtaining sequencing data derived from a plurality of cell-free nucleic acid molecules that is obtained or derived from a subject; (b) processing the sequencing data to identify one or more cell-free nucleic acid molecules of the plurality of cell-free nucleic acid molecules with a limit of detection of less than about 1 out of 50,000 observations from the sequencing data; and (c) analyzing the identified one or more cell-free nucleic acid molecules to determine a condition of the subject.

In some embodiments of any one of the methods disclosed herein, the limit of detection of the identification step is less than about 1 out of 100,000, less than about 1 out of 500,000, less than about 1 out of 1,000,000, less than about 1 out of 1,500,000, or less than about 1 out of 2,000,000 observations from the sequencing data.

In some embodiments of any one of the methods disclosed herein, each of the one or more cell-free nucleic acid molecules comprises a plurality of phased variants relative to a reference genomic sequence. In some embodiments of any one of the methods disclosed herein, a first phased variant of the plurality of phased variants and a second phased variant of the plurality of phased variants are separated by at least one nucleotide.

In some embodiments of any one of the methods disclosed herein, the processes (a) to (c) are performed by a computer system.

In some embodiments of any one of the methods disclosed herein, the sequencing data is generated based on nucleic acid amplification. In some embodiments of any one of the methods disclosed herein, the sequencing data is generated based on polymerase chain reaction. In some embodiments of any one of the methods disclosed herein, the sequencing data is generated based on amplicon sequencing.

In some embodiments of any one of the methods disclosed herein, the sequencing data is generated based on next-generation sequencing (NGS). Alternatively, in some embodiments of any one of the methods disclosed herein, the sequencing data is generated based on non-hybridization-based NGS.

In some embodiments of any one of the methods disclosed herein, the sequencing data is generated without use of molecular barcoding of at least a portion of the plurality of cell-free nucleic acid molecules. In some embodiments of any one of the methods disclosed herein, the sequencing data is obtained without use of sample barcoding of at least a portion of the plurality of cell-free nucleic acid molecules.

In some embodiments of any one of the methods disclosed herein, the sequencing data is obtained without in silico removal or suppression of (i) background error or (ii) sequencing error.

In one aspect, the present disclosure provides a method of treating a condition of a subject, the method comprising: (a) identifying the subject for treatment of the condition, wherein the subject has been determined to have the condition based on identification of one or more cell-free nucleic acid molecules from a plurality of cell-free nucleic acid molecules that is obtained or derived from the subject, wherein each of the one or more cell-free nucleic acid molecules identified comprises a plurality of phased variants relative to a reference genomic sequence that are separated by at least one nucleotide, and wherein a presence of the plurality of phased variants is indicative of the condition of the subject; and (b) subjecting the subject to the treatment based on the identification in (a).

In one aspect, the present disclosure provides a method of monitoring a progress of a condition of a subject, the method comprising: (a) determining a first state of the condition of the subject based on identification of a first set of one or more cell-free nucleic acid molecules from a first plurality of cell-free nucleic acid molecules that is obtained or derived from the subject; (b) determining a second state of the condition of the subject based on identification of a second set of one or more cell-free nucleic acid molecules from a second plurality of cell-free nucleic acid molecules that is obtained or derived from the subject, wherein the second plurality of cell-free nucleic acid molecules are obtained from the subject subsequent to obtaining the first plurality of cell-free nucleic acid molecules from the subject; and (c) determining the progress of the condition based on the first state of the condition and the second state of the condition, wherein each of the one or more cell-free nucleic acid molecules comprises a plurality of phased variants relative to a reference genomic sequence that are separated by at least one nucleotide.

In some embodiments of any one of the methods disclosed herein, the progress of the condition is worsening of the condition.

In some embodiments of any one of the methods disclosed herein, the progress of the condition is at least a partial remission of the condition.

In some embodiments of any one of the methods disclosed herein, a presence of the plurality of phased variants is indicative of the first state or the second state of the condition of the subject.

In some embodiments of any one of the methods disclosed herein, the second plurality of cell-free nucleic acid molecules is obtained from the subject at least about 1 week, at least about 2 weeks, at least about 3 weeks, at least about 4 weeks, at least about 2 months, or at least about 3 months subsequent to obtaining the first plurality of cell-free nucleic acid molecules from the subject.

In some embodiments of any one of the methods disclosed herein, the subject is subjected to a treatment for the condition (i) prior to obtaining the second plurality of cell-free nucleic acid molecules from the subject and (ii) subsequent to obtaining the first plurality of cell-free nucleic acid molecules from the subject.

In some embodiments of any one of the methods disclosed herein, the progress of the condition is indicative of minimal residual disease of the condition of the subject. In some embodiments of any one of the methods disclosed herein, the progress of the condition is indicative of tumor burden or cancer burden of the subject.

In some embodiments of any one of the methods disclosed herein, the one or more cell-free nucleic acid molecules are captured from among the plurality of cell-free nucleic acid molecules with a set of nucleic acid probes, wherein the set of nucleic acid probes is configured to hybridize to at least a portion of cell-free nucleic acid molecules comprising one or more genomic regions associated with the condition.

In one aspect, the present disclosure provides a method comprising: (a) providing a mixture comprising (1) a set of nucleic acid probes and (2) a plurality of cell-free nucleic acid molecules that is obtained or derived from a subject, wherein an individual nucleic acid probe of the set of nucleic acid probes is designed to hybridize to at least a portion of a target cell-free nucleic acid molecule comprising a plurality of phased variants relative to a reference genomic sequence that are separated by at least one nucleotide, and wherein the individual nucleic acid probe comprises an activatable reporter agent, activation of the activatable reporter agent being selected from the group consisting of: (i) hybridization of the individual nucleic acid probe to the plurality of phased variants and (ii) dehybridization of at least a portion of the individual nucleic acid probe that has been hybridized to the plurality of phased variants; (b) detecting the activatable reporter agent that is activated, to identify one or more cell-free nucleic acid molecules of the plurality of cell-free nucleic acid molecules, wherein each of the one or more cell-free nucleic acid molecules comprises the plurality of phased variants; and (c) analyzing the identified one or more cell-free nucleic acid molecules to determine a condition of the subject.

In one aspect, the present disclosure provides a method comprising: (a) providing a mixture comprising (1) a set of nucleic acid probes and (2) a plurality of cell-free nucleic acid molecules that is obtained or derived from a subject, wherein an individual nucleic acid probe of the set of nucleic acid probes is designed to hybridize to at least a portion of a target cell-free nucleic acid molecule comprising a plurality of phased variants relative to a reference genomic sequence, and wherein the individual nucleic acid probe comprises an activatable reporter agent, activation of the activatable reporter agent being selected from the group consisting of: (i) hybridization of the individual nucleic acid probe to the plurality of phased variants and (ii) dehybridization of at least a portion of the individual nucleic acid probe that has been hybridized to the plurality of phased variants; (b) detecting the activatable reporter agent that is activated, to identify one or more cell-free nucleic acid molecules of the plurality of cell-free nucleic acid molecules, wherein each of the one or more cell-free nucleic acid molecules comprises the plurality of phased variants, wherein a limit of detection of the identification step is less than about 1 out of 50,000 cell-free nucleic acid molecules of the plurality of cell-free nucleic acid molecules; and (c) analyzing the identified one or more cell-free nucleic acid molecules to determine a condition of the subject.

In some embodiments of any one of the methods disclosed herein, the limit of detection of the identification step is less than about 1 out of 100,000, less than about 1 out of 500,000, less than about 1 out of 1,000,000, less than about 1 out of 1,500,000, or less than about 1 out of 2,000,000 cell-free nucleic acid molecules of the plurality of cell-free nucleic acid molecules.

In some embodiments of any one of the methods disclosed herein, a first phased variant of the plurality of phased variants and a second phased variant of the plurality of phased variants are separated by at least one nucleotide.

In some embodiments of any one of the methods disclosed herein, the activatable reporter agent is activated upon hybridization of the individual nucleic acid probe to the plurality of phased variants.

In some embodiments of any one of the methods disclosed herein, the activatable reporter agent is activated upon dehybridization of at least a portion of the individual nucleic acid probe that has been hybridized to the plurality of phased variants.

In some embodiments of any one of the methods disclosed herein, the method further comprises mixing (1) the set of nucleic acid probes and (2) the plurality of cell-free nucleic acid molecules.

In some embodiments of any one of the methods disclosed herein, the activatable reporter agent is a fluorophore.

In some embodiments of any one of the methods disclosed herein, analyzing the identified one or more cell-free nucleic acid molecules comprises analyzing (i) the identified one or more cell-free nucleic acid molecules and (ii) other cell-free nucleic acid molecules of the plurality of cell-free nucleic acid molecules that do not comprise the plurality of phased variants as different variables.

In some embodiments of any one of the methods disclosed herein, the analyzing of the identified one or more cell-free nucleic acid molecules is not based on other cell-free nucleic acid molecules of the plurality of cell-free nucleic acid molecules that do not comprise the plurality of phased variants.

In some embodiments of any one of the methods disclosed herein, a number of the plurality of phased variants from the identified one or more cell-free nucleic acid molecules is indicative of the condition of the subject. In some embodiments, a ratio of (i) the number of the plurality of phased variants from the one or more cell-free nucleic acid molecules and (ii) a number of single nucleotide variants (SNVs) from the one or more cell-free nucleic acid molecules is indicative of the condition of the subject.

In some embodiments of any one of the methods disclosed herein, a frequency of the plurality of phased variants in the identified one or more cell-free nucleic acid molecules is indicative of the condition of the subject. In some embodiments, the frequency is indicative of a diseased cell associated with the condition. In some embodiments, the condition is diffuse large B-cell lymphoma, and wherein the frequency is indicative of whether the one or more cell-free nucleic acid molecules are derived from germinal center B-cell (GCB) or activated B-cell (ABC).

In some embodiments of any one of the methods disclosed herein, genomic origin of the identified one or more cell-free nucleic acid molecules is indicative of the condition of the subject.

In some embodiments of any one of the methods disclosed herein, the first and second phased variants are separated by at least 2, at least 3, at least 4, at least 5, at least 6, at least 7, or at least 8 nucleotides. In some embodiments of any one of the methods disclosed herein, the first and second phased variants are separated by at most about 180, at most about 170, at most about 160, at most about 150, or at most about 140 nucleotides.

In some embodiments of any one of the methods disclosed herein, at least about 10%, at least about 20%, at least about 30%, at least about 40%, or at least about 50% of the one or more cell-free nucleic acid molecules comprising a plurality of phased variants comprises a single nucleotide variant (SNV) that is at least 2 nucleotides away from an adjacent SNV.

In some embodiments of any one of the methods disclosed herein, the plurality of phased variants comprises at least 3, at least 4, at least 5, at least 10, at least 15, at least 20, or at least 25 phased variants within the same cell-free nucleic acid molecule.

In some embodiments of any one of the methods disclosed herein, the one or more cell-free nucleic acid molecules identified comprises at least 2, at least 3, at least 4, at least 5, at least 10, at least 50, at least 100, at least 500, or at least 1,000 cell-free nucleic acid molecules.

In some embodiments of any one of the methods disclosed herein, the reference genomic sequence is derived from a reference cohort. In some embodiments, the reference genomic sequence comprises a consensus sequence from the reference cohort. In some embodiments, the reference genomic sequence comprises at least a portion of hg19 human genome, hg18 genome, hg17 genome, hg16 genome, or hg38 genome.

In some embodiments of any one of the methods disclosed herein, the reference genomic sequence is derived from a sample of the subject.

In some embodiments of any one of the methods disclosed herein, the sample is a healthy sample. In some embodiments, the sample comprises a healthy cell. In some embodiments, the healthy cell comprises a healthy leukocyte.

In some embodiments of any one of the methods disclosed herein, the sample is a diseased sample. In some embodiments, the diseased sample comprises a diseased cell. In some embodiments, the diseased cell comprises a tumor cell. In some embodiments, the diseased sample comprises a solid tumor.

In some embodiments of any one of the methods disclosed herein, the set of nucleic acid probes is designed based on the plurality of phased variants that are identified by comparing (i) sequencing data from a solid tumor, lymphoma, or blood tumor of the subject and (ii) sequencing data from a healthy cell of the subject or a healthy cohort. In some embodiments, the healthy cell is from the subject. In some embodiments, the healthy cell is from the healthy cohort.

In some embodiments of any one of the methods disclosed herein, the set of nucleic acid probes are designed to hybridize to at least a portion of sequences of genomic loci associated with the condition. In some embodiments, the genomic loci associated with the condition are known to exhibit aberrant somatic hypermutation when the subject has the condition.

In some embodiments of any one of the methods disclosed herein, the set of nucleic acid probes are designed to hybridize to at least about 5%, at least about 10%, at least about 20%, at least about 30%, at least about 40%, at least about 50%, at least about 60%, at least about 70%, at least about 80%, at least about 90%, or about 100% of (i) the genomic regions identified in Table 1, (ii) the genomic regions identified in Table 3, or (iii) the genomic regions identified to have a plurality of phased variants in Table 3.

In some embodiments of any one of the methods disclosed herein, each nucleic acid probe of the set of nucleic acid probes has at least about 70%, at least about 80%, at least about 90% sequence identity, at least about 95% sequence identity, or about 100% sequence identity to a probe sequence selected from Table 6.

In some embodiments of any one of the methods disclosed herein, the set of nucleic acid probes comprises at least about 5%, at least about 10%, at least about 20%, at least about 30%, at least about 40%, at least about 50%, at least about 60%, at least about 70%, at least about 80%, or at least about 90% of probe sequences in Table 6.

In some embodiments of any one of the methods disclosed herein, the method further comprises determining that the subject has the condition or determining a degree or status of the condition of the subject, based on the identified one or more cell-free nucleic acid molecules comprising the plurality of phased variants. In some embodiments, the method further comprises determining that the one or more cell-free nucleic acid molecules are derived from a sample associated with the condition, based on performing a statistical model analysis of the identified one or more cell-free nucleic acid molecules. In some embodiments, the statistical model analysis comprises a Monte Carlo statistical analysis.

In some embodiments of any one of the methods disclosed herein, the method further comprises monitoring a progress of the condition of the subject based on the identified one or more cell-free nucleic acid molecules.

In some embodiments of any one of the methods disclosed herein, the method further comprises performing a different procedure to confirm the condition of the subject. In some embodiments, the different procedure comprises a blood test, genetic test, medical imaging, physical exam, or tissue biopsy.

In some embodiments of any one of the methods disclosed herein, the method further comprises determining a treatment for the condition of the subject based on the identified one or more cell-free nucleic acid molecules.

In some embodiments of any one of the methods disclosed herein, the subject has been subjected to a treatment for the condition prior to (a).

In some embodiments of any one of the methods disclosed herein, the treatment comprises chemotherapy, radiotherapy, chemoradiotherapy, immunotherapy, adoptive cell therapy, hormone therapy, targeted drug therapy, surgery, transplant, transfusion, or medical surveillance.

In some embodiments of any one of the methods disclosed herein, the plurality of cell-free nucleic acid molecules comprise a plurality of cell-free deoxyribonucleic acid (DNA) molecules.

In some embodiments of any one of the methods disclosed herein, condition comprises a disease.

In some embodiments of any one of the methods disclosed herein, the plurality of cell-free nucleic acid molecules are derived from a bodily sample of the subject. In some embodiments, the bodily sample comprises plasma, serum, blood, cerebrospinal fluid, lymph fluid, saliva, urine, or stool.

In some embodiments of any one of the methods disclosed herein, the subject is a mammal. In some embodiments of any one of the methods disclosed herein, the subject is a human.

In some embodiments of any one of the methods disclosed herein, the condition comprises neoplasm, cancer, or tumor. In some embodiments, the condition comprises a solid tumor. In some embodiments, the condition comprises a lymphoma. In some embodiments, the condition comprises a B-cell lymphoma. In some embodiments, the condition comprises a sub-type of B-cell lymphoma selected from the group consisting of diffuse large B-cell lymphoma, follicular lymphoma, Burkitt lymphoma, and B-cell chronic lymphocytic leukemia.

In some embodiments of any one of the methods disclosed herein, the plurality of phased variants have been previously identified as tumor-derived from sequencing a prior tumor sample or cell-free nucleic acid sample.

In one aspect, the present disclosure provides a composition comprising a bait set comprising a set of nucleic acid probes designed to capture cell-free DNA molecules derived from at least about 5% of genomic regions set forth in (i) the genomic regions identified in Table 1, (ii) the genomic regions identified in Table 3, or (iii) the genomic regions identified to have a plurality of phased variants in Table 3.

In some embodiments of any of the compositions disclosed herein, the set of nucleic acid probes are designed to pull down cell-free DNA molecules derived from at least about 10%, at least about 20%, at least about 30%, at least about 40%, at least about 50%, at least about 60%, at least about 70%, at least about 80%, at least about 90%, or about 100% of the genomic regions set forth in (i) the genomic regions identified in Table 1, (ii) the genomic regions identified in Table 3, or (iii) the genomic regions identified to have a plurality of phased variants in Table 3.

In some embodiments of any of the compositions disclosed herein, the set of nucleic acid probes are designed to capture the one or more cell-free DNA molecules derived from at most about 10%, at most about 20%, at most about 30%, at most about 40%, at most about 50%, at most about 60%, at most about 70%, at most about 80%, at most about 90%, or about 100% of the genomic regions set forth in (i) the genomic regions identified in Table 1, (ii) the genomic regions identified in Table 3, or (iii) the genomic regions identified to have a plurality of phased variants in Table 3.

In some embodiments of any of the compositions disclosed herein, the bait set comprises at most 5, at most 10, at most 50, at most 100, at most 500, at most 1000, or at most 2000 nucleic acid probes.

In some embodiments of any of the compositions disclosed herein, an individual nucleic acid probe of the set of nucleic acid probes comprises a pull-down tag.

In some embodiments of any of the compositions disclosed herein, the pull-down tag comprises a nucleic acid barcode.

In some embodiments of any of the compositions disclosed herein, the pull-down tag comprises biotin.

In some embodiments of any of the compositions disclosed herein, each of the cell-free DNA molecules is between about 100 nucleotides and about 180 nucleotides in length.

In some embodiments of any of the compositions disclosed herein, the genomic regions are associated with a condition.

In some embodiments of any of the compositions disclosed herein, the genomic regions exhibit aberrant somatic hypermutation when a subject has the condition.

In some embodiments of any of the compositions disclosed herein, the condition comprises a B-cell lymphoma. In some embodiments, the condition comprises a sub-type of B-cell lymphoma selected from the group consisting of diffuse large B-cell lymphoma, follicular lymphoma, Burkitt lymphoma, and B-cell chronic lymphocytic leukemia.

In some embodiments of any of the compositions disclosed herein, the composition further comprises a plurality of cell-free DNA molecules obtained or derived from a subject.

In one aspect, the present disclosure provides a method to perform a clinical procedure on an individual, the method comprising: (a) obtaining or having obtained a targeted sequencing result of a collection of cell-free nucleic acid molecules, wherein the collection of cell-free nucleic acid molecules are sourced from a liquid or waste biopsy of an individual, and wherein the targeting sequencing is performed utilizing nucleic acid probes to pull down sequences of genomic loci known to experience aberrant somatic hypermutation in a B-cell cancer; (b) identifying or having identified a plurality of variants in phase within the cell-free nucleic acid sequencing result; (c) determining or having determined, utilizing a statistical model and the identified phased variants, that the cell-free nucleic acid sequencing result contains nucleotides derived from a neoplasm; and (d) performing a clinical procedure on the individual to confirm the presence of the B-cell cancer, based upon determining that the cell-free nucleic acid sequencing result contains nucleic acid sequences likely derived from the B-cell cancer.

In some embodiments of any of the compositions disclosed herein, the biopsy is one of blood, serum, cerebrospinal fluid, lymph fluid, urine, or stool.

In some embodiments of any of the compositions disclosed herein, the genomic loci are selected from (i) the genomic regions identified in Table 1, (ii) the genomic regions identified in Table 3, or (iii) the genomic regions identified to have a plurality of phased variants in Table 3.

In some embodiments of any of the compositions disclosed herein, the sequences of the nucleic acid probes are selected from Table 6.

In some embodiments of any of the compositions disclosed herein, the clinical is procedure is a blood test, medical imaging, or a physical exam.

In one aspect, the present disclosure provides a method to treat an individual for a B-cell cancer, the method comprising: (a) obtaining or having obtained a targeted sequencing result of a collection of cell-free nucleic acid molecules, wherein the collection of cell-free nucleic acid molecules are sourced from a liquid or waste biopsy of an individual, and wherein the targeting sequencing is performed utilizing nucleic acid probes to pull down sequences of genomic loci known to experience aberrant somatic hypermutation in a B-cell cancer; (b) identifying or having identified a plurality of variants in phase within the cell-free nucleic acid sequencing result; (c) determining or having determined, utilizing a statistical model and the identified phased variants, that the cell-free nucleic acid sequencing result contains nucleotides derived from a neoplasm; and (d) treating the individual to curtail the B-cell cancer, based upon determining that the cell-free nucleic acid sequencing result contains nucleic acid sequences derived from the B-cell cancer.

In some embodiments of any of the compositions disclosed herein, the biopsy is one of blood, serum, cerebrospinal fluid, lymph fluid, urine or stool.

In some embodiments of any of the compositions disclosed herein, the genomic loci are selected from (i) the genomic regions identified in Table 1, (ii) the genomic regions identified in Table 3, or (iii) the genomic regions identified to have a plurality of phased variants in Table 3.

In some embodiments of any of the compositions disclosed herein, the sequences of the nucleic acid probes are selected from Table 6.

In some embodiments of any of the compositions disclosed herein, the treatment is chemotherapy, radiotherapy, immunotherapy, hormone therapy, targeted drug therapy, or medical surveillance.

In one aspect, the present disclosure provides a method to detect cancerous minimal residual disease in an individual and to treat the individual for a cancer, the method comprising: (a) obtaining or having obtained a targeted sequencing result of a collection of cell-free nucleic acid molecules, wherein the collection of cell-free nucleic acid molecules are sourced from a liquid or waste biopsy of an individual, wherein the liquid or waste biopsy is sourced after a series of treatments in order to detect minimal residual disease, and wherein the targeting sequencing is performed utilizing nucleic acid probes to pull down sequences of genomic loci determined to contain a plurality of variants in phase, as determined by a prior sequencing result on a prior biopsy derived from the cancer; (b) identifying or having identified at least one set of the plurality of variants in phase within the cell-free nucleic acid sequencing result; and (c) treating the individual to curtail the cancer, based upon determining that the cell-free nucleic acid sequencing result contains nucleic acid sequences derived from the cancer.

In some embodiments of any of the compositions disclosed herein, the liquid or waste biopsy is one of blood, serum, cerebrospinal fluid, lymph fluid, urine or stool.

In some embodiments of any of the compositions disclosed herein, the treatment is chemotherapy, radiotherapy, immunotherapy, hormone therapy, targeted drug therapy, or medical surveillance.

In one aspect, the present disclosure provides a computer program product comprising a non-transitory computer-readable medium having computer-executable code encoded therein, the computer-executable code adapted to be executed to implement any one of the methods disclosed herein.

In one aspect, the present disclosure provides a system comprising one or more computer processors and computer memory coupled thereto, wherein the computer memory comprises machine executable code that, upon execution by the one or more computer processors, implements any one of the methods disclosed herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

Various features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1A. is a cartoon depicting the difference between detection of a single nucleotide variant (SNV) (top) and multiple variants 'in-phase' (phased variants, PVs; bottom) on individual cell-free DNA molecules. In theory, detection of a PV is a more specific event than detection of an isolated SNV. FIG. 1B. is a scatter plot showing the distribution of the number of PVs from WGS data for 24 different histologies of cancer, normalized by the total number of SNVs. Bars show the median value and interquartile range. (FL-NHL, follicular lymphoma; DLBCL-NHL, diffuse large B-cell lymphoma; Burkitt-NHL, Burkitt lymphoma; Lung-SCC, squamous cell lung cancer; Lung-Adeno, lung adenocarcinoma; Kidney-RCC, renal cell carcinoma; Bone-Osteosarc, osteosarcoma; Liver-HCC, hepatocellular carcinoma; Breast-Adeno, breast adenocarcinoma; Panc-Adeno, pancreatic adenocarcinoma; Head-SCC, head and neck squamous cell carcinoma; Ovary-Adeno, ovarian adenocarcinoma; Eso-Adeno, esophageal adenocarcinoma; Uterus-Adeno, uterine adenocarcinoma; Stomach-Adeno, stomach adenocarcinoma; CLL, chronic lymphocytic leukemia; ColoRect-Adeno, colorectal adenocarcinoma; Prost-Adeno, prostate adenocarcinoma; CNS-GBM, glioblastoma multiforme; Panc-Endocrine, pancreatic neuroendocrine tumor; Thy-Adeno, thyroid adenocarcinoma; CNS-PiloAstro, piloastrocytoma; CNS-Medullo, medulloblastoma.) FIG. 1C. is a heatmap demonstrating the enrichment in single base substitution (SBS) mutational signatures for PVs versus single SNVs across multiple cancer types. Blue represents signatures which are enriched in PVs in specific histologies; darker gray represents signatures where un-phased, single SNVs are enriched; and red represents SNVs occurring in isolation. Only signatures which have a significant difference between PVs and unphased SNVs after correcting for multiple hypotheses are shown; other signatures are grey. Signatures associated with smoking, AID/AICDA, and APOBEC are indicated. FIG. 1D. demonstrate bar plots showing the distribution of PVs occurring in stereotyped regions across the genome in B-lymphoid malignancies and lung adenocarcinoma. In this plot, the genome was divided into 1000 bp bins, and the fraction of samples of a given histology with a PV in each 1000 bp bin was calculated. Only bins that have at least a 2 percent recurrence frequency in any cancer subtype are shown. Key genomic loci are also labeled. FIG. 1E. is a comparison of duplex sequencing to phased variant sequencing. A schema comparing error-suppressed sequencing by duplex sequencing vs. recovery of phased variants. In duplex sequencing, recovery of a single SNV observed on both strands of an original DNA double-helix (i.e., in trans) is required. This requires independent recovery of two molecules by sequencing as the plus and minus strands of the original DNA molecule go through library preparation and PCR independently. In contrast, recovery of PVs requires multiple SNVs observed on the same single strand of DNA (i.e., in cis). Thus, recovery of only the plus or the minus strand (rather than both) is sufficient for identification of PVs.

FIG. 2A is a schematic of the design for PhasED-Seq. WGS data from DLBCL tumor samples were aggregated (left), and areas of recurrent putative PVs were identified (middle). An assay capturing the genomic regions most recurrently containing PVs was then designed (right), resulting in an ~7500× enrichment in PVs compared to WGS. The top right panel shows the in silico expected number of PVs per case per kilobase of panel size (y-axis) for increasing panel sizes (x-axis). The dashed line shows the selected regions in the PhasED-Seq panel. The bottom right panel shows the total number of expected PVs per case (y-axis, assessed in silico from WGS data, for increasing panel sizes (y-axis). The dark area shows the selected regions in the PhasED-Seq panel. FIG. 2B illustrate two panels showing the yield of SNVs (left) and PVs (right) for sequencing tumor DNA and matched germline by a previously established lymphoma CAPP-Seq panel or PhasED-Seq; values are assessed in silico by limiting WGS to the targeted space of interest. PVs reported in the right panel include doublet, triplet, and quadruplet phased events. FIG. 2C shows the yield of SNVs (left) and PVs (right) from experimental sequencing of tumor and/or cell-free DNA from CAPP-Seq versus PhasED-Seq, similar to FIG. 2B. FIG. 2D is a scatterplot showing the frequency of PVs by genomic location (in 1000 bp bins) for patients with DLBCL, identified either by WGS or identified by PhasED-Seq. PVs in IGH, BCL2, MYC, and BCL6 are highlighted. FIG. 2E illustrate scatterplots comparing the frequency of PVs by genomic location (in 50 bp bins) for patients with different types of lymphomas. The colored circles show the relative frequency of PVs in 50 bp bins from a specific gene of interest; the other (gray) circles show the relative frequency of PVs in 50 bp bins from the remainder of the PhasED-Seq sequencing panel. FIG. 2F illustrate volcano plots summarizing the difference in relative frequency of PVs in specific genetic loci between types of lymphoma, including ABC-DLBCL vs. GCB-DLBCL (dark Gray, left); PMBCL vs DLBCL (dark gray, middle); and HL vs. DLBCL (dark gray, right). The x-axis demonstrates the relative enrichment in PVs in a specific locus, while the y-axis demonstrates the statistical significance of this association. (Example 10).

FIG. 3A illustrates bar plot showing the performance of hybrid capture sequencing for recovery of synthetic 150 bp oligonucleotides from two loci (MYC and BCL6) with increasing degree of mutation/non-reference bases. Error bars represent the 95% confidence interval (n=3 replicates of each condition in distinct samples). FIG. 3B illustrates plot demonstrating the background error-rate (Example 10) for different types of error-suppression from 12 healthy control cell-free DNA samples sequenced on the PhasED-Seq panel. 'PhasED-Seq 2×' or 'doublets' represents detection of two mutations in-phase on the same DNA molecule; 'PhasED-Seq 3×' or 'triplets' represents detection of three mutations in-phase on the same DNA molecule. FIG. 3C illustrates bar plot showing the depth of unique molecular recovery (e.g., depth after barcode-mediated PCR duplicate removal) from sequencing data from 12 cell-free DNA samples for different types of error-suppression, including barcode deduplication, duplex sequencing, and recovery of PVs of increasing maximal distance between SNVs in-phase. FIG. 3D illustrates bar plot showing the cumulative fraction of PVs that have a maximal distance between SNVs less than the number of base-pairs shown on the x-axis. FIG. 3E illustrates a plot demonstrating the results of a limiting dilution series simulating cell-free DNA samples containing patient-specific tumor fractions of $1\times10^{-3}$ to $0.5\times10^{-6}$; cfDNA from 3 independent patients samples were used in each dilution. The same sequencing data was analyzed using a variety of error-suppression methods for recovery of expected tumor fractions, including iDES, duplex sequencing, and PhasED-Seq (both for recovery of doublet and triplet molecules). Points and error-bars represent the mean, minimum, and maximum across the three patient-specific tumor mutations considered. The difference between observed and expected tumor fractions for sample<1:10,000 were compared via paired t-test. *, P<0.05, , P<0.005, *, P<0.0005. FIG. 3F illustrates plot demonstrating the background signal for detection of tumor-specific alleles in 12 unrelated, healthy cell-free DNA samples, and the healthy cfDNA sample used for limiting dilution series (n=13 total samples). In each sample, tumor-specific SNVs or PVs from the 3 patient samples utilized in the limiting dilution experiment shown in FIG. 3E, for a total of 39 assessments were assessed. Bars represent the arithmetic mean across all 39 assessments; statistical comparison performed by Wilcoxon rank-sum test. *, P<0.05, , P<0.005, *, P<0.0005. FIG. 3G illustrates plot showing the theoretical rate of detection for a sample with a given number of PV-containing regions, according to simple binomial sampling. This plot is produced by assuming a unique sequencing depth of 5000$\chi$ (line), along with a varying number of independent 150 bp PV-containing regions, from 3 regions (blue) to 67 regions (purple). Confidence envelopes consider depth from 4000-6000×; a 5% false-positive rate is also assumed. FIG. 3H illustrates plot showing the observed rate of detection (y-axis) for sample of a given true tumor fraction (x-axis), with varying numbers of PV-containing regions. For each number of tumor-reporter regions ranging from 3 to 67, this number of 150 bp windows was randomly sampled from each of 3 patient-specific PV reporter lists 25 times and used to assess tumor-detection at each dilution. Filled-in points represent 'wet' dilution series experiments, while open points represent in silico dilution experiments. Points and error-bars represent the mean, minimum, and maximum across the three patient-specific PV reporter lists used in the original sampling. FIG. 3I illustrates scatter plot compares the predicted vs observed rate of detection for samples from the dilution series shown in panels FIG. 3G and FIG. 3H. Additional details of this experiment are provided in Example 10.

FIG. 4A illustrates plot showing ctDNA levels for a patient with DLBCL responding to, and subsequently relapsing after, first-line immuno-chemotherapy. Levels measured by CAPP-Seq are shown in darker gray circles while levels measured by PhasED-Seq are shown in lighter gray circles. Open circles represent undetectable levels by CAPP-Seq. FIG. 4B illustrates a univariate scatter plot showing the mean tumor allele fraction measured by PhasED-Seq for clinical samples at time-points of minimal disease (i.e., after 1 or 2 cycles of therapy). The plot is divided by samples detected vs undetected by standard CAPP-Seq; P-value from Wilcoxon rank-sum test. FIG. 4C illustrates bar plot showing the fraction of DLBCL patients who have detectable ctDNA by CAPP-Seq after 1 or 2 cycles of treatment (dark gray bars), as well as the fraction of additional patients with detectable disease when adding PhasED-Seq to standard CAPP-Seq (medium gray bars). P-value represents a Fisher's Exact Test for detection by CAPP-Seq alone versus the combination of PhasED-Seq and CAPP-Seq in 171 samples after 1 or 2 cycles of treatment. FIG. 4D illustrates a waterfall plot showing the change in ctDNA levels measured by CAPP-Seq after 2 cycles of first-line therapy in patients with DLBCL. Patients with undetectable ctDNA by CAPP-Seq are shown as "ND" ("not detected"), in darker colors. The colors of the bars also indicate the eventual clinical outcomes for these patients. FIG. 4E illustrates a Kaplan-Meier plot showing the event-free survival for 52 DLBCL patients with undetectable ctDNA measured by CAPP-Seq after 2 cycles. FIG. 4F illustrates a Kaplan-Meier plot showing the event-free survival of 52 patients shown in FIG. 4E (undetectable ctDNA by CAPP-Seq) stratified by ctDNA detection via PhasED-Seq at this same time-point (cycle 3, day 1). FIG. 4G illustrates a Kaplan-Meier plot showing the event-free survival for 89 patients with DLBCL stratified by ctDNA at cycle 3, day 1 separated into 3 strata—patients failing to achieve a major molecular response (dark gray), patients with a major molecular response who still have detectable ctDNA by PhasED-Seq and/or CAPP-Seq (light grey), and patients who have a stringent molecular remission (undetectable ctDNA by PhasED-Seq and CAPP-Seq; medium gray).

FIG. 5A-C illustrate Univariate scatter plots showing the number of SNVs (FIG. 5A), PVs (FIG. 5B), and PVs, controlling for total number of SNVs (FIG. 5C), from WGS data for 24 different histologies of cancer. Bars show the median value and interquartile range. (FL-NHL, follicular lymphoma; DLBCL-NHL, diffuse large B cell lymphoma; Burkitt-NHL, Burkitt lymphoma; Lung-SCC, squamous cell lung cancer; Lung-Adeno, lung adenocarcinoma; Kidney-RCC, renal cell carcinoma; Bone-Osteosarc, osteosarcoma; Liver-HCC, hepatocellular carcinoma; Breast-Adeno, breast adenocarcinoma; Panc-Adeno, pancreatic adenocarcinoma; Head-SCC, head and neck squamous cell carcinoma; Ovary-Adeno, ovarian adenocarcinoma; Eso-Adeno, esophageal adenocarcinoma; Uterus-Adeno, uterine adenocarcinoma; Stomach-Adeno, stomach adenocarcinoma; CLL, chronic lymphocytic leukemia; ColoRect-Adeno, colorectal adenocarcinoma; Prost-Adeno, prostate adenocarcinoma; CNS-GBM, glioblastoma multiforme; Panc-Endocrine, pancreatic neuroendocrine tumor; Thy-Adeno, thyroid adenocarcinoma; CNS-PiloAstro, piloastrocytoma; CNS-Medullo, medulloblastoma).

FIG. 8A. illustrates bar plot showing the number of independent 1000 bp regions across the genome that recurrently contain PVs for DLBCL, FL, BL, and CLL (n=68, 74, 36, and 151 respectively). FIG. 8B-D illustrate plots showing the frequency of PVs for multiple lymphoid malignancies with relationships to specific genetic loci, including FIG. 8B: BCL2, FIG. 8C: MYC, and FIG. 8D: ID3. The location of the transcript for a given gene is shown below the plot in grey; exons are shown in darker gray. *indicates a region with significantly more PVs in a given cancer histology compared to all other histologies by Fisher's Exact Test (P<0.05). FIG. 8E, similar to FIG. 8B-D, these plots show the frequency of PVs across lymphoma subtypes. Here, it is shown the IGH locus, consisting of IGHV, IGHD, and IGHJ parts, for ABC and GCB subtype DLBCLs (n=25 and 25, respectively). Coding regions for Ig parts, including Ig-constant regions and V-genes, are shown. (DLBCL, diffuse large B-cell lymphoma; FL, follicular lymphoma; BL, Burkitt lymphoma, CLL, chronic lymphocytic leukemia).

FIG. 9A illustrates univariate scatter plot showing the fraction of all PVs across the genome identified by WGS (n=79) that were recovered by previously reported lymphoma CAPP-Seq panel[8] (left) compared to PhasED-Seq (right). FIG. 9B illustrates the expected yield of SNVs per case identified from WGS using a previously established lymphoma CAPP-Seq panel or the PhasED-Seq panel. FIG. 9C illustrates the expected yield of PVs per case identified from WGS using a previously established lymphoma CAPP-Seq panel or the PhasED-Seq panel. Data from three independent publicly available cohorts are shown in FIGS. 9A-9C. FIGS. 9D-9F illustrate plots showing the improvement in recovery of PVs by PhasED-Seq compared to CAPP-Seq in 16 patients sequenced by both assays. This includes improvement in d) two SNVs in phase (e.g., 2× or 'doublet PVs'), e) three SNVs in phase (3× or 'triplet PVs') and f) four SNVs in phase (e.g., 4× or 'quadruplet PVs'). FIGS. 9G-9K. illustrate panels showing the number of SNVs and PVs identified for patients with different types of lymphomas. These panels show the number of g) SNVs, h) doublet PVs, i) triplet PVs, j) quadruplet PVs, and k) all PVs. *, P<0.05; , P<0.01, *, P<0.001. (DLBCL, diffuse large B-cell lymphoma; GCB, germinal center B-cell like DLBCL; ABC, activated B-cell like DLBCL; PMBCL, primary mediastinal B-cell lymphoma; HL, Hodgkin lymphoma).

FIG. 14A shows a plot of the theoretical energy of binding for typical 150-mers across the genome with increasing fraction of bases mutated from the reference genome. Mutations were spread throughout the 150-mer either clustered to one end of the sequence, clustered in the middle of the sequence, or randomly throughout the sequence. Point and error-bars represent the median and interquartile ranges from 10,000 in silico simulations. FIG. 14B illustrates a plot showing two histograms of summary metrics of the mutation rate of 151-bp windows across the PhasED-Seq panel across all patients in this study. The light gray histogram shows the maximum percent mutated in any 151-bp window for all patients in this study; the dark gray histogram shows the $95^{th}$ percentile mutation rate across all mutated 151-bp windows. FIG. 14C is a plot showing the percentile of mutation rate across all mutated 151-bp windows across all patients in this study. FIG. 14D illustrates heatmaps showing the relative error rate (as log 10(error rate)) for single SNVs (left, "RED"), doublet PVs (middle, "YELLOW"), and triplet PVs (right, "BLUE"). FIG. 14D demonstrates that analysis based on the plurality of phased variants (e.g., double or triplet PVs) yields a lower error rate than analysis based on single SNVs. In addition, FIG. 14D demonstrates that analysis using a higher number of phased variant sets (e.g., triplet PVs labeled as "BLUE") yields a lower error rate than analysis based on a lower number of phased variant sets (e.g., doublet PVs labeled as "YELLOW"). The error rate of single SNVs from sequencing with multiple error suppression methods is shown, including barcode deduplication, iDES, and duplex sequencing. Error rates are summarized by the type of mutation. In the case of triplet PVs, the x and y-axis of the heatmap represent the first and second type of base alteration in the PV; the third alteration is averaged over all 12 possible base changes. FIG. 14E illustrates a plot showing the error rate for doublet/2×PVs as a function of the genomic distance between the component SNVs.

FIGS. 15 and 16A-16B illustrates comparison of ctDNA quantitation by PhasED-Seq to CAPP-Seq and clinical applications. FIG. 15 illustrates the detection-rate of ctDNA from pretreatment samples across 107 patients with large-B cell lymphomas by standard CAPP-Seq (green), as well as PhasED-Seq using doublets (light blue), triplets (medium blue), and quadruplets (dark blue). The specificity of ctDNA detection is also shown. In the lower two plots, the false-detection rate in 40 withheld healthy control cfDNA samples is shown. The size of each bar in these two plots shows the detection-rate for patient-specific cfDNA mutations in these 40-withheld controls, across all 107 cases. FIG. 16A illustrates table summarizing the sensitivity and specificity for ctDNA detection in pretreatment samples by CAPP-Seq and PhasED-Seq using doublets, triplets, and quadruplets, shown in panel A. Sensitivity is calculated across all 107 cases, while specificity is calculated across the 40 withheld control samples, assessing for each of the 107 independent patient-specific mutation lists, for a total of 4280 independent tests. FIG. 16B illustrates a scatterplot showing the quantity of ctDNA (measured as log 10(haploid genome equivalents/mL)) as measured by CAPP-Seq vs. PhasED-Seq in individual samples. Samples taken prior to cycle 1 of RCHOP therapy (i.e., pretreatment), prior to cycle 2, and prior to cycle 3, are shown in independent colors (blue, green, and red respectively; 278 total samples). Undetectable levels fall on the axes. Spearman correlation and P-value are shown.

FIG. 17A illustrates a scatter plot showing the log-fold change in ctDNA after 2 cycles of therapy (i.e., the Major Molecular Response or MMR) measured by CAPP-Seq or PhasED-Seq for patients receiving RCHOP therapy. Dotted lines show the previously established threshold of a 2.5-log reduction in ctDNA for MMR. Undetectable samples fall on the axes; the correlation coefficient represents a Spearman rho for the 33 samples detected by both CAPP-Seq and PhasED-Seq. FIG. 17B illustrates 2 by 2 tables summarizing the detection rate of ctDNA samples after 2 cycles of therapy by PhasED-Seq vs CAPP-Seq. Patients with eventual disease progression are shown in bottom panel, while patients without eventual disease progression are shown in upper panel. FIG. 17C illustrates bar-plots showing the area under the receiver operator curve (AUC) for classification of patients for event-free survival at 24 months based on CAPP-Seq (light colors) or PhasED-Seq (dark colors) after 2 cycles of therapy. Classification of all patient (n=89, left) and only patients achieving a MMR (n=69, right) are both shown. FIG. 17D illustrates Kaplan-Meier plots showing the event-free survival of 69 patients achieving a MMR stratified by ctDNA detection with CAPP-Seq (top) or PhasED-Seq (bottom).

FIG. 18A illustrates scatterplot showing the log-fold change in ctDNA after 1 cycle of therapy (i.e., the Early Molecular Response or EMR) measured by CAPP-Seq or PhasED-Seq for patients receiving RCHOP therapy. Dotted lines show the previously established threshold of a 2-log reduction in ctDNA for EMR. Undetectable samples fall on the axes; the correlation coefficient represents a Spearman rho for the 45 samples detected by both CAPP-Seq and PhasED-Seq. FIG. 18B illustrates 2 by 2 tables summarizing the detection rate of ctDNA samples after 1 cycle of therapy by PhasED-Seq vs CAPP-Ceq. Patients with eventual disease progression are shown in red, while patients without eventual disease progression are shown in blue. FIG. 18C illustrates bar-plots showing the area under the receiver operator curve (AUC) for classification of patients for event-free survival at 24 months based on CAPP-Seq (light colors) or PhasED-Seq (dark colors) after 1 cycle of therapy. Classification of all patient (n=82, left) and only patients achieving an EMR (n=63, right) are both shown. FIG. 18D illustrates Kaplan-Meier plots showing the event-free survival of 63 patients achieving an EMR stratified by ctDNA detection with CAPP-Seq (top) or PhasED-Seq (bottom). FIG. 18E illustrates waterfall plot showing the change in ctDNA levels measured by CAPP-Seq after 1 cycle of first-line therapy in patients with DLBCL. Patients with undetectable ctDNA by CAPP-Seq are shown as "ND" ("not detected"), in darker colors. The colors of the bars also indicate the eventual clinical outcomes for these patients. FIG. 18F illustrates a Kaplan-Meier plot showing the event-free survival for 33 DLBCL patients with undetectable ctDNA measured by CAPP-Seq after 1 cycle of therapy. FIG. 18G illustrates a Kaplan-Meier plot showing the event-free survival of 33 patients shown in FIG. 18F (undetectable ctDNA by CAPP-Seq) stratified by ctDNA detection via PhasED-Seq at this same time-point (cycle 2, day 1). FIG. 18H illustrates a Kaplan-Meier plot showing the event-free survival for 82 patients with DLBCL stratified by ctDNA at cycle 2, day 1 separated into 3 strata—patients failing to achieve an early molecular response, patients with an early molecular response who still have detectable ctDNA by PhasED-Seq and/or CAPP-Seq, and patients who have a stringent molecular remission (undetectable ctDNA by PhasED-Seq and CAPP-Seq).

FIGS. 25A-25C show example flowcharts of methods for determining a condition of a subject based on one or more cell-free nucleic acid molecules comprising a plurality of variants.

FIG. 25D shows an example flowchart of a method for treating a condition of a subject based on one or more cell-free nucleic acid molecules comprising a plurality of variants.

FIGS. 25F and 25G show example flowcharts of methods for determining a condition of a subject based on one or more cell-free nucleic acid molecules comprising a plurality of variants.

DETAILED DESCRIPTION

Figure 1A:
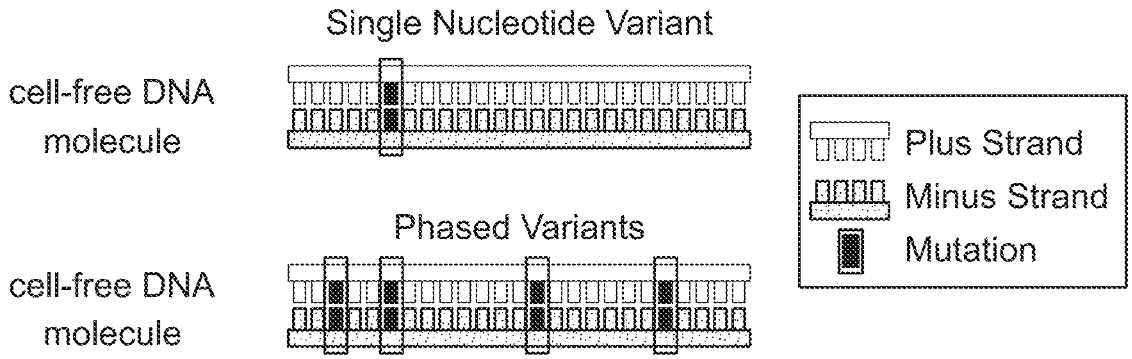
FIGS. 1A-1E illustrate discovery of phased variants and their mutational signatures via analysis of whole-genome sequencing data.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "about" or "approximately" generally mean within an acceptable error range for the particular value, which may depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value may be assumed.

The term "phased variants," "variants in phase," "PV," or "somatic variants in phase," as used interchangeably herein, generally refers to two or more mutations (e.g., SNVs or indels) that occur in cis (i.e., on the same strand of a nucleic acid molecule) within a single cell-free nucleic acid molecule. In some cases, a cell-free nucleic acid molecule can be a cell-free deoxyribonucleic acid (cfDNA) molecule. In some cases, a cfDNA molecule can be derived from a diseased tissue, such as a tumor (e.g., a circulating tumor DNA (ctDNA) molecule).

The term "biological sample" or "bodily sample," as used interchangeably herein, generally refers to a tissue or fluid sample derived from a subject. A biological sample can be directly obtained from the subject. Alternatively, a biological sample can be derived from the subject (e.g., by processing an initial biological sample obtained from the subject). The biological sample can be or can include one or more nucleic acid molecules, such as DNA or ribonucleic acid (RNA) molecules. The biological sample can be derived from any organ, tissue or biological fluid. A biological sample can comprise, for example, a bodily fluid or a solid tissue sample. An example of a solid tissue sample is a tumor sample, e.g., from a solid tumor biopsy. Non-limiting examples of bodily fluids include blood, serum, plasma, tumor cells, saliva, urine, cerebrospinal fluid, lymphatic fluid, prostatic fluid, seminal fluid, milk, sputum, stool, tears, and derivatives of these. In some cases, one or more cell-free nucleic acid molecules as disclosed herein can be derived from a biological sample.

The term "subject," as used herein, generally refers to any animal, mammal, or human. A subject can have, potentially have, or be suspected of having one or more conditions, such as a disease. In some cases, a condition of the subject can be cancer, a symptom(s) associated with cancer, or asymptomatic with respect to cancer or undiagnosed (e.g., not diagnosed for cancer). In some cases, the subject can have cancer, the subject can show a symptom(s) associated with cancer, the subject can be free from symptoms associated with cancer, or the subject may not be diagnosed with cancer. In some examples, the subject is a human.

The term "cell-free DNA" or "cfDNA," as used interchangeably herein, generally refers to DNA fragments circulating freely in a blood stream of a subject. Cell-free DNA fragments can have dinucleosomal protection (e.g., a fragment size of at least 240 base pairs ("bp")). These cfDNA fragments with dinucleosomal protection were likely not cut between the nucleosome, resulting in a longer fragment length (e.g., with a typical size distribution centered around 334 bp). Cell-free DNA fragments can have mononucleosomal protection (e.g., a fragment size of less than 240 base pairs ("bp")). These cfDNA fragments with mononucleosomal protection were likely cut between the nucleosome, resulting in a shorter fragment length (e.g., with a typical size distribution centered around 167 bp).

The term "sequencing data," as used herein, generally refers to "raw sequence reads" and/or "consensus sequences" of nucleic acids, such as cell-free nucleic acids or derivatives thereof. Raw sequence reads are the output of a DNA sequencer, and typically include redundant sequences of the same parent molecule, for example after amplification. "Consensus sequences" are sequences derived from redundant sequences of a parent molecule intended to represent the sequence of the original parent molecule. Consensus sequences can be produced by voting (wherein each majority nucleotide, e.g., the most commonly observed nucleotide at a given base position, among the sequences is the consensus nucleotide) or other approaches such as comparing to a reference genome. In some cases, consensus sequences can be produced by tagging original parent molecules with unique or non-unique molecular tags, which allow tracking of the progeny sequences (e.g., after amplification) by tracking of the tag and/or use of sequence read internal information.

The term "reference genomic sequence," as used herein, generally refers to a nucleotide sequence against which a subject's nucleotide sequences are compared.

The term "genomic region," as used herein, generally refers to any region (e.g., range of base pair locations) of a genome, e.g., an entire genome, a chromosome, a gene, or an exon. A genomic region can be a contiguous or a non-contiguous region. A "genetic locus" (or "locus") can be a portion or entirety of a genomic region (e.g., a gene, a portion of a gene, or a single nucleotide of a gene).

The term "likelihood," as used herein, generally refers to a probability, a relative probability, a presence or an absence, or a degree.

The term "liquid biopsy," as used herein, generally refers to a non-invasive or minimally invasive laboratory test or assay (e.g., of a biological sample or cell-free nucleic acids). The "liquid biopsy" assays can report detections or measurements (e.g., minor allele frequencies, gene expression, or protein expression) of one or more marker genes associated with a condition of a subject (e.g., cancer or tumor-associated marker genes).

A. Introduction

Modifications (e.g., mutations) of genomic DNA can be manifested in a formation and/or progression of one or more conditions (e.g., a disease, such as cancer or tumor) of a subject. The present disclosure provides methods and systems for analyzing cell-free nucleic acid molecules, such as cfDNA, from a subject to determine the presence or absence of a condition of the subject, prognosis of a diagnosed condition of the subject, progress of the condition of the subject over time, therapeutic treatment of a diagnosed condition of the subject, or predicted treatment outcome for a condition of the subject.

Analysis of cell-free nucleic acids, such as cfDNA, have been developed with broad applications in, e.g., prenatal testing, organ transplantation, infectious disease, and oncology. In the context of detecting or monitoring a disease of a subject, such as cancer, circulating tumor DNA (ctDNA) can be a sensitive and specific biomarker in numerous cancer types. In some cases, ctDNA can be used to detect the presence of minimal residual disease (MRD) or tumor burden after treatment, such as chemotherapies or surgical resection of solid tumors. However, the limit of detection (LOD) for ctDNA analysis can be restricted by a number of factors including (i) low input DNA amounts from a typical blood collection and (ii) background error rates from sequencing.

In some cases, ctDNA-based cancer detection can be improved by tracking multiple somatic mutations with error-suppressed sequencing, e.g., with LOD of about 2 parts in 100,000 from cfDNA input while using off-the-shelf panels or personalized assays. However, in some cases, current LOD of ctDNA of interest can be insufficient to universally detect MRD in patients destined for disease relapse or progression. For example, such 'loss of detection' can be exemplified in diffuse large B-cell lymphoma (DLBCL). For DLBCL, interim ctDNA detection after only two cycles of curative-intent therapy can represent a major molecular response (MMR), and can be a strong prognostic marker for ultimate clinical outcomes. Despite this, nearly one-third of patients ultimately experiencing disease progression do not have detectable ctDNA at this interim landmark using available techniques (e.g., Cancer Personalized Profiling by Deep Sequencing (CAPP-Seq)), thus representing 'false-negative' measurements. Such high false-negative rates have also been observed in DLBCL patients by alternative methods, such as monitoring ctDNA through immunoglobulin gene rearrangements. Therefore, there exists a need for improved methods of ctDNA-based cancer detection with greater sensitivity.

Somatic variants detected on both of the complementary strands of parental DNA duplexes can be used to lower the LOD of ctDNA detection, thereby advantageously increasing the sensitivity of ctDNA detection. Such 'duplex sequencing' can reduce background error profile due to the requirement of two concordant events for detection of a single nucleotide variant (SNV). However, the duplex sequencing approach alone can be limited by inefficient recovery of DNA duplexes as recovery of both original strands can occur in a minority of all recovered molecules. Thus, duplex sequencing may be suboptimal and inefficient for real-world ctDNA detection with limited amount of starting sample, where input DNA from practical blood volumes (e.g., between about 4,000 to about 8,000 genomes per standard 10 milliliter (mL) blood collection tube) is limited and maximal recovery of genomes is essential.

Thus, there remains a significant unmet need for detection and analysis of ctDNA with low LOD (e.g., thereby yielding high sensitivity) for determining, for example, presence or absence of a disease of a subject, prognosis of the disease, treatment for the disease, and/or predicted outcome of the treatment.

B. Methods and Systems for Determining or Monitoring a Condition

The present disclosure describes methods and systems for detecting and analyzing cell free nucleic acids with a plurality of phased variants as a characteristic of a condition of a subject. In some aspects, the cell-free nucleic acid molecules can comprise cfDNA molecules, such as ctDNA molecules. The methods and systems disclosed herein can utilize sequencing data derived from a plurality of cell-free nucleic acid molecules of the subject to identify a subset of the plurality of cell-free nucleic acid molecules having the plurality of phased variants, thereby to determine the condition of the subject. The methods and systems disclosed herein can directly detect and, in some cases, pull down (or capture) such subset of the plurality of cell-free nucleic acid molecules that exhibit the plurality of phased variants, thereby to determine the condition of the subject with or without sequencing. The methods and systems disclosed herein can reduce background error rate often involved during detection and analysis of cell-free nucleic acid molecules, such as cfDNA.

In some aspects, methods and systems for cell-free nucleic acid sequencing and detection of cancer are provided. In some embodiments, cell-free nucleic acids (e.g., cfDNA or cfRNA) can be extracted from a liquid biopsy of an individual and prepared for sequencing. Sequencing results of the cell-free nucleic acids can be analyzed to detect somatic variants in phase (i.e., phased variants, as disclosed herein) as an indication of circulating-tumor nucleic acid (ctDNA or ctRNA) sequences (i.e., sequences that derived or are originated from nucleic acids of a cancer cell). Accordingly, in some cases, cancer can be detected in the individual by extracting a liquid biopsy from the individual and sequencing the cell-free nucleic acids derived from that liquid biopsy to detect circulating-tumor nucleic acid sequences, and the presence of circulating-tumor nucleic acid sequences can indicate that the individual has a cancer (e.g., a specific type of cancer). In some cases, a clinical intervention and/or treatment can be determined and/or performed on the individual based on the detection of the cancer.

As disclosed herein, a presence of somatic variants in phase can be a strong indication that the nucleic acids containing such phased variants are derived from a bodily sample with a condition, such as a cancerous cell (or alternatively, that the nucleic acids are from derived from a bodily sample obtained or derived from a subject with a condition, such as cancer). Detection of phased somatic variants can enhance the signal-to-noise ratio of cell-free nucleic acid detection methods (e.g., by reducing or eliminating spurious "noise" signals) as it may be unlikely that phased mutations would occur within a small genetic window that is approximately the size of a typical cell-free nucleic acid molecule (e.g., about 170 bp or less).

In some aspects, a number of genomic regions can be used as hotspots for detection of phased variants, especially in various cancers, e.g., lymphomas. In some cases, enzymes (e.g., AID, Apobec3a) can stereotypically mutagenize DNA in specific genes and locations, leading to development of particular cancers. Accordingly, cell-free nucleic acids derived from such hotspot genomic regions can be captured or targeted (e.g., with or without deep sequencing) for cancer detection and/or monitoring. Alternatively, capture or targeted sequencing can performed on regions in which phased variants have been previously detected from a cancerous source (e.g., tumor) of a particular individual in order to detect cancer in that individual.

In some aspects, capture sequencing on cell-free nucleic acids can be performed as a screening diagnostic. In some cases, a screening diagnostic can be developed and used to detect circulating-tumor nucleic acids for cancers that have stereotypical regions of phased variants. In some cases, capture sequencing on cell-free nucleic acids is performed as a diagnostic to detect MRD or tumor burden to determine if a particular disease is present during or after treatment. In some cases, capture sequencing on cell-free nucleic acids can be performed as a diagnostic to determine progress (e.g., progression or regression) of a treatment.

In some aspects, cell-free nucleic acid sequencing results can be analyzed to detect whether phased somatic single nucleotide variants (SNVs) or other mutations or variants (e.g., indels) exist within the cell-free nucleic acid sample. In some cases, the presence of particular somatic SNVs or other variants can be indicative of circulating-tumor nucleic acid sequences, and thus indicative of a tumor present in the subject. In some cases, a minimum of two variants can be detected in phase on a cell-free nucleic acid molecule. In some cases, a minimum of three variants can be detected in phase on a cell-free nucleic acid molecule. In some cases, a minimum of four variants can be detected in phase on a cell-free nucleic acid molecule. In some cases, a minimum of five or more variants can be detected in phase on a cell-free nucleic acid molecule. In some cases, the greater number of phased variants detected on a cell-free nucleic acid molecule, the greater the likelihood that the cell-free nucleic acid molecule is derived from cancer, as opposed to detecting an innocuous sequence of somatic variants that arise from molecular preparation of the sequence library or random biological errors. Accordingly, the likelihood of false-positive detection can decrease with detection of more variants in phase within a molecule (e.g., thereby increasing specificity of detection).

In some aspects, a cell-free nucleic acid sequencing result can be analyzed to detect whether an insertion or deletion of one or more nucleobases (i.e., indel) exist within the cell-free nucleic acid sample, e.g., relative to a reference genomic sequence. Without wishing to be bound by theory, in some cases, presence of indels in a cell-free nucleic acid molecule (e.g., cfDNA) can be indicative of a condition of a subject, e.g., a disease such as cancer. In some cases, a genetic variation as a result of an indel can be treated as a variant or mutation, and thus two indels can be treated a two phased variants, as disclosed herein. In some examples, within a cell-free nucleic acid molecule, a first genetic variation from a first indel (a first phase variant) and a second genetic variation from a second indel (a second phase variant) can be separated from each other by at least 1 nucleotide.

Within a single cell-free nucleic acid molecule (e.g., a single cfDNA molecule), as disclosed herein, a first phased variant can be a SNV and a second phased variant can be a part of a different small nucleotide polymorphism, e.g., another SNV or a part of a multi-nucleotide variant (MNV). A multi-nucleotide variant can be a cluster of two or more (e.g., at least 2, 3, 4, 5, or more) adjacent variants existing within the same stand of nucleic acid molecule. In some cases, the first phased variant and the second phased variant can be parts of the same MNV within the single cell-free nucleic acid molecule. In some cases, the first phased variant and the second phased variant can be from two different MNVs within the single cell-free nucleic acid molecule.

In some aspects, a statistical method can be utilized to calculate the likelihood that detected phased variants are from a cancer and not random or artificial (e.g., from sample prep or sequencing error). In some cases, a Monte Carlo sampling method can be utilized to determine the likelihood that detected phased variants are from a cancer and not random or artificial.

Aspects of the present disclosure provide identification or detection of cell-free nucleic acids (e.g., cfDNA molecule) with a plurality of phased variants, e.g., from a liquid biopsy of a subject. In some cases, a first phased variant of the plurality of phased variants and a second phased variant of the plurality of phased variants can be directly adjacent to each other (e.g., neighboring SNVs). In some cases, a first phased variant of the plurality of phased variants and a second phased variant of the plurality of phased variants can be separated by at least one nucleotide. The spacing between the first phased variant and the second phased variant can be limited by the length of the cell-free nucleic acid molecule.

Within a single cell-free nucleic acid molecule (e.g., a single cfDNA molecule), as disclosed herein, a first phased variant and a second phased variant can be separated from each other by at least or up to about 1 nucleotide, at least or up to about 2 nucleotides, at least or up to about 3 nucleotides, at least or up to about 4 nucleotides, at least or up to about 5 nucleotides, at least or up to about 6 nucleotides, at least or up to about 7 nucleotides, at least or up to about 8 nucleotides, at least or up to about 9 nucleotides, at least or up to about 10 nucleotides, at least or up to about 11 nucleotides, at least or up to about 12 nucleotides, at least or up to about 13 nucleotides, at least or up to about 14 nucleotides, at least or up to about 15 nucleotides, at least or up to about 20 nucleotides, at least or up to about 25 nucleotides, at least or up to about 30 nucleotides, at least or up to about 35 nucleotides, at least or up to about 40 nucleotides, at least or up to about 45 nucleotides, at least or up to about 50 nucleotides, at least or up to about 60 nucleotides, at least or up to about 70 nucleotides, at least or up to about 80 nucleotides, at least or up to about 90 nucleotides, at least or up to about 100 nucleotides, at least or up to about 110 nucleotides, at least or up to about 120 nucleotides, at least or up to about 130 nucleotides, at least or up to about 140 nucleotides, at least or up to about 150 nucleotides, at least or up to about 160 nucleotides, at least or up to about 170 nucleotides, or at least or up to about 180 nucleotides. Alternatively or in addition to, within a single cell-free nucleic acid molecule, a first phased variant and a second phased variant may not or need not be separated by one or more nucleotides and thus can be directly adjacent to one another.

A single cell-free nucleic acid molecule (e.g., a single cfDNA molecule), as disclosed herein, can comprise at least or up to about 2 phased variants, at least or up to about 3 phased variants, at least or up to about 4 phased variants, at least or up to about 5 phased variants, at least or up to about 6 phased variants, at least or up to about 7 phased variants, at least or up to about 8 phased variants, at least or up to about 9 phased variants, at least or up to about 10 phased variants, at least or up to about 12 phased variants, at least or up to about 12 phased variants, at least or up to about 13 phased variants, at least or up to about 14 phased variants, at least or up to about 15 phased variants, at least or up to about 20 phased variants, or at least or up to about 25 phased variants within the same molecule.

From a plurality of cell-free nucleic acid molecules obtained (e.g., from a liquid biopsy of a subject), two or more (e.g., 10 or more, 1,000 or more, 10,000 or more) cell-free nucleic acid molecules can be identified to have an average of at least or up to about 2 phased variants, at least or up to about 3 phased variants, at least or up to about 4 phased variants, at least or up to about 5 phased variants, at least or up to about 6 phased variants, at least or up to about 7 phased variants, at least or up to about 8 phased variants, at least or up to about 9 phased variants, at least or up to about 10 phased variants, at least or up to about 12 phased variants, at least or up to about 12 phased variants, at least or up to about 13 phased variants, at least or up to about 14 phased variants, at least or up to about 15 phased variants, at least or up to about 20 phased variants, or at least or up to about 25 phased variants per each cell-free nucleic acid molecule identified to comprise a plurality of phased variants.

In some cases, a plurality of cell-free nucleic acid molecules (e.g., cfDNA molecules) can be obtained from a biological sample of a subject (e.g., solid tumor or liquid biopsy). Out of the plurality of cell-free nucleic acid molecules, at least or up to 1, at least or up to 2, at least or up to 3, at least or up to 4, at least or up to 5, at least or up to 6, at least or up to 7, at least or up to 8, at least or up to 9, at least or up to 10, at least or up to 15, at least or up to 20, at least or up to 25, at least or up to 30, at least or up to 35, at least or up to 40, at least or up to 45, at least or up to 50, at least or up to 60, at least or up to 70, at least or up to 80, at least or up to 90, at least or up to 100, at least or up to 150, at least or up to 200, at least or up to 300, at least or up to 400, at least or up to 500, at least or up to 600, at least or up to 700, at least or up to 800, at least or up to 900, at least or up to 1,000, at least or up to 5,000, at least or up to, 10,000, at least or up to 50,000, or at least or up to 100,000 cell-free nucleic acid molecules can be identified, such that each identified cell-free nucleic acid molecule comprises the plurality of phased variants, as disclosed herein.

In some cases, a plurality of cell-free nucleic acid molecules (e.g., cfDNA molecules) can be obtained from a biological sample of a subject (e.g., solid tumor or liquid biopsy). Out of the plurality of cell-free nucleic acid molecules, at least or up to 1, at least or up to 2, at least or up to 3, at least or up to 4, at least or up to 5, at least or up to 6, at least or up to 7, at least or up to 8, at least or up to 9, at least or up to 10, at least or up to 15, at least or up to 20, at least or up to 25, at least or up to 30, at least or up to 35, at least or up to 40, at least or up to 45, at least or up to 50, at least or up to 60, at least or up to 70, at least or up to 80, at least or up to 90, at least or up to 100, at least or up to 150, at least or up to 200, at least or up to 300, at least or up to 400, at least or up to 500, at least or up to 600, at least or up to 700, at least or up to 800, at least or up to 900, or at least or up to 1,000 cell-free nucleic acid molecules can be identified from a target genomic region (e.g., a target genomic locus), such that each identified cell-free nucleic acid molecule comprises the plurality of phased variants, as disclosed herein.

Figure 1B:
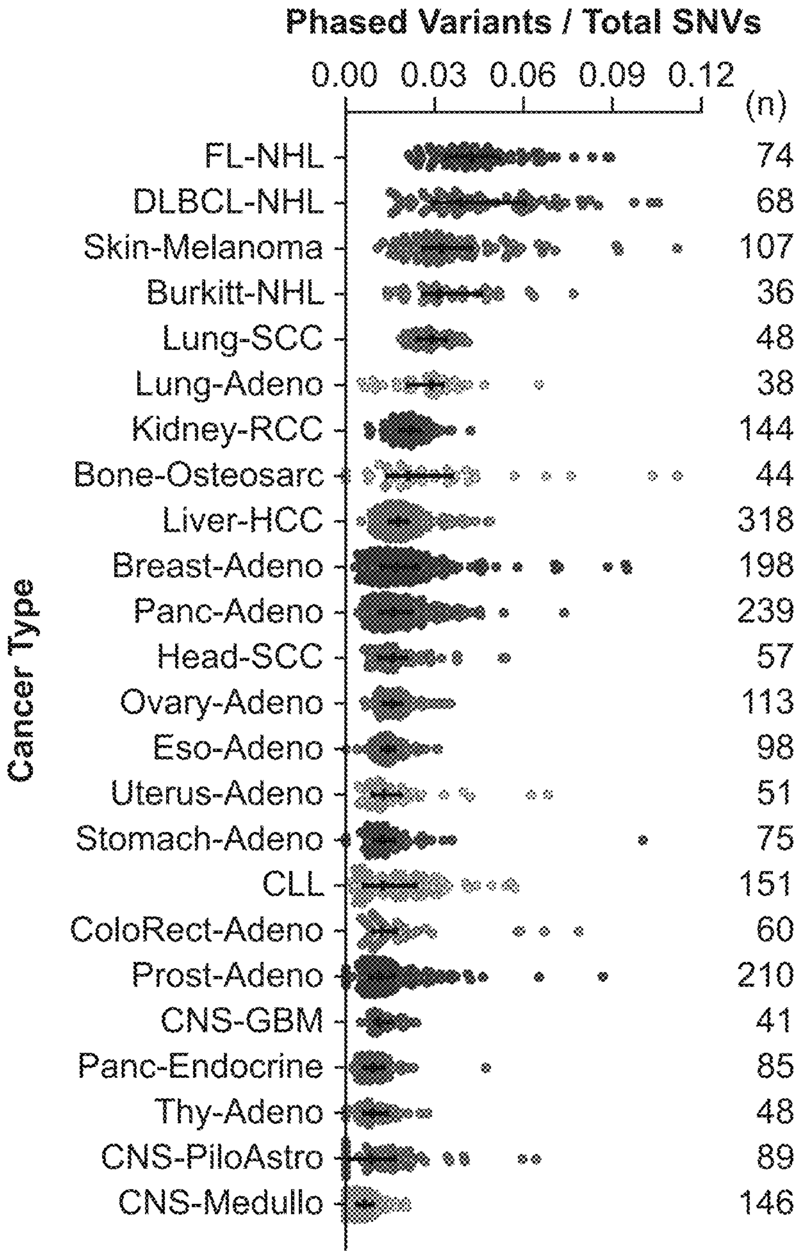
Figure 1C:
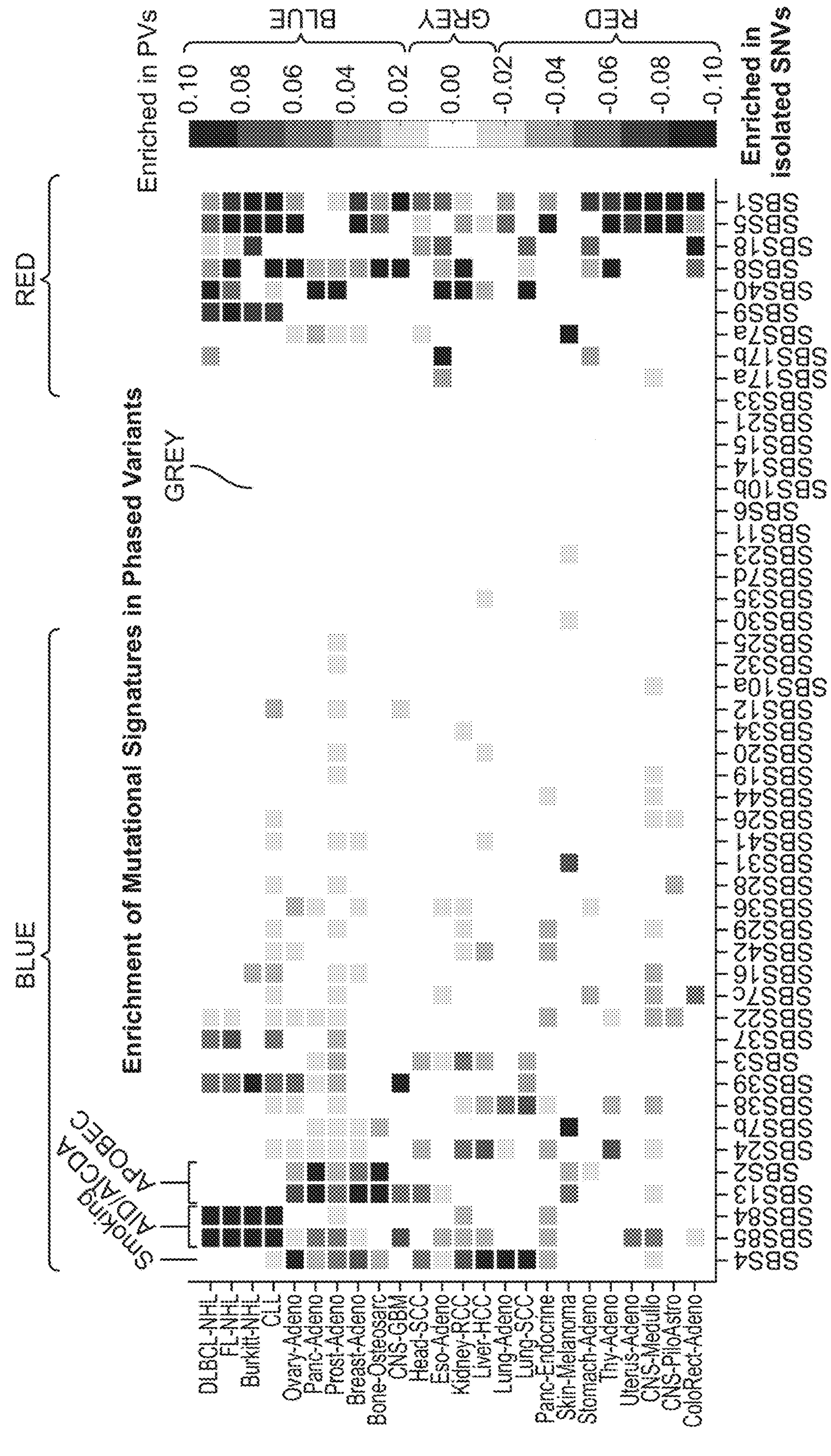
Figure 1D:
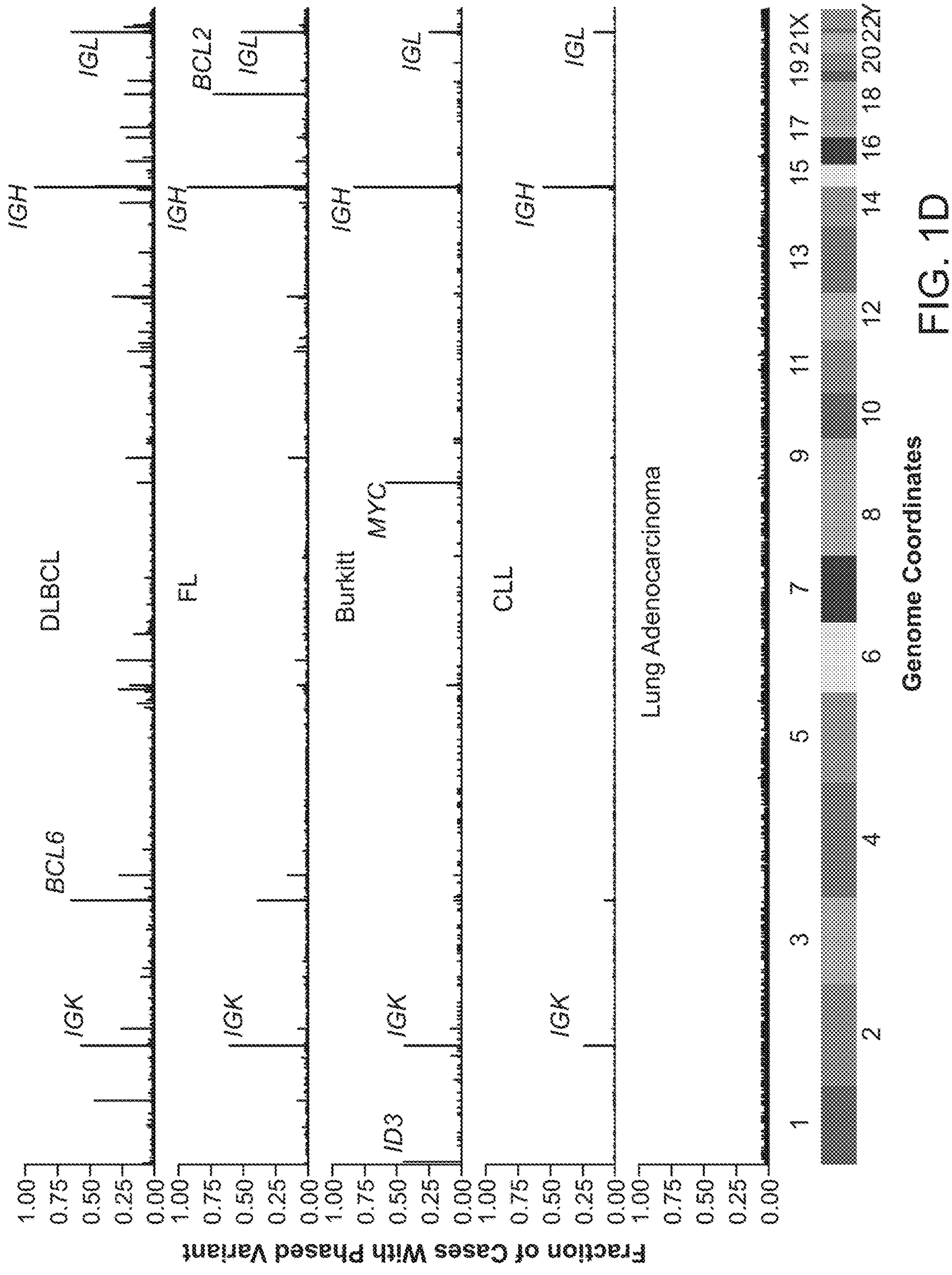
Figure 1E:
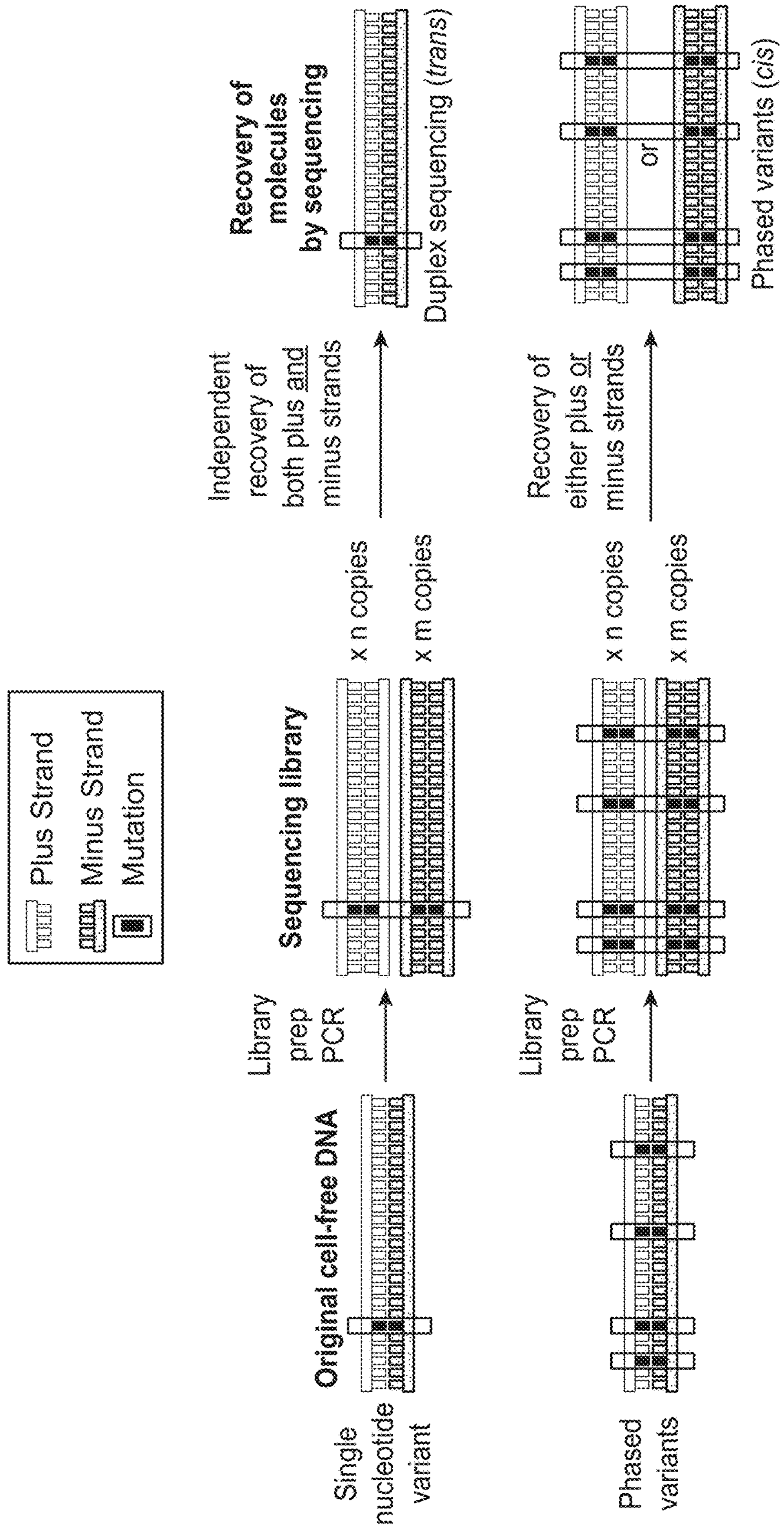

FIGS. 1A and 1E schematically illustrate examples of (i) a cfDNA molecule comprising a SNV and (ii) another cfDNA molecule comprising a plurality of phased variants. Each variant identified within the cfDNA can indicate a presence of one more genetic mutations in the cell that the cfNDA is originated from. In alternative embodiments, one or more of the phased variants may be an insertion or deletion (indel) instead of an SNV.

In one aspect, the present disclosure provides a method for determining a condition of a subject, as shown by flowchart 2510 in FIG. 25A. The method can comprise (a) obtaining, by a computer system, sequencing data derived from a plurality of cell-free nucleic acid molecules that is obtained or derived from the subject (process 2512). The method can further comprise (b) processing, by the computer system, the sequencing data to identify one or more cell-free nucleic acid molecules of the plurality of cell-free nucleic acid molecules, wherein each of the one or more cell-free nucleic acid molecules identified comprises a plurality of phased variants relative to a reference genomic sequence (process 2514). In some cases, at least a portion of the one or more cell-free nucleic acid molecules can comprise a first phased variant of the plurality of phased variants and a second phased variant of the plurality of phased variants that are separated by at least one nucleotide, as disclosed herein. The method can optionally comprise (c) analyzing, by the computer system, at least a portion of the identified one or more cell-free nucleic acid molecules to determine the condition of the subject (process 2516).

In some cases, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, at least or up to about 50%, at least or up to about 60%, at least or up to about 70%, at least or up to about 80%, at least or up to about 90%, at least or up to about 95%, at least or up to about 99%, or about 100% of the one or more cell-free nucleic acid molecules can comprise a first phased variant of the plurality of phased variants and a second phased variant of the plurality of phased variants that are separated by at least one nucleotide, as disclosed herein. In some examples, a plurality of phased variants within a single cfDNA molecule can comprise (i) a first plurality of phased variants that are separated by at least one nucleotide from one another and (ii) a second plurality of phased variants that are adjacent to one another (e.g., two phased variants within a MNV). In some examples, a plurality of phased variants within a single cfDNA molecule can consist of phased variants that are separate by at least one nucleotide from one another.

Figure 25B:
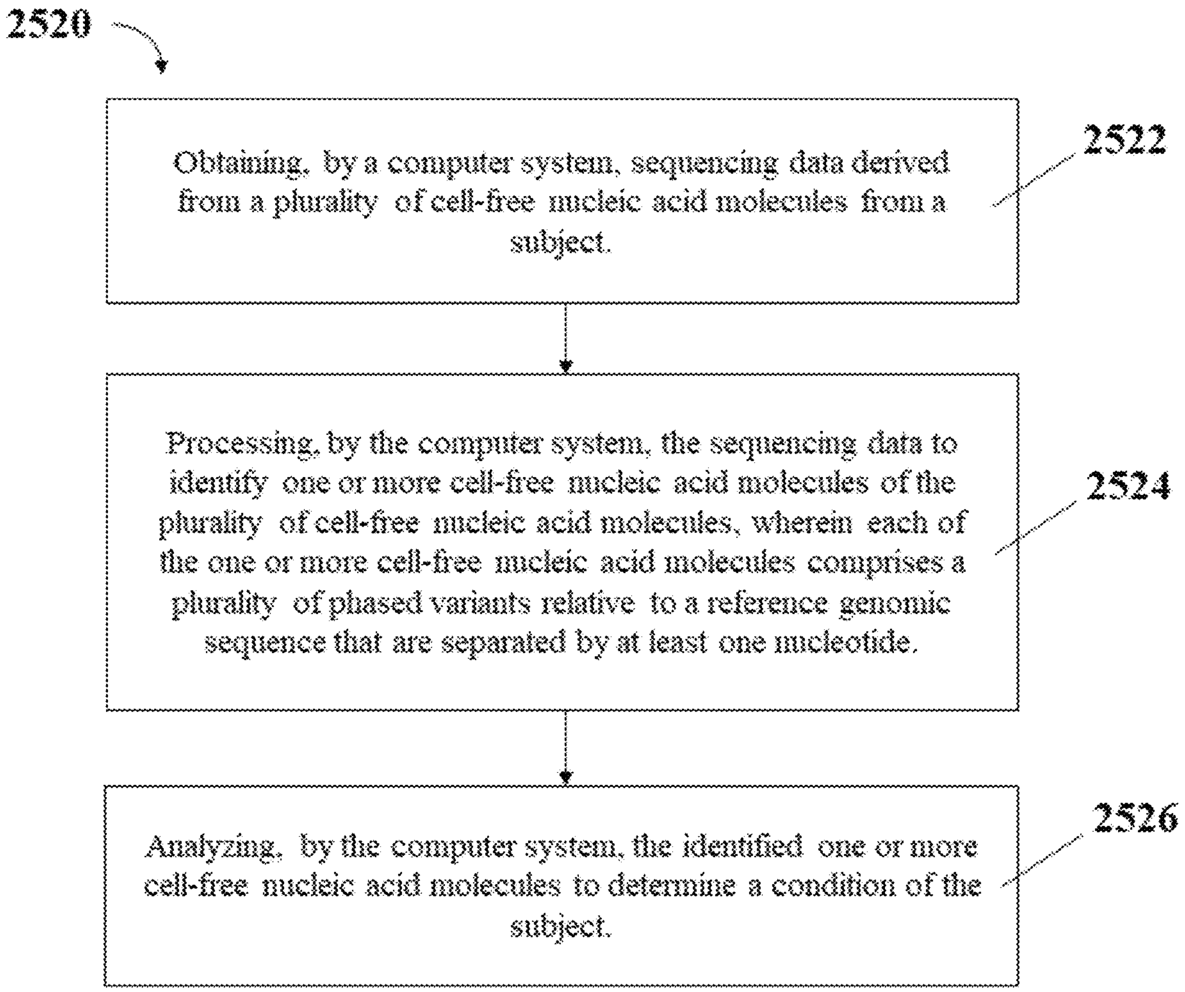

In one aspect, the present disclosure provides a method for determining a condition of the subject, as shown by flowchart 2520 in FIG. 25B. The method can comprise (a) obtaining, by a computer system, sequencing data derived from a plurality of cell-free nucleic acid molecules that is obtained or derived from a subject (process 2522). The method can further comprise (b) processing, by the computer system, the sequencing data to identify one or more cell-free nucleic acid molecules of the plurality of cell-free nucleic acid molecules, wherein each of the one or more cell-free nucleic acid molecules comprises a plurality of phased variants relative to a reference genomic sequence (process 2524). In some cases, a first phased variant of the plurality of phased variant and a second phased variant of the plurality of phased variant can be separated by at least one nucleotide, as disclosed herein. The method can optionally comprise (c) analyzing, by the computer system, at least a portion of the identified one or more cell-free nucleic acid molecules to determine the condition of the subject (process 2526).

Figure 25C:
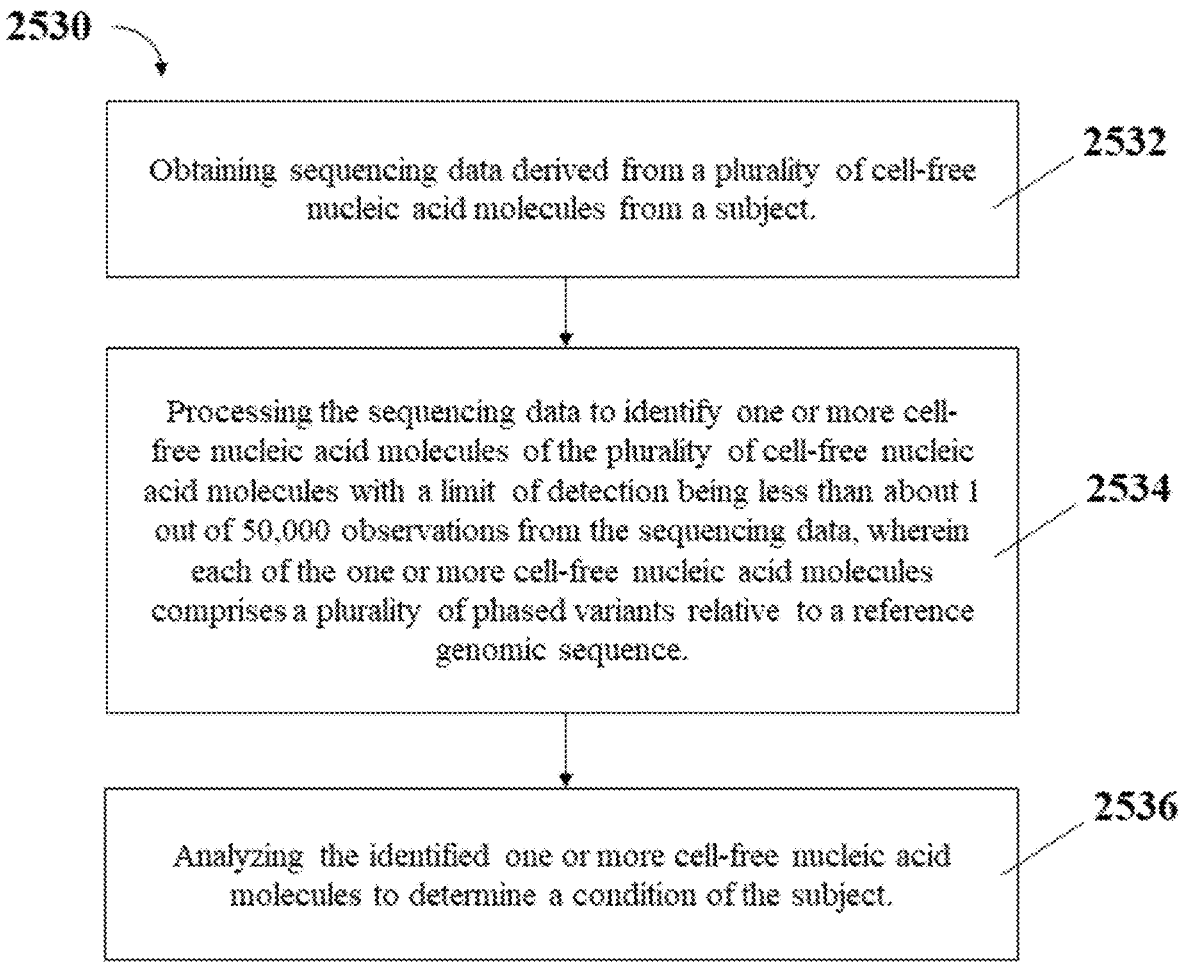

In one aspect, the present disclosure provides a method for determining a condition of a subject, as shown by flowchart 2530 in FIG. 25C. The method can comprise (a) obtaining sequencing data derived from a plurality of cell-free nucleic acid molecules that is obtained or derived from the subject (process 2532). The method can further comprise (b) processing the sequencing data to identify one or more cell-free nucleic acid molecules of the plurality of cell-free nucleic acid molecules with a LOD being less than about 1 out of 50,000 observations (or cell-free nucleic acid molecules) from the sequencing data (process 2534). In some cases, each of the one or more cell-free nucleic acid molecules comprises a plurality of phased variants relative to a reference genomic sequence. The method can optionally comprise (c) analyzing at least a portion of the identified one or more cell-free nucleic acid molecules to determine the condition of the subject (process 2536).

In some cases, the LOD of the operation of identifying the one or more cell-free nucleic acid molecules, as disclosed herein, can be less than about 1 out of 60,000, less than 1 out of 70,000, less than 10 out of 80,000, less than 1 out of 90,000, less than 1 out of 100,000, less than 1 out of 150,000, less than 1 out of 200,000, less than 1 out of 300,000, less than 1 out of 400,000, less than 1 out of 500,000, less than 1 out of 600,000, less than 1 out of 700,000, less than 1 out of 800,000, less than 1 out of 900,000, less than 1 out of 1,000,000, less than 1 out of 1,000,000, less than 1 out of 1,100,000, less than 1 out of 1,200,000, less than 1 out of 1,300,000, less than 1 out of 1,400,000, less than 1 out of 1,500,000, or less than 1 out of 2,000,000 observations from the sequencing data.

In some cases, at least one cell-free nucleic acid molecule of the identified one or more cell-free nucleic acid molecules can comprise a first phased variant of the plurality of phased variants and a second phased variant of the plurality of phased variants that are separated by at least one nucleotide, as disclosed herein.

In some cases, one or more of the operations (a) through (c) of the subject method can be performed by a computer system. In an example, all of the operations (a) through (c) of the subject method can be performed by the computer system.

The sequencing data, as disclosed herein, can be obtained from one or more sequencing methods. A sequencing method can be a first-generation sequencing method (e.g., Maxam-Gilbert sequencing, Sanger sequencing). A sequencing method can be a high-throughput sequencing method, such as next-generation sequencing (NGS) (e.g., sequencing by synthesis). A high-throughput sequencing method can sequence simultaneously (or substantially simultaneously) at least about 10,000, at least about 100,000, at least about 1 million, at least about 10 million, at least about 100 million, at least about 1 billion, or more polynucleotide molecules (e.g., cell-free nucleic acid molecules or derivatives thereof). NGS can be any generation number of sequencing technologies (e.g., second-generation sequencing technologies, third-generation sequencing technologies, fourth-generation sequencing technologies, etc.). Non-limiting examples of high-throughput sequencing methods include massively parallel signature sequencing, polony sequencing, pyrosequencing, sequencing-by-synthesis, combinatorial probe anchor synthesis (cPAS), sequencing-by-ligation (e.g., sequencing by oligonucleotide ligation and detection (SOLiD) sequencing), semiconductor sequencing (e.g., Ion Torrent semiconductor sequencing), DNA nanoball sequencing, and single-molecule sequencing, sequencing-by-hybridization.

In some embodiments of any one of the methods disclosed herein, the sequencing data can be obtained based on any of the disclosed sequencing methods that utilizes nucleic acid amplification (e.g., polymerase chain reaction (PCR)). Non-limiting examples of such sequencing methods can include 454 pyrosequencing, polony sequencing, and SoLiD sequencing. In some cases, amplicons (e.g., derivatives of the plurality of cell-free nucleic acid molecules that is obtained or derived from the subject, as disclosed herein) that correspond to a genomic region of interest (e.g., a genomic region associated with a disease) can be generated by PCR, optionally pooled, and subsequently sequenced to generating sequencing data. In some examples, because the regions of interest are amplified into amplicons by PCR before being sequenced, the nucleic acid sample is already enriched for the region of interest, and thus any additional pooling (e.g., hybridization) may not and need not be needed prior to sequencing (e.g., non-hybridization based NGS). Alternatively, pooling via hybridization can further be performed for additional enrichment prior to sequencing. Alternatively, the sequencing data can be obtained without generating PCR copies, e.g., via cPAS sequencing.

A number of embodiments utilize capture hybridization techniques to perform targeted sequencing. When performing sequencing on cell-free nucleic acids, in order to enhance resolution on particular genomic loci, library products can be captured by hybridization prior to sequencing. Capture hybridization can be particularly useful when trying to detect rare and/or somatic phased variants from a sample at particular genomic loci. In some situations, detection of rare and/or somatic phased variants is indicative of the source of nucleic acids, including nucleic acids derived from a cancer source. Accordingly, capture hybridization is a tool that can enhance detection of circulating-tumor nucleic acids within cell-free nucleic acids.

Various types of cancers repeatedly experience aberrant somatic hypermutation in particular genomic loci. For instance, the enzyme activation-induced deaminase induces aberrant somatic hypermutation in B-cells, which leads to various B-cell lymphomas, including (but not limited to) diffuse large B-cell lymphoma (DLBCL), follicular lymphoma (FL), Burkitt lymphoma (BL), and B-cell chronic lymphocytic leukemia (CLL). Accordingly, in numerous embodiments, probes are designed to pull down (or capture)

genomic loci known to experience aberrant somatic hypermutation in a lymphoma. FIG. 1D and Table 1 describe a number of regions that experience aberrant somatic hypermutation in DLBCL, FL, BL and CLL. Provided in Table 6 is list of nucleic acid probes that can be utilized to pull down (or capture) genomic loci to detect aberrant somatic hypermutation in B-cell cancers.

Capture sequencing can also be performed utilizing personalized nucleic acid probes designed to detect the existence of an individual's cancer. An individual having a cancer can have their cancer biopsied and sequenced to detect somatic phased variants that have accumulated in the cancer. Based on the sequencing result, in accordance with a number of embodiments, nucleic acid probes are designed and synthesized capable of pulling down the genomic loci inclusive of the positions of where the phased variants. These personalized designed and synthesized nucleic acid probes can be utilized to detect circulating-tumor nucleic acids from a liquid biopsy of that individual. Accordingly, the personalized nucleic acid probes can be useful for determining treatment response and/or detecting MRD after treatment.

In some embodiments of any one of the methods disclosed herein, the sequencing data can be obtained based on any sequencing method that utilizes adapters. Nucleic acid samples (e.g., the plurality of cell-free nucleic acid molecules from the subject, as disclosed herein) can be conjugated with one or more adapters (or adapter sequences) for recognizing (e.g., via hybridization) of the sample or any derivatives thereof (e.g., amplicons). In some examples, the nucleic acid samples can be tagged with a molecular barcode, e.g., such that each cell-free nucleic acid molecule of the plurality of cell-free nucleic acid molecules can have a unique barcode. Alternatively or in addition to, the nucleic acid samples can be tagged with a sample barcode, e.g., such that the plurality of cell-free nucleic acid molecules from the subject (e.g., a plurality of cell-free nucleic acid molecules obtained from a specific bodily tissue of the subject) can have the same barcode.

In alternative embodiments, the methods of identifying one or more cell-free nucleic acid molecules comprising the plurality of phased variants, as disclosed herein, can be performed without molecular barcoding, without sample barcoding, or without molecular barcoding and sample barcoding, at least in part due to high specificity and low LOD achieved by relying on identifying the phased variants as opposed to, e.g., a single SNV.

In some embodiments of any one of the methods disclosed herein, the sequencing data can be obtained and analyzed without in silico removal or suppression of (i) background error and/or (ii) sequencing error, at least in part due to high specificity and low LOD achieved by relying on identifying the phased variants as opposed to, e.g., a single SNV or indel.

In some embodiments of any one of the methods disclosed herein, using the plurality of variants as a condition to identify target cell-free nucleic acid molecules with specific mutations of interest without in silico methods of error suppression can yield a background error-rate that is lower than that of (i) barcode-deduplication, (ii) integrated digital error suppression, or (iii) duplex sequencing by at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 200-fold, at least about 400-fold, at least about 600-fold, at least about 800-fold, or at least about 1,000-fold. This approach may advantageously increase signal-to-noise ratio (thereby increasing sensitivity and/or specificity) of identifying target cell-free nucleic acid molecules with specific mutations of interest.

In some embodiments of any one of the methods disclosed herein, increasing a minimum number of phased variants (e.g., increasing from at least two phased variants to at least three phased variants) per cell-free nucleic acid molecule required as a condition to identify target cell-free nucleic acid molecules with specific mutations of interest can reduce the background error-rate by at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, or at least about 100-fold. This approach may advantageously increase signal-to-noise ratio (thereby increasing sensitivity and/or specificity) of identifying target cell-free nucleic acid molecules with specific mutations of interest.

In one aspect, the present disclosure provides a method of treating a condition of a subject, as shown in flowchart 2540 in FIG. 25D. The method can comprise (a) identifying the subject for treatment of the condition, wherein the subject has been determined to have the condition based on identification of one or more cell-free nucleic acid molecules from a plurality of cell-free nucleic acid molecules that is obtained or derived from the subject (Process 2542). Each of the identified one or more cell-free nucleic acid molecules can comprise a plurality of phased variants relative to a reference genomic sequence. At least a portion (e.g., partial or all) of the plurality of phased variants can be separated by at least one nucleotide, such that a first phased variant of the plurality of phased variants and a second phased variant of the plurality of phased variants are separated by at least one nucleotide, as disclosed herein. In some cases, a presence of the plurality of phased variants is indicative of the condition (e.g., a disease, such as cancer) of the subject. The method can further comprise (b) subjecting the subject to the treatment based on the step (a) (process 2544). Examples of such treatment of the condition of the subject are disclosed elsewhere in the present disclosure.

Figure 25E:
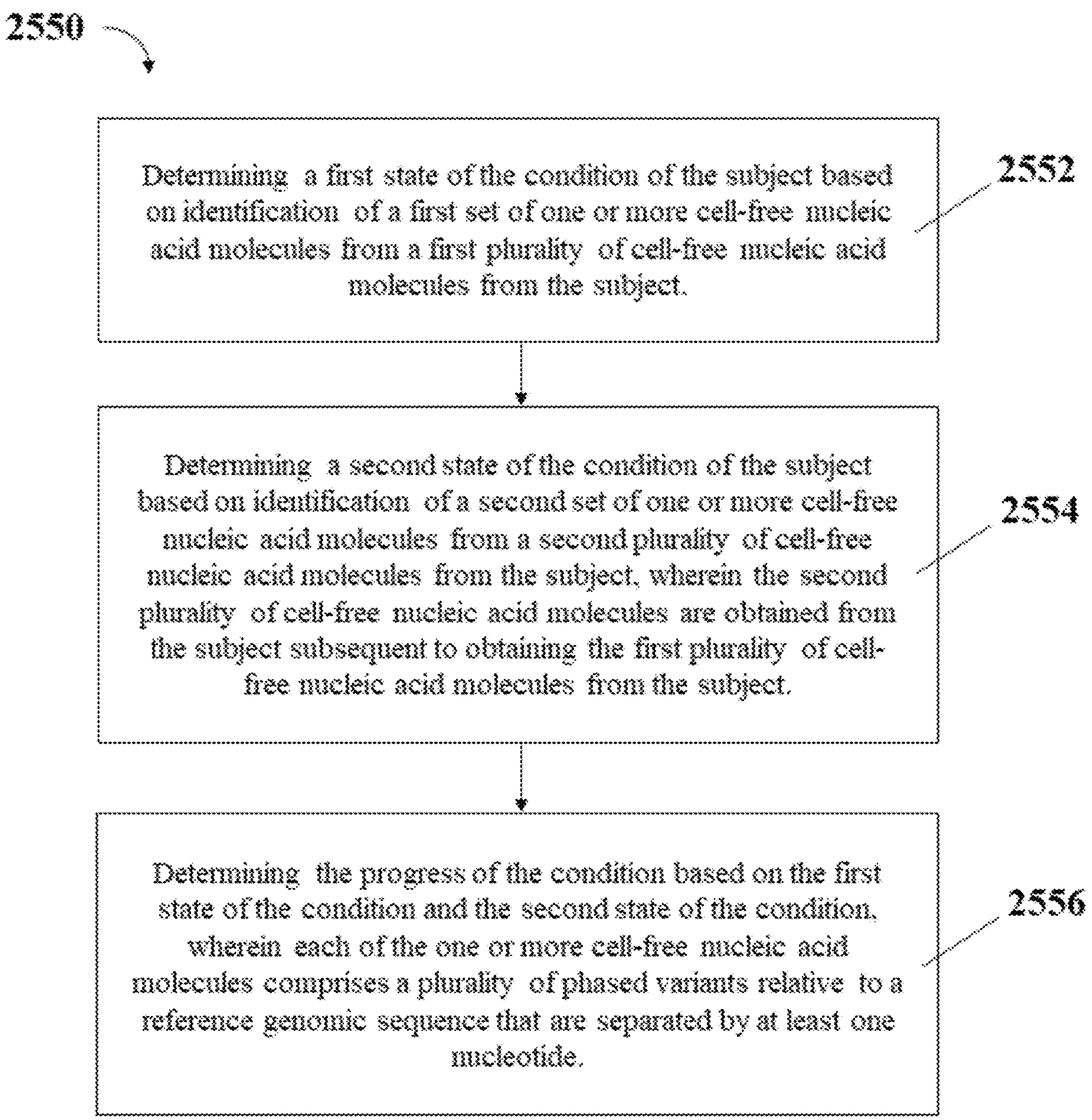
FIG. 25E shows an example flowchart of a method for determining a progress (e.g., progression or regression) of a condition of a subject based on one or more cell-free nucleic acid molecules comprising a plurality of variants.

In one aspect, the present disclosure provides a method of monitoring a progress (e.g., progression or regression) of a condition of a subject, as shown in flowchart 2550 in FIG. 25E. The method can comprise (a) determining a first state of the condition of the subject based on identification of a first set of one or more cell-free nucleic acid molecules from a first plurality of cell-free nucleic acid molecules that is obtained or derived from the subject (process 2552). The method can further comprise (b) determining a second state of the condition of the subject based on identification of a second set of one or more cell-free nucleic acid molecules from a second plurality of cell-free nucleic acid molecules that is obtained or derived from the subject (process 2554). The second plurality of cell-free nucleic acid molecules can be obtained from the subject subsequent to obtaining the first plurality of cell-free nucleic acid molecules from the subject. The method can optionally comprise (c) determining the progress (e.g., progression or regression) of the condition based at least in part on the first state of the condition and the second state of the condition (process 2556). In some cases, each of the one or more cell-free nucleic acid molecules identified (e.g., each of the first set of one or more cell-free nucleic acid molecules identified, each of the second set of one or more cell-free nucleic acid molecules identified) can comprise a plurality of phased variants relative to a reference genomic sequence. At least a portion (e.g., partial or all) of the one or more cell-free nucleic acid molecules identified can be separated by at least one nucleotide, as disclosed herein. In some cases, presence of the plurality of phased variants can be indicative of a state of the condition of the subject.

In some cases, the first plurality of cell-free nucleic acid molecules from the subject can be obtained (e.g., via blood biopsy) and analyzed to determine (e.g., diagnose) a first state of the condition (e.g., a disease, such as cancer) of the subject. The first plurality of cell-free nucleic acid molecules can be analyzed via any of the methods disclosed herein (e.g., with or without sequencing) to identify the first set of one or more cell-free nucleic acid molecules comprising the plurality of phased variants, and the presence or characteristics of the first set of one or more cell-free nucleic acid molecules can be used to determine the first state of the condition (e.g., an initial diagnosis) of the subject. Based on the determined first state of the condition, the subject can be subjected to one or more treatments (e.g., chemotherapy) as disclosed herein. Subsequent to the one or more treatments, the second plurality of cell-free nucleic acid molecules can be obtained from the subject.

In some cases, the subject can be subjected to at least or up to about 1 treatment, at least or up to about 2 treatments, at least or up to about 3 treatments, at least or up to about 4 treatments, at least or up to about 5 treatments, at least or up to about 6 treatments, at least or up to about 7 treatments, at least or up to about 8 treatments, at least or up to about 9 treatments, or at least or up to about 10 treatments based on the determined first state of the condition. In some cases, the subject can be subjected to a plurality of treatments based on the determined first state of the condition, and a first treatment of the plurality of treatments and a second treatment of the plurality of treatments can be separated by at least or up to about 1 day, at least or up to about 7 days, at least or up to about 2 weeks, at least or up to about 3 weeks, at least or up to about 4 weeks, at least or up to about 2 months, at least or up to about 3 months, at least or up to about 4 months, at least or up to about 5 months, at least or up to about 6 months, at least or up to about 12 months, at least or up to about 2 years, at least or up to about 3 years, at least or up to about 4 years, at least or up to about 5 years, or at least or up to about 10 years. The plurality of treatments for the subject can be the same. Alternatively, the plurality of treatments can be different by drug type (e.g., different chemotherapeutic drugs), drug dosage (e.g., increasing dosage, decreasing dosage), presence or absence of a co-therapeutic agent (e.g., chemotherapy and immunotherapy), modes of administration (e.g., intravenous vs oral administrations), frequency of administration (e.g., daily, weekly, monthly), etc.

In some cases, the subject may not and need not be treated for the condition between determination of the first state of the condition and determination of the second state of the condition. For example, without any intervening treatment, the second plurality of cell-free nucleic acid molecules may be contained (e.g., via liquid biopsy) from the subject to confirm whether the subject still exhibits indications of the first state of the condition.

In some cases, the second plurality of cell-free nucleic acid molecules from the subject can be obtained (e.g., via blood biopsy) at least or up to about 1 day, at least or up to about 7 days, at least or up to about 2 weeks, at least or up to about 3 weeks, at least or up to about 4 weeks, at least or up to about 2 months, at least or up to about 3 months, at least or up to about 4 months, at least or up to about 5 months, at least or up to about 6 months, at least or up to about 12 months, at least or up to about 2 years, at least or up to about 3 years, at least or up to about 4 years, at least or up to about 5 years, or at least or up to about 10 years after obtaining the first plurality of cell-free nucleic acid molecules from the subject.

In some cases, at least or up to about 2, at least or up to about 3, at least or up to about 4, at least or up to about 5, at least or up to about 6, at least or up to about 7, at least or up to about 8, at least or up to about 9, or at least or up to about 10 different samples comprising a plurality of nucleic acid molecules (e.g., at least the first plurality of cell-free nucleic acid molecules and the second plurality of cell-free nucleic acid molecules) can be obtained over time (e.g., once every month for 6 months, once every two months for a year, once every three months for a year, once every 6 months for one or more years, etc.) to monitor the progress of the condition of the subject, as disclosed herein.

In some cases, the step of determining the progress of the condition based on the first state of the condition and the second state of the condition can comprise comparing one or more characteristics of the first state and the second state of the condition, such as, for example, (i) a total number of cell-free nucleic acid molecules identified to comprise the plurality of phased variants in each state (e.g., per equal weight or volume of the biological sample of origin, per equal number of initial cell-free nucleic acid molecules analyzed, etc.), (ii) an average number of the plurality of phased variants per each cell-free nucleic acid molecule identified to comprise a plurality of phased variants (i.e., two or more phased variants), or (iii) a number of cell-free nucleic acid molecules identified to comprise the plurality of phased variants divided by a total number of cell-free nucleic acid molecules that comprise a mutation that overlaps with some of the plurality of phased variants (i.e., phased variant allele frequency). Based on such comparison, MRD of the condition (e.g., cancer or tumor) of the subject can be determined. For example, tumor burden or cancer burden of the subject can be determined based on such comparison.

In some cases, the progress of the condition can be progression or worsening of the condition. In an example, the worsening of the condition can comprise developing of a cancer from an earlier stage to a later stage, such as from stage I cancer to stage III cancer. In another example, the worsening of the condition can comprise increasing size (e.g., volume) of a solid tumor. Yet in a different example, the worsening of the condition can comprise cancer metastasis from once location to another location within the subject's body.

In some examples, (i) a total number of cell-free nucleic acid molecules identified to comprise the plurality of phased variants from the second state of the condition of the subject can be higher than (ii) a total number of cell-free nucleic acid molecules identified to comprise the plurality of phased variants from the first state of the condition of the subject by at least or up to about 0.1-fold, at least or up to about 0.2-fold, at least or up to about 0.3-fold, at least or up to about 0.4-fold, at least or up to about 0.5-fold, at least or up to about 0.6-fold, at least or up to about 0.7-fold, at least or up to about 0.8-fold, at least or up to about 0.9-fold, at least or up to about 1-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 200-fold, at least or up to about 300-fold, at least or up to about 400-fold, or at least or up to about 500-fold.

In some examples, (i) an average number of the plurality of phased variants per each cell-free nucleic acid molecule identified to comprise a plurality of phased variants from the second state of the condition of the subject can be higher than (ii) an average number of the plurality of phased variants per each cell-free nucleic acid molecule identified to comprise a plurality of phased variants from the first state of the condition of the subject by at least or up to about 0.1-fold, at least or up to about 0.2-fold, at least or up to about 0.3-fold, at least or up to about 0.4-fold, at least or up to about 0.5-fold, at least or up to about 0.6-fold, at least or up to about 0.7-fold, at least or up to about 0.8-fold, at least or up to about 0.9-fold, at least or up to about 1-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 200-fold, at least or up to about 300-fold, at least or up to about 400-fold, or at least or up to about 500-fold.

In some cases, the progress of the condition can be regression or at least a partial remission of the condition. In an example, the at least the partial remission of the condition can comprise downstaging of a cancer from a later stage to an earlier stage, such as from stage IV cancer to stage II cancer. Alternatively, the at least the partial remission of the condition can be full remission from cancer. In another example, the at least the partial remission of the condition can comprise decreasing size (e.g., volume) of a solid tumor.

In some examples, (i) a total number of cell-free nucleic acid molecules identified to comprise the plurality of phased variants from the second state of the condition of the subject can be lower than (ii) a total number of cell-free nucleic acid molecules identified to comprise the plurality of phased variants from the first state of the condition of the subject by at least or up to about 0.1-fold, at least or up to about 0.2-fold, at least or up to about 0.3-fold, at least or up to about 0.4-fold, at least or up to about 0.5-fold, at least or up to about 0.6-fold, at least or up to about 0.7-fold, at least or up to about 0.8-fold, at least or up to about 0.9-fold, at least or up to about 1-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 200-fold, at least or up to about 300-fold, at least or up to about 400-fold, or at least or up to about 500-fold.

In some examples, (i) an average number of the plurality of phased variants per each cell-free nucleic acid molecule identified to comprise a plurality of phased variants from the second state of the condition of the subject can be lower than (ii) an average number of the plurality of phased variants per each cell-free nucleic acid molecule identified to comprise a plurality of phased variants from the first state of the condition of the subject by at least or up to about 0.1-fold, at least or up to about 0.2-fold, at least or up to about 0.3-fold, at least or up to about 0.4-fold, at least or up to about 0.5-fold, at least or up to about 0.6-fold, at least or up to about 0.7-fold, at least or up to about 0.8-fold, at least or up to about 0.9-fold, at least or up to about 1-fold, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 15-fold, at least or up to about 20-fold, at least or up to about 30-fold, at least or up to about 40-fold, at least or up to about 50-fold, at least or up to about 60-fold, at least or up to about 70-fold, at least or up to about 80-fold, at least or up to about 90-fold, at least or up to about 100-fold, at least or up to about 200-fold, at least or up to about 300-fold, at least or up to about 400-fold, or at least or up to about 500-fold.

In some cases, the progress of the condition can remain substantially the same between the two states of the condition of the subject. In some examples, (i) a total number of cell-free nucleic acid molecules identified to comprise the plurality of phased variants from the second state of the condition of the subject can be about the same as (ii) a total number of cell-free nucleic acid molecules identified to comprise the plurality of phased variants from the first state of the condition of the subject. In some examples, (i) an average number of the plurality of phased variants per each cell-free nucleic acid molecule identified to comprise a plurality of phased variants from the second state of the condition of the subject can about the same as (ii) an average number of the plurality of phased variants per each cell-free nucleic acid molecule identified to comprise a plurality of phased variants from the first state of the condition of the subject.

In some embodiments of any one of the methods disclosed herein, the one or more cell-free nucleic acid molecules comprising the plurality of phased variants can be identified from the plurality of cell-free nucleic acid molecules by one or more sequencing methods. Alternatively or in addition to, the one or more cell-free nucleic acid molecules comprising the plurality of phased variants can be identified by being pulled down from (or captured from among) the plurality of cell-free nucleic acid molecules with a set of nucleic acid probes. The pull down (or capture) method via the set of nucleic acid probes can be sufficient to identify the one or more cell-free nucleic acid molecules of interest without sequencing. In some cases, the set of nucleic acid probes can be configured to hybridize to at least a portion of cell-free nucleic acid (e.g., cfDNA) molecules from one or more genomic regions associated with the condition of the subject. As such, a presence of one or more cell-free nucleic acid molecules that have been pulled down by the set of nucleic acid probes can be an indication that the one or more cell-free nucleic acid molecules are derived from the condition (e.g., ctDNA or ctRNA). Additional details of the set of nucleic probes are disclosed elsewhere the present disclosure.

In some embodiments of any one of the methods disclosed herein, based the sequencing data derived from the plurality of cell-free nucleic acid molecules (e.g., cfDNA) that is obtained or derived from the subject, (i) the one or more cell-free nucleic acid molecules identified to comprise the plurality of phased variants can be separated, in silico, from (ii) one or more other cell-free nucleic acid molecules that are not identified to comprise the plurality of phased variants (or one or more other cell-free nucleic acid molecules that do not comprise the plurality of phased variants). In some cases, the method can further comprise generating an additional data comprising sequencing information of only (i) the one or more cell-free nucleic acid molecules identified to comprise the plurality of phased variants. In some cases, the method can further comprise generating a different data comprising sequencing information of only (ii) the one or more other cell-free nucleic acid molecules that are not identified to comprise the plurality of phased variants (or the one or more other cell-free nucleic acid molecules that do not comprise the plurality of phased variants).

In one aspect, the present disclosure provides a method for determining a condition of the subject, as shown by flowchart 2560 in FIG. 25F. The method can comprise (a) providing a mixture comprising (1) a set of nucleic acid probes and (2) a plurality of cell-free nucleic acid molecules obtained or derived from the subject (process 2562). In some cases, an individual nucleic acid probe of the set of nucleic acid probes can be designed to hybridize to a target cell-free nucleic acid molecule comprising a plurality of phased variants relative to a reference genomic sequence that are separated by at least one nucleotide. As such, a first phased variant of the plurality of phased variants and a second phased variant of the plurality of phased variants can be separated by at least one nucleotide, as disclosed herein. In some cases, the individual nucleic acid probe can comprise an activatable reporter agent. The activatable reporter agent can be activated by either one of (i) hybridization of the individual nucleic acid probe to the plurality of phased variants and (ii) dehybridization of at least a portion of the individual nucleic acid probe that has been hybridized to the plurality of phased variants. The method can further comprise (b) detecting the reporter agent that is activated, to identify one or more cell-free nucleic acid molecules of the plurality of cell-free nucleic acid molecules (process 2564). Each of the one or more cell-free nucleic acid molecules can comprise the plurality of phased variants. The method can optionally comprise (c) analyzing at least a portion of the identified one or more cell-free nucleic acid molecules to determine the condition of the subject (process 2566).

In one aspect, the present disclosure provides a method for determining a condition of the subject, as shown by flowchart 2570 in FIG. 25G. The method can comprise (a) providing a mixture comprising (1) a set of nucleic acid probes and (2) a plurality of cell-free nucleic acid molecules obtained or derived from the subject (process 2572). In some cases, an individual nucleic acid probe of the set of nucleic acid probes can be designed to hybridize to a target cell-free nucleic acid molecule comprising a plurality of phased variants relative to a reference genomic sequence. In some cases, the individual nucleic acid probe can comprise an activatable reporter agent. The activatable reporter agent can be activated by either one of (i) hybridization of the individual nucleic acid probe to the plurality of phased variants and (ii) dehybridization of at least a portion of the individual nucleic acid probe that has been hybridized to the plurality of phased variants. The method can further comprise (b) detecting the reporter agent that is activated, to identify one or more cell-free nucleic acid molecules of the plurality of cell-free nucleic acid molecules (process 2574). Each of the one or more cell-free nucleic acid molecules can comprise the plurality of phased variants, and a LOD of the identification step can be less than about 1 out of 50,000 cell-free nucleic acid molecules of the plurality of cell-free nucleic acid molecules, as disclosed herein. The method can optionally comprise (c) analyzing at least a portion of the identified one or more cell-free nucleic acid molecules to determine the condition of the subject (process 2576).

In some cases, a first phased variant of the plurality of phased variants and a second phased variant of the plurality of phased variants are separated by at least one nucleotide, as disclosed herein.

In some cases, the LOD of the step of identifying the one or more cell-free nucleic acid molecules, as disclosed herein, can be less than about 1 out of 60,000, less than 1 out of 70,000, less than 10 out of 80,000, less than 1 out of 90,000, less than 1 out of 100,000, less than 1 out of 150,000, less than 1 out of 200,000, less than 1 out of 300,000, less than 1 out of 400,000, less than 1 out of 500,000, less than 1 out of 600,000, less than 1 out of 700,000, less than 1 out of 800,000, less than 1 out of 900,000, less than 1 out of 1,000,000, less than 1 out of 1,000,000, less than 1 out of 1,100,000, less than 1 out of 1,200,000, less than 1 out of 1,300,000, less than 1 out of 1,400,000, less than 1 out of 1,500,000, less than 1 out of 2,000,000, less than 1 out of 2,500,000, less than 1 out of 3,000,000, less than 1 out of 4,000,000, or less than 1 out of 5,000,000 cell-free nucleic acid molecules of the plurality of cell-free nucleic acid molecules. Generally, a detection method with a lower LOD has a greater sensitivity of such detection.

In some embodiments of any one of the methods disclosed herein, the method can further comprise mixing (1) the set of nucleic acid probes and (2) the plurality of cell-free nucleic acid molecules.

In some embodiments of any one of the methods disclosed herein, the activatable reporter agent of a nucleic acid probe can be activated upon hybridization of the individual nucleic acid probe to the plurality of phased variants. Non-limiting examples of such nucleic acid probe can include a molecular beacon, eclipse probe, amplifluor probe, scorpions PCR primer, and light upon extension fluorogenic PCR primer (LUX primer).

Figure 26A:
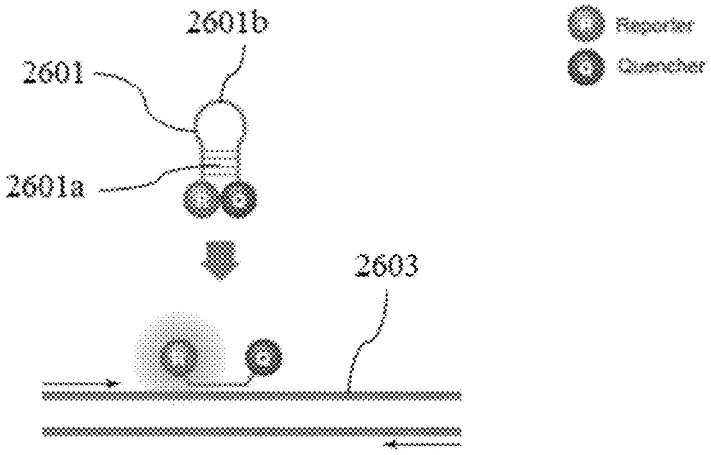
FIGS. 26A and 26B schematically illustrate different fluorescent probes for identifying one or more cell-free nucleic acid molecules comprising a plurality of phased variants.

For example, the nucleic acid probe can be a molecular beacon, as shown in FIG. 26A. The molecular beacon can be fluorescently labeled (e.g., dye-labeled) oligonucleotide probe that comprises complementarity to a target cell-free nucleic acid molecule 2603 in a region that comprises the plurality of phased variants. The molecular beacon can have a length between about 25 nucleotides to about 50 nucleotides. The molecular beacon can also be designed to be partially self-complimentary, such that it form a hairpin structure with a stem 2601*a* and a loop 2601*b*. The 5' and 3' ends of the molecular beacon probe can have complementary sequences (e.g., about 5-6 nucleotides) that form the stem structure 2601*a*. The loop portion 2601*b* of the hairpin can be designed to specifically hybridize to a portion (e.g., about 15-30 nucleotides) of the target sequence comprising two or more phased variants. The hairpin can be designed to hybridize to a portion that comprises at least 2, 3, 4, 5, or more phased variants. A fluorescent reporter molecule can be attached to the 5' end of the molecular beacon probe, and a quencher that quenches fluorescence of the fluorescent reporter can be attached to the 3' end of the molecular beacon probe. Formation of the hairpin therefore can bring the fluorescent reporter and quencher together, such that no fluorescence is emitted. However, during annealing operation of amplification reaction of the plurality of cell-free nucleic acid molecules that is obtained or derived from the subject, the loop portion of the molecular beacon can bind to its target sequence, causing the stem to denature. Thus, the reporter and quencher can be separated, abolishing quenching, and the fluorescent reporter is activated and detectable. Because fluorescence of the fluorescent reporter is emitted from the molecular beacon probe only when the probe is bound to the target sequence, the amount or level of fluorescence detected can be proportional to the amount of target in the reaction (e.g., (i) a total number of cell-free nucleic acid molecules identified to comprise the plurality of phased variants in each state or (ii) an average number of the plurality of phased variants per each cell-free nucleic acid molecule identified to comprise a plurality of phased variants, as disclosed herein).

In some embodiments of any one of the methods disclosed herein, the activatable reporter agent can be activated upon dehybridization of at least a portion of the individual nucleic acid probe that has been hybridized to the plurality of phased variants. In other words, once the individual nucleic acid probe is hybridized to target cell-free nucleic acid molecule's portion that comprises the plurality of phased variants, dehybridization of at least a portion of the individual nucleic acid prob and the target cell-free nucleic acid can activate the activatable reporter agent. Non-limiting examples of such nucleic acid probe can include a hydrolysis probe (e.g., TaqMan prob), dual hybridization probes, and QZyme PCR primer.

Figure 26B:
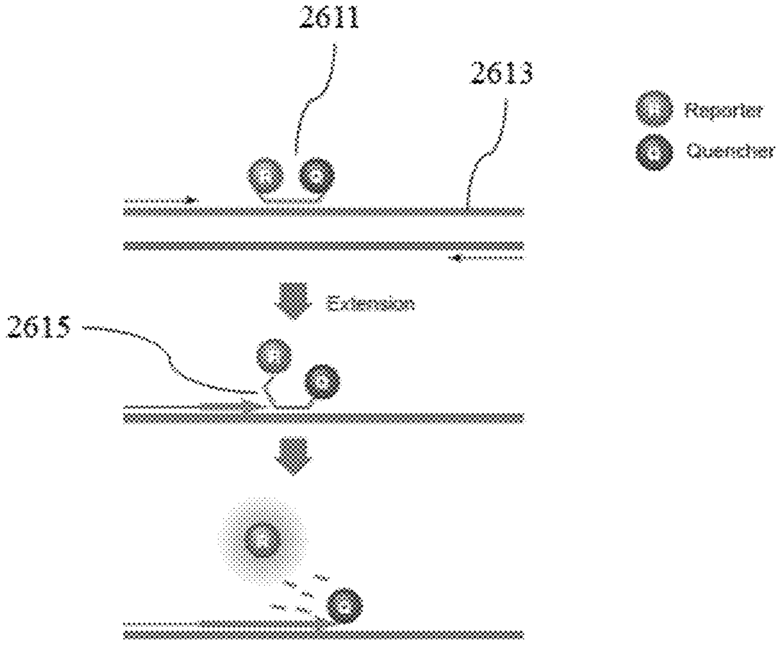

For example, the nucleic acid probe can be a hydrolysis probe, as shown in FIG. 26B. The hydrolysis probe 2611 can be a fluorescently labeled oligonucleotide probe that can specifically hybridize to a portion (e.g., between about 10 and about 25 nucleotides) of the target cell-free nucleic acid molecule 2613, wherein the hybridized portion comprises two or more phased variants. The hydrolysis probe 2611 can be labeled with a fluorescent reporter at the 5' end and a quencher at the 3' end. When the hydrolysis probe is intact (e.g., not cleaved), the fluorescence of the reporter is quenched due to its proximity to the quencher (FIG. 26B). During annealing operation of amplification reaction of the plurality of cell-free nucleic acid molecules obtained or derived from the subject, 5'→3' exonuclease activity of certain thermostable polymerases (e.g., Taq or Tth) The amplification reaction of the plurality of cell-free nucleic acid molecules obtained or derived from the subject can include a combined annealing/extension operation during which the hydrolysis probe hybridizes to the target cell-free nucleic acid molecule, and the dsDNA-specific 5'→3' exonuclease activity of a thermostable polymerase (e.g., Taq or Tth) cleaves off the fluorescent reporter from the hydrolysis probe. As a result, the fluorescent reporter is separated from the quencher, resulting in a fluorescence signal that is proportional to the amount of target in the sample (e.g., (i) a total number of cell-free nucleic acid molecules identified to comprise the plurality of phased variants in each state or (ii) an average number of the plurality of phased variants per each cell-free nucleic acid molecule identified to comprise a plurality of phased variants, as disclosed herein).

In some embodiments of any one of the methods disclosed herein, the reporter agent can comprise a fluorescent reporter. Non-limiting examples of a fluorescent reporter include fluorescein amidite (FAM, 2-[3-(dimethylamino)-6-dimethyliminio-xanthen-9-yl]benzoate TAN/IRA, (2E)-2-[(2E,4E)-5-(2-tert-butyl-9-ethyl-6,8,8-trimethyl-pyrano[3,2-g]quinolin-1-ium-4-yl)penta-2,4-dienylidene]-1-(6-hydroxy-6-oxo-hexyl)-3,3-dimethyl-indoline-5-sulfonate Dy 750, 6-carboxy-2',4,4',5',7,7'-hexachlorofluorescein, 4,5,6,7-Tetrachlorofluorescein TET™, sulforhodamine 101 acid chloride succinimidyl ester Texas Red-X, ALEXA Dyes, Bodipy Dyes, cyanine Dyes, Rhodamine 123 (hydrochloride), Well RED Dyes, MAX, and TEX 613. In some cases, the reporter agent further comprises a quencher, as disclosed herein. Non-limiting examples of a quencher can include Black Hole Quencher, Iowa Black Quencher, and 4-dimethylaminoazobenzene-4'-sulfonyl chloride (DABCYL).

In some embodiments of any one of the methods disclosed herein, any PCR reaction utilizing the set of nucleic acid probes can be performed using real-time PCR (qPCR). Alternatively, the PCR reaction utilizing the set of nucleic acid probes can be performed using digital PCR (dPCR).

Figure 24:
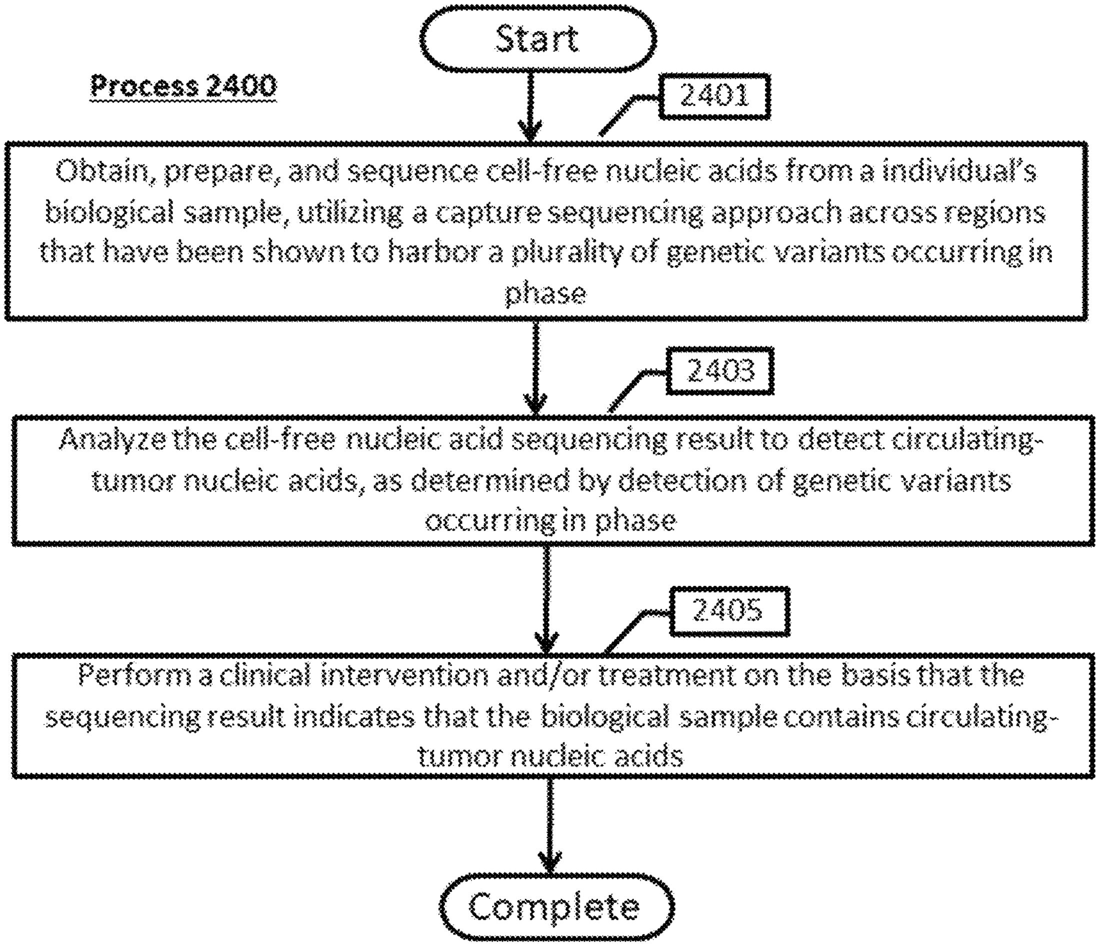
FIG. 24 illustrates a flow diagram of a process to perform a clinical intervention and/or treatment on an individual based on detecting circulating-tumor nucleic acid sequences in a sequencing result in accordance with an embodiment.

Provided in FIG. 24 is an example flowchart of a process to perform a clinical intervention and/or treatment based on detecting circulating-tumor nucleic acids in an individual's biological sample. In several embodiments, detection of circulating-tumor nucleic acids is determined by the detection of somatic variants in phase in a cell-free nucleic acid sample. In many embodiments, detection of circulating-tumor nucleic acids indicates cancer is present, and thus appropriate clinical intervention and/or treatment can be performed.

Referring to FIG. 24, process 2400 can begin with obtaining, preparing, and sequencing (2401) cell-free nucleic acids obtained from a non-invasive biopsy (e.g., liquid or waste biopsy), utilizing a capture sequencing approach across regions shown to harbor a plurality of genetic mutations or variants occurring in phase. In several embodiments, cfDNA and/or cfRNA is extracted from plasma, blood, lymph, saliva, urine, stool, and/or other appropriate bodily fluid. Cell-free nucleic acids can be isolated and purified by any appropriate means. In some embodiments, column purification is utilized (e.g., QIAamp Circulating Nucleic Acid Kit from Qiagen, Hilden, Germany). In some embodiments, isolated RNA fragments can be converted into complementary DNA for further downstream analysis.

In some embodiments, a biopsy is extracted prior to any indication of cancer. In some embodiments, a biopsy is extracted to provide an early screen in order to detect a cancer. In some embodiments, a biopsy is extracted to detect if residual cancer exists after a treatment. In some embodiments, a biopsy is extracted during treatment to determine whether the treatment is providing the desired response. Screening of any particular cancer can be performed. In some embodiments, screening is performed to detect a cancer that develops somatic phased variants in stereotypical regions in the genome, such as (for example) lymphoma. In some embodiments, screening is performed to detect a cancer in which somatic phased variants were discovered utilizing a prior extracted cancer biopsy.

In some embodiments, a biopsy is extracted from an individual with a determined risk of developing cancer, such as those with a familial history of the disorder or have determined risk factors (e.g., exposure to carcinogens). In many embodiments, a biopsy is extracted from any individual within the general population. In some embodiments, a biopsy is extracted from individuals within a particular age group with higher risk of cancer, such as, for example, aging individuals above the age of 50. In some embodiments, a biopsy is extracted from an individual diagnosed with and treated for a cancer.

In some embodiments, extracted cell-free nucleic acids are prepared for sequencing. Accordingly, cell-free nucleic acids are converted into a molecular library for sequencing. In some embodiments, adapters and/or primers are attached onto cell-free nucleic acids to facilitate sequencing. In some embodiments, targeted sequencing of particular genomic loci is to be performed, and thus particular sequences corresponding to the particular loci are captured via hybridization prior to sequencing (e.g., capture sequencing). In some embodiments, capture sequencing is performed utilizing a set of probes that pull down (or capture) regions that have been discovered to commonly harbor phased variants for a particular cancer (e.g., lymphoma). In some embodiments, capture sequencing is performed utilizing a set of probes that pull down (or capture) regions that have been discovered to harbor phased variants as determined prior by sequencing a biopsy of the cancer. More detailed discussion of capture sequencing and probes is provided in the section entitled “Capture Sequencing.”

In some embodiments, any appropriate sequencing technique can be utilized that can detect phased variants indicative of circulating-tumor nucleic acids. Sequencing techniques include (but are not limited to) 454 sequencing, Illumina sequencing, SOLiD sequencing, Ion Torrent sequencing, single-read sequencing, paired-end sequencing, etc.

Process 2400 analyzes (2403) the cell-free nucleic acid sequencing result to detect circulating-tumor nucleic acid sequences, as determined by detection of somatic variants occurring in phase. Because cancers are actively growing and expanding, neoplastic cells are often releasing biomolecules (especially nucleic acids) into the vasculature, lymph, and/or waste systems. In addition, due to biophysical constraints in their local environment, neoplastic cells are often rupturing, releasing their inner cell contents into the vasculature, lymph, and/or waste systems. Accordingly, it is possible to detect distal primary tumors and/or metastases from a liquid or waste biopsy.

Detection of circulating-tumor nucleic acid sequences indicates that a cancer is present in the individual being examined. Accordingly, based on detection of circulating-tumor nucleic acids, a clinical intervention and/or treatment may be performed (2405). In a number of embodiments, a clinical procedure is performed, such as (for example) a blood test, genetic test, medical imaging, physical exam, a tumor biopsy, or any combination thereof. In several embodiments, diagnostics are preformed to determine the particular stage of cancer. In a number of embodiments, a treatment is performed, such as (for example) chemotherapy, radiotherapy, chemoradiotherapy, immunotherapy, hormone therapy, targeted drug therapy, surgery, transplant, transfusion, medical surveillance, or any combination thereof. In some embodiments, an individual is assessed and/or treated by medical professional, such as a doctor, physician, physician's assistant, nurse practitioner, nurse, caretaker, dietician, or similar.

Various embodiments of the present disclosure are directed towards utilizing detection of cancer to perform clinical interventions. In a number of embodiments, an individual has a liquid or waste biopsy screened and processed by methods described herein to indicate that the individual has cancer and thus an intervention is to be performed. Clinical interventions include clinical procedures and treatments. Clinical procedures include (but are not limited to) blood tests, genetic test, medical imaging, physical exams, and tumor biopsies. Treatments include (but are not limited to) chemotherapy, radiotherapy, chemoradiotherapy, immunotherapy, hormone therapy, targeted drug therapy, surgery, transplant, transfusion, and medical surveillance. In several embodiments, diagnostics are performed to determine the particular stage of cancer. In some embodiments, an individual is assessed and/or treated by medical professional, such as a doctor, physician, physician's assistant, nurse practitioner, nurse, caretaker, dietician, or similar.

In several embodiments as described herein a cancer can be detected utilizing a sequencing result of cell-free nucleic acids derived from blood, serum, cerebrospinal fluid, lymph fluid, urine or stool. In many embodiments, cancer is detected when a sequencing result has one or more somatic variants present in phase within a short genetic window, such as the length of a cell-free molecule (e.g., about 170 bp). In numerous embodiments, a statistical method is utilized to determine whether the presence of phased variants is derived from a cancerous source (as opposed to molecular artifact or other biological source). Various embodiments utilize a Monte Carlo sampling method as the statistical method to determine whether a sequencing result of cell-free nucleic acids includes sequences of circulating-tumor nucleic acids based on a score as determined by the presence of phased variants. Accordingly, in a number of embodiments, cell-free nucleic acids are extracted, processed, and sequenced, and the sequencing result is analyzed to detect cancer. This process is especially useful in a clinical setting to provide a diagnostic scan.

An exemplary procedure for a diagnostic scan of an individual for a B-cell cancer is as follows:

(a) extract liquid or waste biopsy from individual,
(b) prepare and perform targeted sequencing of cell-free nucleic acids from biopsy utilizing nucleic acid probes specific for the B-cell cancer,
(c) detect phased variants in a sequencing results that are indicative of circulating-tumor nucleic acid sequences, and
(d) perform clinical intervention based on detection of circulating-tumor nucleic acid sequences.

An exemplary procedure for a personalized diagnostic scan of an individual for a cancer that has been previously sequenced to detect phased variants in particular genomic loci is as follows:

extract cancer biopsy from individual sequence cancer biopsy to detect phased variants that have accumulated in the cancer (a) design and synthesize nucleic acid probes for genomic loci that include the positions of the detected phased variants,
(b) extract liquid or waste biopsy from individual,
(c) prepare and perform targeted sequencing of cell-free nucleic acids from biopsy utilizing the designed and synthesized nucleic acid probes,
(d) detect phased variants in a sequencing results that are indicative of circulating-tumor nucleic acid sequences, and
(e) perform clinical intervention based on detection of circulating-tumor nucleic acid sequences.

In some embodiments of any one of the methods disclosed herein, at least a portion of the identified one or more cell-free nucleic acid molecules comprising the plurality of phased variants can be further analyzed for determining the condition of the subject. In such analysis, (i) the identified one or more cell-free nucleic acid molecules and (ii) other cell-free nucleic acid molecules of the plurality of cell-free nucleic acid molecules that do not comprise the plurality of phased variants can be analyzed as different variables. In some cases, a ratio of (i) a number the identified one or more cell-free nucleic acid molecules and (ii) a number of the other cell-free nucleic acid molecules of the plurality of cell-free nucleic acid molecules that do not comprise the plurality of phased variants can be used a factor to determine the condition of the subject. In some cases, comparison of (i) a position(s) of the identified one or more cell-free nucleic acid molecules relative to the reference genomic sequence and (ii) a position(s) of the other cell-free nucleic acid molecules of the plurality of cell-free nucleic acid molecules that do not comprise the plurality of phased variants relative to the reference genomic sequence can be used a factor to determine the condition of the subject.

Alternatively, in some cases, the analysis of the identified one or more cell-free nucleic acid molecules comprising the plurality of phased variants for determining the condition of the subject may not and need not be based on the other cell-free nucleic acid molecules of the plurality of cell-free nucleic acid molecules that do not comprise the plurality of phased variants. As disclosed herein, non-limiting examples of information or characteristics of the one or more cell-free nucleic acid molecules comprising the plurality of phased variants can include (i) a total number of such cell-free nucleic acid molecules and (ii) an average number of the plurality of phased variations per each nucleic acid molecule in the population of identified cell-free nucleic acid molecules.

Thus, in some embodiments of any one of the methods disclosed herein, a number of the plurality of phased variants from the one or more cell-free nucleic acid molecules that have been identified to have the plurality of phased variants can be indicative of the condition of the subject. In some cases, a ratio of (i) the number of the plurality of phased variants from the one or more cell-free nucleic acid molecules and (ii) a number of single nucleotide variants from the one or more cell-free nucleic acid molecules can be indicative of the condition of the subject. For instance, a particular condition (e.g., follicular lymphoma) can exhibit a signature ratio that is different than that of another condition (e.g., breast cancer). In some examples, for cancer or solid tumor, the ratio as disclosed herein can be between about 0.01 and about 0.20. In some examples, for cancer or solid tumor, the ratio as disclosed herein can be about 0.01, about 0.02, about 0.03, about 0.04, about 0.05, about 0.06, about 0.07, about 0.08, about 0.09, about 0.10, about 0.11, about 0.12, about 0.13, about 0.14, about 0.15, about 0.16, about 0.17, about 0.18, about 0.19, or about 0.20. In some examples, for cancer or solid tumor, the ratio as disclosed herein can be at least or up to about 0.01, at least or up to about 0.02, at least or up to about 0.03, at least or up to about 0.04, at least or up to about 0.05, at least or up to about 0.06, at least or up to about 0.07, at least or up to about 0.08, at least or up to about 0.09, at least or up to about 0.10, at least or up to about 0.11, at least or up to about 0.12, at least or up to about 0.13, at least or up to about 0.14, at least or up to about 0.15, at least or up to about 0.16, at least or up to about 0.17, at least or up to about 0.18, at least or up to about 0.19, or at least or up to about 0.20.

In some embodiments of any one of the methods disclosed herein, a frequency of the plurality of phased variants in the one or more cell-free nucleic acid molecules that have been identified can be indicative of the condition of the subject. In some cases, based on the sequencing data disclosed herein, an average frequency of the plurality of phased variant per a predetermined bin length (e.g., a bin of about 50 base pairs) within each of the identified cell-free nucleic acid molecule can be indicative of the condition of the subject. In some cases, based on the sequencing data disclosed herein, an average frequency of the plurality of phased variant per a predetermined bin length (e.g., a bin of about 50 base pairs) within each of the identified cell-free nucleic acid molecule that is associated with a particular gene (e.g., BCL2, PIM1) can be indicative of the condition of the subject. The size of the bin can be about 30, about 40, about 50, about 60, about 70, or about 80.

In some examples, a first condition (e.g., Hodgkin lymphoma or HL) can exhibit a first average frequency and a second condition (e.g., DLBCL) can exhibit a different average frequency, thereby allowing identification and/or determination of whether the subject has or is suspected of having a particular condition. In some examples, a first sub-type of a disease can exhibit a first average frequency and a second sub-type of the same disease can exhibit a different average frequency, thereby allowing identification and/or determination of whether the subject has or is suspected of having a particular sub-type of the disease. For example, the subject can have DLBCL, and one or more cell-free nucleic acid molecules derived from germinal center B-cell (GCB) DLBCL or activated B-cell (ABC) DLBCL can have different average frequency of the plurality of phased variant per a predetermined bin length, as disclosed herein.

In some example, a condition of the subject may have a predetermined number of phased variants spanning predetermined genomic loci (i.e., a predetermined frequency of phased variants). When the predetermined frequency of phased variants match a frequency of the plurality of phased variants in the one or more cell-free nucleic acid molecules that have been identified from a plurality of cell-free nucleic acid molecules from the subject, it may indicate that the subject has such condition.

In some embodiments of any one of the methods disclosed herein, the one or more cell-free nucleic acid molecules identified to comprise the plurality of phased variants can be analyzed to determine their genomic origin (e.g., which gene locus they are from). The genomic origin of the one or more cell-free nucleic acid molecules that have been identified can be indicative of the condition of the subject, as different disease can have the plurality of phased variants in different signature genes. For example, a subject can have GCB DLBCL, and one or more cell-free nucleic acid molecules originated from GCBs of the subject can have the phased variants prevalent in BCL2 gene, while one or more cell-free nucleic acid molecules originated from ABCs of the same subject may not comprise as many phased variants in the BCL2 gene as those from GCBs. On the other hand, a subject can have ABC DLBCL, and one or more cell-free nucleic acid molecules originated from ABCs of the subject can have the phased variants prevalent in PIM1 gene, while one or more cell-free nucleic acid molecules originated from GCBs of the same subject may not comprise as many phased variants in the PIM1 gene as those from ABCs.

In some embodiments of any one of the methods disclosed herein, at least or up to about 10%, at least or up to about 15%, at least or up to about 20%, at least or up to about 25%, at least or up to about 30%, at least or up to about 35%, at least or up to about 40%, at least or up to about 45%, at least or up to about 50%, at least or up to about 55%, at least or up to about 60%, at least or up to about 65%, at least or up to about 70%, at least or up to about 75%, at least or up to about 80%, at least or up to about 85%, at least or up to about 90%, at least or up to about 95%, at least or up to about 99%, or about 100% of the one or more cell-free nucleic acid molecules comprising the plurality of phased variants can comprise a single nucleotide variant (SNV) that is at least 2 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 3 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 4 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 5 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 6 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 7 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 8 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 9 nucleotides away from an adjacent SNV.

In some embodiments of any one of the methods disclosed herein, at least or up to about 5%, at least or up to about 10%, at least or up to about 15%, at least or up to about 20%, at least or up to about 25%, at least or up to about 30%, at least or up to about 35%, at least or up to about 40%, at least or up to about 45%, or at least or up to about 50% of the one or more cell-free nucleic acid molecules comprising the plurality of phased variants can comprise a single nucleotide variant (SNV) that is at least 10 nucleotides away from an adjacent SNV.

C. Reference Genomic Sequence

In some embodiments of any one of the methods disclosed herein, the reference genomic sequence can be at least a portion of a nucleic acid sequence database (i.e., a reference genome), which database is assembled from genetic data and intended to represent the genome of a reference cohort. In some cases, a reference cohort can be a collection of individuals from a specific or varying genotype, haplotype, demographics, sex, nationality, age, ethnicity, relatives, physical condition (e.g., healthy or having been diagnosed to have the same or different condition, such as a specific type of cancer), or other groupings. A reference genomic sequence as disclosed herein can be a mosaic (or a consensus sequence) of the genomes of two or more individuals. The reference genomic sequence can comprise at least a portion of a publicly available reference genome or a private reference genome. Non-limiting examples of a human reference genome include hg19, hg18, hg17, hg16, and hg38.

In some examples, the reference genomic sequence can comprise at least or up to about 500 nucleobases, at least or up to about 1 kilobase (kb), at least or up to about 2 kb, at least or up to about 3 kb, at least or up to about 4 kb, at least or up to about 5 kb, at least or up to about 6 kb, at least or up to about 7 kb, at least or up to about 8 kb, at least or up to about 9 kb, at least or up to about 10 kb, at least or up to about 20 kb, at least or up to about 30 kb, at least or up to about 40 kb, at least or up to about 50 kb, at least or up to about 60 kb, at least or up to about 70 kb, at least or up to about 80 kb, at least or up to about 90 kb, at least or up to about 100 kb, at least or up to about 200 kb, at least or up to about 300 kb, at least or up to about 400 kb, at least or up to about 500 kb, at least or up to about 600 kb, at least or up to about 700 kb, at least or up to about 800 kb, at least or up to about 900 kb, at least or up to about 1,000 kb, at least or up to about 2,000 kb, at least or up to about 3,000 kb, at least or up to about 4,000 kb, at least or up to about 5,000 kb, at least or up to about 6,000 kb, at least or up to about 7,000 kb, at least or up to about 8,000 kb, at least or up to about 9,000 kb, at least or up to about 10,000 kb, at least or up to about 20,000 kb, at least or up to about 30,000 kb, at least or up to about 40,000 kb, at least or up to about 50,000 kb, at least or up to about 60,000 kb, at least or up to about 70,000 kb, at least or up to about 80,000 kb, at least or up to about 90,000 kb, or at least or up to about 100,000 kb.

In some cases, the reference genomic sequence can be whole reference genome or a portion (e.g., a portion relevant to the condition of interest) of the genome. For example, the reference genomic sequence can consist of at least 1, 2, 3, 4, 5, or more genes that experience aberrant somatic hypermutation under certain types of cancer. In some cases, the reference genomic sequence can be a whole chromosomal sequence, or a fragment thereof. In some cases, the reference genomic sequence can comprise two or more (e.g., at least 2, 3, 4, 5, or more) different portions of the reference genome that are not adjacent to one another (e.g., within the same chromosome or from different chromosomes).

In some embodiments of any one of the methods disclosed herein, the reference genomic sequence can be at least a portion of a reference genome of a selected individual, such as a healthy individual or the subject of any of the methods as disclosed herein.

In some cases, the reference genomic sequence can be derived from an individual who is not the subject (e.g., a healthy control individual). Alternatively, in some cases, the reference genomic sequence can be derived from a sample of the subject. In some examples, the sample can be a healthy sample of the subject. The healthy sample of the subject can be any subject cell that is healthy, e.g., a healthy leukocyte. By comparing sequencing data of the plurality of cell-free nucleic acid molecules (e.g., cfDNA molecules) of the subject against at least a portion of the genomic sequence of a healthy cell of the same subject, one or more cell-free nucleic acid molecules that comprise the plurality of phased variants can be identified and analyzed, as disclosed herein. In some examples, the sample can be a diseased sample of the subject, such as a diseased cell (e.g., a tumor cell) or a solid tumor. The reference genomic sequence can be obtained from sequencing at least a portion of a diseased cell of the subject or from sequencing a plurality of cell-free nucleic acid molecules obtained from the solid tumor of the subject. Once the subject is diagnosed to have a particular condition (e.g., a disease), the reference genomic sequence of the subject that comprises the plurality of phased variants can be used to determine whether the subject still exhibits the same phased variants at future time points. In this context, any new phased variants identified between the "diseased" reference genomic sequence of the subject and new cell-free nucleic acid molecules obtained or derived from the subject can indicate a reduced degree of aberrant somatic hypermutation in particular genomic loci (e.g., at least a partial remission).

In various embodiments, diagnostic scans can be performed for any neoplasm type, including (but not limited to) acute lymphoblastic leukemia (ALL), acute myeloid leukemia (AML), anal cancer, astrocytomas, basal cell carcinoma, bile duct cancer, bladder cancer, breast cancer, Burkitt's lymphoma, cervical cancer, chronic lymphocytic leukemia (CLL) chronic myelogenous leukemia (CIVIL), chronic myeloproliferative neoplasms, colorectal cancer, diffuse large B-cell lymphoma, endometrial cancer, ependymoma, esophageal cancer, esthesioneuroblastoma, Ewing sarcoma, fallopian tube cancer, follicular lymphoma, gallbladder cancer, gastric cancer, gastrointestinal carcinoid tumor, hairy cell leukemia, hepatocellular cancer, Hodgkin lymphoma, hypopharyngeal cancer, Kaposi sarcoma, Kidney cancer, Langerhans cell histiocytosis, laryngeal cancer, leukemia, liver cancer, lung cancer, lymphoma, melanoma, Merkel cell cancer, mesothelioma, mouth cancer, neuroblastoma, non-Hodgkin lymphoma, non-small cell lung cancer, osteosarcoma, ovarian cancer, pancreatic cancer, pancreatic neuroendocrine tumors, pharyngeal cancer, pituitary tumor, prostate cancer, rectal cancer, renal cell cancer, retinoblastoma, skin cancer, small cell lung cancer, small intestine cancer, squamous neck cancer, T-cell lymphoma, testicular cancer, thymoma, thyroid cancer, uterine cancer, vaginal cancer, and vascular tumors.

In a number of embodiments, a diagnostic scan is utilized to provide an early detection of cancer. In some embodiments, a diagnostic scan detects cancer in individuals having stage I, II, or III cancer. In some embodiments, a diagnostic scan is utilized to detect MRD or tumor burden. In some embodiments, a diagnostic scan is utilized to determine progress (e.g., progression or regression) of treatment. Based on the diagnostic scan, a clinical procedure and/or treatment may be performed.

D. Nucleic Acid Probes

In some embodiments of any one of the methods disclosed herein, the set of nucleic acid probes can be designed based on the any of the subject reference genomic sequences of the present disclosure. In some cases, the set of nucleic acid probes can be designed based on the plurality of phased variants that have been identified by comparing (i) sequencing data from a solid tumor of the subject and (ii) sequencing data from a healthy cell of the subject or a healthy cohort, as disclosed herein. The set of nucleic acid probes can be designed based on the plurality of phased variants that have been identified by comparing (i) sequencing data from a solid tumor of the subject and (ii) sequencing data from a healthy cell of the subject. The set of nucleic acid probes can be designed based on the plurality of phased variants that have been identified by comparing (i) sequencing data from a solid tumor of the subject and (ii) sequencing data from a healthy cell of a healthy cohort.

In some embodiments of any one of the methods disclosed herein, the set of nucleic acid probes are designed to hybridize to sequences of genomic loci associated with the condition. As disclosed herein, the genomic loci associated with the condition can be determined to experience or exhibit aberrant somatic hypermutation when the subject has the condition. Alternatively, the set of nucleic acid probes are designed to hybridize to sequences of stereotyped regions.

In some embodiments of any one of the methods disclosed herein, the set of nucleic acid probes can be designed to hybridize to at least about 5%, at least about 10%, at least about 20%, at least about 30%, at least about 40%, at least about 50%, at least about 60%, at least about 70%, at least about 80%, at least about 90%, at least about 95%, at least about 99%, or about 100% of the genomic regions identified in Table 1.

In some embodiments of any one of the methods disclosed herein, the set of nucleic acid probes can be designed to hybridize to at least a portion of cell-free nucleic acid (e.g., cfDNA) molecules derived from at least about 5%, at least about 10%, at least about 20%, at least about 30%, at least about 40%, at least about 50%, at least about 60%, at least about 70%, at least about 80%, at least about 90%, at least about 95%, at least about 99%, or about 100% of the genomic regions identified in Table 1.

In some embodiments of any one of the methods disclosed herein, each nucleic acid probe of the set of nucleic acid probes can have at least about 50%, at least about 55%, at least about 60%, at least about 65%, at least about 70%, at least about 75%, at least about 80%, at least about 85%, at least about 90% sequence identity, at least about 95% sequence identity, at least about 99%, or about 100% sequence identity to a probe sequence selected from Table 6.

In some embodiments of any one of the methods disclosed herein, the set of nucleic acid probes can comprise at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or about 100% of probe sequences in Table 6.

In some embodiments of any one of the methods disclosed herein, the set of nucleic acid probes can be designed to cover one or more target genomic regions comprising at least or up to about 500 nucleobases, at least or up to about 1 kilobase (kb), at least or up to about 2 kb, at least or up to about 3 kb, at least or up to about 4 kb, at least or up to about 5 kb, at least or up to about 6 kb, at least or up to about 7 kb, at least or up to about 8 kb, at least or up to about 9 kb, at least or up to about 10 kb, at least or up to about 20 kb, at least or up to about 30 kb, at least or up to about 40 kb, at least or up to about 50 kb, at least or up to about 60 kb, at least or up to about 70 kb, at least or up to about 80 kb, at least or up to about 90 kb, at least or up to about 100 kb, at least or up to about 200 kb, at least or up to about 300 kb, at least or up to about 400 kb, or at least or up to about 500 kb.

In some embodiments of any one of the methods disclosed herein, a target genomic region (e.g., a target genomic locus) of the one or more target genomic regions can comprise at most about 200 nucleobases, at most about 300 nucleobases, 400 nucleobases, at most about 500 nucleobases, at most about 600 nucleobases, at most about 700 nucleobases, at most about 800 nucleobases, at most about 900 nucleobases, at most about 1 kb, at most about 2 kb, at most about 3 kb, at most about 4 kb, at most about 5 kb, at most about 6 kb, at most about 7 kb, at most about 8 kb, at most about 9 kb, at most about 10 kb, at most about 11 kb, at most about 12 kb, at most about 13 kb, at most about 14 kb, at most about 15 kb, at most about 16 kb, at most about 17 kb, at most about 18 kb, at most about 19 kb, at most about 20 kb, at most about 25 kb, at most about 30 kb, at most about 35 kb, at most about 40 kb, at most about 45 kb, at most about 50 kb, or at most about 100 kb.

In some embodiments of any one of the methods disclosed herein, the set of nucleic acid probes can comprise at least or up to about 10, at least or up to about 20, at least or up to about 30, at least or up to about 40, at least or up to about 50, at least or up to about 60, at least or up to about 70, at least or up to about 80, at least or up to about 90, at least or up to about 100, at least or up to about 200, at least or up to about 300, at least or up to about 400, at least or up to about 500, at least or up to about 600, at least or up to about 700, at least or up to about 800, at least or up to about 900, at least or up to about 1,000, at least or up to about 2,000, at least or up to about 3,000, at least or up to about 4,000, or at least or up to about 5,000 different nucleic acid probes designed to hybridize to different target nucleic acid sequences.

In some embodiments of any one of the methods disclosed herein, the set of nucleic acid probes can have a length of at least or up to about 50, at least or up to about 55, at least or up to about 60, at least or up to about 65, at least or up to about 70, at least or up to about 75, at least or up to about 80, at least or up to about 85, at least or up to about 90, at least or up to about 95, or at least or up to about 100 nucleotides.

In one aspect, the present disclosure provides a composition comprising a bait set comprising any one of the set of nucleic acid probes disclosed herein. The composition comprising such bait set can be used for any of the methods disclosed herein. In some cases, the set of nucleic acid probes can be designed to pull down (or capture) cfDNA molecules. In some cases, the set of nucleic acid probes can be designed to pull down (or capture) cfRNA molecules.

In some embodiments, the bait set can comprise a set of nucleic acid probes designed to pull down cell-free nucleic acid (e.g., cfDNA) molecules derived from genomic regions set forth in Table 1. The set of nucleic acid probes can be designed to pull down cell-free nucleic acid molecules derived from at least or up to about 1%, at least or up to about 2%, at least or up to about 3%, at least or up to about 4%, at least or up to about 5%, at least or up to about 6%, at least or up to about 7%, at least or up to about 8%, at least or up to about 9%, at least or up to about 10%, at least or up to about 15%, at least or up to about 20%, at least or up to about 25%, at least or up to about 30%, at least or up to about 35%, at least or up to about 40%, at least or up to about 45%, at least or up to about 50%, at least or up to about 55%, at least or up to about 60%, at least or up to about 65%, at least or up to about 70%, at least or up to about 75%, at least or up to about 80%, at least or up to about 85%, at least or up to about 90%, at least or up to about 95%, at least or up to about 99%, or about 100% of the genomic regions set forth in Table 1. In some cases, the set of nucleic acid probes can be designed to pull down cfDNA molecules. In some cases, the set of nucleic acid probes can be designed to pull down cfRNA molecules.

In some embodiments of any one of the compositions disclosed herein, an individual nucleic acid probe (or each nucleic acid probe) of the set of nucleic acid probes can comprise a pull-down tag. The pull-down tag can be used to enrich a sample (e.g., a sample comprising the plurality of nucleic acid molecules obtained or derived from the subject) for a specific subset (e.g., for cell-free nucleic acid molecules comprising the plurality of phased variants as disclosed herein).

In some cases, pull-down tag can comprise a nucleic acid barcode (e.g., on either or both sides of the nucleic acid probe). By utilizing beads or substrates comprising nucleic acid sequences having complementarity to the nucleic acid barcode, the nucleic acid barcode can be used to pull-down and enrich for any nucleic acid probe that is hybridized to a target cell-free nucleic acid molecule. Alternatively or in addition to, the nucleic acid barcode can be used to identify the target cell-free nucleic acid molecule from any sequencing data (e.g., sequencing by amplification) obtained by using any of the set of nucleic acid probes disclosed herein.

In some cases, the pull-down tag can comprise an affinity target moiety that can be specifically recognized and bound by an affinity binding moiety. The affinity binding moiety specifically can bind the affinity target moiety to form an affinity pair. In some cases, by utilizing beads or substrates comprising the affinity binding moiety, the affinity target moiety can be used to pull-down and enrich for any nucleic acid probe that is hybridized to a target cell-free nucleic acid molecule. Alternatively, the pull-down tag can comprise the affinity binding moiety, while the beads/substrates can comprise the affinity target moiety. Non-limiting examples of the affinity pair can include biotin/avidin, antibody/antigen, biotin/streptavidin, metal/chelator, ligand/receptor, nucleic acid and binding protein, and complementary nucleic acids. In an example, the pull-down tag can comprise biotin.

In some embodiments of any one of the compositions disclosed herein, a length of a target cell-free nucleic acid (e.g., cfDNA) molecule that is to be pulled down by any subject nucleic acid probe can be about 100 nucleotides to about 200 nucleotides. The length of the target cell-free nucleic acid molecule can be at least about 100 nucleotides. The length of the target cell-free nucleic acid molecule can be at most about 200 nucleotides. The length of the target cell-free nucleic acid molecule can be about 100 nucleotides to about 110 nucleotides, about 100 nucleotides to about 120 nucleotides, about 100 nucleotides to about 130 nucleotides, about 100 nucleotides to about 140 nucleotides, about 100 nucleotides to about 150 nucleotides, about 100 nucleotides to about 160 nucleotides, about 100 nucleotides to about 170 nucleotides, about 100 nucleotides to about 180 nucleotides, about 100 nucleotides to about 190 nucleotides, about 100 nucleotides to about 200 nucleotides, about 110 nucleotides to about 120 nucleotides, about 110 nucleotides to about 130 nucleotides, about 110 nucleotides to about 140 nucleotides, about 110 nucleotides to about 150 nucleotides, about 110 nucleotides to about 160 nucleotides, about 110 nucleotides to about 170 nucleotides, about 110 nucleotides to about 180 nucleotides, about 110 nucleotides to about 190 nucleotides, about 110 nucleotides to about 200 nucleotides, about 120 nucleotides to about 130 nucleotides, about 120 nucleotides to about 140 nucleotides, about 120 nucleotides to about 150 nucleotides, about 120 nucleotides to about 160 nucleotides, about 120 nucleotides to about 170 nucleotides, about 120 nucleotides to about 180 nucleotides, about 120 nucleotides to about 190 nucleotides, about 120 nucleotides to about 200 nucleotides, about 130 nucleotides to about 140 nucleotides, about 130 nucleotides to about 150 nucleotides, about 130 nucleotides to about 160 nucleotides, about 130 nucleotides to about 170 nucleotides, about 130 nucleotides to about 180 nucleotides, about 130 nucleotides to about 190 nucleotides, about 130 nucleotides to about 200 nucleotides, about 140 nucleotides to about 150 nucleotides, about 140 nucleotides to about 160 nucleotides, about 140 nucleotides to about 170 nucleotides, about 140 nucleotides to about 180 nucleotides, about 140 nucleotides to about 190 nucleotides, about 140 nucleotides to about 200 nucleotides, about 150 nucleotides to about 160 nucleotides, about 150 nucleotides to about 170 nucleotides, about 150 nucleotides to about 180 nucleotides, about 150 nucleotides to about 190 nucleotides, about 150 nucleotides to about 200 nucleotides, about 160 nucleotides to about 170 nucleotides, about 160 nucleotides to about 180 nucleotides, about 160 nucleotides to about 190 nucleotides, about 160 nucleotides to about 200 nucleotides, about 170 nucleotides to about 180 nucleotides, about 170 nucleotides to about 190 nucleotides, about 170 nucleotides to about 200 nucleotides, about 180 nucleotides to about 190 nucleotides, about 180 nucleotides to about 200 nucleotides, or about 190 nucleotides to about 200 nucleotides. The length of the target cell-free nucleic acid molecule can be about 100 nucleotides, about 110 nucleotides, about 120 nucleotides, about 130 nucleotides, about 140 nucleotides, about 150 nucleotides, about 160 nucleotides, about 170 nucleotides, about 180 nucleotides, about 190 nucleotides, or about 200 nucleotides. In some examples, the length of the target cell-free nucleic acid molecule can range between about 100 nucleotides and about 180 nucleotides.

In some embodiments of any one of the compositions disclosed herein, the genomic regions can be associated with a condition. The genomic regions can be determined to exhibit aberrant somatic hypermutation when a subject has the condition. For example, the condition can comprise B-cell lymphoma or a sub-type thereof, such as diffuse large B-cell lymphoma, follicular lymphoma, Burkitt lymphoma, and B-cell chronic lymphocytic leukemia. Additional details of the condition are provided below.

In some embodiments of any one of the compositions disclosed herein, the composition further comprises the plurality of cell-free nucleic acid (e.g., cfDNA) molecules obtained or derived from the subject.

E. Diagnostic or Therapeutic Applications

A number of embodiments are directed towards performing a diagnostic scan on cell-free nucleic acids of an individual and then based on results of the scan indicating cancer, performing further clinical procedures and/or treating the individual. In accordance with various embodiments, numerous types of neoplasms can be detected.

In some embodiments of any one of the methods disclosed herein, the method can comprise determining that the subject has the condition or determining a degree or status of the condition of the subject, based on the one or more cell-free nucleic acid molecules comprising the plurality of phased variants. In some cases, the method can further comprise determining that the one or more cell-free nucleic acid molecules (each identified to comprise a plurality of phased variants) are derived from a sample associated with the condition (e.g., cancer), based on a statistical model analysis (i.e., molecular analysis). For example, the method can comprise using one or more algorithms (e.g., Monte Carlos simulation) to determine a first probability of a cell-free nucleic acid identified to have a plurality of phased variants being associated with or originated from a first condition (e.g., 80%) and a second probability of the same cell-free nucleic acid being associated with or originated from a second condition (or from a healthy cell) (e.g., 20%). In some cases, the method can comprise determining a likelihood or probability that the subject has one or more conditions based on analysis of the one or more cell-free nucleic acid molecules each identified to comprise a plurality of phased variants (i.e., macro- or global analysis). For example, the method can comprise using one or more algorithms (e.g., comprising one or more mathematical models as disclosed herein, such as binomial sampling) to analyze a plurality of cell-free nucleic acid molecules each identified to comprise a plurality of phased variants, thereby to determine a first probability of the subject having a first condition (e.g., 80%) and a second probability of the subject having a second condition (or being healthy) (e.g., 20%).

The statistical model analysis as disclosed herein can be an approximate solution by a numerical approximation such as a binomial model, a ternary model, a Monte Carlo simulation, or a finite difference method. In an example, the statistical model analysis as used herein can be a Monte Carlo statistical analysis. In another example, the statistical model analysis as used herein can be a binomial or ternary model analysis.

In some embodiments of any one of the methods disclosed herein, the method can comprise monitoring a progress of the condition of the subject based on the one or more cell-free nucleic acid molecules identified, such that each of the identified cell-free nucleic acid molecule comprises a plurality of phased variants. In some cases, the progress of the condition can be worsening of the condition, as described in the present disclosure (e.g., developing from stage I cancer to stage III cancer). In some cases, the progress of the condition can be at least a partial remission of the condition, as described in the present disclosure (e.g., downstaging from stage IV cancer to stage II cancer). Alternatively, in some cases, the progress of the condition can remain substantially the same between two different time points, as described in the present disclosure. In an example, the method can comprise determining likelihoods or probabilities of different progresses of the condition of the subject. For example, the method can comprise using one or more algorithms (e.g., comprising one or more mathematical models as disclosed herein, such as binomial sampling) to determine a first probability of the subject's condition being worse than before (e.g., 20%), a second probability of at least partial remission of the condition (e.g., 70%), and a third probability that the subject's condition is the same as before (e.g., 10%).

In some embodiments of any one of the methods disclosed herein, the method can comprise comprising performing a different procedure (e.g., follow-up diagnostic procedures) to confirm the condition of the subject, which condition has been determined and/or monitored progress thereof, as provided in the present disclosure. Non-limiting examples of a different procedure can include physical exam, medical imaging, genetic test, mammography, endoscopy, stool sampling, pap test, alpha-fetoprotein blood test, CA-125 test, prostate-specific antigen (PSA) test, biopsy extraction, bone marrow aspiration, and tumor marker detection tests. Medical imaging includes (but is not limited to) X-ray, magnetic resonance imaging (MM), computed tomography (CT), ultrasound, and positron emission tomography (PET). Endoscopy includes (but is not limited to) bronchoscopy, colonoscopy, colposcopy, cystoscopy, esophagoscopy, gastroscopy, laparoscopy, neuroendoscopy, proctoscopy, and sigmoidoscopy.

In some embodiments of any one of the methods disclosed herein, the method can comprise determining a treatment for the condition of the subject based on the one or more cell-free nucleic acid molecules identified, each identified cell-free nucleic acid molecule comprising a plurality of phased variants. In some cases, the treatment can be determined based on (i) the determined condition of the subject and/or (ii) the determined progress of the condition of the subject. In addition, the treatment can be determined based on one or more additional factors of the following: sex, nationality, age, ethnicity, and other physical conditions of the subject. In some examples, the treatment can be determined based on one or more features of the plurality of phased variants of the identified cell-free nucleic acid molecules, as disclosed herein.

In some embodiments of any one of the methods disclosed herein, the subject may not have been subjected to any treatment for the condition, e.g., the subject may not have been diagnosed with the condition (e.g., a lymphoma). In some embodiments of any one of the methods disclosed herein, the subject may been subjected to a treatment for the condition prior to any subject method of the present disclosure. In some cases, the methods disclosed herein can be performed to monitor progress of the condition that the subject has been diagnosed with, thereby to (i) determine efficacy of the previous treatment and (ii) assess whether to keep the treatment, modify the treatment, or cancel the treatment in favor of a new treatment.

In some embodiments of any one of the methods disclosed herein, non-limiting examples of a treatment (e.g., prior treatment, new treatment to be determined based on the methods of the present disclosure, etc.) can include chemotherapy, radiotherapy, chemoradiotherapy, immunotherapy, adoptive cell therapy (e.g., chimeric antigen receptor (CAR) T cell therapy, CAR NK cell therapy, modified T cell receptor (TCR) T cell therapy, etc.) hormone therapy, targeted drug therapy, surgery, transplant, transfusion, or medical surveillance.

In some embodiments of any one of the methods disclosed herein, the condition can comprise a disease. In some embodiments of any one of the methods disclosed herein, the condition can comprise neoplasm, cancer, or tumor. In an example, the condition can comprise a solid tumor. In another example, the condition can comprise a lymphoma, such as B-cell lymphoma (BCL). Non-limiting examples of BCL can include diffuse large B-cell lymphoma (DLBCL), follicular lymphoma (FL), Burkitt lymphoma (BL), B-cell chronic lymphocytic leukemia (CLL), Marginal zone B-cell lymphoma (MZL), and Mantle cell lymphoma (MCL).

As disclosed herein, a treatment for a condition of subject can comprise administering the subject with one or more therapeutic agents. The one or more therapeutic drugs can be administered to the subject by one or more of the following: orally, intraperitoneally, intravenously, intraarterially, transdermally, intramuscularly, liposomally, via local delivery by catheter or stent, subcutaneously, intraadiposally, and intrathecally.

Non-limiting examples of the therapeutic drugs can include cytotoxic agents, chemotherapeutic agents, growth inhibitory agents, agents used in radiation therapy, anti-angiogenesis agents, apoptotic agents, anti-tubulin agents, and other agents to treat cancer, for example, anti-CD20 antibodies, anti-PD1 antibodies (e.g., Pembrolizumab) platelet derived growth factor inhibitors (e.g., GLEEVEC™ (imatinib mesylate)), a COX-2 inhibitor (e.g., celecoxib), interferons, cytokines, antagonists (e.g., neutralizing antibodies) that bind to one or more of the following targets PDGFR-β, BlyS, APRIL, BCMA receptor(s), TRAIL/Apo2, other bioactive and organic chemical agents, and the like.

Non-limiting examples of a cytotoxic agent can include radioactive isotopes (e.g., At211, I131, I125, Y90, Re186, Re188, Sm153, Bi212, P32, and radioactive isotopes of Lu), chemotherapeutic agents, e.g., methotrexate, adriamycin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin.

Non-limiting examples of a chemotherapeutic agent can include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolmelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics; dynemicin, including dynemicin A; an espiramicina; as well as neocarzinostatin chromophore and related chromoprotein enediyne antibiotic chromophores), aclacinomycins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; eflornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verrucarin A, roridin A and anguidine); urethan; vindesine (ELDISINE®, FILDESIN®); dacarbazine; mannomustine; mitobronitol; mitolactol; pipobroman; gacytosine; arabinoside (“Ara-C”); thiotepa; taxoids, for example taxanes including TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhone-Poulenc Rorer, Antony, France); chlorambucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Examples of a chemotherapeutic agent can also include “anti-hormonal agents” or “endocrine therapeutics” that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD) leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGFR); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Examples of a chemotherapeutic agent can also include antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, feMzumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1λ antibody genetically modified to recognize interleukin-12 p40 protein.

Examples of a chemotherapeutic agent can also include “tyrosine kinase inhibitors” such as an EGFR-targeting agent (e.g., small molecule, antibody, etc.); small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline);

multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g., those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone); and rapamycin (sirolimus, RAPAMUNE®).

Examples of a chemotherapeutic agent can also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Examples of a chemotherapeutic agent can also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate: immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNF$\alpha$) blockers such as etanercept (ENBREL®), infliximab (REMICADE®), adalimumab (HUMIRA®), certolizumab pegol (CIMZIA®), golimumab (SIMPONI®), Interleukin 1 (IL-1) blockers such as anakinra (KINERET®), T-cell costimulation blockers such as abatacept (ORENCIA®), Interleukin 6 (IL-6) blockers such as tocilizumab (ACTEMERA®); Interleukin 13 (IL-13) blockers such as lebrikizumab; Interferon alpha (IFN) blockers such as rontalizumab; beta 7 integrin blockers such as rhuMAb Beta7; IgE pathway blockers such as Anti-M1 prime; Secreted homotrimeric LTa3 and membrane bound heterotrimer LTa/$\beta$2 blockers such as Anti-lymphotoxin alpha (LTa); miscellaneous investigational agents such as thioplatin, PS-341, phenylbutyrate, ET-18-OCH3, or famesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g., celecoxib or etoricoxib), proteosome inhibitor (e.g., PS341); CCI-779; tipifamib (R11577); orafenib, ABT510; Bcl-2 inhibitor such as oblimersen sodium (GENASENSE®); pixantrone; famesyltransferase inhibitors such as lonafamib (SCH 6636, SARASAR™); and pharmaceutically acceptable salts, acids or derivatives of any of the above; as well as combinations of two or more of the above.

In accordance with many embodiments, once a diagnosis of cancer is indicated, a number of treatments can be performed, including (but not limited to) surgery, resection, chemotherapy, radiation therapy, immunotherapy, targeted therapy, hormone therapy, stem cell transplant, and blood transfusion. In some embodiments, an anti-cancer and/or chemotherapeutic agent is administered, including (but not limited to) alkylating agents, platinum agents, taxanes, vinca agents, anti-estrogen drugs, aromatase inhibitors, ovarian suppression agents, endocrine/hormonal agents, bisphophonate therapy agents and targeted biological therapy agents. Medications include (but are not limited to) cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolomide, topotecan, vincristine, vinblastine, eribulin, mutamycin, capecitabine, capecitabine, anastrozole, exemestane, letrozole, leuprolide, abarelix, buserelin, goserelin, megestrol acetate, risedronate, pamidronate, ibandronate, alendronate, zoledronate, tykerb, daunorubicin, doxorubicin, epirubicin, idarubicin, valrubicin mitoxantrone, bevacizumab, cetuximab, ipilimumab, ado-trastuzumab emtansine, afatinib, aldesleukin, alectinib, alemtuzumab, atezolizumab, avelumab, axtinib, belimumab, belinostat, bevacizumab, blinatumomab, bortezomib, bosutinib, brentuximab vedotin, brigatinib, cabozantinib, canakinumab, carfilzomib, certinib, cetuximab, cobimetinib, crizotinib, dabrafenib, daratumumab, dasatinib, denosumab, dinutuximab, durvalumab, elotuzumab, enasidenib, erlotinib, everolimus, gefitinib, ibritumomab tiuxetan, ibrutinib, idelalisib, imatinib, ipilimumab, ixazomib, lapatinib, lenvatinib, midostaurin, necitumumab, neratinib, nilotinib, niraparib, nivolumab, obinutuzumab, ofatumumab, olaparib, olaratumab, osimertinib, palbociclib, panitumumab, panobinostat, pembrolizumab, pertuzumab, ponatinib, ramucirumab, regorafenib, ribociclib, rituximab, romidepsin, rucaparib, ruxolitinib, siltuximab, sipuleucel-T, sonidegib, sorafenib, temsi rolimus, tocilizumab, tofacitinib, tositumomab, trametinib, trastuzumab, vandetanib, vemurafenib, venetoclax, vismodegib, vorinostat, and ziv-aflibercept. In accordance with various embodiments, an individual may be treated, by a single medication or a combination of medications described herein. A common treatment combination is cyclophosphamide, methotrexate, and 5-fluorouracil (CMF).

In some embodiments of any one of the methods disclosed herein, any of the cell-free nucleic acid molecules (e.g., cfDNA, cfRNA) can be derived from a cell. For example, a cell sample or tissue sample may be obtained from a subject and processed to remove all cells from the sample, thereby producing cell-free nucleic acid molecules derived from the sample.

In some embodiments of any one of the methods disclosed herein, a reference genomic sequence can be derived from a cell of an individual. The individual can be a healthy control or the subject who is being subjected to the methods disclosed herein for determining or monitoring progress of a condition.

A cell can be a healthy cell. Alternatively, a cell can be a diseased cell. A diseased cell can have altered metabolic, gene expression, and/or morphologic features. A diseased cell can be a cancer cell, a diabetic cell, and an apoptotic cell. A diseased cell can be a cell from a diseased subject. Exemplary diseases can include blood disorders, cancers, metabolic disorders, eye disorders, organ disorders, musculoskeletal disorders, cardiac disease, and the like.

A cell can be a mammalian cell or derived from a mammalian cell. A cell can be a rodent cell or derived from a rodent cell. A cell can be a human cell or derived from a human cell. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a pluripotent stem cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a microbe cell or derived from a microbe cell. A cell can be a fungi cell or derived from a fungi cell. A cell can be from a specific organ or tissue.

Non-limiting examples of a cell(s) can include lymphoid cells, such as B cell, T cell (Cytotoxic T cell, Natural Killer T cell, Regulatory T cell, T helper cell), Natural killer cell, cytokine induced killer (CIK) cells; myeloid cells, such as granulocytes (Basophil granulocyte, Eosinophil granulocyte, Neutrophil granulocyte/Hypersegmented neutrophil), Monocyte/Macrophage, Red blood cell (Reticulocyte), Mast cell, Thrombocyte/Megakaryocyte, Dendritic cell; cells from the endocrine system, including thyroid (Thyroid epithelial cell, Parafollicular cell), parathyroid (Parathyroid chief cell, Oxyphil cell), adrenal (Chromaffin cell), pineal (Pinealocyte) cells; cells of the nervous system, including glial cells (Astrocyte, Microglia), Magnocellular neurosecretory cell, Stellate cell, Boettcher cell, and pituitary (Gonadotrope, Corticotrope, Thyrotrope, Somatotrope, Lactotroph); cells of the Respiratory system, including Pneumocyte (Type I pneumocyte, Type II pneumocyte), Clara cell, Goblet cell, Dust cell; cells of the circulatory system, including Myocardiocyte, Pericyte; cells of the digestive system, including stomach (Gastric chief cell, Parietal cell), Goblet cell, Paneth cell, G cells, D cells, ECL cells, I cells, K cells, S cells; enteroendocrine cells, including enterochromaffm cell, APUD cell, liver (Hepatocyte, Kupffer cell), Cartilage/bone/muscle; bone cells, including Osteoblast, Osteocyte, Osteoclast, teeth (Cementoblast, Ameloblast); cartilage cells, including Chondroblast, Chondrocyte; skin cells, including Trichocyte, Keratinocyte, Melanocyte (Nevus cell); muscle cells, including Myocyte; urinary system cells, including Podocyte, Juxtaglomerular cell, Intraglomerular mesangial cell/Extraglomerular mesangial cell, Kidney proximal tubule brush border cell, Macula densa cell; reproductive system cells, including Spermatozoon, Sertoli cell, Leydig cell, Ovum; and other cells, including Adipocyte, Fibroblast, Tendon cell, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell), Wet stratified barrier epithelial cells, Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts), Exocrine secretory epithelial cells, Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion). Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), Paneth cell of small intestine (lysozyme secretion), Type II pneumocyte of lung (surfactant secretion), Clara cell of lung, Hormone secreting cells, Anterior pituitary cells, Somatotropes, Lactotropes, Thyrotropes, Gonadotropes, Corticotropes, Intermediate pituitary cell, Magnocellular neurosecretory cells, Gut and respiratory tract cells, Thyroid gland cells, thyroid epithelial cell, parafollicular cell, Parathyroid gland cells, Parathyroid chief cell, Oxyphil cell, Adrenal gland cells, chromaffin cells, Ley dig cell of testes, Theca interna cell of ovarian follicle, Corpus luteum cell of ruptured ovarian follicle, Granulosa lutein cells, Theca lutein cells, Juxtaglomerular cell (renin secretion), Macula densa cell of kidney, Metabolism and storage cells, Barrier function cells (Lung, Gut, Exocrine Glands and Urogenital Tract), Kidney, Type I pneumocyte (lining air space of lung), Pancreatic duct cell (centroacinar cell), Nonstriated duct cell (of sweat gland, salivary gland, mammary gland, etc.), Duct cell (of seminal vesicle, prostate gland, etc.), Epithelial cells lining closed internal body cavities, Ciliated cells with propulsive function, Extracellular matrix secretion cells, Contractile cells; Skeletal muscle cells, stem cell, Heart muscle cells, Blood and immune system cells, Erythrocyte (red blood cell), Megakaryocyte (platelet precursor), Monocyte, Connective tissue macrophage (various types), Epidermal Langerhans cell, Osteoclast (in bone), Dendritic cell (in lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types), Pluripotent stem cells, Totipotent stem cells, Induced pluripotent stem cells, adult stem cells, Sensory transducer cells, Autonomic neuron cells, Sense organ and peripheral neuron supporting cells, Central nervous system neurons and glial cells, Lens cells, Pigment cells, Melanocyte, Retinal pigmented epithelial cell, Germ cells, Oogonium/Oocyte, Spermatid, Spermatocyte, Spermatogonium cell (stem cell for spermatocyte), Spermatozoon, Nurse cells, Ovarian follicle cell, Sertoli cell (in testis), Thymus epithelial cell, Interstitial cells, and Interstitial kidney cells.

In some embodiments of any one of the methods disclosed herein, the condition can be a cancer or tumor. Non-limiting examples of such condition can include Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, and Wilms' tumor.

In accordance with various embodiments, numerous types of neoplasms can be detected, including (but not limited to) acute lymphoblastic leukemia (ALL), acute myeloid leukemia (AML), anal cancer, astrocytomas, basal cell carcinoma, bile duct cancer, bladder cancer, breast cancer, Burkitt's lymphoma, cervical cancer, chronic lymphocytic leukemia (CLL) chronic myelogenous leukemia (CIVIL), chronic myeloproliferative neoplasms, colorectal cancer, diffuse large B-cell lymphoma, endometrial cancer, ependymoma, esophageal cancer, esthesioneuroblastoma, Ewing sarcoma, fallopian tube cancer, follicular lymphoma, gallbladder cancer, gastric cancer, gastrointestinal carcinoid tumor, hairy cell leukemia, hepatocellular cancer, Hodgkin lymphoma, hypopharyngeal cancer, Kaposi sarcoma, Kidney cancer, Langerhans cell histiocytosis, laryngeal cancer, leukemia, liver cancer, lung cancer, lymphoma, melanoma, Merkel cell cancer, mesothelioma, mouth cancer, neuroblastoma, non-Hodgkin lymphoma, non-small cell lung cancer, osteosarcoma, ovarian cancer, pancreatic cancer, pancreatic neuroendocrine tumors, pharyngeal cancer, pituitary tumor, prostate cancer, rectal cancer, renal cell cancer, retinoblastoma, skin cancer, small cell lung cancer, small intestine cancer, squamous neck cancer, T-cell lymphoma, testicular cancer, thymoma, thyroid cancer, uterine cancer, vaginal cancer, and vascular tumors.

Many embodiments are directed to diagnostic or companion diagnostic scans performed during cancer treatment of an individual. When performing diagnostic scans during treatment, the ability of agent to treat the cancer growth can be monitored. Most anti-cancer therapeutic agents result in death and necrosis of neoplastic cells, which should release higher amounts nucleic acids from these cells into the samples being tested. Accordingly, the level of circulating-tumor nucleic acids can be monitored over time, as the level should increase during early treatments and begin to decrease as the number of cancerous cells are decreased. In some embodiments, treatments are adjusted based on the treatment effect on cancer cells. For instance, if the treatment isn't cytotoxic to neoplastic cells, a dosage amount may be increased or an agent with higher cytotoxicity can be administered. In the alternative, if cytotoxicity of cancer cells is good but unwanted side effects are high, a dosage amount can be decreased or an agent with less side effects can be administered.

Various embodiments are also directed to diagnostic scans performed after treatment of an individual to detect residual disease and/or recurrence of cancer. If a diagnostic scan indicates residual and/or recurrence of cancer, further diagnostic tests and/or treatments may be performed as described herein. If the cancer and/or individual is susceptible to recurrence, diagnostic scans can be performed frequently to monitor any potential relapse.

F. Computer Systems

In one aspect, the present disclosure provides a computer program product comprising a non-transitory computer-readable medium having computer-executable code encoded therein, the computer-executable code adapted to be executed to implement any one of the preceding methods.

The present disclosure provides computer systems that are programmed to implement methods of the disclosure. The system can, in some cases, include components such as a processor, an input module for inputting sequencing data or data derived therefrom, a computer-readable medium containing instructions that, when executed by the processor, perform an algorithm on the input regarding one or more cell-free nucleic acids molecules, and an output module providing one or more indicia associated with the condition.

Figure 27:
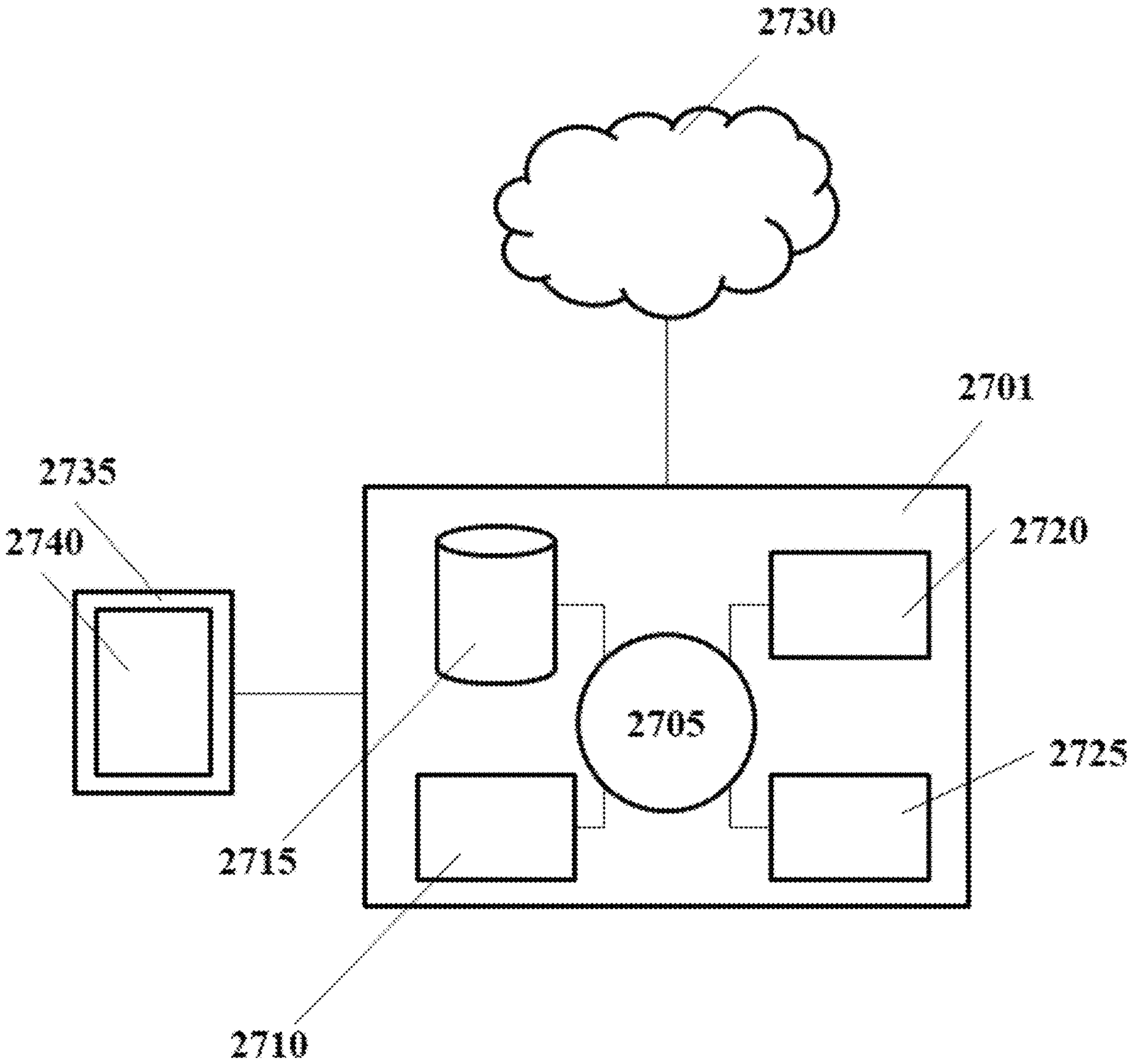
FIG. 27 shows a computer system that is programmed or otherwise configured to implement methods provided herein.

FIG. 27 shows a computer system 2701 that is programmed or otherwise configured to implement partial or all of the methods disclosed herein. The computer system 2701 can regulate various aspects of the present disclosure, such as, for example, (i) identify, from sequencing data derived from a plurality of cell-free nucleic acid molecules, one or more cell-free nucleic acid molecules comprising the plurality of phased variants, (ii) analyze any of the identified cell-free nucleic acid molecules, (iii) determine a condition of the subject based at least in part on the identified cell-free nucleic acid molecules, (iv) monitor a progress of the condition of the subject based at least in part on the identified cell-free nucleic acid molecules, (v) identify the subject based at least in part on the identified cell-free nucleic acid molecules, or (vi) determine an appropriate treatment of the condition of the subject based at least in part on the identified cell-free nucleic acid molecules. The computer system 2701 can be an electronic device of a user or a computer system that is remotely located with respect to the electronic device. The electronic device can be a mobile electronic device.

The computer system 2701 includes a central processing unit (CPU, also "processor" and "computer processor" herein) 2705, which can be a single core or multi core processor, or a plurality of processors for parallel processing. The computer system 2701 also includes memory or memory location 2710 (e.g., random-access memory, read-only memory, flash memory), electronic storage unit 2715 (e.g., hard disk), communication interface 2720 (e.g., network adapter) for communicating with one or more other systems, and peripheral devices 2725, such as cache, other memory, data storage and/or electronic display adapters. The memory 2710, storage unit 2715, interface 2720 and peripheral devices 2725 are in communication with the CPU 2705 through a communication bus (solid lines), such as a motherboard. The storage unit 2715 can be a data storage unit (or data repository) for storing data. The computer system 2701 can be operatively coupled to a computer network ("network") 2730 with the aid of the communication interface 2720. The network 2730 can be the Internet, an internet and/or extranet, or an intranet and/or extranet that is in communication with the Internet. The network 2730 in some cases is a telecommunication and/or data network. The network 2730 can include one or more computer servers, which can enable distributed computing, such as cloud computing. The network 2730, in some cases with the aid of the computer system 2701, can implement a peer-to-peer network, which may enable devices coupled to the computer system 2701 to behave as a client or a server.

The CPU 2705 can execute a sequence of machine-readable instructions, which can be embodied in a program or software. The instructions may be stored in a memory location, such as the memory 2710. The instructions can be directed to the CPU 2705, which can subsequently program or otherwise configure the CPU 2705 to implement methods of the present disclosure. Examples of operations performed by the CPU 2705 can include fetch, decode, execute, and writeback.

The CPU 2705 can be part of a circuit, such as an integrated circuit. One or more other components of the system 2701 can be included in the circuit. In some cases, the circuit is an application specific integrated circuit (ASIC).

The storage unit 2715 can store files, such as drivers, libraries and saved programs. The storage unit 2715 can store user data, e.g., user preferences and user programs. The computer system 2701 in some cases can include one or more additional data storage units that are external to the computer system 2701, such as located on a remote server that is in communication with the computer system 2701 through an intranet or the Internet.

The computer system 2701 can communicate with one or more remote computer systems through the network 2730. For instance, the computer system 2701 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2701 via the network 2730.

Methods as described herein can be implemented by way of machine (e.g., computer processor) executable code stored on an electronic storage location of the computer system 2701, such as, for example, on the memory 2710 or electronic storage unit 2715. The machine executable or machine readable code can be provided in the form of software. During use, the code can be executed by the processor 2705. In some cases, the code can be retrieved from the storage unit 2715 and stored on the memory 2710 for ready access by the processor 2705. In some situations, the electronic storage unit 2715 can be precluded, and machine-executable instructions are stored on memory 2710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2701 can include or be in communication with an electronic display 2735 that comprises a user interface (UI) 2740 for providing, for example, (i) analysis of any of the identified cell-free nucleic acid molecules, (ii) a determined condition of the subject based at least in part on the identified cell-free nucleic acid molecules, (iii) a determined progress of the condition of the subject based at least in part on the identified cell-free nucleic acid molecules, (iv) the identified subject suspected of having the condition based at least in part on the identified cell-free nucleic acid molecules, or (v) a determined treatment of the condition of the subject based at least in part on the identified cell-free nucleic acid molecules. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2705. The algorithm can, for example, (i) identify, from sequencing data derived from a plurality of cell-free nucleic acid molecules, one or more cell-free nucleic acid molecules comprising the plurality of phased variants, (ii) analyze any of the identified cell-free nucleic acid molecules, (iii) determine a condition of the subject based at least in part on the identified cell-free nucleic acid molecules, (iv) monitor a progress of the condition of the subject based at least in part on the identified cell-free nucleic acid molecules, (v) identify the subject based at least in part on the identified cell-free nucleic acid molecules, or (vi) determine an appropriate treatment of the condition of the subject based at least in part on the identified cell-free nucleic acid molecules.

EXAMPLES

The following illustrative examples are representative of embodiments of the stimulation, systems, and methods described herein and are not meant to be limiting in any way.

Example 1: Genomic Distribution of Phased Variants

Described is an alternative to duplex sequencing for reducing the background error rate that involves detection of 'phased variants' (PVs), where two or more mutations occur in cis (i.e., on the same strand of DNA FIG. 1A and FIG. 1E). Similar to duplex sequencing, this method provides lower error profiles due to the concordant detection of two separate non-reference events in individual molecules. However, unlike duplex sequencing, both events occur on the same sequencing read-pair, thereby increasing the efficiency of genome recovery. Phased mutations are present in diverse cancer types, but occur in stereotyped portions of the genome in B-cell malignancies, likely due to on-target and aberrant somatic hypermutation (aSHM) driven by activation-induced deaminase (AID). The most common regions of aSHM in B-cell non-Hodgkin lymphomas (NHL) are identified. Described herein is phased variant Enrichment and Detection Sequencing (PhasED-Seq), a novel method to detect ctDNA through phased variants to tumor fractions on the order of parts per million. Described herein is demonstration that PhasED-Seq can meaningfully improve detection of ctDNA in clinical samples both during therapy and prior to disease relapse.

To identify malignancies where PVs may potentially improve disease detection, the frequency of PVs across cancer types were assessed. Publicly available whole-genome sequencing data was analyzed to identify sets of variants occurring at a distance of <170 bp apart, which represents the typical length of a single cfDNA fragment consisting of a single core nucleosome and associated linker. The frequency of these 'putative phased variants," (Example 10) controlling for the total number of SNVs, from 2538 tumors across 24 cancer histologies including solid tumors and hematological malignancies (FIG. 1B, FIG. 5, and Table 1) was identified and summarized. PVs were most significantly enriched in two B-cell lymphomas (DLBCL and follicular lymphoma, FL, $P<0.05$ vs all other histologies), a group of diseases with hypermutation driven by AID/AICDA.

Example 2: Mutational Mechanisms Underlying PVs

Figure 6A:
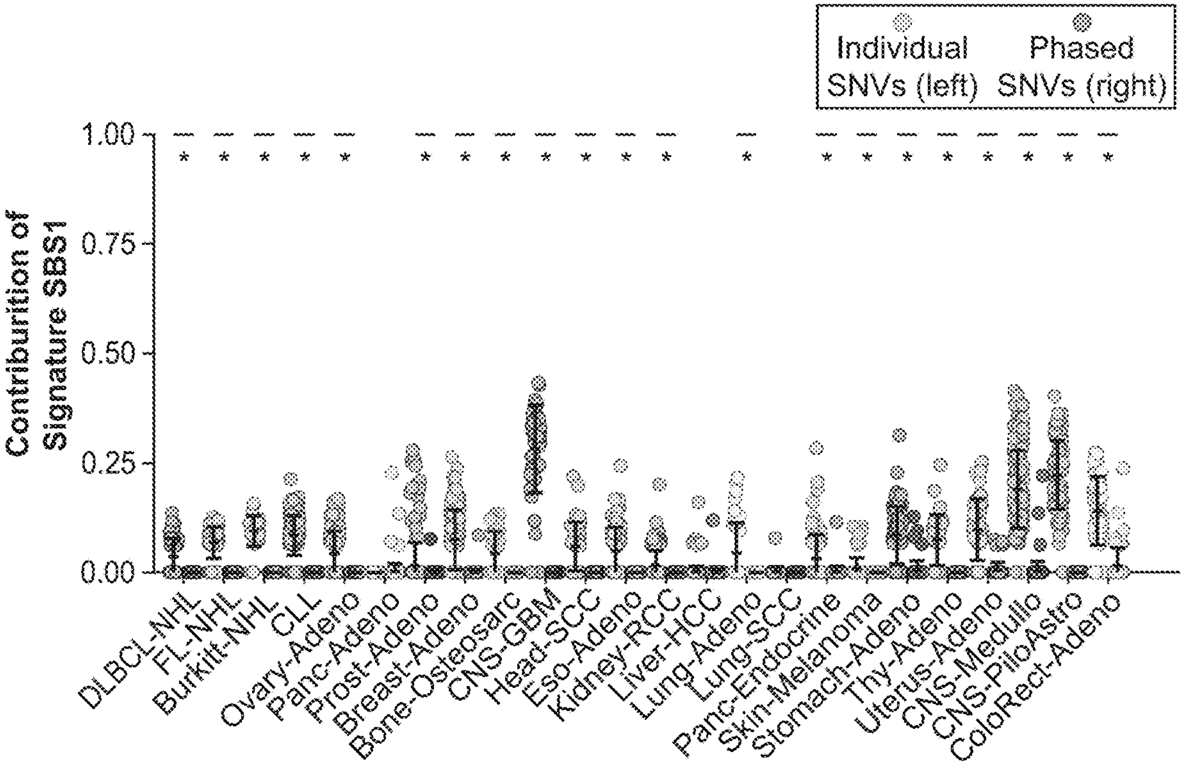
FIGS. 6A-6WW illustrate contribution of mutational signatures in phased and un-phased SNVs in WGS (FIGS. 6A-6WW.) Scatterplots showing the contribution of established single base substitution (SBS) mutational signatures to SNVs seen in PVs, shown in dark colors, and SNVs seen outside of possible phased relationships, shown in light colors, from WGS. This is presented for 49 SBS mutational signatures across 24 subtypes of cancer. Mutational signatures that show a significant difference in contribution between phased and un-phased SNVs after multiple hypothesis testing correction are indicated with a *. These figures represent the raw data summarized in FIG. 1C.
Figure 6B:
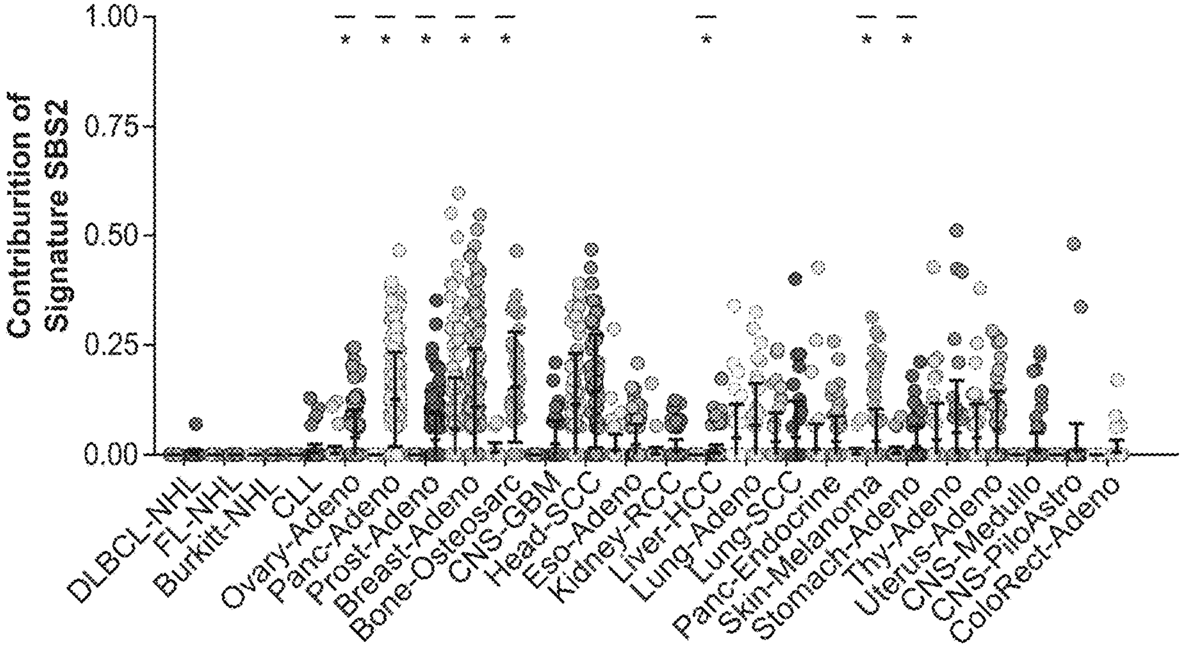
Figure 6C:
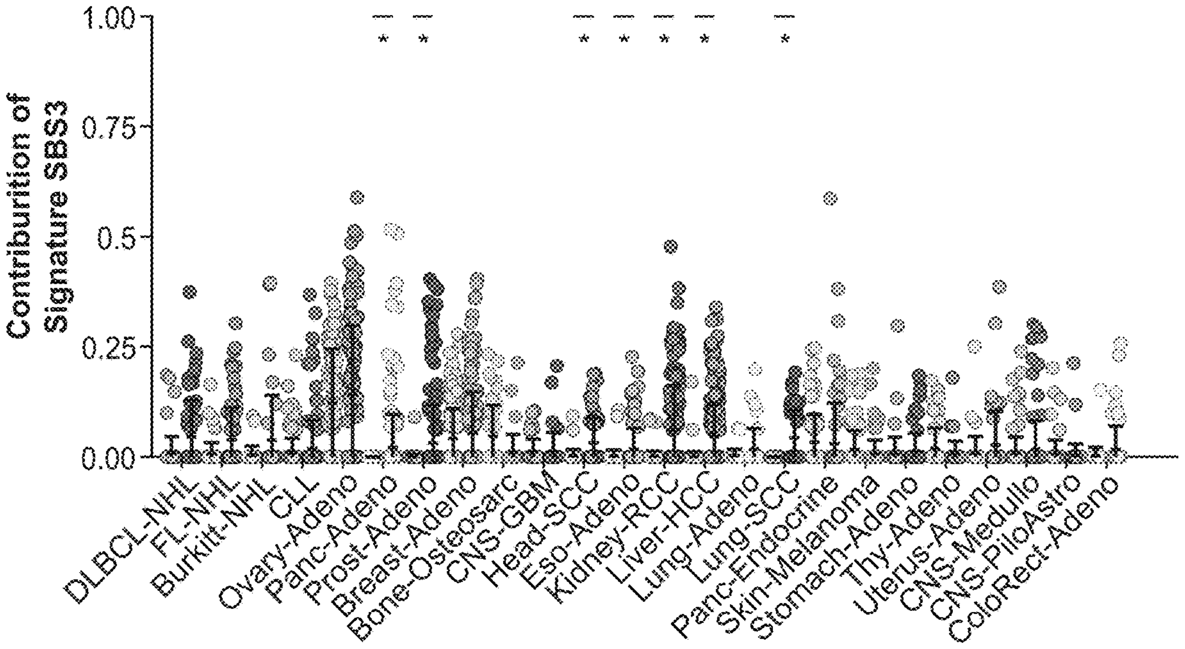
Figure 6D:
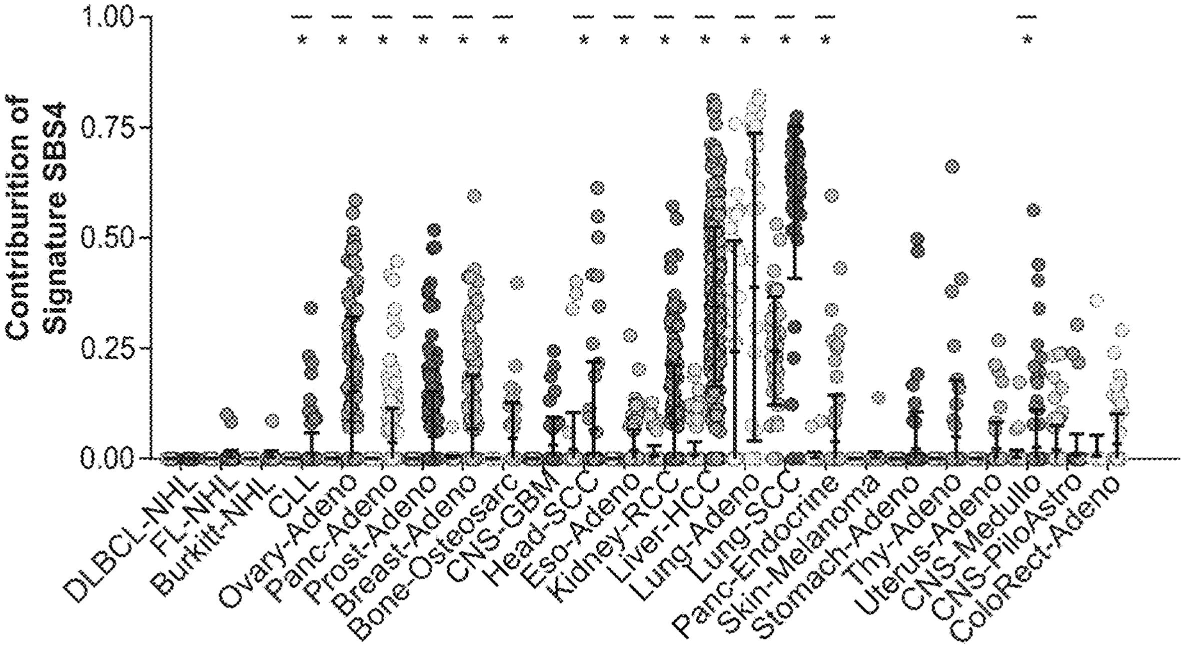
Figure 6E:
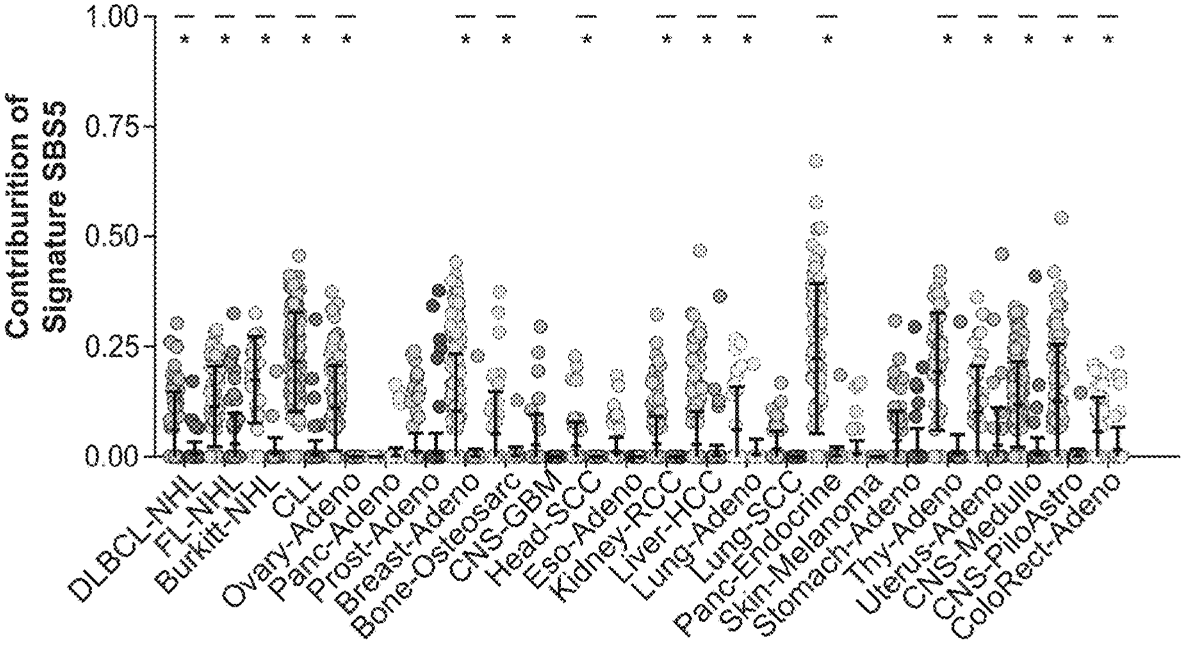
Figure 6F:
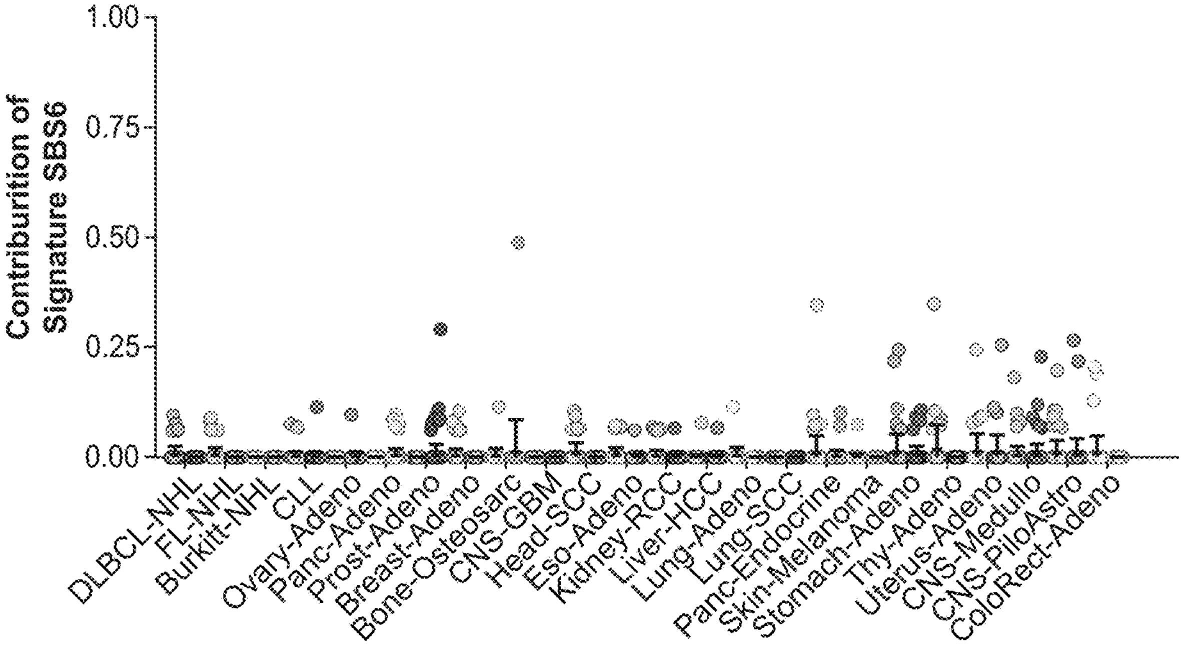
Figure 6G:
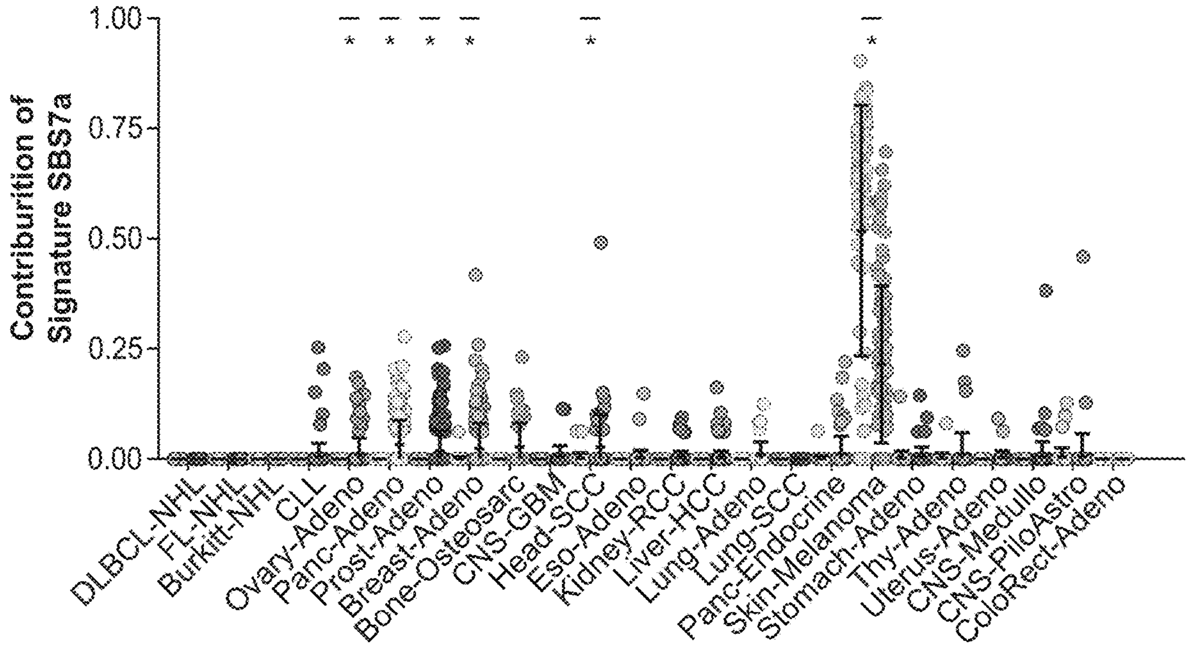
Figure 6H:
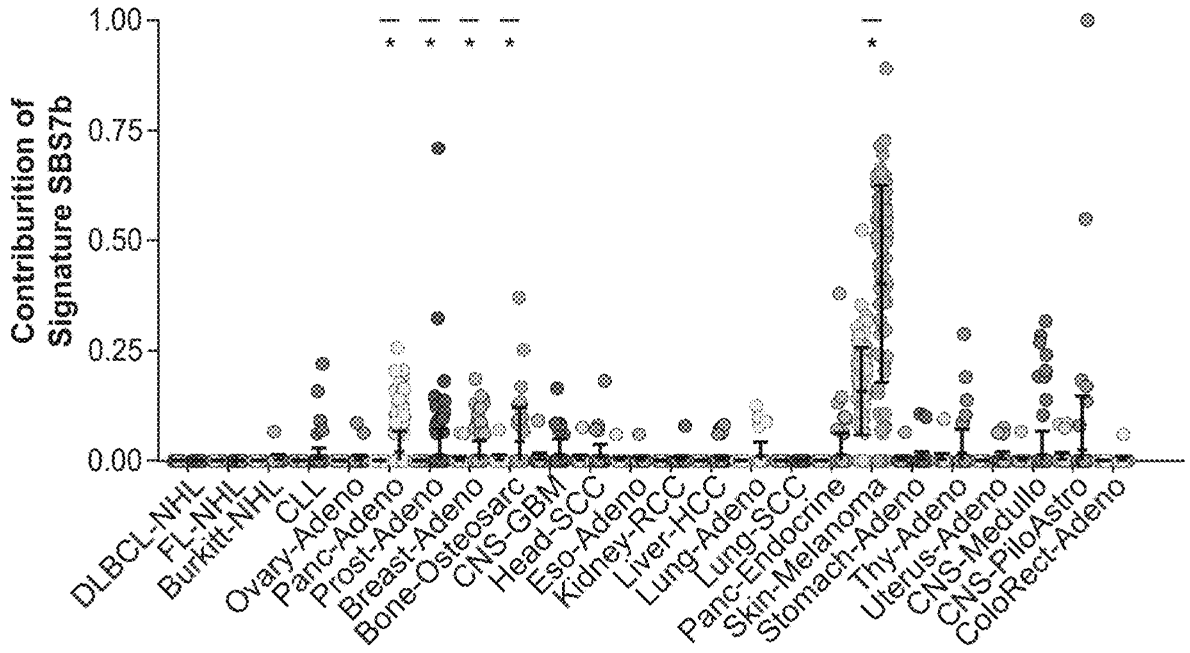
Figure 6I:
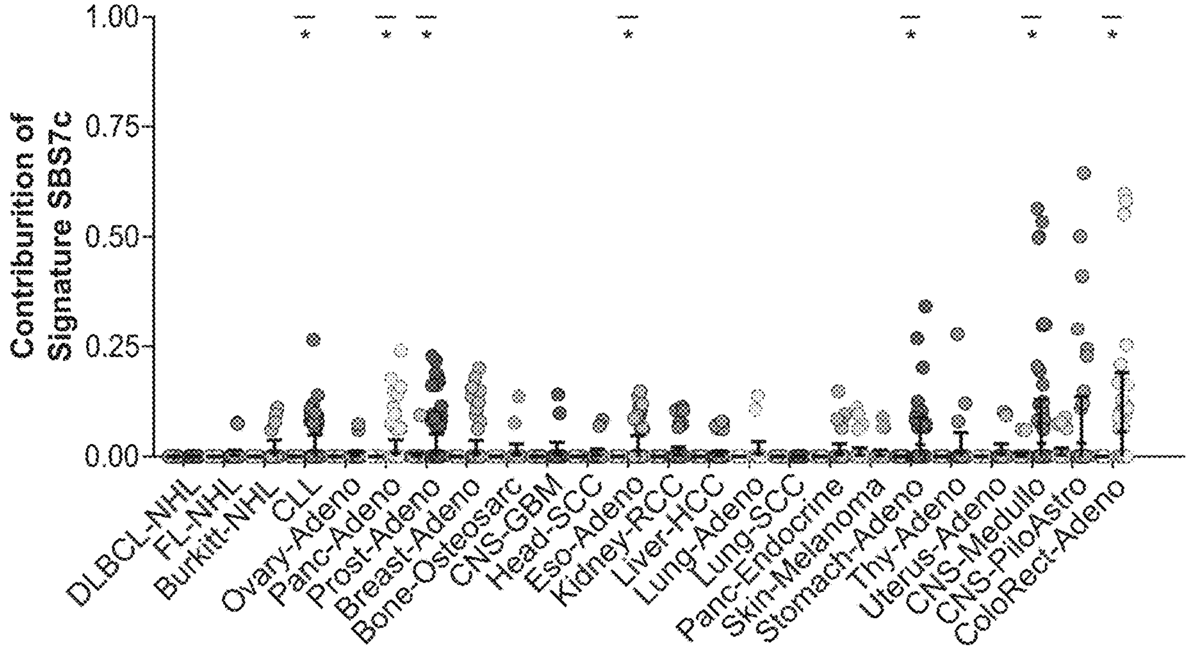
Figure 6J:
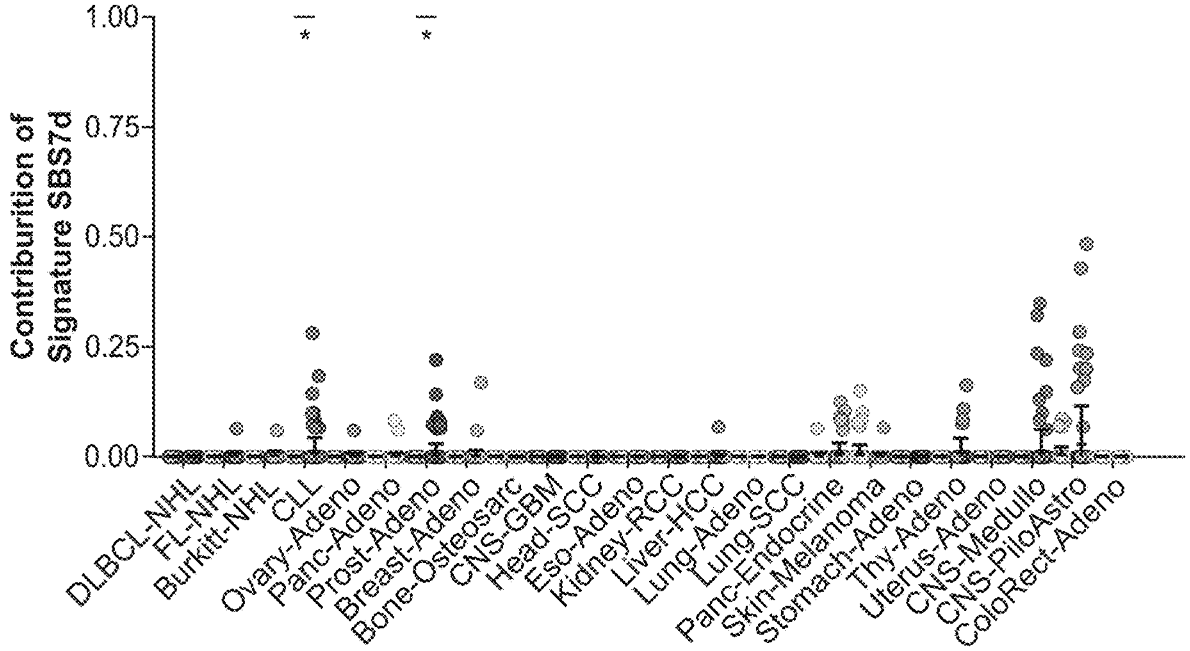
Figure 6K:
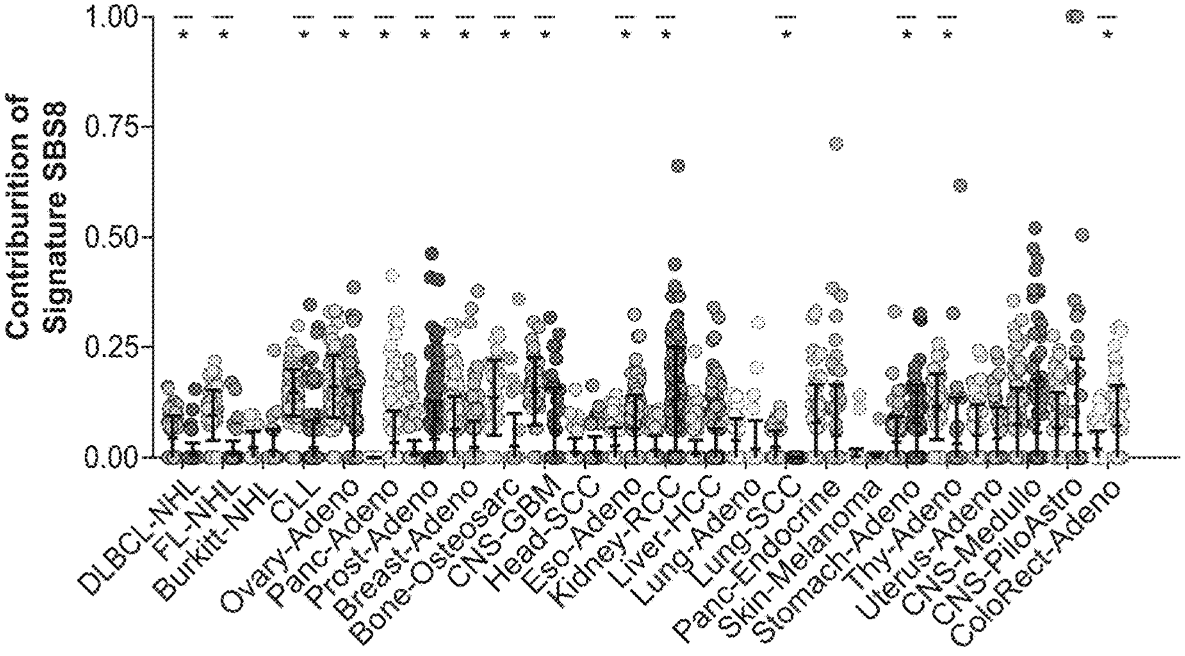
Figure 6L:
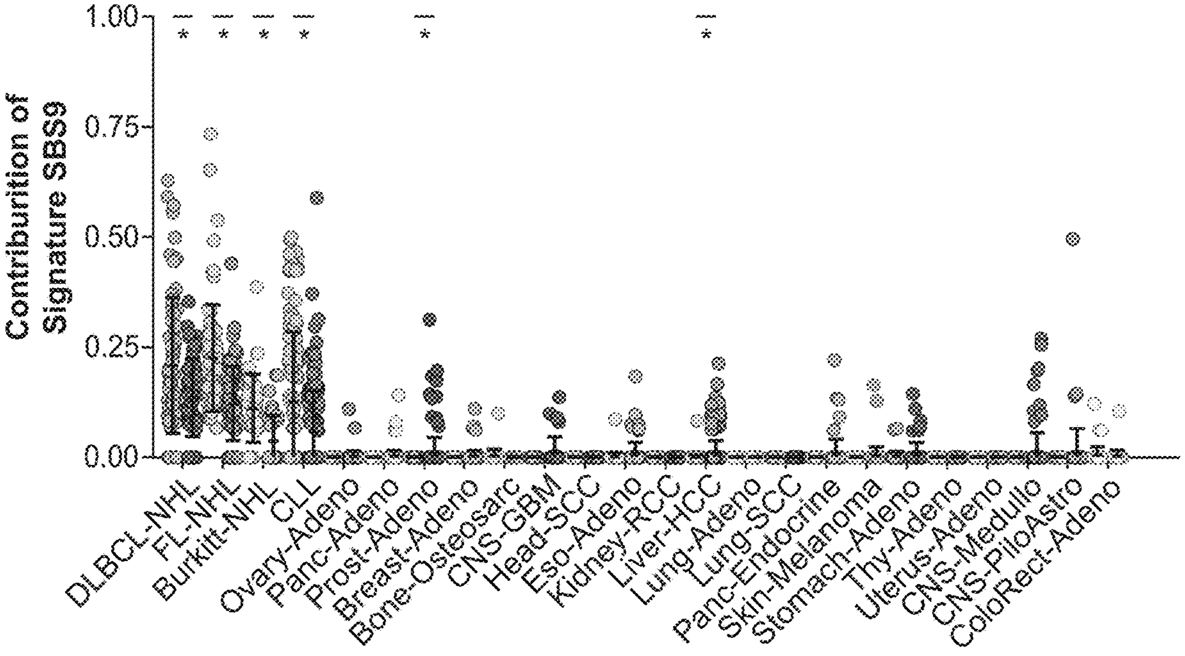
Figure 6M:
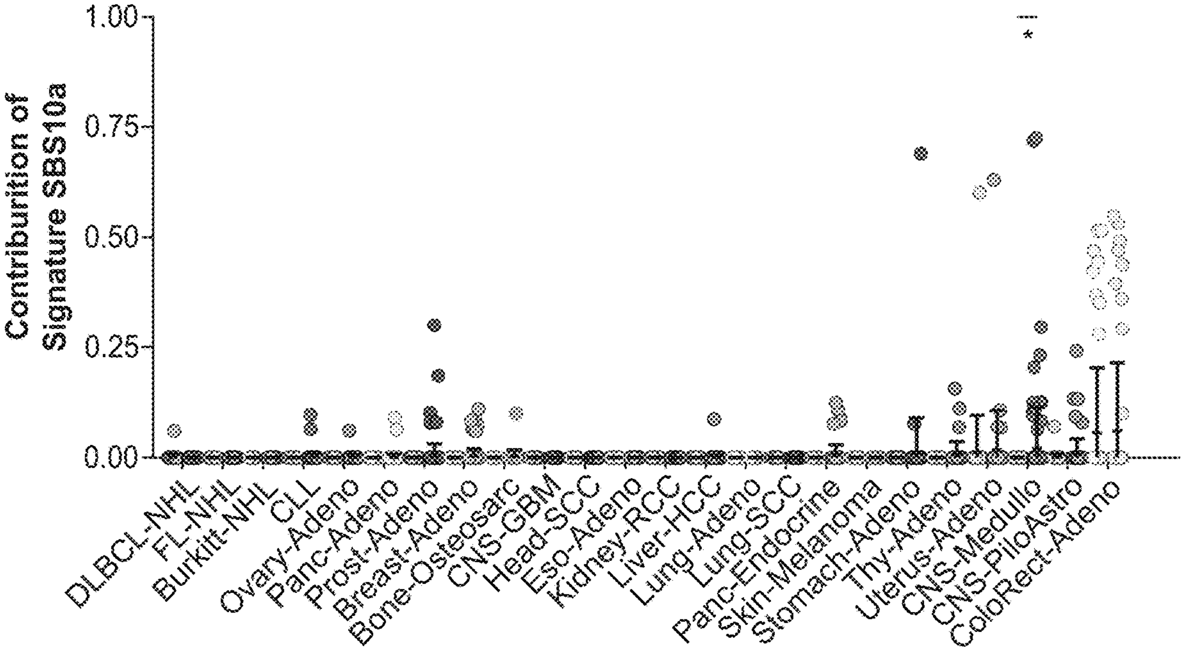
Figure 6N:
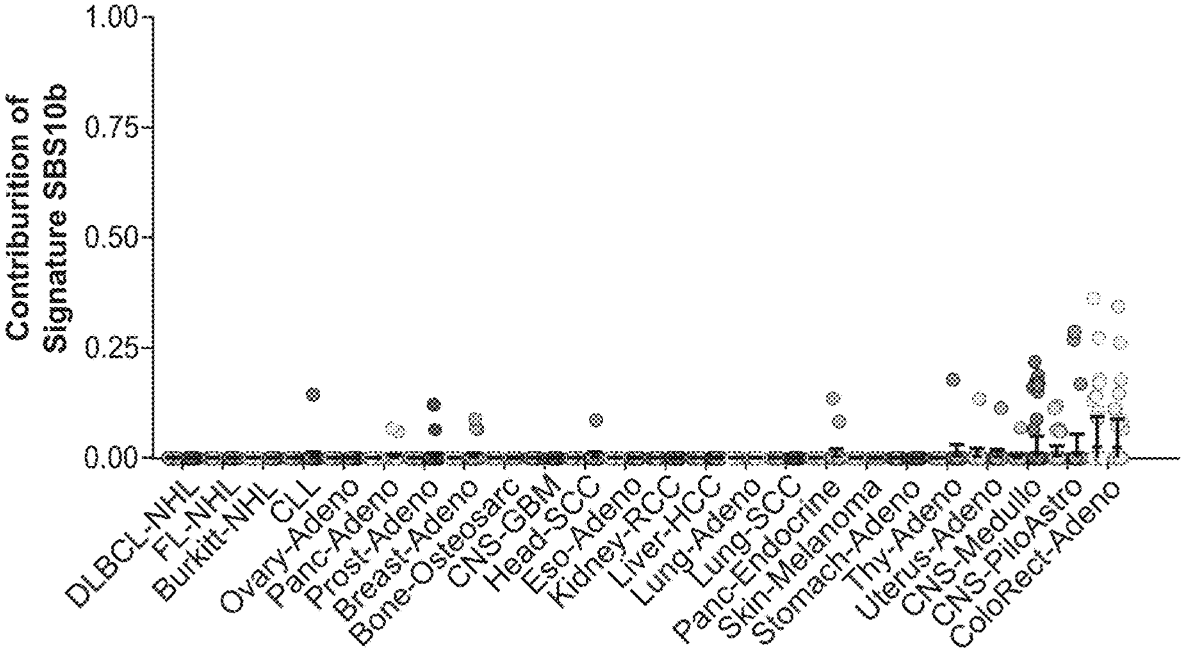
Figure 6O:
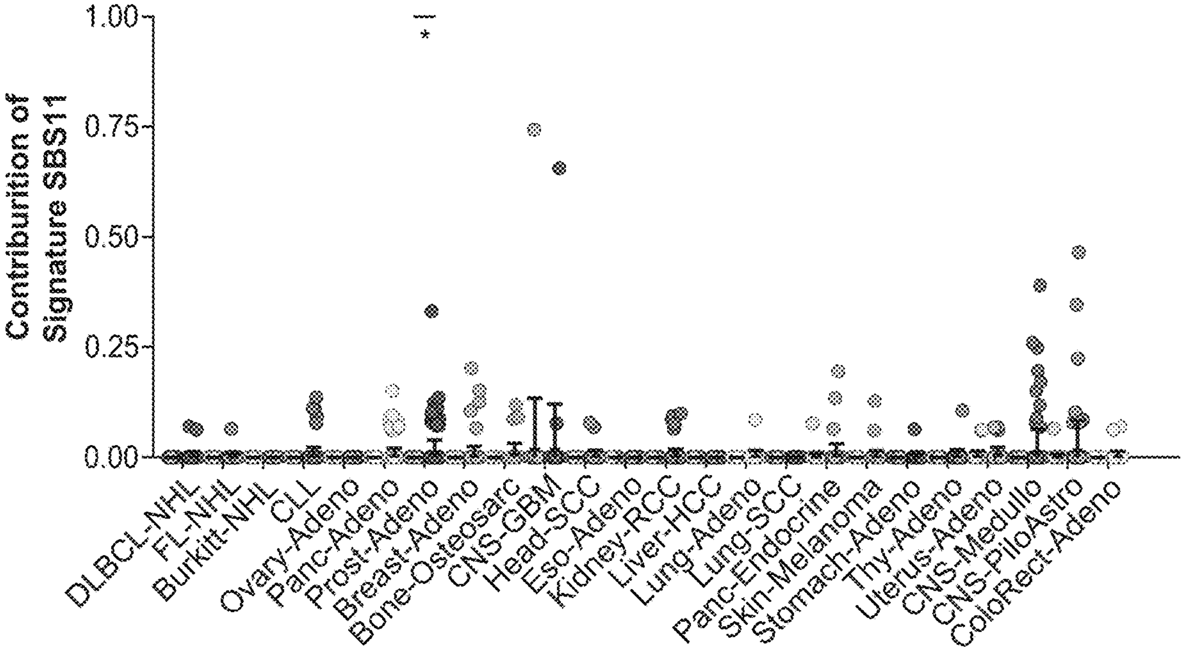
Figure 6P:
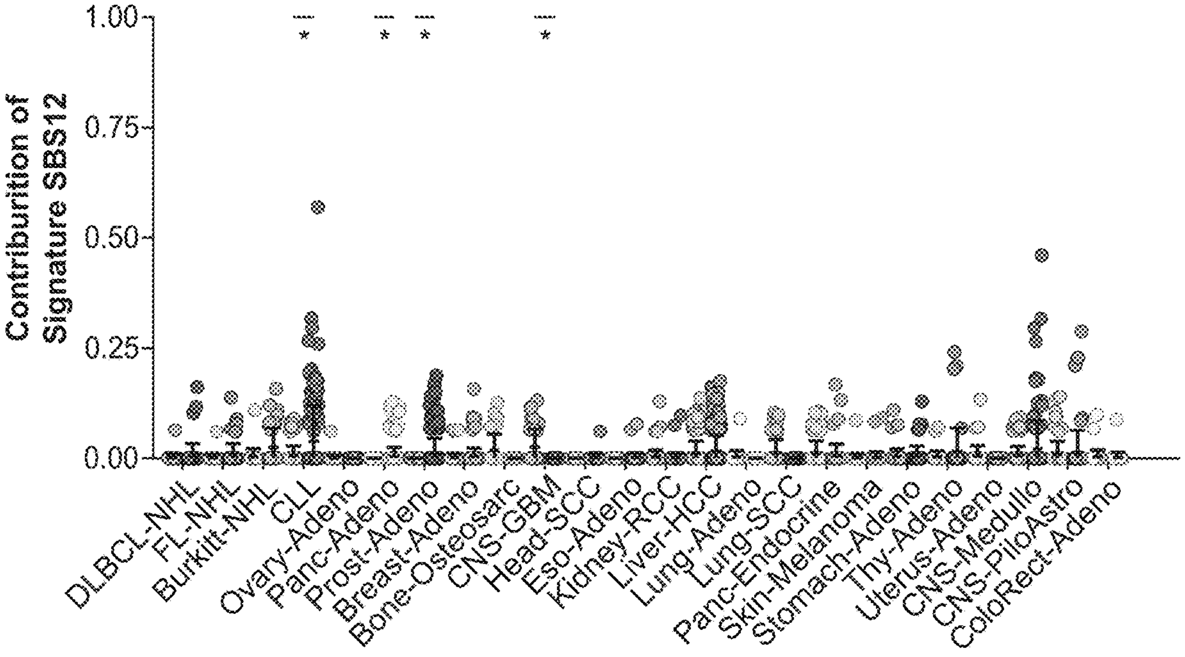
Figure 6Q:
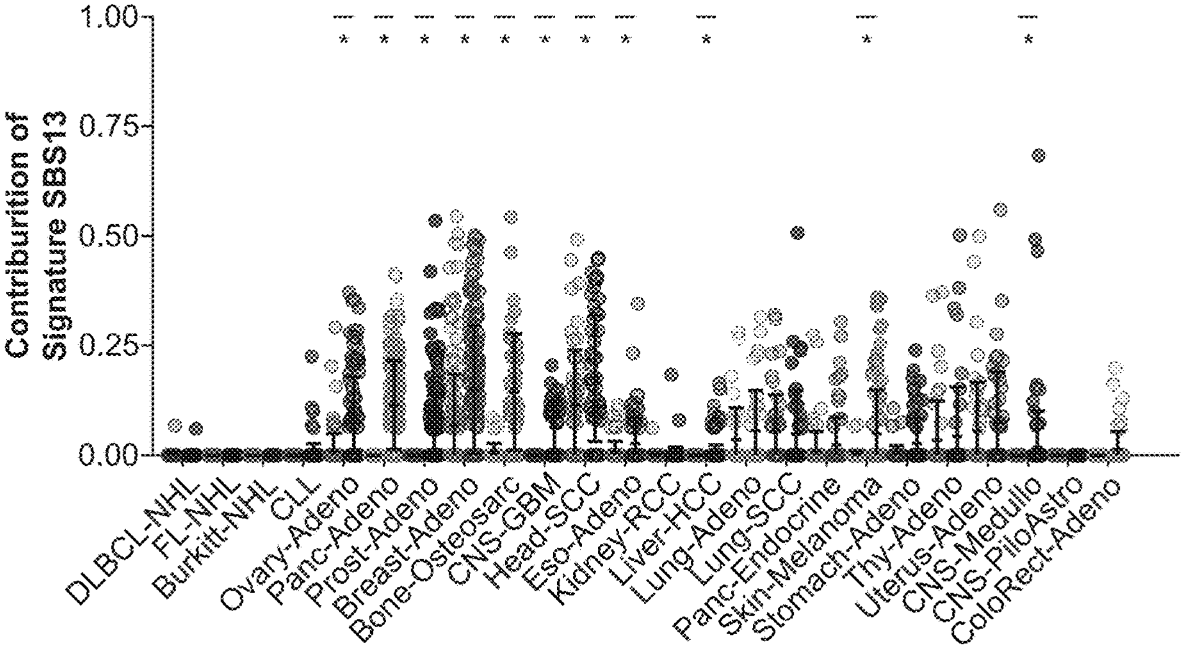
Figure 6R:
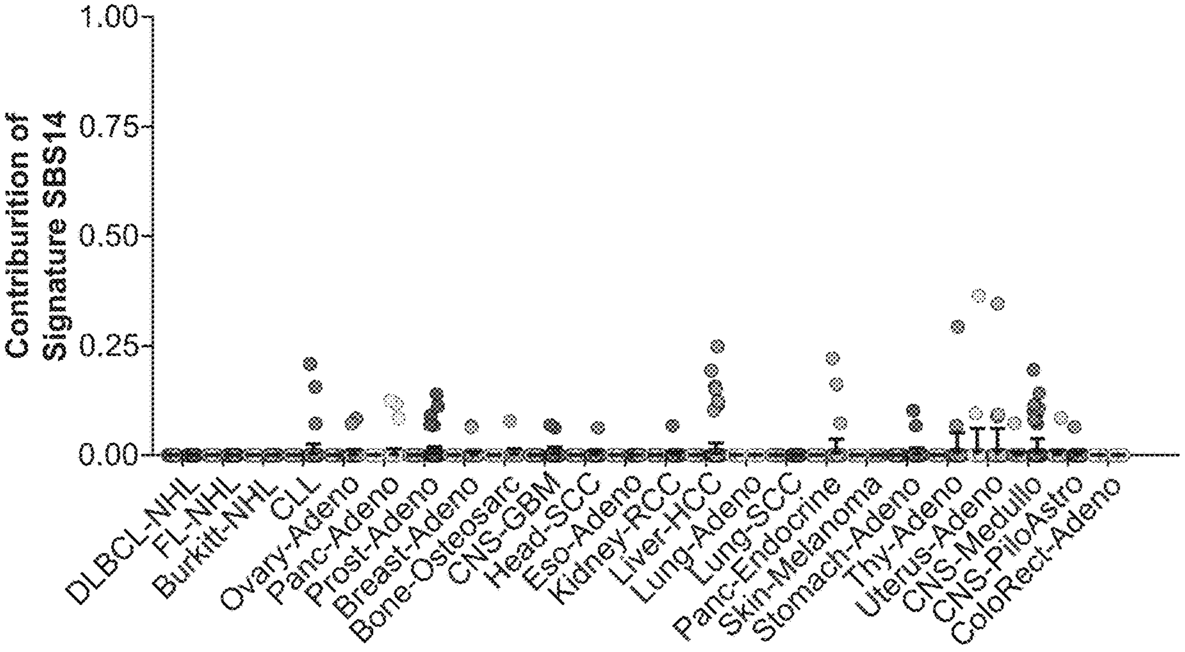
Figure 6S:
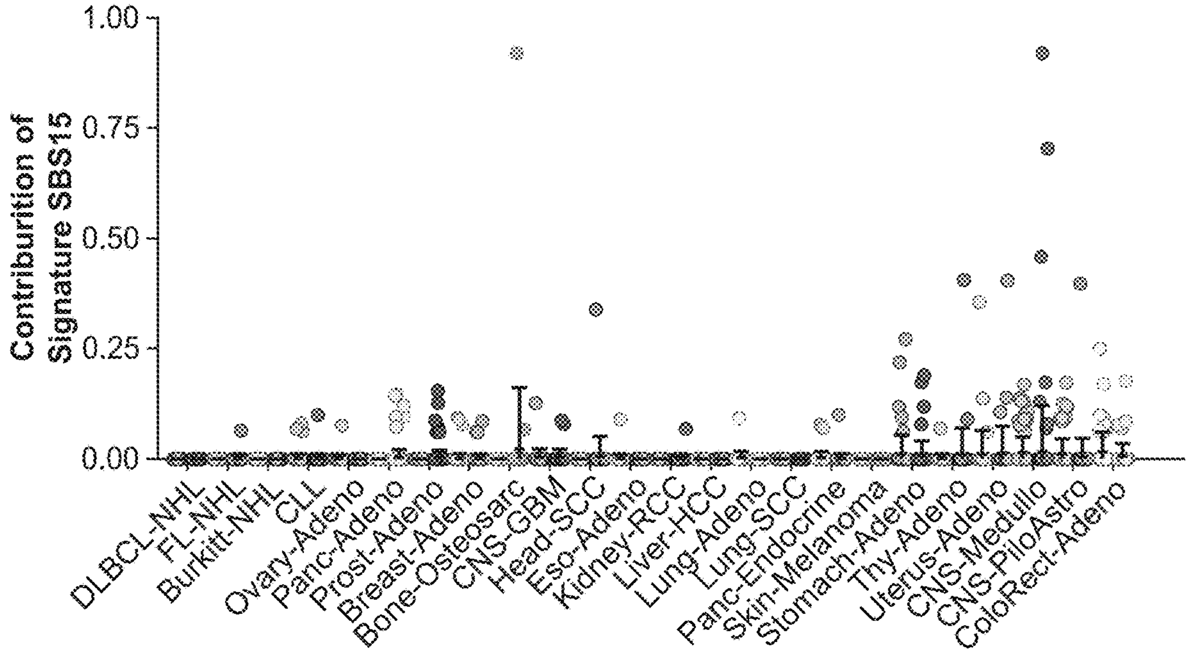
Figure 6T:
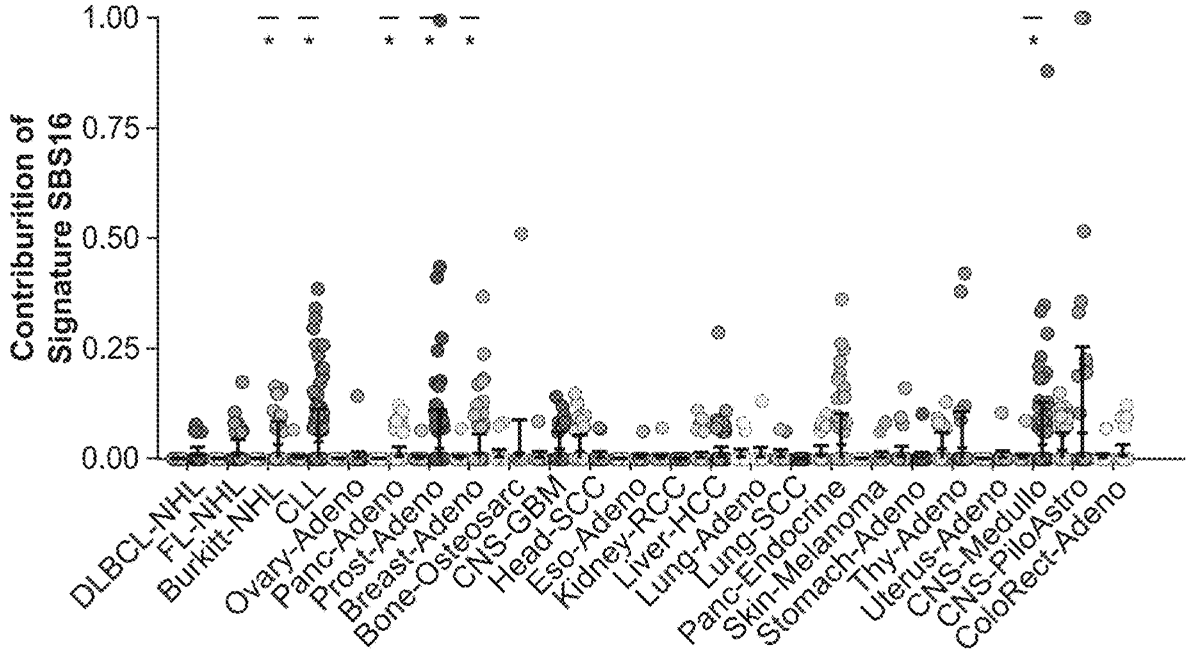
Figure 6U:
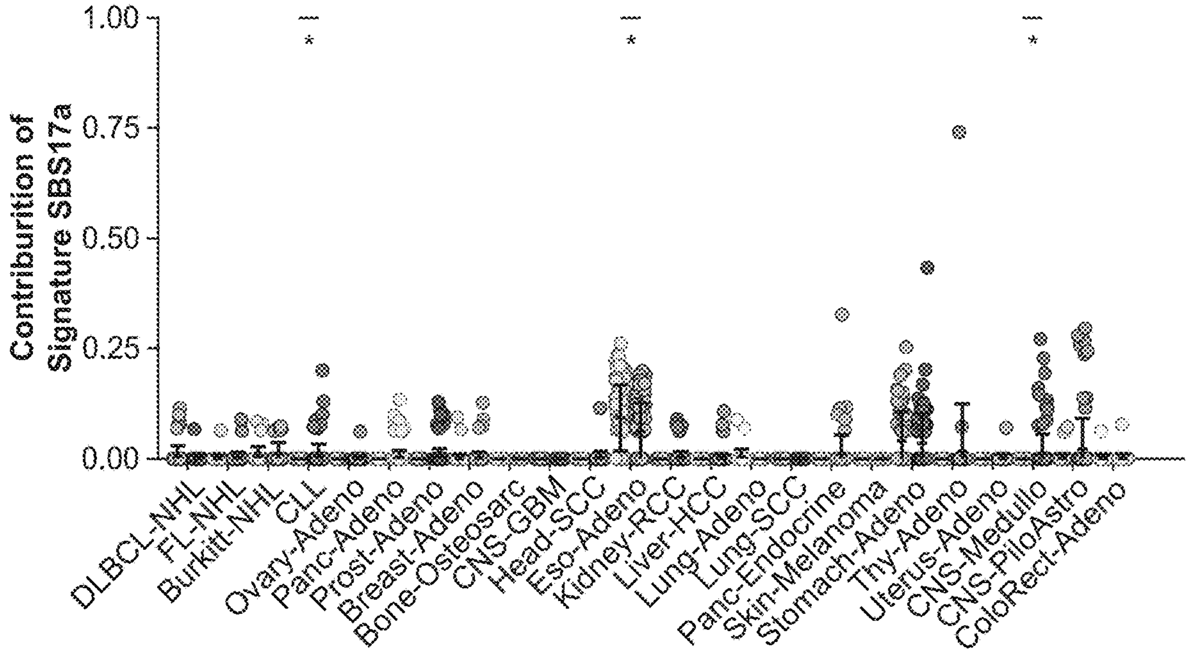
Figure 6V:
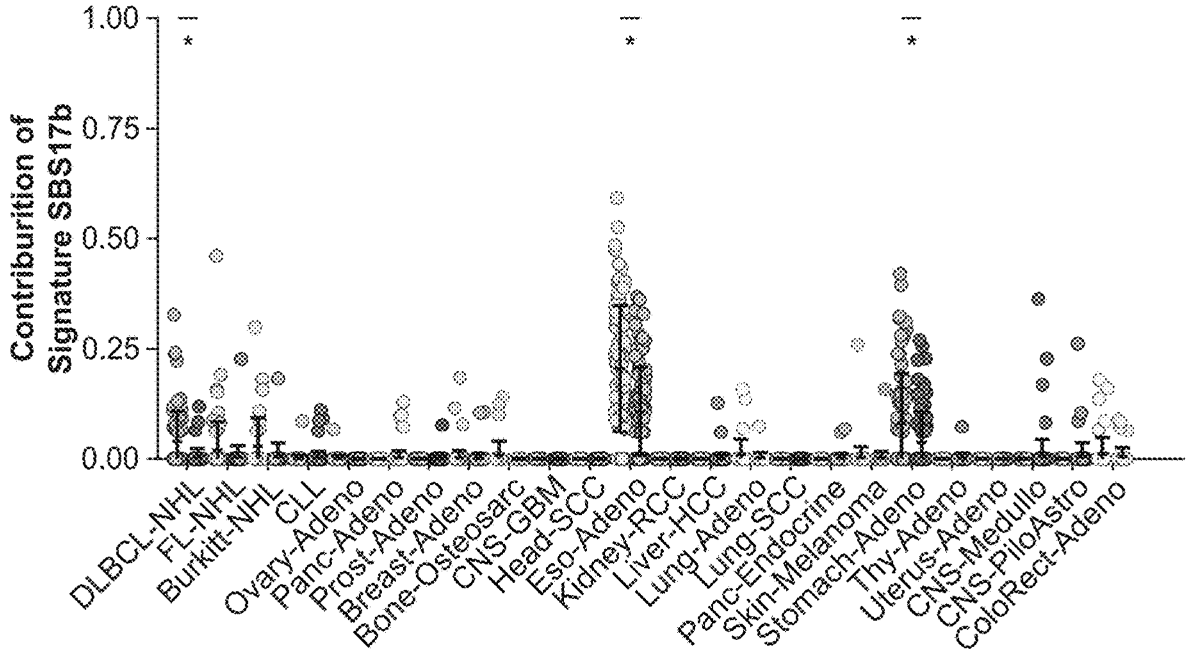
Figure 6W:
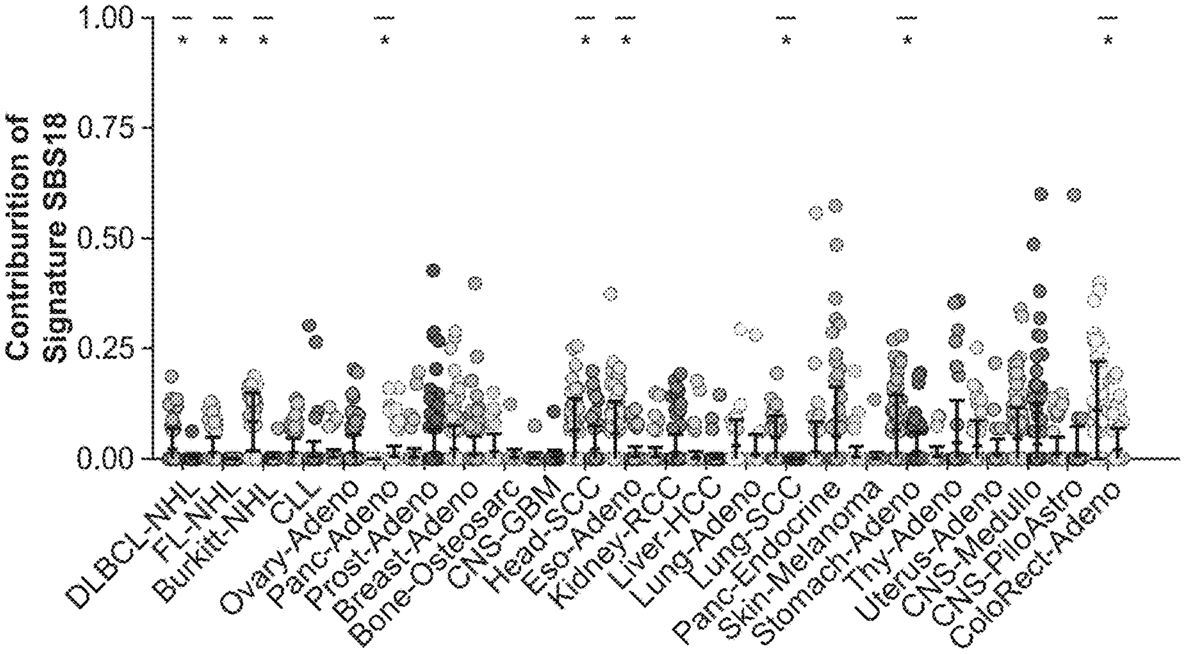
Figure 6X:
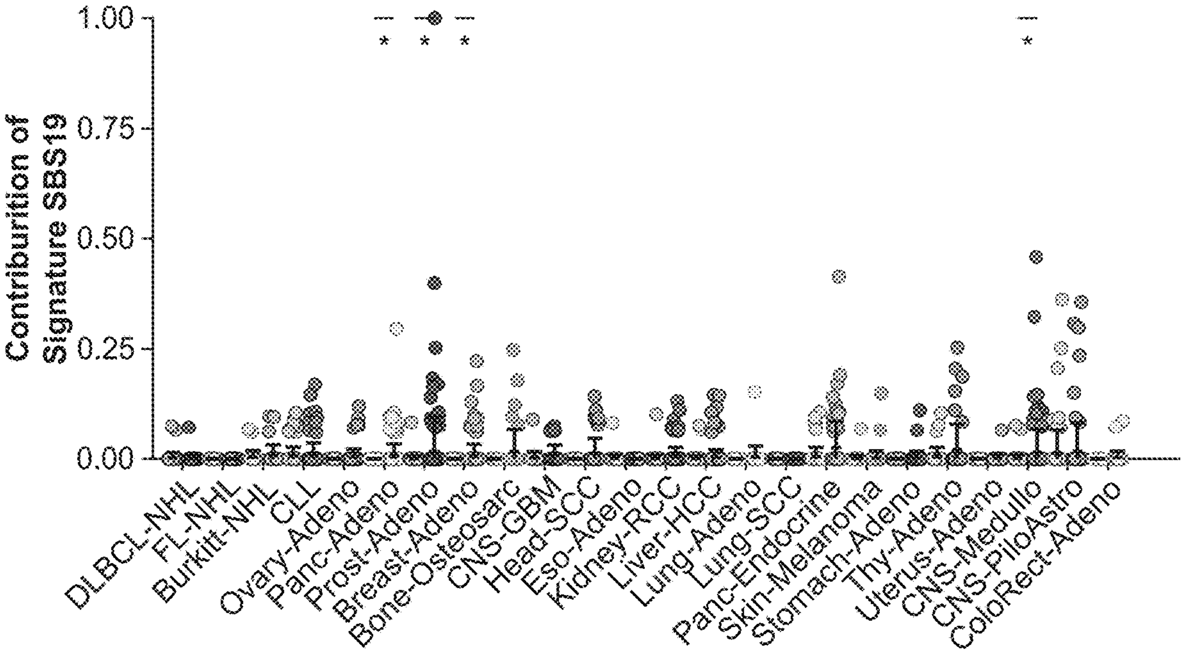
Figure 6Y:
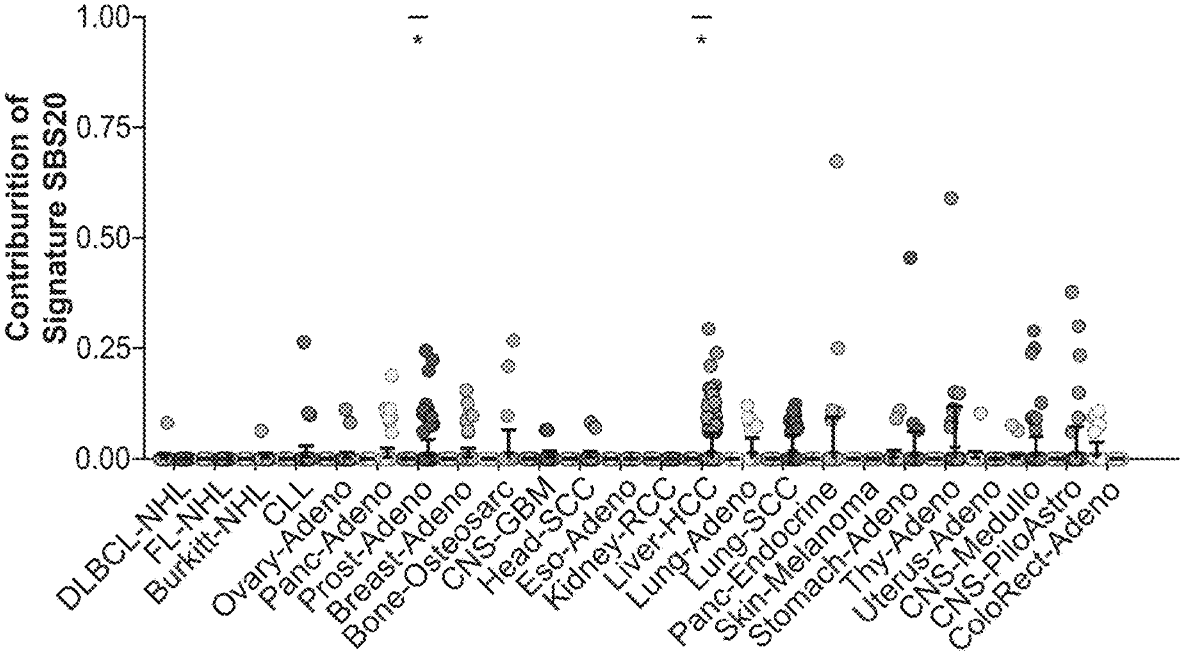
Figure 6Z:
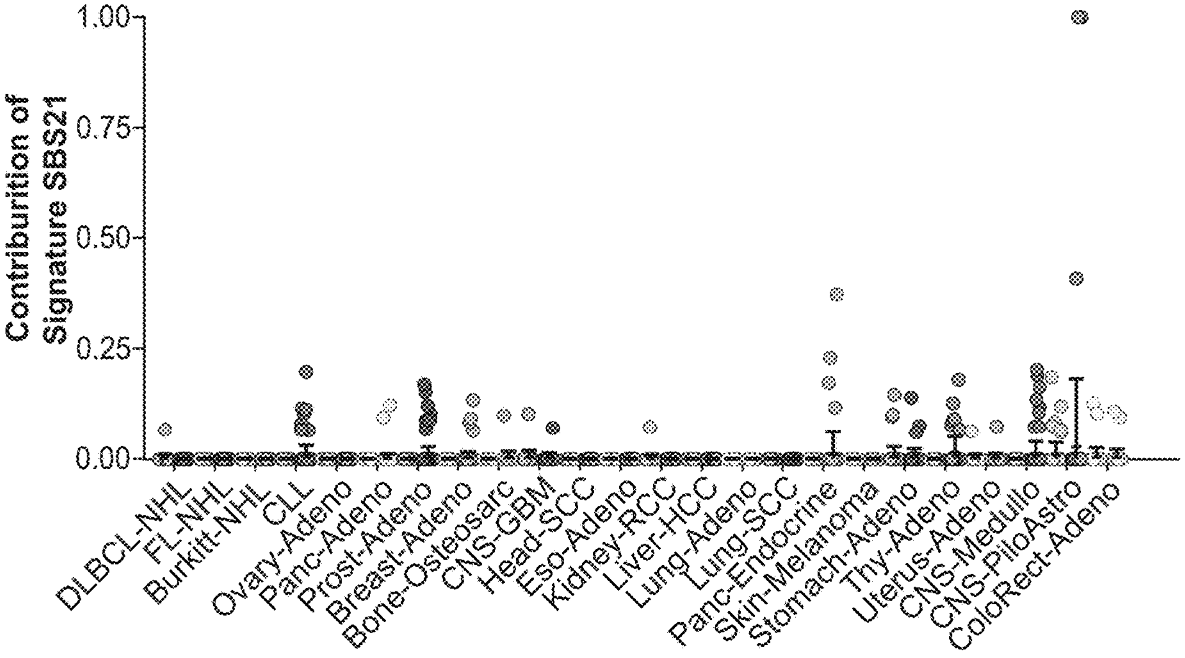
Figure 6A:
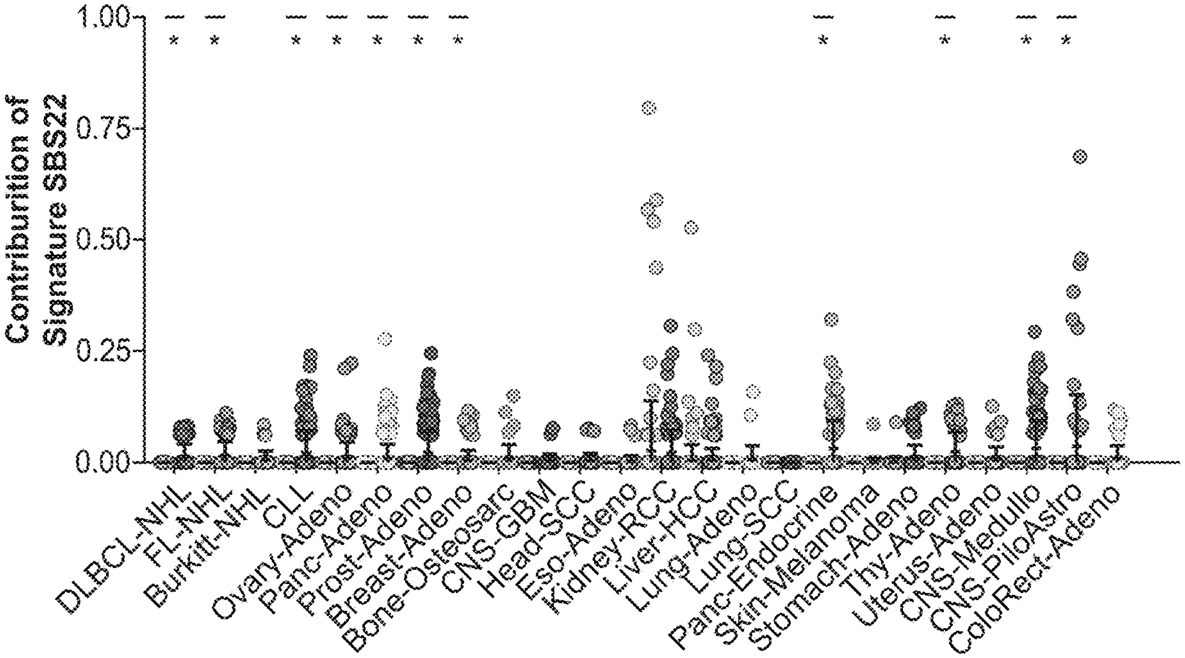
Figure 6B:
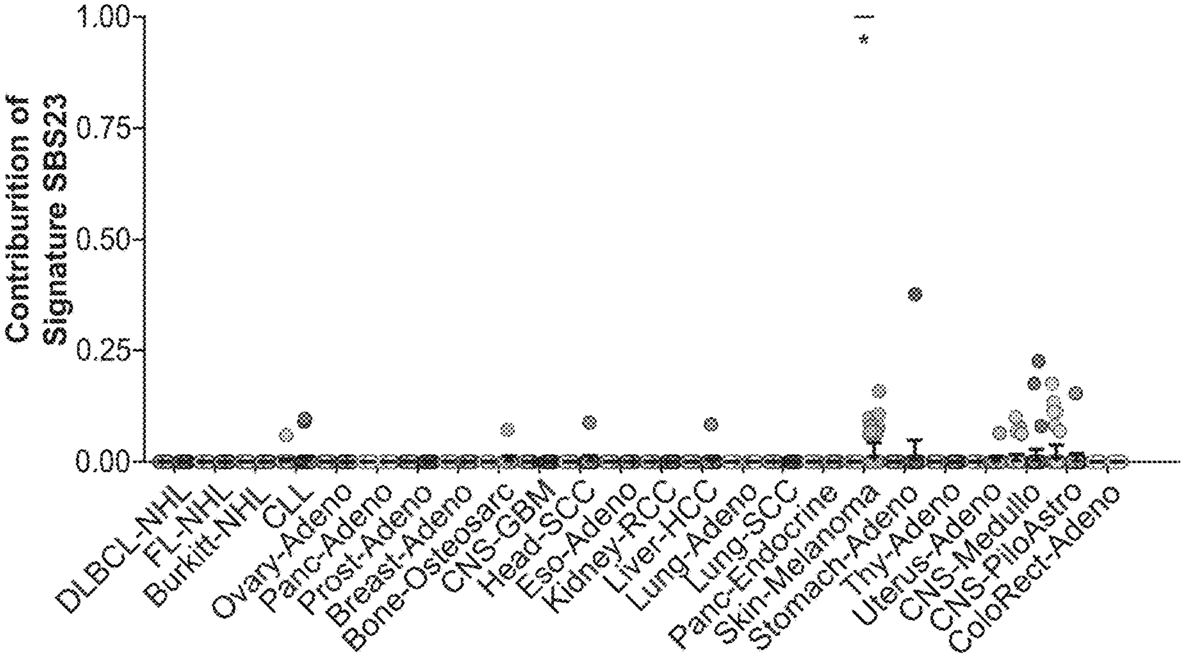
Figure 6C:
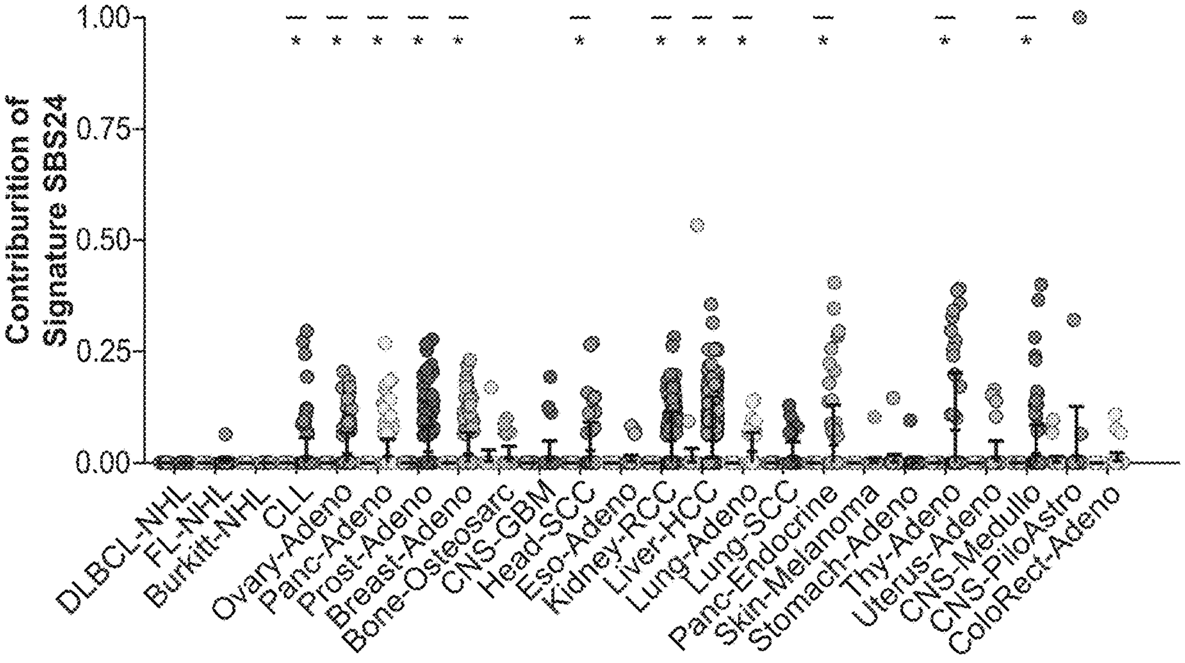
Figure 6D:
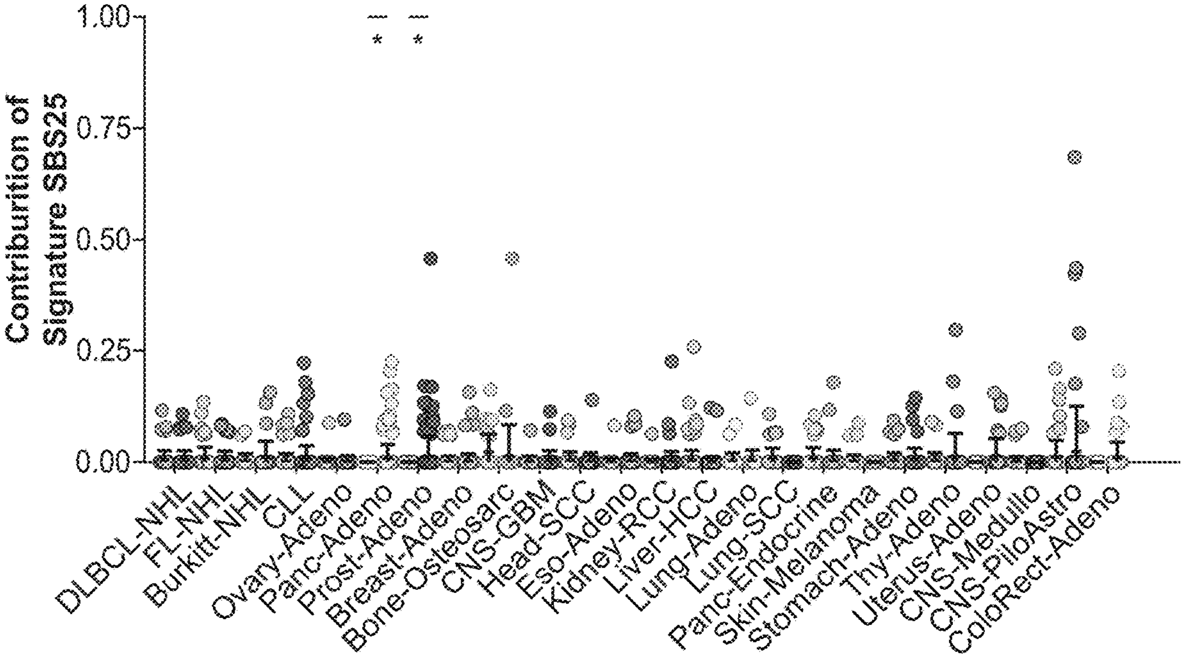
Figure 6E:
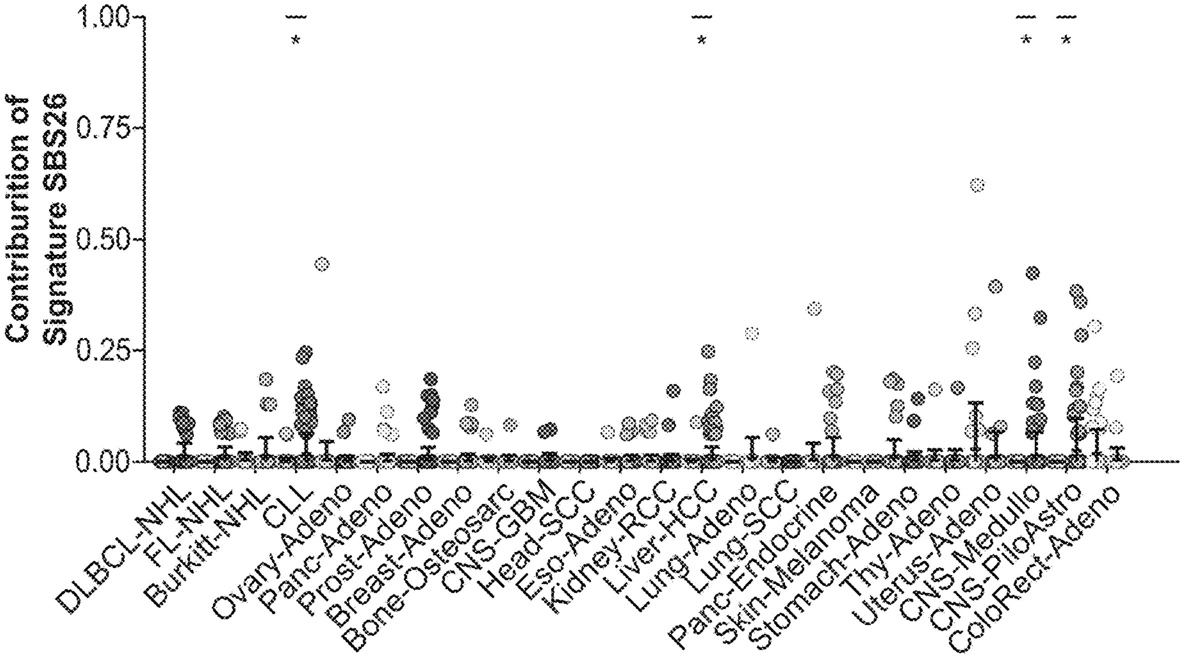
Figure 6F:
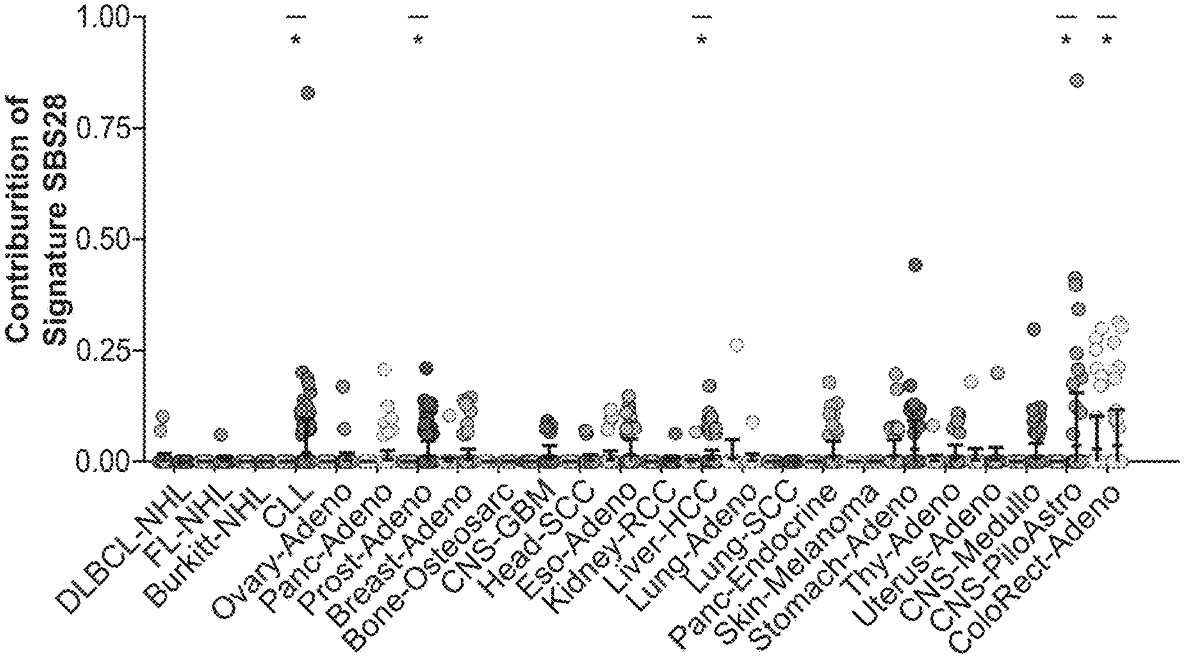
Figure 6G:
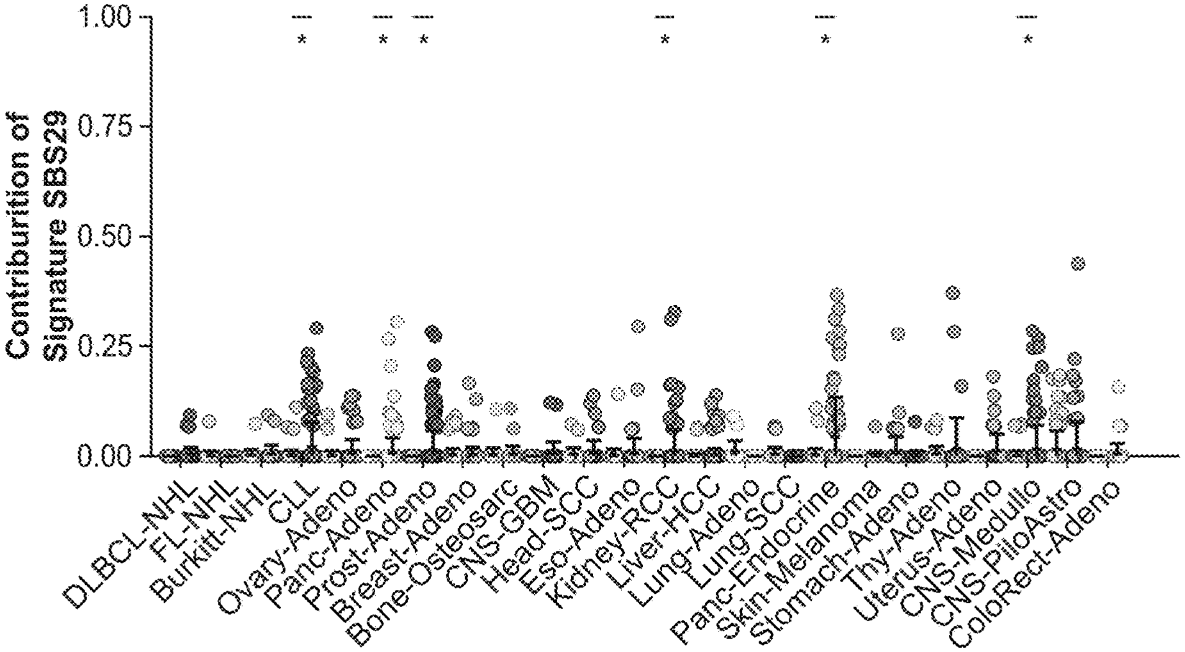
Figure 6H:
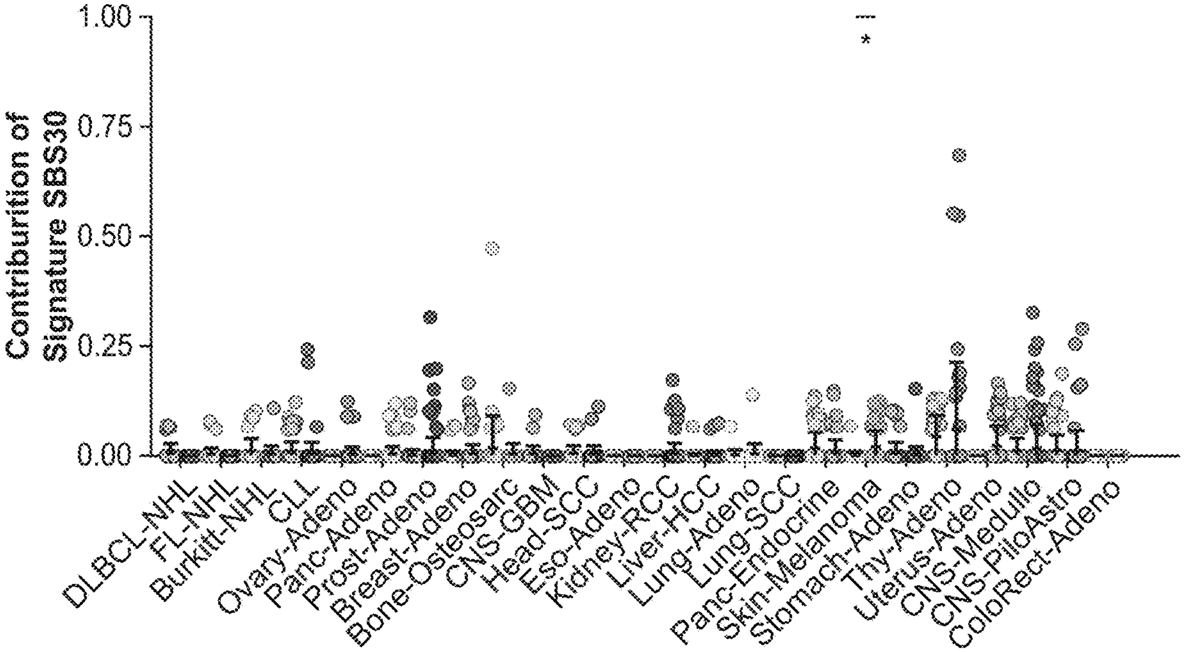
Figure 6I:
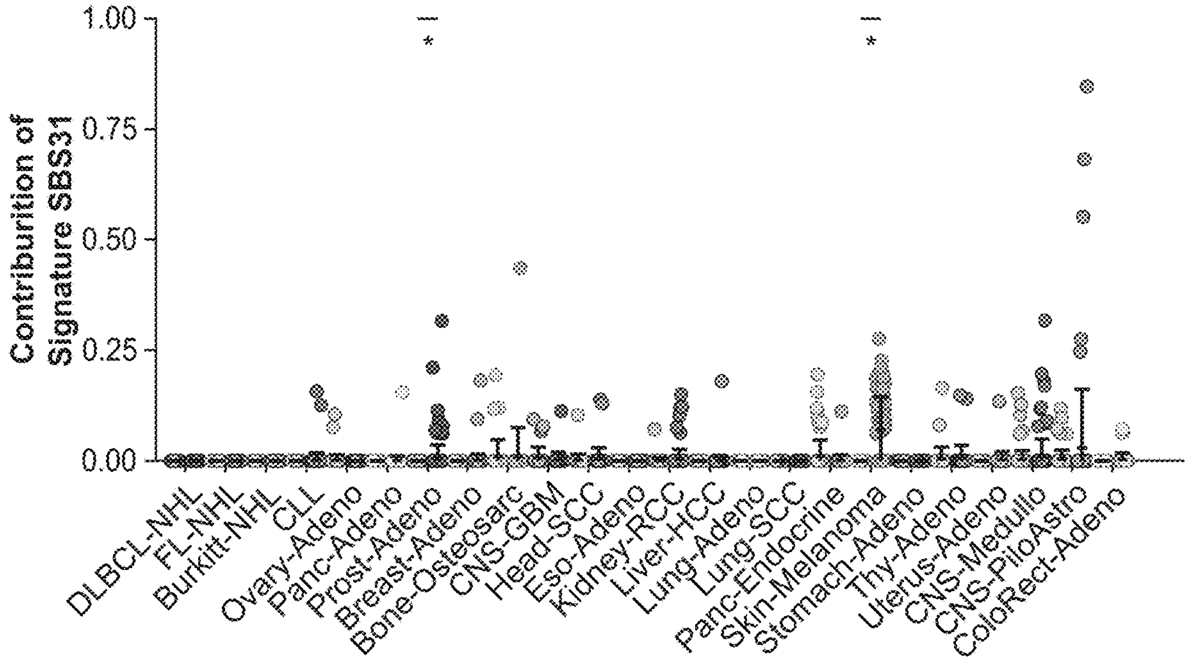
Figure 6J:
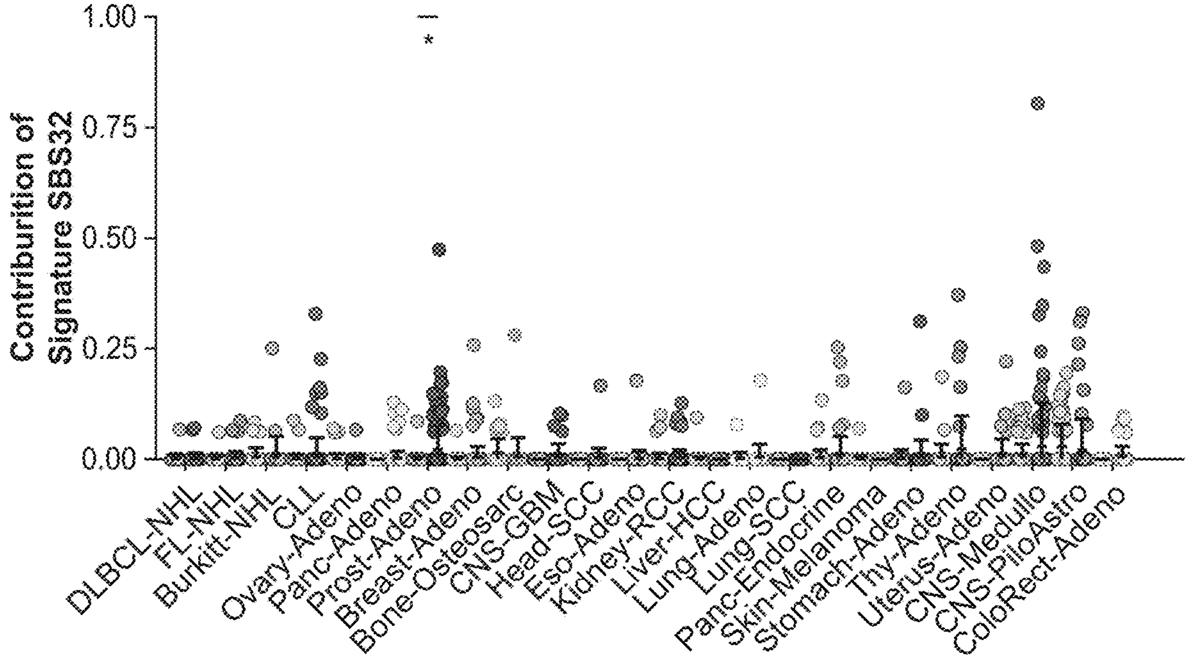
Figure 6K:
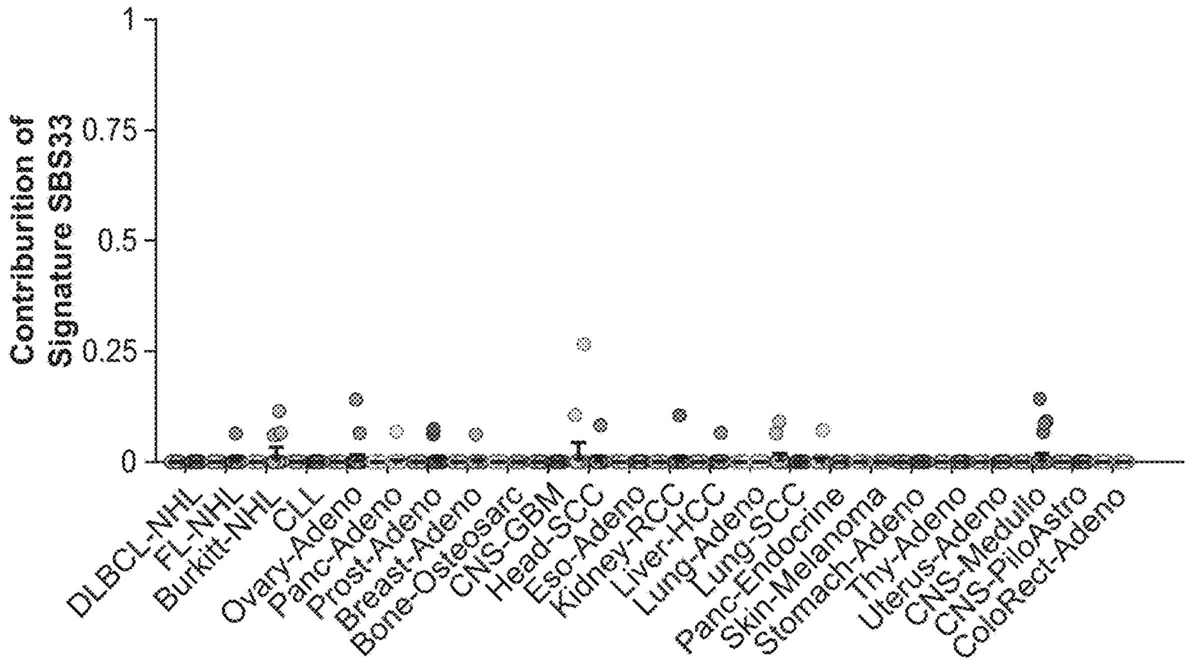
Figure 6L:
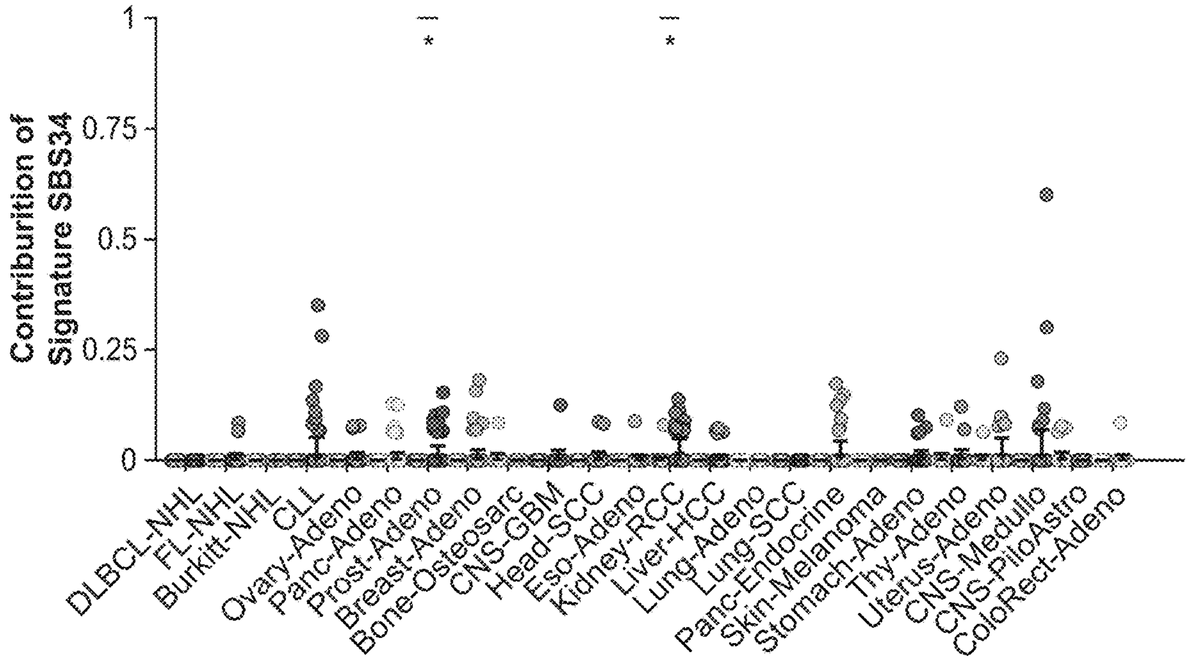
Figure 6M:
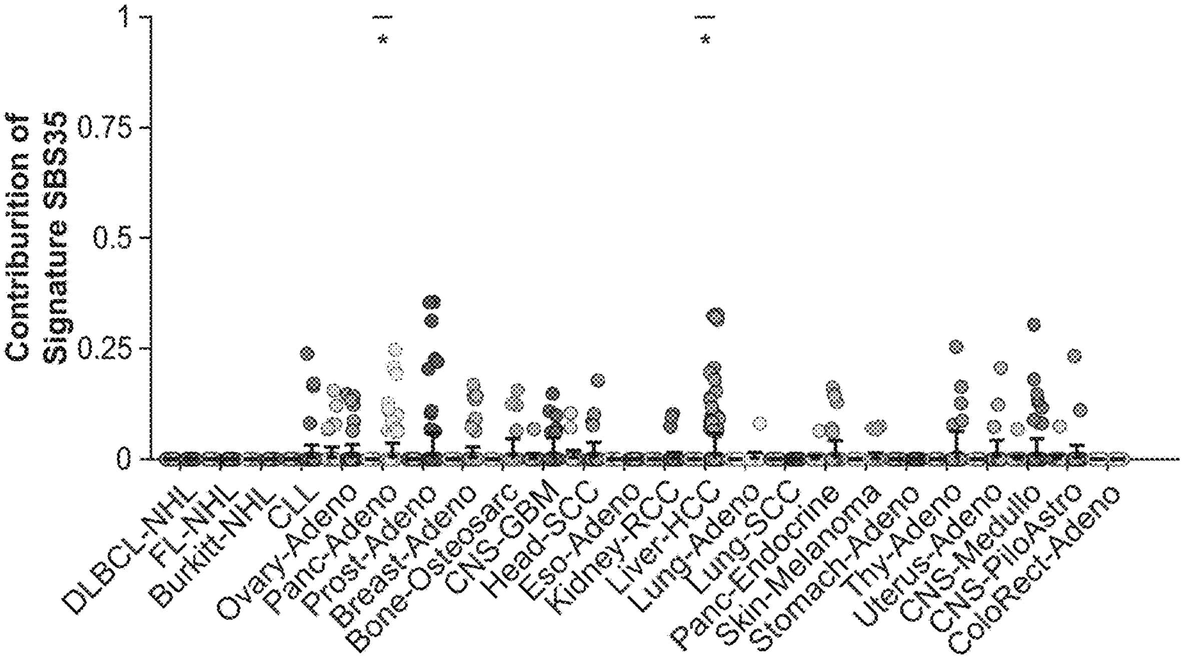
Figure 6N:
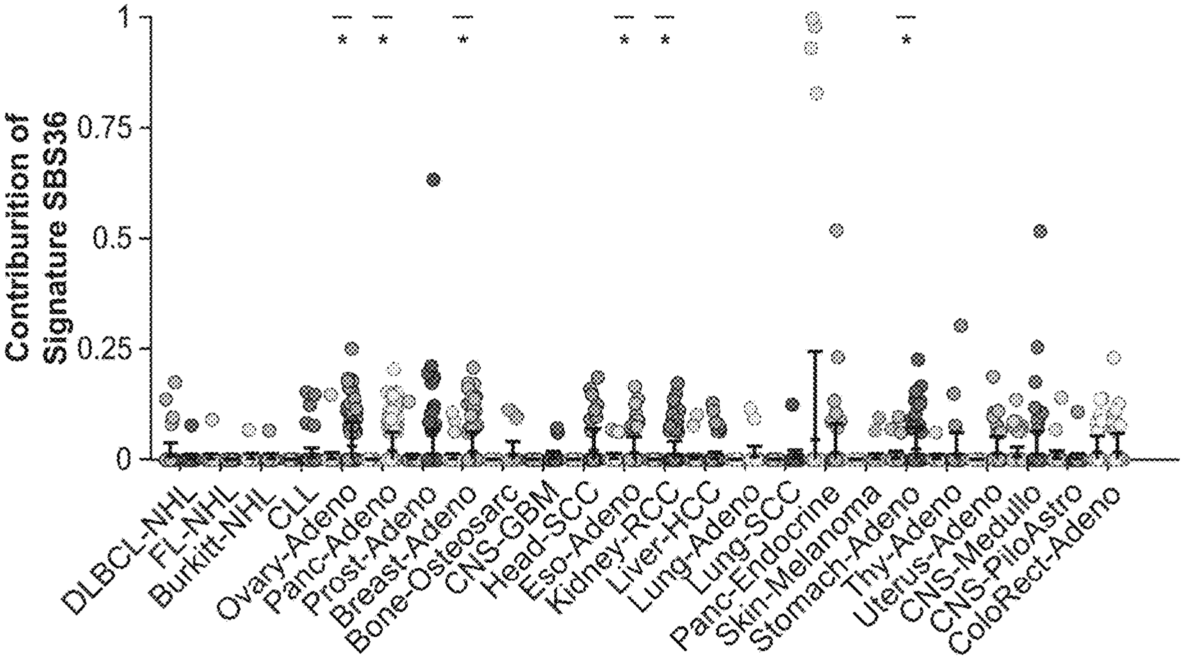
Figure 6O:
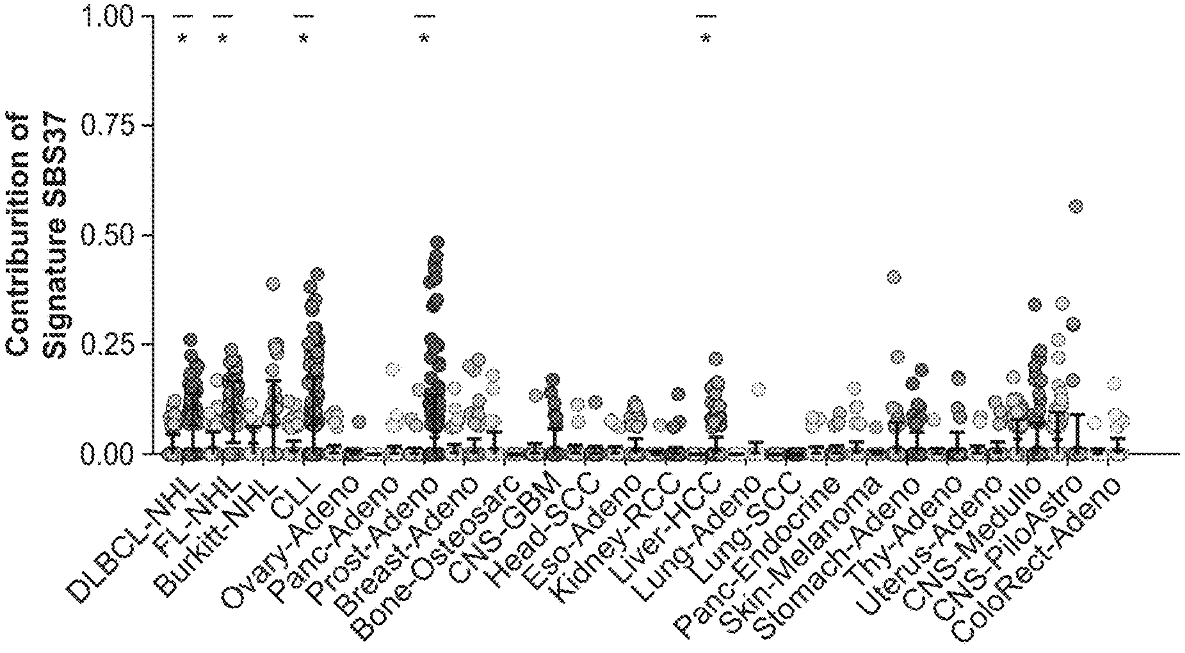
Figure 6P:
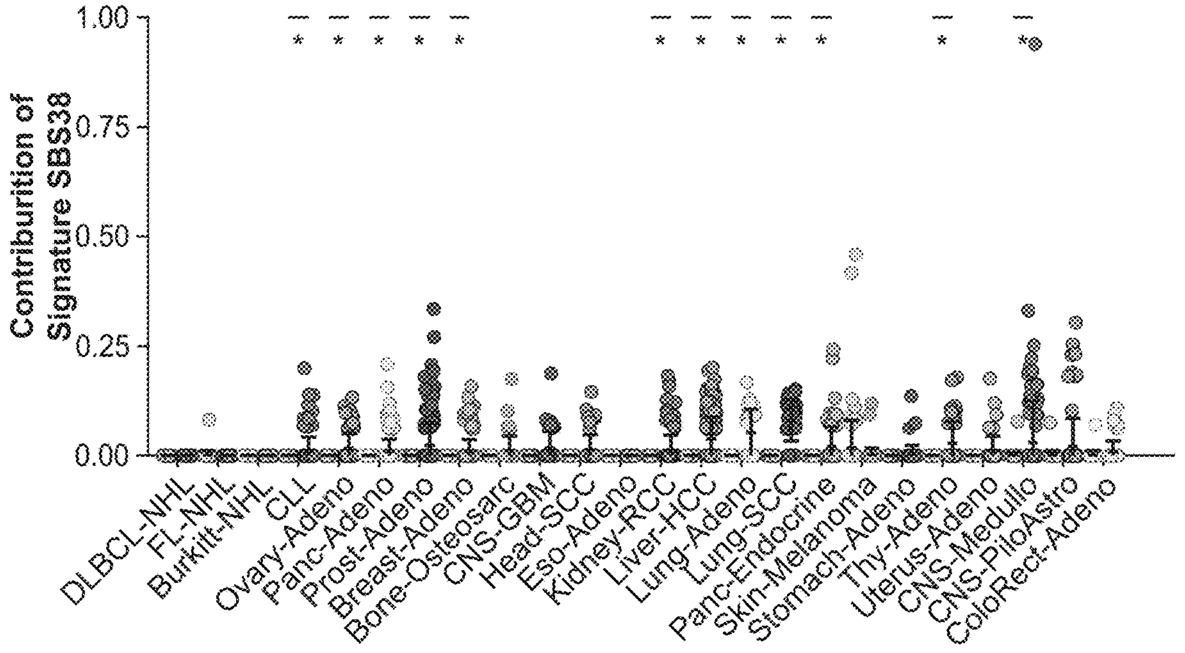
Figure 6Q:
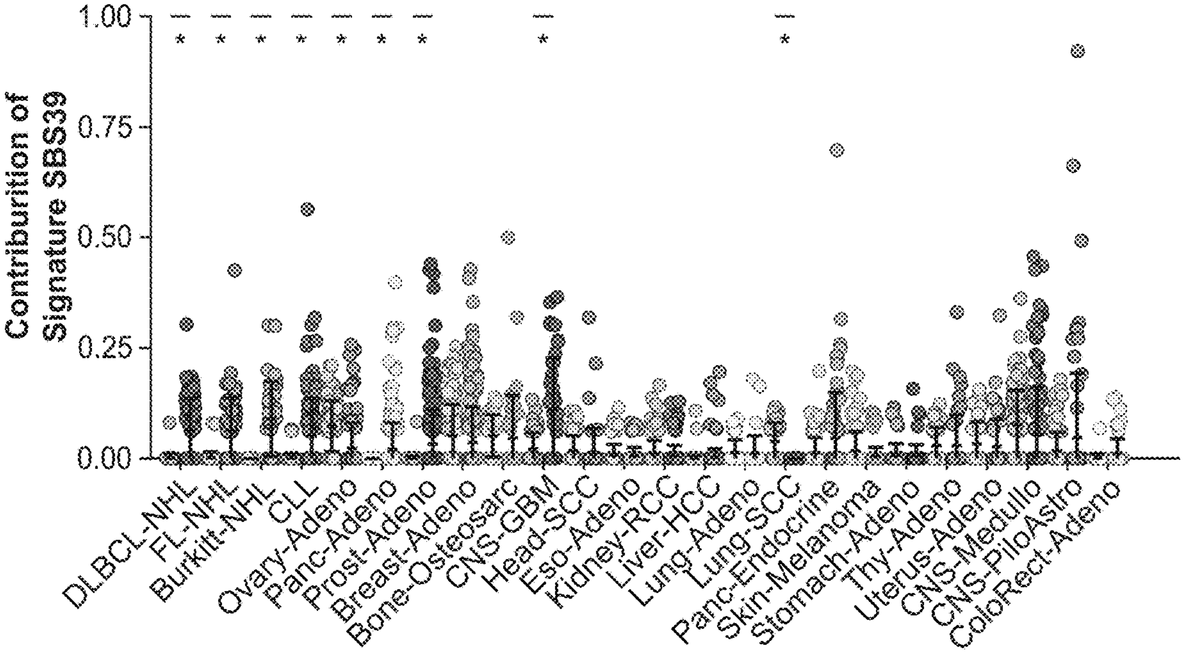
Figure 6R:
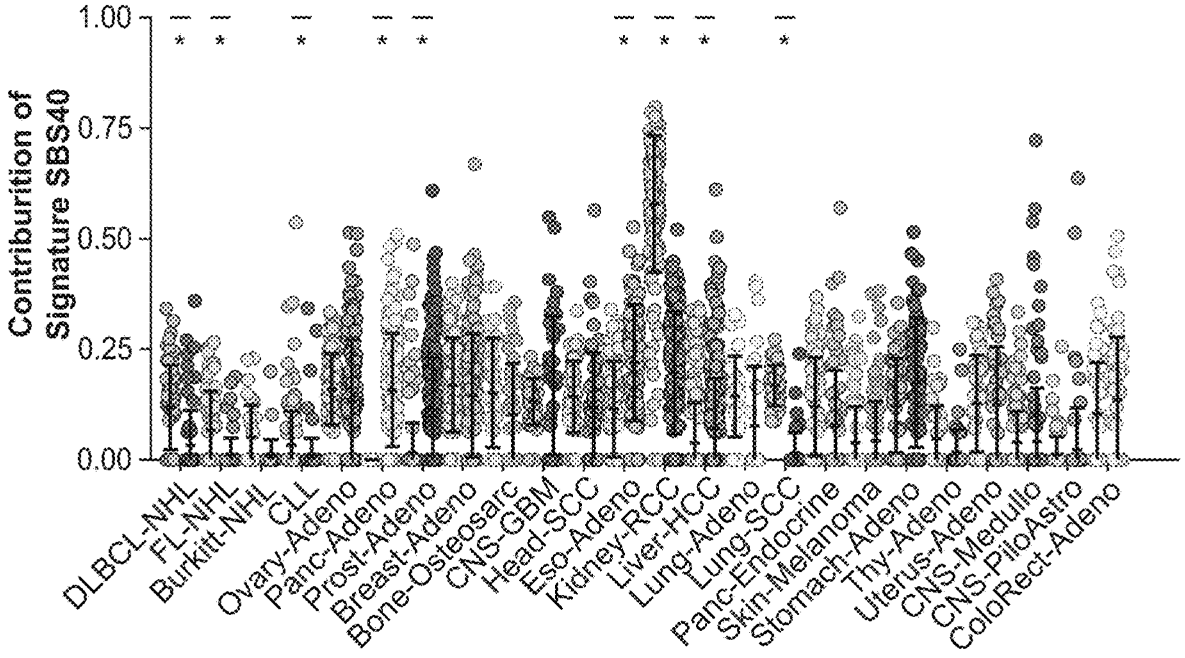
Figure 6S:
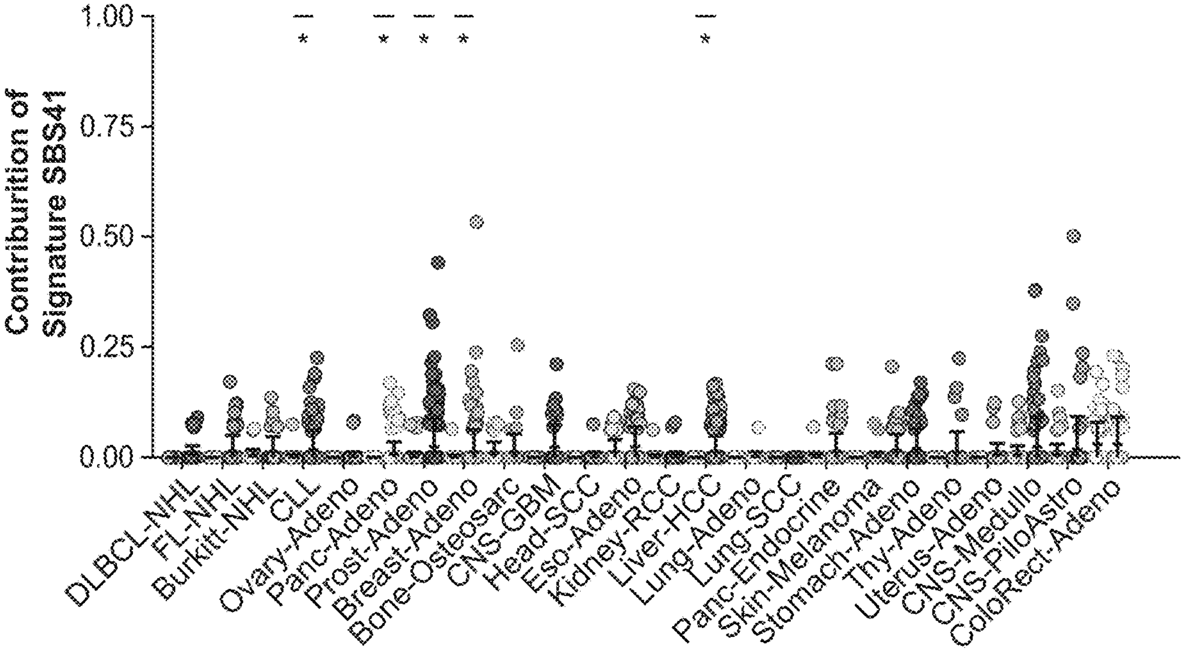
Figure 6T:
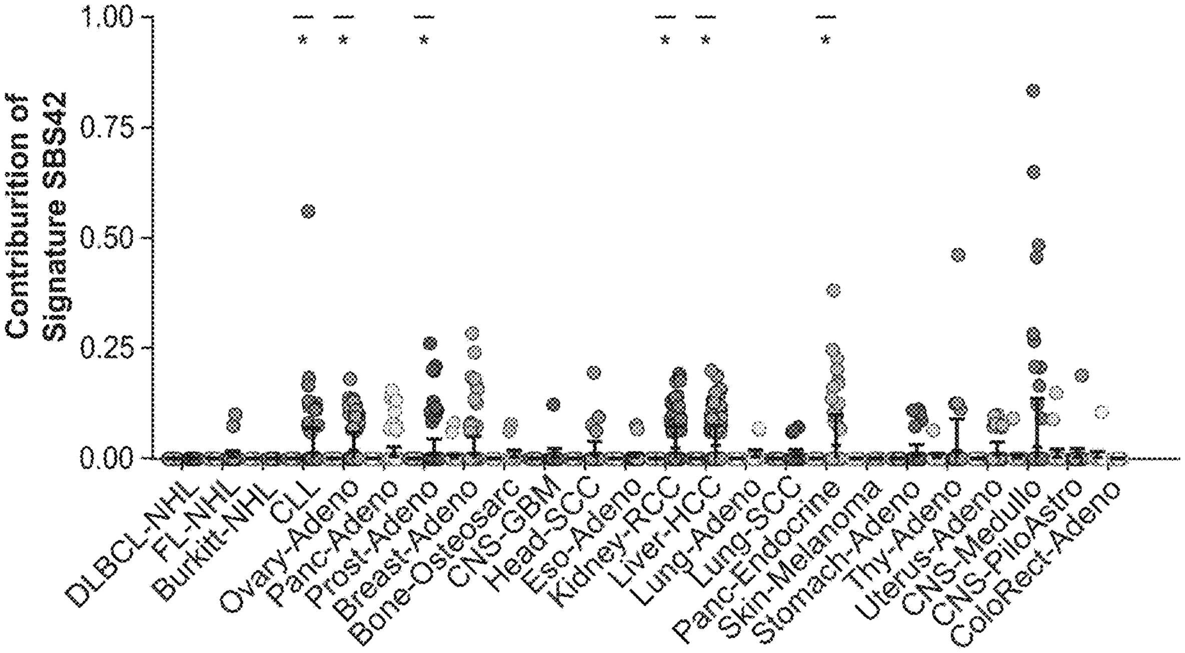
Figure 6U:
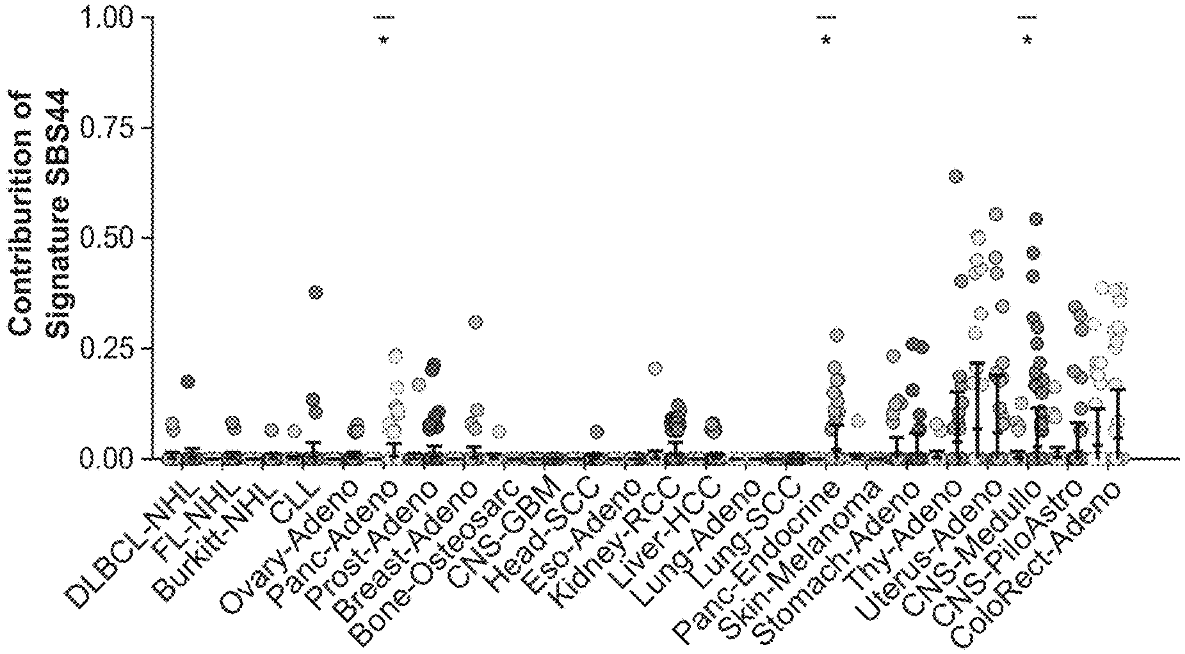
Figure 6V:
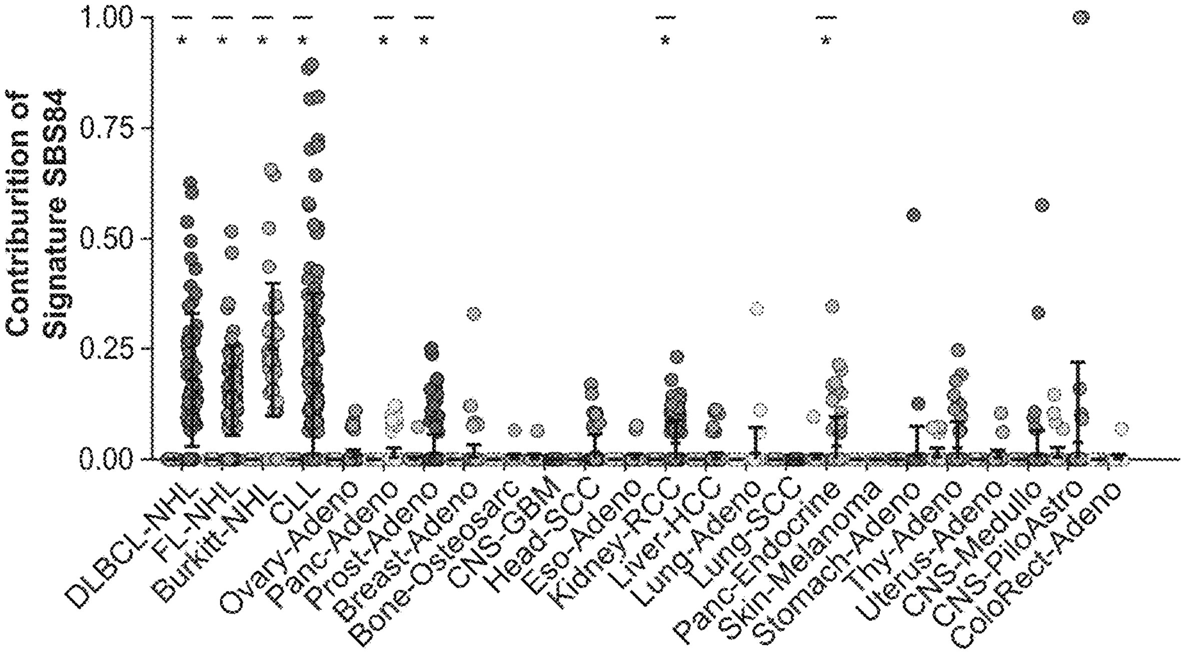
Figure 6W:
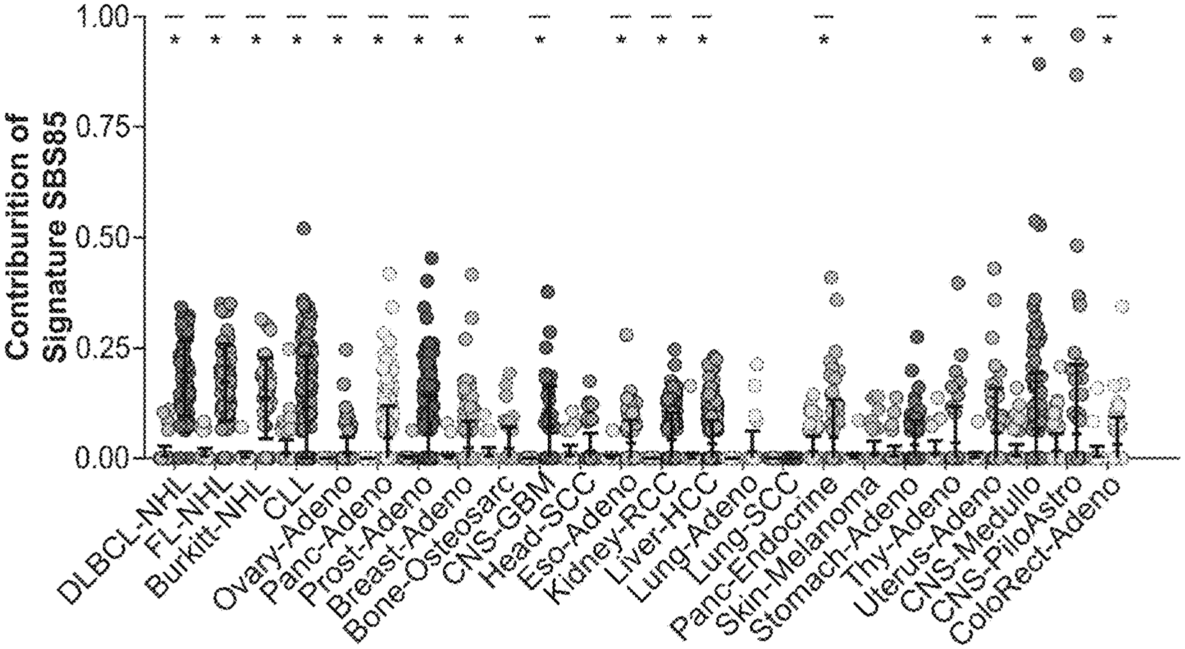

To investigate the origin of PVs, the single base substitution (SBS) mutational signatures contributing to SNVs occurring within 170 bp of another SNV, and SNVs occurring in isolation (e.g., not having another SNV within 170 bp) (Example 10) were compared. As expected, PVs were highly enriched in several mutational signatures associated with clustered mutations. Signatures of clustered mutations associated with activity of AID (SBS84 and SBS85) were significantly enriched in PVs from B-cell lymphomas and CLL, while signatures associated with activity of APOBEC3B (SBS2 and SBS13)—another mechanism of kataegis hypermutation—were significantly enriched in PVs from multiple solid cancer histologies, including ovarian, pancreatic, prostate, and breast adenocarcinomas (FIG. 1C and FIGS. 6A-6WW). Signatures of clustered mutations associated with activity of AID (SBS84 and SBS85) were enriched in PVs found in lymphomas and CLL, while signatures associated with activity of APOBEC3B (SBS2 and SBS13) were significantly enriched in breast cancer (FIG. 1C and FIGS. 6A-6WW). PVs from multiple tumor types were also associated with SBS4, a signature associated with tobacco use. Furthermore, among PVs across multiple tumor histologies, it was observed that novel enrichments in several other signatures without clearly associated mechanisms (e.g., SBS24, SBS37, SBS38, and SBS39). In contrast, aging-associated mutational signatures such as SBS1 and SBS5 were significantly enriched in isolated SNVs.

Example 3: PVs Occur in Stereotyped Genomic Regions in Lymphoid Cancers

Figure 7:
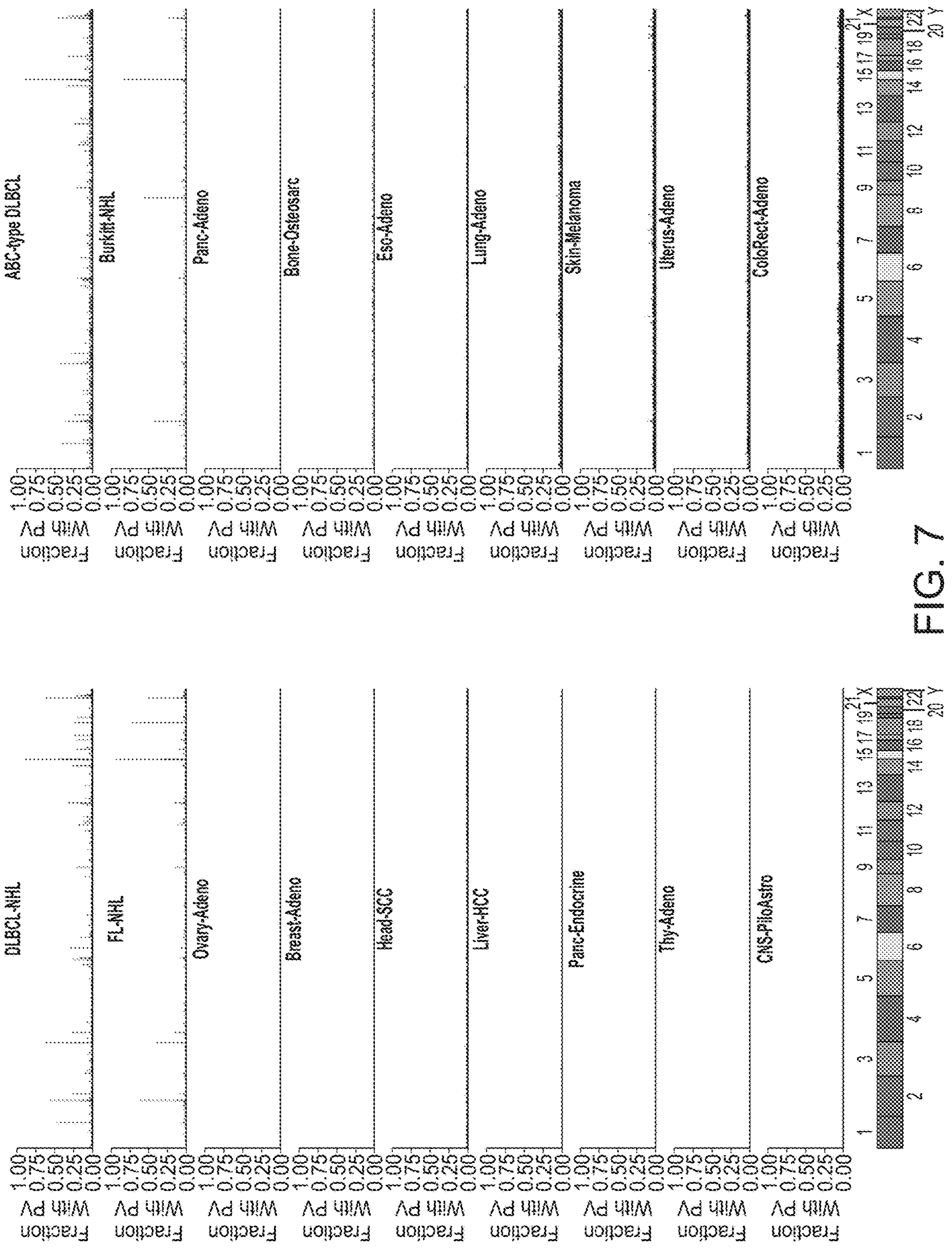
FIG. 7 illustrates distribution of PVs in stereotyped regions across the genome. Bar plots show the distribution of PVs occurring in stereotyped regions across the genome of multiple cancer types. In this plot, the genome was divided into 1000 bp bins, and the fraction of samples of a given histology with a PV in each 1000 bp bin was calculated. Only bins that have at least a 2 percent recurrence frequency in any cancer subtype are shown. Histologies shown are as in FIG. 1E; activated B-cell (ABC) and germinal center B-cell (GCB) subtypes of DLBCL are also shown.
Figure 7:
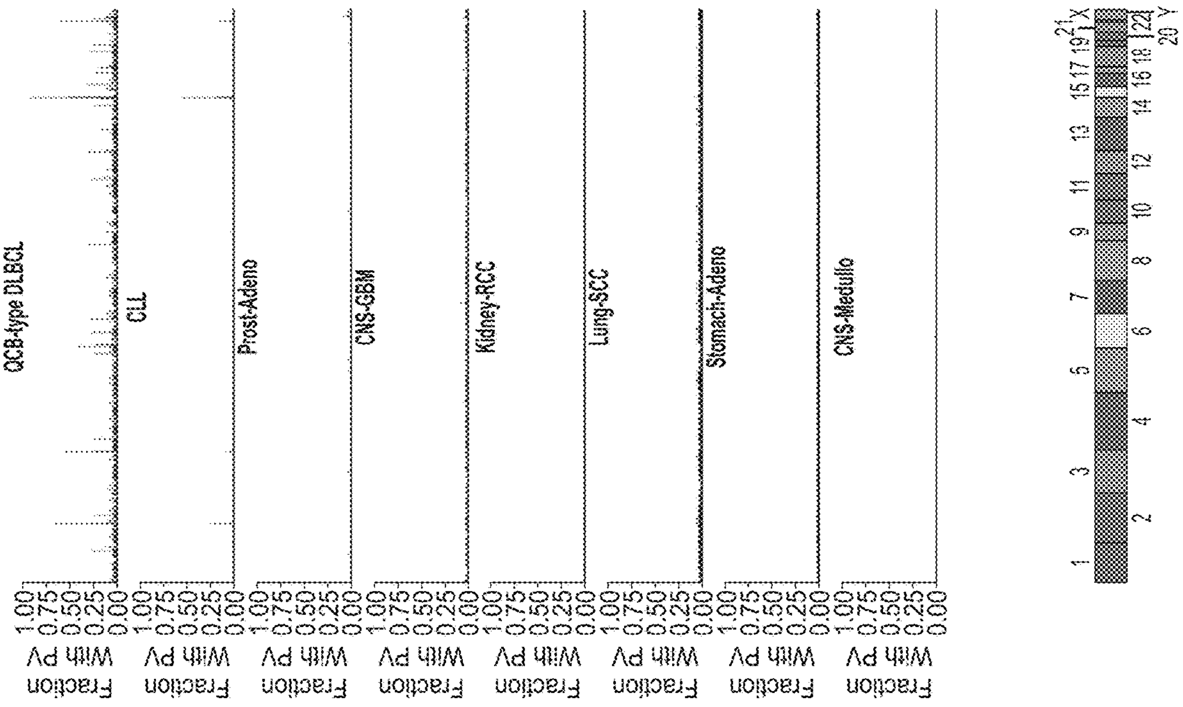

To assess the genomic distribution of putative PVs, these events were first binned into 1-kb regions to visualize their frequency across tumor types. It was observed that a strikingly stereotyped distribution of PVs in individual lymphoid neoplasms (e.g., DLBCL, FL, Burkitt lymphoma (BL), and chronic lymphocytic leukemia (CLL); FIG. 1D and FIG. 7). In contrast, non-lymphoid cancers generally did not exhibit substantial recurrence of clustered PVs in stereotyped regions. This lack of stereotype in the position of PVs was true even when considering melanomas and lung cancers, diseases with frequent PVs.

Figure 8A:
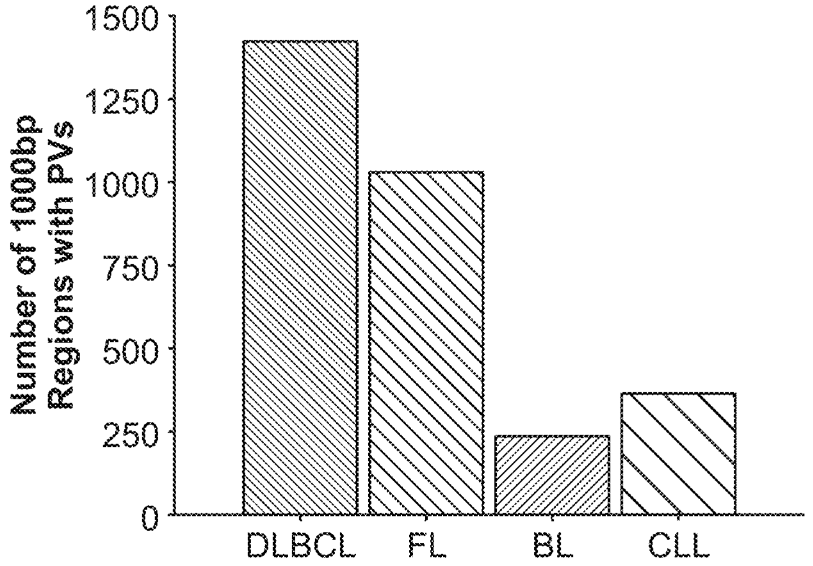
FIGS. 8A-8E illustrate quantity and genomic location of PVs from WGS in lymphoid malignancies.

Notably, the majority of hypermutated regions were shared between all three lymphoma subtypes, with the highest densities seen in known targets of aSHM including BCL2, BCL6, and MYC, as well as the immunoglobulin (Ig) loci encoding the heavy and light chains IGH, IGK, and IGL (Table 2). Strikingly, certain regions within Ig loci were densely mutated in nearly all lymphoma patients as well as in patients with CLL (FIG. 1D). Among lymphoma subtypes, DLBCL tumors harbored the most 1-kb regions recurrently containing PVs (FIG. 8A), consistent with the highest number of recurrently mutated genes being observed in this tumor type. In total, 1639 unique 1-kb regions recurrently containing PVs in B-lymphoid malignancies were identified. Among these lymphoma-associated 1-kb regions, nearly one-third fell into genomic areas previously associated with physiological or aberrant SHM in B-cells. Specifically, 19% (315/1639) were located in Ig regions, while 13% (218/1639) were in portions of 68 previously identified targets of aSHM (Table 2). While most PVs fell into noncoding regions of the genome, additional recurrently affected loci not previously described as targets of aSHM, including XBP1, LPP, and AICDA, among others, were also identified.

Figure 8B:
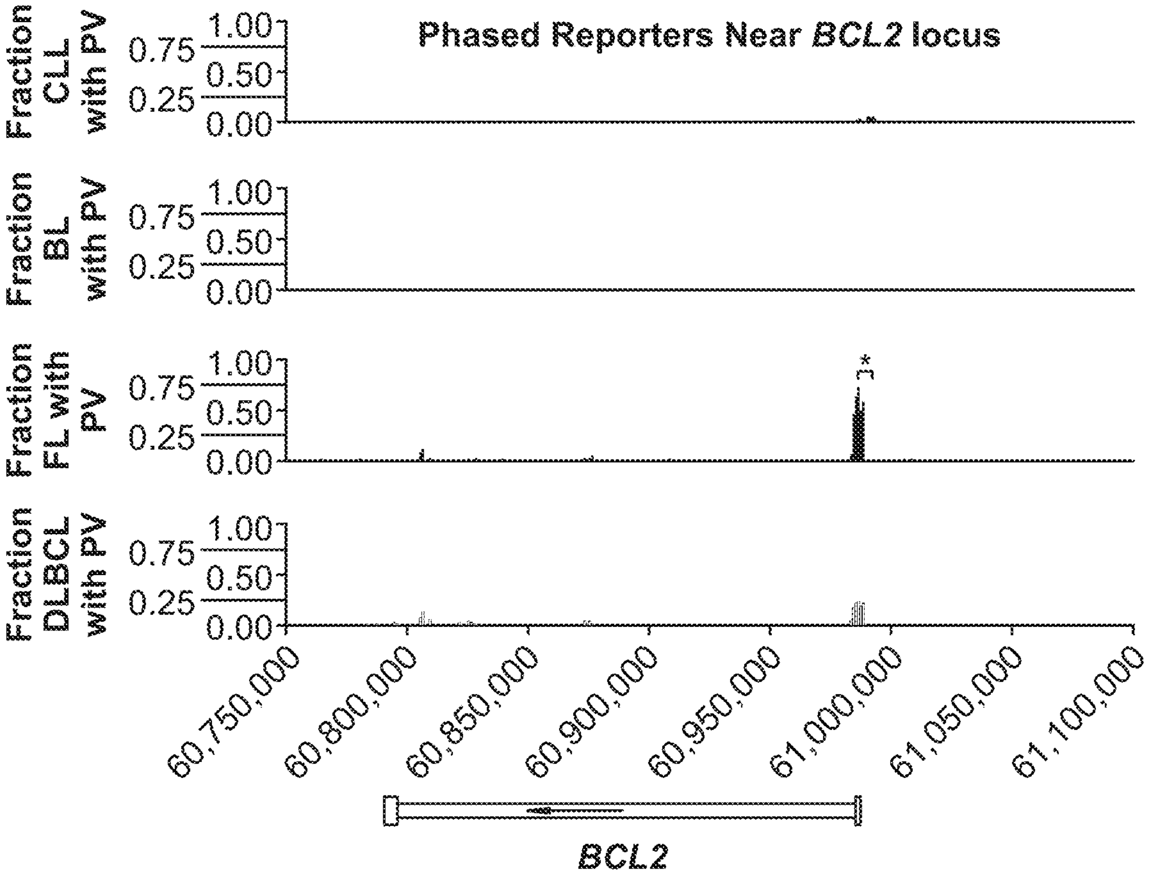
Figure 8C:
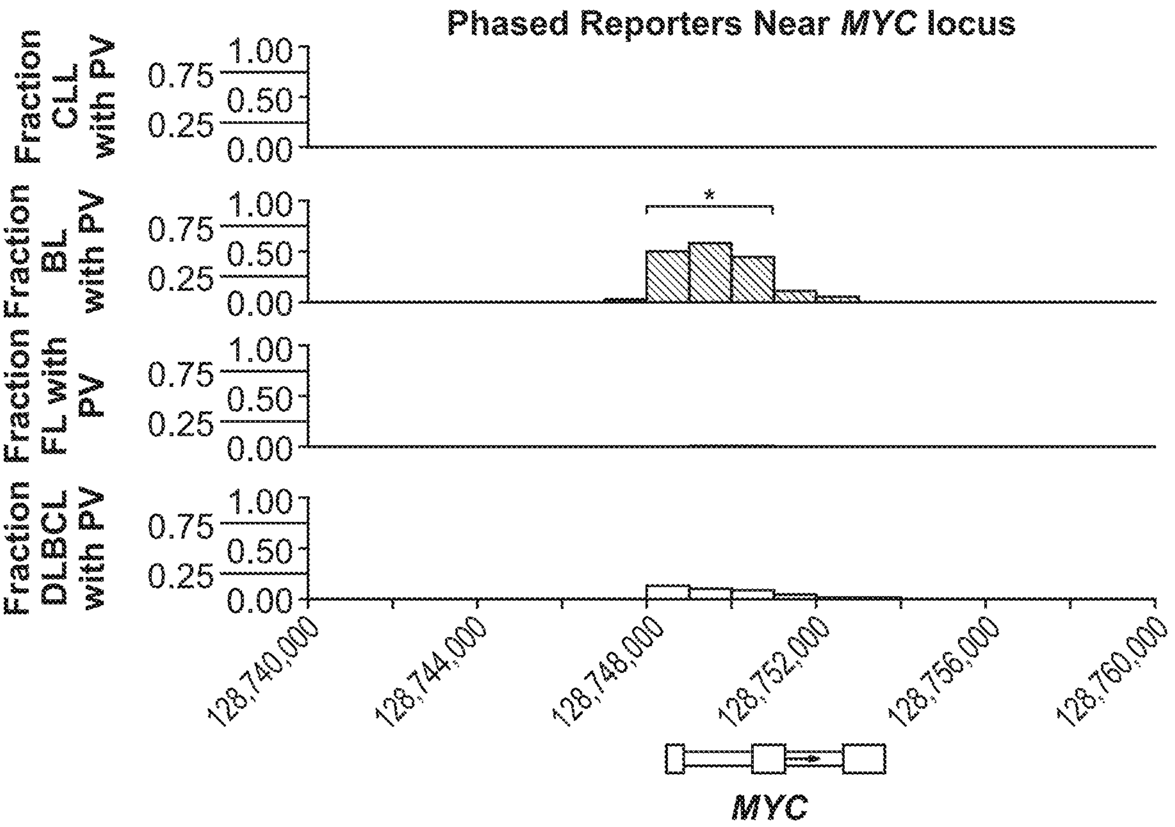
Figure 8D:
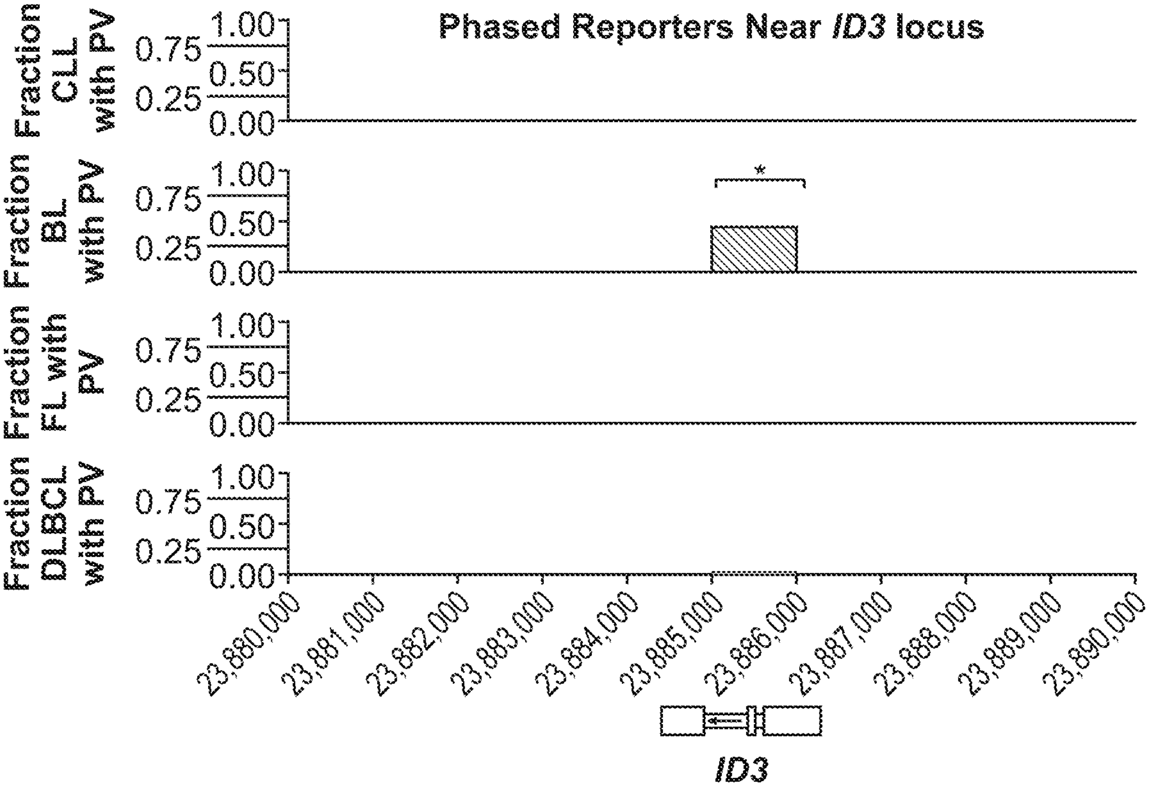
Figure 8E:
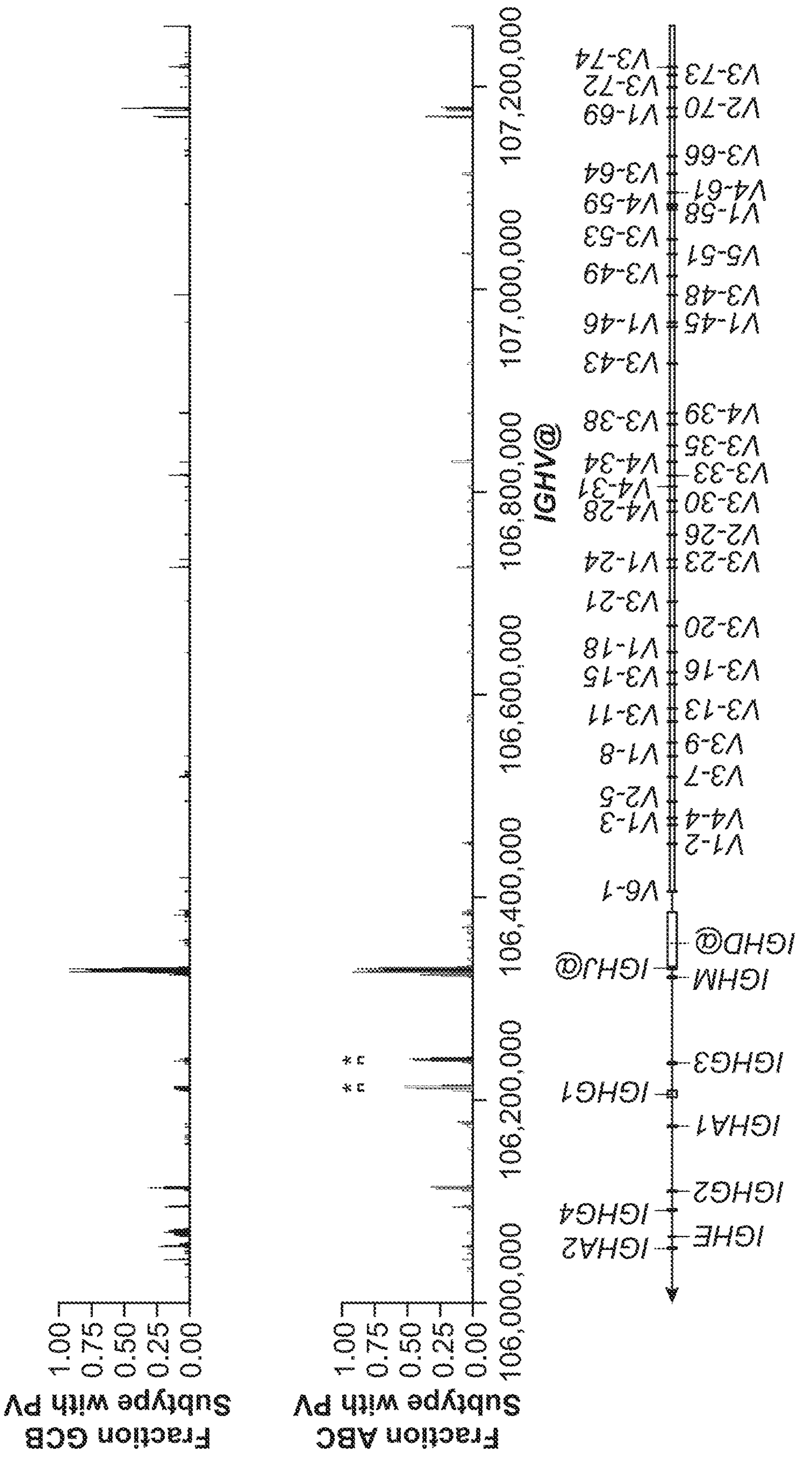

The distribution of PVs within each lymphoid malignancy correlated with oncogenic features associated with the distinct pathophysiology of the corresponding disease. For example, cases of FL—where more than 90% of tumors harbor oncogenic BCL2 fusions—were significantly more likely to contain phased variants in BCL2 than other lymphoid malignancies (FIG. 1D and FIG. 8B). Similarly, significantly more Burkitt lymphomas (BL) harbored PVs in MYC and ID3, two driver genes strongly associated with the BL pathogenesis, than other lymphoid malignancies (FIG. 1D and FIGS. 8C-8D). DLBCL molecular subtypes associated with distinct cell-of-origin also demonstrated distinct distributions of PVs (Table 2). Specifically, while germinal center B-cell like (GCB) and activated B-cell like (ABC) DLBCLs harbored similar frequencies of PVs overall (median 798 vs 516, P=0.37), significant enrichment for PVs in the telomeric IGH class-switch regions (Sγ1, and Sγ3) in ABC-DLBCLs, consistent with previous reports41 (FIG. 8E), was found. Conversely, GCB-DLBCLs harbored more phased haplotypes in centromeric IGH class switch regions (Sα2 and Sε) and in BCL2.

Example 4: Design and Validation of PhasED-Seq Panel for Lymphoma

Figure 2A:
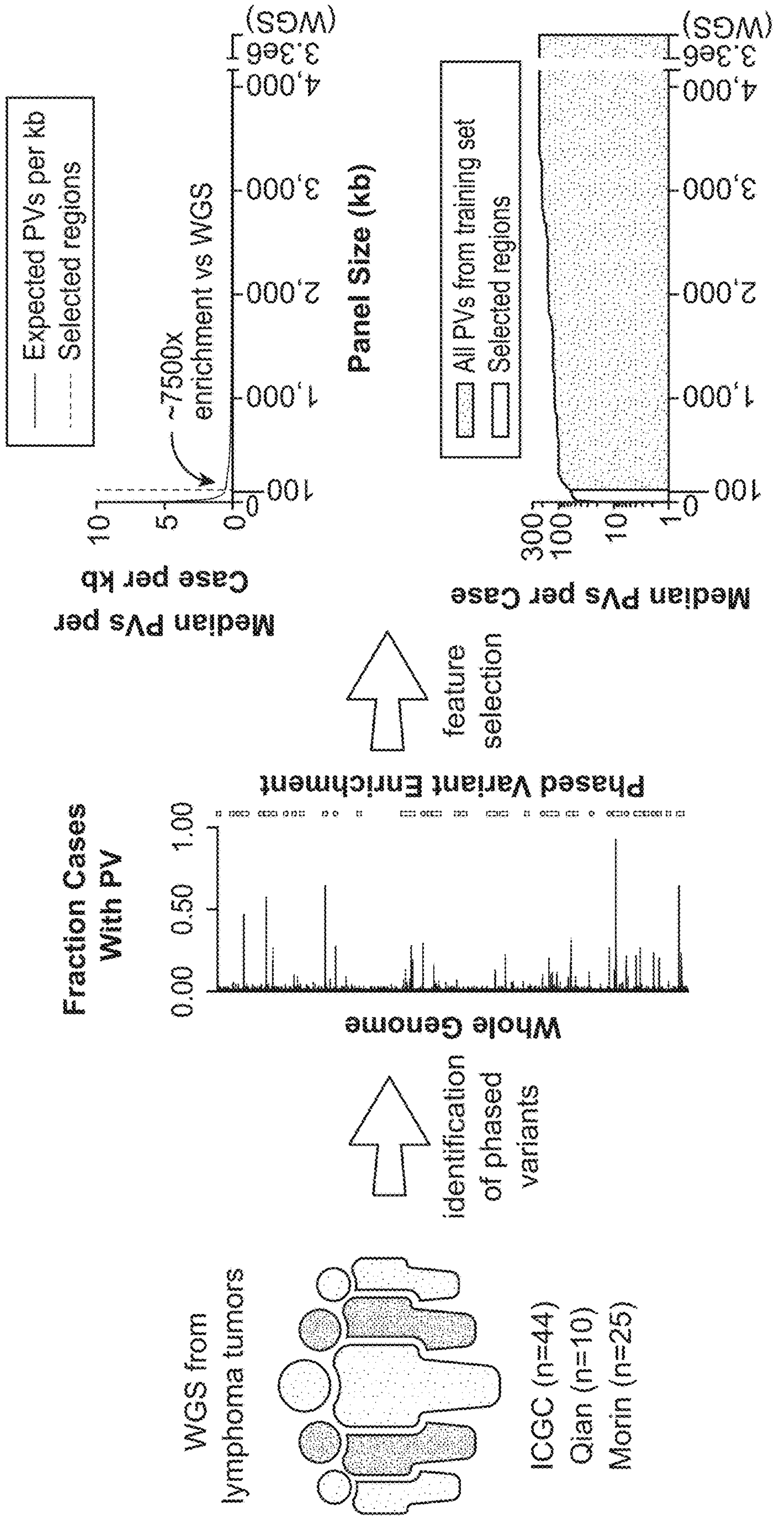
FIGS. 2A-2F illustrate design, validation, and application of phased variant enrichment sequencing.

To validate these PV-rich regions and assess their utility for disease detection from ctDNA, a sequencing panel targeting putative PVs identified within WGS from three independent cohorts of patients with DLBCL, as well as in patients with CLL (FIG. 2A and Example 10) was designed. This final Phased variant Enrichment and Detection Sequencing (PhasED-Seq) panel targeted ~115 kb of genomic space focused on PVs, along with an additional ~200 kb targeting genes that are recurrently mutated in B-NHLs (Table 3). While the 115 kb of space dedicated to PV-capture targets only 0.0035% of the human genome, it captures 26% of phased variants observed in mature B-cell neoplasms profiled by WGS (FIG. 9A), thus yielding a 7500-fold PV enrichment by PhasED-Seq over WGS.

Figure 2B:
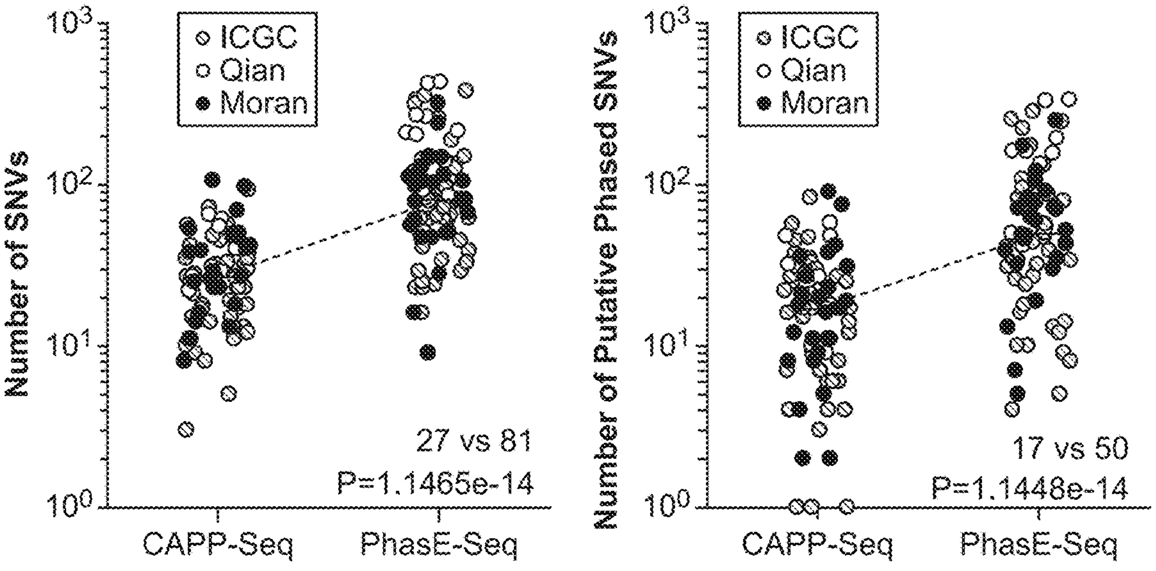
Figure 2C:
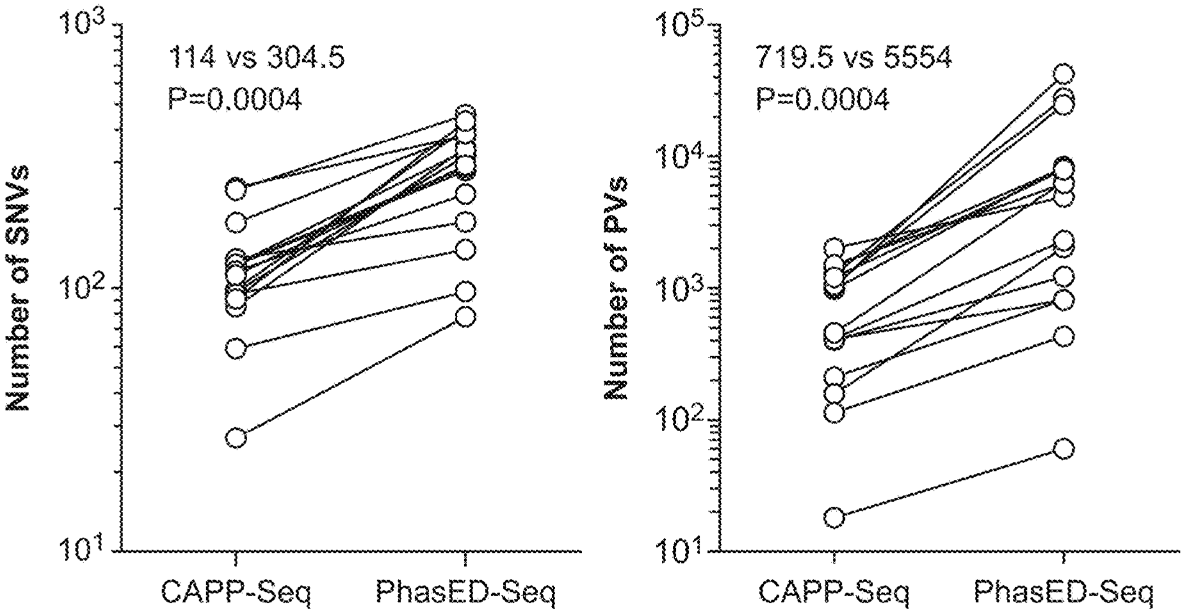
Figure 2D:
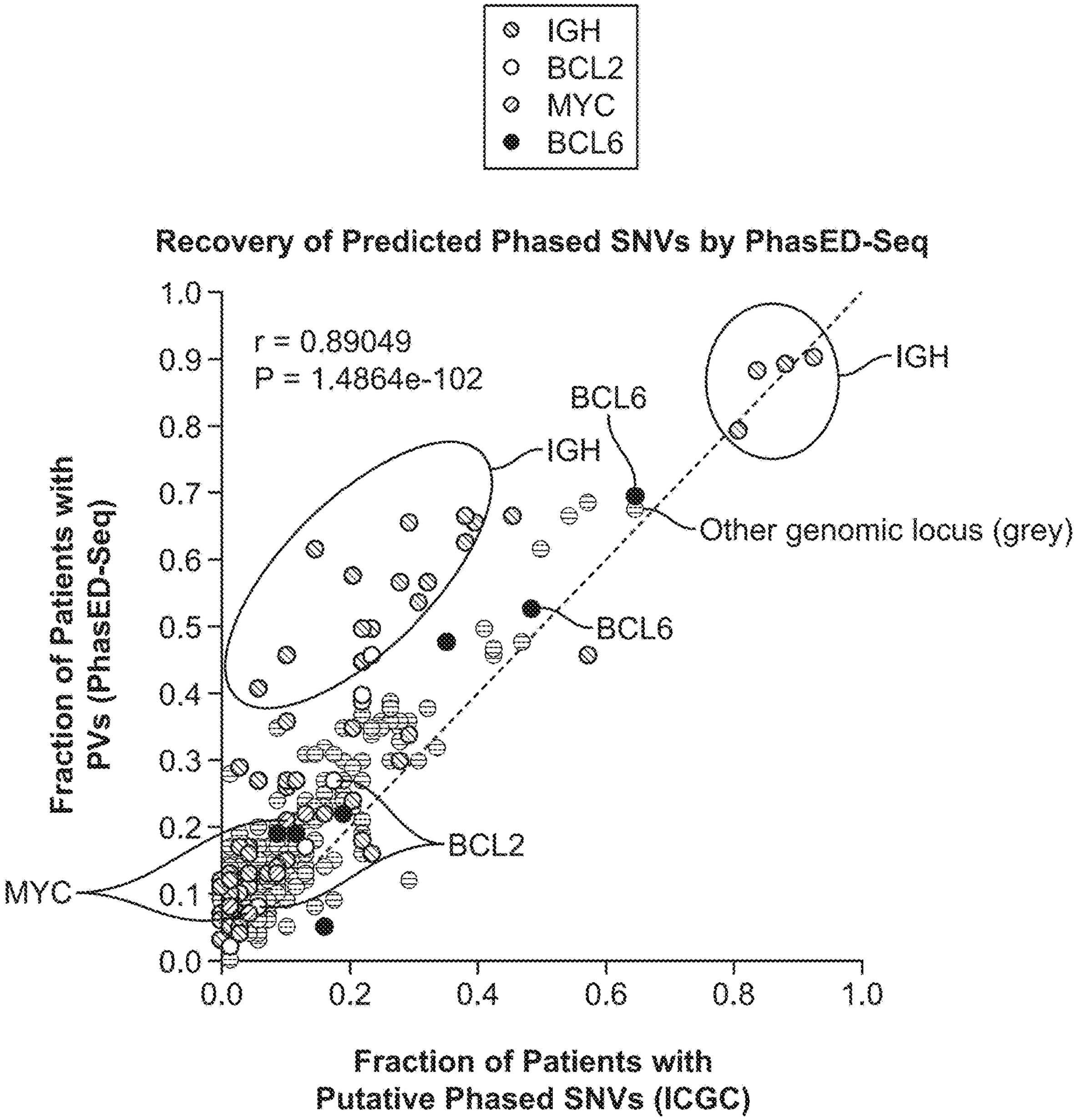
Figure 9A:
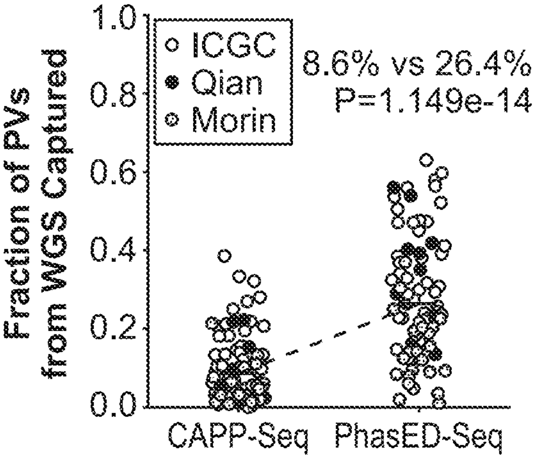
FIGS. 9A-9K illustrate performance of PhasED-Seq for recovery of PVs across lymphomas.
Figure 9B:
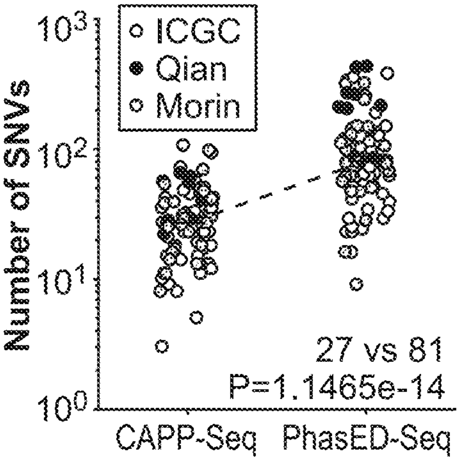
Figure 9C:
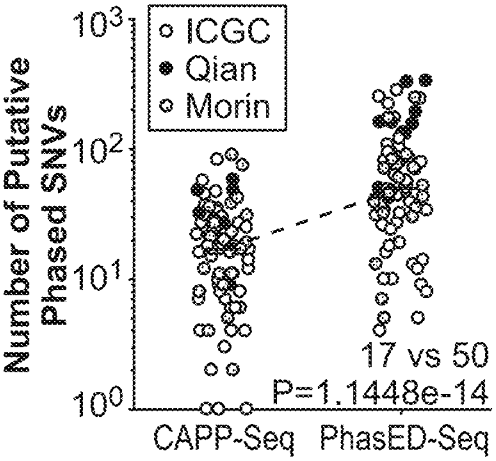
Figure 9D:
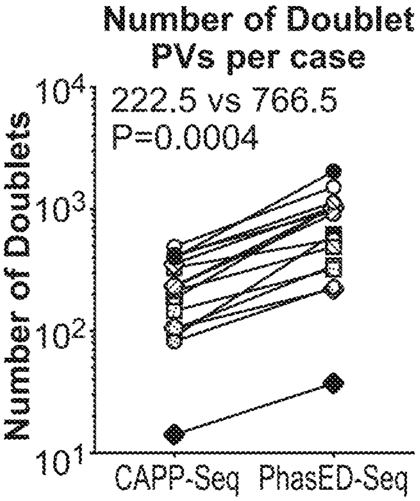
Figure 9E:
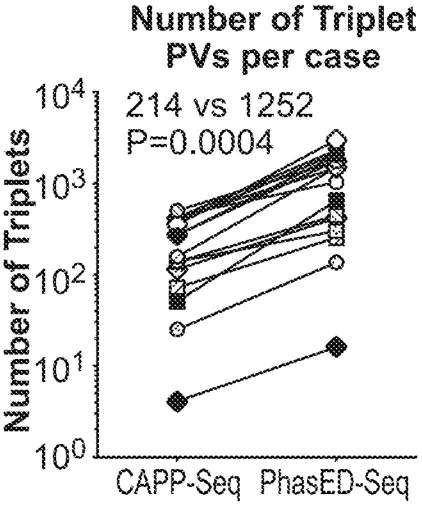
Figure 9F:
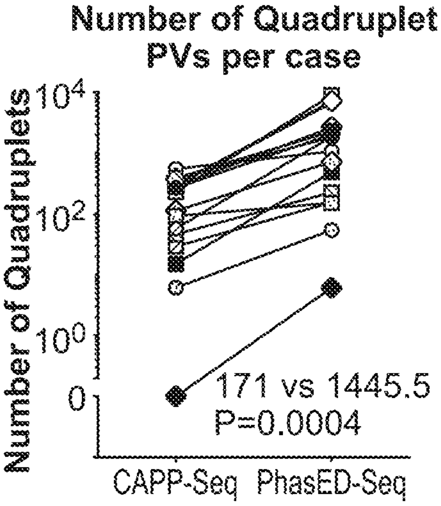
Figure 9G:
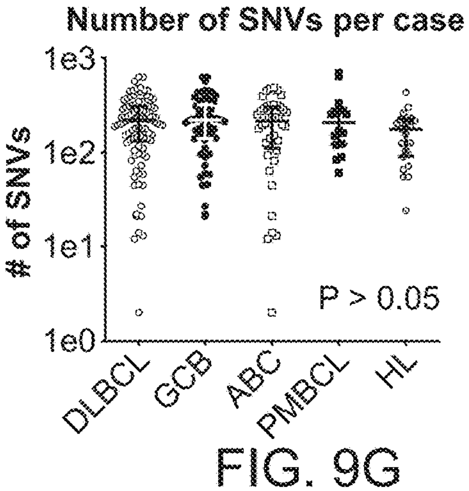
Figure 9H:
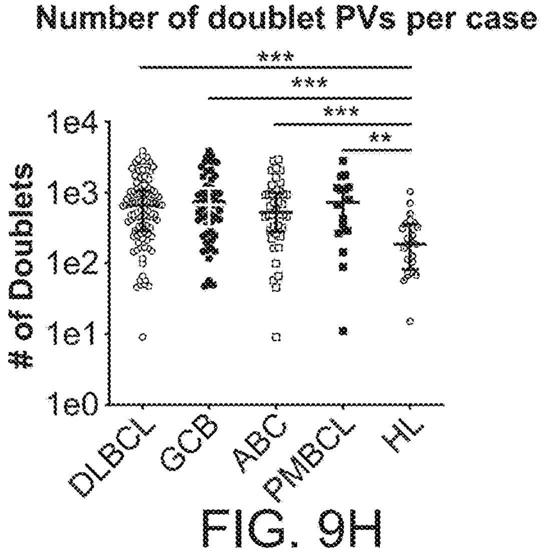
Figure 9I:
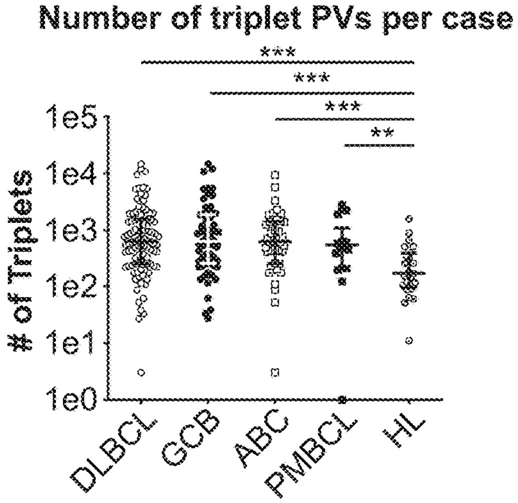
Figure 9J:
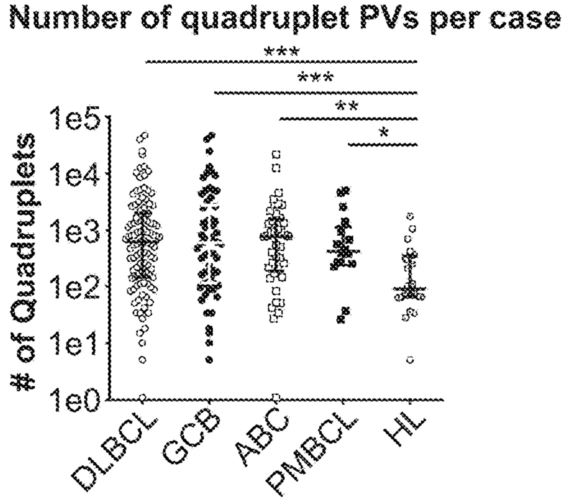
Figure 9K:
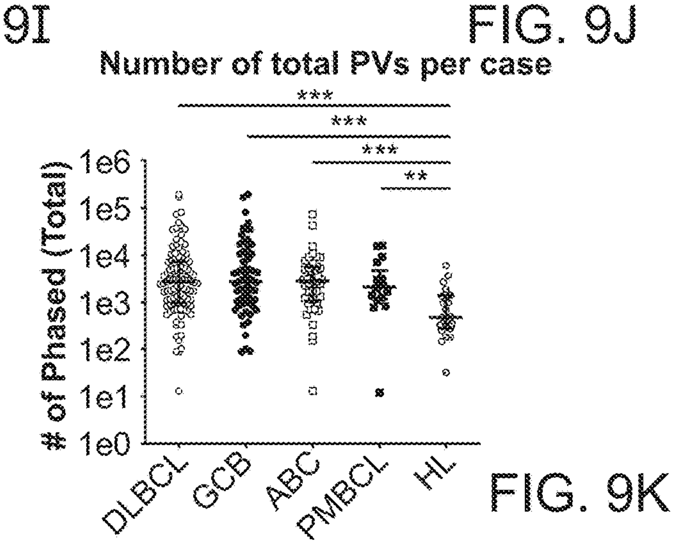
Figure 10A:
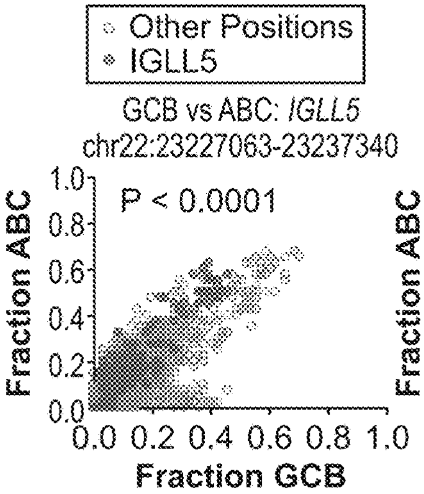
FIGS. 10A-10Y illustrate location-specific differences in PVs between ABC-DLBCL and GCB-DLBC (FIGS. 10A-10Y.) Similar to FIG. 2D, these scatterplots compare the frequency of PVs by genomic location (in 50 bp bins) for patients with different types of lymphomas; in this figure, the difference between ABC-DLBCL and GCB-DLBCL is shown. The red circles show the relative frequency of PVs in 50 bp bins from a specific gene of interest; the other (grey) circles show the relative frequency of PVs in 50 bp bins from the remainder of the PhasED-Seq sequencing panel. Only genes with a statistically significant difference in PVs between ABC-DLBCL and GCB-DLBCL are shown. P-values represent a Wilcoxon rank-sum test of 50 bp bins from a given gene against all other 50 bp bins; see Example 10.
Figure 10B:
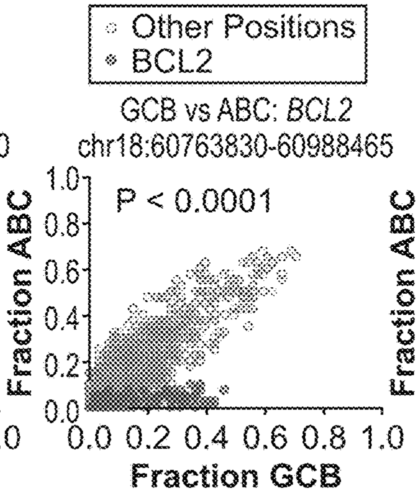
Figure 10C:
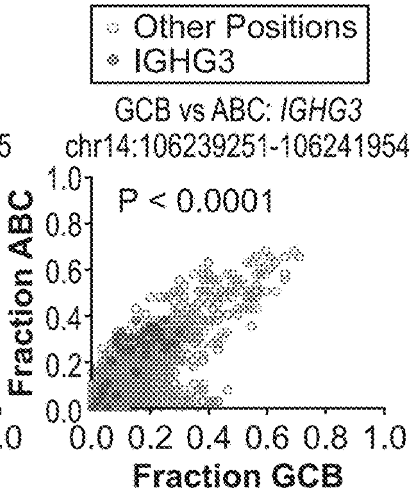
Figure 10D:
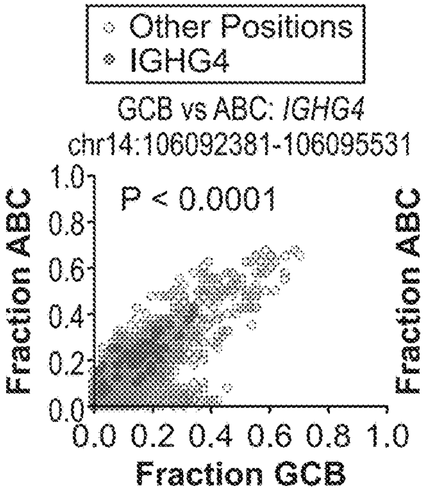
Figure 10E:
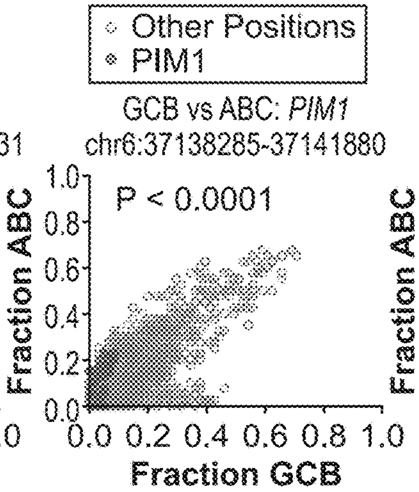
Figure 10F:
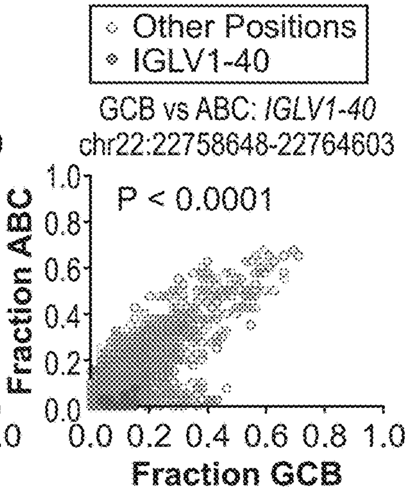
Figure 10G:
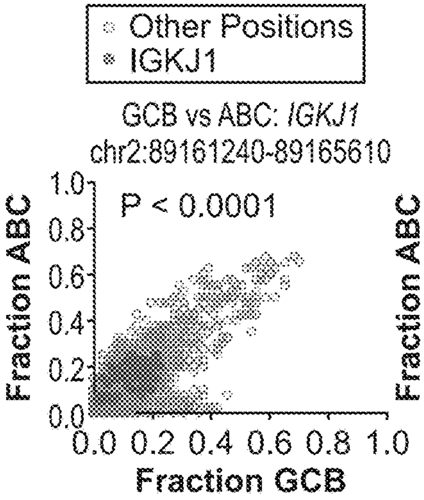
Figure 10H:
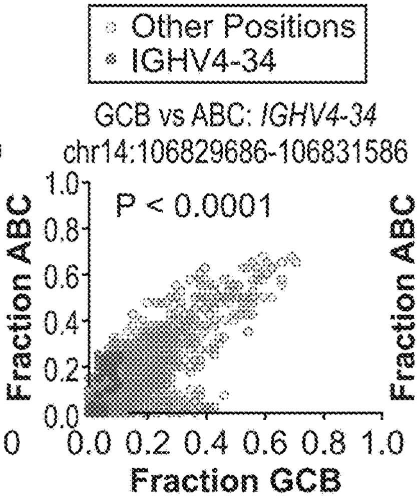
Figure 10I:
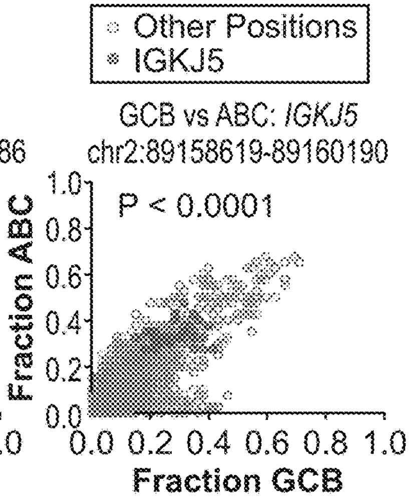
Figure 10J:
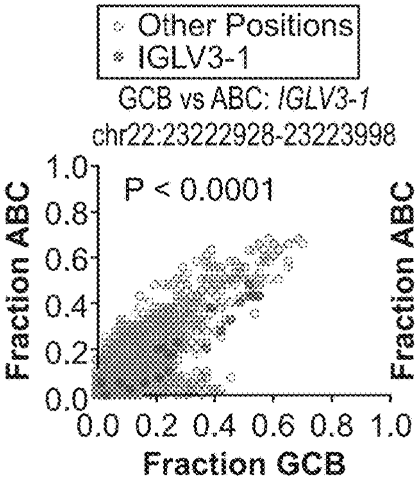
Figure 10K:
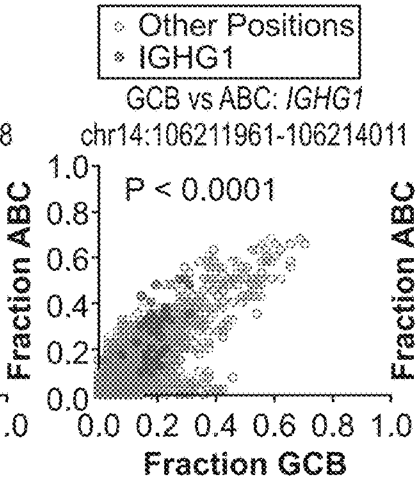
Figure 10L:
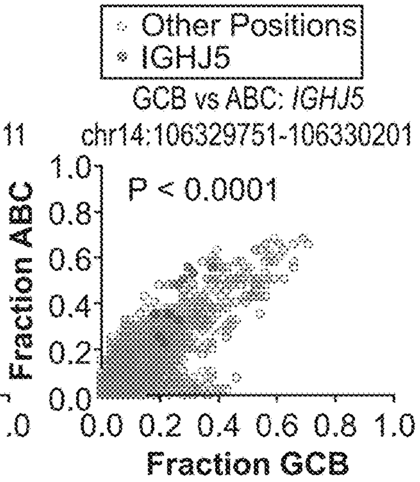
Figure 10M:
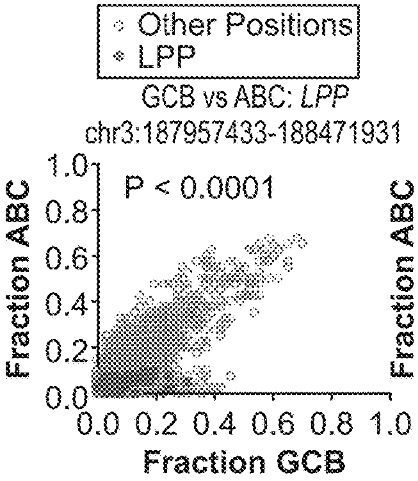
Figure 10N:
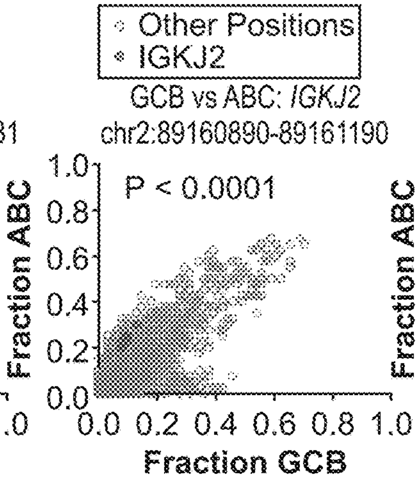
Figure 10O:
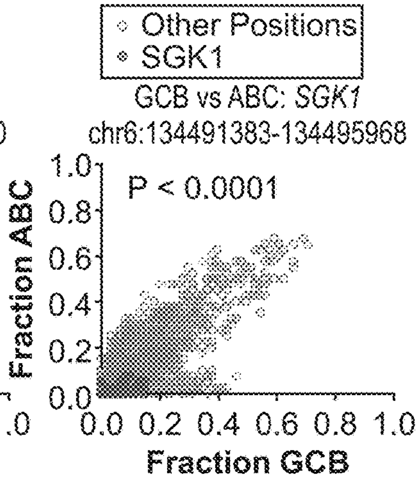
Figure 10P:
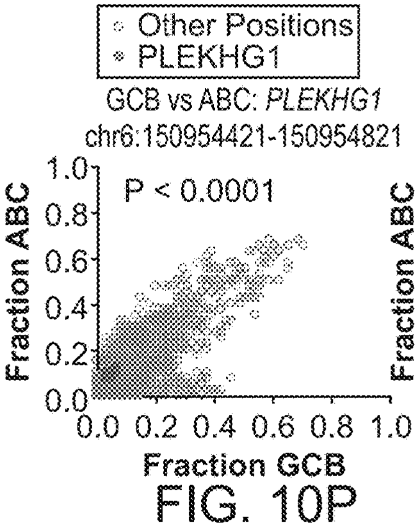
Figure 10Q:
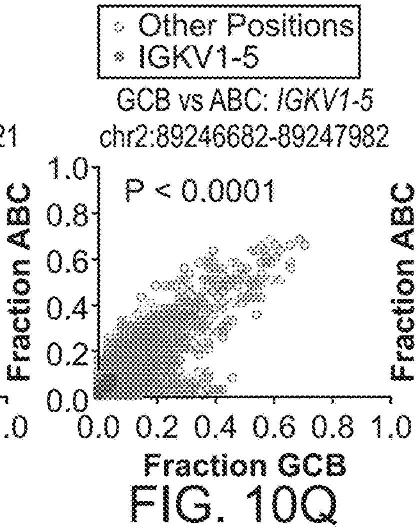
Figure 10R:
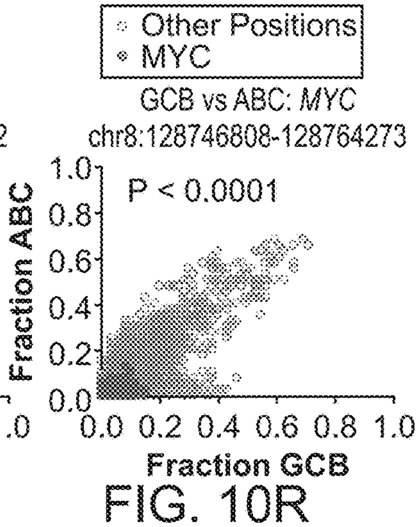
Figure 10S:
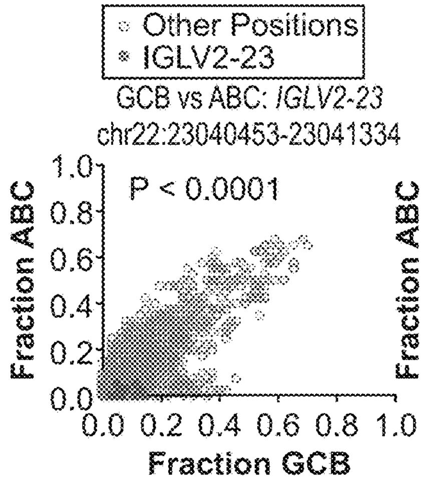
Figure 10T:
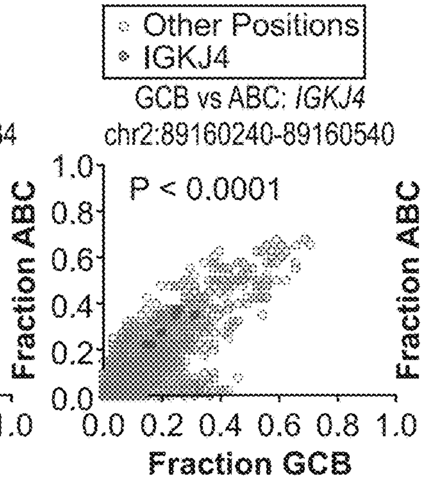
Figure 10U:
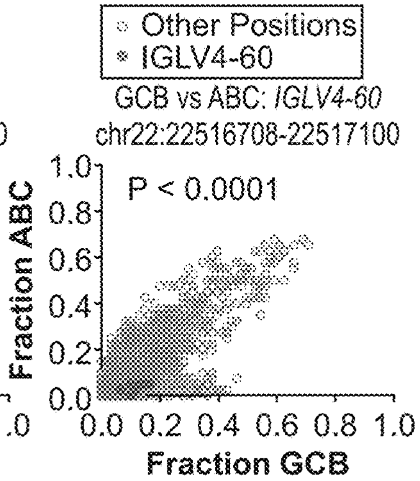
Figure 10V:
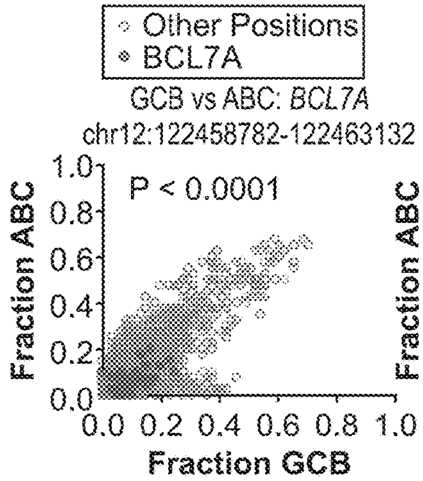
Figure 10W:
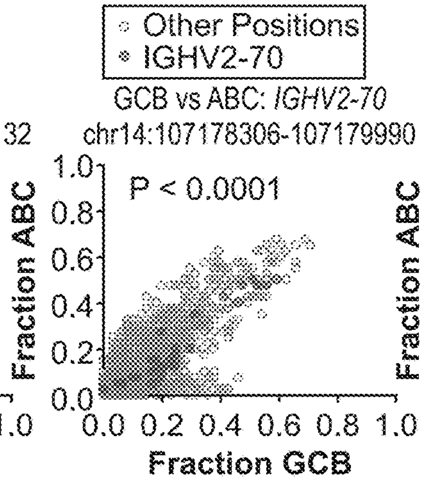
Figure 10X:
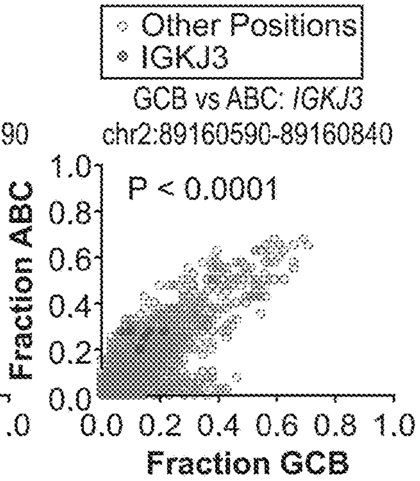
Figure 10Y:
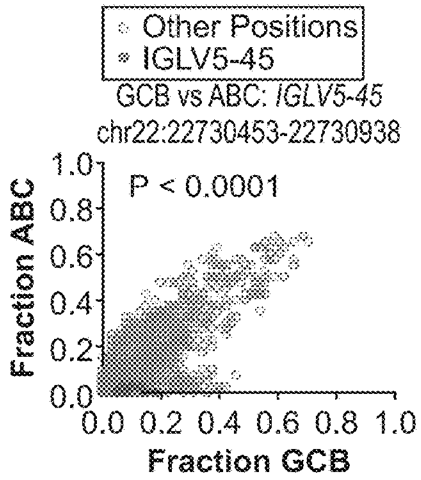
Figure 11A:
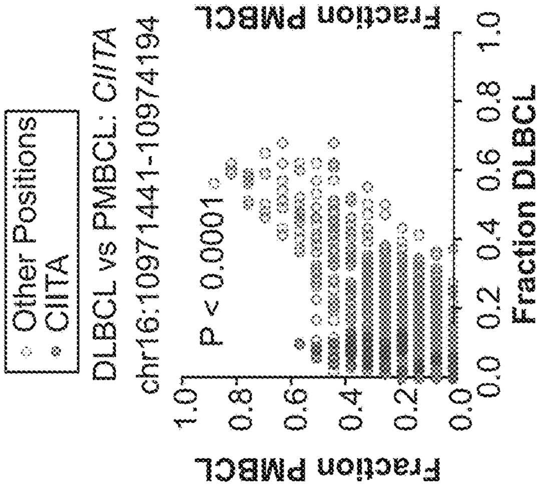
FIGS. 11A-11X illustrate Location-specific differences in PVs between DLBCL and PMBCL (FIGS. 11A-11X). Similar to FIG. 2D, these scatterplots compare the frequency of PVs by genomic location (in 50 bp bins) for patients with different types of lymphomas; in this figure, the difference between DLBCL and PMBCL is shown. The blue circles show the relative frequency of PVs in 50 bp bins from a specific gene of interest; the other (gray) circles show the relative frequency of PVs in 50 bp bins from the remainder of the PhasED-Seq sequencing panel. Only genes with a statistically significant difference in PVs between DLBCL and PMBCL are shown. P-values represent a Wilcoxon rank-sum test of 50 bp bins from a given gene against all other 50 bp bins; see Example 10.
Figure 11B:
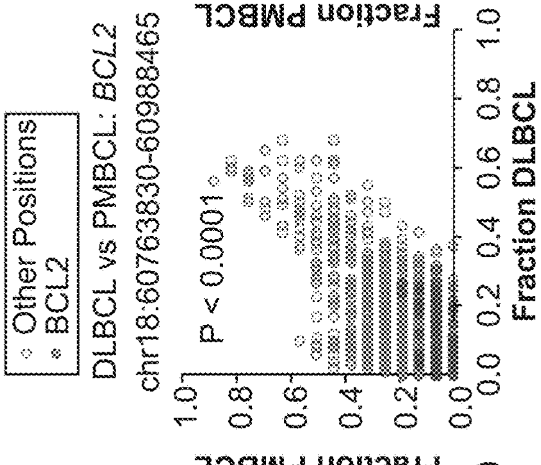
Figure 11C:
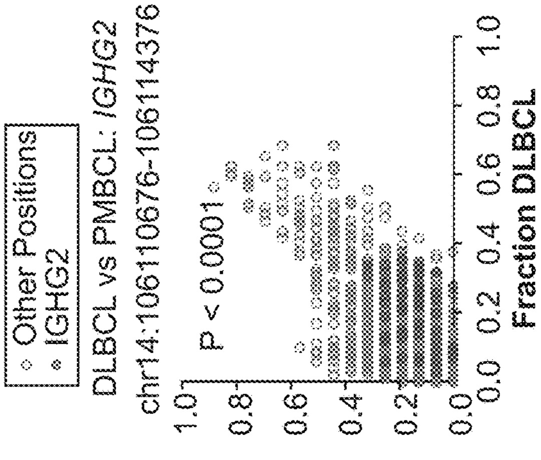
Figure 11D:
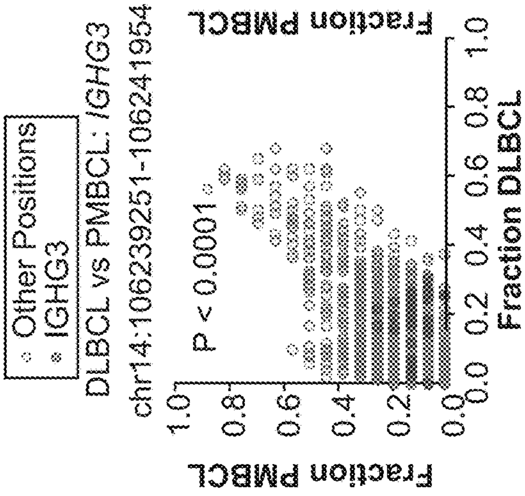
Figure 11E:
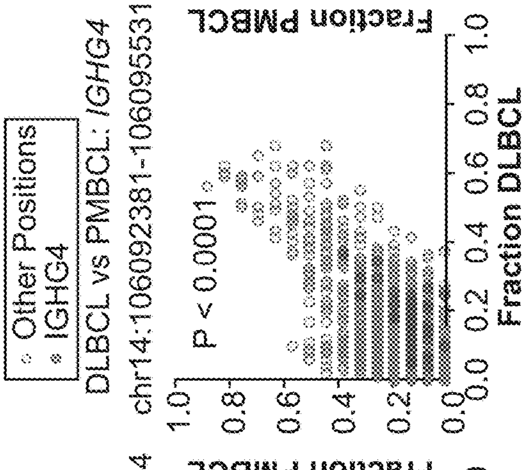
Figure 11F:
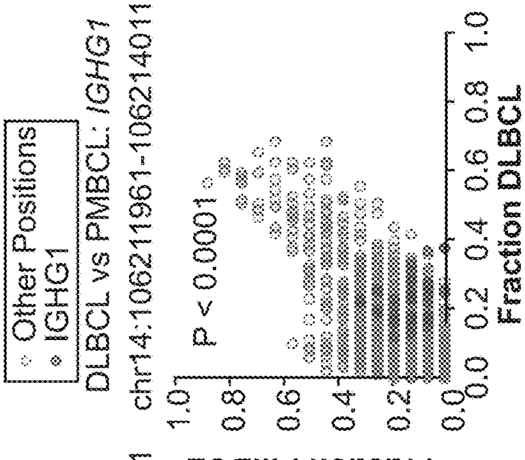
Figure 11G:
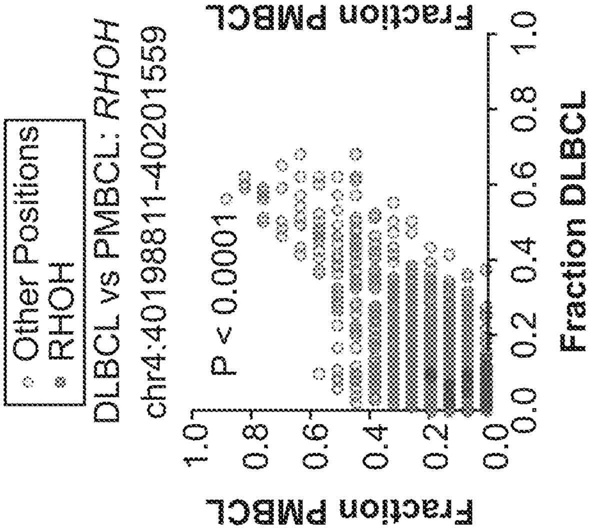
Figure 11H:
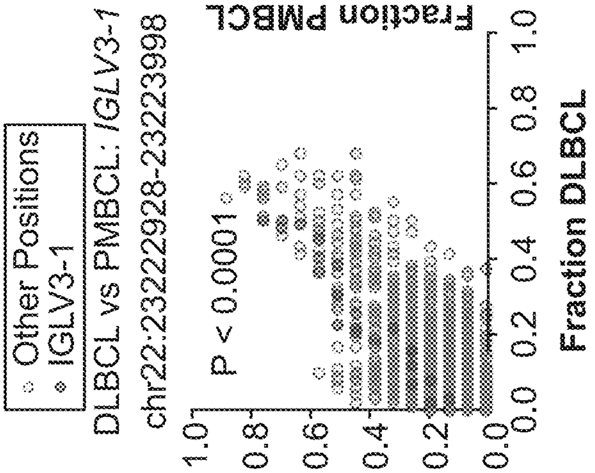
Figure 11I:
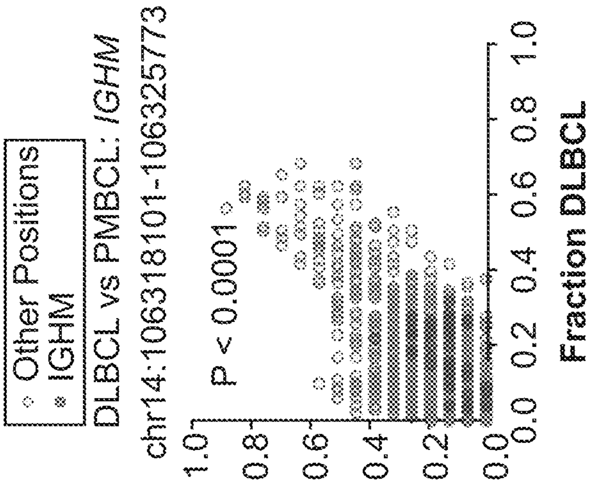
Figures 11J, 11K, 11L, 11M, 11N, 11O:
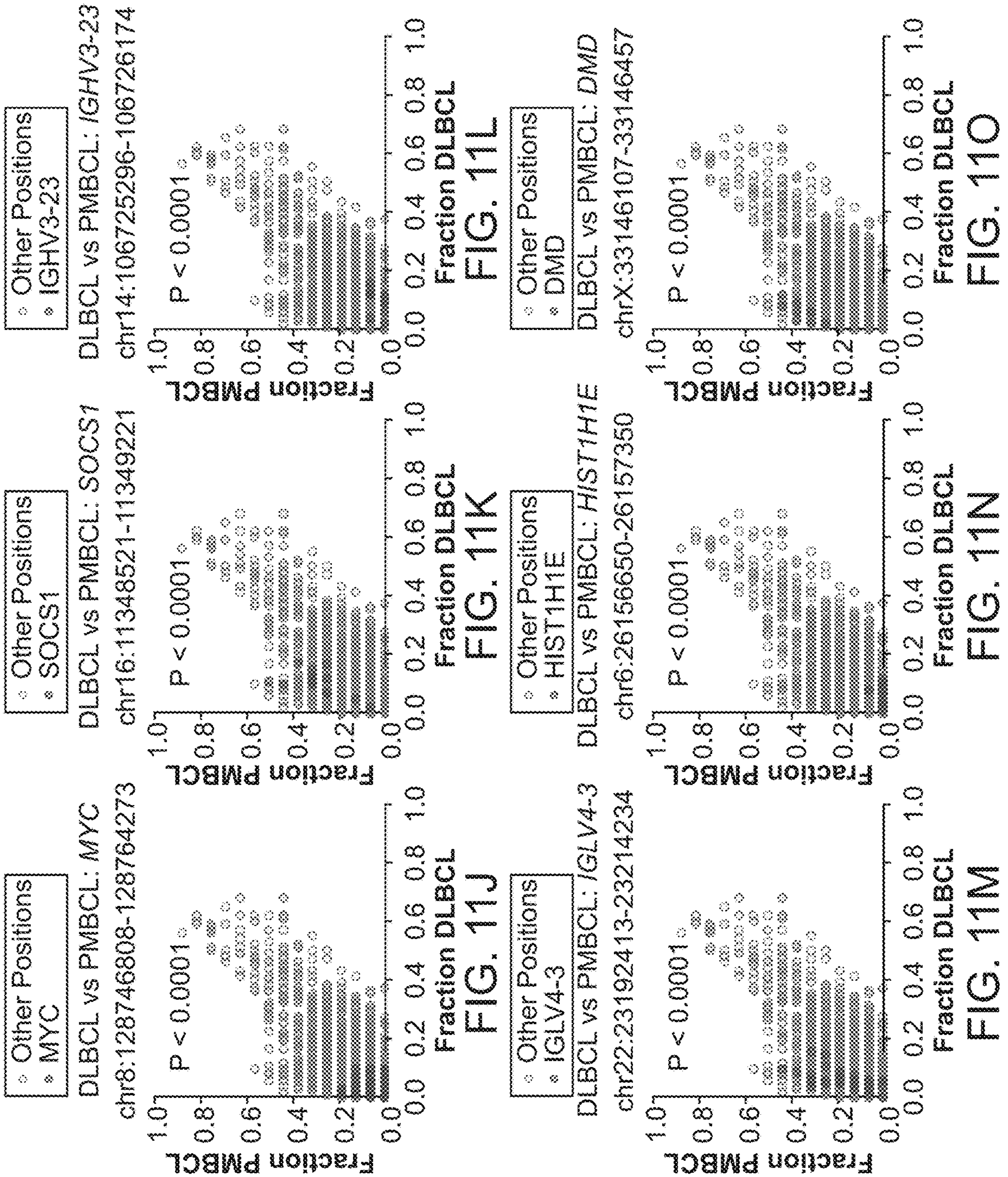
Figure 11R:
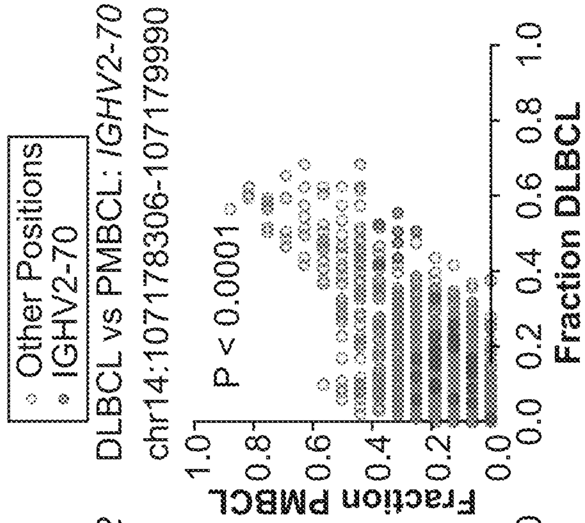
Figure 11Q:
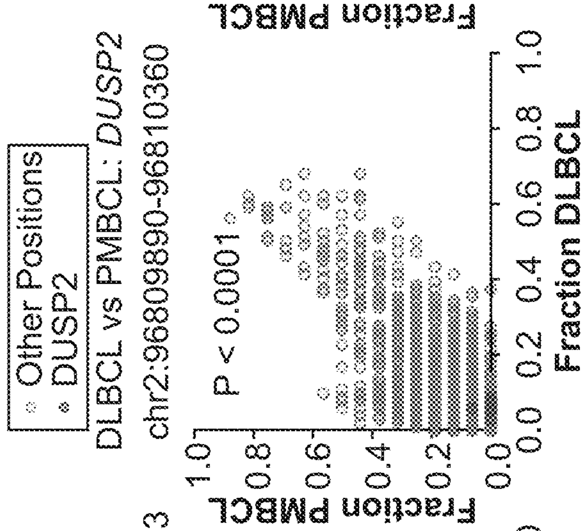
Figure 11P:
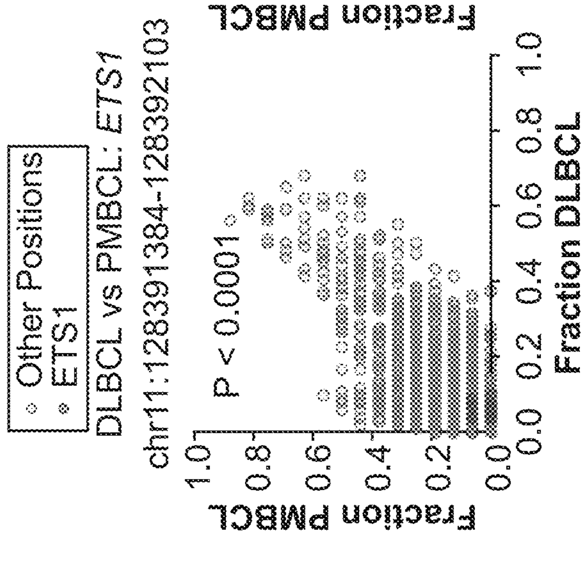
Figure 11S:
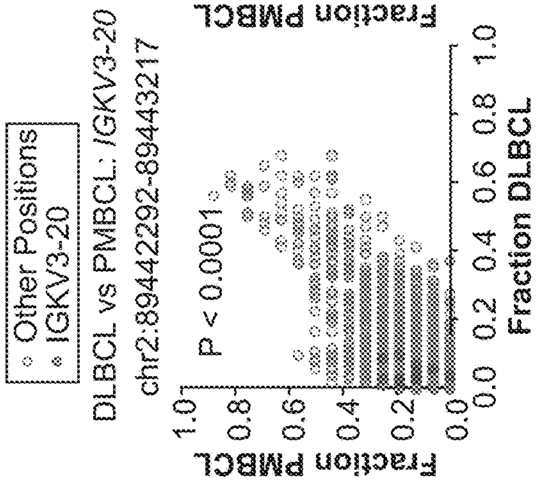
Figure 11T:
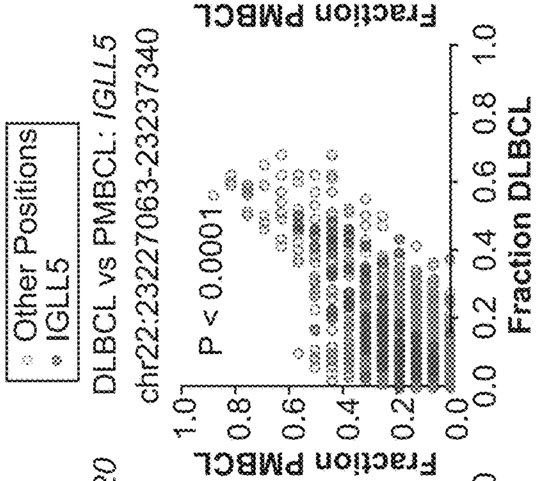
Figure 11U:
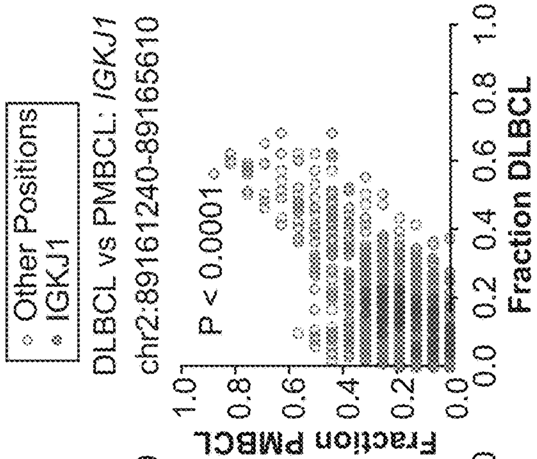
Figure 11V:
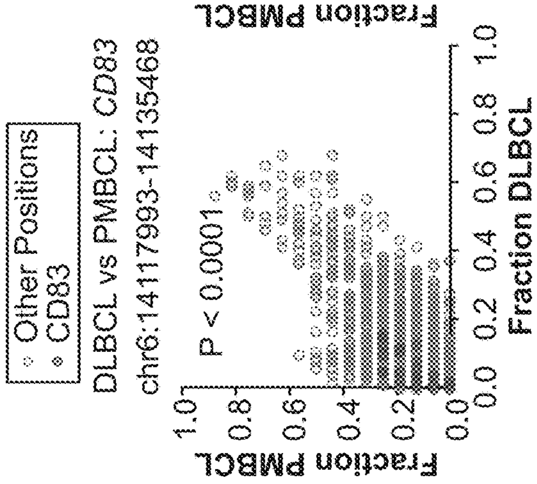
Figure 11W:
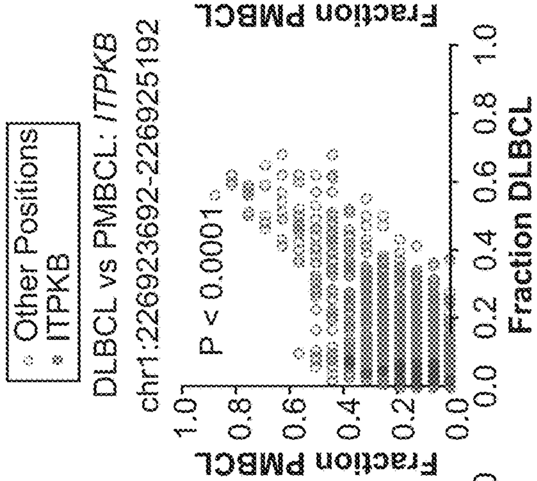
Figure 11X:
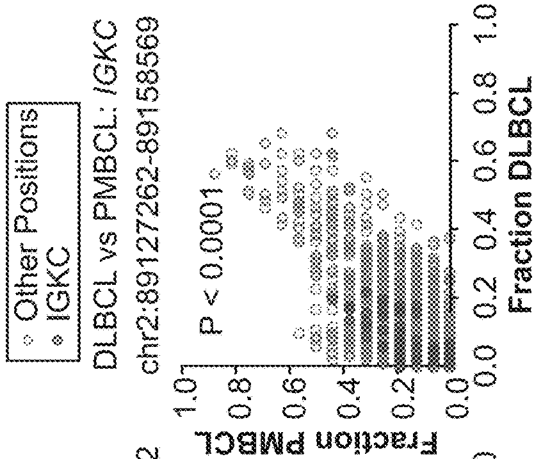
Figures 12A, 12B, 12C, 12D, 12E, 12F:
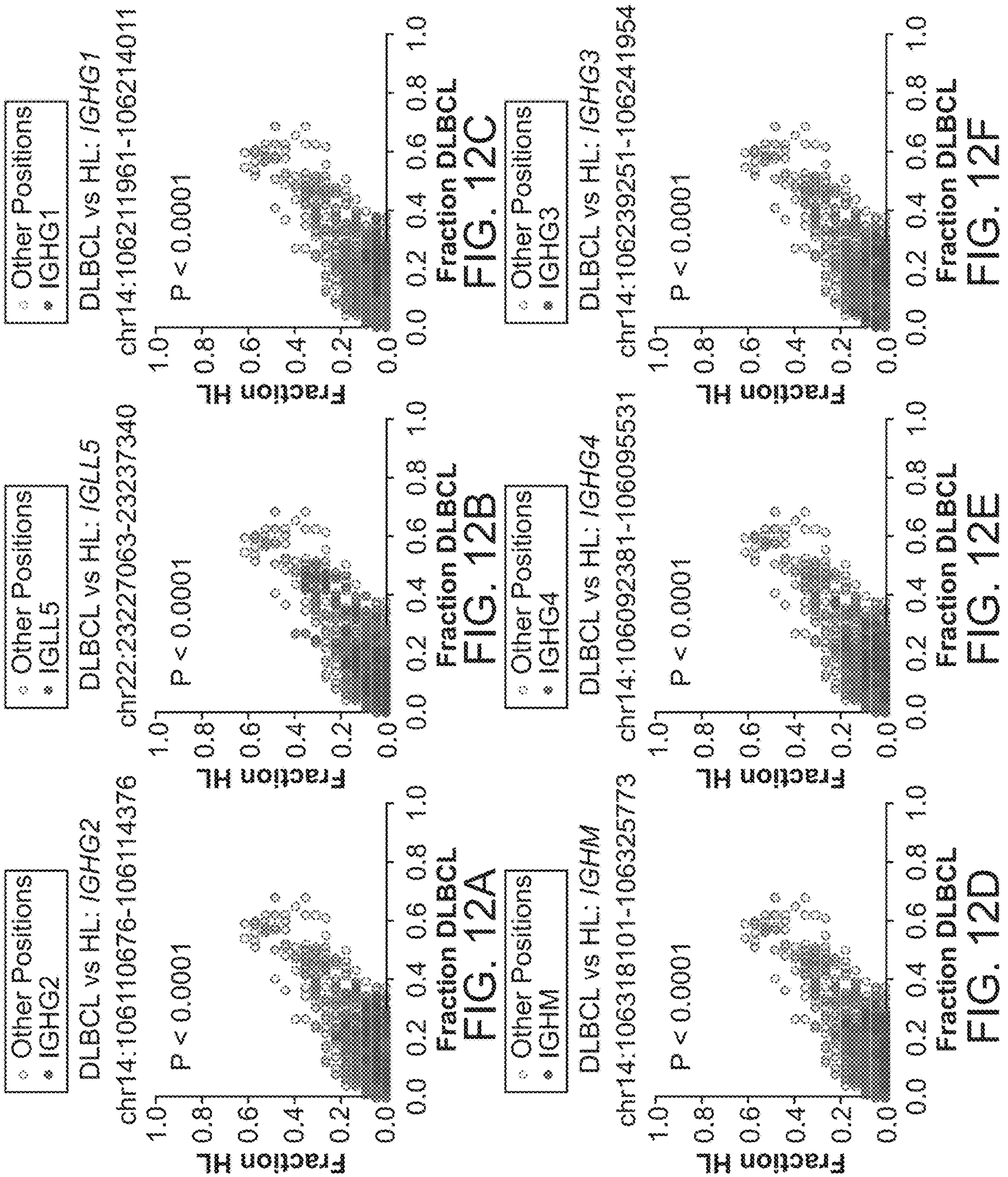
FIGS. 12A-12NN illustrate Location-specific differences in PVs between DLBCL and HL. Similar to FIG. 2D, scatterplots of FIGS. 12A-12NN compare the frequency of PVs by genomic location (in 50 bp bins) for patients with different types of lymphomas; in this figure, the difference between DLBCL and HL is shown. The green circles show the relative frequency of PVs in 50 bp bins from a specific gene of interest; the other (grey) circles show the relative frequency of PVs in 50 bp bins from the remainder of the PhasED-Seq sequencing panel. Only genes with a statistically significant difference in PVs between DLBCL and HL are shown. P-values represent a Wilcoxon rank sum test of 50 bp bins from a given gene against all other 50 bp bins; see Example 10.
Figure 12G:
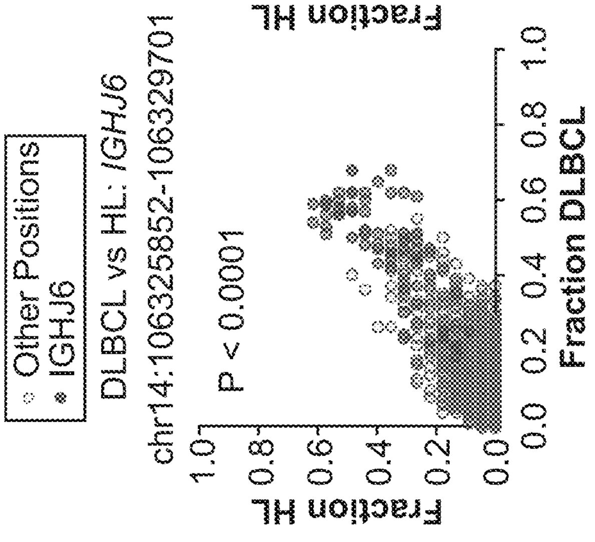
Figure 12H:
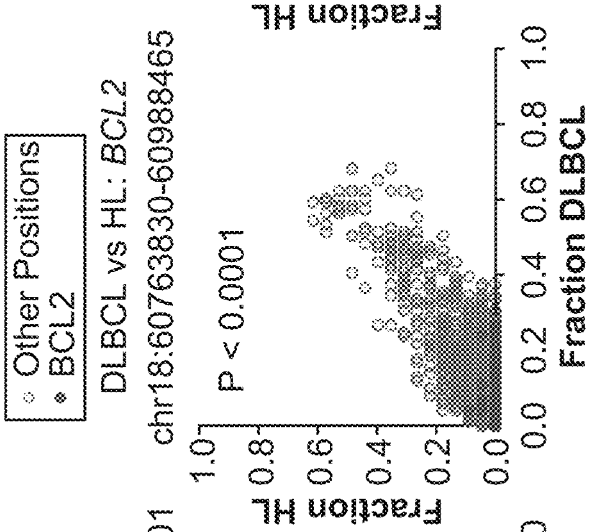
Figure 12I:
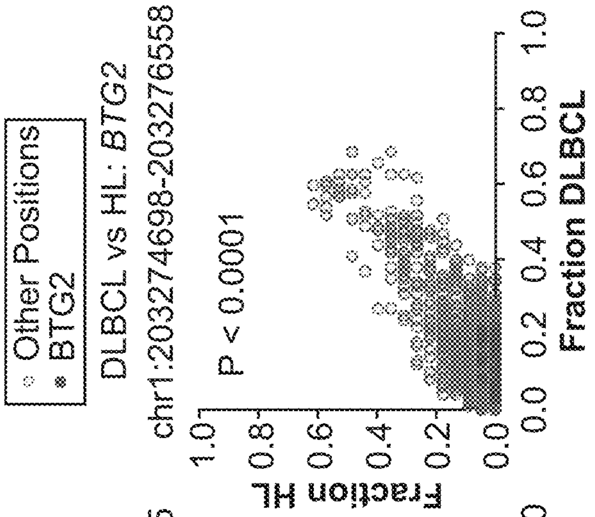
Figures 12J, 12K, 12L, 12M, 12N, 12O:
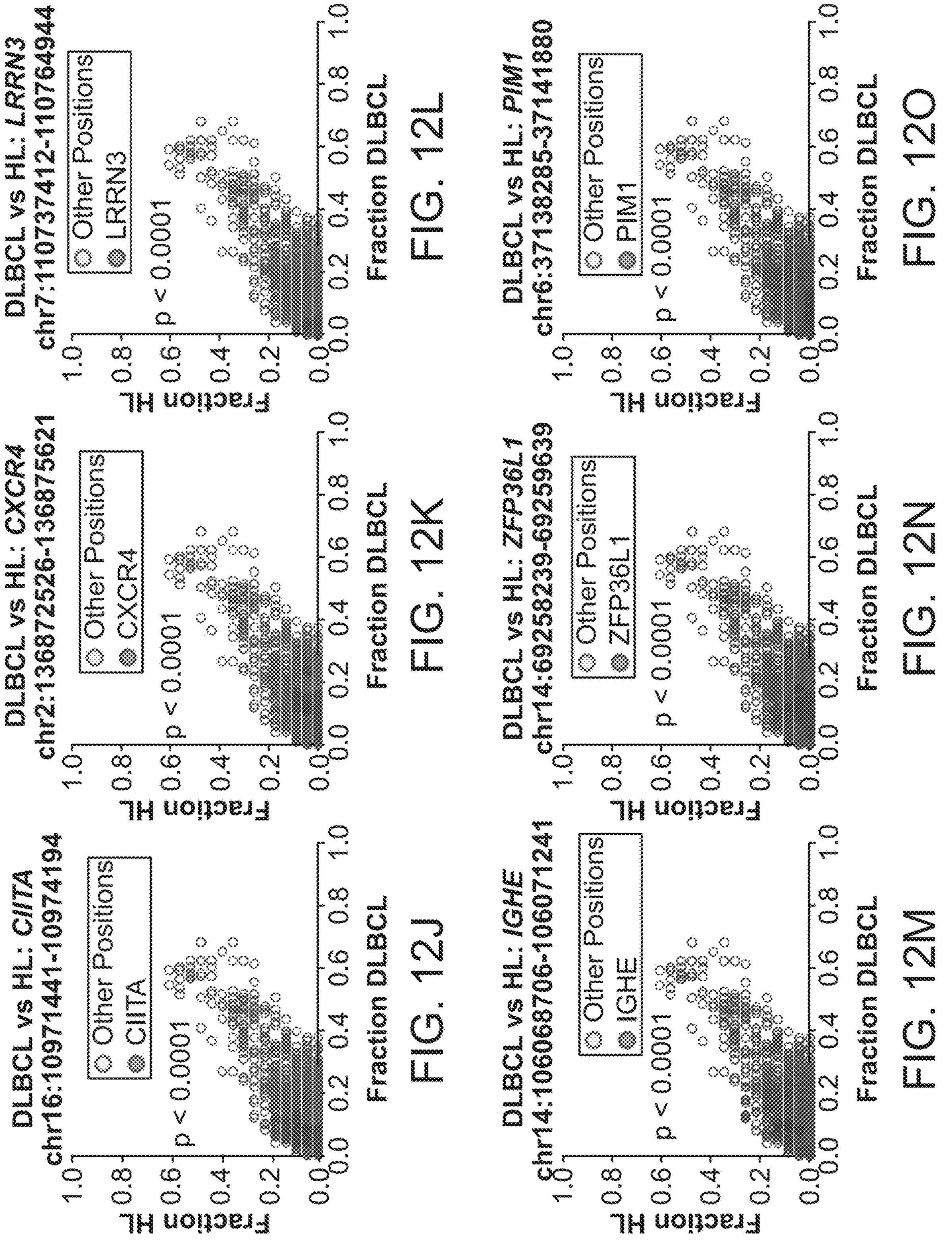
Figure 12P:
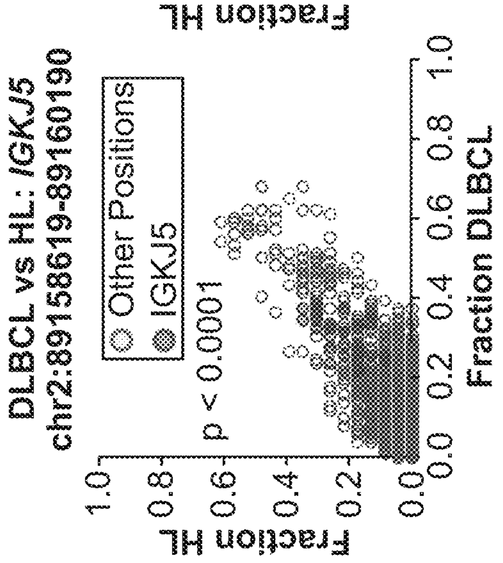
Figure 12Q:
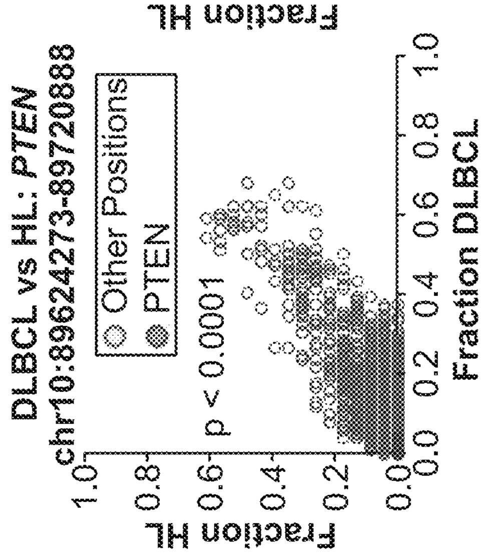
Figure 12R:
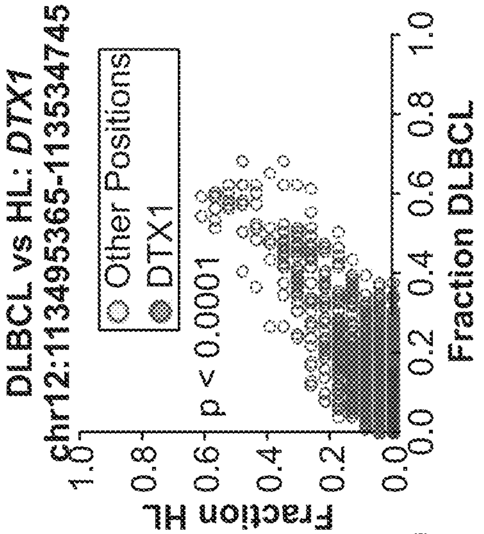
Figure 12S:
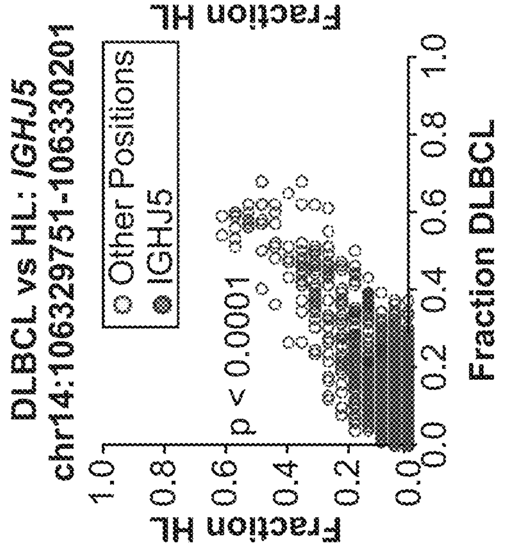
Figure 12T:
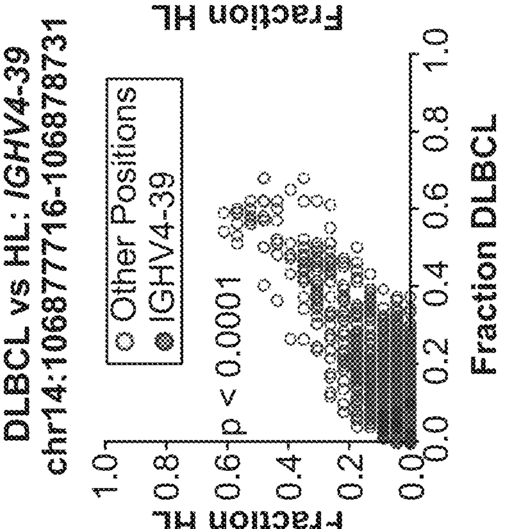
Figure 12U:
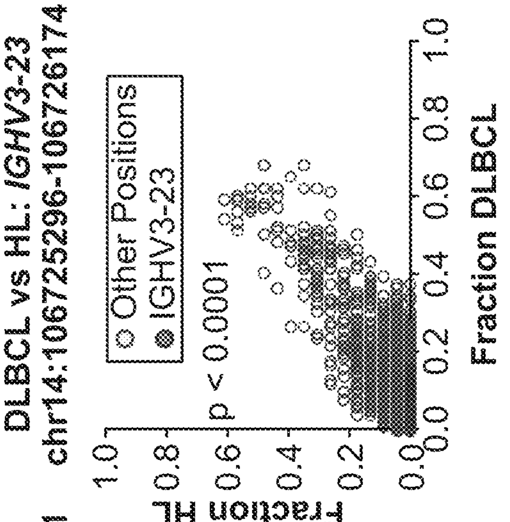
Figure 12V:
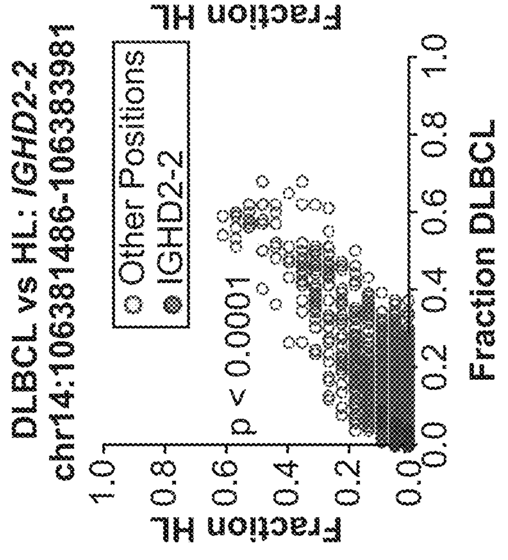
Figure 12W:
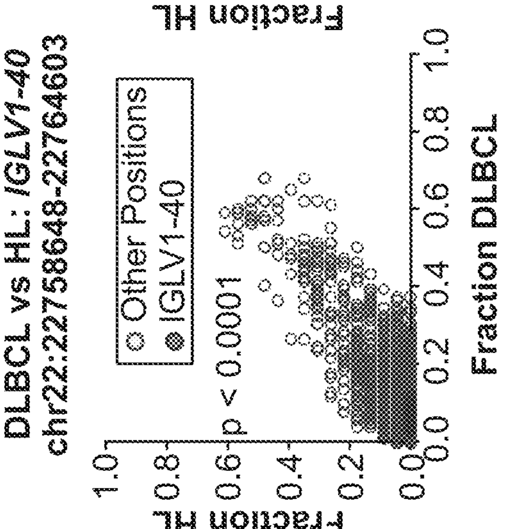
Figure 12X:
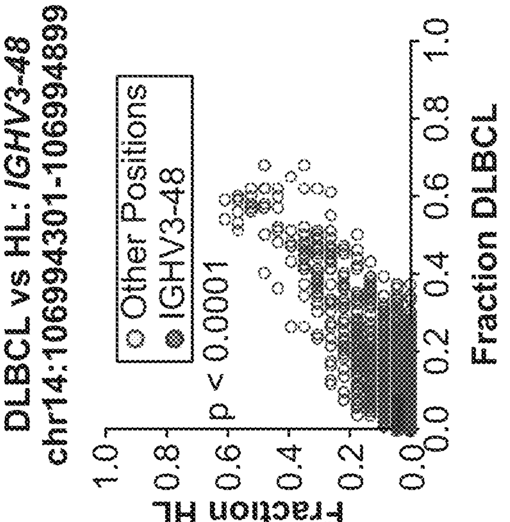
Figure 12Y:
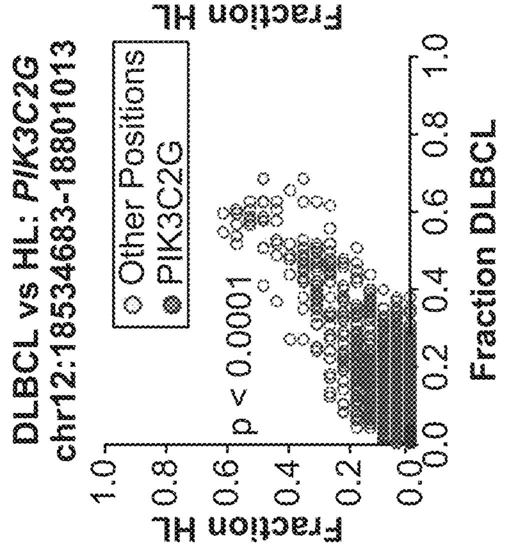
Figure 12Z:
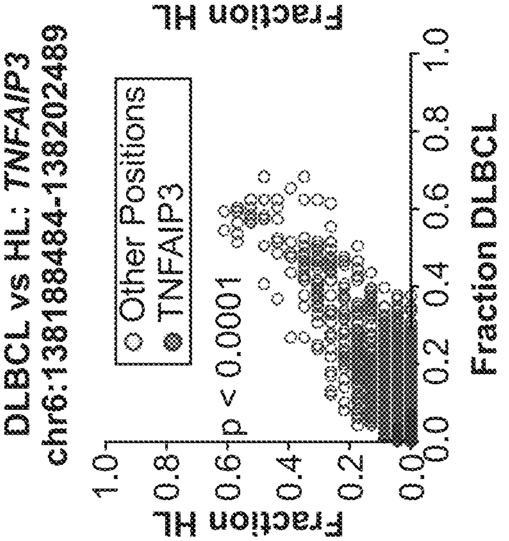
Figure 12A:
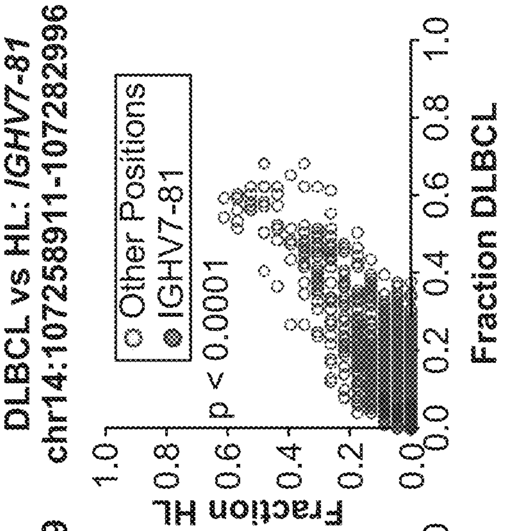
Figure 12B:
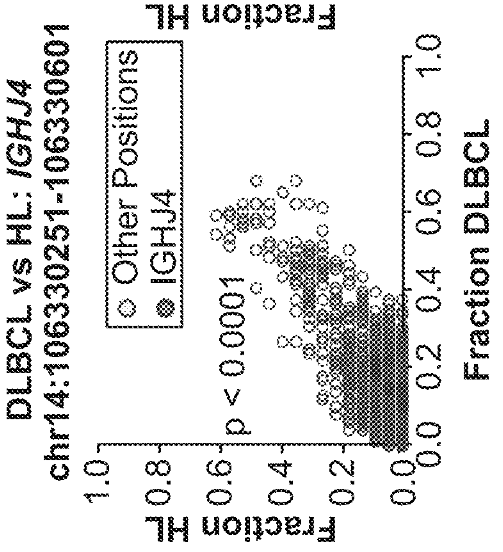
Figure 12C:
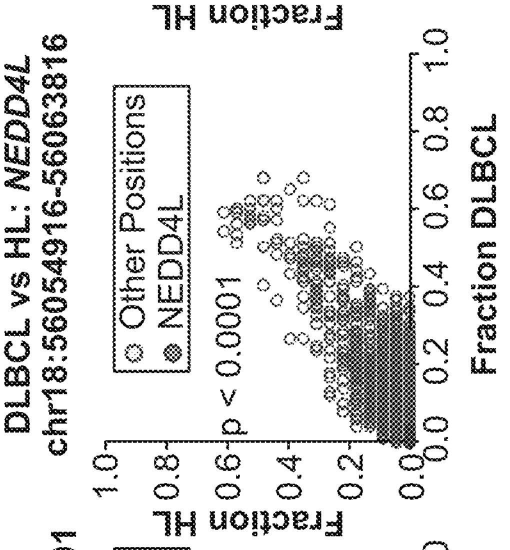
Figure 12D:
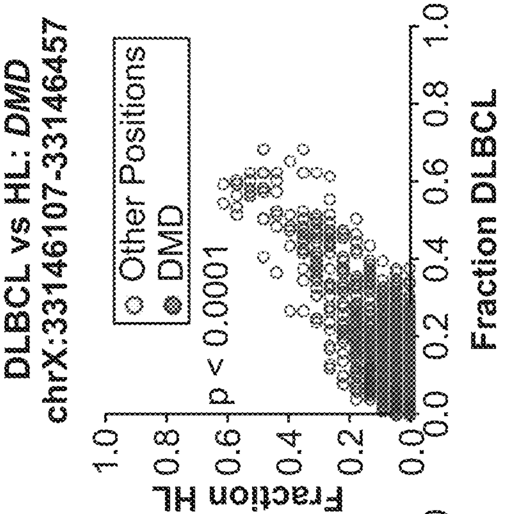
Figure 12E:
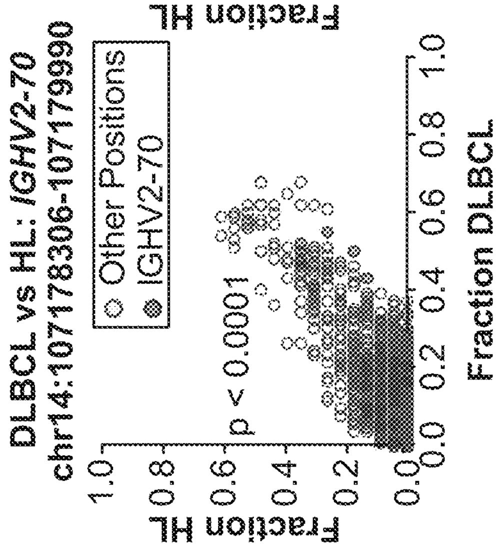
Figure 12F:
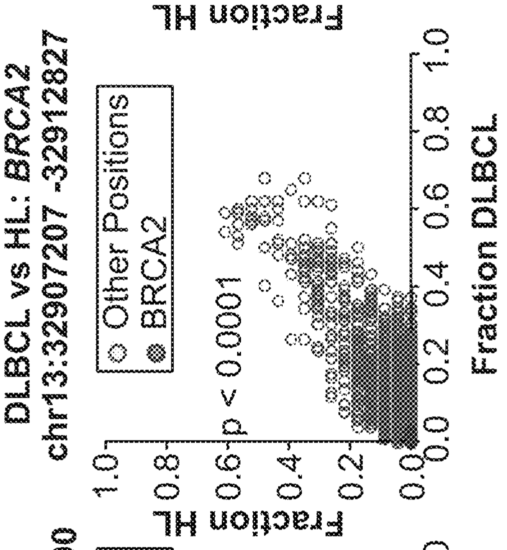
Figure 12G:
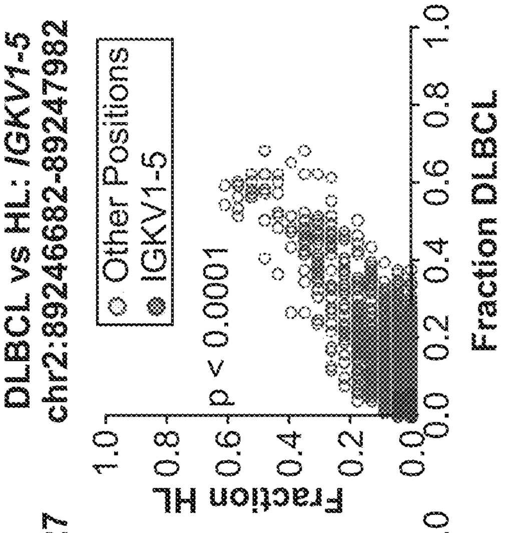
Figure 12H:
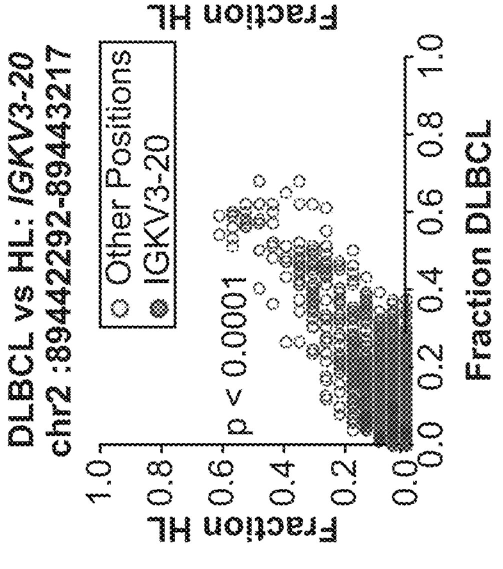
Figure 12I:
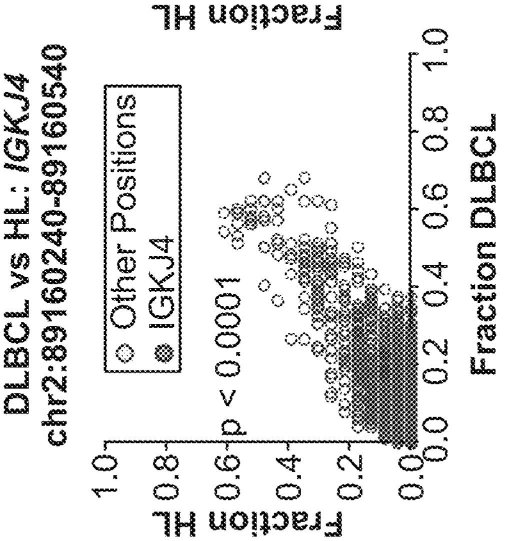
Figure 12J:
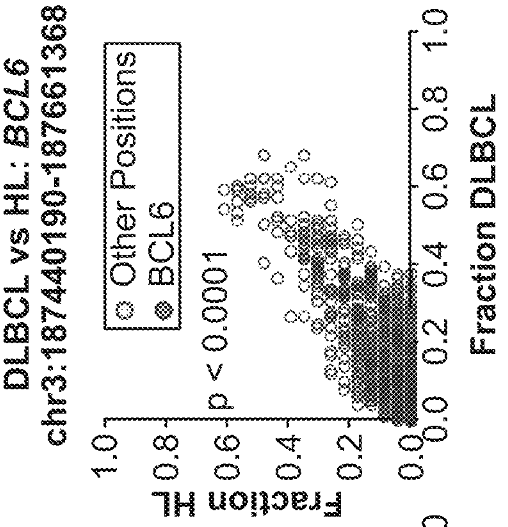
Figure 12K:
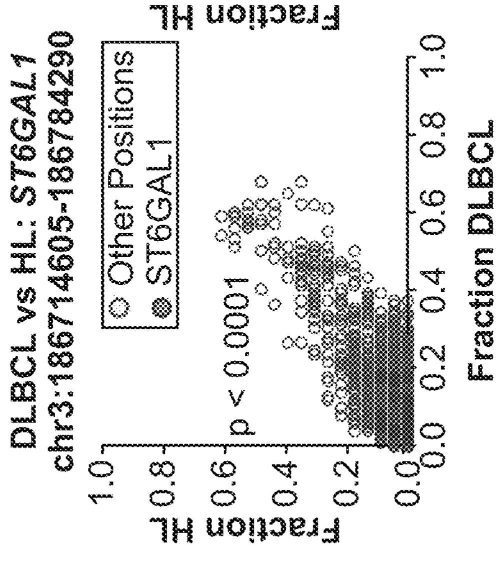
Figure 12L:
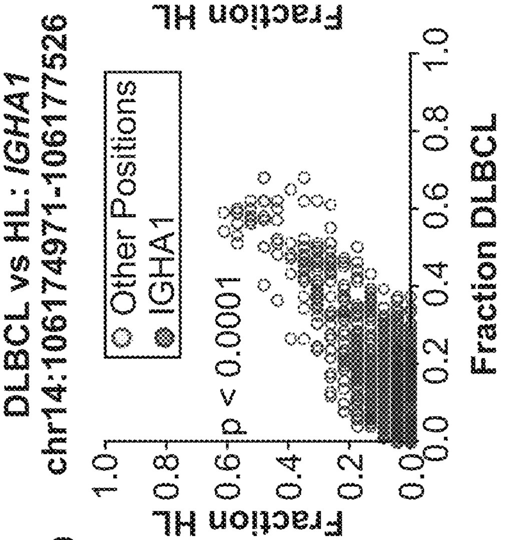
Figure 12M:
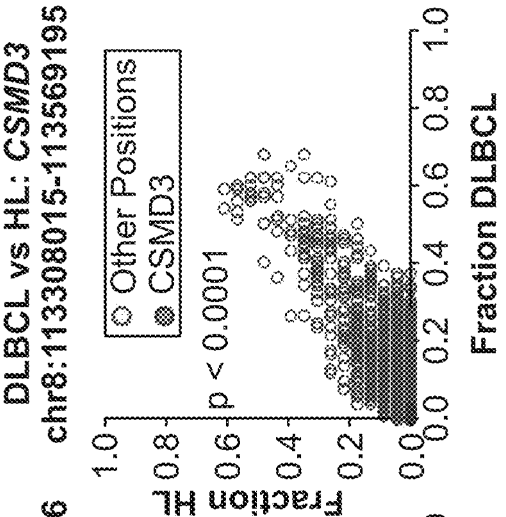
Figure 12N:
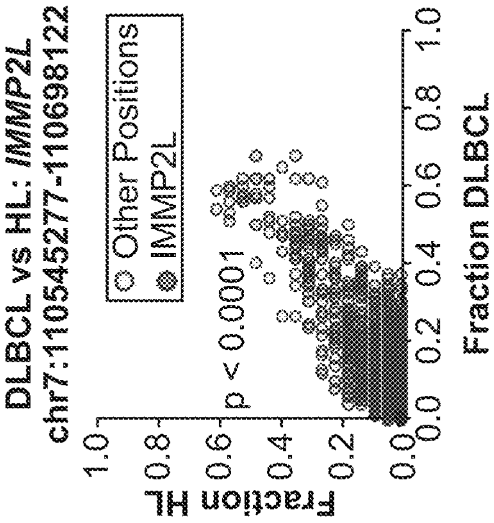

Expected SNV and PV recovery was compared to previously reported CAPP-Seq selector designed to maximize SNVs per patient in B-cell lymphomas (FIG. 9A-C). When considering diverse B-NHLs with available WGS data, PhasED-Seq recovered 3.0× more SNVs (81 vs. 27) and 2.9× more PVs (50 vs. 17) in the median case than previous CAPP-Seq panel. This observation highlights the importance of including non-coding portions of the genome for maximal mutation recovery. To validate these yield improvements experimentally, 16 pretreatment tumor or plasma DNA samples from patients with DLBCL (Table 4) were profiled. Both CAPP-Seq and PhasED-Seq panels were applied to each specimen in parallel and then sequenced them to high unique molecular depths (FIG. 2B). Compared to the expected enrichment established from WGS, similar improvements in yield of SNVs by PhasED-Seq compared to CAPP-Seq (2.7×; median 304.5 vs. 114) were observed. However, when enumerating PVs observed in individual sequenced DNA fragments, an improvement in favor of PhasED-Seq beyond the expected improvement from WGS (7.7×; median 5554 vs 719.5 PVs/case) was found. This improvement is potentially due to either 1) the higher sequencing depth in targeted sequencing which leads to improvement in rare allele detection, or 2) enumeration of higher order PVs in targeted sequencing with PhasED-Seq or CAPP-Seq, which was not accounted for in the WGS design (i.e., >2 SNVs per fragment; FIGS. 9D-9F). Furthermore, across 1-kb windows in the panel, robust correlation between the frequency of putative PVs in WGS data and PVs from targeted sequencing by PhasED-Seq across 101 DLBCL samples (FIG. 2C) was observed, further validating the frequency and distribution of PVs in B-cell malignancies.

Example 5: Differences in Phased Variants Between Lymphoma Subtypes

Figure 2E:
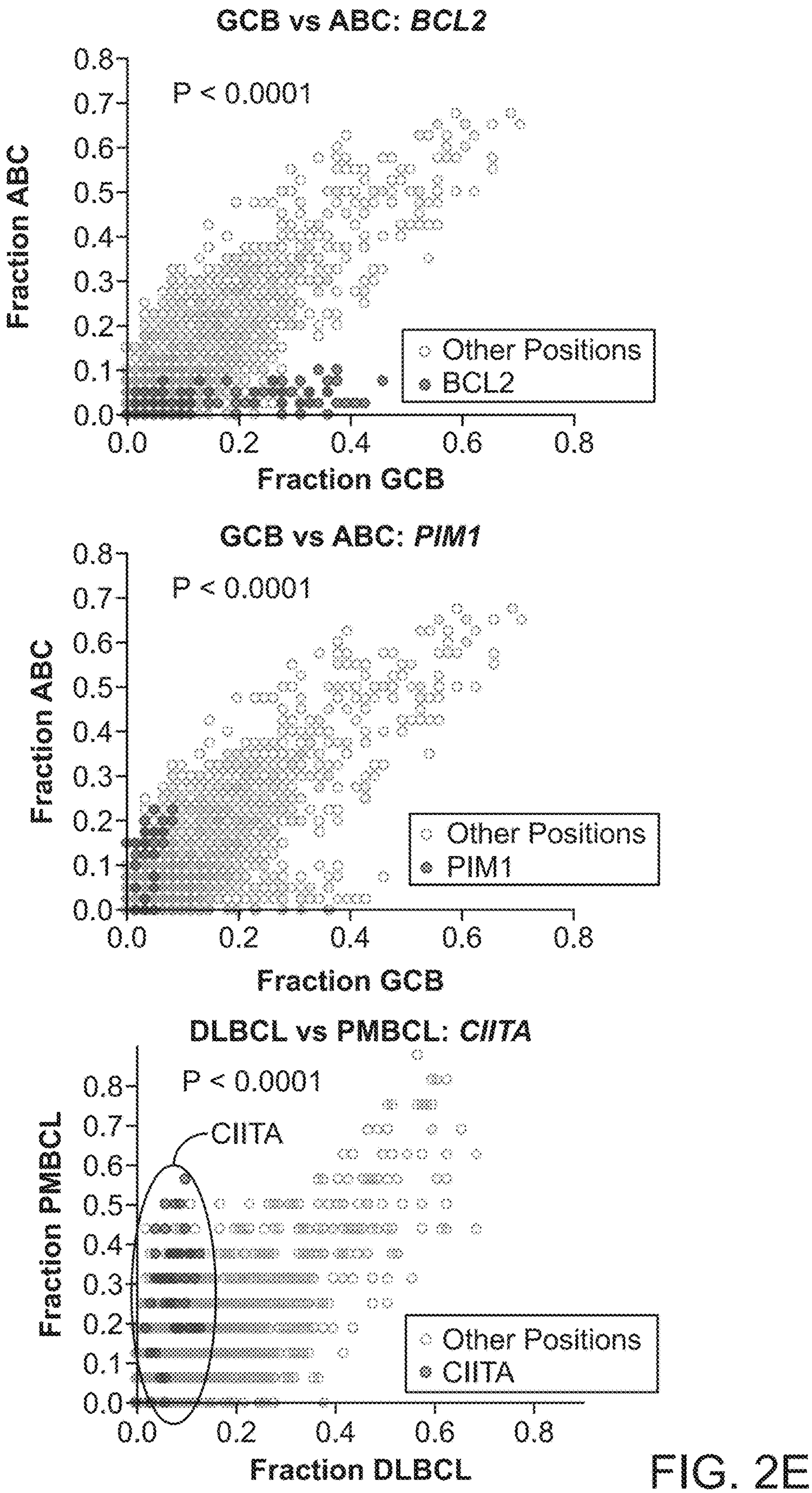
Figure 2F:
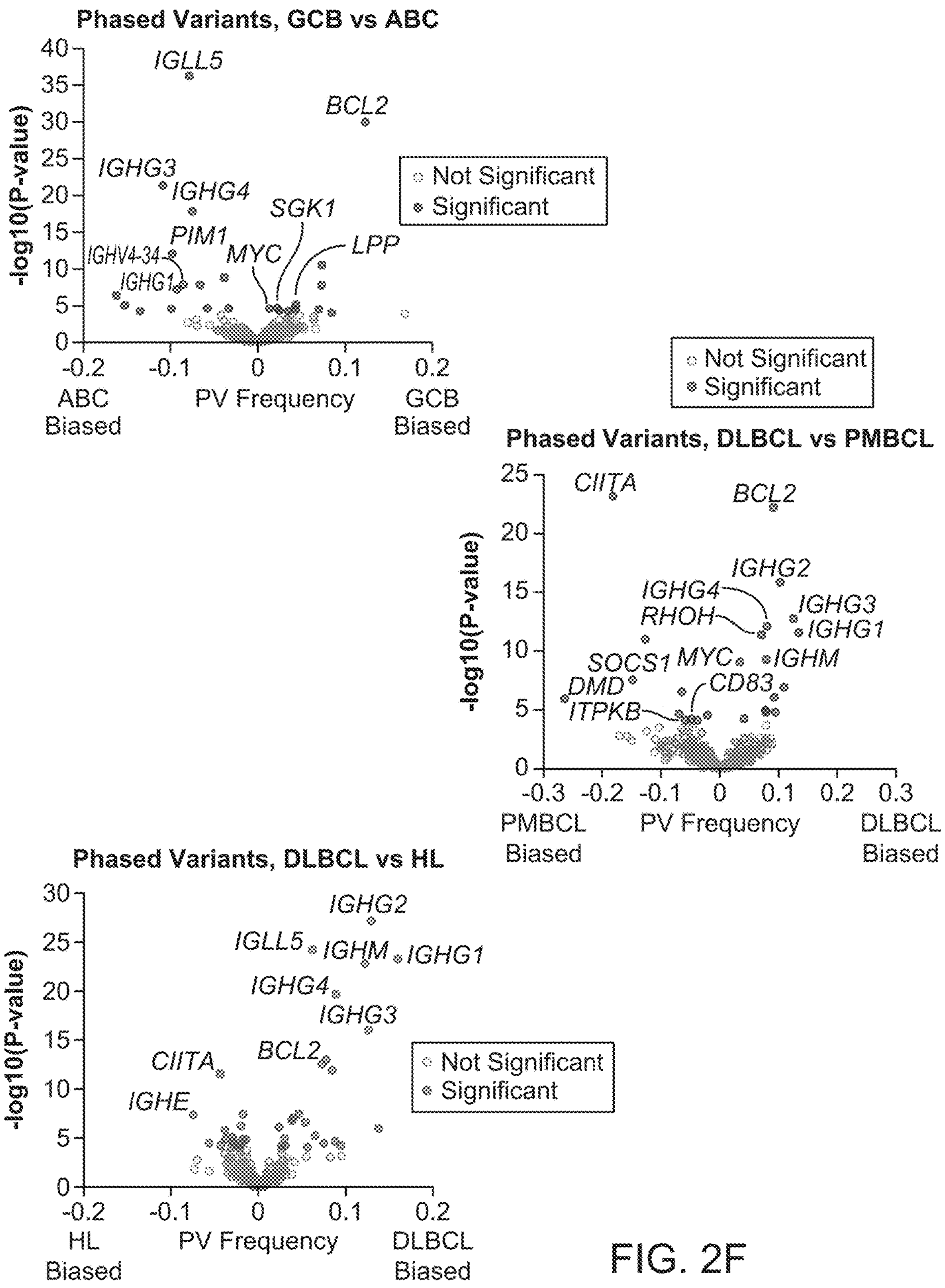
Figure 13:
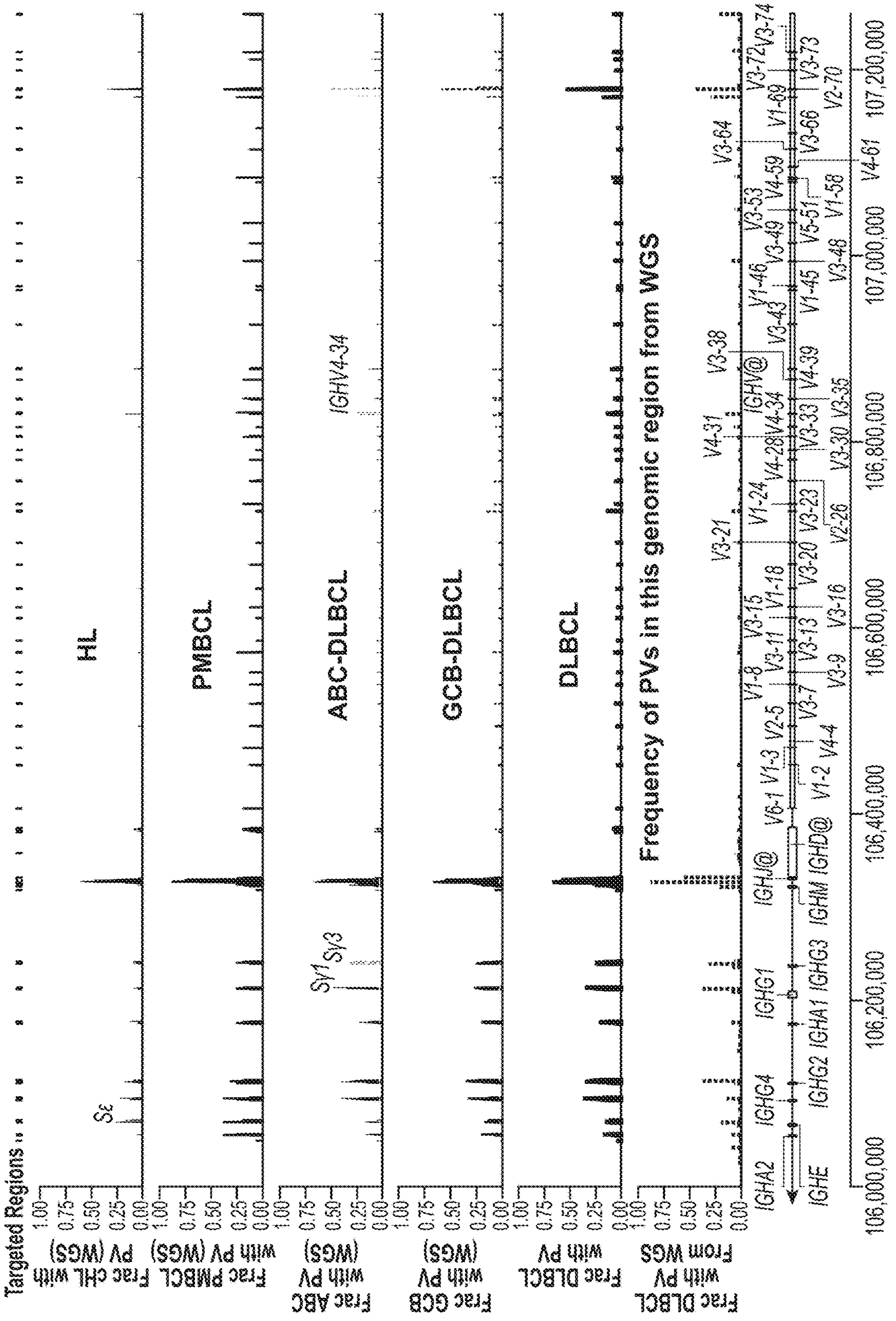
FIG. 13 illustrates differences in PVs between lymphoma types in mutations in the IGH locus. This figure shows the frequency of PVs from PhasED-Seq across the @IGH locus for different types of B-cell lymphomas. The bottom track shows the structure of the @IGH locus and gene-parts, including Ig-constant genes and V-genes. The next (outlined) track shows the frequency of PVs in this genomic region from WGS data (ICGC cohort). The remainder of the tracks show the frequency of PVs from PhasED-Seq targeted sequencing data, including 1) DLBCL, GCB-DLBCL, ABC-DLBCL, PMBCL, and HL. The regions targeted by the PhasED-Seq panel are shown at the top. Selected immunoglobulin parts with PVs enriched in specific histologies are labeled (i.e., IGHV4-34, Sε, Sγ3 and Sγ1).

Having validated the PhasED-Seq panel, the biological differences in PVs between various B-cell malignancies, including DLBCL (n=101), primary mediastinal B-cell lymphoma (PMBCL) (n=16), and classical Hodgkin lymphoma (cHL) (n=23) were examined. The number of SNVs identified per case was not significantly different between lymphoma subtypes (FIGS. 9G-9K). However, when considering mutational haplotypes, cHL had a significantly lower burden of PVs than either DLBCL or PMBCL. In addition to this quantitative disparity, differences in the genomic locations of PVs between different B-cell lymphoma subtypes were also observed (FIGS. 2D-2E and FIGS. 10-12). This included previously established biological associations in DLBCL subtypes, including more frequent PVs in BCL2 in GCB-type than ABC-type DLBCL, with the opposite association seen for PIM1. More frequent PVs in CIITA in PMBCL compared with DLBCL, a gene in which breakpoints are common in PMBCL, was also observed. Relative enrichments were also observed throughout the IGH locus, with more frequent PVs seen in Sγ3 and Sγ1 regions in ABC-DLBCL (compared with GCB-DLBCL) and interestingly, more frequent PVs in the Sc locus in cHL compared with DLBCL (FIG. 2E and FIG. 13). In total, after correcting for testing multiple hypotheses, significant relative enrichments in 25 genetic loci between ABC- and GCB-DLBCL, 24 between DLBCL and PMBCL, and 40 between DLBCL and cHL were found (FIG. 10-12).

Example 6: Recovery of Phased Variants Through PhasED-Seq

Figure 3A:
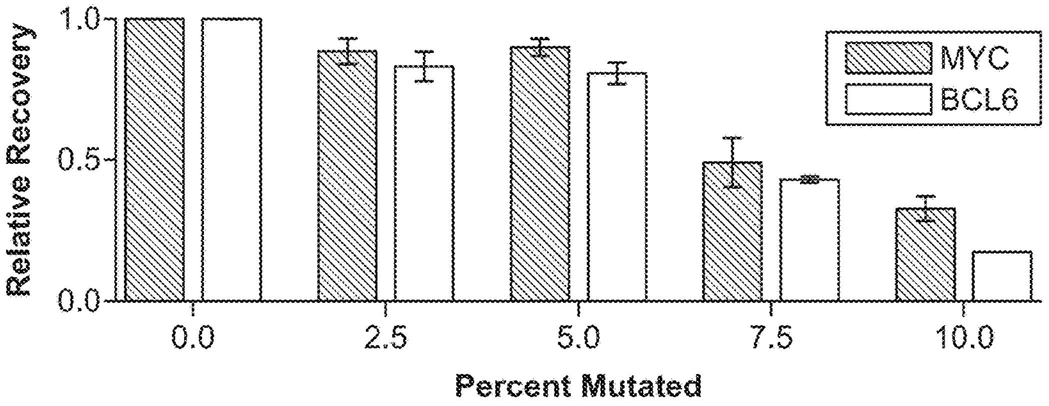
FIGS. 3A-3I illustrate technical performance of PhasED-Seq for disease detection.
Figure 14A:
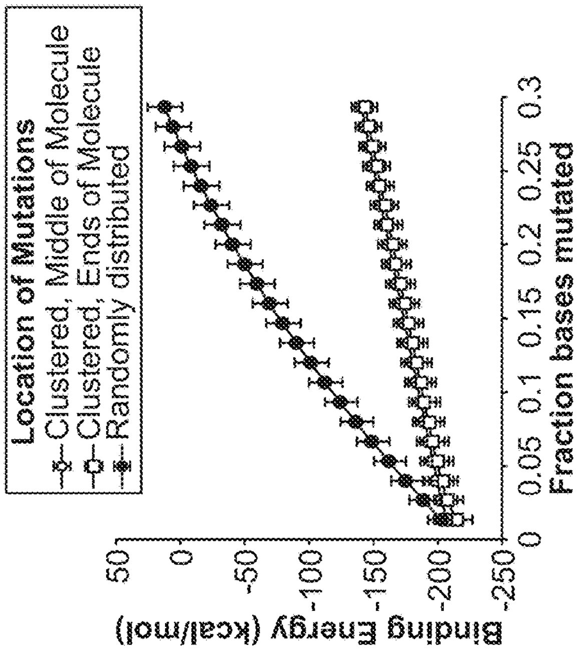
FIGS. 14A-14E illustrate Technical aspects of PhasED-Seq by hybrid-capture sequencing.
Figure 14B:
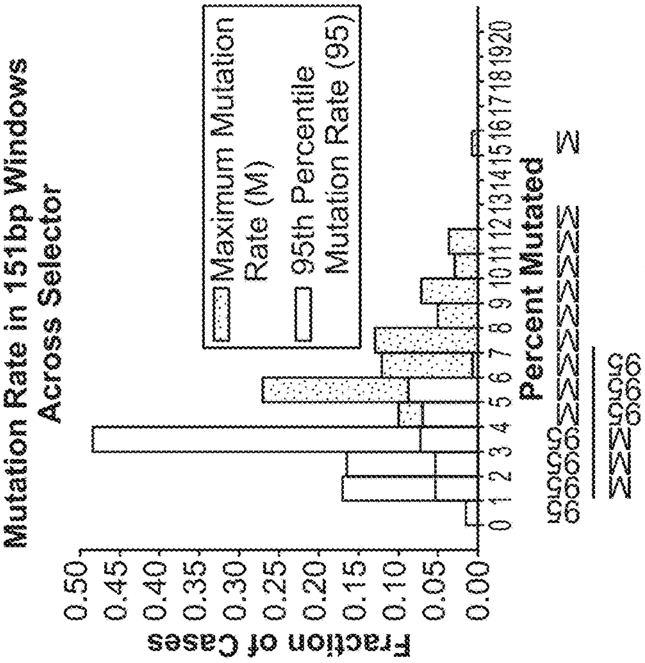
Figure 14C:
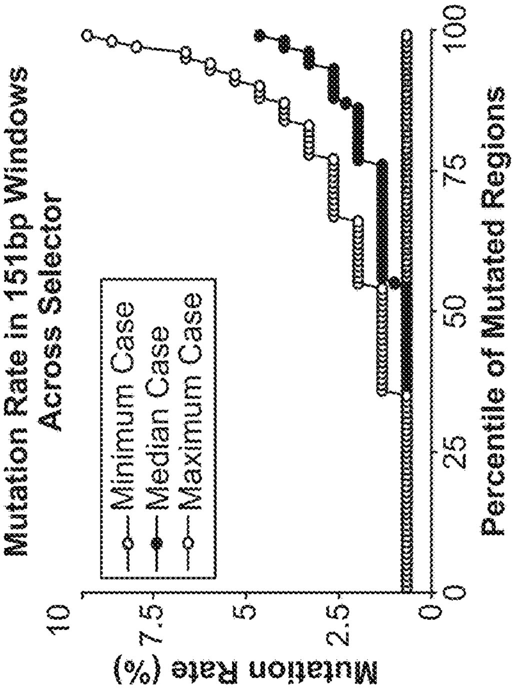

To facilitate detection of ctDNA using PVs, efficient recovery of DNA molecules is desired. Hybrid-capture sequencing is potentially sensitive to DNA mismatches, with increasing mutations decreasing hybridization efficiency. Indeed, AID hotspots can contain a 5-10% local mutation rate, with even higher rates in certain regions of IGH. To empirically assess the effect of mutation rate on capture efficiency, DNA hybridization of 150-mers with varying mutation rates in silico was simulated. As expected, predicted binding energy decreased with an increasing number of mutations (FIG. 14A). Notably, randomly distributed mutations had a greater effect on binding energy than clustered mutations. To assess the effect of this decreased binding affinity, 150-mer DNA oligonucleotides with 0 to 10% difference from the reference sequence in MYC and BCL6, two loci that are targets of aSHM were synthesized. To assess the worst-case scenario for hybridization, non-reference bases were randomly distributed rather than in clusters (Example 10). An equimolar mixture of these oligonucleotides were then captured with PhasED-Seq panel. Concordant with the in silico predictions, increased mutational rates resulted in decreased capture efficiency (FIG. 3A). Molecules with a 5% mutation rate were captured with 85% efficiency relative to fully-wildtype counterparts, while molecules with 10% mutation were captured with only 27% relative efficiency. To assess the prevalence of this degree of mutation in human tumors, the distribution of variants in panel in 140 patients with B-cell lymphomas, calculating the fraction of mutated bases in overlapping 151-bp windows (Example 10) was examined. Only 7% (10/140) of patients had any 151-bp window exceeding 10% mutation rate (FIG. 14B-C). Indeed, in the experiment with synthetic oligonucleotides, a 5% mutation rate was recovered nearly as efficiently as the wild-type sequence. In over half of all cases considered, no locus had >5% mutation rate at any window, while in all cases>90% of windows had <5% mutations. Overall, these observations indicate that the majority of phased mutations are recoverable by efficient hybrid capture, despite hybridization biases.

Example 7: Error Profile and Limit of Detection for Phased Variant Sequencing

Figure 3B:
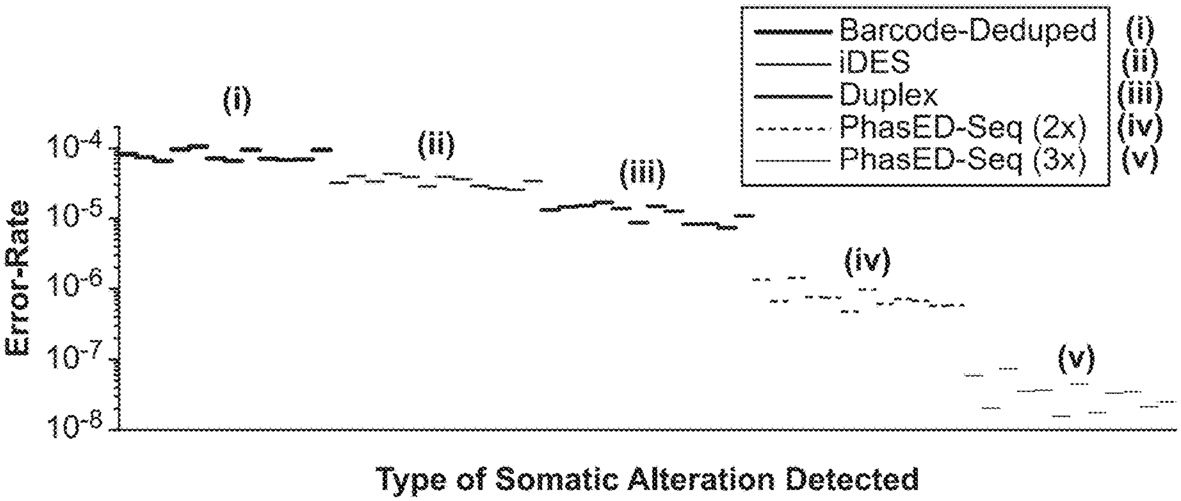
Figure 3C:
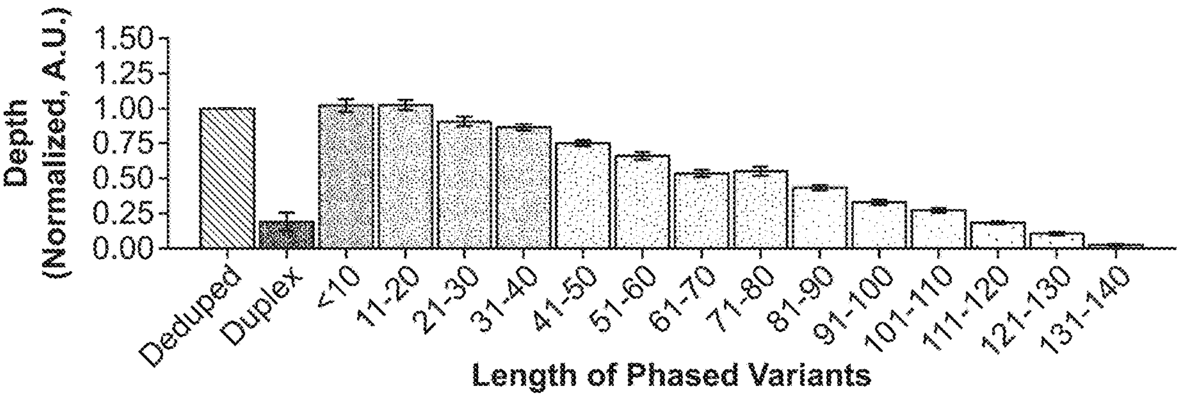
Figure 3D:
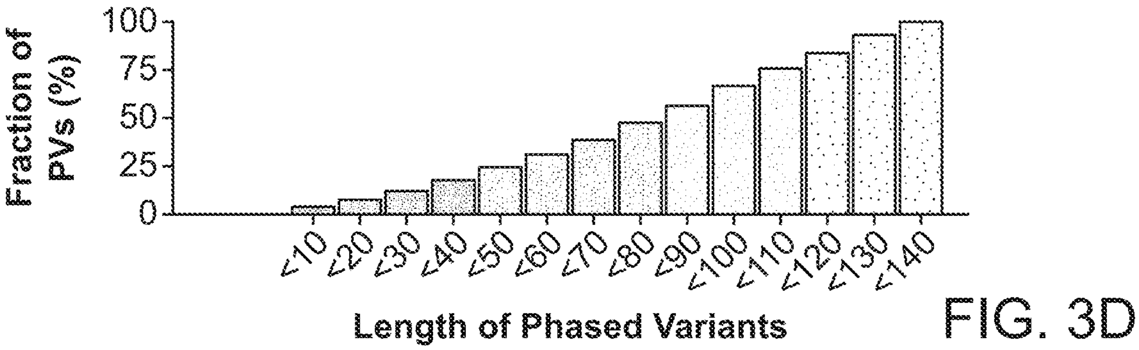
Figure 14D:
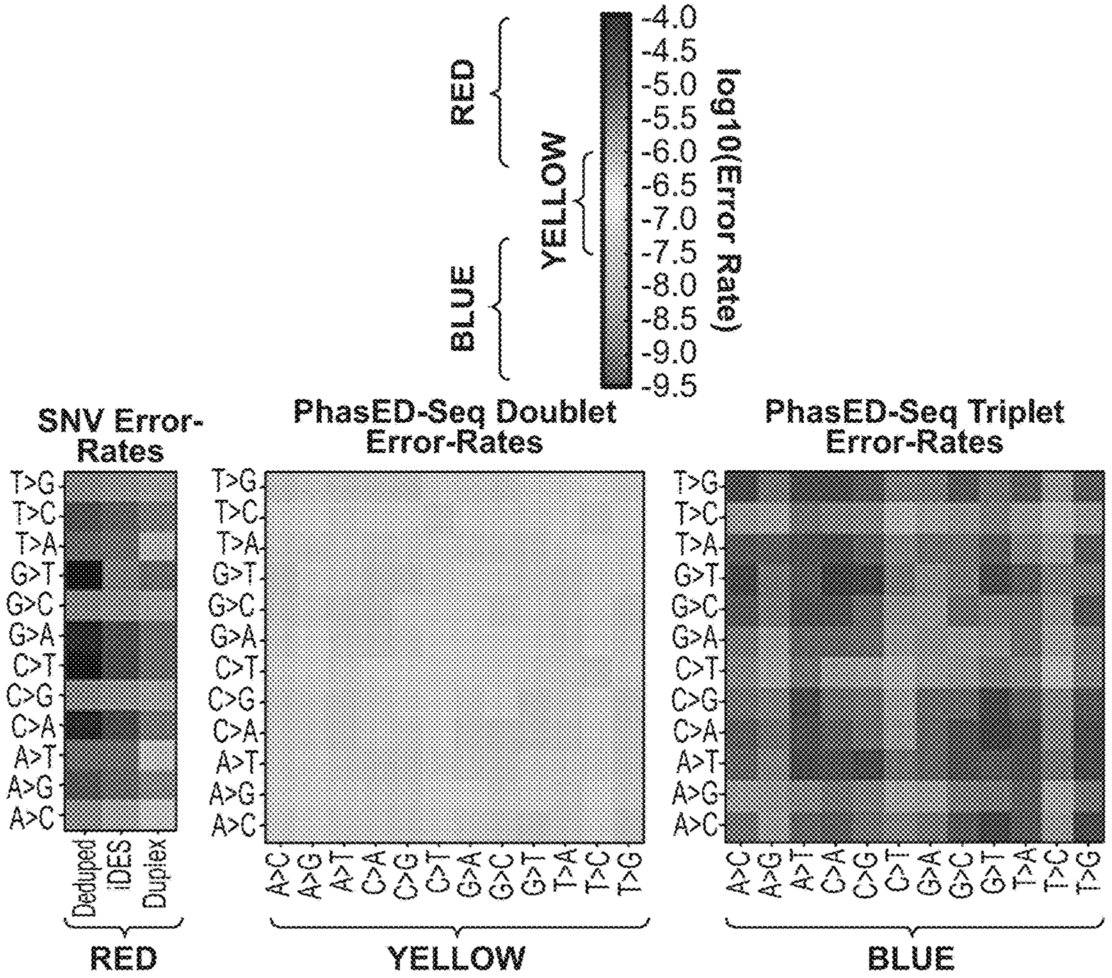
Figure 14E:
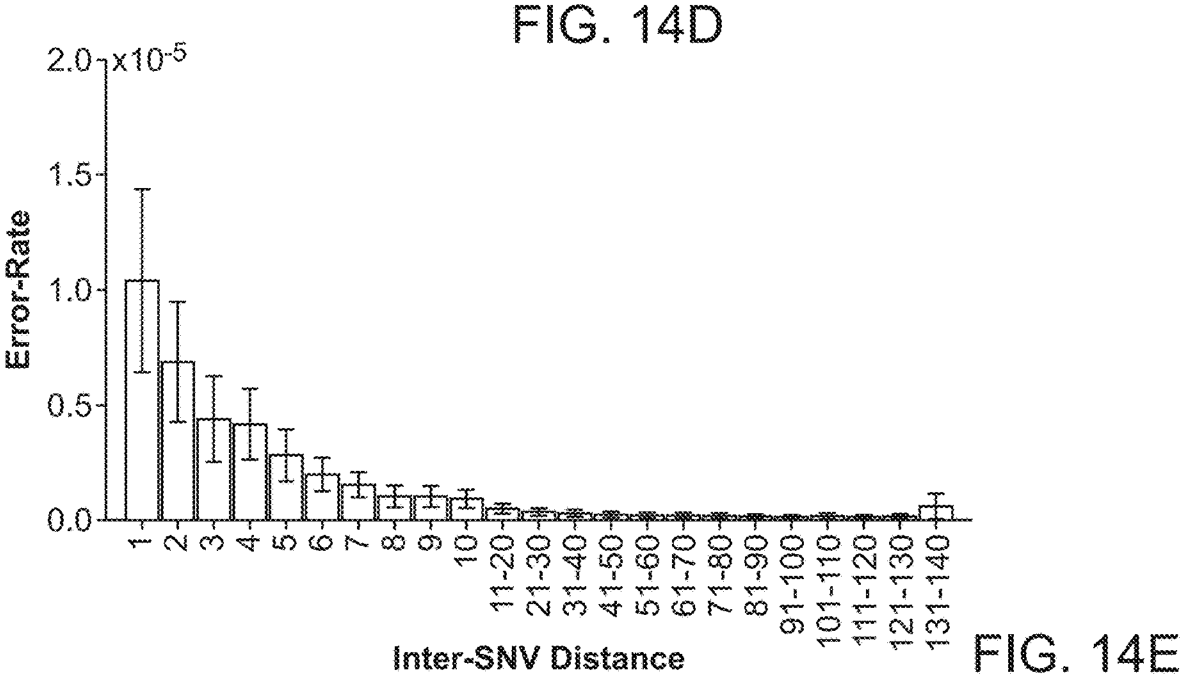
Figure 17A:
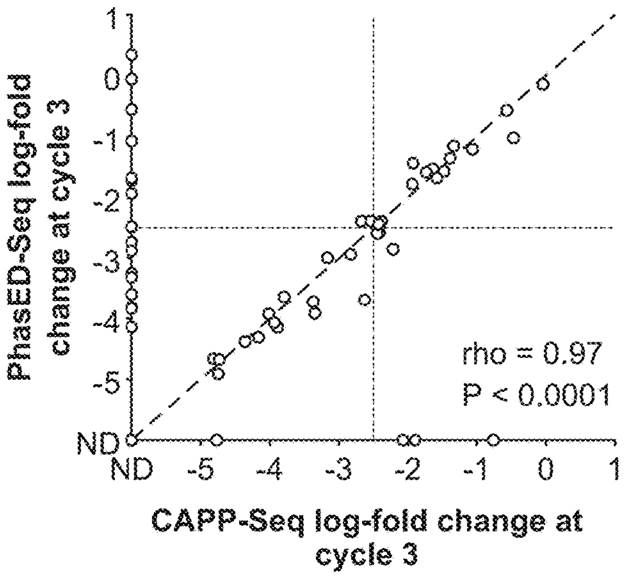
FIGS. 17A-17D illustrate detection of ctDNA after two cycles of systemic therapy.
Figure 17B:
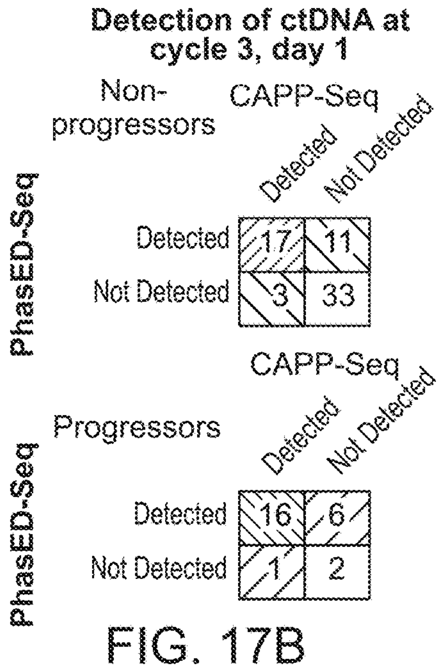
Figure 17C:
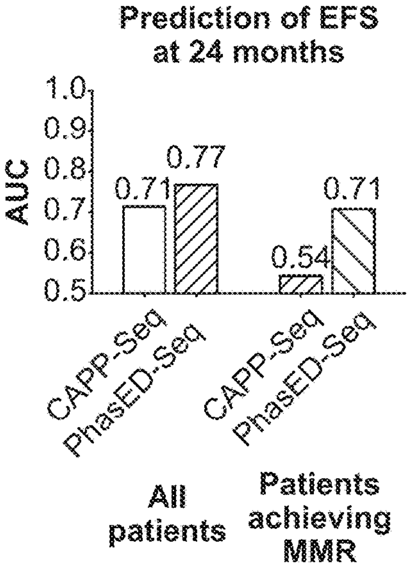
Figure 17D:
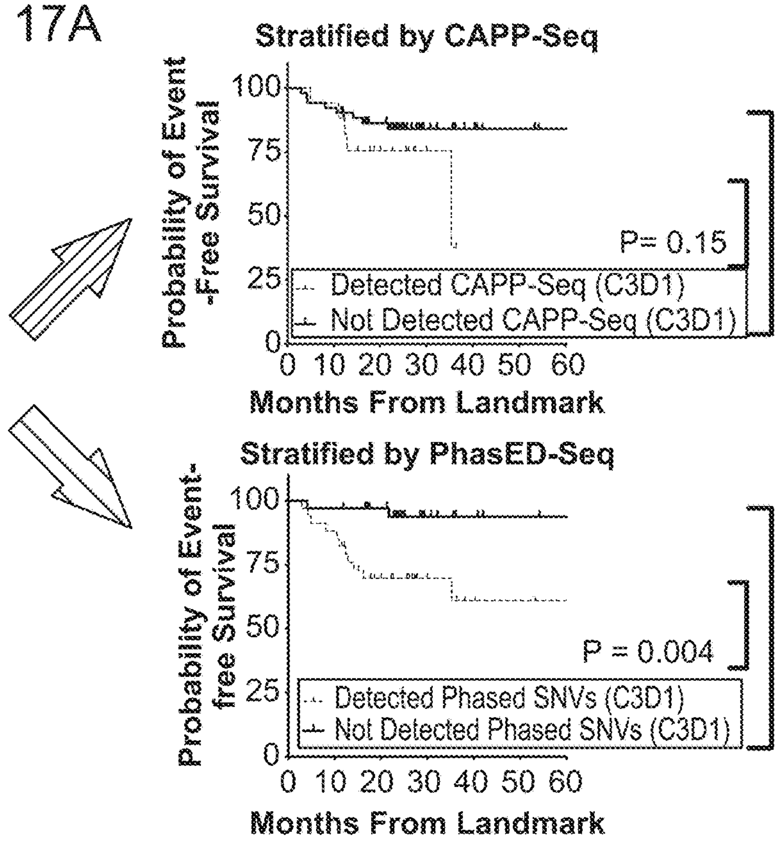

Previous methods for highly error-suppressed sequencing applied to cfDNA have utilized either a combination of molecular and in silico methods for error suppression (e.g., integrated digital error suppression, iDES) or duplex molecular recovery. However, each of these has limitations, either for detecting events at ultra-low tumor fractions or for efficient recovery of original DNA molecules, which are important considerations for cfDNA analysis where input DNA is limited. The error profile and recovery of input genomes from plasma cfDNA samples form 12 heathy adults by PhasED-Seq were compared with both iDES-CAPP-Seq and duplex sequencing. While iDES-enhanced CAPP-Seq had a lower background error profile than barcode-deduplication alone, duplex sequencing offered the lowest background error rate for non-reference single nucleotide substitutions (FIG. 3B, $3.3\times10^{-5}$ vs. $1.2\times10^{-5}$, P<0.0001). However, the rate of phased errors—e.g., multiple non-reference bases occurring on the same sequencing fragment—was significantly lower than the rate of single errors in either iDES-enhanced CAPP-Seq or duplex sequencing data. This was true for the incidence of both two (2× or 'doublet' PVs) or three (3× or 'triplet' PVs) substitutions on the same DNA molecule (FIG. 3B, $8.0\times10^{-7}$ and $3.4\times10^{-8}$ respectively, P<0.0001). Phased errors containing C to T or T to C transition substitutions were more common than other types of PVs (FIG. 14D). Notably, the rate doublet PVs errors in cfDNA was also correlated with distance between positions, with the highest PV error-rate consisting of neighboring SNVs (e.g., DNVs) and decreasing error rate with increasing distance between constituent variants (FIG. 14E). When considering unique molecular depth, duplex sequencing recovered only 19% of all unique cfDNA fragments (FIG. 3C). In contrast, the unique depth of PVs within a genomic distance of <20 bp was nearly identical to the depth of individual positions (e.g., molecules covering individual SNVs). Similarly, PVs up to 80 bps in size had depth greater than 50% of the median unique molecular depth for a sample. Importantly, almost half (48%) of all PVs were within 80 bp of each other, demonstrating their utility for disease detection from input-limited cfDNA samples (FIG. 3D).

Figure 3E:
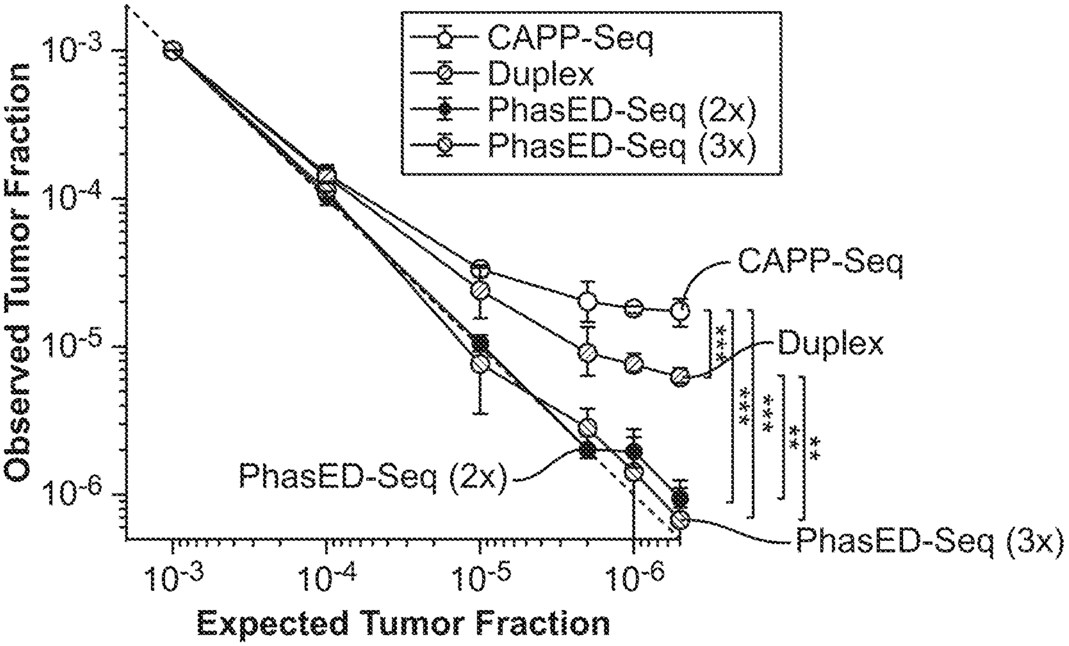
Figure 3F:
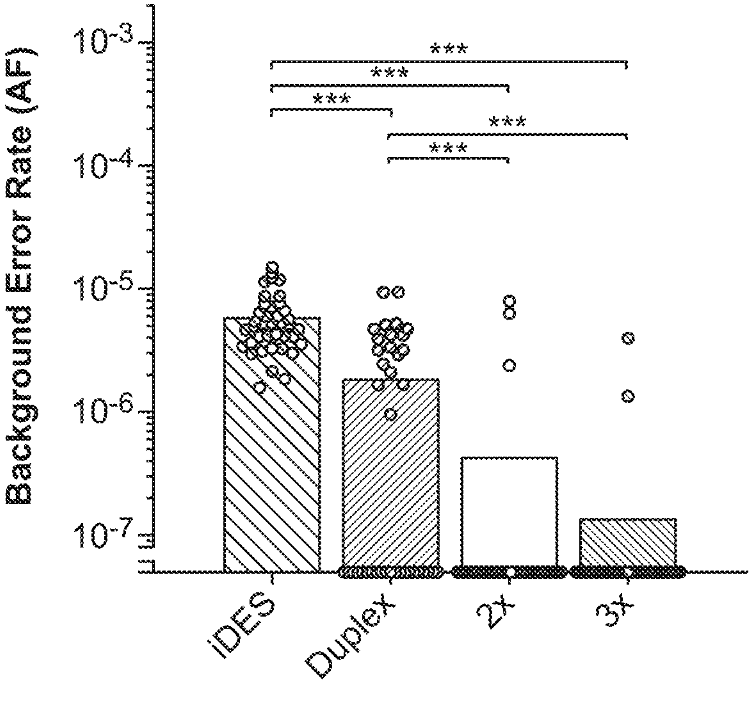
Figure 23A:
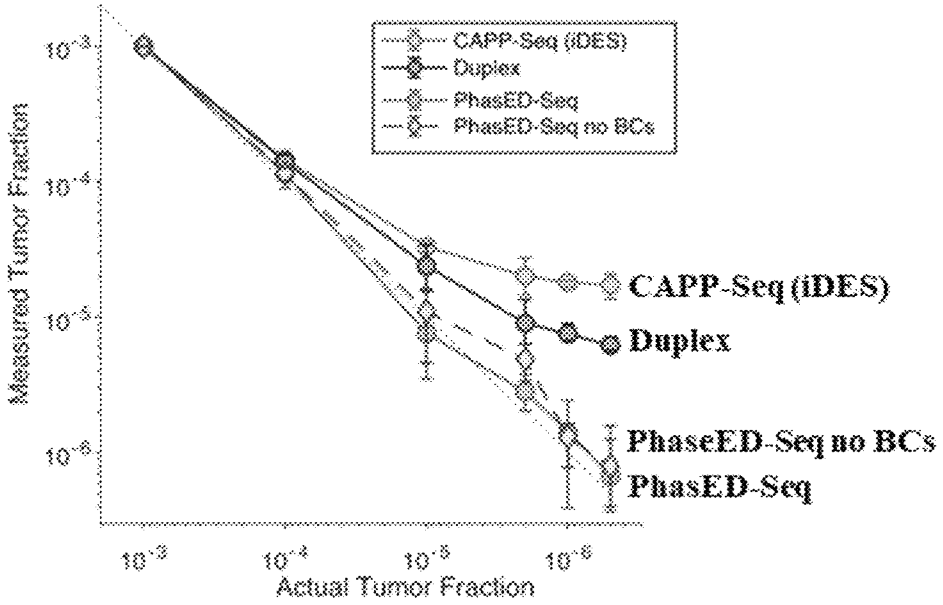
FIGS. 23A-23B illustrate that the method describe herein (e.g. method depicted yielding FIG. 3E and FIG. 3F) does not require barcode meditated error suppression.
Figure 23B:
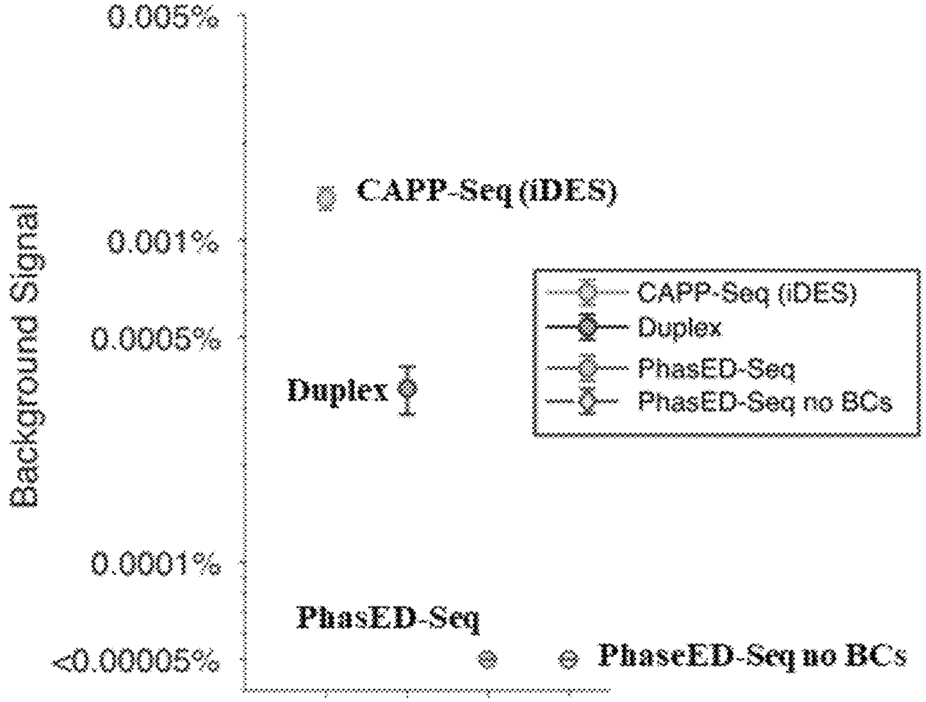

To quantitatively compare the performance of PhasED-Seq to alternative methods for ctDNA detection, limiting dilutions of ctDNA from 3 lymphoma patients into healthy control cfDNA were generated, resulting in expected tumor fractions between 0.1% and 0.00005% (1 part in 2,000,000; (Example 10). The expected tumor fraction was compared to the estimated tumor content in each of these dilutions using PhasED-Seq to track tumor-derived PVs, as well as to error-suppressed detection methods depending on individual SNVs (e.g. iDES-enhanced CAPP-Seq or duplex sequencing; FIG. 3E). All methods performed equally well down to tumor fractions of 0.01% (1 part in 10,000). However, below this level (e.g., 0.001%, 0.0002%, 0.0001%, and 0.00005%), both PhasED-Seq and duplex sequencing significantly outperformed iDES-enhanced CAPP-Seq (P<0.0001 for duplex, '2×' PhasED-Seq, and '3×' PhasED-Seq; FIG. 3E). In addition, when compared to duplex-sequencing, tracking either 2 or 3 variants in-phase (e.g., 2× and 3× PhasED-Seq) more accurately identified expected tumor content, with superior linearity down to 1 part in 2,000,000 (P=0.005 for duplex vs 2×PhasED-Seq, P=0.002 for 3χ PhasED-Seq) (Example 10). Specificity of PVs by looking for evidence of tumor-derived SNVs or PVs in cfDNA samples from 12 unrelated healthy control subjects and the healthy control used for the limiting dilution was assessed. Here again, both 2×- or 3×-PhasED-Seq showed significantly lower background signal levels than did CAPP-Seq and duplex sequencing (FIG. 3F). This lower error rate and background from PVs improves the detection limit for ctDNA disease detection. In some instances, the method of sequencing-based cfDNA assays described herein (e.g. the method depicted in FIG. 3E and FIG. 3F) does not require molecular barcodes to achieve exquisite error-suppression and low limits of detection. Signal assessed by the method without barcode used limiting dilution series from 1:1,000 to 5:10,000,000, and 'blank' controls (FIGS. 23A-23B).

Figure 3G:
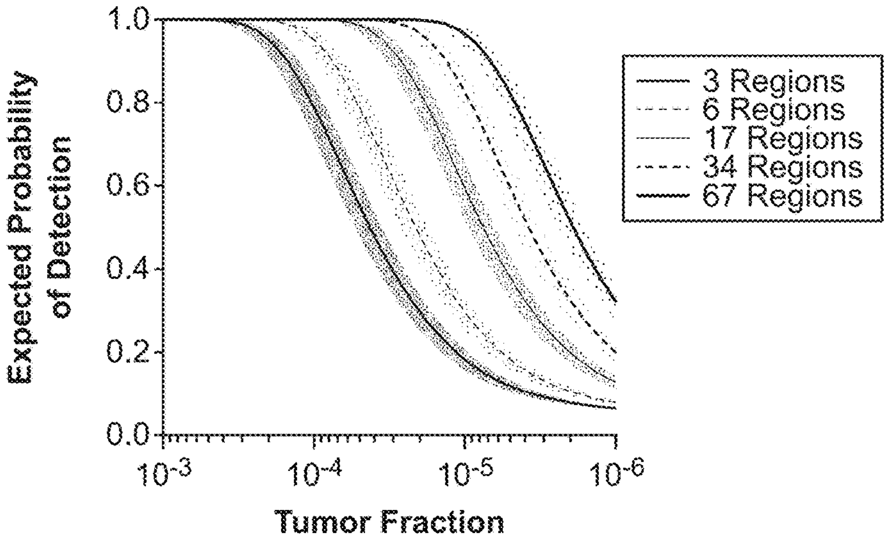
Figure 3H:
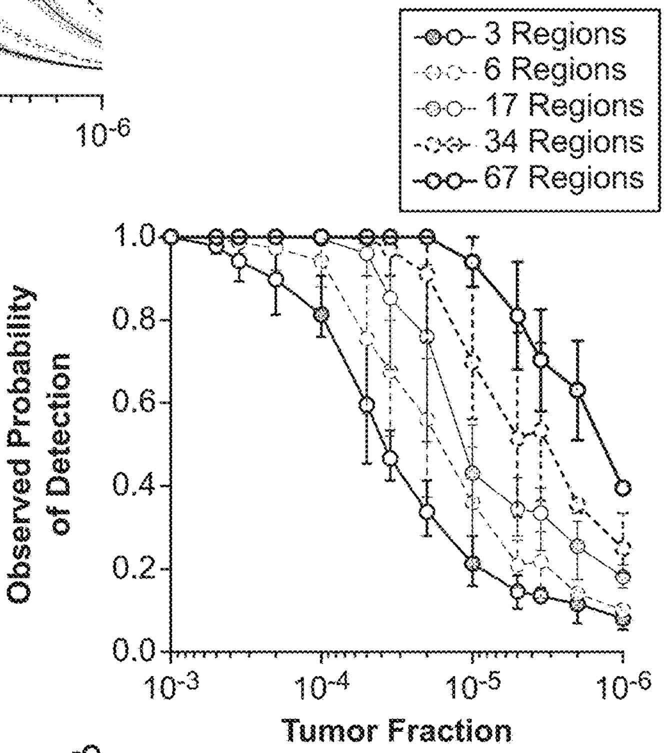
Figure 3I:
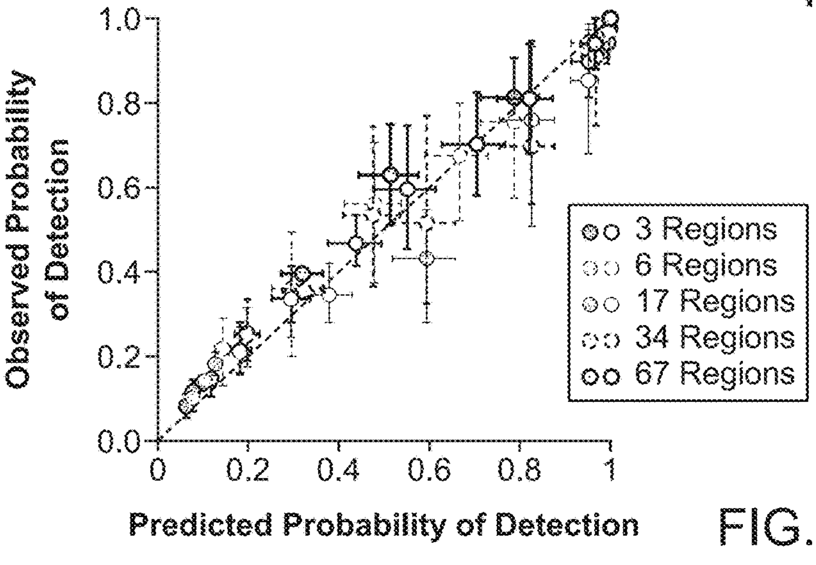

This dilution series was used to assess the limit of detection for a given number of PVs (FIGS. 3G-3I). When considering a set of PVs within 150 base pair (bp) regions, the probability of detection for a given sample may be accurately modelled by binomial sampling, considering both the depth of sequencing and the number of 150 bp regions with PVs (Example 10).

Example 8: Improvements in Detection of Low-Burden Minimal Residual Disease

Figure 4A:
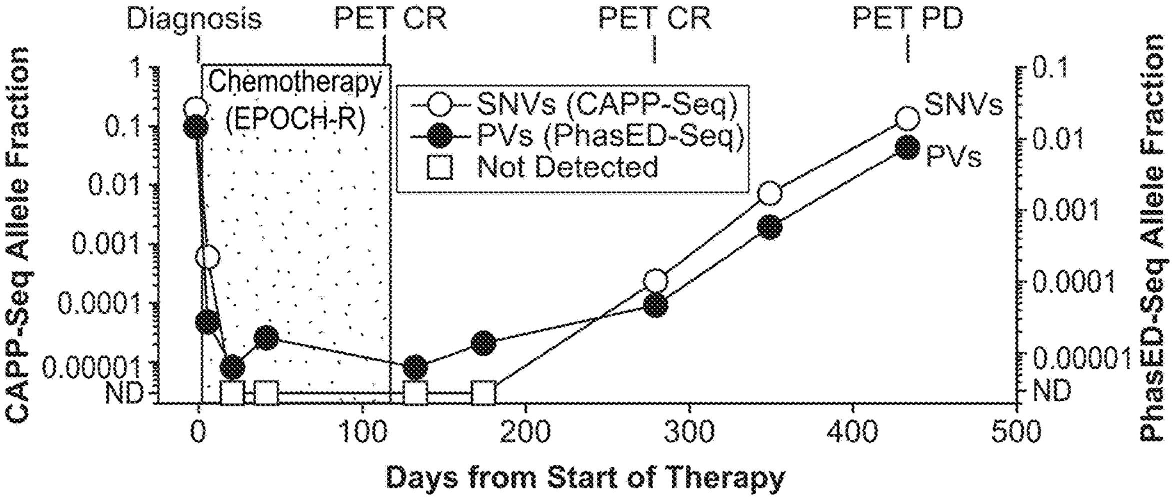
FIGS. 4A-4G illustrate clinical application of PhasED-Seq for ultra-sensitive disease detection and response monitoring in DLBCL.

To test the utility of the lower LOD afforded by PhasED-Seq for detection of ultra-low burden MRD from cfDNA, Serial cell-free DNA samples were sequenced from a patient undergoing front-line therapy for DLBCL (FIG. 4A). Using CAPP-Seq, this patient had undetectable ctDNA after only one cycle of therapy, with multiple subsequent samples during and after treatment also remaining undetectable. This patient had subsequent re-emergence of detectable ctDNA>250 days after the start of therapy, with eventual clinical and radiographic disease progression 5 months later, indicating falsely negative serial measurements with CAPP-Seq. Strikingly, all four of the plasma samples that were undetectable by CAPP-Seq during and after treatment had detectable ctDNA levels by PhasED-Seq, with mean allelic fractions as low as 6 parts in 1,000,000. This increased sensitivity improved the lead-time of disease detection by ctDNA compared to radiographic surveillance from 5 with CAPP-Seq to 10 months with PhasED-Seq.

Figure 4B:
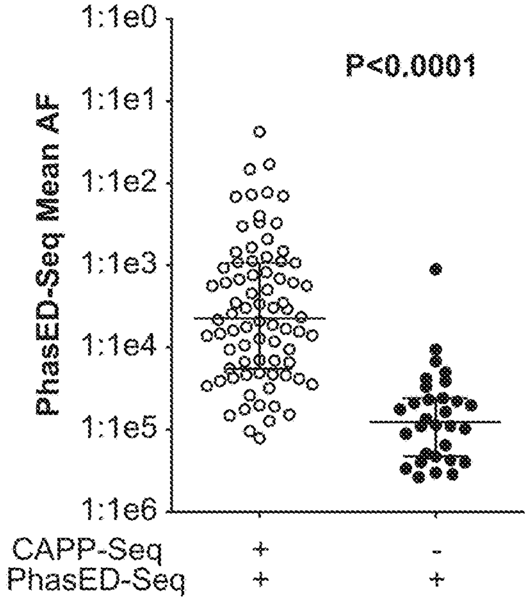
Figure 4C:
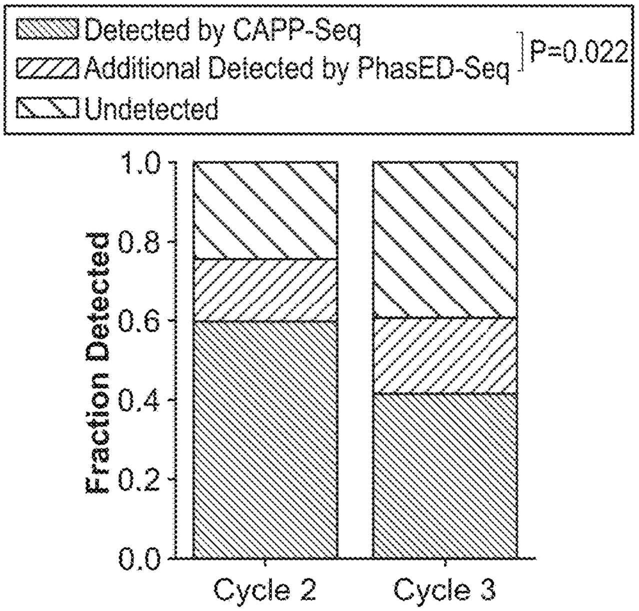
Figures 4D, 4E, 4F, 4G:
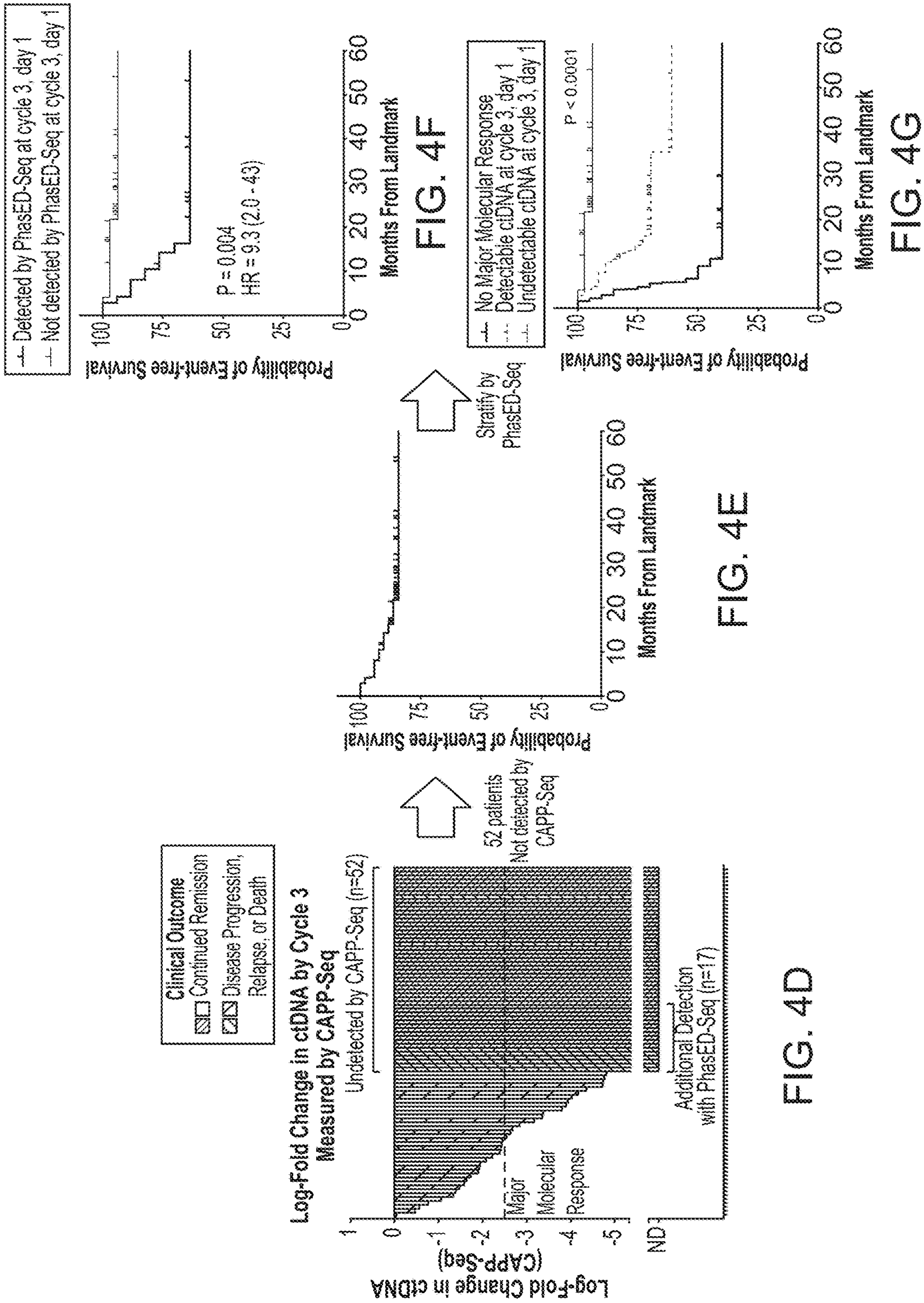

Next, the performance of PhasED-Seq ctDNA detection in a cohort of 107 patients with large B-cell lymphomas and blood samples available after 1 or 2 cycles of standard immuno-chemotherapy was next assessed. Importantly, ctDNA levels measured by PhasED-Seq were highly correlated with those measured by CAPP-Seq. In total, 443 tumor, germ-line, and cell-free DNA samples, including cfDNA prior to therapy (n=107) and after 1 or 2 cycles of treatment (n=82 and 89), were assessed. Prior to therapy, patient-specific PVs were detectable by PhaseED-Seq in 98% of samples, with 95% specificity in cfDNA from healthy controls (FIGS. 15 and 16A). Importantly, ctDNA levels measured by PhasED-Seq were highly correlated with those measured by CAPP-Seq, considering both pretreatment and post treatment samples (Spearman rho=0.91, FIG. 16B). Next, quantitative levels of ctDNA measured by PhasED-Seq and CAPP-Seq from cfDNA samples after initiation of therapy were compared. In total, 72% (78/108) of samples with detectable ctDNA by PhasED-Seq after 1 or 2 cycles were also detected by conventional CAPP-Seq (FIG. 4B). Among 108 samples detected by PhasED-Seq, disease burden was significantly lower for those with undetectable (28%) vs. detectable (72%) ctDNA levels using conventional CAPP-Seq, with a >10χ difference in median ctDNA levels (tumor fraction $2.2\times10^{-4}$ vs $1.2\times10^{-5}$, P<0.001, FIG. 4B). In total, an additional 16% (13/82) of samples after 1 cycle of therapy and 19% (17/89) of samples after 2 cycles of therapy had detectable ctDNA when comparing PhasED-Seq with CAPP-Seq (FIG. 4C).

ctDNA molecular response criteria was previously described for DLBCL patients using CAPP-Seq, including Major Molecular Response (MMR), defined as a 2.5-log reduction in ctDNA after 2 cycles of therapy22. While MMR at this time-point is prognostic for outcomes, many patients have undetectable ctDNA by CAPP-Seq at this landmark (FIGS. 4D-4E). Importantly, even in patients with undetectable ctDNA by CAPP-Seq, detection of occult ultra-low ctDNA levels by PhasED-Seq was prognostic for outcomes including event-free and overall survival (FIG. 4D). Indeed, in the 89 patients with a sample available from this time-point, 58% (52/89) had undetectable ctDNA by CAPP-Seq at their interim MMR assessment, after completing 2 of 6 planned cycles of therapy. Using PhasED-Seq, 33% (17/52) of samples not detected by CAPP-Seq had evidence of ctDNA as evidenced by PVs, with levels as low as 3:1,000,000 (FIGS. 17A-17D)—these 17 cases additionally detected by PhasED-Seq represent potential false negative tests by CAPP-Seq. Similar results were seen at the Early Molecular Response (EMR) time-point (i.e., after 1 cycle of therapy, FIGS. 18A-18H).

Figure 18A:
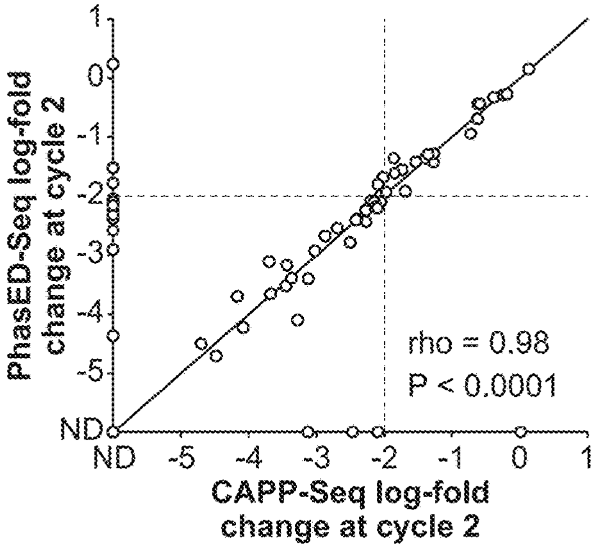
FIGS. 18A-18H illustrate detection of ctDNA after one cycle of systemic therapy.
Figure 18B:
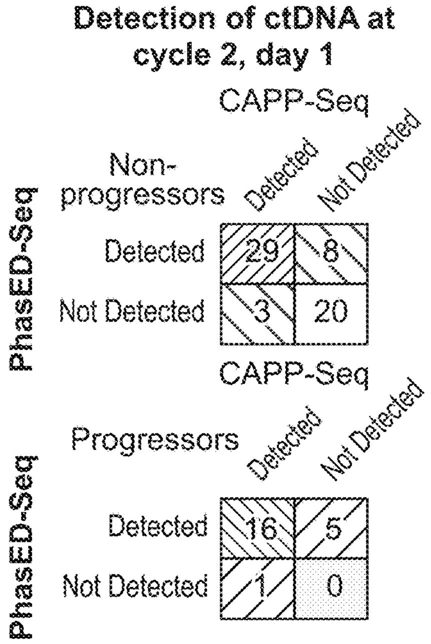
Figure 18C:
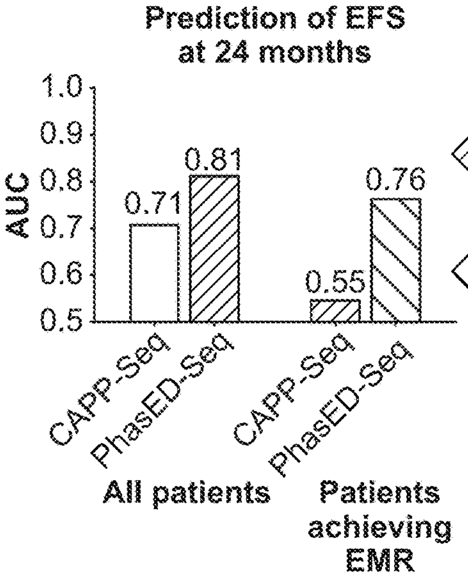
Figure 18D:
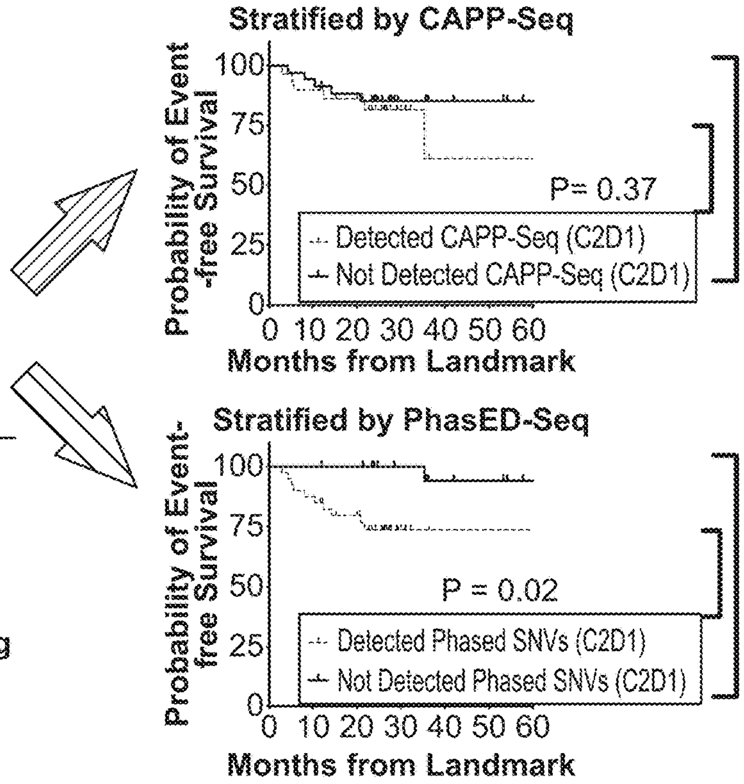
Figure 18E:
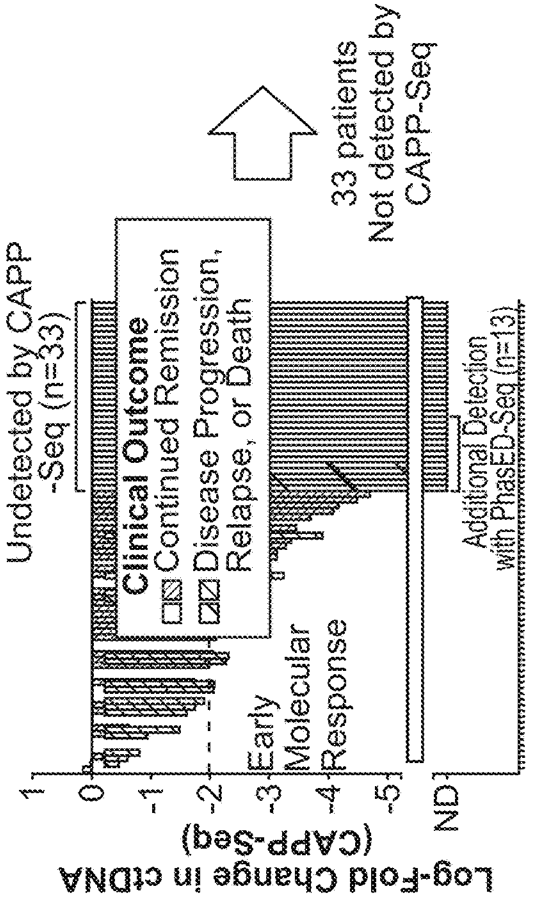
Figure 18F:
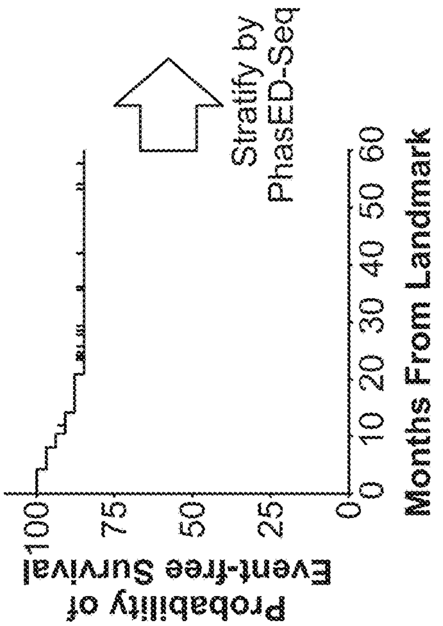
Figure 18G:
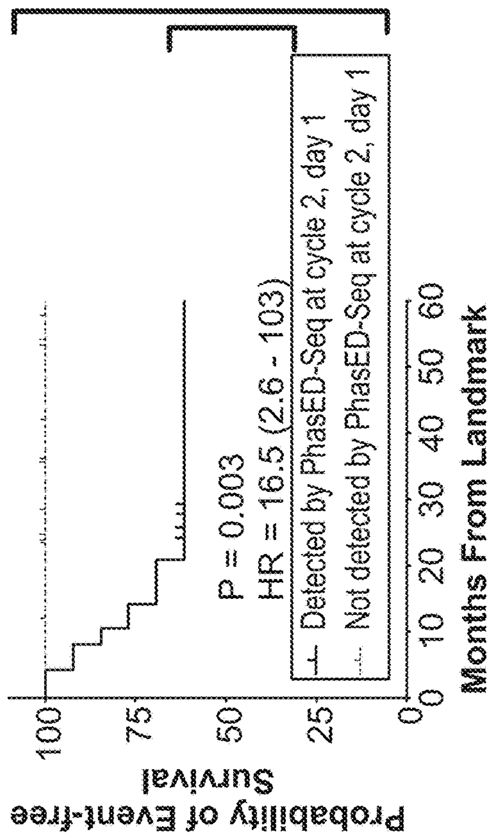
Figure 18H:
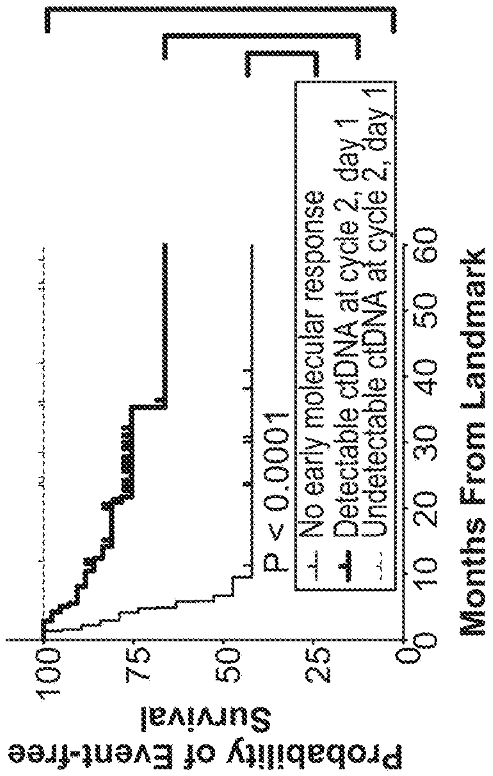

While detection of ctDNA in DLBCL after 1 or 2 cycles of therapy is a known adverse prognostic marker outcomes for patients with undetectable ctDNA at these time-points are heterogeneous (FIG. 4E and FIG. 18F). Importantly, even in patients with undetectable ctDNA by CAPP-Seq after 1 or 2 cycles of therapy, detection of ultra-low ctDNA levels by PhasED-Seq was strongly prognostic for outcomes including event-free survival (FIG. 4F, FIG. 17C-D, FIG. 18C-D, and FIG. 18G). When combining detection by PhasED-Seq with previously described MMR threshold, patients could be stratified into three groups—patients not achieving MMR, patients achieving MMR but with persistent ctDNA, and patients with undetectable ctDNA (FIG. 4G). Interestingly, while patients not achieving MMR were at especially high risk for early events despite additional planned first line therapy (e.g., within the first year of treatment), patients with persistent low levels of ctDNA appeared to have a higher risk of later relapse or progression events. In contrast, patients with undetectable ctDNA after 2 cycles of therapy by PhasED-Seq had overwhelmingly favorable outcomes, with 95% being event-free and 97% overall survival at 5 years. Similar results were seen at the EMR time-point after 1 cycle of therapy (FIG. 18H).

Example 9: Exemplary Embodiments of Mutation Detection Using Next Generation Sequencing (NGS) when the Mutation is not a Single Base Substation, but Rather a Pair of Mutations In Many Instances, a Limitation of cfDNA Tracking May be the Limitation on the Number of molecules available for detection. Additionally, there are multiple potential limitations on tracking tumor molecules from cell-free DNA, including not only the sequencing error profile, but also the number of molecules available for detection. The number of molecules available for detection—here termed the number of "evaluable fragments"—can be thought of as both a function of the number of recovered unique genomes (e.g., unique depth of sequencing) and the number of somatic mutations being tracked. More specifically, the number of evaluable fragments is equal to: EF=d*n.

Where d=the unique molecular depth considered and n=the number of somatic alterations tracked. For the typical cell-free DNA samples, less than 10,000 unique genomes are often recovered (d), requiring any sensitive method to track multiple alterations (n). Furthermore, as stated above, the major limitation for duplex sequencing is difficulty recovering sufficient unique molecular depth (d); thus, from a typical plasma sample with duplex depth of ~1,500×, even if following 100 somatic alterations, there are only 150,000 evaluable fragments. Thus, in this scenario, sensitivity is limited by the number of molecules available for detection. In contrast, other methods such as iDES-enhanced CAPP-Seq consider all molecules recovered. Here, as many as 5,000-6,000× unique haploid genomes can be recovered. Therefore, the number of evaluable fragments, tracking the same 100 somatic alterations, may be 500,000-600,000×. However, the error profile of single-stranded sequencing, even with error suppression, allows detection to levels of at best 1 part in 50,000. Therefore, methods aiming to improve on the detection limits for ctDNA must overcome both the error-profile of sequencing and the recovery of sufficient evaluable fragments to utilize said lower error-profiles.

To remedy this apparent deficiency, the method of PhasED-Seq, as described in the instant disclosure, allows for lymphoid malignancies and was applicable to other cancer histologies, (e.g., using a "personalized" approach). For a personalized approach, customized hybrid-capture oligonucleotides (or primers for PCR amplicons) were used to capture personalized somatic mutations identified from whole exome or genome sequencing. The PCAWG dataset assessed for SNVs occurring within 170 bp of each other in genomic space was re-analyzed. It was found that in 14 of 24 cancer histologies considered, the median case contained >100 possible phased variants, including in several solid tumors such as Melanoma (median 2072), lung squamous cell carcinoma (1268), lung adenocarcinoma (644.5), and colorectal adenocarcinoma (216.5).

Figure 19:
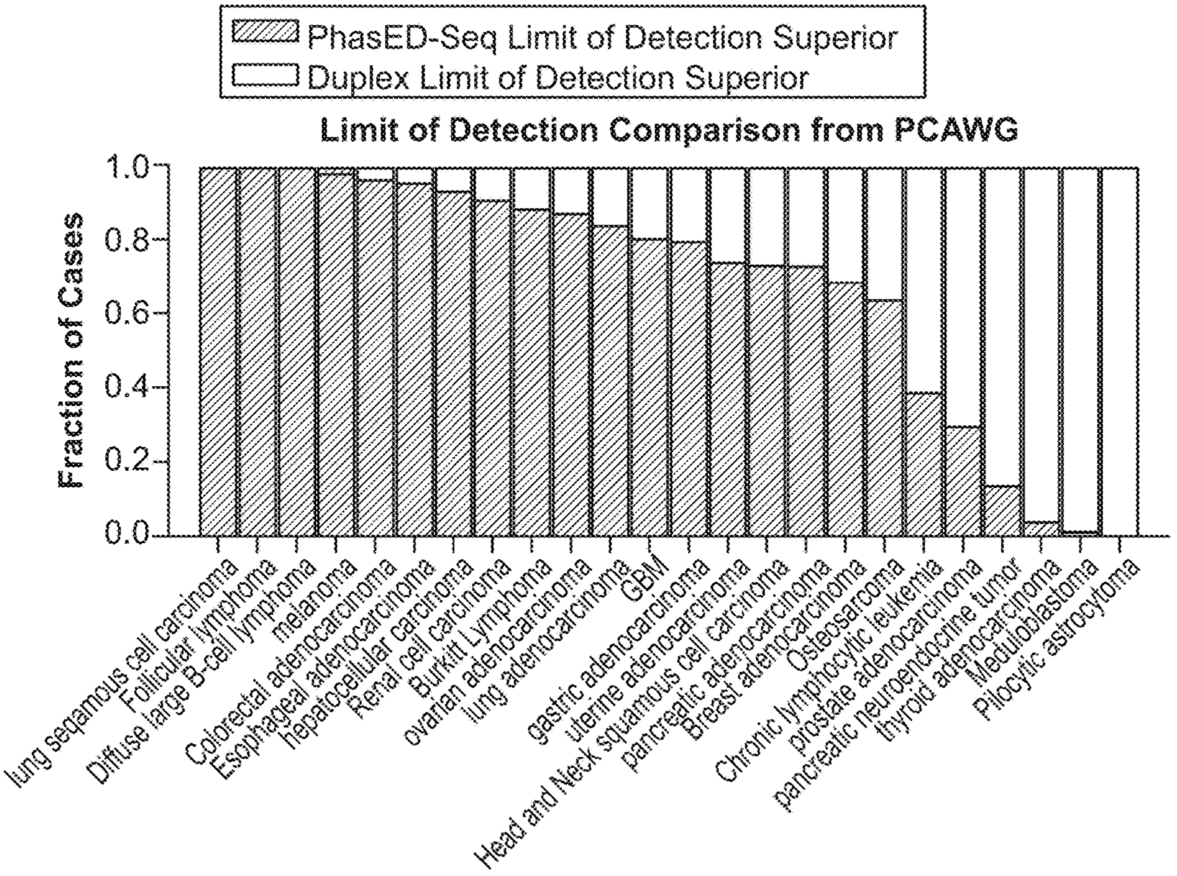
FIG. 19 illustrates a fraction of patients where PhasED-Seq would achieve a lower LOD than duplex sequencing tracking SNVs based on PCAWG data (whole genome sequencing) from which the number of SNVs and phased variants (PVs) in different tumor types was quantified.
Figure 20:
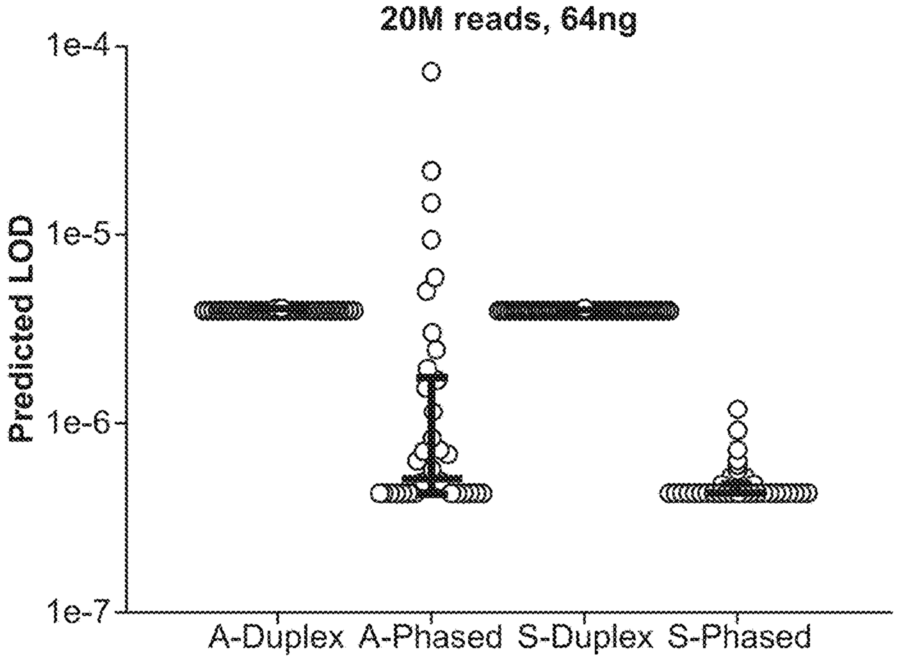
FIG. 20 illustrates improved LODs achieved in lung cancers (adenocarcinoma, abbreviated 'A', and squamous cell carcinoma, abbreviated S'), compared to duplex sequencing of whole genome sequencing data.

Next, the expected limit of detection in all cases in the PCAWG dataset using either duplex sequencing or PhasED-Seq was assessed. Again, the limit of detection was defined by the expected number of evaluable fragments, and thus depends on both the number of variants tracked and the expected depth of sequencing. Utilizing the data from optimized hybrid capture conditions, a model to predict the expected deduplicated (single-stranded) and duplex (double-stranded) molecular depth with a given DNA input and number of sequencing reads was constructed. Using this, along with the number of SNVs or possible PVs from the PCAWG dataset, for each case, which method would lead to a greater number of evaluable fragments, and therefore a superior limit of detection was assessed. The results of this exercise, assuming 64 nanograms (ng) of total cfDNA input and a total of 20 million sequencing reads are shown in FIG. 19. Notably, in the majority of cancer types (18/24 histologies), PhasED-Seq had a lower limit of detection than duplex sequencing. This importantly included not only B-cell lymphomas, but common solid tumors, including lung squamous cell carcinoma and adenocarcinoma, colorectal adenocarcinoma, esophageal and gastric adenocarcinoma, and breast adenocarcinoma, among others. Indeed, taking lung cancers as a specific example, an almost 10-fold lower limit of detection was found for the median squamous cell and adenocarcinoma lung cancer case using PhasED-Seq compared to duplex sequencing (FIG. 20). Both PhasED-Seq and duplex sequencing using a personalized approach had a lower limit of detection than non-personalized approaches (e.g., iDES-enhanced CAPP-Seq).

Figure 21:
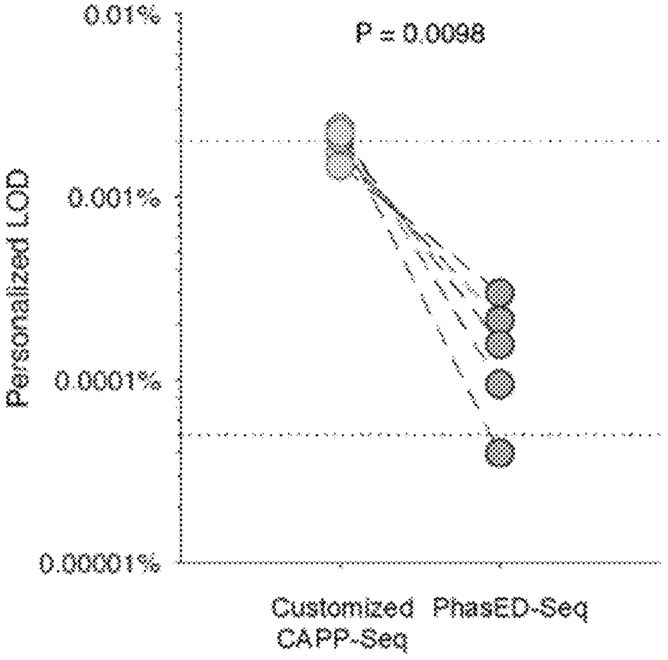
FIG. 21 illustrates empiric data from an experiment where WGS was performed on tumor tissue and custom panels were designed for 5 patients with solid tumors (5 lung cancers) to examine and compare the LODs of custom CAPP-Seq vs PhasED-Seq, showing a ~10× lower LOD using PhasED-Seq in 5/5 patients.

To further confirm the applicability of phased variants and PhasED-Seq in diverse solid tumors, WGS (20-30×) was performed on paired tumor and normal DNA to identify PVs from five solid tumor patients predicted to have low ctDNA burden prior to treatment (lung cancer (n=5)). After identifying putative PVs in each case, a set of personalized hybrid capture oligonucleotides was subsequently designed to performed targeted resequencing of tumor and normal DNA to validate candidate PVs. Finally, plasma samples were sequenced from all 5 patients to high unique molecular depth using personalized PhasED-Seq to detect ctDNA. Considering these five lung cancer cases the PhasED-Seq approach achieved a ~10-fold improvement in analytical sensitivity, achieving a median LOD of 0.00018% compared to 0.0019% using customized CAPP-Seq (FIG. 21).

Figure 22A:
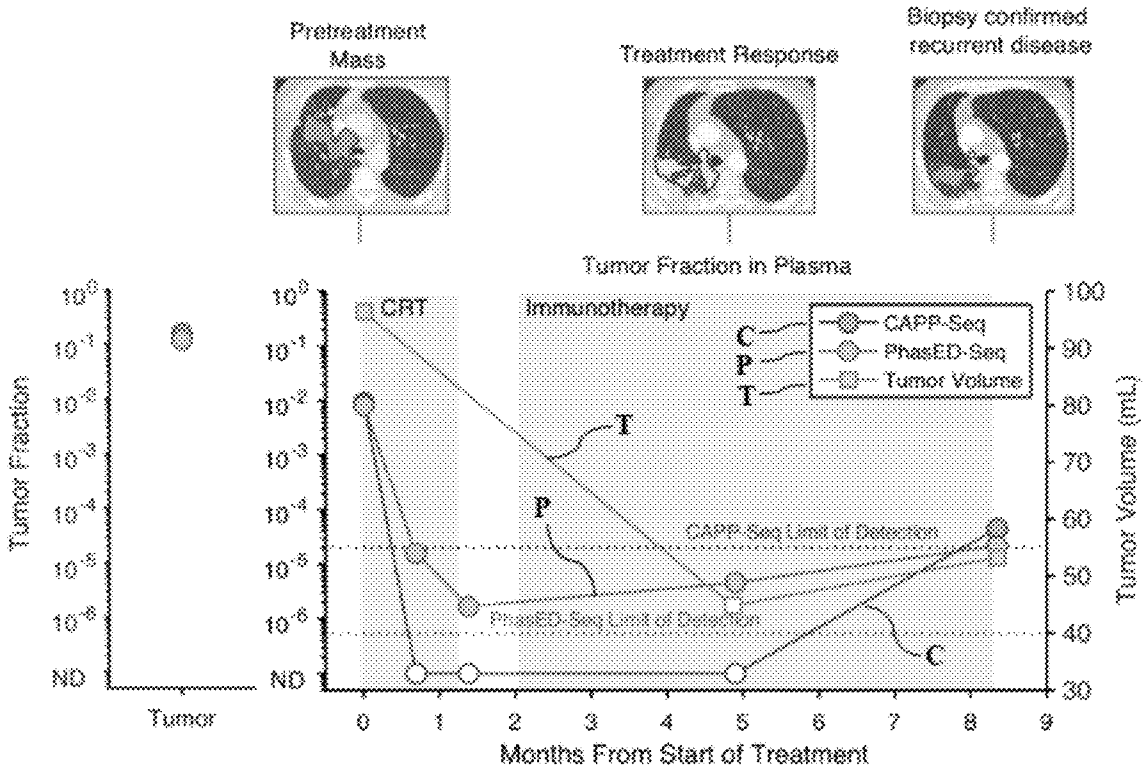
FIG. 22A illustrates proof of principle example patient vignette comparing using custom CAPP-Seq and PhasED-Seq for disease surveillance in lung cancer showing earlier detection of relapse using PhasED-Seq.
Figure 22B:
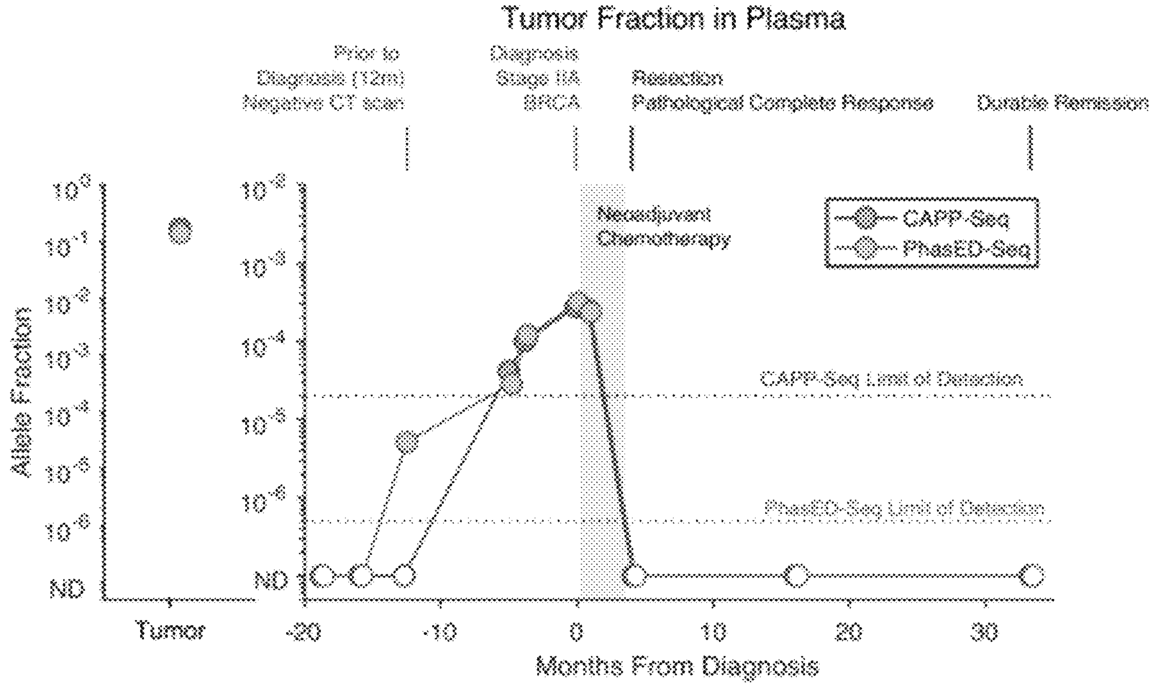
FIG. 22B illustrates proof of principle example patient vignette comparing using custom CAPP-Seq and PhasED-Seq for early detection of disease in breast cancer, showing earlier detection of disease with PhasED-Seq.

To demonstrate the clinical significance of this improved limit of detection for ctDNA from PhasED-Seq in solid tumors, serial plasma samples from a patient with stage 3 adenocarcinoma of the lung treated with chemoradiotherapy with curative intent (LUP814) were analyzed using both CAPP-Seq and PhasED-Seq. As outlined above, both CAPP-Seq and PhasED-Seq quantified a similar level of ctDNA prior to therapy (~1% tumor fraction). However, 3 subsequent samples after beginning therapy had undetectable ctDNA by standard CAPP-Seq, including samples during and after chemoradiation and during adjuvant immunotherapy with Durvalumab. Despite the lack of detectable disease by CAPP-Seq, the patient had biopsy-confirmed recurrent disease after an initial radiographic response. However, when analyzing these same samples with PhasED-Seq, molecular residual disease in 3/3 (100%) of samples was detected, with mean tumor fraction as low as 0.00016% (1.6 parts per million). Furthermore, the trend in ctDNA quantitation mirrored the patient's disease course, with an initial response to chemoradiotherapy but disease progression during immunotherapy. Importantly, this patient's disease remained detectable at all timepoints, with detectable disease at the completion of chemoradiotherapy 8 months prior to the patient's biopsy-confirmed disease progression (FIG. 22).

Figure 5A:
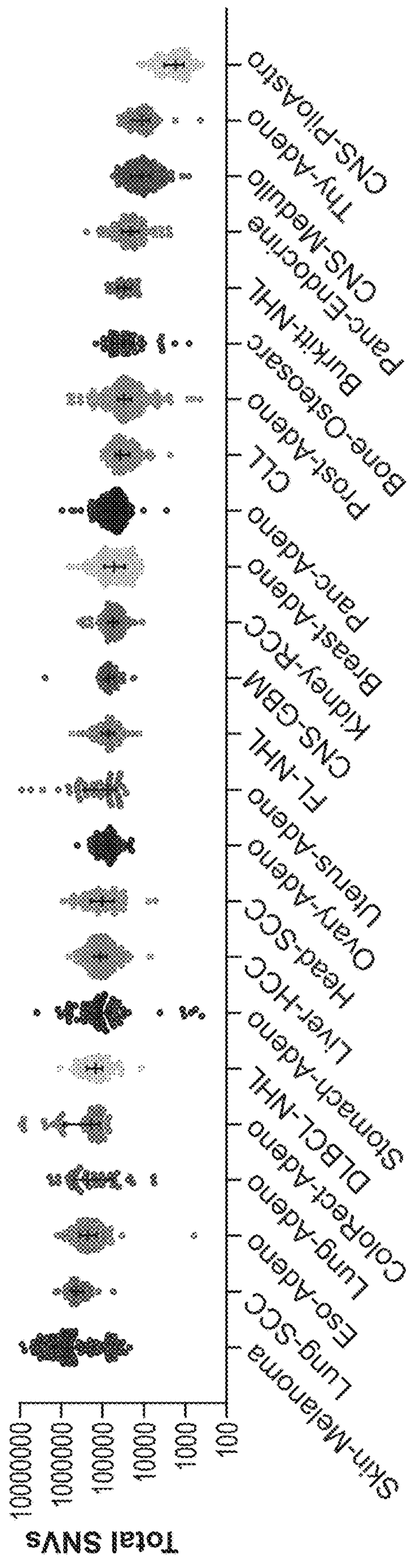
FIGS. 5A-5C illustrate enumeration of SNVs and PVs in diverse cancers from WGS.
Figure 5B:
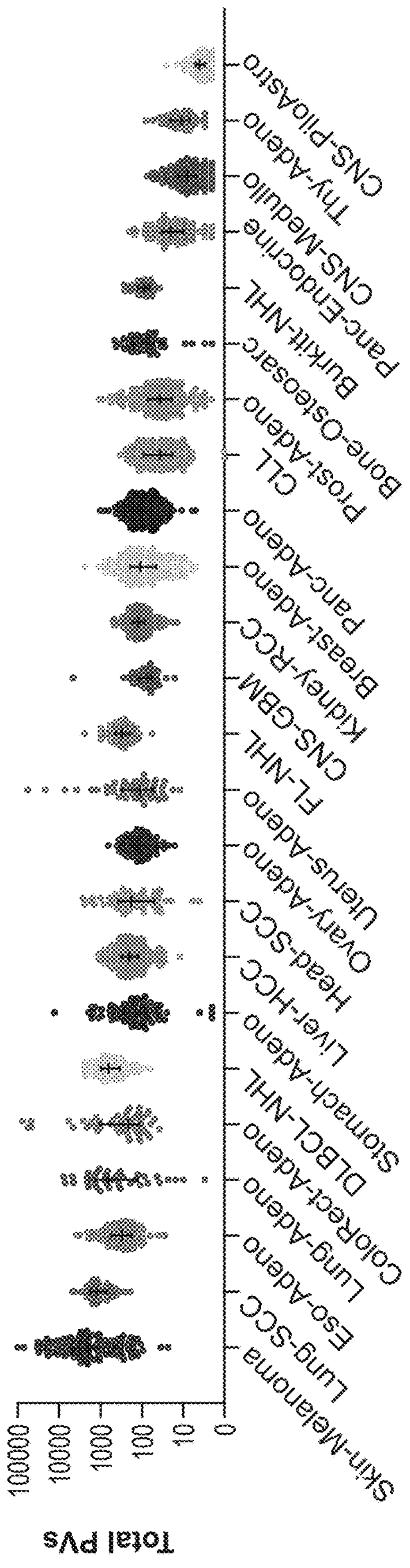
Figure 5C:
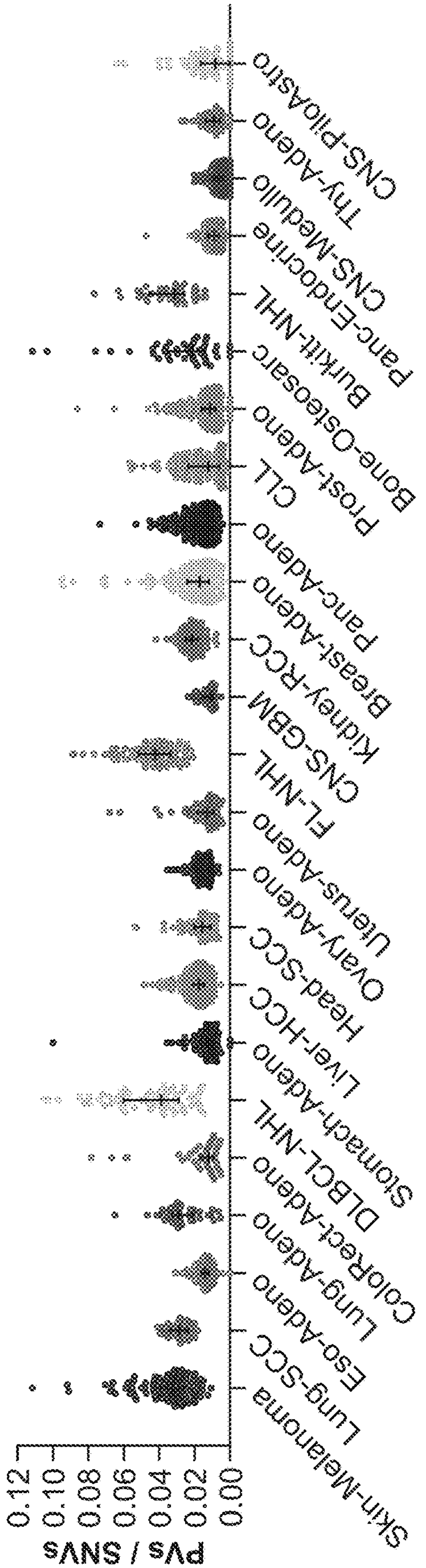

Example 10: Methods of Phased Variant Enrichment for Enhanced Disease Detection from Cell-Free DNA 10(a): Whole-Genome Sequencing Analysis 10(a)(1): Whole-Genome Sequencing Data Putative Phased Variant Identification Whole-genome sequencing data were obtained from two sources. Data for lymphoid malignancies (diffuse large B-cell lymphoma, DLBCL; follicular lymphoma, FL; Burkitt lymphoma, BL; chronic lymphocytic leukemia, CLL) were downloaded from the International Cancer Genome Consortium (ICGC) data portal on May 7, 2018. Data from all other histologies were part of the pan-Cancer analysis of whole genomes (PCAWG) and downloaded on Nov. 11, 2019. Only cancer histologies with at least 35 available cases were considered; details of the dataset considered are provided in Table 1. All samples had somatic mutations called from WGS using matched tumor and normal genotyping. Queries were limited to base substitutions obtained from WGS (single, double, triple, and oligo nucleotide variants; SNVs, DNVs, TNVs, and ONVs). Having thus identified the cases and variants of interest, the number of putative phased variants (PVs) in each tumor was next identified. To function as a PV on a single cell-free DNA (cfDNA) molecule, two variants, such as two single nucleotide variants (SNVs) generally must occur within a genomic distance less than the length of a typical cfDNA molecule (~170 bp). Therefore, putative PVs were defined as two variants occurring on the same chromosome within a genomic distance of <170 bp. DNVs, TNVs, and ONVs were considered as the set of their respective component SNVs. The number of SNVs as well as the identity of putative PVs for each case are detailed in Table 1. The raw number of SNVs and putative PVs, as well as the number of putative PVs controlling for the number of SNVs, is shown in FIG. 5A-C.

10(a)(2): Mutational Signatures of Phased Variants from WGS

To assess the mutational processes associated with phased and non-phased mutations across different cancer types/subtypes, the mutational signatures of single base substitutions (SBS) were enumerated for each WGS case described above using the R package 'deconstructSigs'. The list of SNVs for each patient was first divided into two groups: 1) SNVs contained within a possible PV; that is, with an adjacent or 'nearest neighbor' SNV<170 bp away, and 2) isolated SNVs (i.e., non-phased), defined as those occurring ≥170 bp in distance from the closest adjacent SNV. 'DeconstructSigs' was then applied using the 49 SBS signatures described in COSMIC (excluding signatures linked to possible sequencing artefacts) to assess the contribution of each SBS signature to both candidate phased SNVs and un-phased SNVs for each patient. To compare the contribution of each SBS signature to phased and isolated SNVs, a Wilcoxon signed rank test was performed to compare the relative contribution of each SBS signature between these two categories for each cancer type (FIGS. 6A-6WW). To account for multiple hypotheses, Bonferroni's correction was applied, by considering any SBS signature that differed in contribution to phased vs. un-phased SNVs to be significant if the Wilcoxon signed rank test resulted in a P-value of <0.05/49 or 0.001. The distributions of these comparisons, along with significance testing, are depicted in FIGS. 6A-6WW. A summary of this analysis is also shown in FIG. 1C using a heat-map display, where the 'heat' represents the difference between the mean contribution of the SBS signature to phased variants to the mean contribution to isolated/un-phased variants.

10(a)(3): Genomic Distribution of Phased Variants from WGS

The recurrence frequency for PVs was assessed in each cancer type across the genome within each tumor type. Specifically, the human genome (build GRCh37/hg19) was first divided into 1-kb bins (3,095,689 total bins); then, for each sample, the number of PVs (as defined above) contained in each 1-kb bin was counted. For this analysis, any PV with at least one of its constituent SNVs falling within the 1-kb bin of interest was included. The fraction of patients whose tumors harbored a PV for each cancer type within each genomic bin was then calculated. To identify 1-kb bins recurrently harboring PVs across patients, the fraction of patients containing PVs in each 1-kb bin vs. genomic coordinates (FIG. 1D and FIG. 7) was plotted; for this analysis, only bins where at least 2% of samples contained a PV in at least one cancer subtype were plotted.

10(a)(4): Identification of Recurrent 1-kb Bins with Phased Variants

To identify 1-kb bins that recurrently contain PVs in B-lymphoid malignancies, WGS data was utilized from the following diseases: DLBCL, FL, BL, and CLL. Any 1-kb bin where >1 sample from these tumor types was considered to recurrently contain PVs from B-lymphoid malignancies. The genomic coordinates of 1-kb bins containing recurrent PVs in lymphoid malignancies are enumerated in Table 2, and are plotted in FIG. 8A.

10(b): Design of PhasED-Seq Panel for B-Lymphoid Malignancies

10(b)(1): Identification of Recurrent PVs from WGS Data at Higher Resolution

Given the prevalence of recurrent putative PVs from WGS data in B-cell malignancies, a targeted sequencing approach was designed for their hybridization-mediated capture—Phased variant Enrichment Sequencing (PhasED-Seq)—to enrich these specific PV events from tumor or cell-free DNA. In addition to the ICGC data described above, WGS data was also utilized from other sources in this design, including both B-cell NHLs as well as CLL.

Previous experience with targeted sequencing from cfDNA in NHLs was also examined. Pairs of SNVs occurring at a distance of <170 bp apart in each B-cell tumor sample were identified. Then, genomic "windows" that contained PVs was identified as follows: for each chromosome, the PVs were sorted by genomic coordinates relative to reference genome. Then, the lowest (i.e., left-most) position was identified for any PV in any patient; this defined the left-hand (5') coordinate seeding a desired window of interest, to be captured from the genome. This window was then extended by growing its 3' end to capture successive PVs until a gap of ≥340 bp was reached, with 340-bp chosen as capturing two successive chromatosomal sized fragments of ~170-bp. When such a gap was reached, a new window was started, and this iterative process of adding neighboring PVs was repeated again until the next gap of ≥340 bp was reached. This resulted in a BED file of genomic windows containing all possible PVs from all samples considered. Finally, each window was additionally padded by 50 bp on each side, to enable efficient capture from flanking sequences in rare scenarios when repetitive or poorly mapping intervening sequences might preclude their direct targeting for enrichment.

Having identified the regions of interest containing putative PVs, each window was then into 170 bp segments (e.g., the approximate size of a chromatosomal cfDNA molecule). Then, the number of cases containing a PV was enumerated in each case. For each 170 bp region, the region in final sequencing panel design was included if one or more of the following criteria was met: 1) at least one patient contained a PV in the 170 bp region in 3 of 5 independent data-sets, 2) at least one patient contained a PV in the region in 2 of 5 independent data-sets if one dataset was prior CAPP-Seq experience, or 3) at least one patient contained a PV in the region in 2 of 5 independent data-sets, with a total of at least 3 patients containing a PV in the region. This resulted in 691 'tiles', with each tile representing a 170 bp genomic region. These tiles, along with an additional ~200 kb of genomic space targeting driver genes recurrently mutated in B-NHL, were combined into a unified targeted sequencing panel as previously described for both tumor and cfDNA genotyping using NimbleDesign (Roche NimbleGen). The final coordinates of this panel are provided in Table 3.

10(b)(2). Comparison of PhasED-Seq and CAPP-Seq Performance in PV Yield

To evaluate the performance of PhasED-Seq for capturing both SNVs and PVs compared to previously reported CAPP-Seq selector for B-cell lymphomas, the predicted number of both SNVs and PVs that may be recovered with each panel by limiting WGS in silico to the capture targets of each approach (FIG. 9A-C) was quantified. The predicted number of variants was then compared using the Wilcoxon signed rank test. Both CAPP-Seq and PhasED-Seq were also performed on 16 samples from patients with DLBCL. In these samples, tumor or plasma DNA, along with matched germline DNA, was sequenced. The resulting number of variants were again compared by the Wilcoxon signed rank text (FIG. 2B, and FIGS. 9D-9E). The sequencing depth for the samples included in this analysis are provided in Tables 4.

10(c): Identification of Phased Variants from Targeted Sequencing Data

10(c)(1): Patient Enrollment and Clinical Sample Collection

Patients with B-cell lymphomas undergoing front-line therapy were enrolled on this study from six centers across North America and Europe, including Stanford University, MD Anderson Cancer Center, the National Cancer Institute, University of Eastern Piedmont (Italy), Essen University Hospital (Germany), and CHU Dijon (France). In total, 343 cell-free DNA, 73 tumor, and 183 germ-line samples from 183 patients were included in this study. All patient samples were collected with written informed consent for research use and were approved by the corresponding Institutional Review Boards in accordance with the Declaration of Helsinki. Cell-free, tumor, and germ-line DNA were isolated as previously described. All radiographic imaging was performed as part of standard clinical care.

10(c)(2): Library Preparation and Sequencing

To generate sequencing libraries and targeted sequencing data, CAPP-Seq was applied as previously described. Briefly, cell-free, tumor, and germ-line DNA were used to construct sequencing libraries through end repair, A-tailing, and adapter ligation following the KAPA Hyper Prep Kit manufacturer's instructions with ligation performed overnight at 4° C. CAPP-Seq adapters with unique molecular identifiers (UMIDs) were used for barcoding of unique DNA duplexes and subsequent deduplication of sequencing read pairs. Hybrid capture was then performed (SeqCap EZ Choice; NimbleGen) using the PhasED-Seq panel described above. Affinity capture was performed according to the manufacturer's protocol, with all 47° C. hybridizations conducted on an Eppendorf thermal cycler. Following enrichment, libraries were sequenced using an Illumina HiSeq4000 instrument with 2×150 bp paired-end (PE) reads.

10(c)(3): Pre-Processing and Alignment

FASTQ files were de-multiplexed and UMIDs were extracted using a custom pipeline as previously described. Following demultiplexing, reads were aligned to the human genome (build GRCh37/hg19) using BWA ALN. Molecular barcode-mediated error suppression and background polishing (i.e., integrated digital error suppression; iDES) were then performed as previously described.

10(c)(4): Identification of Phased Variants and Allelic Quantitation

After generating UMID error-suppressed alignment files (e.g., BAM files), PVs were identified from each sample as follows. First, matched germ-line sequencing of uninvolved peripheral blood mononuclear cells (PBMCs) was performed to identify patient-specific constitutional single nucleotide polymorphisms (SNPs). These were defined as non-reference positions with a variant allele fraction (VAF) above 40% with a depth of at least 10, or a VAF of above 0.25% with a depth of at least 100. Next, PVs were identified from read-level data for a sample of interest. Following UMID-mediated error suppression, each individual paired-end (PE) read and identified all non-reference positions were using 'samtools calmd'. PE data was used rather than single reads to identify variants occurring on the same template DNA molecule, which may subsequently fall into either read 1 or read 2. Any read-pair containing ≥2 non-reference positions was considered to represent a possible somatic PV. For reads with >2 non-reference positions, each permutation of size≥2 was considered independently: i.e., if 4 non-reference positions were identified in a read-pair, all combinations of 2 SNVs (i.e., 'doublet' phased variants) and all combinations of 3 SNVs (i.e., 'triplet' phased variants) were independently considered. PVs containing putative germ-line SNPs were also removed as follows: if in a given n-mer (i.e., n SNVs in phase on a given molecule)≥n−1 of the component variants were identified as germ-line SNPs, the PV was redacted. This filtering strategy ensures that for any remaining PV, at least 2 of the component SNVs were not seen in the germ-line, as relevant for both sensitivity and specificity.

Putative somatic PVs were filtered using a heuristic blacklisting approach in considering sequencing data from 170 germ-line DNA samples serving as controls. In each of these samples, PVs were identified on read-pairs as described above, but without filtering for matched germ-line. Any PV that occurred in one or greater paired-end read, in one or more of these control samples, was included in the blacklist and removed from patient-specific somatic PV lists.

To calculate the VAF of each PV, a numerator representing the number of DNA molecules containing a PV of interest was calculated over a denominator representing the total number of DNA molecules that covered the genomic region of interest. That is, the numerator is simply the total number of deduplicated read-pairs that contain a given PV while the denominator is the number of read-pairs that span the genomic locus of a given PV.

10(c)(5): Genotyping Phased Variants from Pretreatment Samples

The above strategy resulted in a list of PVs of ≥1 read-depth in each sample. To identify PVs serving as tumor-specific somatic reporters for disease monitoring, for each case a 'best genotyping' specimen—either DNA from a tumor tissue biopsy (preferred), or pretreatment cell-free DNA was identified. After identifying all possible PVs in the 'best genotyping sample', the list for specificity was further filtered as follows. For any n-mer PV set, if ≥n−1 of the constituent SNVs were present as germ-line SNPs in the 170 control samples described above, the PV was removed. Furthermore, only PVs that meet the following criteria were considered: 1) AF>1%; 2) depth of the PV locus of ≥100 read-pairs, and 3) at least one component SNV must be in the on-target space. Finally, 4) any PV meeting these criteria was assessed for read-support in a cohort of 12 healthy control cfDNA samples. If any read-support was present in >1 of these 12 samples, the PV was removed. For genotyping from cell-free DNA samples identified as low tumor fraction by SNVs (i.e., <1% mean AF across all SNVs), the AF threshold for determining PVs was relaxed to >0.2%. This filtering resulted in the PV lists used for disease monitoring and MRD detection.

10(c)(6): Determination of Tumor Fraction in a Sample from Phased Variants

For evaluation of a sample for minimal residual disease (MRD) detection with prior knowledge of the tumor genotype, the presence of any PV identified in the best pretreatment genotyping sample in the MRD sample of interest can be assessed. Given a list of k possible tumor-derived PVs observed in the best genotyping sample, all read-pairs covering at least 1 of the k possible PVs were determined. This value, d, can be thought of as the aggregated 'informative depth' across all PVs spanned by cfDNA molecules in a PhasED-Seq experiment. It was then assessed how many of these d read-pairs actually contained 1 or more of the k possible PVs—this value, x, represents the number of tumor-derived molecules containing somatic PVs in a given sample. The number of tumor-derived molecules containing PVs divided by the informative depth—x/d—is therefore the phased-variant tumor fraction (PVAF) in a given sample. For detection of MRD in each sample, PVAF was calculated independently for doublet, triplet, and quadruplet PVs.

10(c) (7): Monte Carlo Simulation for Empirical Significance of PV Detection within a Specimen To assess the statistical significance of the detection of tumor-derived PVs in any sample, an empiric significance testing approach was implemented. A test statistic f was first defined as follows—from a given list of k possible tumor-derived PVs observed in the best genotyping sample, the arithmetic mean of allele fractions was calculated across all k PVs (allele fraction defined as the number of read-pairs containing an individual PV (xi) over the number of read-pairs spanning the PV positions (d)):

$$f = \frac{\sum_{i=1}^{k} \frac{x_i}{d_i}}{k} \quad (1)$$

to assess the hypothesis that f is not significantly different from the background error-rate of similar PVs assessed from the same sample. A Monte Carlo approach was used to develop a null distribution and perform statistical testing as follows:

1. Given a set of k PVs, $\{pv_1 \ldots pv_i \ldots pv_k\}$, an 'alternate' list of PVs, $\{pv'_1 \ldots pv'_i \ldots pv'_k\}$, was generated such that for each alternate PV had the same type of base change and distance between SNVs as the test PV. For example, if a doublet PV, chr14:106329929 C>T and chr14:106329977 G>A, was identified in the genotyping sample and searched for an alternate two positions at the same genomic distance (here, 48 bp) with reference bases C and G, and assessed for read-pairs with the same types of base changes (i.e., C>T and G>A), using the heuristic search scheme below.
2. For each tumor $pv_i$ in the set of k, 50 such alternates were identified. This was performed with a random search algorithm to scan the genomic space and identify alternates. To find these 50 alternates, a random position on the same chromosome as the test $pv_i$ was identified and then searched for the same types of reference bases at the same genomic distance as described above. Synteny of observed/alternate PVs was used to control for regional variation in SHM/aSHM as well as copy number variation, as potential confounders of the null distribution. Alternate positions that were identified as a germ-line SNP, defined as having AF>5%, were excluded.

3. After identifying 50 such alternates for each $pv_i$, 10,000 random permutations of 1 alternate were generated for each of the k original PVs and calculated the phased-variant fraction f' for these alternate lists in the sample of interest being evaluated for presence of MRD, as described above.
4. An empiric P-value was calculated, defined as the fraction of times the true phased-variant fraction f is observed to be less than or equal to the alternate f' across the 10,000 random PV lists as an empirical measure of significance of MRD significance in the blood sample of interest.

While this resulting comparison is a measure of the significance for PV detection of tumor-reporter list compared to the empirically defined background PV error-rate within the sample of interest, its relationship to specificity of detection across cases and control samples was also evaluated, as described below.

10(c)(8): Assessment of Specificity of PhasED-Seq

To determine the specificity of disease and MRD detection through PhasED-Seq, patient-specific PVs from 107 patients with DLBCL were first identified using pretreatment tumor or plasma DNA along with paired germ-line samples. 40 independent plasma DNA samples were then assessed from healthy individuals for presence of these patient-specific PVs, using the Monte Carlo approach outlined above. A threshold for P-values was empirically determined from Monte Carlo such that 95% specificity was achieved for disease detection from doublet, triplet, and quadruplet PVs. The P-value threshold yielding 95% specificity for each size of PV was as follows: <0.041 for doublets, <1 for triplets, and <1 for quadruplets. The results of this specificity in control cfDNA analysis is shown in FIGS. 15 and 16.

10(c)(9): Calculation of Error Rates

To assess the error profile of both isolated SNVs and PVs, the non-reference base observation rate of each type of variant was examined across all reads. For isolated SNVs, the error-rate for each possible base change $e_{n1>n1'}$ was calculated as the fraction of on-target bases with reference allele n1 that are mutated to alternate allele n1', when considering all possible base-changes of the reference allele. Positions with a non-reference allele rate exceeding 5% were classified as probable germ-line events, and excluded from the error-rate analysis. A global error rate, defined as the rate of mutation from the hg19 reference allele to any alternate allele, was also calculated.

For phased variants, a similar calculation was performed. For the error-rate of a given type of phased variant composed of k constituent base-changes $\{e_{n1>n1'}, \ldots e_{nk>nk'}\}$, the error-rate was calculated by determining both the number of instances of the type of base change (i.e., the numerator), as well as the number of possible instances for the base change (i.e., the denominator). To calculate the numerator, N, the number of occurrences of the PV of interest over all read-pairs was counted in a given sample. For example, to calculate the error-rate of C>T and G>A phased doublets, the number of read-pairs that include both a reference C mutated to a T as well as a reference G mutated to an A was first counted.

To calculate the denominator, D, the number of possible instances of this type of phased variant was also calculated; this was performed first for each read-pair i, and then summed over all read pairs. A PV with k components can be summarized as having certain set of reference bases $p_A$, $p_C$, $p_G$, $p_T$, where $p_N$ is the number of each reference base in the PV. Similarly, a given read pair contains a certain set of reference bases $b_A$, $b_C$, $b_G$, $b_T$, where $b_N$ is the number of each reference base in the read pair. Therefore, for each read pair in a given sample, the number of possible occurrences of PV type of interest can be calculated combinatorically as:

$$D_i = \binom{b_A}{p_A}\binom{b_C}{p_C}\binom{b_G}{p_G}\binom{b_T}{p_T} \quad (2)$$

For example, consider a read-pair with 40 reference As, 50 reference Cs, 45 reference Gs, and 35 reference Ts. The number of positions for a C>T and G>A PV is:

$$D_i = \binom{40}{0}\binom{50}{1}\binom{45}{1}\binom{35}{0} = 2250 \quad (3)$$

The aggregated denominator, D, for error rate calculation is then simply the sum of this value over all read pairs. The error rate for this type of PV is then simply N/D.

10(d): Differences in Phased Variants Between Lymphoma Subtypes

To compare the distribution of phased variants in different types of lymphomas, tumor-specific PVs were identified in 101 DLBCL, 16 PMBCL, and 23 cHL patients via sequencing of tumor biopsy specimens and/or pre-treatment cell-free DNA and paired germ-line specimens. After identifying these tumor-specific PVs, their distribution was the assessed across the targeted sequencing panel. The panel was first divided into 50 bp bins; for each patient, it was then determined if each patient had evidence of a PV within the 50 bp bin, defined as having at least one component of the PV within the bin. The nearest gene to each 50 bp bin was further determined, based on GENCODEv19 annotation of the reference genome.

To assess how the distribution of PVs between subtypes of lymphoma varies at the level of specific genes, the distribution of PVs was examined across the 50 bp bins spanning each gene (or nearest gene). For example, consider a given gene with n such 50 bp bins represented in targeted sequencing panel. For each bin, it was first determined the fraction of patients, f in each type of lymphoma with a PV falling within the 50 bp bin—i.e., determining $\{f_{type1,1}, \ldots f_{type1,n}\}$ and $\{f_{type2,1}, \ldots f_{type2,n}\}$. Then, any two histologies were then compared for the fraction of cases harboring PVs in the set of 50 bp bins assigned to each gene. These comparisons are depicted for individual genes on gene-specific plots in FIG. 2D and FIGS. 10-12.

The enrichment in PVs was statistically compared in a specific lymphoma type or subtype vs. another by calculating the difference in the fraction of patients which contain a PV in each 50 bp bin across all bins assigned to a gene (i.e., overlapping a given gene or with a given nearest gene). Specifically, for any comparison between two lymphoma types ($type_1$ and $type_2$), this set of differences in PV-rate was first identified between histologies if $\{f_{type1,1}-f_{type2,1}, \ldots f_{type1,n}-f_{type2,n}\}$. This set of gene-specific differences in frequency of PVs was the compared between types of lymphoma against the distribution of all other 50 bp bins in the sequencing panel by the Wilcoxon rank sum test. For this test, the set of n 50 bp bins assigned to a given gene was compared to all other 50 bp bins (i.e., 6755−n, since there are 6755 50 bp bins in sequencing panel). This P-value, along with the mean difference in fraction of patients with a PV in each bin for each gene between histologies, is depicted as a volcano plot in FIG. 2E. To account for the global difference in rate of PVs between different histologies, the mean difference in fraction of patients with a PV between histologies was centered on 0 by subtracting the mean difference across all genes.

10(e): Hybridization Bias

To assess the effect of mutations on hybridization efficiency, the affinity of mutated molecules to wildtype capture baits in silico was first estimated by considering DNA fragments harboring 0-30% mutations across the entire fragment. For each mutation condition across this range, 10,000 regions were first randomly sampled, each 150 bp in length, from across the whole genome. These 150-mers were then mutated in silico to simulate the desired mutation rate in 3 different ways: 1) mutating 'clustered' or contiguous bases starting from the ends of a sequence, 2) mutating clustered bases started from the middle of the sequence, or 3) mutating bases selected at random positions throughout the sequence. The energy.c package was then used to calculate the theoretical binding energy (kcal/mol) between the mutated and wild-type sequences, in relying on a nearest-neighbor model employing established thermodynamic parameters (FIG. 14A).

This in silico experiment was then replicated by testing the effects of same mutation rates in vitro. Specifically, oligonucleotides (IDT) were synthesized and annealed to form DNA duplexes harboring 0-10% mutations at defined positions relative to the human reference genome sequence. These synthetic DNA molecules were then captured together at equimolar concentrations and quantified the relative capture efficiency of mutated duplexes compared to the wild-type, unmutated species (FIG. 3A). Two sets of oligonucleotide sequences were selected from coding regions of BCL6 and MYC to capture AID-mediated aberrant somatic hypermutations associated with each gene (Table 5); the preserved mappability of the mutated species was ensured by BWA ALN. These synthetic oligonucleotide duplexes were then subjected to library preparation, then captured and sequenced using PhasED-Seq, performed in triplicate using distinct samples. This allowed assessment of the relative efficiency of hybrid capture and molecular recovery as directly compared to wildtype molecules identical to the reference genome.

10(f): Assessment of Limit of Detection with Limiting Dilution Series

To empirically define the analytical sensitivity of PhasED-Seq, a limited dilution series of cell-free DNA from 3 patients that were spiked into healthy control cell-free DNA at defined concentrations was utilized. The dilution series contained samples with an expected mean tumor fraction of 0.1%, 0.01%, 0.001%, 0.0002%, 0.0001%, and 0.00005% or ranging from 1 part in 1,000 to 1 part in 2,000,000. The sequencing characteristics and ctDNA quantification via CAPP-Seq, duplex sequencing, and PhasED-Seq are provided. To compare the performance of each method, the difference was calculated, δ, between the observed and expected tumor fraction for each patient i at each dilution concentration j:

$$\delta_{i,j} = \widehat{tumorfrac}_{i,j} - \mathrm{tumorfrac}_{i,j} \quad (4)$$

This value was calculated for patients i={1,2,3} and concentrations j={0.001%, 0.0002%, 0.0001%, 0.00005%} for each ctDNA detection method (CAPP-Seq, duplex, doublet PhasED-Seq, and triplet PhasED-Seq). The performance of each method was then compared to each other by paired t-test across this set of patients and concentrations.

10(g): Model to Predict the Probability of Detection for a Given Set of Phased Variants To build a mathematical model to predict the probability of detection for a given sample of interest, it began with the common assumption that cfDNA detection can be considered a random process based on binomial sampling. However, unlike SNVs occurring at large genomic distances apart from one another, detection of PVs can be highly inter-dependent, especially when PVs are degenerate (i.e., when two PVs share component SNVs) or occur in close proximity. To account for this, only PVs occurring >150 bp apart from each other was considered as independent 'tumor reporters'. The number of 'tumor reporters' to allow for disease detection in a given sample can thus be determined as follows. The PhasED-Seq panel was broken apart into 150 bp bins. Each PV in a given patient's reporter list was then turned into a BED coordinate, consisting of the start position (defined as the left-most component SNV) and end position (defined as the right-most component SNV). For each PV, the 150 bp bin from the PhasED-Seq selector panel containing the PV was determined; if a PV spanned two or more 150 bp bins, it was assigned to both bins. The number of independent tumor reporters was then defined as the number of separate 150 bp bins containing a tumor-specific PV.

A mathematical model was then developed comparing the expected probability of detection for a given sample at a given tumor fraction with a given number of independent tumor reporters (e.g., 150 bp bins). With a given number of tumor reporters r, at a given tumor fraction f, with a given sequencing depth d, the probability of detecting 1 or more cell-free DNA molecule containing a tumor-specific PV containing can be defined as:

$$Pr(\text{detection}) = 1 - Pr(\text{nondetection}) \quad (5)$$

$$= 1 - \binom{d*r}{0} f^0 (1-f)^{d*r} \quad (6)$$

based on simple binomial sampling. However, as ctDNA detection method was trained to have a 5% false positive rate, this false positive rate term was added to the model as well:

$$Pr(\text{detection}) = 1 - Pr(\text{nondetection}) + 0.05 * Pr(\text{nondetection}) \quad (7)$$

$$Pr(\text{detection}) = 1 - 0.95 * Pr(\text{nondetection}) \quad (8)$$

$$= 1 - 0.95 * \binom{d*r}{0} f^0 (1-f)^{d*r} \quad (9)$$

FIG. 3G shows the results of this model for a range of tumor reporters r from 3 to 67 at depth d of 5000. The confidence envelope on this plot shows solutions for a range of depth d from 4000 to 6000.

To empirically validate this model assessing the probability of disease detection, samples from limiting dilution series were utilized. In this dilution series, 3 patient cfDNA samples, each containing patient-specific PVs, were spiked into healthy control cfDNA. For each list of patient specific PVs, 25 random subsamplings of the 150 bp bins containing patient-specific PVs were performed to generate reporter lists containing variable numbers of tumor-specific reporters. A maximum bin number of 67 was selected to allow sampling from all 3 patient-specific PV lists, followed by scaling down the number of bins by 2× or 3× per operation. This resulted in reporter lists containing patient-specific PVs from 3, 6, 17, 34, or 67 independent 150 bp bins. Disease detection was then assessed using each of these patient-specific PV lists of increasing size in each of 'wet' limiting dilution samples from 1:1,000 to 1:1,000,000 (FIG. 3H, closed circles). In silico mixtures was further created using sequencing reads from limiting dilution samples with varying expected tumor-content, and again assessed for the probability of disease detection using patient-specific subsampled PV reporter lists of varying lengths (open circles). For this experiment, both the 'wet' and 'in-silico' dilution barn files were down-sampled to achieve a depth of ~4000-6000× to correspond with modeled depth. The final mean and standard deviation of depth across all down-sampled barn files was 4214×±789. The probability of detection was summarized across all tests at a given expected tumor fraction, for a given patient-specific PV list. For each given dilution, multiple independently sampled sets of reads were considered to allow superior estimation of the true probability of detection. Specifically, the following number of replicates at each dilution indicated was considered in Table 7.

TABLE 7

Replicates at each dilution for predicting the probability of detection for a given set of phased variants.

| Dilution | Replicates | Number of Tests (Replicates * 25) | Wet or In silico |
|---|---|---|---|
| 1:1,000 | 1 | 25 | Wet |
| 5:10,000 | 3 | 75 | In silico |
| 3.5:10,000 | 3 | 75 | In silico |
| 2:10,000 | 3 | 75 | In silico |
| 1:10,000 | 3 | 75 | Wet |
| 5:100,000 | 3 | 75 | In silico |
| 3.5:100,000 | 3 | 75 | In silico |
| 2:100,000 | 3 | 75 | In silico |
| 1:100,000 | 3 | 75 | Wet |
| 5:1,000,000 | 8 | 200 | In silico |
| 3.5:1,000,000 | 8 | 200 | In silico |
| 2:1,000,000 | 8 | 200 | Wet |
| 1:1,000,000 | 8 | 200 | Wet |

The total number of tests, for each patient-specific PV list, is therefore the number of randomly subsampled PV lists (e.g., 25) times the number of independently downsampled barn files; this number is provided in the table above. In FIG. 3H, the points and error-bars represent the mean, minimum, and maximum across all three patients. The concordance between the predicted probability of disease detection from theoretical mathematical model and wet and in silico samples validating this model, is shown in FIG. 3I.

10(h): Statistical Analyses & Software Availability

All P-values reported in this manuscript are 2-sided unless otherwise noted. Comparisons of matched samples and populations were performed using the Wilcoxon signed rank test; comparisons of samples drawn from unrelated populations were performed using the Wilcoxon rank-sum test. Comparisons of paired samples were performed by paired t-test. Survival probabilities were estimated using the Kaplan-Meier method; survival of groups of patients based on ctDNA levels were compared using the log-rank test. Other statistical tests are noted in the manuscript text where utilized. All analyses were performed with the use of MATLAB, version 2018b, R Statistical Software version 3.4.1, and GraphPad Prism, version 8.0.2. The contribution of known mutational processes to phased and isolated SNVs from WGS was assessed with the deconstruct Sigs R package using the COSMIC signature set (v2) as described. Calculation of AUC accounting for survival and censorship was performed using the R 'survivalROC' package version 1.0.3 with default settings. An executable version of the PhasED-Seq software, developed in C++ 17, is available at phasedseq(dot)stanford(dot)edu.

Example 11

Additional details of the tables described throughout the present disclosure are provided herein:

TABLE 1: 1000 bp regions of interest throughout the genome containing putative phased variants (PV) in various lymphoid neoplasms. Only regions containing >1 subject with a PV are shown. Coordinates are in hg19. Regions from genes that were previously identified as targets of activation-induced deaminase (AID) are labeled. Regions that contain PVs in >5% of subjects in any histology (BL, CLL, DLBCL, FL) are also labeled. BL, Burkitt lymphoma; CLL, chronic lymphocytic leukemia; DLBCL, diffuse large B-cell lymphoma; FL, follcicular lymphoma.

TABLE 2: 1000 bp regions of interest throughout the genome containing putative phased variants (PV) in the ABC and GCB subtypes of DLBCL. Only regions containing >1 subject with a PV are shown. Coordinates are in hg19. Regions from genes that were previously identified as targets of AID are labeled. ABC, activated B-cell subtype; GCB, germinal center B-cell subtype.

TABLE 3: Regions used for the PhasED-Seq capture reagent described in this paper focused on lymphoid malignancies. Coordinates are in hg19. The closest gene and the reason for inclusion (Phased Variants vs general DLBCL genotyping) is also shown.

TABLE 4: Enrichment of PVs at genetic loci throughout the PhasED-Seq targeted sequencing panel for different types of B-cell lymphomas (DLBCL including ABC and GCB subtypes, PMBCL, and cHL). The PhasED-Seq selector was binned into 50 bp bins in hg19 coordinates, and each bin was labelled by gene or nearest gene. The mean of the fraction of cases of a given histology with a PV across all 50 bp bins is shown. Significance was determined by rank-sum (Mann-Whitney U) test of 50 bp bins for a given gene against the remainder of the sequencing panel. Uncorrected P-values are shown; multiple-hypothesis testing correction was performed by Bonferroni method. DLBCL, diffuse large B-cell lymphoma; PMBCL, primary mediastinal B-cell lymphoma; cHL, classical Hodgkin lymphoma; ABC, activated B-cell DLBCL; GCB, germinal center B-cell DLBCL.

TABLE 5: Sequences of oligonucleotides synthesized to assess hybridization and molecular recovery bias with increasing mutational burden (SEQ ID NOs. 1331-1358).

TABLE 6: Nucleic acid probes for Capture Sequencing of B-cell Cancers (SEQ ID NOs. 0001-1330).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 1 | chr1 | 756000 | 757000 | 0.028 | 0.000 | 0.015 | 0.000 | AL669831.1 | 0.47887 | 1.00000 | 0.29694 | 0 | 0 |
| 2 | chr1 | 1963000 | 1964000 | 0.028 | 0.000 | 0.015 | 0.000 | GABRD | 0.47887 | 1.00000 | 0.29694 | 0 | 0 |
| 3 | chr1 | 2052000 | 2053000 | 0.028 | 0.000 | 0.000 | 0.014 | PRKCZ | 1.00000 | 0.34615 | 1.00000 | 0 | 0 |
| 4 | chr1 | 3789000 | 3790000 | 0.000 | 0.000 | 0.029 | 0.000 | DFFB | 0.22755 | 0.54294 | 0.08726 | 0 | 0 |
| 5 | chr1 | 6613000 | 6614000 | 0.000 | 0.000 | 0.044 | 0.014 | NOL9 | 0.34948 | 0.54966 | 0.02537 | 1 | 0 |
| 6 | chr1 | 6614000 | 6615000 | 0.000 | 0.000 | 0.088 | 0.027 | NOL9 | 0.15270 | 0.09031 | 0.00058 | 1 | 1 |
| 7 | chr1 | 6661000 | 6662000 | 0.000 | 0.000 | 0.029 | 0.014 | KLHL21 | 0.60686 | 0.54294 | 0.08726 | 0 | 0 |
| 8 | chr1 | 6662000 | 6663000 | 0.000 | 0.000 | 0.044 | 0.014 | KLHL21 | 0.34948 | 0.54966 | 0.02537 | 0 | 0 |
| 9 | chr1 | 9129000 | 9130000 | 0.000 | 0.000 | 0.044 | 0.000 | SLC2A5 | 0.10727 | 0.54966 | 0.02537 | 0 | 0 |
| 10 | chr1 | 10894000 | 10895000 | 0.028 | 0.000 | 0.000 | 0.014 | C1orf127 | 1.00000 | 0.34615 | 1.00000 | 0 | 0 |
| 11 | chr1 | 17019000 | 17020000 | 0.028 | 0.000 | 0.000 | 0.014 | AL137798.1 | 1.00000 | 0.34615 | 1.00000 | 0 | 0 |
| 12 | chr1 | 17231000 | 17232000 | 0.000 | 0.000 | 0.015 | 0.014 | CROCC | 1.00000 | 1.00000 | 0.29694 | 0 | 0 |
| 13 | chr1 | 19935000 | 19936000 | 0.000 | 0.000 | 0.029 | 0.000 | MINOS1-NBL1 | 0.22755 | 0.54294 | 0.08726 | 0 | 0 |
| 14 | chr1 | 21091000 | 21092000 | 0.000 | 0.000 | 0.015 | 0.014 | HPIBP3 | 1.00000 | 1.00000 | 0.29694 | 0 | 0 |
| 15 | chr1 | 23885000 | 23886000 | 0.444 | 0.000 | 0.015 | 0.000 | ID3 | 0.47887 | 0.00000 | 0.29694 | 1 | 1 |
| 16 | chr1 | 28408000 | 28409000 | 0.000 | 0.000 | 0.029 | 0.000 | EYA3 | 0.22755 | 0.54294 | 0.08726 | 0 | 0 |
| 17 | chr1 | 32373000 | 32374000 | 0.000 | 0.000 | 0.029 | 0.000 | PTP4A2 | 0.22755 | 0.54294 | 0.08726 | 0 | 0 |
| 18 | chr1 | 36722000 | 36723000 | 0.000 | 0.012 | 0.015 | 0.000 | THRAP3 | 0.47887 | 1.00000 | 1.00000 | 0 | 0 |
| 19 | chr1 | 46576000 | 46577000 | 0.000 | 0.000 | 0.015 | 0.014 | PIK3R3 | 1.00000 | 1.00000 | 0.29694 | 0 | 0 |
| 20 | chr1 | 51965000 | 51966000 | 0.000 | 0.006 | 0.015 | 0.000 | EPS15 | 0.47887 | 1.00000 | 0.50663 | 0 | 0 |
| 21 | chr1 | 51978000 | 51979000 | 0.000 | 0.000 | 0.029 | 0.000 | EPS15 | 0.22755 | 0.54294 | 0.08726 | 0 | 0 |
| 22 | chr1 | 51983000 | 51984000 | 0.000 | 0.006 | 0.029 | 0.000 | EPS15 | 0.22755 | 0.54294 | 0.21104 | 0 | 0 |
| 23 | chr1 | 72393000 | 72394000 | 0.000 | 0.000 | 0.015 | 0.014 | NEGR1 | 1.00000 | 1.00000 | 0.29694 | 0 | 0 |
| 24 | chr1 | 73719000 | 73720000 | 0.000 | 0.000 | 0.029 | 0.000 | LRRIQ3 | 0.22755 | 0.54294 | 0.08726 | 0 | 0 |
| 25 | chr1 | 77315000 | 77316000 | 0.028 | 0.006 | 0.000 | 0.000 | ST6GALNAC5 | 1.00000 | 0.34615 | 1.00000 | 0 | 0 |
| 26 | chr1 | 81306000 | 81307000 | 0.000 | 0.000 | 0.015 | 0.014 | LPHN2 | 1.00000 | 1.00000 | 0.29694 | 0 | 0 |
| 77 | chr1 | 81527000 | 81528000 | 0.000 | 0.000 | 0.029 | 0.000 | LPHN2 | 0.22755 | 0.54294 | 0.08726 | 0 | 0 |
| 28 | chr1 | 82009000 | 82010000 | 0.028 | 0.000 | 0.015 | 0.000 | LPHN2 | 0.47887 | 1.00000 | 0.29694 | 0 | 0 |
| 29 | chr1 | 84106000 | 84107000 | 0.000 | 0.006 | 0.015 | 0.000 | TTLL7 | 0.47887 | 1.00000 | 0.50663 | 0 | 0 |
| 30 | chr1 | 87524000 | 87525000 | 0.000 | 0.006 | 0.015 | 0.000 | HS2ST1; HS2ST1LOC339524; | 0.47887 | 1.00000 | 0.50663 | 0 | 0 |
| 31 | chr1 | 94551000 | 94552000 | 0.000 | 0.000 | 0.029 | 0.000 | ABCA4 | 0.22755 | 0.54294 | 0.08726 | 0 | 0 |
| 32 | chr1 | 94552000 | 94553000 | 0.000 | 0.000 | 0.029 | 0.000 | ABCA4 | 0.22755 | 0.54294 | 0.08726 | 0 | 0 |
| 33 | chr1 | 103696000 | 103697000 | 0.000 | 0.000 | 0.000 | 0.027 | COL11A1 | 0.49735 | 1.00000 | 1.00000 | 0 | 0 |
| 34 | chr1 | 116979000 | 116980000 | 0.000 | 0.000 | 0.044 | 0.041 | ATP1A1 | 1.00000 | 0.54966 | 0.02537 | 0 | 0 |
| 35 | chr1 | 149784000 | 149785000 | 0.000 | 0.000 | 0.015 | 0.014 | HIST2H3D | 1.00000 | 1.00000 | 0.29694 | 1 | 0 |
| 36 | chr1 | 149821000 | 149822000 | 0.000 | 0.000 | 0.044 | 0.000 | HIST2H2AA4 | 0.10727 | 0.54966 | 0.02537 | 1 | 0 |
| 37 | chr1 | 149857000 | 149858000 | 0.000 | 0.000 | 0.015 | 0.014 | HIST2H2BE | 1.00000 | 1.00000 | 0.29694 | 1 | 0 |
| 38 | chr1 | 149858000 | 149859000 | 0.000 | 0.000 | 0.059 | 0.000 | HIST2H2AC; HIST2H2BE; | 0.05016 | 0.29551 | 0.00730 | 0 | 1 |
| 39 | chr1 | 160616000 | 160617000 | 0.000 | 0.000 | 0.015 | 0.014 | SLAMF1 | 1.00000 | 1.00000 | 0.29694 | 0 | 0 |
| 40 | chr1 | 162711000 | 162712000 | 0.000 | 0.000 | 0.015 | 0.014 | DDR2 | 1.00000 | 1.00000 | 0.29694 | 0 | 0 |
| 41 | chr1 | 163684000 | 163685000 | 0.000 | 0.000 | 0.015 | 0.014 | NUF2 | 1.00000 | 1.00000 | 0.29694 | 0 | 0 |
| 42 | chr1 | 167598000 | 167599000 | 0.000 | 0.000 | 0.044 | 0 014 | RCSD1 | 0.34948 | 0.54966 | 0.02537 | 0 | 0 |
| 43 | chr1 | 167599000 | 167600000 | 0.000 | 0.000 | 0.029 | 0.014 | RCSD1 | 0.60686 | 0.54294 | 0.08726 | 0 | 0 |
| 44 | chr1 | 167600000 | 167601000 | 0.000 | 0.000 | 0.044 | 0.000 | RCSD1 | 0.10727 | 0.54966 | 0.02537 | 0 | 0 |
| 45 | chr1 | 174333000 | 174334000 | 0.000 | 0.000 | 0.015 | 0.014 | RABGAPIL | 1.00000 | 1.00000 | 0.29694 | 0 | 0 |
| 46 | chr1 | 187263000 | 187264000 | 0.000 | 0.000 | 0.044 | 0.000 | PLA2G4A | 0.10727 | 0.54966 | 0.02537 | 0 | 0 |
| 47 | chr1 | 187283000 | 187284000 | 0.000 | 0.000 | 0.029 | 0.000 | PLA2G4A | 0.22755 | 0.54294 | 0.08726 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 48 | chr1 | 187892000 | 187893000 | 0.028 | 0.000 | 0.015 | 0.000 | PLA2G4A | 0.47887 | 1.00000 | 0.29694 | 0 | 0 |
| 49 | chr1 | 195282000 | 195283000 | 0.000 | 0.000 | 0.015 | 0.014 | KCNT2 | 1.00000 | 1.00000 | 0.29694 | 0 | 0 |
| 50 | chr1 | 198591000 | 198592000 | 0.000 | 0.000 | 0.029 | 0.000 | PTPRC | 0.22755 | 0.54294 | 0.08726 | 0 | 0 |
| 51 | chr1 | 198608000 | 198609000 | 0.000 | 0.000 | 0 029 | 0.000 | PTPRC | 0.22755 | 0.54294 | 0.08726 | 0 | 0 |
| 52 | chr1 | 198609000 | 198610000 | 0.000 | 0.000 | 0.029 | 0.000 | PTPRC | 0.22755 | 0.54294 | 0.08726 | 0 | 0 |
| 53 | chr1 | 202004000 | 202005000 | 0.028 | 0.000 | 0.029 | 0.000 | ELF3 | 0.22755 | 1.00000 | 0.08726 | 0 | 0 |
| 54 | chr1 | 203273000 | 203274000 | 0.000 | 0.000 | 0.029 | 0.000 | BTG2 | 0.22755 | 0.54294 | 0.08726 | 1 | 0 |
| 55 | chr1 | 203274000 | 203275000 | 0.000 | 0.000 | 0.176 | 0.014 | BTG2 | 0.00078 | 0.00730 | 0.00000 | 1 | 1 |
| 56 | chr1 | 203275000 | 203276000 | 0.028 | 0.006 | 0.471 | 0.081 | BTG2 | 0.00000 | 0.00000 | 0.00000 | 1 | 1 |
| 57 | chr1 | 203276000 | 203277000 | 0.028 | 0.000 | 0.059 | 0.000 | BTG2 | 0.05016 | 0.65667 | 0.00730 | 1 | 1 |
| 58 | chr1 | 205780000 | 205781000 | 0.000 | 0.000 | 0.000 | 0.027 | SLC41A1 | 0.49735 | 1.00000 | 1.60000 | 0 | 0 |
| 59 | chr1 | 205781000 | 205782000 | 0.000 | 0.000 | 0.000 | 0.027 | SLC41A1 | 0.49735 | 1.00000 | 1.00000 | 0 | 0 |
| 60 | chr1 | 206283000 | 206284000 | 0.000 | 0.000 | 0.015 | 0.014 | CTSE | 1.00000 | 1.00000 | 0.29694 | 0 | 0 |
| 61 | chr1 | 206286000 | 206287000 | 0.000 | 0.000 | 0.029 | 0.014 | CTSE | 0.60686 | 0.54294 | 0.08726 | 0 | 0 |
| 62 | chr1 | 217044000 | 217045000 | 0.000 | 0.000 | 0.029 | 0.000 | ESRRG | 0.22755 | 0.54294 | 0.08726 | 0 | 0 |
| 63 | chr1 | 226924000 | 226925000 | 0.000 | 0.000 | 0.029 | 0.000 | ITPKB | 0.22755 | 0.54294 | 0.08726 | 1 | 0 |
| 64 | chr1 | 226925000 | 226926000 | 0.000 | 0.000 | 0.044 | 0.000 | ITPKB | 0.10727 | 0.54966 | 0.02537 | 1 | 0 |
| 65 | chr1 | 226926000 | 226927000 | 0.000 | 0.000 | 0.029 | 0.000 | ITPKB | 0.22755 | 0.54294 | 0.08726 | 1 | 0 |
| 66 | chr1 | 229974000 | 229975000 | 0.028 | 0.000 | 0.015 | 0.027 | URB2 | 1.00000 | 1.00000 | 0.29694 | 0 | 0 |
| 67 | chr1 | 235131000 | 235132000 | 0.000 | 0.000 | 0.000 | 0.027 | TOMM20 | 0.49735 | 1.00000 | 1.00000 | 0 | 0 |
| 68 | chr1 | 235141000 | 235142000 | 0.000 | 0.000 | 0.015 | 0.014 | TOMM20 | 1.00000 | 1.00000 | 0.29694 | 0 | 0 |
| 69 | chr1 | 238787000 | 238788000 | 0.000 | 0.000 | 0.029 | 0.000 | MTRNR2L11 | 0.22755 | 0.54294 | 0.08726 | 0 | 0 |
| 70 | chr1 | 248088000 | 248089000 | 0.028 | 0.000 | 0.015 | 0.000 | OR2TS | 0.47887 | 1.00000 | 0.29694 | 0 | 0 |
| 71 | chr2 | 630000 | 631000 | 0.000 | 0.000 | 0.000 | 0.027 | TMEM1S | 0.49735 | 1.00000 | 1.00000 | 0 | 0 |
| 72 | chr2 | 1484000 | 1485000 | 0.000 | 0.000 | 0.000 | 0.027 | TPO | 0.49735 | 1.00000 | 1.00000 | 0 | 0 |
| 73 | chr2 | 7991000 | 7992000 | 0.056 | 0.000 | 0.000 | 0.000 | RNF144A | 1.00000 | 0.11763 | 1.00000 | 0 | 1 |
| 74 | chr2 | 12173000 | 12174000 | 0.000 | 0.000 | 0.044 | 0.000 | LPIN1 | 0.10727 | 0.54966 | 0.02537 | 0 | 0 |
| 76 | chr2 | 12175000 | 12176000 | 0.000 | 0.000 | 0.029 | 0.000 | LPIN1 | 0.22755 | 0.54294 | 0.08726 | 0 | 0 |
| 76 | chr2 | 12249000 | 12250000 | 0.000 | 0.000 | 0.029 | 0.000 | LPIN1 | 0.22755 | 0.54294 | 0.08726 | 0 | 0 |
| 77 | chr2 | 14113000 | 14114000 | 0.000 | 0.000 | 0.000 | 0.027 | FAM84A | 0.49735 | 1.00000 | 1.00000 | 0 | 0 |
| 78 | chr2 | 17577000 | 17578000 | 0.000 | 0.000 | 0.015 | 0.014 | RAD51AP2 | 1.00000 | 1.60000 | 0.29694 | 0 | 0 |
| 79 | chr2 | 19253000 | 19254000 | 0.000 | 0.000 | 0.029 | 0.000 | OSR1 | 0.22755 | 0.54294 | 0.08726 | 0 | 0 |
| 80 | chr2 | 24802000 | 24803000 | 0.000 | 0.000 | 0.029 | 0.000 | NCOA1 | 0.22755 | 0.54294 | 0.08726 | 0 | 0 |
| 81 | chr2 | 31478000 | 31479000 | 0.000 | 0.000 | 0.015 | 0.014 | EHD3 | 1.00000 | 1.00000 | 0.29694 | 0 | 0 |
| 82 | chr2 | 41728000 | 41729000 | 0.000 | 0.000 | 0.015 | 0.014 | C2orf91 | 1.60000 | 1.00000 | 0.29694 | 0 | 0 |
| 83 | chr2 | 45404000 | 45405000 | 0.000 | 0.000 | 0.000 | 0.027 | SIX2 | 0.49735 | 1.00000 | 1.00000 | 0 | 0 |
| 84 | chr2 | 47923000 | 47924000 | 0.000 | 0.000 | 0.015 | 0.014 | MSH6 | 1.00000 | 1.00000 | 0.29694 | 0 | 0 |
| 85 | chr2 | 47944000 | 47945000 | 0.000 | 0.000 | 0.029 | 0.000 | MSH6 | 0.22755 | 0.54294 | 0.08726 | 0 | 0 |
| 86 | chr2 | 51360000 | 51361000 | 0.000 | 0.000 | 0.015 | 0.014 | NRXNI | 1.00000 | 1.60000 | 0.29694 | 0 | 0 |
| 87 | chr2 | 51655000 | 51656000 | 0.000 | 0.000 | 0.000 | 0.027 | NRXNI | 0.49735 | 1.00000 | 1.00000 | 0 | 0 |
| 88 | chr2 | 56565000 | 56566000 | 0.000 | 0.000 | 0.029 | 0.000 | CCDC85A | 0.22755 | 0.54294 | 0.08726 | 0 | 0 |
| 89 | chr2 | 57800000 | 57801000 | 0.000 | 0.000 | 0.015 | 0.014 | VRK2 | 1.00000 | 1.00000 | 0.29694 | 0 | 0 |
| 90 | chr2 | 60779000 | 60780000 | 0.000 | 0.000 | 0.029 | 0.027 | BCL11A | 1.60000 | 0.54294 | 0.08726 | 0 | 0 |
| 91 | chr2 | 60780000 | 60781000 | 0.000 | 0.000 | 0.029 | 0.000 | BCL11A | 0.22755 | 0.54294 | 0.08726 | 0 | 0 |
| 92 | chr2 | 63802000 | 63803000 | 0.000 | 0.000 | 0.000 | 0.027 | WDPCP | 0.49735 | 1.00000 | 1.00000 | 0 | 0 |
| 93 | chr2 | 63827000 | 63828000 | 0.000 | 0.000 | 0.015 | 0.014 | MDH1 | 1.00000 | 1.00000 | 0.29694 | 0 | 0 |
| 94 | chr2 | 64319000 | 64320000 | 0.000 | 0.000 | 0.044 | 0.000 | PELII | 0.10727 | 0.54966 | 0.02537 | 0 | 0 |
| 95 | chr2 | 65593000 | 65594000 | 0.000 | 0.000 | 0.044 | 0.054 | SPRED2 | 1.00000 | 0.54966 | 0.02537 | 1 | 1 |
| 96 | chr2 | 67002000 | 67003000 | 0.028 | 0.000 | 0.029 | 0.000 | MEISI | 0.22755 | 1.00000 | 0.08726 | 0 | 0 |
| 97 | chr2 | 70315000 | 70316000 | 0.083 | 0.000 | 0.000 | 0.000 | PCBP1 | 1.00000 | 0.03921 | 1.00000 | 0 | 1 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 98 | chr2 | 79502000 | 79503000 | 0.028 | 0.000 | 0.015 | 0.000 | REG3A | 0.47887 | 1.00000 | 0.29694 | 0 | 0 |
| 99 | chr2 | 79644000 | 79645000 | 0.000 | 0.000 | 0.000 | 0.027 | CTNNA2 | 0.49735 | 1.00000 | 1.00000 | 0 | 0 |
| 100 | chr2 | 81818000 | 81819000 | 0.000 | 0.000 | 0.000 | 0.027 | CTNNA2 | 0.49735 | 1.00000 | 1.00000 | 0 | 0 |
| 101 | chr2 | 82310000 | 82311000 | 0.028 | 0.000 | 0.015 | 0.000 | CTNNA2 | 0.47887 | 1.00000 | 0.29694 | 0 | 0 |
| 102 | chr2 | 82948000 | 82949000 | 0.000 | 0.000 | 0.029 | 0.000 | SUCLG1 | 0.22755 | 0.54294 | 0.08726 | 0 | 0 |
| 103 | chr2 | 85335000 | 85336000 | 0.000 | 0.000 | 0.000 | 0.027 | TCF7L1 | 0.49735 | 1.00000 | 1.00 000 | 0 | 0 |
| 104 | chr2 | 88905000 | 88906000 | 0.000 | 0.000 | 0.059 | 0.000 | EIF2AK3 | 0.05016 | 0.29551 | 0.00730 | 0 | 1 |
| 105 | chr2 | 88906000 | 88907000 | 0.000 | 0.006 | 0.074 | 0.014 | EIF2AK3 | 0.10420 | 0.16101 | 0.00953 | 0 | 1 |
| 106 | chr2 | 88907000 | 88908000 | 0.000 | 0.000 | 0.059 | 0.000 | EIF2AK3 | 0.05016 | 0.29551 | 0.00730 | 0 | 1 |
| 107 | chr2 | 89052000 | 89053000 | 0.000 | 0.006 | 0.015 | 0.000 | RPIA | 0.47887 | 1.00000 | 0.50663 | 0 | 0 |
| 108 | chr2 | 89065000 | 89066000 | 0.000 | 0.000 | 0.015 | 0.027 | RPIA | 1.00000 | 1.00000 | 0.29694 | 0 | 0 |
| 109 | chr2 | 89066000 | 89067000 | 0.000 | 0.000 | 0.015 | 0.014 | RPIA | 1.00000 | 1.00000 | 0.29694 | 0 | 0 |
| 110 | chr2 | 89095000 | 89096000 | 0.000 | 0.000 | 0.015 | 0.014 | RPIA | 1.00000 | 1.00000 | 0.29694 | 0 | 0 |
| 111 | chr2 | 89127000 | 89128000 | 0.000 | 0.006 | 0.147 | 0.041 | IGKC | 0.03985 | 0.01404 | 0.00003 | 0 | 1 |
| 112 | chr2 | 89128000 | 89129000 | 0.028 | 0.006 | 0.176 | 0.041 | IGKC | 0.01224 | 0.03142 | 0.00000 | 0 | 1 |
| 113 | chr2 | 89129000 | 89130000 | 0.000 | 0.000 | 0.044 | 0.041 | IGKC | 1.00000 | 0.54966 | 0.02537 | 0 | 0 |
| 114 | chr2 | 89130000 | 89131000 | 0.000 | 0.000 | 0.044 | 0.000 | IGKC | 0.10727 | 0.54966 | 0.02537 | 0 | 0 |
| 115 | chr2 | 89131000 | 89132000 | 0.000 | 0.000 | 0.029 | 0.000 | IGKC | 0.22755 | 0.54294 | 0.08726 | 0 | 0 |
| 116 | chr2 | 89132000 | 89133000 | 0.000 | 0.006 | 0.015 | 0.014 | IGKC | 1.00000 | 1.00000 | 0.50663 | 0 | 0 |
| 117 | chr2 | 89133000 | 89134000 | 0.000 | 0.000 | 0.029 | 0.041 | IGKC | 1.00000 | 0.54294 | 0.08726 | 0 | 0 |
| 118 | chr2 | 89137000 | 89338000 | 0.000 | 0.000 | 0.044 | 0.014 | IGKC | 0.34948 | 0 54966 | 0.02537 | 0 | 0 |
| 119 | chr2 | 89138000 | 89139000 | 0.000 | 0.000 | 0.015 | 0.014 | IGKC | 1.00000 | 1.00000 | 0.29694 | 0 | 0 |
| 120 | chr2 | 89139000 | 89140000 | 0.000 | 0.000 | 0.044 | 0.014 | IGKC | 0.34948 | 0.54966 | 0.02537 | 0 | 0 |
| 121 | chr2 | 89140000 | 89141000 | 0.000 | 0.000 | 0.088 | 0.054 | IGKC | 0.52007 | 0.09031 | 0.00058 | 0 | 1 |
| 122 | chr2 | 89141000 | 89142000 | 0.000 | 0.006 | 0.103 | 0.027 | IGKC | 0.08710 | 0.09269 | 0.00099 | 0 | 1 |
| 123 | chr2 | 89142000 | 89143000 | 0.000 | 0.000 | 0.088 | 0.000 | IGKC | 0.01070 | 0.09031 | 0.00058 | 0 | 1 |
| 124 | chr2 | 89143000 | 89144000 | 0.000 | 0.000 | 0.029 | 0.000 | IGKC | 0.22755 | 0.54294 | 0.084’26 | 0 | 0 |
| 125 | chr2 | 89144000 | 89145000 | 0.000 | 0.000 | 0.015 | 0.014 | IGKC | 1.00000 | 1.00000 | 0.29694 | 0 | 0 |
| 126 | chr2 | 89145000 | 39146000 | 0.000 | 0.000 | 0.029 | 0.014 | IGKC | 0.60686 | 054294 | 0.08726 | 0 | 0 |
| 127 | chr2 | 89146000 | 89147000 | 0.000 | 0.000 | 0.029 | 0.014 | IGKC | 0.60686 | 0.54294 | 0.08726 | 0 | 0 |
| 128 | chr2 | 89153000 | 89154000 | 0.000 | 0.000 | 0.029 | 0.000 | IGKC | 0.22755 | 0.54294 | 0.08726 | 0 | 0 |
| 129 | chr2 | 89155000 | 89156000 | 0.000 | 0.000 | 0.059 | 0.014 | IGKC | 0.19371 | 0.29551 | 0.00730 | 0 | 1 |
| 130 | chr2 | 89156000 | 89157000 | 0.000 | 0.000 | 0.103 | 0.014 | IGKC | 002808 | 0.09269 | 0.00016 | 0 | 1 |
| 131 | chr2 | 89157000 | 89158000 | 0.000 | 0.000 | 0.250 | 0.149 | IGKC | 0.14439 | 0.00048 | 0.00000 | 0 | 1 |
| 132 | chr2 | 89158000 | 89159000 | 0.028 | 0.019 | 0.426 | 0.270 | IGKC | 0.05462 | 0.00001 | 0.00000 | 0 | 1 |
| 133 | chr2 | 89159000 | 89160000 | 0.222 | 0.180 | 0.574 | 0.473 | IGKJ5 | 0.24418 | 0.00083 | 0.00000 | 0 | 1 |
| 134 | chr2 | 89160000 | 89161000 | 0.444 | 0.242 | 0.500 | 0.608 | IGKJ3; IGKJ4; IGKJ5; | 0.23729 | 0.68125 | 0.00019 | 0 | 1 |
| 135 | chr2 | 89161000 | 89162000 | 0.222 | 0.08 E | 0.265 | 0.405 | IGKJ1; IGKJ2; | 0.10957 | 0.81234 | 0.00049 | 0 | 1 |
| 136 | chr2 | 89162000 | 89163000 | 0.056 | 0.012 | 0.221 | 0.108 | IGKJ1 | 0.10913 | 0.04835 | 0.00000 | 0 | 1 |
| 137 | chr2 | 89163000 | 89164000 | 0.000 | 0.068 | 0.235 | 0.176 | IGKJ1 | 0.41068 | 0.00098 | 0.00117 | 0 | 1 |
| 138 | chr2 | 89164000 | 89165000 | 0.028 | 0.137 | 0.294 | 0.216 | IGKJ1 | 0.33637 | 0.00075 | 0.00821 | 0 | 1 |
| 139 | chr2 | 89165000 | 89166000 | 0.083 | 0.143 | 0.279 | 0.216 | IGKJ1 | 0.43812 | 0.02316 | 0.02379 | 0 | 1 |
| 140 | chr2 | 89166000 | 89167000 | 0.028 | 0.012 | 0.044 | 0.027 | IGKJ1 | 0.67043 | 1.00000 | 0.15671 | 0 | 0 |
| 141 | chr2 | 89169000 | 89170000 | 0.000 | 0.000 | 0.015 | 0.014 | IGKJ1 | 1.00000 | 1.00000 | 0.29694 | 0 | 0 |
| 142 | chr2 | 89184000 | 89185000 | 0.000 | 0.006 | 0.015 | 0.054 | IGKV4-1 | 0.36833 | 1.00000 | 0.50663 | 0 | 1 |
| 143 | chr2 | 89185000 | 89186000 | 0.028 | 0.056 | 0.162 | 0.135 | IGKV4-1 | 0.81354 | 0.05349 | 0.01836 | 0 | 1 |
| 144 | chr2 | 89196000 | 89197000 | 0.000 | 0.000 | 0.059 | 0.014 | IGKV5-2 | 0.19371 | 0.29551 | 0.00730 | 0 | 1 |
| 145 | chr2 | 89197000 | 89198000 | 0.000 | 0.000 | 0.000 | 0.027 | IGKV5-2 | 0.49735 | 1.00000 | 1.00000 | 0 | 0 |
| 146 | chr2 | 89214000 | 89215000 | 0.000 | 0.012 | 0.000 | 0.000 | IGKV5-2 | 1.00000 | 1.00000 | 1.00000 | 0 | 0 |
| 147 | chr2 | 89246000 | 89247000 | 0.000 | 0.031 | 0.029 | 0.027 | IGKV1-5 | 1.00000 | 0.54294 | 1.00000 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 148 | chr2 | 89247000 | 89248000 | 0.028 | 0.019 | 0.118 | 0.054 | IGKV1-5 | 0.23086 | 0.15803 | 0.00321 | 0 | 1 |
| 149 | chr2 | 89248000 | 89249000 | 0.028 | 0.000 | 0.044 | 0.000 | IGKV1-5 | 0.10727 | 1.00000 | 0.02537 | 0 | 0 |
| 150 | chr2 | 89266000 | 89267000 | 0.000 | 0.000 | 0.015 | 0.014 | IGKV1-6 | 1.00000 | 1.00000 | 0.29694 | 0 | 0 |
| 151 | chr2 | 89291000 | 89292000 | 0.000 | 0.019 | 0.029 | 0.000 | IGKV1-8 | 0.22755 | 0.54294 | 0.63492 | 0 | 0 |
| 152 | chr2 | 89292000 | 89293000 | 0.000 | 0.025 | 0.044 | 0.000 | IGKV1-8 | 0.10727 | 0.54966 | 0.42650 | 0 | 0 |
| 153 | chr2 | 89326000 | 89327000 | 0.000 | 0.019 | 0.000 | 0.041 | IGKV3-11 | 0.24693 | 1.00000 | 0.55662 | 0 | 0 |
| 154 | chr2 | 89327000 | 89328000 | 0.000 | 0.012 | 0.015 | 0.027 | IGKV3-11 | 1.00000 | 1.00000 | 1.00000 | 0 | 0 |
| 155 | chr2 | 89442000 | 89443000 | 0.111 | 0.050 | 0.074 | 0.122 | IGKV3-20 | 0.40586 | 0.71556 | 0.53493 | 0 | 1 |
| 156 | chr2 | 89443000 | 89444000 | 0.000 | 0.000 | 0.015 | 0.041 | IGKV3-20 | 0.62100 | 1.00990 | 0.29694 | 0 | 0 |
| 157 | chr2 | 89476000 | 89477000 | 0.028 | 0.000 | 0.000 | 0.014 | IGKV2-24 | 1.00000 | 0.34615 | 1.00000 | 0 | 0 |
| 158 | chr2 | 89513000 | 89514000 | 0.000 | 0.000 | 0.029 | 0.000 | IGKV1-27 | 0.22755 | 0.54294 | 0.08726 | 0 | 0 |
| 159 | chr2 | 89521000 | 89522000 | 0.028 | 0.000 | 0.015 | 0.014 | IGKV2-28 | 1.00000 | 1.00000 | 0.29694 | 0 | 0 |
| 160 | chr2 | 89533000 | 89534000 | 0.028 | 0.000 | 0.044 | 0.014 | IGKV2-30 | 0.34948 | 1.00000 | 0.02537 | 0 | 0 |
| 161 | chr2 | 89534000 | 89535000 | 0.000 | 0.000 | 0.029 | 0.014 | IGKV2-30 | 0.60686 | 0.54294 | 0.08726 | 0 | 0 |
| 162 | chr2 | 89544000 | 89545000 | 0.028 | 0.012 | 0.059 | 0.014 | IGKV2-30 | 0.19371 | 0.65667 | 0.06548 | 0 | 1 |
| 163 | chr2 | 89545000 | 89546000 | 0.000 | 0.006 | 0.029 | 0.000 | IGKV2-30 | 0.22755 | 0.54294 | 0.21104 | 0 | 0 |
| 164 | chr2 | 90259000 | 90260000 | 0.000 | 0.000 | 0.015 | 0.014 | IGKV1D-8 | 1.00000 | 1.00000 | 0.29694 | 0 | 0 |
| 165 | chr2 | 90260000 | 90261000 | 0.000 | 0.000 | 0.059 | 0.014 | IGKV1D-8 | 0.19371 | 0.29551 | 0.00730 | 0 | 1 |
| 166 | chr2 | 96809000 | 96810000 | 0.000 | 0.000 | 0.044 | 0.000 | DUSP2 | 0.10727 | 0.54966 | 0.02537 | 1 | 0 |
| 167 | chr2 | 96810000 | 96811000 | 0.000 | 0.000 | 0.044 | 0.014 | DUSP2 | 0.34948 | 0.54966 | 0.02537 | 1 | 0 |
| 168 | chr2 | 96811000 | 96812000 | 0.000 | 0.000 | 0.029 | 0.000 | DUSP2 | 0.22755 | 0.54294 | 0.08726 | 1 | 0 |
| 169 | chr2 | 98611000 | 98612000 | 0.000 | 0.000 | 0.015 | 0.014 | TMEM131 | 1.00000 | 1.00000 | 0.29694 | 0 | 0 |
| 170 | chr2 | 100757000 | 100758000 | 0.000 | 0.000 | 0.029 | 0.027 | AFF3 | 1.00000 | 0.54294 | 0.08726 | 0 | 0 |
| 171 | chr2 | 100758000 | 100759000 | 0.000 | 0.000 | 0.044 | 0.014 | AFF3 | 0.34948 | 0.54966 | 0.02537 | 0 | 0 |
| 172 | chr2 | 106144000 | 106145000 | 0.000 | 0.000 | 0.029 | 0.000 | FHL2 | 0.22755 | 0.54294 | 0.08726 | 0 | 0 |
| 173 | chr2 | 111878000 | 111879000 | 0.000 | 0.000 | 0.029 | 0.014 | BCL2L11 | 0.60686 | 0.54294 | 0.08726 | 0 | 0 |
| 174 | chr2 | 111879000 | 111880000 | 0.000 | 0.000 | 0.044 | 0.014 | BCL2L11 | 0.34948 | 0.54966 | 0.02537 | 0 | 0 |
| 175 | chr2 | 112305000 | 112306000 | 0.000 | 0.000 | 0.015 | 0.014 | ANAPC1 | 1.00000 | 1.00000 | 0.29694 | 0 | 0 |
| 176 | chr2 | 116234000 | 116235000 | 0.000 | 0.000 | 0.015 | 0.014 | DPP10 | 1.00000 | 1.00000 | 0.29694 | 0 | 0 |
| 177 | chr2 | 116439000 | 116440000 | 0.028 | 0.000 | 0.000 | 0.014 | DPP10 | 1.00000 | 0.34615 | 1.00000 | 0 | 0 |
| 178 | chr2 | 124697000 | 124698000 | 0.028 | 0.000 | 0.015 | 0.000 | CNTNAP5 | 0.47887 | 1.00000 | 0.29694 | 0 | 0 |
| 179 | chr2 | 125235000 | 125236000 | 0.000 | 0.000 | 0.029 | 0.000 | CNTNAP5 | 0.22755 | 0.54294 | 0.08726 | 0 | 0 |
| 180 | chr2 | 127538000 | 127539000 | 0.028 | 0.000 | 0.015 | 0.000 | GYPC | 0.47887 | 1.00000 | 0.29694 | 0 | 0 |
| 181 | chr2 | 136874000 | 136875000 | 0.000 | 0.000 | 0.191 | 0.014 | CXCR4 | 0.00036 | 0.00372 | 0.00000 | 1 | 1 |
| 182 | chr2 | 136875000 | 136876000 | 0.083 | 0.019 | 0.265 | 0.081 | CXCR4 | 0.00626 | 0.03882 | 0.00000 | 1 | 1 |
| 183 | chr2 | 136996000 | 136997000 | 0.000 | 0.000 | 0.029 | 0.000 | CXCR4 | 0.22755 | 0.54294 | 0.08726 | 1 | 0 |
| 184 | chr2 | 137082000 | 137083000 | 0.000 | 0.000 | 0.015 | 0.014 | CXCR4 | 1.00000 | 1.00000 | 0.29694 | 1 | 0 |
| 185 | chr2 | 140951000 | 140952000 | 0.000 | 0.000 | 0.029 | 0.000 | LRP1B | 0.22755 | 0.54294 | 0.08726 | 0 | 0 |
| 186 | chr2 | 141335000 | 141336000 | 0.000 | 0.000 | 0.015 | 0.014 | LRP1B | 1.00000 | 1.00000 | 0.29694 | 0 | 0 |
| 187 | chr2 | 141770000 | 141771000 | 0.000 | 0.000 | 0.029 | 0.000 | LRP1B | 0.22755 | 0.54294 | 0.08726 | 0 | 0 |
| 188 | chr2 | 146445000 | 146446000 | 0.000 | 0.000 | 0.029 | 0.090 | ZEB2 | 0.22755 | 0.54294 | 0.08726 | 0 | 0 |
| 189 | chr2 | 146446000 | 146447000 | 0.000 | 0.000 | 0.029 | 0.014 | ZEB2 | 0.60686 | 0.54294 | 0.08726 | 0 | 0 |
| 190 | chr2 | 156443000 | 156444000 | 0.000 | 0.000 | 0.029 | 0.000 | KCNJ3 | 0.22755 | 0.54294 | 0.08726 | 0 | 0 |
| 191 | chr2 | 172590000 | 172591000 | 0.000 | 0.000 | 0.029 | 0.000 | DYNCII2 | 0.22755 | 0.54294 | 0.08726 | 0 | 0 |
| 192 | chr2 | 176581000 | 176582000 | 0.028 | 0.000 | 9.000 | 0.014 | KIAA1715 | 1.00000 | 0.34615 | 1.00000 | 0 | 0 |
| 193 | chr2 | 179880000 | 179881000 | 0.000 | 0.000 | 9.015 | 0.014 | CCDC141 | 1.00000 | 1.00000 | 0.29694 | 0 | 0 |
| 194 | chr2 | 180358000 | 180359000 | 0.000 | 0.000 | 0.029 | 0.000 | ZNF385B | 0.22755 | 0.54294 | 0.08726 | 0 | 0 |
| 195 | chr2 | 189285000 | 189286000 | 0.000 | 0.000 | 0.915 | 0.014 | GULP1 | 1.00000 | 1.00000 | 0.29694 | 0 | 0 |
| 196 | chr2 | 189432000 | 189433000 | 0.028 | 0.000 | 0.990 | 0.014 | GULP1 | 1.00000 | 0.34615 | 1.00000 | 0 | 0 |
| 197 | chr2 | 194115000 | 194116000 | 0.000 | 0.000 | 0.015 | 0.014 | TMEFF2 | 1.00000 | 1.00000 | 0.29694 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 198 | chr2 | 197035000 | 197036000 | 0.000 | 0.000 | 0.044 | 0.014 | STK17B | 0.34948 | 0.54966 | 0.02537 | 0 | 0 |
| 199 | chr2 | 197041000 | 197042000 | 0.000 | 0.000 | 0.029 | 0.000 | STK17B | 0.22755 | 0.54294 | 0.08726 | 0 | 0 |
| 200 | chr2 | 215999000 | 216000000 | 0.000 | 0.006 | 0.015 | 0.000 | ABCA12 | 0.47887 | 1.00000 | 0.50663 | 0 | 0 |
| 201 | chr2 | 216973000 | 216974000 | 0.028 | 0.000 | 0.000 | 0.014 | XRCC5 | 1.00000 | 0.34615 | 1.00000 | 0 | 0 |
| 202 | chr2 | 217247000 | 217248000 | 0.028 | 0.000 | 0.000 | 0.014 | 4-Mar-19 | 1.00000 | 0.34615 | 1.00000 | 0 | 0 |
| 203 | chr2 | 225386000 | 225387000 | 0.000 | 0.000 | 0.029 | 0.000 | CUL3 | 0.22755 | 0.54294 | 0.08726 | 0 | 0 |
| 204 | chr2 | 225524000 | 225525000 | 0.000 | 0.000 | 0.029 | 0.000 | CUL3 | 0.22755 | 0.54294 | 0.08726 | 0 | 0 |
| 205 | chr2 | 233478000 | 233479000 | 0.028 | 0.000 | 0.015 | 0.000 | EFHD1 | 0.47887 | 1.00000 | 0.29694 | 0 | 0 |
| 200 | chr2 | 233980000 | 233981000 | 0.028 | 0.000 | 0.029 | 0.000 | INPP5D | 0.22755 | 1.00000 | 0.08726 | 0 | 0 |
| 207 | chr2 | 240641000 | 240642000 | 0.028 | 0.000 | 0.000 | 0.027 | AC093802.1 | 0.49735 | 0.34615 | 1.00000 | 0 | 0 |
| 208 | chr2 | 241125000 | 241126000 | 0.000 | 0.000 | 0.000 | 0.027 | OTOS | 0.49735 | 1.00000 | 1.00000 | 0 | 0 |
| 209 | chr3 | 8739000 | 8740000 | 0.000 | 0.000 | 0.000 | 0.027 | CAV3 | 0.49735 | 1.00000 | 1.00000 | 0 | 0 |
| 210 | chr3 | 16407000 | 16408000 | 0.000 | 0.000 | 0.000 | 0.027 | RFTN1 | 0.49735 | 1.00000 | 1.00000 | 1 | 0 |
| 211 | chr3 | 16409000 | 16410000 | 0.028 | 0.000 | 0.000 | 0.041 | RFTN1 | 0.24603 | 0.34615 | 1.00000 | 1 | 0 |
| 212 | chr3 | 16419000 | 16420000 | 0.000 | 0.006 | 0.044 | 0.000 | RFTN1 | 0.10727 | 0.54966 | 0.07959 | 1 | 0 |
| 213 | chr3 | 16472000 | 16473000 | 0.000 | 0.000 | 0.015 | 0.014 | RFTN1 | 1.00000 | 1.00000 | 0.29694 | 1 | 0 |
| 214 | chr3 | 16495000 | 16496000 | 0.000 | 0.000 | 0.029 | 0.000 | RFTN1 | 0.22755 | 0.54294 | 0.08726 | 1 | 0 |
| 215 | chr3 | 16552000 | 16553000 | 0.000 | 0.012 | 0.029 | 0.014 | RFTN1 | 0.60686 | 0.54294 | 0.58408 | 1 | 0 |
| 216 | chr3 | 16554000 | 16555000 | 0.000 | 0.000 | 0.103 | 0.027 | RFTN1 | 0.08710 | 0.09269 | 0.00016 | 1 | 1 |
| 21" | chr3 | 16555000 | 16556000 | 0.000 | 0.000 | 0.029 | 0.000 | RFTN1 | 0.22755 | 0.54294 | 0.08726 | 1 | 0 |
| 218 | chr3 | 21658000 | 21659000 | 0.000 | 0.000 | 0.029 | 0.000 | ZNF385D | 0.22755 | 0.54294 | 0.08726 | 0 | 0 |
| 219 | chr3 | 25691000 | 25692000 | 0.000 | 0.000 | 0.029 | 0.000 | TOP2B | 0.22755 | 0.54294 | 0.08726 | 0 | 0 |
| 220 | chr3 | 31969000 | 31970000 | 0.000 | 0.000 | 0.029 | 0.000 | OSBPL10 | 0.22755 | 0.54294 | 0.08726 | 1 | 0 |
| 221 | chr3 | 31993000 | 31994000 | 0.000 | 0.000 | 0.044 | 0.000 | OSBPL10 | 0.10727 | 0.54966 | 0.02537 | 1 | 0 |
| 222 | chr3 | 32001000 | 32002000 | 0.000 | 0.000 | 0.044 | 0.000 | OSBPL10 | 0.10727 | 0.54966 | 0.02537 | 1 | 0 |
| 223 | chr3 | 32022000 | 32023000 | 0.000 | 0.000 | 0.088 | 0.014 | OSBPL10 | 0.05468 | 0.09031 | 0.00058 | 1 | 1 |
| 224 | chr3 | 32023000 | 32024000 | 0.000 | 0.000 | 0.029 | 0.000 | OSBPL10 | 0.22755 | 0.54294 | 0.08726 | 1 | 0 |
| 225 | chr3 | 50128000 | 50129000 | 0.000 | 0.000 | 0.029 | 0.000 | RBM5 | 0.22755 | 0.54294 | 0.08726 | 0 | 0 |
| 226 | chr3 | 54913000 | 54914000 | 0.000 | 0.006 | 0.015 | 0.000 | CACNA2D3 | 0.47887 | 1.00000 | 0.50663 | 0 | 0 |
| 707 | chr3 | 56074000 | 56075000 | 0.028 | 0.000 | 0.000 | 0.014 | ERC2 | 1.00000 | 0.34615 | 1.00000 | 0 | 0 |
| 228 | chr3 | 59577000 | 59578000 | 0.000 | 0.000 | 0.029 | 0.000 | FHIT | 0.22755 | 0.54294 | 0.08726 | 0 | 0 |
| 229 | chr3 | 60351000 | 60352000 | 0.000 | 0.000 | 0.044 | 0.000 | FHIT | 0.10727 | 0.54966 | 0.02537 | 0 | 0 |
| 230 | chr3 | 60356000 | 60357000 | 0.028 | 0.000 | 0.000 | 0.014 | FHIT | 1.00000 | 0.34615 | 1.00000 | 0 | 0 |
| 231 | chr3 | 60357000 | 60358000 | 0.000 | 0.000 | 0.015 | 0.014 | FHIT | 1.00000 | 1.00000 | 0.29694 | 0 | 0 |
| 232 | chr3 | 60358000 | 60359000 | 0.000 | 0.000 | 0.015 | 0.014 | FHIT | 1.00000 | 1.00000 | 0.29694 | 0 | 0 |
| 233 | chr3 | 60359000 | 60360000 | 0.000 | 0.000 | 0.029 | 0.000 | FHIT | 0.22755 | 0.54294 | 0.08726 | 0 | 0 |
| 234 | chr3 | 60389000 | 60390000 | 0.000 | 0.000 | 0.015 | 0.027 | FHIT | 1.00000 | 1.00000 | 0.29694 | 0 | 0 |
| 235 | chr3 | 60392000 | 60393000 | 0.000 | 0.000 | 0.029 | 0.000 | FHIT | 0.22755 | 0.54294 | 0.08726 | 0 | 0 |
| 236 | chr3 | 60395000 | 60396000 | 0.000 | 0.000 | 0.000 | 0.027 | FHIT | 0.49735 | 1.00000 | 1.00000 | 0 | 0 |
| 237 | chr3 | 60404000 | 60405000 | 0.000 | 0.000 | 0.029 | 0.000 | FHIT | 0.22755 | 0.54294 | 0.08726 | 0 | 0 |
| 238 | chr3 | 60436000 | 60437000 | 0.000 | 0.000 | 0.000 | 0.027 | FHIT | 0.49735 | 1.00000 | 1.00000 | 0 | 0 |
| 239 | chr3 | 60437000 | 60438000 | 0.000 | 0.000 | 0.029 | 0.000 | FHIT | 0.22755 | 0.54294 | 0.08726 | 0 | 0 |
| 240 | chr3 | 60477000 | 60478000 | 0.000 | 0.000 | 0.029 | 0.000 | FHIT | 0.22755 | 0.54294 | 0.08726 | 0 | 0 |
| 241 | chr3 | 60485000 | 60486000 | 0.000 | 0.000 | 0.015 | 0.014 | FHIT | 1.00000 | 1.00000 | 0.29694 | 0 | 0 |
| 242 | chr3 | 60515000 | 60516000 | 0.000 | 0.000 | 0.015 | 0.014 | FHIT | 1.00000 | 1.00000 | 0.29694 | 0 | 0 |
| 243 | chr3 | 60535000 | 60536000 | 0.000 | 0.006 | 0.015 | 0.000 | FHIT | 0.47887 | 1.00000 | 0.50663 | 0 | 0 |
| 244 | chr3 | 60602000 | 60603000 | 0.000 | 0.000 | 0.029 | 0.014 | FHIT | 0.60686 | 0.54294 | 0.08726 | 0 | 0 |
| 245 | chr3 | 60613000 | 60614000 | 0.000 | 0.000 | 0.029 | 0.014 | FHIT | 0.60686 | 0.54294 | 0.08726 | 0 | 0 |
| 246 | chr3 | 60614000 | 60615000 | 0.000 | 0.000 | 0.029 | 0.000 | FHIT | 0.22755 | 0.54294 | 0.08726 | 0 | 0 |
| 247 | chr3 | 60632000 | 60633000 | 0.000 | 0.000 | 0.000 | 0.027 | FHIT | 0.49735 | 1.00000 | 1.00000 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 248 | chr3 | 60635000 | 60636000 | 0.000 | 0.000 | 0.029 | 0.000 | FHIT | 0.22755 | 0.54294 | 0.08726 | 0 | 0 |
| 249 | chr3 | 60640000 | 60641000 | 0.000 | 0.000 | 0.000 | 0.027 | FHIT | 0.49735 | 1.00000 | 1.00000 | 0 | 0 |
| 250 | chr3 | 60647000 | 60648000 | 0.000 | 0.000 | 0.015 | 0.014 | FHIT | 1.00000 | 1.00000 | 0.29694 | 0 | 0 |
| 251 | chr3 | 60648000 | 60649000 | 0.000 | 0.000 | 0.015 | 0.014 | FHIT | 1.00000 | 1.00000 | 0.29694 | 0 | 0 |
| 252 | chr3 | 60652000 | 60653000 | 0.000 | 0.000 | 0.000 | 0.027 | FHIT | 0.49735 | 1.00000 | 1.00000 | 0 | 0 |
| 253 | chr3 | 60660000 | 60661009 | 0.000 | 0.000 | 0.029 | 0.014 | FHIT | 0.60686 | 0.54294 | 0.08726 | 0 | 0 |
| 254 | chr3 | 60665000 | 69666009 | 0.000 | 0.000 | 0.015 | 0.027 | FHIT | 1.00000 | 1.00000 | 0.29694 | 0 | 0 |
| 255 | chr3 | 60666000 | 60667009 | 0.000 | 0.000 | 0.015 | 0.014 | FHIT | 1.00000 | 1.00000 | 0.29694 | 0 | 0 |
| 256 | chr3 | 60671000 | 60672000 | 0.000 | 0.000 | 0.000 | 0.041 | FHIT | 0.24603 | 1.00000 | 1.00000 | 0 | 0 |
| 257 | chr3 | 69673090 | 60674900 | 0.000 | 0.000 | 0.044 | 0.000 | FHIT | 0.10727 | 0.54966 | 0.02537 | 0 | 0 |
| 258 | chr3 | 69675090 | 60676000 | 0.000 | 0.000 | 0.015 | 0.014 | FHIT | 1.00000 | 1.00000 | 0.29694 | 0 | 0 |
| 259 | chr3 | 69678090 | 60679900 | 0.000 | 0.000 | 0.044 | 0.000 | FHIT | 0.10727 | 0.54966 | 0.92537 | 0 | 0 |
| 260 | chr3 | 60683000 | 60684000 | 0.000 | 0.000 | 0.015 | 0.027 | FHIT | 1.00000 | 1.00000 | 0.29694 | 0 | 0 |
| 261 | chr3 | 60684000 | 60685009 | 0.000 | 0.000 | 0.015 | 0.041 | FHIT | 0.62100 | 1.00000 | 0.29694 | 0 | 0 |
| 262 | chr3 | 60688000 | 69689009 | 0.000 | 0.000 | 0.015 | 0.014 | FHIT | 1.00000 | 1.00000 | 0.29694 | 0 | 0 |
| 263 | chr3 | 60717000 | 60718009 | 0.000 | 0.000 | 0.000 | 0.027 | FHIT | 0.49735 | 1.00000 | 1.00000 | 0 | 0 |
| 264 | chr3 | 60740000 | 60741000 | 0.000 | 0.000 | 0.029 | 0.000 | FHIT | 0.22755 | 0.54294 | 0.08726 | 0 | 0 |
| 265 | chr3 | 69774090 | 60775900 | 0.000 | 0.000 | 0.029 | 0.000 | FHIT | 0.22755 | 0.54294 | 0.08726 | 0 | 0 |
| 266 | chr3 | 60792090 | 60793000 | 0.000 | 0.000 | 0.000 | 0.027 | FHIT | 0.49735 | 1.00000 | 1.00000 | 0 | 0 |
| 267 | chr3 | 69806090 | 60807900 | 0.028 | 0.000 | 0.000 | 0.014 | FHIT | 1.00000 | 0.34615 | 1.00000 | 0 | 0 |
| 268 | chr3 | 60812000 | 60813000 | 0.000 | 0.000 | 0.000 | 0.027 | FHIT | 0.49735 | 1.00000 | 1.00000 | 0 | 0 |
| 269 | chr3 | 60860000 | 60861009 | 0.000 | 0.000 | 0.000 | 0.027 | FHIT | 0.49735 | 1.00000 | 1.00000 | 0 | 0 |
| 270 | chr3 | 71551000 | 71552099 | 0.000 | 0.000 | 0.000 | 0.027 | EIF4E3 | 0.49735 | 1.00000 | 1.00000 | 0 | 0 |
| 271 | chr3 | 78274000 | 78275009 | 0.000 | 0.000 | 0.015 | 0.014 | ROBO1 | 1.00000 | 1.00000 | 0.29694 | 0 | 0 |
| 272 | chr3 | 80273000 | 80274000 | 0.000 | 0.006 | 0.015 | 0.000 | ROBO1 | 0.47887 | 1.00000 | 9.50663 | 0 | 0 |
| 273 | chr3 | 83094090 | 83095900 | 0.028 | 0.000 | 0.015 | 0.000 | GBE1 | 0.47887 | 1.00000 | 9.29694 | 0 | 0 |
| 274 | chr3 | 83924000 | 83925900 | 0.028 | 0.000 | 0.000 | 0.014 | CADM2 | 1.00000 | 0.34615 | 1.00000 | 0 | 0 |
| 275 | chr3 | 84293090 | 84294900 | 0.000 | 0.000 | 0.015 | 0.014 | CADM2 | 1.00000 | 1.00000 | 0.29694 | 0 | 0 |
| 276 | chr3 | 85260000 | 85261000 | 0.000 | 0.000 | 0.044 | 0.000 | CADM2 | 0.10727 | 0.54966 | 0.02537 | 0 | 0 |
| 277 | chr3 | 85261000 | 85262009 | 0.000 | 0.000 | 0.029 | 0.000 | CADM2 | 0.22755 | 0.54294 | 0.08726 | 0 | 0 |
| 278 | chr3 | 85799000 | 85800099 | 0.000 | 0.000 | 0.029 | 0.000 | CADM2 | 0.22755 | 0.54294 | 0.08726 | 0 | 0 |
| 279 | chr3 | 86226000 | 86227900 | 0.000 | 0.000 | 0.029 | 0.000 | CADM2 | 0.22755 | 0.54294 | 0.08726 | 0 | 0 |
| 280 | chr3 | 88146000 | 88147000 | 0.000 | 0.000 | 0.029 | 0.000 | CGGBP1 | 0.22755 | 0.54294 | 0.08726 | 0 | 0 |
| 281 | chr3 | 94709090 | 94719900 | 0.000 | 0.000 | 0.029 | 0.000 | NSUN3 | 0.22755 | 0.54294 | 0.08726 | 0 | 0 |
| 282 | chr3 | 95460000 | 95461900 | 0.028 | 0.000 | 0.015 | 0.000 | MTRNR2L12 | 0.47887 | 1.00000 | 0.29694 | 0 | 0 |
| 283 | chr3 | 95724090 | 95725900 | 0.000 | 0.000 | 0.029 | 0.000 | MTRNR2L12 | 0.22755 | 0.54294 | 0.08726 | 0 | 0 |
| 284 | chr3 | 101569000 | 101570000 | 0.028 | 0.000 | 0.015 | 0.000 | NFKBIZ | 0.47887 | 1.00000 | 0.29694 | 0 | 0 |
| 285 | chr3 | 111851000 | 111852000 | 0.000 | 0.000 | 0.044 | 0.000 | GCSAM | 0.10727 | 0.54966 | 0.02537 | 0 | 0 |
| 286 | chr3 | 111852000 | 111853099 | 0.000 | 0.000 | 0.059 | 0.000 | GCSAM | 0.05016 | 0.29551 | 0.00730 | 0 | 1 |
| 287 | chr3 | 122377000 | 122378009 | 0.028 | 0.000 | 0.044 | 0.000 | PARP14 | 0.10727 | 1.00000 | 0.02537 | 0 | 0 |
| 288 | chr3 | 150478000 | 150479000 | 0.000 | 0.000 | 0.029 | 0.000 | SIAH2 | 0.22755 | 0.54294 | 0.08726 | 0 | 0 |
| 289 | chr3 | 150479990 | 150489000 | 0.000 | 0.000 | 0.029 | 0.000 | SIAH2 | 0.22755 | 0.54294 | 0.08726 | 0 | 0 |
| 290 | chr3 | 150480000 | 150481000 | 0.000 | 0.000 | 0.015 | 0.014 | SIAH2 | 1.00000 | 1.00000 | 0.29694 | 0 | 0 |
| 291 | chr3 | 163237990 | 163238000 | 0.000 | 0.000 | 0.000 | 0.027 | SI | 0.49735 | 1.00000 | 1.00000 | 0 | 0 |
| 292 | chr3 | 163238000 | 163239000 | 0.000 | 0.000 | 0.029 | 0.000 | SI | 0.22755 | 9.54294 | 0.08726 | 0 | 0 |
| 293 | chr3 | 163615000 | 163616000 | 0.000 | 0.000 | 0.029 | 0.000 | SI | 0.22755 | 9.54294 | 0.08726 | 0 | 0 |
| 294 | chr3 | 183270000 | 183271000 | 0.000 | 0.000 | 0.029 | 0.000 | KLHL6 | 0.22755 | 0.54294 | 0.08726 | 0 | 0 |
| 295 | chr3 | 183271000 | 183272009 | 0.000 | 0.000 | 0.029 | 0.014 | KLHL6 | 0.60686 | 0.54294 | 0.08726 | 0 | 0 |
| 296 | chr3 | 183272000 | 183273000 | 0.000 | 0.000 | 0.029 | 0.014 | KLHL6 | 0.60686 | 0.54294 | 0.08726 | 0 | 0 |
| 297 | chr3 | 183273900 | 183274000 | 0.000 | 0.019 | 0.044 | 0.027 | KLHL6 | 0.67043 | 0.54966 | 0.36534 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 298 | chr3 | 186648900 | 186649000 | 0.000 | 0.000 | 0.044 | 0.014 | ADIPOQ | 0.34948 | 0.54966 | 0.02537 | 0 | 0 |
| 299 | chr3 | 186714990 | 186715000 | 0.000 | 0.006 | 0.132 | 0.027 | ST6GAL1 | 0.02624 | 0.02564 | 0.00009 | 1 | 1 |
| 300 | chr3 | 186715000 | 186716000 | 0.000 | 0.000 | 0.044 | 0.014 | ST6GAL1 | 0.34948 | 0.54966 | 0.02537 | 1 | 0 |
| 301 | chr3 | 186739000 | 186740009 | 0.000 | 0.006 | 0.074 | 0.014 | ST6GAL1 | 0.10420 | 0.16101 | 0.00953 | 1 | 1 |
| 302 | chr3 | 186740000 | 186741000 | 0.056 | 0.006 | 0.074 | 0.027 | ST6GAL1 | 0.25970 | 1.00000 | 0.00953 | 1 | 1 |
| 303 | chr3 | 186742000 | 186743000 | 0.000 | 0.000 | 0.029 | 0.000 | ST6GAL1 | 0.22755 | 0.54294 | 0.08726 | 1 | 0 |
| 304 | chr3 | 186783000 | 186784000 | 0.000 | 0.050 | 0.338 | 0.041 | ST6GAL1 | 0.00001 | 0.00001 | 0.00000 | 1 | 1 |
| 305 | chr3 | 186784000 | 186785000 | 0.000 | 0.025 | 0.044 | 0.000 | ST6GAL1 | 0.10727 | 0.54966 | 0.42650 | 1 | 0 |
| 306 | chr3 | 187458000 | 187459000 | 0.000 | 0.000 | 0.029 | 0.000 | BCL6 | 0.22755 | 0.54294 | 0.08726 | 1 | 0 |
| 307 | chr3 | 187459000 | 187460000 | 0.000 | 0.000 | 0.029 | 0.000 | BCL6 | 0.22755 | 0.54294 | 0.08726 | 1 | 0 |
| 308 | chr3 | 187460000 | 187461000 | 0.000 | 0.000 | 0.088 | 0.041 | BCL6 | 0.31126 | 0.09031 | 0.00058 | 1 | 1 |
| 309 | chr3 | 187461000 | 187462000 | 0.000 | 0.006 | 0.353 | 0.122 | BCL6 | 0.00137 | 0.00001 | 0.00000 | 1 | 1 |
| 310 | chr3 | 187462000 | 187463000 | 0.056 | 0.081 | 0.647 | 0.392 | BCL6 | 0.00266 | 0.00000 | 0.00000 | 1 | 1 |
| 311 | chr3 | 187463000 | 187464000 | 0.000 | 0.037 | 0.485 | 0.230 | BCL6 | 0.00164 | 0.00000 | 0.00000 | 1 | 1 |
| 312 | chr3 | 187464000 | 187465000 | 0.028 | 0.000 | 0.162 | 0.000 | BCL6 | 0.00019 | 0.05349 | 0.00000 | 1 | 1 |
| 313 | chr3 | 187468000 | 187469000 | 0.000 | 0.000 | 0.044 | 0.000 | BCL6 | 0.10727 | 0.54966 | 0.02537 | 1 | 0 |
| 314 | chr3 | 187635000 | 187636000 | 0.000 | 0.000 | 0.029 | 0.000 | BCL6 | 0.22755 | 0.54294 | 0.08726 | 1 | 0 |
| 315 | chr3 | 187636000 | 187637000 | 0.000 | 0.000 | 0.000 | 0.027 | BCL6 | 0.49735 | 1.00000 | 1.00000 | 1 | 0 |
| 310 | chr3 | 187653000 | 187654000 | 0.000 | 0.000 | 0.044 | 0.014 | BCL6 | 0.34948 | 0.54966 | 0.02537 | 1 | 0 |
| 317 | chr3 | 187658000 | 187659000 | 0.000 | 0.000 | 0.029 | 0.000 | BCL6 | 0.22755 | 0.54294 | 0.08726 | 1 | 0 |
| 318 | chr3 | 187660000 | 187661000 | 0.000 | 0.019 | 0.118 | 0.054 | BCL6 | 0.23086 | 0.04825 | 0.00321 | 1 | 1 |
| 319 | chr3 | 187661000 | 187662000 | 0.000 | 0.012 | 0.191 | 0.081 | BCL6 | 0.08249 | 0.00372 | 0.00000 | 1 | 1 |
| 320 | chr3 | 187664000 | 187665000 | 0.000 | 0.000 | 0.044 | 0.000 | BCL6 | 0.10727 | 0.54966 | 0.02537 | 1 | 0 |
| 321 | chr3 | 187686000 | 187687000 | 0.028 | 0.000 | 0.029 | 0.014 | AC022498.1 | 0.60686 | 1.00000 | 0.08726 | 0 | 0 |
| 322 | chr3 | 187687000 | 187688000 | 0.000 | 0.006 | 0.000 | 0.014 | AC022498.1 | 1.00000 | 1.00000 | 1.00 000 | 0 | 0 |
| 323 | chr3 | 187693000 | 187694000 | 0.000 | 0.000 | 0.015 | 0.014 | AC022498.1 | 1.00000 | 1.00000 | 0.29694 | 0 | 0 |
| 324 | chr3 | 187696000 | 187697000 | 0.000 | 0.006 | 0.059 | 0.000 | AC022498.1 | 0.05016 | 0.29551 | 0.02818 | 0 | 1 |
| 325 | chr3 | 187697000 | 187698000 | 0.000 | 0.000 | 0.044 | 0.000 | AC022498.1 | 0.10727 | 0.54966 | 0.02537 | 0 | 0 |
| 326 | chr3 | 187803000 | 187804000 | 0.000 | 0.000 | 0.029 | 0.000 | AC022498.1 | 0.22755 | 0.54294 | 0.08726 | 0 | 0 |
| 327 | chr3 | 187806000 | 187807000 | 0.000 | 0.000 | 0.059 | 0.014 | AC022498.1 | 0.19371 | 0.29551 | 0.00730 | 0 | 1 |
| 328 | chr3 | 187957000 | 187958000 | 0.000 | 0.006 | 0.132 | 0.014 | AC022498.1 | 0.00701 | 0.02564 | 0.00009 | 0 | 1 |
| 329 | chr3 | 187958000 | 187959000 | 0.028 | 0.025 | 0.221 | 0.095 | AC022498.1 | 0.06156 | 0.00936 | 0.00000 | 0 | 1 |
| 330 | chr3 | 187959000 | 187960000 | 0.000 | 0.012 | 0.118 | 0.000 | AC022498.1 | 0.00220 | 0.04825 | 0.00116 | 0 | 1 |
| 331 | chr3 | 187960000 | 187961000 | 0.000 | 0.000 | 0.029 | 0.000 | AC022498.1 | 0.22755 | 0.54294 | 0.08726 | 0 | 0 |
| 332 | chr3 | 188222000 | 188223000 | 0.000 | 0.000 | 0.029 | 0.000 | LPP | 0.22755 | 0.54294 | 0.08726 | 0 | 0 |
| 333 | chr3 | 188298000 | 188299000 | 0.000 | 0.000 | 0.015 | 0.014 | LPP | 1.00000 | 1.00000 | 0.29694 | 0 | 0 |
| 334 | chr3 | 188299000 | 188300000 | 0.000 | 0.006 | 0.088 | 0.027 | LPP | 0.15270 | 0.09031 | 0 00311 | 0 | 1 |
| 335 | chr3 | 188471000 | 188472000 | 0.000 | 0.006 | 0.191 | 0.068 | LPP | 0.04150 | 0.00372 | 0.00000 | 0 | 1 |
| 336 | chr3 | 188472000 | 188473000 | 0.000 | 0.000 | 0.044 | 0.027 | LPP | 0.67043 | 0.54966 | 0.02537 | 0 | 0 |
| 337 | chr4 | 50000 | 51000 | 0.000 | 0.000 | 0.029 | 0.000 | ZNF595; ZNF718; | 0.22755 | 0.54294 | 0.08726 | 0 | 0 |
| 338 | chr4 | 51000 | 52000 | 0.000 | 0.000 | 0.044 | 0.014 | ZNF595; ZNF718; | 0.34948 | 0.54966 | 0.02537 | 0 | 0 |
| 339 | chr4 | 54000 | 55000 | 0.000 | 0.000 | 0.029 | 0.000 | ZNF595; ZNF718; | 0.22755 | 0.54294 | 0.08726 | 0 | 0 |
| 340 | chr4 | 290000 | 291000 | 0.056 | 0.000 | 0.000 | 0.000 | ZNF732 | 1.00000 | 0.11763 | 1.00000 | 0 | 1 |
| 341 | chr4 | 385000 | 386000 | 0.000 | 0.000 | 0.029 | 0.000 | ZNF141 | 0.22755 | 0.54294 | 0.08726 | 0 | 0 |
| 342 | chr4 | 550000 | 551000 | 0.000 | 0.000 | 0.000 | 0.027 | PIGG | 0.49735 | 1.00000 | 1.00000 | 0 | 0 |
| 343 | chr4 | 2707000 | 2708000 | 0.028 | 0.000 | 0.015 | 0.000 | FAMI93A | 0.47887 | 1.00 000 | 0.29694 | 0 | 0 |
| 344 | chr4 | 5206000 | 5207000 | 0.000 | 0.000 | 0.029 | 0.000 | STK32B | 0.22755 | 0.54294 | 0.08726 | 0 | 0 |
| 345 | chr4 | 25863000 | 25864000 | 0.000 | 0.000 | 0.059 | 0.014 | SEL1L3 | 0.19371 | 0.29551 | 0.00730 | 0 | 1 |
| 346 | chr4 | 25864000 | 25865000 | 0.000 | 0.006 | 0.044 | 0.027 | SEL1L3 | 0.67043 | 0.54966 | 0.07959 | 0 | 0 |
| 347 | chr4 | 25865000 | 25866000 | 0.000 | 0.000 | 0.074 | 0.027 | SEL1L3 | 0.25970 | 0.16101 | 0.00208 | 0 | 1 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 348 | chr4 | 29657000 | 29658000 | 0.000 | 0.000 | 0.015 | 0.014 | PCDH7 | 1.00000 | 1.00000 | 0.29694 | 0 | 0 |
| 349 | chr4 | 30356000 | 30357000 | 0.000 | 0.006 | 0.015 | 0.000 | PCDH7 | 0.47887 | 1.00000 | 0.50663 | 0 | 0 |
| 350 | chr4 | 33418000 | 33419000 | 0.000 | 0.000 | 0.029 | 0.000 | PCDH7 | 0.22755 | 0.54294 | 0.08726 | 0 | 0 |
| 351 | chr4 | 33449000 | 33450000 | 0.028 | 0.000 | 0.015 | 0.000 | PCDH7 | 0.47887 | 1.00000 | 0.29694 | 0 | 0 |
| 352 | chr4 | 39348000 | 39349000 | 0.000 | 0.000 | 0.015 | 0.014 | RFC1 | 1.00000 | 1.00000 | 0.29694 | 0 | 0 |
| 353 | chr4 | 39974000 | 39975000 | 0.000 | 0.000 | 0.000 | 0.027 | PDS5A | 0.49735 | 1.00000 | 1.00000 | 0 | 0 |
| 354 | chr4 | 40194000 | 40195000 | 0.000 | 0.000 | 0.044 | 0.027 | N4BP2 | 0.67043 | 0.54966 | 0.02537 | 0 | 0 |
| 355 | chr4 | 40195000 | 40196000 | 0.000 | 0.000 | 0.015 | 0.027 | N4BP2 | 1.00000 | 1.00000 | 0.29694 | 0 | 0 |
| 356 | chr4 | 40196000 | 40197000 | 0.000 | 0.000 | 0.074 | 0.014 | N4BP2 | 0.10420 | 0.16101 | 0.00208 | 0 | 1 |
| 357 | chr4 | 40197000 | 40198000 | 0.000 | 0.000 | 0.015 | 0.027 | N4BP2 | 1.00000 | 1.00000 | 0.29694 | 0 | 0 |
| 358 | chr4 | 40198000 | 40199000 | 0.000 | 0.000 | 0.088 | 0.041 | N4BP2 | 0.31126 | 0.09031 | 0.00058 | 0 | 1 |
| 359 | chr4 | 40199000 | 40200000 | 0.056 | 0.000 | 0.279 | 0.162 | N4BP2 | 0.10628 | 0.00895 | 0.00000 | 0 | 1 |
| 360 | chr4 | 40200000 | 40201000 | 0.000 | 0.006 | 0.118 | 0.041 | RHOH | 0.11795 | 0.04825 | 0.00030 | 1 | 1 |
| 361 | chr4 | 40201000 | 40202000 | 0.000 | 0.000 | 0.088 | 0.041 | RHOH | 0.31126 | 0.09031 | 0.00058 | 1 | 1 |
| 362 | chr4 | 40202000 | 40203000 | 0.000 | 0.000 | 0.029 | 0.014 | RHOH | 0.60686 | 0.54294 | 0.08726 | 1 | 0 |
| 363 | chr4 | 40204000 | 40205000 | 0.000 | 0.000 | 0.029 | 0.000 | RHOH | 0.22755 | 0.54294 | 0.08726 | 1 | 0 |
| 364 | chr4 | 45308000 | 45309000 | 0.000 | 0.000 | 0.029 | 0.000 | GNPDA2 | 0.22755 | 0.54294 | 0.08726 | 0 | 0 |
| 365 | chr4 | 46360000 | 46361000 | 0.000 | 0.000 | 0.015 | 0.014 | GABRA2 | 1.00000 | 1.00000 | 0.29694 | 0 | 0 |
| 366 | chr4 | 62375000 | 62376000 | 0.000 | 0.000 | 0.029 | 0.000 | LPHN3 | 0.22755 | 0.54294 | 0.08726 | 0 | 0 |
| 367 | chr4 | 62530000 | 62531000 | 0.000 | 0.000 | 0.029 | 0.000 | LPHN3 | 0.22755 | 0.54294 | 0.08726 | 0 | 0 |
| 368 | chr4 | 62911000 | 62912000 | 0.000 | 0.000 | 0.029 | 0.000 | LPHN3 | 0.22755 | 0.54294 | 0.08726 | 0 | 0 |
| 369 | chr4 | 63120000 | 63121000 | 0.000 | 0.000 | 0.029 | 0.000 | LPHN3 | 0.22755 | 0.54294 | 0 08726 | 0 | 0 |
| 370 | chr4 | 64015000 | 64016000 | 0.000 | 0.000 | 0.029 | 0.000 | LPHN3 | 0.22755 | 0.54294 | 0.08726 | 0 | 0 |
| 371 | chr4 | 65038000 | 65039000 | 0.000 | 0.000 | 0.015 | 0.014 | TECRL | 1.00000 | 1.00000 | 0.29694 | 0 | 0 |
| 372 | chr4 | 65165000 | 65166000 | 0.000 | 0.000 | 0.015 | 0.014 | TECRL | 1.00000 | 1.00000 | 0.29694 | 0 | 0 |
| 373 | chr4 | 65966000 | 65967000 | 0.000 | 0.006 | 0.000 | 0.014 | EPHA5 | 1.00000 | 1.00000 | 1.00000 | 0 | 0 |
| 374 | chr4 | 66827000 | 66828000 | 0.000 | 0.000 | 0.029 | 0.000 | EPHA5 | 0.22755 | 0.54294 | 0.08726 | 0 | 0 |
| 375 | chr4 | 71531000 | 71532000 | 0.000 | 0.000 | 0.015 | 0.041 | IGJ | 0.62100 | 1.00000 | 0.29694 | 0 | 0 |
| 376 | chr4 | 71532000 | 71533000 | 0.000 | 0.000 | 0.000 | 0.027 | IGJ | 0.49735 | 1.00000 | 1.00000 | 0 | 0 |
| 377 | chr4 | 74456000 | 74457000 | 0.000 | 0.000 | 0.029 | 0.000 | RASSF6 | 0.22755 | 0.54294 | 0.08726 | 0 | 0 |
| 378 | chr4 | 74483000 | 74484000 | 0.000 | 0.006 | 0.015 | 0.000 | RASSF6 | 0.47887 | 1.00000 | 0.50663 | 0 | 0 |
| 379 | chr4 | 74484000 | 74485000 | 0.000 | 0.000 | 0.044 | 0.000 | RASSF6 | 0.10727 | 0.54966 | 0.02537 | 0 | 0 |
| 380 | chr4 | 74485000 | 74486000 | 0.000 | 0.000 | 0.088 | 0.000 | RASSF6 | 0.01070 | 0.09031 | 0.00058 | 0 | 1 |
| 381 | chr4 | 91886000 | 91887000 | 0.000 | 0.000 | 0.015 | 0.014 | CCSER1 | 1.00000 | 1.00000 | 0.29694 | 0 | 0 |
| 382 | chr4 | 92787000 | 92788000 | 0.000 | 0.000 | 0.029 | 0.000 | CCSER1 | 0.22755 | 0.54294 | 0.08726 | 0 | 0 |
| 383 | chr4 | 113206000 | 113207000 | 0.000 | 0.000 | 0.029 | 0.000 | TIFA | 0.22755 | 0.54294 | 0.08726 | 1 | 0 |
| 384 | chr4 | 114466000 | 114467000 | 0.000 | 0.000 | 0.029 | 0.000 | CAMK2D | 0.22755 | 0.54294 | 0.08726 | 0 | 0 |
| 385 | chr4 | 114681000 | 114682000 | 0.000 | 0.000 | 0.044 | 0.000 | CAMK2D | 0.10727 | 0.54966 | 0.02537 | 0 | 0 |
| 386 | chr4 | 117928000 | 117929000 | 0.000 | 0.000 | 0.029 | 0.000 | TRAMIL1 | 0.22755 | 0.54294 | 0.08726 | 0 | 0 |
| 387 | chr4 | 123637000 | 123638000 | 0.000 | 0.000 | 0.000 | 0.027 | BBS12 | 0.49735 | 1.00000 | 1.00000 | 0 | 0 |
| 388 | chr4 | 125227000 | 125228000 | 0.000 | 0.000 | 0.015 | 0.014 | ANKRD50 | 1.00000 | 1.00000 | 0.29694 | 0 | 0 |
| 389 | chr4 | 12737E000 | 127372000 | 0.000 | 0.000 | 0.029 | 0.000 | FAT4 | 0.22755 | 0.54294 | 0.08726 | 0 | 0 |
| 390 | chr4 | 133455000 | 133456000 | 0.000 | 0.000 | 0.000 | 0.027 | PCDH10 | 0.49735 | 1.00000 | 1.00000 | 0 | 0 |
| 391 | chr4 | 134538000 | 134539000 | 0.000 | 0.000 | 0.015 | 0.014 | PCDH10 | 1.00000 | 1.00000 | 0.29694 | 0 | 0 |
| 392 | chr4 | 134743000 | 134744000 | 0.000 | 0.000 | 0.029 | 0.000 | PABPC4L | 0.22755 | 0.54294 | 0.08726 | 0 | 0 |
| 393 | chr4 | 134867000 | 134868000 | 0.000 | 0.000 | 0.029 | 0.000 | PABPC4L | 0.22755 | 0.54294 | 0.08726 | 0 | 0 |
| 394 | chr4 | 134949000 | 134950000 | 0.000 | 0.000 | 0.029 | 0.000 | PABPC4L | 0.22755 | 0.54294 | 0.08726 | 0 | 0 |
| 395 | chr4 | 135064000 | 135065000 | 0.000 | 0.000 | 0.015 | 0.014 | PABPC4L | 1.00000 | 1.00000 | 0.29694 | 0 | 0 |
| 396 | chr4 | 135077000 | 135078000 | 0.000 | 0.000 | 0.029 | 0.000 | PABPC4L | 0.22755 | 0.54294 | 0.08726 | 0 | 0 |
| 397 | chr4 | 136799000 | 136800000 | 0.028 | 0.006 | 0.000 | 0.000 | PCDH18 | 1.00000 | 0.34615 | 1.00000 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 398 | chr4 | 136867000 | 136868000 | 0.000 | 0.000 | 0.015 | 0.014 | PCDH18 | 1.00 000 | 1.00000 | 0.29694 | 0 | 0 |
| 399 | chr4 | 140236000 | 140237000 | 0.000 | 0.000 | 0.015 | 0.014 | NAA15 | 1.00000 | 1.00000 | 0.29694 | 0 | 0 |
| 400 | chr4 | 151723000 | 151724000 | 0.000 | 0.000 | 0.029 | 0.000 | LRBA | 0.22755 | 0.54294 | 0.08726 | 0 | 0 |
| 401 | chr4 | 151950000 | 151951000 | 0.000 | 0.000 | 0.000 | 0.027 | LRBA | 0.49735 | 1.00000 | 1.00000 | 0 | 0 |
| 402 | chr4 | 152125000 | 152126000 | 0.028 | 0.000 | 0.029 | 0.000 | SH3D19 | 0.22755 | t.00000 | 0.08726 | 0 | 0 |
| 403 | chr4 | 157246000 | 157247000 | 0.000 | 0.000 | 0.015 | 0.014 | CTSO | 1.00000 | 1.00000 | 0.29694 | 0 | 0 |
| 404 | chr4 | 164532000 | 164533000 | 0.000 | 0.000 | 0.000 | 0.027 | 1-Mar-19 | 0.49735 | 1.00000 | 1.00000 | 0 | 0 |
| 405 | chr4 | 178732000 | 178733000 | 0.028 | 0.000 | 0.000 | 0.014 | AGA | 1.00000 | 0.34635 | 1.00000 | 0 | 0 |
| 406 | chr4 | 178885000 | 178886000 | 0.000 | 0.000 | 0.029 | 0.000 | AGA | 0.22755 | 0.54294 | 0.08726 | 0 | 0 |
| 407 | chr4 | 179898000 | 179899000 | 0.000 | 0.000 | 0.029 | 0.000 | AGA | 0.22755 | 0.54294 | 0.08726 | 0 | 0 |
| 408 | chr4 | 180885000 | 180886000 | 0.000 | 0.006 | 0.029 | 0.000 | TENM3 | 0.22755 | 0.54294 | 0.21304 | 0 | 0 |
| 409 | chr4 | 181554000 | 181555000 | 0.000 | 0.000 | 0.029 | 0.000 | TENM3 | 0.22755 | 0.54294 | 0.08726 | 0 | 0 |
| 410 | chr4 | 182122000 | 182123000 | 0.000 | 0.000 | 0.015 | 0.014 | TENM3 | 1.00000 | 1.00000 | 0.29694 | 0 | 0 |
| 411 | chr5 | 436000 | 437000 | 0.028 | 0.000 | 0.000 | 0.014 | AHRR | 1.00000 | 0.34615 | 1.00000 | 0 | 0 |
| 412 | chr5 | 3982000 | 3983000 | 0.000 | 0.000 | 0.029 | 0.000 | IRX1 | 0.22755 | 0.54294 | 0.08726 | 0 | 0 |
| 413 | chr5 | 17218000 | 17219000 | 0.000 | 0.000 | 0.029 | 0.000 | BASP1 | 0.22755 | 0.54294 | 0.08726 | 0 | 0 |
| 414 | chr5 | 17219000 | 17220000 | 0.000 | 0.000 | 0.029 | 0.000 | BASP1 | 0.22755 | 0.54294 | 0.08726 | 0 | 0 |
| 415 | chr5 | 18514000 | 18515000 | 0.028 | 0.000 | 0.000 | 0.014 | CDH18 | 1.00000 | 0.34615 | 1.00000 | 0 | 0 |
| 416 | chr5 | 22356000 | 22357000 | 0.000 | 0.000 | 0.029 | 0.000 | CDH12 | 0.22755 | 0.54294 | 0.08726 | 0 | 0 |
| 417 | chr5 | 22517000 | 22518000 | 0.000 | 0.000 | 0.015 | 0.014 | CDH12 | 1.00000 | 1.00000 | 0.29694 | 0 | 0 |
| 418 | chr5 | 24632000 | 24633000 | 0.000 | 0.000 | 0.029 | 0.000 | CDH10 | 0.22755 | 0.54294 | 0.08726 | 0 | 0 |
| 419 | chr5 | 25275000 | 25276000 | 0.000 | 0.000 | 0.015 | 0.014 | CDH10 | 1.00000 | 1.00000 | 0.29694 | 0 | 0 |
| 420 | chr5 | 25541000 | 25542000 | 0.000 | 0.000 | 0.029 | 0.000 | CDH10 | 0.22755 | 0.54294 | 0.08726 | 0 | 0 |
| 421 | chr5 | 26119000 | 26120000 | 0.000 | 0.000 | 0.015 | 0.014 | CDH9 | 1.00000 | 1.00000 | 0.29694 | 0 | 0 |
| 422 | chr5 | 26450000 | 26451000 | 0.000 | 0.000 | 0.029 | 0.000 | CDH9 | 0.22755 | 0.54294 | 0.08726 | 0 | 0 |
| 423 | chr5 | 29224000 | 29225000 | 0.000 | 0.000 | 0.029 | 0.000 | CDH6 | 0.22755 | 0.54294 | 0.08726 | 0 | 0 |
| 424 | chr5 | 29492000 | 29493000 | 0.000 | 0.000 | 0.029 | 0.000 | CDH6 | 0.22755 | 0 54294 | 0.08726 | 0 | 0 |
| 425 | chr5 | 29648000 | 29649000 | 0.000 | 0.000 | 0.029 | 0.000 | CDH6 | 0.22755 | 0.54294 | 0.08726 | 0 | 0 |
| 426 | chr5 | 51521000 | 51522000 | 0.000 | 0.000 | 0.044 | 0.014 | CTD-2203A3.1 | 0.34948 | 0.54966 | 0.02537 | 0 | 0 |
| 427 | chr5 | 83841000 | 83842000 | 0.000 | 0.000 | 0.029 | 0.000 | EDIL3 | 0.22755 | 0.54294 | 0.08726 | 0 | 0 |
| 428 | chr5 | 88177000 | 88178000 | 0.000 | 0.000 | 0.029 | 0.000 | MEF2C | 0.22755 | 0.54294 | 0 08726 | 0 | 0 |
| 429 | chr5 | 88178000 | 88179000 | 0.000 | 0.000 | 0.015 | 0.014 | MEF2C | 1.00000 | 1.00000 | 029694 | 0 | 0 |
| 430 | chr5 | 91417000 | 91418000 | 0.000 | 0.000 | 0.000 | 0.027 | ARRDC3 | 0.49735 | 1.00000 | 1.00000 | 0 | 0 |
| 431 | chr5 | 103678000 | 103679000 | 0.000 | 0.000 | 0.015 | 0.014 | NUDT12 | 1.00000 | 1.00000 | 0.29694 | 0 | 0 |
| 432 | chr5 | 123696000 | 123697000 | 0.000 | 0.000 | 0.000 | 0.027 | ZNF608 | 0.49735 | 1.00000 | 1.00000 | 1 | 0 |
| 433 | chr5 | 124079000 | 124080000 | 0.000 | 0.000 | 0.029 | 0.014 | ZNF608 | 0.60686 | 0.54294 | 0.08726 | 1 | 0 |
| 434 | chr5 | 124080000 | 124081000 | 0.000 | 0.000 | 0.029 | 0.014 | ZNF608 | 0.60686 | 0.54294 | 0.08726 | 1 | 0 |
| 435 | chr5 | 127594000 | 127595000 | 0.000 | 0.000 | 0.015 | 0.014 | FBN2 | 1.00000 | 1.00000 | 0.29694 | 0 | 0 |
| 436 | chr5 | 127875000 | 327876000 | 0.000 | 0.000 | 0.000 | 0.027 | FBN2 | 0.49735 | 1.00000 | 1.00000 | 0 | 0 |
| 437 | chr5 | 131825000 | 131826000 | 0.000 | 0.000 | 0.074 | 0.000 | IRF1 | 0.02326 | 0.16101 | 0.00208 | 0 | 1 |
| 438 | chr5 | 131826000 | 131827000 | 0.000 | 0.000 | 0.029 | 0.000 | IRF1 | 0.22755 | 0.54294 | 0.08726 | 0 | 0 |
| 439 | chr5 | 149791000 | 149792000 | 0.000 | 0.000 | 0.132 | 0.014 | CD74 | 0.00701 | 0.02564 | 0.00001 | 1 | 1 |
| 440 | chr5 | 149792000 | 149793000 | 0.000 | 0.000 | 0.015 | 0.014 | CD74 | 1.00000 | 1.00000 | 0.29694 | 1 | 0 |
| 441 | chr5 | 158380000 | 158381000 | 0.028 | 0.000 | 0.015 | 0.000 | EBF1 | 0.47887 | 1.00000 | 0.29694 | 0 | 0 |
| 442 | chr5 | 158479000 | 158480000 | 0.000 | 0.000 | 0.029 | 0.000 | EBF1 | 0.22755 | 0.54294 | 0.08726 | 0 | 0 |
| 443 | chr5 | 158526000 | 158527000 | 0.028 | 0.000 | 0.044 | 0.000 | EBF1 | 0.10727 | 1.00000 | 0.02537 | 0 | 0 |
| 444 | chr5 | 158527000 | 158528000 | 0.000 | 0.000 | 0.029 | 0.000 | EBF1 | 0.22755 | 0.54294 | 0.08726 | 0 | 0 |
| 445 | chr5 | 158528000 | 158529000 | 0.000 | 0.000 | 0.059 | 0.000 | EBF1 | 0.05016 | 0.29551 | 0.00730 | 0 | 1 |
| 446 | chr5 | 164247000 | 164248000 | 0.000 | 0.000 | 0.029 | 0.000 | MAT2B | 0.22755 | 0.54294 | 0.08726 | 0 | 0 |
| 447 | chr5 | 164441000 | 164442000 | 0.028 | 0.000 | 0.015 | 0.000 | MAT2B | 0.47887 | 1.00000 | 0.29694 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 448 | chr5 | 165932000 | 165933000 | 0.000 | 0.000 | 0.015 | 0.014 | TENM2 | 1.00000 | 1.00000 | 0.29694 | 0 | 0 |
| 449 | chr5 | 173300000 | 173301000 | 0.000 | 0.000 | 0.000 | 0.027 | CPEB4 | 0.49735 | 1.00000 | 1.00000 | 0 | 0 |
| 450 | chr5 | 179166000 | 179167000 | 0.000 | 0.000 | 0.015 | 0.027 | MAML1 | 1.00000 | 1.00000 | 0.29694 | 0 | 0 |
| 451 | chr5 | 180102000 | 180103000 | 0.000 | 0.000 | 0.015 | 0.014 | FLT4 | 1.00000 | 1.00000 | 0.29694 | 0 | 0 |
| 452 | chr6 | 392000 | 393000 | 0.000 | 0.000 | 0.074 | 0.000 | IRF4 | 0.02326 | 0.16101 | 0.00208 | 1 | 1 |
| 453 | chr6 | 393000 | 394000 | 0.000 | 0.000 | 0.074 | 0.000 | IRF4 | 0.02326 | 0.16101 | 0.00208 | 1 | 1 |
| 454 | chr6 | 14118000 | 14119000 | 0.000 | 0.000 | 0.279 | 0.041 | CD83 | 0.00011 | 0.00013 | 0.00000 | 1 | 1 |
| 455 | chr6 | 14119000 | 14120000 | 0.000 | 0.000 | 0.044 | 0.027 | CD83 | 0.67043 | 0.54966 | 0.02537 | 1 | 0 |
| 456 | chr6 | 18111000 | 18112000 | 0.028 | 0.000 | 0.044 | 0.000 | NHLRC1 | 0.10727 | 1.00000 | 0.02537 | 0 | 0 |
| 457 | chr6 | 18387000 | 18388000 | 0.000 | 0.000 | 0.000 | 0.027 | RNF144B | 0.49735 | 1.00000 | 1.00000 | 1 | 0 |
| 458 | chr6 | 18388000 | 18389000 | 0.000 | 0.000 | 0.000 | 0.027 | RNF144B | 0.49735 | 1.00000 | 1.00000 | 1 | 0 |
| 459 | chr6 | 19573000 | 19574000 | 0.000 | 0.000 | 0.029 | 0.000 | ID4 | 0.22755 | 0.54294 | 0.08726 | 0 | 0 |
| 460 | chr6 | 22873000 | 22874000 | 0.000 | 0.000 | 0.015 | 0.014 | HDGFL1 | 1.00000 | 1.00000 | 0.29694 | 0 | 0 |
| 461 | chr6 | 26031000 | 26032000 | 0.000 | 0.000 | 0.000 | 0.027 | HIST1H3B | 0.49735 | 1.00000 | 1.00000 | 1 | 0 |
| 462 | chr6 | 26032000 | 26033000 | 0.000 | 0.000 | 0.000 | 0.027 | HIST1H3B | 0.49735 | 1.00000 | 1.00000 | 1 | 0 |
| 463 | chr6 | 26056000 | 26057000 | 0.000 | 0.000 | 0.059 | 0.027 | HIST1H1C | 0.42627 | 0.29551 | 0.00730 | 1 | 1 |
| 464 | chr6 | 26123000 | 26124000 | 0.000 | 0.000 | 0.059 | 0.014 | HIST1H2BC | 0.19371 | 0.29551 | 0.00730 | 1 | 1 |
| 465 | chr6 | 26124000 | 26125000 | 0.000 | 0.000 | 0.074 | 0.000 | HIST1H2AC; HIST1H2BC; | 0.02326 | 0.16101 | 0.00208 | 0 | 1 |
| 466 | chr6 | 26125000 | 26126000 | 0.000 | 0.000 | 0.015 | 0.014 | HIST1H2AC | 1.00000 | 1.00000 | 0.29694 | 1 | 0 |
| 467 | chr6 | 26156000 | 26157000 | 0.000 | 0.000 | 0.074 | 0.014 | HIST1H1E | 0.10420 | 0.16101 | 0.00208 | 1 | 1 |
| 468 | chr6 | 26157000 | 26158000 | 0.000 | 0.000 | 0.029 | 0.014 | HIST1H1E | 0.60686 | 0.54294 | 0.08726 | 1 | 0 |
| 469 | chr6 | 26216000 | 26217000 | 0.000 | 0.000 | 0.029 | 0.000 | HIST1H2BG | 0.22755 | 0.54294 | 0.08726 | 1 | 0 |
| 470 | chr6 | 26234000 | 26235000 | 0.000 | 0.000 | 0.044 | 0.000 | HIST1H1D | 0.10727 | 0.54966 | 0.02537 | 0 | 0 |
| 471 | chr6 | 27101000 | 27102000 | 0.000 | 0.000 | 0.029 | 0.000 | HIST1H2AG | 0.22755 | 0.54294 | 0.08726 | 1 | 0 |
| 472 | chr6 | 27114000 | 27115000 | 0.000 | 0.000 | 0.059 | 0.014 | HIST1H2AH; HIST1H2BK: | 0.19371 | 0.29551 | 0.00730 | 0 | 1 |
| 473 | chr6 | 27792000 | 27793000 | 0.000 | 0.000 | 0.044 | 0.014 | HIST1H4J | 0.34948 | 0.54966 | 0.02537 | 0 | 0 |
| 474 | chr6 | 27833000 | 27834000 | 0.000 | 0.000 | 0.015 | 0.014 | HIST1H2AL | 1.00000 | 1.00000 | 0.29694 | 1 | 0 |
| 475 | chr6 | 27860000 | 27861000 | 0.000 | 0.000 | 0.029 | 0.027 | HIST1H2AM | 1.00000 | 0.54294 | 0.08726 | 1 | 0 |
| 476 | chr6 | 27861000 | 27862000 | 0.000 | 0.000 | 0.015 | 0.014 | HIST1H2BO | 1.00000 | 1.00000 | 0.29694 | 1 | 0 |
| 477 | chr6 | 29778000 | 29779000 | 0.028 | 0.000 | 0.000 | 0.014 | LOC554223 | 1.00000 | 0.34615 | 1.00000 | 0 | 0 |
| 478 | chr6 | 29780000 | 29781000 | 0.000 | 0.000 | 0.015 | 0.014 | HLA-G | 1.00000 | 1.00000 | 0.29694 | 0 | 0 |
| 479 | chr6 | 29911000 | 29912000 | 0.000 | 0.000 | 0.044 | 0.000 | HLA-A | 0.10727 | 0.54966 | 0.02537 | 0 | 0 |
| 480 | chr6 | 29927000 | 29928000 | 0.000 | 0.000 | 0.015 | 0.014 | HLA-A | 1.00000 | 1.00000 | 0.29694 | 0 | 0 |
| 481 | chr6 | 31324000 | 31325000 | 0.000 | 0.000 | 0.029 | 0.014 | HLA-B | 0.60686 | 0 54294 | 0.08726 | 1 | 0 |
| 482 | chr6 | 31325000 | 31326000 | 0.028 | 0.000 | 0.000 | 0.014 | HLA-B | 1.00000 | 0.34615 | 1.00000 | 1 | 0 |
| 483 | chr6 | 31543000 | 31544000 | 0.000 | 0.000 | 0.029 | 0.000 | TNF | 0.22755 | 0.54294 | 0.08726 | 1 | 0 |
| 484 | chr6 | 31549000 | 31550000 | 0.000 | 0.006 | 0.191 | 0.068 | LTB | 0.04150 | 0.00372 | 0.00000 | 1 | 1 |
| 485 | chr6 | 31550000 | 31551000 | 0.000 | 0.000 | 0.044 | 0.000 | LTB | 0.10727 | 0.54966 | 0.02537 | 1 | 0 |
| 486 | chr6 | 32440000 | 32441000 | 0.000 | 0.000 | 0.044 | 0.027 | HLA-DRA | 0.67043 | 0.54966 | 0.02537 | 0 | 0 |
| 487 | chr6 | 32451000 | 32452000 | 0.056 | 0.000 | 0.000 | 0.000 | HLA-DRB5 | 1.00000 | 0.11763 | 1.00000 | 0 | 1 |
| 488 | chr6 | 32452000 | 32453000 | 0.028 | 0.000 | 0.015 | 0.000 | HLA-DRB5 | 0.47887 | 1.00000 | 0.29694 | 0 | 0 |
| 489 | chr6 | 32455000 | 32456000 | 0.028 | 0.000 | 0.015 | 0.000 | HLA-DRB5 | 0.47887 | 1.00000 | 0.29694 | 0 | 0 |
| 490 | chr6 | 32457000 | 32458000 | 0.000 | 0.000 | 0.000 | 0.027 | HLA-DRB5 | 0.49735 | 1.00000 | 1.00000 | 0 | 0 |
| 491 | chr6 | 32498000 | 32499000 | 0.000 | 0.000 | 0.000 | 0.027 | HLA-DRB5 | 0.49735 | 1.00000 | 1.00000 | 0 | 0 |
| 492 | chr6 | 32505000 | 32506000 | 0.000 | 0.000 | 0.029 | 0.014 | HLA-DRB5 | 0.60686 | 0.54294 | 0.08726 | 0 | 0 |
| 493 | chr6 | 32511000 | 32512000 | 0.000 | 0.000 | 0.000 | 0.041 | HLA-DRB5 | 0.24603 | 1.00000 | 1.00000 | 0 | 0 |
| 494 | chr6 | 32522000 | 32523000 | 0.028 | 0.000 | 0.015 | 0.027 | HLA-DRB1 | 1.00000 | 1.00000 | 0.29694 | 0 | 0 |
| 495 | chr6 | 32525000 | 32526000 | 0.000 | 0.000 | 0.029 | 0.014 | HLA-DRB1 | 0.60686 | 0.54294 | 0.08726 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 496 | chr6 | 32526000 | 32527000 | 0.000 | 0.000 | 0.000 | 0.041 | HLA-DRB1 | 0.24603 | 1.00000 | 1.00000 | 0 | 0 |
| 497 | chr6 | 32527000 | 32528000 | 0.000 | 0.000 | 0.000 | 0.027 | HLA-DRB1 | 0.49735 | 1.00000 | 1.00000 | 0 | 0 |
| 498 | chr6 | 32548000 | 32549000 | 0.000 | 0.000 | 0.029 | 0.014 | HLA-DRB1 | 0.60686 | 0.54294 | 0.08726 | 0 | 0 |
| 499 | chr6 | 32552000 | 32553000 | 0.056 | 0.000 | 0.015 | 0.027 | HLA-DRB1 | 1.00000 | 0.27446 | 0.29694 | 0 | 1 |
| 500 | chr6 | 32557000 | 32558000 | 0.028 | 0.000 | 0.000 | 0.041 | HLA-DRB1 | 0.24603 | 0.34615 | 1.00000 | 0 | 0 |
| 501 | chr6 | 32609000 | 32610000 | 0.028 | 0.000 | 0.059 | 0.014 | HLA-DQA1 | 0.19371 | 0.65667 | 0.00730 | 0 | 1 |
| 502 | chr6 | 32630000 | 32631000 | 0.000 | 0.000 | 0.015 | 0.014 | HLA-DQB1 | 1.00000 | 1.00000 | 0.29694 | 0 | 0 |
| 503 | chr6 | 32632000 | 32633000 | 0.111 | 0.000 | 0.029 | 0.027 | HLA-DQB1 | 1.00000 | 0.17874 | 0.08726 | 0 | 1 |
| 504 | chr6 | 32727000 | 32728000 | 0.056 | 0.000 | 0.015 | 0.000 | HLA-DQB2 | 0.47887 | 0.27446 | 0.29694 | 0 | 1 |
| 505 | chr6 | 32729000 | 32730000 | 0.056 | 0.000 | 0.029 | 0.014 | HLA-DQB2 | 0.60686 | 0.60763 | 0.08726 | 0 | 1 |
| 506 | chr6 | 33048000 | 33049000 | 0.000 | 0.000 | 0.015 | 0.014 | HLA-DPB1 | 1.00000 | 1.00000 | 0.29694 | 0 | 0 |
| 507 | chr6 | 34179000 | 34180000 | 0.000 | 0.000 | 0.029 | 0.000 | HMGA1 | 0.22755 | 0.54294 | 0.08726 | 0 | 0 |
| 508 | chr6 | 37138000 | 37139000 | 0.000 | 0.000 | 0.191 | 0.081 | PIM1 | 0.08249 | 0.00372 | 0.00000 | 1 | 1 |
| 509 | chr6 | 37139000 | 37140000 | 0.000 | 0.000 | 0.088 | 0.041 | PIM1 | 0.31126 | 0.09031 | 0.00058 | 1 | 1 |
| 510 | chr6 | 37140000 | 37141000 | 0.000 | 0.000 | 0.029 | 0.014 | PIM1 | 0.60686 | 0.54294 | 0.08726 | 1 | 0 |
| 511 | chr6 | 58001000 | 58002000 | 0.000 | 0.000 | 0.015 | 0.014 | PRIM2 | 1.00000 | 1.00000 | 0.29694 | 0 | 0 |
| 512 | chr6 | 67923000 | 67924000 | 0.000 | 0.000 | 0.015 | 0.014 | BAI3 | 1.00000 | 1.00000 | 0.29694 | 0 | 0 |
| 513 | chr6 | 77256000 | 77257000 | 0.000 | 0.000 | 0.029 | 0.000 | IMPG1 | 0.22755 | 0.54294 | 0.08726 | 0 | 0 |
| 514 | chr6 | 81437000 | 81438000 | 0.000 | 0.000 | 0.015 | 0.014 | BCKDHB | 1.00000 | 1.00000 | 0.29694 | 0 | 0 |
| 515 | chr6 | 88468000 | 88469000 | 0.000 | 0.000 | 0.015 | 0.014 | AKIRIN2 | 1.00000 | 1.00000 | 0.29694 | 0 | 0 |
| 516 | chr6 | 88630000 | 88631000 | 0.000 | 0.000 | 0.044 | 0.014 | SPACA1 | 0.34948 | 0.54966 | 0.02537 | 0 | 0 |
| 517 | chr6 | 88876000 | 88877000 | 0.028 | 0.000 | 0.015 | 0.000 | CNR1 | 0.47887 | 1.00000 | 0.29694 | 0 | 0 |
| 518 | chr6 | 89323000 | 89324000 | 0.000 | 0.000 | 0.029 | 0.014 | RNGTT | 0.60686 | 0.54294 | 0.08726 | 0 | 0 |
| 519 | chr6 | 89338000 | 89339000 | 0.000 | 0.000 | 0.029 | 0.000 | RNGTT | 0.22755 | 0.54294 | 0.08726 | 0 | 0 |
| 520 | chr6 | 89348000 | 89349000 | 0.000 | 0.000 | 0.044 | 0.000 | RNGTT | 0.10727 | 0.54966 | 0.02537 | 0 | 0 |
| 521 | chr6 | 89470000 | 89471000 | 0.000 | 0.000 | 0.029 | 0.000 | RNGTT | 0.22755 | 0.54294 | 0.08726 | 0 | 0 |
| 522 | chr6 | 89471000 | 89472000 | 0.000 | 0.000 | 0.029 | 0.000 | RNGTT | 0.22755 | 0.54294 | 0.08726 | 0 | 0 |
| 523 | chr6 | 90061000 | 90062000 | 0.000 | 0.000 | 0.059 | 0.000 | UBE2J1 | 0.05016 | 0.29551 | 0.00730 | 1 | 1 |
| 524 | chr6 | 90062000 | 90063000 | 0.000 | 0.000 | 0.029 | 0.000 | UBE2J1 | 0.22755 | 0 54294 | 0.08726 | 1 | 0 |
| 525 | chr6 | 90994000 | 90995000 | 0.000 | 0.000 | 0.029 | 0.014 | MAP3K7 | 0.60686 | 0.54294 | 0.08726 | 0 | 0 |
| 526 | chr6 | 91004000 | 91005000 | 0.000 | 0.000 | 0.059 | 0.014 | MAP3K7 | 0.19371 | 0.29551 | 0.00730 | 0 | 1 |
| 527 | chr6 | 91005000 | 91006000 | 0.000 | 0.019 | 0.294 | 0.095 | MAP3K7 | 0.00279 | 0.00011 | 0.00000 | 0 | 1 |
| 528 | chr6 | 91006000 | 91007000 | 0.000 | 0.006 | 0.118 | 0.027 | MAP3K7 | 004838 | 0.04825 | 0.00030 | 0 | 1 |
| 529 | chr6 | 91007000 | 91008000 | 0.000 | 0.012 | 0.029 | 0.000 | MAP3K7 | 0.22755 | 0.54294 | 0.58408 | 0 | 0 |
| 530 | chr6 | 94822000 | 94823000 | 0.028 | 0.000 | 0.015 | 0.000 | EPHA7 | 0.47887 | 1.00000 | 0.29694 | 0 | 0 |
| 531 | chr6 | 107704000 | 107705000 | 0.028 | 0.000 | 0.000 | 0.014 | PDSS2 | 1.00000 | 0.34615 | 1.00000 | 0 | 0 |
| 532 | chr6 | 112885000 | 112886000 | 0.000 | 0.000 | 0.015 | 0.014 | RFPL4B | 1.00000 | 1 00000 | 0.29694 | 0 | 0 |
| 533 | chr6 | 118244000 | 118245000 | 0.000 | 0.000 | 0.015 | 0.014 | SLC35F1 | 1.00000 | 1.00000 | 0.29694 | 0 | 0 |
| 534 | chr6 | 121288000 | 121289000 | 0.000 | 0.000 | 0.000 | 0.027 | C6orf170 | 0.49735 | 1.00000 | 1.00000 | 0 | 0 |
| 535 | chr6 | 121489000 | 121490000 | 0.000 | 0.000 | 0.029 | 0.000 | C6orf170 | 0.22755 | 0.54294 | 0.08726 | 0 | 0 |
| 536 | chr6 | 123504000 | 123505000 | 0.000 | 0.006 | 0.015 | 0.000 | TRDN | 0.47887 | 1.00000 | 0.50663 | 0 | 0 |
| 537 | chr6 | 127313000 | 127314000 | 0.000 | 0.006 | 0.015 | 0.000 | RSPO3 | 0.47887 | 1.00000 | 0.50663 | 0 | 0 |
| 538 | chr6 | 133785000 | 133786000 | 0.000 | 0.000 | 0.029 | 0.000 | EYA4 | 0.22755 | 0.54294 | 0.08726 | 0 | 0 |
| 539 | chr6 | 134491000 | 134492000 | 0.000 | 0.000 | 0.029 | 0.000 | SGK1 | 0.22755 | 0.54294 | 0.08726 | 1 | 0 |
| 540 | chr6 | 134492000 | 134493000 | 0.000 | 0.000 | 0.044 | 0.014 | SGK1 | 0.34948 | 0.54966 | 0.02537 | 1 | 0 |
| 541 | chr6 | 134493000 | 134494000 | 0.000 | 0.000 | 0.029 | 0.000 | SGK1 | 0.22755 | 0.54294 | 0.08726 | 1 | 0 |
| 542 | chr6 | 134494000 | 134495000 | 0.000 | 0.000 | 0.029 | 0.000 | SGK1 | 0.22755 | 0.54294 | 0.08726 | 1 | 0 |
| 543 | chr6 | 134495000 | 134496000 | 0.000 | 0.000 | 0.162 | 0.041 | SGK1 | 0.02233 | 0.01471 | 0.00000 | 1 | 1 |
| 544 | chr6 | 134496000 | 134497000 | 0.000 | 0.000 | 0.029 | 0.000 | SGK1 | 0.22755 | 0.54294 | 0.08726 | 1 | 0 |
| 545 | chr6 | 142046000 | 142047000 | 0.000 | 0.000 | 0.059 | 0.000 | NMBR | 0.05016 | 0.29551 | 0.00730 | 0 | 1 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 546 | chr6 | 147860000 | 147861000 | 0.028 | 0.000 | 0.015 | 0.000 | SAMD5 | 0.47887 | 1.00000 | 0.29694 | 0 | 0 |
| 547 | chr6 | 150954000 | 150955000 | 0.000 | 0.000 | 0.044 | 0.014 | PLEKHG1 | 0.34948 | 0.54966 | 0.02537 | 0 | 0 |
| 548 | chr6 | 159238000 | 159239000 | 0.000 | 0.012 | 0.044 | 0.014 | EZR | 0.34948 | 0.54966 | 0.15671 | 0 | 0 |
| 549 | chr6 | 159239000 | 159240000 | 0.000 | 0.000 | 0.029 | 0.014 | EZR | 0.60686 | 0.54294 | 0.08726 | 0 | 0 |
| 550 | chr6 | 159240000 | 159241000 | 0.000 | 0.000 | 0.029 | 0.014 | EZR | 0.60686 | 0.54294 | 0.08726 | 0 | 0 |
| 551 | chr6 | 159464000 | 159465000 | 0.000 | 0.000 | 0.015 | 0.014 | TAGAP | 1.00000 | 1.00000 | 0.29694 | 0 | 0 |
| 552 | chr6 | 159465000 | 159466000 | 0.000 | 0.000 | 0.029 | 0.000 | TAGAP | 0.22755 | 0.54294 | 0.08726 | 0 | 0 |
| 553 | chr6 | 161265000 | 161266000 | 0.028 | 0.000 | 0.000 | 0.027 | PLG | 0.49735 | 0.34615 | 1.00000 | 0 | 0 |
| 554 | chr6 | 161833000 | 161834000 | 0.028 | 0.000 | 0.000 | 0.027 | PARK2 | 0.49735 | 0.34615 | 1.00000 | 0 | 0 |
| 555 | chr6 | 162712000 | 162713000 | 0.000 | 0.000 | 0.029 | 0.000 | PARK2 | 0.22755 | 0.54294 | 0.08726 | 0 | 0 |
| 556 | chr6 | 164941000 | 164942000 | 0.000 | 0.000 | 0.029 | 0.000 | C6orf118 | 0.22755 | 0.54294 | 0.08726 | 0 | 0 |
| 557 | chr6 | 168813000 | 168814000 | 0.028 | 0.000 | 0.015 | 0.000 | SMOC2 | 0.47887 | 1.00000 | 0.29694 | 0 | 0 |
| 558 | chr7 | 1898000 | 1899000 | 0.000 | 0.000 | 0.029 | 0.000 | AC110781.3 | 0.22755 | 0.54294 | 0.08726 | 0 | 0 |
| 559 | chr7 | 1963000 | 1964000 | 0.028 | 0.000 | 0.015 | 0.000 | MAD1L1 | 0.47887 | 1.00000 | 0.29694 | 0 | 0 |
| 560 | chr7 | 2080000 | 2081000 | 0.000 | 0.000 | 0.015 | 0.014 | MAD1L1 | 1.00000 | 1.00000 | 0.29694 | 0 | 0 |
| 561 | chr7 | 5568000 | 5569000 | 0.000 | 0.000 | 0.059 | 0.014 | ACTB | 0.19371 | 0.29551 | 0.00730 | 1 | 1 |
| 562 | chr7 | 5569000 | 5570000 | 0.000 | 0.000 | 0.059 | 0.014 | ACTB | 0.19371 | 0.29551 | 0.00730 | 1 | 1 |
| 563 | chr7 | 5570000 | 5571000 | 0.000 | 0.000 | 0.015 | 0.027 | ACTB | 1.00000 | 1.00000 | 0.29694 | 1 | 0 |
| 564 | chr7 | 9933000 | 9934000 | 0.000 | 0.000 | 0.029 | 0.014 | NDUFA4 | 0.60686 | 0.54294 | 0.08726 | 0 | 0 |
| 565 | chr7 | 13017000 | 13018000 | 0.028 | 0.000 | 0.015 | 0.000 | ARL4A | 0.47887 | 1.00000 | 0.29694 | 0 | 0 |
| 566 | chr7 | 13346000 | 13347000 | 0.000 | 0.000 | 0.000 | 0.027 | ETV1 | 0.49735 | 1.00000 | 1.00000 | 0 | 0 |
| 567 | chr7 | 15459000 | 15460000 | 0.000 | 0.000 | 0.000 | 0.027 | AGMO | 0.49735 | 1.00000 | 1.00000 | 0 | 0 |
| 568 | chr7 | 16382000 | 16383000 | 0.000 | 0.000 | 0.015 | 0.014 | ISPD | 1.00000 | 1.00000 | 0.29694 | 0 | 0 |
| 569 | chr7 | 28600000 | 28601000 | 0.028 | 0.000 | 0.015 | 0.000 | CREB5 | 0.47887 | 1.00000 | 0.29694 | 0 | 0 |
| 570 | chr7 | 40846000 | 40847000 | 0.000 | 0.000 | 0.015 | 0.041 | C7orf10 | 0.62100 | 1.00000 | 0.29694 | 0 | 0 |
| 571 | chr7 | 50349000 | 50350000 | 0.000 | 0.000 | 0.059 | 0.014 | IKZF1 | 0.19371 | 0.29551 | 0.00730 | 0 | 1 |
| 572 | chr7 | 50350000 | 50351000 | 0.000 | 0.000 | 0.044 | 0.000 | IKZF1 | 0.10727 | 0.54966 | 0.02537 | 0 | 0 |
| 573 | chr7 | 53335000 | 53336000 | 0.000 | 0.000 | 0.000 | 0.027 | POM121L12 | 0.49735 | 1.00000 | 1.00000 | 0 | 0 |
| 574 | chr7 | 57713000 | 57714000 | 0.000 | 0.000 | 0.029 | 0.000 | ZNF716 | 0.22755 | 0.54294 | 0.08726 | 0 | 0 |
| 575 | chr7 | 62475000 | 62476000 | 0.000 | 0.000 | 0.015 | 0.027 | AC006455.1 | 1.00000 | 1.00000 | 0.29694 | 0 | 0 |
| 576 | chr7 | 70669000 | 70670000 | 0.000 | 0.000 | 0.029 | 0.000 | WBSCR17 | 0.22755 | 0.54294 | 0.08726 | 0 | 0 |
| 577 | chr7 | 71553000 | 71554000 | 0.000 | 0.000 | 0.015 | 0.014 | CALN1 | 1.00000 | 1.00000 | 0.29694 | 0 | 0 |
| 578 | chr7 | 79847000 | 79848000 | 0.000 | 0.000 | 0.015 | 0.014 | GNAI1 | 1.00000 | 1.00000 | 0.29694 | 0 | 0 |
| 579 | chr7 | 80694000 | 80695000 | 0.000 | 0.000 | 0.029 | 0.000 | AC005008.2 | 0.22755 | 0.54294 | 0.08726 | 0 | 0 |
| 580 | chr7 | 81556000 | 81557000 | 0.000 | 0.000 | 0.000 | 0.027 | CACNA2D1 | 0.49735 | 1.00000 | 1.00000 | 0 | 0 |
| 581 | chr7 | 84127000 | 84128000 | 0.028 | 0.000 | 0.015 | 0.000 | SEMA3A | 0.47887 | 1.00000 | 0.29694 | 0 | 0 |
| 582 | chr7 | 84247000 | 84248000 | 0.000 | 0.000 | 0.029 | 0.000 | SEMA3D | 0.22755 | 0.54294 | 0.08726 | 0 | 0 |
| 583 | chr7 | 84257000 | 84258000 | 0.028 | 0.000 | 0.015 | 0.000 | SEMA3D | 0.47887 | 1.00000 | 0.29694 | 0 | 0 |
| 584 | chr7 | 86914000 | 86915000 | 0.000 | 0.000 | 0.015 | 0.014 | CROT | 1.00000 | 1.00000 | 0.29694 | 0 | 0 |
| 585 | chr7 | 90356000 | 90357000 | 0.000 | 0.000 | 0.029 | 0.000 | CDK14 | 0.22755 | 0.54294 | 0.08726 | 0 | 0 |
| 586 | chr7 | 93304000 | 93305000 | 0.000 | 0.000 | 0.029 | 0.000 | CALCR | 0.22755 | 0.54294 | 0.08726 | 0 | 0 |
| 587 | chr7 | 93682000 | 93683000 | 0.000 | 0.000 | 0.015 | 0.014 | BET1 | 1.00000 | 1.00000 | 0.29694 | 0 | 0 |
| 588 | chr7 | 102644000 | 102645000 | 0.028 | 0.000 | 0.000 | 0.014 | FBXL13 | 1.00000 | 0.34615 | 1.00000 | 0 | 0 |
| 589 | chr7 | 105699000 | 105700000 | 0.000 | 0.000 | 0.015 | 0.027 | CDHR3 | 1.00000 | 1.00000 | 0.29694 | 0 | 0 |
| 590 | chr7 | 110521000 | 110522000 | 0.000 | 0.000 | 0.029 | 0.000 | IMMP2L | 0.22755 | 0.54294 | 0.08726 | 0 | 0 |
| 591 | chr7 | 110543000 | 110544000 | 0.000 | 0.000 | 0.029 | 0.000 | IMMP2L | 0.22755 | 0.54294 | 0.08726 | 0 | 0 |
| 592 | chr7 | 110545000 | 110546000 | 0.000 | 0.000 | 0.015 | 0.014 | IMMP2L | 1.00000 | 1.00000 | 0.29694 | 0 | 0 |
| 593 | chr7 | 110597000 | 110598000 | 0.000 | 0.000 | 0.015 | 0.014 | IMMP2L | 1.00000 | 1.00000 | 0.29694 | 0 | 0 |
| 594 | chr7 | 110601000 | 110602000 | 0.000 | 0.000 | 0.029 | 0.000 | IMMP2L | 0.22755 | 0.54294 | 0.08726 | 0 | 0 |
| 595 | chr7 | 110602000 | 110603000 | 0.000 | 0.000 | 0.029 | 0.000 | IMMP2L | 0.22755 | 0.54294 | 0.08726 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 596 | chr7 | 110609000 | 110610000 | 0.000 | 0.000 | 0.029 | 0.000 | IMMP2L | 0.22755 | 0.54294 | 0.08726 | 0 | 0 |
| 597 | chr7 | 110610000 | 110611000 | 0.000 | 0.000 | 0.044 | 0.000 | IMMP2L | 0.10727 | 0.54966 | 0.02537 | 0 | 0 |
| 598 | chr7 | 110617000 | 110618000 | 0.000 | 0.000 | 0.029 | 0.000 | IMMP2L | 0.22755 | 0.54294 | 0.08726 | 0 | 0 |
| 599 | chr7 | 110618000 | 110619000 | 0.000 | 0.000 | 0.044 | 0.000 | IMMP2L | 0.10727 | 0.54966 | 0.02537 | 0 | 0 |
| 600 | chr7 | 110619000 | 110620000 | 0.000 | 0.000 | 0.029 | 0.000 | IMMP2L | 0.22755 | 0.54294 | 0.08726 | 0 | 0 |
| 601 | chr7 | 110621000 | 110622000 | 0.000 | 0.000 | 0.029 | 0.000 | IMMP2L | 0.22755 | 0.54294 | 0.08726 | 0 | 0 |
| 602 | chr7 | 110628000 | 110629000 | 0.000 | 0.000 | 0.029 | 0.000 | IMMP2L | 0.22755 | 0.54294 | 0.08726 | 0 | 0 |
| 603 | chr7 | 110629000 | 110630000 | 0.000 | 0.000 | 0.015 | 0.027 | IMMP2L | 1.00000 | 1.00000 | 0.29694 | 0 | 0 |
| 604 | chr7 | 110631000 | 110632000 | 0.000 | 0.000 | 0.044 | 0.000 | IMMP2L | 0.10727 | 0.54966 | 0.02537 | 0 | 0 |
| 605 | chr7 | 110632000 | 110633000 | 0.000 | 0.000 | 0.029 | 0.014 | IMMP2L | 0.60686 | 0.54294 | 0.08726 | 0 | 0 |
| 606 | chr7 | 110636000 | 110637000 | 0.000 | 0.000 | 0.029 | 0.014 | IMMP2L | 0.60686 | 0.54294 | 0.08726 | 0 | 0 |
| 607 | chr7 | 110637000 | 110638000 | 0.000 | 0.000 | 0.029 | 0.014 | IMMP2L | 0.60686 | 0.54294 | 0.08726 | 0 | 0 |
| 608 | chr7 | 110638000 | 110639000 | 0.000 | 0.000 | 0.029 | 0.027 | IMMP2L | 1.00000 | 0.54294 | 0.08726 | 0 | 0 |
| 609 | chr7 | 110639000 | 110640000 | 0.000 | 0.000 | 0.044 | 0.000 | IMMP2L | 0.10727 | 0.54966 | 0.02537 | 0 | 0 |
| 610 | chr7 | 110641000 | 110642000 | 0.000 | 0.000 | 0.029 | 0.000 | IMMP2L | 0.22755 | 0.54294 | 0.08726 | 0 | 0 |
| 611 | chr7 | 110650000 | 110651000 | 0.000 | 0.000 | 0.029 | 0.000 | IMMP2L | 0.22755 | 0.54294 | 0.08726 | 0 | 0 |
| 612 | chr7 | 110651000 | 110652000 | 0.000 | 0.000 | 0.029 | 0.014 | IMMP2L | 0.60686 | 0.54294 | 0.08726 | 0 | 0 |
| 613 | chr7 | 110666000 | 110667000 | 0.000 | 0.006 | 0.000 | 0.027 | IMMP2L | 0.49735 | 1.00000 | 1.00000 | 0 | 0 |
| 614 | chr7 | 110671000 | 110672000 | 0.000 | 0.000 | 0.029 | 0.000 | IMMP2L | 0.22755 | 0.54294 | 0.08726 | 0 | 0 |
| 615 | chr7 | 110677000 | 110678000 | 0.000 | 0.000 | 0.029 | 0.014 | IMMP2L | 0.60686 | 0.54294 | 0.08726 | 0 | 0 |
| 616 | chr7 | 110679000 | 110680000 | 0.000 | 0.000 | 0.029 | 0.000 | IMMP2L | 0.22755 | 0.54294 | 0.08726 | 0 | 0 |
| 617 | chr7 | 110680000 | 110681000 | 0.000 | 0.000 | 0.074 | 0.000 | IMMP2L | 0.02326 | 0.16101 | 0.00208 | 0 | 1 |
| 618 | chr7 | 110685000 | 110686000 | 0.000 | 0.000 | 0.029 | 0.000 | LRRN3 | 0.22755 | 0.54294 | 0.08726 | 0 | 0 |
| 619 | chr7 | 110686000 | 110687000 | 0.028 | 0.000 | 0.044 | 0.027 | LRRN3 | 0.67043 | 1.00000 | 0.02537 | 0 | 0 |
| 620 | chr7 | 110688000 | 110689000 | 0.000 | 0.000 | 0.029 | 0.000 | LRRN3 | 0.22755 | 0.54294 | 0.08726 | 0 | 0 |
| 621 | chr7 | 110699000 | 110700000 | 0.000 | 0.000 | 0.059 | 0.000 | LRRN3 | 0.05016 | 0.29551 | 0.00730 | 0 | 1 |
| 622 | chr7 | 110700000 | 110701000 | 0.000 | 0.000 | 0.029 | 0.000 | LRRN3 | 0.22755 | 0.54294 | 0.08726 | 0 | 0 |
| 623 | chr7 | 110709000 | 110710000 | 0.000 | 0.000 | 0.029 | 0.000 | LRRN3 | 0.22755 | 0.54294 | 0.08726 | 0 | 0 |
| 624 | chr7 | 110711000 | 110712000 | 0.000 | 0.000 | 0.044 | 0.000 | LRRN3 | 0.10727 | 0.54966 | 0.02537 | 0 | 0 |
| 625 | chr7 | 110714000 | 110715000 | 0.000 | 0.000 | 0.015 | 0.014 | LRRN3 | 1.00000 | 1.00000 | 0.29694 | 0 | 0 |
| 626 | chr7 | 110727000 | 110728000 | 0.000 | 0.000 | 0.029 | 0.000 | LRRN3 | 0.22755 | 0.54294 | 0.08726 | 0 | 0 |
| 627 | chr7 | 110728000 | 110729000 | 0.000 | 0.000 | 0.015 | 0.014 | LRRN3 | 1.00000 | 1.00000 | 0.29694 | 0 | 0 |
| 628 | chr7 | 110729000 | 110730000 | 0.000 | 0.000 | 0.029 | 0.014 | LRRN3 | 0.60686 | 0.54294 | 0.08726 | 0 | 0 |
| 629 | chr7 | 110734000 | 110735000 | 0.000 | 0.000 | 0.015 | 0.014 | LRRN3 | 1.00000 | 1.00000 | 0.29694 | 0 | 0 |
| 630 | chr7 | 110737000 | 110738000 | 0.000 | 0.000 | 0.015 | 0.027 | LRRN3 | 1.00000 | 1.00000 | 0.29694 | 0 | 0 |
| 631 | chr7 | 110740000 | 110741000 | 0.000 | 0.000 | 0.029 | 0.027 | LRRN3 | 1.00000 | 0.54294 | 0.08726 | 0 | 0 |
| 632 | chr7 | 110744000 | 110745000 | 0.000 | 0.000 | 0.029 | 0.000 | LRRN3 | 0.22755 | 0.54294 | 0.08726 | 0 | 0 |
| 633 | chr7 | 110746000 | 110747000 | 0.000 | 0.000 | 0.029 | 0.014 | LRRN3 | 0.60686 | 0.54294 | 0.08726 | 0 | 0 |
| 634 | chr7 | 110747000 | 110748000 | 0.000 | 0.000 | 0.029 | 0.000 | LRRN3 | 0.22755 | 0.54294 | 0.08726 | 0 | 0 |
| 635 | chr7 | 110748000 | 110749000 | 0.000 | 0.000 | 0.029 | 0.000 | LRRN3 | 0.22755 | 0.54294 | 0.08726 | 0 | 0 |
| 636 | chr7 | 110755000 | 110756000 | 0.000 | 0.000 | 0.044 | 0.000 | LRRN3 | 0.10727 | 0.54966 | 0.02537 | 0 | 0 |
| 637 | chr7 | 110764000 | 110765000 | 0.000 | 0.000 | 0.029 | 0.000 | LRRN3 | 0.22755 | 0.54294 | 0.08726 | 0 | 0 |
| 638 | chr7 | 110767000 | 110768000 | 0.000 | 0.000 | 0.029 | 0.014 | LRRN3 | 0.60686 | 0.54294 | 008726 | 0 | 0 |
| 639 | chr7 | 110769000 | 110770000 | 0.000 | 0.000 | 0.044 | 0.000 | LRRN3 | 0.10727 | 0.54966 | 0.02537 | 0 | 0 |
| 640 | chr7 | 110771000 | 110772000 | 0.000 | 0.000 | 0.029 | 0.014 | LRRN3 | 0.60686 | 0.54294 | 0.08726 | 0 | 0 |
| 641 | chr7 | 110779000 | 110780000 | 0.000 | 0.000 | 0.015 | 0.027 | LRRN3 | 1.00000 | 1.00000 | 0.29694 | 0 | 0 |
| 642 | chr7 | 110780000 | 110781000 | 0.000 | 0.000 | 0.029 | 0.000 | LRRN3 | 0.22755 | 0.54294 | 0.08726 | 0 | 0 |
| 643 | chr7 | 110783000 | 110784000 | 0.000 | 0.000 | 0.044 | 0.000 | LRRN3 | 0.10727 | 0.54966 | 0.02537 | 0 | 0 |
| 644 | chr7 | 110785000 | 110786000 | 0.000 | 0.000 | 0.029 | 0.000 | LRRN3 | 0.22755 | 0.54294 | 0.08726 | 0 | 0 |
| 645 | chr7 | 110801000 | 110802000 | 0.000 | 0.000 | 0.015 | 0.027 | LRRN3 | 1.00000 | 1.00000 | 0.29694 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 646 | chr7 | 110802000 | 110803000 | 0.000 | 0.000 | 0.029 | 0.000 | LRRN3 | 0.22755 | 0.54294 | 0.08726 | 0 | 0 |
| 647 | chr7 | 110810000 | 110811000 | 0.000 | 0.000 | 0.029 | 0.000 | LRRN3 | 0.22755 | 0.54294 | 0.08726 | 0 | 0 |
| 648 | chr7 | 110816000 | 110817000 | 0.000 | 0.000 | 0.044 | 0.000 | LRRN3 | 0.10727 | 0.54966 | 0.02537 | 0 | 0 |
| 649 | chr7 | 110821000 | 110822000 | 0.000 | 0.000 | 0.029 | 0.000 | LRRN3 | 0.22755 | 0.54294 | 0.08726 | 0 | 0 |
| 650 | chr7 | 110824000 | 110825000 | 0.000 | 0.000 | 0.029 | 0.000 | LRRN3 | 0.22755 | 0.54294 | 0.08726 | 0 | 0 |
| 651 | chr7 | 110827000 | 110828000 | 0.000 | 0.000 | 0.015 | 0.014 | LRRN3 | 1.00000 | 1.00000 | 0.29694 | 0 | 0 |
| 652 | chr7 | 110836000 | 110837000 | 0.000 | 0.000 | 0.044 | 0.000 | LRRN3 | 0.10727 | 0.54966 | 0.02537 | 0 | 0 |
| 653 | chr7 | 110847000 | 110848000 | 0.000 | 0.000 | 0.029 | 0.000 | LRRN3 | 0.22755 | 0.54294 | 0.08726 | 0 | 0 |
| 654 | chr7 | 111567000 | 111568000 | 0.028 | 0.000 | 0.000 | 0.014 | DOCK4 | 1.00000 | 0.34615 | 1.00000 | 0 | 0 |
| 655 | chr7 | 119056000 | 119057000 | 0.000 | 0.000 | 0.015 | 0.014 | KCND2 | 1.00000 | 1.00000 | 0.29694 | 0 | 0 |
| 656 | chr7 | 121380000 | 121381000 | 0.000 | 0.006 | 0.015 | 0.014 | PTPR21 | 1.00900 | 1.00000 | 0.50663 | 0 | 0 |
| 657 | chr7 | 123887000 | 123888000 | 0.000 | 0.000 | 0.029 | 0.000 | TMEM229A | 0.22755 | 0.54294 | 0.08726 | 0 | 0 |
| 658 | chr7 | 125262000 | 125263000 | 0.000 | 0.000 | 0.015 | 0.014 | POT1 | 1.00000 | 1.00000 | 0.29694 | 0 | 0 |
| 659 | chr7 | 145723000 | 145724000 | 0.000 | 0.000 | 0.029 | 0.000 | CNTNAP2 | 0.22755 | 0.54294 | 0.08726 | 0 | 0 |
| 660 | chr7 | 148508000 | 148509000 | 0.000 | 0.000 | 0.000 | 0.041 | EZH2 | 0.24603 | 1.00000 | 1.00000 | 0 | 0 |
| 661 | chr7 | 155127000 | 155128000 | 0.000 | 0.000 | 0.000 | 0.027 | BLACE | 0.49735 | 1.00000 | 1.00000 | 0 | 0 |
| 662 | chr7 | 157162000 | 157163000 | 0.056 | 0.000 | 0.000 | 0.000 | DNAJB6 | t.00000 | 0.11763 | 1.00000 | 0 | 1 |
| 663 | chr7 | 158684000 | 158685000 | 0.000 | 0.000 | 0.015 | 0.014 | WDR60 | 1.00000 | 1.00000 | 0.29694 | 0 | 0 |
| 664 | chr8 | 1646000 | 1647000 | 0.000 | 0.000 | 0.015 | 0.027 | DLGAP2 | 1.00000 | 1.00000 | 0.29694 | 0 | 0 |
| 665 | chr8 | 5558000 | 5559000 | 0.000 | 0.000 | 0.029 | 0.000 | MCPH1 | 0.22755 | 0.54294 | 0.08726 | 0 | 0 |
| 666 | chr8 | 5612000 | 5613000 | 0.000 | 0.000 | 0.000 | 0.027 | MCPH1 | 0.49735 | t.00000 | 1.00000 | 0 | 0 |
| 667 | chr8 | 8602000 | 8603000 | 0.000 | 0.000 | 0.029 | 0.014 | MFHAS1 | 0.60686 | 0.54294 | 0.08726 | 0 | 0 |
| 668 | chr8 | 8706000 | 8707000 | 0.000 | 0.000 | 0.029 | 0.000 | MFHAS1 | 0.22755 | 0.54294 | 0.08726 | 0 | 0 |
| 669 | chr8 | 8717000 | 8718000 | 0.000 | 0.000 | 0.029 | 0.000 | MFHAS1 | 0.22755 | 0.54294 | 0.08726 | 0 | 0 |
| 670 | chr8 | 11352000 | 11353000 | 0.000 | 0.000 | 0.029 | 0.014 | BLK | 0.60686 | 0.54294 | 0.08726 | 0 | 0 |
| 671 | chr8 | 14080000 | 14081000 | 0.000 | 0.000 | 0.015 | 0.014 | SGCZ | 1.00000 | 1.00000 | 0.29694 | 0 | 0 |
| 672 | chr8 | 14796000 | 14797000 | 0.000 | 0.006 | 0.015 | 0.000 | SGCZ | 0.47887 | 1.00000 | 0.50663 | 0 | 0 |
| 673 | chr8 | 16090000 | 16091000 | 0.000 | 0.000 | 0.015 | 0.014 | MSR1 | 1.00000 | 1.00000 | 0 29694 | 0 | 0 |
| 674 | chr8 | 16187000 | 16188000 | 0.028 | 0.000 | 0.015 | 0.000 | MSR1 | 0.47887 | 1.00000 | 0.29694 | 0 | 0 |
| 675 | chr8 | 23101000 | 23102000 | 0.000 | 0.000 | 0.015 | 0.014 | CHMP7 | 1.00000 | 1.00000 | 0.29694 | 0 | 0 |
| 676 | chr8 | 24207000 | 24208000 | 0.000 | 0.000 | 0.029 | 0.000 | ADAM28 | 0.22755 | 0.54294 | 0.08726 | 0 | 0 |
| 677 | chr8 | 29155000 | 29156000 | 0.028 | 0.000 | 0.000 | 0.014 | KIF13B | 1.00000 | 0.34615 | 1.00000 | 0 | 0 |
| 678 | chr8 | 35657000 | 35658000 | 0.000 | 0.000 | 0.029 | 0.000 | AC012215.1 | 0.22755 | 0.54294 | 0.08726 | 0 | 0 |
| 679 | chr8 | 38759000 | 38760000 | 0.000 | 0.000 | 0.029 | 0.000 | PLEKHA2 | 0.22755 | 0.54294 | 0.08726 | 0 | 0 |
| 680 | chr8 | 54986000 | 54987000 | 0.000 | 0.000 | 0.029 | 0.000 | LYPLA1 | 0.22755 | 0.54294 | 0.08726 | 0 | 0 |
| 681 | chr8 | 60031000 | 60032000 | 0.000 | 0.000 | 0.015 | 0.014 | TOX | 1.00000 | 1.00000 | 029694 | 0 | 6 |
| 682 | chr8 | 67525000 | 67526000 | 0.000 | 0.000 | 0.015 | 0.014 | MYBL1 | 1.00000 | 1.00000 | 0.29694 | 0 | 0 |
| 683 | chr8 | 77105000 | 77106000 | 0.000 | 0.000 | 0.029 | 0.000 | ZFHX4 | 0.22755 | 0.54294 | 0.08726 | 0 | 0 |
| 684 | chr8 | 78400000 | 78401000 | 0.000 | 0.000 | 0.029 | 0.000 | PEX2 | 0.22755 | 0.54294 | 0.08726 | 0 | 0 |
| 685 | chr8 | 90322000 | 90323000 | 0.000 | 0.000 | 0.029 | 0.000 | RIPK2 | 0.22755 | 054294 | 0.08726 | 0 | 0 |
| 686 | chr8 | 93199000 | 93200000 | 0.000 | 0.000 | 0.029 | 0.000 | RUNX1T1 | 0.22755 | 0.54294 | 0.08726 | 0 | 0 |
| 687 | chr8 | 94618000 | 94619000 | 0.028 | 0.000 | 0.015 | 0.000 | FAM92A1 | 0.47887 | 1.00000 | 0.29694 | 0 | 0 |
| 688 | chr8 | 110586000 | 110587000 | 0.000 | 0.000 | 0.015 | 0.014 | SYBU | 1.00000 | 1.00000 | 0.29694 | 0 | 0 |
| 689 | chr8 | 126687000 | 126688000 | 0.028 | 0.000 | 0.015 | 0.014 | TPIB1 | 1.00000 | 1.00000 | 0.29694 | 0 | 0 |
| 690 | chr8 | 128748000 | 128749000 | 0.500 | 0.000 | 0.132 | 0.000 | MYC | 0.00099 | 0.00010 | 0.00001 | 1 | 1 |
| 691 | chr8 | 128749000 | 128750000 | 0.583 | 0.000 | 0.103 | 0.014 | MYC | 0.02808 | 0.00000 | 0.00016 | 1 | 1 |
| 692 | chr8 | 128750000 | 128751000 | 0.444 | 0.000 | 0.088 | 0.014 | MYC | 0.05468 | 0.00007 | 0.00058 | 1 | 1 |
| 693 | chr8 | 128751000 | 128752000 | 0.111 | 0.000 | 0.044 | 0.000 | MYC | 0.10727 | 0.23165 | 0.02537 | 1 | 1 |
| 694 | chr8 | 128752000 | 128753000 | 0.056 | 0.000 | 0.015 | 0.000 | MYC | 0.47887 | 0.27446 | 0.29694 | 1 | 1 |
| 695 | chr8 | 137918000 | 137919000 | 0.028 | 0.000 | 0.015 | 0.000 | FAM135B | 0.47887 | 1.00000 | 0.29694 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 696 | chr8 | 138274000 | 138275000 | 0.000 | 0.000 | 0.000 | 0.027 | FAM135B | 0.49735 | 1.00000 | 1.00000 | 0 | 0 |
| 697 | chr8 | 143183000 | 143184009 | 0.028 | 0.000 | 0.015 | 0.000 | TSNARE1 | 0.47887 | 1.00000 | 0.29694 | 0 | 0 |
| 698 | chr8 | 144123000 | 144124000 | 0.000 | 0.000 | 0.029 | 0.000 | C8orf31 | 0.22755 | 0.54294 | 0.08726 | 0 | 0 |
| 699 | chr9 | 6411000 | 6412000 | 0.000 | 0.000 | 0.029 | 0.000 | UHRF2 | 0.22755 | 0.54294 | 0.08726 | 0 | 0 |
| 700 | chr9 | 6413000 | 6414000 | 0.000 | 0.000 | 0.015 | 0.014 | UHRF2 | 1.00000 | 1.00000 | 0.29694 | 0 | 0 |
| 701 | chr9 | 6414000 | 6415000 | 0.000 | 0.000 | 0.029 | 0.014 | UHRF2 | 0.60686 | 0.54294 | 0.08726 | 0 | 0 |
| 702 | chr9 | 9928000 | 9929000 | 0.000 | 0.000 | 0.000 | 0.027 | PTPRD | 0.49735 | 1.00000 | 1.00000 | 0 | 0 |
| 703 | chr9 | 13965000 | 13966000 | 0.000 | 0.000 | 0.029 | 0.000 | NFIB | 0.22755 | 0.54294 | 0.08726 | 0 | 0 |
| 704 | chr9 | 22824000 | 22825000 | 0.000 | 0.000 | 0.029 | 0.000 | DMRTA1 | 0.22755 | 0.54294 | 0.08726 | 0 | 0 |
| 705 | chr9 | 25260000 | 25261000 | 0.000 | 0.000 | 0.029 | 0.000 | TUSC1 | 0.22755 | 0.54294 | 0.08726 | 0 | 0 |
| 706 | chr9 | 29890000 | 29891000 | 0.000 | 0.000 | 0.015 | 0.014 | LINGO2 | 1.00000 | 1.00000 | 0.29694 | 0 | 0 |
| 707 | chr9 | 30656000 | 30657000 | 0.000 | 0.000 | 0.015 | 0.014 | ACO1 | 1.00000 | 1.00000 | 0.29694 | 0 | 0 |
| 708 | chr9 | 37003000 | 37004000 | 0.000 | 0.006 | 0.015 | 0.000 | PAX5 | 0.47887 | 1.00000 | 0.50663 | 1 | 0 |
| 709 | chr9 | 37005000 | 37006000 | 0.000 | 0.000 | 0.015 | 0.014 | PAX5 | 1.00000 | 1.00000 | 0.29694 | 1 | 0 |
| 710 | chr9 | 37024000 | 37025000 | 0.000 | 0.000 | 0.044 | 0.027 | PAX5 | 0.67043 | 0.54966 | 0.02537 | 1 | 0 |
| 711 | chr9 | 37025000 | 37026000 | 0.000 | 0.000 | 0.132 | 0.054 | PAX5 | 0.14640 | 0.02564 | 0.00001 | 1 | 1 |
| 712 | chr9 | 37026000 | 37027000 | 0.000 | 0.006 | 0.221 | 0.108 | PAX5 | 0.10913 | 0.00107 | 0.00000 | 1 | 1 |
| 713 | chr9 | 37027000 | 37028000 | 0.000 | 0.000 | 0.029 | 0.014 | PAX5 | 0.60686 | 0.54294 | 0.08726 | 1 | 0 |
| 714 | chr9 | 37033000 | 37034000 | 0.000 | 0.000 | 0.044 | 0.014 | PAX5 | 0.34948 | 0.54966 | 0.02537 | 1 | 0 |
| 715 | chr9 | 37034000 | 37035000 | 0.000 | 0.000 | 0.074 | 0.041 | PAX5 | 0.47996 | 0.16101 | 0.00208 | 1 | 1 |
| 716 | chr9 | 37035000 | 37036000 | 0.000 | 0.000 | 0.015 | 0.014 | PAX5 | 1.00000 | 1.00000 | 0.29694 | 1 | 0 |
| 717 | chr9 | 37196000 | 37197000 | 0.000 | 0.000 | 0.029 | 0.014 | ZCCHC7 | 0.60686 | 0.54294 | 0.08726 | 0 | 0 |
| 718 | chr9 | 37197000 | 37198000 | 0.000 | 0.000 | 0.029 | 0.000 | ZCCHC7 | 0.22755 | 0.54294 | 0.08726 | 0 | 0 |
| 719 | chr9 | 37293000 | 37294000 | 0.000 | 0.000 | 0.029 | 0.027 | ZCCHC7 | 1.00000 | 0.54294 | 0.08726 | 0 | 0 |
| 720 | chr9 | 37294000 | 37295000 | 0.000 | 0.000 | 0.044 | 0.027 | ZCCHC7 | 0.67043 | 0.54966 | 0.02537 | 0 | 0 |
| 721 | chr9 | 37327000 | 37328000 | 0.000 | 0.000 | 0.015 | 0.014 | ZCCHC7 | 1.00000 | 1.00000 | 0.29694 | 0 | 0 |
| 722 | chr9 | 37336000 | 37337000 | 0.000 | 0.000 | 0.044 | 0.014 | ZCCHC7 | 0.34948 | 0.54966 | 0.02537 | 0 | 0 |
| 723 | chr9 | 37337000 | 37338000 | 0.000 | 0.012 | 0.015 | 0.041 | ZCCHC7 | 0.62100 | 1.00000 | 1.00000 | 0 | 0 |
| 724 | chr9 | 37338000 | 37339000 | 0.000 | 0.000 | 0.029 | 0.014 | ZCCHC7 | 0.60686 | 0.54294 | 0 08726 | 0 | 0 |
| 725 | chr9 | 37369000 | 37370000 | 0.000 | 0.000 | 0.029 | 0.000 | ZCCHC7 | 0.22755 | 0.54294 | 0.08726 | 0 | 0 |
| 726 | chr9 | 37371000 | 37372000 | 0.028 | 0.025 | 0.118 | 0.068 | ZCCHC7 | 0.38669 | 0.15803 | 0.00732 | 0 | 1 |
| 727 | chr9 | 37372000 | 37373000 | 0.000 | 0.000 | 0.015 | 0.014 | ZCCHC7 | 1.00000 | 1.00000 | 0.29694 | 0 | 0 |
| 728 | chr9 | 37383000 | 37384000 | 0.000 | 0.000 | 0.059 | 0.027 | ZCCHC7 | 0.42627 | 0.29551 | 0.00730 | 0 | 1 |
| 729 | chr9 | 37384000 | 37385000 | 0.000 | 0.000 | 0.059 | 0.054 | ZCCHC7 | 1.00000 | 0.29551 | 0.00730 | 0 | 1 |
| 739 | chr9 | 37385000 | 37386000 | 0.000 | 0.000 | 0.029 | 0.014 | ZCCHC7 | 0.60686 | 0.54294 | 0.08726 | 0 | 0 |
| 731 | chr9 | 37387000 | 37388000 | 0.000 | 0.000 | 0.059 | 0.014 | ZCCHC7 | 0.19371 | 0.29551 | 0.00730 | 0 | 1 |
| 732 | chr9 | 37397000 | 37398000 | 0.000 | 0.000 | 0.044 | 0.000 | GRHPR | 0.10727 | 0.54966 | 0.02537 | 0 | 0 |
| 733 | chr9 | 37398000 | 37399000 | 0.000 | 0.000 | 0.029 | 0.000 | GRHPR | 0.22755 | 0.54294 | 0.08726 | 0 | 0 |
| 734 | chr9 | 37399000 | 37400000 | 0.000 | 0.000 | 0.029 | 0.000 | GRHPR | 0.22755 | 0.54294 | 0.08726 | 0 | 0 |
| 735 | chr9 | 37402000 | 37403000 | 0.000 | 0.006 | 0.029 | 0.000 | GRHPR | 0.22755 | 0.54294 | 0.21104 | 0 | 0 |
| 736 | chr9 | 37406000 | 37407000 | 0.000 | 0.000 | 0.015 | 0.014 | GRHPR | 1.00000 | 1.00000 | 0.29694 | 0 | 0 |
| 737 | chr9 | 37407000 | 37408000 | 0.000 | 0.000 | 0.132 | 0.149 | GRHPR | 0.81382 | 0.02564 | 0.00001 | 0 | 1 |
| 738 | chr9 | 37408000 | 37409000 | 0.000 | 0.006 | 0.029 | 0.027 | GRHPR | 1.00000 | 0.54294 | 0.21104 | 0 | 0 |
| 739 | chr9 | 37410000 | 37411000 | 0.000 | 0.000 | 0.029 | 0.000 | GRHPR | 0.22755 | 0.54294 | 0.08726 | 0 | 0 |
| 740 | chr9 | 37424000 | 37425000 | 0.000 | 0.000 | 0.044 | 0.000 | GRHPR | 0.10727 | 0.54966 | 0.02537 | 0 | 0 |
| 741 | chr9 | 37425000 | 37426000 | 0.000 | 0.000 | 0.029 | 0.000 | GRHPR | 0.22755 | 0.54294 | 0.08726 | 0 | 0 |
| 742 | chr9 | 112811000 | 112812000 | 0.000 | 0.000 | 0.059 | 0.014 | AKAP2 | 0.19371 | 0.29551 | 0.00730 | 0 | 1 |
| 743 | chr9 | 117037000 | 117038000 | 0.056 | 0.000 | 0.000 | 0.014 | COL27A1 | 1.00000 | 0.11763 | 1.00000 | 0 | 1 |
| 744 | chr9 | 119779000 | 119780000 | 0.000 | 0.000 | 0.044 | 0.000 | ASTN2 | 0.10727 | 0.54966 | 0.02537 | 0 | 0 |
| 745 | chr9 | 126232000 | 126233000 | 0.056 | 0.000 | 0.000 | 0.000 | DENND1A | 1.00000 | 0.11763 | 1.00000 | 0 | 1 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 746 | chr9 | 130741000 | 130742000 | 0.000 | 0.000 | 0.059 | 0.000 | FAM102A | 0.05016 | 0.29551 | 0.00730 | 1 | 1 |
| 747 | chr9 | 130742000 | 130743000 | 0.000 | 0.000 | 0.059 | 0.027 | FAM102A | 0.42627 | 0.29551 | 0.00730 | 1 | 1 |
| 748 | chr9 | 132767000 | 132768000 | 0.000 | 0.000 | 0.015 | 0.014 | FNBP1 | 1.00000 | 1.00000 | 0.29694 | 0 | 0 |
| 749 | chr9 | 132785000 | 132786000 | 0.000 | 0.000 | 0.029 | 0.000 | FNBP1 | 0.22755 | 0.54294 | 0.08726 | 0 | 0 |
| 750 | chr9 | 132803000 | 132804000 | 0.000 | 0.000 | 0.015 | 0.014 | FNBP1 | 1.00000 | 1.00900 | 0.29694 | 0 | 0 |
| 751 | chr9 | 132804000 | 132805000 | 0.000 | 0.000 | 0.029 | 0.027 | FNBP1 | 1.00000 | 0.54294 | 0.08726 | 0 | 0 |
| 752 | chr9 | 134551000 | 134552000 | 0.000 | 0.000 | 0.029 | 0.000 | RAPGEF1 | 0.22755 | 0.54294 | 0.08726 | 0 | 0 |
| 753 | chr9 | 138874000 | 138875000 | 0.056 | 0.000 | 0.029 | 0.014 | UBAC1 | 0.60686 | 0.60763 | 0.08726 | 0 | 1 |
| 754 | chr10 | 3333000 | 3334000 | 0.000 | 0.000 | 0.000 | 0.027 | PITRM1 | 0.49735 | 1.00000 | 1.00000 | 0 | 0 |
| 755 | chr10 | 5707000 | 5708000 | 0.000 | 0.000 | 0.029 | 0.014 | ASB13 | 0.60686 | 0.54294 | 0.08726 | 0 | 0 |
| 756 | chr10 | 5728000 | 5729000 | 0.000 | 0.006 | 0.015 | 0.000 | ASB13 | 0.47887 | 1.00000 | 0.50663 | 0 | 0 |
| 757 | chr10 | 15393000 | 5394000 | 0.028 | 0.000 | 0.015 | 0.000 | FAM171A1 | 0.47887 | 1.00000 | 0.29694 | 0 | 0 |
| 758 | chr10 | 20796000 | 20797000 | 0.000 | 0.006 | 0.015 | 0.000 | PLXDC2 | 0.47887 | 1.00000 | 0.50663 | 0 | 0 |
| 759 | chr10 | 35424000 | 35425900 | 0.000 | 0.000 | 0.029 | 0.000 | CREM | 0.22755 | 0.54294 | 0.08726 | 0 | 0 |
| 760 | chr10 | 56678000 | 56679900 | 0.000 | 0.000 | 0.000 | 0.027 | PCDH15 | 0.49735 | 1.00000 | 1.00000 | 0 | 0 |
| 761 | chr10 | 63440000 | 63441000 | 0.028 | 0.000 | 0.015 | 0.000 | C10orf107 | 0.47887 | 1.00000 | 0.29694 | 0 | 0 |
| 762 | chr10 | 63659000 | 63660000 | 0.000 | 0.000 | 0.044 | 0.014 | ARID5B | 0.34948 | 0.54966 | 0.02537 | 1 | 0 |
| 763 | chr10 | 63669000 | 63661000 | 0.000 | 0.000 | 0.059 | 0.014 | ARID5B | 0.19371 | 0.29551 | 0.00730 | 1 | 1 |
| 764 | chr10 | 63662000 | 63663000 | 0.000 | 0.000 | 0.029 | 0.014 | ARID5B | 0.60686 | 0.54294 | 0.08726 | 1 | 0 |
| 765 | chr10 | 63720090 | 63723000 | 0.000 | 0.000 | 0.029 | 0.000 | ARID5B | 0.22755 | 0.54294 | 0.08726 | 1 | 0 |
| 766 | chr10 | 63803990 | 63804000 | 0.000 | 0.000 | 0.009 | 0.027 | ARID5B | 0.49735 | 1.00000 | 1.00000 | 1 | 0 |
| 767 | chr10 | 63809090 | 63810900 | 0.000 | 0.000 | 0.015 | 0.014 | ARID5B | 1.00000 | 1.00000 | 0.29694 | 1 | 0 |
| 768 | chr10 | 63810000 | 63811000 | 0.000 | 0.000 | 0.009 | 0.027 | ARID5B | 0.49735 | 1.00000 | 1.00000 | 1 | 0 |
| 769 | chr10 | 67997000 | 67908000 | 0.000 | 0.006 | 0.015 | 0.000 | CTNNA3 | 0.47887 | 1.00000 | 0.50663 | 0 | 0 |
| 770 | chr10 | 68474000 | 68475000 | 0.000 | 0.000 | 0.000 | 0.027 | CTNNA3 | 0.49735 | 1.00000 | 1.00000 | 0 | 0 |
| 771 | chr10 | 98519000 | 98511000 | 0.000 | 0.000 | 0.029 | 0.000 | PIK3AP1 | 0.22755 | 0.54294 | 0.08726 | 0 | 0 |
| 772 | chr10 | 101384000 | 101385000 | 0.028 | 0.000 | 0.015 | 0.014 | SLC25A28 | 1.00000 | 1.00000 | 0.29694 | 0 | 0 |
| 773 | chr10 | 198276900 | 108277000 | 0.000 | 0.000 | 0.029 | 0.000 | SORCS1 | 0.22755 | 0.54294 | 0.08726 | 0 | 0 |
| 774 | chr10 | 113473900 | 113474000 | 0.028 | 0.000 | 0.015 | 0.000 | GPAM | 0.47887 | 1.00000 | 0.29694 | 0 | 0 |
| 775 | chr10 | 113636990 | 113637000 | 0.000 | 0.000 | 0.029 | 0.000 | GPAM | 0.22755 | 0.54294 | 0.08726 | 0 | 0 |
| 776 | chr10 | 116458000 | 16459000 | 0.000 | 0.000 | 0.044 | 0.000 | ABLIM1 | 0.10727 | 0.54966 | 0.02537 | 0 | 0 |
| 777 | chr10 | 121623009 | 121624099 | 0.000 | 0.000 | 0.029 | 0.000 | MCMBP | 0.22755 | 0.54294 | 0.08726 | 0 | 0 |
| 778 | chr10 | 132973009 | 132974099 | 0.000 | 0.000 | 0.015 | 0.027 | TCERG1L | 1.00000 | 1.00000 | 0.29694 | 0 | 0 |
| 779 | chr10 | 134326000 | 134327009 | 0.028 | 0.000 | 0.015 | 0.000 | INPP5A | 0.47887 | 1.00000 | 0.29694 | 0 | 0 |
| 780 | chr11 | 871000 | 872000 | 0.028 | 0.000 | 0.029 | 0.000 | CHID1 | 0.22755 | 1.00000 | 0.08726 | 0 | 0 |
| 781 | chr11 | 1149000 | 1150000 | 0.028 | 0.000 | 0.015 | 0.000 | MUC5AC | 0.47887 | 1.00000 | 0.29694 | 0 | 0 |
| 782 | chr11 | 25065000 | 25066000 | 0.000 | 0.000 | 0.029 | 0.000 | LUZP2 | 0.22755 | 0.54294 | 0.08726 | 0 | 0 |
| 783 | chr11 | 25289009 | 25290900 | 0.000 | 0.000 | 0.029 | 0.000 | LUZP2 | 0.22755 | 0.54294 | 0.08726 | 0 | 0 |
| 784 | chr11 | 27216000 | 27217000 | 0.028 | 0.000 | 0.029 | 0.014 | BBOX1 | 0.60686 | 1.00000 | 0.08726 | 0 | 0 |
| 785 | chr11 | 28849000 | 28850009 | 0.000 | 0.000 | 0.000 | 0.027 | METTL15 | 0.49735 | 1.00000 | 1.00000 | 0 | 0 |
| 786 | chr11 | 29253000 | 29254009 | 0.000 | 0.000 | 0.029 | 0.000 | KCNA4 | 0.22755 | 0.54294 | 0.08726 | 0 | 0 |
| 787 | chr11 | 29909000 | 29901009 | 0.000 | 0.000 | 0.029 | 0.000 | KCNA4 | 0.22755 | 0.54294 | 0.08726 | 0 | 0 |
| 788 | chr11 | 40626000 | 40627000 | 0.000 | 0.000 | 0.029 | 0.000 | LRRC4C | 0.22755 | 0.54294 | 0.08726 | 0 | 0 |
| 789 | chr11 | 40845000 | 40846000 | 0.000 | 0.000 | 0.029 | 0.000 | LRRC4C | 0.22755 | 0.54294 | 0.08726 | 0 | 0 |
| 790 | chr11 | 40868000 | 40869900 | 0.000 | 0.000 | 0.029 | 0.000 | LRRC4C | 0.22755 | 0.54294 | 0.08726 | 0 | 0 |
| 791 | chr11 | 41066000 | 41067900 | 0.000 | 0.000 | 0.029 | 0.000 | LRRC4C | 0.22755 | 0.54294 | 0.08726 | 0 | 0 |
| 792 | chr11 | 41844000 | 41845000 | 0.028 | 0.000 | 0.015 | 0.000 | API5 | 0.47887 | 1.00000 | 0.29694 | 0 | 0 |
| 793 | chr11 | 57171000 | 57172009 | 0.000 | 0.000 | 0.029 | 0.014 | SLC43A3 | 0.60686 | 0.54294 | 0.08726 | 0 | 0 |
| 794 | chr11 | 60224000 | 69225009 | 0.000 | 0.000 | 0.074 | 0.014 | MS4A1 | 0.10420 | 0.16101 | 0.00208 | 1 | 1 |
| 795 | chr11 | 65190000 | 65191009 | 0.000 | 0.000 | 0.074 | 0.027 | FRMD8 | 0.25970 | 0.16101 | 0.00298 | 0 | 1 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 796 | chr11 | 65191000 | 65192000 | 0.000 | 0.000 | 0.103 | 0.014 | FRMD8 | 0.02808 | 0.09269 | 0.00016 | 0 | 1 |
| 797 | chr11 | 65266000 | 65267000 | 0.000 | 0.000 | 0.029 | 0.014 | SCYL1 | 0.60686 | 0.54294 | 0.08726 | 0 | 0 |
| 798 | chr11 | 65267000 | 65268900 | 0.000 | 0.000 | 0.103 | 0.000 | SCYL1 | 0.00488 | 0.09269 | 0.00016 | 0 | 1 |
| 799 | chr11 | 85963000 | 85964900 | 0.000 | 0.000 | 0.029 | 0.000 | EED | 0.22755 | 0.54294 | 0.08726 | 0 | 0 |
| 809 | chr11 | 92261000 | 92262000 | 0.000 | 0.000 | 0.029 | 0.000 | FAT3 | 0.22755 | 0.54294 | 0.08726 | 0 | 0 |
| 801 | chr11 | 102117000 | 102118000 | 0.000 | 0.000 | 0.000 | 0.027 | YAP1 | 0.49735 | 1.00000 | 1.00000 | 0 | 0 |
| 802 | chr11 | 102188000 | 102189000 | 0.000 | 0.012 | 0.206 | 0.108 | BIRC3 | 0.16270 | 0.00197 | 0.00000 | 1 | 1 |
| 803 | chr11 | 102189000 | 102190009 | 0.000 | 0.000 | 0.059 | 0.000 | BIRC3 | 0.05016 | 0.29551 | 0.00730 | 1 | 1 |
| 804 | chr11 | 107497000 | 107498000 | 0.028 | 0.000 | 0.015 | 0.000 | ELMOD1 | 0.47887 | 1.00000 | 0.29694 | 0 | 0 |
| 805 | chr11 | 108781000 | 108782000 | 0.000 | 0.000 | 0.015 | 0.014 | DDX10 | 1.00000 | 1.00000 | 0.29694 | 0 | 0 |
| 806 | chr11 | 108975000 | 108976000 | 0.000 | 0.000 | 0.015 | 0.014 | DDX10 | 1.00000 | 1.00000 | 0.29694 | 0 | 0 |
| 807 | chr11 | 109066000 | 109067000 | 0.028 | 0.000 | 0.015 | 0.000 | C11orf87 | 0.47887 | 1.00000 | 0.29694 | 0 | 0 |
| 808 | chr11 | 111248000 | 111249000 | 0.000 | 0.000 | 0.029 | 0.014 | POU2AF1 | 0.60686 | 0.54294 | 0.08726 | 1 | 0 |
| 809 | chr11 | 111249000 | 111250000 | 0.000 | 0.012 | 0.103 | 0.081 | POU2AF1 | 0.77363 | 0.09269 | 0.00337 | 1 | 1 |
| 810 | chr11 | 115761000 | 115762000 | 0.028 | 0.000 | 0.015 | 0.041 | CADM1 | 0.62100 | 1.00000 | 0.29694 | 0 | 0 |
| 811 | chr11 | 118723000 | 118724000 | 0.000 | 0.000 | 0.029 | 0.000 | CXCR5 | 0.22755 | 0.54294 | 0.08726 | 0 | 0 |
| 812 | chr11 | 126496000 | 126497099 | 0.028 | 0.000 | 0.015 | 0.014 | KIRREL3 | 1.00000 | 1.00000 | 0.29694 | 0 | 0 |
| 813 | chr11 | 128390000 | 128391009 | 0.000 | 0.000 | 0.044 | 0.014 | ETS1 | 0.34948 | 0.54966 | 0.02537 | 1 | 0 |
| 814 | chr11 | 128391000 | 128392000 | 0.000 | 0.000 | 0.118 | 0.014 | ETS1 | 0.01415 | 0.04825 | 0.00004 | 1 | 1 |
| 815 | chr12 | 6554000 | 6555000 | 0.000 | 0.000 | 0.029 | 0.000 | CD27 | 0.22755 | 0.54294 | 0.08726 | 0 | 0 |
| 816 | chr12 | 8762000 | 8763900 | 0.000 | 0.000 | 0.015 | 0.014 | AICDA | 1.00000 | 1.00000 | 0.29694 | 0 | 0 |
| 817 | chr12 | 8763099 | 8764900 | 0.000 | 0.000 | 0.044 | 0.041 | AICDA | 1.00000 | 0.54966 | 0.02537 | 0 | 0 |
| 818 | chr12 | 8764000 | 8765000 | 0.000 | 0.000 | 0.029 | 0.068 | AICDA | 0.44431 | 0.54294 | 0.08726 | 0 | 1 |
| 819 | chr12 | 8765000 | 8766000 | 0.000 | 0.000 | 0.015 | 0.027 | AICDA | 1.00000 | 1.00000 | 0.29694 | 0 | 0 |
| 820 | chr12 | 9823000 | 9824000 | 0.000 | 0.000 | 0.015 | 0.014 | CLEC2D | 1.00000 | 1.00000 | 0.29694 | 0 | 0 |
| 821 | chr12 | 11710000 | 11711000 | 0.000 | 0.000 | 0.029 | 0.000 | ETV6 | 0.22755 | 0.54294 | 0.08726 | 1 | 0 |
| 822 | chr12 | 11803000 | 11804000 | 0.000 | 0.000 | 0.015 | 0.014 | ETV6 | 1.00000 | 1.00000 | 0.29694 | 1 | 0 |
| 823 | chr12 | 14923000 | 14924000 | 0.000 | 0.000 | 0.015 | 0.014 | HIST4H4 | 1.00009 | 1.00000 | 0.29694 | 1 | 0 |
| 824 | chr12 | 16717900 | 16718000 | 0.000 | 0.000 | 0.000 | 0.027 | LMO3 | 0.49735 | 1.00000 | 1.00000 | 0 | 0 |
| 825 | chr12 | 23805090 | 23806000 | 0.000 | 0.000 | 0.029 | 0.000 | SOX5 | 0.22755 | 0.54294 | 0.98726 | 0 | 0 |
| 826 | chr12 | 25149000 | 25150000 | 0.000 | 0.000 | 0.029 | 0.000 | C12orf77 | 0.22755 | 0.54294 | 0.08726 | 0 | 0 |
| 827 | chr12 | 25151000 | 25152000 | 0.000 | 0.000 | 0.015 | 0.014 | C12orf77 | 1.00000 | 1.00000 | 0.29694 | 0 | 0 |
| 828 | chr12 | 25174000 | 25175000 | 0.000 | 0.000 | 0.044 | 0.000 | C12orf77 | 0.19727 | 0.54966 | 0.02537 | 0 | 0 |
| 829 | chr12 | 25205000 | 25206000 | 0.000 | 0.006 | 0.015 | 0.000 | LRMP | 0.47887 | 1.00000 | 0.50663 | 1 | 0 |
| 830 | chr12 | 25206000 | 25207000 | 0.000 | 0.006 | 0.103 | 0.014 | LRMP | 0.02808 | 0.09269 | 1.00000 | 1 | 1 |
| 831 | chr12 | 25207000 | 25208000 | 0.000 | 0.006 | 0.118 | 0.014 | LRMP | 0.01415 | 0.04825 | 0.00030 | 1 | 1 |
| 832 | chr12 | 25208000 | 25209000 | 0.000 | 0.000 | 0.029 | 0.014 | LRMP | 0.60686 | 0.54294 | 008726 | 1 | 0 |
| 833 | chr12 | 25665000 | 25666000 | 0.028 | 0.000 | 0.015 | 0.000 | IFLTD1 | 0.47887 | 1.00090 | 0.29694 | 0 | 0 |
| 834 | chr12 | 38920000 | 38921000 | 0.000 | 0.000 | 0.029 | 0.000 | CPNE8 | 0.22755 | 0.54294 | 0.08726 | 0 | 0 |
| 835 | chr12 | 48027000 | 48028000 | 0.028 | 0.000 | 0.059 | 0.027 | RPAP3 | 0.42627 | 0.65667 | 0.00730 | 0 | 1 |
| 836 | chr12 | 57496000 | 57497000 | 0.000 | 0.000 | 0.015 | 0.014 | STAT6 | 1.00000 | 1.00000 | 0.29694 | 0 | 0 |
| 837 | chr12 | 69203000 | 69204000 | 0.000 | 0.006 | 0.015 | 0.000 | MDM2 | 0.47887 | 1.00000 | 0.50663 | 0 | 0 |
| 838 | chr12 | 76202000 | 76203000 | 0.000 | 0.000 | 0.000 | 0.027 | PHLDA1 | 0.49735 | 1.00000 | 1.00000 | 0 | 0 |
| 839 | chr12 | 79270000 | 79271000 | 0.000 | 0.000 | 0.029 | 0.027 | SYT1 | 1.00000 | 0.54294 | 0.08726 | 0 | 0 |
| 840 | chr12 | 82572000 | 82573000 | 0.000 | 0.000 | 0.015 | 0.014 | CCDC59 | 1.00000 | 1.00000 | 0.29694 | 0 | 0 |
| 841 | chr12 | 84837090 | 84838000 | 0.000 | 0.000 | 0.090 | 0.027 | SLC6A15 | 0.49735 | 1.00000 | 1.00000 | 0 | 0 |
| 842 | chr12 | 86114000 | 86115000 | 0.000 | 0.000 | 0.029 | 0.000 | RASSF9 | 0.22755 | 0.54294 | 0.08726 | 0 | 0 |
| 843 | chr12 | 86115000 | 86116000 | 0.000 | 0.000 | 0.029 | 0.000 | RASSF9 | 0.22755 | 0.54294 | 0.08726 | 0 | 0 |
| 844 | chr12 | 92538000 | 92539000 | 0.000 | 0.000 | 0.088 | 0.027 | BTG1 | 0.15270 | 0.09031 | 0.00958 | 1 | 1 |
| 845 | chr12 | 92539000 | 92540000 | 0.000 | 0.000 | 0.074 | 0.014 | BTG1 | 0.10420 | 0.16101 | 0.00298 | 1 | 1 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 846 | chr12 | 96030000 | 96031000 | 0.028 | 0.000 | 0.015 | 0.000 | NTN4 | 0.47887 | 1.00000 | 0.29694 | 0 | 0 |
| 847 | chr12 | 110171000 | 110172000 | 0.000 | 0.006 | 0.015 | 0.000 | FAM222A | 0.47887 | 1.00000 | 0.50663 | 0 | 0 |
| 848 | chr12 | 110980000 | 110981000 | 0.000 | 0.000 | 0.015 | 0.014 | PPTC7 | 1.00000 | 1.00000 | 0.29694 | 0 | 0 |
| 849 | chr12 | 113493000 | 113494000 | 0.000 | 0.000 | 0.059 | 0.009 | DTX1 | 0.05016 | 0.29551 | 0.00730 | 1 | 1 |
| 850 | chr12 | 113494000 | 113495000 | 0.000 | 0.000 | 0.176 | 0.041 | DTX1 | 0.01224 | 0.00730 | 0.00000 | 1 | I |
| 851 | chr12 | 113495000 | 113496000 | 0.000 | 0.000 | 0.162 | 0.068 | DTX1 | 0.11904 | 0.01471 | 0.00000 | 1 | 1 |
| 852 | chr12 | 113496000 | 113497090 | 0.000 | 0.000 | 0.132 | 0.054 | DTX1 | 0.14640 | 0.02564 | 0.00001 | 1 | 1 |
| 853 | chr12 | 113497000 | 113498000 | 0.000 | 0.000 | 0.074 | 0.000 | DTX1 | 0.02326 | 0.16101 | 0.00208 | 1 | 1 |
| 854 | chr12 | 113499000 | 113500000 | 0.000 | 0.000 | 0.029 | 0.000 | DTX1 | 0.22755 | 0.54294 | 0.08726 | 1 | 0 |
| 855 | chr12 | 113512000 | 113513000 | 0.000 | 0.000 | 0.029 | 0.000 | DTX1 | 0.22755 | 0.54294 | 0.08726 | 1 | 0 |
| 856 | chr12 | 115966000 | 115967000 | 0.000 | 0.000 | 0.099 | 0.027 | MED13L | 0.49735 | 1.00000 | 1.00000 | 0 | 0 |
| 857 | chr12 | 122432000 | 122433000 | 0.000 | 0.000 | 0.029 | 0.009 | WDR66 | 0.22755 | 0.54294 | 0.08726 | 0 | 0 |
| 858 | chr12 | 122433000 | 122434000 | 0.000 | 0.000 | 0.059 | 0.014 | WDR66 | 0.19371 | 0.29551 | 0.00730 | 0 | 1 |
| 859 | chr12 | 122447000 | 122448000 | 0.000 | 0.000 | 0.000 | 0.027 | WDR66 | 0.49735 | 1.00000 | 1.00000 | 0 | 0 |
| 860 | chr12 | 122458000 | 122459090 | 0.000 | 0.006 | 0.118 | 0.068 | BCL7A | 0.38669 | 0.94825 | 0.00730 | 1 | 1 |
| 861 | chr12 | 122459000 | 122460000 | 0.000 | 0.006 | 0.324 | 0.108 | BCL7A | 0.00197 | 0.00003 | 0.00000 | 1 | 1 |
| 862 | chr12 | 122460000 | 122461000 | 0.000 | 0.000 | 0.176 | 0.081 | BCL7A | 0.12879 | 0.00730 | 0.00000 | 1 | 1 |
| 863 | chr12 | 122461000 | 122462000 | 0.000 | 0.006 | 0.279 | 0.162 | BCL7A | 0.10628 | 0.00013 | 0.00000 | 1 | 1 |
| 864 | chr12 | 122462000 | 122463000 | 0.000 | 0.012 | 0.191 | 0.027 | BCL7A | 0.00186 | 0.00372 | 0.00000 | 1 | 1 |
| 865 | chr12 | 122463000 | 122464000 | 0.000 | 0.012 | 0.132 | 0.054 | BCL7A | 0.14640 | 0.02564 | 0.00038 | 1 | 1 |
| 866 | chr12 | 124054000 | 124055000 | 0.028 | 0.000 | 0.015 | 0.014 | TMED2 | 1.00000 | 1.00000 | 0.29694 | 0 | 0 |
| 867 | chr12 | 127965000 | 127966000 | 0.000 | 0.000 | 0.000 | 0.027 | TMEM132C | 0.49735 | 1.00000 | 1.00000 | 0 | 0 |
| 868 | chr12 | 131303000 | 131304000 | 0.056 | 0.000 | 0.015 | 0.014 | STX2 | 1.00000 | 0.27446 | 0.29694 | 0 | 1 |
| 869 | chr12 | 131649000 | 131650000 | 0.000 | 0.000 | 0.000 | 0.027 | GPR133 | 0.49735 | 1.00000 | 1.00000 | 0 | 0 |
| 870 | chr12 | 133306000 | 133307000 | 0.028 | 0.000 | 0.015 | 0.027 | ANKLE2 | 1.00000 | 1.00000 | 0.29694 | 0 | 0 |
| 871 | chr13 | 21913000 | 21914000 | 0.000 | 0.000 | 0.029 | 0.000 | ZDHHC20 | 0.22755 | 0.54294 | 0.08726 | 0 | 0 |
| 872 | chr13 | 32116000 | 32117000 | 0.028 | 0.000 | 0.015 | 0.000 | RXFP2 | 0.47887 | 1.00000 | 0.29694 | 0 | 0 |
| 873 | chr13 | 35498000 | 35499000 | 0.000 | 0.000 | 0.015 | 0.027 | NBEA | 1.00000 | 1.00000 | 0.29694 | 0 | 0 |
| 874 | chr13 | 38371000 | 38372000 | 0.028 | 0.000 | 0.015 | 0.000 | TRPC4 | 0.47887 | 1.00000 | 0.29694 | 0 | 0 |
| 875 | chr13 | 38630000 | 38631000 | 0.000 | 0.000 | 0.029 | 0.000 | TRPC4 | 0.22755 | 0.54294 | 0.08726 | 0 | 0 |
| 876 | chr13 | 41156000 | 41157000 | 0.000 | 0.000 | 0.029 | 0.000 | FOXO1 | 0.22755 | 0.54294 | 0.08726 | 1 | 0 |
| 877 | chr13 | 41240000 | 41241000 | 0.028 | 0.000 | 0.029 | 0.000 | FOXO1 | 0.22755 | 1.00000 | 0.08726 | 1 | 0 |
| 878 | chr13 | 46958000 | 46959000 | 0.000 | 0.000 | 0.029 | 0.000 | KIAA0226L | 0.22755 | 0.54294 | 0.08726 | 0 | 0 |
| 879 | chr13 | 46959000 | 46960000 | 0.000 | 0.000 | 0.029 | 0.000 | KIAA0226L | 0.22755 | 0.54294 | 0.08726 | 0 | 0 |
| 880 | chr13 | 46960000 | 46961000 | 0.000 | 0.000 | 0.088 | 0.027 | KIAA0226L | 0.15270 | 0.09031 | 0.00058 | 0 | 1 |
| 881 | chr13 | 46961000 | 46962000 | 0.000 | 0.000 | 0.015 | 0.014 | KIAA0226L | 1.00000 | 1.00000 | 0.29694 | 0 | 0 |
| 882 | chr13 | 46962000 | 46963000 | 0.000 | 0.000 | 0.015 | 0.014 | KIAA0226L | 1.00000 | 1.00000 | 0.29694 | 0 | 0 |
| 883 | chr13 | 55239000 | 55240000 | 0.000 | 0.000 | 0.029 | 0.000 | OLFM4 | 0.22755 | 0.54294 | 0.08726 | 0 | 0 |
| 884 | chr13 | 55386000 | 55387000 | 0.000 | 0.000 | 0.029 | 0.000 | OLFM4 | 0.22755 | 0.54294 | 0.08726 | 0 | 0 |
| 885 | chr13 | 55598000 | 55599000 | 0.000 | 0.000 | 0.029 | 0.000 | OLFM4 | 0.22755 | 0.54294 | 0.08726 | 0 | 0 |
| 886 | chr13 | 57222000 | 57223000 | 0.000 | 0.000 | 0.029 | 0.000 | PRR20A; PRR20DPRR20BPRR20B; | 0.22755 | 0.54294 | 0.08726 | 0 | 0 |
| 887 | chr13 | 61343000 | 61344000 | 0.028 | 0.000 | 0.015 | 0.000 | TDRD3 | 0.47887 | 1.00000 | 0.29694 | 0 | 0 |
| 888 | chr13 | 62830000 | 62831000 | 0.000 | 0.000 | 0.000 | 0.027 | PCDH20 | 0.49735 | 1.00000 | 1.00000 | 0 | 0 |
| 889 | chr13 | 63049000 | 63050000 | 0.000 | 0.000 | 0.029 | 0.000 | PCDH20 | 0.22755 | 0.54294 | 0.08726 | 0 | 0 |
| 890 | chr13 | 63157000 | 63158000 | 0.028 | 0.000 | 0.015 | 0.000 | AL445989.1 | 0.47887 | 1.00000 | 0.29694 | 0 | 0 |
| 891 | chr13 | 63214000 | 63215000 | 0.028 | 0.000 | 0.015 | 0.000 | AL445989.1 | 0.47887 | 1.00000 | 0.29694 | 0 | 0 |
| 892 | chr13 | 64802000 | 64803000 | 0.000 | 0.000 | 0.015 | 0.014 | AL445989.1 | 1.00000 | 1.00000 | 0.29694 | 0 | 0 |
| 893 | chr13 | 65637000 | 65638000 | 0.000 | 0.000 | 0.029 | 0.000 | PCDH9 | 0.22755 | 0.54294 | 0.08726 | 0 | 0 |
| 894 | chr13 | 68656000 | 68657000 | 0.000 | 0.000 | 0.000 | 0.027 | PCDH9 | 0.49735 | 1.00000 | 1.00000 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 895 | chr13 | 69418000 | 69419000 | 0.000 | 0.000 | 0.029 | 0.014 | KLHL1 | 0.60686 | 0.54294 | 0.08726 | 0 | 0 |
| 896 | chr13 | 70956000 | 70957000 | 0.000 | 0.012 | 0.015 | 0.000 | KLHLI | 0.47887 | 1.00000 | 1.00000 | 0 | 0 |
| 897 | chr13 | 74542000 | 74543000 | 0.000 | 0.000 | 0.029 | 0.000 | KLF12 | 0.22755 | 0.54294 | 0.08726 | 0 | 0 |
| 898 | chr13 | 75983000 | 75984000 | 0.000 | 0.000 | 0.074 | 0.014 | TBC1D4 | 0.10420 | 0.16101 | 0.00208 | 0 | 1 |
| 899 | chr13 | 75984000 | 75985000 | 0.000 | 0.000 | 0.118 | 0.027 | TBC1D4 | 0.04838 | 0.04825 | 0.00004 | 0 | 1 |
| 900 | chr13 | 83450000 | 83451000 | 0.000 | 0.000 | 0.029 | 0.000 | SLITRK1 | 0.22755 | 0.54294 | 0.08726 | 0 | 0 |
| 901 | chr13 | 84641000 | 84642000 | 0.000 | 0.000 | 0.015 | 0.014 | SLITRK1 | 1.00000 | 1.00000 | 0.29694 | 0 | 0 |
| 902 | chr13 | 87793000 | 87794000 | 0.000 | 0.000 | 0.015 | 0.014 | SLITRK5 | 1.00000 | 1.00000 | 0.29694 | 0 | 0 |
| 903 | chr13 | 91480000 | 91481000 | 0.000 | 0.000 | 0.000 | 0.027 | GPC5 | 0.49735 | 1.00000 | 1.00000 | 0 | 0 |
| 904 | chr13 | 106081000 | 106082000 | 0.000 | 0.000 | 0.015 | 0.014 | DAOA | 1.00000 | 1.00000 | 0.29694 | 0 | 0 |
| 905 | chr13 | 114786000 | 114787000 | 0.000 | 0.000 | 0.015 | 0.027 | RASA3 | 1.00000 | 1.00000 | 0.29694 | 0 | 0 |
| 906 | chr13 | 114916000 | 114917000 | 0.028 | 0.000 | 0.000 | 0.014 | RASA3 | 1.00000 | 0.34615 | 1.00000 | 0 | 0 |
| 907 | chr14 | 22948000 | 22949000 | 0.000 | 0.000 | 0.029 | 0.000 | TRAJ56 | 0.22755 | 0.54294 | 0.08726 | 0 | 0 |
| 908 | chr14 | 22949000 | 22950000 | 0.000 | 0.000 | 0.044 | 0.000 | TRAJ56 | 0.10727 | 0.54966 | 0.02537 | 0 | 0 |
| 909 | chr14 | 22950000 | 22951000 | 0.000 | 0.000 | 0.029 | 0.000 | TRAJ54 | 0.22755 | 0.54294 | 0.08726 | 0 | 0 |
| 910 | chr14 | 22977000 | 22978000 | 0.000 | 0.000 | 0.015 | 0.014 | TRAJ33 | 1.00000 | 1.00000 | 0.29694 | 0 | 0 |
| 911 | chr14 | 27286000 | 27287000 | 0.000 | 0.000 | 0.029 | 0.000 | NOVA1 | 0.22755 | 0.54294 | 0.98726 | 0 | 0 |
| 912 | chr14 | 28645000 | 28646000 | 0.000 | 0.000 | 0.000 | 0.027 | FOXG1 | 0.49735 | 1.00000 | 1.00000 | 0 | 0 |
| 913 | chr14 | 49497000 | 49408009 | 0.000 | 0.000 | 0.000 | 0.041 | RPS29 | 0.24603 | 1.00000 | 1.00000 | 0 | 0 |
| 914 | chr14 | 50864000 | 59865009 | 0.000 | 0.000 | 0.029 | 0.000 | CDKL1 | 0.22755 | 0.54294 | 0.08726 | 0 | 0 |
| 915 | chr14 | 54812000 | 54813009 | 0.000 | 0.000 | 0.000 | 0.027 | CDKN3 | 0.49735 | 1.00000 | 1.00000 | 0 | 0 |
| 916 | chr14 | 55348000 | 55349000 | 0.000 | 0.000 | 0.029 | 0.000 | GCH1 | 0.22755 | 0.54294 | 0.08726 | 0 | 0 |
| 917 | chr14 | 59827090 | 59828900 | 0.000 | 0.000 | 0.029 | 0.000 | DAAM1 | 0.22755 | 0.54294 | 0.08726 | 0 | 0 |
| 918 | chr14 | 63143990 | 63144900 | 0.000 | 0.000 | 0.015 | 0.014 | KCNH5 | 1.00000 | 1.00000 | 0.29694 | 0 | 0 |
| 919 | chr14 | 64194090 | 64195900 | 0.000 | 0.000 | 0.015 | 0.014 | SGPP1 | 1.00000 | 1.00000 | 0.29694 | 0 | 0 |
| 920 | chr14 | 69258000 | 69259000 | 0.000 | 0.000 | 0.191 | 0.027 | ZFP36L1 | 0.00186 | 0.00372 | 0.00000 | 1 | 1 |
| 921 | chr14 | 69259000 | 69260009 | 0.000 | 0.012 | 0.265 | 0.068 | ZFP36L1 | 0.00244 | 0.00024 | 0.00000 | 1 | 1 |
| 922 | chr14 | 78418000 | 78419009 | 0.000 | 0.000 | 0.029 | 0.000 | ADCK1 | 0.22755 | 0.54294 | 0.08726 | 0 | 0 |
| 003 | chr14 | 81685000 | 81686009 | 0.028 | 0.000 | 0.015 | 0.000 | GTF2A1 | 0.47887 | 1.00000 | 0.29694 | 0 | 0 |
| 924 | chr14 | 84420000 | 84421000 | 0.000 | 0.006 | 0.015 | 0.000 | FLRT2 | 0.47887 | 1.00000 | 0.50663 | 0 | 0 |
| 925 | chr14 | 91883990 | 91884900 | 0.000 | 0.000 | 0.015 | 0.014 | CCDC88C | 1.00000 | 1.00000 | 0.29694 | 0 | 0 |
| 926 | chr14 | 94941990 | 94942900 | 0.000 | 0.006 | 0.029 | 0.014 | SERPINA9 | 0.60686 | 0.54294 | 0.21104 | 1 | 0 |
| 927 | chr14 | 94942090 | 94943900 | 0.000 | 0.000 | 0.118 | 0.014 | SERPINA9 | 0.91415 | 0.04825 | 0.90004 | 1 | 1 |
| 928 | chr14 | 96179000 | 96180000 | 0.028 | 0.037 | 0.132 | 0.108 | TCL1A | 0.79702 | 0.15881 | 0.01566 | 1 | 1 |
| 929 | chr14 | 96180000 | 96181009 | 0.028 | 0.025 | 0.088 | 0.054 | TCL1A | 0.52997 | 0.41714 | 0.06858 | 1 | 1 |
| 930 | chr14 | 101597000 | 101598099 | 0.000 | 0.000 | 0.000 | 0.027 | AL117190.3 | 0.49735 | 1.00000 | 1.00000 | 0 | 0 |
| 931 | chr14 | 102285000 | 102286009 | 0.000 | 0.000 | 0.015 | 0.014 | PPP2R5C | 1.00000 | 1.00000 | 0.29694 | 0 | 0 |
| 932 | chr14 | 105954000 | 105955000 | 0.000 | 0.000 | 0.044 | 0.014 | CRIP1 | 0.34948 | 0.54966 | 0.02537 | 0 | 0 |
| 933 | chr14 | 196031990 | 106032000 | 0.000 | 0.000 | 0.015 | 0.014 | IGHA2 | 1.00000 | 1.00000 | 0.29694 | 0 | 0 |
| 934 | chr14 | 196042990 | 106043000 | 0.000 | 0.019 | 0.193 | 0.041 | IGHA2 | 0.19468 | 0.09269 | 0.00855 | 0 | 1 |
| 935 | chr14 | 196048990 | 106649000 | 0.000 | 0.006 | 0.015 | 0.000 | IGHA2 | 0.47887 | 1.00000 | 0.50663 | 0 | 0 |
| 936 | chr14 | 106054000 | 106055090 | 0.000 | 0.000 | 0.029 | 0.014 | IGHA2 | 0.60686 | 0.54294 | 0.08726 | 0 | 0 |
| 937 | chr14 | 106955009 | 106956099 | 0.056 | 0.000 | 0.103 | 0.027 | IGHA2 | 0.08710 | 0.49207 | 0.00916 | 0 | 1 |
| 938 | chr14 | 106956009 | 106957099 | 0.056 | 0.006 | 0.074 | 0.027 | IGHA2 | 0.25970 | 1.00000 | 0.00953 | 0 | 1 |
| 939 | chr14 | 106057000 | 106958009 | 0.000 | 0.000 | 0.059 | 0.000 | IGHA2 | 0.05016 | 0.29551 | 0.00730 | 0 | 1 |
| 949 | chr14 | 106058000 | 106059000 | 0.000 | 0.000 | 0.029 | 0.000 | IGHA2 | 0.22755 | 0.54294 | 0.08726 | 0 | 0 |
| 941 | chr14 | 196066990 | 106067000 | 0.000 | 0.000 | 0.059 | 0.000 | IGHE | 0.05016 | 0.29551 | 0.00730 | 0 | 1 |
| 942 | chr14 | 196067990 | 106068000 | 0.000 | 0.000 | 0.044 | 0.014 | IGHE | 0.34948 | 0.54966 | 0.02537 | 0 | 0 |
| 943 | chr14 | 106068000 | 106069000 | 0.000 | 0.000 | 0.103 | 0.027 | IGHE | 0.08710 | 0.09269 | 0.00016 | 0 | 1 |
| 944 | chr14 | 106069000 | 106070000 | 0.000 | 0.006 | 0.206 | 0.216 | IGHE | 1.00000 | 0.00197 | 0.00000 | 0 | 1 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 945 | chr14 | 106070000 | 106971009 | 0.000 | 0.000 | 0.088 | 0.068 | IGHE | 0.75773 | 0.09031 | 0.00958 | 0 | 1 |
| 946 | chr14 | 106971000 | 106972099 | 0.000 | 0.000 | 0.074 | 0.068 | IGHE | 1.00000 | 0.16101 | 0.00298 | 0 | 1 |
| 947 | chr14 | 106072000 | 106973009 | 0.000 | 0.000 | 0.029 | 0.014 | IGHE | 0.60686 | 0.54294 | 0.08726 | 0 | 0 |
| 948 | chr14 | 106082000 | 106083000 | 0.000 | 0.000 | 0.015 | 0.027 | IGHG4 | 1.00009 | 1.00000 | 0.29694 | 0 | 0 |
| 949 | chr14 | 196092990 | 106093900 | 0.000 | 0.000 | 0.029 | 0.000 | IGHG4 | 0.22755 | 0.54294 | 0.08726 | 0 | 0 |
| 950 | chr14 | 196094990 | 106095900 | 0.000 | 0.006 | 0.147 | 0.027 | IGHG4 | 0.01393 | 0.01494 | 0.00003 | 0 | 1 |
| 951 | chr14 | 196095090 | 106096900 | 0.000 | 0.000 | 0.103 | 0.081 | IGHG4 | 0.77363 | 0.09269 | 0.00016 | 0 | 1 |
| 952 | chr14 | 106110000 | 106111000 | 0.000 | 0.000 | 0.074 | 0.014 | IGHG2 | 0.10420 | 0.16101 | 0.00208 | 0 | 1 |
| 953 | chr14 | 106111000 | 106112009 | 0.000 | 0.000 | 0.015 | 0.014 | IGHG2 | 1.00000 | 1.00000 | 0.29694 | 0 | 0 |
| 954 | chr14 | 106112000 | 106113699 | 0.000 | 0.056 | 0.294 | 0.257 | IGHG2 | 0.70749 | 0.90011 | 0.00000 | 0 | 1 |
| 955 | chr14 | 106113000 | 106114009 | 0.028 | 0.068 | 0.397 | 0.284 | IGHG2 | 0.16121 | 0.00002 | 0.00000 | 0 | 1 |
| 956 | chr14 | 106114000 | 106115000 | 0.000 | 0.000 | 0.279 | 0.122 | IGHG2 | 0.02111 | 0.00013 | 0.00000 | 0 | 1 |
| 957 | chr14 | 196146990 | 106147900 | 0.000 | 0.000 | 0.029 | 0.000 | IGHA1 | 0.22755 | 0.54294 | 0.08726 | 0 | 0 |
| 958 | chr14 | 196151990 | 106152900 | 0.000 | 0.006 | 0.015 | 0.014 | IGHA1 | 1.00000 | 1.00000 | 0.50663 | 0 | 0 |
| 959 | chr14 | 196152090 | 106153900 | 0.000 | 0.006 | 0.015 | 0.027 | IGHA1 | 1.00000 | 1.00000 | 0.50663 | 0 | 0 |
| 960 | chr14 | 106161000 | 106162000 | 0.000 | 0.000 | 0.015 | 0.014 | IGHA1 | 1.00000 | 1.00000 | 0.29694 | 0 | 0 |
| 961 | chr14 | 106173000 | 106174009 | 0.028 | 0.006 | 0.029 | 0.027 | IGHA1 | 1.00000 | 1.00000 | 0.21104 | 0 | 0 |
| 962 | chr14 | 106174000 | 106175000 | 0.000 | 0.006 | 0.029 | 0.000 | IGHA1 | 0.22755 | 0.54294 | 0.21104 | 0 | 0 |
| 963 | chr14 | 106175000 | 106176000 | 0.028 | 0.006 | 0.059 | 0.014 | IGHA1 | 0.19371 | 0.65667 | 0.02818 | 0 | 1 |
| 964 | chr14 | 106176000 | 106177000 | 0.139 | 0.031 | 0.103 | 0.068 | IGHA1 | 0.55139 | 0.74810 | 0.04551 | 0 | 1 |
| 965 | chr14 | 106177000 | 106178000 | 0.000 | 0.019 | 0.059 | 0.027 | IGHA1 | 0.42627 | 0.29551 | 0.20027 | 0 | 1 |
| 966 | chr14 | 106178000 | 106179000 | 0.000 | 0.006 | 0.059 | 0.014 | IGHA1 | 0.19371 | 0.29551 | 0.02818 | 0 | 1 |
| 967 | chr14 | 106208000 | 106209000 | 0.000 | 0.000 | 0.103 | 0.027 | IGHG1 | 0.08710 | 0.09269 | 0.00016 | 0 | 1 |
| 968 | chr14 | 106209000 | 106210000 | 0.000 | 0.006 | 0.118 | 0.054 | IGHG1 | 0.23086 | 0.04825 | 0.00030 | 0 | 1 |
| 969 | chr14 | 106210000 | 106211000 | 0.000 | 0.000 | 0.118 | 0.068 | IGHG1 | 0.38669 | 0.04825 | 0.00004 | 0 | 1 |
| 970 | chr14 | 106211000 | 106212000 | 0.000 | 0.056 | 0.235 | 0.149 | IGHG1 | 0.20587 | 0.00098 | 0.00025 | 0 | 1 |
| 971 | chr14 | 106212000 | 106213000 | 0.028 | 0.106 | 0.309 | 0.270 | IGHG1 | 0.71144 | 0.00070 | 0.00035 | 0 | 1 |
| 972 | chr14 | 106213000 | 106214000 | 0.056 | 0.068 | 0.382 | 0.216 | IGHG1 | 0.04243 | 0.00034 | 0.00000 | 0 | 1 |
| 973 | chr14 | 106214000 | 106215000 | 0.000 | 0.000 | 0.147 | 0.000 | IGHG1 | 0.00044 | 0.01404 | 0.00000 | 0 | 1 |
| 974 | chr14 | 106237000 | 106238000 | 0.000 | 0.000 | 0.088 | 0.000 | IGHG3 | 0.01070 | 0.09031 | 0.00058 | 0 | 1 |
| 975 | chr14 | 106238000 | 106239000 | 0.000 | 0.000 | 0.176 | 0.027 | IGHG3 | 0.00370 | 0.00730 | 0.00000 | 0 | 1 |
| 976 | chr14 | 106239000 | 106240000 | 0.056 | 0.062 | 0.206 | 0.135 | IGHG3 | 0.27339 | 0.04910 | 0.00349 | 0 | 1 |
| 977 | chr14 | 106240000 | 106241000 | 0.028 | 0.130 | 0.324 | 0.230 | IGHG3 | 0.25971 | 0.00034 | 0.00136 | 0 | 1 |
| 978 | chr14 | 106241000 | 106242000 | 0.000 | 0.025 | 0.221 | 0.081 | IGHG3 | 0.03144 | 0.00107 | 0.00000 | 0 | 1 |
| 979 | chr14 | 106242000 | 106243000 | 0.000 | 0.000 | 0.044 | 0.014 | IGHG3 | 0.34948 | 0.54966 | 0.02537 | 0 | 0 |
| 980 | chr14 | 106321000 | 106322000 | 0.000 | 0.000 | 0.059 | 0.000 | IGHM | 0.05016 | 0.29551 | 0.00730 | 0 | 1 |
| 981 | chr14 | 106322000 | 106323000 | 0.000 | 0.006 | 0.221 | 0.054 | IGHM | 0.00556 | 0.00107 | 0.00000 | 0 | 1 |
| 982 | chr14 | 106323000 | 106324000 | 0.056 | 0.062 | 0.235 | 0.162 | IGHM | 0.29797 | 0.02782 | 0.00040 | 0 | 1 |
| 983 | chr14 | 106324000 | 106325000 | 0.250 | 0.193 | 0.221 | 0.284 | IGHM | 0.44266 | 0.80827 | 0.71834 | 0 | 1 |
| 984 | chr14 | 106325000 | 106326000 | 0.694 | 0.335 | 0.279 | 0.365 | IGHM | 0.28848 | 0.00006 | 0.44111 | 0 | 1 |
| 985 | chr14 | 106326000 | 106327000 | 0.833 | 0.540 | 0.838 | 0.838 | IGHJ6 | 1.00000 | 1.00000 | 0.00001 | 0 | 1 |
| 986 | chr14 | 106327000 | 106328000 | 0.333 | 0.335 | 0.926 | 0.905 | IGHJ6 | 0.76698 | 0.00000 | 0.00000 | 0 | 1 |
| 987 | chr14 | 106328000 | 106329000 | 0.250 | 0.248 | 0.809 | 0.730 | IGHJ6 | 0.32171 | 0.00000 | 0.00000 | 0 | 1 |
| 988 | chr14 | 106329000 | 106330000 | 0.694 | 0.441 | 0.882 | 0.932 | IGHJ6 | 0.38669 | 0.03086 | 0.00000 | 0 | 1 |
| 989 | chr14 | 106330000 | 106331000 | 0.694 | 0.298 | 0.574 | 0.649 | IGHJ3; IGHJ4; IGHJ5; | 0.39187 | 0.29080 | 0.00017 | 0 | 1 |
| 990 | chr14 | 106331000 | 106332000 | 0.028 | 0.012 | 0.044 | 0.027 | IGHD7-27; IGHJ1; IGHJ2; | 0.67043 | 1.00000 | 0.15671 | 0 | 0 |
| 991 | chr14 | 106338000 | 106339000 | 0.028 | 0.006 | 0.000 | 0.000 | IGHD7-27 | 1.00000 | 0.34615 | 1.00000 | 0 | 0 |
| 992 | chr14 | 106350000 | 106351000 | 0.000 | 0.006 | 0.029 | 0.000 | IGHD4-23 | 0.22755 | 0.54294 | 0.21104 | 0 | 0 |
| 993 | chr14 | 106352000 | 106353000 | 0.000 | 0.000 | 0 029 | 0.000 | IGHD3-22 | 0.22755 | 0.54294 | 0.08726 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 994 | chr14 | 106353000 | 106354000 | 0.000 | 0.006 | 0.029 | 0.000 | IGHD2-21 | 0.22755 | 0.54294 | 0.21104 | 0 | 0 |
| 995 | chr14 | 106354000 | 106355000 | 0.000 | 0.006 | 0.015 | 0.000 | IGHD2-21 | 0.47887 | 1.00000 | 0.50663 | 0 | 0 |
| 996 | chr14 | 106355000 | 106356000 | 0.000 | 0.000 | 0.044 | 0.000 | IGHD2-21 | 0.10727 | 0.54966 | 0.02537 | 0 | 0 |
| 997 | chr14 | 106357000 | 106358000 | 0.028 | 0.000 | 0.059 | 0.000 | IGHD1-20; IGHD6-19; | 0.05016 | 0.65667 | 0.00730 | 0 | 1 |
| 998 | chr14 | 106358000 | 106359000 | 0.000 | 0.006 | 0.029 | 0.000 | IGHD5-18 | 0.22755 | 0.54294 | 0.21104 | 0 | 0 |
| 999 | chr14 | 106362000 | 106363000 | 0.028 | 0.006 | 0.000 | 0.000 | IGHD3-16 | 1.00000 | 0.34615 | 1.00000 | 0 | 0 |
| 1000 | chr14 | 106364000 | 106365000 | 0.000 | 0.000 | 0.029 | 0.000 | IGHD2-15 | 0.22755 | 0.54294 | 0.08726 | 0 | 0 |
| 1001 | chr14 | 106367000 | 106368000 | 0.000 | 0.000 | 0.029 | 0.000 | IGHD6-13 | 0.22755 | 0.54294 | 0.08726 | 0 | 0 |
| 1002 | chr14 | 106370000 | 106371000 | 0.000 | 0.012 | 0.044 | 0.014 | IGHD3-10; IGHD3-9; | 0.34948 | 0.54966 | 0.15671 | 0 | 0 |
| 1003 | chr14 | 106371000 | 106372000 | 0.000 | 0.012 | 0.029 | 0.014 | IGHD3-9 | 0.60686 | 0.54294 | 0.58408 | 0 | 0 |
| 1004 | chr14 | 106372000 | 106373000 | 0.000 | 0.006 | 0.015 | 0.000 | IGHD2-8 | 0.47887 | 1.00000 | 0.50663 | 0 | 0 |
| 1005 | chr14 | 106375000 | 106376000 | 0.000 | 0.019 | 0.015 | 0.000 | IGHD1-7 | 0.47887 | 1.00000 | 1.00000 | 0 | 0 |
| 1006 | chr14 | 106376000 | 106377000 | 0.000 | 0.012 | 0.015 | 0.000 | IGHD6-6 | 0.47887 | 1.00000 | 1.00000 | 0 | 0 |
| 1007 | chr14 | 106380000 | 106381000 | 0.000 | 0.031 | 0.000 | 0.000 | IGHD3-3 | 1.00000 | 1.00000 | 0.32529 | 0 | 0 |
| 1008 | chr14 | 106381000 | 106382000 | 0.000 | 0.031 | 0.000 | 0.000 | IGHD2-2 | 1.00000 | 1.00000 | 0.32529 | 0 | 0 |
| 1009 | chr14 | 106382000 | 106383000 | 0.000 | 0.037 | 0.044 | 0.014 | IGHD2-2 | 0.34948 | 0.54966 | 0.72719 | 0 | 0 |
| 1010 | chr14 | 106383000 | 106384000 | 0.000 | 0.000 | 0.044 | 0.014 | IGHD2-2 | 0.34948 | 0.54966 | 0.02537 | 0 | 0 |
| 1011 | chr14 | 106384000 | 106385000 | 0.000 | 0.012 | 0.044 | 0.014 | IGHD1-1 | 0.34948 | 0.54966 | 0.15671 | 0 | 0 |
| 1012 | chr14 | 106385000 | 106386000 | 0.000 | 0.000 | 0.029 | 0.014 | IGHD1-1 | 0.60686 | 0.54294 | 0.08726 | 0 | 0 |
| 1013 | chr14 | 106387000 | 106388000 | 0.000 | 0.000 | 0.029 | 0.014 | KIAA0125 | 0.60686 | 0.54294 | 0.08726 | 0 | 0 |
| 1014 | chr14 | 106405000 | 106406000 | 0.000 | 0.006 | 0.015 | 0.014 | IGHV6-1 | 1.00000 | 1.00000 | 0.50663 | 0 | 0 |
| 1015 | chr14 | 106406000 | 106407000 | 0.000 | 0.006 | 0.015 | 0.014 | IGHV6-1 | 1.00000 | 1.00000 | 0.50663 | 0 | 0 |
| 1016 | chr14 | 106419000 | 106420000 | 0.000 | 0.006 | 0.015 | 0.000 | IGHV6-1 | 0.47887 | 1.00000 | 0.50663 | 0 | 0 |
| 1017 | chr14 | 106452000 | 106453000 | 0.000 | 0.006 | 0.029 | 0.000 | IGHV1-2 | 0.22755 | 0.54294 | 0.21104 | 0 | 0 |
| 1018 | chr14 | 106453000 | 106454000 | 0.000 | 0.006 | 0.044 | 0.000 | IGHV1-2 | 0.10727 | 0.54966 | 0.07959 | 0 | 0 |
| 1019 | chr14 | 106454000 | 106455000 | 0.000 | 0.000 | 0.029 | 0.000 | IGHV1-2 | 0.22755 | 0.54294 | 0.08726 | 0 | 0 |
| 1020 | chr14 | 106494000 | 106495000 | 0.000 | 0.019 | 0.000 | 0.014 | IGHV2-5 | 1.00000 | 1.00000 | 0.55662 | 0 | 0 |
| 1021 | chr14 | 106518000 | 106519000 | 0.028 | 0.037 | 0.000 | 0.054 | IGHV3-7 | 0.12104 | 0.34615 | 0.18288 | 0 | 1 |
| 1022 | chr14 | 106519000 | 106520000 | 0.000 | 0.012 | 0.000 | 0.027 | IGHV3-7 | 0.49735 | 1.00000 | 1.00000 | 0 | 0 |
| 1023 | chr14 | 106539000 | 106540000 | 0.000 | 0.031 | 0.015 | 0.000 | IGHV1-8 | 0.47887 | 1.00000 | 0.67240 | 0 | 0 |
| 1024 | chr14 | 106552000 | 106553000 | 0.000 | 0.006 | 0.029 | 0.014 | IGHV3-9 | 0.60686 | 0.54294 | 0.21104 | 0 | 0 |
| 1025 | chr14 | 106573000 | 106574000 | 0.000 | 0.019 | 0.029 | 0.068 | IGHV3-11 | 0.44431 | 0.54294 | 0.63492 | 0 | 1 |
| 1026 | chr14 | 106574000 | 106575000 | 0.000 | 0.006 | 0.029 | 0.041 | IGHV3-11 | 1.00000 | 0.54294 | 0.21104 | 0 | 0 |
| 1027 | chr14 | 106578000 | 106579000 | 0.000 | 0.000 | 0.015 | 0.027 | IGHV3-11 | 1.00000 | 1.00000 | 0.29694 | 0 | 0 |
| 1028 | chr14 | 106579000 | 106580000 | 0.000 | 0.000 | 0.015 | 0.027 | IGHV3-11 | 1.00000 | 1.00000 | 0.29694 | 0 | 0 |
| 1029 | chr14 | 106610000 | 106611000 | 0.056 | 0.012 | 0.029 | 0.000 | IGHV3-15 | 0.22755 | 0.60763 | 0.58408 | 0 | 1 |
| 1030 | chr14 | 106641000 | 106642000 | 0.000 | 0.019 | 0.015 | 0.000 | IGHV1-18 | 0.47887 | 1.00000 | 1.00000 | 0 | 0 |
| 1031 | chr14 | 106642000 | 106643000 | 0.000 | 0.012 | 0.015 | 0.000 | IGHV1-18 | 0.47887 | 1.00000 | 1.00000 | 0 | 0 |
| 1032 | chr14 | 106691000 | 106692000 | 0.000 | 0.012 | 0.029 | 0.027 | IGHV3-21 | 1.00 000 | 0.54294 | 0.58408 | 0 | 0 |
| 1033 | chr14 | 106692000 | 106693000 | 0.000 | 0.006 | 0.015 | 0.041 | IGHV3-2 1 | 0.62100 | 1.00000 | 0.50663 | 0 | 0 |
| 1034 | chr14 | 106725000 | 106726000 | 0.083 | 0.068 | 0.103 | 0.135 | IGHV3-23 | 0.61250 | 1.00000 | 0.42238 | 0 | I |
| 1035 | chr14 | 106726000 | 106727000 | 0.028 | 0.019 | 0.088 | 0.095 | IGHV3-23 | 1.00000 | 0.41714 | 0.02173 | 0 | 1 |
| 1036 | chr14 | 106733000 | 106734000 | 0.028 | 0.006 | 0.015 | 0.027 | IGHV1-24 | 1.00000 | 1.00000 | 0.50663 | 0 | 0 |
| 1037 | chr14 | 106757000 | 106758000 | 0.056 | 0.000 | 0.015 | 0.000 | IGHV2-26 | 0.47887 | 0.27446 | 0.29694 | 0 | 1 |
| 1038 | chr14 | 106758000 | 106759000 | 0.056 | 0.000 | 0.000 | 0.000 | IGHV2-26 | 1.00000 | 0.11763 | 1.00000 | 0 | 1 |
| 1039 | chr14 | 106791000 | 106792000 | 0.056 | 0.006 | 0.015 | 0.000 | IGHV3-30 | 0.47887 | 0.27446 | 0.50663 | 0 | I |
| 1040 | chr14 | 106804000 | 106805000 | 0.000 | 0.006 | 0.029 | 0.000 | IGHV4-31 | 0.22755 | 0.54294 | 0.21104 | 0 | 0 |
| 1041 | chr14 | 106805000 | 106806000 | 0.000 | 0.006 | 0.044 | 0.014 | IGHV4-31 | 0.34948 | 0.54966 | 0.07959 | 0 | 0 |
| 1042 | chr14 | 106806000 | 106807000 | 0.000 | 0.006 | 0.015 | 0.000 | IGHV4-31 | 0.47887 | 1.00000 | 0.50663 | 0 | 0 |
| 1043 | chr14 | 106815000 | 106816000 | 0.000 | 0.012 | 0.044 | 0.027 | IGHV3-33 | 0.67043 | 0.54966 | 0.15671 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 1044 | chr14 | 106816000 | 106817000 | 0.000 | 0.006 | 0.074 | 0.014 | IGHV3-33 | 0.10420 | 0.16101 | 0.00953 | 0 | 1 |
| 1045 | chr14 | 106817000 | 106818000 | 0.000 | 0.000 | 0.029 | 0.000 | IGHV3-33 | 0.22755 | 0.54294 | 0.08726 | 0 | 0 |
| 1046 | chr14 | 106829000 | 106830000 | 0.167 | 0.050 | 0.162 | 0.135 | IGHV4-34 | 0.81354 | 1.00000 | 0.00804 | 0 | 1 |
| 1047 | chr14 | 106830000 | 106831000 | 0.028 | 0.043 | 0.118 | 0.135 | IGHV4-34 | 0.80514 | 0.15803 | 0.07447 | 0 | I |
| 1048 | chr14 | 106877000 | 106878000 | 0.056 | 0.006 | 0.015 | 0.041 | IGHV4-39 | 0.62100 | 0.27446 | 0.50663 | 0 | 1 |
| 1049 | chr14 | 106878000 | 106879000 | 0.028 | 0.012 | 0.044 | 0.041 | IGHV4-39 | 1.00000 | 1.00000 | 0.15671 | 0 | 0 |
| 1050 | chr14 | 106967000 | 106968000 | 0.056 | 0.000 | 0.015 | 0.000 | IGHV1-46 | 0.47887 | 0.27446 | 0.29694 | 0 | I |
| 1051 | chr14 | 106994000 | 106995000 | 0.028 | 0.012 | 0.088 | 0.122 | IGHV3-48 | 0.59201 | 0.41714 | 0.00949 | 0 | 1 |
| 1052 | chr14 | 106995000 | 106996000 | 0.000 | 0.000 | 0.000 | 0.027 | IGHV3-48 | 0.49735 | 1.00000 | 1.00000 | 0 | 0 |
| 1053 | chr14 | 107034000 | 107035000 | 0.028 | 0.000 | 0.000 | 0.014 | IGHV5-51 | 1.00000 | 0.34615 | 1.00000 | 0 | 0 |
| 1054 | chr14 | 107035000 | 107036000 | 0.000 | 0.006 | 0.029 | 0.014 | IGHV5-51 | 0.60686 | 0.54294 | 0.21104 | 0 | 0 |
| 1055 | chr14 | 107048000 | 107049000 | 0.028 | 0.006 | 0.000 | 0.000 | IGHV3-53 | 1.00000 | 0.34615 | 1.00000 | 0 | 0 |
| 1056 | chr14 | 107049000 | 107650000 | 0.000 | 0.012 | 0.044 | 0.027 | IGHV3-53 | 0.67043 | 0.54966 | 0.15671 | 0 | 0 |
| 1057 | chr14 | 107083000 | 107084000 | 0.000 | 0.006 | 0.044 | 0.054 | IGHV4-59 | 1.00000 | 0.54966 | 0.07959 | 0 | 1 |
| 1058 | chr14 | 107084000 | 107085000 | 0.000 | 0.006 | 0.029 | 0.027 | IGHV4-59 | 1.00000 | 0.54294 | 0.21104 | 0 | 0 |
| 1059 | chr14 | 107095000 | 107096000 | 0.000 | 0.006 | 0.015 | 0.000 | IGHV4-61 | 0.47887 | 1.00000 | 0.50663 | 0 | 0 |
| 1060 | chr14 | 107113000 | 107114000 | 0.000 | 0.000 | 0.029 | 0.000 | IGHV3-64 | 0.22755 | 0.54294 | 0.08726 | 0 | 0 |
| 1061 | chr14 | 107114000 | 107115000 | 0.000 | 0.000 | 0.029 | 0.000 | IGHV3-64 | 0.22755 | 0.54294 | 0.08726 | 0 | 0 |
| 1062 | chr14 | 107169000 | 107170000 | 0.056 | 0.068 | 0.206 | 0.041 | IGHV1-69 | 0.00346 | 0.04910 | 0.00442 | 0 | 1 |
| 1063 | chr14 | 107170000 | 107173000 | 0.028 | 0.075 | 0.294 | 0.095 | IGHV1-69 | 0.00279 | 0.00075 | 0.00004 | 0 | 1 |
| 1064 | chr14 | 107176000 | 107177000 | 0.028 | 0.006 | 0.118 | 0.027 | IGHV2-70 | 0.04838 | 0.15803 | 0.00930 | 0 | 1 |
| 1065 | chr14 | 107177000 | 107178000 | 0.000 | 0.000 | 0.044 | 0.027 | IGHV2-70 | 0.67043 | 0.54966 | 0.02537 | 0 | 0 |
| 1066 | chr14 | 107178000 | 107179000 | 0.056 | 0.161 | 0.456 | 0.284 | IGHV2-70 | 0.03781 | 0.00002 | 0.00001 | 0 | 1 |
| 1067 | chr14 | 107179000 | 107180000 | 0.056 | 0.380 | 0.382 | 0.338 | IGHV2-70 | 0.60350 | 0.00034 | 0.00206 | 0 | 1 |
| 1068 | chr14 | 107183000 | 107384000 | 0.000 | 0.006 | 0.029 | 0.000 | IGHV2-70 | 0.22755 | 0.54294 | 0.21104 | 0 | 0 |
| 1069 | chr14 | 107199000 | 107200000 | 0.000 | 0.012 | 0.015 | 0.090 | IGHV3-72 | 0.47887 | 1.00000 | 1.00000 | 0 | 0 |
| 1070 | chr14 | 107218000 | 107219000 | 0.028 | 0.012 | 0.015 | 0.000 | IGHV3-74 | 0.47887 | 1.00000 | 1.00000 | 0 | 0 |
| 1071 | chr14 | 107219000 | 107220000 | 0.000 | 0.012 | 0.074 | 0.027 | IGHV3-74 | 0.25970 | 0.16101 | 0.02559 | 0 | 1 |
| 1072 | chr14 | 107221000 | 107222000 | 0.000 | 0.000 | 0.059 | 0.000 | IGHV3-74 | 0.05016 | 0.29551 | 0.00730 | 0 | 1 |
| 1073 | chr14 | 107232000 | 107233000 | 0.000 | 0.000 | 0.029 | 0.000 | IGHV3-74 | 0.22755 | 9.54294 | 0.08726 | 0 | 0 |
| 1074 | chr14 | 107253000 | 107254000 | 0.000 | 0.000 | 0.044 | 0.014 | IGHV7-81 | 0.34948 | 0.54966 | 0.02537 | 0 | 0 |
| 1075 | chr14 | 107258000 | 107259000 | 0.000 | 0.000 | 0.015 | 0.014 | IGHV7-81 | 1.00000 | 1.00000 | 0.29694 | 0 | 0 |
| 1076 | chr14 | 107259000 | 107260000 | 0.000 | 0.025 | 0.235 | 0.027 | IGHV7-81 | 0.00021 | 0.00998 | 0.00000 | 0 | 1 |
| 1077 | chr15 | 45003000 | 45004000 | 0.000 | 0.000 | 0.044 | 0.000 | B2M | 0.10727 | 0.54966 | 0.02537 | 0 | 0 |
| 1078 | chr15 | 45007000 | 45008000 | 0.000 | 0.000 | 0.044 | 0.000 | B2M | 0.10727 | 0.54966 | 0.02537 | 0 | 0 |
| 1079 | chr15 | 45814000 | 45815000 | 0.000 | 0.000 | 0.015 | 0.014 | SLC30A4 | 1.00000 | 1.00000 | 0.29694 | 0 | 0 |
| 1080 | chr15 | 59664000 | 59665000 | 0.000 | 0.000 | 0.044 | 0.041 | MYO1E | 1.00000 | 0.54966 | 0.02537 | 0 | 0 |
| 1081 | chr15 | 65588000 | 65589000 | 0.028 | 0.000 | 0.000 | 0.014 | PARP16 | 1.00000 | 0.34615 | 1.00000 | 0 | 0 |
| 1082 | chr15 | 78332000 | 78333000 | 0.028 | 0.000 | 0.000 | 0.014 | TBC1D2B | 1.00000 | 0.34615 | 1.00000 | 0 | 0 |
| 1083 | chr15 | 83227000 | 83228000 | 0.000 | 0.000 | 0.029 | 0.000 | CPEB1 | 0.22755 | 0.54294 | 0.08726 | 0 | 0 |
| 1084 | chr15 | 86226000 | 86227000 | 0.000 | 0.000 | 0.044 | 0.000 | AKAP13 | 0.10727 | 0.54966 | 0.02537 | 0 | 0 |
| 1085 | chr15 | 86233000 | 86234000 | 0.000 | 0.000 | 0.029 | 0.014 | AKAP13 | 0.60686 | 0.54294 | 0.98726 | 0 | 0 |
| 1086 | chr15 | 86245000 | 86246000 | 0.000 | 0.000 | 0.059 | 0.000 | AKAP13 | 0.05016 | 0.29551 | 0.90730 | 0 | 1 |
| 1087 | chr16 | 368000 | 369000 | 0.000 | 0.000 | 0.015 | 0.014 | AXIN1 | 1.00000 | 1.00000 | 0.29694 | 0 | 0 |
| 1088 | chr16 | 3788000 | 3789000 | 0.000 | 0.000 | 0.015 | 0.014 | CREBBP | 1.00000 | 1.00000 | 0.29694 | 0 | 0 |
| 1089 | chr16 | 10971000 | 10972000 | 0.000 | 0.000 | 0.162 | 0.041 | CIITA | 0.02233 | 0.01471 | 0.00000 | 1 | 1 |
| 1090 | chr16 | 10972000 | 10973000 | 0.000 | 0.000 | 0.191 | 0.081 | CIITA | 0.08249 | 0.00372 | 0.00000 | 1 | 1 |
| 1091 | chr16 | 10973000 | 10974000 | 0.000 | 0.000 | 0.162 | 0.095 | CIITA | 0.31342 | 0.01471 | 0.00000 | 1 | 1 |
| 1092 | chr16 | 10974000 | 10975000 | 0.000 | 0.000 | 0.059 | 0.000 | CIITA | 0.05016 | 0.29551 | 0.00730 | 1 | 1 |
| 1093 | chr16 | 11348000 | 11349000 | 0.000 | 0.000 | 0.191 | 0.027 | SOCS1 | 0.00186 | 0.00372 | 0.00000 | 1 | 1 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 1094 | chr16 | 11349000 | 11350000 | 0.000 | 0.000 | 0.221 | 0.041 | SOCS1 | 0.00179 | 0.00107 | 0.00000 | 1 | 1 |
| 1095 | chr16 | 21167000 | 21168000 | 0.000 | 0.000 | 0.015 | 0.014 | DNAH3 | 1.00000 | 1.00000 | 0.29694 | 0 | 0 |
| 1096 | chr16 | 27325000 | 27326000 | 0.000 | 0.000 | 0.029 | 0.041 | CTD-3203P2.2 | 1.00000 | 0.54294 | 0.08726 | 0 | 0 |
| 1097 | chr16 | 27326000 | 27327000 | 0.000 | 0.000 | 0.088 | 0.041 | CTD-3203P2.2 | 0.31126 | 0.09031 | 0.00958 | 0 | 1 |
| 1098 | chr16 | 27327000 | 27328000 | 0.000 | 0.000 | 0.029 | 0.000 | IL4R | 0.22755 | 0.54294 | 0.08726 | 0 | 0 |
| 1099 | chr16 | 27434000 | 27415000 | 0.000 | 0.000 | 0.029 | 0.000 | IL21R | 0.22755 | 0.54294 | 0.08726 | 0 | 0 |
| 1100 | chr16 | 29248000 | 29249000 | 0.000 | 0.000 | 0.029 | 0.000 | 61E3.4 | 0.22755 | 0.54294 | 0.08726 | 0 | 0 |
| 1101 | chr16 | 31910000 | 31911000 | 0.000 | 0.000 | 0.015 | 0.014 | ZNF267 | 1.00000 | 1.00000 | 0.29694 | 0 | 0 |
| 1102 | chr16 | 46821000 | 46822000 | 0.000 | 0.000 | 0.015 | 0.014 | C16orf87 | 1.00000 | 1.00000 | 0.29694 | 0 | 0 |
| 1103 | chr16 | 50985000 | 50986000 | 0.000 | 0.000 | 0.035 | 0.014 | CYLD | 1.00000 | 1.00000 | 0.29694 | 0 | 0 |
| 1104 | chr16 | 64351000 | 64352000 | 0.000 | 0.000 | 0.029 | 0.014 | CDH11 | 0.60686 | 0.54294 | 0.08726 | 0 | 0 |
| 1105 | chr16 | 78398000 | 78399000 | 0.000 | 0.000 | 0.000 | 0.027 | WWOX | 0.49735 | 1.00000 | 1.00990 | 0 | 0 |
| 1106 | chr16 | 78615000 | 78616000 | 0.000 | 0.000 | 0.015 | 0.014 | WWOX | 1.00000 | 1.00000 | 0.29694 | 0 | 0 |
| 1107 | chr16 | 78753000 | 78754000 | 0.000 | 0.000 | 0.015 | 0.014 | WWOX | 1.00000 | 1.00000 | 0.29694 | 0 | 0 |
| 1108 | chr16 | 78833000 | 78812000 | 0.000 | 0.000 | 0.000 | 0.027 | WWOX | 0.49735 | 1.00000 | 1.00000 | 0 | 0 |
| 1109 | chr16 | 79988000 | 79989000 | 0.000 | 0.000 | 0.015 | 0.014 | MAF | 1.00000 | 1.00000 | 0.29694 | 0 | 0 |
| 1110 | chr16 | 81836000 | 81837000 | 0.000 | 0.000 | 0.029 | 0.000 | PLCG2 | 0.22755 | 0.54294 | 0.08726 | 0 | 0 |
| 1111 | chr16 | 85932000 | 85933000 | 0.000 | 0.000 | 0.059 | 0.027 | IRF8 | 0.42627 | 0.29551 | 0.00730 | 1 | 1 |
| 1112 | chr16 | 85933000 | 85934000 | 0.000 | 0.012 | 0.223 | 0.083 | IRF8 | 0.03144 | 0.00107 | 0.00000 | 1 | 1 |
| 1113 | chr16 | 85934000 | 85935000 | 0.000 | 0.006 | 0.015 | 0.027 | IRF8 | 1.00900 | 1.00000 | 0.50663 | 1 | 0 |
| 1114 | chr16 | 85936000 | 85937000 | 0.000 | 0.000 | 0.029 | 0.000 | IRF8 | 0.22755 | 0.54294 | 0.08726 | 1 | 0 |
| 1115 | chr16 | 88441000 | 88442000 | 0.000 | 0.000 | 0.015 | 0.014 | ZNF469 | 1.00000 | 1.00000 | 0.29694 | 0 | 0 |
| 1116 | chr17 | 3598000 | 3599000 | 0.000 | 0.000 | 0.029 | 0.014 | P2RX5; P2RX5-TAX1BP3P2RX5; | 0.60686 | 0.54294 | 0.08726 | 0 | 0 |
| 1117 | chr17 | 37286000 | 37287000 | 0.000 | 0.000 | 0.029 | 0.000 | SMCR9 | 0.22755 | 0.54294 | 0.08726 | 0 | 0 |
| 1118 | chr17 | 23194000 | 21195000 | 0.000 | 0.000 | 0.015 | 0.041 | MAP2K3 | 0.62100 | 1.00000 | 0.29694 | 0 | 0 |
| 1119 | chr17 | 29646000 | 29647000 | 0.000 | 0.000 | 0.029 | 0.014 | EVI2A | 0.60686 | 0.54294 | 0.08726 | 0 | 0 |
| 1120 | chr17 | 38020000 | 38021000 | 0.000 | 0.000 | 0.029 | 0.014 | IKZF3 | 0.60686 | 0.54294 | 0.08726 | 0 | 0 |
| 1121 | chr17 | 43662000 | 43663000 | 0.000 | 0.000 | 0.029 | 0.000 | PLEKHM1 | 0.22755 | 0.54294 | 0.08726 | 0 | 0 |
| 1122 | chr17 | 56408000 | 56409000 | 0.000 | 0.006 | 0.059 | 0.027 | BZRAP1 | 0.42627 | 0.29551 | 0.02818 | 0 | 1 |
| 1123 | chr17 | 56409000 | 56410000 | 0.000 | 0.000 | 0.265 | 0.027 | BZRAP1 | 0.00005 | 0.00024 | 0.00000 | 0 | 1 |
| 1124 | chr17 | 57916000 | 57917000 | 0.000 | 0.000 | 0.029 | 0.014 | VMP1 | 0.60686 | 0.54294 | 0.08726 | 1 | 0 |
| 1125 | chr17 | 57917000 | 57918000 | 0.000 | 0.000 | 0.029 | 0.000 | VMP1 | 0.22755 | 0.54294 | 0.08726 | 1 | 0 |
| 1126 | chr17 | 62007000 | 62008000 | 0.000 | 0.000 | 0.029 | 0.000 | CD79B | 0.22755 | 0.54294 | 0.08726 | 0 | 0 |
| 1127 | chr17 | 62008000 | 62009000 | 0.000 | 0.000 | 0.044 | 0.014 | CD79B | 0.34948 | 0.54966 | 0.02537 | 0 | 0 |
| 1128 | chr17 | 63067000 | 63068000 | 0.000 | 0.000 | 0.015 | 0.014 | GNA13 | 1.00000 | 1.00000 | 0.29694 | 0 | 0 |
| 1129 | chr17 | 65676000 | 65677000 | 0.000 | 0.000 | 0.029 | 0.000 | PITPNC1 | 0.22755 | 0.54294 | 0.08726 | 0 | 0 |
| 1130 | chr17 | 69365000 | 69366000 | 0.000 | 0.000 | 0.015 | 0.014 | AC007461.1 | 1.00000 | 1.00000 | 0.29694 | 0 | 0 |
| 1131 | chr17 | 70083000 | 70084000 | 0.028 | 0.000 | 0.000 | 0.014 | SOX9 | 1.00000 | 0.34615 | 1.00000 | 0 | 0 |
| 1132 | chr17 | 74733000 | 74734000 | 0.000 | 0.000 | 0.000 | 0.027 | SRSF2 | 0.49735 | 1.00000 | 1.00000 | 0 | 0 |
| 1133 | chr17 | 75447000 | 75448000 | 0.000 | 0.000 | 0.044 | 0.000 | 9-Sep-19 | 0.30727 | 0.54966 | 0.02537 | 0 | 0 |
| 1134 | chr17 | 75448000 | 75449000 | 0.000 | 0.000 | 0.044 | 0.000 | 9-Sep-19 | 0.10727 | 0.54966 | 0.02537 | 0 | 0 |
| 1135 | chr17 | 76775000 | 76776000 | 0.000 | 0.000 | 0.000 | 0.027 | CYTH1 | 0.49735 | 1.00000 | 1.00000 | 0 | 0 |
| 1136 | chr17 | 80928000 | 80929000 | 0.000 | 0.000 | 0.029 | 0.090 | B3GNTL1 | 0.22755 | 0.54294 | 0.08726 | 0 | 0 |
| 1137 | chr17 | 80976000 | 80977000 | 0.000 | 0.000 | 0.015 | 0.014 | B3GNTL1 | 1.00000 | 1.00000 | 0.29694 | 0 | 0 |
| 1138 | chr18 | 2709000 | 2730000 | 0.000 | 0.000 | 0.029 | 0.000 | SMCHD1 | 0.22755 | 0.54294 | 0.08726 | 0 | 0 |
| 1139 | chr18 | 3600000 | 3601000 | 0.000 | 0.000 | 0.015 | 0.014 | DLGAP1 | 1.00000 | 1.00000 | 0.29694 | 0 | 0 |
| 1140 | chr18 | 12062000 | 12063000 | 0.000 | 0.000 | 0.000 | 0.041 | ANKRD62 | 0.24603 | 1.00000 | 1.00000 | 0 | 0 |
| 1141 | chr18 | 27771000 | 27772000 | 0.000 | 0.000 | 0.029 | 0.000 | DSC3 | 0.22755 | 0.54294 | 0.08726 | 0 | 0 |
| 1142 | chr18 | 28066000 | 28067000 | 0.000 | 0.000 | 0.029 | 0.000 | DSC3 | 0.22755 | 0.54294 | 0.08726 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 1143 | chr18 | 30349000 | 30350000 | 0.000 | 0.000 | 0.000 | 0.027 | AC012123.1; KLHL14; | 0.49735 | 1.00000 | 1.00000 | 0 | 0 |
| 1144 | chr18 | 36806000 | 36807000 | 0.000 | 0.000 | 0.029 | 0.090 | CELF4 | 0.22755 | 0.54294 | 0.08726 | 0 | 0 |
| 1145 | chr18 | 37753000 | 37752000 | 0.000 | 0.000 | 0.015 | 0.014 | PIK3C3 | 1.00000 | 1.00000 | 0.29694 | 0 | 0 |
| 1146 | chr18 | 38672000 | 38673000 | 0.028 | 0.000 | 0.000 | 0.014 | PIK3C3 | 1.00000 | 0.34615 | 1.00000 | 0 | 0 |
| 1147 | chr18 | 42168000 | 42169000 | 0.028 | 0.000 | 0.000 | 0.014 | SETBP1 | 1.00000 | 0.34615 | 1.00000 | 0 | 0 |
| 1148 | chr18 | 51952000 | 51953000 | 0.000 | 0.000 | 0.029 | 0.000 | C18orf54 | 0.22755 | 0.54294 | 0.08726 | 0 | 0 |
| 1149 | chr18 | 52447000 | 52448000 | 0.000 | 0.000 | 0.015 | 0.014 | RAB27B | 1.00000 | 1.00000 | 0.29694 | 0 | 0 |
| 1150 | chr18 | 52988000 | 52989000 | 0.000 | 0.000 | 0.029 | 0.000 | TCF4 | 0.22755 | 0.54294 | 0.08726 | 0 | 0 |
| 1153 | chr18 | 54653000 | 54654000 | 0.000 | 0.000 | 0.000 | 0.027 | WDR7 | 0.49735 | 1.00000 | 1.00000 | 0 | 0 |
| 1152 | chr18 | 60794000 | 60795000 | 0.000 | 0.000 | 0.029 | 0.090 | BCL2 | 0.22755 | 0.54294 | 0.08726 | 1 | 0 |
| 1153 | chr18 | 60805000 | 60806000 | 0.000 | 0.000 | 0.074 | 0.081 | BCL2 | 1.00000 | 0.16101 | 0.00208 | 1 | 1 |
| 1154 | chr18 | 60806000 | 60807000 | 0.000 | 0.006 | 0.132 | 0.122 | BCL2 | 1.00000 | 0.02564 | 0.00009 | 1 | 1 |
| 1155 | chr18 | 60809000 | 60810000 | 0.000 | 0.000 | 0.059 | 0.027 | BCL2 | 0.42627 | 0.29551 | 0.00730 | 1 | 1 |
| 1156 | chr18 | 60821000 | 60822000 | 0.000 | 0.000 | 0.029 | 0.000 | BCL2 | 0.22755 | 0.54294 | 0.08726 | 1 | 0 |
| 1157 | chr18 | 60825000 | 60826000 | 0.000 | 0.000 | 0.044 | 0.027 | BCL2 | 0.67043 | 0.54966 | 0.02537 | 1 | 0 |
| 1158 | chr18 | 60826000 | 60827000 | 0.000 | 0.000 | 0.029 | 0.000 | BCL2 | 0.22755 | 0.54294 | 0.08726 | 1 | 0 |
| 1159 | chr18 | 60828000 | 60829000 | 0.000 | 0.000 | 0.015 | 0.027 | BCL2 | 1.00000 | 1.00000 | 0.29694 | 1 | 0 |
| 1160 | chr18 | 60873000 | 60874000 | 0.000 | 0.000 | 0.044 | 0.027 | BCL2 | 0.67043 | 0.54966 | 0.02537 | 1 | 0 |
| 1161 | chr18 | 60875000 | 60876000 | 0.000 | 0.000 | 0.044 | 0.027 | BCL2 | 0.67043 | 0.54966 | 0.02537 | 1 | 0 |
| 1162 | chr18 | 60876000 | 60877000 | 0.000 | 0.000 | 0.015 | 0.054 | BCL2 | 0.36833 | 1.00000 | 0.29694 | 1 | 1 |
| 1163 | chr18 | 60983000 | 60984000 | 0.000 | 0.006 | 0.059 | 0.068 | BCL2 | 1.00000 | 0.29551 | 0.02818 | 1 | 1 |
| 1164 | chr18 | 60984000 | 60985000 | 0.000 | 0.012 | 0.176 | 0.459 | BCL2 | 0.00034 | 0.00730 | 0.00001 | 1 | 1 |
| 1165 | chr18 | 60985000 | 60986000 | 0.000 | 0.060 | 0.223 | 0.635 | BCL2 | 0.00060 | 0.60107 | 0.00000 | 1 | 1 |
| 1166 | chr18 | 60986000 | 60987000 | 0.000 | 0.019 | 0.235 | 0.736 | BCL2 | 0.60000 | 0.00098 | 0.00000 | 1 | 1 |
| 1167 | chr18 | 60987000 | 60988000 | 0.000 | 0.019 | 0.191 | 0.500 | BCL2 | 0.00019 | 0.00372 | 0.00001 | 1 | 1 |
| 1168 | chr18 | 60988000 | 60989000 | 0.000 | 0.032 | 0.221 | 0.595 | BCL2 | 0.00001 | 0.00167 | 0.00000 | 1 | 1 |
| 1169 | chr18 | 61810000 | 61811000 | 0.000 | 0.000 | 0.015 | 0.014 | SERPINB8 | 1.00000 | 1.00060 | 0.29694 | 0 | 0 |
| 1170 | chr18 | 63080000 | 63081000 | 0.000 | 0.000 | 0.029 | 0.000 | CDH7 | 0.22755 | 0.54294 | 0.08726 | 0 | 0 |
| 1171 | chr18 | 63791000 | 63792000 | 0.028 | 0.060 | 0.015 | 0.000 | CDH7 | 0.47887 | 1.00000 | 0.29694 | 0 | 0 |
| 1172 | chr18 | 63875000 | 63876000 | 0.000 | 0.000 | 0.029 | 0.000 | CDH19 | 0.22755 | 0.54294 | 0.08726 | 0 | 0 |
| 1173 | chr18 | 64643000 | 64644000 | 0.000 | 0.000 | 0.029 | 0.000 | CDH19 | 0.22755 | 0.54294 | 0.08726 | 0 | 0 |
| 1174 | chr18 | 65863000 | 65864000 | 0.000 | 0.000 | 0.000 | 0.027 | TMX3 | 0.49735 | 1.00000 | 1.00000 | 0 | 0 |
| 1175 | chr18 | 66328000 | 66329000 | 0.000 | 6.000 | 0.015 | 0.014 | TMX3 | 1.00000 | 1.00000 | 0.29694 | 0 | 0 |
| 1176 | chr18 | 70462000 | 70463000 | 0.000 | 6.000 | 0.015 | 0.014 | NETO1 | 1.00000 | 1.00000 | 0.29694 | 0 | 0 |
| 1177 | chr18 | 73767000 | 73768000 | 0.000 | 6.000 | 0.015 | 0.014 | ZNF516 | 1.00000 | 1.00060 | 0.29694 | 0 | 0 |
| 1178 | chr18 | 76515000 | 76516000 | 0.000 | 0.000 | 0.029 | 0.014 | SALL3 | 0.60686 | 0.54294 | 0.08726 | 0 | 0 |
| 1179 | chr18 | 76724000 | 76725000 | 0.000 | 0.060 | 0.015 | 0.014 | SALL3 | 1.00060 | 1.60000 | 0.29694 | 0 | 0 |
| 1180 | chr18 | 76725000 | 76726000 | 0.000 | 0.060 | 0.015 | 0.014 | SALL3 | 1.00000 | 1.00 000 | 0.29694 | 0 | 0 |
| 1181 | chr19 | 1612000 | 1613000 | 0.056 | 0.060 | 0.000 | 0.000 | TCF3 | 1.00060 | 0.11763 | 1.00060 | 0 | 1 |
| 1182 | chr19 | 2476000 | 2477000 | 0.000 | 0.000 | 0.029 | 0.000 | GADD45B | 0.22755 | 0.54294 | 0.08726 | 1 | 0 |
| 1183 | chr19 | 10304000 | 10305000 | 0.000 | 0.000 | 0.059 | 0.000 | DNMT1 | 0.05016 | 0.29551 | 0.00730 | 0 | 1 |
| 1184 | chr19 | 10305000 | 10306000 | 0.000 | 0.000 | 0.044 | 0.006 | DNMT1 | 0.10727 | 0.54966 | 0.02537 | 0 | 0 |
| 1185 | chr19 | 10335000 | 10336000 | 0.000 | 0.000 | 0.015 | 0.014 | S1PR2 | 1.00000 | 1.00060 | 0.29694 | 1 | 0 |
| 1186 | chr19 | 10340000 | 10341000 | 0.000 | 0.000 | 0.118 | 0.041 | S1PR2 | 0.11795 | 0.04825 | 0.00094 | 1 | 1 |
| 1187 | chr19 | 10341000 | 10342000 | 0.000 | 0.012 | 0.206 | 0.054 | S1PR2 | 0.01013 | 0.00197 | 0.00000 | 1 | 1 |
| 1188 | chr19 | 16030000 | 36031000 | 0.028 | 0.000 | 0.03 5 | 0.000 | CYP4F11 | 0.47887 | 1.00000 | 0.29694 | 0 | 0 |
| 1189 | chr19 | 16436000 | 16437000 | 0.000 | 0.000 | 0.02.9 | 0.014 | KLF2 | 0.60686 | 0.54294 | 0.08726 | 1 | 0 |
| 1190 | chr19 | 20889000 | 20890000 | 0.000 | 0.006 | 0.015 | 0.000 | ZNF626 | 0.47887 | 1.00900 | 0.50663 | 0 | 0 |
| 1191 | chr19 | 21073000 | 21074000 | 0.000 | 0.000 | 0.015 | 0.027 | ZNF85 | 1.60000 | 1.00000 | 0.29694 | 0 | 0 |
| 1192 | chr19 | 21092000 | 21093000 | 0.000 | 0.000 | 0.029 | 0.006 | ZNF85 | 0.22755 | 0.54294 | 0.68726 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 1193 | chr19 | 23841000 | 23842000 | 0.000 | 0.000 | 0.015 | 0.027 | ZNF675 | 1.00000 | 1.00060 | 0.29694 | 0 | 0 |
| 1194 | chr19 | 29256000 | 29257000 | 0.000 | 0.000 | 0.029 | 0.000 | UQCRFS1 | 0.22755 | 0.54294 | 0.08726 | 0 | 0 |
| 1195 | chr19 | 44183000 | 44184000 | 0.000 | 0.000 | 0.029 | 0.000 | PLAUR | 0.22755 | 0.54294 | 0.08726 | 0 | 0 |
| 1196 | chr19 | 50399000 | 50400000 | 0.000 | 0.000 | 0.029 | 0.000 | IL4I1 | 0.22755 | 0.54294 | 0.08726 | 0 | 0 |
| 1197 | chr19 | 53419000 | 53420000 | 0.028 | 0.000 | 0.015 | 0.014 | ZNF321P; ZNF816; ZNF816- ZNF321PZNF321PZNF 816-ZNF321P; | 1.00000 | 1.00000 | 0.29694 | 0 | 0 |
| 1198 | chr20 | 15470000 | 15471000 | 0.028 | 0.006 | 0.006 | 0.006 | MACROD2 | 1.00000 | 0.34615 | 1.00000 | 0 | 0 |
| 1199 | chr20 | 23359000 | 23360000 | 0.056 | 0.000 | 0.000 | 0.000 | NAPB | 1.00000 | 0.11763 | 1.00000 | 0 | 1 |
| 1200 | chr20 | 23912000 | 23913000 | 0.000 | 0.000 | 0.000 | 0.027 | CST5 | 0.49735 | 1.60000 | 1.00000 | 0 | 0 |
| 1201 | chr20 | 46131000 | 46132000 | 0.000 | 0.000 | 0.059 | 0.014 | NCOA3 | 0.39373 | 0.29551 | 0.00730 | 1 | 1 |
| 1202 | chr20 | 49127000 | 49128000 | 0.000 | 0.000 | 0.029 | 0.014 | PTPN1 | 0.60686 | 0.54294 | 0.08726 | 0 | 0 |
| 1203 | chr20 | 49648000 | 49649000 | 0.000 | 0.000 | 0.029 | 0.000 | KCNG1 | 0.22755 | 0.54294 | 0.08726 | 0 | 0 |
| 1204 | chr20 | 61607000 | 61608000 | 0.000 | 0.000 | 0.006 | 0.027 | SLC17A9 | 0.49735 | 1.00060 | 1.00000 | 0 | 0 |
| 1205 | chr21 | 21597000 | 21598000 | 0.000 | 0.000 | 0.029 | 0.006 | NCAM2 | 0.22755 | 0.54294 | 0.08726 | 0 | 0 |
| 1206 | chr21 | 23458000 | 23459000 | 0.000 | 0.000 | 0.029 | 0.006 | NCAM2 | 0.22755 | 0.54294 | 0.08726 | 0 | 0 |
| 1207 | chr21 | 24998000 | 24999000 | 0.000 | 0.000 | 0.029 | 0.000 | MRPL39 | 0.22755 | 0.54294 | 0.08726 | 0 | 0 |
| 1208 | chr21 | 26935000 | 26936000 | 0.000 | 0.000 | 0.015 | 0.014 | MRPL39 | 1.00000 | 1.00000 | 0.29694 | 0 | 0 |
| 1209 | chr21 | 35779000 | 35780000 | 0.000 | 0.000 | 0.000 | 0.027 | SMIM11 | 0.49735 | 1.00000 | 1.00000 | 0 | 0 |
| 1210 | chr21 | 38779000 | 38780000 | 0.000 | 0.000 | 0.000 | 0.027 | DYRK1A | 0.49735 | 1.00000 | 1.00000 | 0 | 0 |
| 1211 | chr21 | 43254000 | 43255000 | 0.000 | 0.000 | 0.029 | 0.000 | PRDM15 | 0.22755 | 0.54294 | 0.08726 | 0 | 0 |
| 1212 | chr21 | 44612000 | 44613000 | 0.000 | 0.000 | 0.000 | 0.027 | CRYAA | 0.49735 | 1.00000 | 1.00000 | 0 | 0 |
| 1213 | chr21 | 45381000 | 45382000 | 0.000 | 0.000 | 0.029 | 0.000 | AGPAT3 | 0.22755 | 0.54294 | 0.08726 | 0 | 0 |
| 1214 | chr21 | 46058000 | 46059000 | 0.000 | 0.000 | 0.015 | 0.027 | KRTAP10-10 | 1.00000 | 1.00000 | 0.29694 | 0 | 0 |
| 1215 | chr22 | 19050000 | 19051000 | 0.000 | 0.006 | 0.000 | 0.027 | DGCR2 | 0.49735 | 1.00000 | 1.00000 | 0 | 0 |
| 1216 | chr22 | 20212000 | 20213000 | 0.000 | 0.000 | 0.029 | 0.014 | RTN4R | 0.60686 | 0.54294 | 0.08726 | 0 | 0 |
| 1217 | chr22 | 20708000 | 20709000 | 0.000 | 0.000 | 0.029 | 0.000 | FAM230A | 0.22755 | 0.54294 | 0.08726 | 0 | 0 |
| 1218 | chr22 | 21994000 | 21995000 | 0.028 | 0.000 | 0.015 | 0.000 | SDF2L1 | 0.47887 | 1.00000 | 0.29694 | 0 | 0 |
| 1219 | chr22 | 22379000 | 22380000 | 0.000 | 0.000 | 0.029 | 0.027 | IGLV4-69 | 1.00000 | 0.54294 | 0.08726 | 0 | 0 |
| 1220 | chr22 | 22380000 | 22381000 | 0.000 | 0.012 | 0.044 | 0.068 | IGLV4-69 | 0.72064 | 0.54966 | 0.35671 | 0 | 1 |
| 1221 | chr22 | 22381000 | 22382000 | 0.000 | 0.012 | 0.015 | 0.027 | IGLV4-69 | 1.00000 | 1.00000 | 1.00000 | 0 | 0 |
| 1222 | chr22 | 22385000 | 22386000 | 0.028 | 0.031 | 0.029 | 0.068 | IGLV4-69 | 0.44431 | 1.00000 | 1.00000 | 0 | 1 |
| 1223 | chr22 | 22452000 | 22453000 | 0.000 | 0.012 | 0.015 | 0.014 | IGLV8-61 | 1.00000 | 1.00000 | 1.00000 | 0 | 0 |
| 1224 | chr22 | 22453000 | 22454000 | 0.000 | 0.012 | 0 015 | 0 014 | IGLV8-61 | 1.00000 | 1.00000 | 1.00000 | 0 | 0 |
| 1225 | chr22 | 22516000 | 22517000 | 0.000 | 0.025 | 0.015 | 0.054 | IGLV4-60 | 0.36833 | 1.00000 | 1.00000 | 0 | 1 |
| 1226 | chr22 | 22517000 | 22518000 | 0.000 | 0.019 | 0.000 | 0.014 | IGLV4-60 | 1.00000 | 1.00000 | 0.55662 | 0 | 0 |
| 1227 | chr22 | 22550000 | 22551000 | 0.056 | 0.006 | 0.044 | 0.054 | IGLV6-57 | 1.00000 | 1.00000 | 0.07959 | 0 | 1 |
| 1228 | chr22 | 22569000 | 22570000 | 0.000 | 0.006 | 0.015 | 0.014 | IGLV10-54 | 1.00000 | 1.00000 | 0.50663 | 0 | 0 |
| 1229 | chr22 | 22676000 | 22677000 | 0.028 | 0.000 | 0.015 | 0.000 | IGLV1-51 | 0.47887 | 1.00000 | 0.29694 | 0 | 0 |
| 1230 | chr22 | 22677000 | 22678000 | 0.083 | 0.012 | 0.015 | 0.014 | IGLV1-51 | 1.00000 | 0.11840 | 1.00000 | 0 | 1 |
| 1231 | chr22 | 22707000 | 22708000 | 0.028 | 0.006 | 0.044 | 0.014 | IGLV5-48 | 0.34948 | 1.00000 | 0.07959 | 0 | 0 |
| 1232 | chr22 | 22712000 | 22713000 | 0.083 | 0.012 | 0 088 | 0.041 | IGLV1-47 | 0.31126 | 1.00000 | 0.00949 | 0 | 1 |
| 1233 | chr22 | 22723000 | 22724000 | 0.000 | 0.006 | 0.015 | 0.027 | IGLV7-46 | 1.00000 | 1.00000 | 0.50663 | 0 | 0 |
| 1234 | chr22 | 22724000 | 22725000 | 0.028 | 0.012 | 0.088 | 0.041 | IGLV7-46 | 0.31126 | 0.41714 | 0.00949 | 0 | 1 |
| 1235 | chr22 | 22730000 | 22731000 | 0.000 | 0.006 | 0.059 | 0.054 | IGLV5-45 | 1.00000 | 0.29551 | 0.02818 | 0 | 1 |
| 1236 | chr22 | 22731000 | 22732000 | 0.000 | 0.006 | 0.029 | 0.000 | IGLV5-45 | 0.22755 | 0.54294 | 0.21104 | 0 | 0 |
| 1237 | chr22 | 22735000 | 22736000 | 0.028 | 0.037 | 0.059 | 0.068 | IGLV1-44 | 1.00000 | 0.65667 | 0.48849 | 0 | 1 |
| 1238 | chr22 | 22749000 | 22750000 | 0.000 | 0.006 | 0.059 | 0.027 | IGLV7-43 | 0.42627 | 0.29551 | 0.02818 | 0 | 1 |
| 1239 | chr22 | 22758000 | 22759000 | 0.028 | 0.006 | 0.029 | 0.014 | IGLV1-40 | 0.60686 | 1.00000 | 0.21104 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 1240 | chr22 | 22759000 | 22760000 | 0.056 | 0.006 | 0 044 | 0..027 | tGLV1-40 | 0.67043 | 1.00000 | 0.07959 | 0 | 1 |
| 1241 | chr22 | 22764000 | 22765000 | 0.111 | 0.006 | 0.044 | 0.068 | IGLV1-40 | 0.72064 | 0.23165 | 0.07959 | 0 | 1 |
| 1242 | chr22 | 23028000 | 23029000 | 0.000 | 0.006 | 0.015 | 0.000 | IGLV3-25 | 0.47887 | 1.00000 | 0.50663 | 0 | 0 |
| 1243 | chr22 | 23029000 | 23030000 | 0.028 | 0.062 | 0.132 | 0.108 | IGLV3-25 | 0.79702 | 0.15881 | 0.11274 | 0 | 1 |
| 1244 | chr22 | 23035000 | 23036000 | 0.000 | 0.000 | 0.015 | 0.014 | IGLV2-23 | 1.00000 | 1.00000 | 0.29694 | 0 | 0 |
| 1245 | chr22 | 23039000 | 23040000 | 0.000 | 0.000 | 0.000 | 0.027 | IGLV2-23 | 0.49735 | 1.00000 | 1.00000 | 0 | 0 |
| 1246 | chr22 | 23040000 | 23041000 | 0.000 | 0.043 | 0.103 | 0.054 | IGLV2-23 | 0.35266 | 0.09269 | 0.12716 | 0 | 1 |
| 1247 | chr22 | 23041000 | 23042000 | 0.000 | 0.006 | 0.044 | 0.000 | IGLV2-23 | 0.10727 | 0.54966 | 0.07959 | 0 | 0 |
| 1248 | chr22 | 23055000 | 23056000 | 0.028 | 0.056 | 0.059 | 0.014 | IGLV3-21 | 0.19371 | 0.65667 | 1.00000 | 0 | 1 |
| 1249 | chr22 | 23063000 | 23064000 | 0.000 | 0.000 | 0.074 | 0.041 | IGLV3-19 | 0.47996 | 0.16101 | 0.00208 | 0 | 1 |
| 1250 | chr22 | 23090000 | 23091000 | 0.000 | 0.000 | 0.059 | 0.041 | IGLV3-16 | 0.70990 | 0.29551 | 0.00730 | 0 | 1 |
| 1251 | chr22 | 23100000 | 23101000 | 0.000 | 0.019 | 0.044 | 0.054 | IGLV2-14 | 1.00000 | 0.54966 | 0.36534 | 0 | 1 |
| 1252 | chr22 | 23101000 | 23102000 | 0.028 | 0.031 | 0.074 | 0.081 | IGLV2-14 | 1.00000 | 0.66188 | 0.16714 | 0 | 1 |
| 1253 | chr22 | 23114000 | 23115000 | 0.000 | 0.000 | 0.015 | 0.027 | IGLV3-12 | 1.00000 | 1.00000 | 0.29694 | 0 | 0 |
| 1254 | chr22 | 23134000 | 23135000 | 0.000 | 0.000 | 0.029 | 0.014 | IGLV2-11 | 0.60686 | 0.54294 | 0.08726 | 0 | 0 |
| 1255 | chr22 | 23154000 | 23155000 | 0.000 | 0.019 | 0.074 | 0.027 | IGLV3-10 | 0.25970 | 0.16101 | 0.05242 | 0 | 1 |
| 1256 | chr22 | 23161000 | 23162000 | 0.000 | 0.006 | 0 000 | 0 014 | IGLV3-9 | 1.00000 | 1.00000 | 1.00000 | 0 | 0 |
| 1257 | chr22 | 23162000 | 23163000 | 0.000 | 0.012 | 0.000 | 0.014 | IGLV3-9 | 1.00000 | 1.00000 | 1.00000 | 0 | 0 |
| 1258 | chr22 | 23165000 | 23166000 | 0.000 | 0.012 | 0.000 | 0.041 | IGLV2-8 | 0.24603 | 1.00000 | 1.00000 | 0 | 0 |
| 1259 | chr22 | 23192000 | 23193000 | 0.000 | 0.006 | 0.088 | 0.041 | IGLV4-3 | 0.31126 | 0.09031 | 0.00311 | 0 | 1 |
| 1260 | chr22 | 23197000 | 23198000 | 0.000 | 0.006 | 0.015 | 0.000 | IGLV4-3 | 0.47887 | 1.00000 | 0.50663 | 0 | 0 |
| 1261 | chr22 | 23198000 | 23199000 | 0.000 | 0.025 | 0.147 | 0.068 | IGLV4-3 | 0.17231 | 0.01404 | 0.00108 | 0 | 1 |
| 1262 | chr22 | 23199000 | 23200000 | 0.000 | 0.031 | 0.221 | 0.068 | IGLV4-3 | 0.01424 | 0.00107 | 0.00002 | 0 | 1 |
| 1263 | chr22 | 23203000 | 23204000 | 0.000 | 0.006 | 0.029 | 0.600 | IGLV4-3 | 0.22755 | 0.54294 | 0.08726 | 0 | 0 |
| 1264 | chr22 | 23204000 | 23205000 | 0.056 | 0.000 | 0.059 | 0.041 | IGLV4-3 | 0.70990 | 1.00000 | 0.00730 | 0 | 1 |
| 1265 | chr22 | 23205000 | 23206000 | 0.000 | 0.000 | 0.015 | 0.027 | IGLV4-3 | 1.00000 | 1.00000 | 0.29694 | 0 | 0 |
| 1266 | chr22 | 23207000 | 23208000 | 0.000 | 0.000 | 0.029 | 0.000 | IGLV4-3 | 0.22755 | 0.54294 | 0.08726 | 0 | 0 |
| 1267 | chr22 | 23209000 | 23210000 | 0.000 | 0.000 | 0.029 | 0.000 | IGLV4-3 | 0.22755 | 0.54294 | 0.08726 | 0 | 0 |
| 1268 | chr22 | 23213000 | 23214000 | 0.000 | 0.000 | 0.088 | 0.027 | IGLV4-3 | 0.15270 | 0.09031 | 0.00058 | 0 | 1 |
| 1269 | chr22 | 23214000 | 23215000 | 0.000 | 0.000 | 0.074 | 0.027 | IGLV4-3 | 0.25970 | 0.16101 | 0.00208 | 0 | 1 |
| 1270 | chr22 | 23219000 | 23220000 | 0.000 | 0.000 | 0.044 | 0.000 | IGLV3-1 | 0.10727 | 0.54966 | 0.02537 | 0 | 0 |
| 1271 | chr22 | 23220000 | 23221000 | 0.000 | 0.000 | 0.059 | 0.000 | IGLV3-1 | 0.05016 | 0.29551 | 0.00730 | 0 | 1 |
| 1272 | chr22 | 23222000 | 23223000 | 0.000 | 0.006 | 0.147 | 0.014 | IGLV3-1 | 0.00342 | 0.01404 | 0.00003 | 0 | 1 |
| 1273 | chr22 | 23223000 | 23224000 | 0.083 | 0.149 | 0.544 | 0.432 | IGLV3-1 | 0.23940 | 0.00000 | 0.00000 | 0 | 1 |
| 1274 | chr22 | 23224000 | 23225600 | 0.000 | 0.000 | 0.118 | 0.027 | IGLV3-1 | 0.04838 | 0.04825 | 0.00004 | 0 | 1 |
| 1275 | chr22 | 23226000 | 23227000 | 0.000 | 0.000 | 0.029 | 0.000 | IGLV3-1 | 0.22755 | 0.54294 | 0.08726 | 0 | 0 |
| 1276 | chr22 | 23227000 | 23228000 | 0.028 | 0.056 | 0.412 | 0.257 | IGLL5 | 0.07371 | 0.00001 | 0.00000 | 0 | 1 |
| 1277 | chr22 | 23228000 | 23229000 | 0.028 | 0.019 | 0.309 | 0.095 | IGLL5 | 0.00152 | 0.00070 | 0.00000 | 0 | 1 |
| 1278 | chr22 | 23229000 | 23230000 | 0.000 | 0.000 | 0.118 | 0.041 | IGLL5 | 0.11795 | 0.64825 | 0.00004 | 0 | 1 |
| 1279 | chr22 | 23230000 | 23231000 | 0.222 | 0.161 | 0.647 | 0.514 | IGLL5 | 0.12719 | 0.66007 | 0.00000 | 0 | 1 |
| 1280 | chr22 | 23231000 | 23232000 | 0.250 | 0.155 | 0.647 | 0.514 | IGLL5 | 0.12719 | 0.00017 | 0.00000 | 0 | 1 |
| 1281 | chr22 | 23232000 | 23233000 | 0.000 | 0.012 | 0.426 | 0.162 | IGLL5 | 0.00075 | 0.00000 | 0.00000 | 0 | 1 |
| 1282 | chr22 | 23233000 | 23234600 | 0.000 | 0.006 | 0.162 | 0.054 | IGLJ1 | 0.05410 | 0.01471 | 0.00001 | 0 | 1 |
| 1283 | chr22 | 23234000 | 23235000 | 0.056 | 0.000 | 0.147 | 0.041 | IGLJ1 | 0.63985 | 0.20979 | 0.00000 | 0 | 1 |
| 1284 | chr22 | 23235000 | 23236000 | 0.056 | 0.031 | 0.176 | 0.068 | IGLJ1; IGLL5; | 0.66843 | 0.13046 | 0.00035 | 0 | 1 |
| 1285 | chr22 | 23236000 | 23237000 | 0.111 | 0.043 | 0.250 | 0.095 | IGLJ1; IGLL5; | 0.02356 | 0.12484 | 0.00001 | 0 | 1 |
| 1286 | chr22 | 23237000 | 23238000 | 0.083 | 0.006 | 0.103 | 0.054 | IGLC1; IGLL5; | 0.35266 | 1.60000 | 0.00099 | 0 | 1 |
| 1287 | chr22 | 23241000 | 23242000 | 0.028 | 0.012 | 0.074 | 0.000 | IGLJ2 | 0.02326 | 0.66188 | 0.02559 | 0 | 1 |
| 1288 | chr22 | 23242000 | 23243000 | 0.028 | 0.050 | 0.147 | 0.108 | IGLC2 | 0.61516 | 0.09212 | 0.02792 | 0 | 1 |
| 1289 | chr22 | 23243000 | 23244000 | 0.000 | 0.000 | 0.029 | 0.000 | IGLC2 | 0.22755 | 0.54294 | 0.08726 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 1290 | chr22 | 23244000 | 23245600 | 0.000 | 0.012 | 0.015 | 0.014 | IGLC2 | 1.60000 | 1.00060 | 1.00000 | 0 | 0 |
| 1291 | chr22 | 23247000 | 23248000 | 0.111 | 0.099 | 0.088 | 0.122 | IGLJ3 | 0.59201 | 0.73421 | 1.00000 | 0 | 1 |
| 1292 | chr22 | 23248000 | 23249000 | 0.000 | 0.012 | 0.015 | 0.027 | IGLC3 | 1.00 000 | 1.00000 | 1.00000 | 0 | 0 |
| 1293 | chr22 | 23249000 | 23250000 | 0.000 | 0.006 | 0.029 | 0.027 | IGLC3 | 1.00060 | 0.54294 | 0.21104 | 0 | 0 |
| 1294 | chr22 | 23260000 | 23261000 | 0.000 | 0.025 | 0.015 | 0.000 | IGLJ6 | 0.47887 | 1.60000 | 1.00000 | 0 | 0 |
| 1295 | chr22 | 23261000 | 23262000 | 0.000 | 0.012 | 0.015 | 0.014 | IGLJ6 | 1.00060 | 1.00000 | 1.00000 | 0 | 0 |
| 1296 | chr22 | 23263000 | 23264000 | 0.000 | 0.006 | 0.044 | 0.014 | IGLJ7 | 0.34948 | 0.54966 | 0.07959 | 0 | 0 |
| 1297 | chr22 | 23264000 | 23265000 | 0.000 | 0.006 | 0.044 | 0.027 | IGLC7 | 0.67043 | 0.54966 | 0.07959 | 0 | 0 |
| 1298 | chr22 | 23273000 | 23274600 | 0.000 | 0.000 | 0.044 | 0.000 | IGLC7 | 0.10727 | 0.54966 | 0.02537 | 0 | 0 |
| 1299 | chr22 | 23277000 | 23278000 | 0.000 | 0.000 | 0.029 | 0.014 | IGLC7 | 0.60686 | 0.54294 | 0.08726 | 0 | 0 |
| 1300 | chr22 | 23278000 | 23279000 | 0.000 | 0.006 | 0.059 | 0.014 | IGLC7 | 0.19371 | 0.29551 | 0.02818 | 0 | 1 |
| 1301 | chr22 | 23281000 | 23282000 | 0.000 | 0.000 | 0.029 | 0.014 | IGLC7 | 0.60686 | 0.54294 | 0.08726 | 0 | 0 |
| 1302 | chr22 | 23282000 | 23283000 | 0.000 | 0.006 | 0.147 | 0.027 | IGLC7 | 0.01393 | 0.61404 | 0.00663 | 0 | 1 |
| 1303 | chr22 | 23284000 | 23285000 | 0.000 | 0.000 | 0.029 | 0.000 | IGLC7 | 0.22755 | 0.54294 | 0.08726 | 0 | 0 |
| 1304 | chr22 | 23523000 | 23524000 | 0.000 | 0.000 | 0.015 | 0.041 | BCR | 0.62160 | 1.00 000 | 0.29694 | 0 | 0 |
| 1305 | chr22 | 23524000 | 23525000 | 0.000 | 0.000 | 0.029 | 0.014 | BCR | 0.60686 | 0.54294 | 0.08726 | 0 | 0 |
| 1306 | chr22 | 27236000 | 27237600 | 0.028 | 0.000 | 0.029 | 0.000 | CRYBA4 | 0.22755 | 1.00060 | 0.08726 | 0 | 0 |
| 1307 | chr22 | 29195000 | 29196000 | 0.000 | 0.000 | 0.088 | 0.000 | XBP1 | 0.01070 | 0.09031 | 0.00058 | 0 | 1 |
| 1308 | chr22 | 29196000 | 29197000 | 0.000 | 0.000 | 0.059 | 0.041 | XBP1 | 0.70990 | 0.29551 | 0.00730 | 0 | 1 |
| 1309 | chr22 | 31826000 | 31827000 | 0.000 | 0.000 | 0.029 | 0.000 | DRG1 | 0.22755 | 0.54294 | 0.08726 | 0 | 0 |
| 1310 | chr22 | 32982000 | 32983000 | 0.028 | 0.000 | 0.015 | 0.000 | SYN3 | 0.47887 | 1.60000 | 0.29694 | 0 | 0 |
| 1311 | chr22 | 39852000 | 39853000 | 0.000 | 0.000 | 0.029 | 0.000 | TAB1 | 0.22755 | 0.54294 | 0.08726 | 0 | 0 |
| 1312 | chr22 | 39854000 | 39855000 | 0.000 | 0.000 | 0.029 | 0.000 | TAB1 | 0.22755 | 0.54294 | 0.08726 | 0 | 0 |
| 1313 | chr22 | 43360000 | 43361000 | 0.000 | 0.000 | 0.029 | 0.000 | PACSIN2 | 0.22755 | 0.54294 | 0.08726 | 0 | 0 |
| 1314 | chr22 | 47186000 | 47187000 | 0.000 | 0.000 | 0.029 | 0.000 | TBC1D22A | 0.22755 | 0.54294 | 0.08726 | 0 | 0 |
| 1315 | chr22 | 47738000 | 47739000 | 0.000 | 0.000 | 0.000 | 0.027 | LL22NC03-75H12.2 | 0.49735 | 1.00000 | 1.00000 | 0 | 0 |
| 1316 | chr22 | 50336000 | 50337000 | 0.028 | 0.000 | 0.015 | 0.000 | CRELD2 | 0.47887 | 1.00000 | 0.29694 | 0 | 0 |
| 1317 | chrX | 228000 | 229000 | 0.000 | 0.000 | 0.000 | 0.027 | GTPBP6 | 0.49735 | 1.00000 | 1.00000 | 0 | 0 |
| 1318 | chrX | 1514000 | 1515000 | 0.000 | 0.000 | 0.015 | 0.014 | SLC25A6 | 1.00000 | 1.00000 | 0.29694 | 0 | 0 |
| 1319 | chrX | 1611000 | 1612060 | 0.000 | 0.000 | 0.029 | 0.000 | P2RY8 | 0.22755 | 0.54294 | 0.08726 | 1 | 0 |
| 1320 | chrX | 12993000 | 12994000 | 0.000 | 0.000 | 0.235 | 0.041 | TMSB4X | 0.00091 | 0.00098 | 0.00000 | 1 | 1 |
| 1321 | chrX | 12994000 | 12995000 | 0.000 | 0.000 | 0.221 | 0.027 | TMSB4X | 0.00045 | 0.00107 | 0.00000 | 1 | 1 |
| 1322 | chrX | 13419000 | 13420006 | 0.028 | 0.000 | 0.029 | 0.027 | ATXN3L | 1.00000 | 1.00000 | 0.08726 | 0 | 0 |
| 1323 | chrX | 27031000 | 27032000 | 0.006 | 0.000 | 0.059 | 0.000 | DCAF8L2 | 0.05016 | 0.29551 | 0.00730 | 0 | 1 |
| 1324 | chrX | 32315000 | 32316000 | 0.000 | 0.000 | 0.000 | 0.027 | DMD | 0.49735 | 1.00000 | 1.00000 | 1 | 0 |
| 1325 | chrX | 32317000 | 32318000 | 0.028 | 0.000 | 0.000 | 0.014 | DMD | 1.00000 | 0.34615 | 1.00000 | 1 | 0 |
| 1326 | chrX | 33144000 | 33145660 | 0.000 | 0.000 | 0.029 | 0.014 | DMD | 0.60686 | 0.54294 | 0.08726 | 1 | 0 |
| 1327 | chrX | 33145000 | 33146660 | 0.000 | 0.000 | 0.044 | 0.027 | DMD | 0.67043 | 0.54966 | 0.02537 | 1 | 0 |
| 1328 | chrX | 33146000 | 33147000 | 0.000 | 0.000 | 0.162 | 0.068 | DMD | 0.11004 | 0.01471 | 0.00000 | 1 | 1 |
| 1329 | chrX | 41366000 | 41367000 | 0.000 | 0.000 | 0.015 | 0.027 | CASK | 1.00000 | 1.00000 | 0.29694 | 0 | 0 |
| 1330 | chrX | 42862000 | 42863006 | 0.000 | 0.000 | 0.074 | 0.027 | MAOA | 0.25970 | 0.16101 | 0.00268 | 0 | 1 |
| 1331 | chrX | 48775000 | 48776000 | 0.000 | 0.000 | 0.044 | 0.014 | PIM2 | 0.34948 | 0.54966 | 0.02537 | 1 | 0 |
| 1332 | chrX | 48776000 | 48777000 | 0.000 | 0.000 | 0.029 | 0.014 | PIM2 | 0.60686 | 0.54294 | 0.08726 | 1 | 0 |
| 1333 | chrX | 64071000 | 64072000 | 0.000 | 0.000 | 0.059 | 0.014 | ZC4H2 | 0.19371 | 0.29551 | 0.00730 | 0 | 1 |
| 1334 | chrX | 67630060 | 67031660 | 0.028 | 0.000 | 0.015 | 0.000 | AR | 0.47887 | 1.00000 | 0.29694 | 0 | 0 |
| 1335 | chrX | 86258000 | 80259660 | 0.000 | 0.000 | 0.000 | 0.027 | HMGN5 | 0.49735 | 1.00060 | 1.00000 | 0 | 0 |
| 1336 | chrX | 81172000 | 81173000 | 0.000 | 0.000 | 0.015 | 0.027 | SW3BGRL | 1.00000 | 1.00000 | 0.29694 | 0 | 0 |
| 1337 | chrX | 87742000 | 87743000 | 0.000 | 0.000 | 0.029 | 0.000 | CPXCR1 | 0.22755 | 0.54294 | 0.08726 | 0 | 0 |
| 1338 | chrX | 87831000 | 87832006 | 0.000 | 0.000 | 0.000 | 0.027 | CPXCRI | 0.49735 | 1.00000 | 1.00000 | 0 | 0 |
| 1339 | chrX | 88263000 | 88264000 | 0.000 | 0.000 | 0.000 | 0.027 | CPXCRI | 0.49735 | 1.00000 | 1.00060 | 0 | 0 |

-continued

| # | Chromosome | Region Start | Region End | BL | CLL | DLBCL | FL | ClosestGene | Fisher_p_ DLBCL_vs_FL | Fisher _p_ DLBCL_vs_BL | Fisher _p_ DLBCL_vs_CLL | Previously Identified | over5PctInAny Histology |
|---|---|---|---|---|---|---|---|---|---|---|---|---|---|
| 1340 | chrX | 88458000 | 88459000 | 0.000 | 0.000 | 0.029 | 0.000 | CPXCRI | 0.22755 | 0.54294 | 0.08726 | 0 | 0 |
| 1341 | chrX | 92647000 | 92648000 | 0.000 | 0.000 | 0.000 | 0.027 | NAPIL3 | 0.49735 | 1.00000 | 1.00000 | 0 | 0 |
| 1342 | chrX | 93279060 | 93280000 | 0.000 | 0.000 | 0.015 | 0.014 | FAM133A | 1.00000 | 1.00000 | 0.29694 | 0 | 0 |
| 1343 | chrX | 94679006 | 94080000 | 0.000 | 0.000 | 0.015 | 0.014 | FAM133A | 1.00000 | 1.00000 | 0.29694 | 0 | 0 |
| 1344 | chrX | 104006000 | 104007000 | 0.000 | 0.000 | 0.015 | 0.014 | ILIRAFL2 | 1.00000 | 1.00000 | 0.29694 | 0 | 0 |
| 1345 | chrX | 104269000 | 104270000 | 0.000 | 0.000 | 0.015 | 0.014 | ILIRAPL2 | 1.00000 | 1.00000 | 0.29694 | 0 | 0 |
| 1346 | chrX | 106132000 | 106133000 | 0.000 | 0.000 | 0.000 | 0.027 | RIPPLYI | 0.49735 | 1.00000 | 1.00000 | 0 | 0 |
| 1347 | chrX | 113095000 | 113096000 | 0.000 | 0.006 | 0.015 | 0.000 | HTR2C | 0.47887 | 1.00000 | 0.50663 | 0 | 0 |
| 1348 | chrX | 115676000 | 115677000 | 0.000 | 0.000 | 0.015 | 0.014 | CXorf6l | 1.00000 | 1.00000 | 0.29694 | 0 | 0 |
| 1349 | chrX | 124996000 | 124997000 | 0.000 | 0.000 | 0.029 | 0.000 | DCAFL2L2 | 0.22755 | 0.54294 | 0.08726 | 0 | 0 |
| 1350 | chrX | 125708660 | 125709000 | 0.000 | 0.000 | 0.029 | 0.000 | DCAFI2LI | 0.22755 | 0.54294 | 0.68726 | 0 | 0 |
| 1351 | chrX | 128560000 | 128566000 | 0.000 | 0.000 | 0.015 | 0.014 | SMARCAI | 1.00000 | 1.00060 | 0.29694 | 0 | 0 |
| 1352 | chrX | 129643000 | 129644000 | 0.000 | 0.000 | 0.015 | 0.027 | RBMX2 | 1.00000 | 1.00000 | 0.29694 | 0 | 0 |
| 1353 | chrX | 134903000 | 134904000 | 0.000 | 0.000 | 0.029 | 0.014 | CT45A3;CT45A4; | 0.60686 | 0.54294 | 0.08726 | 0 | 0 |
| 1354 | chrX | 140846000 | 140847000 | 0.000 | 0.000 | 0.029 | 0.000 | SPANXD.SPANXE; | 0.22755 | 0.54294 | 0.08726 | 0 | 0 |
| 1355 | chrX | 143750000 | 143751000 | 0.000 | 0.000 | 0.000 | 0.027 | SPANXNI | 0.49735 | 1.00000 | 1.00000 | 0 | 0 |
| 1356 | chrX | 145016000 | 145017000 | 0.028 | 0.000 | 0.000 | 0.027 | TMEM257 | 0.49735 | 0.34615 | 1.00000 | 0 | 0 |

| # | Chromosome | Region Start | Region End | ABC-subtype | GCB-subtype | ClosestGene | p_ABC_vs_GCB | PreviouslyIdentified |
|---|---|---|---|---|---|---|---|---|
| 1 | chr1 | 756000 | 757000 | 0.040 | 0.000 | AL669831.1 | 1.00000 | 0 |
| 2 | chr1 | 1963000 | 1964000 | 0.000 | 0.000 | GABRD | 1.00000 | 0 |
| 3 | chr1 | 2052000 | 2053000 | 0.000 | 0.040 | PRKCZ | 1.00000 | 0 |
| 4 | chr1 | 3789000 | 3790000 | 0.000 | 0.000 | DFFB | 1.00000 | 0 |
| 5 | chr1 | 6613000 | 6614000 | 0.000 | 0.000 | NOL9 | 1.00000 | 1 |
| 6 | chr1 | 6614000 | 6615000 | 0.120 | 0.040 | NOL9 | 0.60921 | 1 |
| 7 | chr1 | 6661000 | 6662000 | 0.000 | 0.000 | KLHL21 | 1.00000 | 0 |
| 8 | chr1 | 6662000 | 6663000 | 0.120 | 0.000 | KLHL21 | 0.23469 | 0 |
| 9 | chr1 | 9129000 | 9130000 | 0.000 | 0.080 | SLC2A5 | 0.48980 | 0 |
| 10 | chr1 | 10894000 | 10895000 | 0.040 | 0.000 | C1orf127 | 1.00000 | 0 |
| 11 | chr1 | 17019000 | 17020000 | 0.000 | 0.000 | AL137798.1 | 1.00000 | 0 |
| 12 | chr1 | 17231000 | 17232000 | 0.040 | 0.000 | CROCC | 1.00000 | 0 |
| 13 | chr1 | 19935000 | 19936000 | 0.080 | 0.000 | MINOS1-NBL1 | 0.48980 | 0 |
| 14 | chr1 | 21091000 | 21092000 | 0.040 | 0.000 | HP1BP3 | 1.00000 | 0 |
| 15 | chr1 | 23885000 | 23886000 | 0.080 | 0.040 | ID3 | 1.00000 | 1 |
| 16 | chr1 | 28408000 | 28409000 | 0.000 | 0.040 | EYA3 | 1.00000 | 0 |
| 17 | chr1 | 32373000 | 32374000 | 0.000 | 0.040 | PTP4A2 | 1.00000 | 0 |
| 18 | chr1 | 36722000 | 36723000 | 0.040 | 0.000 | THRAP3 | 1.00000 | 0 |
| 19 | chr1 | 46576000 | 46577000 | 0.040 | 0.000 | PIK3R3 | 1.00000 | 0 |
| 20 | chr1 | 51965000 | 51966000 | 0.000 | 0.040 | EPS15 | 1.00000 | 0 |
| 21 | chr1 | 51978000 | 51979000 | 0.040 | 0.080 | EPS15 | 1.00000 | 0 |
| 22 | chr1 | 51983000 | 51984000 | 0.040 | 0.000 | EPS15 | 1.00000 | 0 |
| 23 | chr1 | 72393000 | 72394000 | 0.040 | 0.000 | NEGR1 | 1.00000 | 0 |
| 24 | chr1 | 73719000 | 73720000 | 0.040 | 0.040 | LRR1Q3 | 1.00000 | 0 |
| 25 | chr1 | 77315000 | 77316000 | 0.000 | 0.040 | ST6GALNAC5 | 1.00000 | 0 |
| 26 | chr1 | 81306000 | 81307000 | 0.040 | 0.000 | LPHN2 | 1.00000 | 0 |
| 27 | chr1 | 81527000 | 81528000 | 0.000 | 0.000 | LPHN2 | 1.00000 | 0 |
| 28 | chr1 | 82009000 | 82010000 | 0.000 | 0.000 | LPHN2 | 1.00000 | 0 |
| 29 | chr1 | 84106000 | 84107000 | 0.040 | 0.000 | TTLL7 | 1.00000 | 0 |
| 30 | chr1 | 87524000 | 87525000 | 0.000 | 0.040 | HS2STL; HS2ST 1LOC339524; | 1.00000 | 0 |
| 31 | chr1 | 94551000 | 94552000 | 0.000 | 0.040 | ABCA4 | 1.00000 | 0 |
| 32 | chr1 | 94552000 | 94553000 | 0.000 | 0.040 | ABCA4 | 1.00000 | 0 |
| 33 | chr1 | 103696000 | 103697000 | 0.000 | 0.000 | COL11A1 | 1.00000 | 0 |
| 34 | chr1 | 116979000 | 116980000 | 0.000 | 0.040 | ATP1A1 | 1.00000 | 0 |
| 35 | chr1 | 149784000 | 149785000 | 0.040 | 0.040 | HIST2H3D | 1.00000 | 1 |
| 36 | chr1 | 149821000 | 149822000 | 0.040 | 0.000 | HIST2H2AA4 | 1.00000 | 1 |
| 37 | chr1 | 149857000 | 149858000 | 0.000 | 0.040 | HIST2H2BE | 1.00000 | 1 |
| 38 | chr1 | 149858000 | 149859000 | 0.080 | 0.040 | HIST2H2AC; HIST2H2BE; | 1.00000 | 0 |
| 39 | chr1 | 160616000 | 160617000 | 0.040 | 0.040 | SLAMF1 | 1.00000 | 0 |
| 40 | chr1 | 162711000 | 162712000 | 0.040 | 0.000 | DDR2 | 1.00000 | 0 |
| 41 | chr1 | 163684000 | 163685000 | 0.040 | 0.000 | NUF2 | 1.00000 | 0 |
| 42 | chr1 | 167598000 | 167599000 | 0.080 | 0.000 | RCSD1 | 0.48980 | 0 |
| 43 | chr1 | 167599000 | 167600000 | 0.040 | 0.000 | RCSD1 | 1.00000 | 0 |
| 44 | chr1 | 167600000 | 167601000 | 0.040 | 0.040 | RCSD1 | 1.00000 | 0 |
| 45 | chr1 | 174333000 | 174334000 | 0.040 | 0.000 | RABGAP1L | 1.00000 | 0 |
| 46 | chr1 | 187263000 | 187264000 | 0.000 | 0.000 | PLA2G4A | 1.00000 | 0 |
| 47 | chr1 | 187283000 | 187284000 | 0.040 | 0.000 | PLA2G4A | 1.00000 | 0 |
| 48 | chr1 | 187892000 | 187893000 | 0.040 | 0.000 | PLA2G4A | 1.00000 | 0 |
| 49 | chr1 | 195282000 | 195283000 | 0.000 | 0.040 | KCNT2 | 1.00000 | 0 |
| 50 | chr1 | 198591000 | 198592000 | 0.000 | 0.040 | PTPRC | 1.00000 | 0 |
| 51 | chr1 | 198608000 | 198609000 | 0.040 | 0.000 | PTPRC | 1.00000 | 0 |
| 52 | chr1 | 198609000 | 198610000 | 0.080 | 0.000 | PTPRC | 0.48980 | 0 |
| 53 | chr1 | 202004000 | 202005000 | 0.040 | 0.040 | ELF3 | 1.00000 | 0 |
| 54 | chr1 | 203273000 | 203274000 | 0.040 | 0.000 | BTG2 | 1.00000 | 1 |
| 55 | chr1 | 203274000 | 203275000 | 0.160 | 0.160 | BTG2 | 1.00000 | 1 |
| 56 | chr1 | 203275000 | 203276000 | 0.400 | 0.280 | BTG2 | 0.55122 | 1 |
| 57 | chr1 | 203276000 | 203277000 | 0.080 | 0.040 | BTG2 | 1.00000 | 1 |
| 58 | chr1 | 205780000 | 205781000 | 0.000 | 0.000 | SLC41A1 | 1.00000 | 0 |
| 59 | chr1 | 205781000 | 205782000 | 0.000 | 0.000 | SLC41Al | 1.00000 | 0 |
| 60 | chr1 | 206283000 | 206284000 | 0.000 | 0.040 | CTSE | 1.00000 | 0 |
| 61 | chr1 | 206286000 | 206287000 | 0.040 | 0.000 | CTSE | 1.00000 | 0 |
| 62 | chr1 | 217044000 | 217045000 | 0.040 | 0.000 | ESRRG | 1.00000 | 0 |
| 63 | chr1 | 226924000 | 226925000 | 0.080 | 0.120 | ITPKB | 1.00000 | 1 |
| 64 | chr1 | 226925000 | 226926000 | 0.120 | 0.000 | ITPKB | 0.23469 | 1 |
| 65 | chr1 | 226926000 | 226927000 | 0.120 | 0.000 | ITPKB | 0.23469 | 1 |
| 66 | chr1 | 229974000 | 229975000 | 0.040 | 0.040 | URB2 | 1.00000 | 0 |
| 67 | chr1 | 235131000 | 235132000 | 0.000 | 0.000 | TOMM20 | 1.00000 | 0 |
| 68 | chr1 | 235141000 | 235142000 | 0.040 | 0.000 | TOMM20 | 1.00000 | 0 |
| 69 | chr1 | 238787000 | 238788000 | 0.040 | 0.000 | MTRNR2L11 | 1.00000 | 0 |
| 70 | chr1 | 248088000 | 248089000 | 0.040 | 0.000 | OR2T8 | 1.00000 | 0 |
| 71 | chr2 | 630000 | 631000 | 0.000 | 0.000 | TMEM18 | 1.00000 | 0 |
| 72 | chr2 | 1484000 | 1485000 | 0.000 | 0.000 | TPO | 1.00000 | 0 |
| 73 | chr2 | 7991000 | 7992000 | 0.000 | 0.040 | RNF144A | 1.00000 | 0 |
| 74 | chr2 | 12173000 | 12174000 | 0.000 | 0.040 | LPIN1 | 1.00000 | 0 |
| 75 | chr2 | 12175000 | 12176000 | 0.000 | 0.000 | LPIN1 | 1.00000 | 0 |
| 76 | chr2 | 12249000 | 12250000 | 0.000 | 0.040 | LPIN1 | 1.00000 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 77 | chr2 | 14113000 | 14114000 | 0.000 | 0.000 | FAM84A | 1.00000 | 0 |
| 78 | chr2 | 17577000 | 17578000 | 0.000 | 0.040 | RAD51AP2 | 1.00000 | 0 |
| 79 | chr2 | 19253000 | 19254000 | 0.000 | 0.000 | OSR1 | 1.00000 | 0 |
| 80 | chr2 | 24802000 | 24803000 | 0.040 | 0.000 | NCOA1 | 1.00000 | 0 |
| 81 | chr2 | 31478000 | 31479000 | 0.040 | 0.000 | EHD3 | 1.00000 | 0 |
| 82 | chr2 | 41728000 | 41729000 | 0.040 | 0.000 | C2orf91 | 1.00000 | 0 |
| 83 | chr2 | 45404000 | 45405000 | 0.000 | 0.000 | SIX2 | 1.00000 | 0 |
| 84 | chr2 | 47923000 | 47924000 | 0.000 | 0.040 | MSH6 | 1.00000 | 0 |
| 85 | chr2 | 47944000 | 47945000 | 0.000 | 0.000 | MSH6 | 1.00000 | 0 |
| 86 | chr2 | 51360000 | 51361000 | 0.040 | 0.000 | NRXN1 | 1.00000 | 0 |
| 87 | chr2 | 51655000 | 51656000 | 0.000 | 0.000 | NRXN1 | 1.00000 | 0 |
| 88 | chr2 | 56565000 | 56566000 | 0.040 | 0.000 | CCDC85A | 1.00000 | 0 |
| 89 | chr2 | 57800000 | 57801000 | 0.040 | 0.000 | VRK2 | 1.00000 | 0 |
| 90 | chr2 | 60779000 | 60780000 | 0.000 | 0.040 | BCL11A | 1.00000 | 0 |
| 91 | chr2 | 60780000 | 60781000 | 0.080 | 0.000 | BCL11A | 0.48980 | 0 |
| 92 | chr2 | 63802000 | 63803000 | 0.000 | 0.000 | WDPCP | 1.00000 | 0 |
| 93 | chr2 | 63827000 | 63828000 | 0.000 | 0.040 | MDH1 | 1.00000 | 0 |
| 94 | chr2 | 64319000 | 64320000 | 0.000 | 0.040 | PELI1 | 1.00000 | 0 |
| 95 | chr2 | 65593000 | 65594000 | 0.000 | 0.040 | SPRED2 | 1.00000 | 1 |
| 96 | chr2 | 67002000 | 67003000 | 0.040 | 0.040 | MEIS1 | 1.00000 | 0 |
| 97 | chr2 | 70315000 | 70316000 | 0.040 | 0.000 | PCBP1 | 1.00000 | 0 |
| 98 | chr2 | 79502000 | 79503000 | 0.000 | 0.000 | REG3A | 1.00000 | 0 |
| 99 | chr2 | 79644000 | 79645000 | 0.000 | 0.000 | CTNNA2 | 1.00000 | 0 |
| 100 | chr2 | 81818000 | 81819000 | 0.000 | 0.000 | CTNNA2 | 1.00000 | 0 |
| 101 | chr2 | 82310000 | 82311000 | 0.000 | 0.000 | CTNNA2 | 1.00000 | 0 |
| 102 | chr2 | 82948000 | 82949000 | 0.000 | 0.040 | SUCLG1 | 1.00000 | 0 |
| 103 | chr2 | 85335000 | 85336000 | 0.000 | 0.000 | TCF7L1 | 1.00000 | 0 |
| 104 | chr2 | 88905000 | 88906000 | 0.080 | 0.000 | EIF2AK3 | 0.48980 | 0 |
| 105 | chr2 | 88906000 | 88907000 | 0.160 | 0.040 | EIF2AK3 | 0.34868 | 0 |
| 106 | chr2 | 88907000 | 88908000 | 0.040 | 0.040 | EIF2AK3 | 1.00000 | 0 |
| 107 | chr2 | 89052000 | 89053000 | 0.000 | 0.080 | RPIA | 0.48980 | 0 |
| 108 | chr2 | 89065000 | 89066000 | 0.000 | 0.000 | RPIA | 1.00000 | 0 |
| 109 | chr2 | 89066000 | 89067000 | 0.040 | 0.000 | RPIA | 1.00000 | 0 |
| 110 | chr2 | 89095000 | 89096000 | 0.000 | 0.040 | RPIA | 1.00000 | 0 |
| 111 | chr2 | 89127000 | 89128000 | 0.120 | 0.080 | IGKC | 1.00000 | 0 |
| 112 | chr2 | 89128000 | 89129000 | 0.160 | 0.160 | IGKC | 1.00000 | 0 |
| 113 | chr2 | 89129000 | 89130000 | 0.120 | 0.000 | IGKC | 0.23469 | 0 |
| 114 | chr2 | 89130000 | 89131000 | 0.080 | 0.000 | IGKC | 0.48980 | 0 |
| 115 | chr2 | 89131000 | 89132000 | 0.040 | 0.040 | IGKC | 1.00000 | 0 |
| 116 | chr2 | 89132000 | 89133000 | 0.040 | 0.000 | IGKC | 1.00000 | 0 |
| 117 | chr2 | 89133000 | 89134000 | 0.000 | 0.040 | IGKC | 1.00000 | 0 |
| 118 | chr2 | 89137000 | 89138000 | 0.000 | 0.040 | IGKC | 1.00000 | 0 |
| 119 | chr2 | 89138000 | 89139000 | 0.040 | 0.000 | IGKC | 1.00000 | 0 |
| 120 | chr2 | 89139000 | 89140000 | 0.000 | 0.040 | IGKC | 1.00000 | 0 |
| 121 | chr2 | 89140000 | 89141000 | 0.040 | 0.120 | IGKC | 0.60921 | 0 |
| 122 | chr2 | 89141000 | 89142000 | 0.080 | 0.120 | IGKC | 1.00000 | 0 |
| 123 | chr2 | 89142000 | 89143000 | 0.040 | 0.200 | IGKC | 0.18946 | 0 |
| 124 | chr2 | 89143000 | 89144000 | 0.000 | 0.080 | IGKC | 0.48980 | 0 |
| 125 | chr2 | 89144000 | 89145000 | 0.040 | 0.040 | IGKC | 1.00000 | 0 |
| 126 | chr2 | 89145000 | 89146000 | 0.040 | 0.000 | IGKC | 1.00000 | 0 |
| 127 | chr2 | 89146000 | 89147000 | 0.000 | 0.000 | IGKC | 1.00000 | 0 |
| 128 | chr2 | 89153000 | 89154000 | 0.000 | 0.000 | IGKC | 1.00000 | 0 |
| 129 | chr2 | 89155000 | 89156000 | 0.080 | 0.080 | IGKC | 1.00000 | 0 |
| 130 | chr2 | 89156000 | 89157000 | 0.120 | 0.000 | IGKC | 0.23469 | 0 |
| 131 | chr2 | 89157000 | 89158000 | 0.240 | 0.160 | IGKC | 0.72520 | 0 |
| 132 | chr2 | 89158000 | 89159000 | 0.240 | 0.280 | IGKC | 1.00000 | 0 |
| 133 | cht2 | 89159000 | 89160000 | 0.360 | 0.640 | IGKJ5 | 0.08874 | 0 |
| 134 | chr2 | 89160000 | 89161000 | 0.320 | 0.680 | IGKJ3; IGKJ4; IGKJ5; | 0.02271 | 0 |
| 135 | chr2 | 89161000 | 89162000 | 0.240 | 0.320 | IGKJ1; IGKJ2; | 0.75361 | 0 |
| 136 | chr2 | 89162000 | 89163000 | 0.200 | 0.200 | IGKJ1 | 1.00000 | 0 |
| 137 | chr2 | 89163000 | 89164000 | 0.120 | 0.240 | IGKJ1 | 0.46349 | 0 |
| 138 | chr2 | 89164000 | 89165000 | 0.160 | 0.280 | IGKJ1 | 0.49620 | 0 |
| 139 | chr2 | 89165000 | 89166000 | 0.160 | 0.360 | IGKJ1 | 0.19633 | 0 |
| 140 | chr2 | 89166000 | 89167000 | 0.000 | 0.040 | IGKJ1 | 1.00000 | 0 |
| 141 | chr2 | 89169000 | 89170000 | 0.000 | 0.040 | IGKJ1 | 1.00000 | 0 |
| 142 | chr2 | 89184000 | 89185000 | 0.000 | 0.000 | IGKV4-1 | 1.00000 | 0 |
| 143 | chr2 | 89185000 | 89186000 | 0.120 | 0.320 | IGKV4-1 | 0.17062 | 0 |
| 144 | chr2 | 89196000 | 89197000 | 0.000 | 0.160 | IGKV5-2 | 0.10986 | 0 |
| 145 | chr2 | 89197000 | 89198000 | 0.000 | 0.040 | IGKV5-2 | 1.00000 | 0 |
| 146 | chr2 | 89214000 | 89215000 | 0.000 | 0.040 | IGKV5-2 | 1.00000 | 0 |
| 147 | chr2 | 89246000 | 89247000 | 0.040 | 0.000 | IGKV1-5 | 1.00000 | 0 |
| 148 | chr2 | 89247000 | 89248000 | 0.160 | 0.000 | IGKVI-5 | 0.10986 | 0 |
| 149 | chr2 | 89248000 | 89249000 | 0.040 | 0.000 | IGKV1-5 | 1.00000 | 0 |
| 150 | chr2 | 89266000 | 89267000 | 0.000 | 0.040 | IGKV1-6 | 1.00000 | 0 |
| 151 | chr2 | 89291000 | 89292000 | 0.040 | 0.040 | IGKV1-8 | 1.00000 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 152 | chr2 | 89292000 | 89293000 | 0.000 | 0.040 | IGKV1-8 | 1.00000 | 0 |
| 153 | chr2 | 89326000 | 89327000 | 0.040 | 0.000 | IGKV3-11 | 1.00000 | 0 |
| 154 | chr2 | 89327000 | 89328000 | 0.040 | 0.000 | IGKV3-11 | 1.00000 | 0 |
| 155 | chr2 | 89442000 | 89443000 | 0.040 | 0.160 | IGKV3-20 | 0.34868 | 0 |
| 156 | chr2 | 89443000 | 89444000 | 0.000 | 0.000 | IGKV3-20 | 1.00000 | 0 |
| 157 | chr2 | 89476000 | 89477000 | 0.000 | 0.000 | IGKV2-24 | 1.00000 | 0 |
| 158 | chr2 | 89513000 | 89514000 | 0.040 | 0.000 | IGKV1-27 | 1.00000 | 0 |
| 159 | chr2 | 89521000 | 89522000 | 0.040 | 0.040 | IGKV2-28 | 1.00000 | 0 |
| 160 | chr2 | 89533000 | 89534000 | 0.040 | 0.000 | IGKV2-30 | 1.00000 | 0 |
| 161 | chr2 | 89534000 | 89535000 | 0.080 | 0.000 | IGKV2-30 | 0.48980 | 0 |
| 162 | chr2 | 89544000 | 89545000 | 0.000 | 0.080 | IGKV2-30 | 0.48980 | 0 |
| 163 | chr2 | 89545000 | 89546000 | 0.040 | 0.000 | IGKV2-30 | 1.00000 | 0 |
| 164 | chr2 | 90259000 | 90260000 | 0.040 | 0.000 | IGKV1D-8 | 1.00000 | 0 |
| 165 | chr2 | 90260000 | 90261000 | 0.120 | 0.000 | IGKV1D-8 | 0.23469 | 0 |
| 166 | chr2 | 96809000 | 96810000 | 0.040 | 0.080 | DUSP2 | 1.00000 | 1 |
| 167 | chr2 | 96810000 | 96811000 | 0.080 | 0.120 | DUSP2 | 1.00000 | 1 |
| 168 | chr2 | 96811000 | 96812000 | 0.000 | 0.080 | DUSP2 | 0.48980 | 1 |
| 169 | chr2 | 98611000 | 98612000 | 0.000 | 0.040 | TMEM131 | 1.00000 | 0 |
| 170 | chr2 | 100757000 | 100758000 | 0.080 | 0.000 | AFF3 | 0.48980 | 0 |
| 171 | chr2 | 100758000 | 100759000 | 0.120 | 0.000 | AFF3 | 0.23469 | 0 |
| 172 | chr2 | 106144000 | 106145000 | 0.000 | 0.080 | FHL2 | 0.48980 | 0 |
| 173 | chr2 | 111878000 | 111879000 | 0.000 | 0.120 | BCL2L11 | 0.23469 | 0 |
| 174 | chr2 | 111879000 | 111880000 | 0.040 | 0.120 | BCL2L11 | 0.60921 | 0 |
| 175 | chr2 | 112305000 | 112306000 | 0.000 | 0.040 | ANAPC1 | 1.00000 | 0 |
| 176 | chr2 | 116234000 | 116235000 | 0.040 | 0.000 | DPP10 | 1.00000 | 0 |
| 177 | chr2 | 116439000 | 116440000 | 0.040 | 0.000 | DPP10 | 1.00000 | 0 |
| 178 | chr2 | 124697000 | 124698000 | 0.000 | 0.040 | CNTNAP5 | 1.00000 | 0 |
| 179 | chr2 | 125235000 | 125236000 | 0.000 | 0.000 | CNTNAP5 | 1.00000 | 0 |
| 180 | chr2 | 127538000 | 127539000 | 0.000 | 0.000 | GYPC | 1.00000 | 0 |
| 181 | chr2 | 136874000 | 136875000 | 0.200 | 0.120 | CXCR4 | 0.70194 | 1 |
| 182 | chr2 | 136875000 | 136876000 | 0.240 | 0.240 | CXCR4 | 1.00000 | 1 |
| 183 | chr2 | 136996000 | 136997000 | 0.000 | 0.040 | CXCR4 | 1.00000 | 1 |
| 184 | chr2 | 137082000 | 137083000 | 0.040 | 0.000 | CXCR4 | 1.00000 | 1 |
| 185 | chr2 | 140951000 | 140952000 | 0.040 | 0.000 | LRP1B | 1.00000 | 0 |
| 186 | chr2 | 141335000 | 141336000 | 0.040 | 0.000 | LRP1B | 1.00000 | 0 |
| 187 | chr2 | 141770000 | 141771000 | 0.000 | 0.000 | LRP1B | 1.00000 | 0 |
| 188 | chr2 | 146445000 | 146446000 | 0.000 | 0.000 | ZEB2 | 1.00000 | 0 |
| 189 | chr2 | 146446000 | 146447000 | 0.000 | 0.080 | ZEB2 | 0.48980 | 0 |
| 190 | chr2 | 156443000 | 156444000 | 0.000 | 0.000 | KCNJ3 | 1.00000 | 0 |
| 191 | chr2 | 172590000 | 172591000 | 0.040 | 0.000 | DYNC1I2 | 1.00000 | 0 |
| 192 | chr2 | 176581000 | 176582000 | 0.000 | 0.000 | KIAA1715 | 1.00000 | 0 |
| 193 | chr2 | 179880000 | 179881000 | 0.000 | 0.040 | CCDC141 | 1.00000 | 0 |
| 194 | chr2 | 180358000 | 180359000 | 0.040 | 0.000 | ZNF385B | 1.00000 | 0 |
| 195 | chr2 | 189285000 | 189286000 | 0.040 | 0.000 | GULP1 | 1.00000 | 0 |
| 196 | chr2 | 189432000 | 189433000 | 0.000 | 0.040 | GULP1 | 1.00000 | 0 |
| 197 | chr2 | 194115000 | 194116000 | 0.040 | 0.000 | TMEFF2 | 1.00000 | 0 |
| 198 | chr2 | 197035000 | 197036000 | 0.040 | 0.080 | STK17B | 1.00000 | 0 |
| 199 | chr2 | 197041000 | 197042000 | 0.080 | 0.000 | STK17B | 0.48980 | 0 |
| 200 | chr2 | 215999000 | 216000000 | 0.040 | 0.000 | ABCA12 | 1.00000 | 0 |
| 201 | chr2 | 216973000 | 216974000 | 0.000 | 0.000 | XRCC5 | 1.00000 | 0 |
| 202 | chr2 | 217247000 | 217248000 | 0.000 | 0.000 | 4-Mar-19 | 1.00000 | 0 |
| 203 | chr2 | 225386000 | 225387000 | 0.040 | 0.000 | CUL3 | 1.00000 | 0 |
| 204 | chr2 | 225524000 | 225525000 | 0.000 | 0.040 | CUL3 | 1.00000 | 0 |
| 205 | chr2 | 233478000 | 233479000 | 0.040 | 0.000 | EFHD1 | 1.00000 | 0 |
| 206 | chr2 | 233980000 | 233981000 | 0.000 | 0.080 | INPP5D | 0.48980 | 0 |
| 207 | chr2 | 240641000 | 240642000 | 0.000 | 0.000 | AC093802.1 | 1.00000 | 0 |
| 208 | chr2 | 241125000 | 241126000 | 0.000 | 0.000 | OTOS | 1.00000 | 0 |
| 209 | chr3 | 8739000 | 8740000 | 0.000 | 0.000 | CAV3 | 1.00000 | 0 |
| 210 | chr3 | 16407000 | 16408000 | 0.000 | 0.000 | RFTN1 | 1.00000 | 1 |
| 211 | chr3 | 16409000 | 16410000 | 0.000 | 0.000 | RFTN1 | 1.00000 | 1 |
| 212 | chr3 | 16419000 | 16420000 | 0.040 | 0.080 | RFTN1 | 1.00000 | 1 |
| 213 | chr3 | 16472000 | 16473000 | 0.040 | 0.000 | RFTN1 | 1.00000 | 1 |
| 214 | chr3 | 16495000 | 16496000 | 0.000 | 0.080 | RFTN1 | 0.48980 | 1 |
| 215 | chr3 | 16552000 | 16553000 | 0.000 | 0.080 | RFTN1 | 0.48980 | 1 |
| 216 | chr3 | 16554000 | 16555000 | 0.120 | 0.120 | RFTN1 | 1.00000 | 1 |
| 217 | chr3 | 16555000 | 16556000 | 0.000 | 0.040 | RFTN1 | 1.00000 | 1 |
| 218 | chr3 | 21658000 | 21659000 | 0.040 | 0.000 | ZNF385D | 1.00000 | 0 |
| 219 | chr3 | 25691000 | 25692000 | 0.040 | 0.040 | TOP2B | 1.00000 | 0 |
| 220 | chr3 | 31969000 | 31970000 | 0.000 | 0.040 | OSBPL10 | 1.00000 | 1 |
| 221 | chr3 | 31993000 | 31994000 | 0.040 | 0.000 | OSBPL10 | 1.00000 | 1 |
| 222 | chr3 | 32001000 | 32002000 | 0.080 | 0.040 | OSBPL10 | 1.00000 | 1 |
| 223 | chr3 | 32022000 | 32023000 | 0.120 | 0.080 | OSBPL10 | 1.00000 | 1 |
| 224 | chr3 | 32023000 | 32024000 | 0.080 | 0.000 | OSBPL10 | 0.48980 | 1 |
| 225 | chr3 | 50128000 | 50129000 | 0.000 | 0.040 | RBM5 | 1.00000 | 0 |
| 226 | chr3 | 54913000 | 54914000 | 0.040 | 0.000 | CACNA2D3 | 1.00000 | 0 |
| 227 | chr3 | 56074000 | 56075000 | 0.040 | 0.040 | ERC2 | 1.00000 | 0 |
| 228 | chr3 | 59577000 | 59578000 | 0.000 | 0.000 | FHIT | 1.00000 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 229 | chr3 | 60351000 | 60352000 | 0.000 | 0.040 | FHIT | 1.00000 | 0 |
| 230 | chr3 | 60356000 | 60357000 | 0.000 | 0.000 | FHIT | 1.00000 | 0 |
| 231 | chr3 | 60357000 | 60358000 | 0.040 | 0.000 | FHIT | 1.00000 | 0 |
| 232 | chr3 | 60358000 | 60359000 | 0.040 | 0.000 | FHIT | 1.00000 | 0 |
| 233 | chr3 | 60359000 | 60360000 | 0.000 | 0.000 | FHIT | 1.00000 | 0 |
| 234 | chr3 | 60389000 | 60390000 | 0.000 | 0.040 | FHIT | 1.00000 | 0 |
| 235 | chr3 | 60392000 | 60393000 | 0.040 | 0.000 | FHIT | 1.00000 | 0 |
| 236 | chr3 | 60395000 | 60396000 | 0.000 | 0.000 | FHIT | 1.00000 | 0 |
| 237 | chr3 | 60404000 | 60405000 | 0.040 | 0.000 | FHIT | 1.00000 | 0 |
| 238 | chr3 | 60436000 | 60437000 | 0.000 | 0.000 | FHIT | 1.00000 | 0 |
| 239 | chr3 | 60437000 | 60438000 | 0.000 | 0.040 | FHIT | 1.00000 | 0 |
| 240 | chr3 | 60477000 | 60478000 | 0.040 | 0.040 | FHIT | 1.00000 | 0 |
| 241 | chr3 | 60485000 | 60486000 | 0.040 | 0.000 | FHIT | 1.00000 | 0 |
| 242 | chr3 | 60515000 | 60516000 | 0.000 | 0.040 | FHIT | 1.00000 | 0 |
| 243 | chr3 | 60535000 | 60536000 | 0.040 | 0.000 | FHIT | 1.00000 | 0 |
| 244 | chr3 | 60602000 | 60603000 | 0.000 | 0.000 | FHIT | 1.00000 | 0 |
| 245 | chr3 | 60613000 | 60614000 | 0.000 | 0.040 | FHIT | 1.00000 | 0 |
| 246 | chr3 | 60614000 | 60615000 | 0.000 | 0.040 | FHIT | 1.00000 | 0 |
| 247 | chr3 | 60632000 | 60633000 | 0.000 | 0.000 | FHIT | 1.00000 | 0 |
| 248 | chr | 60635000 | 60636000 | 0.000 | 0.000 | FHIT | 1.00000 | 0 |
| 249 | chr3 | 60640000 | 60641000 | 0.000 | 0.000 | FHIT | 1.00000 | 0 |
| 250 | chr3 | 60647000 | 60648000 | 0.000 | 0.040 | FHIT | 1.00000 | 0 |
| 251 | chr3 | 60648000 | 60649000 | 0.000 | 0.040 | FHIT | 1.00000 | 0 |
| 252 | chr3 | 60652000 | 60653000 | 0.000 | 0.000 | FHIT | 1.00000 | 0 |
| 253 | chr3 | 60660000 | 60661000 | 0.040 | 0.000 | FHIT | 1.00000 | 0 |
| 254 | chr3 | 60665000 | 60666000 | 0.000 | 0.040 | FHIT | 1.00000 | 0 |
| 255 | chr3 | 60666000 | 60667000 | 0.000 | 0.040 | FHIT | 1.00000 | 0 |
| 256 | chr3 | 60671000 | 60672000 | 0.000 | 0.000 | FHIT | 1.00000 | 0 |
| 257 | chr3 | 60673000 | 60674000 | 0.040 | 0.000 | FHIT | 1.00000 | 0 |
| 258 | chr3 | 60675000 | 60676000 | 0.000 | 0.040 | FHIT | 1.00000 | 0 |
| 259 | chr3 | 60678000 | 60679000 | 0.000 | 0.040 | FHIT | 1.00000 | 0 |
| 260 | chr3 | 60683000 | 60684000 | 0.000 | 0.000 | FHIT | 1.00000 | 0 |
| 261 | chr3 | 60684000 | 60685000 | 0.000 | 0.040 | FHIT | 1.00000 | 0 |
| 262 | chr3 | 60688000 | 60689000 | 0.040 | 0.000 | FHIT | 1.00000 | 0 |
| 263 | chr3 | 60717000 | 60718000 | 0.000 | 0.000 | FHIT | 1.00000 | 0 |
| 264 | chr3 | 60740000 | 60741000 | 0.040 | 0.000 | FHIT | 1.00000 | 0 |
| 265 | chr3 | 60774000 | 60775000 | 0.000 | 0.040 | FHIT | 1.00000 | 0 |
| 266 | chr3 | 60792000 | 60793000 | 0.000 | 0.000 | FHIT | 1.00000 | 0 |
| 267 | chr3 | 60806000 | 60807000 | 0.040 | 0.000 | FHIT | 1.00000 | 0 |
| 268 | chr3 | 60812000 | 60813000 | 0.000 | 0.000 | FHIT | 1.00000 | 0 |
| 269 | chr3 | 60860000 | 60861000 | 0.000 | 0.000 | FHIT | 1.00000 | 0 |
| 270 | chr3 | 71551000 | 71552000 | 0.040 | 0.000 | EIF4E3 | 1.00000 | 0 |
| 271 | chr3 | 78274000 | 78275000 | 0.000 | 0.040 | ROBO1 | 1.00000 | 0 |
| 272 | chr3 | 80273000 | 80274000 | 0.000 | 0.000 | ROBO1 | 1.00000 | 0 |
| 273 | chr3 | 83094000 | 83095000 | 0.000 | 0.000 | GBE1 | 1.00000 | 0 |
| 274 | chr3 | 83924000 | 83925000 | 0.000 | 0.000 | CADM2 | 1.00000 | 0 |
| 275 | chr3 | 84293000 | 84294000 | 0.000 | 0.040 | CADM2 | 1.00000 | 0 |
| 276 | chr3 | 85260000 | 85261000 | 0.000 | 0.040 | CADM2 | 1.00000 | 0 |
| 277 | chr3 | 85261000 | 85262000 | 0.000 | 0.000 | CADM2 | 1.00000 | 0 |
| 278 | chr3 | 85799000 | 85800000 | 0.040 | 0.000 | CADM2 | 1.00000 | 0 |
| 279 | chr3 | 86226000 | 86227000 | 0.000 | 0.000 | CADM2 | 1.00000 | 0 |
| 280 | chr3 | 88146000 | 88147000 | 0.040 | 0.000 | CGGBP1 | 1.00000 | 0 |
| 281 | chr3 | 94709000 | 94710000 | 0.000 | 0.000 | NSUN3 | 1.00000 | 0 |
| 282 | chr3 | 95460000 | 95461000 | 0.000 | 0.000 | MTRNR2L12 | 1.00000 | 0 |
| 283 | chr3 | 95724000 | 95725000 | 0.080 | 0.000 | MTRNR2L12 | 0.48980 | 0 |
| 284 | chr3 | 101569000 | 101570000 | 0.000 | 0.040 | NFKBIZ | 1.00000 | 0 |
| 285 | chr3 | 111851000 | 111852000 | 0.000 | 0.000 | GCSAM | 1.00000 | 0 |
| 286 | chr3 | 111852000 | 111853000 | 0.040 | 0.040 | GCSAM | 1.00000 | 0 |
| 287 | chr3 | 122377000 | 122378000 | 0.080 | 0.040 | PARP14 | 1.00000 | 0 |
| 288 | chr3 | 150478000 | 150479000 | 0.000 | 0.000 | SIAH2 | 1.00000 | 0 |
| 289 | chr3 | 150479000 | 150480000 | 0.000 | 0.040 | SIAH2 | 1.00000 | 0 |
| 290 | chr3 | 150480000 | 150481000 | 0.000 | 0.120 | SIAH2 | 0.23469 | 0 |
| 291 | chr3 | 163237000 | 163238000 | 0.000 | 0.000 | SI | 1.00000 | 0 |
| 292 | chr3 | 163238000 | 163239000 | 0.000 | 0.000 | SI | 1.00000 | 0 |
| 293 | chr3 | 163615000 | 163616000 | 0.040 | 0.040 | SI | 1.00000 | 0 |
| 294 | chr3 | 183270000 | 183271000 | 0.000 | 0.000 | KLHL6 | 1.00000 | 0 |
| 295 | chr3 | 183271000 | 183272000 | 0.000 | 0.040 | KLHL6 | 1.00000 | 0 |
| 296 | chr3 | 183272000 | 183273000 | 0.000 | 0.120 | KLHL6 | 0.23469 | 0 |
| 297 | chr3 | 183273000 | 183274000 | 0.000 | 0.040 | KLHL6 | 1.00000 | 0 |
| 298 | chr3 | 186648000 | 186649000 | 0.000 | 0.040 | ADIPOQ | 1.00000 | 0 |
| 299 | chr3 | 186714000 | 186715000 | 0.080 | 0.160 | ST6GAL1 | 0.66710 | 1 |
| 300 | chr3 | 186715000 | 186716000 | 0.080 | 0.000 | STGGAL1 | 0.48980 | 1 |
| 301 | chr3 | 186739000 | 186740000 | 0.120 | 0.040 | ST6GAL1 | 0.60921 | 1 |
| 302 | chr3 | 186740000 | 186741000 | 0.160 | 0.080 | ST6GAL1 | 0.66710 | 1 |
| 303 | chr3 | 186742000 | 186743000 | 0.000 | 0.000 | ST6GAL1 | 1.00000 | 1 |
| 304 | chr3 | 186783000 | 186784000 | 0.160 | 0.240 | STGGAL1 | 0.72520 | 1 |
| 305 | chr3 | 186784000 | 186785000 | 0.040 | 0.040 | ST6GAL1 | 1.00000 | 1 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 306 | chr3 | 187458000 | 187459000 | 0.000 | 0.000 | BCL6 | 1.00000 | 1 |
| 307 | chr3 | 187459000 | 187460000 | 0.000 | 0.000 | BCL6 | 1.00000 | 1 |
| 308 | chr3 | 187460000 | 187461000 | 0.040 | 0.040 | BCL6 | 1.00000 | 1 |
| 309 | chr3 | 187461000 | 187462000 | 0.240 | 0.360 | BCL6 | 0.53803 | 1 |
| 310 | chr3 | 187462000 | 187463000 | 0.440 | 0.560 | BCL6 | 0.57214 | 1 |
| 311 | chr3 | 187463000 | 187464000 | 0.360 | 0.440 | BCL6 | 0.77329 | 1 |
| 312 | chr3 | 187464000 | 187465000 | 0.200 | 0.200 | BCL6 | 1.00000 | 1 |
| 313 | chr3 | 187468000 | 187469000 | 0.120 | 0.000 | BCL6 | 0.23469 | 1 |
| 314 | chr3 | 187635000 | 187636000 | 0.040 | 0.000 | BCL6 | 1.00000 | 1 |
| 315 | chr3 | 187636000 | 187637000 | 0.000 | 0.000 | BCL6 | 1.00000 | 1 |
| 316 | chr3 | 187653000 | 187654000 | 0.040 | 0.040 | BCL6 | 1.00000 | 1 |
| 317 | chr3 | 187658000 | 187659000 | 0.000 | 0.040 | BCL6 | 1.00000 | 1 |
| 318 | chr3 | 187660000 | 187661000 | 0.040 | 0.160 | BCL6 | 0.34868 | 1 |
| 319 | chr3 | 187661000 | 187662000 | 0.040 | 0.240 | BCL6 | 0.09828 | 1 |
| 320 | chr3 | 187664000 | 187665000 | 0.040 | 0.080 | BCL6 | 1.00000 | 1 |
| 321 | chr3 | 187686000 | 187687000 | 0.040 | 0.000 | AC022498.1 | 1.00000 | 0 |
| 322 | chr3 | 187687000 | 187688000 | 0.000 | 0.040 | AC022498.1 | 1.00000 | 0 |
| 323 | chr3 | 187693000 | 187694000 | 0.040 | 0.040 | AC022498.1 | 1.00000 | 0 |
| 324 | chr3 | 187696000 | 187697000 | 0.040 | 0.000 | AC022498.1 | 1.00000 | 0 |
| 325 | chr3 | 187697000 | 187698000 | 0.040 | 0.000 | AC022498.1 | 1.00000 | 0 |
| 326 | chr3 | 187803000 | 187804000 | 0.000 | 0.000 | AC022498.1 | 1.00000 | 0 |
| 327 | chr3 | 187806000 | 187807000 | 0.080 | 0.080 | AC022498.1 | 1.00000 | 0 |
| 328 | chr3 | 187957000 | 187958000 | 0.120 | 0.160 | AC022498.1 | 1.00000 | 0 |
| 329 | chr3 | 187958000 | 187959000 | 0.240 | 0.280 | AC022498.1 | 1.00000 | 0 |
| 330 | chr3 | 187959000 | 187960000 | 0.120 | 0.040 | AC022498.1 | 0.60921 | 0 |
| 331 | chr3 | 187960000 | 187961000 | 0.000 | 0.040 | AC022498.1 | 1.00000 | 0 |
| 332 | chr3 | 188222000 | 188223000 | 0.000 | 0.000 | LPP | 1.00000 | 0 |
| 333 | chr3 | 188298000 | 188299000 | 0.040 | 0.000 | LPP | 1.00000 | 0 |
| 334 | chr3 | 188299000 | 188300000 | 0.080 | 0.080 | LPP | 1.00000 | 0 |
| 335 | chr3 | 188471000 | 188472000 | 0.120 | 0.240 | LPP | 0.46349 | 0 |
| 336 | chr3 | 188472000 | 188473000 | 0.000 | 0.080 | LPP | 0.48980 | 0 |
| 337 | chr4 | 50000 | 51000 | 0.080 | 0.000 | ZNF595; ZNF718; | 0.48980 | 0 |
| 338 | chr4 | 51000 | 52000 | 0.120 | 0.040 | ZNF595; ZNF718; | 0.60921 | 0 |
| 339 | chr4 | 54000 | 55000 | 0.080 | 0.000 | ZN F595 ZNF718; | 0.48980 | 0 |
| 340 | chr4 | 290000 | 291000 | 0.000 | 0.000 | ZNF732 | 1.00000 | 0 |
| 341 | chr4 | 385000 | 386000 | 0.080 | 0.000 | ZNF141 | 0.48980 | 0 |
| 342 | chr4 | 550000 | 551000 | 0.000 | 0.000 | PIGG | 1.00000 | 0 |
| 343 | chr4 | 2707000 | 2708000 | 0.000 | 0.040 | FAM193A | 1.00000 | 0 |
| 344 | chr4 | 5206000 | 5207000 | 0.080 | 0.000 | STK32B | 0.48980 | 0 |
| 345 | chr4 | 25863000 | 25864000 | 0.080 | 0.040 | SEL1L3 | 1.00000 | 0 |
| 346 | chr4 | 25864000 | 25865000 | 0.000 | 0.040 | SEL1L3 | 1.00000 | 0 |
| 347 | chr4 | 25865000 | 25866000 | 0.040 | 0.000 | SEL1L3 | 1.00000 | 0 |
| 348 | chr4 | 29657000 | 29658000 | 0.040 | 0.000 | PCDH7 | 1.00000 | 0 |
| 349 | chr4 | 30356000 | 30357000 | 0.040 | 0.000 | PCDH7 | 1.00000 | 0 |
| 350 | chr4 | 33418000 | 33419000 | 0.000 | 0.000 | PCDH7 | 1.00000 | 0 |
| 351 | chr4 | 33449000 | 33450000 | 0.000 | 0.040 | PCDH7 | 1.00000 | 0 |
| 352 | chr4 | 39348000 | 39349000 | 0.000 | 0.040 | RFC1 | 1.00000 | 0 |
| 353 | chr4 | 39974000 | 39975000 | 0.000 | 0.000 | PDS5A | 1.00000 | 0 |
| 354 | chr4 | 40194000 | 40195000 | 0.000 | 0.120 | N4BP2 | 0.23469 | 0 |
| 355 | chr4 | 40195000 | 40196000 | 0.000 | 0.040 | N4BP2 | 1.00000 | 0 |
| 356 | chr4 | 40196000 | 40197000 | 0.040 | 0.000 | N4BP2 | 1.00000 | 0 |
| 357 | chr4 | 40197000 | 40198000 | 0.000 | 0.000 | N4BP2 | 1.00000 | 0 |
| 358 | chr4 | 40198000 | 40199000 | 0.120 | 0.080 | N4BP2 | 1.00000 | 0 |
| 359 | chr4 | 40199000 | 40200000 | 0.280 | 0.240 | N4BP2 | 1.00000 | 0 |
| 360 | chr4 | 40200000 | 40201000 | 0.080 | 0.080 | RHOH | 1.00000 | 1 |
| 361 | chr4 | 40201000 | 40202000 | 0.120 | 0.120 | RHOH | 1.00000 | 1 |
| 362 | chr4 | 40202000 | 40203000 | 0.080 | 0.000 | RHOH | 0.48980 | 1 |
| 363 | chr4 | 40204000 | 40205000 | 0.000 | 0.040 | RHOH | 1.00000 | 1 |
| 364 | chr4 | 45308000 | 45309000 | 0.000 | 0.000 | GNPDA2 | 1.00000 | 0 |
| 365 | chr4 | 46360000 | 46361000 | 0.000 | 0.040 | GABRA2 | 1.00000 | 0 |
| 366 | chr4 | 62375000 | 62376000 | 0.000 | 0.000 | LPHN3 | 1.00000 | 0 |
| 367 | chr4 | 62530000 | 62531000 | 0.000 | 0.000 | LPHN3 | 1.00000 | 0 |
| 368 | chr4 | 62911000 | 62912000 | 0.000 | 0.040 | LPHN3 | 1.00000 | 0 |
| 369 | chr4 | 63120000 | 63121000 | 0.040 | 0.040 | LPHN3 | 1.00000 | 0 |
| 370 | chr4 | 64015000 | 64016000 | 0.000 | 0.000 | LPHN3 | 1.00000 | 0 |
| 371 | chr4 | 65038000 | 65039000 | 0.040 | 0.000 | TECRL | 1.00000 | 0 |
| 372 | chr4 | 65165000 | 65166000 | 0.000 | 0.040 | TECRL | 1.00000 | 0 |
| 373 | chr4 | 65966000 | 65967000 | 0.000 | 0.040 | EPHA5 | 1.00000 | 0 |
| 374 | chr4 | 66827000 | 66828000 | 0.000 | 0.080 | EPHA5 | 0.48980 | 0 |
| 375 | chr4 | 71531000 | 71532000 | 0.000 | 0.040 | IGJ | 1.00000 | 0 |
| 376 | chr4 | 71532000 | 71533000 | 0.000 | 0.000 | IGJ | 1.00000 | 0 |
| 377 | chr4 | 74456000 | 74457000 | 0.040 | 0.000 | RASSF6 | 1.00000 | 0 |
| 378 | chr4 | 74483000 | 74484000 | 0.040 | 0.000 | RASSF6 | 1.00000 | 0 |
| 379 | chr4 | 74484000 | 74485000 | 0.040 | 0.000 | RASSF6 | 1.00000 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 380 | chr4 | 74485000 | 74486000 | 0.120 | 0.000 | RASSF6 | 0.23469 | 0 |
| 381 | chr4 | 91886000 | 91887000 | 0.040 | 0.000 | CCSER1 | 1.00000 | 0 |
| 382 | chr4 | 92787000 | 92788000 | 0.000 | 0.040 | CCSERI | 1.00000 | 0 |
| 383 | chr4 | 113206000 | 113207000 | 0.000 | 0.000 | TIFA | 1.00000 | 0 |
| 384 | chr4 | 114466000 | 114467000 | 0.000 | 0.000 | CAMK2D | 1.00000 | 0 |
| 385 | chr4 | 114681000 | 114682000 | 0.000 | 0.080 | CAMK2D | 0.48980 | 0 |
| 386 | chr4 | 117928000 | 117929000 | 0.040 | 0.000 | TRAM1L1 | 1.00000 | 0 |
| 387 | chr4 | 123637000 | 123638000 | 0.000 | 0.000 | BBS12 | 1.00000 | 0 |
| 388 | chr4 | 125227000 | 125228000 | 0.040 | 0.000 | ANKRD50 | 1.00000 | 0 |
| 389 | chr4 | 127371000 | 127372000 | 0.000 | 0.000 | FAT4 | 1.00000 | 0 |
| 390 | chr4 | 133455000 | 133456000 | 0.000 | 0.000 | PCDH10 | 1.00000 | 0 |
| 391 | chr4 | 134538000 | 134539000 | 0.000 | 0.040 | PCDH10 | 1.00000 | 0 |
| 392 | chr4 | 134743000 | 134744000 | 0.040 | 0.040 | PABPC4L | 1.00000 | 0 |
| 393 | chr4 | 134867000 | 134868000 | 0.000 | 0.000 | PABPC4L | 1.00000 | 0 |
| 394 | chr4 | 134949000 | 134950000 | 0.080 | 0.000 | PABPC4L | 0.48980 | 0 |
| 395 | chr4 | 135064000 | 135065000 | 0.040 | 0.000 | PABPC4L | 1.00000 | 0 |
| 396 | chr4 | 135077000 | 135078000 | 0.000 | 0.000 | PABPC4L | 1.00000 | 0 |
| 397 | chr4 | 136799000 | 136800000 | 0.000 | 0.000 | PCDH18 | 1.00000 | 0 |
| 398 | chr4 | 136867000 | 136868000 | 0.000 | 0.040 | PCDH18 | 1.00000 | 0 |
| 399 | chr4 | 140236000 | 140237000 | 0.040 | 0.000 | NAA15 | 1.00000 | 0 |
| 400 | chr4 | 151723000 | 151724000 | 0.000 | 0.000 | LRBA | 1.00000 | 0 |
| 401 | chr4 | 151950000 | 151951000 | 0.000 | 0.000 | LRBA | 1.00000 | 0 |
| 402 | chr4 | 152125000 | 152126000 | 0.040 | 0.040 | SH3D19 | 1.00000 | 0 |
| 403 | chr4 | 157246000 | 157247000 | 0.040 | 0.000 | CTSO | 1.00000 | 0 |
| 404 | chr4 | 164532000 | 164533000 | 0.000 | 0.000 | 1-Mar-19 | 1.00000 | 0 |
| 405 | chr4 | 178732000 | 178733000 | 0.040 | 0.040 | AGA | 1.00000 | 0 |
| 406 | chr4 | 178885000 | 178886000 | 0.040 | 0.000 | AGA | 1.00000 | 0 |
| 407 | chr4 | 179898000 | 179899000 | 0.000 | 0.040 | AGA | 1.00000 | 0 |
| 408 | chr4 | 180885000 | 180886000 | 0.040 | 0.000 | TENM3 | 1.00000 | 0 |
| 409 | chr4 | 181554000 | 181555000 | 0.040 | 0.040 | TENM3 | 1.00000 | 0 |
| 410 | chr4 | 182122000 | 182123000 | 0.000 | 0.040 | TENM3 | 1.00000 | 0 |
| 411 | chr5 | 436000 | 437000 | 0.000 | 0.000 | AHRR | 1.00000 | 0 |
| 412 | chr5 | 3982000 | 3983000 | 0.040 | 0.000 | IRX1 | 1.00000 | 0 |
| 413 | chr5 | 17218000 | 17219000 | 0.040 | 0.000 | BASP1 | 1.00000 | 0 |
| 414 | chr5 | 17219000 | 17220000 | 0.080 | 0.000 | BASP1 | 0.48980 | 0 |
| 415 | chr5 | 18514000 | 18515000 | 0.040 | 0.000 | CDH18 | 1.00000 | 0 |
| 416 | chr5 | 22356000 | 22357000 | 0.040 | 0.000 | CDH12 | 1.00000 | 0 |
| 417 | chr5 | 22517000 | 22518000 | 0.040 | 0.000 | CDH12 | 1.00000 | 0 |
| 418 | chr5 | 24632000 | 24633000 | 0.000 | 0.000 | CDH10 | 1.00000 | 0 |
| 419 | chr5 | 25275000 | 25276000 | 0.000 | 0.040 | CDH10 | 1.00000 | 0 |
| 420 | chr5 | 25541000 | 25542000 | 0.000 | 0.000 | CDH10 | 1.00000 | 0 |
| 421 | chr5 | 26119000 | 26120000 | 0.000 | 0.080 | CDH9 | 0.48980 | 0 |
| 422 | chr5 | 26450000 | 26451000 | 0.000 | 0.000 | CDH9 | 1.00000 | 0 |
| 423 | chr5 | 29224000 | 29225000 | 0.080 | 0.000 | CDH6 | 0.48980 | 0 |
| 424 | chr5 | 29492000 | 29493000 | 0.000 | 0.000 | CDH6 | 1.00000 | 0 |
| 425 | chr5 | 29648000 | 29649000 | 0.000 | 0.000 | CDH6 | 1.00000 | 0 |
| 426 | chr5 | 51521000 | 51522000 | 0.000 | 0.040 | CTD-2203A3.1 | 1.00000 | 0 |
| 427 | chr5 | 83841000 | 83842000 | 0.040 | 0.000 | EDIL3 | 1.00000 | 0 |
| 428 | chr5 | 88177000 | 88178000 | 0.040 | 0.000 | MEF2C | 1.00000 | 0 |
| 429 | chr5 | 88178000 | 88179000 | 0.040 | 0.000 | MEF2C | 1.00000 | 0 |
| 430 | chr5 | 91417000 | 91418000 | 0.000 | 0.000 | ARRDC3 | 1.00000 | 0 |
| 431 | chr5 | 103678000 | 103679000 | 0.040 | 0.000 | NUDT12 | 1.00000 | 0 |
| 432 | chr5 | 123696000 | 123697000 | 0.000 | 0.000 | ZNF608 | 1.00000 | 1 |
| 433 | chr5 | 124079000 | 124080000 | 0.000 | 0.040 | ZNF608 | 1.00000 | 1 |
| 434 | chr5 | 124080000 | 124081000 | 0.040 | 0.000 | ZNF608 | 1.00000 | 1 |
| 435 | chr5 | 127594000 | 127595000 | 0.000 | 0.040 | FBN2 | 1.00000 | 0 |
| 436 | chr5 | 127875000 | 127876000 | 0.000 | 0.000 | FBN2 | 1.00000 | 0 |
| 437 | chr5 | 131825000 | 131826000 | 0.120 | 0.040 | IRF1 | 0.60921 | 0 |
| 438 | chr5 | 131826000 | 131827000 | 0.040 | 0.040 | IRF1 | 1.00000 | 0 |
| 439 | chr5 | 149791000 | 149792000 | 0.160 | 0.240 | CD74 | 0.72520 | 1 |
| 440 | chr5 | 149792000 | 149793000 | 0.040 | 0.080 | CD74 | 1.00000 | 1 |
| 441 | chr5 | 158380000 | 158381000 | 0.000 | 0.080 | EBF1 | 0.48980 | 0 |
| 442 | chr5 | 158479000 | 158480000 | 0.000 | 0.000 | EBF1 | 1.00000 | 0 |
| 443 | chr5 | 158526000 | 158527000 | 0.040 | 0.080 | EBF1 | 1.00000 | 0 |
| 444 | chr5 | 158527000 | 158528000 | 0.040 | 0.040 | EBF1 | 1.00000 | 0 |
| 445 | chr5 | 158528000 | 158529000 | 0.040 | 0.000 | EBF1 | 1.00000 | 0 |
| 446 | chr5 | 164247000 | 164248000 | 0.040 | 0.040 | MAT2B | 1.00000 | 0 |
| 447 | chr5 | 164441000 | 164442000 | 0.000 | 0.000 | MAT2B | 1.00000 | 0 |
| 448 | chr5 | 165932000 | 165933000 | 0.000 | 0.000 | TENM2 | 1.00000 | 0 |
| 449 | chr5 | 173300000 | 173301000 | 0.000 | 0.000 | CPEB4 | 1.00000 | 0 |
| 450 | chr5 | 179166000 | 179167000 | 0.040 | 0.040 | MAML1 | 1.00000 | 0 |
| 451 | chr5 | 180102000 | 180103000 | 0.040 | 0.000 | FLT4 | 1.00000 | 0 |
| 452 | chr6 | 392000 | 393000 | 0.120 | 0.080 | IRF4 | 1.00000 | 1 |
| 453 | chr6 | 393000 | 394000 | 0.080 | 0.080 | IRF4 | 1.00000 | 1 |
| 454 | chr6 | 14118000 | 14119000 | 0.160 | 0.440 | CD83 | 0.06222 | 1 |
| 455 | chr6 | 14119000 | 14120000 | 0.000 | 0.120 | CD83 | 0.23469 | 1 |
| 456 | chr6 | 18111000 | 18112000 | 0.000 | 0.080 | NHLRC1 | 0.48980 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 457 | chr6 | 18387000 | 18388000 | 0.000 | 0.040 | RNF144B | 1.00000 | 1 |
| 458 | chr6 | 18388000 | 18389000 | 0.000 | 0.040 | RNF144B | 1.00000 | 1 |
| 459 | chr6 | 19573000 | 19574000 | 0.040 | 0.040 | ID4 | 1.00000 | 0 |
| 460 | chr6 | 22873000 | 22874000 | 0.040 | 0.000 | HDGFL1 | 1.00000 | 0 |
| 461 | chr6 | 26031000 | 26032000 | 0.000 | 0.040 | HIST1H3B | 1.00000 | 1 |
| 462 | chr6 | 26032000 | 26033000 | 0.000 | 0.040 | HIST1H3B | 1.00000 | 1 |
| 463 | chr6 | 26056000 | 26057000 | 0.120 | 0.040 | HIST1HIC | 0.60921 | 1 |
| 464 | chr6 | 26123000 | 26124000 | 0.120 | 0.040 | HIST1H2BC | 0.60921 | 1 |
| 465 | chr6 | 26124000 | 26125000 | 0.120 | 0.080 | HIST1H2AC; HIST1H2BC; | 1.00000 | 0 |
| 466 | chr6 | 26125000 | 26126000 | 0.000 | 0.040 | HIST1H2AC | 1.00000 | 1 |
| 467 | chr6 | 26156000 | 26157000 | 0.120 | 0.080 | HIST1HIE | 1.00000 | 1 |
| 468 | chr6 | 26157000 | 26158000 | 0.080 | 0.040 | HIST1HIE | 1.00000 | 1 |
| 469 | chr6 | 26216000 | 26217000 | 0.040 | 0.040 | HIST1H2BG | 1.00000 | 1 |
| 470 | chr6 | 26234000 | 26235000 | 0.080 | 0.040 | HIST1H1D | 1.00000 | 0 |
| 471 | chr6 | 27101000 | 27102000 | 0.040 | 0.040 | HIST1H2AG | 1.00000 | 1 |
| 472 | chr6 | 27114000 | 27115000 | 0.080 | 0.040 | HIST1H2AH; HIST1H2BK; | 1.00000 | 0 |
| 473 | chr6 | 27792000 | 27793000 | 0.120 | 0.040 | HIST1H4J | 0.60921 | 0 |
| 474 | chr6 | 27833000 | 27834000 | 0.040 | 0.000 | HIST1H2AL | 1.00000 | 1 |
| 475 | chr6 | 27860000 | 27861000 | 0.000 | 0.080 | HIST1H2AM | 0.48980 | 1 |
| 476 | chr6 | 27861000 | 27862000 | 0.000 | 0.040 | HIST1H2BO | 1.00000 | 1 |
| 477 | chr6 | 29778000 | 29779000 | 0.000 | 0.040 | LOC55422.3 | 1.00000 | 0 |
| 478 | chr6 | 29780000 | 29781000 | 0.040 | 0.000 | HLA-G | 1.00000 | 0 |
| 479 | chr6 | 29911000 | 29912000 | 0.080 | 0.040 | HLA-A | 1.00000 | 0 |
| 480 | chr6 | 29927000 | 29928000 | 0.040 | 0.000 | HLA-A | 1.00000 | 0 |
| 481 | chr6 | 31324000 | 31325000 | 0.040 | 0.040 | HLA-B | 1.00000 | 1 |
| 482 | chr6 | 31325000 | 31326000 | 0.000 | 0.000 | HLA-B | 1.00000 | 1 |
| 483 | chr6 | 31543000 | 31544000 | 0.080 | 0.000 | TNF | 0.48980 | 1 |
| 484 | chr6 | 31549000 | 31550000 | 0.200 | 0.240 | LTB | 1.00000 | 1 |
| 485 | chr6 | 31550000 | 31551000 | 0.040 | 0.040 | LTB | 1.00000 | 1 |
| 486 | chr6 | 32440000 | 32441000 | 0.120 | 0.000 | HLA-DRA | 0.23469 | 0 |
| 487 | chr6 | 32451000 | 32452000 | 0.040 | 0.000 | HLA-DRB5 | 1.00000 | 0 |
| 488 | chr6 | 32452000 | 32453000 | 0.080 | 0.000 | HLA-DRB5 | 0.48980 | 0 |
| 489 | chr6 | 32455000 | 32456000 | 0.040 | 0.040 | HLA-DRB5 | 1.00000 | 0 |
| 490 | chr6 | 32457000 | 32458000 | 0.000 | 0.000 | HLA-DRB5 | 1.00000 | 0 |
| 491 | chr6 | 32498000 | 32499000 | 0.000 | 0.040 | HLA-DRB5 | 1.00000 | 0 |
| 492 | chr6 | 32505000 | 32506000 | 0.040 | 0.000 | HLA-DRB5 | 1.00000 | 0 |
| 493 | chr6 | 32511000 | 32512000 | 0.000 | 0.000 | HLA-DRB5 | 1.00000 | 0 |
| 494 | chr6 | 32522000 | 32523000 | 0.040 | 0.000 | HLA-DRB1 | 1.00000 | 0 |
| 495 | chr6 | 32525000 | 32526000 | 0.040 | 0.000 | HLA-DRB1 | 1.00000 | 0 |
| 496 | chr6 | 32526000 | 32527000 | 0.000 | 0.000 | HLA-DRB1 | 1.00000 | 0 |
| 497 | chr6 | 32527000 | 32528000 | 0.000 | 0.000 | HLA-DRB1 | 1.00000 | 0 |
| 498 | chr6 | 32548000 | 32549000 | 0.000 | 0.000 | HLA-DRB1 | 1.00000 | 0 |
| 499 | chr6 | 32552000 | 32553000 | 0.040 | 0.000 | HLA-DRB1 | 1.00000 | 0 |
| 500 | chr6 | 32557000 | 32558000 | 0.000 | 0.080 | HLA-DRB1 | 0.48980 | 0 |
| 501 | chr6 | 32609000 | 32610000 | 0.000 | 0.040 | HLA-DQA1 | 1.00000 | 0 |
| 502 | chr6 | 32630000 | 32631000 | 0.000 | 0.040 | HLA-DQB1 | 1.00000 | 0 |
| 503 | chr6 | 32632000 | 32633000 | 0.080 | 0.040 | HLA-DQB1 | 1.00000 | 0 |
| 504 | chr6 | 32727000 | 32728000 | 0.040 | 0.040 | HLA-DQB2 | 1.00000 | 0 |
| 505 | chr6 | 32729000 | 32730000 | 0.000 | 0.040 | HLA-DQB2 | 1.00000 | 0 |
| 506 | chr6 | 33048000 | 33049000 | 0.000 | 0.040 | HLA-DPB1 | 1.00000 | 0 |
| 507 | chr6 | 34179000 | 34180000 | 0.000 | 0.040 | HMGA1 | 1.00000 | 0 |
| 508 | chr6 | 37138000 | 37139000 | 0.200 | 0.200 | PIM1 | 1.00000 | 1 |
| 509 | chr6 | 37139000 | 37140000 | 0.120 | 0.120 | PIM1 | 1.00000 | 1 |
| 510 | chr6 | 37140000 | 37141000 | 0.040 | 0.000 | PIM1 | 1.00000 | 1 |
| 511 | chr6 | 58001000 | 58002000 | 0.040 | 0.000 | PRIM2 | 1.00000 | 0 |
| 512 | chr6 | 67923000 | 67924000 | 0.040 | 0.000 | BAI3 | 1.00000 | 0 |
| 513 | chr6 | 77256000 | 77257000 | 0.040 | 0.000 | IMPG1 | 1.00000 | 0 |
| 514 | chr6 | 81437000 | 81438000 | 0.040 | 0.000 | BCKDHB | 1.00000 | 0 |
| 515 | chr6 | 88468000 | 88469000 | 0.000 | 0.040 | AKIRIN2 | 1.00000 | 0 |
| 516 | chr6 | 88630000 | 88631000 | 0.040 | 0.080 | SPACA1 | 1.00000 | 0 |
| 517 | chr6 | 88876000 | 88877000 | 0.000 | 0.000 | CNR1 | 1.00000 | 0 |
| 518 | chr6 | 89323000 | 89324000 | 0.000 | 0.000 | RNGTT | 1.00000 | 0 |
| 519 | chr6 | 89338000 | 89339000 | 0.080 | 0.000 | RNGTT | 0.48980 | 0 |
| 520 | chr6 | 89348000 | 89349000 | 0.080 | 0.000 | RNGTT | 0.48980 | 0 |
| 521 | chr6 | 89470000 | 89471000 | 0.080 | 0.000 | RNGTT | 0.48980 | 0 |
| 522 | chr6 | 89471000 | 89472000 | 0.000 | 0.000 | RNGTT | 1.00000 | 0 |
| 523 | chr6 | 90061000 | 90062000 | 0.040 | 0.040 | UBE2J1 | 1.00000 | 1 |
| 524 | chr6 | 90062000 | 90063000 | 0.040 | 0.000 | UBE2J1 | 1.00000 | 1 |
| 525 | chr6 | 90994000 | 90995000 | 0.000 | 0.080 | MAP3K7 | 0.48980 | 0 |
| 526 | chr6 | 91004000 | 91005000 | 0.040 | 0.040 | MAP3K7 | 1.00000 | 0 |
| 527 | chr6 | 91005000 | 91006000 | 0.120 | 0.280 | MAP3K7 | 0.28902 | 0 |
| 528 | chr6 | 91006000 | 91007000 | 0.040 | 0.120 | MAP3K7 | 0.60921 | 0 |
| 529 | chr6 | 91007000 | 91008000 | 0.000 | 0.040 | MAP3K7 | 1.00000 | 0 |
| 530 | chr6 | 94822000 | 94823000 | 0.000 | 0.040 | EPHA7 | 1.00000 | 0 |
| 531 | chr | 107704000 | 107705000 | 0.000 | 0.000 | PDSS2 | 1.00000 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 532 | chr6 | 112885000 | 112886000 | 0.040 | 0.000 | RFPL4B | 1.00000 | 0 |
| 533 | chr6 | 118244000 | 118245000 | 0.040 | 0.000 | SLC35F1 | 1.00000 | 0 |
| 534 | chr6 | 121288000 | 121289000 | 0.000 | 0.000 | C6orf170 | 1.00000 | 0 |
| 535 | chr6 | 121489000 | 121490000 | 0.000 | 0.080 | C6orf170 | 0.48980 | 0 |
| 536 | chr6 | 123504000 | 123505000 | 0.040 | 0.000 | TRDN | 1.00000 | 0 |
| 537 | chr6 | 127313000 | 127314000 | 0.040 | 0.000 | RSPO3 | 1.00000 | 0 |
| 538 | chr6 | 133785000 | 133786000 | 0.080 | 0.000 | EYA4 | 0.48980 | 0 |
| 539 | chr6 | 134491000 | 134492000 | 0.000 | 0.080 | SGK1 | 0.48980 | 1 |
| 540 | chr6 | 134492000 | 134493000 | 0.080 | 0.040 | SGK1 | 1.00000 | 1 |
| 541 | chr6 | 134493000 | 134494000 | 0.040 | 0.080 | SGK1 | 1.00000 | 1 |
| 542 | chr6 | 134494000 | 134495000 | 0.040 | 0.080 | SGK1 | 1.00000 | 1 |
| 543 | chr6 | 134495000 | 134496000 | 0.160 | 0.280 | SGK1 | 0.49620 | 1 |
| 544 | chr6 | 134496000 | 134497000 | 0.000 | 0.200 | SGK1 | 0.05015 | 1 |
| 545 | chr6 | 142046000 | 142047000 | 0.000 | 0.080 | NMBR | 0.48980 | 0 |
| 546 | chr6 | 147860000 | 147861000 | 0.000 | 0.040 | SAMD5 | 1.00000 | 0 |
| 547 | chr6 | 150954000 | 150955000 | 0.040 | 0.040 | PLEKHG1 | 1.00000 | 0 |
| 548 | chr6 | 159238000 | 159239000 | 0.000 | 0.080 | EZR | 0.48980 | 0 |
| 549 | chr6 | 159239000 | 159240000 | 0.040 | 0.000 | EZR | 1.00000 | 0 |
| 550 | chr6 | 159240000 | 159241000 | 0.040 | 0.000 | EZR | 1.00000 | 0 |
| 551 | chr6 | 159464000 | 159465000 | 0.040 | 0.000 | TAGAP | 1.00000 | 0 |
| 552 | chr6 | 159465000 | 159466000 | 0.040 | 0.000 | TAGAP | 1.00000 | 0 |
| 553 | chr6 | 161265000 | 161266000 | 0.000 | 0.040 | PEG | 1.00000 | 0 |
| 554 | chr6 | 161833000 | 161834000 | 0.000 | 0.000 | PARK2 | 1.00000 | 0 |
| 555 | chr6 | 162712000 | 162713000 | 0.000 | 0.000 | PARK2 | 1.00000 | 0 |
| 556 | chr6 | 164941000 | 164942000 | 0.000 | 0.000 | C6orf118 | 1.00000 | 0 |
| 557 | chr6 | 168813000 | 168814000 | 0.000 | 0.000 | SMOC2 | 1.00000 | 0 |
| 558 | chr7 | 1898000 | 1899000 | 0.040 | 0.040 | AC110781.3 | 1.00000 | 0 |
| 559 | chr 7 | 1963000 | 1964000 | 0.040 | 0.000 | MAD1L1 | 1.00000 | 0 |
| 560 | chr7 | 2080000 | 2081000 | 0.000 | 0.040 | MADI1L1 | 1.00000 | 0 |
| 561 | chr7 | 5568000 | 5569000 | 0.040 | 0.080 | ACTB | 1.00000 | 1 |
| 562 | chr7 | 5569000 | 5570000 | 0.040 | 0.120 | ACTB | 0.60921 | 1 |
| 563 | chr7 | 5570000 | 5571000 | 0.040 | 0.040 | ACTB | 1.00000 | 1 |
| 564 | chr7 | 9933000 | 9934000 | 0.040 | 0.040 | NDUFA4 | 1.00000 | 0 |
| 565 | chr7 | 13017000 | 13018000 | 0.000 | 0.040 | ARL4A | 1.00000 | 0 |
| 566 | chr7 | 13346000 | 13347000 | 0.000 | 0.000 | ETVI | 1.00000 | 0 |
| 567 | chr7 | 15459000 | 15460000 | 0.000 | 0.000 | AGMO | 1.00000 | 0 |
| 568 | chr7 | 16382000 | 16383000 | 0.040 | 0.000 | ISPD | 1.00000 | 0 |
| 569 | chr7 | 28600000 | 28601000 | 0.040 | 0.000 | CREB5 | 1.00000 | 0 |
| 570 | chr7 | 40846000 | 40847000 | 0.040 | 0.000 | C7orf10 | 1.00000 | 0 |
| 571 | chr7 | 50349000 | 50350000 | 0.040 | 0.040 | IKZF1 | 1.00000 | 0 |
| 572 | chr7 | 50350000 | 50351000 | 0.080 | 0.040 | IKZF1 | 1.00000 | 0 |
| 573 | chr7 | 53335000 | 53336000 | 0.000 | 0.000 | POM121L12 | 1.00000 | 0 |
| 574 | chr7 | 57713000 | 57714000 | 0.080 | 0.040 | ZNF716 | 1.00000 | 0 |
| 575 | chr7 | 62475000 | 62476000 | 0.040 | 0.040 | AC006455.1 | 1.00000 | 0 |
| 576 | chr7 | 70669000 | 70670000 | 0.040 | 0.000 | WBSCR17 | 1.00000 | 0 |
| 577 | chr7 | 71553000 | 71554000 | 0.000 | 0.040 | CALN1 | 1.00000 | 0 |
| 578 | chr7 | 79847000 | 79848000 | 0.040 | 0.000 | GNAI1 | 1.00000 | 0 |
| 579 | chr7 | 80694000 | 80695000 | 0.040 | 0.000 | AC005008.2 | 1.00000 | 0 |
| 580 | chr7 | 81556000 | 81557000 | 0.000 | 0.000 | CACNA2D1 | 1.00000 | 0 |
| 581 | chr7 | 84127000 | 84128000 | 0.040 | 0.000 | SEMA3A | 1.00000 | 0 |
| 582 | chr7 | 84247000 | 84248000 | 0.000 | 0.040 | SEMA3D | 1.00000 | 0 |
| 583 | chr7 | 84257000 | 84258000 | 0.000 | 0.000 | SEMA3D | 1.00000 | 0 |
| 584 | chr7 | 86914000 | 86915000 | 0.000 | 0.040 | CROT | 1.00000 | 0 |
| 585 | chr7 | 90356000 | 90357000 | 0.000 | 0.040 | CDK14 | 1.00000 | 0 |
| 586 | chr7 | 93304000 | 93305000 | 0.000 | 0.000 | CALCR | 1.00000 | 0 |
| 587 | chr7 | 93682000 | 93683000 | 0.040 | 0.000 | BET1 | 1.00000 | 0 |
| 588 | chr7 | 102644000 | 102645000 | 0.000 | 0.000 | FBXL13 | 1.00000 | 0 |
| 589 | chr7 | 105699000 | 105700000 | 0.000 | 0.040 | CDHR3 | 1.00000 | 0 |
| 590 | chr7 | 110521000 | 110522000 | 0.040 | 0.040 | IMMP2L | 1.00000 | 0 |
| 591 | chr7 | 110543000 | 110544000 | 0.040 | 0.000 | IMMP2L | 1.00000 | 0 |
| 592 | chr7 | 110545000 | 110546000 | 0.040 | 0.000 | IMMP2L | 1.00000 | 0 |
| 593 | chr7 | 110597000 | 110598000 | 0.000 | 0.040 | IMMP2L | 1.00000 | 0 |
| 594 | chr7 | 110601000 | 110602000 | 0.000 | 0.000 | IMMP2L | 1.00000 | 0 |
| 595 | chr7 | 110602000 | 110603000 | 0.040 | 0.000 | IMMP2L | 1.00000 | 0 |
| 596 | chr7 | 110609000 | 110610000 | 0.040 | 0.000 | IMMP2L | 1.00000 | 0 |
| 597 | chr7 | 110610000 | 110611000 | 0.040 | 0.000 | IMMP2L | 1.00000 | 0 |
| 598 | chr7 | 110617000 | 110618000 | 0.040 | 0.000 | IMMP2L | 1.00000 | 0 |
| 599 | chr7 | 110618000 | 110619000 | 0.000 | 0.000 | IMMP2L | 1.00000 | 0 |
| 600 | chr7 | 110619000 | 110620000 | 0.040 | 0.000 | IMMP2L | 1.00000 | 0 |
| 601 | chr7 | 110621000 | 110622000 | 0.000 | 0.040 | IMMP2L | 1.00000 | 0 |
| 602 | chr7 | 110628000 | 110629000 | 0.040 | 0.000 | IMMP2L | 1.00000 | 0 |
| 603 | chr7 | 110629000 | 110630000 | 0.000 | 0.000 | IMMP2L | 1.00000 | 0 |
| 604 | chr7 | 110631000 | 110632000 | 0.000 | 0.040 | IMMP2L | 1.00000 | 0 |
| 605 | chr7 | 110632000 | 110633000 | 0.040 | 0.000 | IMMP2L | 1.00000 | 0 |
| 606 | chr7 | 110636000 | 110637000 | 0.040 | 0.000 | IMMP2L | 1.00000 | 0 |
| 607 | chr 7 | 110637000 | 110638000 | 0.000 | 0.000 | IMMP2L | 1.00000 | 0 |
| 608 | chr7 | 110638000 | 110639000 | 0.000 | 0.040 | IMMP2L | 1.00000 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 609 | chr7 | 110639000 | 110640000 | 0.000 | 0.040 | IMMP2L | 1.00000 | 0 |
| 610 | chr7 | 110641000 | 110642000 | 0.000 | 0.000 | IMMP2L | 1.00000 | 0 |
| 611 | chr7 | 110650000 | 110651000 | 0.000 | 0.000 | IMMP2L | 1.00000 | 0 |
| 612 | chr7 | 110651000 | 110652000 | 0.000 | 0.040 | IMMP2L | 1.00000 | 0 |
| 613 | chr7 | 110666000 | 110667000 | 0.000 | 0.000 | IMMP2L | 1.00000 | 0 |
| 614 | chr7 | 110671000 | 110672000 | 0.000 | 0.080 | IMMP2L | 0.48980 | 0 |
| 615 | chr7 | 110677000 | 110678000 | 0.000 | 0.000 | IMMP2L | 1.00000 | 0 |
| 616 | chr7 | 110679000 | 110680000 | 0.000 | 0.000 | IMMP2L | 1.00000 | 0 |
| 617 | chr7 | 110680000 | 110681000 | 0.000 | 0.000 | IMMP2L | 1.00000 | 0 |
| 618 | chr7 | 110685000 | 110686000 | 0.000 | 0.000 | LRRN3 | 1.00000 | 0 |
| 619 | chr7 | 110686000 | 110687000 | 0.000 | 0.040 | LRRN3 | 1.00000 | 0 |
| 620 | chr7 | 110688000 | 110689000 | 0.000 | 0.000 | LRRN3 | 1.00000 | 0 |
| 621 | chr7 | 110699000 | 110700000 | 0.080 | 0.000 | LRRN3 | 0.48980 | 0 |
| 622 | chr7 | 110700000 | 110701000 | 0.040 | 0.000 | LRRN3 | 1.00000 | 0 |
| 623 | chr7 | 110709000 | 110710000 | 0.000 | 0.040 | LRRN3 | 1.00000 | 0 |
| 624 | chr7 | 110711000 | 110712000 | 0.000 | 0.040 | LRRN3 | 1.00000 | 0 |
| 625 | chr7 | 110714000 | 110715000 | 0.000 | 0.040 | LRRN3 | 1.00000 | 0 |
| 626 | chr7 | 110727000 | 110728000 | 0.000 | 0.040 | LRRN3 | 1.00000 | 0 |
| 627 | chr7 | 110728000 | 110729000 | 0.040 | 0.000 | LRRN3 | 1.00000 | 0 |
| 628 | chr7 | 110729000 | 110730000 | 0.000 | 0.040 | LRRN3 | 1.00000 | 0 |
| 629 | chr7 | 110734000 | 110735000 | 0.000 | 0.040 | LRRN3 | 1.00000 | 0 |
| 630 | chr7 | 110737000 | 110738000 | 0.000 | 0.000 | LRRN3 | 1.00000 | 0 |
| 631 | chr7 | 110740000 | 110741000 | 0.040 | 0.080 | LRRN3 | 1.00000 | 0 |
| 632 | chr7 | 110744000 | 110745000 | 0.000 | 0.000 | LRRN3 | 1.00000 | 0 |
| 633 | chr7 | 110746000 | 110747000 | 0.000 | 0.040 | LRRN3 | 1.00000 | 0 |
| 634 | chr7 | 110747000 | 110748000 | 0.000 | 0.000 | LRRN3 | 1.00000 | 0 |
| 635 | chr7 | 110748000 | 110749000 | 0.000 | 0.000 | LRRN3 | 1.00000 | 0 |
| 636 | chr7 | 110755000 | 110756000 | 0.000 | 0.000 | LRRN3 | 1.00000 | 0 |
| 637 | chr7 | 110764000 | 110765000 | 0.000 | 0.000 | LRRN3 | 1.00000 | 0 |
| 638 | chr7 | 110767000 | 110768000 | 0.040 | 0.000 | LRRN3 | 1.00000 | 0 |
| 639 | chr7 | 110769000 | 110770000 | 0.000 | 0.040 | LRRN3 | 1.00000 | 0 |
| 640 | chr7 | 110771000 | 110772000 | 0.040 | 0.040 | LRRN3 | 1.00000 | 0 |
| 641 | chr7 | 110779000 | 110780000 | 0.000 | 0.000 | LRRN3 | 1.00000 | 0 |
| 642 | chr7 | 110780000 | 110781000 | 0.000 | 0.040 | LRRN3 | 1.00000 | 0 |
| 643 | chr 7 | 110783000 | 110784000 | 0.000 | 0.040 | LRRN3 | 1.00000 | 0 |
| 644 | chr7 | 110785000 | 110786000 | 0.000 | 0.080 | LRRN3 | 0.48980 | 0 |
| 645 | chr7 | 110801000 | 110802000 | 0.000 | 0.040 | LRRN3 | 1.00000 | 0 |
| 646 | chr7 | 110802000 | 110803000 | 0.000 | 0.040 | LRRN3 | 1.00000 | 0 |
| 647 | chr7 | 110810000 | 110811000 | 0.000 | 0.000 | LRRN3 | 1.00000 | 0 |
| 648 | chr7 | 110816000 | 110817000 | 0.000 | 0.000 | LRRN3 | 1.00000 | 0 |
| 649 | chr7 | 110821000 | 110822000 | 0.000 | 0.040 | LRRN3 | 1.00000 | 0 |
| 650 | chr7 | 110824000 | 110825000 | 0.000 | 0.000 | LRRN3 | 1.00000 | 0 |
| 651 | chr7 | 110827000 | 110828000 | 0.040 | 0.000 | LRRN3 | 1.00000 | 0 |
| 652 | chr7 | 110836000 | 110837000 | 0.040 | 0.040 | LRRN3 | 1.00000 | 0 |
| 653 | chr7 | 110847000 | 110848000 | 0.000 | 0.040 | LRRN3 | 1.00000 | 0 |
| 654 | chr7 | 111567000 | 111568000 | 0.000 | 0.000 | DOCK4 | 1.00000 | 0 |
| 655 | chr7 | 119056000 | 119057000 | 0.040 | 0.000 | KCND2 | 1.00000 | 0 |
| 656 | chr7 | 121380000 | 121381000 | 0.040 | 0.000 | PTPRZ1 | 1.00000 | 0 |
| 657 | chr7 | 123887000 | 123888000 | 0.000 | 0.000 | TMEM229A | 1.00000 | 0 |
| 658 | chr7 | 125262000 | 125263000 | 0.000 | 0.040 | POT1 | 1.00000 | 0 |
| 659 | chr7 | 145723000 | 145724000 | 0.000 | 0.000 | CNTNAP2 | 1.00000 | 0 |
| 660 | chr7 | 148508000 | 148509000 | 0.000 | 0.000 | EZH2 | 1.00000 | 0 |
| 661 | chr7 | 155127000 | 155128000 | 0.000 | 0.000 | BLACE | 1.00000 | 0 |
| 662 | chr7 | 157162000 | 157163000 | 0.040 | 0.000 | DNAJB6 | 1.00000 | 0 |
| 663 | chr7 | 158684000 | 158685000 | 0.000 | 0.040 | WDR60 | 1.00000 | 0 |
| 664 | chr8 | 1646000 | 1647000 | 0.000 | 0.040 | DLGAP2 | 1.00000 | 0 |
| 665 | chr8 | 5558000 | 5559000 | 0.000 | 0.040 | MCPH1 | 1.00000 | 0 |
| 666 | chr8 | 5612000 | 5613000 | 0.000 | 0.000 | MCPH1 | 1.00000 | 0 |
| 667 | chr8 | 8602000 | 8603000 | 0.000 | 0.120 | MFHAS1 | 0.23469 | 0 |
| 668 | chr8 | 8706000 | 8707000 | 0.000 | 0.000 | MFHAS1 | 1.00000 | 0 |
| 669 | chr8 | 8717000 | 8718000 | 0.000 | 0.040 | MFHAS1 | 1.00000 | 0 |
| 670 | chr8 | 11352000 | 11353000 | 0.040 | 0.040 | BLK | 1.00000 | 0 |
| 671 | chr8 | 14080000 | 14081000 | 0.000 | 0.040 | SGCZ | 1.00000 | 0 |
| 672 | chr8 | 14796000 | 14797000 | 0.040 | 0.000 | SGCZ | 1.00000 | 0 |
| 673 | chr8 | 16090000 | 16091000 | 0.000 | 0.040 | MSR1 | 1.00000 | 0 |
| 674 | chr8 | 16187000 | 16188000 | 0.000 | 0.080 | MSR1 | 0.48980 | 0 |
| 675 | chr8 | 23101000 | 23102000 | 0.000 | 0.040 | CHMP7 | 1.00000 | 0 |
| 676 | chr8 | 24207000 | 24208000 | 0.000 | 0.000 | ADAM28 | 1.00000 | 0 |
| 677 | chr8 | 29155000 | 29156000 | 0.000 | 0.040 | KIF13B | 1.00000 | 0 |
| 678 | chr8 | 35657000 | 35658000 | 0.000 | 0.000 | AC012215.1 | 1.00000 | 0 |
| 679 | chr8 | 38759000 | 38760000 | 0.040 | 0.000 | PLEKHA2 | 1.00000 | 0 |
| 680 | chr8 | 54986000 | 54987000 | 0.040 | 0.000 | LYPLA1 | 1.00000 | 0 |
| 681 | chr8 | 60031000 | 60032000 | 0.040 | 0.000 | TOX | 1.00000 | 0 |
| 682 | chr8 | 67525000 | 67526000 | 0.040 | 0.000 | MYBL1 | 1.00000 | 0 |
| 683 | chr8 | 77105000 | 77106000 | 0.000 | 0.000 | ZFHX4 | 1.00000 | 0 |
| 684 | chr8 | 78400000 | 78401000 | 0.000 | 0.040 | PEX2 | 1.00000 | 0 |
| 685 | chr8 | 90322000 | 90323000 | 0.040 | 0.000 | RIPK2 | 1.00000 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 686 | chr8 | 93199000 | 93200000 | 0.000 | 0.040 | RUNX1T1 | 1.00000 | 0 |
| 687 | chr8 | 94618000 | 94619000 | 0.000 | 0.040 | FAM92A1 | 1.00000 | 0 |
| 688 | chr8 | 110586000 | 110587000 | 0.000 | 0.040 | SYBU | 1.00000 | 0 |
| 689 | chr8 | 126687000 | 126688000 | 0.000 | 0.000 | TRIB1 | 1.00000 | 0 |
| 690 | chr8 | 128748000 | 128749000 | 0.080 | 0.280 | MYC | 0.13833 | 1 |
| 691 | chr8 | 128749000 | 128750000 | 0.080 | 0.320 | MYC | 0.07375 | 1 |
| 692 | chr8 | 128750000 | 128751000 | 0.080 | 0.120 | MYC | 1.00000 | 1 |
| 693 | chr8 | 128751000 | 128752000 | 0.040 | 0.080 | MYC | 1.00000 | 1 |
| 694 | chr8 | 128752000 | 128753000 | 0.000 | 0.000 | MYC | 1.00000 | 1 |
| 695 | chr8 | 137918000 | 137919000 | 0.000 | 0.040 | FAM135B | 1.00000 | 0 |
| 696 | chr8 | 138274000 | 138275000 | 0.000 | 0.000 | FAM135B | 1.00000 | 0 |
| 697 | chr8 | 143183000 | 143184000 | 0.000 | 0.040 | TSNARE1 | 1.00000 | 0 |
| 698 | chr8 | 144123000 | 144124000 | 0.000 | 0.040 | C8orf31 | 1.00000 | 0 |
| 699 | chr9 | 6411000 | 6412000 | 0.040 | 0.040 | UHRF2 | 1.00000 | 0 |
| 700 | chr9 | 6413000 | 6414000 | 0.040 | 0.040 | UHRF2 | 1.00000 | 0 |
| 701 | chr9 | 6414000 | 6415000 | 0.000 | 0.000 | UHRF2 | 1.00000 | 0 |
| 702 | chr9 | 9928000 | 9929000 | 0.000 | 0.000 | PTPRD | 1.00000 | 0 |
| 703 | chr9 | 13965000 | 13966000 | 0.040 | 0.000 | NFIB | 1.00000 | 0 |
| 704 | chr9 | 22824000 | 22825000 | 0.040 | 0.000 | DMRTA1 | 1.00000 | 0 |
| 705 | chr9 | 25260000 | 25261000 | 0.040 | 0.000 | TUSC1 | 1.00000 | 0 |
| 706 | chr9 | 29890000 | 29891000 | 0.040 | 0.000 | LINGO2 | 1.00000 | 0 |
| 707 | chr9 | 30656000 | 30657000 | 0.000 | 0.040 | ACO1 | 1.00000 | 0 |
| 708 | chr9 | 37003000 | 37004000 | 0.040 | 0.000 | PAX5 | 1.00000 | 1 |
| 709 | chr9 | 37005000 | 37006000 | 0.040 | 0.000 | PAX5 | 1.00000 | 1 |
| 710 | chr9 | 37024000 | 37025000 | 0.040 | 0.040 | PAX5 | 1.00000 | 1 |
| 711 | chr9 | 37025000 | 37026000 | 0.160 | 0.120 | PAX5 | 1.00000 | 1 |
| 712 | chr9 | 37026000 | 37027000 | 0.240 | 0.120 | PAX5 | 0.46349 | 1 |
| 713 | chr9 | 37027000 | 37028000 | 0.080 | 0.040 | PAX5 | 1.00000 | 1 |
| 714 | chr9 | 37033000 | 37034000 | 0.120 | 0.040 | PAX5 | 0.60921 | 1 |
| 715 | chr9 | 37034000 | 37035000 | 0.120 | 0.040 | PAX5 | 0.60921 | 1 |
| 716 | chr9 | 37035000 | 37036000 | 0.000 | 0.040 | PAX5 | 1.00000 | 1 |
| 717 | chr9 | 37196000 | 37197000 | 0.040 | 0.000 | ZCCHC7 | 1.00000 | 0 |
| 718 | chr9 | 37197000 | 37198000 | 0.040 | 0.000 | ZCCHC7 | 1.00000 | 0 |
| 719 | chr9 | 37293000 | 37294000 | 0.000 | 0.000 | ZCCHC7 | 1.00000 | 0 |
| 720 | chr9 | 37294000 | 37295000 | 0.080 | 0.000 | ZCCHC7 | 0.48980 | 0 |
| 721 | chr9 | 37327000 | 37328000 | 0.040 | 0.000 | ZCCHC7 | 1.00000 | 0 |
| 722 | chr9 | 37336000 | 37337000 | 0.080 | 0.000 | ZCCHC7 | 0.48980 | 0 |
| 723 | chr9 | 37337000 | 37338000 | 0.000 | 0.000 | ZCCHC7 | 1.00000 | 0 |
| 724 | chr9 | 37338000 | 37339000 | 0.000 | 0.040 | ZCCHC7 | 1.00000 | 0 |
| 725 | chr9 | 37369000 | 37370000 | 0.040 | 0.000 | ZCCHC7 | 1.00000 | 0 |
| 726 | chr9 | 37371000 | 37372000 | 0.080 | 0.080 | ZCCHC7 | 1.00000 | 0 |
| 727 | chr9 | 37372000 | 37373000 | 0.000 | 0.000 | ZCCHC7 | 1.00000 | 0 |
| 728 | chr9 | 37383000 | 37384000 | 0.080 | 0.080 | ZCCHC7 | 1.00000 | 0 |
| 729 | chr9 | 37384000 | 37385000 | 0.120 | 0.040 | ZCCHC7 | 0.60921 | 0 |
| 730 | chr9 | 37385000 | 37386000 | 0.040 | 0.000 | ZCCHC7 | 1.00000 | 0 |
| 731 | chr9 | 37387000 | 37388000 | 0.080 | 0.040 | ZCCHC7 | 1.00000 | 0 |
| 732 | chr9 | 37397000 | 37398000 | 0.040 | 0.120 | GRHPR | 0.60921 | 0 |
| 733 | chr9 | 37398000 | 37399000 | 0.040 | 0.000 | GRHPR | 1.00000 | 0 |
| 734 | chr9 | 37399000 | 37400000 | 0.080 | 0.000 | GRHPR | 0.48980 | 0 |
| 735 | chr9 | 37402000 | 37403000 | 0.000 | 0.040 | GRHPR | 1.00000 | 0 |
| 736 | chr9 | 37406000 | 37407000 | 0.000 | 0.040 | GRHPR | 1.00000 | 0 |
| 737 | chr9 | 37407000 | 37408000 | 0.200 | 0.080 | GRHPR | 0.41743 | 0 |
| 738 | chr9 | 37408000 | 37409000 | 0.080 | 0.000 | GRHPR | 0.48980 | 0 |
| 739 | chr9 | 37410000 | 37411000 | 0.000 | 0.000 | GRHPR | 1.00000 | 0 |
| 740 | chr9 | 37424000 | 37425000 | 0.040 | 0.040 | GRHPR | 1.00000 | 0 |
| 741 | chr9 | 37425000 | 37426000 | 0.000 | 0.040 | GRHPR | 1.00000 | 0 |
| 742 | chr9 | 112811000 | 112812000 | 0.080 | 0.080 | AKAP2 | 1.00000 | 0 |
| 743 | chr9 | 117037000 | 117038000 | 0.000 | 0.040 | COL27A1 | 1.00000 | 0 |
| 744 | chr9 | 119779000 | 119780000 | 0.040 | 0.000 | ASTN2 | 1.00000 | 0 |
| 745 | chr9 | 126232000 | 126233000 | 0.040 | 0.000 | DENND1A | 1.00000 | 0 |
| 746 | chr9 | 130741000 | 130742000 | 0.040 | 0.000 | FAM102A | 1.00000 | 1 |
| 747 | chr9 | 130742000 | 130743000 | 0.040 | 0.080 | FAM102A | 1.00000 | 1 |
| 748 | chr9 | 132767000 | 132768000 | 0.000 | 0.040 | FNBP1 | 1.00000 | 0 |
| 749 | chr9 | 132785000 | 132786000 | 0.040 | 0.000 | FNBP1 | 1.00000 | 0 |
| 750 | chr9 | 132803000 | 132804000 | 0.000 | 0.040 | FNBP1 | 1.00000 | 0 |
| 751 | chr9 | 132804000 | 132805000 | 0.040 | 0.120 | FNBP1 | 0.60921 | 0 |
| 752 | chr9 | 134551000 | 134552000 | 0.040 | 0.000 | RAPGEF1 | 1.00000 | 0 |
| 753 | chr9 | 138874000 | 138875000 | 0.000 | 0.040 | UBAC1 | 1.00000 | 0 |
| 754 | chr10 | 3333000 | 3334000 | 0.000 | 0.000 | PITRM1 | 1.00000 | 0 |
| 755 | chr10 | 5707000 | 5708000 | 0.040 | 0.040 | ASB13 | 1.00000 | 0 |
| 756 | chr10 | 5728000 | 5729000 | 0.000 | 0.040 | ASB13 | 1.00000 | 0 |
| 757 | chr10 | 15393000 | 15394000 | 0.000 | 0.000 | FAM171A1 | 1.00000 | 0 |
| 758 | chr10 | 20796000 | 20797000 | 0.040 | 0.000 | PLXDC2 | 1.00000 | 0 |
| 759 | chr10 | 35424000 | 35425000 | 0.000 | 0.000 | CREM | 1.00000 | 0 |
| 760 | chr10 | 56678000 | 56679000 | 0.000 | 0.000 | PCDH15 | 1.00000 | 0 |
| 761 | chr10 | 63440000 | 63441000 | 0.000 | 0.040 | C10orf107 | 1.00000 | 0 |
| 762 | chr10 | 63659000 | 63660000 | 0.040 | 0.000 | ARID5B | 1.00000 | 1 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 763 | chr10 | 63660000 | 63661000 | 0.040 | 0.080 | ARID5B | 1.00000 | 1 |
| 764 | chr10 | 63662000 | 63663000 | 0.000 | 0.000 | ARID5B | 1.00000 | 1 |
| 765 | chr10 | 63720000 | 63721000 | 0.000 | 0.000 | ARID5B | 1.00000 | 1 |
| 766 | chr10 | 63803000 | 63804000 | 0.000 | 0.000 | ARID5B | 1.00000 | 1 |
| 767 | chr10 | 63809000 | 63810000 | 0.000 | 0.080 | ARID5B | 0.48980 | 1 |
| 768 | chr10 | 63810000 | 63811000 | 0.000 | 0.040 | ARID5B | 1.00000 | 1 |
| 769 | chr10 | 67907000 | 67908000 | 0.000 | 0.040 | CTNNA3 | 1.00000 | 0 |
| 770 | chr10 | 68474000 | 68475000 | 0.000 | 0.000 | CTNNA3 | 1.00000 | 0 |
| 771 | chr10 | 98510000 | 98511000 | 0.080 | 0.000 | PIK3AP1 | 0.48980 | 0 |
| 772 | chr10 | 101384000 | 101385000 | 0.000 | 0.000 | SLC25A28 | 1.00000 | 0 |
| 773 | chr10 | 108276000 | 108277000 | 0.040 | 0.000 | SORCS1 | 1.00000 | 0 |
| 774 | chr10 | 113473000 | 113474000 | 0.040 | 0.040 | GPAM | 1.00000 | 0 |
| 775 | chr10 | 113636000 | 113637000 | 0.040 | 0.000 | GPAM | 1.00000 | 0 |
| 776 | chr10 | 116458000 | 116459000 | 0.000 | 0.040 | ABLIM1 | 1.00000 | 0 |
| 777 | chr10 | 121623000 | 121624000 | 0.040 | 0.000 | MCMBP | 1.00000 | 0 |
| 778 | chr10 | 132973000 | 132974000 | 0.040 | 0.000 | TCERG1L | 1.00000 | 0 |
| 779 | chr10 | 134326000 | 134327000 | 0.000 | 0.000 | INPP5A | 1.00000 | 0 |
| 780 | chr11 | 871000 | 872000 | 0.040 | 0.040 | CHID1 | 1.00000 | 0 |
| 781 | chr11 | 1149000 | 1150000 | 0.000 | 0.000 | MUC5AC | 1.00000 | 0 |
| 782 | chr11 | 25065000 | 25066000 | 0.040 | 0.000 | LUZP2 | 1.00000 | 0 |
| 783 | chr11 | 25289000 | 25290000 | 0.040 | 0.040 | LUZP2 | 1.00000 | 0 |
| 784 | chr11 | 27216000 | 27217000 | 0.000 | 0.040 | BBOX1 | 1.00000 | 0 |
| 785 | chr11 | 28849000 | 28850000 | 0.000 | 0.000 | METTL15 | 1.00000 | 0 |
| 786 | chr11 | 29253000 | 29254000 | 0.040 | 0.000 | KCNA4 | 1.00000 | 0 |
| 787 | chr11 | 29900000 | 29901000 | 0.000 | 0.000 | KCNA4 | 1.00000 | 0 |
| 788 | chr11 | 40626000 | 40627000 | 0.000 | 0.000 | LRRC4C | 1.00000 | 0 |
| 789 | chr11 | 40845000 | 40846000 | 0.000 | 0.000 | LRRC4C | 1.00000 | 0 |
| 790 | chr11 | 40868000 | 40869000 | 0.000 | 0.000 | LRRC4C | 1.00000 | 0 |
| 791 | chr11 | 41066000 | 41067000 | 0.000 | 0.000 | LRRC4C | 1.00000 | 0 |
| 792 | chr11 | 41844000 | 41845000 | 0.000 | 0.000 | API5 | 1.00000 | 0 |
| 793 | chr11 | 57171000 | 57172000 | 0.040 | 0.000 | SLC43A3 | 1.00000 | 0 |
| 794 | chr11 | 60224000 | 60225000 | 0.040 | 0.080 | MS4A1 | 1.00000 | 1 |
| 795 | chr11 | 65190000 | 65191000 | 0.080 | 0.120 | FRMD8 | 1.00000 | 0 |
| 796 | chr11 | 65191000 | 65192000 | 0.080 | 0.120 | FRMD8 | 1.00000 | 0 |
| 797 | chr11 | 65266000 | 65267000 | 0.000 | 0.040 | SCYL1 | 1.00000 | 0 |
| 798 | chr11 | 65267000 | 65268000 | 0.120 | 0.040 | SCYL1 | 0.60921 | 0 |
| 799 | chr11 | 85963000 | 85964000 | 0.000 | 0.000 | EED | 1.00000 | 0 |
| 800 | chr11 | 92261000 | 92262000 | 0.000 | 0.040 | FAT3 | 1.00000 | 0 |
| 801 | chr11 | 102117000 | 102118000 | 0.000 | 0.000 | YAP1 | 1.00000 | 0 |
| 802 | chr11 | 102188000 | 102189000 | 0.200 | 0.280 | BIRC3 | 0.74164 | 1 |
| 803 | chr11 | 102189000 | 102190000 | 0.040 | 0.080 | BIRC3 | 1.00000 | 1 |
| 804 | chr11 | 107497000 | 107498000 | 0.000 | 0.000 | ELMODI | 1.00000 | 0 |
| 805 | chr11 | 108781000 | 108782000 | 0.000 | 0.040 | DDX10 | 1.00000 | 0 |
| 806 | chr11 | 108975000 | 108976000 | 0.040 | 0.000 | DDX10 | 1.00000 | 0 |
| 807 | chr11 | 109066000 | 109067000 | 0.000 | 0.000 | C11orf87 | 1.00000 | 0 |
| 808 | chr11 | 111248000 | 111249000 | 0.000 | 0.040 | POU2AF1 | 1.00000 | 1 |
| 809 | chr11 | 111249000 | 111250000 | 0.120 | 0.160 | POU2AF1 | 1.00000 | 1 |
| 810 | chr11 | 115761000 | 115762000 | 0.000 | 0.040 | CADM1 | 1.00000 | 0 |
| 811 | chr11 | 118723000 | 118724000 | 0.040 | 0.000 | CXCR5 | 1.00000 | 0 |
| 812 | chr11 | 126496000 | 126497000 | 0.040 | 0.000 | KIRREL3 | 1.00000 | 0 |
| 813 | chr11 | 12,8390000 | 128391000 | 0.040 | 0.040 | ETS1 | 1.00000 | 1 |
| 814 | chr11 | 128391000 | 128392000 | 0.160 | 0.040 | ETS1 | 0.34868 | 1 |
| 815 | chr12 | 6554000 | 6555000 | 0.000 | 0.040 | CD27 | 1.00000 | 0 |
| 816 | chr12 | 8762000 | 8763000 | 0.040 | 0.000 | AICDA | 1.00000 | 0 |
| 817 | chr12 | 8763000 | 8764000 | 0.080 | 0.040 | AICDA | 1.00000 | 0 |
| 818 | chr12 | 8764000 | 8765000 | 0.080 | 0.000 | AICDA | 0.48980 | 0 |
| 819 | chr12 | 8765000 | 8766000 | 0.040 | 0.000 | AICDA | 1.00000 | 0 |
| 820 | chr12 | 9823000 | 9824000 | 0.040 | 0.000 | CLEC2D | 1.00000 | 0 |
| 821 | chr12 | 11710000 | 11711000 | 0.000 | 0.040 | ETV6 | 1.00000 | 1 |
| 822 | chr12 | 11803000 | 11804000 | 0.040 | 0.000 | ETV6 | 1.00000 | 1 |
| 823 | chr12 | 14923000 | 14924000 | 0.040 | 0.040 | HIST4H4 | 1.00000 | 1 |
| 824 | chr12 | 16717000 | 16718000 | 0.000 | 0.000 | LMO3 | 1.00000 | 0 |
| 825 | chr12 | 23805000 | 23806000 | 0.000 | 0.040 | SOX5 | 1.00000 | 0 |
| 826 | chr12 | 25149000 | 25150000 | 0.000 | 0.040 | C12orf77 | 1.00000 | 0 |
| 827 | chr12 | 25151000 | 25152000 | 0.000 | 0.040 | C12orf77 | 1.00000 | 0 |
| 828 | chr12 | 25174000 | 25175000 | 0.040 | 0.040 | C12orf77 | 1.00000 | 0 |
| 829 | chr12 | 25205000 | 25206000 | 0.040 | 0.040 | LRMP | 1.00000 | 1 |
| 830 | chr12 | 25206000 | 25207000 | 0.080 | 0.120 | LRMP | 1.00000 | 1 |
| 831 | chr12 | 25207000 | 25208000 | 0.080 | 0.12.0 | LRMP | 1.00000 | 1 |
| 832 | chr12 | 25208000 | 25209000 | 0.000 | 0.040 | LRMP | 1.00000 | 1 |
| 833 | chr12 | 25665000 | 25666000 | 0.000 | 0.000 | IFLTD1 | 1.00000 | 0 |
| 834 | chr12 | 38920000 | 38921000 | 0.000 | 0.000 | CPNE8 | 1.00000 | 0 |
| 835 | chr12 | 48027000 | 48028000 | 0.080 | 0.080 | RPAP3 | 1.00000 | 0 |
| 836 | chr12 | 57496000 | 57497000 | 0.040 | 0.000 | STAT6 | 1.00000 | 0 |
| 837 | chr12 | 69203000 | 69204000 | 0.000 | 0.040 | MDM2 | 1.00000 | 0 |
| 838 | chr12 | 76202000 | 76203000 | 0.000 | 0.000 | PHLDA1 | 1.00000 | 0 |
| 839 | chr12 | 79270000 | 79271000 | 0.000 | 0.000 | SYT1 | 1.00000 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 840 | chr12 | 82572000 | 82573000 | 0.000 | 0.040 | CCDC59 | 1.00000 | 0 |
| 841 | chr12 | 84837000 | 84838000 | 0.000 | 0.000 | SLC6A15 | 1.00000 | 0 |
| 842 | chr12 | 86114000 | 86115000 | 0.040 | 0.000 | RASSF9 | 1.00000 | 0 |
| 843 | chr12 | 86115000 | 86116000 | 0.040 | 0.000 | RASSF9 | 1.00000 | 0 |
| 844 | chr12 | 92538000 | 92539000 | 0.080 | 0.080 | BTG1 | 1.00000 | 1 |
| 845 | chr12 | 92539000 | 92540000 | 0.080 | 0.040 | BTG1 | 1.00000 | 1 |
| 846 | chr12 | 96030000 | 96031000 | 0.000 | 0.040 | NTN4 | 1.00000 | 0 |
| 847 | chr12 | 110171000 | 110172000 | 0.000 | 0.040 | FAM222A | 1.00000 | 0 |
| 848 | chr12 | 110980000 | 110981000 | 0.000 | 0.040 | PPTC7 | 1.00000 | 0 |
| 849 | chr12 | 113493000 | 113494000 | 0.080 | 0.000 | DTX1 | 0.48980 | 1 |
| 850 | chr12 | 113494000 | 113495000 | 0.240 | 0.040 | DTX1 | 0.09828 | 1 |
| 851 | chr12 | 113495000 | 113496000 | 0.160 | 0.080 | DTX1 | 0.66710 | 1 |
| 852 | chr12 | 113496000 | 113497000 | 0.160 | 0.040 | DTX1 | 0.34868 | 1 |
| 853 | chr12 | 113497000 | 113498000 | 0.080 | 0.040 | DTX1 | 1.00000 | 1 |
| 854 | chr12 | 113499000 | 113500000 | 0.000 | 0.000 | DTX1 | 1.00000 | 1 |
| 855 | chr12 | 113512000 | 113513000 | 0.000 | 0.000 | DTX1 | 1.00000 | 1 |
| 856 | chr12 | 115966000 | 115967000 | 0.000 | 0.000 | MED13L | 1.00000 | 0 |
| 857 | chr12 | 122432000 | 122433000 | 0.040 | 0.000 | WDR66 | 1.00000 | 0 |
| 858 | chr12 | 122433000 | 122434000 | 0.080 | 0.000 | WDR66 | 0.48980 | 0 |
| 859 | chr12 | 122447000 | 122448000 | 0.000 | 0.040 | WDR66 | 1.00000 | 0 |
| 860 | chr12 | 122458000 | 122459000 | 0.080 | 0.120 | BCL7A | 1.00000 | 1 |
| 861 | chr12 | 122459000 | 122460000 | 0.240 | 0.320 | BCL7A | 0.75361 | 1 |
| 862 | chr12 | 122460000 | 122461000 | 0.120 | 0.280 | BCL7A | 0.28902 | 1 |
| 863 | chr12 | 122461000 | 122462000 | 0.240 | 0.240 | BCL7A | 1.00000 | 1 |
| 864 | chr12 | 122462000 | 122463000 | 0.160 | 0.200 | BCL7A | 1.00000 | 1 |
| 865 | chr12 | 122463000 | 122464000 | 0.120 | 0.200 | BCL7A | 0.70194 | 1 |
| 866 | chr12 | 124054000 | 124055000 | 0.000 | 0.080 | TMED2 | 0.48980 | 0 |
| 867 | chr12 | 127965000 | 127966000 | 0.000 | 0.000 | TMEM132C | 1.00000 | 0 |
| 868 | chr12 | 131303000 | 131304000 | 0.000 | 0.120 | STX2 | 0.23469 | 0 |
| 869 | chr12 | 131649000 | 131650000 | 0.000 | 0.000 | GPR133 | 1.00000 | 0 |
| 870 | chr12 | 133306000 | 133307000 | 0.000 | 0.000 | ANKLE2 | 1.00000 | 0 |
| 871 | chr13 | 21913000 | 21914000 | 0.040 | 0.040 | ZDHHC20 | 1.00000 | 0 |
| 872 | chr13 | 32116000 | 32117000 | 0.040 | 0.040 | RXFP2 | 1.00000 | 0 |
| 873 | chr13 | 35498000 | 35499000 | 0.000 | 0.000 | NBEA | 1.00000 | 0 |
| 874 | chr13 | 38371000 | 38372000 | 0.040 | 0.000 | TRPC4 | 1.00000 | 0 |
| 875 | chr13 | 38630000 | 38631000 | 0.040 | 0.000 | TRPC4 | 1.00000 | 0 |
| 876 | chr13 | 41156000 | 41157000 | 0.000 | 0.040 | FOXO1 | 1.00000 | 1 |
| 877 | chr13 | 41240000 | 41241000 | 0.000 | 0.040 | FOXO1 | 1.00000 | 1 |
| 878 | chr13 | 46958000 | 46959000 | 0.000 | 0.000 | KIAA0226L | 1.00000 | 0 |
| 879 | chr13 | 46959000 | 46960000 | 0.040 | 0.000 | KIAA0226L | 1.00000 | 0 |
| 880 | chr13 | 46960000 | 46961000 | 0.160 | 0.040 | KIAA0226L | 0.34868 | 0 |
| 881 | chr13 | 46961000 | 46962000 | 0.000 | 0.040 | KIAA0226L | 1.00000 | 0 |
| 882 | chr13 | 46962000 | 46963000 | 0.000 | 0.040 | KIAA0226L | 1.00000 | 0 |
| 883 | chr13 | 55239000 | 55240000 | 0.040 | 0.000 | OLFM4 | 1.00000 | 0 |
| 884 | chr13 | 55386000 | 55387000 | 0.040 | 0.000 | OLFM4 | 1.00000 | 0 |
| 885 | chr13 | 55598000 | 55599000 | 0.000 | 0.000 | OLFM4 | 1.00000 | 0 |
| 886 | chr13 | 57222000 | 57223000 | 0.000 | 0.040 | PRR20A; PRR20 DPRR20 BPRR20E; | 1.00000 | 0 |
| 887 | chr13 | 61343000 | 61344000 | 0.000 | 0.000 | TDRD3 | 1.00000 | 0 |
| 888 | chr13 | 62830000 | 62831000 | 0.000 | 0.000 | PCDH20 | 1.00000 | 0 |
| 889 | chr13 | 63049000 | 63050000 | 0.080 | 0.000 | PCDH20 | 0.48980 | 0 |
| 890 | chr13 | 63157000 | 63158000 | 0.000 | 0.000 | AL445989.1 | 1.00000 | 0 |
| 891 | chr13 | 63214000 | 63215000 | 0.040 | 0.000 | AL445989.1 | 1.00000 | 0 |
| 892 | chr13 | 64802000 | 64803000 | 0.000 | 0.040 | AL445989.1 | 1.00000 | 0 |
| 893 | chr13 | 65637000 | 65638000 | 0.000 | 0.040 | PCDH9 | 1.00000 | 0 |
| 894 | chr13 | 68656000 | 68657000 | 0.000 | 0.000 | PCDH9 | 1.00000 | 0 |
| 895 | chr13 | 69418000 | 69419000 | 0.000 | 0.000 | KLHL1 | 1.00000 | 0 |
| 896 | chr13 | 70956000 | 70957000 | 0.040 | 0.000 | KLHL1 | 1.00000 | 0 |
| 897 | chr13 | 74542000 | 74543000 | 0.000 | 0.040 | KLF12 | 1.00000 | 0 |
| 898 | chr13 | 75983000 | 75984000 | 0.000 | 0.040 | TBC1D4 | 1.00000 | 0 |
| 899 | chr13 | 75984000 | 75985000 | 0.000 | 0.160 | TBC1D4 | 0.10986 | 0 |
| 900 | chr13 | 83450000 | 83451000 | 0.000 | 0.000 | SLITRK1 | 1.00000 | 0 |
| 901 | chr13 | 84641000 | 84642000 | 0.040 | 0.000 | SLITRK1 | 1.00000 | 0 |
| 902 | chr13 | 87793000 | 87794000 | 0.040 | 0.000 | SLITRK5 | 1.00000 | 0 |
| 903 | chr13 | 91480000 | 91481000 | 0.000 | 0.000 | GPC5 | 1.00000 | 0 |
| 904 | chr13 | 106081000 | 106082000 | 0.040 | 0.000 | DAOA | 1.00000 | 0 |
| 905 | chr13 | 114786000 | 114787000 | 0.040 | 0.000 | RASA3 | 1.00000 | 0 |
| 906 | chr13 | 114916000 | 114917000 | 0.000 | 0.000 | RASA3 | 1.00000 | 0 |
| 907 | chr14 | 22948000 | 22949000 | 0.040 | 0.000 | TRAJ56 | 1.00000 | 0 |
| 908 | chr14 | 22949000 | 22950000 | 0.040 | 0.000 | TRAJ56 | 1.00000 | 0 |
| 909 | chr14 | 22950000 | 22951000 | 0.040 | 0.000 | TRAJ54 | 1.00000 | 0 |
| 910 | chr14 | 22977000 | 22978000 | 0.000 | 0.040 | TRAJ33 | 1.00000 | 0 |
| 911 | chr14 | 27286000 | 27287000 | 0.000 | 0.000 | NOVA1 | 1.00000 | 0 |
| 912 | chr14 | 28645000 | 28646000 | 0.000 | 0.000 | FOXG1 | 1.00000 | 0 |
| 913 | chr14 | 49407000 | 49408000 | 0.000 | 0.000 | RPS29 | 1.00000 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 914 | chr14 | 50864000 | 50865000 | 0.000 | 0.000 | CDKL1 | 1.00000 | 0 |
| 915 | chr14 | 54812000 | 54813000 | 0.000 | 0.000 | CDKN3 | 1.00000 | 0 |
| 916 | chr14 | 55348000 | 55349000 | 0.040 | 0.000 | GCH1 | 1.00000 | 0 |
| 917 | chr14 | 59827000 | 59828000 | 0.000 | 0.040 | DAAM1 | 1.00000 | 0 |
| 918 | chr14 | 63143000 | 63144000 | 0.000 | 0.040 | KCNH5 | 1.00000 | 0 |
| 919 | chr14 | 64194000 | 64195000 | 0.000 | 0.040 | SGPP1 | 1.00000 | 0 |
| 920 | chr14 | 69258000 | 69259000 | 0.240 | 0.200 | ZFP36L1 | 1.00000 | 1 |
| 921 | chr14 | 69259000 | 69260000 | 0.360 | 0.240 | ZFP36L1 | 0.53803 | 1 |
| 922 | chr14 | 78418000 | 78419000 | 0.000 | 0.040 | ADCK1 | 1.00000 | 0 |
| 923 | chr14 | 81685000 | 81686000 | 0.000 | 0.040 | GTF2A1 | 1.00000 | 0 |
| 924 | chr14 | 84420000 | 84421000 | 0.040 | 0.000 | FLRT2 | 1.00000 | 0 |
| 925 | chr14 | 91883000 | 91884000 | 0.040 | 0.000 | CCDC88C | 1.00000 | 0 |
| 926 | chr14 | 94941000 | 94942000 | 0.000 | 0.120 | SERPINA9 | 0.23469 | 1 |
| 927 | chr14 | 94942000 | 94943000 | 0.040 | 0.200 | SERPINA9 | 0.18946 | 1 |
| 928 | chr14 | 96179000 | 96180000 | 0.160 | 0.120 | TCL1A | 1.00000 | 1 |
| 929 | chr14 | 96180000 | 96181000 | 0.080 | 0.160 | TCL1A | 0.66710 | 1 |
| 930 | chr14 | 101597000 | 101598000 | 0.000 | 0.000 | AL117190.3 | 1.00000 | 0 |
| 931 | chr14 | 102285000 | 102286000 | 0.040 | 0.000 | PPP2R5C | 1.00000 | 0 |
| 932 | chr14 | 105954000 | 105955000 | 0.040 | 0.040 | CRIP1 | 1.00000 | 0 |
| 933 | chr14 | 106031000 | 106032000 | 0.040 | 0.000 | IGHA2 | 1.00000 | 0 |
| 934 | chr14 | 106042000 | 106043000 | 0.080 | 0.200 | IGHA2 | 0.41743 | 0 |
| 935 | chr14 | 106048000 | 106049000 | 0.040 | 0.040 | IGHA2 | 1.00000 | 0 |
| 936 | chr14 | 106054000 | 106055000 | 0.040 | 0.040 | IGHA2 | 1.00000 | 0 |
| 937 | chr14 | 106055000 | 106056000 | 0.080 | 0.240 | IGHA2 | 0.24672 | 0 |
| 938 | chr14 | 106056000 | 106057000 | 0.040 | 0.200 | IGHA2 | 0.18946 | 0 |
| 939 | chr14 | 106057000 | 106058000 | 0.000 | 0.080 | IGHA2 | 0.48980 | 0 |
| 940 | chr14 | 106058000 | 106059000 | 0.000 | 0.080 | IGHA2 | 0.48980 | 0 |
| 941 | chr14 | 106066000 | 106067000 | 0.000 | 0.120 | IGHE | 0.23469 | 0 |
| 942 | chr14 | 106067000 | 106068000 | 0.000 | 0.120 | IGHE | 0.23469 | 0 |
| 943 | chr14 | 106068000 | 106069000 | 0.040 | 0.120 | IGHE | 0.60921 | 0 |
| 944 | chr14 | 106069000 | 106070000 | 0.040 | 0.200 | IGHE | 0.18946 | 0 |
| 945 | chr14 | 106070000 | 106071000 | 0.000 | 0.160 | IGHE | 0.10986 | 0 |
| 946 | chr14 | 106071000 | 106072000 | 0.000 | 0.160 | IGHE | 0.10986 | 0 |
| 947 | chr14 | 106072000 | 106073000 | 0.000 | 0.120 | IGHE | 0.23469 | 0 |
| 948 | chr14 | 106082000 | 106083000 | 0.000 | 0.000 | IGHG4 | 1.00000 | 0 |
| 949 | chr14 | 106092000 | 106093000 | 0.040 | 0.000 | IGHG4 | 1.00000 | 0 |
| 950 | chr14 | 106094000 | 106095000 | 0.160 | 0.200 | IGHG4 | 1.00000 | 0 |
| 951 | chr14 | 106095000 | 106096000 | 0.080 | 0.160 | IGHG4 | 0.66710 | 0 |
| 952 | chr14 | 106110000 | 106111000 | 0.080 | 0.040 | IGHG2 | 1.00000 | 0 |
| 953 | chr14 | 106111000 | 106112000 | 0.000 | 0.040 | IGHG2 | 1.00000 | 0 |
| 954 | chr14 | 106112000 | 106113000 | 0.280 | 0.200 | IGHG2 | 0.74164 | 0 |
| 955 | chr14 | 106113000 | 106114000 | 0.240 | 0.320 | IGHG2 | 0.75361 | 0 |
| 956 | chr14 | 106114000 | 106115000 | 0.320 | 0.200 | IGHG2 | 0.52019 | 0 |
| 957 | chr14 | 106146000 | 106147000 | 0.000 | 0.000 | IGHA1 | 1.00000 | 0 |
| 958 | chr14 | 106151000 | 106152000 | 0.040 | 0.000 | IGHA1 | 1.00000 | 0 |
| 959 | chr14 | 106152000 | 106153000 | 0.040 | 0.000 | IGHA1 | 1.00000 | 0 |
| 960 | chr14 | 106161000 | 106162000 | 0.000 | 0.040 | IGHA1 | 1.00000 | 0 |
| 961 | chr14 | 106173000 | 106174000 | 0.040 | 0.040 | IGHA1 | 1.00000 | 0 |
| 962 | chr14 | 106174000 | 106175000 | 0.040 | 0.000 | IGHA1 | 1.00000 | 0 |
| 963 | chr14 | 106175000 | 106176000 | 0.040 | 0.000 | IGHA1 | 1.00000 | 0 |
| 964 | chr14 | 106176000 | 106177000 | 0.080 | 0.040 | IGHA1 | 1.00000 | 0 |
| 965 | chr14 | 106177000 | 106178000 | 0.000 | 0.000 | IGHA1 | 1.00000 | 0 |
| 966 | chr14 | 106178000 | 106179000 | 0.120 | 0.000 | IGHA1 | 0.23469 | 0 |
| 967 | chr14 | 106208000 | 106209000 | 0.040 | 0.040 | IGHG1 | 1.00000 | 0 |
| 968 | chr14 | 106209000 | 106210000 | 0.160 | 0.080 | IGHG1 | 0.66710 | 0 |
| 969 | chr14 | 106210000 | 106211000 | 0.160 | 0.120 | IGHG1 | 1.00000 | 0 |
| 970 | chr14 | 106211000 | 106212000 | 0.440 | 0.120 | IGHG1 | 0.02548 | 0 |
| 971 | chr14 | 106212000 | 106213000 | 0.520 | 0.120 | IGHG1 | 0.00544 | 0 |
| 972 | chr14 | 106213000 | 106214000 | 0.520 | 0.120 | IGHG1 | 0.00544 | 0 |
| 973 | chr14 | 106214000 | 106215000 | 0.240 | 0.000 | IGHG1 | 0.02229 | 0 |
| 974 | chr14 | 106237000 | 106238000 | 0.080 | 0.040 | IGHG3 | 1.00000 | 0 |
| 975 | chr14 | 106238000 | 106239000 | 0.320 | 0.120 | IGHG3 | 0.17062 | 0 |
| 976 | chr14 | 106239000 | 106240000 | 0.440 | 0.040 | IGHG3 | 0.00192 | 0 |
| 977 | chr14 | 106240000 | 106241000 | 0.480 | 0.080 | IGHG3 | 0.00361 | 0 |
| 978 | chr14 | 106241000 | 106242000 | 0.320 | 0.040 | IGHG3 | 0.02322 | 0 |
| 979 | chr14 | 106242000 | 106243000 | 0.040 | 0.000 | IGHG3 | 1.00000 | 0 |
| 980 | chr14 | 106321000 | 106322000 | 0.040 | 0.000 | IGHM | 1.00000 | 0 |
| 981 | chr14 | 106322000 | 106323000 | 0.240 | 0.040 | IGHM | 0.09828 | 0 |
| 982 | chr14 | 106323000 | 106324000 | 0.400 | 0.160 | IGHM | 0.11366 | 0 |
| 983 | chr14 | 106324000 | 106325000 | 0.320 | 0.120 | IGHM | 0.17062 | 0 |
| 984 | chr14 | 106325000 | 106326000 | 0.160 | 0.320 | IGHM | 0.32089 | 0 |
| 985 | chr14 | 106326000 | 106327000 | 0.920 | 0.920 | IGHJ6 | 1.00000 | 0 |
| 986 | chr14 | 106327000 | 106328000 | 0.800 | 0.760 | IGHJ6 | 1.00000 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 987 | chr14 | 106328000 | 106329000 | 0.680 | 0.800 | IGHJ6 | 0.52019 | 0 |
| 988 | chr14 | 106329000 | 106330000 | 0.880 | 0.920 | IGHJ6 | 1.00000 | 0 |
| 989 | chr14 | 106330000 | 106331000 | 0.720 | 0.520 | IGHJ3; IGHJ4; IGHJ5; | 0.24363 | 0 |
| 990 | chr14 | 106331000 | 106332000 | 0.120 | 0.080 | IGHD7-27; IGHJ1; IGHJ2 | 1.00000 | 0 |
| 991 | chr14 | 106338000 | 106339000 | 0.040 | 0.000 | IGHD7-27 | 1.00000 | 0 |
| 992 | chr14 | 106350000 | 106351000 | 0.040 | 0.000 | IGHD4-23 | 1.00000 | 0 |
| 993 | chr14 | 106352000 | 106353000 | 0.000 | 0.040 | IGHD3-22 | 1.00000 | 0 |
| 994 | chr14 | 106353000 | 106354000 | 0.000 | 0.000 | IGHD2-21 | 1.00000 | 0 |
| 995 | chr14 | 106354000 | 106355000 | 0.000 | 0.040 | IGHD2-21 | 1.00000 | 0 |
| 996 | chr14 | 106355000 | 106356000 | 0.000 | 0.040 | IGHD2-21 | 1.00000 | 0 |
| 997 | chr14 | 106357000 | 106358000 | 0.040 | 0.080 | IGHD1-20; IGHD6-19; | 1.00000 | 0 |
| 998 | chr14 | 106358000 | 106359000 | 0.000 | 0.040 | IGHD5-18 | 1.00000 | 0 |
| 999 | chr14 | 106362000 | 106363000 | 0.000 | 0.000 | IGHD3-16 | 1.00000 | 0 |
| 1000 | chr14 | 106364000 | 106365000 | 0.040 | 0.000 | IGHD2-15 | 1.00000 | 0 |
| 1001 | chr14 | 106367000 | 106368000 | 0.040 | 0.000 | IGHD6-13 | 1.00000 | 0 |
| 1002 | chr14 | 106370000 | 106371000 | 0.080 | 0.000 | IGHD3-10; IGHD3-9; | 0.48980 | 0 |
| 1003 | chr14 | 106371000 | 106372000 | 0.040 | 0.000 | IGHD3-9 | 1.00000 | 0 |
| 1004 | chr14 | 106372000 | 106373000 | 0.040 | 0.000 | IGHD2-8 | 1.00000 | 0 |
| 1005 | chr14 | 106375000 | 106376000 | 0.000 | 0.000 | IGHD1-7 | 1.00000 | 0 |
| 1006 | chr14 | 106376000 | 106377000 | 0.000 | 0.040 | IGHD6-6 | 1.00000 | 0 |
| 1007 | chr14 | 106380000 | 106381000 | 0.000 | 0.040 | IGHD3-3 | 1.00000 | 0 |
| 1008 | chr14 | 106381000 | 106382000 | 0.000 | 0.040 | IGHD2-2 | 1.00000 | 0 |
| 1009 | chr14 | 106382000 | 106383000 | 0.040 | 0.120 | IGHD2-2 | 0.60921 | 0 |
| 1010 | chr14 | 106383000 | 106384000 | 0.080 | 0.040 | IGHD2-2 | 1.00000 | 0 |
| 1011 | chr14 | 106384000 | 106385000 | 0.040 | 0.040 | IGHD1-1 | 1.00000 | 0 |
| 1012 | chr14 | 106385000 | 106386000 | 0.080 | 0.040 | IGHD1-1 | 1.00000 | 0 |
| 1013 | chr14 | 106387000 | 106388000 | 0.040 | 0.080 | KIAA0125 | 1.00000 | 0 |
| 1014 | chr14 | 106405000 | 106406000 | 0.000 | 0.040 | IGHV6-1 | 1.00000 | 0 |
| 1015 | chr14 | 106406000 | 106407000 | 0.000 | 0.040 | IGHV6-1 | 1.00000 | 0 |
| 1016 | chr14 | 106419000 | 106420000 | 0.000 | 0.080 | IGHV6-1 | 0.48980 | 0 |
| 1017 | chr14 | 106452000 | 106453000 | 0.040 | 0.000 | IGHV1-2 | 1.00000 | 0 |
| 1018 | chr14 | 106453000 | 106454000 | 0.080 | 0.000 | IGHV1-2 | 0.48980 | 0 |
| 1019 | chr14 | 106454000 | 106455000 | 0.040 | 0.000 | IGHV1-2 | 1.00000 | 0 |
| 1020 | chr14 | 106494000 | 106495000 | 0.000 | 0.040 | IGHV2-5 | 1.00000 | 0 |
| 1021 | chr14 | 106518000 | 106519000 | 0.000 | 0.080 | IGHV3-7 | 0.48980 | 0 |
| 1022 | chr14 | 106519000 | 106520000 | 0.000 | 0.080 | IGHV3-7 | 0.48980 | 0 |
| 1023 | chr14 | 106539000 | 106540000 | 0.000 | 0.040 | IGHV1-8 | 1.00000 | 0 |
| 1024 | chr14 | 106552000 | 106553000 | 0.000 | 0.000 | IGHV3-9 | 1.00000 | 0 |
| 1025 | chr14 | 106573000 | 106574000 | 0.040 | 0.000 | IGHV3-11 | 1.00000 | 0 |
| 1026 | chr14 | 106574000 | 106575000 | 0.040 | 0.000 | IGHV3-11 | 1.00000 | 0 |
| 1027 | chr14 | 106578000 | 106579000 | 0.040 | 0.000 | IGHV3-11 | 1.00000 | 0 |
| 1028 | chr14 | 106579000 | 106580000 | 0.040 | 0.000 | IGHV3-11 | 1.00000 | 0 |
| 1029 | chr14 | 106610000 | 106611000 | 0.000 | 0.000 | IGHV3-15 | 1.00000 | 0 |
| 1030 | chr14 | 106641000 | 106642000 | 0.040 | 0.040 | IGHV1-18 | 1.00000 | 0 |
| 1031 | chr14 | 106642000 | 106643000 | 0.040 | 0.000 | IGHVI-18 | 1.00000 | 0 |
| 1032 | chr14 | 106691000 | 106692000 | 0.000 | 0.000 | IGHV3-21 | 1.00000 | 0 |
| 1033 | chr14 | 106692000 | 106693000 | 0.000 | 0.040 | IGHV3-21 | 1.00000 | 0 |
| 1034 | chr14 | 106725000 | 106726000 | 0.120 | 0.160 | IGHV3-23 | 1.00000 | 0 |
| 1035 | chr14 | 106726000 | 106727000 | 0.040 | 0.080 | IGHV3-23 | 1.00000 | 0 |
| 1036 | chr14 | 106733000 | 106734000 | 0.000 | 0.080 | IGHV1-24 | 0.48980 | 0 |
| 1037 | chr14 | 106757000 | 106758000 | 0.000 | 0.040 | IGHV2-26 | 1.00000 | 0 |
| 1038 | chr14 | 106758000 | 106759000 | 0.000 | 0.040 | IGHV2-26 | 1.00000 | 0 |
| 1039 | chr14 | 106791000 | 106792000 | 0.040 | 0.040 | IGHV3-30 | 1.00000 | 0 |
| 1040 | chr14 | 106804000 | 106805000 | 0.040 | 0.040 | IGHV4-31 | 1.00000 | 0 |
| 1041 | chr14 | 106805000 | 106806000 | 0.040 | 0.040 | IGHV4-31 | 1.00000 | 0 |
| 1042 | chr14 | 106806000 | 106807000 | 0.000 | 0.000 | IGHV4-31 | 1.00000 | 0 |
| 1043 | chr14 | 106815000 | 106816000 | 0.000 | 0.040 | IGHV3-33 | 1.00000 | 0 |
| 1044 | chr14 | 106816000 | 106817000 | 0.000 | 0.160 | IGHV3-33 | 0.10986 | 0 |
| 1045 | chr14 | 106817000 | 106818000 | 0.000 | 0.080 | IGHV3-33 | 0.48980 | 0 |
| 1046 | chr14 | 106829000 | 106830000 | 0.160 | 0.080 | IGHV4-34 | 0.66710 | 0 |
| 1047 | chr14 | 106830000 | 106831000 | 0.160 | 0.000 | IGHV4-34 | 0.10986 | 0 |
| 1048 | chr14 | 106877000 | 106878000 | 0.040 | 0.080 | IGHV4-39 | 1.00000 | 0 |
| 1049 | chr14 | 106878000 | 106879000 | 0.000 | 0.080 | IGHV4-39 | 0.48980 | 0 |
| 1050 | chr14 | 106967000 | 106968000 | 0.040 | 0.040 | IGHV1-46 | 1.00000 | 0 |
| 1051 | chr14 | 106994000 | 106995000 | 0.000 | 0.120 | IGHV3-48 | 0.23469 | 0 |
| 1052 | chr14 | 106995000 | 106996000 | 0.000 | 0.000 | IGHV3-48 | 1.00000 | 0 |
| 1053 | chr14 | 107034000 | 107035000 | 0.040 | 0.000 | IGHV5-51 | 1.00000 | 0 |
| 1054 | chr14 | 107035000 | 107036000 | 0.080 | 0.000 | IGHV5-51 | 0.48980 | 0 |
| 1055 | chr14 | 107048000 | 107049000 | 0.000 | 0.000 | IGHV3-53 | 1.00000 | 0 |
| 1056 | chr14 | 107049000 | 107050000 | 0.000 | 0.000 | IGHV3-53 | 1.00000 | 0 |
| 1057 | chr14 | 107083000 | 107084000 | 0.040 | 0.040 | IGHV4-59 | 1.00000 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 1058 | chr14 | 107084000 | 107085000 | 0.000 | 0.040 | IGHV4-59 | 1.00000 | 0 |
| 1059 | chr14 | 107095000 | 107096000 | 0.040 | 0.000 | IGHV4-61 | 1.00000 | 0 |
| 1060 | chr14 | 107113000 | 107114000 | 0.080 | 0.000 | IGHV3-64 | 0.48980 | 0 |
| 1061 | chr14 | 107114000 | 107115000 | 0.080 | 0.000 | IGHV3-64 | 0.48980 | 0 |
| 1062 | chr14 | 107169000 | 107170000 | 0.200 | 0.240 | IGHV1-69 | 1.00000 | 0 |
| 1063 | chr14 | 107170000 | 107171000 | 0.360 | 0.280 | IGHV1-69 | 0.76241 | 0 |
| 1064 | chr14 | 107176000 | 107177000 | 0.200 | 0.200 | IGHV2-70 | 1.00000 | 0 |
| 1065 | chr14 | 107177000 | 107178000 | 0.080 | 0.040 | IGHV2-70 | 1.00000 | 0 |
| 1066 | chr14 | 107178000 | 107179000 | 0.200 | 0.520 | IGHV2-70 | 0.03776 | 0 |
| 1067 | chr14 | 107179000 | 107180000 | 0.240 | 0.360 | IGHV2-70 | 0.53803 | 0 |
| 1068 | chr14 | 107183000 | 107184000 | 0.000 | 0.000 | IGHV2-70 | 1.00000 | 0 |
| 1069 | chr14 | 107199000 | 107200000 | 0.000 | 0.080 | IGHV3-72 | 0.48980 | 0 |
| 1070 | chr14 | 107218000 | 107219000 | 0.000 | 0.080 | IGHV3-74 | 0.48980 | 0 |
| 1071 | chr14 | 107219000 | 107220000 | 0.000 | 0.160 | IGHV3-74 | 0.10986 | 0 |
| 1072 | chr14 | 107221000 | 107222000 | 0.000 | 0.080 | IGHV3-74 | 0.48980 | 0 |
| 1073 | chr14 | 107232000 | 107233000 | 0.000 | 0.000 | IGHV3-74 | 1.00000 | 0 |
| 1074 | chr14 | 107253000 | 107254000 | 0.000 | 0.000 | IGHV7-81 | 1.00000 | 0 |
| 1075 | chr14 | 107258000 | 107259000 | 0.000 | 0.040 | IGHV7-81 | 1.00000 | 0 |
| 1076 | chr14 | 107259000 | 107260000 | 0.160 | 0.200 | IGHV7-81 | 1.00000 | 0 |
| 1077 | chr15 | 45003000 | 45004000 | 0.040 | 0.040 | B2M | 1.00000 | 0 |
| 1078 | chr15 | 45007000 | 45008000 | 0.000 | 0.000 | B2M | 1.00000 | 0 |
| 1079 | chr15 | 45814000 | 45815000 | 0.000 | 0.040 | SLC30A4 | 1.00000 | 0 |
| 1080 | chr15 | 59664000 | 59665000 | 0.000 | 0.080 | MYO1E | 0.48980 | 0 |
| 1081 | chr15 | 65588000 | 65589000 | 0.040 | 0.000 | PARP16 | 1.00000 | 0 |
| 1082 | chr15 | 78332000 | 78333000 | 0.000 | 0.000 | TBC1D2B | 1.00000 | 0 |
| 1083 | chr15 | 83227000 | 83228000 | 0.000 | 0.040 | CPEB1 | 1.00000 | 0 |
| 1084 | chr15 | 86226000 | 86227000 | 0.040 | 0.040 | AKAP13 | 1.00000 | 0 |
| 1085 | chr15 | 86233000 | 86234000 | 0.040 | 0.000 | AKAP13 | 1.00000 | 0 |
| 1086 | chr15 | 86245000 | 86246000 | 0.080 | 0.120 | AKAP13 | 1.00000 | 0 |
| 1087 | chr16 | 368000 | 369000 | 0.000 | 0.040 | AXIN1 | 1.00000 | 0 |
| 1088 | chr16 | 3788000 | 3789000 | 0.040 | 0.000 | CREBBP | 1.00000 | 0 |
| 1089 | chr16 | 10971000 | 10972000 | 0.080 | 0.120 | CIITA | 1.00000 | 1 |
| 1090 | chr16 | 10972000 | 10973000 | 0.120 | 0.320 | CIITA | 0.17062 | 1 |
| 1091 | chr16 | 10973000 | 10974000 | 0.120 | 0.240 | CIITA | 0.46349 | 1 |
| 1092 | chr16 | 10974000 | 10975000 | 0.080 | 0.120 | CIITA | 1.00000 | 1 |
| 1093 | chr16 | 11348000 | 11349000 | 0.080 | 0.200 | SOCS1 | 0.41743 | 1 |
| 1094 | chr16 | 11349000 | 11350000 | 0.120 | 0.240 | SOCS1 | 0.46349 | 1 |
| 1095 | chr16 | 21167000 | 21168000 | 0.040 | 0.000 | DNAH3 | 1.00000 | 0 |
| 1096 | chr16 | 27325000 | 27326000 | 0.000 | 0.040 | CTD-3203P2.2 | 1.00000 | 0 |
| 1097 | chr16 | 27326000 | 27327000 | 0.080 | 0.080 | CTD-3203P2.2 | 1.00000 | 0 |
| 1098 | chr16 | 27327000 | 27328000 | 0.000 | 0.000 | IL4R | 1.00000 | 0 |
| 1099 | chr16 | 27414000 | 27415000 | 0.040 | 0.000 | IL21R | 1.00000 | 0 |
| 1100 | chr16 | 29248000 | 29249000 | 0.000 | 0.000 | 61E3.4 | 1.00000 | 0 |
| 1101 | chr16 | 31910000 | 31911000 | 0.040 | 0.000 | ZNF267 | 1.00000 | 0 |
| 1102 | chr16 | 46821000 | 46822000 | 0.000 | 0.040 | C16or87 | 1.00000 | 0 |
| 1103 | chr16 | 50985000 | 50986000 | 0.040 | 0.000 | CYLD | 1.00000 | 0 |
| 1104 | chr16 | 64351000 | 64352000 | 0.000 | 0.040 | CDH11 | 1.00000 | 0 |
| 1105 | chr16 | 78398000 | 78399000 | 0.000 | 0.000 | WWOX | 1.00000 | 0 |
| 1106 | chr16 | 78615000 | 78616000 | 0.040 | 0.000 | WWOX | 1.00000 | 0 |
| 1107 | chr16 | 78753000 | 78754000 | 0.000 | 0.040 | WWOX | 1.00000 | 0 |
| 1108 | chr16 | 78811000 | 78812000 | 0.000 | 0.040 | WWOX | 1.00000 | 0 |
| 1109 | chr16 | 79988000 | 79989000 | 0.000 | 0.040 | MAF | 1.00000 | 0 |
| 1110 | chr16 | 81836000 | 81837000 | 0.000 | 0.000 | PLCG2 | 1.00000 | 0 |
| 1111 | chr16 | 85932000 | 85933000 | 0.040 | 0.040 | IRF8 | 1.00000 | 1 |
| 1112 | chr16 | 85933000 | 85934000 | 0.080 | 0.240 | IRF8 | 0.24672 | 1 |
| 1113 | chr16 | 85934000 | 85935000 | 0.040 | 0.000 | IRF8 | 1.00000 | 1 |
| 1114 | chr16 | 85936000 | 85937000 | 0.000 | 0.000 | IRF8 | 1.00000 | 1 |
| 1115 | chr16 | 88441000 | 88442000 | 0.040 | 0.000 | ZNF469 | 1.00000 | 0 |
| 1116 | chr17 | 3598000 | 3599000 | 0.040 | 0.040 | P2RXS; P2RX5-TAX1BP3 P2RX5; | 1.00000 | 0 |
| 1117 | chr17 | 17286000 | 17287000 | 0.080 | 0.000 | SMCR9 | 0.48980 | 0 |
| 1118 | chr17 | 21194000 | 21195000 | 0.000 | 0.040 | MAP2K3 | 1.00000 | 0 |
| 1119 | chr17 | 29646000 | 29647000 | 0.000 | 0.000 | EVI2A | 1.00000 | 0 |
| 1120 | chr17 | 38020000 | 38021000 | 0.000 | 0.040 | IKZF3 | 1.00000 | 0 |
| 1121 | chr17 | 43662000 | 43663000 | 0.040 | 0.000 | PLEKHM1 | 1.00000 | 0 |
| 1122 | chr17 | 56408000 | 56409000 | 0.120 | 0.040 | BZRAP1 | 0.60921 | 0 |
| 1123 | chr17 | 56409000 | 56410000 | 0.360 | 0.200 | BZRAP1 | 0.34513 | 0 |
| 1124 | chr17 | 57916000 | 57917000 | 0.040 | 0.080 | VMP1 | 1.00000 | 1 |
| 1125 | chr17 | 57917000 | 57918000 | 0.040 | 0.080 | VMP1 | 1.00000 | 1 |
| 1126 | chr17 | 62007000 | 62008000 | 0.040 | 0.000 | CD79B | 1.00000 | 0 |
| 1127 | chr17 | 62008000 | 62009000 | 0.040 | 0.000 | CD79B | 1.00000 | 0 |
| 1128 | chr17 | 63067000 | 63068000 | 0.040 | 0.000 | GNA13 | 1.00000 | 0 |
| 1129 | chr17 | 65676000 | 65677000 | 0.040 | 0.000 | PITPNC1 | 1.00000 | 0 |
| 1130 | chr17 | 69365000 | 69366000 | 0.000 | 0.040 | AC007461.1 | 1.00000 | 0 |
| 1131 | chr17 | 70083000 | 70084000 | 0.000 | 0.000 | SOX9 | 1.00000 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 1132 | chr17 | 74733000 | 74734000 | 0.000 | 0.000 | SRSF2 | 1.00000 | 0 |
| 1133 | chr17 | 75447000 | 75448000 | 0.080 | 0.000 | 9-Sep-19 | 0.48980 | 0 |
| 1134 | chr17 | 75448000 | 75449000 | 0.040 | 0.000 | 9-Sep-19 | 1.00000 | 0 |
| 1135 | chr17 | 76775000 | 76776000 | 0.000 | 0.000 | CYTH1 | 1.00000 | 0 |
| 1136 | chr17 | 80928000 | 80929000 | 0.000 | 0.000 | B3GNTL1 | 1.00000 | 0 |
| 1137 | chr17 | 80976000 | 80977000 | 0.000 | 0.040 | B3GNTL1 | 1.00000 | 0 |
| 1138 | chr18 | 2709000 | 2710000 | 0.000 | 0.000 | SMCHD1 | 1.00000 | 0 |
| 1139 | chr18 | 3600000 | 3601000 | 0.040 | 0.000 | DLGAP1 | 1.00000 | 0 |
| 1140 | chr18 | 12062000 | 12,063000 | 0.000 | 0.000 | ANKRD62 | 1.00000 | 0 |
| 1141 | chr18 | 27771000 | 27772000 | 0.040 | 0.000 | DSC3 | 1.00000 | 0 |
| 1142 | chr18 | 28066000 | 28067000 | 0.000 | 0.040 | DSC3 | 1.00000 | 0 |
| 1143 | chr18 | 30349000 | 30350000 | 0.000 | 0.000 | AC012123.1; KLHL14; | 1.00000 | 0 |
| 1144 | chr18 | 36806000 | 36807000 | 0.040 | 0.000 | CELF4 | 1.00000 | 0 |
| 1145 | chr18 | 37751000 | 37752000 | 0.000 | 0.040 | PIK3C3 | 1.00000 | 0 |
| 1146 | chr18 | 38672000 | 38673000 | 0.000 | 0.040 | PIK3C3 | 1.00000 | 0 |
| 1147 | chr18 | 42168000 | 42169000 | 0.000 | 0.000 | SETBP1 | 1.00000 | 0 |
| 1148 | chr18 | 51952000 | 51953000 | 0.040 | 0.000 | C18orf54 | 1.00000 | 0 |
| 1149 | chr18 | 52447000 | 52448000 | 0.000 | 0.080 | RAB27B | 0.48980 | 0 |
| 1150 | chr18 | 52988000 | 52989000 | 0.040 | 0.000 | TCF4 | 1.00000 | 0 |
| 1151 | chr18 | 54653000 | 54654000 | 0.000 | 0.000 | WDR7 | 1.00000 | 0 |
| 1152 | chr18 | 60794000 | 60795000 | 0.000 | 0.080 | BCL2 | 0.48980 | 1 |
| 1153 | chr18 | 60805000 | 60806000 | 0.000 | 0.000 | BCL2 | 1.00000 | 1 |
| 1154 | chr18 | 60806000 | 60807000 | 0.000 | 0.120 | BCL2 | 0.23469 | 1 |
| 1155 | chr18 | 60809000 | 60810000 | 0.000 | 0.080 | BCL2 | 0.48980 | 1 |
| 1156 | chr18 | 60821000 | 60822000 | 0.000 | 0.040 | BCL2 | 1.00000 | 1 |
| 1157 | chr18 | 60825000 | 60826000 | 0.000 | 0.080 | BCL2 | 0.48980 | 1 |
| 1158 | chr18 | 60826000 | 60827000 | 0.000 | 0.040 | BCL2 | 1.00000 | 1 |
| 1159 | chr18 | 60828000 | 60829000 | 0.000 | 0.000 | BCL2 | 1.00000 | 1 |
| 1160 | chr18 | 60873000 | 60874000 | 0.000 | 0.040 | BCL2 | 1.00000 | 1 |
| 1161 | chr18 | 60875000 | 60876000 | 0.000 | 0.000 | BCL2 | 1.00000 | 1 |
| 1162 | chr18 | 60876000 | 60877000 | 0.000 | 0.040 | BCL2 | 1.00000 | 1 |
| 1163 | chr18 | 60983000 | 60984000 | 0.000 | 0.040 | BCL2 | 1.00000 | 1 |
| 1164 | chr18 | 60984000 | 60985000 | 0.000 | 0.240 | BCL2 | 0.02229 | 1 |
| 1165 | chr18 | 60985000 | 60986000 | 0.040 | 0.320 | BCL2 | 0.02322 | 1 |
| 1166 | chr18 | 60986000 | 60987000 | 0.080 | 0.320 | BCL2 | 0.07375 | 1 |
| 1167 | chr18 | 60987000 | 60988000 | 0.080 | 0.320 | BCL2 | 0.07375 | 1 |
| 1168 | chr18 | 60988000 | 60989000 | 0.080 | 0.280 | BCL2 | 0.13833 | 1 |
| 1169 | chr18 | 61810000 | 61811000 | 0.040 | 0.000 | SERPINB8 | 1.00000 | 0 |
| 1170 | chr18 | 63080000 | 63081000 | 0.000 | 0.000 | CDH7 | 1.00000 | 0 |
| 1171 | chr18 | 63791000 | 63792000 | 0.000 | 0.000 | CDH7 | 1.00000 | 0 |
| 1172 | chr18 | 63875000 | 63876000 | 0.040 | 0.000 | CDH19 | 1.00000 | 0 |
| 1173 | chr18 | 64643000 | 64644000 | 0.000 | 0.000 | CDH19 | 1.00000 | 0 |
| 1174 | chr18 | 65863000 | 65864000 | 0.000 | 0.000 | TMX3 | 1.00000 | 0 |
| 1175 | chr18 | 66328000 | 66329000 | 0.040 | 0.000 | TMX3 | 1.00000 | 0 |
| 1176 | chr18 | 70462000 | 70463000 | 0.000 | 0.040 | NETO1 | 1.00000 | 0 |
| 1177 | chr18 | 73767000 | 73768000 | 0.040 | 0.000 | ZNF516 | 1.00000 | 0 |
| 1178 | chr18 | 76515000 | 76516000 | 0.040 | 0.000 | SALL3 | 1.00000 | 0 |
| 1179 | chr18 | 76724000 | 76725000 | 0.040 | 0.000 | SALL3 | 1.00000 | 0 |
| 1180 | chr18 | 76725000 | 76726000 | 0.040 | 0.000 | SALL3 | 1.00000 | 0 |
| 1181 | chr19 | 1612000 | 1613000 | 0.000 | 0.040 | TCF3 | 1.00000 | 0 |
| 1182 | chr19 | 2476000 | 2477000 | 0.040 | 0.040 | GADD45B | 1.00000 | 1 |
| 1183 | chr19 | 10304000 | 10305000 | 0.040 | 0.080 | DNMT1 | 1.00000 | 0 |
| 1184 | chr19 | 10305000 | 10306000 | 0.000 | 0.080 | DNMT1 | 0.48980 | 0 |
| 1185 | chr19 | 10335000 | 10336000 | 0.000 | 0.040 | S1PR2 | 1.00000 | 1 |
| 1186 | chr19 | 10340000 | 10341000 | 0.080 | 0.160 | S1PR2 | 0.66710 | 1 |
| 1187 | chr19 | 10341000 | 10342000 | 0.120 | 0.280 | S1PR2 | 0.28902 | 1 |
| 1188 | chr19 | 16030000 | 16031000 | 0.000 | 0.000 | CYP4F11 | 1.00000 | 0 |
| 1189 | chr19 | 16436000 | 16437000 | 0.040 | 0.000 | KLF2 | 1.00000 | 1 |
| 1190 | chr19 | 20889000 | 20890000 | 0.000 | 0.040 | ZNF626 | 1.00000 | 0 |
| 1191 | chr19 | 21073000 | 21074000 | 0.040 | 0.000 | ZNF85 | 1.00000 | 0 |
| 1192 | chr19 | 21092000 | 21093000 | 0.000 | 0.040 | ZNF85 | 1.00000 | 0 |
| 1193 | chr19 | 23841000 | 23842000 | 0.040 | 0.000 | ZNF675 | 1.00000 | 0 |
| 1194 | chr19 | 29256000 | 29257000 | 0.040 | 0.000 | UQCRFS1 | 1.00000 | 0 |
| 1195 | chr19 | 44183000 | 44184000 | 0.040 | 0.000 | PLAUR | 1.00000 | 0 |
| 1196 | chr19 | 50399000 | 50400000 | 0.040 | 0.040 | IL4I1 | 1.00000 | 0 |
| 1197 | chr19 | 53419000 | 53420000 | 0.000 | 0.000 | ZNF321P; ZNF86; 1ZNF816-ZNF321PZNF321PZNF816-ZNF321P; | 1.00000 | 0 |
| 1198 | chr20 | 15470000 | 15471000 | 0.000 | 0.040 | MACROD2 | 1.00000 | 0 |
| 1199 | chr20 | 23359000 | 23360000 | 0.000 | 0.000 | NAPB | 1.00000 | 0 |
| 1200 | chr20 | 23912000 | 23913000 | 0.000 | 0.000 | CST5 | 1.00000 | 0 |
| 1201 | chr20 | 46131000 | 46132000 | 0.040 | 0.120 | NCOA3 | 0.60921 | 1 |
| 1202 | chr20 | 49127000 | 49128000 | 0.000 | 0.000 | PTPN1 | 1.00000 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 1203 | chr20 | 49648000 | 49649000 | 0.040 | 0.000 | KCNG1 | 1.00000 | 0 |
| 1204 | chr20 | 61607000 | 61608000 | 0.000 | 0.000 | SLC17A9 | 1.00000 | 0 |
| 1205 | chr21 | 21597000 | 21598000 | 0.000 | 0.000 | NCAM2 | 1.00000 | 0 |
| 1206 | chr21 | 23458000 | 23459000 | 0.000 | 0.040 | NCAM2 | 1.00000 | 0 |
| 1207 | chr21 | 24998000 | 24999000 | 0.000 | 0.040 | MRPL39 | 1.00000 | 0 |
| 1208 | chr21 | 26935000 | 26936000 | 0.000 | 0.080 | MRPL39 | 0.48980 | 0 |
| 1209 | chr21 | 35779000 | 35780000 | 0.000 | 0.000 | SMIM11 | 1.00000 | 0 |
| 1210 | chr21 | 38779000 | 38780000 | 0.000 | 0.000 | DYRK1A | 1.00000 | 0 |
| 1211 | chr21 | 43254000 | 43255000 | 0.000 | 0.040 | PRDM15 | 1.00000 | 0 |
| 1212 | chr21 | 44612000 | 44613000 | 0.000 | 0.000 | CRYAA | 1.00000 | 0 |
| 1213 | chr21 | 45381000 | 45382000 | 0.040 | 0.000 | AGPAT3 | 1.00000 | 0 |
| 1214 | chr21 | 46058000 | 46059000 | 0.000 | 0.000 | KRTAP10-10 | 1.00000 | 0 |
| 1215 | chr22 | 19050000 | 19051000 | 0.000 | 0.000 | DGCR2 | 1.00000 | 0 |
| 1216 | chr22 | 20212000 | 20213000 | 0.040 | 0.000 | RTN4R | 1.00000 | 0 |
| 1217 | chr22 | 20708000 | 20709000 | 0.040 | 0.040 | FAM230A | 1.00000 | 0 |
| 1218 | chr22 | 21994000 | 21995000 | 0.000 | 0.000 | SDF2L1 | 1.00000 | 0 |
| 1219 | chr22 | 22379000 | 22380000 | 0.040 | 0.040 | IGLV4-69 | 1.00000 | 0 |
| 1220 | chr22 | 22380000 | 22381000 | 0.040 | 0.080 | IGLV4-69 | 1.00000 | 0 |
| 1221 | chr22 | 22381000 | 22382000 | 0.040 | 0.040 | IGLV4-69 | 1.00000 | 0 |
| 1222 | chr22 | 22385000 | 22386000 | 0.040 | 0.080 | IGLV4-69 | 1.00000 | 0 |
| 1223 | chr22 | 22452000 | 22453000 | 0.000 | 0.040 | IGLV8-61 | 1.00000 | 0 |
| 1224 | chr22 | 22453000 | 22454000 | 0.000 | 0.040 | IGLV8-61 | 1.00000 | 0 |
| 1225 | chr22 | 22516000 | 22517000 | 0.000 | 0.160 | IGLV4-60 | 0.10986 | 0 |
| 1226 | chr22 | 22517000 | 22518000 | 0.000 | 0.080 | IGLV4-60 | 0.48980 | 0 |
| 1227 | chr22 | 22550000 | 22551000 | 0.160 | 0.000 | IGLV6-57 | 0.10986 | 0 |
| 1228 | chr22 | 22569000 | 22570000 | 0.040 | 0.000 | IGLV10-54 | 1.00000 | 0 |
| 1229 | chr22 | 22676000 | 22677000 | 0.040 | 0.000 | IGLV1-51 | 1.00000 | 0 |
| 1230 | chr22 | 22677000 | 22678000 | 0.040 | 0.000 | IGLV1-51 | 1.00000 | 0 |
| 1231 | chr22 | 22707000 | 22708000 | 0.040 | 0.080 | IGLV5-48 | 1.00000 | 0 |
| 1232 | chr22 | 22712000 | 22713000 | 0.160 | 0.040 | IGLV1-47 | 0.34868 | 0 |
| 1233 | chr22 | 22723000 | 22724000 | 0.000 | 0.000 | IGLV7-46 | 1.00000 | 0 |
| 1234 | chr22 | 22724000 | 22725000 | 0.080 | 0.040 | IGLV7-46 | 1.00000 | 0 |
| 1235 | chr22 | 22730000 | 22731000 | 0.040 | 0.040 | IGLV5-45 | 1.00000 | 0 |
| 1236 | chr22 | 22731000 | 22732000 | 0.000 | 0.000 | IGLV5-45 | 1.00000 | 0 |
| 1237 | chr22 | 22735000 | 22736000 | 0.080 | 0.120 | IGLV1-44 | 1.00000 | 0 |
| 1238 | chr22 | 22749000 | 22750000 | 0.120 | 0.040 | IGLV7-43 | 0.60921 | 0 |
| 1239 | chr22 | 22758000 | 22759000 | 0.080 | 0.040 | IGLV1-40 | 1.00000 | 0 |
| 1240 | chr22 | 22759000 | 22760000 | 0.080 | 0.080 | IGLV1-40 | 1.00000 | 0 |
| 1241 | chr22 | 22764000 | 22765000 | 0.120 | 0.080 | IGLV1-40 | 1.00000 | 0 |
| 1242 | chr22 | 23028000 | 23029000 | 0.000 | 0.040 | IGLV3-25 | 1.00000 | 0 |
| 1243 | chr22 | 23029000 | 23030000 | 0.040 | 0.120 | IGLV3-25 | 0.60921 | 0 |
| 1244 | chr22 | 23035000 | 23036000 | 0.000 | 0.040 | IGLV2-23 | 1.00000 | 0 |
| 1245 | chr22 | 23039000 | 23040000 | 0.000 | 0.000 | IGLV2-23 | 1.00000 | 0 |
| 1246 | chr22 | 23040000 | 23041000 | 0.120 | 0.040 | IGLV2-23 | 0.60921 | 0 |
| 1247 | chr22 | 23041000 | 23042000 | 0.040 | 0.000 | IGLV2-23 | 1.00000 | 0 |
| 1248 | chr22 | 23055000 | 23056000 | 0.040 | 0.000 | IGLV3-21 | 1.00000 | 0 |
| 1249 | chr22 | 23063000 | 23064000 | 0.040 | 0.000 | IGLV3-19 | 1.00000 | 0 |
| 1250 | chr22 | 23090000 | 23091000 | 0.120 | 0.000 | IGLV3-16 | 0.23469 | 0 |
| 1251 | chr22 | 23100000 | 23101000 | 0.040 | 0.000 | IGLV2-14 | 1.00000 | 0 |
| 1252 | chr22 | 23101000 | 23102000 | 0.120 | 0.040 | IGLV2-14 | 0.60921 | 0 |
| 1253 | chr22 | 23114000 | 23115000 | 0.000 | 0.000 | IGLV3-12 | 1.00000 | 0 |
| 1254 | chr22 | 23134000 | 23135000 | 0.000 | 0.000 | IGLV2-11 | 1.00000 | 0 |
| 1255 | chr22 | 23154000 | 23155000 | 0.120 | 0.000 | IGLV3-10 | 0.23469 | 0 |
| 1256 | chr22 | 23161000 | 23162000 | 0.000 | 0.000 | IGLV3-9 | 1.00000 | 0 |
| 1257 | chr22 | 23162000 | 23163000 | 0.000 | 0.000 | IGLV3-9 | 1.00000 | 0 |
| 1258 | chr22 | 23165000 | 23166000 | 0.000 | 0.000 | IGLV2-8 | 1.00000 | 0 |
| 1259 | chr22 | 23192000 | 23193000 | 0.080 | 0.080 | IGLV4-3 | 1.00000 | 0 |
| 1260 | chr22 | 23197000 | 23198000 | 0.040 | 0.000 | IGLV4-3 | 1.00000 | 0 |
| 1261 | chr22 | 23198000 | 23199000 | 0.160 | 0.040 | IGLV4-3 | 0.34868 | 0 |
| 1262 | chr22 | 23199000 | 23200000 | 0.200 | 0.200 | IGLV4-3 | 1.00000 | 0 |
| 1263 | chr22 | 23203000 | 23204000 | 0.000 | 0.000 | IGLV4-3 | 1.00000 | 0 |
| 1264 | chr22 | 23204000 | 23205000 | 0.080 | 0.000 | IGLV4-3 | 0.48980 | 0 |
| 1265 | chr22 | 23205000 | 23206000 | 0.000 | 0.000 | IGLV4-3 | 1.00000 | 0 |
| 1266 | chr22 | 23207000 | 23208000 | 0.000 | 0.040 | IGLV4-3 | 1.00000 | 0 |
| 1267 | chr22 | 23209000 | 23210000 | 0.000 | 0.040 | IGLV4-3 | 1.00000 | 0 |
| 1268 | chr22 | 23213000 | 23214000 | 0.120 | 0.040 | IGLV4-3 | 0.60921 | 0 |
| 1269 | chr22 | 23214000 | 23215000 | 0.040 | 0.040 | IGLV4-3 | 1.00000 | 0 |
| 1270 | chr22 | 23219000 | 23220000 | 0.080 | 0.000 | IGLV3-1 | 0.48980 | 0 |
| 1271 | chr22 | 23220000 | 23221000 | 0.080 | 0.000 | IGLV3-1 | 0.48980 | 0 |
| 1272 | chr22 | 23222000 | 23223000 | 0.040 | 0.120 | IGLV3-1 | 0.60921 | 0 |
| 1273 | chr22 | 23223000 | 23224000 | 0.320 | 0.520 | IGLV3-1 | 0.25159 | 0 |
| 1274 | chr22 | 23224000 | 23225000 | 0.080 | 0.080 | IGLV3-1 | 1.00000 | 0 |
| 1275 | chr22 | 23226000 | 23227000 | 0.120 | 0.000 | IGLV3-1 | 0.23469 | 0 |
| 1276 | chr22 | 23227000 | 23228000 | 0.200 | 0.360 | IGLL5 | 0.34513 | 0 |
| 1277 | chr22 | 23228000 | 23229000 | 0.240 | 0.200 | IGLL5 | 1.00000 | 0 |
| 1278 | chr22 | 23229000 | 23230000 | 0.040 | 0.160 | IGLL5 | 0.34868 | 0 |
| 1279 | chr22 | 23230000 | 23231000 | 0.440 | 0.600 | IGLL5 | 0.39610 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 1280 | chr22 | 23231000 | 23232000 | 0.480 | 0.440 | IGLL5 | 1.00000 | 0 |
| 1281 | chr22 | 23232000 | 23233000 | 0.320 | 0.240 | IGLL5 | 0.75361 | 0 |
| 1282 | chr22 | 23233000 | 23234000 | 0.200 | 0.040 | IGLJ1 | 0.18946 | 0 |
| 1283 | chr22 | 23234000 | 23235000 | 0.200 | 0.080 | IGLJ1 | 0.41743 | 0 |
| 1284 | chr22 | 23235000 | 23236000 | 0.320 | 0.080 | IGLJ1; IGLL5; | 0.07375 | 0 |
| 1285 | chr22 | 23236000 | 23237000 | 0.240 | 0.200 | IGLJ1; IGLL5; | 1.00000 | 0 |
| 1286 | chr22 | 23237000 | 23238000 | 0.040 | 0.160 | IGLC1; IGLL5; | 0.34868 | 0 |
| 1287 | chr22 | 23241000 | 23242000 | 0.040 | 0.040 | IGLJ2 | 1.00000 | 0 |
| 1288 | chr22 | 23242000 | 23243000 | 0.120 | 0.040 | IGLC2 | 0.60921 | 0 |
| 1289 | chr22 | 23243000 | 23244000 | 0.080 | 0.040 | IGLC2 | 1.00000 | 0 |
| 1290 | chr22 | 23244000 | 23245000 | 0.000 | 0.040 | IGLC2 | 1.00000 | 0 |
| 1291 | chr22 | 23247000 | 23248000 | 0.280 | 0.160 | IGLJ3 | 0.49620 | 0 |
| 1292 | chr22 | 23248000 | 23249000 | 0.040 | 0.000 | IGLC3 | 1.00000 | 0 |
| 1293 | chr22 | 23249000 | 23250000 | 0.040 | 0.000 | IGLC3 | 1.00000 | 0 |
| 1294 | chr22 | 23260000 | 23261000 | 0.000 | 0.000 | IGLJ6 | 1.00000 | 0 |
| 1295 | chr22 | 23261000 | 23262000 | 0.000 | 0.000 | IGLJ6 | 1.00000 | 0 |
| 1296 | chr22 | 23263000 | 23264000 | 0.000 | 0.040 | IGLJ7 | 1.00000 | 0 |
| 1297 | chr22 | 23264000 | 23265000 | 0.000 | 0.040 | IGLC7 | 1.00000 | 0 |
| 1298 | chr22 | 23273000 | 23274000 | 0.000 | 0.040 | IGLC7 | 1.00000 | 0 |
| 1299 | chr22 | 23277000 | 23278000 | 0.040 | 0.040 | IGLC7 | 1.00000 | 0 |
| 1300 | chr22 | 23278000 | 23279000 | 0.000 | 0.120 | IGLC7 | 0.23469 | 0 |
| 1301 | chr22 | 23281000 | 23282000 | 0.040 | 0.000 | IGLC7 | 1.00000 | 0 |
| 1302 | chr22 | 23282000 | 23283000 | 0.080 | 0.160 | IGLC7 | 0.66710 | 0 |
| 1303 | chr22 | 23284000 | 23285000 | 0.000 | 0.000 | IGLC7 | 1.00000 | 0 |
| 1304 | chr22 | 23523000 | 23524000 | 0.000 | 0.080 | BCR | 0.48980 | 0 |
| 1305 | chr22 | 23524000 | 23525000 | 0.000 | 0.000 | BCR | 1.00000 | 0 |
| 1306 | chr22 | 27236000 | 27237000 | 0.000 | 0.000 | CRYBA4 | 1.00000 | 0 |
| 1307 | chr22 | 29195000 | 29196000 | 0.040 | 0.040 | XBP1 | 1.00000 | 0 |
| 1308 | chr22 | 29196000 | 29197000 | 0.040 | 0.040 | XBP1 | 1.00000 | 0 |
| 1309 | chr22 | 31826000 | 31827000 | 0.040 | 0.000 | DRG1 | 1.00000 | 0 |
| 1310 | chr22 | 32982000 | 32983000 | 0.000 | 0.040 | SYN3 | 1.00000 | 0 |
| 1311 | chr22 | 39852000 | 39853000 | 0.040 | 0.000 | TAB1 | 1.00000 | 0 |
| 1312 | chr22 | 39854000 | 39855000 | 0.000 | 0.000 | TAB1 | 1.00000 | 0 |
| 1313 | chr22 | 43360000 | 43361000 | 0.000 | 0.000 | PACSIN2 | 1.00000 | 0 |
| 1314 | chr22 | 47186000 | 47187000 | 0.000 | 0.000 | TBC1D22A | 1.00000 | 0 |
| 1315 | chr22 | 47738000 | 47739000 | 0.000 | 0.000 | LL22NC03-75H12.2 | 1.00000 | 0 |
| 1316 | chr22 | 50336000 | 50337000 | 0.000 | 0.000 | CRELD2 | 1.00000 | 0 |
| 1317 | chrX | 228000 | 229000 | 0.000 | 0.000 | GTPBP6 | 1.00000 | 0 |
| 1318 | chrX | 1514000 | 1515000 | 0.000 | 0.040 | SLC25A6 | 1.00000 | 0 |
| 1319 | chrX | 1611000 | 1612000 | 0.040 | 0.040 | P2RY8 | 1.00000 | 1 |
| 1320 | chrX | 12993000 | 12994000 | 0.320 | 0.280 | TMSB4X | 1.00000 | 1 |
| 1321 | chrX | 12994000 | 12995000 | 0.200 | 0.160 | TMSB4X | 1.00000 | 1 |
| 1322 | chrX | 13419000 | 13420000 | 0.000 | 0.040 | ATXN3L | 1.00000 | 0 |
| 1323 | chrX | 27031000 | 27032000 | 0.080 | 0.040 | DCAF8L2 | 1.00000 | 0 |
| 1324 | chrX | 32315000 | 32316000 | 0.000 | 0.000 | DMD | 1.00000 | 1 |
| 1325 | chrX | 32317000 | 32318000 | 0.000 | 0.000 | DMD | 1.00000 | 1 |
| 1326 | chrX | 33144000 | 33145000 | 0.000 | 0.000 | DMD | 1.00000 | 1 |
| 1327 | chrX | 33145000 | 33146000 | 0.000 | 0.040 | DMD | 1.00000 | 1 |
| 1328 | chrX | 33146000 | 33147000 | 0.080 | 0.120 | DMD | 1.00000 | 1 |
| 1329 | chrX | 41366000 | 41367000 | 0.040 | 0.000 | CASK | 1.00000 | 0 |
| 1330 | chrX | 42802000 | 42803000 | 0.080 | 0.120 | MAOA | 1.00000 | 0 |
| 1331 | chrX | 48775000 | 48776000 | 0.120 | 0.040 | PIM2 | 0.60921 | 1 |
| 1332 | chrX | 48776000 | 48777000 | 0.080 | 0.000 | PIM2 | 0.48980 | 1 |
| 1333 | chrX | 64071000 | 64072000 | 0.120 | 0.080 | ZC4H2 | 1.00000 | 0 |
| 1334 | chrX | 67030000 | 67031000 | 0.000 | 0.000 | AR | 1.00000 | 0 |
| 1335 | chrX | 80258000 | 80259000 | 0.000 | 0.000 | HMGN5 | 1.00000 | 0 |
| 1336 | chrX | 81172000 | 81173000 | 0.040 | 0.000 | SH3BGRL | 1.00000 | 0 |
| 1337 | chrX | 87742000 | 87743000 | 0.040 | 0.000 | CPXCR1 | 1.00000 | 0 |
| 1338 | chrX | 87831000 | 87832000 | 0.000 | 0.000 | CPXCR1 | 1.00000 | 0 |
| 1339 | chrX | 88263000 | 88264000 | 0.000 | 0.000 | CPXCR1 | 1.00000 | 0 |
| 1340 | chrX | 88458000 | 88459000 | 0.040 | 0.000 | CPXCR1 | 1.00000 | 0 |
| 1341 | chrX | 92647000 | 92648000 | 0.000 | 0.000 | NAP1L3 | 1.00000 | 0 |
| 1342 | chrX | 93279000 | 93280000 | 0.040 | 0.000 | FAM133A | 1.00000 | 0 |
| 1343 | chrX | 94079000 | 94080000 | 0.040 | 0.000 | FAM133A | 1.00000 | 0 |
| 1344 | chrX | 104006000 | 104007000 | 0.040 | 0.000 | IL1RAPL2 | 1.00000 | 0 |
| 1345 | chrX | 104269000 | 104270000 | 0.040 | 0.000 | IL1RAPL2 | 1.00000 | 0 |
| 1346 | chrX | 106132000 | 106133000 | 0.000 | 0.000 | RIPPLY1 | 1.00000 | 0 |
| 1347 | chrX | 113095000 | 113096000 | 0.000 | 0.040 | HTR2C | 1.00000 | 0 |
| 1348 | chrX | 115676000 | 115677000 | 0.040 | 0.000 | CXorf61 | 1.00000 | 0 |
| 1349 | chrX | 124996000 | 124997000 | 0.000 | 0.000 | DCAF12L2 | 1.00000 | 0 |
| 1350 | chrX | 125708000 | 125709000 | 0.000 | 0.000 | DCAF12L1 | 1.00000 | 0 |
| 1351 | chrX | 128565000 | 128566000 | 0.040 | 0.040 | SMARCA1 | 1.00000 | 0 |

-continued

| # | Chromosome | Region Start | Region End | ABC-subtype | GCB-subtype | ClosestGene | p_ABC_vs_GCB | PreviouslyIdentified |
|---|---|---|---|---|---|---|---|---|
| 1352 | chrX | 129643000 | 129644000 | 0.000 | 0.040 | RBMX2 | 1.00000 | 0 |
| 1353 | chrX | 134903000 | 134904000 | 0.000 | 0.000 | CT45A3; CT45A4; | 1.00000 | 0 |
| 1354 | chrX | 140846000 | 140847000 | 0.040 | 0.000 | SPANXD; SPANXE; | 1.00000 | 0 |
| 1355 | chrX | 143750000 | 143751000 | 0.000 | 0.000 | SPANXN1 | 1.00000 | 0 |
| 1356 | chrX | 145016000 | 145017000 | 0.040 | 0.000 | TMEM257 | 1.00000 | 0 |

| # | Chromosome | Region Start | Region End | Closest Gene | Reason for Inclusion |
|---|---|---|---|---|---|
| 1 | chr1 | 2306311 | 2306832 | MORN1 | Genotyping |
| 2 | chr1 | 2334441 | 2334664 | RER1 | Genotyping |
| 3 | chr1 | 2334671 | 2335161 | RER1 | Genotyping |
| 4 | chr1 | 2488006 | 2488247 | TNFRSF14 | Phased Variants |
| 5 | chr1 | 2489111 | 2489330 | TNFRSF14 | Genotyping |
| 6 | chr1 | 2489726 | 2489973 | TNFRSF14 | Genotyping |
| 7 | chr1 | 2491206 | 2491455 | TNFRSF14 | Genotyping |
| 8 | chr1 | 2492036 | 2492175 | TNFRSF14 | Genotyping |
| 9 | chr1 | 2493051 | 2493333 | TNFRSF14 | Genotyping |
| 10 | chr1 | 2494241 | 2494376 | TNFRSF14 | Genotyping |
| 11 | chr1 | 2494556 | 2494745 | TNFRSF14 | Genotyping |
| 12 | chr1 | 3547350 | 3547715 | WRAP73 | Genotyping |
| 13 | chr1 | 3747620 | 3747798 | CEP104 | Genotyping |
| 14 | chr1 | 3800045 | 3800148 | DFFB | Genotyping |
| 15 | chr1 | 3800155 | 3800363 | DFFB | Genotyping |
| 16 | chr1 | 4472438 | 4472621 | AJAP1 | Genotyping |
| 17 | chr1 | 4476348 | 4476627 | AJAP1 | Genotyping |
| 18 | chr1 | 9784432 | 9784540 | PIK3CD | Genotyping |
| 19 | chr1 | 23885407 | 23885541 | ID3 | Genotyping |
| 20 | chr1 | 23885582 | 23885938 | ID3 | Genotyping |
| 21 | chr1 | 27059146 | 27059321 | ARID1A | Genotyping |
| 22 | chr1 | 27101071 | 27101294 | ARID1A | Genotyping |
| 23 | chr1 | 27101401 | 27101613 | AMD1A | Genotyping |
| 24 | chr1 | 27105466 | 27105671 | AMD1A | Genotyping |
| 25 | chr1 | 27106311 | 27106523 | ARID1A | Genotyping |
| 26 | chr1 | 27106711 | 27106920 | ARID1A | Genotyping |
| 27 | chr1 | 29069531 | 29070185 | YTHDF2 | Genotyping |
| 28 | chr1 | 34404022 | 34404171 | CSMD2 | Phased Variants |
| 29 | chr1 | 35472492 | 35472739 | ZMYM6 | Genotyping |
| 30 | chr1 | 61553802 | 61554330 | NFIA | Genotyping |
| 31 | chr1 | 72334891 | 72335045 | NEGR1 | Phased Variants |
| 32 | chr1 | 72335051 | 72335120 | NEGR1 | Phased Variants |
| 33 | chr1 | 85733207 | 85733640 | BCL10 | Phased Variants |
| 34 | chr1 | 85736272 | 85736619 | BCL10 | Genotyping |
| 35 | chr1 | 85741932 | 85742068 | BCL10 | Genotyping |
| 36 | chr1 | 86591437 | 86591909 | COL24A1 | Genotyping |
| 37 | chr1 | 107866871 | 107867579 | NTNG1 | Genotyping |
| 38 | chr1 | 109649126 | 109649304 | C1orf194 | Genotyping |
| 39 | chr1 | 109822181 | 109822805 | PSRC1 | Genotyping |
| 40 | chr1 | 110561141 | 110561757 | ARCYL1 | Genotyping |
| 41 | chr1 | 111441722 | 111442219 | CD53 | Genotyping |
| 42 | chr1 | 111715727 | 111715908 | CEPT1 | Genotyping |
| 43 | chr1 | 117078642 | 117078856 | CD58 | Genotyping |
| 44 | chr1 | 117086927 | 117087172 | CD58 | Genotyping |
| 45 | chr1 | 120457960 | 120459297 | NOTCH2 | Genotyping |
| 46 | chr1 | 160319283 | 160319532 | NCSTN | Genotyping |
| 47 | chr1 | 181452914 | 181453131 | CACNA1E | Genotyping |
| 48 | chr1 | 185833555 | 185833832 | HMCN1 | Genotyping |
| 49 | chr1 | 185972790 | 185973006 | HMCN1 | Genotyping |
| 50 | chr1 | 186062580 | 186062797 | HMCN1 | Genotyping |
| 51 | chr1 | 186083050 | 186083301 | HMCN1 | Genotyping |
| 52 | chr1 | 186143590 | 186143828 | HMCN1 | Genotyping |
| 53 | chr1 | 186158895 | 186159102 | HMCN1 | Genotyping |
| 54 | chr1 | 190067139 | 190068194 | FAM5C | Genotyping |
| 55 | chr1 | 201038552 | 201038756 | CACNA1S | Genotyping |
| 56 | chr1 | 203274697 | 203275926 | BTG2 | Phased Variants |
| 57 | chr1 | 203276207 | 203276586 | BTG2 | Genotyping |
| 58 | chr1 | 226923691 | 226925200 | ITPKB | Phased Variants |
| 59 | chr1 | 227842646 | 227842718 | ZNF678 | Genotyping |
| 60 | chr2 | 1652010 | 1652858 | PXDN | Genotyping |
| 61 | chr2 | 48027958 | 48028159 | MSH6 | Genotyping |
| 62 | chr2 | 48059883 | 48060051 | FBXO11 | Genotyping |
| 63 | chr2 | 48065973 | 48066184 | FBXO11 | Genotyping |
| 64 | chr2 | 55237198 | 55237610 | RTN4 | Genotyping |

-continued

| # | Chromosome | Region Start | Region End | Closest Gene | Reason for Inclusion |
|---|---|---|---|---|---|
| 65 | chr2 | 56149510 | 56150116 | EFEMP1 | Genotyping |
| 66 | chr2 | 58520800 | 58521222 | FANCL | Genotyping |
| 67 | chr2 | 59821914 | 59822083 | BCL11A | Genotyping |
| 68 | chr2 | 60773084 | 60773479 | BCL11A | Genotyping |
| 69 | chr2 | 61118794 | 61118998 | REL | Genotyping |
| 70 | chr2 | 61145504 | 61145785 | REL | Genotyping |
| 71 | chr2 | 61148869 | 61149644 | REL | Genotyping |
| 72 | chr2 | 61441169 | 61441870 | USP34 | Genotyping |
| 73 | chr2 | 61719434 | 61719642 | XPO1 | Genotyping |
| 74 | chr2 | 62934009 | 62934460 | EHBP1 | Genotyping |
| 75 | chr2 | 63217829 | 63218002 | EHBP1 | Genotyping |
| 76 | chr2 | 63335242 | 63335600 | WDPCP | Genotyping |
| 77 | chr2 | 63631157 | 63631817 | WDPCP | Genotyping |
| 78 | chr2 | 63826277 | 63826429 | MDH1 | Genotyping |
| 79 | chr2 | 65258145 | 65258367 | SLC1A4 | Phased Variants |
| 80 | chr2 | 65593035 | 65593153 | SPRED2 | Phased Variants |
| 81 | chr2 | 65593180 | 65593250 | SPRED2 | Phased Variants |
| 82 | chr2 | 77746602 | 77746988 | LRRTM4 | Genotyping |
| 83 | chr2 | 80801235 | 80801513 | CTNNA2 | Genotyping |
| 84 | chr2 | 88906681 | 88906861 | EIF2AK3 | Phased Variants |
| 85 | chr2 | 89127261 | 89127335 | IGKC | Phased Variants |
| 86 | chr2 | 89127461 | 89127946 | IGKC | Phased Variants |
| 87 | chr2 | 89128431 | 89128574 | IGKC | Phased Variants |
| 88 | chr2 | 89131726 | 89132295 | IGKC | Phased Variants |
| 89 | chr2 | 89140556 | 89140755 | IGKC | Phased Variants |
| 90 | chr2 | 89140886 | 89141350 | IGKC | Phased Variants |
| 91 | chr2 | 89157326 | 89157609 | IGKC | Phased Variants |
| 92 | chr2 | 89157626 | 89158011 | IGKC | Phased Variants |
| 93 | chr2 | 89158036 | 89158938 | IGKC | Phased Variants |
| 94 | chr2 | 89158941 | 89159493 | IGKJ5 | Phased Variants |
| 95 | chr2 | 89159511 | 89161445 | IGKJ1 | Phased Variants |
| 96 | chr2 | 89161926 | 89162149 | IGKJ1 | Phased Variants |
| 97 | chr2 | 89162776 | 89163285 | IGKJ1 | Phased Variants |
| 98 | chr2 | 89163306 | 89163837 | IGKJ1 | Phased Variants |
| 99 | chr2 | 89163861 | 89164838 | IGKJ1 | Phased Variants |
| 100 | chr2 | 89164866 | 89165181 | IGKJ1 | Phased Variants |
| 101 | chr2 | 89165191 | 89165644 | IGKJ1 | Phased Variants |
| 102 | chr2 | 89184966 | 89185186 | IGKV4-1 | Phased Variants |
| 103 | chr2 | 89185196 | 89185704 | IGKV4-1 | Phased Variants |
| 104 | chr2 | 89196226 | 89196411 | IGKV5-2 | Phased Variants |
| 105 | chr2 | 89196851 | 89197324 | IGKV5-2 | Phased Variants |
| 106 | chr2 | 89214836 | 89215040 | IGKV5-2 | Phased Variants |
| 107 | chr2 | 89246681 | 89246772 | IGKVG5 | Phased Variants |
| 108 | chr2 | 89246786 | 89246857 | IGKV1-5 | Phased Variants |
| 109 | chr2 | 89246911 | 89247053 | IGKV1-5 | Phased Variants |
| 110 | chr2 | 89247096 | 89247215 | IGKV1-5 | Phased Variants |
| 111 | chr2 | 89247526 | 89247628 | IGKV1-5 | Phased Variants |
| 112 | chr2 | 89247641 | 89247735 | IGKV1-5 | Phased Variants |
| 113 | chr2 | 89247831 | 89248010 | IGKV1-5 | Phased Variants |
| 114 | chr2 | 89265756 | 89265829 | IGKV1-6 | Genotyping |
| 115 | chr2 | 89265936 | 89266013 | IGKV1-6 | Genotyping |
| 116 | chr2 | 89291906 | 89291981 | IGKV1-8 | Phased Variants |
| 117 | chr2 | 89292131 | 89292217 | IGKV1-8 | Phased Variants |
| 118 | chr2 | 89442291 | 89442561 | IGKV3-20 | Phased Variants |
| 119 | chr2 | 89442616 | 89443259 | IGKV3-20 | Phased Variants |
| 120 | chr2 | 89475781 | 89476009 | IGKV2-24 | Genotyping |
| 121 | chr2 | 89476041 | 89476122 | IGKV2-24 | Genotyping |
| 122 | chr2 | 89544331 | 89544608 | IGKV2-30 | Genotyping |
| 123 | chr2 | 89544656 | 89544899 | IGKV2-30 | Phased Variants |
| 124 | chr2 | 89976276 | 89976426 | IGKV2D-30 | Genotyping |
| 125 | chr2 | 89986776 | 89987023 | IGKV2D-29 | Genotyping |
| 126 | chr2 | 89987031 | 89987108 | IGKV2D-29 | Genotyping |
| 127 | chr2 | 90025206 | 90025289 | IGKV2D-26 | Genotyping |
| 128 | chr2 | 90025296 | 90025378 | IGKV2D-26 | Genotyping |
| 129 | chr2 | 90025471 | 90025554 | IGKV2D-26 | Genotyping |
| 130 | chr2 | 90077981 | 90078054 | IGKV3D-20 | Genotyping |
| 131 | chr2 | 90078136 | 90078222 | IGKV3D-20 | Genotyping |
| 132 | chr2 | 90078251 | 90078335 | IGKV3D-20 | Genotyping |
| 133 | chr2 | 90121891 | 90122008 | IGKVID-17 | Genotyping |
| 134 | chr2 | 90122021 | 90122157 | IGKVID-17 | Genotyping |
| 135 | chr2 | 90212016 | 90212093 | IGKV3D-11 | Genotyping |
| 136 | chr2 | 90212196 | 90212278 | IGKV3D-11 | Genotyping |
| 137 | chr2 | 90249151 | 90249275 | IGKV1D-43 | Genotyping |
| 138 | chr2 | 90249346 | 90249419 | IGKV1D-43 | Genotyping |
| 139 | chr2 | 90259931 | 90260059 | IGKV1D-8 | Genotyping |
| 140 | chr2 | 90260181 | 90260258 | IGKV1D-8 | Genotyping |
| 141 | chr2 | 96809889 | 96810144 | DUSP2 | Genotyping |

-continued

| # | Chromosome | Region Start | Region End | Closest Gene | Reason for Inclusion |
|---|---|---|---|---|---|
| 142 | chr2 | 96810164 | 96810374 | DUSP2 | Phased Variants |
| 143 | chr2 | 100758483 | 100758660 | AFF3 | Phased Variants |
| 144 | chr2 | 103148733 | 103148948 | SLC9A4 | Genotyping |
| 145 | chr2 | 117951919 | 117952057 | DDX18 | Phased Variants |
| 146 | chr2 | 136872525 | 136872740 | CXCR4 | Genotyping |
| 147 | chr2 | 136874415 | 136874797 | CXCR4 | Phased Variants |
| 148 | chr2 | 136874920 | 136875662 | CXCR4 | Phased Variants |
| 149 | chr2 | 141245127 | 141245373 | LRP1B | Genotyping |
| 150 | chr2 | 145162401 | 145162624 | ZEB2 | Genotyping |
| 151 | chr2 | 145187091 | 145187638 | ZEB2 | Genotyping |
| 152 | chr2 | 145270956 | 145271394 | ZEB2 | Genotyping |
| 153 | chr2 | 145275631 | 145275744 | ZEB2 | Genotyping |
| 154 | chr2 | 145275756 | 145276174 | ZEB2 | Genotyping |
| 155 | chr2 | 145278026 | 145278305 | ZEB2 | Genotyping |
| 156 | chr2 | 145278311 | 145278659 | ZEB2 | Genotyping |
| 157 | chr2 | 145692901 | 145693081 | ZEB2 | Genotyping |
| 158 | chr2 | 148680516 | 148680692 | ACVR2A | Genotyping |
| 159 | chr2 | 169781120 | 169781352 | ABCB11 | Genotyping |
| 160 | chr2 | 170101185 | 170101401 | LRP2 | Genotyping |
| 161 | chr2 | 198950434 | 198951003 | PLCL1 | Genotyping |
| 162 | chr2 | 242793232 | 242793447 | PDCD1 | Genotyping |
| 163 | chr2 | 242794037 | 242794192 | PDCD1 | Genotyping |
| 164 | chr2 | 242794317 | 242794537 | PDCD1 | Genotyping |
| 165 | chr2 | 242794822 | 242795040 | PDCD1 | Genotyping |
| 166 | chr2 | 242800887 | 242801093 | PDCD1 | Genotyping |
| 167 | chr3 | 7620223 | 7620990 | GRM7 | Genotyping |
| 168 | chr3 | 16419204 | 16419479 | RFTN1 | Phased Variants |
| 169 | chr3 | 38180129 | 38180549 | MYD88 | Genotyping |
| 170 | chr3 | 38181334 | 38181509 | MYD88 | Genotyping |
| 171 | chr3 | 38181854 | 38182099 | MYD88 | Genotyping |
| 172 | chr3 | 38182194 | 38182407 | MYD88 | Genotyping |
| 173 | chr3 | 38182554 | 38182844 | MYD88 | Genotyping |
| 174 | chr3 | 49397608 | 49397717 | RHOA | Genotyping |
| 175 | chr3 | 49397718 | 49397827 | RHOA | Genotyping |
| 176 | chr3 | 49399903 | 49400084 | RHOA | Genotyping |
| 177 | chr3 | 49405833 | 49406013 | RHOA | Genotyping |
| 178 | chr3 | 49412838 | 49413046 | RHOA | Genotyping |
| 179 | chr3 | 64547204 | 64547477 | ADAMTS9 | Genotyping |
| 180 | chr3 | 64579889 | 64580094 | ADAMTS9 | Genotyping |
| 181 | chr3 | 71551101 | 71551497 | EIF4E3 | Phased Variants |
| 182 | chr3 | 140281598 | 140281875 | CLSTN2 | Genotyping |
| 183 | chr3 | 164730700 | 164730888 | SI | Genotyping |
| 184 | chr3 | 165548198 | 165548680 | BCHE | Genotyping |
| 185 | chr3 | 176750699 | 176750928 | TBLIXR1 | Genotyping |
| 186 | chr3 | 176767759 | 176767977 | TBLIXR1 | Genotyping |
| 187 | chr3 | 176769304 | 176769543 | TBLIXR1 | Genotyping |
| 188 | chr3 | 176771659 | 176771732 | TBLIXR1 | Genotyping |
| 189 | chr3 | 183209758 | 183209937 | KLHL6 | Genotyping |
| 190 | chr3 | 183210258 | 183210544 | KLHL6 | Genotyping |
| 191 | chr3 | 183272308 | 183272521 | KLHL6 | Phased Variants |
| 192 | chr3 | 183273063 | 183273456 | KLHL6 | Phased Variants |
| 193 | chr3 | 184580663 | 184580872 | VPS8 | Genotyping |
| 194 | chr3 | 185146278 | 185146873 | MAP3K13 | Genotyping |
| 195 | chr3 | 185197923 | 185198317 | MAP3K13 | Genotyping |
| 196 | chr3 | 185236908 | 185237109 | LIPH | Genotyping |
| 197 | chr3 | 185446223 | 185446389 | C3orf65 | Genotyping |
| 198 | chr3 | 185538773 | 185538951 | IGF2BP2 | Genotyping |
| 199 | chr3 | 185697423 | 185697669 | TRA2B | Genotyping |
| 200 | chr3 | 186714604 | 186715001 | ST6GAL1 | Phased Variants |
| 201 | chr3 | 186782529 | 186782790 | ST6GAL1 | Phased Variants |
| 202 | chr3 | 186783389 | 186784291 | ST6GAL1 | Phased Variants |
| 203 | chr3 | 187440189 | 187440445 | BCL6 | Genotyping |
| 204 | chr3 | 187442669 | 187442920 | BCL6 | Genotyping |
| 205 | chr3 | 187443239 | 187443438 | BCL6 | Genotyping |
| 206 | chr3 | 187446814 | 187447831 | BCL6 | Genotyping |
| 207 | chr3 | 187449434 | 187449655 | BCL6 | Genotyping |
| 208 | chr3 | 187451284 | 187451667 | BCL6 | Genotyping |
| 209 | chr3 | 187460134 | 187460530 | BCL6 | Phased Variants |
| 210 | chr3 | 187460824 | 187461302 | BCL6 | Phased Variants |
| 211 | chr3 | 187461319 | 187461381 | BCL6 | Phased Variants |
| 212 | chr3 | 187461454 | 187461918 | BCL6 | Phased Variants |
| 213 | chr3 | 187461924 | 187462343 | BCL6 | Phased Variants |
| 214 | chr3 | 187462374 | 187462887 | BCL6 | Phased Variants |
| 215 | chr3 | 187462924 | 187462999 | BCL6 | Phased Variants |
| 216 | chr3 | 187463004 | 187463525 | BCL6 | Phased Variants |
| 217 | chr3 | 187463709 | 187463781 | BCL6 | Phased Variants |
| 218 | chr3 | 187463794 | 187464109 | BCL6 | Phased Variants |

-continued

| # | Chromosome | Region Start | Region End | Closest Gene | Reason for Inclusion |
|---|---|---|---|---|---|
| 219 | chr3 | 187619334 | 187619708 | BCL6 | Phased Variants |
| 220 | chr3 | 187660817 | 187661390 | BCL6 | Phased Variants |
| 221 | chr3 | 187957432 | 187957507 | AC022498.1 | Phased Variants |
| 222 | chr3 | 187957512 | 187957754 | AC022498.1 | Phased Variants |
| 223 | chr3 | 187957767 | 187958110 | AC022498.1 | Phased Variants |
| 224 | chr3 | 187958282 | 187958675 | AC022498.1 | Phased Variants |
| 225 | chr3 | 187958787 | 187959184 | AC022498.1 | Phased Variants |
| 226 | chr3 | 187959462 | 187959686 | AC022498.1 | Phased Variants |
| 227 | chr3 | 188299217 | 188299605 | LPP | Phased Variants |
| 228 | chr3 | 188471412 | 188471549 | LPP | Phased Variants |
| 229 | chr3 | 188471567 | 188471937 | LPP | Phased Variants |
| 230 | chr4 | 7728456 | 7728661 | SORCS2 | Genotyping |
| 231 | chr4 | 40198810 | 40199653 | N4BP2 | Phased Variants |
| 232 | chr4 | 40199660 | 40199873 | N4BP2 | Phased Variants |
| 233 | chr4 | 40199990 | 40200211 | N4BP2 | Phased Variants |
| 234 | chr4 | 40200505 | 40200727 | RHOH | Phased Variants |
| 235 | chr4 | 40200730 | 40201571 | RHOH | Phased Variants |
| 236 | chr4 | 80327792 | 80328151 | GK2 | Genotyping |
| 237 | chr4 | 88011077 | 88011285 | AFF1 | Genotyping |
| 238 | chr4 | 106157604 | 106157813 | TET2 | Genotyping |
| 239 | chr4 | 134727698 | 134727916 | PABPC4L | Phased Variants |
| 240 | chr4 | 153249285 | 153249507 | FBXW7 | Genotyping |
| 241 | chr4 | 154624670 | 154625050 | TLR2 | Genotyping |
| 242 | chr4 | 187509884 | 187510410 | FAT1 | Genotyping |
| 243 | chr4 | 187557779 | 187557985 | FAT1 | Genotyping |
| 244 | chr4 | 188924114 | 188924897 | ZFP42 | Genotyping |
| 245 | chr5 | 5182145 | 5182494 | ADAMTS16 | Genotyping |
| 246 | chr5 | 11110990 | 11111137 | CTNND2 | Genotyping |
| 247 | chr5 | 11236740 | 11236956 | CTNND2 | Genotyping |
| 248 | chr5 | 11364700 | 11364923 | CTNND2 | Genotyping |
| 249 | chr5 | 11397080 | 11397377 | CTNND2 | Genotyping |
| 250 | chr5 | 11411600 | 11411807 | CTNND2 | Genotyping |
| 251 | chr5 | 13864465 | 13864696 | DNAH5 | Genotyping |
| 252 | chr5 | 21783415 | 21783668 | CDH12 | Genotyping |
| 253 | chr5 | 54964698 | 54964921 | SLC38A9 | Phased Variants |
| 254 | chr5 | 67590966 | 67591183 | PIK3R1 | Genotyping |
| 255 | chr5 | 75913716 | 75914448 | F2RL2 | Genotyping |
| 256 | chr5 | 83258967 | 83259183 | EDIL3 | Genotyping |
| 257 | chr5 | 112176756 | 112176958 | APC | Genotyping |
| 258 | chr5 | 124079827 | 124080721 | ZNF608 | Phased Variants |
| 259 | chr5 | 131825017 | 131825239 | IRF1 | Genotyping |
| 260 | chr5 | 135381969 | 135382218 | TGFBI | Genotyping |
| 261 | chr5 | 137801487 | 137801637 | EGR1 | Genotyping |
| 262 | chr5 | 137801697 | 137801804 | EGR1 | Genotyping |
| 263 | chr5 | 140208033 | 140208874 | PCDHA6 | Genotyping |
| 264 | chr5 | 158527642 | 158528019 | EBF1 | Phased Variants |
| 265 | chr5 | 176522449 | 176522613 | FGFR4 | Genotyping |
| 266 | chr6 | 392760 | 392967 | IRF4 | Phased Variants |
| 267 | chr6 | 393090 | 393309 | IRF4 | Phased Variants |
| 268 | chr6 | 394815 | 395025 | IRF4 | Genotyping |
| 269 | chr6 | 14117992 | 14118654 | CD83 | Phased Variants |
| 270 | chr6 | 14131732 | 14132021 | CD83 | Genotyping |
| 271 | chr6 | 14133857 | 14133996 | CD83 | Genotyping |
| 272 | chr6 | 14135317 | 14135496 | CD83 | Genotyping |
| 273 | chr6 | 26020709 | 26020958 | HIST1H3A | Genotyping |
| 274 | chr6 | 26032014 | 26032217 | HIST1H3B | Genotyping |
| 275 | chr6 | 26045744 | 26046077 | HIST1H3C | Genotyping |
| 276 | chr6 | 26056034 | 26056315 | HIST1H1C | Genotyping |
| 277 | chr6 | 26056319 | 26056558 | HIST1H1C | Genotyping |
| 278 | chr6 | 26123614 | 26123778 | HIST1H2BC | Phased Variants |
| 279 | chr6 | 26123879 | 26124098 | HIST1H2BC | Genotyping |
| 280 | chr6 | 26124544 | 26124640 | HIST1H2AC | Genotyping |
| 281 | chr6 | 26124714 | 26124889 | HIST1H2AC | Genotyping |
| 282 | chr6 | 26156649 | 26157377 | HIST1H1E | Phased Variants |
| 283 | chr6 | 26158529 | 26158608 | HIST1H2BD | Genotyping |
| 284 | chr6 | 26158739 | 26158835 | HIST1H2BD | Genotyping |
| 285 | chr6 | 26197104 | 26197182 | HIST1H3D | Genotyping |
| 286 | chr6 | 26197189 | 26197465 | HIST1H3D | Genotyping |
| 287 | chr6 | 26216779 | 26216920 | HIST1H2BG | Genotyping |
| 288 | chr6 | 26217214 | 26217431 | HIST1H2AE | Genotyping |
| 289 | chr6 | 26234654 | 26234976 | HIST1H1D | Genotyping |
| 290 | chr6 | 26250459 | 26250537 | HIST1H3F | Genotyping |
| 291 | chr6 | 26250594 | 26250703 | HIST1H3F | Genotyping |
| 292 | chr6 | 26252154 | 26252232 | HIST1H2BH | Genotyping |
| 293 | chr6 | 27100079 | 27100185 | HIST1H2BJ | Genotyping |
| 294 | chr6 | 27100939 | 27101039 | HIST1H2AG | Genotyping |
| 295 | chr6 | 27101159 | 27101300 | HIST1H2AG | Genotyping |

-continued

| # | Chromosome | Region Start | Region End | Closest Gene | Reason for Inclusion |
|---|---|---|---|---|---|
| 296 | chr6 | 27114004 | 27114216 | HIST1H2BK | Phased Variants |
| 297 | chr6 | 27114319 | 27114396 | HIST1H2BK | Genotyping |
| 298 | chr6 | 27114494 | 27114592 | HIST1H2BK | Genotyping |
| 299 | chr6 | 27277284 | 27277495 | POM121L2 | Genotyping |
| 300 | chr6 | 27777783 | 27777900 | HIST1W3H | Genotyping |
| 301 | chr6 | 27777928 | 27778106 | HIST1H3H | Genotyping |
| 302 | chr6 | 27782718 | 27782926 | HIST1H2BM | Genotyping |
| 303 | chr6 | 27799168 | 27799381 | HIST1H4K | Genotyping |
| 304 | chr6 | 27833408 | 27833516 | HIST1H2AL | Genotyping |
| 305 | chr6 | 27834968 | 27835075 | HIST1H1B | Genotyping |
| 306 | chr6 | 27839658 | 27839805 | HIST1H3I | Genotyping |
| 307 | chr6 | 27860479 | 27860659 | HIST1H2AM | Genotyping |
| 308 | chr6 | 27860794 | 27860938 | HIST1H2AM | Genotyping |
| 309 | chr6 | 27861244 | 27861344 | HIST1H2BO | Genotyping |
| 310 | chr6 | 27861399 | 27861485 | HIST1H2BO | Genotyping |
| 311 | chr6 | 37138284 | 37139559 | PIM1 | Phased Variants |
| 312 | chr6 | 37140749 | 37140956 | PIM1 | Genotyping |
| 313 | chr6 | 37141679 | 37141903 | PIM1 | Genotyping |
| 314 | chr6 | 41903611 | 41903834 | CCND3 | Genotyping |
| 315 | chr6 | 41904271 | 41904477 | CCND3 | Genotyping |
| 316 | chr6 | 41904941 | 41905155 | CCND3 | Genotyping |
| 317 | chr6 | 41908071 | 41908365 | CCND3 | Genotyping |
| 318 | chr6 | 41909196 | 41909441 | CCND3 | Genotyping |
| 319 | chr6 | 75965846 | 75966046 | TMEM30A | Genotyping |
| 320 | chr6 | 75969006 | 75969288 | TMEM30A | Genotyping |
| 321 | chr6 | 91004618 | 91004828 | MAP3K7 | Phased Variants |
| 322 | chr6 | 91005793 | 91005998 | MAP3K7 | Phased Variants |
| 323 | chr6 | 94120219 | 94120743 | EPHA7 | Genotyping |
| 324 | chr6 | 106534266 | 106534477 | PRDM1 | Genotyping |
| 325 | chr6 | 106536046 | 106536340 | PRDM1 | Genotyping |
| 326 | chr6 | 106543466 | 106543637 | PRDM1 | Genotyping |
| 327 | chr6 | 106547146 | 106547437 | PRDM1 | Genotyping |
| 328 | chr6 | 106552761 | 106552932 | PRDM1 | Genotyping |
| 329 | chr6 | 106552961 | 106553841 | PRDM1 | Genotyping |
| 330 | chr6 | 106554221 | 106554400 | PRDM1 | Genotyping |
| 331 | chr6 | 106554766 | 106555383 | PRDM1 | Genotyping |
| 332 | chr6 | 108040228 | 108040856 | SCML4 | Genotyping |
| 333 | chr6 | 108041553 | 108042219 | SCML4 | Genotyping |
| 334 | chr6 | 110777718 | 110778244 | SLC22A16 | Genotyping |
| 335 | chr6 | 134491382 | 134491589 | SGK1 | Genotyping |
| 336 | chr6 | 134491892 | 134492111 | SGK1 | Genotyping |
| 337 | chr6 | 134492132 | 134492333 | SGK1 | Genotyping |
| 338 | chr6 | 134492717 | 134492923 | SGK1 | Genotyping |
| 339 | chr6 | 134493307 | 134493474 | SGK1 | Genotyping |
| 340 | chr6 | 134493732 | 134494308 | SGK1 | Phased Variants |
| 341 | chr6 | 134494342 | 134494514 | SGK1 | Genotyping |
| 342 | chr6 | 134494552 | 134494718 | SGK1 | Phased Variants |
| 343 | chr6 | 134494722 | 134494795 | SGK1 | Phased Variants |
| 344 | chr6 | 134494967 | 134495974 | SGK1 | Phased Variants |
| 345 | chr6 | 138188483 | 138188650 | TNFAIP3 | Genotyping |
| 346 | chr6 | 138192338 | 138192683 | TNFAIP3 | Genotyping |
| 347 | chr6 | 138195963 | 138196172 | TNFAIP3 | Genotyping |
| 348 | chr6 | 138196803 | 138197021 | TNFAIP3 | Genotyping |
| 349 | chr6 | 138197108 | 138197313 | TNFAIP3 | Genotyping |
| 350 | chr6 | 138198193 | 138198407 | TNFAIP3 | Genotyping |
| 351 | chr6 | 138199548 | 138200525 | TNFAIP3 | Genotyping |
| 352 | chr6 | 138201178 | 138201404 | TNFAIP3 | Genotyping |
| 353 | chr6 | 138202138 | 138202494 | TNFAIP3 | Genotyping |
| 354 | chr6 | 150954420 | 150954823 | PLEKHG1 | Phased Variants |
| 355 | chr6 | 159238415 | 159238794 | EZR | Phased Variants |
| 356 | chr7 | 2963818 | 2963952 | CARD11 | Genotyping |
| 357 | chr7 | 2963953 | 2964056 | CARD11 | Genotyping |
| 358 | chr7 | 2969593 | 2969738 | CARD11 | Genotyping |
| 359 | chr7 | 2976668 | 2976876 | CARD11 | Genotyping |
| 360 | chr7 | 2977493 | 2977712 | CARD11 | Genotyping |
| 361 | chr7 | 2978258 | 2978502 | CARD11 | Genotyping |
| 362 | chr7 | 2979398 | 2979601 | CARD11 | Genotyping |
| 363 | chr7 | 2983918 | 2984199 | CARD11 | Genotyping |
| 364 | chr7 | 2985403 | 2985610 | CARD11 | Genotyping |
| 365 | chr7 | 2987163 | 2987382 | CARD11 | Genotyping |
| 366 | chr7 | 5569095 | 5569200 | ACTB | Genotyping |
| 367 | chr7 | 5569210 | 5569359 | ACTB | Genotyping |
| 368 | chr7 | 80285799 | 80286074 | CD36 | Genotyping |
| 369 | chr7 | 82387830 | 82388061 | PCLO | Genotyping |
| 370 | chr7 | 82453520 | 82453733 | PCLO | Genotyping |
| 371 | chr7 | 82763800 | 82764050 | PCLO | Genotyping |
| 372 | chr7 | 82784490 | 82784643 | PCLO | Genotyping |

-continued

| # | Chromosome | Region Start | Region End | Closest Gene | Reason for Inclusion |
|---|---|---|---|---|---|
| 373 | chr7 | 106508490 | 106509161 | PIK3CG | Genotyping |
| 374 | chr7 | 110545276 | 110545445 | IMMP2L | Phased Variants |
| 375 | chr7 | 110697971 | 110698144 | LRRN3 | Phased Variants |
| 376 | chr7 | 110737411 | 110737634 | LRRN3 | Phased Variants |
| 377 | chr7 | 110746681 | 110746893 | LRRN3 | Phased Variants |
| 378 | chr7 | 110762936 | 110764629 | LRRN3 | Genotyping |
| 379 | chr7 | 110764636 | 110764981 | LRRN3 | Genotyping |
| 380 | chr7 | 119915406 | 119915800 | KCND2 | Genotyping |
| 381 | chr7 | 122634905 | 122635140 | TAS2R16 | Genotyping |
| 382 | chr7 | 140453012 | 140453121 | BRAF | Genotyping |
| 383 | chr7 | 140453162 | 140453268 | BRAF | Genotyping |
| 384 | chr7 | 146997183 | 146997422 | CNTNAP2 | Genotyping |
| 385 | chr7 | 148506318 | 148506416 | EZH2 | Genotyping |
| 386 | chr7 | 148506448 | 148506551 | EZH2 | Genotyping |
| 387 | chr7 | 148508658 | 148508867 | EZH2 | Genotyping |
| 388 | chr7 | 148513738 | 148513900 | EZH2 | Genotyping |
| 389 | chr7 | 148523533 | 148523743 | EZH2 | Genotyping |
| 390 | chr7 | 151943421 | 151943500 | KMT2C | Phased Variants |
| 391 | chr8 | 623880 | 624090 | ERICH1 | Genotyping |
| 392 | chr8 | 3141724 | 3141942 | CSMD1 | Genotyping |
| 393 | chr8 | 4494931 | 4495105 | CSMD1 | Genotyping |
| 394 | chr8 | 8748687 | 8749284 | MFHAS1 | Genotyping |
| 395 | chr8 | 8750067 | 8750281 | MFHAS1 | Genotyping |
| 396 | chr8 | 18729445 | 18729937 | PSD3 | Genotyping |
| 397 | chr8 | 75898190 | 75898400 | CRISPED1 | Genotyping |
| 398 | chr8 | 101730376 | 101730457 | PABPC1 | Genotyping |
| 399 | chr8 | 103663491 | 103664160 | KLF10 | Genotyping |
| 400 | chr8 | 104897561 | 104898479 | RIMS2 | Genotyping |
| 401 | chr8 | 113308014 | 113308283 | CSMD3 | Genotyping |
| 402 | chr8 | 113364624 | 113364791 | CSMD3 | Genotyping |
| 403 | chr8 | 113568994 | 113569205 | CSMD3 | Genotyping |
| 404 | chr8 | 116616145 | 116616886 | TRPS1 | Genotyping |
| 405 | chr8 | 122626847 | 122627163 | HAS2 | Genotyping |
| 406 | chr8 | 128492947 | 128493338 | POUSF1B | Genotyping |
| 407 | chr8 | 128746807 | 128748893 | MYC | Genotyping |
| 408 | chr8 | 128748902 | 128749969 | MYC | Genotyping |
| 409 | chr8 | 128750367 | 128751183 | MYC | Phased Variants |
| 410 | chr8 | 128752612 | 128753235 | MYC | Genotyping |
| 411 | chr8 | 128754007 | 128754731 | MYC | Genotyping |
| 412 | chr8 | 128754752 | 128756424 | MYC | Genotyping |
| 413 | chr8 | 128756707 | 128756931 | MYC | Genotyping |
| 414 | chr8 | 128756947 | 128757361 | MYC | Genotyping |
| 415 | chr8 | 128757737 | 128757921 | MYC | Genotyping |
| 416 | chr8 | 128764072 | 128764292 | MYC | Genotyping |
| 417 | chr8 | 128951724 | 128951896 | TMEM75 | Genotyping |
| 418 | chr8 | 130692149 | 130692503 | GSDMC | Genotyping |
| 419 | chr8 | 130760594 | 130761023 | GSDMC | Genotyping |
| 420 | chr8 | 131373024 | 131373443 | ASAP1 | Genotyping |
| 421 | chr8 | 136569669 | 136569842 | KHDRBS3 | Genotyping |
| 422 | chr8 | 136659204 | 136659414 | KHDRBS3 | Genotyping |
| 423 | chr8 | 137101252 | 137101464 | KHDRBS3 | Genotyping |
| 424 | chr8 | 137528187 | 137528570 | KHDRBS3 | Genotyping |
| 425 | chr8 | 138849937 | 138850149 | FAM135B | Genotyping |
| 426 | chr8 | 139600457 | 139601255 | COL22A1 | Genotyping |
| 427 | chr8 | 139601392 | 139601569 | COL22A1 | Genotyping |
| 428 | chr9 | 5450474 | 5450616 | CD274 | Genotyping |
| 429 | chr9 | 5456059 | 5456200 | CD274 | Genotyping |
| 430 | chr9 | 5457054 | 5457446 | CD274 | Genotyping |
| 431 | chr9 | 5462809 | 5463160 | CD274 | Genotyping |
| 432 | chr9 | 5465489 | 5465622 | CD274 | Genotyping |
| 433 | chr9 | 5466724 | 5466867 | CD274 | Genotyping |
| 434 | chr9 | 5467814 | 5468022 | CD274 | Genotyping |
| 435 | chr9 | 5510589 | 5510804 | PDCD1LG2 | Genotyping |
| 436 | chr9 | 5522484 | 5522636 | PDCD1LG2 | Genotyping |
| 437 | chr9 | 5534764 | 5535047 | PDCD1LG2 | Genotyping |
| 438 | chr9 | 5549309 | 5549627 | PDCD1LG2 | Genotyping |
| 439 | chr9 | 5557589 | 5557762 | PDCD1LG2 | Genotyping |
| 440 | chr9 | 5563119 | 5563251 | PDCD1LG2 | Genotyping |
| 441 | chr9 | 5569929 | 5570140 | PDCD1LG2 | Genotyping |
| 442 | chr9 | 13222185 | 13222409 | MPDZ | Genotyping |
| 443 | chr9 | 16435498 | 16436307 | BNC2 | Genotyping |
| 444 | chr9 | 19957356 | 19958178 | SLC24A2 | Genotyping |
| 445 | chr9 | 20820916 | 20821095 | FOCAD | Genotyping |
| 446 | chr9 | 20946676 | 20946849 | FOCAD | Genotyping |
| 447 | chr9 | 21808814 | 21808891 | MTAP | Genotyping |
| 448 | chr9 | 21808894 | 21808973 | MTAP | Genotyping |
| 449 | chr9 | 21859249 | 21859469 | MTAP | Genotyping |

-continued

| # | Chromosome | Region Start | Region End | Closest Gene | Reason for Inclusion |
|---|---|---|---|---|---|
| 450 | chr9 | 21970834 | 21971023 | CDKN2A | Genotyping |
| 451 | chr9 | 21971069 | 21971170 | CDKN2A | Genotyping |
| 452 | chr9 | 21974409 | 21974881 | CDKN2A | Genotyping |
| 453 | chr9 | 21989304 | 21989976 | CDKN2A | Genotyping |
| 454 | chr9 | 21994084 | 21994405 | CDKN2A | Genotyping |
| 455 | chr9 | 22005929 | 22006067 | CDKN2B | Genotyping |
| 456 | chr9 | 22006109 | 22006187 | CDKN2B | Genotyping |
| 457 | chr9 | 22008649 | 22009012 | CDKN2B | Genotyping |
| 458 | chr9 | 24545399 | 24545922 | IZUMO3 | Genotyping |
| 459 | chr9 | 24905444 | 24905729 | IZUMO3 | Genotyping |
| 460 | chr9 | 27950144 | 27950532 | LINGO2 | Genotyping |
| 461 | chr9 | 37024919 | 37025642 | PAX5 | Phased Variants |
| 462 | chr9 | 37025829 | 37025996 | PAX5 | Phased Variants |
| 463 | chr9 | 37026269 | 37027015 | PAX5 | Phased Variants |
| 464 | chr9 | 37033619 | 37033797 | PAX5 | Phased Variants |
| 465 | chr9 | 37293169 | 37293378 | ZCCHC7 | Phased Variants |
| 466 | chr9 | 37371494 | 37371879 | ZCCHC7 | Phased Variants |
| 467 | chr9 | 37384684 | 37384911 | ZCCHC7 | Phased Variants |
| 468 | chr9 | 37407369 | 37407588 | GRHPR | Phased Variants |
| 469 | chr9 | 78686579 | 78686854 | PCSK5 | Genotyping |
| 470 | chr9 | 139390582 | 139390950 | NOTCH1 | Genotyping |
| 471 | chr9 | 139390952 | 139391172 | NOTCH1 | Genotyping |
| 472 | chr9 | 139402662 | 139402868 | NOTCH1 | Genotyping |
| 473 | chr9 | 5755066 | 5755273 | FAM208B | Phased Variants |
| 474 | chr10 | 89500957 | 89501139 | PAPSS2 | Genotyping |
| 475 | chr10 | 89603602 | 89604077 | KLLN | Genotyping |
| 476 | chr10 | 89624272 | 89624350 | PTEN | Genotyping |
| 477 | chr10 | 89653752 | 89653825 | PTEN | Genotyping |
| 478 | chr10 | 89653832 | 89653909 | PTEN | Genotyping |
| 479 | chr10 | 89685272 | 89685379 | PTEN | Genotyping |
| 480 | chr10 | 89690752 | 89690894 | PTEN | Genotyping |
| 481 | chr10 | 89692737 | 89692810 | PTEN | Genotyping |
| 482 | chr10 | 89692877 | 89692951 | PTEN | Genotyping |
| 483 | chr10 | 89692972 | 89693037 | PTEN | Genotyping |
| 484 | chr10 | 89711837 | 89711966 | PTEN | Genotyping |
| 485 | chr10 | 89711982 | 89712058 | PTEN | Genotyping |
| 486 | chr10 | 89717577 | 89717714 | PTEN | Genotyping |
| 487 | chr10 | 89717742 | 89717811 | PTEN | Genotyping |
| 488 | chr10 | 89720637 | 89720904 | PTEN | Genotyping |
| 489 | chr10 | 90074239 | 90074419 | RNLS | Genotyping |
| 490 | chr10 | 90537736 | 90538027 | LIPN | Genotyping |
| 491 | chr10 | 90579966 | 90580319 | LIPM | Genotyping |
| 492 | chr10 | 90699126 | 90699647 | ACTA2 | Genotyping |
| 493 | chr10 | 90773866 | 90774076 | FAS | Genotyping |
| 494 | chr10 | 91092211 | 91092423 | IFIT3 | Genotyping |
| 495 | chr10 | 91358986 | 91359298 | PANK1 | Genotyping |
| 496 | chr10 | 131640289 | 131640505 | EBF3 | Genotyping |
| 497 | chr11 | 58978692 | 58978791 | MPEG1 | Genotyping |
| 498 | chr11 | 58978927 | 58979095 | MPEG1 | Genotyping |
| 499 | chr11 | 58979112 | 58979365 | MPEG1 | Genotyping |
| 500 | chr11 | 65190342 | 65190557 | FRMD8 | Phased Variants |
| 501 | chr11 | 65266552 | 65266924 | SCYL1 | Phased Variants |
| 502 | chr11 | 65267397 | 65267603 | SCYL1 | Phased Variants |
| 503 | chr11 | 65623422 | 65623506 | CFL1 | Genotyping |
| 504 | chr11 | 69346691 | 69346940 | CCND1 | Genotyping |
| 505 | chr11 | 102188381 | 102188945 | BIRC3 | Phased Variants |
| 506 | chr11 | 111234536 | 111235068 | POU2AF1 | Genotyping |
| 507 | chr11 | 111249311 | 111249530 | POU2AF1 | Phased Variants |
| 508 | chr11 | 111613196 | 111613432 | PPP2R1B | Genotyping |
| 509 | chr11 | 111781036 | 111781641 | CRYAB | Genotyping |
| 510 | chr11 | 111904096 | 111904291 | DLAT | Genotyping |
| 511 | chr11 | 112405016 | 112405330 | AP002884.2 | Genotyping |
| 512 | chr11 | 112405341 | 112405621 | AP002884.2 | Genotyping |
| 513 | chr11 | 117101043 | 117101217 | PCSK7 | Genotyping |
| 514 | chr11 | 117712683 | 117712997 | FXYD6 | Genotyping |
| 515 | chr11 | 118754793 | 118755011 | CXCR5 | Phased Variants |
| 516 | chr11 | 118764838 | 118765408 | CXCR5 | Genotyping |
| 517 | chr11 | 118967323 | 118968029 | DPAGT1 | Genotyping |
| 518 | chr11 | 120127163 | 120127588 | POU2F3 | Genotyping |
| 519 | chr11 | 120189028 | 120189629 | POU2F3 | Genotyping |
| 520 | chr11 | 125472640 | 125472915 | STT3A | Genotyping |
| 521 | chr11 | 128391383 | 128391629 | ETS1 | Phased Variants |
| 522 | chr11 | 128391648 | 128392132 | ETS1 | Phased Variants |
| 523 | chr11 | 129739778 | 129740102 | NFRKB | Genotyping |
| 524 | chr11 | 131747549 | 131748030 | NTM | Genotyping |
| 525 | chr11 | 134027789 | 134027980 | NCAPD3 | Genotyping |
| 526 | chr11 | 134118684 | 134118873 | THYN1 | Genotyping |

-continued

| # | Chromosome | Region Start | Region End | Closest Gene | Reason for Inclusion |
|---|---|---|---|---|---|
| 527 | chr11 | 134129469 | 134130211 | ACAD8 | Genotyping |
| 528 | chr11 | 134130464 | 134131097 | ACAD8 | Genotyping |
| 529 | chr11 | 134133389 | 134133972 | ACAD8 | Genotyping |
| 530 | chr12 | 6439713 | 6439920 | TNFRSF1A | Genotyping |
| 531 | chr12 | 15813487 | 15813687 | EPS8 | Genotyping |
| 532 | chr12 | 18534682 | 18534856 | PIK3C2G | Genotyping |
| 533 | chr12 | 18544037 | 18544241 | PIK3C2G | Genotyping |
| 534 | chr12 | 18573807 | 18574017 | PIK3C2G | Genotyping |
| 535 | chr12 | 18699197 | 18699459 | PIK3C2G | Genotyping |
| 536 | chr12 | 18747397 | 18747562 | PIK3C2G | Genotyping |
| 537 | chr12 | 18800762 | 18801046 | PIK3C2G | Genotyping |
| 538 | chr12 | 18891267 | 18891560 | CAPZA3 | Genotyping |
| 539 | chr12 | 25205888 | 25206105 | LRMP | Phased Variants |
| 540 | chr12 | 25206398 | 25206616 | LRMP | Phased Variants |
| 541 | chr12 | 25206748 | 25206877 | LRMP | Phased Variants |
| 542 | chr12 | 25207088 | 25207474 | LRMP | Phased Variants |
| 543 | chr12 | 25398218 | 25398299 | KRAS | Genotyping |
| 544 | chr12 | 48190731 | 48190983 | HDAC7 | Genotyping |
| 545 | chr12 | 49415991 | 49416144 | KMT2D | Genotyping |
| 546 | chr12 | 49418306 | 49418550 | KMT2D | Genotyping |
| 547 | chr12 | 49420531 | 49420750 | KMT2D | Genotyping |
| 548 | chr12 | 49426451 | 49426592 | KMT2D | Genotyping |
| 549 | chr12 | 49427886 | 49428116 | KMT2D | Genotyping |
| 550 | chr12 | 49433331 | 49433507 | KMT2D | Genotyping |
| 551 | chr12 | 49437926 | 49438391 | KMT2D | Genotyping |
| 552 | chr12 | 49444391 | 49444595 | KMT2D | Genotyping |
| 553 | chr12 | 49447196 | 49447491 | KMT2D | Genotyping |
| 554 | chr12 | 57496552 | 57496735 | STAT6 | Genotyping |
| 555 | chr12 | 57498222 | 57498396 | STAT6 | Genotyping |
| 556 | chr12 | 57498912 | 57499150 | STAT6 | Genotyping |
| 557 | chr12 | 86198698 | 86199622 | RASSF9 | Genotyping |
| 558 | chr12 | 92537875 | 92538647 | BTG1 | Phased Variants |
| 559 | chr12 | 92538790 | 92539374 | BTG1 | Phased Variants |
| 560 | chr12 | 113495364 | 113496458 | DTX1 | Phased Variants |
| 561 | chr12 | 113496509 | 113496679 | DTX1 | Phased Variants |
| 562 | chr12 | 113496694 | 113496945 | DTX1 | Phased Variants |
| 563 | chr12 | 113497059 | 113497278 | DTX1 | Phased Variants |
| 564 | chr12 | 113515199 | 113515658 | DTX1 | Genotyping |
| 565 | chr12 | 113515664 | 113515934 | DTX1 | Genotyping |
| 566 | chr12 | 113530924 | 113531055 | DTX1 | Genotyping |
| 567 | chr12 | 113531319 | 113531531 | DTX1 | Genotyping |
| 568 | chr12 | 113531799 | 113531930 | DTX1 | Genotyping |
| 569 | chr12 | 113532569 | 113532781 | DTX1 | Genotyping |
| 570 | chr12 | 113532809 | 113533032 | DTX1 | Genotyping |
| 571 | chr12 | 113533099 | 113533237 | DTX1 | Genotyping |
| 572 | chr12 | 113534494 | 113534778 | DTX1 | Genotyping |
| 573 | chr12 | 122458781 | 122459524 | BCL7A | Phased Variants |
| 574 | chr12 | 122460811 | 122461193 | BCL7A | Phased Variants |
| 575 | chr12 | 122461316 | 122461882 | BCL7A | Phased Variants |
| 576 | chr12 | 122462001 | 122462210 | BCL7A | Phased Variants |
| 577 | chr12 | 122462716 | 122462935 | BCL7A | Phased Variants |
| 578 | chr12 | 122463031 | 122463137 | BCL7A | Phased Variants |
| 579 | chr13 | 32907206 | 32907376 | BRCA2 | Genotyping |
| 580 | chr13 | 32912226 | 32912828 | BRCA2 | Genotyping |
| 581 | chr13 | 41133662 | 41133842 | FOXO1 | Genotyping |
| 582 | chr13 | 41133922 | 41135026 | FOXO1 | Genotyping |
| 583 | chr13 | 41239682 | 41239755 | FOXO1 | Genotyping |
| 584 | chr13 | 41239827 | 41240356 | FOXO1 | Genotyping |
| 585 | chr13 | 41240362 | 41240788 | FOXO1 | Genotyping |
| 586 | chr13 | 46959165 | 46959379 | KIAA0226L | Phased Variants |
| 587 | chr13 | 46961680 | 46962067 | KIAA0226L | Phased Variants |
| 588 | chr13 | 51915233 | 51915552 | SERPINE3 | Genotyping |
| 589 | chr13 | 58207131 | 58209129 | PCDH17 | Genotyping |
| 590 | chr13 | 84453542 | 84455255 | SLITRK1 | Genotyping |
| 591 | chr13 | 113516229 | 113516436 | ATP11A | Phased Variants |
| 592 | chr14 | 23344697 | 23345206 | LRP10 | Genotyping |
| 593 | chr14 | 32615405 | 32615617 | ARHGAP5 | Genotyping |
| 594 | chr14 | 35873671 | 35873838 | NFKBIA | Genotyping |
| 595 | chr14 | 64330252 | 64330462 | SYNE2 | Phased Variants |
| 596 | chr14 | 69258238 | 69259642 | ZFP36L1 | Phased Variants |
| 597 | chr14 | 84420586 | 84420796 | FLRT2 | Phased Variants |
| 598 | chr14 | 96179592 | 96180295 | TCL1A | Phased Variants |
| 599 | chr14 | 106048955 | 106049032 | IGHA2 | Phased Variants |
| 600 | chr14 | 106054695 | 106055541 | IGHA2 | Genotyping |
| 601 | chr14 | 106055740 | 106055827 | IGHA2 | Genotyping |
| 602 | chr14 | 106055910 | 106055995 | IGHA2 | Genotyping |
| 603 | chr14 | 106056035 | 106056121 | IGHA2 | Genotyping |

-continued

| # | Chromosome | Region Start | Region End | Closest Gene | Reason for Inclusion |
|---|---|---|---|---|---|
| 604 | chr14 | 106068705 | 106068911 | IGHE | Phased Variants |
| 605 | chr14 | 106069045 | 106069384 | IGHE | Phased Variants |
| 606 | chr14 | 106071060 | 106071135 | IGHE | Phased Variants |
| 607 | chr14 | 106071190 | 106071271 | IGHE | Phased Variants |
| 608 | chr14 | 106092380 | 106092608 | IGHG4 | Genotyping |
| 609 | chr14 | 106092670 | 106093406 | IGHG4 | Genotyping |
| 610 | chr14 | 106093435 | 106093575 | IGHG4 | Genotyping |
| 611 | chr14 | 106093610 | 106094215 | IGHG4 | Genotyping |
| 612 | chr14 | 106094235 | 106094479 | IGHG4 | Genotyping |
| 613 | chr14 | 106094580 | 106094654 | IGHG4 | Genotyping |
| 614 | chr14 | 106094675 | 106094915 | IGHG4 | Genotyping |
| 615 | chr14 | 106095335 | 106095417 | IGHG4 | Phased Variants |
| 616 | chr14 | 106095480 | 106095560 | IGHG4 | Phased Variants |
| 617 | chr14 | 106110675 | 106110814 | IGHG2 | Phased Variants |
| 618 | chr14 | 106110830 | 106110904 | IGHG2 | Phased Variants |
| 619 | chr14 | 106110950 | 106111025 | IGHG2 | Phased Variants |
| 620 | chr14 | 106111100 | 106111311 | IGHG2 | Genotyping |
| 621 | chr14 | 106111390 | 106112121 | IGHG2 | Genotyping |
| 622 | chr14 | 106112160 | 106112302 | IGHG2 | Genotyping |
| 623 | chr14 | 106112335 | 106113010 | IGHG2 | Phased Variants |
| 624 | chr14 | 106113020 | 106113438 | IGHG2 | Phased Variants |
| 625 | chr14 | 106113450 | 106113625 | IGHG2 | Phased Variants |
| 626 | chr14 | 106113695 | 106113901 | IGHG2 | Phased Variants |
| 627 | chr14 | 106113905 | 106113984 | IGHG2 | Phased Variants |
| 628 | chr14 | 106114175 | 106114414 | IGHG2 | Phased Variants |
| 629 | chr14 | 106174970 | 106175819 | IGHA1 | Genotyping |
| 630 | chr14 | 106175820 | 106176042 | IGHA1 | Genotyping |
| 631 | chr14 | 106176070 | 106176217 | IGHA1 | Genotyping |
| 632 | chr14 | 106176235 | 106176320 | IGHA1 | Genotyping |
| 633 | chr14 | 106176375 | 106176932 | IGHA1 | Phased Variants |
| 634 | chr14 | 106176985 | 106177069 | IGHA1 | Phased Variants |
| 635 | chr14 | 106177425 | 106177536 | IGHA1 | Genotyping |
| 636 | chr14 | 106211960 | 106212864 | IGHG1 | Phased Variants |
| 637 | chr14 | 106212870 | 106212948 | IGHG1 | Phased Variants |
| 638 | chr14 | 106212980 | 106213124 | IGHGI | Phased Variants |
| 639 | chr14 | 106213125 | 106213200 | IGHG1 | Phased Variants |
| 640 | chr14 | 106213210 | 106213525 | IGHG1 | Phased Variants |
| 641 | chr14 | 106213660 | 106214042 | IGHG1 | Phased Variants |
| 642 | chr14 | 106239250 | 106239357 | IGHG3 | Phased Variants |
| 643 | chr14 | 106239455 | 106239900 | IGHG3 | Phased Variants |
| 644 | chr14 | 106239990 | 106240155 | IGHG3 | Phased Variants |
| 645 | chr14 | 106240170 | 106240815 | IGHG3 | Phased Variants |
| 646 | chr14 | 106240820 | 106240892 | IGHG3 | Phased Variants |
| 647 | chr14 | 106240915 | 106241118 | IGHG3 | Phased Variants |
| 648 | chr14 | 106241200 | 106241278 | IGHG3 | Phased Variants |
| 649 | chr14 | 106241345 | 106241627 | IGHG3 | Phased Variants |
| 650 | chr14 | 106241630 | 106241705 | IGHG3 | Genotyping |
| 651 | chr14 | 106241710 | 106241975 | IGHG3 | Genotyping |
| 652 | chr14 | 106318100 | 106318327 | IGHM | Phased Variants |
| 653 | chr14 | 106322055 | 106322271 | IGHM | Phased Variants |
| 654 | chr14 | 106322905 | 106323129 | IGHM | Phased Variants |
| 655 | chr14 | 106323470 | 106323656 | IGHM | Phased Variants |
| 656 | chr14 | 106323805 | 106323896 | IGHM | Phased Variants |
| 657 | chr14 | 106324010 | 106324087 | IGHM | Phased Variants |
| 658 | chr14 | 106324155 | 106324245 | IGHM | Phased Variants |
| 659 | chr14 | 106324290 | 106324369 | IGHM | Phased Variants |
| 660 | chr14 | 106324490 | 106324577 | IGHM | Phased Variants |
| 661 | chr14 | 106324750 | 106325340 | IGHM | Phased Variants |
| 662 | chr14 | 106325360 | 106325513 | IGHM | Phased Variants |
| 663 | chr14 | 106325515 | 106325791 | IGHM | Phased Variants |
| 664 | chr14 | 106325820 | 106326095 | IGHJ6 | Phased Variants |
| 665 | chr14 | 106326245 | 106326338 | IGHJ6 | Phased Variants |
| 666 | chr14 | 106326450 | 106331808 | IGHD7-27 | Phased Variants |
| 667 | chr14 | 106357890 | 106357967 | IGHD6-19 | Phased Variants |
| 668 | chr14 | 106380360 | 106380541 | IGHD3-3 | Phased Variants |
| 669 | chr14 | 106380550 | 106380901 | IGHD3-3 | Phased Variants |
| 670 | chr14 | 106380910 | 106381109 | IGHD3-3 | Phased Variants |
| 671 | chr14 | 106381275 | 106381351 | IGHD3-3 | Phased Variants |
| 672 | chr14 | 106381485 | 106381633 | IGHD2-2 | Phased Variants |
| 673 | chr14 | 106381655 | 106381724 | IGHD2-2 | Phased Variants |
| 674 | chr14 | 106381890 | 106381968 | IGHD2-2 | Phased Variants |
| 675 | chr14 | 106381990 | 106382161 | IGHD2-2 | Phased Variants |
| 676 | chr14 | 106382325 | 106382403 | IGHD2-2 | Phased Variants |
| 677 | chr14 | 106382905 | 106383014 | IGHD2-2 | Phased Variants |
| 678 | chr14 | 106383030 | 106383140 | IGHD2-2 | Phased Variants |
| 679 | chr14 | 106383980 | 106384142 | IGHD1-1 | Phased Variants |
| 680 | chr14 | 106384630 | 106384702 | IGHD1-1 | Phased Variants |

-continued

| # | Chromosome | Region Start | Region End | Closest Gene | Reason for Inclusion |
|---|---|---|---|---|---|
| 681 | chr14 | 106384720 | 106384798 | IGHD1-1 | Phased Variants |
| 682 | chr14 | 106384825 | 106384957 | IGHD1-1 | Phased Variants |
| 683 | chr14 | 106405615 | 106405963 | IGHV6-1 | Genotyping |
| 684 | chr14 | 106452660 | 106452748 | IGHV1-2 | Genotyping |
| 685 | chr14 | 106452755 | 106452907 | IGHV1-2 | Genotyping |
| 686 | chr14 | 106452940 | 106453023 | IGHV1-2 | Genotyping |
| 687 | chr14 | 106471395 | 106471476 | IGHV1-3 | Genotyping |
| 688 | chr14 | 106471510 | 106471609 | IGHV1-3 | Genotyping |
| 689 | chr14 | 106494090 | 106494168 | IGHV2-5 | Phased Variants |
| 690 | chr14 | 106494210 | 106494365 | IGHV2-5 | Phased Variants |
| 691 | chr14 | 106494445 | 106494553 | IGHV2-5 | Phased Variants |
| 692 | chr14 | 106494565 | 106494640 | IGHV2-5 | Phased Variants |
| 693 | chr14 | 106494650 | 106494806 | IGHV2-5 | Phased Variants |
| 694 | chr14 | 106518495 | 106518570 | IGHV3-7 | Phased Variants |
| 695 | chr14 | 106518855 | 106518962 | IGHV3-7 | Phased Variants |
| 696 | chr14 | 106518970 | 106519111 | IGHV3-7 | Phased Variants |
| 697 | chr14 | 106539175 | 106539315 | IGHV1-8 | Genotyping |
| 698 | chr14 | 106552365 | 106552502 | IGHV3-9 | Genotyping |
| 699 | chr14 | 106573315 | 106573414 | IGHV3-11 | Genotyping |
| 700 | chr14 | 106573445 | 106573524 | IGHV3-11 | Genotyping |
| 701 | chr14 | 106573540 | 106573645 | IGHV3-11 | Phased Variants |
| 702 | chr14 | 106573685 | 106574021 | IGHV3-11 | Phased Variants |
| 703 | chr14 | 106586200 | 106586343 | IGHV3-13 | Genotyping |
| 704 | chr14 | 106610380 | 106610479 | IGHV3-15 | Genotyping |
| 705 | chr14 | 106610480 | 106610557 | IGHV3-15 | Genotyping |
| 706 | chr14 | 106610690 | 106610765 | IGHV3-15 | Phased Variants |
| 707 | chr14 | 106621885 | 106622026 | IGHV3-16 | Genotyping |
| 708 | chr14 | 106622035 | 106622108 | IGHV3-16 | Genotyping |
| 709 | chr14 | 106641655 | 106641789 | IGHV1-18 | Genotyping |
| 710 | chr14 | 106642110 | 106642265 | IGHV1-18 | Phased Variants |
| 711 | chr14 | 106667545 | 106667628 | IGHV3-20 | Genotyping |
| 712 | chr14 | 106667675 | 106667750 | IGHV3-20 | Genotyping |
| 713 | chr14 | 106667805 | 106667882 | IGHV3-20 | Genotyping |
| 714 | chr14 | 106691755 | 106691904 | IGHV3-21 | Genotyping |
| 715 | chr14 | 106725295 | 106725442 | IGHV3-23 | Phased Variants |
| 716 | chr14 | 106725550 | 106725663 | IGHV3-23 | Phased Variants |
| 717 | chr14 | 106725780 | 106725952 | IGHV3-23 | Phased Variants |
| 718 | chr14 | 106725995 | 106726188 | IGHV3-23 | Phased Variants |
| 719 | chr14 | 106/32970 | 106733077 | IGHV1-24 | Phased Variants |
| 720 | chr14 | 106733185 | 106733270 | IGHV1-24 | Phased Variants |
| 721 | chr14 | 106733275 | 106733487 | IGHV1-24 | Phased Variants |
| 722 | chr14 | 106757725 | 106757888 | IGHV2-26 | Genotyping |
| 723 | chr14 | 106758470 | 106758653 | IGHV2-26 | Phased Variants |
| 724 | chr14 | 106780610 | 106780752 | IGHV4-28 | Genotyping |
| 725 | chr14 | 106791090 | 106791169 | IGHV3-30 | Phased Variants |
| 726 | chr14 | 106805290 | 106805428 | IGHV4-31 | Genotyping |
| 727 | chr14 | 106805945 | 106806076 | IGHV4-31 | Phased Variants |
| 728 | chr14 | 106806120 | 106806219 | IGHV4-31 | Phased Variants |
| 729 | chr14 | 106815805 | 106815910 | IGHV3-33 | Phased Variants |
| 730 | chr14 | 106829685 | 106829757 | IGHV4-34 | Phased Variants |
| 731 | chr14 | 106829765 | 106829986 | IGHV4-34 | Phased Variants |
| 732 | chr14 | 106830125 | 106830196 | IGHV4-34 | Phased Variants |
| 733 | chr14 | 106830240 | 106830312 | IGHV4-34 | Phased Variants |
| 734 | chr14 | 106830315 | 106830884 | IGHV4-34 | Phased Variants |
| 735 | chr14 | 106831185 | 106831594 | IGHV4-34 | Phased Variants |
| 736 | chr14 | 106845300 | 106845540 | IGHV3-35 | Genotyping |
| 737 | chr14 | 106846385 | 106846557 | IGHV3-35 | Phased Variants |
| 738 | chr14 | 106866380 | 106866461 | IGHV3-38 | Genotyping |
| 739 | chr14 | 106866475 | 106866638 | IGHV3-38 | Genotyping |
| 740 | chr14 | 106877715 | 106877858 | IGHV4-39 | Phased Variants |
| 741 | chr14 | 106877930 | 106878498 | IGHV4-39 | Phased Variants |
| 742 | chr14 | 106878540 | 106878612 | IGHV4-39 | Phased Variants |
| 743 | chr14 | 106878680 | 106878759 | IGHV4-39 | Phased Variants |
| 744 | chr14 | 106926180 | 106926405 | IGHV3-43 | Genotyping |
| 745 | chr14 | 106962965 | 106963167 | IGHV1-45 | Genotyping |
| 746 | chr14 | 106963170 | 106963280 | IGHVI-45 | Genotyping |
| 747 | chr14 | 106967130 | 106967209 | IGHV1-46 | Genotyping |
| 748 | chr14 | 106967315 | 106967397 | IGHV1-46 | Genotyping |
| 749 | chr14 | 106994300 | 106994376 | IGHV3-48 | Phased Variants |
| 750 | chr14 | 106994430 | 106994534 | IGHV3-48 | Phased Variants |
| 751 | chr14 | 106994545 | 106994618 | IGHV3-48 | Phased Variants |
| 752 | chr14 | 106994660 | 106994745 | IGHV3-48 | Phased Variants |
| 753 | chr14 | 106994760 | 106994904 | IGHV3-48 | Phased Variants |
| 754 | chr14 | 107013035 | 107013204 | IGHV3-49 | Genotyping |
| 755 | chr14 | 107034665 | 107034845 | IGHV5-51 | Genotyping |
| 756 | chr14 | 107034955 | 107035097 | IGHV5-51 | Genotyping |
| 757 | chr14 | 107078455 | 107078631 | IGHV1-58 | Genotyping |

-continued

| # | Chromosome | Region Start | Region End | Closest Gene | Reason for Inclusion |
|---|---|---|---|---|---|
| 758 | chr14 | 107083565 | 107083726 | IGHV4-59 | Phased Variants |
| 759 | chr14 | 107083790 | 107083923 | IGHV4-59 | Phased Variants |
| 760 | chr14 | 107113405 | 107113560 | IGHV3-64 | Phased Variants |
| 761 | chr14 | 107113820 | 107113922 | IGHV3-64 | Phased Variants |
| 762 | chr14 | 107114095 | 107114238 | IGHV3-64 | Phased Variants |
| 763 | chr14 | 107136755 | 107136899 | IGHV3-66 | Phased Variants |
| 764 | chr14 | 107169645 | 107169841 | IGHV1-69 | Phased Variants |
| 765 | chr14 | 107169970 | 107170195 | IGHV1-69 | Phased Variants |
| 766 | chr14 | 107170220 | 107170472 | IGHV1-69 | Phased Variants |
| 767 | chr14 | 107170475 | 107170563 | IGHV1-69 | Phased Variants |
| 768 | chr14 | 107170660 | 107170871 | IGHV1-69 | Phased Variants |
| 769 | chr14 | 107178305 | 107178377 | IGHV2-70 | Phased Variants |
| 770 | chr14 | 107178415 | 107178869 | IGHV2-70 | Phased Variants |
| 771 | chr14 | 107178880 | 107179116 | IGHV2-70 | Phased Variants |
| 772 | chr14 | 107179130 | 107179339 | IGHV2-70 | Phased Variants |
| 773 | chr14 | 107179360 | 107180001 | IGHV2-70 | Phased Variants |
| 774 | chr14 | 107199020 | 107199094 | IGHV3-72 | Genotyping |
| 775 | chr14 | 107199095 | 107199173 | IGHV3-72 | Genotyping |
| 776 | chr14 | 107210955 | 107211159 | IGHV3-73 | Genotyping |
| 777 | chr14 | 107218755 | 107218891 | IGHV3-74 | Genotyping |
| 778 | chr14 | 107258910 | 107259078 | IGHV7-81 | Phased Variants |
| 779 | chr14 | 107259100 | 107259206 | IGHV7-81 | Phased Variants |
| 780 | chr14 | 107259235 | 107259444 | IGHV7-81 | Phased Variants |
| 781 | chr14 | 107259555 | 107259635 | IGHV7-81 | Phased Variants |
| 782 | chr14 | 107282770 | 107282884 | IGHV7-81 | Genotyping |
| 783 | chr14 | 107282945 | 107283018 | IGHV7-81 | Genotyping |
| 784 | chr15 | 45003678 | 45003861 | B2M | Genotyping |
| 785 | chr15 | 45007718 | 45007927 | B2M | Genotyping |
| 786 | chr15 | 45008463 | 45008603 | B2M | Genotyping |
| 787 | chr15 | 66727354 | 66727536 | MAP2K1 | Genotyping |
| 788 | chr15 | 66729014 | 66729123 | MAP2K1 | Genotyping |
| 789 | chr15 | 66729139 | 66729292 | MAP2K1 | Genotyping |
| 790 | chr15 | 86312062 | 86312565 | KLHL25 | Genotyping |
| 791 | chr16 | 2812096 | 2812786 | SRRM2 | Genotyping |
| 792 | chr16 | 3779106 | 3779320 | CREBBP | Genotyping |
| 793 | chr16 | 3781171 | 3781464 | CREBBP | Genotyping |
| 794 | chr16 | 3781756 | 3781972 | CREBBP | Genotyping |
| 795 | chr16 | 3786011 | 3786223 | CREBBP | Genotyping |
| 796 | chr16 | 3786591 | 3786885 | CREBBP | Genotyping |
| 797 | chr16 | 3788511 | 3788716 | CREBBP | Genotyping |
| 798 | chr16 | 3789521 | 3789770 | CREBBP | Genotyping |
| 799 | chr16 | 3790376 | 3790580 | CREBBP | Genotyping |
| 800 | chr16 | 3794846 | 3794994 | CREBBP | Genotyping |
| 801 | chr16 | 3808801 | 3809009 | CREBBP | Genotyping |
| 802 | chr16 | 3817706 | 3817915 | CREBBP | Genotyping |
| 803 | chr16 | 3823711 | 3823942 | CREBBP | Genotyping |
| 804 | chr16 | 3824536 | 3824719 | CREBBP | Genotyping |
| 805 | chr16 | 3832716 | 3832942 | CREBBP | Genotyping |
| 806 | chr16 | 3900236 | 3900462 | CREBBP | Genotyping |
| 807 | chr16 | 3900561 | 3900914 | CREBBP | Genotyping |
| 808 | chr16 | 10971440 | 10973882 | CIITA | Phased Variants |
| 809 | chr16 | 10973885 | 10974203 | CIITA | Phased Variants |
| 810 | chr16 | 11348520 | 11349249 | SOCS1 | Phased Variants |
| 811 | chr16 | 30093722 | 30093935 | PPP4C | Genotyping |
| 812 | chr16 | 33523607 | 33523675 | IGHV3OR16-12 | Phased Variants |
| 813 | chr16 | 81946175 | 81946356 | PLCG2 | Genotyping |
| 814 | chr16 | 81953055 | 81953307 | PLCG2 | Genotyping |
| 815 | chr16 | 81962120 | 81962263 | PLCG2 | Genotyping |
| 816 | chr16 | 85933003 | 85933569 | IRF8 | Phased Variants |
| 817 | chr16 | 85936563 | 85936836 | IRF8 | Genotyping |
| 818 | chr16 | 85942563 | 85942821 | IRF8 | Genotyping |
| 819 | chr16 | 85945108 | 85945330 | IRF8 | Genotyping |
| 820 | chr16 | 85946708 | 85946887 | IRF8 | Genotyping |
| 821 | chr16 | 85948018 | 85948170 | IRF8 | Genotyping |
| 822 | chr16 | 85951993 | 85952448 | IRF8 | Genotyping |
| 823 | chr16 | 85953683 | 85953837 | IRF8 | Genotyping |
| 824 | chr16 | 85954723 | 85954937 | IRF8 | Genotyping |
| 825 | chr17 | 5366796 | 5367031 | DHX33 | Genotyping |
| 826 | chr17 | 7576949 | 7577197 | TP53 | Genotyping |
| 827 | chr17 | 7577444 | 7577683 | TP53 | Genotyping |
| 828 | chr17 | 7578129 | 7578336 | TP53 | Genotyping |
| 829 | chr17 | 7578344 | 7578591 | TP53 | Genotyping |
| 830 | chr17 | 7579259 | 7579428 | TP53 | Genotyping |
| 831 | chr17 | 18001529 | 18001704 | DRG2 | Genotyping |
| 832 | chr17 | 18022119 | 18022791 | MYO15A | Genotyping |
| 833 | chr17 | 40467709 | 40467857 | STAT3 | Genotyping |
| 834 | chr17 | 40469104 | 40469321 | STAT3 | Genotyping |

-continued

| # | Chromosome | Region Start | Region End | Closest Gene | Reason for Inclusion |
|---|---|---|---|---|---|
| 835 | chr17 | 40474309 | 40474530 | STAT3 | Genotyping |
| 836 | chr17 | 40474974 | 40475190 | STAT3 | Genotyping |
| 837 | chr17 | 40475254 | 40475394 | STAT3 | Genotyping |
| 838 | chr17 | 40478074 | 40478252 | STAT3 | Genotyping |
| 839 | chr17 | 40485844 | 40486132 | STAT3 | Genotyping |
| 840 | chr17 | 40489754 | 40489903 | STAT3 | Genotyping |
| 841 | chr17 | 40491284 | 40491489 | STAT3 | Genotyping |
| 842 | chr17 | 41847058 | 41847241 | DUSP3 | Genotyping |
| 843 | chr17 | 51900441 | 51900897 | KIF2B | Genotyping |
| 844 | chr17 | 56408574 | 56408755 | BZRAP1 | Phased Variants |
| 845 | chr17 | 56408884 | 56409615 | BZRAP1 | Phased Variants |
| 846 | chr17 | 62006520 | 62006919 | CD79B | Genotyping |
| 847 | chr17 | 62007105 | 62007279 | CD79B | Genotyping |
| 848 | chr17 | 62007410 | 62007761 | CD79B | Genotyping |
| 849 | chr17 | 62008645 | 62008786 | CD79B | Genotyping |
| 850 | chr17 | 62009505 | 62009659 | CD79B | Genotyping |
| 851 | chr17 | 63010240 | 63010308 | GNA13 | Phased Variants |
| 852 | chr17 | 63010315 | 63010973 | GNA13 | Phased Variants |
| 853 | chr17 | 63014313 | 63014461 | GNA13 | Genotyping |
| 854 | chr17 | 63049573 | 63049774 | GNA13 | Genotyping |
| 855 | chr17 | 63052443 | 63052678 | GNA13 | Genotyping |
| 856 | chr17 | 75447868 | 75448421 | 9-Sep | Phased Variants |
| 857 | chr17 | 78343503 | 78343715 | RNF213 | Genotyping |
| 858 | chr17 | 79478953 | 79479026 | ACTG1 | Genotyping |
| 859 | chr18 | 1477565 | 1477666 | ADCYAP1 | Phased Variants |
| 860 | chr18 | 6947104 | 6947347 | LAMA1 | Genotyping |
| 861 | chr18 | 6980464 | 6980680 | LAMA1 | Genotyping |
| 862 | chr18 | 13825915 | 13826461 | MC5R | Genotyping |
| 863 | chr18 | 30349775 | 30350300 | AC012123.1 | Phased Variants |
| 864 | chr18 | 48231684 | 48232112 | MAPK4 | Genotyping |
| 865 | chr18 | 48327694 | 48327901 | MRO | Genotyping |
| 866 | chr18 | 48512954 | 48513347 | ELAC1 | Genotyping |
| 867 | chr18 | 48591759 | 48592011 | SMAD4 | Genotyping |
| 868 | chr18 | 48593364 | 48593571 | SMAD4 | Genotyping |
| 869 | chr18 | 48604604 | 48604852 | SMAD4 | Genotyping |
| 870 | chr18 | 48703169 | 48703965 | MEX3C | Genotyping |
| 871 | chr18 | 53804515 | 53804796 | TXNL1 | Genotyping |
| 872 | chr18 | 55274405 | 55274580 | NARS | Genotyping |
| 873 | chr18 | 55319680 | 55319999 | ATP8B1 | Genotyping |
| 874 | chr18 | 55329690 | 55329857 | ATP8B1 | Genotyping |
| 875 | chr18 | 55359005 | 55359259 | ATP8B1 | Genotyping |
| 876 | chr18 | 56054915 | 56055594 | NEDD4L | Genotyping |
| 877 | chr18 | 56063365 | 56063826 | NEDD4L | Genotyping |
| 878 | chr18 | 60763829 | 60764032 | BCL2 | Genotyping |
| 879 | chr18 | 60764299 | 60764540 | BCL2 | Genotyping |
| 880 | chr18 | 60774414 | 60774660 | BCL2 | Genotyping |
| 881 | chr18 | 60793369 | 60793654 | BCL2 | Genotyping |
| 882 | chr18 | 60795829 | 60796006 | BCL2 | Genotyping |
| 883 | chr18 | 60806264 | 60806836 | BCL2 | Phased Variants |
| 884 | chr18 | 60983784 | 60983991 | BCL2 | Phased Variants |
| 885 | chr18 | 60984454 | 60986731 | BCL2 | Phased Variants |
| 886 | chr18 | 60986844 | 60987047 | BCL2 | Phased Variants |
| 887 | chr18 | 60987964 | 60988511 | BCL2 | Phased Variants |
| 888 | chr18 | 64172116 | 64172531 | CDH19 | Genotyping |
| 889 | chr18 | 64176241 | 64176518 | CDH19 | Genotyping |
| 890 | chr18 | 64239166 | 64239357 | CDH19 | Genotyping |
| 891 | chr18 | 65179856 | 65181824 | DSEL | Genotyping |
| 892 | chr18 | 73944893 | 73945380 | ZNF516 | Genotyping |
| 893 | chr18 | 75683734 | 75684502 | GALR1 | Genotyping |
| 894 | chr18 | 77092820 | 77093034 | ATP9B | Genotyping |
| 895 | chr18 | 77170715 | 77171032 | NFATC1 | Genotyping |
| 896 | chr18 | 77208755 | 77208996 | NFATC1 | Genotyping |
| 897 | chr18 | 77227415 | 77227661 | NFATC1 | Genotyping |
| 898 | chr18 | 77288040 | 77288611 | NFATC1 | Genotyping |
| 899 | chr18 | 77794425 | 77795130 | RBFA | Genotyping |
| 900 | chr19 | 1376440 | 1376662 | MUM1 | Genotyping |
| 901 | chr19 | 6586161 | 6586445 | CD70 | Genotyping |
| 902 | chr19 | 6590026 | 6590238 | CD70 | Genotyping |
| 903 | chr19 | 6590786 | 6591079 | CD70 | Genotyping |
| 904 | chr19 | 8028408 | 8028583 | ELAVL1 | Genotyping |
| 905 | chr19 | 10334563 | 10335187 | S1PR2 | Genotyping |
| 906 | chr19 | 10335308 | 10335585 | S1PR2 | Genotyping |
| 907 | chr19 | 10340823 | 10341376 | S1PR2 | Phased Variants |
| 908 | chr19 | 10341833 | 10341984 | S1PR2 | Genotyping |
| 909 | chr19 | 12902574 | 12902861 | JUNB | Genotyping |
| 910 | chr19 | 19256469 | 19256851 | MEF2B | Genotyping |
| 911 | chr19 | 19257044 | 19257222 | MEF2B | Genotyping |

-continued

| # | Chromosome | Region Start | Region End | Closest Gene | Reason for Inclusion |
|---|---|---|---|---|---|
| 912 | chr19 | 19257339 | 19257480 | MEF2B | Genotyping |
| 913 | chr19 | 19257489 | 19257741 | MEF2B | Genotyping |
| 914 | chr19 | 19257824 | 19258036 | MEF2B | Genotyping |
| 915 | chr19 | 19258484 | 19258662 | MEF2B | Genotyping |
| 916 | chr19 | 19259984 | 19260176 | MEF2B | Genotyping |
| 917 | chr19 | 19261414 | 19261588 | MEF2B | Genotyping |
| 918 | chr19 | 19293309 | 19293478 | MEF2BNB | Genotyping |
| 919 | chr19 | 42599890 | 42600121 | POU2F2 | Genotyping |
| 920 | chr19 | 51525626 | 51525937 | KLK11 | Genotyping |
| 921 | chr19 | 51559441 | 51560040 | KLK13 | Genotyping |
| 922 | chr19 | 51561771 | 51561943 | KLK13 | Genotyping |
| 923 | chr19 | 52381611 | 52381786 | ZNF577 | Genotyping |
| 924 | chr19 | 52403336 | 52403586 | ZNF649 | Genotyping |
| 925 | chr19 | 52961146 | 52961224 | ZNF534 | Genotyping |
| 926 | chr19 | 52961226 | 52961578 | ZNF534 | Genotyping |
| 927 | chr19 | 53598586 | 53599055 | ZNF160 | Genotyping |
| 928 | chr20 | 23028372 | 23028858 | THBD | Genotyping |
| 929 | chr20 | 25003526 | 25003774 | ACSS1 | Genotyping |
| 930 | chr20 | 46131072 | 46131213 | NCOA3 | Phased Variants |
| 931 | chr20 | 46131217 | 46131287 | NCOA3 | Phased Variants |
| 932 | chr21 | 18981233 | 18981504 | BTG3 | Genotyping |
| 933 | chr21 | 28213258 | 28213536 | ADAMTS1 | Genotyping |
| 934 | chr21 | 28216763 | 28217005 | ADAMTS1 | Genotyping |
| 935 | chr22 | 22380472 | 22381038 | IGLV4-69 | Phased Variants |
| 936 | chr22 | 22385622 | 22385767 | IGLV4-69 | Genotyping |
| 937 | chr22 | 22385777 | 22385898 | IGLV4-69 | Genotyping |
| 938 | chr22 | 22453287 | 22453502 | IGLV8-61 | Genotyping |
| 939 | chr22 | 22453527 | 22453608 | IGLV8-61 | Genotyping |
| 940 | chr22 | 22516707 | 22516785 | IGLV4-60 | Phased Variants |
| 941 | chr22 | 22516827 | 22517113 | IGLV4-60 | Phased Variants |
| 942 | chr22 | 22550337 | 22550812 | IGLV6-57 | Genotyping |
| 943 | chr22 | 22556227 | 22556630 | IGLV11-55 | Genotyping |
| 944 | chr22 | 22569332 | 22569655 | IGLV10-54 | Genotyping |
| 945 | chr22 | 22673242 | 22673607 | IGLV5-52 | Genotyping |
| 946 | chr22 | 22677077 | 22677216 | IGLV1-51 | Phased Variants |
| 947 | chr22 | 22677227 | 22677337 | IGLV1-51 | Genotyping |
| 948 | chr22 | 22681927 | 22682007 | IGLV1-50 | Genotyping |
| 949 | chr22 | 22682097 | 22682213 | IGLV1-50 | Genotyping |
| 950 | chr22 | 22697727 | 22698123 | IGLV9-49 | Genotyping |
| 951 | chr22 | 22707427 | 22707509 | IGLV5-48 | Genotyping |
| 952 | chr22 | 22707517 | 22707658 | IGLV5-48 | Phased Variants |
| 953 | chr22 | 22707742 | 22707823 | IGLV5-48 | Genotyping |
| 954 | chr22 | 22712077 | 22712496 | IGLV1-47 | Phased Variants |
| 955 | chr22 | 22712512 | 22712625 | IGLV1-47 | Genotyping |
| 956 | chr22 | 22723897 | 22724189 | IGLV7-46 | Phased Variants |
| 957 | chr22 | 22724207 | 22724494 | IGLV7-46 | Phased Variants |
| 958 | chr22 | 22730452 | 22730552 | IGLV5-45 | Phased Variants |
| 959 | chr22 | 22730607 | 22730756 | IGLV5-45 | Phased Variants |
| 960 | chr22 | 22730887 | 22730955 | IGLV5-45 | Phased Variants |
| 961 | chr22 | 22735417 | 22735604 | IGLV1-44 | Phased Variants |
| 962 | chr22 | 22735792 | 22735878 | IGLV1-44 | Phased Variants |
| 963 | chr22 | 22749602 | 22749701 | IGLV7-43 | Phased Variants |
| 964 | chr22 | 22749732 | 22749853 | IGLV7-43 | Phased Variants |
| 965 | chr22 | 22749857 | 22749939 | IGLV7-43 | Phased Variants |
| 966 | chr22 | 22749942 | 22750074 | IGLV7-43 | Phased Variants |
| 967 | chr22 | 22750092 | 22750342 | IGLV7-43 | Phased Variants |
| 968 | chr22 | 22758647 | 22759294 | IGLV1-40 | Phased Variants |
| 969 | chr22 | 22759297 | 22759377 | IGLV1-40 | Phased Variants |
| 970 | chr22 | 22764167 | 22764309 | IGLV1-40 | Phased Variants |
| 971 | chr22 | 22764367 | 22764450 | IGLV1-40 | Phased Variants |
| 972 | chr22 | 22764552 | 22764634 | IGLV1-40 | Phased Variants |
| 973 | chr22 | 22782037 | 22782325 | IGLV5-37 | Genotyping |
| 974 | chr22 | 22786477 | 22786702 | IGLV1-36 | Genotyping |
| 975 | chr22 | 22786727 | 22786842 | IGLV1-36 | Genotyping |
| 976 | chr22 | 22930852 | 22931173 | IGLV2-33 | Genotyping |
| 977 | chr22 | 22937192 | 22937341 | IGLV3-32 | Genotyping |
| 978 | chr22 | 22937347 | 22937548 | IGLV3-32 | Genotyping |
| 979 | chr22 | 23010977 | 23011143 | IGLV3-27 | Genotyping |
| 980 | chr22 | 23011172 | 23011316 | IGLV3-27 | Genotyping |
| 981 | chr22 | 23029497 | 23029581 | IGLV3-25 | Genotyping |
| 982 | chr22 | 23029622 | 23029778 | IGLV3-25 | Genotyping |
| 983 | chr22 | 23040452 | 23040527 | IGLV2-23 | Phased Variants |
| 984 | chr22 | 23040592 | 23040811 | IGLV2-23 | Phased Variants |
| 985 | chr22 | 23040852 | 23041365 | IGLV2-23 | Phased Variants |
| 986 | chr22 | 23047067 | 23047329 | IGLV3-22 | Genotyping |
| 987 | chr22 | 23055367 | 23055445 | IGLV3-21 | Genotyping |
| 988 | chr22 | 23055497 | 23055577 | IGLV3-21 | Phased Variants |

-continued

| # | Chromosome | Region Start | Region End | Closest Gene | Reason for Inclusion |
|---|---|---|---|---|---|
| 989 | chr22 | 23055727 | 23055857 | IGLV3-21 | Phased Variants |
| 990 | chr22 | 23063307 | 23063661 | IGLV3-19 | Genotyping |
| 991 | chr22 | 23077337 | 23077435 | IGLV2-18 | Genotyping |
| 992 | chr22 | 23077537 | 23077615 | IGLV2-18 | Genotyping |
| 993 | chr22 | 23090122 | 23090205 | IGLV3-16 | Genotyping |
| 994 | chr22 | 23090287 | 23090372 | IGLV3-16 | Genotyping |
| 995 | chr22 | 23101392 | 23101473 | IGLV2-14 | Phased Variants |
| 996 | chr22 | 23101532 | 23101605 | IGLV2-14 | Phased Variants |
| 997 | chr22 | 23101652 | 23101735 | IGLV2-14 | Genotyping |
| 998 | chr22 | 23114792 | 23114874 | IGLV3-12 | Genotyping |
| 999 | chr22 | 23114947 | 23115052 | IGLV3-12 | Genotyping |
| 1000 | chr22 | 23135152 | 23135230 | IGLV2-11 | Genotyping |
| 1001 | chr22 | 23135247 | 23135399 | IGLV2-11 | Genotyping |
| 1002 | chr22 | 23135437 | 23135521 | IGLV2-11 | Genotyping |
| 1003 | chr22 | 23154347 | 23154477 | IGLV3-10 | Phased Variants |
| 1004 | chr22 | 23154597 | 23154815 | IGLV3-10 | Phased Variants |
| 1005 | chr22 | 23161917 | 23162052 | IGLV3-9 | Genotyping |
| 1006 | chr22 | 23162072 | 23162290 | IGLV3-9 | Genotyping |
| 1007 | chr22 | 23165422 | 23165496 | IGLV2-8 | Phased Variants |
| 1008 | chr22 | 23165542 | 23165680 | IGLV2-8 | Phased Variants |
| 1009 | chr22 | 23165727 | 23165811 | IGLV2-8 | Phased Variants |
| 1010 | chr22 | 23192412 | 23192818 | IGLV4-3 | Phased Variants |
| 1011 | chr22 | 23197917 | 23198053 | IGLV4-3 | Phased Variants |
| 1012 | chr22 | 23198067 | 23198475 | IGLV4-3 | Phased Variants |
| 1013 | chr22 | 23198587 | 23198732 | IGLV4-3 | Phased Variants |
| 1014 | chr22 | 23198797 | 23198869 | IGLV4-3 | Phased Variants |
| 1015 | chr22 | 23199022 | 23199127 | IGLV4-3 | Phased Variants |
| 1016 | chr22 | 23199182 | 23199261 | IGLV4-3 | Phased Variants |
| 1017 | chr22 | 23199277 | 23199671 | IGLV4-3 | Phased Variants |
| 1018 | chr22 | 23213857 | 23214141 | IGLV4-3 | Genotyping |
| 1019 | chr22 | 23214167 | 23214249 | IGLV4-3 | Genotyping |
| 1020 | chr22 | 23222927 | 23223065 | IGLV3-1 | Phased Variants |
| 1021 | chr22 | 23223077 | 23223319 | IGLV3-1 | Phased Variants |
| 1022 | chr22 | 23223327 | 23224010 | IGLV3-1 | Phased Variants |
| 1023 | chr22 | 23227062 | 23227279 | IGLL5 | Phased Variants |
| 1024 | chr22 | 23227567 | 23227896 | IGLL5 | Phased Variants |
| 1025 | chr22 | 23227897 | 23228624 | IGLL5 | Phased Variants |
| 1026 | chr22 | 23229332 | 23229550 | IGLL5 | Phased Variants |
| 1027 | chr22 | 23229562 | 23229739 | IGLL5 | Phased Variants |
| 1028 | chr22 | 23230012 | 23231063 | IGLL5 | Phased Variants |
| 1029 | chr22 | 23231072 | 23231764 | IGLL5 | Phased Variants |
| 1030 | chr22 | 23231927 | 23232005 | IGLL5 | Phased Variants |
| 1031 | chr22 | 23232062 | 23232346 | IGLL5 | Phased Variants |
| 1032 | chr22 | 23232362 | 23232465 | IGLL5 | Phased Variants |
| 1033 | chr22 | 23232517 | 23232737 | IGLL5 | Phased Variants |
| 1034 | chr22 | 23234612 | 23235837 | IGLJ1 | Phased Variants |
| 1035 | chr22 | 23235847 | 23236276 | IGLJ1 | Phased Variants |
| 1036 | chr22 | 23236277 | 23236378 | IGLJ1 | Phased Variants |
| 1037 | chr22 | 23236387 | 23236526 | IGLJ1 | Phased Variants |
| 1038 | chr22 | 23236557 | 23236851 | IGLJ1 | Phased Variants |
| 1039 | chr22 | 23236877 | 23237366 | IGLC1 | Phased Variants |
| 1040 | chr22 | 23241762 | 23241835 | IGLJ2 | Genotyping |
| 1041 | chr22 | 23242602 | 23242981 | IGLC2 | Phased Variants |
| 1042 | chr22 | 23244157 | 23244373 | IGLC2 | Phased Variants |
| 1043 | chr22 | 23247137 | 23247209 | IGLJ3 | Genotyping |
| 1044 | chr22 | 23247257 | 23247444 | IGLJ3 | Phased Variants |
| 1045 | chr22 | 23247467 | 23247630 | IGLJ3 | Phased Variants |
| 1046 | chr22 | 23248182 | 23248404 | IGLC3 | Phased Variants |
| 1047 | chr22 | 23252687 | 23252824 | IGLJ4 | Genotyping |
| 1048 | chr22 | 23256362 | 23256504 | IGLJ5 | Genotyping |
| 1049 | chr22 | 23260267 | 23260399 | IGLJ6 | Genotyping |
| 1050 | chr22 | 23263507 | 23263653 | IGLJ7 | Genotyping |
| 1051 | chr22 | 23263872 | 23264263 | IGLJ7 | Phased Variants |
| 1052 | chr22 | 23278157 | 23278381 | IGLC7 | Phased Variants |
| 1053 | chr22 | 23282767 | 23282839 | IGLC7 | Phased Variants |
| 1054 | chr22 | 23282842 | 23282956 | IGLC7 | Phased Variants |
| 1055 | chr22 | 23523567 | 23524204 | BCR | Genotyping |
| 1056 | chr22 | 23524212 | 23524419 | BCR | Genotyping |
| 1057 | chr22 | 23610547 | 23610791 | BCR | Genotyping |
| 1058 | chr22 | 29191136 | 29191455 | XBP1 | Genotyping |
| 1059 | chr22 | 29191461 | 29191746 | XBP1 | Genotyping |
| 1060 | chr22 | 29192006 | 29192215 | XBP1 | Genotyping |
| 1061 | chr22 | 29193041 | 29193205 | XBP1 | Genotyping |
| 1062 | chr22 | 29196261 | 29196547 | XBPI | Genotyping |
| 1063 | chr22 | 41513340 | 41513562 | EP300 | Genotyping |
| 1064 | chr22 | 41525845 | 41526047 | EP300 | Genotyping |
| 1065 | chr22 | 41527440 | 41527664 | EP300 | Genotyping |

-continued

| # | Chromosome | Region Start | Region End | Closest Gene | Reason for Inclusion |
|---|---|---|---|---|---|
| 1066 | chr22 | 41536110 | 41536291 | EP300 | Genotyping |
| 1067 | chr22 | 41545740 | 41545940 | EP300 | Genotyping |
| 1068 | chr22 | 41545995 | 41546223 | EP300 | Genotyping |
| 1069 | chr22 | 41565485 | 41565650 | EP300 | Genotyping |
| 1070 | chr22 | 41566385 | 41566592 | EP300 | Genotyping |
| 1071 | chr22 | 41568480 | 41568693 | EP300 | Genotyping |
| 1072 | chr22 | 41569600 | 41569814 | EP300 | Genotyping |
| 1073 | chr22 | 41572225 | 41572436 | EP300 | Genotyping |
| 1074 | chr22 | 41572800 | 41573022 | EP300 | Genotyping |
| 1075 | chr22 | 41573300 | 41573515 | EP300 | Genotyping |
| 1076 | chr22 | 41574255 | 41574486 | EP300 | Genotyping |
| 1077 | chr22 | 41574685 | 41574904 | EP300 | Genotyping |
| 1078 | chr22 | 47570209 | 47570414 | TBC1D22A | Phased Variants |
| 1079 | chrX | 1584324 | 1585521 | P2RY8 | Genotyping |
| 1080 | chrX | 1655789 | 1656029 | AKAP17A | Genotyping |
| 1081 | chrX | 12993264 | 12993539 | TMSB4X | Phased Variants |
| 1082 | chrX | 12993544 | 12994173 | TMSB4X | Phased Variants |
| 1083 | chrX | 12994289 | 12994397 | TMSB4X | Phased Variants |
| 1084 | chrX | 12994444 | 12994514 | TMSB4X | Phased Variants |
| 1085 | chrX | 33146106 | 33146490 | DMD | Phased Variants |
| 1086 | chrX | 35820576 | 35821268 | MAGEB16 | Genotyping |
| 1087 | chrX | 70347816 | 70348034 | MED12 | Genotyping |
| 1088 | chrX | 70612661 | 70612778 | TAF1 | Genotyping |
| 1089 | chrX | 73962123 | 73963110 | KIAA2022 | Genotyping |
| 1090 | chrX | 86772953 | 86773345 | KLHL4 | Genotyping |
| 1091 | chrX | 90026453 | 90026652 | PABPC5 | Phased Variants |
| 1092 | chrX | 100610984 | 100611308 | BTK | Genotyping |
| 1093 | chrX | 119509280 | 119509492 | ATP1B4 | Genotyping |
| 1094 | chrX | 141291052 | 141291326 | MAGEC2 | Genotyping |
| 1095 | chrX | 141291357 | 141291566 | MAGEC2 | Genotyping |
| 1096 | chrX | 153997383 | 153997622 | DKC1 | Genotyping |

| # | Chromosome | Region Start | Region End | Number of 50 bp bins | Gene | Mean frac DLBCL with PV | Mean frac GCB with PV |
|---|---|---|---|---|---|---|---|
| 1 | chr22 | 23227063 | 23237340 | 135 | IGLL5 | 0.184 | 0.158 |
| 2 | chr18 | 60763830 | 60988465 | 104 | BCL2 | 0.111 | 0.165 |
| 3 | chr14 | 106239251 | 106241954 | 49 | IGHG3 | 0.193 | 0.155 |
| 4 | chr14 | 106092381 | 106095531 | 51 | IGHG4 | 0.179 | 0.155 |
| 5 | chr6 | 37138285 | 37141880 | 36 | PIM1 | 0.073 | 0.039 |
| 6 | chr22 | 22758648 | 22764603 | 22 | IGLV1-40 | 0.064 | 0.098 |
| 7 | chr2 | 89161240 | 89165610 | 66 | IGKJ1 | 0.144 | 0.134 |
| 8 | chr14 | 106829686 | 106831586 | 30 | IGHV4-34 | 0.077 | 0.049 |
| 9 | chr2 | 89158619 | 89160190 | 32 | IGKJ5 | 0.307 | 0.286 |
| 10 | chr22 | 23222928 | 23223998 | 22 | IGLV3-1 | 0.266 | 0.300 |
| 11 | chr14 | 106211961 | 106214011 | 39 | IGHG1 | 0.229 | 0.197 |
| 12 | chr14 | 106329751 | 106330201 | 10 | IGHJ5 | 0.320 | 0.261 |
| 13 | chr3 | 187957433 | 188471931 | 54 | LPP | 0.080 | 0.102 |
| 14 | chr2 | 89160890 | 89161190 | 7 | IGKJ2 | 0.151 | 0.096 |
| 15 | chr6 | 134491383 | 134495968 | 64 | SGK1 | 0.039 | 0.053 |
| 16 | chr6 | 150954421 | 150954821 | 9 | PLEKHG1 | 0.067 | 0.049 |
| 17 | chr2 | 89246682 | 89247982 | 18 | IGKV1-5 | 0.031 | 0.023 |
| 18 | chr8 | 128746808 | 128764273 | 164 | MYC | 0.037 | 0.047 |
| 19 | chr22 | 23040453 | 23041334 | 17 | IGLV2-23 | 0.051 | 0.073 |
| 20 | chr2 | 89160240 | 89160540 | 7 | IGKJ4 | 0.259 | 0.225 |
| 21 | chr22 | 22516708 | 22517100 | 8 | IGLV4-60 | 0.084 | 0.117 |
| 22 | chr12 | 122458782 | 122463132 | 48 | BCL7A | 0.091 | 0.106 |
| 23 | chr14 | 107178306 | 107179990 | 33 | IGHV2-70 | 0.224 | 0.242 |
| 24 | chr2 | 89160590 | 89160840 | 6 | IGKJ3 | 0.185 | 0.137 |
| 25 | chr22 | 22730453 | 22730938 | 7 | IGLV5-45 | 0.069 | 0.108 |
| 26 | chr22 | 23248183 | 23248383 | 5 | IGLC3 | 0.164 | 0.236 |
| 27 | chr2 | 89127262 | 89158569 | 66 | IGKC | 0.089 | 0.077 |
| 28 | chr9 | 37293170 | 37384885 | 18 | ZCCHC7 | 0.055 | 0.075 |
| 29 | chr14 | 106732971 | 106733441 | 9 | IGHV1-24 | 0.036 | 0.060 |
| 30 | chr2 | 89184967 | 89185677 | 15 | IGKV4-1 | 0.103 | 0.133 |
| 31 | chr2 | 59821915 | 60773435 | 12 | BCL11A | 0.035 | 0.053 |
| 32 | chr20 | 46131073 | 46131277 | 5 | NCOA3 | 0.071 | 0.102 |
| 33 | chr22 | 23165423 | 23165766 | 6 | IGLV2-8 | 0.045 | 0.022 |
| 34 | chr8 | 8748688 | 8750268 | 17 | MFHAS1 | 0.033 | 0.051 |
| 35 | chr19 | 52961147 | 52961549 | 9 | ZNF534 | 0.029 | 0.018 |
| 36 | chr9 | 16435499 | 16436299 | 17 | BNC2 | 0.034 | 0.049 |
| 37 | chr22 | 23264173 | 23282921 | 11 | IGLC7 | 0.041 | 0.061 |
| 38 | chr14 | 106318101 | 106325773 | 50 | IGHM | 0.181 | 0.175 |

-continued

| | | | | | | | |
|---|---|---|---|---|---|---|---|
| 39 | chr22 | 23235813 | 23235973 | 4 | IGLJ1 | 0.059 | 0.033 |
| 40 | chr16 | 11348521 | 11349221 | 15 | SOCS1 | 0.108 | 0.126 |
| 41 | chr16 | 10971441 | 10974194 | 56 | CIITA | 0.072 | 0.084 |
| 42 | chr5 | 13864466 | 13864666 | 5 | DNAH5 | 0.034 | 0.056 |
| 43 | chr6 | 27777784 | 27778062 | 6 | HIST1H3H | 0.041 | 0.025 |
| 44 | chr22 | 23192413 | 23214234 | 46 | IGLV4-3 | 0.061 | 0.074 |
| 45 | chr14 | 106330251 | 106330601 | 8 | IGHJ4 | 0.166 | 0.143 |
| 46 | chr14 | 106877716 | 106878731 | 18 | IGHV4-39 | 0.050 | 0.064 |
| 47 | chr10 | 90773867 | 90774067 | 5 | FAS | 0.042 | 0.066 |
| 48 | chr22 | 22723898 | 22724466 | 12 | IGLV7-46 | 0.057 | 0.081 |
| 49 | chr5 | 137801488 | 137801798 | 6 | EGR1 | 0.031 | 0.052 |
| 50 | chr22 | 23242603 | 23244358 | 13 | IGLC2 | 0.139 | 0.164 |
| 51 | chr22 | 22930853 | 22931153 | 7 | IGLV2-33 | 0.030 | 0.021 |
| 52 | chr14 | 106325852 | 106329701 | 73 | IGHJ6 | 0.474 | 0.471 |
| 53 | chr3 | 185697424 | 185697624 | 5 | TRA2B | 0.040 | 0.059 |
| 54 | chr6 | 26056035 | 26056539 | 11 | HIST1H1C | 0.059 | 0.079 |
| 55 | chr3 | 71551102 | 71551452 | 8 | FOXP1 | 0.015 | 0.006 |
| 56 | chr3 | 187440190 | 187661368 | 137 | BCL6 | 0.106 | 0.116 |
| 57 | chr11 | 128391384 | 128392103 | 15 | ETS1 | 0.061 | 0.059 |
| 58 | chr13 | 46959166 | 46962031 | 13 | KIAA0226L | 0.034 | 0.029 |
| 59 | chr11 | 118754794 | 118765389 | 17 | CXCR5 | 0.035 | 0.029 |
| 60 | chr17 | 62006521 | 62009656 | 27 | CD79B | 0.041 | 0.039 |
| 61 | chr1 | 2334442 | 2335149 | 15 | RER1 | 0.019 | 0.016 |
| 62 | chr8 | 139600458 | 139601543 | 20 | COL22A1 | 0.031 | 0.043 |
| 63 | chr1 | 34404023 | 34404123 | 3 | CSMD2 | 0.073 | 0.104 |
| 64 | chr6 | 26216780 | 26216880 | 3 | HIST1H2BG | 0.040 | 0.066 |
| 65 | chr19 | 52381612 | 52381762 | 4 | ZNF577 | 0.032 | 0.053 |
| 66 | chr11 | 65266553 | 65267598 | 13 | SCYL1 | 0.030 | 0.045 |
| 67 | chr22 | 23029498 | 23029739 | 5 | IGLV3-25 | 0.085 | 0.108 |
| 68 | chr9 | 78686580 | 78686830 | 6 | PCSK5 | 0.035 | 0.052 |
| 69 | chr14 | 106048956 | 106056101 | 25 | IGHA2 | 0.071 | 0.071 |
| 70 | chr14 | 69258239 | 69259639 | 29 | ZFP36L1 | 0.088 | 0.103 |
| 71 | chr5 | 75913717 | 75914417 | 15 | F2RL2 | 0.030 | 0.044 |
| 72 | chr14 | 106926181 | 106926381 | 5 | IGHV3-43 | 0.038 | 0.056 |
| 73 | chr6 | 27782719 | 27782919 | 5 | HIST1H2BM | 0.032 | 0.052 |
| 74 | chr2 | 100758484 | 100758634 | 4 | AFF3 | 0.037 | 0.025 |
| 75 | chr8 | 136569670 | 137528538 | 22 | KHDRBS3 | 0.029 | 0.041 |
| 76 | chr6 | 392761 | 395016 | 15 | IRF4 | 0.035 | 0.031 |
| 77 | chr8 | 3141725 | 4495082 | 9 | CSMD1 | 0.034 | 0.051 |
| 78 | chr14 | 106330651 | 106331101 | 10 | IGHJ3 | 0.057 | 0.075 |
| 79 | chr16 | 30093723 | 30093923 | 5 | PPP4C | 0.034 | 0.023 |
| 80 | chr12 | 92537876 | 92539341 | 28 | BTG1 | 0.058 | 0.057 |
| 81 | chr17 | 5366797 | 5366997 | 5 | DHX33 | 0.022 | 0.010 |
| 82 | chr22 | 22697728 | 22698078 | 8 | IGLV9-49 | 0.041 | 0.035 |
| 83 | chr22 | 23256363 | 23256463 | 3 | IGLJ5 | 0.059 | 0.082 |
| 84 | chr5 | 176522450 | 176522600 | 4 | FGFR4 | 0.037 | 0.025 |
| 85 | chr13 | 113516230 | 113516430 | 5 | ATP11A | 0.050 | 0.069 |
| 86 | chr14 | 106331551 | 106331651 | 3 | IGHJ1 | 0.046 | 0.033 |
| 87 | chr2 | 117951920 | 117952020 | 3 | DDX18 | 0.033 | 0.055 |
| 88 | chr14 | 107210956 | 107211156 | 5 | IGHV3-73 | 0.046 | 0.033 |
| 89 | chr12 | 6439714 | 6439914 | 5 | TNFRSF1A | 0.038 | 0.056 |
| 90 | chr2 | 136872526 | 136875621 | 28 | CXCR4 | 0.105 | 0.101 |
| 91 | chr3 | 165548199 | 165548649 | 10 | BCHE | 0.012 | 0.008 |
| 92 | chr4 | 188924115 | 188924865 | 16 | ZFP42 | 0.033 | 0.046 |
| 93 | chr20 | 25003527 | 25003727 | 5 | ACSS1 | 0.032 | 0.049 |
| 94 | chr14 | 106994301 | 106994899 | 11 | IGHV3-48 | 0.041 | 0.036 |
| 95 | chr16 | 3779107 | 3900912 | 82 | CREBBP | 0.035 | 0.043 |
| 96 | chr2 | 89544332 | 89544880 | 11 | IGKV2-30 | 0.029 | 0.042 |
| 97 | chr5 | 112176757 | 112176957 | 5 | APC | 0.028 | 0.046 |
| 98 | chr3 | 185146279 | 185198274 | 20 | MAP3K13 | 0.022 | 0.033 |
| 99 | chr11 | 129739779 | 129740079 | 7 | NFRKB | 0.037 | 0.030 |
| 100 | chr12 | 86198699 | 86199599 | 19 | RASSF9 | 0.035 | 0.047 |
| 101 | chr12 | 15813488 | 15813638 | 4 | EPS8 | 0.035 | 0.025 |
| 102 | chr2 | 63826278 | 63826428 | 4 | MDH1 | 0.017 | 0.008 |
| 103 | chr14 | 107083566 | 107083891 | 7 | IGHV4-59 | 0.040 | 0.054 |
| 104 | chr22 | 22735418 | 22735843 | 6 | IGLV1-44 | 0.059 | 0.079 |
| 105 | chr12 | 18891268 | 18891518 | 6 | CAPZA3 | 0.012 | 0.005 |
| 106 | chr14 | 106174971 | 106177526 | 44 | IGHA1 | 0.117 | 0.117 |
| 107 | chr13 | 58207132 | 58209082 | 40 | PCDH17 | 0.038 | 0.047 |
| 108 | chr6 | 26156650 | 26157350 | 15 | HIST1H1E | 0.064 | 0.077 |
| 109 | chr8 | 75898191 | 75898391 | 5 | CRISPLD1 | 0.012 | 0.007 |
| 110 | chr9 | 37024920 | 37033770 | 38 | PAX5 | 0.059 | 0.060 |
| 111 | chr17 | 18001530 | 18001680 | 4 | DRG2 | 0.015 | 0.008 |
| 112 | chr10 | 91092212 | 91092412 | 5 | IFIT3 | 0.026 | 0.016 |
| 113 | chr2 | 56149511 | 56150111 | 13 | EFEMP1 | 0.030 | 0.029 |
| 114 | chr6 | 26032015 | 26032215 | 5 | HIST1H3B | 0.030 | 0.046 |
| 115 | chrX | 1584325 | 1655990 | 29 | P2RY8 | 0.031 | 0.041 |
| 116 | chr4 | 187509885 | 187557980 | 16 | FAT1 | 0.028 | 0.039 |
| 117 | chr5 | 11110991 | 11411801 | 24 | CTNND2 | 0.031 | 0.040 |

-continued

| | | | | | | | |
|---|---|---|---|---|---|---|---|
| 118 | chr14 | 106110676 | 106114376 | 65 | IGHG2 | 0.213 | 0.210 |
| 119 | chr1 | 4472439 | 4476599 | 10 | AJAP1 | 0.030 | 0.026 |
| 120 | chr1 | 110561142 | 110561742 | 13 | AHCYL1 | 0.019 | 0.018 |
| 121 | chr14 | 106725296 | 106726174 | 14 | IGHV3-23 | 0.099 | 0.111 |
| 122 | chr1 | 111715728 | 111715878 | 4 | CEPT1 | 0.022 | 0.016 |
| 123 | chr11 | 118967324 | 118968024 | 15 | DPAGT1 | 0.032 | 0.044 |
| 124 | chr2 | 55237199 | 55237599 | 9 | RTN4 | 0.047 | 0.060 |
| 125 | chr11 | 111781037 | 111781637 | 13 | CRYAB | 0.025 | 0.037 |
| 126 | chr14 | 106573316 | 106574003 | 13 | IGHV3-11 | 0.041 | 0.054 |
| 127 | chr18 | 48231685 | 48232085 | 9 | MAPK4 | 0.022 | 0.020 |
| 128 | chr2 | 62934010 | 63217980 | 14 | EHBP1 | 0.030 | 0.042 |
| 129 | chr22 | 22677078 | 22677289 | 5 | IGLV1-51 | 0.046 | 0.066 |
| 130 | chr7 | 119915407 | 119915757 | 8 | KCND2 | 0.038 | 0.053 |
| 131 | chr22 | 23154348 | 23154798 | 8 | IGLV3-10 | 0.024 | 0.020 |
| 132 | chr6 | 26045745 | 26046045 | 7 | HIST1H3C | 0.030 | 0.026 |
| 133 | chr10 | 131640290 | 131640490 | 5 | EBF3 | 0.040 | 0.036 |
| 134 | chr1 | 109822182 | 109822782 | 13 | PSRC1 | 0.027 | 0.038 |
| 135 | chr17 | 18022120 | 18022770 | 14 | MYO15A | 0.039 | 0.036 |
| 136 | chr16 | 85933004 | 85954924 | 56 | IRF8 | 0.037 | 0.047 |
| 137 | chr2 | 89986777 | 89987085 | 7 | IGKV2D-29 | 0.024 | 0.021 |
| 138 | chr2 | 90249152 | 90249397 | 5 | IGKV1D-43 | 0.040 | 0.033 |
| 139 | chr2 | 242793233 | 242801088 | 24 | PDCD1 | 0.047 | 0.048 |
| 140 | chr6 | 27100080 | 27100180 | 3 | HIST1H2BJ | 0.033 | 0.027 |
| 141 | chr7 | 110545277 | 110698122 | 8 | IMMP2L | 0.004 | 0.002 |
| 142 | chr1 | 111441723 | 111442173 | 10 | CD53 | 0.027 | 0.038 |
| 143 | chrX | 70612662 | 70612762 | 3 | TAF1 | 0.007 | 0.000 |
| 144 | chr21 | 18981234 | 18981484 | 6 | BTG3 | 0.020 | 0.033 |
| 145 | chr14 | 107113406 | 107114196 | 10 | IGHV3-64 | 0.015 | 0.013 |
| 146 | chr22 | 22380473 | 22385883 | 18 | IGLV4-69 | 0.044 | 0.054 |
| 147 | chr9 | 5510590 | 5570130 | 34 | PDCD1LG2 | 0.026 | 0.028 |
| 148 | chr1 | 27059147 | 27106912 | 29 | ARID1A | 0.035 | 0.043 |
| 149 | chr13 | 32907207 | 32912827 | 17 | BRCA2 | 0.013 | 0.013 |
| 150 | chr18 | 48703170 | 48703920 | 16 | MEX3C | 0.022 | 0.023 |
| 151 | chr1 | 203274698 | 203276558 | 33 | BTG2 | 0.131 | 0.129 |
| 152 | chr8 | 128492948 | 128493298 | 8 | POU5F1B | 0.022 | 0.035 |
| 153 | chr6 | 27834969 | 27835069 | 3 | HIST1H1B | 0.043 | 0.038 |
| 154 | chr22 | 23010978 | 23011307 | 7 | IGLV3-27 | 0.045 | 0.059 |
| 155 | chr1 | 117078643 | 117087128 | 10 | CD58 | 0.022 | 0.021 |
| 156 | chr14 | 106380361 | 106381326 | 17 | IGHD3-3 | 0.040 | 0.040 |
| 157 | chr12 | 49415992 | 49447447 | 47 | KMT2D | 0.029 | 0.031 |
| 158 | chr22 | 22782038 | 22782288 | 6 | IGLV5-37 | 0.051 | 0.066 |
| 159 | chr8 | 18729446 | 18729896 | 10 | PSD3 | 0.036 | 0.048 |
| 160 | chr14 | 106552366 | 106552466 | 3 | IGHV3-9 | 0.020 | 0.011 |
| 161 | chrX | 35820577 | 35821227 | 14 | MAGEB16 | 0.021 | 0.032 |
| 162 | chr16 | 81946176 | 81962221 | 13 | PLCG2 | 0.027 | 0.028 |
| 163 | chr22 | 22712078 | 22712594 | 11 | IGLV1-47 | 0.050 | 0.063 |
| 164 | chr3 | 16419205 | 16419455 | 6 | RFTN1 | 0.050 | 0.046 |
| 165 | chr11 | 111613197 | 111613397 | 5 | PPP2R1B | 0.026 | 0.039 |
| 166 | chr14 | 106331151 | 106331501 | 8 | IGHJ2 | 0.048 | 0.047 |
| 167 | chr1 | 226923692 | 226925192 | 31 | ITPKB | 0.044 | 0.053 |
| 168 | chr6 | 27100940 | 27101260 | 5 | HIST1H2AG | 0.024 | 0.020 |
| 169 | chr10 | 91358987 | 91359287 | 7 | PANK1 | 0.021 | 0.019 |
| 170 | chr14 | 32615406 | 32615606 | 5 | ARHGAP5 | 0.020 | 0.033 |
| 171 | chrX | 119509281 | 119509481 | 5 | ATP1B4 | 0.016 | 0.013 |
| 172 | chr18 | 77794426 | 77795126 | 15 | RBFA | 0.014 | 0.014 |
| 173 | chr10 | 89624273 | 89720888 | 32 | PTEN | 0.015 | 0.016 |
| 174 | chr14 | 64330253 | 64330453 | 5 | SYNE2 | 0.006 | 0.003 |
| 175 | chr9 | 24545400 | 24905695 | 17 | IZUMO3 | 0.030 | 0.039 |
| 176 | chr5 | 54964699 | 54964899 | 5 | SLC38A9 | 0.002 | 0.000 |
| 177 | chr8 | 101730377 | 101730427 | 2 | PABPC1 | 0.015 | 0.008 |
| 178 | chr8 | 131373025 | 131373425 | 9 | ASAP1 | 0.030 | 0.040 |
| 179 | chr22 | 23101393 | 23101730 | 6 | IGLV2-14 | 0.048 | 0.044 |
| 180 | chr1 | 109649127 | 109649277 | 4 | C1orf194 | 0.047 | 0.045 |
| 181 | chr11 | 65623423 | 65623473 | 2 | CFL1 | 0.025 | 0.041 |
| 182 | chr22 | 22707428 | 22707793 | 7 | IGLV5-48 | 0.035 | 0.047 |
| 183 | chr14 | 106331701 | 106331801 | 3 | IGHD7-27 | 0.026 | 0.022 |
| 184 | chr14 | 96179593 | 96180293 | 15 | TCL1A | 0.050 | 0.050 |
| 185 | chr22 | 23063308 | 23063658 | 8 | IGLV3-19 | 0.031 | 0.029 |
| 186 | chr17 | 7576950 | 7579410 | 24 | TP53 | 0.040 | 0.051 |
| 187 | chr2 | 148680517 | 148680667 | 4 | ACVR2A | 0.025 | 0.037 |
| 188 | chr19 | 10334564 | 10341984 | 35 | S1PR2 | 0.064 | 0.077 |
| 189 | chr6 | 108040229 | 108042204 | 27 | SCML4 | 0.025 | 0.026 |
| 190 | chr6 | 27277285 | 27277485 | 5 | POM121L2 | 0.042 | 0.039 |
| 191 | chr3 | 186714605 | 186784290 | 33 | ST6GAL1 | 0.084 | 0.091 |
| 192 | chr19 | 12902575 | 12902825 | 6 | JUNB | 0.053 | 0.052 |
| 193 | chr14 | 107199021 | 107199172 | 4 | IGHV3-72 | 0.045 | 0.041 |
| 194 | chr11 | 102188382 | 102188932 | 12 | BIRC3 | 0.104 | 0.123 |
| 195 | chr1 | 185833556 | 186159096 | 32 | HMCN1 | 0.021 | 0.023 |
| 196 | chr12 | 18534683 | 18801013 | 30 | PIK3C2G | 0.017 | 0.020 |

-continued

| | | | | | | | |
|---|---|---|---|---|---|---|---|
| 197 | chrX | 100610985 | 100611285 | 7 | BTK | 0.021 | 0.021 |
| 198 | chr18 | 64172117 | 64239317 | 19 | CDH19 | 0.023 | 0.032 |
| 199 | chr2 | 1652011 | 1652811 | 17 | PXDN | 0.045 | 0.054 |
| 200 | chr11 | 111904097 | 111904247 | 4 | DLAT | 0.037 | 0.049 |
| 201 | chr22 | 22556228 | 22556628 | 9 | IGLV11-55 | 0.039 | 0.038 |
| 202 | chr2 | 103148734 | 103148934 | 5 | SLC9A4 | 0.024 | 0.036 |
| 203 | chr2 | 48027959 | 48028159 | 5 | MSH6 | 0.012 | 0.010 |
| 204 | chr4 | 134727699 | 134727899 | 5 | PABPC4L | 0.012 | 0.010 |
| 205 | chr11 | 134027790 | 134027940 | 4 | NCAPD3 | 0.047 | 0.061 |
| 206 | chr2 | 77746603 | 77746953 | 8 | LRRTM4 | 0.026 | 0.037 |
| 207 | chr1 | 160319284 | 160319484 | 5 | NCSTN | 0.044 | 0.039 |
| 208 | chr18 | 65179857 | 65181807 | 40 | DSEL | 0.021 | 0.029 |
| 209 | chr15 | 45003679 | 45008564 | 12 | B2M | 0.035 | 0.046 |
| 210 | chr1 | 29069532 | 29070182 | 14 | YTHDF2 | 0.043 | 0.052 |
| 211 | chr4 | 80327793 | 80328143 | 8 | GK2 | 0.030 | 0.041 |
| 212 | chr5 | 158527643 | 158527993 | 8 | EBF1 | 0.052 | 0.064 |
| 213 | chr1 | 3747621 | 3747771 | 4 | CEP104 | 0.025 | 0.037 |
| 214 | chr2 | 48059884 | 48066174 | 9 | FBXO11 | 0.014 | 0.015 |
| 215 | chrX | 33146107 | 33146457 | 8 | DMD | 0.059 | 0.059 |
| 216 | chr6 | 16124545 | 26124865 | 6 | HIST1H2AC | 0.051 | 0.063 |
| 217 | chr14 | 106791091 | 106791141 | 2 | IGHV3-30 | 0.045 | 0.041 |
| 218 | chr3 | 183209759 | 183273414 | 23 | KLHL6 | 0.036 | 0.036 |
| 219 | chr17 | 79478954 | 79479004 | 2 | ACTG1 | 0.005 | 0.000 |
| 220 | chr22 | 47570210 | 47570410 | 5 | TBC1D22A | 0.030 | 0.043 |
| 221 | chr6 | 27799169 | 27799369 | 5 | HIST1H4K | 0.022 | 0.033 |
| 222 | chr2 | 65258146 | 65258346 | 5 | SLC1A4 | 0.018 | 0.030 |
| 223 | chr14 | 106586201 | 106586301 | 3 | IGHV3-13 | 0.033 | 0.027 |
| 224 | chr6 | 26158530 | 26358790 | 4 | HIST1H2BD | 0.030 | 0.041 |
| 225 | chr14 | 106691756 | 106691856 | 3 | IGHV3-21 | 0.053 | 0.066 |
| 226 | chr10 | 90579967 | 90580317 | 8 | LIPM | 0.035 | 0.035 |
| 227 | chr7 | 82387831 | 82784641 | 19 | PCLO | 0.035 | 0.044 |
| 228 | chr22 | 23090123 | 23090338 | 4 | IGLV3-16 | 0.030 | 0.041 |
| 229 | chr2 | 89475782 | 89476114 | 7 | 1GKV2-24 | 0.044 | 0.042 |
| 230 | chr2 | 90121892 | 90122155 | 6 | IGKV1D-17 | 0.030 | 0.041 |
| 231 | chr14 | 107034666 | 107035056 | 7 | IGHV5-51 | 0.038 | 0.049 |
| 232 | chr6 | 26217215 | 26217415 | 5 | HIST1H2AE | 0.024 | 0.023 |
| 233 | chr14 | 84420587 | 84420787 | 5 | FLRT2 | 0.000 | 0.000 |
| 234 | chr4 | 40198811 | 40201559 | 49 | RHOH | 0.062 | 0.068 |
| 235 | chr14 | 106539176 | 106539276 | 3 | IGHV1-8 | 0.040 | 0.038 |
| 236 | chr5 | 83258968 | 83259168 | 5 | EDIL3 | 0.022 | 0.033 |
| 237 | chrX | 70347817 | 70348017 | 5 | MED12 | 0.022 | 0.033 |
| 238 | chr18 | 48512955 | 48513305 | 8 | ELAC1 | 0.026 | 0.027 |
| 239 | chrX | 12993265 | 12994487 | 23 | TMSB4X | 0.098 | 0.108 |
| 240 | chr19 | 6586162 | 6591037 | 17 | CD70 | 0.052 | 0.064 |
| 241 | chr9 | 13222186 | 13222386 | 5 | MPDZ | 0.018 | 0.016 |
| 242 | chr19 | 8028409 | 8028559 | 4 | ELAVL1 | 0.037 | 0.049 |
| 243 | chr17 | 63010241 | 63052644 | 28 | GNA13 | 0.033 | 0.035 |
| 244 | chr6 | 75965847 | 75969257 | 10 | TMEM30A | 0.017 | 0.018 |
| 245 | chr2 | 61118795 | 61149620 | 27 | REL | 0.024 | 0.030 |
| 246 | chr8 | 103663492 | 103664142 | 14 | KLF10 | 0.032 | 0.034 |
| 247 | chr7 | 122634906 | 122635106 | 5 | TAS2R16 | 0.040 | 0.036 |
| 248 | chr7 | 106508491 | 106509141 | 14 | PIK3CG | 0.043 | 0.044 |
| 249 | chr19 | 1376441 | 1376641 | 5 | MUM1 | 0.053 | 0.066 |
| 250 | chr10 | 90074240 | 90074390 | 4 | RNLS | 0.012 | 0.012 |
| 251 | chr17 | 56408575 | 56409585 | 19 | BZRAP1 | 0.107 | 0.116 |
| 252 | chr18 | 48327695 | 48327895 | 5 | MRO | 0.034 | 0.033 |
| 253 | chr2 | 90212017 | 90212247 | 4 | IGKV3D-11 | 0.000 | 0.000 |
| 254 | chr3 | 164730701 | 164730851 | 4 | SI | 0.000 | 0.000 |
| 255 | chr18 | 75683735 | 75684485 | 16 | GALR1 | 0.025 | 0.026 |
| 256 | chr10 | 90699127 | 90699627 | 11 | ACTA2 | 0.022 | 0.030 |
| 257 | chr7 | 146997184 | 146997384 | 5 | CNTNAP2 | 0.020 | 0.030 |
| 258 | chr10 | 90537737 | 90537987 | 6 | LIPN | 0.021 | 0.022 |
| 259 | chr8 | 116616146 | 116616846 | 15 | TRPS1 | 0.033 | 0.042 |
| 260 | chr6 | 14117993 | 14135468 | 27 | CD83 | 0.061 | 0.069 |
| 261 | chr14 | 106610381 | 106610741 | 6 | IGHV3-15 | 0.036 | 0.046 |
| 262 | chr14 | 106962966 | 106963269 | 7 | IGHV1-45 | 0.023 | 0.023 |
| 263 | chr6 | 27833409 | 27833509 | 3 | HIST1H2AL | 0.017 | 0.027 |
| 264 | chr7 | 2963819 | 2987364 | 44 | CARD11 | 0.047 | 0.055 |
| 265 | chr11 | 134118685 | 134118835 | 4 | THYN1 | 0.017 | 0.016 |
| 266 | chr14 | 107258911 | 107282996 | 17 | IGHV7-81 | 0.031 | 0.040 |
| 267 | chrX | 73962124 | 73963074 | 20 | KIAA2022 | 0.020 | 0.028 |
| 268 | chr3 | 185236909 | 185237109 | 5 | LIPH | 0.022 | 0.033 |
| 269 | chr3 | 64547205 | 64580090 | 11 | ADAMTS9 | 0.028 | 0.030 |
| 270 | chr14 | 106405616 | 106405916 | 7 | IGHV6-1 | 0.028 | 0.037 |
| 271 | chr11 | 117712684 | 117712984 | 7 | FXYD6 | 0.035 | 0.035 |
| 272 | chr8 | 130692150 | 130760995 | 17 | GSDMC | 0.029 | 0.037 |
| 273 | chr22 | 22749603 | 22750309 | 14 | IGLV7-43 | 0.021 | 0.022 |
| 274 | chr22 | 23135153 | 23135508 | 7 | IGLV2-11 | 0.020 | 0.021 |
| 275 | chr6 | 26234655 | 26234955 | 7 | HIST1H1D | 0.042 | 0.044 |

-continued

| | | | | | | | |
|---|---|---|---|---|---|---|---|
| 276 | chr11 | 112405017 | 112405578 | 12 | C11orf34 | 0.029 | 0.037 |
| 277 | chr1 | 2488007 | 2494707 | 36 | TNFRSF14 | 0.035 | 0.042 |
| 278 | chr18 | 48591760 | 48604805 | 16 | SMAD4 | 0.019 | 0.020 |
| 279 | chr18 | 55274406 | 55274556 | 4 | NARS | 0.015 | 0.025 |
| 280 | chrX | 90026454 | 90026604 | 4 | PABPC5 | 0.015 | 0.025 |
| 281 | chr8 | 623881 | 624081 | 5 | ERICH1 | 0.020 | 0.020 |
| 282 | chr18 | 1477566 | 1477666 | 3 | ADCYAP1 | 0.043 | 0.055 |
| 283 | chr12 | 48190732 | 48190982 | 6 | HDAC7 | 0.043 | 0.041 |
| 284 | chr14 | 106381486 | 106383981 | 18 | IGHD2-2 | 0.029 | 0.032 |
| 285 | chr5 | 135381970 | 135382170 | 5 | TGFBI | 0.034 | 0.030 |
| 286 | chr3 | 184580664 | 184580864 | 5 | VPS8 | 0.006 | 0.007 |
| 287 | chr14 | 106805291 | 106806190 | 8 | IGHV4-31 | 0.038 | 0.041 |
| 288 | chr22 | 23077338 | 23077588 | 4 | IGLV2-18 | 0.025 | 0.025 |
| 289 | chr11 | 134129470 | 134133940 | 40 | ACAD8 | 0.027 | 0.034 |
| 290 | chr1 | 190067140 | 190068190 | 22 | FAM5C | 0.028 | 0.035 |
| 291 | chr19 | 52403337 | 52403537 | 5 | ZNF649 | 0.026 | 0.026 |
| 292 | chr15 | 66727355 | 66729281 | 10 | MAP2K1 | 0.035 | 0.044 |
| 293 | chr6 | 94120220 | 94120720 | 11 | EPHA7 | 0.024 | 0.027 |
| 294 | chr20 | 23028373 | 23028823 | 10 | THBD | 0.044 | 0.052 |
| 295 | chr19 | 42599891 | 42600091 | 5 | POU2F2 | 0.038 | 0.049 |
| 296 | chrX | 86772954 | 86773304 | 8 | KLHL4 | 0.026 | 0.035 |
| 297 | chr9 | 37407370 | 37407570 | 5 | GRHPR | 0.046 | 0.056 |
| 298 | chr9 | 20820917 | 20946827 | 8 | FOCAD | 0.015 | 0.016 |
| 299 | chr6 | 91004619 | 91005994 | 10 | BACH2 | 0.051 | 0.061 |
| 300 | chr9 | 139390583 | 139402863 | 17 | NOTCH1 | 0.038 | 0.045 |
| 301 | chr14 | 106452661 | 106453001 | 7 | IGHV1-2 | 0.020 | 0.021 |
| 302 | chr6 | 26020710 | 26020910 | 5 | HIST1H3A | 0.036 | 0.036 |
| 303 | chr9 | 27950145 | 27950495 | 8 | LINGO2 | 0.022 | 0.031 |
| 304 | chr7 | 80285800 | 80286050 | 6 | CD36 | 0.013 | 0.022 |
| 305 | chr18 | 13825916 | 13826416 | 11 | MC5R | 0.035 | 0.043 |
| 306 | chr9 | 5450475 | 5468015 | 33 | CD274 | 0.026 | 0.029 |
| 307 | chr3 | 185446224 | 185538924 | 8 | IGF2BP2 | 0.019 | 0.027 |
| 308 | chr1 | 3800046 | 3800353 | 7 | DFFB | 0.042 | 0.044 |
| 309 | chr22 | 23055368 | 23055828 | 7 | IGLV3-21 | 0.034 | 0.035 |
| 310 | chr6 | 27114005 | 27114545 | 9 | HIST1H2BK | 0.023 | 0.031 |
| 311 | chr14 | 107013036 | 107013186 | 4 | IGHV3-49 | 0.020 | 0.029 |
| 312 | chr22 | 22453288 | 22453563 | 6 | IGLV8-61 | 0.053 | 0.055 |
| 313 | chr14 | 106357891 | 106357941 | 2 | IGHD6-19 | 0.000 | 0.000 |
| 314 | chr16 | 33523608 | 33523658 | 2 | IGHV3OR16-12 | 0.000 | 0.000 |
| 315 | chr7 | 151943422 | 151943472 | 2 | KMT2C | 0.000 | 0.000 |
| 316 | chr22 | 23114793 | 23115048 | 5 | IGLV3-12 | 0.018 | 0.026 |
| 317 | chr2 | 80801236 | 80801486 | 6 | CTNNA2 | 0.017 | 0.025 |
| 318 | chr22 | 23161918 | 23162288 | 8 | IGLV3-9 | 0.036 | 0.039 |
| 319 | chr12 | 113495365 | 113534745 | 80 | DTX1 | 0.058 | 0.065 |
| 320 | chr11 | 65190343 | 65190543 | 5 | FRMD8 | 0.050 | 0.049 |
| 321 | chr14 | 106967131 | 106967366 | 4 | IGHV1-46 | 0.022 | 0.033 |
| 322 | chr12 | 25205889 | 25207439 | 21 | LRMP | 0.038 | 0.041 |
| 323 | chr14 | 106780611 | 106780711 | 3 | IGHV4-28 | 0.036 | 0.038 |
| 324 | chr11 | 125472641 | 125472891 | 6 | STT3A | 0.046 | 0.055 |
| 325 | chr11 | 69346692 | 69346892 | 5 | CCND1 | 0.024 | 0.026 |
| 326 | chr13 | 51915234 | 51915534 | 7 | SERPINE3 | 0.035 | 0.044 |
| 327 | chr5 | 21783416 | 21783666 | 6 | CDH12 | 0.020 | 0.022 |
| 328 | chr12 | 25398219 | 25398269 | 2 | KRAS | 0.015 | 0.025 |
| 329 | chr1 | 85733208 | 85742033 | 19 | BCL10 | 0.021 | 0.025 |
| 330 | chr1 | 107866872 | 107867572 | 15 | NTNG1 | 0.013 | 0.015 |
| 331 | chr1 | 86591438 | 86591888 | 10 | COL24A1 | 0.029 | 0.036 |
| 332 | chr18 | 30349776 | 30350276 | 11 | KLHL14 | 0.033 | 0.036 |
| 333 | chr14 | 106641656 | 106642261 | 7 | IGHV1-18 | 0.023 | 0.026 |
| 334 | chr17 | 78343504 | 78343704 | 5 | RNF213 | 0.014 | 0.016 |
| 335 | chr1 | 120457961 | 120459261 | 27 | NOTCH2 | 0.036 | 0.039 |
| 336 | chr17 | 40467710 | 40491485 | 39 | STAT3 | 0.034 | 0.040 |
| 337 | chr9 | 19957357 | 19958157 | 17 | SLC24A2 | 0.027 | 0.031 |
| 338 | chr3 | 38180130 | 38182805 | 29 | MYD88 | 0.045 | 0.053 |
| 339 | chr18 | 73944894 | 73945344 | 10 | ZNF516 | 0.018 | 0.025 |
| 340 | chr7 | 140453013 | 140453254 | 5 | BRAF | 0.012 | 0.020 |
| 341 | chr6 | 159238416 | 159238766 | 8 | EZR | 0.050 | 0.057 |
| 342 | chr18 | 77092821 | 77093021 | 5 | ATP9B | 0.008 | 0.010 |
| 343 | chr22 | 23523568 | 23610748 | 22 | BCR | 0.038 | 0.045 |
| 344 | chr22 | 22673243 | 22673593 | 8 | IGLV5-52 | 0.027 | 0.035 |
| 345 | chr4 | 88011078 | 88011278 | 5 | AFF1 | 0.014 | 0.016 |
| 346 | chr11 | 131747550 | 131748000 | 10 | NTM | 0.029 | 0.036 |
| 347 | chr2 | 90077982 | 90078316 | 6 | IGKV3D-20 | 0.025 | 0.033 |
| 348 | chr2 | 96809890 | 96810360 | 10 | DUSP2 | 0.063 | 0.066 |
| 349 | chr2 | 89265757 | 89265987 | 4 | IGKV1-6 | 0.010 | 0.012 |
| 350 | chr19 | 53598587 | 53599037 | 10 | ZNF160 | 0.024 | 0.031 |
| 351 | chr2 | 63335243 | 63631808 | 22 | WDPCP | 0.026 | 0.033 |
| 352 | chr9 | 21808815 | 21859450 | 9 | MTAP | 0.019 | 0.026 |
| 353 | chr6 | 27860480 | 27860895 | 7 | HIST1H2AM | 0.030 | 0.033 |
| 354 | chr6 | 27839659 | 27839759 | 3 | HIST1H3I | 0.036 | 0.038 |

-continued

| | | | | | | | |
|---|---|---|---|---|---|---|---|
| 355 | chr6 | 26252155 | 26252205 | 2 | HIST1H2BH | 0.015 | 0.016 |
| 356 | chr19 | 19256470 | 19293460 | 41 | MEF2B | 0.040 | 0.045 |
| 357 | chr14 | 107169646 | 107170861 | 21 | IGHV1-69 | 0.091 | 0.098 |
| 358 | chr8 | 113308015 | 113569195 | 15 | CSMD3 | 0.013 | 0.020 |
| 359 | chr22 | 22550338 | 22550788 | 10 | IGLV6-57 | 0.042 | 0.049 |
| 360 | chr4 | 153249286 | 153249486 | 5 | FBXW7 | 0.026 | 0.026 |
| 361 | chr11 | 120127164 | 120189629 | 22 | POU2F3 | 0.027 | 0.033 |
| 362 | chr12 | 57496553 | 57499113 | 13 | STAT6 | 0.046 | 0.054 |
| 363 | chr22 | 22937193 | 22937499 | 7 | IGLV3-32 | 0.018 | 0.026 |
| 364 | chr6 | 138188484 | 138202489 | 64 | TNFAIP3 | 0.024 | 0.028 |
| 365 | chr8 | 138849938 | 138850138 | 5 | FAM135B | 0.020 | 0.023 |
| 366 | chr14 | 107218756 | 107218856 | 3 | IGHV3-74 | 0.073 | 0.082 |
| 367 | chr14 | 23344698 | 23345198 | 11 | LRP10 | 0.059 | 0.063 |
| 368 | chr14 | 106866381 | 106866595 | 5 | IGHV3-38 | 0.032 | 0.033 |
| 369 | chr1 | 3547351 | 3547701 | 8 | WRAP73 | 0.024 | 0.027 |
| 370 | chr21 | 28213259 | 28216964 | 11 | ADAMTS1 | 0.028 | 0.036 |
| 371 | chr2 | 169781121 | 169781321 | 5 | ABCB11 | 0.016 | 0.023 |
| 372 | chr22 | 41513341 | 41574886 | 72 | EP300 | 0.031 | 0.037 |
| 373 | chr18 | 56054916 | 56063816 | 24 | NEDD4L | 0.016 | 0.020 |
| 374 | chr14 | 106845301 | 106846536 | 9 | IGHV3-35 | 0.055 | 0.064 |
| 375 | chr14 | 107136756 | 107136856 | 3 | IGHV3-66 | 0.030 | 0.038 |
| 376 | chr22 | 23047068 | 23047318 | 6 | IGLV3-22 | 0.043 | 0.049 |
| 377 | chr22 | 22786478 | 22786803 | 7 | IGLV1-36 | 0.040 | 0.047 |
| 378 | chr8 | 122626848 | 122627148 | 7 | HAS2 | 0.030 | 0.033 |
| 379 | chr5 | 131825018 | 131825218 | 5 | IRF1 | 0.026 | 0.030 |
| 380 | chr22 | 23252688 | 23252788 | 3 | IGLJ4 | 0.020 | 0.022 |
| 381 | chr14 | 107078456 | 107078606 | 4 | IGHV1-58 | 0.050 | 0.053 |
| 382 | chr4 | 154624671 | 154625021 | 8 | TLR2 | 0.017 | 0.020 |
| 383 | chr1 | 89196227 | 89215037 | 19 | IGKV5-2 | 0.024 | 0.028 |
| 384 | chr18 | 55319681 | 55359256 | 17 | ATP8B1 | 0.028 | 0.031 |
| 385 | chr1 | 61553803 | 61554303 | 11 | NFIA | 0.030 | 0.033 |
| 386 | chr10 | 89603603 | 89604053 | 10 | KLLN | 0.024 | 0.028 |
| 387 | chr22 | 23247138 | 23247609 | 9 | IGLJ3 | 0.165 | 0.169 |
| 388 | chr11 | 117101044 | 117101194 | 4 | PCSK7 | 0.042 | 0.049 |
| 389 | chr6 | 27861245 | 27861450 | 4 | HIST1H2BO | 0.037 | 0.045 |
| 390 | chr2 | 61441170 | 61441870 | 15 | USP34 | 0.025 | 0.028 |
| 391 | chr11 | 111234537 | 111249512 | 16 | POU2AF1 | 0.030 | 0.034 |
| 392 | chr5 | 5182146 | 5182446 | 7 | ADAMTS16 | 0.038 | 0.044 |
| 393 | chr14 | 106667546 | 106667856 | 6 | IGHV3-20 | 0.021 | 0.025 |
| 394 | chr2 | 145162402 | 145693052 | 53 | ZEB2 | 0.041 | 0.046 |
| 395 | chr14 | 106494091 | 106494768 | 12 | IGHV2-5 | 0.027 | 0.034 |
| 396 | chr2 | 65593036 | 65593213 | 4 | SPRED2 | 0.057 | 0.061 |
| 397 | chr2 | 141245128 | 141245328 | 5 | LRP1B | 0.010 | 0.016 |
| 398 | chr22 | 23241763 | 23241813 | 2 | IGLJ2 | 0.030 | 0.033 |
| 399 | chrX | 153997384 | 153997584 | 5 | DKC1 | 0.042 | 0.046 |
| 400 | chr10 | 5755067 | 5755267 | 5 | FAM208B | 0.016 | 0.020 |
| 401 | chr1 | 35472493 | 35472693 | 5 | ZMYM6 | 0.016 | 0.020 |
| 402 | chr6 | 26250460 | 26250695 | 5 | HIST1H3F | 0.028 | 0.033 |
| 403 | chr3 | 176750700 | 176771710 | 17 | TBL1XR1 | 0.020 | 0.024 |
| 404 | chr18 | 77170716 | 77288591 | 29 | NFATC1 | 0.038 | 0.043 |
| 405 | chr13 | 41133663 | 41240784 | 49 | FOXO1 | 0.025 | 0.031 |
| 406 | chr8 | 128951725 | 128951875 | 4 | TMEM75 | 0.042 | 0.049 |
| 407 | chr22 | 22681928 | 22682198 | 5 | IGLV1-50 | 0.020 | 0.026 |
| 408 | chr2 | 89976277 | 89976377 | 3 | IGKV2D-30 | 0.066 | 0.071 |
| 409 | chr14 | 106757726 | 106758621 | 8 | IGHV2-26 | 0.026 | 0.033 |
| 410 | chr1 | 2306312 | 2306812 | 11 | MORN1 | 0.028 | 0.034 |
| 411 | chr14 | 106384031 | 106384926 | 9 | IGHD1-1 | 0.039 | 0.046 |
| 412 | chr8 | 104897562 | 104898462 | 19 | RIMS2 | 0.030 | 0.036 |
| 413 | chr10 | 89500958 | 89501108 | 4 | PAPSS2 | 0.025 | 0.029 |
| 414 | chr1 | 201038553 | 201038753 | 5 | CACNA1S | 0.034 | 0.033 |
| 415 | chr13 | 84453543 | 84455243 | 35 | SLITRK1 | 0.034 | 0.039 |
| 416 | chr22 | 23263508 | 23264123 | 9 | IGLJ7 | 0.062 | 0.069 |
| 417 | chr5 | 140208034 | 140208834 | 17 | PCDHA6 | 0.026 | 0.031 |
| 418 | chr1 | 23885408 | 23885899 | 10 | ID3 | 0.015 | 0.020 |
| 419 | chr14 | 106518496 | 106519064 | 7 | IGHV3-7 | 0.035 | 0.040 |
| 420 | chr9 | 22005930 | 22009000 | 13 | CDKN2B | 0.031 | 0.035 |
| 421 | chr11 | 58978693 | 58979345 | 11 | MPEG1 | 0.032 | 0.036 |
| 422 | chr1 | 227842647 | 227842697 | 2 | ZNF678 | 0.010 | 0.016 |
| 423 | chr6 | 106534267 | 106555367 | 60 | PRDM1 | 0.031 | 0.036 |
| 424 | chr2 | 198950435 | 198950985 | 12 | PLCL1 | 0.021 | 0.027 |
| 425 | chr18 | 6947105 | 6980665 | 10 | LAMA1 | 0.027 | 0.033 |
| 426 | chr6 | 26197105 | 26197462 | 8 | HIST1H3D | 0.021 | 0.027 |
| 427 | chr19 | 51525627 | 51525927 | 7 | KLK11 | 0.028 | 0.033 |
| 428 | chr2 | 61719435 | 61719635 | 5 | XPO1 | 0.012 | 0.016 |
| 429 | chrX | 141291053 | 141291534 | 10 | MAGEC2 | 0.019 | 0.023 |
| 430 | chr14 | 35873672 | 35873822 | 4 | NFKBIA | 0.035 | 0.041 |
| 431 | chr2 | 89442292 | 89443217 | 19 | IGKV3-20 | 0.042 | 0.047 |
| 432 | chr1 | 72334892 | 72335098 | 5 | NEGR1 | 0.014 | 0.020 |
| 433 | chr1 | 9784433 | 9784533 | 3 | PIK3CD | 0.007 | 0.011 |

-continued

| | | | | | | | |
|---|---|---|---|---|---|---|---|
| 434 | chr2 | 170101186 | 170101386 | 5 | LRP2 | 0.032 | 0.036 |
| 435 | chr7 | 110737412 | 110764944 | 51 | LRRN3 | 0.019 | 0.024 |
| 436 | chr3 | 7620224 | 7620974 | 16 | GRM7 | 0.032 | 0.038 |
| 437 | chr22 | 22569333 | 22569633 | 7 | IGLV10-54 | 0.031 | 0.037 |
| 438 | chr17 | 75447869 | 75448419 | 12 | 9-Sep | 0.031 | 0.037 |
| 439 | chr7 | 148506319 | 148523734 | 19 | EZH2 | 0.019 | 0.025 |
| 440 | chr14 | 106621886 | 106622095 | 5 | IGHV3-16 | 0.024 | 0.030 |
| 441 | chr1 | 181452915 | 181453115 | 5 | CACNA1E | 0.032 | 0.036 |
| 442 | chr2 | 58520801 | 58521201 | 9 | FANCL | 0.029 | 0.035 |
| 443 | chr19 | 51559442 | 51561922 | 16 | KLK13 | 0.032 | 0.038 |
| 444 | chr16 | 2812097 | 2812747 | 14 | SRRM2 | 0.056 | 0.062 |
| 445 | chr6 | 41903612 | 41909397 | 26 | CCND3 | 0.041 | 0.047 |
| 446 | chr14 | 106068706 | 106071241 | 16 | IGHE | 0.118 | 0.124 |
| 447 | chr6 | 110777719 | 110778219 | 11 | SLC22A16 | 0.027 | 0.033 |
| 448 | chr9 | 21970835 | 21994385 | 37 | CDKN2A | 0.027 | 0.031 |
| 449 | chr2 | 90025207 | 90025522 | 6 | IGKV2D-26 | 0.012 | 0.016 |
| 450 | chr4 | 7728457 | 7728657 | 5 | SORCS2 | 0.034 | 0.039 |
| 451 | chr7 | 5569096 | 5569356 | 6 | ACTB | 0.048 | 0.055 |
| 452 | chr3 | 140281599 | 140281849 | 6 | CLSTN2 | 0.036 | 0.038 |
| 453 | chr2 | 89291907 | 89292182 | 4 | IGKV1-8 | 0.020 | 0.025 |
| 454 | chr22 | 23260268 | 23260368 | 3 | IGLJ6 | 0.043 | 0.049 |
| 455 | chr14 | 106815806 | 106815906 | 3 | IGHV3-33 | 0.059 | 0.066 |
| 456 | chr6 | 26123615 | 26124080 | 9 | HIST1H2BC | 0.031 | 0.036 |
| 457 | chr3 | 49397609 | 49413039 | 18 | RHOA | 0.030 | 0.035 |
| 458 | chr22 | 29191137 | 29196512 | 28 | XBP1 | 0.032 | 0.039 |
| 459 | chr14 | 106471396 | 106471580 | 4 | IGHV1-3 | 0.007 | 0.012 |
| 460 | chr17 | 41847059 | 41847209 | 4 | DUSP3 | 0.032 | 0.037 |
| 461 | chr17 | 51900442 | 51900892 | 10 | KIF2B | 0.035 | 0.039 |
| 462 | chr15 | 86312063 | 86312563 | 11 | KLHL25 | 0.032 | 0.037 |
| 463 | chr18 | 53804516 | 53804766 | 6 | TXNL1 | 0.036 | 0.041 |
| 464 | chr5 | 67590967 | 67591167 | 5 | PIK3R1 | 0.018 | 0.023 |
| 465 | chr5 | 124079828 | 124080678 | 18 | ZNF608 | 0.026 | 0.031 |
| 466 | chr2 | 90259932 | 90260232 | 5 | IGKV1D-8 | 0.034 | 0.039 |
| 467 | chr2 | 88906682 | 88906832 | 4 | EIF2AK3 | 0.059 | 0.066 |
| 468 | chr4 | 106157605 | 106157805 | 5 | TET2 | 0.018 | 0.023 |

| # | Mean frac ABC with PV | Mean frac PMBCL with PV | Mean frac cHL with PV | ranksumP ABCvsGCB | ranksumP PMBCLvsDLBCL | ranksumP cHLvsDLBCL |
|---|---|---|---|---|---|---|
| 1 | 0.224 | 0.242 | 0.088 | 0.00000 | 0.00003 | 0.00000 |
| 2 | 0.029 | 0.056 | 0.004 | 0.00000 | 0.00000 | 0.00000 |
| 3 | 0.251 | 0.105 | 0.032 | 0.00000 | 0.00000 | 0.00000 |
| 4 | 0.217 | 0.136 | 0.056 | 0.00000 | 0.00000 | 0.00000 |
| 5 | 0.124 | 0.068 | 0.000 | 0.00000 | 0.00251 | 0.00000 |
| 6 | 0.013 | 0.102 | 0.000 | 0.00000 | 0.46986 | 0.00001 |
| 7 | 0.160 | 0.140 | 0.109 | 0.00000 | 0.00006 | 0.36296 |
| 8 | 0.121 | 0.100 | 0.012 | 0.00000 | 0.10144 | 0.01432 |
| 9 | 0.339 | 0.350 | 0.219 | 0.00000 | 0.28398 | 0.00000 |
| 10 | 0.215 | 0.429 | 0.208 | 0.00000 | 0.00000 | 0.22589 |
| 11 | 0.277 | 0.131 | 0.035 | 0.00000 | 0.00000 | 0.00000 |
| 12 | 0.410 | 0.375 | 0.148 | 0.00000 | 0.24822 | 0.00000 |
| 13 | 0.046 | 0.168 | 0.062 | 0.00001 | 0.00027 | 0.00345 |
| 14 | 0.236 | 0.116 | 0.062 | 0.00001 | 0.02569 | 0.00086 |
| 15 | 0.018 | 0.075 | 0.001 | 0.00002 | 0.58192 | 0.99403 |
| 16 | 0.094 | 0.063 | 0.000 | 0.00002 | 0.11666 | 0.00114 |
| 17 | 0.043 | 0.097 | 0.024 | 0.00003 | 0.01798 | 0.00005 |
| 18 | 0.021 | 0.039 | 0.001 | 0.00003 | 0.00000 | 0.86966 |
| 19 | 0.018 | 0.088 | 0.005 | 0.00003 | 0.77724 | 0.04594 |
| 20 | 0.311 | 0.241 | 0.130 | 0.00003 | 0.04157 | 0.00006 |
| 21 | 0.034 | 0.078 | 0.022 | 0.00003 | 0.17854 | 0.01628 |
| 22 | 0.068 | 0.173 | 0.041 | 0.00005 | 0.00033 | 0.01552 |
| 23 | 0.195 | 0.182 | 0.115 | 0.00006 | 0.00002 | 0.00004 |
| 24 | 0.258 | 0.135 | 0.109 | 0.00006 | 0.00291 | 0.00284 |
| 25 | 0.011 | 0.107 | 0.019 | 0.00010 | 0.70241 | 0.37522 |
| 26 | 0.055 | 0.113 | 0.035 | 0.00014 | 0.00837 | 0.00072 |
| 27 | 0.107 | 0.164 | 0.041 | 0.00022 | 0.00008 | 0.04625 |
| 28 | 0.025 | 0.069 | 0.002 | 0.00023 | 0.36871 | 0.42872 |
| 29 | 0.000 | 0.090 | 0.000 | 0.00026 | 0.33149 | 0.77291 |
| 30 | 0.057 | 0.133 | 0.078 | 0.00035 | 0.83189 | 0.36813 |
| 31 | 0.008 | 0.089 | 0.000 | 0.00075 | 0.19138 | 0.80319 |
| 32 | 0.025 | 0.025 | 0.009 | 0.00085 | 0.00670 | 0.02848 |
| 33 | 0.079 | 0.083 | 0.043 | 0.00090 | 0.90873 | 0.01148 |
| 34 | 0.004 | 0.055 | 0.000 | 0.00099 | 0.48925 | 0.69644 |
| 35 | 0.044 | 0.063 | 0.000 | 0.00113 | 0.75367 | 0.44231 |
| 36 | 0.012 | 0.077 | 0.000 | 0.00119 | 0.51920 | 0.84956 |
| 37 | 0.011 | 0.131 | 0.000 | 0.00129 | 0.00884 | 0.29860 |
| 38 | 0.190 | 0.139 | 0.024 | 0.00192 | 0.00000 | 0.00000 |
| 39 | 0.100 | 0.266 | 0.000 | 0.00225 | 0.00168 | 0.05724 |

-continued

| | | | | | | |
|---|---|---|---|---|---|---|
| 40 | 0.080 | 0.2.92 | 0.046 | 0.00303 | 0.00000 | 0.07342 |
| 41 | 0.054 | 0.289 | 0.082 | 0.00307 | 0.00000 | 0.00000 |
| 42 | 0.000 | 0.088 | 0.000 | 0.00408 | 0.40676 | 0.90937 |
| 43 | 0.067 | 0.042 | 0.000 | 0.00488 | 0.21081 | 0.62256 |
| 44 | 0.042 | 0.162 | 0.025 | 0.00501 | 0.00000 | 0.65960 |
| 45 | 0.200 | 0.180 | 0.043 | 0.00606 | 0.43909 | 0.00002 |
| 46 | 0.028 | 0.059 | 0.053 | 0.00685 | 0.08333 | 0.00000 |
| 47 | 0.005 | 0.038 | 0.000 | 0.00715 | 0.19681 | 0.45229 |
| 48 | 0.021 | 0.094 | 0.000 | 0.00728 | 0.81618 | 0.00596 |
| 49 | 0.000 | 0.167 | 0.000 | 0.00799 | 0.01126 | 0.75859 |
| 50 | 0.100 | 0.163 | 0.094 | 0.00835 | 0.72971 | 0.51511 |
| 51 | 0.043 | 0.045 | 0.000 | 0.00870 | 0.55261 | 0.56841 |
| 52 | 0.478 | 0.470 | 0.362 | 0.00948 | 0.02862 | 0.00000 |
| 53 | 0.010 | 0.075 | 0.000 | 0.00954 | 0.90180 | 0.48859 |
| 54 | 0.027 | 0.017 | 0.000 | 0.00967 | 0.00022 | 0.00680 |
| 55 | 0.028 | 0.031 | 0.011 | 0.00999 | 0.57172 | 0.00116 |
| 56 | 0.089 | 0.126 | 0.044 | 0.01002 | 0.04210 | 0.00007 |
| 57 | 0.065 | 0.021 | 0.000 | 0.01042 | 0.00001 | 0.00039 |
| 58 | 0.042 | 0.067 | 0.000 | 0.01112 | 0.97915 | 0.84801 |
| 59 | 0.044 | 0.077 | 0.000 | 0.01378 | 0.40303 | 0.93788 |
| 60 | 0.044 | 0.083 | 0.002 | 0.01401 | 0.66941 | 0.59741 |
| 61 | 0.023 | 0.088 | 0.000 | 0.01514 | 0.02024 | 0.00677 |
| 62 | 0.011 | 0.078 | 0.000 | 0.01532 | 0.28495 | 0.48626 |
| 63 | 0.025 | 0.042 | 0.000 | 0.01556 | 0.06834 | 0.05288 |
| 64 | 0.000 | 0.063 | 0.000 | 0.01575 | 0.79954 | 0.58401 |
| 65 | 0.000 | 0.063 | 0.000 | 0.01627 | 0.93639 | 0.94029 |
| 66 | 0.008 | 0.048 | 0.003 | 0.01646 | 0.43210 | 0.34042 |
| 67 | 0.050 | 0.113 | 0.043 | 0.01712 | 0.97583 | 0.80122 |
| 68 | 0.008 | 0.073 | 0.000 | 0.01813 | 0.77106 | 0.87235 |
| 69 | 0.072 | 0.180 | 0.007 | 0.01828 | 0.00255 | 0.02269 |
| 70 | 0.065 | 0.159 | 0.013 | 0.01945 | 0.03212 | 0.00000 |
| 71 | 0.010 | 0.108 | 0.000 | 0.01980 | 0.01754 | 0.55332 |
| 72 | 0.010 | 0.038 | 0.000 | 0.01981 | 0.22178 | 0.96725 |
| 73 | 0.000 | 0.000 | 0.000 | 0.02014 | 0.01525 | 0.81176 |
| 74 | 0.056 | 0.078 | 0.033 | 0.02064 | 0.69126 | 0.04169 |
| 75 | 0.011 | 0.065 | 0.000 | 0.02090 | 0.60391 | 0.32890 |
| 76 | 0.042 | 0.021 | 0.000 | 0.02146 | 0.00420 | 0.95404 |
| 77 | 0.008 | 0.076 | 0.000 | 0.02188 | 0.57834 | 0.96296 |
| 78 | 0.030 | 0.150 | 0.009 | 0.02210 | 0.00851 | 0.25752 |
| 79 | 0.050 | 0.050 | 0.000 | 0.02254 | 0.59983 | 0.95843 |
| 80 | 0.059 | 0.074 | 0.012 | 0.02452 | 0.27041 | 0.12731 |
| 81 | 0.040 | 0.025 | 0.000 | 0.02494 | 0.30467 | 0.19851 |
| 82 | 0.050 | 0.047 | 0.000 | 0.02532 | 0.32106 | 0.47874 |
| 83 | 0.025 | 0.042 | 0.000 | 0.02682 | 0.15950 | 0.08878 |
| 84 | 0.056 | 0.063 | 0.000 | 0.02722 | 0.79786 | 0.74613 |
| 85 | 0.020 | 0.113 | 0.000 | 0.02729 | 0.27017 | 0.10654 |
| 86 | 0.067 | 0.104 | 0.029 | 0.02734 | 0.59010 | 0.16336 |
| 87 | 0.000 | 0.063 | 0.000 | 0.02815 | 0.98381 | 0.97542 |
| 88 | 0.065 | 0.113 | 0.000 | 0.02872 | 0.30080 | 0.42892 |
| 89 | 0.010 | 0.050 | 0.000 | 0.02933 | 0.46779 | 0.82988 |
| 90 | 0.113 | 0.100 | 0.025 | 0.03071 | 0.00337 | 0.00000 |
| 91 | 0.018 | 0.081 | 0.000 | 0.03118 | 0.04749 | 0.00098 |
| 92 | 0.014 | 0.066 | 0.000 | 0.03190 | 0.74698 | 0.62135 |
| 93 | 0.005 | 0.138 | 0.000 | 0.03215 | 0.03660 | 0.87436 |
| 94 | 0.048 | 0.125 | 0.043 | 0.03245 | 0.00471 | 0.00001 |
| 95 | 0.022 | 0.070 | 0.001 | 0.03490 | 0.47515 | 0.61294 |
| 96 | 0.009 | 0.091 | 0.000 | 0.03816 | 0.14785 | 0.41409 |
| 97 | 0.000 | 0.088 | 0.000 | 0.03821 | 0.23210 | 0.50694 |
| 98 | 0.006 | 0.103 | 0.000 | 0.03855 | 0.00439 | 0.01617 |
| 99 | 0.046 | 0.054 | 0.000 | 0.03877 | 0.49619 | 0.72943 |
| 100 | 0.017 | 0.066 | 0.000 | 0.04167 | 0.79797 | 0.81991 |
| 101 | 0.050 | 0.031 | 0.000 | 0.04189 | 0.24118 | 0.93977 |
| 102 | 0.031 | 0.203 | 0.000 | 0.04203 | 0.00443 | 0.12932 |
| 103 | 0.018 | 0.179 | 0.043 | 0.04206 | 0.00035 | 0.00040 |
| 104 | 0.029 | 0.073 | 0.000 | 0.04311 | 0.62445 | 0.18113 |
| 105 | 0.021 | 0.125 | 0.000 | 0.04368 | 0.00589 | 0.00868 |
| 106 | 0.116 | 0.125 | 0.027 | 0.04581 | 0.05495 | 0.00009 |
| 107 | 0.024 | 0.092 | 0.000 | 0.04705 | 0.03043 | 0.23893 |
| 108 | 0.045 | 0.008 | 0.000 | 0.04776 | 0.00000 | 0.00658 |
| 109 | 0.020 | 0.050 | 0.000 | 0.04779 | 0.61717 | 0.01894 |
| 110 | 0.059 | 0.107 | 0.015 | 0.04840 | 0.84733 | 0.06185 |
| 111 | 0.025 | 0.031 | 0.000 | 0.04924 | 0.70570 | 0.06008 |
| 112 | 0.040 | 0.050 | 0.000 | 0.05027 | 0.89626 | 0.41400 |
| 113 | 0.031 | 0.115 | 0.000 | 0.05115 | 0.00217 | 0.49133 |
| 114 | 0.005 | 0.013 | 0.000 | 0.05360 | 0.05680 | 0.72269 |
| 115 | 0.016 | 0.093 | 0.001 | 0.05546 | 0.01173 | 0.29622 |
| 116 | 0.013 | 0.094 | 0.000 | 0.05661 | 0.05492 | 0.36536 |
| 117 | 0.016 | 0.060 | 0.000 | 0.05690 | 0.95068 | 0.19315 |
| 118 | 0.217 | 0.147 | 0.049 | 0.05698 | 0.00000 | 0.00000 |

-continued

| | | | | | | |
|---|---|---|---|---|---|---|
| 119 | 0.035 | 0.031 | 0.000 | 0.05889 | 0.10905 | 0.59078 |
| 120 | 0.021 | 0.058 | 0.000 | 0.05908 | 0.58438 | 0.01312 |
| 121 | 0.080 | 0.027 | 0.000 | 0.05952 | 0.00000 | 0.00001 |
| 122 | 0.031 | 0.047 | 0.000 | 0.06085 | 0.91905 | 0.26127 |
| 123 | 0.013 | 0.046 | 0.000 | 0.06151 | 0.19789 | 0.69126 |
| 124 | 0.028 | 0.063 | 0.000 | 0.06231 | 0.41805 | 0.17702 |
| 125 | 0.008 | 0.082 | 0.000 | 0.06377 | 0.11838 | 0.14383 |
| 126 | 0.021 | 0.082 | 0.007 | 0.06792 | 0.84332 | 0.93964 |
| 127 | 0.025 | 0.021 | 0.000 | 0.07104 | 0.07945 | 0.10112 |
| 128 | 0.013 | 0.080 | 0.000 | 0.07190 | 0.51773 | 0.62080 |
| 129 | 0.015 | 0.113 | 0.000 | 0.07234 | 0.37625 | 0.20872 |
| 130 | 0.016 | 0.039 | 0.000 | 0.07723 | 0.12619 | 0.48614 |
| 131 | 0.028 | 0.102 | 0.000 | 0.07866 | 0.03037 | 0.15798 |
| 132 | 0.036 | 0.045 | 0.019 | 0.08101 | 0.47189 | 0.03046 |
| 133 | 0.045 | 0.100 | 0.000 | 0.08357 | 0.26942 | 0.76490 |
| 134 | 0.012 | 0.072 | 0.000 | 0.08367 | 0.51165 | 0.24502 |
| 135 | 0.043 | 0.085 | 0.000 | 0.08686 | 0.51095 | 0.37846 |
| 136 | 0.024 | 0.065 | 0.012 | 0.08712 | 0.41154 | 0.04982 |
| 137 | 0.029 | 0.045 | 0.000 | 0.09053 | 0.66530 | 0.22260 |
| 138 | 0.050 | 0.063 | 0.009 | 0.09076 | 0.87053 | 0.96927 |
| 139 | 0.046 | 0.083 | 0.000 | 0.09248 | 0.64737 | 0.01000 |
| 140 | 0.042 | 0.000 | 0.029 | 0.09735 | 0.05014 | 0.09524 |
| 141 | 0.006 | 0.063 | 0.000 | 0.10148 | 0.15804 | 0.00010 |
| 142 | 0.010 | 0.100 | 0.000 | 0.10715 | 0.04221 | 0.30553 |
| 143 | 0.017 | 0.063 | 0.000 | 0.10731 | 0.45417 | 0.02634 |
| 144 | 0.000 | 0.073 | 0.000 | 0.10744 | 0.29340 | 0.11987 |
| 145 | 0.018 | 0.050 | 0.000 | 0.10843 | 0.80649 | 0.00490 |
| 146 | 0.029 | 0.073 | 0.000 | 0.10860 | 0.97247 | 0.18279 |
| 147 | 0.024 | 0.057 | 0.000 | 0.11075 | 0.98596 | 0.05983 |
| 148 | 0.023 | 0.073 | 0.006 | 0.11182 | 0.58280 | 0.43378 |
| 149 | 0.013 | 0.088 | 0.000 | 0.11539 | 0.00502 | 0.00005 |
| 150 | 0.022 | 0.059 | 0.000 | 0.11749 | 0.74407 | 0.02655 |
| 151 | 0.133 | 0.133 | 0.012 | 0.11791 | 0.01136 | 0.00000 |
| 152 | 0.003 | 0.047 | 0.000 | 0.11971 | 0.87638 | 0.11243 |
| 153 | 0.050 | 0.042 | 0.000 | 0.12081 | 0.31080 | 0.40430 |
| 154 | 0.025 | 0.045 | 0.000 | 0.12123 | 0.15843 | 0.35845 |
| 155 | 0.023 | 0.025 | 0.000 | 0.12266 | 0.14627 | 0.06157 |
| 156 | 0.040 | 0.022 | 0.010 | 0.12443 | 0.00226 | 0.54240 |
| 157 | 0.026 | 0.097 | 0.000 | 0.12454 | 0.00102 | 0.09879 |
| 158 | 0.029 | 0.052 | 0.000 | 0.12900 | 0.22779 | 0.08945 |
| 159 | 0.018 | 0.100 | 0.000 | 0.12911 | 0.49227 | 0.67922 |
| 160 | 0.033 | 0.063 | 0.000 | 0.12919 | 0.69275 | 0.24178 |
| 161 | 0.005 | 0.080 | 0.000 | 0.13076 | 0.08392 | 0.03514 |
| 162 | 0.027 | 0.058 | 0.000 | 0.13686 | 0.98920 | 0.29436 |
| 163 | 0.032 | 0.108 | 0.000 | 0.13854 | 0.36497 | 0.04398 |
| 164 | 0.054 | 0.063 | 0.000 | 0.14045 | 0.43890 | 0.10024 |
| 165 | 0.005 | 0.000 | 0.000 | 0.14058 | 0.02490 | 0.46424 |
| 166 | 0.050 | 0.102 | 0.027 | 0.14335 | 0.33135 | 0.15651 |
| 167 | 0.031 | 0.139 | 0.000 | 0.14412 | 0.00007 | 0.03739 |
| 168 | 0.030 | 0.038 | 0.000 | 0.14525 | 0.54138 | 0.28737 |
| 169 | 0.025 | 0.107 | 0.000 | 0.15224 | 0.01412 | 0.10864 |
| 170 | 0.000 | 0.100 | 0.000 | 0.15384 | 0.16273 | 0.16433 |
| 171 | 0.020 | 0.088 | 0.000 | 0.15508 | 0.23890 | 0.07712 |
| 172 | 0.013 | 0.075 | 0.000 | 0.15602 | 0.08296 | 0.00029 |
| 173 | 0.013 | 0.023 | 0.000 | 0.15663 | 0.04633 | 0.00000 |
| 174 | 0.010 | 0.025 | 0.000 | 0.15837 | 0.74245 | 0.00357 |
| 175 | 0.016 | 0.037 | 0.000 | 0.15955 | 0.10765 | 0.43759 |
| 176 | 0.005 | 0.013 | 0.000 | 0.16320 | 0.46997 | 0.00144 |
| 177 | 0.025 | 0.000 | 0.000 | 0.16445 | 0.26379 | 0.18377 |
| 178 | 0.014 | 0.028 | 0.000 | 0.16655 | 0.08650 | 0.59884 |
| 179 | 0.054 | 0.073 | 0.022 | 0.16893 | 0.83695 | 0.56495 |
| 180 | 0.050 | 0.078 | 0.022 | 0.17014 | 0.88867 | 0.40591 |
| 181 | 0.000 | 0.031 | 0.000 | 0.17060 | 0.58174 | 0.54924 |
| 182 | 0.018 | 0.071 | 0.000 | 0.17227 | 0.95304 | 0.82874 |
| 183 | 0.033 | 0.125 | 0.000 | 0.17412 | 0.05590 | 0.56584 |
| 184 | 0.050 | 0.071 | 0.000 | 0.17445 | 0.59106 | 0.01278 |
| 185 | 0.034 | 0.039 | 0.000 | 0.17496 | 0.31060 | 0.64225 |
| 186 | 0.023 | 0.107 | 0.000 | 0.17822 | 0.03641 | 0.51953 |
| 187 | 0.006 | 0.031 | 0.000 | 0.18073 | 0.41320 | 0.38140 |
| 188 | 0.044 | 0.104 | 0.002 | 0.18105 | 0.40386 | 0.00014 |
| 189 | 0.023 | 0.060 | 0.005 | 0.18315 | 0.54097 | 0.01195 |
| 190 | 0.045 | 0.050 | 0.000 | 0.18414 | 0.38135 | 0.41604 |
| 191 | 0.072 | 0.087 | 0.018 | 0.18556 | 0.01425 | 0.00007 |
| 192 | 0.054 | 0.010 | 0.000 | 0.18604 | 0.00259 | 0.04452 |
| 193 | 0.050 | 0.000 | 0.000 | 0.18636 | 0.00860 | 0.27305 |
| 194 | 0.075 | 0.104 | 0.043 | 0.18760 | 0.23061 | 0.02703 |
| 195 | 0.018 | 0.074 | 0.000 | 0.18799 | 0.04332 | 0.00092 |
| 196 | 0.013 | 0.054 | 0.000 | 0.18947 | 0.52931 | 0.00001 |
| 197 | 0.021 | 0.116 | 0.000 | 0.18957 | 0.01363 | 0.10957 |

-continued

| | | | | | | |
|---|---|---|---|---|---|---|
| 198 | 0.009 | 0.072 | 0.002 | 0.19120 | 0.37384 | 0.02195 |
| 199 | 0.031 | 0.092 | 0.000 | 0.19342 | 0.57240 | 0.03398 |
| 200 | 0.019 | 0.016 | 0.000 | 0.19688 | 0.06546 | 0.70963 |
| 201 | 0.039 | 0.111 | 0.000 | 0.19910 | 0.04960 | 0.53925 |
| 202 | 0.005 | 0.063 | 0.000 | 0.20039 | 0.78808 | 0.29891 |
| 203 | 0.015 | 0.000 | 0.000 | 0.20189 | 0.09865 | 0.01894 |
| 204 | 0.015 | 0.150 | 0.000 | 0.20189 | 0.02007 | 0.01894 |
| 205 | 0.025 | 0.078 | 0.000 | 0.20429 | 0.99130 | 0.21830 |
| 206 | 0.009 | 0.047 | 0.000 | 0.20711 | 0.60835 | 0.35208 |
| 207 | 0.050 | 0.025 | 0.000 | 0.21582 | 0.05416 | 0.28073 |
| 208 | 0.009 | 0.073 | 0.000 | 0.21609 | 0.19591 | 0.00018 |
| 209 | 0.017 | 0.031 | 0.007 | 0.21616 | 0.04427 | 0.31773 |
| 210 | 0.030 | 0.040 | 0.006 | 0.21620 | 0.03795 | 0.84925 |
| 211 | 0.013 | 0.117 | 0.000 | 0.21872 | 0.01766 | 0.70075 |
| 212 | 0.034 | 0.055 | 0.000 | 0.22009 | 0.11870 | 0.13982 |
| 213 | 0.006 | 0.109 | 0.000 | 0.22034 | 0.26105 | 0.39687 |
| 214 | 0.014 | 0.063 | 0.000 | 0.22199 | 0.44292 | 0.00401 |
| 215 | 0.059 | 0.359 | 0.082 | 0.22404 | 0.00000 | 0.00004 |
| 216 | 0.033 | 0.010 | 0.000 | 0.22855 | 0.00394 | 0.11588 |
| 217 | 0.050 | 0.063 | 0.000 | 0.24046 | 0.72117 | 0.43844 |
| 218 | 0.036 | 0.052 | 0.006 | 0.24437 | 0.12177 | 0.41139 |
| 219 | 0.013 | 0.125 | 0.043 | 0.24604 | 0.05674 | 0.01689 |
| 220 | 0.010 | 0.175 | 0.000 | 0.24818 | 0.00334 | 0.70762 |
| 221 | 0.005 | 0.038 | 0.000 | 0.24870 | 0.54640 | 0.19851 |
| 222 | 0.000 | 0.050 | 0.000 | 0.25016 | 0.78384 | 0.08170 |
| 223 | 0.042 | 0.021 | 0.000 | 0.25073 | 0.17545 | 0.97542 |
| 224 | 0.013 | 0.016 | 0.000 | 0.25147 | 0.13295 | 0.69509 |
| 225 | 0.033 | 0.042 | 0.000 | 0.25208 | 0.23957 | 0.18828 |
| 226 | 0.034 | 0.047 | 0.000 | 0.25854 | 0.32941 | 0.85606 |
| 227 | 0.022 | 0.049 | 0.000 | 0.25896 | 0.17138 | 0.85294 |
| 228 | 0.013 | 0.063 | 0.065 | 0.26082 | 0.88005 | 0.00186 |
| 229 | 0.046 | 0.125 | 0.000 | 0.26354 | 0.03650 | 0.25182 |
| 230 | 0.013 | 0.083 | 0.000 | 0.26708 | 0.50393 | 0.47148 |
| 231 | 0.021 | 0.071 | 0.000 | 0.26981 | 0.83901 | 0.54622 |
| 232 | 0.025 | 0.038 | 0.000 | 0.26983 | 0.53539 | 0.29891 |
| 233 | 0.000 | 0.025 | 0.000 | 0.27098 | 0.90753 | 0.00089 |
| 234 | 0.053 | 0.028 | 0.015 | 0.27123 | 0.00000 | 0.12156 |
| 235 | 0.042 | 0.063 | 0.000 | 0.27246 | 0.79783 | 0.70059 |
| 236 | 0.005 | 0.063 | 0.000 | 0.27662 | 0.67082 | 0.19851 |
| 237 | 0.005 | 0.075 | 0.000 | 0.27662 | 0.38460 | 0.19851 |
| 238 | 0.025 | 0.102 | 0.000 | 0.27685 | 0.05340 | 0.35208 |
| 239 | 0.083 | 0.177 | 0.057 | 0.27705 | 0.03023 | 0.53439 |
| 240 | 0.035 | 0.121 | 0.000 | 0.27742 | 0.02768 | 0.05558 |
| 241 | 0.020 | 0.050 | 0.000 | 0.27845 | 0.92556 | 0.10149 |
| 242 | 0.019 | 0.094 | 0.000 | 0.28231 | 0.39328 | 0.68881 |
| 243 | 0.029 | 0.051 | 0.005 | 0.29192 | 0.20921 | 0.55174 |
| 244 | 0.015 | 0.063 | 0.000 | 0.29877 | 0.61973 | 0.01289 |
| 245 | 0.014 | 0.053 | 0.006 | 0.29909 | 0.79282 | 0.00093 |
| 246 | 0.029 | 0.103 | 0.000 | 0.29943 | 0.04753 | 0.77217 |
| 247 | 0.045 | 0.050 | 0.000 | 0.30121 | 0.42497 | 0.50451 |
| 248 | 0.041 | 0.058 | 0.000 | 0.30584 | 0.28865 | 0.12742 |
| 249 | 0.035 | 0.063 | 0.000 | 0.30591 | 0.40617 | 0.10207 |
| 250 | 0.013 | 0.141 | 0.000 | 0.30697 | 0.04146 | 0.05611 |
| 251 | 0.095 | 0.122 | 0.050 | 0.31066 | 0.24386 | 0.00835 |
| 252 | 0.035 | 0.088 | 0.000 | 0.32051 | 0.36874 | 0.94107 |
| 253 | 0.000 | 0.063 | 0.000 | 0.32488 | 0.18259 | 0.00295 |
| 254 | 0.000 | 0.031 | 0.000 | 0.32488 | 0.89232 | 0.00295 |
| 255 | 0.023 | 0.055 | 0.000 | 0.32688 | 0.88862 | 0.08570 |
| 256 | 0.009 | 0.074 | 0.000 | 0.32826 | 0.22549 | 0.05225 |
| 257 | 0.005 | 0.063 | 0.000 | 0.33654 | 0.72508 | 0.12531 |
| 258 | 0.021 | 0.063 | 0.000 | 0.33950 | 0.63054 | 0.15262 |
| 259 | 0.020 | 0.088 | 0.000 | 0.34027 | 0.10857 | 0.96046 |
| 260 | 0.049 | 0.146 | 0.006 | 0.34145 | 0.00006 | 0.25221 |
| 261 | 0.021 | 0.042 | 0.000 | 0.34253 | 0.25513 | 0.68243 |
| 262 | 0.021 | 0.036 | 0.000 | 0.34439 | 0.45188 | 0.16111 |
| 263 | 0.000 | 0.042 | 0.000 | 0.34503 | 0.82367 | 0.13637 |
| 264 | 0.035 | 0.075 | 0.000 | 0.34677 | 0.68708 | 0.00272 |
| 265 | 0.019 | 0.094 | 0.000 | 0.35301 | 0.26225 | 0.10870 |
| 266 | 0.019 | 0.088 | 0.026 | 0.35469 | 0.15903 | 0.00002 |
| 267 | 0.009 | 0.103 | 0.000 | 0.35514 | 0.00284 | 0.00632 |
| 268 | 0.005 | 0.038 | 0.000 | 0.35786 | 0.57454 | 0.20093 |
| 269 | 0.025 | 0.091 | 0.000 | 0.35888 | 0.08153 | 0.38328 |
| 270 | 0.014 | 0.098 | 0.000 | 0.36129 | 0.28061 | 0.53891 |
| 271 | 0.036 | 0.045 | 0.000 | 0.36200 | 0.39501 | 0.93264 |
| 272 | 0.018 | 0.051 | 0.000 | 0.36490 | 0.59248 | 0.38946 |
| 273 | 0.018 | 0.067 | 0.000 | 0.36721 | 0.26604 | 0.01881 |
| 274 | 0.018 | 0.098 | 0.000 | 0.36740 | 0.03964 | 0.07222 |
| 275 | 0.039 | 0.018 | 0.000 | 0.36781 | 0.01092 | 0.23508 |
| 276 | 0.017 | 0.099 | 0.000 | 0.36795 | 0.03866 | 0.51208 |

-continued

| | | | | | | |
|---|---|---|---|---|---|---|
| 277 | 0.024 | 0.082 | 0.000 | 0.37037 | 0.15033 | 0.73903 |
| 278 | 0.016 | 0.035 | 0.000 | 0.37088 | 0.36837 | 0.00422 |
| 279 | 0.000 | 0.047 | 0.000 | 0.37631 | 0.84014 | 0.07298 |
| 280 | 0.000 | 0.031 | 0.000 | 0.37790 | 0.70713 | 0.06008 |
| 281 | 0.020 | 0.025 | 0.000 | 0.38591 | 0.34374 | 0.13521 |
| 282 | 0.025 | 0.000 | 0.000 | 0.38723 | 0.02764 | 0.48180 |
| 283 | 0.046 | 0.021 | 0.000 | 0.38786 | 0.03107 | 0.34087 |
| 284 | 0.025 | 0.059 | 0.024 | 0.39142 | 0.82914 | 0.00001 |
| 285 | 0.040 | 0.038 | 0.000 | 0.39274 | 0.28309 | 0.98151 |
| 286 | 0.005 | 0.075 | 0.000 | 0.40112 | 0.15248 | 0.00357 |
| 287 | 0.034 | 0.117 | 0.000 | 0.40201 | 0.02655 | 0.49158 |
| 288 | 0.025 | 0.063 | 0.000 | 0.40450 | 0.82223 | 0.42774 |
| 289 | 0.016 | 0.063 | 0.000 | 0.40456 | 0.61602 | 0.02024 |
| 290 | 0.017 | 0.077 | 0.000 | 0.40678 | 0.18209 | 0.12955 |
| 291 | 0.025 | 0.075 | 0.000 | 0.41027 | 0.52307 | 0.41005 |
| 292 | 0.020 | 0.069 | 0.000 | 0.41169 | 0.93852 | 0.81159 |
| 293 | 0.020 | 0.119 | 0.000 | 0.41348 | 0.00251 | 0.10186 |
| 294 | 0.030 | 0.075 | 0.009 | 0.41401 | 0.97196 | 0.91852 |
| 295 | 0.020 | 0.125 | 0.000 | 0.41703 | 0.03149 | 0.68257 |
| 296 | 0.013 | 0.086 | 0.000 | 0.41822 | 0.64743 | 0.29530 |
| 297 | 0.030 | 0.113 | 0.000 | 0.42725 | 0.84925 | 0.34749 |
| 298 | 0.013 | 0.078 | 0.000 | 0.43273 | 0.41122 | 0.00842 |
| 299 | 0.038 | 0.100 | 0.017 | 0.43292 | 0.62927 | 0.61655 |
| 300 | 0.028 | 0.140 | 0.000 | 0.44217 | 0.00038 | 0.66264 |
| 301 | 0.018 | 0.080 | 0.000 | 0.44604 | 0.33603 | 0.09047 |
| 302 | 0.035 | 0.000 | 0.000 | 0.44876 | 0.01256 | 0.96541 |
| 303 | 0.009 | 0.117 | 0.000 | 0.45177 | 0.00957 | 0.11783 |
| 304 | 0.000 | 0.135 | 0.000 | 0.45506 | 0.00452 | 0.01644 |
| 305 | 0.023 | 0.085 | 0.000 | 0.45807 | 0.35320 | 0.85391 |
| 306 | 0.020 | 0.049 | 0.000 | 0.46045 | 0.38390 | 0.02293 |
| 307 | 0.006 | 0.102 | 0.000 | 0.47564 | 0.05373 | 0.03579 |
| 308 | 0.039 | 0.107 | 0.000 | 0.47590 | 0.23069 | 0.43666 |
| 309 | 0.032 | 0.107 | 0.000 | 0.47614 | 0.19555 | 0.90440 |
| 310 | 0.011 | 0.021 | 0.000 | 0.48388 | 0.09402 | 0.14560 |
| 311 | 0.006 | 0.109 | 0.000 | 0.48557 | 0.05983 | 0.17265 |
| 312 | 0.050 | 0.083 | 0.000 | 0.48567 | 0.96231 | 0.04559 |
| 313 | 0.000 | 0.000 | 0.000 | 0.48646 | 0.45288 | 0.03556 |
| 314 | 0.000 | 0.125 | 0.022 | 0.48646 | 0.05020 | 0.02436 |
| 315 | 0.000 | 0.125 | 0.000 | 0.48646 | 0.10655 | 0.03556 |
| 316 | 0.005 | 0.000 | 0.000 | 0.49420 | 0.05467 | 0.09497 |
| 317 | 0.004 | 0.146 | 0.000 | 0.50036 | 0.00472 | 0.03774 |
| 318 | 0.031 | 0.063 | 0.000 | 0.50251 | 0.65174 | 0.76665 |
| 319 | 0.047 | 0.075 | 0.000 | 0.50409 | 0.06246 | 0.00000 |
| 320 | 0.050 | 0.038 | 0.009 | 0.51163 | 0.10472 | 0.60740 |
| 321 | 0.006 | 0.063 | 0.000 | 0.51321 | 0.66087 | 0.32094 |
| 322 | 0.033 | 0.080 | 0.027 | 0.51555 | 0.36573 | 0.00948 |
| 323 | 0.033 | 0.125 | 0.000 | 0.51984 | 0.19368 | 0.92185 |
| 324 | 0.033 | 0.052 | 0.000 | 0.52125 | 0.24640 | 0.20117 |
| 325 | 0.020 | 0.113 | 0.000 | 0.52233 | 0.04449 | 0.30659 |
| 326 | 0.021 | 0.152 | 0.000 | 0.53028 | 0.03239 | 0.74664 |
| 327 | 0.017 | 0.083 | 0.000 | 0.53207 | 0.16100 | 0.13344 |
| 328 | 0.000 | 0.000 | 0.000 | 0.53308 | 0.26379 | 0.18377 |
| 329 | 0.016 | 0.056 | 0.000 | 0.53493 | 0.60987 | 0.00831 |
| 330 | 0.010 | 0.063 | 0.000 | 0.53686 | 0.17297 | 0.00018 |
| 331 | 0.018 | 0.075 | 0.000 | 0.53874 | 0.54478 | 0.46033 |
| 332 | 0.030 | 0.091 | 0.000 | 0.53960 | 0.49213 | 0.94697 |
| 333 | 0.018 | 0.063 | 0.019 | 0.54851 | 0.55397 | 0.01550 |
| 334 | 0.010 | 0.038 | 0.000 | 0.54949 | 0.86764 | 0.04664 |
| 335 | 0.031 | 0.053 | 0.000 | 0.55999 | 0.22789 | 0.63380 |
| 336 | 0.023 | 0.059 | 0.000 | 0.56418 | 0.51376 | 0.71754 |
| 337 | 0.022 | 0.063 | 0.000 | 0.56498 | 0.75617 | 0.22788 |
| 338 | 0.033 | 0.073 | 0.000 | 0.56578 | 0.70668 | 0.03867 |
| 339 | 0.008 | 0.056 | 0.000 | 0.56926 | 0.67544 | 0.01359 |
| 340 | 0.000 | 0.075 | 0.000 | 0.56966 | 0.30182 | 0.01894 |
| 341 | 0.038 | 0.016 | 0.000 | 0.57311 | 0.00246 | 0.08463 |
| 342 | 0.005 | 0.075 | 0.000 | 0.57396 | 0.16232 | 0.00549 |
| 343 | 0.028 | 0.097 | 0.000 | 0.57399 | 0.04814 | 0.27043 |
| 344 | 0.016 | 0.117 | 0.000 | 0.57479 | 0.00701 | 0.30927 |
| 345 | 0.010 | 0.038 | 0.000 | 0.57733 | 0.89980 | 0.03303 |
| 346 | 0.018 | 0.119 | 0.000 | 0.57801 | 0.02773 | 0.42832 |
| 347 | 0.013 | 0.031 | 0.000 | 0.57996 | 0.26904 | 0.32350 |
| 348 | 0.060 | 0.006 | 0.000 | 0.58190 | 0.00002 | 0.00216 |
| 349 | 0.006 | 0.047 | 0.000 | 0.59812 | 0.84325 | 0.02299 |
| 350 | 0.013 | 0.063 | 0.000 | 0.60291 | 0.98122 | 0.12855 |
| 351 | 0.016 | 0.091 | 0.000 | 0.60661 | 0.01199 | 0.09457 |
| 352 | 0.008 | 0.042 | 0.000 | 0.61688 | 0.80480 | 0.03120 |
| 353 | 0.025 | 0.045 | 0.000 | 0.61920 | 0.45404 | 0.60865 |
| 354 | 0.033 | 0.021 | 0.000 | 0.62267 | 0.15955 | 0.75106 |
| 355 | 0.013 | 0.063 | 0.000 | 0.62577 | 0.55784 | 0.18377 |

-continued

| | | | | | | |
|---|---|---|---|---|---|---|
| 356 | 0.032 | 0.091 | 0.000 | 0.62683 | 0.04274 | 0.29098 |
| 357 | 0.082 | 0.107 | 0.029 | 0.63032 | 0.38178 | 0.00266 |
| 358 | 0.003 | 0.046 | 0.000 | 0.63047 | 0.85436 | 0.00010 |
| 359 | 0.030 | 0.131 | 0.017 | 0.64049 | 0.04005 | 0.29687 |
| 360 | 0.025 | 0.038 | 0.000 | 0.64551 | 0.50853 | 0.39977 |
| 361 | 0.018 | 0.091 | 0.000 | 0.64824 | 0.02013 | 0.09628 |
| 362 | 0.035 | 0.072 | 0.013 | 0.65115 | 0.71967 | 0.94722 |
| 363 | 0.007 | 0.063 | 0.000 | 0.65348 | 0.49810 | 0.05644 |
| 364 | 0.018 | 0.035 | 0.004 | 0.65552 | 0.00591 | 0.00002 |
| 365 | 0.015 | 0.038 | 0.000 | 0.65643 | 0.70665 | 0.12531 |
| 366 | 0.058 | 0.104 | 0.058 | 0.66142 | 0.98960 | 0.26299 |
| 367 | 0.052 | 0.034 | 0.000 | 0.66215 | 0.00576 | 0.01137 |
| 368 | 0.030 | 0.163 | 0.000 | 0.66584 | 0.01626 | 0.86538 |
| 369 | 0.019 | 0.063 | 0.000 | 0.66789 | 0.68610 | 0.19690 |
| 370 | 0.016 | 0.108 | 0.012 | 0.67094 | 0.03930 | 0.06299 |
| 371 | 0.005 | 0.125 | 0.000 | 0.67664 | 0.00990 | 0.06041 |
| 372 | 0.022 | 0.067 | 0.000 | 0.67996 | 0.51033 | 0.09373 |
| 373 | 0.009 | 0.031 | 0.000 | 0.68133 | 0.24138 | 0.00003 |
| 374 | 0.042 | 0.097 | 0.000 | 0.68499 | 0.76566 | 0.05591 |
| 375 | 0.017 | 0.021 | 0.000 | 0.68512 | 0.22171 | 0.79848 |
| 376 | 0.033 | 0.042 | 0.014 | 0.68905 | 0.16524 | 0.80319 |
| 377 | 0.029 | 0.080 | 0.000 | 0.69080 | 0.82010 | 0.41665 |
| 378 | 0.025 | 0.063 | 0.000 | 0.70243 | 0.90117 | 0.66520 |
| 379 | 0.020 | 0.138 | 0.000 | 0.70868 | 0.00725 | 0.42851 |
| 380 | 0.017 | 0.021 | 0.000 | 0.71377 | 0.39782 | 0.24178 |
| 381 | 0.044 | 0.063 | 0.000 | 0.71737 | 0.53128 | 0.17192 |
| 382 | 0.013 | 0.125 | 0.000 | 0.72168 | 0.00257 | 0.03397 |
| 383 | 0.017 | 0.036 | 0.007 | 0.73228 | 0.12196 | 0.02080 |
| 384 | 0.024 | 0.044 | 0.000 | 0.73256 | 0.29761 | 0.29755 |
| 385 | 0.025 | 0.097 | 0.000 | 0.73331 | 0.11994 | 0.58902 |
| 386 | 0.018 | 0.044 | 0.000 | 0.73666 | 0.57207 | 0.12653 |
| 387 | 0.158 | 0.153 | 0.048 | 0.73794 | 0.02871 | 0.00093 |
| 388 | 0.031 | 0.016 | 0.000 | 0.73868 | 0.05815 | 0.47968 |
| 389 | 0.025 | 0.031 | 0.000 | 0.74033 | 0.21815 | 0.85767 |
| 390 | 0.020 | 0.042 | 0.000 | 0.74279 | 0.23146 | 0.11749 |
| 391 | 0.023 | 0.105 | 0.008 | 0.74326 | 0.02352 | 0.08875 |
| 392 | 0.029 | 0.107 | 0.000 | 0.75162 | 0.19189 | 0.54007 |
| 393 | 0.017 | 0.063 | 0.000 | 0.75404 | 0.64784 | 0.15262 |
| 394 | 0.032 | 0.048 | 0.008 | 0.76200 | 0.00643 | 0.47223 |
| 395 | 0.017 | 0.063 | 0.014 | 0.76623 | 0.78849 | 0.01259 |
| 396 | 0.050 | 0.250 | 0.033 | 0.77068 | 0.00195 | 0.40243 |
| 397 | 0.000 | 0.088 | 0.000 | 0.77497 | 0.10161 | 0.00830 |
| 398 | 0.025 | 0.094 | 0.000 | 0.77602 | 0.38252 | 0.80404 |
| 399 | 0.035 | 0.075 | 0.000 | 0.77946 | 0.93861 | 0.49207 |
| 400 | 0.010 | 0.000 | 0.000 | 0.77955 | 0.06988 | 0.04606 |
| 401 | 0.010 | 0.025 | 0.000 | 0.77955 | 0.46246 | 0.04606 |
| 402 | 0.020 | 0.013 | 0.000 | 0.78052 | 0.07461 | 0.50252 |
| 403 | 0.013 | 0.051 | 0.003 | 0.78556 | 0.88935 | 0.00559 |
| 404 | 0.031 | 0.082 | 0.000 | 0.78831 | 0.61891 | 0.47180 |
| 405 | 0.016 | 0.042 | 0.000 | 0.78900 | 0.09626 | 0.00465 |
| 406 | 0.031 | 0.016 | 0.000 | 0.78980 | 0.05059 | 0.43332 |
| 407 | 0.010 | 0.088 | 0.000 | 0.79643 | 0.39142 | 0.12531 |
| 408 | 0.058 | 0.125 | 0.000 | 0.79654 | 0.28677 | 0.06295 |
| 409 | 0.016 | 0.039 | 0.000 | 0.80101 | 0.48691 | 0.27328 |
| 410 | 0.018 | 0.102 | 0.000 | 0.80151 | 0.03618 | 0.25568 |
| 411 | 0.028 | 0.132 | 0.024 | 0.81269 | 0.00673 | 0.00968 |
| 412 | 0.021 | 0.099 | 0.000 | 0.81294 | 0.04875 | 0.36772 |
| 413 | 0.019 | 0.047 | 0.000 | 0.81562 | 0.75051 | 0.38140 |
| 414 | 0.035 | 0.113 | 0.000 | 0.82537 | 0.08167 | 0.99310 |
| 415 | 0.026 | 0.073 | 0.000 | 0.82863 | 0.60871 | 0.95353 |
| 416 | 0.050 | 0.042 | 0.000 | 0.84212 | 0.02446 | 0.00290 |
| 417 | 0.019 | 0.051 | 0.000 | 0.84499 | 0.73711 | 0.13168 |
| 418 | 0.008 | 0.081 | 0.000 | 0.84648 | 0.06666 | 0.00452 |
| 419 | 0.029 | 0.054 | 0.000 | 0.84779 | 0.54879 | 0.79096 |
| 420 | 0.025 | 0.038 | 0.000 | 0.85460 | 0.20627 | 0.52500 |
| 421 | 0.025 | 0.080 | 0.000 | 0.85627 | 0.50475 | 0.70735 |
| 422 | 0.000 | 0.156 | 0.000 | 0.85664 | 0.04034 | 0.09510 |
| 423 | 0.023 | 0.065 | 0.000 | 0.86083 | 0.99103 | 0.15072 |
| 424 | 0.013 | 0.094 | 0.000 | 0.86126 | 0.14473 | 0.05072 |
| 425 | 0.018 | 0.094 | 0.000 | 0.86312 | 0.22629 | 0.28027 |
| 426 | 0.013 | 0.000 | 0.000 | 0.86864 | 0.00995 | 0.09168 |
| 427 | 0.021 | 0.089 | 0.000 | 0.87219 | 0.14799 | 0.45199 |
| 428 | 0.005 | 0.000 | 0.000 | 0.87795 | 0.09496 | 0.02531 |
| 429 | 0.013 | 0.081 | 0.000 | 0.88059 | 0.07959 | 0.02755 |
| 430 | 0.025 | 0.000 | 0.000 | 0.88119 | 0.02331 | 0.96205 |
| 431 | 0.036 | 0.148 | 0.050 | 0.88608 | 0.00002 | 0.00006 |
| 432 | 0.005 | 0.025 | 0.000 | 0.88638 | 0.51822 | 0.02712 |
| 433 | 0.000 | 0.083 | 0.000 | 0.89151 | 0.14993 | 0.02634 |
| 434 | 0.025 | 0.100 | 0.000 | 0.89564 | 0.18901 | 0.76737 |

-continued

| | | | | | | |
|---|---|---|---|---|---|---|
| 435 | 0.011 | 0.086 | 0.002 | 0.90183 | 0.00080 | 0.00000 |
| 436 | 0.023 | 0.078 | 0.000 | 0.90333 | 0.28646 | 0.77891 |
| 437 | 0.021 | 0.063 | 0.000 | 0.90702 | 0.86839 | 0.77523 |
| 438 | 0.021 | 0.036 | 0.000 | 0.90976 | 0.14194 | 0.64487 |
| 439 | 0.011 | 0.082 | 0.000 | 0.91143 | 0.05741 | 0.00268 |
| 440 | 0.015 | 0.063 | 0.000 | 0.91521 | 0.67996 | 0.28737 |
| 441 | 0.025 | 0.025 | 0.000 | 0.91767 | 0.14135 | 0.76209 |
| 442 | 0.019 | 0.069 | 0.000 | 0.92005 | 0.73186 | 0.57669 |
| 443 | 0.023 | 0.113 | 0.000 | 0.92076 | 0.04033 | 0.89701 |
| 444 | 0.046 | 0.045 | 0.000 | 0.92192 | 0.02154 | 0.01164 |
| 445 | 0.033 | 0.058 | 0.000 | 0.92504 | 0.14949 | 0.21095 |
| 446 | 0.108 | 0.215 | 0.158 | 0.92648 | 0.00059 | 0.00000 |
| 447 | 0.018 | 0.034 | 0.000 | 0.92796 | 0.19315 | 0.23193 |
| 448 | 0.020 | 0.039 | 0.000 | 0.92888 | 0.04082 | 0.03393 |
| 449 | 0.004 | 0.031 | 0.000 | 0.92990 | 0.73921 | 0.01161 |
| 450 | 0.025 | 0.038 | 0.000 | 0.93035 | 0.30875 | 0.99310 |
| 451 | 0.038 | 0.208 | 0.007 | 0.93481 | 0.00069 | 0.95055 |
| 452 | 0.033 | 0.031 | 0.000 | 0.94099 | 0.11813 | 0.72422 |
| 453 | 0.013 | 0.047 | 0.022 | 0.94155 | 0.86146 | 0.00511 |
| 454 | 0.033 | 0.063 | 0.000 | 0.94574 | 0.74604 | 0.48180 |
| 455 | 0.050 | 0.063 | 0.043 | 0.94598 | 0.41907 | 0.10857 |
| 456 | 0.022 | 0.028 | 0.000 | 0.95616 | 0.07091 | 0.75304 |
| 457 | 0.022 | 0.045 | 0.000 | 0.95622 | 0.26281 | 0.40030 |
| 458 | 0.022 | 0.085 | 0.003 | 0.95630 | 0.05799 | 0.16891 |
| 459 | 0.000 | 0.141 | 0.000 | 0.95914 | 0.00935 | 0.01524 |
| 460 | 0.025 | 0.094 | 0.000 | 0.96078 | 0.74050 | 0.94029 |
| 461 | 0.028 | 0.088 | 0.000 | 0.96080 | 0.24029 | 0.71768 |
| 462 | 0.025 | 0.074 | 0.000 | 0.96521 | 0.83987 | 0.74482 |
| 463 | 0.029 | 0.115 | 0.000 | 0.96529 | 0.05667 | 0.84317 |
| 464 | 0.010 | 0.075 | 0.009 | 0.97792 | 0.39415 | 0.02207 |
| 465 | 0.019 | 0.063 | 0.000 | 0.98245 | 0.74836 | 0.14794 |
| 466 | 0.025 | 0.163 | 0.000 | 0.98690 | 0.17514 | 0.96394 |
| 467 | 0.050 | 0.063 | 0.000 | 0.98750 | 0.34568 | 0.07429 |
| 468 | 0.010 | 0.075 | 0.000 | 0.99542 | 0.34309 | 0.09635 |

| Reference Coordinates | Nearest Gene | Percent Non-Reference | Total Non-Reference Bases | Plus Strand Oligonucleotide | SEQ ID NOS: |
|---|---|---|---|---|---|
| chr8: 128,750,550-128,750,699 | MYC | 0 | 0 | CGACTACGACTCGGTGCAGCCGTATTTCTACTGCGACGAGGAGGAGAACTT CTACCAGCAGCAGCAGCAGAGCGAGCTGCAGCCCCCGGCGCCCAGCGAGG ATATCTGGAAGAAATTCGAGCTGCTGCCCACCCCGCCCCTGTCCCCTAG | 1331 |
| chr8: 128,750,550-128,750,699 | MYC | 2.5 | 4 | CGACTACGACTCGGTGCAGCCGTAGTTCTACTGCGACGAGGAGGAAAACT TCTACCAGCAGCAGCAGCAGAGCGAGCTGCAGCCCCTGGCGCCCAGCGAG GATATCTGGAAGAACTTCGAGCTGCTGCCCACCCCGCCCCTGTCCCCTAG | 1332 |
| chr8: 128,750,550-128,750,699 | MYC | 5 | 8 | CGACTACGACTCGGTGCAGCCGTAGTTCTACTGCGACGAGGAGGAATACTT CTACCAGCAGCAGCCGCAGAGCGAGCTGCAGCCCCTGGCGCCCAGCGAGG GTATCTGGAAGAACTTCGAGCTACTGCCCACCCCGCCCCTGTCCCCTAG | 1333 |
| chr8: 128,750,550-128,750,699 | MYC | 7.5 | 11 | CGACTACGACTCGTTGCAGCCGTAGTTCTACTGCGACGAGGAGGAATACTT CTACCAGCAGCAGCCGCAGAGCGAGCTGCAGCGCCTGGCGCCCAGCGAGG GTATCTGGAAGAACTTCGAGCTACAGCCCACCCCGCCCCTGTCCCCTAG | 1334 |
| chr8: 128,750,550-128,750,699 | MYC | 10 | 15 | CGACTACGACTCGTTGCAGCCGTAGATCTACTGCGACGAGGAGGAATACTT CTACCTGCAGCAGCCGCAGAGCGAGCTGCAGCGCCTGGCGCCCAGCGAGC GTATCTGGAAGAACTTCGAGCTACAGCCCACCCCGCCCTTGTCCCCTAG | 1335 |
| chr8: 128,750,550-128,750,699 | MYC | 12.5 | 19 | CGACAACGACTCGTTGCACCCGTAGATCTACTGCGACGAGGAGGAATACTT CTACCTGCAGCAGCCGCAGAGCGAGCTGCAGCGCCTGGCGCCCAGCGAGC GTATCTGAAAGAACTTCGAGCTACAGCCCACGCCGCCCTTGTCCCCTAG | 1336 |
| chr8: 128,750,550-128,750,699 | MYC | 15 | 23 | CGACAACGACTCGTTGCACCCGTAGATCTACTGCGACGAGGAGGAATACTT CTACCTGCAGCAGCCGCAGAGCGAGCTGCAGCGCCTGGCGCCCAGCGAGC GTATCTGAAAGAACTTCGAGCTACAGCCCACGCCGCCCTTGTCCCCTAG | 1337 |
| chr3: 187,443,281-187,443,430 | BCL6 | 0 | 0 | GCTCACCTGTACAAATCTGGCTCCGCAGGTTTCGCATTTGTAGGGCTTCTCT CCAGAGTGAATTCGAGTGTGGGTTTTCAGGTTGGCTGGCCGGTTGAACTGG GCCCCACAGATGTTGCAACGATAGGGTTTCTCACCTATTACCAAGAA | 1338 |
| chr3: 187,443,281-187,443,430 | BCL6 | 2.5 | 4 | GCTCACCTGTACAAATCTGCCTCCGCAGGTTTCGCATTTGTAGGGCTCCTCT CCAGAGTGAATTCGAGTGTGGGTTTTCAGGTTGGCTGGGCGGTTGAACTGG GCCCCACAGATGTTGCAACGCTAGGGTTTCTCACCTATTACCAAGAA | 1339 |

-continued

| | | | | | |
|---|---|---|---|---|---|
| chr3: 187,443,281-187,443,430 | BCL6 | 5 | 8 | GCTCACCTGTACAAATCTGCCTCCGCAGGTTTCGCCTTTGTAGGGCTCCTCTCCAGAGTGAATTCGAGTGTAGGITTCAAGTTGGCTGGGCGGTTGAACTGGGCCCCACGGATGTTGCAACGCTAGGGTTTCTCACCTATTACCAAGAA | 1340 |
| chr3: 187,443,281-187,443,430 | BCL6 | 7.5 | 11 | GCTCACCTGTACAAATCTGCCTCCGCCGGTTTCGCCITTTTAGGGCTCCTCTCCAGAGTGAATTCGAGTGTAGGTTTTCAAGTTGGCTGGGCGGTTGAACTGGGCCCCACGGATGTTGCAACGCTAGGGTTTCTCACCTATTTCCAAGAA | 1341 |
| chr3: 187,443,281-187,443,430 | BCL6 | 10 | 15 | GCTCACCTGTACAAGTCTGCCTCCGCCGGTTACGCCTTTTTAGGGCTCCTCTCCAGAGTGAATTCGAGTGTAGGTTTTCAAGTTGGCTGGGCGGTTGAACTGGGCTCCACGGATGTTGCAACGCTAGGGATTCTCACCTATTTCCAAGAA | 1342 |
| chr3: 187,443,281-187,443,430 | BCL6 | 12.5 | 19 | GCTCACCTGGACAAGTCTGCCTCCGCCGGTTACGACTTTTTAGGGCTCCTCTCCAGAGTGAATTCGAGTGTAGGCTTTCAAGTTGGCTGGGCGGTTGAACTGGGCTCCACGGCTGTTGCAACGCTAGGGATTCTCACCTATTTOCAAGAA | 1343 |
| chr3: 187,443,281-187,443,430 | BCL6 | 15 | 23 | GCTCACCTGGACAAGTCTGCCTCCGCCGGTTACGACTTTTTAGGGCACCTCTCCAGAGTGAATTCGAGTGTAGGCTTTCAAGTTGGCTGGGAGCTTGAACTGGGCTGCACGGCTGTTGCAACGCTAGGGATTCTCACCTATITCCAAGAA | 1344 |
| — | — | — | — | Minus Strand Oligonucleotide | |
| chr8: 128,750,550-128,750,699 | MYC | 0 | 0 | CTAGGGGACAGGGGCGGGGTGGGCAGCAGCTCGAATTTCTTCCAGATATCCTCGCTGGGCGCCGGGGGCTGCAGCTCGCTCTGCTGCTGCTGCTGGTAGAAGTTCTCCTCCTCGTCGCAGTAGAAATACGGCTGCACCGAGTCGTAGTCG | 1345 |
| chr8: 128,750,550-128,750,699 | MYC | 2.5 | 4 | CTAGGGGACAGGGGCGGGGTGGGCAGCAGCTCGAAGTTCTTCCAGATATCCTCGCTGGGCGCCAGGGGCTGCAGCTCGCTCTGCTGCTGCTGCTGGTAGAAGTTTTCCTCCTCGTCGCAGTAGAACTACGGCTGCACCGAGTCGTAGTCG | 1346 |
| chr8: 128,750,550-128,750,699 | MYC | 5 | 8 | CTAGGGGACAGGGGCGGGGTGGGCAGTAGCTCGAAGTTCTTCCAGATACCCTCGCTGGGCGCCAGGGGCTGCAGCTCGCTCTGCGGCTGCTGCTGGTAGAAGTATTCCTCCTCGTCGCAGTAGAACTACGGCTGCACCGAGTCGTAGTCG | 1347 |
| chr8: 128,750,550-128,750,699 | MYC | 7.5 | 11 | CTAGGGGACAGGGGCGGGGTGGGCTGTAGCTCGAAGTTCTTCCAGATACCCTCGCTGGGCGCCAGGCGCTGCAGCTCGCTCTGCGGCTGCTGCTGGTAGAAGTATTCCTCCTCGTCGCAGTAGAACTACGGCTGCAACGAGTCGTAGTCG | 1348 |
| chr8: 128,750,550-128,750,699 | MYC | 10 | 15 | CTAGGGGACAAGGGCGGGGTGGGCTGTAGCTCGAAGTTCTTCCAGATACGCTCGCTGGGCGCCAGGCGCTGCAGCTCGCTCTGCGGCTGCTGCAGGTAGAAGTATTCCTCCTCGTCGCAGTAGATCTACGGCTGCAACGAGTCGTAGTCG | 1349 |
| chr8: 128,750,550-128,750,699 | MYC | 12.5 | 19 | CTAGGGGACAAGGGCGGCGTGGGCTGTAGCTCGAAGTTCTTTCAGATACGCTCGCTGGGCGCCAGGCGCTGCAGCTCGCTCTGCGGCTGCTGCAGGTAGAAGTATTCCTCCTCGTCGCAGTAGATCTACGGGTGCAACGAGTCGTTGTCG | 1350 |
| chr8: 128,750,550-128,750,699 | MYC | 15 | 23 | CTAGGCGACAAGGGCGGCGTGGGCTGTAGCTCGAAGTTCTTTCAGATACGCTCGGTGGGCGCCAGGCGCTGCAGCACGCTCTGCGGCTGCTGCAGGTAGAAGTATTCCTCCTCGTCGCAGTAGATCTACGGGTGCAACGAGTCGCTGTCG | 1351 |
| chr3: 187,443,281-187,443,430 | BCL6 | 0 | 0 | TTCTTGGTAATAGGTGAGAAACCCTATCGTTGCAACATCTGTGGGGCCCAGTTCAACCGGCCAGCCAACCTGAAAACCCACACTCGAATTCACTCTGGAGAGAAGCCCTACAAATGCGAAACCTGCGGAGCCAGATTTGTACAGGTGAGC | 1352 |
| chr3: 187,443,281-187,443,430 | BCL6 | 2.5 | 4 | TTCTTGGTAATAGGTGAGAAACCCTAGCGTTGCAACATCTGTGGGGCCCAGTTCAACCGCCCAGCCAACCTGAAAACCCACACTCGAATTCACTCTGGAGAGGAGCCCTACAAATGCGAAACCTGCGGAGGCAGATTTGTACAGGTGAGC | 1353 |
| chr3: 187,443,281-187,443,430 | BCL6 | 5 | 8 | TTCTTGGTAATAGGTGAGAAACCCTAGCGTTGCAACATCCGTGGGGCCCAGTTCAACCGCCCAGCCAACTTGAAAACCTACACTCGAATTCACTCTGGAGAGGAGCCCTACAAAGGCGAAACCTGCGGAGGCAGATTTGTACAGGTGAGC | 1354 |
| chr3: 187,443,281-187,443,430 | BCL6 | 7.5 | 11 | TTCTTGGAAATAGGTGAGAAACCCTAGCGTTGCAACATCCGTGGGGCCCAGTTCAACCGCCCAGCCAACTTGAAAACCTACACTCGAATTCACTCTGGAGAGGAGCCCTAAAAAGGCGAAACCGGCGGAGGCAGATTTGTACAGGTGAGC | 1355 |
| chr3: 187,443,281-187,443,430 | BCL6 | 10 | 15 | TTCTTGGAAATAGGTGAGAATCCCTAGCGTTGCAACATCCGTGGAGCCCAGTTCAACCGCCCAGCCAACTTGAAAACCTACACTCGAATTCACTCTGGAGAGGAGCCCTAAAAAGGCGTAACCGGCGGAGGCAGACTTGTACAGGTGAGC | 1356 |
| chr3: 187,443,281-187,443,430 | BCL6 | 12.5 | 19 | TTCTTGGAAATAGGTGAGAATCCCTAGCGTTGCAACAGCCGTGGAGCCCAGTTCAACCGCCCAGCCAACTTGAAAGCCTACACTCGAATTCACTCTGGAGAGGAGCCCTAAAAAGTCGTAACCGGCGGAGGCAGACTTGTCCAGGTGAGC | 1357 |
| chr3: 187,443,281-187,443,430 | BCL6 | 15 | 23 | TTCTTGGAAATAGGTGAGAATCCCTAGCGTTGCAACAGCCGTGCAGCCCAGTTCAAGCTCCCAGCCAACTTGAAAGCCTACACTCGAATTCACTCTGGAGAGGTGCCCTAAAAAGTCGTAACCGGCGGAGGCAGACTTGTCCAGGTGAGC | 1358 |

| Name | Sequence | SEQ ID NOs. |
|---|---|---|
| TNFRSF14_chr1: 2488006-2488106 | TCTCTTCTGGCCCACAGCCGCAGCAATGGCGCTGAGTTCCTCTGCTGGAGTTCATCCTGCTAGCTGGGTTC CCGAGCTGCCGGTCTGAGCCTGAGGCATG | 1 |
| TNFRSF14_chr1: 2488106-2488206 | GAGCCTCCTGGAGACTGGGGGCCTCCTCCCTGGAGATCCACCCCCAAAACCGACGTCTTGAGGCTGGTGA GCCCCCGAGCCTCCTCTCCGTCTGCTCGCA | 2 |
| TNFRSF14_chr1: 2488206-2488306 | GATCCCAGTTCTGACCCCAGGGCCTCCCACAGATCTCTTCCCCATGCCCCTGTCCTGGCCGTTGCTGGCTC CGGCGTCCAGCCCGTCCCCTGCTGCCTGG | 3 |
| CSMD2_chr1: 34404022-34404122 | CCATGTTGCTGGCTTACTTGGCATTTCCCATGATCTCACACTGCTGGCTTATTTGGCATTTCCCATGATCCC CTGCTGCTGGTTTACTTGGCATTCCCTA | 4 |
| CSMD2_chr1: 34404122-34404222 | TGATCCCATGTTGCTGGTTTACTTAGCATTTCCCATGATCCCATGTTGCTGGCTTACTTGGCATTTCCCATG ATACCATGTTGCTGGCTTACTTGGCATT | 5 |
| NEGR1_chr1: 72334891-72334991 | ATAGATTAGAGGAAGGAATTCTAGATGAAATTAAGTAAATGAGTTATTTAAGTCAACTAATACAAGTCCT CAAAACTTTGATTATATAGAGAGCTAAACT | 6 |
| NEGR1_chr1: 72334991-72335091 | GATAAATATAGACAAATATAGTGAGCCTATAAATTAAAGCTATACTATGATGAAAAAATAAATGAATAAT TGTGAAATAGCCAAAAATACTAAAATACAG | 7 |
| NEGR1_chr1: 72335051-72335151 | AATGAATAATTGTGAAATAGCCAAAAATACTAAAATACAGCTATAAGGTTAAAAATAAATCTGAATAAAA AATGTAGGAGGGAAAAGTGATTACCTTACC | 8 |
| BCL10_chr1: 85733207-85733307 | GACATGCATCAAATGTAAACAAATGATTACAGCCATTTTATAAAAAGTCATATTCTTTAAAACATTTTTTG TCATCATTAAAAATTAAAAGGCAATAAAG | 9 |
| BCL10_chr1: 85733307-85733407 | TGTCATTGTCGTGAAACAGTACGTGATCTTAAGGGAAGAAACATCTCACTAGAGTTTGCACAAGTTCCTT CTTCTTCTAACTGTAGATCTGGTGGCAAAG | 10 |
| BCL10_chr1: 85733407-85733507 | GAGGAGCCCCTGGGTCCCCAGGTCTGGGAAGTGTAGTTGAAGAGAAGATGGTATTTTCAGTTCTGCCTAC TTCTAGAACAGGCAAATTCAGAGAAGAATT | 11 |
| BCL10_chr1: 85733507-85733607 | AGTAGAAAAAAAGGGCGTCGTGCTGGATTCTCCTTCTGGATGGTACATGACAGTGGATGCCCTCAGTTTT TCAGAGAAATTACTCTCATCTGAATTTGAT | 12 |
| BCL10_chr1: 85733607-85733707 | CTGGAGAGGTTGTTCGTGGCTCCATCTGGAAAAGGTTCACAACTGCTACATTTTAGTCCTACAATAAAATT ATTCAGATGTAAATGAAAAAGTAACTAAA | 13 |
| BTG2_chr1: 203274697-203274797 | ACCCGAGACCTCTCACTGAGCCCGAGCCGCGCGCGACATGAGCCACGGGAAGGGAACCGACATGCTCCC GGAGATCGCCGCCGCCGTGGGCTTCCTCTCC | 14 |
| BTG2_chr1: 203274797-203274897 | AGCCTCCTGAGGACCCGGGGCTGCGTGAGCGAGCAGAGGCTTAAGGTCTTCAGCGGGGCGCTCCAGGAG GCACTCACAGGTGAGCGCATGCCGAGGGGCC | 15 |
| BTG2_chr1: 203274897-203274997 | TGGCGCCACCGGGGGTCGGCCCCATCCCTOCCAGGGCCGTCTTTCTTCTACTCCTGCGGCAGGGTGACCC ACGGGAGCAGCTTTGGGACTCGGTGGCCCT | 16 |

-continued

| Name | Sequence | SEQ ID NOs. |
|---|---|---|
| BTG2_chr1: 203274997-203275097 | CCTCCGACCCCCGGGGCGGCCCGCAGTCCCCAGTTTCCTGGGTCCTCCTCCCCAGCCCTGTGCTCGGGTCT CGGCCGTGGCGGTTCTGATGGGGCGCGCC | 17 |
| BTG2_chr1: 203275097-203275197 | CCTCTACGCTCTCGGAGGCGCAGACCCTGGTCCTGGAGTGCCAGCCCGAGTCCCCAGCTTATGCCCCTGTC TCATTACGGGCTCGTCTCCCTCGCTGGAC | 18 |
| BTG2_chr1: 203275197-203275297 | CCTCGAGATCTTAAGACCCTCGATGGATGTTGTTGCGGGCCGCCCGGTCGGCCGAGGGGTCCCGATGAGG GAAGAAGGTGCAGTCGAGCCTTTTCAACAA | 19 |
| BTG2_chr1: 203275297-203275397 | TTTGGAGTCCCAGTGCGGTTCTTCCTGCCGGTCGGGGTGCGCTGTGCCTGGGGTAGTCCACTGGTTGCTGA CTGGCTTCAAGTTGGAATTTGGGCCCCCT | 20 |
| BTG2_chr1: 203275397-203275497 | TTGTGTTATCTTTGGTTCCCCTTAGCCATCTGCCACCTATTGTGGTAGGGAGGAGAGCCTCGTAGCTCGTG ACCCTGCCGTGCGGGCCTTCAAGTTGGGA | 21 |
| BTG2_chr1: 203275497-203275597 | GGTGAAGAGATAAGCAGCCCGCTCGCTGGCTGGGGAGAGACCTCTCTCCCAGCTGTTTCTAGCTGGTTAC TGTCAGTTTTGGGAAGCGATAGCCATCTCG | 22 |
| BTG2_chr1: 203275597-203275697 | GAACGCACCCACACAGACCCTGCCTTCTGAGGAAAACAGATGTTTCATCAAAACAACCCAGTTTTCACTC CCTTAGGCACTGCTAAGGAAGGTTCTCTGA | 23 |
| BTG2_chr1: 203275697-203275797 | CTCTTCTGAAGGAAGCAGAGGGAACACAGGGTGGGAGGTCCAGTGACTTGCTGTGGACCCAACAATGTTG GCAGCCTTCCTGGCCCTGAAACTTCAGCTC | 24 |
| BTG2_chr1: 203275797-203275897 | ACAGGTCTCCAGAGGCCCTGCCTGGACATGCCAGTCCCAGTCACACCCTTCCCTTGCTTTGGGGGTGTGCC AAAAGCAATACACTGGCCACTAGAGAGTA | 25 |
| BTG2_chr1: 203275897-203275997 | CCCTAGAGCTCTAGAATCCCCTCCCAACACGCACACACACACACACACACACTCTCTCTCTCACACACACA CACTCAGTCACACACACACACACACACAC | 26 |
| ITPKB_chr1: 226923691-226923791 | CTTTCAGATCTTTCGCAGCGTCCCAACAGGGCAAAGGCTCCAGCATTCTGCCAGAAGGAATTCCCGCCTCC ACATTCCCGGTCCCCGGCTGTGCTGAGGG | 27 |
| ITPKB_chr1: 226923791-226923891 | GCTGCCCCCAAGCAAGCCCAGCGTTGGGGACCCTCCCTCCACTCTGTCGGAGAGCTGCCAACGCCCCCCG CCCACGGGGGCCCCACTTCGGGCCTCCTCA | 28 |
| ITPKB_chr1: 226923891-226923991 | GGGCCTACGGAGGCCAGGGCCCTGGGCAGCCTGGACCAGCTCAGGGAATCAGAGGACTCTGCGCTTTGC ACGCTCACAGTCGTCTCCTCTGGCCTTTTGC | 29 |
| ITPKB_chr1: 226923991-226924091 | CCACTTCAGGCTCCCCAGAGCCCGGCATGCCACAGGGCAGATATCCTTTCCCCATCTTCCCAGGGGGTTCT CCATCGCGGGGCCCGCCCCTTTCTGGGGC | 30 |
| ITPKB_chr1: 226924091-226924191 | TGGGCTTGTCTCACTGCCCAGAAACTGCCCCTGCCTCTCCACCAGGGCCTCTGGGGGCTGCAGGTCCTCAA GCTCACGGGCTCTCCCAGACGGCTCAGTG | 31 |
| ITPKB_chr1: 226924191-226924291 | AGGGCAAGATCCTGTGGACGGTGTGGCCCAGTGGATGTAACTCTCGCTGCCACTTCCGTGGCCATCGTTA AGCTAGCTCCGAACAGCCCCAATGAGGGAG | 32 |
| ITPKB_chr1: 226924291-226924391 | CTAGGCAGCTCCGAGTTCCCGGGGTAGGAGAGCCCCTTTTGTCAATTTCCATAGCTGTGGGTGAGCCACA GCGGGGACTGGCAGGGATACCCTTCTCCAT | 33 |

-continued

| Name | Sequence | SEQ ID NOs. |
|---|---|---|
| ITPKB_chr1: 226924391-226924491 | CCTTACAAAAGCGGATGGACCCTGAGCCTCTGATCCTGTAGGGGCAGCCCGGCCGGGAAGAGGTGGCATT CCTTTCTTCACCTGCGAGGAGCATAGGCTG | 34 |
| ITPKB_chr1: 226924491-226924591 | GGCCCTCCTTTCCTCCCGGAGTCGGTTCCTGAAGTCTCTGGACATTGCTCCCCCCAGGACTTTGTCCTCCG TTCCTCGCTCCGGGCGCCCTGAACCAGGA | 35 |
| ITPKB_chr1: 226924591-226924691 | CCCTTCCAGGGGGCTGACTGCTGCTGCGGAAGGGGCACGGGGAGGGCGAGCGAGCCCTGCCCAAACGCG GGCTGCGGGGCGCTTGAATGGCGGAGCTCTG | 36 |
| ITPKB_chr1: 226924691-226924791 | TGCCTGGATGTGCGCCTCAAACATGCCCACTTTCTGGTTCACCTGCACGTTCTGCAACTCGCGCTGCAAGA TCCGCAGCTTCCTCTTGGCCTCCTCCGGC | 37 |
| ITPKB_chr1: 226924791-226924891 | CCTGGCGGGGAGAGGGTACCGGCTGCCACCACCTGCTGCCGGTCCCCTCGCAGGCGACCAGCCCAACTTG GGCTGCTCACGCTACTGCCGCTGCTGCCGC | 38 |
| ITPKB_chr1: 226924891-226924991 | TGCCACTGCCGCTGCTACTATTCAGCCTGCGCCGGCCGCTCCGCCAGCCCCCGGGGCTCCGGGGCTCCTCG GGGGACAGCGACTCGGCTGGGGGGAAGAG | 39 |
| ITPKB_chr1: 226924991-226925091 | GAAAGAGGCGCCTCTCCCGGGGCTGAAAACGCTGCCGGGGCTCAGCACTGCCCTCCTCGGGGGCGGGGG CGTCTCGCTGCCACTGGGCCCCGGGCCOCCG | 40 |
| ITPKB_chr1: 226925091-226925191 | CCGCTCTTCATCTCGTTGGCGCTATTCATGATCACCAGGCTATTGAGCGCATAGCAGTACACAGCCATAGT ACTGGGTCCCGCGCTGCCCGCCGCCGCGG | 41 |
| ITPKB_chr1: 226925191-226925291 | CTCCCGCTCCTGCTCCGCCGCCGGCGCCTCCTCCTCCCGGCGCTCCCGGCTCAGCCCCGGAGGCCCGGCAG CCGCGGCTCCGCGCGCAGATGGGGCGGCA | 42 |
| SLCIA4_chr2: 65258145-65258245 | AAGTGCGAAGGAAGTGTCAGGCTGGATGTCAAAATGAACACCTTGGAGAACTGGATGATGGAACAGACG GTAAAAATCAGCTAAACATCAGAGAAAATGG | 43 |
| SLCIA4_chr2: 65258245-65258345 | AGGAAGAGGTCAAAACTGTGAACAGGAACTAGAAGAAAGTGTAGCAGAAAAAGACTTGTCACAAACTTC GAGAGATTTGGAGAAAATGATGTCAAAACAC | 44 |
| SLCIA4_chr2: 65258345-65258445 | ATCTTCCTCAAGCCCATGCTGAGTATCTCTGATTTGGTTAATTTCTTGGTAAGTGTTCCAAGTACAGACAA CAAAGCAGAAAAGCACTGATTACAGGGAA | 45 |
| SPRED2_chr2: 65593035-65593135 | TATGCAGAATGATCCTTCAGATCATGTGAACGCTATAATTAAATGTTGCTACCAAATCCCCACTACCCTTT CTCCCACCTAGAAAAAGTTAATGCATGAA | 46 |
| SPRED2_chr2: 65593135-65593235 | TTCAGTATGAGCAAATTGTGATTTATAAAAACAAACAAACAAACAAACAAACAAAACCCACCCTATTCAC TCCGTAGGGGAATAAAGCTTTCTTGCATTA | 47 |
| SPRED2_chr2: 65593180-65593280 | AACAAACAAAACCCACCCTATTCACTCCGTAGGGGAATAAAGCTTTCTTGCATTAAGTCACGCATCATGG GGGTAGGAAAAAAGCACAGTACTGAAAGAA | 48 |
| EIF2AK3_chr2: 88906681-88906781 | GTGAAGTGATCCAAATGTAGCCCAGAGATCCTAAAGAAAAAACGATGCTCATGTGTTACAAAACAAAATT TTAAGGCAATCAGTGAGGAATCACAGACAA | 49 |
| EIF2AK3_chr2: 88906781-88906881 | ATTTCCTTAGTGCTTTTATCAAGGTTGAATCTGAATATAAATTACTAGAGGAAAGCAAATCAGATTTCACA TCTGAAAATTAAAAACAAAATTCTTAGCT | 50 |

-continued

| Name | Sequence | SEQ ID NOs. |
|---|---|---|
| IGKC_chr2: 89127261-89127361 | AGGCAACAAAATGAGATCCTGTCCCTAGAAAACATTTCAAAAAATTAACAGCATGGTGACGCACACTTGT AGCCCTAGCTACTTGGGAGGCTGAGTGGGA | 51 |
| IGKC_chr2: 89127461-89127561 | AAGAACTTAAGCAGACTAGGATATAAAGTATAGGAGCGTATTGTGTACAGGAACGGGAAATACTGTTTCC TGGATCTTTTGTTTCACTTACGCACACACC | 52 |
| IGKC_chr2: 89127561-89127661 | CACACCCGCCAGTAGTGTACCAGGTTGCGATGGAAATCTCTCTCTTTCTGTGGATGAGTTTGTGGAAGCCC TTGCTCCAGCATGCCCTCCTTCCTGCCCA | 53 |
| IGKC_chr2: 89127661-89127761 | CCCCTGGACCATTCCTTCCCTTCACAGCACTGTCCCATGGGTAGGCCACAGCCCAGCACAGGCCCCAGCCT GGCGGCTGCAGCAGGAGCCCCATCCCAGG | 54 |
| IGKC_chr2: 89127761-89127861 | GCCTGAGGGGCCATGCGGGGGTCTGGGTGGGAGTGGGAACCGCTGAGGAAGGTGAAGGGAAATATGGTG AGATGACAGGCCCGCTGTCAGGGAGAGTGGG | 55 |
| IGKC_chr2: 89127861-89127961 | AGGAGCCCTGGAGTGCCCTACCTCTGTGGGGCTGGAACTCCCTGTATCCGAGCTAGGGTCTTCCACACGC ATGCTACTACCCCAAGTGCCACAGCTGGAG | 56 |
| IGKC_chr2: 89128431-89128531 | TCATCTCCCACTGGATAACAGTGTTGTCGGGAACTTCCATCCAGCACTGGCGGACACTCCCGTCGCAGCTG CTCCTGACTGAGCAAGTCATTTAAGGGGG | 57 |
| IGKC_chr2: 89128531-89128631 | TCCTTGGCACTCATAAGCACTCACAGAATGGGGCTGGCAGTGCGCCCGGCCTCCCTGGGATGGGTCCAGA ATGGTAGGAAGCGCAGTCCGGGAGGGACCC | 58 |
| IGKC_chr2: 89131726-89131826 | ACTGCTTAGAGCTCTCAGCCCTAGATGGCGTATCACAGTTAATGCTCTATAAAACCCATCATGGCTTTTCC CTAGTAAGCCTCAAATCGCTGCAAGCAAG | 59 |
| IGKC_chr2: 89131826-89131926 | GCTTATATATGAGAGTTTCTGCTGTCTCCTGGAGCCATCTCACCCAAAGCCACTGACTCTGGGAGACCAG CCCAGGCCACAAACCAGCAAAGCACCAGT | 60 |
| IGKC_chr2: 89131926-89132026 | TATAGTTAGAGCTGCATTATAAAGTGGCCAGAGGACATTTCTTTGCAGTGAGATGTGTATCGTGAACGTT TGGGGCCTGTGCTCGCCTAGTCCTCATCTT | 61 |
| IGKC_chr2: 89132026-89132126 | TGCTTTTCTAGGTACACAAAGCCATCCCATGGCTGCAAATGTTAGCTGGGCTGGGCTCCCTACTTGCCTCA AGCCCCTTCATAGACCCTTCAGGCACATG | 62 |
| IGKC_chr2: 89132126-89132226 | CTTTTCTCTGGACGTTTACAGACAGGTCCTCAGAGGTCAGAGCAGGTTGTCCTAGGGAGCAGGGAGGCTT CCTAGGGAGGTCAGACTCCAAATAGTGGAT | 63 |
| IGKC_chr2: 89132226-89132326 | ATGGCAAAAATGCAGCTGCAGACTCATOAGGAGTCGCCCTGGGCTGCCACTAGGGCTCCCACAGTGTGCG CTGCCAACCTGCTGCCCGTGCAGAAACTCT | 64 |
| IGKC_chr2: 89140556-89140656 | CAACTGTGCCCTGCACTGTTAGGGCCCTTGTCAAAACAACACATTTCTCAGTGATTCTGAGACTCTTTCTC TTATCTATAGAAGTCATAACTCAAGAGTA | 65 |
| IGKC_chr2: 89140656-89140756 | AAATCATACCAATATTTTACATAAACCCTAGAATTTTTATAGATCTATTATTTCTTTTTAGAGTACATATTG GAAGTAACTTCACAAGGAACATTTTCTT | 66 |
| IGKC_chr2: 89140886-89140986 | TCTGGTCAAACCACTCCACAAATAAAGTGGACTGATCCTCTTGACTCTATGTGTAAGTGCCCATTGTGTGT GCACAGAGCTGGTGAGAACGGCCATGGTG | 67 |

-continued

| Name | Sequence | SEQ ID NOs. |
| --- | --- | --- |
| IGKC_chr2: 89140986-89141086 | CTAGGTGGGGGTGGTGTTGGTGGAGTTGGACTAGATTATCTGGGATCATGCGAAATGGAAATTCATTTCT AGCTGGCTGGCTTCAGAAGGTGCCATCTCC | 68 |
| IGKC_chr2: 89141086-89141186 | TATTTTATATGAAGCGTGCTTTGGAACTCAGGGCAACGAAGGGTGGGTGTGCTGCACAAGGACAGCAGA AGAGTGAGCTGACTGGTCCCTGAAATCGCA | 69 |
| IGKC_chr2: 89141186-89141286 | GTTGGAAAGTGGATTACCAGTGCAGTAGAACTCTTCACGGAGGCCTGGACCATCAGGTCTAATGGTGTTG TTCCAGGTGGGTGGTCATGTGGAGCAAAAA | 70 |
| IGKC_chr2: 89141286-89141386 | TATTTGAAATCAGCGAGCACGTACCTGAGAGATGACTTTTCCACTTGGGCTAGTCTCTTGATATTTCTGGT CCTGTTTCTTCATCTGTAAACTGGGTTAG | 71 |
| IGKC_chr2: 89157326-89157426 | AAGGAGACCAAGAAGCGTATTTAAAATCTTGATGTTTTGAGTTTCTTCCTAGCTTCCCCCTATTCCTTAAT AAAGTTCTAAATTGTTTTGTTGGAGCTCT | 72 |
| IGKC_chr2: 89157426-89157526 | TTGCAGCCATTCTGAGGGCTTTGCATGCTTTTCTGACCTTGCAGTAAACTCAATGCTTTAGGCAAAGAATG GCCACGTCATCCGACCCCCTCAGAGTTTA | 73 |
| IGKC_chr2: 89157526-89157626 | GAATTCAGAACAGGTCTGAAGAAGACCAGGCAGCGGCTGAGTCAAGGAAAGCCTCCGTCCGCTTTTATTT CCCCTGTGCCTCTTCCAGGACTGTGCTGGG | 74 |
| IGKC_chr2: 89157626-89157726 | ATAACAGGCTCCCGGGGGTTACTTTGGCTGGGCTGGGCTAAAACCTCCCTGCAGAGCAGGCCCTGAGCCC TGCCTCTGCGCCTGGGTGGTGTCAGCCCCT | 75 |
| IGKC_chr2: 89157726-89157826 | CCACCTTCTGACTGTTCCAGCAACTCTCTAAGCCCTCCCAAAGGCCTCAAGGCCTGTAACCATATGCAGCA ATTTTCAGCCATACCAGGAGAGGTCAACT | 76 |
| IGKC_chr2: 89157826-89157926 | GTAATCTTGGCCACCTGCCTAAGAGGAAGTGGCTAGCTTCACTTCTGACCCTCAGCAACTGCCAGGTGGC CTCTTGGAAATCCCCCTCTGGGGGATTCCA | 77 |
| IGKC_chr2: 89157926-89158026 | CCCGTTGGGTGGGAGAGCAGTAGTTAAAATGTAAAATAAGAATCTTTTGCTGGGAGAAGTCAACAGATAG GGAGAAGTCAGCTGATAACAGAAATAGTTT | 78 |
| IGKC_chr2: 89158036-89158136 | TAAAACTAACTTCACTGTTAACCAAGCAGTTCAACATGAAAGACTGATCTCTTATGTTTAATATTTTCTT CTCTTTTAATCTTCATAACTAATTTTTTT | 79 |
| IGKC_chr2: 89358136-89158236 | CAGATAATTGTATAAAATAACCATGGTAGCAAAATAATGTGATCACTGGAAAATAAGCAGGGAAAAACA TGCTATGAAGATACTCCTATCTGGGTGAATT | 80 |
| IGKC_chr2: 89158236-89158336 | CTTGATAGCTTTACATTTTTCATCTGGCATTTAAACATTAAACAGTTAATGTATTTGACATGAAAATTATT TCAAGTTATCTTATTAGTTTTAATAGAGT | 81 |
| IGKC_chr2: 89158336-89158436 | TTAAAAAGTGTTTAAAAGAGTTTTCAAAAGGCTCTAAAATCATTTTGAAATAGTTTAAAACAGTTTTGAAT CGTTGTAAGTTAGTTTTAATAGAGCTTTA | 82 |
| IGKC_chr2: 89158436-89158536 | AAAAGGCCCTAAAATAGTCCTATCAAGTTGTTGCAGACCAAAATAATCTCCTTAAATATCACTTTTGAGAT CAGCTGGGGTAAACGACAGCAACACAATG | 83 |
| IGKC_chr2: 89158536-89158636 | ACAAATCATTAAACTATTTAGAGATTATGAAATTAAAATACTCAGATTAAAATTTTCCTATCACAGAATT AAGGTACTGGAAAATATGTTTAAGTTTTT | 84 |

-continued

| Name | Sequence | SEQ ID NOs. |
|---|---|---|
| IGKJ5_chr2: 89158636-89158736 | ATTAATCACATTGCTATAGGTTTAGATATTTTGTACAACTGAAATAAAATCACACACTGGCAGCTACATTT TTGAAAGTTAAAAACATGGTCACGAATAT | 85 |
| IGKJ5_chr2: 89158736-89158836 | ATCTTATTTTAAAATCAGTTAATATACCTTAATGGTATTTAATGCCAAATTCAAAGTGAATTGATCAAGCC CTCAGTGGCCAGGTCATGGGTGTGATTTT | 86 |
| IGKJ5_chr2: 89158836-89158936 | TACTCTGAAAGAATTACATATTTCTTTCTTTTTGGTTGAGCTTTTGTTATTTAAATACATTTGATGAGAGG ATATTGAAATAATTAAATAGCACTGAAAA | 87 |
| IGKJ5_chr2: 89158936-89159036 | AAAAAAAGCTTTAAATTATTTACAATCCCCTAATGGAAATTTTCACTAATGAGATATCATAATGAATGTGA ATTTTATTTCTGAAATCTCTAATAAATCA | 88 |
| IGKJ5_chr2: 89158941-89159041 | AAGCTTTAAATTATTTACAATCCCCTAATGGAAATTTTCACTAATGAGATATCATAATGAATGTGAATTTT ATTTCTGAAATCTCTAATAAATCAGTCTT | 89 |
| IGKJ5_chr2: 89159041-89159141 | CTCCCTGGTTTTCCCAGCTCAGCGCCCATTACGTTTCTGTTCTCTTTCCCTTAGTGGCATTATTTGTATCAC TGTGCATCAGGAAAGCTGGCTACGGCAG | 90 |
| IGKJ5_chr2: 89159141-89159241 | CATCAATCGGGCAGACACAGGGTGGCCACGGCCACTAGCGGCAAGGCGGCTGCCCOAAGAGCGCOGTGG CATGGCCACCAAAGCCACTCAATCGAGAAAG | 91 |
| IGKJ5_chr2: 89159241-89159341 | ACCGCGGCTCTGTCTACAGCTCGCGGTGCCACGGCCTTCTTGGCAGAATAAAAATGTAGACAAGTAATAA CAGAGGATAATGAAAGAACATACTCTTTAA | 92 |
| IGKJ5_chr2: 89159341-89159441 | AATATTTCCTATTTTTTTCACAGACCCACGGTCATTAAAAAATGCAATTATTTACTTTTTTTCATTTAAACA CATTTCTTTGAGATTGAGCTTTTGGGAA | 93 |
| IGKJ5_chr2: 89159441-89159541 | TAACCACCTTTCCACCATTACAATAAGAGATAATTTCACGTTTAGTCTAATGTACAAATTGGATTTTTAAA AAATGAGCTCTATCTGTGAAGCCCTTATT | 94 |
| IGKJ5_chr2: 89159511-89159611 | AAAATGAGCTCTATCTGTGAAGCCCTTATTCCTATAGAATGTGTCTTTTTGAGTTTATTACTTATTACAGA CTCTAAAAACAACATTGCTGCTGATTTTC | 95 |
| IGKJ5_chr2: 89159611-89159711 | AAGTAAGCTGCCTCTTCTACATAGCAAATAGGTACACTTCACTTTTCCCTGATTTTTCTTAGGGCGTGCTA TTGATTTTTATTGTTGTCTGACAAAATAA | 96 |
| IGKJ5_chr2: 89159711-89159811 | TTTATCAAACAAAAGGGAGAAAGACTAAAAAATGTATTTTTCCACTTTTCTGTATCATGCATAATCAGCAA CAACCAATACAATATTTGGCAAGAGTGAA | 97 |
| IGKJ5_chr2: 89159811-89159911 | CAAAAATAAATTTACTTTTGCTCCTTAGAAATACAAGGGTTCCTTTTTAGTTACACTTTTTTTTTTTACTTT GTGTCATTCAGTTTAGAGCAATTTAATC | 98 |
| IGKJ5_chr2: 89159911-89160011 | TTTTTTTCTCCAAATCCATTTTTGAAGCTGAGTTTAACTTTTGCAACCCATGGCAAATCTTAAATGCCCTCA TTTACCAATCTTTACCAAACTCCTATTT | 99 |
| IGKJ5_chr2: 89160011-89160111 | AAGCCTCTAAAAGTCAATACTGGCCATCAGACCCAAATTTCAGAAGACAATAGTGAAAAATTACTTACGT TTAATCTCCAGTCGTGTCCCTTGGCCGAAG | 100 |
| IGKJ5_chr2: 89160111-89160211 | GTGATCCACAGTGTTAACTTAATTACTTTCCCCTTAACAAAAATCTCTTTTCGCTGTTAATATCACTAACCT GACCGATGCAGAGAAAATCTTGCAATTG | 101 |

-continued

| Name | Sequence | SEQ ID NOs. |
|---|---|---|
| IGKJ4_chr2: 89160211-89160311 | AGATGCCTCACTTAACTGGCTAGCGCTTGGCTGTTCCTTAAGATGAACTAATTTTCTATCCCTTACTCATC TGACTTTTTGAAAGAATCTGGTACTCTTT | 102 |
| IGKJ4_chr2: 89160311-89160411 | GGAATTGACCTGAGCTAATATCTCAAACACAAAAACGCTCCAAATTTAAAACCTTATAAGAAAAAGCATT AGGAAAGTGCACTTACGTTTGATCTCCACC | 103 |
| IGKJ4_chr2: 89160411-89160511 | TTGGTCCCTCCGCCGAAAGTGAGCCACAGTGAGGGATCTCACCCTTTCCCCTCAACAAAAACCTCTCTTGA AGCCAATCATATGAGATAGGCTGCTTGTT | 104 |
| IGKJ4_chr2: 89160511-89160611 | CAGAGAAAAATCTAGCTATTTCTTCCCCATTTCCCCCATGAATCCTATTCTCCTCTCAAACCCAATGATTC GTCTATTTGCTCAGCTTTTTAAGTTCATT | 105 |
| IGKJ3_chr2: 89160611-89160711 | TTCTGGTGTCCTGCTATTTACTTCTGGGTCACCAGGTTTATTCAACCAAAATATCACAAAACTTGCACAAA TGATACAATGGCACTAAAATCTCACGAAT | 106 |
| IGKJ3_chr2: 89160711-89160811 | AATTGAGACAGATGTACTTACGTTTGATATCCACTTTGGTCCCAGGGCCGAAAGTGAATCACAGTGATTC GTCTTAACTTTTCCCTTTACAAAAACCTCC | 107 |
| IGKJ3_chr2: 89160811-89160911 | CTGAAAGCTCAGCAAGCCTCTTTCCCCCAATGAAGTTATTTTGATTTAGAAATCTTAAAAATTAGCCACAA GCTAGCGTCCTGTGGAACAATTTCCCCTC | 108 |
| IGKJ2_chr2: 89160911-89161011 | CTCTGTACCTAACCTGGGAATGAAGTTTGTTAGATCCCTGGCATCCGACTAATGAAAATCCACACAAAGG AACACAAAGTAAACTAATTAGCAACAGTGA | 109 |
| IGKJ2_chr2: 89161011-89161111 | AGAATCAGTGGAAAAAAGTACTTACGTTTGATCTCCAGCTTOGTCCCCTGGCCAAAAGTGTACACACAAT GGTTCCTCTTAACTTCCCTCCTATACAAAA | 110 |
| IGKJ2_chr2: 89161111-89161211 | ACTCCCTTTCTGACAATTGACCAAGGCTCTGTCCAGAACATGTTATGTTCCCCAGGACATTTCTGAAGCTA TTACTTAGACAAGTTATTCTCACCCAATG | 111 |
| IGKJ1_chr2: 89161211-89161311 | ACTGAATCTTGCTTGCTCTTCAAAGAAAATGTGCAATCAATTCTCGAGTTTGACTACAGACTTATCTTTAT CTTTTCCCTGAAGGATATCAGAGGCTGAT | 112 |
| IGKJ1_chr2: 89161311-89161411 | TGCAGAGTCACCTTATAGATCACTTCATAGACACAGGGAACAGAAGACACAGACAACTGAGGAAGCAAA GTTTAAATTCTACTCACGTTTGATTTCCACC | 113 |
| IGKJ1_chr2: 89161411-89161511 | TTGGTCCCTTGGCCGAACGTCCACCACAGTGAGAGCTCTCCATTGTCTTGCTGAACAAAAACCCTTCTCAC CAAAGGGGAACAGAGTCCTGGGTCAGCTG | 114 |
| IGKJ1_chr2: 89161926-89162026 | ATCAACTTAAGGCTCATAACTTTGAAATGCATTTTGAAATGTAGCTCCAGATGGTATACGAAACCAAAGT GAAGACTAATAGAGTAGAAAAGTAGACTTT | 115 |
| IGKJ1_chr2: 89162026-89162126 | ACTTGGTTGGTTTGTCTGTTTTCACAGCACAGGAAGAGCTCAGCTCTTACTGAGCTGGACCAGGCGCATG CCATCTTTGGAGCTGCCATGGAGTCCCAGT | 116 |
| IGKJ1_chr2: 89162126-89162226 | GTTCCATAGTGTTTCCATAGTAATCTCATCAACAACACTGAAGACCTTTTCAGTATTTTCTTTTGAGTCCA GCTCCATTTTTGCAGCCTTGTATCTCTCT | 117 |
| IGKJ1_chr2: 89162776-89162876 | CCGCGCCCAGCCGAGTGCCTGTTTATTTTTACCTGCTTTCAGATTCTCTTCTACCCTTCTAAATTATAAGCT GTTTGATGTTTTATTTGCCCTGTATTTG | 118 |

-continued

| Name | Sequence | SEQ ID NOs. |
|---|---|---|
| IGKJ1_chr2: 89162876-89162976 | GGAGGCTCCGTCCAGTATCTTTACTTAGCAAATGCTTAACAAACATTTTCAGAATAAATAAAAAAAAATA CCTAATTGAAAGTCAATAATAGATCAGAGA | 119 |
| IGKJ1_chr2: 89162976-89163076 | TGCTATCATAGACCAAAGACTAATACTGACTGCCACAACAGTAACTTTTACAACAGAAATCATAACTACA ATTCTAAAGATTAGGGGTAGGTTTATTTGA | 120 |
| IGKJ1_chr2: 89163076-89163176 | TTCTGTCACTGGCAGCTTTGCTAGTTGCCTTGAATAGCAGAATTAGCATTTGGTCTCACCAGAAGATGAGG AAGGAGAGGGATCAAGTTAGAGGTGGAGA | 121 |
| IGKJ1_chr2: 89163176-89163276 | GTTAACATTGGCAAGTGAAATTTAATGTGCAAAATAGCTGACCAAGGGCATAGTCCTTTTTTAAAGGGGA CACAAAGTGATTTTCTCTGCAGACATACAC | 122 |
| IGKJ1_chr2: 89163276-89163376 | GCAATACCAATCATAAAGGGTGACATTTATTGAGCACTTACTAAGTGCCAGACATTGTACATGGATCATC ACATTTAATTATTCCCAAGACTCTATGAAC | 123 |
| IGKJ1_chr2: 89163306-89163406 | TGAGCACTTACTAAGTGCCAGACATTGTACATGGATCATCACATTTAATTATTCCCAAGACTCTATGAACT AGGAACTAATATTATCCCCTACTTTGTAG | 124 |
| IGKJ1_chr2: 89163406-89163506 | GTGCAAAAACTTGAGGGCAGAGAGGTCAAGGAACTGGCTTATGGCAGTAAGTGGCAGAGCTGTGACCTA AACTCAGATCCCATGTTTTTAACTGAACTAT | 125 |
| IGKJ1_chr2: 89163506-89163606 | ATGCAGATTATACTCCAGGAGTAAAGTCACTCAACGGAAGCAACAAGCGTGACAGGGAATGCTGGGATG GGGGAAGGTAAAAGGAACTCCTTAGACTGGG | 126 |
| IGKJ1_chr2: 89163606-89163706 | ATAAGTGTGTACAGACGTATGTATAAGACTACACATGGAAATATTGTTTAAAGAGTGAAAAATAACTAAA ATCCTCATTAATAGGAGTTTGGTTAAACTG | 127 |
| IGKJ1_chr2: 89163706-89163806 | TGCTAGAGCTTTACAATGTAGCACAAAGCAGACATTAAGGGGAAGACGTAGACTTCTATATAGTTACGTG GAAGGTGTTTGTGAAAATGCAGGTCACTGA | 128 |
| IGKJ1_chr2: 89163806-89163906 | AGAGTATGTGTGGTGAGATATCATGATCCCATCTACATTGAATATATATGTATATAAATACGGGCTGAAT TTTAAAAGACATAAATTGTGCTTGGTAGTT | 129 |
| IGKJ1_chr2: 89163861-89163961 | AAATACGGGCTGAATTTTAAAAGACATAAATTGTGCTTGGTAGTTATCTCCTGGGATTGCAGAGGAGGAA CAATGACACTTTATGCCATCTCCTCCTACT | 130 |
| IGKJ1_chr2: 89163961-89164061 | CTTCTGTATGGTGATGTGAATATATTCATTTTATAGTTTTTAGAAATAATAAAACTGTACTAATTTTGAAA AACAGTAAACTCTGACATTGCCTATTAGC | 131 |
| IGKJ1_chr2: 89164061-89164161 | ATTCTCGATATTCCTGTGCAATGCATAAACATAACTTTTTAAAAGATATGTACACACATGTGTGAGTTTTC TTTGTCAAATACTTTTCTATAATCTTTAA | 132 |
| IGKJ1_chr2: 89164161-89164261 | ATCAAGCATGCCAAAAAGGTAAAAGCTTTCCTGTTTCAGTGTAGGAGATAGTCGTCTGCAAAGGAAAGAG ATGTAGGGGATAGAAACAGGAATGAAAAAG | 133 |
| IGKJ1_chr2: 89164261-89164361 | ATGACTGAGCTGTTCGAGGGACTTATGTTCCTAAGTGAGCTAATTGGAAATCTAATATGAACAGTGCAAC CGAATAACTATTGTAAAGCAGTATTTGTAA | 134 |

-continued

| Name | Sequence | SEQ ID NOs. |
|---|---|---|
| IGKJ1_chr2: 89164361-89164461 | ACAATAAAAGATGATTATCATAAGTACCATTGTTGCAAAAACTATTTTATTGATCACATGCAGTGGTGATC TGTAGGAATGATTGTTGTGATGTTTGCTG | 135 |
| IGKJ1_chr2: 89164461-89164561 | TAACATAAAATGAAACATGGGAAGTGGCTGAGATCTTTAGGATGTGTGTGGTTCATTTTTTGAAGCAAA TGTTGTCTCAGAAGCATCTGTGAGACTCTG | 136 |
| IGKJ1_chr2: 89164561-89164661 | CCAGGATCCACCGTTCTACAAAATATCTGTGATGGACATTGATAAGATTGATCTGTTGAGGAAAGGCAAG GTGTCAGTAAGATAGTCTGAGAGCTTCTTG | 137 |
| IGKJ1_chr2: 89164661-89164761 | GATTTCATGTAAAAGAGTGCTGGAAATAGAATTTCTTGGGGAACATTCCAACTAACTCATCACTGAAGGT GCTTTACATTGAACCCTCAGCAAAGTTAGA | 138 |
| IGKJ1_chr2: 89164761-89164861 | TTATCAGAAAAAAAATATAAACTGCTGTGGAGGGGACAGGAAGGAAAGTCAGGGAGGGAGGGGGGCAA GGAGAGAAAGAGCGAGAGAGAGGAGAGAAAGA | 139 |
| IGKJ1_chr2: 89164866-89164966 | AGAGAGGAGAGAGAGAGCACAAGTACACACTTCAATGCACATCTATAAATCATCCTGAAAACTACTGATA AATTATTTTAGCAATGTTCCTCAGATGTAA | 140 |
| IGKJ1_chr2: 89164966-89165066 | CATTTCAAGAAATATCATTTTTGCTTTTATTTGGCATAATTTACTAGCCAATTTAGGAAGTTCCCCTCACA TCAGTAACATACAGTACATCACCCAGTA | 141 |
| IGKJ1_chr2: 89165066-89165166 | TGTCAGAGGACACAATGGCATAAGTTTGCCTTTTGCAAGGTTTGAGGGATGGCCATTTCCCTACCTGACTC AGGAAAGTCTGTAGCTGATATCCATCTTC | 142 |
| IGKJ1_chr2: 89165166-89165266 | AAGTTTGTGGTTCTTTCTCTCTATATATATATTTGAGCTCAGCAGTCATGCTGGAGTCCAGAGTAGGTGAT TCTTTCTGCTTTAGCTTGACTCCTCCTTA | 143 |
| IGKJ1_chr2: 89165191-89165291 | TATATATTTGAGCTCAGCAGTCATGCTGGAGTCCAGAGTAGGTGATTCTTTCTGCTTTAGCTTGACTCCTC CTTAAGATTGTAACTCTCTCAGTTTTACA | 144 |
| IGKJ1_chr2: 89165291-89165391 | TTTTTGTCAGACGTAAGCTGACATTCCACAAGGAGAGGAGGAAATTCTGTGGTTCACATCCAGTGGTGC TTGGAACCTGATTGGTTGTCATTCTTCCAG | 145 |
| IGKJ1_chr2: 89165391-89165491 | CTAGTTTGTCACGAGTGGATATCTGTCCTGGATTCCCAAGGATCAAGGCTGCCCCATTAGCCAGGAAGTA GGGAGATAGAGGAGGTCACTTGAGAAAGAG | 146 |
| IGKJ1_chr2: 89165491-89165591 | CTGCTTCTTTGCCGCCTCCAGGTTGTGTCTGTTTCCTCTCATATCTGAAGACAGATGTGCTGGCAGAAGCA AAGTCCTTTGTCCGGCCACGTGCAAATGC | 147 |
| IGKJ1_chr2: 89165591-89165691 | ATGGGACATAAATATGAACAGAGATTCTTGTCCCACTCTAGAAAATGTAGATGTTCATCTTGTTTCCAAG GGGACAGTAAGGCTGCAGGTGTTTTTTGAC | 148 |
| IGKV4-1_chr2: 89184966-89185066 | CTTTTGTACTCACTGGTTGTTTTTGCATAGGCCCCTCCAGGCCACGACCAGCTGTTTGGATTTTATAAACG GGCCGTTTGCATTGTGAACTGAGCTACAA | 149 |
| IGKV4-1_chr2: 89185066-89185166 | CAGGCAGGCAGGGGCAGCAAGATGGTGTTGCAGACCCAGGTCTTCATTTCTCTGTTGCTCTGGATCTCTG GTGAGGAATTAAAAAGTGCCACAGTCTTTT | 150 |
| IGKV4-1_chr2: 89185166-89185266 | CAGAGTAATATCTGTGTAGAAATAAAAAAAATTAAGATATAGTTGGAAATAATGACTATTTCCAATATGG ATCCAATTATCTGCTGACTTATAATACTAC | 151 |

-continued

| Name | Sequence | SEQ ID NOs. |
|---|---|---|
| IGKV4-1_chr2: 89185196-89185296 | ATTAAGATATAGTTGGAAATAATGACTATTTCCAATATGGATCCAATTATCTGCTGACTTATAATACTACT AGAAAGCAAATTTAAATGACATATTTCAA | 152 |
| IGKV4-1_chr2: 89185296-89185396 | TTATATCTGAGACAGCGTGTATAAGTTTATGTATAATCATTGTCCATTACTGACTACAGGTGCCTACGGGG ACATCGTGATGACCCAGTCTCCAGACTCC | 153 |
| IGKV4-1_chr2: 89185396-89185496 | CTGGCTGTGTCTCTGGGCGAGAGGGCCACCATCAACTGCAAGTCCAGCCAGAGTGTTTTATACAGCTCCA ACAATAAGAACTACTTAGCTTGGTACCAGC | 154 |
| IGKV4-1_chr2: 89185496-89185596 | AGAAACCAGGACAGCCTCCTAAGCTGCTCATTTACTGGGCATCTACCCGGGAATCCGGGGTCCCTGACCG ATTCAGTGGCAGCGGGTCTGGGACAGATTT | 155 |
| IGKV4-1_chr2: 89185596-89185696 | CACTCTCACCATCAGCAGCCTGCAGGCTGAAGATGTGGCAGTTTATTACTGTCAGCAATATTATAGTACTC CTCCCACAGTGCTTCAGCCTCGAACACAA | 156 |
| IGKV4-1_chr2: 89185696-89185796 | ACCTCCTCCCCATACGCTGGGCCAGTAGGTCTTTGCTGCAGCAGCTGCTTCCTCTGCACACAGCCCCCAAC ATGCATGCTTCCTCTGTGTGTTGGGGAGG | 157 |
| IGKV5-2_chr2: 89196226-89196326 | AATACATGAAAACAACTACCGAAATGTTATGAAATTATAGTTTAGTAGAACTAACAAGTGCATTAATGCA AAAGAAAAGTAGGGCTCAGTAATCAGGGAA | 158 |
| IGKV5-2_chr2: 89196326-89196426 | CCAAGTGTGCATTGTAAAAGTGCAGCCTCTCTAACACTGGGTTTCATCACAAGTAACAGAACAGGATGCC TGATGCAGGGAAAAAAGAAAGGCAATTGTT | 159 |
| IGKV5-2_chr2: 89196851-89196951 | GATCTCTGGTAAGAGAAACACTTCCTCTCCTCTGTGCCACCAAGTCCCCTGCATATCCACAAAAATAATAT ATTTTCATAAGGAATTGATTTTCCTCATT | 160 |
| IGKV5-2_chr2: 89196951-89197051 | CTCTGCAAATATGATGCATTTGATTTATGTTTTTTACTTTGCTCCATAATCAGATACCAGGGCAGAAACGA CACTCACGCAGTCTCCAGCATTCATGTCA | 161 |
| IGKV5-2_chr2: 89197051-89197151 | GCGACTCCAGGAGACAAAGTCAACATCTCCTGCAAAGCCAGCCAAGACATTGATGATGATATGAACTGGT ACCAACAGAAACCAGGAGAAGCTGCTATTT | 162 |
| IGKV5-2_chr2: 89197151-89197251 | TCATTATTCAAGAAGCTACTACTCTCGTTCCTGGAATCCCACCTCGATTCAGTGGCAGCGGGTATGGAACA GATTTTACCCTCACAATTAATAACATAGA | 163 |
| IGKV5-2_chr2: 89197251-89197351 | ATCTGAGGATGCTGCATATTACTTCTGTCTACAACATGATAATTTCCCTCTCACAGTGATACACCCTGTTA CAAAAACCTCCAAGTTCTCTCAGTGGGAT | 164 |
| IGKV5-2_chr2: 89214836-89214936 | GCCCTCTGTCCTGGAGACACGGCCAAGGAGGCTGGAGACTGGGTCAGCACAATGTCCCCATTGCAGCCTG AAATGATAAAGACAGATAAATTATATCAGA | 165 |
| IGKV5-2_chr2: 89214936-89215036 | TATACTGAGACTGTCCCCATGTAGGCCATGCATTGGTGACACTTGTAACCACAGTCATATGCAACATCTTG AGTAACCAGAAAACAAAAGATAACTGGGG | 166 |
| IGKV5-2_chr2: 89215036-89215136 | AACTTACAACCTACAATGAGTGCCCTAAATCCAACAACCAAGAATCCAGAGACACAAAAAACAATGATGC CCACATGAGTTTGCCCGATGTTTCCCTATA | 167 |
| IGKV1-5_chr2: 89246681-89246781 | TACCAACACCATCAGAGTGTGGCTGCATCTGAGGACCACTCTCAGCTGATAGAGGCATCAGGAGGAGCAG CTGGGGCAGCCCTGCCTCACACATCTGCTT | 168 |

-continued

| Name | Sequence | SEQ ID NOs. |
|---|---|---|
| IGKV1-5_chr2: 89246786-89246886 | GGGGTTTATGTTCGGGTGTGTAACACTGTGGGAGAATAACTATTATACTGTTGGCAGTAATAAGTTGCAA AATCATCAGGCTGCAGGCTGCTGATGGTGA | 169 |
| IGKV1-5_chr2: 89246911-89247011 | GCCGCTGAACCTTGATGGGACCCCACTTTCTAAACTAGACGCCTTATAGATCAGGAGCTTAGGGGCTTTCC CTGGTTTCTGCTGATACCAGGCCAACCAG | 170 |
| IGKV1-5_chr2: 89247011-89247111 | CTACTAATACTCTGACTGGCCCGGCAAGTGATGGTGACTCTGTCTCCTACAGATGCAGACAGGGTGGAAG GAGACTGGGTCATCTGGATGTCACATTTGG | 171 |
| IGKV1-5_chr2: 89247096-89247196 | GGATGTCACATTTGGCACCTGAGATTGGAAATAGAAACACAAATATTCATACTATTGATCATATTATAGG AAGACTTCCCTGAATAACCAGGCAGTACTG | 172 |
| IGKV1-5_chr2: 89247196-89247296 | AGCACACTGGGCTGAGTAAATTCCTAGTGTTCTCCTTCCTTACCTGGGAGCCAGAGCAGCAGGAGCCCCA GGAGCTGAGCGGGGACCCTCATGTCCATGC | 173 |
| IGKV1-5_chr2: 89247526-89247626 | GGGACTATTTTATTATGAGAAACAATTTTTAGGTATTTTTTTGAGAATTTTAAATATTCCTCAGGAGCCGA TAGAGTAATGTATTTCATTGGTGTATCAG | 174 |
| IGKV1-5_chr2: 89247626-89247726 | GATTATTTAGGAGAATATTCTTGTTTGTAGGAAACACATAGTAAAATGTTAGATGGTAGGATTCTCAAGT CTTCAAAAGACTCTCATAAGATTCCGGGTA | 175 |
| IGKV1-5_chr2: 89247641-89247741 | TATTCTTGTTTGTAGGAAACACATAGTAAAATGTTAGATGGTAGGATTCTCAAGTCTTCAAAAGACTCTCA TAAGATTCCGGGTAGGGAAGGGGGTAATT | 176 |
| IGKV1-5_chr2: 89247831-89247931 | TGTAAGTATTAGGTAATGGTGTTATGCCTTTGTTCTTACTAGTATTAGATCAAGCAATTTATTACAGATAT ACAAAGATGATACCGTGTTGTCTCCATGC | 177 |
| IGKV1-5_chr2: 89247931-89248031 | ATGCAGCACTCACAGATCCACCACTATCAAGAACTGCAGGTCTCTTTAATACCCAGAGACTAAATGAGGT GCACCTTATTCTTGTTTTGGGTACCTTCAT | 178 |
| IGKV1-8_chr2: 89291906-89292006 | TTGGGTGTGTAACACTGTGGGAGGGTAACTATAATACTGTTGACAGTAATAAGTTGCAAAATCTTCAGAC TGCAGGCAGCTGATGGTGAGAGTGAAATCT | 179 |
| IGKV1-8_chr2: 89292131-89292231 | CTGACTCGCCCGACAAGTGATGGTGACTCTGTCTCCTGTAGATGCAGAGAATGAGGATGGAGACTGGGTC ATCCGGATGGCACATCTGGCACCTGAGATT | 180 |
| IGKV3-20_chr2: 89442291-89442391 | CTTTCCCCTGGAGACAAAGACAGGGTGCCTGGAGACTGCGTCAACACAATTTCTCCGGTGGTATCTGAGA TTGGAAATAAAACAGAAAAGTCACCCATGT | 181 |
| IGKV3-20_chr2: 89442391-89442491 | AATCTAAATCAAACCCATTGTCTTCCCAGAAGAGCCAGAATTATTGCTTTATATTGAGCTTTAATTATTGT ATTGACTGAGCAGAGTTGCCAGGTAACAG | 182 |
| IGKV3-20_chr2: 89442491-89442591 | GACTTGAGAGGGTTTTCACTGACATGCAAAACCATCCCATGTTCCCCTCACCTGGGAGCCAGAGTAGCAG GAGGAAGAGAAGCTGCGCTGGGGTTTCCAT | 183 |
| IGKV3-20_chr2: 89442616-89442716 | AGCTCTTCTCCAGAGCTCTGACCCAGGCATTGATATGGGCTCTGGACTGCAGGGCGGCTGGGAGGGACAT GCAAAGCAGCTGGGGCGGGTGCTGGGCTTG | 184 |

-continued

| Name | Sequence | SEQ ID NOs. |
|---|---|---|
| IGKV3-20_chr2: 89442716-89442816 | CAGCTGCAGAGACAATCTGCCTCCCCTTTCTGCTCTCAGCAGCCCATGCCCAGGTGATCAGGCCAGAAAA GGCCGTTGGCTCAGTCTGAGGGTAGAACTT | 185 |
| IGKV3-20_chr2: 89442816-89442916 | CTCCCCTGCGGCCACAGAATTAACCCCTGTGTCCTCTTGTCTCACCATCACCTAGATTGAGCCACAGAAT GTTTGGTACAAGTCTGTTAGAAACAAAAT | 186 |
| IGKV3-20_chr2: 89442916-89443016 | AGAAGGCTGTGGTTTCATTTTTCTCTTTCTGCTCCAACTTGTGCCCAGTCAGCTCCCTAAATGCATGATGG ATCAGGTTGAAAGGAAGAGTCTATTACAA | 187 |
| IGKV3-20_chr2: 89443016-89443116 | CTTTATCTTCCGGATATACTTGTATTTACTTGTTAGTGATCTTTCCTGAGGGTCCAGAAGCTGTCTCATTCT TTGCAGAAATTAAAAGAGTAACATTCAA | 188 |
| IGKV3-20_chr2: 89443116-89443216 | TTAACCTCAGCACTGTGGGTGTGAGGACTTTCACAACTGCACAGATAAGTGAGACCTGGGCTCCAAATCC TCAGGGTAGTGATACCATTTCCCTAAAGAC | 189 |
| IGKV3-20_chr2: 89443216-89443316 | AGAAGATGGTTTTGTCCATGCAGGCAAAGAACTATTTCTTGGGTGATCCTCTAAACTATCCAGTCTTTTTA TTCTGTATAGCTGGTATAGTTTACCCTTA | 190 |
| IGKV2-30_chr2: 89544656-89544756 | GGCTATATATGTATTTGTTCATATTTCAAAAATACACAGTTTCAAAATGGAACTCAAGGGATCCAAGGCTC AAAGGGGTCTCCAGAAGACCCCACACCAT | 191 |
| IGKV2-30_chr2: 89544756-89544856 | CCCCTTTCTGTGTCAGTCTTCCCCAGAGCACAGATCCTTGTTTCTGCTTGAATCTTCCTCACTCTCACAGAT CTGATCATCACATGCCCCACTCTGGAGG | 192 |
| IGKV2-30_chr2: 89544856-89544956 | ACAACATGTGCATGTCCAATACAGGAAAGGAACACACATAGGAGTGTAGTGAGACCCCCAGAGATCACT GTTGTTAGAGGCAGTGGGGCCCCAGAACTCA | 193 |
| DUSP2_chr2: 96810164-96810264 | GGAGCAGCAGCGGGTGGAGACCCCATGGGCTGGCCGAGACAAGAGGACTCCTCAGCCAGTCCTCCTGAC CTGAGACAGGTCTCAGGAATGTGCGGAGGAC | 194 |
| DUSP2_chr2: 96810264-96810364 | ACACCGGGACATACATTTCCCTTCATGCTCCCAACATACACATGCAAACATACACAGACCCATACAGGCA CGCGCGAGCAGCCATGCCCCACCCCCTCCC | 195 |
| DUSP2_chr2: 96810364-96810464 | CCAACACACACACGTATAAAAGTGTGTGTATATGGGCAAACTGCTCGCATCCCCAAATGGCAGGCTCTTT CCCTAGAGGCGCCCAGTCCGCGGCGGGGAG | 196 |
| AFF3_chr2: 100758483-100758583 | AAGCTCACTCACTGGGGCCATTGACTGGGATCCAGTCTGTGGCCATGTCATGGTTTCTATTTTTGAGGTTA TAGCTAATGAGCAACATGAGGTTAAGACA | 197 |
| AFF3_chr2: 100758583-100758683 | CACTTTTCATAAGGCCCCAGCCAGCATCATAAATATGTGTGTGAGCATGTTCACACTCAGGTTATGTCTTC TTTATGTGCACCCTCTACCACACACACAC | 198 |
| DDX18_chr2: 117951919-117952019 | GCCAAGAACCACGACTCTCTAATTTTACTTCCCAGCAGGTATTCAGTGCATAATAGTTCCTACTTAGAAGT ATCATATTTGCCCAAACACAAGGTGATAC | 199 |
| DDX18_chr2: 117952019-117952119 | CCAAAATGAGGTAAGTTTCCTGTTTTCTCAGTGAGATCTTTTGTTGTTGTTGTTGTTGTTGTTGTTTTGTTG TCGATGTTGTTGTTTTTGGTTTTGGTCT | 200 |
| CXCR4_chr2: 136874415-136874515 | CCGGGTCGTCCAGCCCCGGGCCGCCGCGGCTGCCCACTACACCCACGCCAACCGCCCGCAAGCAGCGCTG CAGGGGCTCCGCTGGGCGACACGCCAGGCT | 201 |

-continued

| Name | Sequence | SEQ ID NOs. |
|---|---|---|
| CXCR4_chr2: 136874515-136874615 | CTGTCCCACAGGGTGCTGGGGAGCGACTGGGCGGCTCCGCCGCGAGCGTCTTTGAATTGCGCGCCGCTGC AGGAAACCAAAAACTCCCTAGCAAGAGGGT | 202 |
| CXCR4_chr2: 136874615-136874715 | TTCAAAAGGTTTCTGGAAACCACCGACGGTTAAACATCACAACTGGACTCGGAGAGAGCCAAACGGTTTC CCCACTTGCACCTGCCAGTCTTCGCGGCGG | 203 |
| CXCR4_chr2: 136874715-136874815 | CGACCTGGCAGCCCAGGTGCGGTCTTAACCGCCCCCGCCCCTCACCCCGTACCCGCTCCTATCCCCGGAGC GCAAATCTCAGGGCTGGCAGCTGCOCGGT | 204 |
| CXCR4_chr2: 136874920-136875020 | GGAAGGTTTTCCCCCTCAAACCCAAAGCGCGCOGGCGGATCAACTCCTAGCTGCTGCCACCACTCGATCC CCTCAGAGGATCGGCGCGGTGGGTCCACCC | 205 |
| CXCR4_chr2: 136875020-136875120 | GCCTCTCCCGCCCTCTGCCTACTGTGCTGGGAGACTGGCACAGCTCCGTCGGCCGCACAGAGTTTAACAA ACACGCACCCAGTGTCAAGAACAGTCACCA | 206 |
| CXCR4_chr2: 136875120-136875220 | GGCGCTTAACCCCGAAGTTAAAGCGGGCGCAATCTCCTCCTGGGAACTCAGCCCAGGCACGCCGCCCTCC GCCTCTAAATTCAGACAATGTAACTCGCTC | 207 |
| CXCR4_chr2: 136875220-136875320 | CAAGACATCCCCGCTTCCCCAAGGAAGAGACCGGTGGTCTGAGTCCCGAGGCAGCGCGCACGCCTTCTCT GCACTTGTGCACAGAATGTTCTTACGTTTG | 208 |
| CXCR4_chr2: 136875320-136875420 | CAAACAGCGTGCAAGCCGCCGCGCGCGGCGGGACTCAAGGGGGAGACACATGCAGCCACTGGAACGCTC TTTCCAGTCGTTTCTCCTCGACTCACAGAGA | 209 |
| CXCR4_chr2: 136875420-136875520 | AAAAGATTCCAATCCTGCTCCCCCCCCACCCACCCGCACTATATAGGCATGGTCAAGAAAACTCCTTTCGG TGACCCTTTTTTGGAGTACGGGTACCTCC | 210 |
| CXCR4_chr2: 136875520-136875620 | AATGTCCTGGCCGCTTCTGCCCGCTCGGAGAGGGGCTOCGCTCTAAGTTCAAACGTTTGTACATTTATGAC AAAGCAGGTTGAAACTGGACTTACACTGA | 211 |
| CXCR4_chr2: 136875620-136875720 | TCCCCTCCATGGTAACCGCTGGTTCTCCAGATGCGGTGGCTACTGGAGCACTCACTGCCCTCGGCGTCACTT TGCTACCTGCTGCCGCAGCCAACAAACTG | 212 |
| RFTN1_chr3: 16419204-16419304 | CCCATTGCTGACATACTTACTCCCTGAGAGTGGCTCTTCATGCACCTCCAAGGGGTTGCTCTCCGGTCCAT CCAGTGTCTTGCTCACCCCCTGTGGTGAA | 213 |
| RFTN1_chr3: 16419304-16419404 | AGTTCTCCACCATCTCCCTCTCCGGAGGGTGAGCTGGGCTGCTTGGCGAGGGGCACCTCCCCTCTGGGGC CTGAGCTGGGCTCTGGGCTTTGGTTTCTCC | 214 |
| RFTN1_chr3: 16419404-16419504 | CAGCCGGAGCACTGCACACATCCCCAGTCCCCGGTTTCTCATTCTCCAGTGACGCGTGATCCCCACGTGCG TTTTTTGCATCTCTGGCATCCTCGGTGCT | 215 |
| EIF4E3_chr3: 71551101-71551201 | ATTTGCAGGTTATATCCTGGATGGTGGCACGACAGCCTCCTGGAACACAGAAGGTTGGGAGGCGTGACGCT CATCAGGAAGGCTCTTTTGGGGAGCCAGGA | 216 |
| EIF4E3_chr3: 71551201-71551301 | AGAGTCCCCCAGAAGCCCACTTGGCACCCTATCTATAACAAGTTGCTCTTTAAGAATCATGGGAACTCCA GAATCATTTTCACAAATACCTTCCACTCAT | 217 |

-continued

| Name | Sequence | SEQ ID NOs. |
|---|---|---|
| EIF4E3_chr3: 71551301-71551401 | GATTCAATTAAATGGCAGAAAACACAAACCTTCCGTTCCCACTGGCAAACTGGGTCTAGCTAACTGAGCA CAGCTAGCACAAGGCAGGCCCCCTGCTAGC | 218 |
| EIF4E3_chr3: 71551401-71551501 | AGGGCAAGTGGCGGCCCGGTCCCCAAGGCCCAGGGGAGCCTCTGCAGCTCCCTGGAAGGACGGTCAAGT GAACAGAGAGCTGGCTGCCATCTOGGTTCTT | 219 |
| KLHL6_chr3: 183272308-183272408 | ATGAGATCACCAGTTTATCGTAACTAGAGGCCTCTCCCATCTAAAGCATCTTTGTAACTGCTTTCCCTTTC CCCACACTGCCTACACATAAAGAAGCCCC | 220 |
| KLHL6_chr3: 183272408-183272508 | TAATTTGTAACAAGTCATTTGACAACTCCAGAAGAGGGGCCACATCCTTTTTCTCTATGTCTGTTGATTAA CAAAGACAACATTATGTTTCCAACACCAG | 221 |
| KLHL6_chr3: 183272508-183272608 | TCAGACCAAGGGGGAAAAAAGTCCCCATGACTTCAGTAATTTTCCATCCTTTGGAACAAGGAAATATACA CAAAAGGTTTACTATAGAATGTAAGCATTG | 222 |
| KLHL6_chr3: 183273063-183273163 | AACTGTTCAAGATTGGGCTCTCACACTAACACACCTCTTCCTTGCAACTTGCACCCAATTTGACTCTGGTC CTAGGCATGCTGACCTGAAATAGTTGCTG | 223 |
| KIHL6_chr3: 183273163-183273263 | GCTGCGGCAAGCACCACGCGGTGGCAGGAGAATTCCTGAATGTCCACACACAAGATOACATCTGTCAGAG CGTTTTCCATTCGCAGGGTTTCCAGGCCAT | 224 |
| KLHL6_chr3: 183273263-183273363 | TCTGAAGAATTAAGGAGAGTCCCGCGTCGTCAAATTTGACCTTTTCCCCATTTAAGATCTCGACCAAGTCT CCTGTTTTCTGGGAGGGCTCATCTGTAGA | 225 |
| KLHL6_chr3: 183273363-183273463 | AGGTGCCAGGGGCCCTTCCAAACTCTTCTCGACCACATCACCCATGGTCCAGGCGCCCCTTTGTCCTGCCA TCAACATCGAGACTGAAGGAGCGCCCAAG | 226 |
| ST6GAL1_chr3: 186714604-186714704 | CCTTCCTGTTGGCCACTACATACGTGTCCCCCGCTTCTTGCCCCTCTCTGCTTGGGTCCCTGCTACACTGGT ATCCTGCACTTTCCACCTTGTATTGCCA | 227 |
| ST6GAL1_chr3: 186714704-186714804 | GTTTGTTTCCAAGGCCATCTCCACTTTGAGCTTGTTCATGACCACCTCACACAGCACACTTGGTCTGTGTG GTGGTTTGAGGGGTTCTGTCTGTACACTG | 228 |
| ST6GAL1_chr3: 186714804-186714904 | TGCTTTGGCTGTGTTGGAGGCGGGCAGGTGGGAAGGAAGAAATGTATTCTTGGGGAGATTTGTTTTTAGA GACATGAGACATGGAAAATAGTTAAGTAAT | 229 |
| ST6GAL1_chr3: 186714904-186715004 | AATATAATATGGGAGGCATGGACTATCAGAGGAGGCAGGCAGGACTGCCCAACCTCCTCACTGGGCACGT TACGCTACTTCCTCCTGACCTCTATAGTCC | 230 |
| ST6GAL1_chr3: 186782529-186782629 | CTATCATTGCCCTTTCTTACCTTGATATCCTAAAAAGCTGGTGGTCTGTCTTCTCTATCTTTTGTCCTGGTC AGTTATCCTAACTATTTTGTGTCTGTTT | 231 |
| ST6GAL1_chr3: 186782629-186782729 | CTGTGGATTAGTAAACGGGGTCCCCACCCCCACTCCACAAGGAGAACATCTGGCACCCAGAAGTCACTGA GAGAATAGCTGTTGCTTTGGTAGAATTCTG | 232 |
| ST6GAL1_chr3: 186782729-186782829 | CCTCTGAGTGGCTTGTTCTTTTCCCAGACGGAGAGGTCTCCTGACAGCAGCTCTCTTCTTTTTCTTTTTTTT TTTTTTTGAGACAGAGTTTTGCTCTTGC | 233 |
| ST6GAL1_chr3: 186783389-186783489 | CTCCTGTACCCTGTGGGCCTGAGAGAGGAGACAATGGGACAAGAAGACCCAGTGGCTTCCTTGGAAGCTT TTGTGCTAGCTGGAGAGAGAAGACCTACTT | 234 |

-continued

| Name | Sequence | SEQ ID NOs. |
|---|---|---|
| ST6GAL1_chr3: 186783489-186783589 | CCTATATGCCTAGCAACAGTCCACACTGACTGGACTGCAACCAGGACATTTCCAGATTACTCAGTGGGGC TTATCTTGAAATAATAGTTGATGCCATTTG | 235 |
| ST6GAL1_chr3: 186783589-186783689 | TTAAATATATTATATATACCATCTAAGGGTCTTACATGCCTTCTCTCATTTGATCTTCATGGCAAACCCTGT GAGGTATGACCACCAACCACCATTTTAC | 236 |
| ST6GAL1_chr3: 186783689-186783789 | CTCAGAACTCAGGCTCCCAGAGTTTAAGTTGCTCACAGGAGCCCAGAAAGTAAGCGACAGAGGTGGGATT TGGTTCTAGGTGTTTGCCACCAGCACTTTA | 9377 |
| ST6GAL1_chr3: 186783789-186783889 | AATCACCAAAGCTTTCTGGAAGCTCCAACTTTTCTTCTCAAGATACTGAAAGACAGGTATCTGGATGGGTT GGCAGGGCGGGTGGGAGGTGGGCGAGATT | 238 |
| ST6GAL1_chr3: 186783889-186783989 | TCCATCAACAACGGGTCTAAAACCAGCGATGGTGAGCTGGGTGATTTTGATGGAACCCCTGCCATACAGT CTATTAATATCATAATTGGAGCTAAAATTT | 239 |
| ST6GAL1_chr3: 3186783989-186784089 | AATCATGATGGCAATCATGAGTTCTGGGGCTTCTTGATTTGGGCCAGCAGACACAGTCTCAGTCACTAGTT CTCCGAATCAGAGAAAGGATGCCTTCAGG | 240 |
| ST6GAL1_chr3: 186784089-186784189 | CTGTGTCTTCACATGGCTTTTCCTCTGTGCGTGGTGGAAAGAGAGAGCTCTGCGGGTCTCTTCTTGTTGTA AGGACACTGGCCCCATTGGATTAGGGCCC | 241 |
| ST6GAL1_chr3: 186784189-186784289 | CACCACATGACACATTTAATCCTAATTACCTCCCTCACAGCCCTATTTCCAAACAGGGTATTAGTCACATT AGGGATTAGGGCTTCAACATAGGAATTCT | 242 |
| ST6GAL1_chr3: 186784289-186784389 | GGGGGCACACAATTCAGTCTATAACAGAGGGAAAACAGATTTGAGAAGAAAAAGTCCAAAATATGCAC AGTGGTAATATCTGAAGATGTGCGTGCGTGC | 243 |
| BCL6_chr3: 187460134-187460234 | TCAAGGGCTCAGCAAACGACAACTTAAGCATTTAGAGTCCCATCCCTATCCACCAAACCCAGAATAAGTT AGTCTTTTCAAGAAAGCATTGGTATAAAAC | 244 |
| BCL6_chr3: 187460234-187460334 | CCTTCAAAACTGAAAAGAAGAAAGGGGCAATTGGAGAATTCCCACTTTTTCTGGCTGTCTCCTTCAAGTC GCCCAGTTTTTATGAACAGCATCTAGCCTT | 245 |
| BCL6_chr3: 187460334-187460434 | ACTGTCACTATCAACAACCCTTAAAACTAGCCAATGCTTCGGCCTCTAGTATTGGAAAGTCTTCCAAATAG GATACTGGAAACTTCTATTTATAAGCTTG | 246 |
| BCL6_chr3: 187460434-187460534 | GGGTGGCGGGCGGGGCGGGGAGGTGGAGAGAGAGTTGCCATCTACAGGTTTCTATTTTGGCCTGAAGAC TCAACTGCAGTCATTAGAGTAAGGGAATGCC | 247 |
| BCL6_chr3: 187460824-187460924 | TTATTTATTAAAACCACACACACCTTGCAAAGAAAAAGGGAAACTGGCAGTCTCTGTAGAGGAAGCCGGT GGCATCGCTCAGAGCCACAAACTGTATTTC | 248 |
| BCL6_chr3: 187460924-187461024 | TAAACAGCCCTTTCCCTGGTTCCCTCTCTCCTGCCCCACTTTTTTTAAAATCCAGACTGTAAAAAACACATC TACTGACACTCACTTTACTTTAAAAAAA | 249 |
| BCL6_chr3: 187461024-187461124 | GAAGAGAAAAAGTAAAGCGTIACAAGACTTTCCTCCTGGAAACTATAAACTGAAAAAAAAATCCATAAA AGATTAAATCCTGGCGGGTTGTGGGGTGGCG | 250 |

-continued

| Name | Sequence | SEQ ID NOs. |
|---|---|---|
| BCL6_chr3: 187461124-187461224 | GGGGCCGGCGGGGAGGGGGCGCGGAGTGGAGATTGGCTCTCTGAGGTGGTCAGGGGCCCTGTGACAGCT TGGGACTTTCAGCACCTGGTTTGGGGTCATT | 251 |
| BCL6_chr3: 187461224-187461324 | TATCTGCTCAACTGTCAGGACCCCCCACCCCCAAACCCCAGCCACCAACACAACCATCGTAGAAGGGAAC ACAACACAGAGGGTCTTTTTTCATTTTTTT | 252 |
| BCL6_chr3: 187461319-187461419 | TTTTTAAAAAATCGGTTTGGTTGTGTTTTTGTTTTCCATGGGGGAGCTTTAAAACTCATTATTGCAACACT AGTTCCATTTTTCGCCAGGGTTCCAATAA | 253 |
| BCL6_chr3: 187461454-187461554 | CAAGACATTTACCACGGTCACTACATCCGGCAGCGGGGTGGCCCCTAGCTCCTGCTGCCCCCCCGCCCTTT CTCCCCGCCCGCCCCCGGAGCTCAGCCGA | 254 |
| BCL6_chr3: 187461554-187461654 | TTTCTGAGGCTCCAACTCTACCCACTCCCTCCCCGGGCCGCCGCCGCCGCGCCTTCCCCCATTCTTACTCCC TCGAGGAGAGCCACAGGTTGCAAATCCA | 255 |
| BCL6_chr3: 187461654-187461754 | ACCAACCTCGCAATCTATTTTTGCAAAATCACTCACAAAGATCTCCCTTTCGCGCCCGCGCCCGCTCCTCC CGCGCCGGGTCCCCTCAGCCACGGCCACA | 256 |
| BCL6_chr3: 187461754-187461854 | AAGTGCCCTTCTCTCCTCCTGAGTCTTGCACATAAGGAACGCGGGCTGGGGCTCTGTTCGTCTTTCTCCTC GCCCAAGGTAAGGACCTCGGGAATCTGAA | 257 |
| BCL6_chr3: 187461854-187461954 | GCCTGGCGTCCACTACGCTCAGGCCCGCAGTTCCCTTTTTACAGAGCTTGCACCATGGGAAAAAATAAAA TAAAATTTAGGAAAGGGAGGCAACAGCCAT | 258 |
| BCL6_chr3: 187461924-187462024 | TAAAATTTAGGAAAGGGAGGCAACAGCCATTGGGAGCCAACACAGAGTCACGCAGCGCCCAAAATACAA ACACCGCAGCGGCCAGAAATCCCGCCACCTT | 259 |
| BCL6_chr3: 187462024-187462124 | TCTCGTTCTCCCAGGCTGTCCTGTCGAGGTTCCCTGAGTCCCCCCGCACACTGAAAGGCATCGCAGGTGCA GTGCGCACCCCTTTCCCACCCACCCCAAG | 260 |
| BCL6_chr3: 187462124-187462224 | AAGCCCTGTCCCGCCATCAGTCTCTCTCCTCGGGATGAGCAGGGAGAGCGCGCGGAGGTTCCCGACTCCC TCGACTACAACCAAGAAAGAATAATTTTCA | 261 |
| BCL6_chr3: 187462224-187462324 | AAGTGTTCAACATCCCCGCCCCCAAGCTCCCCAAAACACAGGGGCAGGGAACACCAAAACACTCGGCTCT CATTAGGAAGATCACGGCTCTGAAAGGAAA | 262 |
| BCL6_chr3: 187462324-187462424 | TAGTAGACACGATACTTCATCTCATCTGGATTTATGACCAAAAAAACAAAAACAAAAACCCAAAGAGTTC GCTTGCATTTTTTCCTTCCAAATCTCGGTT | 263 |
| BCL6_chr3: 187462374-187462474 | AACAAAAACCCAAAGAGTTCGCTTGCATTTTTTCCTTCCAAATCTCGGTTCGGCTCGAAGGCAGGGAATCT AAAAGACCGAGGCCGATGGAAGAGAGCCA | 264 |
| BCL6_chr3: 187462474-187462574 | GCGGGGCGAGCGAGCGGGCAGCCTCCCTTTTTGCCTCCCGGAGTTACCCAGAAGGACAGGGGAAGGGAA GGAAGAAGAGGCGAGGAAAAAGAGGAGGGAG | 265 |
| BCL6_chr3: 187462574-187462674 | GGAAGCGGAGGCCAGGAGCGACGGAGCAAGGAAAGCAGTTTGCAAGCGAGAAAAGAGGGAAAAAACAC AGCCGCACGAATCCAGAGAGATCACAAGCCGT | 266 |
| BCL6_chr3: 187462674-187462774 | ACGCAAGCAGCAGCAGAAAGAGCGAGAGCGCGAGCGCGCGTCCTCTCCGCGGTCTGGGGCCAGACAGCC CCCAGACTAGCCCGAATCACCCCCCAAGCAC | 267 |

-continued

| Name | Sequence | SEQ ID NOs. |
| --- | --- | --- |
| BCL6_chr3: 187462774-187462874 | TGTCTCGTCCTCTCTGCTCCGGCCGCCCCCTAATTCCCCTCCTTCCTCTCCTCCACCTCCTTTCCAAAAACC AAAACAACACAAGGGAGGGTGGCAAAAG | 268 |
| BCL6_chr3: 187462874-187462974 | CCTCCCCAAACCGGCCGATTCACTCAAAGACAACAATAATAATAATAAATACATAACAATCTATATCCTA TGGTGGGAGAGACGTGGGACTAATCTTCGG | 269 |
| BCL6_chr3: 187462924-187463024 | ACATAACAATCTATATCCTATGGTGGGAGAGACGTGGGACTAATCTTCGGCATTTATTTAACACCTGACA GCTAGAATAAATAAATATATACATTTATA | 270 |
| BCL6_chr3: 187463004-187463104 | AATAAATATATACATTTATATCAATAGATACACATAGAAAACTTGGAGCCAAAGCATTTGGCAAGAGCGG AAAAAAAAAGAATTAAAAGGTAAAATAATG | 271 |
| BCL6_chr3: 187463104-187463204 | ATCATGAGCAGCGGCGGCGGCAGCGGCACCAGCGGCAACAGCGGCGGCGGCGGCAGTAGCAGCAGCAGC GGCGGCAGCAACAGCAATAATCACCTGGTGT | 272 |
| BCL6_chr3: 187463204-187463304 | CCGGCCTTTCCTAGAAACTTCTTGCATCACCACTTCTAAGAACCCCAGTTCTAAGAATCAACAGAGCTCAA TTCTCGGAATTTGAGCTTCGGACTTTACC | 273 |
| BCL6_chr3: 187463304-187463404 | ACTGCTACGTGGCAGGGGAGGACTTGGTGTCAGCTCTCCGAGATTTTTACTGCCCCTGGCCAACCAAAAG CCCTCAAAGCCACAAGATTTTTCACTGGC | 274 |
| BCL6_chre: 187463404-187463504 | CGGCATATTTCGAGGTCCTCATAAGCAGAGCGTCTCGGATTTGGAGGTTCCGGTTCGAGGCTCGAGGGGC CTGAAGGTGGCTCTCCCTCCCCGGGCCCAA | 275 |
| BCL6_chr3: 187463504-187463604 | GACGATGGTATGGCCTGCTCCGCCACCATCACGTGGGCTCCTCCTCTGTGACGTCGGCGCCTTCGCTGTAG CAAAGCTCGGCCTCTGGAATTCTGAGAAC | 276 |
| BCL6_chr3: 187463709-187463809 | GCACAAAAGGGAGCGAGAGGTTTGAACCACTGGGAAAAGTATGTTATATATATAGTAGGGTTAGAGAGG CGAGTAAGAGAAAAATAAAATAAAATAAACA | 277 |
| BCL6_chr3: 187463794-187463894 | AAAATAAAATAAACATCACAGCTCTTTCCAACTAGAATATTAGGCACCACGAGAAAAATATTTGCCAAGC AGTTTTCGGTGGGTTCATTTGCTTTATTTT | 278 |
| BCL6_chr3: 187463894-187463994 | TATTTAGGACAGGGGTTTTTGCTGTTGTTCTGGGTTTTTTTCTTTCTGGTGTGGTGGCTTGGGATTTTTGGT TTCTGTATTTTGATGGTTTATGGATTTT | 279 |
| BCL6_chr3: 187463994-187464094 | TGCTTCTGATTTTTTGCCTTTTGCAAGTTTGTGGTGTTACGTAAATCACAGGATCGGCATCGGTTGGATTT TTTTGTACGTGCCTTTTCTTTCCCTATCT | 280 |
| BCL6_chr3: 187464094-187464194 | AATCCCTCAAGCGTTTTAAAGATGTATTATTTCAATACTAATACTATTGAAAGAAGCTTAAATTTTTGGCC ATATGTAACAATCCCAGCCCCCACTTTTT | 281 |
| BCL6_chr3: 187619334-187619434 | ATTATCATCATCACCACCAACATCCTCTGCCCTGGAGACCAAGAGAATTCAAACAGGTCAGCACCTCTAA TTGCTGTATAGAACATTGACCCTACTGTCT | 282 |
| BCL6_chr3: 187619434-187619534 | CCCAGTTCCTGAGGATGGTGTGATAATAATACATCTCAGAGTTCTGTAGTTTCTTCACCACTGTGCAGGTG TGGTTGGTGGGAGCAATGCCCTGGATGGA | 283 |

-continued

| Name | Sequence | SEQ ID NOs. |
|---|---|---|
| BCL6_chr3: 187619534-187619634 | TAAGCCAAGCTCTTGTGTCCTGGCAGATAAACAAGGTGAACCCTCAATCCGTGTAGCAGGAGTTTCCAGA CAAACTCACTTTGCATGGAAGGACACTAAC | 284 |
| BCL6_chr3: 187619634-187619734 | CCTTCCAGGTGCATGGAAATATTTTGTAGTTTTTACTGTCTCCCCCTTCCTCCACTGCCTCATCTTTTTTGT TTTTTCCCCTGTGAGACTATTTGCTCTG | 285 |
| BCL6_chr3: 187660817-187660917 | CCTTTCCAACACTGGCCTGCCTTAGGGACTCACCGTCTGCACTCCGCCTGCACAGGTGGAACTGAGTTCAG ATGAGGGAGAATTGCTTTCCATTGTTCAG | 286 |
| BCL6_chr3: 187660917-187661017 | TAGGCTTTTTGTAATTTCTAGTTTTGCTTACCTTTCCTACTCACCACACACACAAAACAGTGTGAGCTTTCT CATTCTAGTGCATAAACACAGGTCGGTC | 287 |
| BCL6_chr3: 187661017-187661117 | AATACCCACAAGTGTTCCAAAAGGTGAGCTGGCATTGCTGCCCAACTGGGCATTATAGTCCCTTCTGTCCC TGCCCATCAGGCTTGCCTTCCTCGGCAAC | 288 |
| BCL6_chr3: 187661117-187661217 | CTTTCTAGCTTGAATTGTACTGTGACTCCTTCTCACGGACCACTCCCGGAGACTGGTGAAAGTTGGGCCCA TTCTTGAAGCCTCTGCTTCTAAATCATGT | 289 |
| BCL6_chr3: 187661217-187661317 | TTTCCATAAAGTCTCCCTCATCGTGCTTGCTTCCACCTTCTCCTATTTGGAATTACTGGTGGGCTCTTCCAC TGTCCCATAGCAAGTGTTCTATACATTC | 290 |
| BCL6_chr3: 187661317-187661417 | TGAAGGCACATTTGAATATATACTTTGTCATGGTTGCTTGGAACCATGTCGTCTTTTCCAAGTAGGCTGTG AACATTCAGTGGCATGGATCATACCGTGC | 291 |
| AC022498.1_chr3: 187957432-187957532 | CCCATTGTTCAAAGAAAGGCATTATGGAGTCTCCAAAAGCCATTGGCAGGTGGTGTCTGTGACTTCCTTA GCCTGGAAATAAACAAATAAACAAGCACAA | 292 |
| AC022498.1_chr3: 187957512-187957612 | AAACAAATAAACAAGCACAAATTAGAAGTCTTTGCCCTATTACTGCACTATTAGTATTGATTGCGCAACA TCATGCAAAAAGTCACTTTAATTTATCTGG | 293 |
| AC022498.1_chr3: 187957612-187957712 | CAGGTCCTATGTAAACACCAATACAGTCAAGAGGGCTTGGATGGGTATTTGCTTTCATTTCTAATGAAATT TCAGGCCTCTAGGGTAGGATATCAAAATT | 294 |
| AC022498.1_chr3: 187957712-187957812 | GGTAGATCATTTGCAATTTATTTTATCCCAAACACCTCACTTTACAGTCAGAGAAACTGAGGCCCAGAGA AGTAAAATGAGTTGCTCAAGGTCTCAGAGA | 295 |
| AC022498.1_chr3: 187957767-187957867 | ACTGAGGCCCAGAGAAGTAAAATGAGTTGCTCAAGGTCTCAGAGAGCAAGAAATAGAGATGGGACTTGA GCACCTAGATCTCTGGTATTGCTGTCCTGTA | 296 |
| AC022498.1_chr3: 187957867-187957967 | GTTCATGGAGCTGGCAGATGGATACATCTGTGACCTGGGATGATGGAGAGACTGCTGGACCCTTCAGAGG ATCTCATCTCAAGGTGGGGTTTATGTGTAA | 297 |
| AC022498.1_chr3: 187957967-187958067 | ATGATATCTGTGTGTTTCATTTTCCTTTCATAAACTAATTTAAAAATCCTTTTGGTATCAAATTTTAAGCCA AAAAGTAGTGAGGGGGAACATGGGTAGG | 298 |
| AC022498.1_chr3: 187958067-187958167 | AATAGCTTACAGCTTGCCTAACAAGGTTGTTGACTGCATAAGAGTCAGGAGTTTTGGGTAAGAGTGTGTG TGTGTGTGTGTGTGTGTGTGTGTGTGTGAG | 299 |
| AC022498.1_chr3: 187958282-187958382 | CGTACTGAATTTGACTGCTTTATTTTGTAGGGAAGGAAACTGATGTGCCTAGAGTAGTTGAGAGCTTTATT CAAACTCATTCCACTGTTATTGAGTAGTT | 300 |

-continued

| Name | Sequence | SEQ ID NOs. |
|---|---|---|
| AC022498.1_chr3: 187958382-187958482 | AGGATATTAGACCAGCAACATATTTGGGTAGAAACTTTCATATAAAAAAGCGTAATCATAACTATCCAATCATGTCAACTAGTAAGGCTGCTCAGGTGGG | 301 |
| AC022498.1_chr3: 187958482-187958582 | ATAACACATCAACCTTCTTTGGGATTCTTCCCTCAGACATGGTTTTGGTGGGAGGAGCATGGCAAGGGAGGGGCGAGCTCCAAATGCAGGGCTGCTCTGT | 302 |
| AC022498.1_chr3: 187958582-187958682 | CCTCGGCGACCTGAGCAGACACACGAGCAGAGATCAGAGACACTCTTAGTGAATGAACCTCCCTATTGGCTATATTAAAGTAATGCTCTGAAAAAGTTCC | 303 |
| AC022498.1_chr3: 187958787-187958887 | TATGTATGCATAGTCTAAAGTGATGATTTTAGAGGTAGCAAGACAGTGAGAATGTCCCTACATGTGAAATGGGCACAGTTTTATCAGGGAAGTGTCAATA | 304 |
| AC022498.1_chr3: 187958887-187958987 | GAGGGTTAATGTTCCACGTAGTGGCTGCAAGAATGATAAGTGGTCATGGGGATAGCCTGACACTCTAGGAGCAGAAGGTGGTGGGTATGGATAGAACTAC | 305 |
| AC022498.1_chr3: 187958987-187959087 | TGATATAGCATGAATCCAACCTGCTGTTATCTGCGCAGGCCTCTCTGCAGCTGTTTGCCCTGAAGTACATGCTGTACGTTTCTCCAGCTGATCCTGCATG | 306 |
| AC022498.1_chr3: 187959087-187959187 | ACTGGGTATAAACGCCTGTCCGCTGTGTGCTGGACAGCCCCAGACACCCTCGGCAGCCTGCTGTGTTTGTGTGAGACATGCTGTGTTAGGGATTTAAGCA | 307 |
| AC022498.1_chr3: 187959462-187959562 | ACAGCTTTCTCATCTACATGGACAACCTATTTTTAAAGAATCTTCAGAGAGTCGTTGACTTTGTTATAACTACTACTATATACGTAATTTCAGATGATAG | 308 |
| AC022498.1_chr3: 187959562-187959662 | AATTGAAAATTTAACTTGTTTTTCTAGAAAGAGTTTATTTTCCCTATAACTTCAAAGAGTAATGGTGGGGAGTAGGACATTCTGAAAATAAGAAGAAACA | 309 |
| AC022498.L1chr3: 187959662-187959762 | TGTCAAATGAATTTCTGACTTCCAGCTAGGCATATGGAATAAAGGTCTTTATTCCAGTGACCTCTGCTCATTGGAAAACTTTGGGCTGGTAGATTTCATG | 310 |
| LPP_chr3: 188299217-188299317 | TCTCTTGCATTCTTAACTTGCAATTTAGTACTGTTTATATTCTGCTTGAAGGTTAGAGACATTCGACTAAATGGTCTTTTCTCCACATTGCTGTCATTCA | 311 |
| LPP_chr3: 188299317-188299417 | TTAATGTCCTGGTCCTGGACTTTACTCATTGACCACAGGACAAGTGGCTCAACTCTCTCCTGCCACTACCCAGGCTGTTAGTCCTGTTGGGAGGCTCAGG | 312 |
| LPP_chr3: 188299417-188299517 | GCCCAACTCACTCATCTGTAACTCTCATCTCCATTCAGCTGCAGCCTCTACAGCCCCTGGTTATACCCTGGATCTTATCATTGCTTCGCTCTATTTTACC | 313 |
| LPP_chr3: 188299517-188299617 | TCCTAAATCGTAAAAATTAAAACCAGCCTCGGAACACAACCCCTCATTCTTCCAGCACTCTCTCTCATTCAGGTAACTCCTATTCTACTTTTCTTCAGCA | 314 |
| LPP_chr3: 188471412-188471512 | TTGTTTTTTTTACTTTACCTTAATTTCTCTTTTTGGACTAAGATGTTAAAATGTTTCTTAATGTGACTGTCTCCGAAACTGTTTTGTGTCTACCACTCA | 315 |
| LPP_chr3: 188471512-188471612 | TCCTAGTGGCAGTCATTGATCCTTTTCTTGTTGCGAGTGTTTGAGTGTGGGTGTGTGTGAGTGTGTATATGTATTTGTAGAGGGAAAAACAAGAGAGAGG | 316 |

-continued

| Name | Sequence | SEQ ID NOs. |
|---|---|---|
| LPP_chr3: 188471567-188471667 | TGTGAGTGTGTATATGTATTTGTAGAGGGAAAAACAAGAGAGAGGGAAACAGACATTGGAGCCACCTTTC CCCCACTAGCCACGTACCTGTTGAACCTTC | 317 |
| LPP_chr3: 188471667-188471767 | AAGCCTCTCTATAGAATCAGATATACACAAGCACAGTGACAGAACTACATGTGTCCTACAGTCCAGCTTT TAAGATATGATAAAAACTCTTGTATTCACA | 318 |
| LPP_chr3: 188471767-188471867 | GAGCTAAATGGCAATAACCATAGGAGATTGCATATTGCTACATTATGTAAAGACAGAGTCCCAAGAAAAT AGTGAGAACTCAGTTTGATGTATGATGTGA | 319 |
| LPP_chr3: 188471867-188471967 | TATGTGATATCTTACTTTACATGGCTAACAGTTGACATTCTTTGTGGATTCTATATTGTCTAAGGCTACAG AAGAGCCATATGATAAATTCATCGGCAAC | 320 |
| N4BP2_chr4: 40198810-40198910 | CAGTGAAAAGGCTTGGGCCGCTTTTGTTTTCACCTGCTTTTGTTGAACAAATTTGATTTCCGGAGTCAGTC ATTTTACTGTCAAGACATTTCTTCGGCAT | 321 |
| N4BP2_chr4: 40198910-40199010 | TCTGCAACAGGTAAGGATTTTGCTTCCTTAAAAGTATTTCTTTGGTGTCAAAAGAAATTTTTCTAATTTTA TTTAGCTTTTACTCTAGGCCAAACATCGT | 322 |
| N4BP2_chr4: 40199010-40199110 | AATGACTCTGAGCTACCTGCTGTAAGGTGTAGAATCAATTTACAGGGGGACGGGGGTCGGGGGGGTGAG TGTTGCTTTGATATTCACTGCCCCTCACCAC | 323 |
| N4BP2_chr4: 40199110-40199210 | AGTCCTAACAAGATTTTTGAAACATGAAAAGTTACAATAGTTGGCTTTTTGGTTTTCCAGATATTCTAGAG AATGCATATGCTTGTGACTGTGGCTGAGC | 324 |
| N4BP2_chr4: 40199210-40199310 | TCAACTGTATOGGTAGTTTAAATACTACCCAAGGTTTGATGAAGTAAATCTAAAGATGCTCTAAGTTGTG CAAATATGAATTTTAAAGTTGTCTAGTTCA | 325 |
| N4BP2_chr4: 40199310-40199410 | GAAAAGAAACAGAACCGAAGTCTAAATGATGTAGATTTCAATCTGGAATTTCTAGCTTGTGTTTTTCACCT ATTGCCAATGTTAATGACCATTTCCCAAA | 326 |
| N4BP2_chr4: 40199410-40199510 | AGTGCTCTATGATGTATAACATGTATTTTTAATTAAATTTAATCTTTCTTCTGAGGTGGTTTGATTTGGAG ATATGCTACGAGGTACCAGTCAGTAGCC | 327 |
| N4BP2_chr4: 40199510-40199610 | TGAGTTGTAACTAAACAAAGTTTGGGAAATCACCGGTTTTAGGTGCTTTACTAAATGAAAGTTGCCATTG ACGTATTCAAGCAGGCAACAAGTAGTTGGT | 328 |
| N4BP2_chr4: 40199610-40199710 | GTCCCCTTATTGGTTCTAAGCTGGTGCCGTGGAGGATATAAGAGAAATATTTTAAAAATCTCTACTTTGAA GGACCCTATAATCTGGTAGTTGTGATAAG | 329 |
| N4BP2_chr4: 40199660-40199760 | TTTAAAAATCTCTACTTTGAAGGACCCTATAATCTGGTAGTTGTGATAAGAAGTAAAATTTAGGAAGCAA TGCAAGATGAGAATTCAGTGATGAGTGGGG | 330 |
| N4BP2_chr4: 40199760-40199860 | CAGCACAGGCTTGAAGAGTTCTGTGAATTCCATGGAGGGGGCCTGGGGGCAAACTGGAGTTGTCAGGAA GATCTGGGCTTTGGAAGAATGCGAAGTGTCG | 331 |
| N4BP2_chr4: 40199860-40199960 | GTAGAAGGAGAAGGGGCAGGTGATTTCAGACTGGGAGGACCTTGTGGGCAAAGGCACAAAGGCGAGACT GACCTGGAGATGATAAGGCCAGTTGAAGAGA | 332 |
| N4BP2_chr4: 40199990-40200090 | ACATTGCAGGAAATCAGATTAGACAGTTAGGGTGTGGACACAAAAGCGAGGACCTTGCAGGCACTGGGG AGAAGTGACCCCATTCAATAGTCCTTGGTCT | 333 |

-continued

| Name | Sequence | SEQ ID NOs. |
|---|---|---|
| N4BP2_chr4: 40200090-40200190 | CCTTCTGCCCTGCGGCTGCGCTTCCTCGGCTCTCACGGCACCAGCAGAATTCCATGTGAGAGGGAGCTTGT CGAGCGTGGCCTCTTCCCACTTGGGGCTG | 334 |
| N4BP2_chr4: 40200190-40200290 | CTTTCTGCATCCCTGTGCCTGGCTGTGGGCCTCCATTTGCCCTCTACTGTCTTCCCTTAGGACATCATTTAT GCAGAGAAAGGTTCGTGTGGCTCGGGGT | 335 |
| RHOH_chr4: 40200505-40200605 | GGACGTTGTTTAGAGAGTCAGTAGATCATAATAATTCAGACACTTTTTTTCTGGACCATAAAATATCTGAA CCCATATAATAACAAACATACAGCACGGT | 336 |
| RHOH_chr4: 40200605-40200705 | GAATAAGAACCCAACTTTTGAGCCAGATCACTTTGCATGGAATCCCCATTCTATCATTCTATCATTTCTGG GCTGTGGGAACCTCAGACAAGTTACTTAA | 337 |
| RHOH_chr4: 40200705-40200805 | CTTCTTCAATGCTCAGATTAAAAAAAAAATTCACAAATATCTCTAATAACAGTAATAATAACTGAAAAT ACCTACCTCAGAGGGTTGTCGTAGAGATCA | 338 |
| RHOH_chr4: 40200730-40200830 | AAAATTCACAAAATATCTCTAATAACAGTAATAATAACTGAAAATACCTACCTCAGAGGGTTGTCGTAGA GATCAAATGAGATAAAAATATGTAAAGCAT | 339 |
| RHOH_chr4: 40200830-40200930 | GTAGCCTAGTGCCTGACTGAAAAAAAAATCTCTCAATAGATGCAACTCTTATGATTCTTATTAAGGACTTG GCTATTGCCACAAATGAAGGTGTTATGAG | 340 |
| RHOH_chr4: 40200930-40201030 | CCCTGGCTTAAGAGCAAGAAGCCTGCAAAGCTAACTCTCCTAATCCCAACATTCCTTTCCAGGGAAAGTA GGGTGACAGGTGGAGGCTGGGAATTAACGT | 341 |
| RHOH_chr4: 40201030-40201130 | TTTTTGAGCACCAAATATGGACAAGGCACAGGGGTTGGGTGTTTTTCTAGTGAGAATACATATGAAAGAA GGAAAACAAACTTGGAAACCGCTATTTTAA | 342 |
| RHOH_chr4: 40201130-40201230 | GCCATTTGGTAACAGTTTCTCTAGCTTATGAGATGAGAGAGGTCCTCTCAGTATCCGCTGCATTACTTGTG GGCCTCCTTGGTTGACGTCGCTCTCTGAA | 343 |
| RHOH_chr4: 40201230-40201330 | CGCTTGGGGTGGAATTCTAGAGGTGCTTTTCATTAGAGGCAGAGAGCATGACCTTTCTTCCTTGCCCAGTT TAAATTAAATTATTTTATCTTACAATGTG | 344 |
| RHOH_chr4: 40201330-40201430 | TTAATTTTAGTGCTAGCAAGGCACAGCTAAAATTCCATTTCTACTTAGGAGTGGGGATCATTGTGGCAGT GAGTGCTTATTTGGGTTTGGGATGCTTGGA | 345 |
| RHOH_chr4: 40201430-40201530 | TCTGGGTGAAAGCCAGGATTAAAAAGCATCCTCCTTCCCCATTCCACTCTCTAGGTTATAAATATTTTTTT GGATTAAAAGCCTCCTTTAAAAAAATGCA | 346 |
| RHOH_chr4: 40201530-40201630 | AATCCACCTGGCATGTTAATTGTGCAGGGGATTCCTAATTATGTGTGCAGATGACGTGAGTCACACGGTG ATAGTGTTCCTTCTAGAGTCCCACTGGTGT | 347 |
| PABPC4L_chr4: 134727698-134727798 | ACTAGGCGTTCATCCTGTGTAATTTGAAAATATGTCACACGTGGTGATGAGAATCTATTTGAGGAACATG GGCAGTTTGAAATAATATATGCAATGTATG | 348 |
| PABPC4L_chr4: 134727798-134727898 | ACTAGTTTATATAATGAAAGGAAGTATTAAAAAGATAGAATGACATAGACTAATCTAATTGAGAAATAT GAAAGTCTAACAGAAATGATTGCTTGTGAA | 349 |

-continued

| Name | Sequence | SEQ ID NOs. |
|---|---|---|
| PABPC4L_chr4: 134727898-134727998 | ATTTTATGAAGAAATCCACAGATAAATTCTCCACCTTGATCTATGTAATCCGAAATTTAGATGTTAAAAAT ATGTTGATTCTGAAAATTTATATTTATTC | 350 |
| SLC38A9_chr5: 54964698-54964798 | TTTGGTATGAATAGGTCAAAACAAGTCACCATTAACTGACAGGAAGCACAGAATTCTCAATTTAGTTTTG GCAAAGACATTATTTTATAAATATGAGTTT | 351 |
| SLC38A9_chr5: 54964798-54964898 | TTAAATGATTCTTATGAAGAAACTAGCACCAAAGTGAATGCACTCTGCAAATAACTCCCAGCTTCTCTGA ATTTCAAAAGCAGCCACTAAATATTATTAG | 352 |
| SLC38A9_chr5: 54964898-54964998 | CAAATCAATTTAGCTGAAAGCGATGATTACAGAAGTAAATCTTTAGGTACAAAGTAGACAGCTGACACA CATGTAGCATATACACACTAGTGATCTGCC | 353 |
| ZNF608_chr5: 124079827-124079927 | TTCCTTCTTTACCAACATAGAGTTTCCCATGAGCCCTGAATCCGGGGCACTTTTGCTAACTTCCCCTGCAG CGGCGACGCTGCCACTCCCAGTGCCCCCG | 354 |
| ZNF608_chr5: 124079927-124080027 | CAGTGGAAGGGGCTCGCGCCACCTCCATTGCTCTTGGCCCCAAAGCCATAGAGGTGCCCCCCGGAAGGGG CCTGGCTGCCACTGCCATTCTGGTGGCCCT | 355 |
| ZNF608_chr5: 124080027-124080127 | GAAGCAGGTCGTGCTTGTCCTTCCTGGATTTCCCCGCATCCTTATCCCGCTTGGCGCCTCGGCTGCTCTGG CTTTTACCTGGCTTCTCCTCTTTGCTTTT | 356 |
| ZNF608_chr5: 124080127-124080227 | CCCACAGGAGCCTGCCCCCGCGGTGGCGGCAGAGGTGCTGGTGCTGGTACTATTGCTGTTTGGGTTGCCG CTGCCGCCGCTGCTCACACTTTGACCCAGC | 357 |
| ZNF608_chr5: 124080227-124080327 | GCTGAATTCATGCCAGTTGCCTCTCCAGGGCGCCCTTGGACTTCCTGCCTCTTGCCAGTGCTGCTGATCTC GGGAATCCCATACAAGGCAGCAGAAGGCA | 358 |
| ZNF608_chr5: 124080327-124080427 | GAGATTTATTAGCATCCTTAGAAGTTTTACTCCTTTTCACTTTTGATTTGCTGGTCTCTTTGTGTGAATTCC CCTGGGGAGCAGAGGCCTGAACAGAAGC | 359 |
| ZNF608_chr5: 124080427-124080527 | AAATTTTAGGCCATCAGCTAAGGCTGCGGTAGCACCAGCCCCACTGGAGGCCGGACCTCCACAATCCTTG GAGTTGCTGCTACTAGTGGTGGTGGTGGAA | 360 |
| ZNF608_chr5: 124080527-124080627 | TTATTCATCTCAAATTTCTGTCTGTCCTTCTCCAAATCAGCGTCCAAATCAATTATTAAATTTCCAACCCCG ATTTCCCAATCATCGCCACTGTCATAAG | 361 |
| ZNF608_chr5: 124080627-124080727 | TATCAACTGTATTTGGATCCACACCTTTTCCTGCAGTAGAAATGTTCACTGACATCCTGAAGATGAGCTCT CTAGAATAAAAATCCGATGAACTTTTCTT | 362 |
| EBF1_chr5: 158527642-158527742 | TTCCTCAGGAATTTGAGCTGGGGATCTOCATCCTGGCCATTGCAGTCCTTTAGCATCCTCGCCGCGCCCTG AGCGCGCTGGAGGCTCGCAGGCTGCGCCC | 363 |
| EBF1_chr5: 158527742-158527842 | TCCCAGGGCTGATGCCGCGTCCTGCTCCGCCGTTCTGGGACGTCGGGGACAAAAGTGGAGGAGACGGGA GAGCCCGGGCAGAAAAAGCAGGACGCGCGTC | 364 |
| EBF1_chr5: 158527842-158527942 | CCAGGTGCCCACCTCTTCGCTTTGAGGCGGGGGCGGTGGGATGGAATATGGGTGCGCGAGGTCGGGGCTG GTAACTCTCGGAGGGGCACGGCCTCCACGC | 365 |
| EBF1_chr5: 158527942-158528042 | TGGGAGGGATGAATGGACGCTGGGCCCCGGCAAATGAGGCGCTGTGGGTCCCCAGGAAGTGGGGTACCA GGCTCTACTCCCACCCCGGCCTCTGAAACGC | 366 |

-continued

| Name | Sequence | SEQ ID NOs. |
|---|---|---|
| IRF4_chr6: 392760-392860 | GGCCAGGAGGGGTGGCGGCTGGGTGGGGAGAGAGGGTGCAAGACGAGCGGCGCGTGTCGGGAGCCTTTG GGCTGCGGGTGCGTTACAGGAGAGCAGGCGG | 367 |
| IRF4_chr6: 392860-392960 | GTAGGAGCCTTCGCGGGGGCCGAGCTCGGAAGGCGGACGGCTGTGCCCGCCCAGGGGATGCGCCCGGGC CGGCCGCGAAGGTGCCTTCTTCCGGGGGCCC | 368 |
| IRF4_chr6: 392960-393060 | GGACGACCCTGACACGGCACGCGCGCGCTTCGCAGCCTCAAAGACTCCGGGGCCTCGTGGTCACTGGCGC AGGGGATCGGGGCGGGGTGCCCGGAGTGCG | 369 |
| IRF4_chr6: 393090-393190 | CCCGCAGTGCAGAGCAGAGCGGGCGGAGGACCCCGGGCGCGGGCGCGGACGGCACGCGGGGCATGAACC TGGAGGGCGGCGGCCGAGGCGGAGAGTTCGG | 370 |
| IRF4_chr6: 393190-393290 | CATGAGCGCGGTGAGCTGCGGCAACGGGAAGCTCCGCCAGTGGCTGATCGACCAGATCGACAGCGGCAA GTACCCCGGGCTGGTGTGGGAGAACGAGGAG | 371 |
| IRF4_chr6: 393290-393390 | AAGAGCATCTTCCGCATCCCCTGGAAGCACGCGGGCAAGCAGGACTACAACCGCGAGGAGGACGCCGCG CTCTTCAAGGTCTCCGGCCTCGGGAGCCGGC | 372 |
| CD83_chr6: 14117992-14118092 | CCCGCGCGCCACAGCTCTGCAGCTCGTGGCAGCGGCGCAGCGCTCCAGCCATGTCGCGCGGCCTCCAGCT TCTGCTCCTGAGCTGCGGTAGGGCTCGCGA | 373 |
| CD83_chr6: 14118092-14118192 | GCGCCTGTCTCGCCTGTCGCCCCCCGCCCCTCCACGACACCCCCTCCCGTCGGTCGCTTGCTCACGACGCG CTCTCTCTTTCTTGTAGCCTACAGCCTGG | 374 |
| CD83_chr6: 14118192-14118292 | CTCCCGCGACGCCGGAGGTGAAGGTGGCTTGCTCCGAAGATGTGGACTTGCCCTGCACCGCCCCCTGGGA TCCGCAGGTTCCCTACACGGTCTCCTGGGT | 375 |
| CD83_chr6: 14118292-14118392 | CAAGGTAGGTGCTGCGATACCCACOGGCTGGGGTTTGGTOGGCTCATTTGAAGACAGCAGGAACCATCTC CCCTAGGCTGGCGACCCTCTGTGGCTGCCA | 376 |
| CD83_chr6: 14118392-14118492 | GGTGGGGGCGAGGGGCGTCTCCCGCAGCTGAACTTGGAGTACCCAGCCTCCCGTCGCGCCTCCCCCACCC CATCCGCATCCAGGTACAGGGCCGAATTAG | 377 |
| CD83_chr6: 14118492-14118592 | GTTTTGCTCTCCGCAGACCTCAATCCCCTTCCTGTCACTGAAGGTGGCCTGAGATGAATGATCCACTTAAG ATGTTTTGGAAGGGCAGAGACTCTCATTT | 378 |
| CD83_chr6: 14118592-14118692 | GGATTAATTCTGGAGGCCACCTGTGGTTGTGGGCCAGCAGGTCAGGAAGAAAGCAACAGGGACCTAGAT TTGGGCATTGGACAGGGGGAATGTCTCCAGA | 379 |
| HIST1H2BC_chr6: 26123614-26123714 | CTCTCCAGTTCCTATATTCTAATACCCCTCCGCCGCCAAATAAAATTTGGCGTCTGGCCACAGCTCTTTTA GTGGGTATCTGGGTGGCTCTTAAAAGAGC | 380 |
| HIST1H2BC_chr6: 26123714-26123814 | CTTTGGGGTTAGGTGTTAAGACGCTTACTTGGAATGTTTACTTGGAGCTGGTGTACTTGGTGACGGCCTTG GTGCCCTCCGACACGGCGTGCTTGGCCAG | 381 |
| HIST1H1E_chr6: 26156649-26156749 | CTCCGGCCCCTGCCGAGAAGACTCCCGTGAAGAAGAAGGCCCGCAAGTCTGCAGGTGCGGCCAAGCGCA AAGCGTCTGGGCCCCCGGTGTCCGAGCTCAT | 382 |
| HIST1H1E_chr6: 26156749-26156849 | TACTAAAGCTGTTGCCGCCTCCAAGGAGCGCAGCGGCGTATCTTTGGCCGCTCTCAAGAAAGCGCTGGCA GCCGCTGGCTATGACGTGGAGAAGAACAAC | 383 |

-continued

| Name | Sequence | SEQ ID NOs. |
|---|---|---|
| HIST1H1E_chr6: 26156849-26156949 | AGCCGCATCAAGCTGGGTCTCAAGAGCCTGGTGAGCAAGGGCACCCTGGTGCAGACCAAGGGCACCGGC GCGTCGGGTTCCTTCAAACTCAACAAGAAGG | 384 |
| HIST1H1E_chr6: 26156949-26157049 | CGGCCTCTGGGGAAGCCAAGCCTAAGGCTAAAAAGGCAGGCGCGGCCAAGGCCAAGAAGCCAGCAGGAG CGGCGAAGAAGCCCAAGAAGGCGACGGGGGC | 385 |
| HIST1H1E_chr6: 26157049-26157149 | GGCCACCCCCAAGAAGAGCGCCAAGAAGACCCCAAAGAAGGCGAAGAAGCCGGCTGCAGCTGCTGGAGC CAAAAAAGCGAAAAGCCCGAAAAAGGCGAAA | 386 |
| HIST1H1E_chr6: 26157149-26157249 | GCAGCCAAGCCAAAAAAGGCGCCCAAGAGCCCAGCGAAGGCCAAAGCAGTTAAACCCAAGGCGGCTAAA CCAAAGACCGCCAAGCCCAAGGCAGCCAAGC | 387 |
| HIST1H1E_chr6: 26157249-26157349 | CAAAGAAGGCGGCAGCCAAGAAAAAGTAGAAAGTTCCTTTGGCCAACTGCTTAGAAGCCCAACACAACC CAAAGGCTCTTLCAGAGCCACCCACCGCTC | 388 |
| HIST1H1E_chr6: 26157349-26157449 | TCAGTAAAAGAGCTGTTGCACTATTAGGGGGCGTGGCTCGGGAAAACGCTGCTAAGCAGGGGCGGGTCT CCCGGGAACAAAGTCGGGGAGAGGAGTGGGA | 389 |
| HIST1H2BK_chr6: 27114004-27114104 | CTCCTTAGCCAGACTCGATTACAAGCACTGCATGCATTACTCAGTGTGATAAGATCATGATAATCCCTTTA AAAAGATCGCCCGAATTTAAGCCTGGATT | 390 |
| HIST1H2BK_chr6: 27114104-27114204 | AGGAACACGTGTTTACAGCTCTAATATCGATAATTTAAGTGGCTCTTAAAAGAGCCTTTGGGGTTGGGCT TTAAGACGCTTACTTGGCAAGTTTACTTAG | 391 |
| HIST1H2BK_chr6: 27114204-27114304 | CGCTGGTGTACTTGGTGACGGCCTTGGTGCCCTCGGACACGGCGTGCTTGGCCAACTCCCCGGGCAGCAG CAGGCGCACGGCCGTCTGGATCTCCCTGGA | 392 |
| PIM1_chr6: 37138284-37138384 | CCCCGGCTCCGGCTCCTGCGGCAGCTCCTCTGGGCACCGTCCCTGCGCCGACATCCTGGAGGTTGGGATG CTCTTGTCCAAAATCAACTCGCTTGCCCAC | 393 |
| PIM1_chr6: 37138384-37138484 | CTGCGCGCCGCGCCCTGCAACGACCTGCACGCCACCAAGCTGGCGCCCGGTGAGAGCACCCCCCGCCTCC GGCCCGGGGATGCGGGGCGGCGGCGGGATC | 394 |
| PIM1_chr6: 37138484-37138584 | TCCTGGGTGGGGAGCTGGCGGCTCGCGGGCCGGCACTGAGTCCCCGTGCTTCCCCCTTTCCTAGGCAAGG AGAAGGAGCCCCTGGAGTCGCAGTACCAGG | 395 |
| PIM1_chr6: 37138584-37138684 | TGGGCCCGCTACTGGGCAGCGGCGGCTTCGGCTCGGTCTACTCAGGCATCCGCGTCTCCGACAACTTGCC GGTGAGTGGGCGCCCCGCGGTGGGGAGGGC | 396 |
| PIM1_chr6: 37138684-37138784 | GCGCCGGGCGGGGGGCGCACGGGCGTGCTTTAGCCCGGACGAGGGAACCTGACGGAGACCCTGGGCTTC CAGGTGGCCATCAAACACGTGGAGAAGGACC | 397 |
| PIM1_chr6: 37138784-37138884 | GGATTTCCGACTGGGGAGAGCTGGTGAGTGCCCTGCAGGAGCGACCCCCAGGATGAGTGGGTGGGGTGA GGGGCGCCCCCGACTCCCGCCCTAACGCGGC | 398 |
| PIM1_chR6: 37138884-37138984 | CCCCTCGCCCCTGCAGCCTAATGGCACTCGAGTGCCCATGGAAGTGGTCCTGCTGAAGAAGGTGAGCTCG GGTTTCTCCGGCGTCATTAGGCTCCTGGAC | 399 |

-continued

| Name | Sequence | SEQ ID NOs. |
|---|---|---|
| PIM1_chr6: 37138984-37139084 | TGGTTCGAGAGGCCCGACAGTTTCGTCCTGATCCTGGAGAGGCCCGAGCCGGTGCAAGATCTCTTCGACT TCATCACGGAAAGGGGAGCCCTGCAAGAGG | 400 |
| PIM1_chr6: 37139084-37139184 | AGCTGGCCCGCAGCTTCTTCTGGCAGGTGCTGGAGGCCGTGCGGCACTGCCACAACTGCGGGGTGCTCCA CCGCGACATCAAGGACGAAAACATCCTTAT | 401 |
| PIM1_chR6: 37139184-37139284 | CGACCTCAATCGCGGCGAGCTCAAGCTCATCGACTTCGGGTCGGGGGCGCTGCTCAAGGACACCGTCTAC ACGGACTTCGATGGTGAGCCAGGCCCGGGA | 402 |
| PIM1_chr6: 37139284-37139384 | GGGAGCTGCCCAGGTGACTCGGCCCGGCCCGGCCCAGTCCGGAGGCCTCGGCCAGTCTCCCGCGCCAGCC TTTTGTAAAGGTCATTGGGCCGCCTGGCTC | 403 |
| PIM1_chr6: 37139384-37139484 | GATGCTAGCCGGGGTGGGACGCAGGAGAGCCTCCCAGCGTAGTAAAGCCGGGGATTTTCAGCCAGCTGA ACCTGTAATGTTTCTGGCATGATTTTATTCT | 404 |
| PIM1_chr6: 37139484-37139584 | TCAAGTGGAATTCAGTTAGTTCCAGGCTTTCCCGATGAATAAGAGGTTGTGGGCAACCGGCGGTAGCCCA GATTTTTCTAAAGTCTGACCCAGTTTCCCC | 405 |
| MAP3K7_ch6: 91004618-91004718 | CTCTAAACAGACAAAAGCAAAATATCTCATTAGGCATCATCTCCGCCAAGGTTCCCACTAGGCAGGAAAG GATTTTTATCTAAAGTAATTACCCTTTTTA | 406 |
| MAP3K7_chr: 91004718-91004818 | GTTAAATACACTCAACAGATGAAATTTACAGAGAGTGAGAGACTGCAGCACTAGACAGCGAAGGTGAAA ACCAGGAACGCCGCGTCTCGCCGCCCGCGGG | 407 |
| MAP3K7_chr6: 91004818-91004918 | CCCGCCGGGAGACTGCGGGTCCGTCTCGCGGGTGGGGCGCCCCGGTCCCTCTCGTTTCCTGGAGGCCACA GGTCACGGCGACGGCGGTGACCGGGAGAGC | 408 |
| MAP3K7_chr6: 91005793-91005893 | CGGGTCTGACAGCTGCTGCGGCTCGCGCGGACGCGCGCCTCCTGCAGCCCGCCCTCCCCATGCCTGACTT ATTACTCTCTGCTCCTCCTCCCTCTGCTGT | 409 |
| MAP3K7_chr6: 91005893-91005993 | TCCAAAACACCCTTCGACGCCAGCAAAATACAATGCGCCTCGGCCGCCGTAAACAGCCGGGAGGGAGAG CACACATTCGGCGCGGCGCGGCCGCCGGCTC | 410 |
| MAP3K7_chr6: 91005993-91006093 | GGCTCCCACCCCCTTCCCGTTCCTAGAAAATGCCATAAAAGCGGGCAGGGCGCGGGGAGGGCGGCTGCGC GCCCGGCGGCCGGGGCTCCCTTCCCGCGCC | 411 |
| SGK1_chr6: 134493732-134493832 | TATGAAACAGCCAGTGCTACGTCTCCTTTATACCAAAACTGGTAGCCTGAAGAGCTCTCAGGCTTACCTAT AAACGATGTTCAGTGAATGCAGGTAGCCC | 412 |
| SGK1_chr6: 134493832-134493932 | AAGGCACTGGCTATTTCAGCAGCATAGAAACGAGCCCGTGGTTCCAGGAAGCAGCGTTCCCTCTGGAGAT GGTAGAACAACTGCAGGAGACAGAACAAAG | 413 |
| SGK1_chr6: 134493932-134494032 | TCATTCTGGGTTGCAAATGAATTTAATTAGTTTTGACATACACAGCAAAAGAACAACTGCAGGAAGTGGC CCCAAGTAATCTATTAACTATAAACCTGAC | 414 |
| SGK1_chr6: 134494032-134494132 | AGGTTGAAGGAAATGCTAATTCTGGTAACATTCTCCCCACCAAAAATCTTTGAAAACTTTTTTCTCAAACT AAAACAAAGCAGGCTGTGCAGAGACACTA | 415 |
| SGK1_chr6: 134494132-134494232 | AGAGTTGACTTCTATCCCCCCTGCTCACCTCTCCACCATTAATGTAGTCTAGGACAAAGTACAATTTGTCA GCAGTCTGGAAAGAGAAGTGAAGGCCCAC | 416 |

-continued

| Name | Sequence | SEQ ID NOs. |
|---|---|---|
| SGK1_chr6: 134494232-134494332 | CAGGAAAGGGTGCTTCACATTCTTCAACAGAACATTCCGCTCCGACATAATATGCTTCTCCTAGGAAAAT GACGATTCAGATTTAGTGGCATGTTTCAAC | 417 |
| SGK1_chr6: 134494552-134494652 | GAGGACATGAAGGAAGTGTACCAAAAGATCTTCAGATTTGAAATTACCTTTCCAAAACTGCCCTTTCCGA TCACTTTCAAGAAGTGAAAGTCAGATGGTT | 418 |
| SGK1_chr6: 134494652-134494752 | TAGCATGAGGATTGGACGACGGGCCAAGGTTGATTTGCTGAGAAGGACTTGGCTAGAAAAAAAAAAAAA GAATTTCTTTTAATACCATTGCTTCAAAGGA | 419 |
| SGK1_chr6: 134494722-134494822 | AATTTCTTTTAATACCATTGCTTCAAAGGAAGACATCTATAACATAAACGATGTAGAAAATGTTACATCTA CAAATGACTGATGCAAATGACCATACATC | 420 |
| SGK1_chr6: 134494967-134495067 | AATAAAATAATACTCTGACTCAATACTTAAATATTTATATCACTTGTTATGCCATAATGAAGCATTCCTGC CTTGATACTAATTTCTAGAAATGCTATTT | 421 |
| SGK1_chr6: 134495067-134495167 | TAATCCATTAATGTAGGAATACTAACTGACTCCCTTACAGTTCTCCACAGATGCACGGCACATACAAAAA CTTACTGGAGGAGAAGGGTTGGCATTCATA | 422 |
| SGK1_chr6: 134495167-134495267 | AGCTCAGGCTCCTGAGGTTGGGAGATCTTCAAGATGGACTGAACTTCAGGGCTGCAGGGAATAAAGGGC ACGATTTAGAATCCAGCTCGCCACTAGGGGG | 423 |
| SGK1_chr6: 134495267-134495367 | CACACCAACATCAAAAGTGAGTTTCTGGCTCTACCGACTTCTACCCGGATAATTCACTGTTTAAACTGAAA ATACCCCAATACATTAGTCAGTTAAAGAA | 424 |
| SGK1_chr6: 134495367-134495467 | AATAATAAACCCCATTAAATACAGAAATAAGGATTGTTGCTCATGGAGAAAGGCCGTGAATTCGGCCAAC ACGAACCATTTATCTTACATCTCCAGTTCA | 425 |
| SGK1_chr6: 134495467-134495567 | AGCCAAATCAGCAAATTAACTTTAATGTTTAAAATGTGTCAAATATATTAGAATTTAAGGAGAAATGAGA TCCCCACCCCAGAAGAAGTCTTCGCCTTCC | 426 |
| SGK1_chr6: 134495567-134495667 | CGATAAACGCCGTGATGAGAATGTTTACCGCTGGCAAATTCAAACTATACTAGTTATTTCCTCAAATCCGG TCAAACTTACTGTTTGCATGCATAGGAGT | 427 |
| SGK1_chr6: 134495667-134495767 | TATTGGCAATCTTCTGAATAAAGTCGTTCAGACCCATCCTCCTCTGCTTCATGAAAGCTGTGGATGAAGGA GGAGAAATAAAGAAACGTTTAGACGGCTT | 428 |
| SGK1_chr6: 134495767-134495867 | CATAACGTCCGGCGCCACACACACTAATCTGATCCGGGACTTTCAAAAATTTCCACTTTGCGTCTCCTGG AGCAGAAGTCCCGCAAGATTCCTGCACTC | 429 |
| SGK1_chr6: 134495867-134495967 | ACCGATGAGAATTGCCACCATGCCCCTCATCCTGGAGTAAGTGAGGGTGCCXnTAGCAGCCTCAGTTTTC ACCGTCATCACCACCGCGGGGAGACAGAAA | 430 |
| SGK1_chr6: 134495967-134496067 | GACGTTAGCGCTCAAAGACCGGCTCGGCGTATGCTGCGCCAGGCCGCGCGCTCGGCCTTATAAAAAAGGC ACCGCCGCGGGGGCGGGGCCTGCGCGACAG | 431 |
| PLEKHG1_chr6: 150954420-150954520 | AGGGTGAGAGGAGTCACCAGGTAAAGATGGGTTGGAAGGACCTGGCAGGCAGAGCAGGGAGCAGGACC CCAGTCCAGGGCAGCAGGGAAGCGGGAGTCTG | 432 |

-continued

| Name | Sequence | SEQ ID NOs. |
|---|---|---|
| PLEKHG1_chr6: 150954520-150954620 | GGCAGAGCTGATTCCAGGCAGCTCAGTATTGCTGGCCTGTGCATCCTGAGACTTATCCGAGTCGCAGGTG AAGCTGGTGGGAATCAGGCAGAGTGCAGAG | 433 |
| PLEKHG1_chr6: 150954620-150954720 | CTTTAGCTGGGGCAGGGTTAGCCAAGAGCCTGTCATGGAGCTGCTCTCTGGGCACTGGGAAACATAAGTC TGGAGGCTTTGGCTGCAGCTGCAGATAAAG | 434 |
| PLEKHG1_chr6: 150954720-150954820 | ATGCAGGGGCCTCTGACGATGGGGGCCTTAGTCATCTCAGAGGTGGTGCAGAGGGTAGAAGCCTGACTG GGGTCAGAGATGAGGAAGGAGAGGGTCAGAA | 435 |
| PLEKHG1_chr6: 150954820-150954920 | ACAGTGATTCTAAACCAATTTGGTTGAGGCAGAAGATACTAATGGCCGAGGGGAGGAGAGAGGGAGCGT AGGCTCTAAAGGGGAAGCTTGTTAGGAATGA | 436 |
| EZR_chr6: 159238415-159238515 | AGACAGAGGCGCAGGCACAGCCCTTTCATCAGCTGACCAGGAGTGCTCGGCCCGGCCTGCCAGGAACCTC TTATCAAACTCCACCGGCTGCCTGCATCTA | |
| EZR_chr6: 159238515-159238615 | CAATTCAAGTCCATGGCTAACCTTCTGTTAGAGACAGAAATTCTGCTGCAGCCAGCAAGTTTGCTGGTGT ACAGGGCACCGCTTCATGGGCCTAGTAGGA | 438 |
| EZR_chr6: 159238615-159238715 | AGCGAAGCTGAAAGGCAACTTCCGAAAGCCAGTCTCCTCTCCCAAACGCCCTTTAATATCTCCCCAGTTG GATCTGGGGCGCCTGTGGTTTCGGACCCTT | 439 |
| EZR_chr6: 159238715-159238815 | AGGAGCTCTGAGAACTGGTGTGTGTGGTCGGAAGCCATCTOAGTCTCCCTGTGATTTGGACTTTTTAAGA AACTTCTAAGTTGTATTACTATACCCTTTA | 440 |
| IMMP2L_chr7: 110545276-110545376 | TTCCCTTGTCATATGACTTCCATCCTCAGCACTACAATATTATCATTAATGTTTAAATCATTGTCAAGTCTG TGATTGCCTTAGAGATTTATTAAGAATA | 441 |
| IMMP2L_chr7: 110545376-110545476 | ACATGCTAGGATTAGGAAAGTTTAACTTTTTACCATCCTTAAAATTAGATTTTTGAAAACTGTCTTATCCC CATTAAAGAAAAAAATAAAAAGGATGAAT | 442 |
| LRRN3_chr7: 110697971-110698071 | TATACATACCTGCACATATATACAGCATATGTATATGTGTCTGTATTATATGTATTAAATGAAAGATTATC CACATTTTGTTCTTTAGGATCTTCAGCAG | 443 |
| LRRN3_chr7: 110698071-110698171 | CTCTCTTCCCATCACAATAGAAAGGCCTGAGCTAACATTTCCATTTCTGCAAAGGCAGATTTTGTTCAAT TAAAAATTATAATGCCTTAAATTTCCACA | 444 |
| LRRN3_chr7: 110737411-110737511 | GACATTTAAGAGACTTCGTTTTCACTGTGATAAACAGGTTTGATTTGGACTTATAACTTTTTTCTAAAATT ATCAAATTAATAACGACTATAATGAAATA | 445 |
| LRRN3_chr6: 110737511-110737611 | GAGGCAAATATTTTAGAGGATTCATTCCTTGGGGTAACATTTGTTCTATAATTTATAGTCTCATAATGTTG AGAGATTAAAGCATTTAAATAACATTGTC | 446 |
| LRRN3_chr7: 110737611-110737711 | AACTAACTTTCAGCTTACCTTTCTTAAGGAAAAAAAACAAAAAAATGTTAAAAATAGACATGTATTTTTC AAACATACAATTCATGTTTTATGTCATTA | 447 |
| LRRN3_chr7: 110746681-110746781 | AAGAGATGTGAGGGACTTATAAATAATATTAAGATAACAGGAATTAAAGTCTCGGTGTGTGAAAATACTG TATATCTAGGATGCACATAAAAACTGCCCT | 448 |

-continued

| Name | Sequence | SEQ ID NOs. |
|---|---|---|
| LRRN3_chr7: 110746781-110746881 | TACAGATCTTGCAGGGAAAAGTACCTGACTATACTGTATAAGACTTCTGCTGTACCATTTAATCATACCAA AAAAAATGGAATCAACACACAAATAGATT | 449 |
| LRRN3_chr7: 110746881-110746981 | TCTTTTCCACTGTTCTCAATTTAAAAATAATTGGAGAAATGTGTGCTTTGTTTAGAAGAGTAAAGGAAAAC ATTCATTCAATAGTACCATGCAGAATGAT | 450 |
| KMT2C_chr7: 151943421-151943521 | CAGAAAAATAGAAAGATTATCATCGGATTTGGGAATCAAAGACAGCTCAGCAAAATACTAGGACATGGC TCATATAAGATGGAATAAGCCTGGAAATACA | 451 |
| MYC_chr8: 128750367-128750467 | CTTTAGGGGATAGCTCTGCAAGGGGAGAGGTTCGGGACTGTGGCGCGCACTGCGCGCTGCGCCAGGTTTC CGCACCAAGACCCCTTTAACTCAAGACTGC | 452 |
| MYC_chr8: 128750467-128750567 | CTCCCGCTTTGTGTGCCCCGCTCCAGCAGCCTCCCGCGACGATGCCCCTCAACGTTAGCTTCACCAACAGG AACTATGACCTCGACTACGACTCGGTGCA | 453 |
| MYC_chr8: 128750567-128750667 | GCCGTATTTCTACTGCGACGAGGAGGAGAACTTCTACCAGCAGCAGCAGCAGAGCGAGCTGCAGCCCCCG GCGCCCAGCGAGGATATCTGGAAGAAATTC | 454 |
| MYC_chr8: 128750667-128750767 | GAGCTGCTGCCCACCCCGCCCCTGTCCCCTAGCCGCCGCTCCGGGCTCTGCTCGCCCTCCTACGTTGCGGT CACACCCTTCTCCCTTCGGGGAGACAACG | 455 |
| MYC_chr8: 128750767-128750867 | ACGGCGGTGGCGGGAGCTTCTCCACGGCCGACCAGCTGGAGATGGTGACCGAGCTGCTGGGAGGAGACA TGGTGAACCAGAGTTTCATCTGCGACCCGGA | 456 |
| MYC_chr8: 128750867-128750967 | CGACGAGACCTTCATCAAAAACATCATCATCCAGGACTGTATGTGGAGCGGCTTCTCGGCCGCCGCCAAG CTCGTCTCAGAGAAGCTGGCCTCCTACCAG | 457 |
| MYC_chr8: 128750967-128751067 | GCTGCGCGCAAAGACAGCGGCAGCCCGAACCCCGCCCGCGGCCACAGCGTCTGCTCCACCTCCAGCTTGT ACCTGCAGGATCTGAGCGCCGCCGCCTCAG | 458 |
| MYC_chr8: 128751067-128751167 | AGTGCATCGACCCCTCGGTGGTCTTCCCCTACCCTCTCAACGACAGCAGCTCGCCCAAGTCCTGCGCCTCG CAAGACTCCAGCGCCTTCTCTCCGTCCTC | 459 |
| MYC_chr8: 328751167-328753267 | GGATTCTCTGCTCTCCTCGACGGAGTCCTCCCCGCAGGGCAGCCCCGAGCCCCTGGTGCTCCATGAGGAG ACACCGCCCACCACCAGCAGCGACTCTGGT | 460 |
| PAX5_chr9: 37024919-37025019 | GCTCCCCATCTGTCCCCACAGTTGCTCCTTGGCTGAGCCAAGGGCTTGCTCACCTCTCAGAGCATTGCCCT AACTGGTTTGTTTTGGGCTTACATTGCAA | 461 |
| PAX5_chr9: 37025019-37025119 | GATCAGGTCCTCCCCAGAGCCAGGCTGGAGTCCGAGGCAGAAAAGGCTGTGGAGGGCACTGGGGTCACC ACAGACTGGAAACCGGTTGGGCGCAGGCCCC | 462 |
| PAX5_chr9: 37025119-37025219 | AAACCTTGAGGAATCGTTTGGGCTGGGACCAGAACAGGGGGCTCCTCTGCACAGAGCTCCCCACCGCTTT GGTGGATTACTTCAGACTCAGAAAATTGAC | 463 |
| PAX5_chr9: 37025219-37025319 | ACAAAGAGAAACTGACCTGCCCGCAGCCAGCCCTGGCTGCCTACACAAGCTTTCCCCTGCTTGCCAGGCC ACTCAGCACTGCGTGGCAGACACGGACATG | 464 |
| PAX5_chr9: 37025319-37025419 | CTCGCCCCGGGAAGCTCACCTTCACTCCAGCCGGGTCTCTGCTGCCTTTGTTAAATAGGGGACCTGCGGCT AGGAAAGCTGGATCCCAGGCTGTTGGGAT | 465 |

-continued

| Name | Sequence | SEQ ID NOs. |
|---|---|---|
| PAX5_chr9: 37025419-37025519 | GGGGGGGAGCGGGGTGGGAGGACCAGGCATGGGGACGGCTCCTAGCCCGGGAGCAACTCCCTGACCTGA AGCCCGCAGAGACCCCGAGCGGCACCCGAGC | 466 |
| PAX5_chr9: 37025519-37025619 | CGAGGCTGCCGAAGCCTGTCACCTTCCTCCAGCCTGGCTCTGCAGCAAACAGAAAGGAAACGCGATTCGT TCCACTTGGAATTTCCTTGAAATCTCCGAA | 467 |
| PAX5_chr9: 37025619-37025719 | TCTAATCCGGCGTTAACTCACCGTGAGAGGAGCGCTCATCTCACAGGAGGCTGTGGTAATGGGTGAATTG GCAGGATCCCTGCGGGCCAGGCAGCCAGGC | 468 |
| PAX5_chr9: 37025829-37025929 | TTTTCGTTTCTTATCCTCTTTTTTTAAAGGGGAGAAGCCATGAGAAAAGGCGTCCTGCAGAGAAGGACCC AATGGGGTCTTTAAGGGTCTCTGTATGAAC | 469 |
| PAX5_chr9: 37025929-37026029 | TGGCCGGCTCCTAAGCAGAAGCTGAACTCAGAAACCGCTACTTCCTTGATTTTTCAAAGCCCCCTCCTCAA CTCCAGGACGCCTTTGGAGCCCTAGCCCC | 470 |
| PAX5_chr9: 37026269-37026369 | TGTCGCCGCCGGAGCCTTGAAAGGCTGCAGCTOGOTGCCCAAGCTACGCGTTGCCGGAGGCGGGATTCCC AGGTGCCTCAGCCCGGGCGGCCAAGTGCGT | 471 |
| PAX5_chr9: 37026369-37026469 | TGTTTCAGGTCCCCTGCCTGGGATCCCTGCACTTTGCAAAGTTAGCTGCGCGGCTGCAGAGGTCCGAGATC CTTCCGGCCTTAGTACCTGACCCACGGTC | 472 |
| PAX5_chr9: 37026469-37026569 | CGGCACCCCCAACCCGGTCCCGGCGGGAGAGTGAGAGAAGCGAGCTCGCCGCCTACTTACTATGCATGGA TGCAAACGGGTCGTGCTTACAGTGTATTTC | 473 |
| PAX5_chr9: 37026569-37026669 | CATCGGGGCGCTCCAGACTGCAGGCCGGCCCACGCCGCCGCCTCCCGGCGCCAAGGGGCTGCCCAGGGCG GATAGGGAGCCTCGCCACCAGGCCAGGCAC | 474 |
| PAX5_chr9: 37026669-37026769 | TGTGCGAGCTGGGCTCAGAAAACACTGCTGGAGCTTCGGGGTCTCTCTCAGAGCCTCCCTGCTGGAGACC GCCCGGAGCTGCGCGGAGAGGCGGGAAATG | 475 |
| PAX5_chr9: 37026769-37026869 | GTGCTAGCGCACCCGGGCTAGGAGCGGGTGCCCAACTCCGGCTGGCTTCCCTCCCTGGCTGGCTCAAGCA GCAGCTCCGGGCCCAGCCCGGGGTAGCTGC | 476 |
| PAX5_chr9: 37026869-37026969 | GGCCAAGGCGCCCGCGGCTTCGGGGGCATAGCGTAGGGGCCCGCCTCCGGGACAGCCAGCAGCCCCCGG CCCCAGGAAGGAGCAGCTTTGAGGAGGCCGC | 477 |
| PAX5_chr9: 37026969-37027069 | CGGAACAATCOGCCCTTGACTTCACTCAGGGGGCGGAGAGACCCGGGCTGCTGCCAGGCTGGTTCCGCGGC CTCGATGCTTCTGAGGTCCCTCCTCGACCC | 478 |
| PAX5_chr9: 37033619-37033719 | CACACAGGCAAACAACTTTTGGACACAAACTCATATATTTTTACATCTTTTAAAAATACATATACTGTAAT GAACACACTGAGTCCCTTATATAAACACA | 479 |
| PAX5_chr9: 37033719-37033819 | CAGGCCCTAACTTGCAGACCCCCGGAAGGACGCCAGCGTGAACATTCAGAAACAGAGAAAAACACAGAC AAACTCACAGATATTTGGACTGATGCAGAAG | 480 |
| ZCCHC7_chr9: 37293169-37293269 | ACAGTTTGAAGTGTGAGCCTGAACATGTTTGATCTAAGGTCTGGAGGAAGATGTGAAGCAAATCTGACCT AAAAAAAATTATAGGAAAAAAGCAAATTGT | 481 |
| ZCCHC7_chr9: 37293269-37293369 | TCTGGATTTGTTTCACCAAGGAACAAGTAAGCAGAGAACCAGACACTGGAGAAAAAAAGGAGTCAGGAA GTAGACAAGGAAATGTTAAAAGAAATAATAG | 482 |

-continued

| Name | Sequence | SEQ ID NOs. |
|---|---|---|
| ZCCHC7_chr9: 37293369-37293469 | GATAACTGAAAGAATGTAGCTTCCAGATTGCTAGCTATCAGCAGATAGATAGAAACTTTTATACAGCCTT TAAATCTTCCCTAGAAACCTTTTTAAAAGT | 483 |
| ZCCHC7_chr9: 37371494-37371594 | CAAGGGCCTGCCAGGATGAGAACGGGCAAACCTGGCCAAGGTGACCCCATTAGGGACTACCCTCCTAGG GACAGCACTCAGGGCCGTTCCCAATCACCCC | 484 |
| ZCCHC7_chr9: 37371594-37371694 | GGATTTCCTGTCCTGCTCGTCTCCTGCCACACCTCCTTTTGATCTACCCCCAAGACACCCCTACCTTTTTAT TCTGTGAAAATTTACTCATGCTGTGGGC | 485 |
| ZCCHC7_chr9: 37371694-37371794 | CCTGCTGGAAATGCCCTCCTACTGTTTCCCCAAACCCCGTCAGAAATTCCACGGGGAAACTCCCTTCCCTT CTGCTGCAGGCACCGTCACTGTGTCTCTC | 486 |
| ZCCHC7_chr9: 37371794-37371894 | AGCTCTGCCCCCCAGCCTCTGAGTACCACCTTATCCTAGCCCTTAGCTACTGGCTTGTCATTGTCTCTTTAC GTTCTCAGCCTCCCACAGAAGCCTGGGA | 487 |
| ZCCHC7_chr9: 37384684-37384784 | AGGCACACTCGCCCCTGGTCTCCAAGGCTCTGGGTCCTCAGACTGGCTGAGTACTGGGGACCAAGGTCAC CCAAGAAGCCCTGAGTGGCCCTCTTGAGGG | 488 |
| ZCCHC7_chr9: 37384784-37384884 | TTAGCAGAGCTTCTCTCTGTCCAAGACAGGTCAGGCTCTCTCCCCTGGCCCCAGCTCCACCGTCACTCAGA GGAGTGGCCTAAACAAACGCTGCAGGTGA | 489 |
| ZCCHC7_chr9: 37384884-37384984 | GGCTCCCGAGCCCCTGACATGGATGTTTATGGAAGAGGACTCTTGGCATCAGCACCTGGGCAAGGTGGGT AGAGGCAGGAGTGGGCAAATGGGAAAGTCT | 490 |
| GRHPR_chr9: 37407369-37407469 | GGAGAGCCGTTTGAGATTCACCAGGTGAATGAACCCCGGTTTTTTCTGGGTAACAGGTCGAATGTGAAT TACTTATTTTCACAAGCTCTTGACATGTTC | 491 |
| GRHPR_chr9: 37407469-37407569 | CGTCAAATTGCTGTTCCCCAAAGAGTGGACTCTGGTGACATATAAGTGTGTGGGACCATTGCATCTTACCC CAGAGATCCACTCCTGATCTGGCATTATT | 492 |
| GRHPR_chr9: 37407569-37407669 | CAAAATCTGCTGAATTCAAAACGATCCTGTACTTCCTGCTCACCAGGTCTGAAAAGAAAAAAGAAAAAAG AAGAAGGAAAGACTACACCTGACAAAAGAC | 493 |
| FAM208B_chr10: 5755066-5755166 | TTCACGGTTTCTCTTTAGTTTTATCTGAAATACATTTGTAAGCTTAGGGTGCAATTTGGATTAAAACAGTT TTCTTTAGTGTCAATAATGGCCTTTACTA | 494 |
| FAM208B_chr10: 5755166-5755266 | GAGTGAATGGATATTTTTCCATTCTGGATTATCGTTTAATCGAAACTTTGTTTCCTGTGGAAATTTTTCTG GTTTAAGTTATTTGATTTGGGAGATAAAT | 495 |
| FAM208B_chr10: 5755266-5755366 | CATGTAACTTAATAAACTTTGGCATCCTGGTTAACTGAAATTGCTTCATTCAATATTTGAAGACTGAAATC TGTATTGTTGCCTGTACCTAAATTATGGG | 496 |
| FRMD8_chr11: 65190342-65190442 | GGACAGACAGGGAGAGATGACTGAGTTAGATGAGACGAGGGGGCGGGCTGGGGGTGCGAGAAGGAAGC TTGGCAAGGAGACTAGGTCTAGGGGGACCACA | 497 |
| FRMD8_chr11: 65190442-65190542 | GTGGGGCAGGCTGCATGGAAAATATCCGCAGGGTCCCCCAGGCAGAACAGCCACGCTCCAGGCCAGGCT GTCCCTACTGCCTGGTGGAGGGGGAACTTGA | 498 |
| FRMD8_chr11: 65190542-65190642 | CCTCTGGGAGGGCGCCGCTCTTGCATAGCTGAGCGAGCCCGGGTGCGCTGGTCTGTGTGGAAGGAGGAA GGCAGGGAGAGGTAGAAGGGGTGGAGGAGTC | 499 |

-continued

| Name | Sequence | SEQ ID NOs. |
|---|---|---|
| SCYL1_chr11: 65266552-65266652 | GGGGCAGGCGGAGCTTGAGGAAACCGCAGATAAGTTTTTTCTCTTTGAAAGATAGAGATTAATACAACT ACTTAAAAAATATAGTCAATAGGTTACTAA | 500 |
| SCYL1_chr11: 65266652-65266752 | GATATTGCTTAGCGTTAAGTTTTTAACGTAATTTTAATAGCTTAAGATTTTAAGAGAAAATATGAAGACTT AGAAGAGTAGCATGAGGAAGGAAAAGATA | 501 |
| SCYL1_chr11: 65266752-65266852 | AAAGGTTTCTAAAACATGACGGAGGTTGAGATGAAGCTTCTTCATGGAGTAAAAAATGTATTTAAAAGAA AATTGAGAGAAAGGACTACAGAGCCCCGAA | 502 |
| SCYL1_chr11: 65266852-65266952 | TTAATACCAATAGAAGGGCAATGCTTTTAGATTAAAATGAAGGTGACTTAAACAGCTTAAAGTTTAGTTT AAAAGTTGTAGGTGATTAAAATAATTTGAA | 503 |
| SCYL1_chr11: 65267397-65267497 | TTGGAGAAGTATAGAAGATAGAAAAATATAAAGCCAAAAATTGGATAAAATAGCACTGAAAAAATGAGG AAATTATTGGTAACCAATTTATTTTAAAAGC | 504 |
| SCYL1_chr11: 65267497-65267597 | CCAACAATTTAATTTCTGGTGGTGCAGAAGTTAGAAGGTAAAGCTTGAGAAGATGAGGGTGTTTACGTAG ACCAGAACCAATTTAGAAGAATACTTGAAG | 505 |
| SCYL1_chr11: 65267597-65267697 | CTAGAAGGGGAAGTTGGTTAAAAATCACATCAAAAAGCTACTAAAAGGACTGGTGTAATTTAAAAAAAA CTAAGGCAGAAGGCTTTTGGAAGAGTTAGAA | 506 |
| BIRC3_chr11: 102188381-102188481 | TGGTGTAAGAGATGTGCCAGCGGCTGGCCGAGGGGCGCTTAGGGCTAGAGCCCGGGGCGCTGCAGAGGT TGAGAGTCAGTGGGTGGGGCGCAGTTATCAA | 507 |
| BIRC3_chr11: 102188481-102188581 | ACACCAGGGCCCAAAAGCAGGCTCTAGATAGGTTCCAGGTGCTCAATTTCTATTTCACGTTTGGAGTGAG CCAGTGGAATTGTGAAGTTGTGGCATTTTG | 508 |
| BIRC3_chr11: 102188581-102188681 | ATTCGGTTGCCAAGAGTTATCACTGGGCCTTTGCAGGTGCCAAATAAATTTCAGGACAGAGCCTAAGGCA GAGCTCTGGCACAGGAAGGAAGTAAAACGT | 509 |
| BIRC3_chr11: 102188681-102188781 | TTAATGAGCAAATGGACGCATGTTTCCAAGCGGTGGTAGGAAGACAGCAGTTTTTGGTTGTCTTCCTGGT GATCAGCATGGAAACCTAGTAGTGCTCTTA | 510 |
| BIRC3_chr11: 102188781-102188881 | CTCTGATCAATACATTGTCGAAGGCATGTACCTGATGCTAACGTAACAATAATATTAAATATTGACTTTAT TTGCTATTATTTATTGCTAACATTAAGTA | 511 |
| BIRC3_chr11: 102188881-102188981 | CTGCTACCTGCTATGTGCTAGGTTTGTCTCTGAAGACTTTACATGTATTTTTCACGTTTAATTATCATAATC TTAAGAAGCAGGTACCATAATTATCTCC | 512 |
| POU2AF1_chr11: 111249311-111249411 | GGGAAAAAGAATGACGAAAGGCAAGACAGTGGAGCAAGTGAGGACACGCTTCACCGAGCCAGATCTCCA CTCCTCCCAGGGTATCCACAGGGACAAGTCA | 513 |
| POU2AF1_chr11: 111249411-111249511 | CACCTGGCAGAAAGCTAAGTCACTCAGCTAGAAACAGGCCCAGGGAATTCAACAGAAGGCTGAAGAGCC ACTGCTTATGGAAATAAAGCCCCTCCTGTAA | 514 |
| POU2AFL_chr11: 111249511-111249611 | AGAACTGCATGGCTTTTCCCTCCCAACCCCAAACCCATCCCACATCTGGCTTTTGTTGTGTGAATCATAAA CTGCCCTTTCTTCACCACAGTGATTCATG | 515 |
| CXCR5_chr11: 118754793-118754893 | AATCCTCTCCCACTGTGGATCTGTAAAATCTAGACAGGTCAGTCAGCTCCCGCCCTTTAAGAGTTTATTTT CCATTCTGTGGAAGAAGCAGATAAGGAGA | 516 |

-continued

| Name | Sequence | SEQ ID NOs. |
|---|---|---|
| CXCR5_chr11: 118754893-118754993 | GCTGCTGTCCTTAGGAGACATCCTTTAGAGGAAGCTGGAAGACACGGGTTCAGGCCCTGCATCCTCCTCT GAGTTGCTATGTGACTGGGAACAGGATACT | 517 |
| CXCR5_chr11: 118754993-118755093 | TCACCTCTCCATTCTTTCTCTCCTTTTCTCTTAGGGTCGGAATATGGAACTAGACAGGAAAGTACTTTGGA GGTTTTCTTACCGTAAGGAGGCTGGCATT | 518 |
| ETS1_chr11: 128391383-128391483 | GGGCCCTCCACCCAGCCTCAGTTCTATGGGGGACGTGGAGTCAGGCGATGATGTCCTCTGAGGCAGCGTC CATCTCCCCTTAACATTAAGGAATAAGGCC | 519 |
| ETS1_chr11: 128391483-128391583 | AGAGGGTTCTCGCTCATTTGGGAAAATAaaaAAAGCAGGAATGGGGCGCTGGAAATTCTATAAGCTTTTC CCCACCACTCACAAAAACACAGCTGTGAAA | 520 |
| ETS1_chr11: 128391583-128391683 | ATAAATACCACCCCCCAAACCAAGGGTCTAGGGCCACCAACAGTCCTCCTCCTCCTCCTCCTCCTCCTTCT CCTCCTCGTCCTCCAGATCCAGCTGCCAA | 521 |
| ETS1_chr11: 128391648-128391748 | CCTTCTCCTCCTCGTCCTCCAGATCCAGCTGCCAACAGCATCCCCCGCTCCTGAAGAAATGCACCGCCCAG AAGGGAACGGCGAAAGGGGGAAGAAGTCC | 522 |
| ETS1_chr11: 128391748-128391848 | AGGGGACCCCCGGCCTCTGGCCGAGAGCTTGGGTGGGGGCCTCGGCCGTCGCCACTCACCCGGGGAGGG GAAAAGCTCCAGATCGACTTTTTCCGTCTTG | 523 |
| ETS1_chr11: 128391848-128391948 | ATGATGGTGAGAGTCGGCTTGAGATCGACGGCCGCCTTCATGGTGCCAGGAGTGGGGGACGTACGGGAT GGTAGCAAGTTTGCAGTTACTGTTGTTTTTC | 524 |
| ETS!_chr11: 128391948-128392048 | TTTTTAATGAGGATTAGTAACAGGGGGAAGGGGACGGGGGAAATCCGACTTTCTTCCCAAAAATCTCAAA TTCCCGCTGCCTTTCTTTCCCCCGCGCCCG | 525 |
| ETS1_chr11: 128392048-128392148 | GACGGTGCGCGCCCGGCACTCCAGGGGAAGTTGGCACTTTGCGGCGAAGTGAGCGCGCTCGGGTCCCAGC CTCGCCCGCGCCGCGCCCGCTCCTCCTGCC | 526 |
| LRMP_chr12: 25205888-25205988 | GAGTGAGTAGCAAATATTCATTTATGACCCAGTTTTTGTCCACCCTCAGGCGGGGCATAGGACTACAGAC ATTTTTCTAGATTACAGCTAGGATATTATT | 527 |
| LRMP_chr12: 25205988-25206088 | CCTGAGTTTATGACAATGAAATGGTTTGAGAAGGCAATATTGTGGGGCTTTCAGAGAGGTTTGCTGAGTG GCTAGGTGCATGCATGGGTTTAACCATTAA | 528 |
| LRMP_chr12: 25206088-25206188 | CTTCCCTTTTTGCCTTTTTATTATAAGCTGGTTTTGTCTGTGGCTGTTTTTTTCTTTTAAAATTAATTAAAAC TTCTCAAAATTTCTAAAAGTAAACAAG | 529 |
| LRMP_chr12: 25206398-25206498 | GCATTCTCTACATACATCTACATACATATTTTGCATTTTAAAAATTGGAATATTTGTCATTTTTCTGTATTA CCCAAAAGTATATAAACAGTTACCAGAG | 530 |
| LRMP_chr12: 25206498-25206598 | ATTTATGTGAGAAGACAGTTGTCACATTACAGATGTCAGATTAGCTATAAAATTGTTTCATTCTAGAAACC TAATATGGTAAAAATAAACCTTACTTATT | 531 |
| LRMP_chr12: 25206598-25206698 | TAGCCATTTATCAGACAATTGCTTTTGTTCAGCCAGTTTCTTGTTCTAGCAGTATAAATATTCTTTTTATAG AAAGTTACTTGGTTTGAGAAATAAACAT | 532 |
| LRMP_chr12: 25206748-25206848 | ATAAGCTTAAGGTAGGCTAGAGATGAAAAATTTCAGACTTGTGTTTGTTTTGGATTTATTGTACCCTTTCT ACTATTATCTGAGAAAGCTATTTAGGAGT | 533 |

-continued

| Name | Sequence | SEQ ID NOs. |
|---|---|---|
| LRMP_chr12: 25206848-25206948 | TTAAGAAATAGTCTAGTTTTAAAATAGCAATGGTTTGCCGGACACAGTGGCTCACCCCTGTAATCCCAGC ATTTTGGGAGGCCGAGGTGGGCAGATTGCT | 534 |
| LRMP_chr12: 25207088-25207188 | GAATTTGCCAGTTTTCAATATTCTGATTCACTCTGTTAAGCTAGTAAGGCAGTCTTTAAATTACACAGTCT GTGTGTTATTTTACTACTGCTCAGAGGGC | 535 |
| LRMP_chr12: 25207188-25207288 | ATTGGAGAAGGTTCCCTTGTGATTAGAACTGTTCATGTTGAGACATGAATCATAAGGCATTCCAAAGTTG GTTTAAGGTGTGTCTGCTTTAGACACTGTG | 536 |
| LRMP_chr12: 25207288-25207388 | CCCAGGACTATTCTTTTGCTCCAGTTTTGCCTTTTGATTAAATCAATATTATACCTGAGTTTTATAAACTAC TAAGAATTTGTTCCCCTTCCTCACTGTG | 537 |
| LRMP_chr12: 25207388-25207488 | ATTTTCTTGCAGTATTTTCTTAGAAGAGTCAACTTTAATAACTTACCCCAAAGTGCACGTTCTTGATATTA TGAACTTGCTATTGTTGTCTTCCCAGTTT | 538 |
| BTG1_chr12: 92537875-92537975 | TATTGTAGTTTTTGGAAGGGCTCGTTCTOCCCAAGAGAAGTTCCTCCTTACAGCTGATTCGGCTGTCTACC ATTTGCACGTTGGTGCTGTTTTGAGTGCT | 539 |
| BTG1_chr12: 92537975-92538075 | ACCTCCTGCTGGTGAGGCTTCATACAGCACACAGATGGAGCCATCCTCTCCAATTCTGTAGGACACTTCAT AGGGGTCAACCCAGAGTGTGAGTTCACTT | 540 |
| BTG1_chr12: 92538075-92538175 | GGGAGAAGCCTGAACAGCTCCTGACTGCTCAGTCCAATCCGCTGTGCTGCCTGTCCAATCAGAGGATCCA TTTTATGGTTGATGCGAATACAACGGTAAC | 541 |
| BTG1_chr12: 92538175-92538275 | CCGATCCCTTGCATGGCTTTTCTGGGAACCAGTGATGTTTATAATGTTCTATAGAAGAAAAGAAGAACAG AGAAACAACGCTTAGGATCGTTAGCTCCCA | 542 |
| BTG1_chr12: 92538275-92538375 | CTGCGGATTCCTCCTACCCCAGGCTCCTTTGAGGAGCGAAAATGAAAACTATCAACTTTTTAAAATGTCCA GGATTGCATCCGTTGTTGTGCATGTGCGG | 543 |
| BTG1_chr12: 92538375-92538475 | GGATGGAAAAAGCGGGCAGGGTTTTAGAAATAACACAGTAGTACCGGACAAAACAATCTCCAGGAACCA ACCGGTTGAGCCGCCAAAACAGGAATCAGGC | 544 |
| BTG1_chr12: 92538475-92538575 | GCGCAGCCTCGGCCAGTCGGGAAGCCACTGGCACCTATGGCCAGGCGAGAAACTGTTTACTTTCTCCACC CCACCCCAGATGCACACAATGGAGTTGATG | 545 |
| BTG1_chr12: 92538575-92538675 | GCTTTGGAGATGAGAAGCGCCACCGGACTGTTAACCCCGAAGGGAAGAAAAACAAGCAACCCTAAACCA CGCTCTGGGCAGGGCTGTTAATTGTOCCGGT | 546 |
| BTG1_chr12: 92538790-92538890 | ACGCAACGGTTGGAGGGGGCTGAGGAAAGGGGACGTCGAACCCACCCCAGCCCCACGGCTCCTTTGTCCC CAAATCCGCCGACGGTCCTCGGACCGCAGC | 547 |
| BTG1_chr12: 92538890-92538990 | TCCCGCCTCGGTGGGCTTAAGTTTCTTTGTTGTGCGTGTTGTCTTCTCCTCTCCGTTTTGCCAGCTGGGGGG AAGGGGGCGCCCTCCGTCCAGCCCCTAA | 548 |
| BTG1_chr12: 92538990-92539090 | AGCCTCGCGGGGAACCGCTGTTAGCGGCCACCCAGCGCAACCACACCGGTCCCGCGGCGGGGCCCAAGC GCGACCGGCCCCGGGGCGCTGCCGAGGTTCC | 549 |
| BTG1_chr12: 92539090-92539190 | CGCAGCCCCGACGGCCGGACTCTGACCCAGGGATGTGGGGCCCGCGTCCCTCCGACGCCCTCGCCCTGCT CACCTGCCAGCAGCTCCTGCAGGCTCTGGC | 550 |

-continued

| Name | Sequence | SEQ ID NOs. |
|---|---|---|
| BTG1_chr12: 92539190-92539290 | TGAAGGTCTGCAGCTGTCGCTCGCTCGTGAGCCCCTTGGTGCGGAGAAACTTGGAGATGAAGGACACGGC GGCGGCGATCTCGCCTATCATGGTGGCGGC | 551 |
| BTG1_chr12: 92539290-92539390 | CCGGGTGTAGAAGGGATGCATGGGGGCGGCGTGCGGGGGCGGCCCGGGGCGGCTGGGGCTCGGCGGCGC GGCCCCGACGGCGGAGCAGCCACCCCGGGCT | 552 |
| DTX1_chr12: 113495364413495464 | ACGCCGCACCCCTCCCCCGTGCGTTCTGCGGCCACCCAGGCCTTCCAGGACACCGTGGAGAGGGAACAAG GGGGCAGGGACGCCCCCTTCGGCAGGAGCC | 553 |
| DTX1_chr12: 113495464-113495564 | GTCGGAGAAGGGGGCCCAGACCGGAGGGAGGCGAGAAGCCCCACTGAAGCCGGGCGCAGGGTCTGGGA CGCAGTTGGGAGTGCAAAGGGCTGGCTGAGAG | 554 |
| DTX1_chr12: 113495564-113495664 | CCGCAGGAGCAGCAGGCTGTGGCCCAGGCCTCCTGGGTGACAGGCCCTGTCTGGCGGGGAAGAGGGACC AAGAGACAACACGGAAGAGGCTGGACCTCGA | 555 |
| DTX1_chr12: 113495664-113495764 | ACAGGGGCGGCTGCCTCACTCCCTACCTGAGCCAGCCGAGGGGGCCAAGGACTTTAGAGCTGTTTCCTCC GGCATAAGAGAGACACTTGCTTTCCAGGGC | 556 |
| DTX1_chr12: 113495764-113495864 | AGCACCCTTTATCGGAGAAGGCTCTACAGGGAAGGGGTCTTTGCAGCCTGGATGGCCATCCCACATTCCT TTAACGGAGGTCTCTAGGCCTCAGAGAGAA | 557 |
| DTX1_chr12: 113495864-113495964 | CCCAGAGTTAGAAAGGAGGCCAGACGGTCCTTGCTGTCCCICCTGGGGAGAGAGGAAGTTGCCGCCTGCTG CCAGGCCCAGGAGGAGCTGGGCCTGCAATA | 558 |
| DTX1_chr12: 113495964-113496064 | GTGGGGGACCTGGCCCCTGAGGCAGTGGCGGCCATGTCACGGCCAGGCCACGGTGGGCTGATGCCTGTG AATGGTCTGGGCTTCCCACCGCAGAACGTGG | 559 |
| DTX1_chr12: 113496064-113496164 | CCCGGGTGGTGGTGTGGGAGTGGCTGAATGAGCACAGCCGCTGGCGGCCCTACACGGCCACCGTGTGCCA CCACATTGAGAACGTGCTGAAGGAGGACGC | 560 |
| DTX1_chr12: 113496164-113496264 | TCGCGGTTCCGTGGTCCTGGGGCAGGTGGACGCCCAGCTTGTGCCCTACATCATCGACCTGCAGTCCATG CACCAGTTTCGCCAGGACACAGGTGAGCAG | 561 |
| DTX1_chr12: 113496264-113496364 | ACACCCACCCCATGCCACCOGCCCCGCCGAGCCATCACTACCTTGCAGCGTAGGATGCTGAAAATCCCAG TAAATCTGCTGATGCCAAATCCCTTCCCCA | 562 |
| DTX1_chr12: 113496364-113496464 | TCTCCCTGCCTCACCTCCAGAAAAACAGGGCAGTCTAACCTTGTCCAGTTTAAGACTTGGATTCCAATGCA GCCTCTGAGCAAGCTGTAGGGCCTTGAGC | 563 |
| DTX1_chr12: 113496509-113496609 | GGGTAGATCAATATCTCTCACAGCTGAGTGAGGATTAAATAAAATTGTGCTCACTGAGCACAGAACCTAG AACAGCAGTAGCATGGGATTGTAGAATAAG | 564 |
| DTX1_chr12: 113496609-113496709 | GGCTTTACATGCACTTCCTCATTTGATTTTTCCCAAGAATCACAGGCAGTAAGTCTGTGTATTGTTGTATT ATTATGAGTCCCATTTTATAGATGAAGAA | 565 |
| DTX1_chr12: 113496694-113496794 | TTTATAGATGAAGAAAACCGAGTCTCCCAGAAGCTGAGTGATTTAAACTCAGAGCTGGGATTTAAACCCAG GCGGTTGAGTTCCAGAACCAAAGTTCTTAA | 566 |

-continued

| Name | Sequence | SEQ ID NOs. |
|---|---|---|
| DTX1_chr12: 113496794-113496894 | CTGGTATCCTATACTGGCTCCAAGTGTTGGTTTGTGGGGTGGAGTCGTGCTGGTGGTAATTAATTGGGGA TGGGGGGCGTTGGTGGTGTTGATGGTGGGG | 567 |
| DTX1_chr12: 113496894-113496994 | TGAGGTGGCAATGATGGAGGAGACAGTGTTAGCGGTTGTGTTGGTGGTGACTCAGTGATAGTATTGATGG TGGTGGGGTCTTGGTGACAATGGAGGGATG | 568 |
| DTX1_chr12: 113497059-113497159 | TGTTGGTGACATTGATAGTTGTGTTGGTGGTGGTGCTGGAAGTGGTGTGATGGGGTGGTGATGATGGAGA AAATGAGAGAATGATGTTGGTGGCAGTCTT | 569 |
| DTX1_chr12: 113497159_113497259 | CGTGGCCATGTGGTGTGGCTGGTAGCCCTGTGTGTGGCTGTTACTTAGTGGTATTGGTGATCCTGTTGTGG TTGTAATGATGGTGATGTTGATGGTTGCG | 570 |
| DTX1_chr12: 113497259-113497359 | TTGGTGGTAATGTGATGGCTGATGATGGAGATAAAATCGATGAGGTCCCACTCTCAGGCCTACTCTCTTTT GTTCTGGAGATTTGTCATCGTTGGGGAGA | 571 |
| BCL7A_chr12: 122458781-122458881 | TGAAATGGCTGCTGTCGGGCTGTCATCTCCAGGCCCGGGGCGCTGACATTTGGCCACTCTCGGTCTCCCT CTTCATTCTGGGCGCGCATTAGCTCTGGT | 572 |
| BCL7A_chr12: 122458881-122458981 | CCGGCCGGTTCCGCTGCAGCTGAACAGCAAGATGCGGCACCCAGGTTACCCTGATCATCGCAGATTTCTC CCCGGGGCTCTGTTCTGAGGCCTCAAAAGT | 573 |
| BCL7A_chr12: 122458981-122459081 | GCTCCTTGTAGATGGGACCAGGGGTCATTTGGGCAGTAGCAGCGCCTGGTCTCAGTCTGGTACTGAAGTC AGGAATGGCTTAAGGTGAAATCGTGGTCCT | 574 |
| BCL7A_chr12: 122459081-122459181 | CTGGTGAAGCTCAGCGAAGACCCCCTCGCCTTGTTTATGACAAGAGAACTTCTGGGGGCGGGAGGAAGAG TCCCTGTTACGATGCTGATCATCATTGAGC | 575 |
| BCL7A_chr12: 122459181-122459281 | TTTTGCTGAGCAGAAAACTCTTTAGTACTCAAGGTCGAGAGTCTCTGGTGGTCTGCCTGGCACCAGGCAC CTTCCTACAACCCTAGTTTTCCAAAAGGAC | 576 |
| BCL7A_chr12: 122459281-122459381 | AAAGCCTGGGGCAGGCGACGTCCTAGCTCGCATTTGAACAGGGCCGCGGGCCAGCAGAGATGCGCGATG CCCAACTCTTTCCAAGAGCACCTCGCGTCCC | 577 |
| BCL7A_chr12: 122459381-122459481 | GAACCGGTGCCTTCAACTCGGAGAAGTCAAGAGACCCGCAAGAAACTTGCACGACTGCACCCGCCGCCGC GCTCTGGGGGCTGGGCAGGGGCAGCTGGGC | 578 |
| BCL7A_chr12: 122459481-122459581 | TGGCTCCCGGGGAACGCGACCCCCCCGCGCCCCGCAGACCGGCTGTCTCCCATGGACCCCTCGGCACCTG CAGCCTCCGAGGAAGGGTCAGCGCGCGTGT | 579 |
| BCL7A_chr12: 122460811-122460911 | GGGGGGCTCGGGCCAGCCGATGTTTTTGGCCAGAAGCCGTTCGTCCTGGGCCGCGGCTGCCTCTCCACAC CGGGAGCTCGTGTTTGTTTTGCGGAGGGAG | 580 |
| BCL7A_chr12: 122460911-122461011 | CTGTTGTTTTTGTTCTCTGCACCGGGGAGAGGGGGACTTGGTGGCGGCCGCGCGTGGTTTTCGGGATCAC ATTAGCGTCCGCCCGGCGTGGCCCGGTCGA | 581 |
| BCL7A_chr12: 122461011-122461111 | CATTAAGGGGATCGAACCTTTCCGCGGCCTCGTCGGGGTCTGCTCGGAATCGGCCCCTGGGCCAGGCCCG AGGCGCAAGCAGATCGCCAGGTTGGGTCAG | 582 |
| BCL7A_chr12: 122461111-122461211 | AGTTGTTGAAAACTCCCCGCTGCCTGATTTCAACTTTATTATTTTTTTCCCACGCCTTCACTGGGGTCCCGG AGGGAGAGGAGCCGCCGCAACGCTGGCT | 583 |

-continued

| Name | Sequence | SEQ ID NOs. |
|---|---|---|
| BCL7A_chr12: 122461316-122461416 | AGTAGCGCCTCGGTCTCTAAAAGCCACTGGGGGCGAGCCTCCGGTGTGGCGGTGTCACAAGTTAGCTGTC CTTTCTGAGTCAAACCCAACAAAAAAGGCA | 584 |
| BCL7A_chr12: 122461416-122461516 | AGAGGAAAATCAATAAAGTCCACGTGCTCCCCGGCCTCCTATGGAAAGGGCTGGCTGCGATGGCCGGATG CCCGGCCGTGGGCTGGGTTTGGCTCCAGTG | 585 |
| BCL7A_chr12: 122461516-122461616 | GGACAAAGAATTTTCAGAACCGTGAGAAGGGGAGGCTTTCCAAAGTTGAGATCCAAGTCGTCGGTGTCTC GGGAGCTCCCCTGGTACACAGGGTGCCCGG | 586 |
| BCL7A_chr12: 122461616-122461716 | TGCCCGACTGGAGCCATTTAAAAATGGCAGAAACAGCTGCAGGCCAACACACACACGCTGGAAAACAAC CCGCAGCCCCCTCTACTGTGGGATTCCCCGC | 587 |
| BCL7A_chr12: 122461716-122461816 | GGGAAGCCCGGAGTTGCTCCCCTCCTTGCCTCAGCCCCTGTGCAAAGAAAGAACTGGTGTCTGTGCCTGG GTCCCTTCTGTCGCCGGCCTGGAGGTTGGG | 588 |
| BCL7A_chr12: 122461816-122461916 | AAACAGCCGGCAAGCCGCCTTTCTCTGCTCGAGGAGGCGTGGTGGGGCCTCCTACTCCAGGTTCCCGGCT GGACAGAGGCTCCTGCACCCTGACAGCTGC | 589 |
| BCL7A_chr12: 122462001-122462101 | GGAGGCCTTCCAGCCCGCTGACCCCGCGGGGACCAGGCCTGTAGTTGGAGCTTGAGGGGCTGTACCTCTG CGCCTCCCTGGGTTTGGGGAAACAACACAT | 590 |
| BCL7A_chr12: 122462101-122462201 | CGTGTCCTCTGAAGACCTCAGGCTTTGGGATCTCATGGTCCAGCTTCCAGTTCACTTCGTTGCCGCGACCT TGGGCATATCATTGTCACTTCTCTAACCA | 591 |
| BCL7A_chr12: 122462201-122462301 | TGGTGACCCGGGGTTTTGTGCTTGGCTTCCAGGTCCCCTCGGGTTATTGAGGACGATTGAGGTCATGCCTC CGAGAGCACCGCGCCCTGGGCGCAGGAGG | 592 |
| BCL7A_chr12: 122462716-122462816 | AATGCAAATTTAACAGGGCACCCTGTATTTTACCCAGAGGGAAGCCGAAGTGTTTGGCAGATCATTTGGC CCCATGAGCCTTGGGTGGGTTTCTCCTCAG | 593 |
| BCL7A_chr12: 122462816-122462916 | CCCTAGTGACCCCTAAAATTACCCCCCCGACCCACCCACTGTCCCCTGATGCTTCCCCCACCCCCGGAAAA AGCTGTGGCCTCCCTCTCATTTGGGGCAG | 594 |
| BCL7A_chr12: 122462916-122463016 | GCTGCCTCCTGTTCTCTTTTTCTGGTGTTTCAGCAAGGCAGGCCAGTGGAGGTGAGGTGACCAGAAGATG GCTAAAGGGAAAACAAAATGGTGGGCCTCT | 595 |
| BCL7A_chr12: 122463031-122463131 | CCAGGGTTTGGGGGCCCTGTGCTGGTGGAGGAGAGAAGACCCCAGGGCGATGGTAGGAGACGAAAGCTT GGGCTGCAGCGTAAGCTTGGAGGCCCGCTGC | 596 |
| BCL7A_chr12: 122463131-122463231 | GGTGGCTCACGCCTGTAATCCCAGAGCTTTGGGAGGCTGAGACAGGAGGATTGCTTGAGCCCAGGAGTTT GAGACCAGCCTGGGTCTCAAACCAAAAAAA | 597 |
| KIAA0226L_chr13: 46959165-46959265 | TAAATATAATTTTAACGCCAATCTGAGAAAAATGACTTATTAGCTGTGTGATTTTGAGCAATGCTCTTAAC CTCCCCCATGAAGGATGGTGTGAGAACGA | 598 |
| KIAA0226L_chr13: 46959265-46959365 | ACAGAATTGTAGCACGTGTATCAGTCTGGTACACAATGTCCTATGAAGGTTAGCTTTATTATCACCATCAT TATTATTGCAGAAAGACTTTCAGTTCAGA | 599 |

-continued

| Name | Sequence | SEQ ID NOs. |
|---|---|---|
| KIAA0226L_chr13: 46959365-46959465 | ATAAGACAGCACAGTTACAGAGACCTGGTTTTATTTTCCAGCTTCTTAACTGAGTCATCTTTCAGCTCCTTTTAATTAAAAAGAAAAAACAATCAGAGAT | 600 |
| KIAA0226L_chr13: 46961680-46961780 | TCAAAGACCTGGCAGAAATGACTTCCCAACCCCAGATGCCCCCAGCAGCAGTATTTAGCAGTCATACAATTGCCTGAAATGAAGAATGAGTAATCTGGAT | 601 |
| KIAA0226L_chr13: 46961780-46961880 | GAGTCGGCCCTGAAATCGACCTGCAACTTACCCGGAACGTGAGCTGTCTCTCTCTGACCTCTOCTGGCTGCTTCACCTGGAGTCTGAGTCCGACTCATGT | 602 |
| KIAA0226L_chr13: 46961880-46961980 | AGCACTTCACTGTCCGCGTTAGTTTAGCCTTCACTGTCAGCAACTCGTCACCTTGTCCTCTTGCAGCGAAGGTTTGGAATCCCATCACGGGTGTGCAGTG | 603 |
| KIAA0226L_chr13: 46961980-46962080 | GTTAGTCCTGAGATCATGGTGGTGCTAGGAGAACCTGCCAACCAATACAGAAAGTTGTCAGGAATAGAAACCTAAGCTCTGGCCGGGTGCGGTGGTTCAA | 604 |
| ATP11A_chr13: 113516229-113516329 | AGATATACTGTTCTAGACATGTGTCTGAAAGGAATCCTGCAAATTCTGTCTTATTGAACAGGCATAAGGTGTCACGTCAGGCGTAAGGTGTCACAGCAGG | 605 |
| ATP11A_chr13: 113516329-113516429 | CGTAAGGCGTCACGTCAGGCGTAAGGTGTCACAGCAGGCGTAAGGCATCACGTCAGGCGTAAGGCGTCACGTCAGGCGTAAGGTGTCACAAGCTCGGTGA | 606 |
| ATP11A_chr13: 113516429-113516529 | ACGTCAGGGGTGTGCCTTGTGTTCTCTGTTCGTTGCTTTCAGAAGCAGCAGCATGTGGCAGCATCTCTGTGCCTATGACGATATTGCAGTGAATATGAGA | 607 |
| SYNE2_chr14: 64330252-64330352 | AATTGTACATTTCAACAACATAAATAAGCTGTTCAAGACTGTCTCCCATGCCTCCAAAACAAATAAAAACCCCCCACAACTCAAATGCATATAAGCTGTT | 608 |
| SYNE2_chr14: 64330352-64330452 | ACTATAGTATAATGGTGAGTTATAGCCAGTGTATGATGGGATTGTTGATAGAATAATGCATATTAGAGCTTTTAGTTCAAAAATTTGAGATAGTGATTCA | 609 |
| SYNE2_chr14: 64330452-64330552 | GAAAGAAAAAAAGGAATGATTATCATGAATTCTGTTTATTAGAATTCTGTTTATTAAAGAGTTAAAGATATGTTTTATTTTTTTATCTTTATTATCATTA | 610 |
| ZFP36L1_chr14: 69258238-69258338 | AATTCTAATGTTGGTCCCTTAGGATCAGCAGGGGGGGACCGGGAATCTGTAACTGCAACCACCCCACCGAGAGGATTACAGGAACCCAGTCGAGAGCTGG | 611 |
| ZFP36L1_chr14: 69258338-69258438 | TTCCCAACAATGAGGTTCATTTAAAAAGTCGTGAGGGGGGAGGGGGGCCAAAGAAAGAAATAGATCAAAGAGCGGGAGAGTCGAGAAAAGAAGGAAGAAA | 612 |
| ZFP36L1_chr14: 69258438-69258538 | TGTTGGGGAGCGCTGGCAGCCGGGCTGGCAAGTGGAGTTTGGGAATGTGCAGGGAGGGAAGGAAGCTGAAAAATTCAAACTTTTTAAATGCTACTCTTCA | 613 |
| ZFP36L1_chr14: 69258538-69258638 | GCTCCTCGGCGTCCCTGCACCCCAACCCTGCAGCCCTGGGGCGTTGGCAGCTGCACCAACAGGAGCAGCAAGCTGGGAAAACAGAGCAACATGACCCGAC | 614 |
| ZFP36L1_chr14: 69258638-69258738 | GTGTTAAGAGAAGGCAAAACACTTCAGCAATTAAAAAGTAGCCCAGCAGCTTCACCCTTTCAAATTGGGAGGGGGAGGTTGGAAAGAAATTTAACAACAT | 615 |
| ZFP36L1_chr14: 69258738-69258838 | CCATAGACTTTTGCTATGTACATTTAAACCGCAGTCCTGGAACATTCCGAGTTTAAAACTTGCTTTTTCAACACTGGCTGACAAGCAACATGTTTTAAGG | 616 |

-continued

| Name | Sequence | SEQ ID NOs. |
|---|---|---|
| ZFP36L1_chr14: 69258838-69258938 | AGCCCCCCATTAAATCCTTACTCGCGGGACTCTCGAGTTCAAGCCAGCATTTTGTCGCCACCTCCCCCCCC AACCCCGCCCGCAATCGATGAGCCGCAAT | 617 |
| ZFP36L1_chr14: 69258938-69259038 | GCCTCGGCAACACAGGTAAGCGGGTCAACCTGAATGCCTCTTTCACCCCAAAGTTTGCTGCACGATCGGC TATCGCGGGAAGAAGCCCAACGGAGCTAGG | 618 |
| ZFP36L1_chr14: 69259038-69259138 | GCGGACTCAAGCCCCACTGCAAACTTGTTCTGCAACATCTTTTTGAATCACAACTTGGCCTTTCTTCCTCG CATATCCCCAGCTCCCCCCAAAGAGTGGA | 619 |
| ZFP36L1_chr14: 69259138-69259238 | GGAAAACATTGTCCCGAGACTCACTTCCCCGAGGGACCTCCCACTCCCAACCCCACGGGTGGGTAATGCC GCTGGACAGACCTAGGGCGCAGACTGGGAA | 620 |
| ZFP36L1_chr14: 69259238-69259338 | CCCGATCAGACCAGCAAACCTGGGATCCAGCAGCACGTTACGTAAAACAGGATCGCCCAAAACTTGTCCC AATCCCAGCCCTCCCCCCGAAGCCCCCGGG | 621 |
| ZFP36L1_chr14: 69259338-69259438 | CTGCCCTGCCAGGCAAACTTCGCCCCTCAAAACCCTGGCCTCCAGATTCACATGTAATCCCCGCCAGCAAC TGTTGAAACTCAAAGGGTGGGAAGGACGG | 622 |
| ZFP36L1_chr14: 69259438-69259538 | GGCCAAATTCCTTCAAACTTGGGAGAAATGCCGGAGGAGAAAAGAATCATCTCGCTGCACCACTTTCCCC ATTGCCTTCCAAGACCCAAACTTTTGGGGG | 623 |
| ZFP36L1_chr14: 69259538-69259638 | TTCTTTCTTAAGGCAAAAGAAAAAGACTTTTTGAAAAGCAAATGCTCCGCCCCCCTTTACCTTGCATAAAA CTTCGCTCAAGTCGAAGATGGTGGCAGAC | 624 |
| ZFP36L1_chr14: 69259638-69259738 | ACGAGGGTGGTGGTCATCCTGTGCGTTCGCGCGAGCCAGGGGCGAGGATCTGGTGTGTCGCGAAGGTCCC GGTGCGGGGAAGGCGCAGCCTCTCCTGTCT | 625 |
| FLRT2_chr14: 84420586-84420686 | TTATTTTTTTATATTAAGATTTATTCTAAATTTTGATTCTTCTAAATATAGTATATATTTAGTATATATATA ATGCACCTCTCTTACCTAATGATCATTT | 626 |
| FLRT2_chr14: 84420686-84420786 | CTAAATAATCATAACAACATCGAGTAAAACTATGTAATAACACATATTATTATTAAGATAAGTATAAGAA ATATAATAATAAATTGTCCCTGTTCTAAAA | 627 |
| FLRT2_chr14: 84420786-84420886 | GGTAATTATATAATGCTGAATGTGTCAGAGGCATTCGAACCAGAGTGACTCCATTTTGAGTGAGGGCTAG GAAAATGAGGCTGAGACTTGCTGGGATGCA | 628 |
| TCL1A_chr14: 96179592-96179692 | TTTAATTTTTATGCTTTCTTCAGTGTATGTTTGGAGAGAGTTTGAACATTTTTTGACTCTTTTTCATTGAGT AAATCCAAATACTTGTAAAAGACTTATC | 629 |
| TCL1A_chr14: 96179692-96179792 | TATTTCTTTAACAAAAACTTAACATGGATTAAGGACCCATCTTAAGGCATCACACATTAAAAAAGTCAAT ATTGATTCAATACCGGCGCTTATACTACGA | 630 |
| TCL1A_chr14: 96179792-96179892 | CATCACTTGTTAAATTTGTTTTCTAAATAAAGCCCAGAGGTAGTGGAAAATACTTCACACTCTAGGCCAGT GTTTGCTATGCCTGGTTGACCCTAAACTG | 631 |
| TCL1A_chr14: 96179892-96179992 | TTGAGGGTTCTTTTTAAAAATACAGATTTCTGGGACCCACCTGAGATGATTCCGATAATCGGCCATATGGA TGAGTCACTTAGAGATACCCATTTTTAAG | 632 |
| TCL1A_chr14: 96179992-96180092 | GATTAGGACCCCGAAGCCCAGAAAATGCCTGCTGTAGTCAACATTATAGTCACACTCCACAGGCACTGGG TCCACCCCTTTGACCGACATTCCTTTGCGG | 633 |

-continued

| Name | Sequence | SEQ ID NOs. |
|---|---|---|
| TCL1A_chr14: 96180092-96180192 | TTTTCCCACCCTTCTTCCCTGCCTGGAGAACTCCTATTCATCCTCCAGAGCCCGGCTCAAAGTGGCTTCATC TGTGGGGATCCTCCCTGCCCCATAGTGA | 634 |
| TCL1A_chr14: 96180192-96180292 | GTGCTCCTTGAGTCCTCGCCCTTCCTAGGGCATCCCAAGCTCCCAGGGGCTGCCCCTGCTGCCTCGCCATC CGCTCCAAAGCTGGCTGTACCTCGATGGT | 635 |
| TCL1A_chr14: 96180292-96180392 | TAAGGGCAGCCAGGCGTGCTGCTTCTCGTCCAAATACACGAACTTCTCCCAGGCCCACAGGCGGTCCGGG TGGTCGGTGACTGCCTCCCCGAGTGTCGGG | 636 |
| IGHA2_chr14: 106048955-106049055 | AGGAATCAGATTTCAAAATGAATATGTATAAGAAAAGAACCGGGGATCAGTGATCAGGAACAGGGATCC ATGATCTGGTCCAGGGCTCAGCGGTCAGGAA | 637 |
| IGHE_chr14: 106068705-106068805 | CCCTGGCCTGGAGTCCCAAGTCCCCAGCCCATCCTGCCCCTGGAGCCCAGTTTAGCTTGGTCTTGAAGTCT GCTCTAGGTACCCCCAAAATCACAGTATC | 638 |
| IGHE_chr14: 106068805-106068905 | CAGCCCCGCTCTGCCCACCGGGACAGCCAAGTTCAGCTGAGACTGGCCTACCGGGGGAGTCGCCCTCTGA AGTTCACTCTAAGCCAGCCTGGTTCAGCCT | 639 |
| IGHE_chr14: 106068905-106069005 | GGCCCAGGTCAGCCCAGGACCTCCCCTTGCAGGCAGCAAACTCTTATTTCAGTCCAGCCAGCTCAACCAG CTTGCTTCTGACTCAGCTCCTCTTAGCCAG | 640 |
| IGHE_chr14: 106069045-106069145 | TTAGCTCAGCAAAGCTGGACCTAAAGTAGCCACCTCACCCCAGCTTCATCCAGATGAATACAGTCCAGAT CAGCTTAGTCAGTTAAGCCTAGCCTAGCTA | 641 |
| IGHE_chr14: 106069145-106069245 | GTTAAATCCAGTTACGACCAGCTCAACTAATCCTGCTCAGCCCTGCTCAGCCCAGCCCAGCTGAACCCAGT TTAGCCGAGGCCAGGCCAGCCCAGCTGAA | 642 |
| IGHE_chr14: 106069245-106069345 | TACAGTTGCCCAGTCTAGCTCAGCCCAGTCCAGCACTGCCCAGTTTAGCTGAGCTCAGCCTGGCCCAGCCC AGCTCATATCAGCCCATCTCAGCTGAACC | 643 |
| IGHE_chr14: 106069345-106069445 | AGTTTGACCCAGTCTAACCCAACCCCGCTCAGCTGAACCCAGCCCAGCCCAGCCCAGCCCAGCCAAACCC AGTTTAGCCTAGCTCAGCTCAGCCCATTTC | 644 |
| IGHE_chr14: 106071060-106071160 | CCTGTCCTAGGGGTGGCAGGCAGTCTGCACCCAGCCTAGCCCTGCCCAGCGTGGGGTCTCTGACCTTCTTG GTCTTGGGCCCAGCCAAGATTCCCAGCCC | 645 |
| IGHE_chr14: 106071190-106071290 | TTCTAGCTTTCCTGTGTCCCCATGCAGGGAAGGGATGCCTAGAGTCCACGCAGTGACCAAGAAGCTTGGT TGATGCTGTGAGGGTGGCCCAGGAGTCCCC | 646 |
| IGHG4_chr14: 106095335-106095435 | CACCTGCTGTCCTTGGTCCTGGCTGAGAGGAGGGCCCTACGGCCAGCTCTGCTGACCCTGCCCTGGGCTCT GGTGATGCTGCCGGCCTGGACAAGCCCCT | 647 |
| IGHG4_chr14: 106095480-106095580 | GAGCTCAGGTCGGTCGTGCCCATCCTGGCATCACCCCACAGCCGGTTCTGCCGCATCCCGTCATGTTCCTC GTGCTCCCAGCCCGGTCGTCCTGGAGGCC | 648 |
| IGHG2_chr14: 106110675-106110775 | TGAGCATGAGTGGGGCGGGCAGAGGCCTCCGGGTGAGGAGACAGATGGGGCCTGCCTTGCTGCCCTGGG CTGGGGCTGCACAGCCGGGGTGCGTCCAGGC | 649 |
| IGHG2_chr14: 106110775-106110875 | AGGAGGGCTGAGCCTGGCTTCCAGCAGACACCCTCCCTCCCTGAGCTGGCCTCTCACCAACTGTCTTGTCC ACCTTGGTGTTGCTGGGCTTGTGATCTAC | 650 |

-continued

| Name | Sequence | SEQ ID NOs. |
|---|---|---|
| IGHG2_chr14: 106110830-106110930 | ACCAACTGTCTTGTCCACCTTGGTGTTGCTGGGCTTGTGATCTACGTTGCAGGTGTAGGTCTGGGTGCCGA AGTTGCTGGAGGGCACGGTCACCACGCTG | 651 |
| IGHG2_chr14: 106110950-106111050 | GGACTGTAGGACAGCCGGGAAGGTGTGCACGCCGCTGGTCAGAGCGCCTGAGTTCCACGACACCGTCACC GGTTCGGGGAAGTAGTCCTTGACCAGGCAG | 652 |
| IGHG2_chr14: 106112335-106112435 | TGCTACACTGCCCTGCACCACCTCCACTCAGCTTCATTGTOCTGGTGGCCCTGGCTCCTGGCAGCCCATCT TGCTCCTTCTGGGGCGCCAGCCTCAGAGG | 653 |
| IGHG2_chr14: 106112435-106112535 | CCTTCCTGCCTAGGGTCCGCTGGGGCCAGCCCTGGGACCCTCCTGGTCTCAAGCACACATTCCCCCTGCAG CCACACCTGCCCCTGCCTGAGAGCTCAGC | 654 |
| IGHG2_chr14: 106112535-106112635 | CCCGAGCCCTGGAATGCCTTCCCTTCTCCATCCCAGCTCACCCTTGCCAACTGCTCAGTGGGATGGGCTCA CACTCCCTTCCTGGCACCAGGAGGCTGCA | 655 |
| IGHG2_chr14: 106112635-106112735 | CTGCACTTTCACCAGCCCTCAGCTGTCTGCTGCCAGCAACTACCCAGCTCCTGCCAAAATCTAGGAGCTGA GTGATGCCTCCCACCGGCCCTGCTCACCT | 656 |
| IGHG2_chr14: 106112735-106112835 | GTGGTTGCCTTGCCCTGAGCTCTAGTGCCTGTCCCCTGCTCGTCCTGCCTCCCACCGGCCCTGCTCACCTG TGGCTGCTCTGCTCTGATTCCCTGAGGCT | 657 |
| IGHG2_chr14: 106112835-106112935 | AAGCCTCAGTCCTGCTCACCTTCTGATGCTCTCCTCTGTCCCCTGAGCTCCAGGGGCTGTCCCCTGCTCGT CCTGCCTCCTACCTGCCCCTGCTTACCTG | 658 |
| IGHG2_chr14: 106112935-106113035 | AGGGTGCTCTGCCCTGGTGCTCTGAGCTCCAGGGGCTGTCCCCTGCTCCTCCTGCTTCCTACCAGCCCCTG CTCACCTGTGGCTGCTCTGCCCTGGTCCC | 659 |
| IGHG2_chr14: 106113020-106113120 | CTCTGCCCTGGTCCCCTGAGCTCCAGGGGCTTCCCCCTGCTCTTCCTGCCCCCACCAGCCCCTGTTCACCTT CAGATGCCCTCCCCTGGTCCCCTGAAGT | 660 |
| IGHG2_chr14: 106113120-106113220 | CCCAGAGCTGCCCCCTGTTCCTCCTGCCTCCCACCAGCCCGTGCTCACICTGCCGCTGCTCTGCCCTGGTCC CGAGTTCCAGGGGCTGCACCCTGTTCGCC | 661 |
| IGHG2_chr14: 106113220-106113320 | CACCTCCCACTAGCCATGCTCAGCTCTTGATGCTCTGTCCTGGTCCCCTGAGCTCCAGGAGCTGTCCCCTA CTCGTCCTGCCACCCACCAGCCCCTGCTC | 662 |
| IGHG2_chr14: 106113320-106113420 | ACCTGAGGCACCTGAGGCTGCTCTGCCCTGGTCCCCTGAGCTCCAGGGTCTTCCCCCTGCTCATCCTGCCT CCCACCTGCCCTTGTTCACCTTCAGTTGC | 663 |
| IGHG2_chr14: 106113420-106113520 | TCTGCCCTGGTCTGCTGAGCTCCAGGAGGTGCCCCCTGCTCCTTCTGCCCCCACCTGCCCTGCTCACCTGT GGCTGCTCGGTCCTGGTACCCTGAACTCC | 664 |
| IGHG2_chr14: 106113450-106113550 | GCCCCCTGCTCCTTCTGCCCCCACCTGCCCTGCTCACCTGTGGCTGCTCGGTCCTGGTACCCTGAACTCCA ATGCCTGCCCCCTGCTCACTCTGCCCTCC | 665 |
| IGHG2_chr14: 106113550-106113650 | CTCAACCCGGGCAGCAATGTCACTCAGGTCACTGTTGCCCCCCTGCCTGTCCTGGCACCCTCTGTCCAGGT TTGGGCTGTTTTTCTGGCCTCATTTTTGT | 666 |
| IGHG2_chr14: 106113695-106113795 | TGTCCAGTCAGGTCTCCCCAACAGAGCCCCTTGCCCTTGCCCATGTGCCCCTCCTGGGTGAGCTCCCAGAT CCTCCCGTCCCTGCACTGCTCCTGCTCTG | 667 |

-continued

| Name | Sequence | SEQ ID NOs. |
|---|---|---|
| IGHG2_chr14: 106113795-106113895 | GAAGCCTCTCCAGAACCTCAGCTCCTCAGTGGCCTCTGCTCTGCTGGGTCAGCTCCCTGAACGCACGGAG CCTCACCCCTCCCCTCGCCCCAGGCCTGCT | 668 |
| IGHG2_chr14: 106113895-106113995 | GCACTCTGGGCCTTTCTGGGCCTCCCTGGACTCTTCCCTCCTCCCATCTGTGCACTCAGCACAGCTCTCCCC TCCACTCCGCTGCTGACCACAGCCCTGC | 669 |
| IGHG2_chr14: 106113905-106114005 | CCTTTCTGGGCCTCCCTGGACTCTTCCCTCCTCCCATCTGTGCACTCAGCACAGCTCTCCCCTCCACTCCGC TGCTGACCACAGCCCTGCTCCCCGCCAG | 670 |
| IGHG2_chr14: 106114175-106114275 | CCCACGGCCAGCACTGCTGACCCTGCCCTGGGCTCCAGTGATGCTGCTGGCCTGGACAAGCCCCTCCGTTC ACCTGGGGCCTCTCCTCCTCCCTCGTTCT | 671 |
| IGHG2_chr14: 106114275-106114375 | ACTGCCTCCTCAGCTCAGGTGGGTCCTGCCCATGCTGGCATCACCCCACGGCCGGCTCTGCCGCATCCCGT CAGGTTCCTCGTGCTCCCAGCCTGGTCGT | 672 |
| IGHG2_chr14: 106114375-106114475 | CATGGAGGCCTCAGTCAGCCTCTGGTGTGTCCTGCCCTGTTGGCTTGGAAGCCCCTGCCCACGGTCCCCGT CATCTTGCACTGGGTGGGCGTTGGTGCCT | 673 |
| IGHA1_chr14: 106176375-106176475 | AGCTCAGCCCAGCCTAGTCCAGCCCAGCCCAGCACAGGTCAGCCCAGCTTAGCTTAGCCCAGGTCAGTCC AGCTCAGCTCAGTCCACTTAAGCTCACCCA | 674 |
| IGHA1_chr14: 106176475-106176575 | GGTCAGCTCCGTCCAGCTCAGCCCAGCCTAGCCCAGCTTAGCCCAGCCCAGCCCAACACAGGTCAGCCCA GCTCAGCCTAGCCCAGCCCAGCTCAGCACA | 675 |
| IGHA1_chr14: 106176575-106176675 | GGTCAGACCAGCTCAGTACAGCTCAGGTCAGCCCAGACCAGTCCAACCCAGCCCAGCGCAGTCCAACCCA GCCCAGCTCAGCTCATCCAAGCCTAGCTCA | 676 |
| IGHA1_chr14: 106176675-106176775 | GCTCAGCCCAGCCCAGGTCAGCCTAGCCCAGCCGAACCCAGCTCAGCCCAGGTCAACCCAATTCAGCTCA GCTCAGCCCAGGTCAACCCAACCAAGCTCA | 677 |
| IGHA1_chr14: 106176775-106176875 | GCTCAGCCTAGCCCAGTCCAGCTCAGCCCAGCTCAGCTCAGCCCAGTCCAGCTCAATCCACCTAAGCTCAC CCAGCTCAGCCCAGTCTGGCTCAGCTTAG | 678 |
| IGHA1_chr14: 106176875-106176975 | GTCAGCCCAGCCCAGCCTAGCCCAGATCAGTCCAGCTTAGCCCAGCCCAGGTCAGCCCAGCCCAGGTCAG CCCAGCTCAGCTCAGCCCAGCCCAGCTCAG | 679 |
| IGHA1_chr14: 106176985-106177085 | CCCAGCCCAGCTCAGCGCAGCCCAGCCTAGCTCACCCCAGCCAGGTCCAGCTTAGCCCAGCTCAGCCCAG CCCAACTCAGCTCAGCCCAGCTCAGCCCAA | 680 |
| IGHG1_chr14: 106211960-106212060 | TCTGAGCTCCAGGGGCTGCCCACCTGCTCCTCCTGCTTCCCACCGGCCCTGCTCACCTGCAGCTGCTCTGC CCTGGCTCCCTGAGGCTGAGCCTCAGTCC | 681 |
| !GHGL_chr14: 106212060-106212160 | TGCTCACCTTCTGATGCTCTCCCCTTGTCCCCTGAGCTCCAGGGGCTGACCCCTGATCTTTCTGCTTCCTAC CTGCCCCTGCTCACCTGTGGCTGCTCTG | 682 |
| IGHG1_chr14: 106212160-106212260 | CCCTGATCCCCTGAGCTCCAGGAGCTGCCTCCTGCTCTTCCTGCCTCCCACCTGCCCCTGCTCACCTGCAG ATCTGCCCTGGCTCTCTGAGGTCCAGGGG | 683 |
| IGHG1_chr14: 106212260-106212360 | CTGCCCCCTGCTCGCCCACCTCCCACCAGCCATGCTGACGTTGTGATGCTCTGCCCTGGTCTCCTGAGGTC CAGGGGCTGTCCCCTGCTTATTCTGCCTC | 684 |

-continued

| Name | Sequence | SEQ ID NOs. |
|---|---|---|
| IGHG1_chr14: 106212360-106212460 | CCACCTGCCCCTTCTCACCTGAGGCTCTTCTGCCCTGGTGCTCTGAGCTCCAAAAGCTGCCCACTTGCTCC TCCTGCTTCCTACCAGCCCCTGCTCTCCT | 685 |
| IGHGL_chr14: 106212460-106212560 | GTGGATGATCTOCCCTGGCTCTCTGAGCTCCAGGGGCTGCCCACCTGCTCCCCATGCTTCCCACCTGCCCC TGCTGACCTGCGGCTGCTCTGCCTTGGCT | 686 |
| IGHG1_chr14: 106212560-106212660 | CCCTGAGCTCCAGGAGCTTCCCCCTGCTCATCCTGCCCCCCACTGGCCCCTGTTCACCTTCAGATGCCCTC CCTGGTCCCCTGAAGTCCAGGAGCTGCCC | 687 |
| IGHG1_chr14: 106212660-106212760 | CCTGTTCCTCCCGCCTCCCACCAGCCCGTGCTCACCTGCGGCTGCTCTGCCCTGGTCCCCTGAGTTCCAGG GGCTGCCCCCTGCTCGCCCACCTCCCACT | 688 |
| IGHG1_chr14: 106212760-106212860 | AGCCATGCTCACCTCCTGATGCTCTGTCCTGGTCCCCTGAGCTCCAGGGGCTGCCCCCTGCTTGCCCATCT CCCACTAGCCATGCTCACCTTCTGATGCT | 689 |
| IGHG1_chr14: 106212860-106212960 | CTGCCCTGGTCCCCTGAGCTCCAGGGTCTTCCCCCTGCTCATCCTGCCGCCCACCAGCCCCTGCTCACCTG AGGCTGCTCTGCCCTGGTCCCCTGAGCTC | 690 |
| IGHG1_chr14: 106212870-106212970 | CCCCTGAGCTCCAGGGTCTTCCCCCTGCTCATCCTGCCGCCCACCAGCCCCTGCTCACCTGAGGCTGCTCT GCCCTGGTCCCCTGAGCTCCAGGAGGTGC | 691 |
| IGHG1_chr14: 106212980-106213080 | TTCTGCCCCCACCTGCCCTGCTCACCTGTGGCTGCTTGGTCCTGGTCCCTGAGCTCCAATGCCTGCTCCCTG CTCACTCTGCCCTCCCTCAACCCGGGCA | 692 |
| IGHG1_chr14: 106213080-106213180 | GCAATGTCACTCAGGTCACTGTTGCCCCCCTGCCTGTCCTGGCACCCTCTGTCCAGGTTTGGGCTGTTTTT CTGCCCTCATTTTTGATTTTGCAGCACTT | 693 |
| IGHG1_chr14: 106213125-106213225 | CCTCTGTCCAGGTTTGGGCTGTTTTTCTGCCCTCATTTTTGATTTTGCAGCACTTGGCGTGTTCCCTATGCT GTGGAGCAGCCCCAGTGTCCAGTCAGGT | 694 |
| IGHG1_chr14: 106213210-106213310 | AGTGTCCAGTCAGGTCTCCCCAACAGAGCCCCTTGCCCTTGCCCATOTOCCCCTCCTGAATGAGCTCCCGG ATCCTCCTGTCCCTGCACTGCTCCTGCTC | 695 |
| IGHG1_chr14: 106213310-106213410 | TGGAAGCCTCTCTGGAACCTCAGCTCCTCAGTGGCCTCTGCTCTGCTGGGTCAGTTCCCTGAACGCACGGA GCCTCAGCCCTTCCCCTCGCCCCAGGCCT | 696 |
| IGHG1_chr14: 106213410-106213510 | GCTGCACTCTGGGCCTTTCTGGGCCTCCCTGGACTCTTCCCTTCTCCCGCCCGTGCACTCAGCACAGCTCT CCCCTCCTCTCCACTGCTGACCACAGCCC | 697 |
| IGHG1_chr14: 106213510-106213610 | TGCTCCCCGCCAGCAGGTGCCCCAACCCCATCAGCTGGCTCTGAGCCCAGCCCCTGTGCCTCCCCTGTCCC TGCCTCTGCCTCTGGGCTCCTTGGCTTCC | 698 |
| IGHG1_chr14: 106213660-106213760 | ACCTGCTGTCCTTGGTCCTGGCTGAGAGGAGGGCCCCACGGCCAGCACTGCTGACCCTGCCCTGGGCTCC GGTGATGCTGCCGGCCTGGACAAGCCCCTC | 699 |
| IGHG1_chr14: 106213760-106213860 | CGTTCACCTGGGGCCTCTCCTCCTCCCTCGCTCTGCTGCCTCCTGAGCTCAGGTCGGTCGTGCCCATCCTG GCATCACCCCACGGCCGGCTCTGCCGCAT | 700 |
| IGHG1_chr14: 106213860-106213960 | CCAGTCATGTTCCTCGTGCTCCCAGCCCGGTCGTCCTGGAGGCCTCAGTCAGCCTCTGGTGTGTCCTGCCC TGTTGGCTTGGAAGCCCCTGCCCACGGTC | 701 |

-continued

| Name | Sequence | SEQ ID NOs. |
|---|---|---|
| IGHG1_chr14: 106213960-106214060 | CCCGTCGTCTCGCACTGGGTGGGCATCGGTGCCTGAAGGCTGCCCACCTCCCCCGTGCTGGCTCCGCTTGG GCCTCCATGTGGGGCCGGCCTCGACCCCA | 702 |
| IGHG3_chr14: 106239250-106239350 | CACTGCACTTTCACCAGCCCTCAGCTGTCTGCTGCCGGCAACTACCCAGCTCCTGCCAAAGTCTAGGAGCT GCGTGCTGCCTCCCACCGTCCCTGCTCAC | 703 |
| IGHG3_chr14: 106239350-106239450 | CTGTGGCTGCTCTGCCCTGGTGCTCTGAGCTCCAGGAGATGCCCCCTGCTCCTCCTGCCCCCCACCTGCCC CTGCTCACCTGCAGCGGCTCTGCCCTGGT | 704 |
| IGHG3_chr14: 106239455-106239555 | GAGCTCCAAGAGCTGCCCCCTGCTCCTCCTGTCCCCTGACCCTGCTCCTGTTTGCCTATGGCTGCTCTGCC CTTGTCCCCTGAGCTCCAGGAGCTGCCCC | 705 |
| IGHG3_chr14: 106239555-106239655 | TGCTCATTCTGCCGCCCACCTGCCCCTGTTCACCTGTGGCTGCTCTTCCCTGGTCCTCTGAGCTCCATGAGC TGCCCCTTGCTCCTCCTGCTTTCCACCA | 706 |
| IGHG3_chr14: 106239655-106239755 | GCCCCTGCTCACCTACCGATGATCTTCCCCGGCTCTCTGAGCTCCAGGGGCTGCCCACCTGCTACCCCTGC TTCCCACCAGCCCTGCTTACCTGCAGCTG | 707 |
| IGHG3_chr14: 106239755-106239855 | CTCTGCCCTGGCTGGCAGAGCTGCAGAAGCTGCCCCCTGCTCTGCAACCTCCCACCGGCCCTTCTCATCTT CTGATGTTCTCCCCTGTTCCCTGAGCTCC | 708 |
| IGHG3_chr14: 106239855-106239955 | AGGAGCTGCCCCCTACTCGTTCTACCTCCCACCAACCCGTGCTCACCTGCGACTGCTCTGCCCTGGTCCCC TGAGCTCCAGGGGCTGCCCCCTGCTCGCC | 709 |
| IGHG3_chr14: 106239990-106240090 | TGCCCTGATCCCCTGAGCTCCAGGACTGCCCCCTGCTCGTCCTOCCCCTCACCTGCCCCTGCTCACCTGAG GCTGCTCTGCCCTGGTCCCCTGAGCTAAA | 710 |
| IGHG3_chr14: 106240090-106240190 | GGGGCTGCCCCTTACTCATCCTGCCTCCCACCAGCCCCTGCTCACCTTCTGATGCCCTCCCCTGGTCCCCTG AGCTCCAGGGGCTGCCCCCTGCTCGTCC | 711 |
| IGHG3_chr14: 106240170-106240270 | GGGCTGCCCCCTGCTCGTCCTGCCTCCCACCAGCCCCTGCTCACCTGCAGCTACACTGCCCTGGTTCCCTG AGCTCCAGGAGCTGCCACCTGCTTGTCCT | 712 |
| IGHG3_chr14: 106240270-106240370 | GCCTTCCACCAGCCCCTGCTCACCTGCAGCTACACTGCCCTGGTTCCCTGAGCTCCGGGAGCTGCCGCCTG CTTGTCCTGCCTCCCACCAGCCCCTGCTC | 713 |
| IGHG3_chr14: 106240370-106240470 | ACCTGTGGCTACACTGCCCTGGTGCCCTGAGCTCCAGGAGCTGCCCCCTGCTTGCCCATCTTCCACTGAGC CCTGCTCACCTGCAACTGCTCTGCCCTGG | 714 |
| IGHG3_chr14: 106240470-106240570 | CTCTATGAGCTCCAGGGGCTGCCCCCTGCTGGTCCTGCCTCCCACCTGCCCTGCGCACCTGTGGCTGCCTC CTCACCTGTGGCTGCTCTGCCCTGGTCCC | 715 |
| IGHG3_chr14: 106240570-106240670 | CTGAGCTCCAGGGTCTTCCTCCTGCTCATCCTGCCCCTCCACCGGCTCCTGTTCACCTTCAGATGCTCTCCC GTGGTCCCCTGAGCTCCAGGAGCTGCCC | 716 |
| IGHG3_chr14: 106240670-106240770 | CCTGTTCTTCCTGCCTCCCACCTGCCCTGTGCACCTGTGGCTGCTTGGTCCTGGTCCCCTGAACTCCAATGC CTGCCCCCTGCTCACTCTGCCCTCCCTC | 717 |
| IGHG3_chr14: 106240770-106240870 | AACCTGGGGCAGCAACGTCACTCGGTCCACTGTTGCCCCCCTGCCTGTCCTGGCACCCTCTGTCCAGGTTT AGGCTGTTTTTCTTGCCTCATTTTTGTTT | 718 |

-continued

| Name | Sequence | SEQ ID NOs. |
|---|---|---|
| IGHG3_chr14: 106240820-106240920 | TGGCACCCTCTGTCCAGGTTTAGGCTGTTTTTCTTGCCTCATTTTTGTTTTTGCAGCACTTGGCGTGTTCCC TATGCTGTGGAGCAGCCCCAGTGTCCAG | 719 |
| IGHG3_chr14: 106240915-106241015 | TCCAGTCAGGTCTCCCCAACAGAGCCCCTTGCCCTTGCCCATGTGCCCCTCCTGGATGAGCTCCCGGATCC TCCCGTCCCTGCACTOCTCCTGCTCTGGA | 720 |
| IGHG3_chr14: 106241015-106241115 | AGCCTCTCCAGAACCTCAGCTCCTCAGTGGCCTCTGCTCTGCTGGGTCAGTTCCCTGAACGCACGGAGCCT CAGCCCCTCCCCTCGCCCCAGGCCTGCTG | 721 |
| IGHG3_chr14: 106241115-106241215 | CACTCTGGGCCTTTCTGGGCCTCCCTGGACTCTTCCCTCCTCCCGCCCGTGCACTCAGCACAGCTCTCCCCT CCTCTCCGCTGCTGACCACAGCCCTGCT | 722 |
| IGHG3_chr14: 106241200-106241300 | GACCACAGCCCTGCTCCCGGCCAGCAGGTGCCCCAACCCCATCAGCTGGCTCTGAGCCCAGCCCCTGTGC CTCCCCTGTCCCTGCCTCTGCCTCTGGGCT | 723 |
| IGHG3_chr14: 106241345-106241445 | GCTCTGCTCCCAGCTCACCTGCTGTCCTTGGTCCTGGCTGAGAGGAGGGCCCTACGGCCAGCTCTGCTGAC CCTCCCCTGGGCTCCGGTGATGCTGCCGG | 724 |
| IGHG3_chr14: 106241445-106241545 | CCTGGACAAGCCCCTCGGTTCACCTGGGGCCTCTCCTCCTCCCTCTCTCTGCTGCCTCCTGAGCTCAGGTC GGTCATGCCCATCCTGGCATCACCCCATG | 725 |
| IGHG3_chr14: 106241545-106241645 | GCTGGCTCTGCCCCATCCCGTCATGTTCCTCACACTCCCAGCCCGGTCGTCCTGGAGGCCTCAGTCAGCCT CTGGTGTGTCCTGCCCTGTTGGCTTGGAA | 726 |
| IGHM_chr14: 106318100-106318200 | GGGTAGAGCCCACCTCGTGGCCTGCAAGCCAGCCAGCCCCTGCCGGTCGAGAAGGAAGCCTGTGTGAGA GCACACAACTGGAGGCCGGGCGGGGAAGAGA | 727 |
| IGHM_chr14: 106318200-106318300 | AACACGTGCCAACAGGCCACGCAGGCCAGGACCCCAGACCCGGAGGCAGCGCCCCTTTGAGTTCCTCTCT CTGGTCTCCGATGTTCTTCTGTTGGGATCA | 728 |
| IGHM_chr14: 106318300-106318400 | TTTCACCTACAGGCAACAGAGACAGTGTGAAATGCTTTCCCTGTGGTCGGGAAGGGAGCCGGGGCAGAG ATGACCCAGTGGGGTGGTGTGGGGGCCTCCG | 729 |
| IGHM_chr14: 106322055-106322155 | CTTTGCACACCACGTGTTCGTCTGTGCCCTGCATGACGTCCTTGGAAGGCAGCAGCACCTGTGAGGTGGCT GCGTACTTGCCCCCTCTCAGGACTGATGG | 730 |
| IGHM_chr14: 106322155-106322255 | GAAGCCCCGGGTGCTGCTGATGTCAGAGTTGTTCTTGTATTTCCAGGAGAAAGTGATGGAGTCGGGAAGG AAGTCCTGTGCGAGGCAGCCAACGGCCACG | 731 |
| IGHM_chr14: 106322255-106322355 | CTGCTCGTATCCGACGGGGAATTCTCACAGGAGACGAGGGGGAAAAGGGTTGGGGCGGATGCACTCCCT GAGGACCCGCAGGACAAAAGAGAAAGGGAGG | 732 |
| IGHM_chr14: 106322905-106323005 | ACTCCAGCTACCCTGAAGTCTCCCCAGGCAGACAACCCAGGCCTGGGAGTGAGTATAGGGAGGGTGGGT GTGATGGGGAACGCAGTGTAGACTCAGCTGA | 733 |
| IGHM_chr14: 106323005-106323105 | GGCTATCCATCTATGTCCAACAAGATCATGAAGATTGGCCCAGTGCCATGTCCTCCAGTTCATCCCAGCCC AGGCCAGCTCAATCCAGTTCATCCCAGCC | 734 |

-continued

| Name | Sequence | SEQ ID NOs. |
|---|---|---|
| IGHM_chr14: 106323105-106323205 | CAGGCCAGCTCAATCCAGCCCAGCCCACCCCACCCCAGCTCAGCAAAGCCAAGCTCAGCTCAGCCCAACT CAGATGAGCTCAGACCAGCTCAGCCCAGCC | 735 |
| IGHM_chr14: 106323470-106323570 | CAGCTCAGCTCAGCCCAACCCAGCCCAGCTCGCTCAACCTTGCTCGGCTCAGCTTAGCCCAGCCCAGCCCA GCTCAATCCAGCCTGGCTCAGCCCAGCCC | 736 |
| IGHM_chr14: 106323570-106323670 | AGCCCAGTTTGGCTCAACCCAGCTTOGCTCAGCCCAGGTCAGCCTGGCTCAACTCAGCCCAGCCCAGCCC AGCTCTGCTCAACCCAGCTCTGCTCAACTC | 737 |
| IGHM_chr14: 106323805-106323905 | AGCCCAGCTCATCCCAGCTCAGCCCAGCCCAGCCTAGCTTAGCTCAACCCAGCTCAGCTCAGTTCAGCTCA GCCCTGCTCAGCACAGCACAGCAGAGCCC | 738 |
| IGHM_chr14: 106324010-106324110 | AGCCCGGATCGGCTCAACCCAGCTTAGCTCAGCCCAGGTCAGCCCAGCTTAACTCAGCCCAGGTCAGCCC AGCTTAACTCAGCCCAGCCCAGCCCAGCTC | 739 |
| IGHM_chr14: 106324155-106324255 | TCAGCCCAGTTCAGCCCAGCTCAGCCCAGCCCAGCCTAGCTTGGCTCAACACAGCTCAGCTCAGCCAGCC CAGACCAGCTCAGCTCAGCCCAGTCCAGCT | 740 |
| IGHM_chr14: 106324290-106324390 | CAACCCAGCCCAGCCCAACCCAGCTCGGCTTAACCCAGCTCGGCTCAGCCCAGATCAGCCTGGCTCAACT CAGCCCAGCCCAGCTCAACCCAGCCCAGTT | 741 |
| IGHM_chr14: 106324490-106324590 | CAGCTCAGCTGAGCCCAGCCCAGCCCAGTCCGGCTCAGCTCAGCCCCGCCCCACTCAGCCCAGCTCAGCT CAGCCCAGCTCAGCCCAGCTCAGCTTAGCC | 742 |
| IGHM_chr14: 106324750-106324850 | CAGCCCAGATCATCCCAGCTCAGCTCAGCTCAGCTCGGCTTAGCCCAGCTCAACCTGGCCCAGCCTGGTCC AGGTCAGCCCAGCCTGGACCACCCAGCCC | 743 |
| IGHM_chr14: 106324850-106324950 | AGCTCAGCTCAGCCCAGCTCATCCTGGTTCAGCTCAGCTCAACCCGGCTCAGCCCAGGTCTGCTCAACCCA GCCCAAATCAGCTCAGCCCAGCCCAGGTC | 744 |
| IGHM_chr14: 106324950-106325050 | ATCCCAGCTCAGCCCAGCACAGCCTACTTCAGCTCAGCTCAGCTCAGCCTAGGTCAGCTCAGTTGAGGTC AGCTCAACTCAGCCCAATCCAGCCTGGCTC | 745 |
| IGHM_chr14: 106325050-106325150 | AGCCCAGCTCACCCTAGCTCAGCTTAGCTCAGCCCAACTCAACCCAGCCCAGCCTTGCCCAACCCAGCTCA GCTCAGCCCAGCCCAGGTTAGCCCAGCCC | 746 |
| IGHM_chr14: 106325150-106325250 | AGCCTCGGCTTAGCTCTGCTCAGCTCGGCCCTGCTCGCCTCAGCCCGTTCAGCCCAGTTCAGCTCAGCTCA GCTCAGCCCAGCTCAGCCCAGCCCTGGTT | 747 |
| IGHM_chr14: 106325250-106325350 | AGCTCAGCCCAGCTAAGCTCAGCTCGGCTTGGCTCTGCTGAGCTTGGCCCAGCTTGGCTTAGCCTGATACA ACCTGCTCAGCCCAGTTCAGCTCGGCTCA | 748 |
| IGHM_chr14: 106325360-106325460 | GCCCAGCGTAGCTCAGCTCAGCTGAGCCCAGCCCAGGTTAGCTCAGCCCCAGTCCAGGTCAGCTCAACTC AGCCCAAACCAGCCTGGCTCGGCCCAGCTC | 749 |
| IGHM_chr14: 106325460-106325560 | ACCCTAGTTCAGCTTAGCTCAGCCCAGCCCAGCCCTGCCCAACCCAGCTCAGCTCAGCCCAGCCCAGGTTA GCCCAGCCCAGCCTCGGCTTAGCTCTGCT | 750 |
| IGHM_chr14: 106325515-106325615 | AGCCCAGCCCAGGTTAGCCCAGCCCAGCCTCGGCTTAGCTCTGCTCAGCTCGGCCCAGCCCAGGTTAGCC CAGCCCAGCCTCGGCTTAGCTCTGCTCAGC | 751 |

-continued

| Name | Sequence | SEQ ID NOs. |
|---|---|---|
| IGHM_chr14: 106325615-106325715 | TCGGCCCTGCTCGCCTCAGCCCGTTCAGCCCAGTTCAGCTCAGCTCAGCTCAGCCCAGCTCAGCCCAGCCC TGGTTAGCTCAGCCCAGCTAAGCTCAGCT | 752 |
| IGHM_chr14: 106325715-106325815 | CGGCTCAGCTCTGCTGAGCTCGGCCCAGCTTGGCTCAGCCCGACACAGCCTGCTCAGCCCAGTTCAGCTC GGCTCAGCCCAGCCCAGCCCAGCGTAGCTC | 753 |
| IGHJ6_chr14: 106325820-106325920 | AGCTGAGCCCAGCCCAGGTTAGCTCAGCCCCAGCCCAGGTTAGCTCAGCCCAGCTCAGCTCTGCCCAGGT TAGCTCAGCCCCAGTCCAGGTTAGCTCAGC | 754 |
| IGHJ6_chr14: 106325920-106326020 | CCAGCTCAGCTCTGCCCAGGTTAGCTCAGCCCCAGTCCAGGTTAGCTCAGCCCAGCTCAGCCTTGCCCAGG TTAGCTCAGCCCAGCTAAGCTCAACTTGG | 755 |
| IGHJ6_chr14: 106326020-106326120 | CTCAGCTCAGCCTAGCTTGGCTCAGCCCAGCACAGCACGCTCAACCCGGTTCAGCTTGGCTCAGCCCAGC CCAGCCCAGCCTAGCTCAGCTCAGCCCCGC | 756 |
| IGHJ6_chr14: 106326245-106326345 | CCAGCTCAGCGCAGCCCAGCTCAGCTCAGCTCAGCCTAGCCTTGCTCGGCCCAGCTCAGCTCAGCCCAGCT CAGCCTAGCCTTGCTCAGCCCAGCTCAGC | 757 |
| IGHJ6_chr14: 106326450-106326550 | TCAGCCCAGCCCTGCCCAGCTCAGCCCAGCTTAGTGCAGCCAAGCCCAGCTCAGCTCAGCTCACCTGGTG CAACTTAGCCCAGCTCAGCTCAGCTCAGCT | 758 |
| IGHJ6_chr14: 106326550-106326650 | CAACCCAGTTCAACTCAGCCCAGTTCAGCTCAGCTCAGCCCAGTTCAGCCTTGTTTAGTCTAGGTCAGCTT AGGTCAGTTTTGCCCATCTGAGTCCATTT | 759 |
| IGHJ6_chr14: 106326650-106326750 | CTGAAAGCTGGATGGAGTTGTCATGGCCAGAAATGGTCAGCCCACCAGACCTGCTTGTCTCAGCTAAAGC CATCTCATTGCCAGGTTCCTGCACAGCCAG | 760 |
| IGHJ6_chr14: 106326750-106326850 | GCTGGCTTCCATCTTTTGTCTCCCTCTACTTGATACCCCAGTTCCCTGCAGTCCTGCCCCAGCGCCACCTGG GTTTTGGTTCCAAAGCATTACCAATCAT | 761 |
| IGHJ6_chr14: 106326850-106326950 | TACCACCCTCCACTACCTGGGTGGAATATTTCTTTGCTGCTTTAAAGTCATTAAAACATCTTGAGAATGAG ACCAAGAATTTAGGAGCCTGTGCTGTGAT | 762 |
| IGHJ6_chr14: 106326950-106327050 | AAAAATGAGCAGGTCCCCTTGCTCTAGAAGTGGCAGCATATCTTCTGCACCAAGAGGAGGGTATTGAGAT GCTCAGAGCCTCCACCTTCCCGGAGCATCC | 763 |
| IGHJ6_chr14: 106327050-106327150 | CCTCCCTTCTGAGTCTGCAGTAAACCCCTGCCTTTAAATTCCCTCTAGATAACAGTCATCATTGGAAACAA CCAAGAAATGCATTTTATCTGAATTTGCC | 764 |
| IGHJ6_chr14: 106327150-106327250 | ACTTAAAATTCTGCCATTTACCATAAATCGCTTTGGAAGGCATGGGCTACTTTCAAGGGTGCGATGATGA CCTACAGTCAATGACTTAGACAAGGGCGAT | 765 |
| IGHJ6_chr14: 106327250-106327350 | GCCAGTGGGGCTTGGTATGTTCTCAAGCATCATTACCCATGCCATCCCCATTCAGAGGTTGTGGAGCAGCT CGTGCGACCTCTCCTTCAAATGGGCTTTA | 766 |
| IGHJ6_chr14: 106327350-106327450 | GGGAAAGTTAAATGGGAGTGACCCAGACAATGGTCACTCAAAAGACTCACATAAATGAGTCTCCTGCTCT TCATCAAGCAATTAAGACCAGTTCCCCTTC | 767 |

-continued

| Name | Sequence | SEQ ID NOs. |
|---|---|---|
| IGHJ6_chr14: 306327450-106327550 | TAGTGGAAATAAGACGTCAAATACAAAGTTTTAAGAGAAGCAAATGCAGCAGCGGCGGCTGCCTGTCTCT TACCATGTCGGGCGCCTGGTCACTGCGAGC | 768 |
| IGHJ6_chr14: 106327550-106327650 | CTTGCAAAGCTTTGGCATGGAATCATTCCTCCAAGTCCATTAACAAGGGCTGGGGCCTGAGCAGCCAGTC GGCCCGGCAGCAGAAGCCACGCATCCCAGC | 769 |
| IGHJ6_chr14: 106327650-106327750 | TCTGGGTAGTCCGGGGAGACCCAAAGCCCAGGCCGGGCCTGGCAGCCACCCTCCCAGAGCCTCCGCTAGG CCAGTCCTGCTGACGCCGCATCGGTGATTC | 770 |
| IGHJ6_chr14: 106327750-106327850 | GGAACAGAATCTGTCCTTCTAAGGTGTCTCCACAGTCCTGTCTTCAGCACTATCTGATTGAGTTTTCTCTT ATGCCACCAACTAACATGCTTAACTGAAA | 771 |
| IGHJ6_chr14: 106327850-106327950 | TAATTCAGGATAATGATGCACATTTTACCTAAAACTTATCCTAAAGTGAGTAGTTGAAAAGTGGTCTTGA AAAATACTAAAATGAAGGCCACTCTATCAG | 772 |
| IGHJ6_chr14: 106327950-106328050 | AATATCAAAGTGTTTCTCCTTAATCACAAAGAGAAAACGAGTTAACCTAAAAAGATTGTGAACACAGTCA TTATGAAAATAATGCTCTGAGGTATCGAAA | 773 |
| IGHJ6_chr14: 106328050-106328150 | AAGTATTTGAGATTAGTTATCACATGAAGGGATAACAAGCTAATTTAAAAAACTTTTTGAATACAGTCAT AAACTCTCCCTAAGACTGTTTAATTTCTTA | 774 |
| IGHJ6_chr14: 106328150-106328250 | AACATCTTACTTTAAAAATGAATGCAGTTTAGAAGTTGATATGCTGTTTGCACAAACTAGCAGTTGATAA GCTAAGATTGGAAATGAAATTCAGATAGTT | 775 |
| IGH16_chr14: 106328250-106328350 | AAAAAAAGCCTTTTCAGTTTCGGTCAGCCTCGCCTTATTTTAGAAACGCAAATTGTCCAGGTGTTGTTTTG CTCAGTAGAGCACTTTCAGATCTGGGCCT | 776 |
| IGHJ6_chr14: 106328350-106328450 | GGGCAAAACCACCTCTTCACAACCAGAAGTGATAAATTTACCAATTGTGTTTTTTTGCTTCCTAAAATAGA CTCTCGCGGTGACCTGCTTCCTGCCACCT | 777 |
| IGHJ6_chr14: 106328450-106328550 | GCTGTGGGTGCCGGAGACCCCCATGCAGCCATCTTGACTCTAATTCATCATCTOCTTCCAGCTTCGCTCAA TTAATTAAAAAAATAAACTTGATTTATGA | 778 |
| IGHJ6_chr14: 106328550-106328650 | TGGTCAAAACGCAGTCCCGCATCGGGGCCGACAGCACTGTGCTAGTATTTCTTAGCTGAGCTTGCTTTGGC CTCAATTCCAGACACATATCACTCATGGG | 779 |
| IGHJ6_chr14: 106328650-106328750 | TGTTAATCAAATGATAAGAATTTCAAATACTTGGACAGTTAAAAAAATTAATATACTTGAAAATCTCTCAC ATTTTTAAGTCATAATTTTCTTAACCATT | 780 |
| IGHJ6_chr14: 106328750-106328850 | TTTCTCAGAAGCCACTTCAAACATATCCTGTCTTTTAACAGTAAGCATGCCTCCTAAGATAAACAATCCTT TTCTCTTGGAAACCAGCTTCAAGGCACTG | 781 |
| IGHJ6_chr14: 106328850-106328950 | AGGTCCTGGAGCCTCCCTAAGCCCCTGTCAGGACGGCAGCCACCGTTTCTOGGCTACCCCTGCCCCCAACC CTGCTCTCATCAAGACCGGGGCTACGCGT | 782 |
| IGHJ6_chr14: 106328950-106329050 | CCCTCCTGGCTGGATTCACCCACTCCGACAGTTCTCTTTCCAGCCAATAAAGAATTTAAGATGCAGGTTGA CACACAGCGCACCTCATAATTCTAAAGAA | 783 |
| IGHJ6_chr14: 106329050-106329150 | AATATTTCACGATTCGCTGCTGTGCAGCGATCTTGCAGTCCTACAGACACCGCTCCTGAGACACATTCCTC AGCCATCACTAAGACCCCTGGTTTGTTCA | 784 |

-continued

| Name | Sequence | SEQ ID NOs. |
|---|---|---|
| IGHJ6_chr14: 106329150-106329250 | GGCATCTCGTCCAAATGTGGCTCCCCAAGCCCCCAGGCTCAGTTACTCCATCAGACGCACCCAACCTGAGT CCCATTTTCCAAAGGCATCGGAAAATCCA | 785 |
| IGHJ6_chr14: 106329250-106329350 | CAGAGGCTCCCAGATCCTCAAGGCACCCCACITGCCCGTCCCCTCCTGGCCAGTCCGCCCAGGTCCCCTCGG AACATGCCCCGAGGACCAACCTGCAATGC | 786 |
| IGHJ6_chr14: 106329350-106329450 | TCAGGAAACCCCACAGGCAGTAGCAGAAAACAAAGGCCCTAGAGTGGCCATTCTTACCTGAGGAGACGG TGACCGTGGTCCCTTTGCCCCAGACGTCCAT | 787 |
| IGHJ6_chr14: 106329450-106329550 | GTAGTAGTAGTAGTAGTAATCACAATGGCAGAATGTCCATCCTCACCCCACAAAAACCCAGCCACCCAGA GACCTTCTGTCTCCGGGCGTCACATGGAAG | 788 |
| IGHJ6_chr14: 106329550-106329650 | CTGACTGTCCGTGGCCCTGTCCTGCCCTTCTCATGGAACCCTCTGCTGGCCTCCCACGTACCCCACATTCT GGCCTGACCCCTCAGAAGCCAGACCACTG | 789 |
| IGHJ6_chr14: 106329650-106329750 | TCGGCCTGGGAAGTCCAACTGCAAGCAGACGGCTGCTAAGTCACCCCCAGGAGTCCAAAAACCCCGGGG GGCACCCGTCCCAGAGAGCGGGTGCCTTGGA | 790 |
| IGHJ5_chr14: 106329750-106329850 | GCGGGACAGAGTCCCACCACGCAATCATCACGACAGCCCCTGAGAATGCTCCAGGTGAAGCGGAGAGAG GTCACCCCAGACCAGCCGAAGGAGCCCCCCA | 791 |
| IGHJ5_chr14: 106329850-106329950 | GCTGCCGACATCTGTGGCCGGACTTGGGGAGGACAGGCTGGGTTCCCATTCGAAGGGTCCCTCTCCCCGG CTTTCTTTCCTGACCTCCAAAATGCCTCCA | 792 |
| IGHJ5_chr14: 106329950-106330050 | AGACTCTGACCCTGAGACCCTGGCAAGCTGAGTCTCCCTAAGTGGACTCAGAGAGGGGGTGGTGAGGACT CACCTGAGGAGACGGTOACCAGGGTTCCCT | 793 |
| IGHJ5_chr14: 106330050-106330150 | GGCCCCAGGGGTCGAACCAGTTGTCACATTGTGACAACAATGCCAGGACCCCAGGCAAGAACTGGCGCCC CGCTACGTCCCTGGGACCCTCTCAGACTGA | 794 |
| IGHJ5_chr14: 106330150-106330250 | GCCCGGGGAGGGCCCGGGGGTTGTTGGGCATTGGACCCCAGAGGCCTAGGGTGGCCCTGGCCACAGAGA GACCCGTGCTGCTGGGCTCAGGAGGAAGGAG | 795 |
| IGHJ4_chr14: 106330250-106330350 | CATCTGGAGCCCTTGCCCCTCGTCTGTGTGGCCGCTGTTGCCTCAGGGCATCCTCCTGAGCCCCCCAGGAT GCTCCGGGGCTCTCTTGGCAGGAGACCCA | 796 |
| IGHJ4_chr14: 106330350-106330450 | GCACCCTTATTTCCCCCCAGAAATGCAGCAAAACCCTTCAGAGTTAAAGCAGGAGAGAGGTTGTGAGGAC TCACCTGAGGAGACGGTGACCAGGGTTCCC | 797 |
| IGHJ4_chr14: 106330450-106330550 | TGGCCCCAGTAGTCAAAGTAGTCACATTGTGGGAGGCCCCATTAAGGGGTGCACAAAAACCTGACTCTCC GACTGTCCCGGGCCGGCCGTGGCAGCCAGC | 798 |
| IGHJ4_chr14: 106330550-106330650 | CCCGTGTCCCAAGGTCATTTTGTCCCCAGCACAAGCATGACTCTGCCCACCCTTTGCCCCAGCAGCAGAGT CCCAGTTCCCAAAGAAAGGCCTTCTGCTG | 799 |
| IGHJ3_chr14: 106330650-106330750 | AACGTGGTCCCAAACAGCCGGAGAAGGAGCCCCGGAGGGCCCCACATGGCCCAGCGCAGACCAAGGAGC CCCCGGACATTATCTCCCAGCTCCAGGACAG | 800 |

-continued

| Name | Sequence | SEQ ID NOs. |
|---|---|---|
| IGHJ3_chr14: 106330750-106330850 | AGGACGCTGGGCCCAGAGAAAGGAGGCAGAAGGAAAGCCATCTTACCTGAAGAGACGGTGACCATTGTC CCTTGGCCCCAGATATCAAAAGCATCACACA | 801 |
| IGHJ3_chr14: 106330850-106330950 | GGGACACAGTCCCTGTTCCTGCCCAGACACAAACCTGTGCCCGTGCAGGACACTCGAATGGGTCACATGG CCCAAGCACAGAGCAGAGGCAGCCGGCGTC | 802 |
| IGHJ3_chr14: 106330950-106331050 | CCTGTCCCCAGCCACACAGACCCCCGGGCTGAGACCCAGGCAGGGAGGGGTGACGTTCCCAGGGAGACG GTGGCCGGGCTGCCCTGGCCCCAGTGCTCCA | 803 |
| IGHJ3_chr14: 106331050-106331150 | AGCACTTGTAGCCACACTAAAGCGCAGGCCTGGTCCCCGGCACATGAACAGCCAGCGCCCAGCCCCAGCC CAGGCTCTGCCCACAACTTCTCCTTCCCGT | 804 |
| IGHJ2_chr14: 106331150-106331250 | CCCTGCCCTCGGCCTGCTTGCTACCTGTGGAGGGTCCCTGACGGGGCTGAAGCCCAGCGGGGTCCCTGCC TGTCCTTGGGGGCTCCAGCTGGCCCCAGGG | 805 |
| IGHJ2_chr14: 106331250-106331350 | CTAAGTGACAGCAGGGCTCTGGCATGCAGCCCATGGCGGAGACCCCAGGGATGGCAGCTGGTGTGGCCTC AGGCCAGACCCAGGCCGGCTGCAGACCCCA | 806 |
| IGHJ2_chr14: 106331350-106331450 | GATACCTGGCCTGGTGCCTGGACAGAGAAGACTGGGAGGGGGCTGCAGTGGGACTCACCTGAGGAGACA GTGACCAGGGTGCCACGGCCCCAGAGATCGA | 807 |
| IGHJ2_chr14: 106331450-106331550 | AGTACCAGTAGCACAGCCTCTGCCCTCCTGCTTCTCCCATACAAAAACACACCCTCCGCCCTCCTGCCGAC CTCCTTTOCTGAGCACCTGTCCCCAAGTC | 808 |
| IGHJ1_chr14: 106331550-106331650 | TGAAGCCAAAGCCCTTGCCTGGCCCAGTACACCTGGCTCCCCOCTATCCCCAGACAGGAGACTCACCTOA GGAGACGGTGACCAGGGTGCCCTGGCCCCA | 809 |
| IGHJI_chr14: 106331650-106331750 | GTGCTGGAAGTATTCAGCCACGGTGAGTCAGCCCTGAGCCAGGGGCTACAGAAACCCACAGCCCGGGGTC CCGGGGGAGCATGGTTTTTGTAGAGCTGCC | 810 |
| IGHD7-27_chr14: 106331750-106331850 | AATCACTGTGTCCCCAGTTAGCACAGTGGTTCTCAGCTCAGCCAAAACCCTGCGGCTGGTAGGGGGCCTG TGGGGCTGGGGGCTGATGTGGCTGCGGTCT | 811 |
| IGHD6-19_chr14: 106357890-106357990 | TGCTGGGTCTGTCCTCTGTGGGAGGGGCTGCTACCCAGGCCCAGGACTGCAGTGGAGGGCTCACTGAGGG GCTTTTGGGTCTGGCCTGAGCCGCTGTGGG | 812 |
| IGHD3-3_chr14: 106380360-106380460 | GCTCTCAGGTCTACTGCGGGGACACTCGGGTCTGCCCCTGGCTTAGGTGGACAGTGTCCGTGCCCACCTG TGCCCTGAGGCTCCATTTCAGGCTGATATC | 813 |
| IGHD3-3_chr14: 106380460-106380560 | TGTCTGTATTGTCCCTACCCGCTGCATGGCCATGTCCTTTTGGGTTTATAAATTGCCCCCAAATCACGCAG GCATCATTCAGGCTTTTTATATTCCCTGG | 814 |
| IGHD3-3_chr14: 106380550-106380650 | TATTCCCTGGGCCACCAGGTGCCTCCACCCAGAAAGCTGAGATGTGGGAGGTTCTAGAGTCATTCTGCAA CCCTGGATGAGCCCCTGCAGCCTCAGTGCT | 815 |
| IGHD3-3_chr14: 106380650-106380750 | ACTGAGGTTCCAGCAAGACCTGGAGCAGGTGCAGATGAGGCCTGAGGCCAGGTGAAGCCCAGGCCAGGT GAGGTCCAGGCCAGTGAGGCCCAGGTCAGAT | 816 |
| IGHD3-3_chr14: 106380750-106380850 | GAGGCCCAGGTCAGGTGAAGCCCAGGTCAGGTGAAACCCAGGTCAGGTGAGGCCCAGATCATGTGAGCT CAGGACAGGCAAGGTCCAAGTCAGGTGAGGC | 817 |

-continued

| Name | Sequence | SEQ ID NOs. |
|---|---|---|
| IGHD3-3_chr14: 106380850-106380950 | CGAGCTCAGGTGAAGCCCAGAGGTGAGGTCTAGGCCAGGTGAGGTCCAGGCCAGGTGAGGTCCAGGTCA GGTGAGGCCCAGGTCAGGCAAGGCTGAGGTA | 818 |
| IGHD3-3_chr14: 106380910-106381010 | TCCAGGTCAGGTGAGGCCCAGGTCAGGCAAGGCTGAGGTAGATGTATGAGACTTCTGTAATTTTCAGTTG GTGCCAACCCTGCCTGGTGTCCCTGCCCCT | 819 |
| IGHD3-3_chr14: 106381010-106381110 | CCTCCCAGCCCATGCTCTGTGCCTGCCAGATOGCGGCCCCTGCACAGGTGCTGCTGGCTGTOGAGGAGCT GGGCTCTGCCTCCCTGTGCATGGGCGTCCC | 820 |
| IGHD3-3_chr14: 106381275-106381375 | GCCTGCAGCCTGTCCGGGGATGCCCAGGGAGGTGAGTGCCACCACATATCAGGCCTTTTCTCTTTAAAGT CATTTCTTTGGGGATACATCATCAATGTCT | 821 |
| lGHD2-2_chr14: 106381485-106381585 | TCTAAACACAGCTGTGTGCATTTTCCTCTTCTTGCAATTTAGAATTTTAACTGCTGTTTTCAAGGTACTGTA ATGTATTTGTTCTCTTCTTGTTAGGAGA | 822 |
| IGHD2-2_chr14: 106381585-106381685 | CTTGCCAACCCTGTGTGTCTCAGTTCATACCCTCTTCCTTCCCCAGTAGAAGTAACGACCACTGTGTTTAT GTGATCATCCTTTTCTTGATTTTCCTTAT | 823 |
| IGHi2-2_chr14: 106381655-106381755 | TGTGATCATCCTTTTCTTGATTTTCCTTATAGTTTTCCTAGTGGAAAGTTTATCCCTTAAGAAGATAGTTCA TTTTGCCGGCTGTAAATTTTATTTAGAA | 824 |
| IGHD2-2_chr14: 106381890-106381990 | CTGCCATCGTTTATTTGCCTGTTTCCTTCAGATGGCTGTTTGCTTCATTCTCAGTTTGGGGCTATGACAAA CATATGTTCTGCACATCTTTGCCCATGA | 825 |
| IGHD2-2_chr14: 106381990-106382090 | GGCTCTCAGGGAGGGCTCTGGAGCTGGCATTGCCTGCAGGGCTCTGCTTTGTTGCAGGGAGTTCCTGCCA AGGCTTTTCAGAGTGTCTGTGCCCAGCCTG | 826 |
| IGHD2-2_chr14: 106382090-106382190 | AAGGTACACACTGTACTTTGCCCTTGCATCAGGCACTTTCCTTGTGCTTGCTTCTGTGTGGCTCCACATTCT GGAGAATTTATTCAGATCTGTGCTGCAA | 827 |
| IGHD2-2_chr14: 106382325-106382425 | CTTCCCACACTGTCCTCCTGGGCTCACTCCCAGCCATCGATCTTGAACACCAGTTTATGGAACTATCTGCA CAGGAAAGCAGAAACAGCAAAAGGCCCTG | 828 |
| 1GHD2-2_chr14: 106382905-106383005 | TTGCGTGGACCCTGTTTTTGGTCAAGGGAAGTACTTGCTGGTGAAGGAGACCTCCCCTCCTTTCTTTCTCA GGAGCCCCCTCTGATGCCGTTGCCTGGTG | 829 |
| IGHD2-2_chr14: 106383005-106383105 | TTTCTCAGGGCTGGTGCTGGGGGCTCAGCAGTGTCTGCCCTGTTCCAGGTGGGAATGTGGGTCTGTTCTGT TTCCACGCGGTGTTCIGGGGCCGCCAGTG | 830 |
| IGHD2-2_chr14: 106383030-106383130 | CAGCAGTGTCTGCCCTGTTCCAGGTGGGAATGTGGGTCTGTTCTGTTTCCACGCGGTGTTCTGGGGCCGCC AGTGAGGGGCTCGGGATGTCAGCGGCTGG | 831 |
| IGHD2-2_chr14: 106383130-106383230 | TCTCTGTCCCTATGGTCTGGGCTCCGGTTCACTGCTCCCCTGCCCTCCAGGTCGGTCACTGACTCAGTTAC TATCCAGCGGGCTCCGTGGCTGTTCAGTG | 832 |
| IGHD2-2_chr14: 106383980-106384080 | GGGAGCAAATGGAGAGGGAAGTGGCAGCGGCCCGAGTGCCAGGCGGTCCCGGTTTGGGGTTGATCTTTG TGGAACAGCTCCCTGGCCCGTGTGTAAGTGG | 833 |

-continued

| Name | Sequence | SEQ ID NOs. |
|---|---|---|
| 3GHD1-1_chr14: 106384080-106384180 | TCGGGGGAGGCACGGAGGTCTGGAGCTACAAGCGGTGGCAGGAAGGCAGGTCCCAGTCTTGGGGGTCTG GAGCTTATCTTCTTCCTGTGAACTGAGTGTG | 834 |
| IGHD1-1_chr14: 106384630-106384730 | ATGGAGGACCTGCCTCGGATGACACCCCTATCTTAAGAAGGTCATGGTGGGTTCCAGCTOGGAGGAAGGG AAGTGGGCCACCTCCTGGGGGTCTTCCACC | 835 |
| IGHD1-1_chr14: 106384720-106384820 | GTCTTCCACCCCCACCACCTCAGCCTGGGGCCTCTGTGATTCCTCTCTGCACAGACCCCAAAGTCTGTGCT GCCGCAGGGCAGGAAGGAAGGGCCTGTGG | 836 |
| IGHD1-1_chr14: 106384825-106384925 | TCGAGGTTGGGGCCACAGTGGTGTTCCCTAAGCCCGAGTCTGGTCTCATGGCCCGCCCCGCAGCAGGTCC TGAGTGAGGGACAGAGACCGGGGCGGGGTC | 837 |
| IGHD1-1_chr14: 106384925-106385025 | TTTGGTCCTGGTGGACTCTGGGGTOGATTCCAGTGGGGAGTCATCAGGGTCGGTGTCCCCCAGGGTACTG GGGTGTCTCTGCTCCTGGAGTCGGCTCTGG | 838 |
| IGHV2-5_chr14: 106494090-106494190 | CCTGGGTTTTTGTACAGGAGGTGCCCTGGGCTGTGTCTTTGTGGTCTGTGTGCACAGTAATATGTGGCTGT GTCCACAGGGTCCATGTTGGTCATTGTAA | 839 |
| IGHV2-5_chr14: 106494210-106494310 | GTGTCCTTGGTGATGGTGAGCCTGCTCTTCAGAGATGGGCTGTAGCGCTTATCATCATTCCAATAAATGAG TGCAAGCCACTCCAGGGCCTTTCCTGGGG | 840 |
| IGHV2-5_chr14: 106494310-106494410 | GCTGACGGATCCAGCCCACACCCACTCCACTAGTGCTGAGTGAGAACCCAGAGAAGGTGCAGGTCAGCGT GAGGGTCTGTGTGGGTTTCACCAGCGTAGG | 841 |
| IGHV2-5_chr14: 106494445-106494545 | CTGTGGAGAAAGCATAAGAAGATGAAGCCCACAAACAAGAAAACTGATGTTTCACCCGTGAAGGAGTCC CTGACCACAGCACTCACATGAAGGGATGGTC | 842 |
| IGHV2-5_chr14: 106494545-106494645 | AGCAGCAGGAGCGTGGAGCAAAGTGTGTCCATGGTGGGGCACAGGAGTCACTGAGCTGGGACCTGTGCT CGGCTTTTTCAACCCAGAGGAGGGTGGAGCT | 843 |
| IGHV2-5_chr14: 106494565-106494665 | AAGTGTGTCCATGGTGGGGCACAGGAGTCACTGAGCTGGGACCTGTGCTCGGCTTTTTCAACCCAGAGGA GGGTGGAGCTGGTGGAGATTTGCATTCCCC | 844 |
| IGHV2-5_chr14: 106494650-106494750 | AGATTTGCATTCCCCTCATCTGTGCCCTACTCTATGGGATGGAGTCAGGTTTCAGGACTCAGGAGGGTGTT GCATCTGTGGTGAGGACCAGTGATAGTAA | 845 |
| IGHV2-5_chr14: 106494750-106494850 | CATGATCAGTGTAATTCAGATGGCATTAATCTAAGGCTGGGCAAGTAGATTCTGAGTAGAAGTCTTTGCA GAAGTCATGATTATGAGGTCATGTTGGTCT | 846 |
| IGHV3-7_chr14: 106518495-106518595 | GCCCTTCACAGAGTCCACATAGTATTTCTCACTTCCATCTTGCTTTATGTTGGCCACCCACTCCAGCCCCTT CCCTGGAGCCTGGCGGACCCAGCTCATC | 847 |
| IGHV3-7_chr14: 106518855-106518955 | TGAGTCCTCTGTGCTCAGTGCTGATCACCAAGTGGAAAGGCCTTGGAGTCCAGGGCTAAGGCTCCTCTCT GAGACCTGCAGGGTCAGGGTTGGGTTGGTT | 848 |
| IGHV3-7_chr14: 106518955-106519055 | TTCATCAGTAGAGGGAGGGCCCTATTTGCATGTCTCCTACTATATAAGAAGCTCTAGTGGGATGCTGGAG GAATAGGCTGTACCCATATAAGAAGACGGT | 849 |
| IGHV3-7_chr14: 106518970-106519070 | AGGGCCCTATTTGCATGTCTCCTACTATATAAGAAGCTCTAGTGGGATGCTGGAGGAATAGGCTGTACCC ATATAAGAAGACGGTGCTCTGCAGAAGTTT | 850 |

-continued

| Name | Sequence | SEQ ID NOs. |
|---|---|---|
| IGHV3-7_chr14: 106519070-106519170 | GCTGACAATGATGGTATTTGGAAAATATGCTGTCTTATGAAATTGTGCTGTOATAAACACTTTGCCCTGAT CACCCTATTACATTTTTTAAAAAATGTGT | 851 |
| IGHV3-11_chr14: 106573540-106573640 | CAAACACAGAGACAACCTAGTCAGAAACTGCCACATATATTCACTGCTTATCTCACTCACGTCCACTCAAT GTCTCTAGTTCTCCATAAATCACCTTTTA | 852 |
| IGHV3-11_chr14: 106573640-106573740 | TAATAGCAACAAGGAAAACCCAGCTCAGCCCAAACTCCATGGTGAGTCCTCTGTGTTCAGTGCTGATCAC CGAATGGAAACTCCTGGGAATTCTGGGGCT | 853 |
| IGHV3-11_chr14: 106573685-106573785 | GTCCTCTGTGTTCAGTGCTGATCACCGAATGGAAACTCCTGGGAATTCTGGGGCTGGGGCTCTTCTCCCAG AGCTGCAGGGTCTGGGCTCGGCTGGTTTT | 854 |
| IGHV3-11_chr14: 106573785-106573885 | TATCAGCAGAGGGAGGGCCCTATTTGCATGTCTCCTACTATATAGCAAGCTCTAGTGGGACGCTGGAGGA GAGGGCAGTGCCCAGAGCAGATGAGAGGGT | 855 |
| IGHV3-11_chr14: 106573885-106573985 | CCCGGAAAACACTGGAGGTAATCCTATCTCTCAGGAAAATATAACTTCAGATTATGTGATTGTGACTTGA TGATCAATTAGCAGTCATCATCTTATTTAA | 856 |
| IGHV3-11_chr14: 106573985-106574085 | TGTTTACATATTTGCAGAATATATTCAGTGCAAGTGTCAATGTTACATTTTTAGAGAAGATGAATTACATA CATAACAGAGCAGTTGTGCAATGTGTCCA | 857 |
| IGHV3-15_chr14: 106610690-106610790 | ACTCACACTTAATCTCTCTAGTTCTCCATAAATCACCTTTTAAAATAGCAGCAAGGAAAATCCAGCTCAGC CCAAACTCCATGGTGAGTCCTCTGTGTTC | 858 |
| IGHV1-18_chr14: 106642110-106642210 | GATGCTATTTAATAGCCCAATTCCTGACCCAGGATGAGAAAGAGCAAATACATGACACATGGACGACACA ATTGTAGAAGCTGAGGGTTCAAGCCGTAAT | 859 |
| IGHV1-18_chr14: 106642210-106642310 | CCTGTTAGAGGCCACGCATCCCCTACCCATCCCTGAACTCTGTGTTGACAGAGCTTCCCCCACTGGAGAAC AAGCTCCCCCAGGACACGCACCTCACTTA | 860 |
| IGHV3-23_chr14: 106725295-106725395 | GGCCCTTCACGGAGTCTGCGTAGTATGTGCTACCACCACTACCACTAATAGCTGAGACCCACTCCAGCCCC TTCCCTGGAGCCTGGCGGACCCAGCTCAT | 861 |
| IGHV3-23_chr14: 106725395-106725495 | GGCATAGCTGCTAAAGGTGAATCCAGAGGCTGCACAGGAGAGTCTCAGGGACCCCCCAGGCTGTACCAA GCCTCCCCCAGACTCCAACAGCTGCACCTCA | 862 |
| IGHV3-23_chr14: 106725550-106725650 | ACTGTTTCTCTCACTCTTATCCATTCACACTCAATTTTTCTATTTCTCCATGAATTACCTTTAAAATAGCC ACAAGAAAAAGCCAGCTCAGCCCAAACT | 863 |
| IGHV3-23_chr14: 106725650-106725750 | CCATGGTGAGTTCTCTCTGTTCAGTCCTGATCACCAAATGAAAACACCTGAAAATCCCAGGGCTGGGCTC CTCTCTCAGAGCTGCAGGGTCAGGGCTGGG | 864 |
| IGHV3-23_chr14: 106725780-106725880 | TTTGCATATCTCCTACTATATAGTAAGCTCTGGGGTGAGAGGCCTTTGGAGATAGTGGGGCTCAGAGCAT GTCAGAATGTCCTCGGGGAGATCTGTGATA | 865 |
| IGHV3-23_chr14: 106725880-106725980 | TTGAAAGCATTGGGAAATTGTGCTTTCCTATTGTCAGTTTGTTTTGTGATAAACTIAAACCTTAAAACCTA AAAATCTTATAATTTTGTAATTTTTATTT | 866 |
| IGHV3-23_chr14: 106725995-106726095 | GAGGTACCATAGATCTACATAAACTGCATATTTTAAAGTTAGCACCAATCATCTTTTATTTACATACG CAGAGAAACCATGGTATATAGTATCAATA | 867 |

-continued

| Name | Sequence | SEQ ID NOs. |
|---|---|---|
| IGHV3-23_chr14: 106726095-106726195 | TTATTTCCATGTTAAAGATGAAAAATTATCAGCAAAAGCACAGGTGGGTTTTACAATGTCCCCAGTGCTC ACTTTTGGTCAGAGTGAGCCTGGGCATCTG | 868 |
| IGHV1-24_chr14: 106732970-106733070 | TCCTACATAATGACAGTGTACACATCTTTCCATTGCTGTTTTACTCAATTACTCAACCCATTTTCTAAACAG ATTTAAACTTCATAAATCCTGTCATCTC | 869 |
| IGHV1-24_chr14: 106733070-106733170 | CTCAGCCTCAGCACAGCTGCCTCATTCCTCAGGGTTTCTGACGCTCTCAGGATGTGGGTTTTCACACTGTG TCTGTTGCACAGTAATACACGGCCGTGTC | 870 |
| IGHV1-24_chr14: 106733185-106733285 | GCTCAGCTCCATGTAGGCTGTGTCTGTAGATGTGTCCTCGGTCATGGTGACTCTGCCCTGGAACTTCTGTG CGTAGATTGTTTCACCATCTTCAGGATCA | 871 |
| IGHV1-24_chr14: 106733275-106733375 | TTCAGGATCAAAACCTCCCATCCACTCAAGCCCTTTTCCAGGAGCCTGTCGCACCCAGTGCATGGATAATT CAGTGAGGGTGTATCCGGAAACCTTGCAG | 872 |
| IGHV1-24_chr14: 106733375-106733475 | GAGACCTTCACTGAGGCCCCAGGCTTCTTCACCTCAGCCCCAGACTGTACCAGCTGGACCTGGGCGTGGG TGCCTGTGGAGAGGACAGAGGAGTGGATGA | 873 |
| IGHV1-24_chr14: 106733475-106733575 | GACACCACTTAACTGGACCCAGTCCCCTCATCAGCCCTGGAACTCAGGATTCTCTTGCCTGTAGCTGCTGC CACCAAGAAGAGGATCCTCCAGGTGCAGT | 874 |
| IGHV2-26_chr14: 106758470-106758570 | GAGGGTGGGAATCTGGGAGAGCAAGGGGCTTCCCATAAGTGTTCTGATAAAAATCCTCTTTGTTTAGGGG GAAAGTGATGATTTTTTTGAATGATAGAGA | 875 |
| IGHV2-26_chr14: 106758570-106758670 | ATACATCACCCAAACATTTAAAAATGTATTGTGTAAAGAAGTGTAAATGGCATCTCAGCCATTTACACAC TGCAAGACACACAGCTTATTAGTGTGCCTG | 876 |
| IGHV3-30_chr14: 106791090-106791190 | TGGTGAATCGGCCCTTCACGGAGTCTGCATAGTATTTATTACTTCCATCATAFGATATAACTGCCACCOAC TCCAGCCCCTTGCCTGGAGCCTGGCGGAC | 877 |
| IGHV4-31_chr14: 106805945-106806045 | ACAATCACTTGAGTTCAGACACACCAGGATTCACTTAATGTTATTTTTAGTTCAGAACCTCTATCAGGTTT AGAGGGAATCGCTCTGTCCCAGGGAGTGG | 878 |
| IGHV4-31_chr14: 106806045-106806145 | ATCTTACAATAGCAAAACGGTCTTAGAAAACCCAACATAATCTACAGCGAGACCTCAGCATGGCAAGCAA GGAATCACTAAAGCCACCAGGGAGATCCGG | 879 |
| IGHV4-31_chr14: 106806120-106806220 | CACTAAAGCCACCAGGGAGATCCGGATGCACTGATACGATCCAGAAACATAGCGAGTCCGGGAACTGAT GCGGACTTTGAGGCAGCCTCTTTTTTTTTTT | 880 |
| IGHV3-33_chr14: 106815805-106815905 | GATGGTGAATCGGCCCTTCACGGAGTCTGCATAGTATTTATTACTTCCATCATACCATATAACTGCCACCC ACTCCAGCCCCTTGCCTGGAGCCTGGCGG | 881 |
| IGHV3-33_chr14: 106815905-106816005 | ACCCAGTGCATGCCATAGCTACTGAAGGTGAATCCAGACGCTGCACAGGAGAGTCTCAGGGACCTCCCAG GCTGGACCACGCCTCCCCCAGACTCCACCA | 882 |
| IGHV4-34_chr14: 106829685-106829785 | CTCGACTCTTGAGGGACGGGTTGTAGTTGGTGCTTCCACTATGATTGATTTCCCCAATCCACTCCAGCCCC TTCCCTGGGGGCTGGCGGATCCAGCTCCA | 883 |
| IGHV4-34_chr14: 106829765-106829865 | GGCTGGCGGATCCAGCTCCAGTAGTAACCACTGAAGGACCCACCATAGACAGCGCAGGTGAGGGACAGG GTCTCCGAAGGCTTCAACAGTCCTGCGCCCC | 884 |

-continued

| Name | Sequence | SEQ ID NOs. |
|---|---|---|
| IGHV4-34_chr14: 106829865-106829965 | ACTGCTGTAGCTGCACCTGGGACAGGACCCCTGTGAACAGAGAAACCCACAGTGAGCCCTGGGATCAGAGGCAGCATCTCATATCTTCATATCCGCATTC | 885 |
| IGHV4-34_chr14: 106829965-106830065 | CTGAGACACTCACATCTGGGAGCTGCCACCAGGAGGAGGAAGAACCACAGGTGTTTCATGTTCTTGTGCAGGAGGTCCATGACTCTCAGAAAGCACTTCC | 886 |
| IGHV4-34_chr14: 106830125-106830225 | GAGGATTTGCATGTGGGTGGTGCCTTTGTATGGATAGGTAAAAAGGGATGAGGGAGGCCCCAGTCTTTTGGGCTCACCCTGGGAGGTGTATGCTGGCTGT | 887 |
| IGHV4-34_chr14: 106830240-106830340 | AGTTCTCTTCCTGTGGCCTCCCCTCACCAAACCCAGAGTCCTCTTCTTCCAGGTAGGAAATGTGCTGAAGGAGCTGGTCTGGGAGACAAGTGTGATCATG | 888 |
| IGHV4-34_chr14: 106830315-106830415 | GGTCTGGGAGACAAGTOTGATCATOGATCAAAGACAGATTTTGGAATACAGTTAATACTGTTCTACATTTAAAGATTCATATAACACCAACCATACACCC | 889 |
| IGHV4-34_chr14: 106830415-106830515 | AGGTCACCTAAATTGTCATTTACCCCTTCAGACATATTGAAACAGCTGCTGAGTGTAATAATCACAGTGAATTGAGACAAACCTGGATCCATGCAATGTG | 890 |
| IGHV4-34_chr14: 106830515-106830615 | TACTGTAGTTCAGAACATCCATCATGGTTAGAAGGATGCTACCTGTCCCAGGAAGTGGGTTATTTTTAAATAGTACCTGAGAGCTGCCCTTCTGAGACCT | 891 |
| IGHV4-34_chr14: 106830615-106830715 | TTTGAAATTTGAGATTGTGTGTGAGATCTCAGGAGAAGGTAGTAGAATATATCTCCATCCTTCTCAATGTGTAACCCTGAGAATATGGCCTGACCTCTAA | 892 |
| IGHV4-34_chr14: 106830715-106830815 | ACATTTCTGTGTGAAAAGATGTACATTGGGGATAGCAGTGACAGCTTCAGATGAAAACTCTATAGTACATCAGCACTGGAGGATAGTCTCATCACCAAGA | 893 |
| IGHV4-34_chr14: 106830815-106830915 | TTAGTGAAATTACCTTTCCTGGGAACCAGAGAGGACCTCTGTGAGCTCTACCCTCTGAGAGAACAAGGAACTCTGGTTCTTCCCTGACAGGTCACACCTG | 894 |
| IGHV4-34_chr14: 106831185-106831285 | AACAAGTGGGCTGGCCTTCTATGAGACGACAGAGGGAAAGAGACAGACTCAATATCCAGAGCGAGGTGAGCTCCTTACCTACCTACCAGGTGGTCTCTGG | 895 |
| IGHV4-34_chr14: 106831285-106831385 | GCCATTTGTTTGAGCAGACCCAGAAGTACCTTCCTCACCCTCAGGAGAATTATGAACATTGAGAGAAACTGAGATACTTTTTTTATTTACAGGGAATATT | 896 |
| IGHV4-34_chr14: 106831385-106831485 | TCATCGGCGTGTTTACATCTACCTGGGTGTGTACAGGGATGCTAGGATGTGCTCATACACAGAAGAGCAAGAATTATATTTCGTGGAAAGAAAACCAAAG | 897 |
| IGHV4-34_chr14: 106831485-106831585 | AGCTTCTGAATTTGTAGGTATTGTTTGCTGCAAATGTGTCAGGTCACTAGATCATGTTATGCTGCTAGAAGAAAAACTTCCCAACATTGTCATGGAGACA | 898 |
| IGHV4-34_chr14: 106831585-106831685 | AAATGCAAAACAGTAAAGATTCAACTGAGATTCCCTTGAAAATCACCAGTAATGAACAGGCCAAAAGAAATCAACCATTGTGGAAAGAGTGGTCATTAAG | 899 |
| IGHV3-35_chr14: 106846385-106846485 | CCCAGTGTCACCTTACACATCCTGCAGGTCACCTOACACATCCACCAGGTCACCOCACATATACCCCACATCACCTCAGACACACCCTGGTCACCTCATA | 900 |
| IGHV3-35_chr14: 106846485-106846585 | CATACGTCAGGTCACCTCACGCTCACCCAAGGTCACCTCACACATCCCGCAGGTCACCTCGTAAATCCCCCAGGTCACCACATACATGCACCAGTTCACC | 901 |

-continued

| Name | Sequence | SEQ ID NOs. |
|---|---|---|
| IGHV4-39_chr14: 106877715-106877815 | CTCTTGAGGGACGGGTTGTAGTAGGTGCTCCCACTATAATAGATACTCCCAATCCACTCCAGCCCCTTCCCTGGGGGCTGGCGGATCCAGCCCCAGTAGT | 902 |
| IGHV4-39_chr14: 106877815-106877915 | AACTACTACTGCTGATGGAGCCACCAGAGACAGTGCAGGTGAGGGACAGGGTCTCCGAAGGCTTCACCAGTCCTGGGCCCGACTCCTGCAGCTGCAGCTG | 903 |
| IGHV4-39_chr14: 106877930-106878030 | GAACAGAAAAACCCACAGTGAGCCCTGGGATCAGAGGCAGCCTCCCATATCTCCATGTCTGCATCCTAGAAACACTCACATCTGGGAGCCGCCACCAGCA | 904 |
| IGHV4-39_chr14: 106878030-106878130 | GGAGGAAGAACCACAGGTGCTTCATTTTCTTGCACATGAGATCCATGACTCTCAGAAAGCATTTCCCTTATGAGTTGGACCTGAATTTAAGGAAATGTGT | 905 |
| IGHV4-39_chr14: 106878130-106878230 | GGTGGCTTCCTGTGGGCGCCTAAGTGAGGATTTGCATGGGGGTGGTGCGTTTGTACGGAGCAGTGAAAAGGGATGAGAGAGGCGCCAGTCTTTTGAGCTC | 906 |
| IGHV4-39_chr14: 106878230-106878330 | ACCCTGGGAGGAGAATGCTGGCTGTGCCCTTTGAGAACTCAGTTCTCTTCTTGGGCCTCCCCTCTCCAAGCCCAGAGTCCTCTTCTTCCAGGTAAAGAGA | 907 |
| IGHV4-39_chr14: 106878330-106878430 | TGTGCTGAAGGAGCTGGTCTOAGAGATGAGTGTGATCCTGGATCAAGGACAGATTTTGGAATAGGGTCAGTACTGTTCAACCCTTAAAGATTCATATAAA | 908 |
| IGHV4-39_chr14: 106878430-106878530 | ACCCACCACACACCCAGGCCATCTAAATAGTCATTTACCCTTTCAGACACATTGAAACAACAGCTGAATGTAATAATGACAGTGACTTCAAACAATACTG | 909 |
| IGHV4-39_chr14: 106878540-106878640 | ATGTTTATTGTAGTTCAGAACATCCACCATGGTTACAGGGAAGCTCACTGTCCCTGGAAGTGGGTCATTTTTTAAAAGCACCTGAGAGCTGTCCTTCTGT | 910 |
| IGHV4-39_chr14: 106878680-106878780 | AAGGTAGTGGGACATATCTCCATACTTCTCAATGTGTGACCTTGAAGATGTGTCCTGCCCTCTAAACACTTCTGATTGAAAATATGTAGATTGGGGATTA | 911 |
| IGHV3-48_chr14: 106994300-106994400 | GTGGAAATGCCTTGGAATCCAGGGCTAAGGCACCTCTCTGAGAGCTGCAGGGTCAGGGTTGGGTTGGTTTTCATCAGTAGAGGGAGGGCCCTATTTGCAT | 912 |
| IGHV3-48_chr14: 106994430-106994530 | GGACCCTTGAGGAGTAGGCTGTACCCAGATAAGACGACGGTGCCCTGTAGAAGTTTGCTGGCAATGATTGCATTTGGAAAATATGCTGTCTTATTATGAA | 913 |
| IGHV3-48_chr14: 106994530-106994630 | ATTGTGCTGTGATAAACACTTTGCACTAATCACCCTATTTCATTTTAAATATTCATGTAAACTATGTTCTGTAGGAGACAATATTTTCTCCATTTACAGA | 914 |
| IGHV3-48_chr14: 106994545-106994645 | ACACTTTGCACTAATCACCCTATTTCATTTTAAATATTCATGTAAACTATGTTCTGTAGGAGACAATATTTTCTCCATTTACAGAAGTGGAAGTAAACCC | 915 |
| IGHV3-48_chr14: 106994660-106994760 | CTGTATGCATCTAGGAGCTCATGTCTGGGATGAGTGAACCCCGGTATCTGGCCCTGTGCTCTTCATCACTGTCTCTGACATCCCCCTAAACCAACTCCAG | 916 |
| IGHV3-48_chr14: 106994760-106994860 | GACAAAGCTGGATGTGTCTAGTGTTTTTATCAGAACCCACTTTCCGTAATAAGAGCATGTGTGGTTTTGCTGCCCTCCAGCACTCTTCTGAAAATATGGA | 917 |
| IGHV3-48_chr14: 106994860-106994960 | GAGAACTAGGATCCAGGCACATTAATTTTCAGGTACTTCTGACATTGAACTTATTTTTTCTATCTTTCTATTACTCTTTCCTTGTCTAAGTTTCCATTTG | 918 |

-continued

| Name | Sequence | SEQ ID NOs. |
|---|---|---|
| IGHV4-59_chr14: 107083565-107083665 | AGAGAGACCCACAGTGAGCCCTGGGATCAGAGGCACCTCCCATATCCCCATGTCTGCATCCCTGAGATAG TCACATCTGGGAGCTGCCACCAGGAGAAGG | 919 |
| IGHV4-59_chr14: 107083665-107083765 | AAGAACCACAGATGTTTCATGTTCTTGCACAGGAGGTCCAGGACTCTCAGAAAGTATTTCCCATGTGAGC TGGAACCTGAATTTAAGGAAATGTGTGGTG | 920 |
| IGHV4-59_chr14: 107083790-107083890 | ATTTGCATGTGGGTGGTGCCTTTGTATGGAGAGGTGAAAAAGGAGGAGGGAGGCCCCAGTCTTTTGGGCT CGCCCTGGGAGTAGGATGCTGGCTGTGCCC | 921 |
| IGHV4-59_chr14: 107083890-107083990 | TTTGAGAACTCAGTTGTCTTCTTGGGGTCTCCCCTCTCCAAGCCCAGAGTCCTCTTCTTTCAGGTAAAGAG ACGTGCTGAAGGACCTGGTCTGGGAGATG | 922 |
| IGHV3-64_chr14: 107113405-107113505 | CTGACAGTGGTGACCATGGTTGAGAACTTTTCATCTCCTCTGTGAGGATCAATCTGCATTTTCTGCATAGG AGAATAGGTTTTCATATTAAAACAATCAT | 923 |
| TGHV3-64_chr14: 107113505-107113605 | TTTAAAAATATGTAGAAATGACCCTAGTAATCACAGAATTCCGAACTTAGGTTCAGTAGAGAAACTTTAA GAAGATGAAGTCCCACATCGTGACAGGAAA | 924 |
| IGHV3-64_chr14: 107113820-107113920 | TGGAGATGGTGAATCTGCCCTTCACAGAGTCTGCATAATATGTGCTACCCCCATTACTACTAATAGCTGAA ACATATTCCAGTCCCTTCCCTGGAGCCTG | 925 |
| IGHV3-64_chr14: 107113920-107114020 | GCGGACCCAGTGCATAGCATAGCTACTGAAGGTGAATCCAGAGGCTGCACAGGAGAGTCTCAGGGACCC CCCAGGCTGGACCAAGCCTTCCCCAGACTCC | 926 |
| IGHV3-64_chr14: 107114095-107114195 | TTCTCTCACTCATGTCCACTCACACTCAATATCTCTATTTCCTCATGAATCACCTTTAAAAATAGCAACAA GGAAAACCCAGCTCAGCCCAAACTCCATC | 927 |
| IGHV3-64_chr14: 107114195-107114295 | ATGACTCTTCTGTGTTCAGTGCTGATCACCAAATGAAAACACCTGGGAATCCCAGGGCGGGGGCTCCTCT CCCAGAGCTGCGGAGTCAGGGCTGGGCTGG | 928 |
| IGHV3-66_chr14: 107136755-107136855 | TAGGGCACATCCTTCCCATCCACTCAAGCCCTTGTGCATGGGCCTGGCGCACCTAGTGCATAGAGTAACT GGTGAAGGTAGGTGTATCCACAAGTCTTGC | 929 |
| IGHV3-66_chr14: 107136855-107136955 | AGGAGACTTTCACTGATGCCCCAGCCTTCTTCATCTCATCCCCAGACTGCACCAGCTGCACCTGGGACTGG GCACCTGTGGAGAGGACACGGGAGTGGAT | 930 |
| IGHV1-69_chr14: 107169645-107169745 | GAAAACTTGTTCACAGTAGCACCTTCATGGAATGTTTGTATCAACGTTATAGAGTGTGGCCTTTTCCACTC TGTGAATTTGGCTTATATTACGACTCTTG | 931 |
| IGHV1-69_chr14: 107169745-107169845 | AATGGAATATTTATCTTAAAATTAGAGTATGTACTTGTTTCTACTGTTCTTTTTTTCTCAAATATATAACCC ATTTTGTAAACAGCCTTAAACCTAATAA | 932 |
| IGHV1-69_chr14: 107169970-107170070 | CTGCTCAGCTCCATGTAGGCTGTGCTCGTGGATTTGTCCGCGGTAATCGTGACTCTGCCCTGGAACTTCTG TGCGTAGTTTGCTGTACCAAAGATAGGGA | 933 |
| IGHV1-69_chr14: 107170070-107170170 | TGATCCCTCCCATCCACTCAAGCCCTTGTCCAGGGGCCTGTCGCACCCAGCTGATAGCATAGCTGCTGAAG GTGCCTCCAGAAGCCTTGCAGGAGACCTT | 934 |
| IGHV1-69_chr14: 107170170-107170270 | CACCGAGGACCCAGGCTTCTTCACCTCAGCCCCAGACTGCACCAGCTGCACCTGGGACTGGACACCTGTG GAGAGGACACAGGGGTGAATAAAATCCTCT | 935 |

-continued

| Name | Sequence | SEQ ID NOs. |
|---|---|---|
| IGHV1-69_chr14: 107170220-107170320 | CCTGGGACTGGACACCTGTGGAGAGGACACAGGGGTGAATAAAATCCTCTTTAACTAAACCAGGATCCCT TCCTCAGCCTTAGGACTAGGAAGCCCCTTA | 936 |
| IGHV1-69_chr14: 107170320-107170420 | CCTGTAGCTGCTGCCACCACAAAGAGGAACCTCCAGGTCCAGTCCATGGTGATGAGCTGTGCTCCCAGGG GCTTCTTCAGAGGAGGAATGTGGTTGTTAT | 937 |
| IGHV1-69_chr14: 107170420-107170520 | GTGATGCTCTCAGOGCACCAATATATCTATATITATCTCAGAAGACCTCAGGTTATTTGCATATGCATGAG GCAGGGTATTTCACAGCTCAAAGCCTGAT | 938 |
| IGHV1-69_chr14: 107170475-107170575 | TTTGCATATGCATGAGGCAGGGTATTTCACAGCTCAAAGCCTGATCTAGGATGAGAAAGAAAACACAGAT GCCACATCAGCTGTACAAGTGTGGGATGCT | 939 |
| IGHV1-69_chr14: 107170660-107170760 | CAGAACAAACCCCAACCCCAGGATGCACTCCTCACTGTGAACCCACATTTTATTGGCCTAAAGATTACCTG GGTTTTTTGTGGGACCATTGCTGTCTCTG | 940 |
| IGHV1-69_chr14: 107170760-107170860 | ACATTGAGCAGGCACCTAGACCCATCCTGGTCCCATTAGGAACACTCAGAGCTCACTGGTAACACTGAAA AGGTGGCCACTCGTTACCCTACATGAGTGT | 941 |
| IGHV1-69_chr14: 107170860-107170960 | CCAGCAGGACCCATGGAGAGTTCTGAGATCTGCTGGGCACTCCCAAGACAGGGTCCCCAGCACTTTCCTG AGGGTCCTGACCTCCOAGGTCCTTCACTGG | 942 |
| IGHV2-70_chr14: 107178305-107178405 | TTATCCATTTCTATGTGTTCTTTTGAAAATGTCTACTCATGTCCTTTGCTCATTTTAACGGAGTTATTTGGT TCTTGTTGCTGTTGTTGTTGTAGAGTTG | 943 |
| IGHV2-70_chr14: 107178415-107178515 | TTGCAAATTCTTCATATTAGTTCCCTGTCACAGGCAAAGTGTGCAAAAGTTTTCTGTCATTCTGTAAATTG CGTATTCACTCTGTTGTTGTGAAAAAAAT | 944 |
| IGHV2-70_chr14: 107178515-107178615 | TATTTAGGTTAATTAAATCTCATCTGTCTATTTTTTTTTAGGTAGCAGGACCTTTCATGCTGAATCTTTGTC AAACAGGATACAGCTTCTGCTTGCATOA | 945 |
| IGHV2-70_chr14: 1071786i5-107178715 | ACCACTAACAGGGGACATGCCATTTATTAGTAAAGAAAAAGGAGGAAAACAAGGCTCTGAGTCAGATGG GGATGGGAAACGCACGCCCTGGGCAGGAAAT | 946 |
| IGHV2-70_chr14: 107178715-107178815 | GGCATCTCAGCCACACTATCCTGTTCTGCAGAAGTGGGGAGGGAGCACCACTGAAAAACACCTGGGTTCT TGTACAGGAAGCGCCCTGGGCTGTGTCTCT | 947 |
| IGHV2-70_chr14: 107178815-107178915 | GTGGTATCCGTGCACAATAATACGTGGCTGTGTCCACAGGGTCCATGTTGGTCATTGTAAGGACCACCTG GTTTTTGGAGGTGTCCTTGGAGATGGTGAG | 948 |
| IGHV2-70_chr14: 107178880-107178980 | ACCTGGTTTTTGGAGGTGTCCTTGGAGATGGTGAGCCTGGTCTTCAGAGATGTGCTGTAGTATTTATCATC ATCCCAATCAATGAGTGCAAGCCACTCCA | 949 |
| IGHV2-70_chr14: 107178980-107179080 | GGGCCTTCCCTGGGGGCTGACGGATCCAGCTCACACACATTCCACTAGTGCTGAGTGAGAACCCAGAGAA GGTGCAGGTCAGTGTGAGGGTCTGTGTGGG | 950 |
| IGHV2-70_chr14: 107179080-107179180 | TTTCACCAGCGCAGGACCAGACTCCCTCAAGGTGACCTGGGATAAGACCCCTGTGGAGAAGACATAAGAA GATGAAGCCCACAAAGGAGAGAATAGATTT | 951 |
| IGHV2-70_chr14: 107179130-107179230 | CTGTGGAGAAGACATAAGAAGATGAAGCCCACAAAGGAGAGAATAGATTTTTTGCTTCTGAAGTACTACC TGACCACAGCACTCACAGGACGGGACAGTC | 952 |

-continued

| Name | Sequence | SEQ ID NOs. |
|---|---|---|
| IGHV2-70_chr14: 107179230-107179330 | AGTAGCAGGAGCGTGGAACAAAGTATGTCCATGGTGGAGAGCAGGATTCACTGAGCGAGGCCCTGTCCT CGTCTTTTGAACCCAGGGGAGGGTGGAGCTG | 953 |
| IGHV2-70_chr14: 107179330-107179430 | GTGGAGATTTGCATCCCCTCATCTGAGCCCTACTCTATGGGGTGCACTCAGGTCTCAGGACTCAGTAGGG GAGTGCATCTGTGGTGAGGAGCAGTGAGCC | 954 |
| IGHV2-70_chr14: 107179360-107179460 | TACTCTATGGGGTGCACTCAGGTCTCAGGACTCAGTAGGGGAGTGCATCTGTGGTGAGGAGCAGTGAGCC CTCAGGTGTGGGGGTCCACGTGTGCTCTCC | 955 |
| IGHV2-70_chr14: 107179460-107179560 | ATCAGGGAATCTATCTCATTTCAGCACCATGGCTCTCAGTCAAGTCTTGACGCTCCTGCTTCTACAGACAG GATCTTCTTCGATGCTCCCGCACCGGACA | 956 |
| IGHV2-70_chr14: 107179560-107179660 | TGCAACCTTCTGGTTTTAGTCCTAGAGGATTAGAGTAGAAATCAAGAGAGCTGCCGTTCCTCCTCCCTTCA AGAATAATGATGGTGGGCATCTGGGGGGC | 957 |
| IGHV2-70_chr14: 107179660-107179760 | AAGGGGCTCCCX3ACAAGCATTCTGATCAAAATCCTCTTTGATTATGGGGAAAAGTGATGAATTTGTGTAA AAAAATTGGAGAGAATAAATAAGAAAATAC | 958 |
| IGHV2-70_chr14: 107179760-107179860 | AGTTACAAGTAATTATGTAAAGAAGTGTGTGCTTAGCAGTGTGTGTGCACACAGCTGCATTCCTAGAGGC ATGTTCCATGAAAAATCGATGTTGTCCTTG | 959 |
| IGHV2-70_chr14: 107179860-107179960 | TGCCCCGTCAGTTCTGTGGAGAGAGTAGACTGCATGAATGACTTCCCTTTTCTCAGCCCATGAATGAGCG GATGCTTTGGACAAGGGAATTGGAAGACTC | 960 |
| IGHV2-70_chr14: 107179960-107180060 | CTGAGGGAGCAGCAGGCTGACTGTTGCAGCCTTGCTCTGCACCTGCACTGGATGTGGTCTCTGTGCTCAT AAGGCCGTGGAAACTCATCAATCCAGGTTC | 961 |
| IGHV7-81_chr14: 107258910-107259010 | CAAAAAGGGGTTAAATGATTTTGGAAAAGTAAGTAGAAAATAAAAGAAGGAGGGAGTAAGAGCGGACA GAAGGGAGGAAGGCAAGCAAGCAATGATGAAC | 962 |
| IGHV7-81_chr14: 107259010-107259110 | TGTGTAAAATTTTCACTAATTAAAAGACTATTATATTGAAGAGGTGCCTATTAGGCAGCCTTTTGATGTTA ACCATGTAATATACACCATGAACAACCTT | 963 |
| IGHV7-81_chr14: 107259100-107259200 | GAACAACCTTGTAGAACACACAAGAGCCCCCTCAGAGAACTGGATGGGTCAGGTCTCCCATCCAGTTGCC TTAGGGGTTAGGAACGCTCCCATGTTGTTC | 964 |
| IGHV7-8i_chr14: 107259200-107259300 | TCTGGTTTTTGCTCCTGAGGACACAAACAGCCAGTGTTTCCTCCCCGGATGAATAGAGAGGCCCCTGGGG AGGGTGTGTCTGGCAGCTCACTCTGCACCT | 965 |
| IGHV7-81_chr14: 107259235-107259335 | GTTTCCTCCCCGGATGAATAGAGAGGCCCCTGGGGAGGGTGTGTCTGGCAGCTCACTCTGCACCTGCACC GCGGAAGGTITTAGATGGTCCCTCTCACAC | 966 |
| IGHV7-81_chr14: 107259335-107259435 | AATAATACATGGCGGCGTCCGAGGCCTTCAGGCTGCTCCACTGCAGGTAGGCGGTGCTGCTGGAGCTGTC GGCTGAGATGGTGACGTGGCCTTGGAAGGA | 967 |
| IGHV7-81_chr14: 107259435-107259535 | TGGGCTGTATCTGGTATCAGAGTTCCCAGGATAGATGCTCCCCATCCACTCCAGTTCTTTCCCGGGCATCT GGCGCACCCAGTGGATCCAGTAGCTGGTA | 968 |
| IGHV7-81_chr14: 107259555-107259655 | ACAGGAGATCCTCAGAGACTCCCCGGGTCTTTTCACCTCTGCTGCAGACTGCAACAGCTGCACCTCGGCA AAGACACCTGTGTGGGAGACACAAAATTTG | 969 |

-continued

| Name | Sequence | SEQ ID NOs. |
|---|---|---|
| CIIUTA_chr16: 10971440-10971540 | GTGTCTGGAGTATGAACCATGTATCAGCACCGAAAGGTTCTAGAAGTCAGACTTTCGGGCAGTGTGTCAC TAACTCTCAGCATGCTGGCCTGGCTCGGCC | 970 |
| CIITA_chr16: 10971540-10971640 | CACAGCAAGGTCTTCTCGCCTCCCTTTGGGTAAATACTGAGGGGTGCCTCTGCAGGACGGGACCTCTGCC AGACTCCACTCCATACCCAGAGAAGCAGGG | 971 |
| CIITA_chr16: 10971640-10971740 | AAACCAAAATTGGAGTCAGCCTTGAGGTGTAGCTGTTGAGCCCTCAGCAGCTGGGGAGAGCTGGCGGAT GCTGCCCTCCCCCCAGTTTCCTAATGGTGTT | 972 |
| CIITA_chr16: 10971740-10971840 | GTTTAAAAAGGGTCAGGGGACGGGGGAACAGATGGTGGGAAGAGCACAGTGCAGACACCTGGCACCGGC TCTGAAGGCAGCATGGCAGCTACACCGTTGG | 973 |
| CIITA_chr16: 10971840-10971940 | CTGGGAAGGGTGTGCCCCTGAAGAAGTCGTTTACATTCTCGAGTCAATTTTCCTGGAGTGTACAATGGAC CTGTGGGAAAGCCTGTATGAAAGGGTAATG | 974 |
| CIITA_chr16: 10971940-10972040 | ATGAGGGACCTAGCACAGTGTCCAATATTTTATAGGAACTGGAATTGAGCTCATAGGAGCTCAATTTTAT TGGCATTGCTGTTGTTGGATGGTTAAAGGG | 975 |
| CIITA_chr16: 10972040-10972140 | GTGGTATCCCTTTTCTCAGACTCCCCTGAAATGTATGGTTTGCTTTGAACCCAGAGACTGATGACAGGTCT GCCGGTGTGGTTGGGTGCAGCCTTAAGTT | 976 |
| CIITA_chr16: 10972140-10972240 | GCTACGGGAAAGTGTTGGAGGGGGAGAAGTCAGAGGTAACCTTGCCCCCTCCCTCAATTCCAGATGAGGA AATTCAGGCCTGAAAAGGGAAAGTGACCAC | 977 |
| CIITA_chr16: 10972240-10972340 | CTCAAAGTCTCATGCCTTGGAGGACCCAGCAGGAATCCAAGACCTCTGAAAAGGACCGGCAGGGCTCTTG CCACGGCTGGGGGTGTGGTCATGGTAACAC | 978 |
| CIITA_chr16: 10972340-10972440 | AGGTTTTCCATCCATGGAAGGTACCTGAGGGATTTTCTCTTCCTCCCTAGGGCCAGCATCAGAGGAGTGA ATAGCTCAGTTAGCTCATCTCAGGGGCCAT | 979 |
| CIITA_chr16: 10972440-10972540 | GTGCCCTCGGAGGTGGTTTGCCACTTTCACGGTTGGACTGAGTTGGAGAGAACAGAGACCCACCCAGGG GTGGGGACAAGCTCCCTGCAACTCAGGACT | 980 |
| CIITA_chr16: 10972540-10972640 | TGCAGATCACTTGCCCAAGTGGCTCCCTAGCTCCTGGCTCCTGGCCCGGGGCCTGGGACTCTCCCCGAAGT GGGGCTGGCCACTGTGAGGAACCGACTGG | 981 |
| CIITA_chr16: 10972640-10972740 | AGGCAGGGACCTCTTGGATGCCCCAGGCAGTTGGGATGCCACTTCTGATAAAGCACGTGGTGGCCACAGT AGGTGCTTGGTTGCTCCACAGCCTGGCCCG | 982 |
| CIITA_chr16: 10972740-10972840 | AGCTCAGCGCTGCAGAAAGAAAGTGAAAGGGAAAAAGAACTGCGGGGAGGCGGGGAGGTAGGATGACC AGCGGACGAGCTGCCACAGACTTGCCGCGGCC | 983 |
| CIITA_chr16: 10972840-10972940 | CCAGAGCTGGCGGGAGGGAGAGGCCACCAGCAGCGCGCGCGGGAGCCCGGGGAACAGCGGTAGGTGAC CAAAGTCTCCTCTGTAACCCCTAAGGTCGGGC | 984 |
| CIITA_chr16: 10972940-10973040 | TGAGAATCGAGGCTCCGAGACTGTCAGCTACTTGCTCAAGGTCACACAGCAAGTCTGGGAGGATGGGGG GATGGAATATGCAAAATGTAGGGCCGGGAAA | 985 |
| CIITA_chr16: 10973040-10973140 | CACCTCGTTTCCAGCATCCCCGCAACGACTCTGCGCGGGAACCAGGAGCCGGGAACCCGGAGCTTGGCTT GCTGTGCCCAGAGCTCCGGGGCCGTGGGCG | 986 |

-continued

| Name | Sequence | SEQ ID NOs. |
| --- | --- | --- |
| CIITA_chr16: 10973140-10973240 | GGTGGCAGGAAAGCCTGGCGGCAGCTTCTGCAGAGAAGCCGGAGCGCAGACTGGGAGCGCGGAGCAGAC ACACTCCCCCGGCCACCCTTGGCCGACTCCG | 987 |
| CIITA_chr16: 10973240-10973340 | CGCGCCCGGGATCCTGCAGAGGTGCGCGCCCTTCTTGTACGCCAGACTTTGGACCAGGGCCGCCGTTCCC TGAGCTTCACTTTCCCTGTTGGGTCATATT | 988 |
| CIITA_chr16: 10973340-10973440 | CCATCTCTAACTCTGGAATCTTGGGTATTGGGCTCTCCAGGCGGGGGGCCCTGCTCAGGGAGGCAGTAGG GAGCCAAACCTTTAACCAGAGGATGGGATA | 989 |
| CIITA_chr16: 10973440-10973540 | AGTCCTCAACTCTCGTTGAACATCTTGGCGAAGGTGTGTGTTGTTGGGAGGGGTGGGGGAGGGATCCCCC CGGACTGAACCGATCTCTTGATCTCTCACT | 990 |
| CIITA_chr16: 10973540-10973640 | TCTCTACCTCGCTTTGGGGCCCTGAGTCACACCCTCTAAGGAGAGAGGCTAAAGCGCCCCGGAAAGCCAG CGTGCGAATGCCGGGGTGGGAGTGGGAGAT | 991 |
| CIITA_chr16: 10973640-10973740 | TGGATCTCCCTGGGGTCCAGGAAAGCCGGAATCGGAGCCACCATGCTTAGCTTAGTCTGGAACTCTTAAA AGCCGCGGTCCTCCTGAGTCCCACAGCCCC | 992 |
| CIITA_chr16: 10973740-10973840 | TCTCCACCCTAGGTGGCACAGGAGAGGTGGCAAAAGCCTAGAAGTTCAAGGCATGGCTCCCTCCCCAGCC GCAGCCTGGAGTGTCTAACTTTGGCAGGAA | 993 |
| CIITA_chr16: 10973840-10973940 | GTCTTCCGTTTCTGCTCCCCACTCCAGAGAAAAAATAAATAAATACTTCTCCGGAGTGAGATTAAGGAAA CAGGTACTTCTTCCTCTTGGAGAAAGAGGA | 994 |
| CIITA_chr16: 10973885-10973985 | CTTCTCCGGAGTGAGATTAAGGAAACAGGTACTTCTTCCTCTTGGAGAAAGAGGAGCCAAAGGAACTTGA CTCCAACAAATGATCACCTTGCAAACCCCC | 995 |
| CIITA_chr16: 10973985-10974085 | GGCTCCCTTAGGGGATGACCTGGTCTCCAACAATCTCAGAGCGTTTGGAGGCAGGGTCTTTGGAGATGAC TGAGTGGGGAATCCCAGGCTCCCCACACAT | 996 |
| CIITA_chr16: 10974085-10974185 | GAACATCACCTGGGATGATCAACCTGTTCAGGATGTAGGTTCCCGGGCTCACCCCCAGGCCCGGTTGGCT AGGCCTGGGGTGAGGCTGAGATCCTGCAGG | 997 |
| CIITA_chr16: 10974185-10974285 | TTAAACCATCTATCCCAGGTGACTCCAATGTTCGTTTGTGGGGCAAAAGTCCCTCAAGTCAGAGACACTG GGAGGCGCTGATGTGGTCTCATCTCTTTAC | 998 |
| SOCS1_chr16: 11348520-11348620 | CAAGAGGTGAGAAGGGGTCTGCGGCCTCGTCTCCAGCCGAGGGCGGGAGGCGCCTCOCCGCTACACCGAT CCGCTCCCTCCAACCCAGGCCGGGGAGGGT | 999 |
| SOCS1_chr16: 11348620-11348720 | ACCCACATGGTTCCAGGCAAGTAATAACAAAATAACACGGCATCCCAGTTAATGCTGCGTGCACGGCGGG CGCTGCCGGTCAAATCTGGAAGGGGAAGGA | 1000 |
| SOCS1_chr16: 11348720-11348820 | GCTCAGGTAGTCGCGGAGGACGGGGTTGAGGGGGATGCGAGCCAGGTTCTCGCGGCCCACGGTGGCCAC GATGCGCTGGCGGCACAGCTCCTGCAGCGGC | 1001 |
| SOCS1_chr16: 11348820-11348920 | CGCACGCGGCGCTGGCGCAGCGGGGCCCCCAGCATGCGGCGCGGCGCCGCCACGTAGTGCTCCAGCAGCT CGAAGAGGCAGTCGAAGCTCTCGCGGCTGC | 1002 |
| SOCS1_chr16: 11348920-11349020 | CATCCAGGTGAAAGCGGCCGGCCTGAAAGTGCACGCGGATGCTCGTGGGTCCCGAGGCCATCTTCACGCT AAGGGCGAAAAAGCAGTTCCGCTGGCGGCT | 1003 |

-continued

| Name | Sequence | SEQ ID NOs. |
|---|---|---|
| SOCS1_chr16: 11349020-11349120 | GTCGCGCACCAGGAAGGTGCCCACGGGCTCGGCGCGCAGCCGCTCGTGCGCCCCGTGCACGCTCAGGGGC CCCCAGTAGAATCCGCAGGCGTCCAGGAGC | 1004 |
| SOCS1_chr16: 11349120-11349220 | GCGCTGGCGCGCGTGATGCGCCGGTAATCGGCGTGCGAACGGAATGTGCGGAAGTGCGTGTCGCCGGGG GCCGGGGCCGGGACCGCGGGGCACGGCCGCG | 1005 |
| SOCS1_chr16: 11349220-11349320 | GGCGCGCGGGGGCCGCGGGCGAGGAGGAGGAAGAGGAGGAAGGTTCTGGCCGCCGTCGGGGCTCTGCTG CTGTGGAGACTGCATTGTCGGCTGCCACCTG | 1006 |
| IGHV3OR16-12_chr16: 33523607-33523707 | TTTAAAATCACCCAAATCAAAATAATTTTATCTTCATTAATAAATAATCATCAGAAGTTTAACTAATTTTT ACTTTATAATACTAGGTTTAAAAATTCTT | 1007 |
| IRF8_chr16: 85933003-85933103 | AATCTGAATGCCCAAGTCGTTGATTGTCGTTTGCCTGTTTCCAAAGATTGGTAGATAGATGCCTTTTTAAA AATCTCATTTTTCTTTAAATCTGGTTTAC | 1008 |
| IRF8_chr16: 85933103-85933203 | ATGGAAAACGTTAGGAGAGCTCATATAATGAACGGCAATAGCAACCCCCTATCTTGAAACGCGCTCTATC ATCCCACTGAAATTCTACCACGTGGAATAA | 1009 |
| IRF8_chr16: 85933203-85933303 | TGCTTGGAGGGTCAGAGTTGTGGAACTGCCCAATAACCAGTCGTTACTGAGGGTTAGTTTGTGAAGGAGG GGACAGACTGCTTCTAAAATTCTGTTTAAT | 1010 |
| IRF8_chr16: 85933303-85933403 | GACAGTCAATTAAGATTTCTGAGTCTGGCTTGAGGGCCTTTGCTTCCATCACAGCCCAGTCGTCCTTGGCA AGAGAGTCTGTATATGGGCCACAGCTCAC | 1011 |
| IRF8_chr16: 85933403-85933503 | AAAAGCATTGTTTGAAAAAAATTTATTGAAAGAACATTGTTTGTAAAATGAGTCCCAATACATAGGACAGA CTTTCCTAAGGTGAGATGTGTTACTTACCC | 1012 |
| IRF8_chr16: 85933503-85933603 | AGAGCTGTGAAAGGCTTTACGGATGGAAACTAGAGACTGAATTTTCCAGAATTTTAAGAAGTCTCCCCAA CCAATGGCCCCCCACTTTCTTTTTTTAAAC | 1013 |
| BZRAP1_chr17: 56408574-56408674 | GGCGTGATCTCCGAAGCCCACAGTACACTCATCCATAAAGTAGGAAACACTACACCCTCCAGTGCTGTTA GTAGTGCTTTCTACTTTATGGGTGACTGCA | 1014 |
| BZRAP1_chr17: 56408674-56408774 | CTGTCTGTCTGTCCGTCGGCGTGTACTCTTCAGGCTGCCCAGGCCTCCTGACTCCTGCTCCAAGAGCCCCC CAGCCCTCCTTGTGGCTTCCTAAGATCCC | 1015 |
| BZRAP1_chr17: 56408884-56408984 | CCCTCTTCCCTTCCCCCTAAAGGCTCCACCCCATCCCCCCAGTTTCAGAGACACTCAGGTAGAGACTAGGG CCTCTGGAGGCCTCACCTTCAGTTCTGTG | 1016 |
| BZRAP1_chr17: 56408984-56409084 | AACCCCTGGCTGGCCGCTTCCAGCCACGCTAGCCACCCTCCAGCGTCCAAATGAGGCAGCCACAGCTCCC CTGCCAAGGTCTTGGTCTCCAGTCCACCCC | 1017 |
| BZRAP1_chr17: 56409084-56409184 | AACCGTGAGGTCCTGACTGCCCAGAGCCTCAGTCCCCACCCTTCAGCCTCCCCACCAGCCCAAGATCCTGA CCCCCCAGGGCCTAAGTCCCCAGCCTCCC | 1018 |
| BZRAP1_chr17: 56409184-56409284 | CAACAGCCCAGGGTCCTGACCCCCCAGGGCCTCAGGCCCTGGCCTCCCCACCAGCCCAAGGTCTTGAACA CACCAGGGCCTCAATTCCCAGCCTCCCCAC | 1019 |
| BZRAP1_chr17: 56409284-56409384 | CAGCTCAAGGTCCTGACTCCCCCAGAGCCTCAGTCCCAGCCTCCATAGCAGCCCAAGGTCCTGACCCCCCA GGGCCTCAGTCCCCAGCCACTCCACCAGC | 1020 |

-continued

| Name | Sequence | SEQ ID NOs. |
|---|---|---|
| BZRAP1_chr17: 56409384-56409484 | CCCAAAGTCCTGACTCCCCAGAGCCTTGATTCTCGGCCTCCCCACCAGCCCAAAGTCCTGACTCCCTCACT GCCCTGCTGTTCCCCTGGCAGGAGCCCAA | 1021 |
| BZRAP1_chr17: 56409484-56409584 | GGCTATCCCAACAAAAATGGTGGCCATGTTGGGCGGAGGAAGAGGCTGGCGCCCCTTGAGACACTGGTCC CACTTCTCAGCCTCTGCGTACCCTCTGCCA | 1022 |
| BZRAP1_chr17: 56409584-56409684 | TCCCCGCCTTACTCTCCAGCCCTCCTCCTTGGACACCTCTTTCCCCGCCTGGGGTCCCGGAGCCATTTTACC TTCCTTCACTAGAGAGGGTTTCAAGGCG | 1023 |
| GNA13_chr17: 63010240-63010340 | CTAAGATTTTCAAGAAGTTAAACGTAGAATTAAGATTGTTCTAATTCTGGTTGTAAACTGCTATTTTAAAA AACAAAACAAACAGAAAACATCAAAAACA | 1024 |
| GNA13_chr17: 63010315-63010415 | AAACAAACAGAAAACATCAAAAACACAAAAAGATATTAAAACAGCAAGTCTTTTGTACATCACTGTAGCA TAAGCTGCTTGAGGTTGTCATGCAGAATAG | 1025 |
| GNA13_chr17: 63010415-63010515 | TATCCTTCACGTCACGGAAAACAAGGCGGATGTTCTCCGTGTTGATAGCAGTGGTGAAGTGGTGGTATAA GGGCTTCTGTTGCTGGTCCCGGCGTTTGTT | 1026 |
| GNA13_chr17: 63010515-63010615 | CCGGAAACATTCCACCAGGAATTTTTGGACGTCTCTTAAGCAGTGGGGATCCCCTTCAAATTCTAGGAAA TAGTCTTTGATGCTCACAATTTGCACCTTC | 1027 |
| GNA13_chr17: 63010615-63010715 | TCCTCAAGCAAGTCTGTCTTGTTTAAGAACAGAATTATGGAGACATTGCTGAAAACCCGGTTATTGACGA TTGTTTCAAAAATGTTCAGAGACTCTGTAA | 1028 |
| GNA13_chr17: 63010715-63010815 | GGCGATTGGTCAGTCGATCTTCCATAAGCACCTGGTCAAATTCACTTGAGGAAACAAGGAAAAGTATTGA TGTCACACTGTCGAAACATTCAAACCAACG | 1029 |
| GNA13_chr17: 63010815-63010915 | TTTCCTTTCTGATCTCTGACCACCTACATCAACCATTTTGAAAGGAACATTTTTATTTCAAAGTCGTATTC ATGGATGCCTTTGGTGGGTCTTCTGGCA | 1030 |
| GNA13_chr17: 63010915-63011015 | AGCAGAATATCTTGTTGTGATGGAATATAATCCTGGAAAAGAAAAAACTTGTTTTATACCTATTAATCCCG AAGTAATGCGAATTTTTAATGGACTACTA | 1031 |
| 43717_chr17: 75447868-75447968 | TGTAAATATTTGGCCAACTAAGCTGAGTGGCTAAGTTCTCCTGCTGCCCGGAGCTTCTTGGAACATGTTTC CTTTTCGCAAGGGGTTTCCCTGGCTTCCA | 1032 |
| 43717_chr17: 75447968-75448068 | GGAGGGCCAGGAAGAAATTCGAATTGGCCACCGCTTTCTCTAAAATCACTCCGCTCAAGTTATCACCCCT CTGGGCTCCCGAAGACCGGCTGGCTGGAGG | 1033 |
| 43717_chr17: 75448068-75448168 | CTGGAGATAGTCTCAATGCTCGAAATGCCGTAACCGAAGCTCCCCGCGGCGCCGGCACTGGGATCCAGGG AGCTGCTGCTACAGCGCAGCTCTGGATTCC | 1034 |
| 43717_chr17: 75448168-75448268 | TGGATGTGTTGGATATGTGCAGGGCGTTCCTGGGAGGAGCGGGGAGGGAGGGTGCTGCTGGCGGGGCTG GTCTGCGTGTGCTTTGCTTCTCTACAATGGC | 1035 |
| 43717_chr17: 75448268-75448368 | ATGCTGCGTGTCGGCCATGCAGAGGCATGTCAGTGAGCAGGGGCTGAGGGATCTCCCTAACGGACCTGCT TTCAGAGGGTCTTTTCATGCTGGGAGAACC | 1036 |
| 43717_chr17: 75448368-75448468 | CCAGAGACTAAATCATGCAGCCAACGGGGTGGTCCCCGGCCTCAAAGCAGGGAGGGGCGAGGAGCTTTG TAGGCAATGCCATCTGCTCCTGAAACGCCGT | 1037 |

-continued

| Name | Sequence | SEQ ID NOs. |
| --- | --- | --- |
| ADCYAP1_chr18: 1477565-1477665 | CAGCCTCCTTAGTAGCTACCGCCTTAGTAAGTACCACTTAGTAAGTACCGCCTTAGTAAGTACCACTTAGT AGCTACCTCCTTAGTAAGTACCACTTAGT | 1038 |
| ADCYAP1_chr18: 1477665-1477765 | AAGTACCTCCTTAGTAAGTACCACTTAGTACTACCACCACGCCTGGCTAATTTCGTATTTTTTTTTTTTTAG TAGAGACGGGGTTTCTCCATATTGGTCA | 1039 |
| AC012123.1_chr18: 30349775-30349875 | AGGTCAGGCGCATACTGCATGCGGGTCTCGCGGTCGTGCTCCAGCCACAGCACGGACATCTGGAAGAGCG CCAGCTCCGACTCCACGGGGGGCGGCAGCG | 1040 |
| AC012123.1_chr18: 30349875-30349975 | AGTCCAGCAGGGCGCGCATCTCCTCGAAGTTGAGCAGCAGCACATCCTCCACCAGGTACTTGTTGGCCAG CTTCTTGGTCTCCTCCAGGCCGTGCAGCGC | 1041 |
| KLHL14_chr18: 30349975-30350075 | GGCGATCTTGCACACCTGCTTGTAGTTCTGCACCGAGATCTGGTCGTTGAGGAACTGCACGCAGAGCTTG GTGACCTGGGGGATGTGCAGGATCTTGCTG | 1042 |
| KLHL14_chr18: 30350075-30350175 | ACCGACAGCACCTCCTCCACCGTGTCCAGGGACAGGGTCACGTTGGCCGTGTAGAGGTACTCGAGCACCA GGCGCAGCCCGATGGACGAGCAGCCCTGCA | 1043 |
| KLHL14_chr18: 30350175-30350275 | GCACCAGGTTGTTGATGGCCCGGGGGCTGGTCAGCAGCTTGTCGTCGGGGGAGGAAGAAGGAGTCCCGG GCTCCTCCTGCGGCGGCGGCTGCTGCTGCTG | 1044 |
| KLHL14_chr18: 30350275-30350375 | TGACGGCTGCTGCTGCGGCGGCTGCTGCTGGTCCTTGGGGGCCCCCAGGCCGTCCTGGCCGCCGACCCCT CCCCCGAGAGGGGGGTGGCTGGAGAAGAGC | 1045 |
| BCL2_chr18: 60806264-60806364 | GAGACTTCAGCCGGAGCTGGCTATTCCAGAGATGGACCTCAGAGGATTCCTTAGTCTAATTACCTTCTGG GCTGGGGTAGAAGATGGTGTCTGGAGGGAA | 1046 |
| BCL2_chr18: 60806364-60806464 | GCACAGAACCAAGTTCCCTACTGCCGCACTAGCTATGCAAATACTGCAGGGCACCTGTGGGCTCATGTCC CTCCTGCAAGAAGGTGTGGTCAGTCCAGTA | 1047 |
| BCL2_chr18: 60806464-60806564 | ATTCAAAAGACGTACTTCTGAAATAGGTGGAGAAATGCATTTATAGCAAAAAGTGCTAAAAATATGTTAA TAGTTATGCTATTTGGTTCACCAGGTTAGT | 1048 |
| BCL2_chr18: 60806564-60806664 | GTAATAAACCATAACAAGAGAGACTAAAGGCCGTATCTATATGACCTTGAAATCTCATCTTCAGCGGGCT TATTCATTCAGTAACCAAACTATTTTTGTA | 1049 |
| BCL2_chr18: 60806664-60806764 | AGGTGCTGAGTATTTAGCTTAAAGCTAAATAAGACACATGCCCTGCCCTATAGTAACTGCTTGGTAATATT CCCAGTGGCTTCCATGGGCCTGATAATTT | 1050 |
| BCL2_chr18: 60806764-60806864 | TCTTAGTACTGAATTCAAAGCACTTTGTGTCTTGTCTGCAGGCCCATTTGCCCAGCAGTGGCCTTGCCAGG AGAGAACAGGCCCATGCTCCTGTCCTCAT | 1051 |
| BCL2_chr18: 60983784-60983884 | CAAACAAACAATTCAAGAAGAGGATTTAAATTTTAGAAATTTAAATTGGGGCATTTTAGTTAATCTTACTT TTAAACACCAAACAGTGGCATCAATATTT | 1052 |
| BCL2_chr18: 60983884-60983984 | TGTCAACTTTGGTCAAATAAGATCAGATGTTCACATCAATCATCTACTTTTCTTGGCCTTTTCTCTATTTGG CCTCCTAGTATGAGCACACTTTGTAAAA | 1053 |

-continued

| Name | Sequence | SEQ ID NOs. |
|---|---|---|
| BCL2_chr18: 60983984-60984084 | TGTAATAAAAACATGTGGTGTGCTTCTTGACATCTAATCCACTTGCAGTAATTTCTAGGCTTTTTGCTCCT GTTAGGTCCTATAAAATAATGACATTAGT | 1054 |
| BCL2_chr18: 60984454-60984554 | ATAGATACCTAGATGCAAATTTTTTTCAGCCGACCACAAAATTAGGTCCACTCTGAGTGGTGAAAAACAA AAGATTCTAACATTCTAGCAAACTGGTAAA | 1055 |
| BCL2_chr18: 60984554-60984654 | CCATACACAAATTATAGAATACAAAGAATGCAGCCGATGCAAATTCTGTCACTGACAAGGTAGCAAAGCC ATAGCCTGATACTCCTCAGGACACCTCATC | 1056 |
| BCL2_chr18: 60984654-60984754 | ACGCCCACTGGGAACATGGCACACACTGGAGATTCCAGTCCAAGGACTTTGGAATGTCAACTTAGCTCTT TACAAACACAACTAAGTTTTTCAGGGAAAA | 1057 |
| BCL2_chr18: 60984754-60984854 | AGACTTACATTGGTTTTCCTCTTTTGGAAAATTTTACCGATTGATGATGCCCTTGGTCTTCTGTGGAGTCT ATTCTTCTAATCGGGTTGTTCTCCAATTT | 1058 |
| BCL2_chr18: 60984854-60984954 | TAGTGTACAACGGGCTTGTTTCAGGGGAGCTTGTTTGGGATGCAGACTGTCAAGACCCAACCTGGTATCT GGTTCATAAGCAGTCCCTGAAACCTCCCTC | 1059 |
| BCL2_chr18: 60984954-60985054 | CGGTTCCAACAAGCTGCTCAAGCCAGGAAACGGTGGTCCTGGGGACTOCTGGACCTTCAGCTTGAGAAAC ACTGAAGGGGTACCATTTACCACCACATCC | 1060 |
| BCL2_chr18: 60985054-60985154 | TACTGGATTACAAACGCTAGATCTTTGGATCTCCACGACTAGCAAGCAAGTTAAAGACTTTTAGATGGCA GGCGTTATCGGTCAGGTTGGGAGTGAACGC | 1061 |
| BCL2_chr18: 60985154-60985254 | TTTGTCCAGAGGAGGAGGTAGGGACGCCGGGAAGCAACAACTCTGATTTTATTTCGCCGGCTCCACAGCC TCCCATTGCCCCAGGAGCCCACCCGCACTC | 1062 |
| BCL2_chr18: 60985254-60985354 | CAACCCCCGCATCTCGGACCTGTGGCCTCAGCCCAGACTCACATCACCAAGTGCACCTACCCAGCCTCCGT TATCCTGGATCCAGGTGTGCAGGTGCCOG | 1063 |
| BCL2_chr18: 60985354-60985454 | TTCAGGTACTCAGTCATCCACAGGGCGATGTTGTCCACCAGGGGCGACATCTCCCGGTTGACGCTCTCCAC ACACATGACCCCACCGAACTCAAAGAAGG | 1064 |
| BCL2_chr18: 60985454-60985554 | CCACAATCCTCCCCCAGTTCACCCCGTCCCTGAAGAGCTCCTCCACCACCGTGGCAAAGCGTCCCCGCGCG GTGAAGGGCGTCAGGTGCAGCTGGCTGGA | 1065 |
| BCL2_chr18: 60985554-60985654 | CATCTCGGCGAAGTCGCGGCGGTAGCGGCGGGAGAAGTCGTCGCCGGCCTGGCGGAGGGTCAGGTGGAC CACAGGTGGCACCGGGCTGAGCGCAGGCCCC | 1066 |
| BCL2_chr18: 60985654-60985754 | GCGGCGGCGCCGGGGGCAGCCGGGGTCTGCAGCGGCGAGGTCCTGGCGACCGGGTCCCGGGATGCGGCT GGATGGGGCGTGTGCCCGGGCTGGGAGGAGA | 1067 |
| BCL2_chr18: 60985754-60985854 | AGATGCCCGGTGCGGGGGCGGCCCCCGGGGGCGCGGCGCCCACATCTCCCGCATCCCACTCGTAGCCCCT CTGCGACAGCTTATAATGGATGTACTTCAT | 1068 |
| BCL2_chr18: 60985854-60985954 | CACTATCTCCCGGTTATCGTACCCTGTTCTCCCAGCGTGCGCCATCCTTCCCAGAGGAAAAGCAACGGGG GCCAACGGCACCTCTCGCCCCAGCTCCCAC | 1069 |
| BCL2_chr18: 60985954-60986054 | CCCACGGCCCCCAGAGAAAGAAGAGGAGTTATAATCCAGCTATTTTATTGGATGTGCTTTGCATTCTTGG ACGAGGGGGTGTCTTCAATCACGCGGAACA | 1070 |

-continued

| Name | Sequence | SEQ ID NOs. |
|---|---|---|
| BCL2_chr18: 60986054-60986154 | CTTGATTCTGGTGTTCCCCCTTGGCATGAGATGCAGGAAATTTTTATTCCAATTCCTTTCGGATCTTTATT TCATGAGGCACGTTATTATTAGTAAGTA | 1071 |
| BCL2_chr18: 60986154-60986254 | TTGTTAATATCAGTCTACTTCCTCTGTGATGCTGAAAGGTTAAAGAAAAAACAAACTAATAAGTAAAAAA TCAGGTGCGTTTCCCTGTACACACTGAGTG | 1072 |
| BCL2_chr18: 60986254-60986354 | AAAGCAGGGCATACACACTACAAGTAACACGGCTAAAAAGAATGTATTAAGCTGCCTGGAAATTAAATTT ACTCGAATGCACTTTAAGTAAAAAATCTCA | 1073 |
| BCL2_chr18: 60986354-60986454 | AAGGTTTCCATTGAAAGTTACATTAAACCAATTTCCTGTGCAGAGAACTTACTTGTATTTTTTAAGTACAG CATGATCCTCTGTCAAGTTTCCTTTTTGT | 1074 |
| BCL2_chr18: 60986454-60986554 | AAAACCAAAACAAATGCATAAGGCAACGATCCCATCAATCTTCAGCACTCTCCAGTTATAGCTGATTTGA AACTTCCCAATGAATCAGGAGTCGCGGGGA | 1075 |
| BCL2_chr18: 60986554-60986654 | GAGGGAGTAAAAATTAGGAGGATTTCCAGATCGATTCCCAGACTTCTGCTTCACAGAAATGTCAATCCGC AGGAATCCCAACCGGAGATCTCAAGAGCTC | 1076 |
| BCL2_chr18: 60986654-60986754 | GAGAAAAAAAAAAAGGCAGCGGCGGCGGCAGATGAATTACAATTTTCAGTCCGGTATTCGCAGAAGTCCT GTGATGTTTTCCCCTTCTCGGCAATTTACAC | 1077 |
| BCL2_chr18: 60986844-60986944 | TGAAGGAGCCGGGGACGGAGGCAGGAATCCTCTTCTGATTAAACTCCGAACAGCAAATGCATTTTCCGAA AAGCTGCTGGATAAATGAAGGCAGGACGCG | 1078 |
| BCL2_chr18: 60986944-60987044 | CCTGGCCCGCCGGTGCCGAGCGCTAGAAGCCCGCGCTGTGTGTGGTGCGGCGAGGGGTGGGGAGAAGGA GGTGGTGGGGGAGGGTTTTATTTTTTCCCTC | 1079 |
| BCL2_chr18: 60987044-60987144 | TTTTCCTAAAAAGGATGACTGCTACGAAGTTCTCCCCCCTGGACCCCCTCTTCCGCTGCACCCCACCGGCG CACCCCGCCTCCGGGCTGCGCACCCTTTC | 1080 |
| BCL2_chr18: 60987964-60988064 | GTGTGTGTCTCGCCTGGACCTTTTCTAGCCGTGTATGTGGGAGTGTGTGTGTCGCCTGGACCCTTTCTAGC CGTGTATGAGAGTGTGTACACGCGCCTAC | 1081 |
| BCL2_chr18: 60988064-60988164 | ACACACACACGTTGTGTTACCGGCGCTCGGCCGCCGGGGGAAGACCCAGGCCAATGCCGCCCCCCACCGC CCCCAGCAGTGGGACCTCAGCGCTGCCCTG | 1082 |
| BCL2_chr18: 60988164-60988264 | CTGTGAAGACAGGTGACTCTGCACGTTTTAAGCAATGTCTAGGGACGCCCCGAGCGTGGTGTTTACTTTC AAGTAGCTTCCTAGGTGTCCGCGCACTACA | 1083 |
| BCL2_chr18: 60988264-60988364 | CACGCACGCGCATCCCCGCCCGTGTCCACCTGAACACCTAGTCCGTGGCCCAGGCCATGCAGAACTCAGC GCTCCAGGGAAGGGGTTTATCAAGGGCTTT | 1084 |
| BCL2_chr18: 60988364-60988464 | ACGACAGTTTAAGTCAATGTTTTCCCTCTGTCCCTAACACCTTTTACACTOGTTTAGTGCTACACGATGAG GACTTCCATATAGTAACTTTCAGGCCCAC | 1085 |
| BCL2_chr18: 60988464-60988564 | CGTCCTAACGCTGGGGTGGGTGGGCTCCTAAAGGTCTCCACCTTTGCCTCGTAGCCAATCCTAGTTGGCCG CACTTTCTCAAATGAGGTACATAGATACA | 1086 |

-continued

| Name | Sequence | SEQ ID NOs. |
|---|---|---|
| SIPR2_chr19: 10340823-10340923 | GTGTCTCCATGGAGATGGCAGCAGGACCCGACCCCGTGCTGGCCCGCACTCTCGGCCTCCTTATCTGGTTT AGGAATGCGCGGTATCCACGCTCGCTCGC | 1087 |
| SIPR2_chr19: 10340923-10341023 | GCGGGAGCCACGCCTCCTCTCCCCCCCGCCCCCGAGACCGCCACACGCGCGGGGCCCCCACGTCTCCAAG CGGCACTGGAAGGATTCCTCTCCGTCCCGC | 1088 |
| SIPR2_chr19: 10341023-10341123 | CAGGGGTCCCGCCTCGAGATTCTGGGAAGACTGGGGGTGGGGGACCAGATCGCAGCAGCAGCTGCACCG CGAGTTCCGCGCCTGGCCGTGTCGCCCCACG | 1089 |
| SIPR2_chr19: 10341123-10341223 | AGGGGGACTGTGGGCTCAGCGCGTGGGGCCCGGAGCATCTGACAAGGACAGAGACAGAGGAGGGGGTG GAAATCCCCGGGTGAGTCAACCCGTGCCTGAG | 1090 |
| SIPR2_chr19: 10341223-10341323 | AAGGGGGCGAGTTCCGACGCTCCGCCCGGCTCGGGGCCACGCGAGGTCCGCGCCACGCGCGCCTTCACCC ACGACCCATCCCTGAGCCGGAGTTGAAAGA | 1091 |
| SIPR2_chr19: 10341323-10341423 | GGAGGCGTCTGAGCCACGCAGTCACTTTCTCTTTCCTTACAAAACAAAGCCACGCCCCCCGCCGGGGGAC CGGAGGAGGCAAACAACTTGGGGAAACCGA | 1092 |
| NCOA3_chr20: 46131072-46131172 | CCCACTTTCCCCTTCTGTCCCTAAAGTTTTTTCTTCCTCTTGCCTCCCCCAGCCCTTTTGAAAGCTCCCCGC GTCGTCCTCCTGCTGCCCCGGCTCCTTA | 1093 |
| NCOA3_chr20: 46131172-46131272 | GCAGCTTCTGGGACGCACGGGAGGGAAAAGCCGCGGGGACCCCCCCCACCCCAGCCTCCCAGCCGGGTG AGATTTGGTTGCTGTGTTTCCTCCTCACTTG | 1094 |
| NCOA3_chr20: 46131217-46131317 | CCACCCCAGCCTCCCAGCCGGGTGAGATTTGGTTGCTGTGTTTCCTCCTCACTTGGGCATTTAAAAAATAT TTTAACACGAATTGTCCGCGGAATTTTCA | 1095 |
| IGLV4-69_chr22: 22380472-22380572 | CATGGCCTGGACCCCTCTCCTCCTCCAGCTTCTCACCCTCTGCTCAGGTGACTGCCTGTGGAATGCCAAAG TGATTATTGGGGACACATGGGATGACTTT | 1096 |
| IGLV4-69_chr22: 22380572-22380672 | TCTCTTATATTTTAACATTGTGGGGTOGGTAGTOAACCCAGACTCACCTCTCTGTGCCTGCCTCCTCTGTT CCAGGGTCCTGGGCACAGTCTGCGCTGAC | 1097 |
| IGLV4-69_chr22: 22380672-22380772 | CCAGGAAGCCTCGGTGTCAGGGACCGfGGGACAGAAGGTCACCCTCTCCTGTACTGGAAACAGCAACAAC GTTGGAAGTTATGCTGTGGGCTGGTACCAA | 1098 |
| IGLV4-69_chr22: 22380772-22380872 | CAGATTTCTCACGGTGCTCCCAAAACTGTGATGTTTGGAAATTCTCTGCCCTCAGGGATCCCTGACCGCTT CTCTGGCTCAAAGTCTGGGACCACAGCCT | 1099 |
| IGLV4-69_chr22: 22380872-22380972 | CCCTGACTATCTCGGGCCTCTAGCCTGAGGACGAGGCTGATTATTACTGTTCAACATGGGACTACAGCCTC AGTGCTCACACAGTGCTGCAGGCACATGG | 1100 |
| IGLV4-69_chr22: 22380972-22381072 | GGAACCGAGACAAAAACCTGCCCTTGGCCTGTCCCGAGGCTGATCACTCCATACTTGCCTATGACAAACA AAGAGGGTGCCTGTGGCTGATCGTACAGTT | 1101 |
| IGLV4-60_chr22: 22516707-22516807 | GAAATGTTGTTTGCTCTTGTCCTTCCTTCAGGCCATAATGAGCGTCTCTGTTTTCAGGGTCTCTCTCCCAGC CTGTGCTGACTCAATCATCCTCTGCCTC | 1102 |
| IGLV4-60_chr22: 22516827-22516927 | TCAAGCTCACCTGCACTCTGAGCAGTGGGCACAGTAGCTACATCATCGCATGGCATCAGCAGCAGCCAGG GAAGGCCCCTCGGTACTTGATGAAGCTTGA | 1103 |

-continued

| Name | Sequence | SEQ ID NOs. |
|---|---|---|
| IGLV4-60_chr22: 22516927-22517027 | AGGTAGTGGAAGCTACAACAAGGGGAGCGGAGTTCCTGATCGCTTCTCAGGCTCCAGCTCTGGGGCTGAC CGCTACCTCACCATCTCCAACCTCCAGTTT | 1104 |
| IGLV4-60_chr22: 22517027-22517127 | GAGGATGAGGCTGATTATTACTGTGAGACCTGGGACAGTAACACTCACACAGTGATACAGGCAGATGAG GAAGTGGGACAAAATCCTCAACCTGCTGAGG | 1105 |
| IGLV1-51_chr22: 22677077-22677177 | AAGGTCACCATCTCCTGCTCTGGAAGCAGCTCCAACATTGGGAATAATTATGTATCCTGGTACCAGCAGC TCCCAGGAACAGCCCCCAAACTCCTCATTT | 1106 |
| IGLV1-51_chr22: 22677177-22677277 | ATGACAATAATAAGCGACCCTCAGGGATTCCTGACCGATTCTCTGGCTCCAAGTCTGGCACGTCAGCCAC CCTGGGCATCACCGGACTCCAGACTGGGGA | 1107 |
| IGLV5-48_chr22: 22707517-22707617 | TCAGCCAGACTCACCTGCACCTTGCGCAGTGGCATCAATCTTGGTAGCTACAGGATATTCTGGTACCAGC AGAAGCCAGAGAGCCCTCCCCGGTATCTCC | 1108 |
| IGLV5-48_chr22: 22707617-22707717 | TGAGCTACTACTCAGACTCAAGTAAGCATCAGGGCTCTGGAGTCCCCAGCCGCTTCTCTGGATCCAAAGA TGCTTCGAGCAATGCAGGGATTTTAGTCAT | 1109 |
| IGLV1-47_chr22: 22712077-22712177 | AGAGATCTGGGGGAAGCTCAGCTTCAGCTGTGGTAGAGAAGACAGGATTCAGGACAATCTCCAGCATGG CCGGCTTCCCTCTCCTCCTCACCCTCCTCAC | 1110 |
| IGLV1-47_chr22: 22712177-22712277 | TCACTGTGCAGGTGACAGGATGGGGACCAAGAGAGGGGCCCTGGGAAGCCCATGGGGCCCTGCTTTCTCC TCTTGTCTCCTTTCGTCTCTTGTCAATCAC | 1111 |
| IGLV1-47_chr22: 22712277-22712377 | CATGTCTGTGTCTCTCTCACTTCCAGGGTCCTGGGCCCAGTCTGTGCTGACTCAGCCACCCTCAGCGTCTG GGACCCCCGGGCAGAGGGTCACCATCTCT | 1112 |
| IGLV1-47_chr22: 22712377-22712477 | TGTTCTGGAAGCAGCTCCAACATCGGAAGTAATTATGTATACTGGTACCAGCAGCTCCCAGGAACGGCCC CCAAACTCCTCATCTATAGTAATAATCAGC | 1113 |
| IGLV1-47_chr22: 22712477-22712577 | GGCCCTCAGGGGTCCCTGACCGATTCTCTGGCTCCAAGTCTGGCACCTCAGCCTCCCTGGCCATCAGTGGG CTCCGGTCCGAGGATGAGGCTGATTATTA | 1114 |
| IGLV7-46_chr22: 22723897-22723997 | ATTTGCATAAAGCAGCACACAGCACACCCCCTCCGTGCGGAGAGCTCAATAGGAGATAAAGAGCCATCAG AATCCAGCCCCAGCTCTGGCACCAGGGGTC | 1115 |
| IGLV7-46_chr22: 22723997-22724097 | CCTTCCAATATCAGCACCATGGCCTGGACTCCTCTCTTTCTGTTCCTCCTCACTTGCTGCCCAGGTTAAGA GAGATTTCAAATACCAGCCTTTGGAGGGA | 1116 |
| IGLV7-46_chr22: 22724097-22724197 | TCCCTTTTTCTCCCTTTCTAATTCCTAATATATGTCTGTTTTTTTTGTTTCAGGGTCCAATTCCCAGGCTGTG GTGACTCAGGAGCCCTCACTGACTGTG | 1117 |
| IGLV7-46_chr22: 22724207-22724307 | GGACAGTCACTCTCACCTGTGGCTCCAGCACTGGAGCTGTCACCAGTGGTCATTATCCCTACTGGTTCCAG CAGAAGCCTGGCCAAGCCCCCAGGACACT | 1118 |
| IGLV7-46_chr22: 22724307-22724407 | GATTTATGATACAAGCAACAAACACTCCTGGACACCTGCCCGGTTCTCAGGCTCCCTCCTTGGGGGCAAA GCTGCCCTGACCCTTTTGGGTGCGCAGCCT | 1119 |

-continued

| Name | Sequence | SEQ ID NOs. |
|---|---|---|
| IGLV7-46_chr22: 22724407-22724507 | GAGGATGAGGCTGAGTATTACTGCTTGCTCTCCTATAGTGGTGCTCGGCACAGTGACAGACCCATGAGAG GAACCAAGACATAAACCTCCCTCGGCCCTT | 1120 |
| IGLV5-45_chr22: 22730452-22730552 | GGTCAGCCACCCAGCCTGATTCTGACTCTTCTGGCAAAGATCCCTGAAAAACTTTACCCTGGTTTCTGCCT TAGCACCCATTAATGTCTGTGTTTCCAGG | 1121 |
| IGLV5-45_chr22: 22730552-22730652 | TTCCCTCTCGCAGGCTGTGCTGACTCAGCCGTCTTCCCTCTCTGCATCTCCTGGAGCATCAGCCAGTCTCA CCTGCACCTTGCGCAGTGGCATCAATGTT | 1122 |
| IGLV5-45_chr22: 22730607-22730707 | GCATCAGCCAGTCTCACCTGCACCTTGCGCAGTGGCATCAATGTTGGTACCTACAGGATATACTGGTACC AGCAGAAGCCAGGGAGTCCTCCCCAGTATC | 1123 |
| IGLV5-45_chr22: 22730707-22730807 | TCCTGAGGTACAAATCAGACTCAGATAAGCAGCAGGGCTCTOGAGTCCCCAGCCGCTTCTCTGGATCCAA AGATGCTTCGGCCAATGCAGGGATTTTACT | 1124 |
| IGLV5-45_chr22: 22730887-22730987 | ACAGATGGGGAAGTGGGACAAAAACCTCACCCTGCTCTGGGTCTTGCTCTGTACCAATTTTTAAATTTTAA AATAACTGGCCTAGGCACAAACTATATTT | 1125 |
| IGLV1-44_chr22: 22735417-22735517 | GCCCAGTCTGTGCTGACTCAGCCACCCTCAGCGTCTGGGACCCCCGGGCAGAGGGTCACCATCTCTTGTTC TGGAAGCAGCTCCAACATCGGAAGTAATA | 1126 |
| IGLV1-44_chr22: 22735517-22735617 | CTGTAAACTGGTACCAGCAGCTCCCAGGAACGGCCCCCAAACTCCTCATCTATAGTAATAATCAGCGGCC CTCAGGGGTCCCTGACCGATTCTCTGGCTC | 1127 |
| IGLV1-44_chr22: 22735792-22735892 | TGCTGCTCAGGCCTGGCCTGTGGCTTCTGCTGCTGCAGCTTCCTTCATGGGTCCAGGGGCATCCAGGGCCC TGCCTGAGAGTGGAGGCTCCTCCTCCCCT | 1128 |
| IGLV7-43_chr22: 22749602-22749702 | TCCAGCACTGGAGCAGTCACCAGTGGTTACTATCCAAACTGGTTCCAGCAGAAACCTGGACAAGCACCCA GGGCACTGATTTATAGTACAAGCAACAAAC | 1129 |
| IGLV7-43_chr22: 22749732-22749832 | CCCTCCTTGGGGGCAAAGCTGCCCTGACACTGTCAGGTGTGCAGCCTGAGGACGAGGCTGAGTATTACTG CCTGCTCTACTATGGTGGTGCTCAGCACAG | 1130 |
| IGLV7-43_chr22: 22749832-22749932 | TGACAGACTCATAAGAGGAACCAAGACATAAACCTCCCTCGGCCCTTGTGATGTGGAGATTGTGTGATCA TACACACCAGCTCTCAAGACAGCCTACATG | 1131 |
| IGLV7-43_chr22: 22749857-22749957 | ACATAAACCTCCCTCGGCCCTTGTGATGTGGAGATTGTGTGATCATACACACCAGCTCTCAAGACAGCCTA CATGTGGACCAGCCATAGAAAGGGGAAGG | 1132 |
| IGLV7-43_chr22: 22749942-22750042 | ATAGAAAGGGGAAGGAAAGGGTCTGAATTGATTTCTATCCCTCCTTGTGCCCTGAAGTGGAGGAAATGTG AGAGTGATTTGCAGTAATTGAATGAGACAA | 1133 |
| IGLV7-43_chr22: 22750042-22750142 | AGCAAAAGTTATTTGTTTTATATGAAAAAAAAAAACAGAAACAGCAGGATCAGATCTAAAGGCTGAGTCT AAATGCATTTCCTCCAGACAGAAGCTTCTT | 1134 |
| IGLV7-43_chr22: 22750092-22750192 | CAGATCTAAAGGCTGAGTCTAAATGCATTTCCTCCAGACAGAAGCTTCTTCAAACGATGGGCTTTCTGAG CTAAGAGCAAAGAAAATAAACTCTCCACGG | 1135 |
| IGLV7-43_chr22: 22750192-22750292 | GTATATTATAAAGTCCATTTTATTGAGTTACTTTCAAAGCAATOCATGACTATTATATAAAGTCAGAAAG TATTAAAAATCACCAAGTTCTCTGCTAAG | 1136 |

-continued

| Name | Sequence | SEQ ID NOs. |
|---|---|---|
| IGLV7-43_chr22: 22750292-22750392 | CTACCTTATCCCATGCAATCAAAATAAGTACTTTTCTTCATTTGGATGCATTTTTTATTTCTGTTTTTAATA TTTCCACAATGGTGATTAAACCTGGTGC | 1137 |
| IGLV1-40_chr22: 22758647-22758747 | ACAGGGTCAGGGGAGGGGTCCAGGAAGCCCATGAGGCCCTGCTTTCTCCTTCTCTCTCTAGACCAAGAAT CACCGTGTCTGTGTCTCTCCTGCTTCCACG | 1138 |
| IGLV1-40_chr22: 22758747-22758847 | GTCCTGGGCCCAGTCTGTGTTGACGCAGCCGCCTTCAGTGTCTGCGGCCCCAGGACAGAAGGTCACCATC TCCTGCTCTGGAAGCAGCTCCGACATGGGG | 1139 |
| IGLV1-40_chr22: 22758847-22758947 | AATTATGCGGTATCCTGGTACCAGCAGCTCCCAGGAACAGCCCCCAAACTCCTCATCTATGAAAATAATA AGCGACCCTCAGGGATTCCTGACCGATTCT | 1140 |
| IGLV1-40_chr22: 22758947-22759047 | CTGGCTCCAAGTCTGGCACCTCAGCCACCCTGGGCATCACTGGCCTCTGGCCTGAGGACTAGGCCGATTA TTACTGCTTAGCATGGGATACCAGCCTGAG | 1141 |
| IGLV1-40_chr22: 22759047-22759147 | AGCTTGCACAGTGCTCCAGGCCAATGGGGAACTGAGACAAGAACCCTCTTCCTCCTCCGCCAGGAGGGTG AGTGCCTGCAGCTGCTGCTCACACCTGACC | 1142 |
| IGLV1-40_chr22: 22759147-22759247 | TGTAGCTTCTGCTGCTGTAGCTTCCCCCATGGGCCTCGGGGCATCCAGGGCCTTGCCTAGGAGTGGAGGC TCCACCACTTTTGTCCTCAGAGTCAGGAAC | 1143 |
| IGLV1-40_chr22: 22759247-22759347 | AGGGACCCCAGGAGACAGAATATCCTGCTCCTCAGCTTGGGACACAGGGTCTCTGCACTGAAATCGTGGG CTGAGGTGGCAGGTCCAACTGTGTCTTCAC | 1144 |
| IGLV1-40_chr22: 22759297-22759397 | CTCTGCACTGAAATCGTGGGCTGAGGTGGCAGGTCCAACTGTGTCTTCACAGTCCTTCCTGTGCCTGCCCA TGGTGTGGGGACGGAGTGAGGAAGTGTGG | 1145 |
| IGLV1-40_chr22: 22764167-22764267 | TCCTCACTCTCCTCGCTCACTGCACAGGTGACTGGATACAGGTCCAGGGGAGGGGCCCTGGGAAGCCTAT GGATTCTTGCTTTCTCCTGTTGTCTCTAGA | 1146 |
| IGLV1-40_chr22: 22764267-22764367 | AGCCGAATAATGATGCCTGTGTCTCTCCCACTTCCAGGGTCCTGGGCCCAGTCTGTGCTGACGCAGCCGCC CTCAGTGTCTGGGGCCCCAGGGCAGAGGG | 1147 |
| IGLV1-40_chr22: 22764367-22764467 | TCACCATCTCCTGCACTGGGAGCAGCTCCAACATCGGGGCAGGTTATGATGTACACTGGTACCAGCAGCT TCCAGGAACAGCCCCCAAACTCCTCATCTA | 1148 |
| IGLV1-40_chr22: 22764552-22764652 | CTCCAGGCTGAGGATGAGGCTGATTATTACTGCCAGTCCTATGACAGCAGCCTGAGTGGTTCCACAGTGC TCCAGGCCCGGGGGGAACTGAGACAAGAAC | 1149 |
| IGLV2-23_chr22: 23040452-23040552 | GCTCCTCACTCTCCTCACTCAGGACACAGGTGACGCCTCCAGGGAAGGGGTCTTGGGGACCTCTGGGCTG ATCCTTGGTCTCCTGCTCCTCAGGCTCACC | 1150 |
| TGLV2-23_chr22: 23040592-23040692 | TTCCAGGGTCCTGGGCCCAGTCTGCCCTGACTCAGCCTGCCTCCGTGTCTGGGTCTCCTGGACAGTCGATC ACCATCTCCTGCACTGGAACCAGCAGTGA | 1151 |
| IGLV2-23_chr22: 23040692-23040792 | TGTTGGGAGTTATAACCTTGTCTCCTGGTACCAACAGCACCCAGGCAAAGCCCCCAAACTCATGATTTATG AGGGCAGTAAGCGGCCCTCAGGGGTTTCT | 1152 |

-continued

| Name | Sequence | SEQ ID NOs. |
|---|---|---|
| IGLV2-23_chr22: 23040792-23040892 | AATCGCTTCTCTGGCTCCAAGTCTGGCAACACGGCCTCCCTGACAATCTCTGGGCTCCAGGCTGAGGACG AGGCTGATTATTACTGCTGCTCATATGCAG | 1153 |
| IGLV2-23_chr22: 23040852-23040952 | GCTGAGGACGAGGCTGATTATTACTGCTGCTCATATGCAGGTAGTAGCACTTTCCACAGTGGTCCAAGTT CATGGGGAACTGAGACCAAAACCTGCCCAG | 1154 |
| IGLV2-23_chr22: 23040952-23041052 | GGCCTTCAGACTTCCTCCTTGCTCTOAAGATGCTTCCTCACCGGGTGCAAGAGGCTTGCTGCAGCGCGGCC TTGAGAATTCTTCTCTCTCAGCTCCTTCC | 1155 |
| IGLV2-23_chr22: 23041052-23041152 | CTTTCCACCATGAATTCCAACAGGAAACCTGCCCTGTGGTTTCCCATCCAGGACAGGGACAGCTTCCTGAT GCTTGTGTGCTGTGGTCCCTGAATGTGCA | 1156 |
| IGLV2-23_chr22: 23041152-23041252 | ACTCTTCCCAGCTCTTCAAATGCAGGGACAGTGACAAGGAGCTGCCTGATTGGTGCAGTCACTGCTTTTTT CAGGGATGTCTTCACCCTACATGTATCAT | 1157 |
| IGLV2-23_chr22: 23041252-23041352 | CATCCCCTACACTGTGGGTAGAATTTTAGCAACTACATTCTAATOGTTATCGCCACAACTTTGATCTTAGA AATAACAGTGCAGTGAACATCCCTATGCA | 1158 |
| IGLV2-23_chr22: 23041352-23041452 | GGCTCCTTTGAGTTCCTGTGTGAATACGACCATAGGATTCATTTCTAAAAGTGAAATTGCGGGTCAGAAA GATGTGTGTTTGTGATTTTCACCCAATGTT | 1159 |
| IGLV3-21_chr22: 23055497-23055597 | ACCAGCAGAAGCCAGGCCAGGCCCCTGTGCTGGTCGTCTATGATGATAGCGACCGGCCCTCAGGGATCCC TGAGCGATTCTCTGGCTCCAACTCTGGGAA | 1160 |
| IGLV3-21_chr22: 23055727-23055827 | CCCAGCCTCGGTCACCCTCTTGCTCCAGCCCCGGGAAGCCTGTTGATAAAGCCATGAGTGAATCTGGCCC AGTTCACCTGGATCTGAGCCTTTCAGGTTG | 1161 |
| IGLV3-21_chr22: 23055827-23055927 | CCCTTCCCTCCAGCCCCCTCCAGGAGTCTCTACAGAAGATACATCAGGCATAAATATGGCCTGGAAGGGC CAGAATCATCTGGTGACTTGGGGCTGTTGT | 1162 |
| IGLV2-14_chr22: 23101392-23101492 | GGTCCTGGGCCCAGTCTGCCCTGACTCAGCCTGCCTCCGTGTCTGGGTCTCCTGGACAGTCGATCACCATC TCCTGCACTGGAACCAGCAGTGACGTTGG | 1163 |
| IGLV2-14_chr22: 23101532-23101632 | AAAGCCCCCAAACTCATGATTTATGAGGTCAGTAATCGGCCCTCAGGGGTTTCTAATCGCTTCTCTGGCTC CAAGTCTGGCAACACGGCCTCCCTGACCA | 1164 |
| IGLV3-10_chr22: 23154347-23154447 | AGGCTCAGTGCCCATAGACCCCAAGTTGGCCCTGCCCTGAACCCTGTGCAAAGCCCAGACACAGTCTTAG GGTAGGACCCCTGGGAATGGGCTCTTGATC | 1165 |
| IGLV3-10_chr22: 23154447-23154547 | TTCAAGCCCCCTCTCCTGTTTTCCTTGCAGTCTCTGAGGCCTCCTATGAGCTGACACAGCCACCCTCGGTG TCAGTGTCCCCAGGACAAACGGCCAGGAT | 1166 |
| IGLV3-10_chr22: 23154597-23154697 | AGAAGTCAGGCCAGGCCCCTGTGCTGGTCATCTATGAGGACAGCAAACGACCCTCCGGGATCCCTGAGAG ATTCTCTGGCTCCAGCTCAGGGACAATGGC | 1167 |
| IGLV3-10_chr22: 23154697-23154797 | CACCTTGACTATCAGTGGGGCCCAGGTGGAGGATGAAGCTGACTACTACTGTTACTCAACAGACAGCAGT GGTAATCATAGCACAGTGACACTGGCAGAT | 1168 |
| IGLV3-10_chr22: 23154797-23154897 | GGGGAAGTGAGACACAAACCCCTTCTTCATCTATTTTACCCTCTCCCTCCAGCCCCAGGACCGCTGTGGAC CAACCCATAAGCAGGTCTGGCAGAATTCA | 1169 |

-continued

| Name | Sequence | SEQ ID NOs. |
| --- | --- | --- |
| IGLV2-8_chr22: 23165422-23165522 | AGGCTCACCTGGGCCCAGCACTGACTCACTAGACTGTGTTTCTCCCTTTCCAGGGTCCTGGGCCCAGTCTG CCCTGACTCAGCCTCCCTCCGCGTCCGGG | 1170 |
| IGLV2-8_chr22: 23165542-23165642 | CATCTCCTGCACTGGAACCAGCAGTGACGTTGGTGGTTATAACTATGTCTCCTGGTACCAACAGCACCCA GGCAAAGCCCCCAAACTCATGATTTATGAG | 1171 |
| IGLV2-8_chr22: 23165642-23165742 | GTCAGTAAGCGGCCCTCAGGGGTCCCTGATCGCTTCTCTGGCTCCAAGTCTGGCAACACGGCCTCCCTGAC CGTCTCTGGGCTCCAGGCTGAGGATGAGG | 1172 |
| IGLV2-8_chr22: 23165727-23165827 | AGGCTGAGGATGAGGCTGATTATTACTGCAGCTCATATGCAGGCAGCAACAATTTCCACAGTGTTTTAAG TCAATGAGGAAGTAAGATCAAAACCTGCCC | 1173 |
| IGLV4-3_chr22: 23192412-23192512 | TCAGGCTCAGAACCCATAGGATCCTGAGCTGGGCCTGCCCAAACATGAGTTCATCCCAGGCACAACCTCA GGGTGGGACCCCCTGGGAACAGATTCATCA | 1174 |
| IGLV4-3_chr22: 23192512-23192612 | TTTACAAGCCTCCTCTCCTGTCCTCTCTTGCAAGCTCCTATGAGCTTACACAGCCACCCTCAGTGTCAGTG TCACCAGGACAGGCAGCCATGATCACCTG | 1175 |
| IGLV4-3_chr22: 23192612-23192712 | CTCTTGAGATAACCTCAAAGATGAGTATGTTTACTGGTTCTGGCAGAAGCCAGACCAGGCCCATACTGGT GATATATGAAGGCAGCAAGCGGCCCTCAGG | 1176 |
| IGLV4-3_chr22: 23192712-23192812 | AATTTCTGATTTTCTGAGTCCAGCTCAGGGAACATGGCCACCCTGACCATCAGCAGGGCTCAGACTGAGG ACGAGGCTGACTATTACTGTCACAGGTACA | 1177 |
| IGLV4-3_chr22: 23192812-23192912 | ATAGAAACAGTGATGAGCCCACAGTGACACAGGCAGATTAGGAAGTGAGACACAAACCCCTTCCCAATCT GTGTCACCCTCTTTCTCCAGCCCCAGGATG | 1178 |
| IGLV4-3_chr22: 23197917-23198017 | GGGATGAGAAGGGACCAGGGGCCTGGGATTGAGCTGTGAAGGGAACCAAAAGGCAGGAGGGACAGGGC AGGGGCTGTCAGCTATGACTCAGGGGAGGTTC | 1179 |
| IGLV4-3_chr22: 23198017-23198117 | CTGGGCCTCAGGATCCTCCCTCTGAGGCCACCAGGGGGCGGGGGTGGCACATGCCTGGACCTGGGAGGTC CCTGCTGGGCTTCACCCTGGGTGGGTCCTA | 1180 |
| IGLV4-3_chr22: 23198067-23198167 | ATGCCTGGACCTGGGAGGTCCCTGCTGGGCTTCACCCTGGGTGGGTCCTAGGAGCTCCTTCCTCCTAAGTC CCCCTAAAGAGACAGAGGCATTCTGGGGT | 1181 |
| IGLV4-3_chr22: 23198167-23198267 | CCTAAATCTGTCATGCCCCCATAAATGCATTTCTACGAGGGCCAATAAATGAACTCCAGGTTTATCCAAGC AGCAGCTTCAGGCGTCTGCAGACACAGAG | 1182 |
| IGLV4-3_chr22: 23198267-23198367 | CGGGGAGGAATTAGCCAACCTGAGGCACCCTAGAAGGGCTGAAGGGGGCTGAAGGGGACTGAAGGGTCC CTGTGGGGCCTGTGGTCCTGGGGAGGGGAGA | 1183 |
| IGLV4-3_chr22: 23198367-23198467 | GCTGGGGTGTCTCCCAGCCACTCTGGGCCCTGTCCTGACACTTCTCCCACAAAGAAGGGAAGGGAAATCC TGGGACCCCACAGCCAGGACCAACCGTGAA | 1184 |
| IGLV4-3_chr22: 23198467-23198567 | CCACAGGACAGGAAGGACAGGGACCCCCAAGGCTGGCTCCATTTCCCAGGCACTGTCATGGGCTGAGTCT CAGGAAATCCAAGTCAAGGAGTTTCAATCC | 1185 |

-continued

| Name | Sequence | SEQ ID NOs. |
|---|---|---|
| IGLV4-3_chr22: 23198587-23198687 | CCAAGGAAACAGAAGTCTACGGGCCCAGGCCCAGGTGAGGGTGGGGTAAGAAGAGGAGCTTAGGATGCA GATTTGCATGGAGGCCCCGCCCTCCTCTGAG | 1186 |
| IGLV4-3_chr22: 23198687-23198787 | GCATCAGGGTAAGACAAGGCTGGGGGCAGGCCCAGTGCTGGGGTCTCAGGAGGCAGCGCTCTGGGGACG TCTCCACCATGGCCTGGGCTCTGCTCCTCCT | 1187 |
| IGLV4-3_chr22: 23198797-23198897 | CTCAGGGCACAGGTGACGCCTCCAGGGAAGGGGCCTCGGGGACCCTTGGGCTGATCCTTGGTCTCCTGCT CCTCAGGCTCACCTGGGCCCAGCACTGACT | 1188 |
| IGLV4-3_chr22: 23199022-23199122 | TTGGGAGTTATGACTATGTCTCCTGGTACCAACAGCACCCAGGCACAGTCCCCAAACCCATGATCTACAA TGTCAATACTCAGCCCTCAGGGGTCCCTGA | 1189 |
| IGLV4-3_chr22: 23199122-23199222 | TCGTTTCTCTGGCTCCAAGTCTGGCAATACGGCCTCCATGACCATCTCTGGACTCCAGGCTGAGGACGAG GCTGATTATTAGTGCTGCTCATATACAAGC | 1190 |
| IGLV4-3_chr22: 23199182-23199282 | TGAGGACGAGGCTGATTATTAGTGCTGCTCATATACAAGCAGTGCCACTTAACCACAGTGGTCCAAGTTC TTGGGGAACTGAGACGAAAACCTGCCCTGG | 1191 |
| IGLV4-3_chr22: 23199277-23199377 | CCTGGGCTCTCAGGCTCCCTTTTTGCTCTGAAGATGTTTCCTCACCCAGTGCAACGGGCTTCCTGAAGCAC AGCCTTGAGAATTCTTCTCCCTCAGCAAC | 1192 |
| IGLVr-3_chr22: 23199377-23199477 | TCTCTTTTCCCACCATGAAATCCAAAGGAAACCTGCTCTGTGGTTTCTCATCCAGGACAGGGACAGCTTCC TTTTGCTTGTGTGTTGTGGTCCCTGAGTG | 1193 |
| IGLV4-3_chr22: 23199477-23199577 | GGTGCAACTCTTCCTAGCTTTTAAATTATGGGAGGGTGACAATGAGCTCCCTGACTGGTGCAGTCCCTGC TGTTTTCAGGAACATCCTCATCCTAAATG | 1194 |
| IGLV4-3_chr22: 23199577-23199677 | CATCTGAATCTCCCACTGTGTGCAGACCAATCTGGACAGATGTTATTAGGGGGAGTTTCCAGAAGCCACA TCTTACTCAACTCTGTATCCACCACACTCT | 1195 |
| IGLV3-1_chr22: 23222927-23223027 | TGCCTCAGCCATGGCATGGATCCCTCTCTTCCTCGGCGTCCTTGCTTACTGCACAGGTGCTGCCCCTAGGG TCCTAGCCACTGGTCCAGTCCCAGGGCTC | 1196 |
| IGLV3-1_chr22: 23223027-23223127 | TGGGTCCAGCCTGGCCCTGACTCTGAGCTCAGCAGGGCCCCCGCCTGTGGTGGGCAGGATGCTCATGACC CTGCTGCAGGTGGATGGGCTCGGCGGGGCT | 1197 |
| IGLV3-1_chr22: 23223077-23223177 | TGGGCAGGATGCTCATGACCCTGCTGCAGGTGGATGGGCTCGGCGGGGCTGAAATCCCCCCACACAGTGC TCATGTGCTCACACTGCCTTAGGGCTCTTT | 1198 |
| IGLV3-1_chr22: 23223177-23223277 | CATCCCTGGATCTGTGTCCAGGCCAGGCACGTGGGAAGATTTACTTGGAGTTCAGCTCCTCAGTTTCAAGC CTTTTCTCTCCCGTTTTCTCTCCTGTAGG | 1199 |
| IGLV3-1_chr22: 23223277-23223377 | ATCCGTGGCCTCCTATGAGCTGACTCAGCCACCCTCAGTGTCCGTGTCCCCAGGACAGACAGCCAGCATC ACCTGCTCTGGAGATAAATTGGGGGATAAA | 1200 |
| IGLV3-1_chr22: 23223327-23223427 | CAGGACAGACAGCCAGCATCACCTGCTCTGGAGATAAATTGGGGGATAAATATGCTTGCTGGTATCAGCA GAAGCCAGGCCAGTCCCCTGTGCTGGTCAT | 1201 |
| IGLV3-1_chr22: 23223427-23223527 | CTATCAAGATAGCAAGCGGCCCTCAGGGATCCCTGAGCGATTCTCTGGCTCCAACTCTGGGAACACAGCC ACTCTGACCATCAGCGGGACCCAGGCTATG | 1202 |

-continued

| Name | Sequence | SEQ ID NOs. |
|---|---|---|
| IGLV3-1_chr22: 23223527-23223627 | GATGAGGCTGACTATTACTGTCAGGCGTGGGACAGCAGCACTGCACACAGTGACACAGGCAGATGCGGA AGTGAGACAGAAACCAGCCACCTCGGCCTGG | 1203 |
| IGLV3-1_chr22: 23223627-23223727 | CTCACAAGACCCTTCCCTCTCTCCTGCCCTGTCACACTGAGCAGGAGGGAGCCTTCCATGTGGAATGGAA GTTTCCAGTCCTATCCCTGCCCTTATGTTC | 1204 |
| IGLV3-1_chr22: 23223727-23223827 | CTGAGAGACGGGAGCAAGTTCCTGCCCACCTCTAGGCTCAGCTTATCCCAGAATAAACTGAGCTAGTCAT TTTGATGATCAAATGCCAGCTCCCAAAAGA | 1205 |
| IGLV3-1_chr22: 23223827-23223927 | CCCCAGAAACCCTGATATCTAAGTAGCACCGACTCTATTAGTATCAAGGGAGACTAGCCCTAGGGTGGAA TCATTTTAGTGTCTCAGAAGGCACAGGGCA | 1206 |
| IGLV3-1_chr22: 23223927-23224027 | ATGGAAAGTGTTTATGAGGTTTCAGGATATGCACGTGAGCAGTTAAAGGCAGGTCTTACAAGGAAGGAA CCTACTAGAATTGGGGCCCATCTGTGACATC | 1207 |
| IGLL5_chr22: 23227062-23227162 | ACATCCCTCTGCTTTOGGAGAGAAGGGCCAGGGCGGGACCCAGAGAGCTCTGCAGAGGCACCACAGACC CTCAGCAGGGGGTCTGCCAAACAGGACAGCT | 1208 |
| IGLL5_chr22: 23227162-23227262 | GGACTTGGCTGCTTCTGCCCAGGCCTGGATCCAGCCCTTGCACATCTCAGGGCAGGGGATAGGCCTGGGT GGCCAGAGCTGCAGCTGCACCTGCTGGGGA | 1209 |
| IGLL5_chr22: 23227262-23227362 | GGCCTAGTCCAGTCCTCCAGGGTCCCCAGACAGACTCGGATTTCCGACTGCAGCCACCATGGAAGGATGT GGTCTGCGGTGACGATGTCTATCCAGAGGC | 1210 |
| IGLL5_chr22: 23227567-23227667 | CCGAATATCCAAGGAGCCCAAGATCAGAGGCAGGAATAGGCCAAGCTCCCCAGTGGAGAAGCTGTGCTG GACCAGGGGTTTCCCAGGGCCCTCCCTTGTG | 1211 |
| IGLL5_chr22: 23227667-23227767 | CCCTGAATGATGTCTGTTAGGGCACCTACACCCTGTTACTGCTCAGTGCCTTGCCTATTTTGAAGGACAGG GATGTGTGGTGATTATTTGTATAATCCAG | 1212 |
| IGLL5_chr22: 23227767-23227867 | CCCCCAGCACCTGGTCCTCAAAAGTTACCCAAGCAATGTGTATAAAGATCCAGCCTGGAGATCTTTGAAA ACCGATTCGATGAGTCGAACCATTAAGTCA | 1213 |
| IGLL5_chr22: 23227867-23227967 | TGATCACCATCCTCAACTTCATCTCTTTCTTCCTCCTCCTCCTCATTATCATCACCTTCAAGAACTGTTAAG AGTCTGAGACTTCATCCTATTTGCAGAC | 1214 |
| IGLL5_chr22: 23227897-23227997 | TCCTCCTCCTCCTCATTATCATCACCTTCAAGAACTGTTAAGAGTCTGAGACTTCATCCTATTTGCAGACTA AAAAGTAAGCCTGCCACAGTGCCATGGA | 1215 |
| IGLL5_chr22: 23227997-23228097 | TGCTGGCAGAAGATACAAGACTCCTGGGTCAGAGACAACGAATAATCTGTTTTTCACAGCAATAGCAGTT GCCAAGGTATCAGCATTGTCTTGCACCAGT | 1216 |
| IGLL5_chr22: 23228097-23228197 | TCCACAAGGTGATGCAAAGAGGGCCAGGTGACATCTGCATGCCAGAGCTCAGGGATCCCAAATATTTCAT ACTTGACAGTAAGCATATATCTGTGTTTTG | 1217 |
| IGLL5_chr22: 23228197-23228297 | CTCCAAAGAGAGGCATTCTCTGTACCTTCCGAGGTTGTTCACTCCACAAACACTCTTGAAAAGATAATCCA CAATCAGTGCCTTTGCCCGAGAGACATGC | 1218 |

-continued

| Name | Sequence | SEQ ID NOs. |
|---|---|---|
| IGLL5_chr22: 23228297-23228397 | AGAAATGCAGAGATCCATAGTAGACCACTGTCTCCCAACAACCATCAACTTTATCAATGAAATGAAGTCT CAGGCTATTTGTCTGTTACCATAGCCCACA | 1219 |
| IGLL5_chr22: 23228397-23228497 | AAAATGTCTGGCTTGATTGTCACCAAATGTATCAAGGAAGTTAAGGAGTATCTGACACAAAATGTGAACC AAGCAATTCTCAAAGGAGCCTCCCAGGAAA | 1220 |
| IGLL5_chr22: 23228497-23228597 | TTCACTTTAGGAAGTCCTAGGAGGCTCCTCTGAGAGTTGCTAAAACAAAACATTGAGAGTCCTAGAGGGC TGCAGATCTGAACTTGAGCAGATATTTTTA | 1221 |
| IGLL5_chr22: 23228597-23228697 | AAGATTTTGTGGCAGAAAAAGAAACTGGAAAGCAAGAGGGCAGACCCTCATTGCAGTTCTGTAATGTAA GGGGGCAGAGCAGGGGCCTTTCTCACCAGAG | 1222 |
| IGLL5_chr22: 23229332-23229432 | GATATTGGACCCTOCATTCATCTTOTCTGGATGGTAATTTTCTCACCTGTAAAACAGAGACACTGGCCCCA AGGACACCCCACAAGTAGTTGTGAATCCC | 1223 |
| IGLL5_chr22: 23229432-23229532 | AAAGTAAGAGAAGAACAAAAAAAGAACCAGAATTTATTCAACACCCACTGAGTGCTTAGCAAACACATG GTTTCTTTAACTCTCATAAGCTTCATGCTGC | 1224 |
| IGLL5_chr22: 23229532-23229632 | AGAGGAACTCTCCCCATTTTACAGATAAGGAAACTGAGGCCCAGAGGTAACCTAGGTCTAGATAGACTCC ACATTTATGACTTCACCACTCTTCCTTGCC | 1225 |
| IGLL5_chr22: 23229562-23229662 | AAACTGAGGCCCAGAGGTAACCTAGGTCTAGATAGACTCCACATTTATGACTTCACCACTCTTCCTTGCCT GAAGGATATAGAATCACTCCCTGCAGGGC | 1226 |
| IGLL5_chr22: 23229662-23229762 | TCTTGCCTGACTCAGGAAAGGGCCACAGGATAGCCAGCCAGGCTTAACCAACCCAGCCAAGAAAGGGCT GGTCCCAACTGGCTGGAGTGCAGTGTACAGG | 1227 |
| IGLL5_chr22: 23230012-23230112 | GTTGGTAGATGCCCCTCTGGGAGAGATCCCCAGGGGTGACAGCCATGGACCCTGGAAGGGCCTGGGCTA GGGACAGGGACCAGAGCCAGTCCAGGGAGAG | 1228 |
| IGLL5_chr22: 23230112-23230212 | GACAGAGCCAATGGACTGGGGTGTACTGTAACAGCCCTGCTGGCGAGAGGGACCAGGGCACCGTCCTCC AGGGAGCCCATGCTGCAAGTCGGGCCAGAGG | 1229 |
| IGLL5_chr22: 23230212-23230312 | TGCCCCTGAACCTGAAGGCCAATGAGACCCAAGACAGGCCAAGTGGGTTGTGAGACCCCTGAGGAGCTG GGCCCTGGTCCCAGGCAGCGCTGGCCCCTOC | 1230 |
| IGLL5_chr22: 23230312-23230412 | TGCTGCTGGGTCTGGCCATGGTCGCCCATGGCCTGCTGCGCCCAATGGTTGCACCGCAAAGCGGGGACCC AGACCCTGGAGCCTCAGTTGGAAGCAGCCG | 1231 |
| IGLL5_chr22: 23230412-23230512 | ATCCAGCCTGCGGAGCCTGTGGGGCAGGTAAGGGGCAAGAGATTCCAGGGGATGTGGGGGTCCTGCAGC AGAGCTGGGAAAGGGTGACCAAGGGGAGACA | 1232 |
| IGLL5_chr22: 23230512-23230612 | AGCCAGAGGAGTGAGGAGGAAGGTTAACCCCTAAGAGGGGCCTGGGCTGACACTGGCTTTAGTAATGGG TTGATATTTTGTCCATCACAGATTTGTTTGA | 1233 |
| IGLL5_chr22: 23230612-23230712 | ATTACTGTTTTTAATATCATATTACGATATTATTTTTCTTGATTTCTGAGTTTTCTGGCGCCACTTAAATTT TCACCAGGGTCAGTGCCTCAATCACCTA | 1234 |
| IGLL5_chr22: 23230712-23230812 | GTCCTAGTCCTCTGGGTAGGGAAGGAACAGAGGCAGGGACAGGACATCCACAGGGGGTGGTGGCCACTG TCCCCACAGGGTGCCCAGGCCTGTTCCTCCC | 1235 |

-continued

| Name | Sequence | SEQ ID NOs. |
|---|---|---|
| IGLL5_chr22: 23230812-23230912 | CCTCCTCCTCTCTGCCCATGTGCCTCCTGCCCAGTGAGGGCAGGGGCCACTCCCTGGAGAAGGCAGCAAG GGCTTGGTTTGGTCTCCCCCAAGGCTGTCT | 1236 |
| IGLL5_chr22: 23230912-23231012 | GTTCACCAACTTGCACATAAATGCTTACTGGGGCCAGGCTCAAGGACACAGGGAGGGTGGGATGAACCG AGGGGAGCTGTCCAGTCATTGGAACAGGCCC | 1237 |
| IGLL5_chr22: 23231012-23231112 | ACGGCCCATGTTTGGAGCAATAAAGGGAGAGGGGATCTCCCTCTGGGATGATGCCCAGGCTGGTCTCACA GATCGAGGGGCACTGGCTGGTGATGGGTGC | 1238 |
| IGLL5_chr22: 23231072-23231172 | TGGTCTCACAGATCGAGGGGCACTGGCTGGTGATGGGTGCCCCCAAAAGACAGAGCAGCGTCAGAGGAG AGGAGAGCACAGGATGAGGCTGGGAGCTCCT | 1239 |
| IGLL5_chr22: 23231172-23231272 | GGGTGACTGGGAAGGGGAGGCAAGAAGACCATAGGGTCCGTGCACCATTCCCAGTCCAGGACGAGTCCT TGGATGGATTTAGGTAGATTGATTATCAGAG | 1240 |
| IGLL5_chr22: 23231272-23231372 | TCAGATTTGTGTTTTTGGAAAAATCAGCACCGGATTGGAGGCTGATGCGACGCCCGATTAGAGGAGGGAG GAGAGGGGGTGATGGCCAAGTCCAGGGTAG | 1241 |
| IGLL5_chr22: 23231372-23231472 | GTGGGGATCCTGGAGGAAGCCGTGCCTTGGGGATGGGGAGGACACTCAGATTCAGAGCACCCAGGGGCC CAGTTTCCTATGAAATGGGAGCATGAAGTTG | 1242 |
| IGLL5_chr22: 23231472-23231572 | AAGTGAGGGCTGAGCAGAGGGGGAGCAGACACGCTCGGGGACTGTCTATGGGCATTAAAAATGTATAACC ATTTTAGCAACAGGCGGCGAGTCAAAAAACA | 1243 |
| IGLL5_chr22: 23231572-23231672 | AAGTGTGTTTATCTAAACTGGGCAATTCCACTTCTAGGAATTTATCCTAAGGGTTGGTTGGGGGAATAATC AAAGCTGTAACCAAATCTTTATAACAAGG | 1244 |
| IGLL5_chr22: 23231672-23231772 | GTGGTTAGCTCAGCATTATTAGTGATGGGAGAAAACTGGAAAAAATCCAAATATCTACCAGAAAGGGTGT GAAAAAACACAATTGTATTTGGGGGACTGT | 1245 |
| IGLL5_chr22: 23231927-23232027 | TGGCTAATTTTGATTAGGATTATTATTAGTTTAGAGACAGAGCCTCGCTATATTGCTCAGGCCTGTCTCAA ATTCCTAAGCTCAAGCAATCTTTCTGCCT | 1246 |
| IGLL5_chr22: 23232062-23232162 | ACTGCACCTGACCCAACTGTGTTTTTAAAGTATATATGCATTTTCAAAAACCTGTCAGAAAATATAGAAAA ATGTCAATGGTGTGTCTGGCTGGCTGATG | 1247 |
| IGLL5_chr22: 23232162-23232262 | GGATTTCACCTAATTTTAATGTGGCTTTATAATTTTCTGGTTTTGTGAAGTTGTTCACAAAAAGAGACATT TCTTCTAATATAATTTTTAATACAACAGT | 1248 |
| IGLL5_chr22: 23232262-23232362 | AATGTACTCATGTGCATTACTCTTTTTGTAATGAGTATATTACAAAATGTAATGACTTTTGTACATTACTCT TTTTTCTTGCCAAAAAAAAAAAAGATTA | 1249 |
| IGLL5_chr22: 23232362-23232462 | AGCAGAGAAGTATATAAAGTAAAAGCAAGTGCTTCTGCTTACCATCTCTCACCTCTTCCCAGAGATAGCC ACTGTCAGGTTGGTCAATATACTTCCAGAA | 1250 |
| IGLL5_chr22: 23232462-23232562 | CTTTCCTGTGTGTGTGTGTGTCCCTGAAAACACACACACACACACACACACACACACACAGTTGGTGC TGGGATTTTATTTTGCAAAAGTAAGAGCC | 1251 |

-continued

| Name | Sequence | SEQ ID NOs. |
|---|---|---|
| IGLL5_chr22: 23232517-23232617 | CACACACAGTTGGTGCTGGGATTTTATTTTGCAAAAGTAAGAGCCATATTCTGCATATTACCAACTTTTAA TCTATTATTGACACTTTCTGTATCAGTCC | 1252 |
| IGLL5_chr22: 23232617-23232717 | ATATGGATTAACCACATTCATTGCTTATAAACTTTGTTTTATAAGCAAAGTTTAGATGAGCCAGAATTTAT TTCCACTAAAAAATCTAAATGACAAATGA | 1253 |
| IGLL5_chr22: 23232717-23232817 | TGCTGCAGTGGAAATTTGTGTGTGTGTGTGTGTGTGTGTGTGTGTGTGTGTGTGTGTGTGTGTATGTGTAC AAAGTGCACTTATATATCTCCCCAGGATA | 1254 |
| IGLJ1_chr22: 23234612-23234712 | TGACCTGGGTGTTTTTCTTTTTCTCTGTAGGATGTTAATAGTATCTTGTGTCATGCTAGGATGTCTAGGAC AGAGGGCAATACAATGAGGGGAAGGCATT | 1255 |
| IGLJ1_chr22: 23234712-23234812 | CTGCGATGTCCCCAGGCCTCTGGCTTGAAGAGTAACTTGCTGAAGTGAGGACTCTGTGGAGGAGCAAGTT ATACAGAAAGAAGTTTAGTTGTGATCTGTT | 1256 |
| IGLJI_chr22: 23234812-23234912 | GAGTTGGAGGTGTCTACAGGGCATCCAAGCAGACATAGGTTGAGGAGGCAGAATATATGTGAATCTGGA GCCAAGAAGAGAGGTAAGGGCTGGAAATAGG | 1257 |
| IGLJ1_chr22: 23234912-23235032 | GATCTAAGACCCCTGGACAGTTGTGAGTGTGCACAATGAGGGTCAGATGCAGAGAAAATTAGGAGACTA CAGAGAGCAGAACCCAGGGTGGGGATCTGGG | 1258 |
| IGLJ1_chr22: 23235012-23235112 | AGTCAGCAGTTGGGCATGGGCCTGGTAGAAAGGGAAGCCAAGGAGGAGGAGAGGGGGCAGTCTCAGAC ACCAAGGAGGGGAGAGTGACTAGAAAGAAAAC | 1259 |
| IGLJ1_chr22: 23235112-23235212 | CTTCTTGCAGAGACATAGGGGATGGGGAAGAACTGCAGACTGAACTGGGGCAAAGGACTGTTGGCCTTA ACCAGAGAGATTTGAGGGAGAGATGAGGCTG | 1260 |
| IGLJ1_chr22: 23235212-23235312 | AGAGCCAGGGGATCCTCCCATGTCCCAGCATAAAAACAGTACCTGACACAGATGGGTGCTTGGGAGCTGT TGTCGGATGAATGAGTGGACAGATGCATGG | 1261 |
| IGLJ1_chr22: 23235332-23235412 | ATGGACGGATGGATGGAAGGATGATAGATTGATGGACAAACAGATGAACAGATGAATAGCTGGATGGAC AACTGGATGGATGGGTAGACAGAATGATCTC | 1262 |
| IGLJ1_chr22: 23235412-23235512 | AGAGATCAGAAAAAGCTTCATGCACTAAGTGGGACTGAACCGCGTCTCCATGGGTAGAAAGCAGAGGAA TCTCCACTTGAGTCAGGAATGACCCAGTGCT | 1263 |
| IGLJ1_chr22: 23235512-23235612 | CTCAATCCAGGGAGAAAGCCAGCCTGGCTTCACTGGGGACACTTGTGTGGGGGACTCAGAGGCCCTTTAA ATGAGGCCAGACGAGGTTGGACAGGTCCAA | 1264 |
| IGLJI_chr22: 23235612-23235712 | GCCAACTCAGCACTCCTCTGCCACACTGCACAGGAGGGGATGTGTCACTCAGGGAGTTGCTGGGACCTAT GGGTCCCAGTGTTGTCATCAGCACCGACAG | 1265 |
| IGLJ1_chr22: 23235712-23235832 | CCTCAGAGAGGAAAGACACACACTGGGGTAACTCCAAGGCTGTGTGTGGCACTTGCCTTGGACAGCAGAC AGGCACAGGGACACCTCTAGGGGGCTGGCC | 1266 |
| IGLJ1_chr22: 23235812-23235912 | ACCCCCCTGCCTCATGTCTAGGTCCCAGCCCCGCCCACTGCAACCCTGTGCCCGTCATGCCCAGCAGGCTC CTGCTCCAGCCCAGCCCCCAGAGAGCAGA | 1267 |
| IGLJ1_chr22: 23235847-23235947 | CACTGCAACCCTGTGCCCGTCATGCCCAGCAGGCTCCTGCTCCAGCCCAGCCCCCAGAGAGCAGACCCCA GGTGCTGGCCCCGGGGGTTTTGGTCTGAGC | 1268 |

-continued

| Name | Sequence | SEQ ID NOs. |
|---|---|---|
| IGLJ1_chr22: 23235947-23236047 | CTCAGTCACTGTGTTATGTCTTCGGAACTGGGACCAAGGTCACCGTCCTAGGTAAGTGGCTCTCAACCTTT CCCAGCCTGTCTCACCCTCTGCTGTCCCT | 1269 |
| IGLJI_chr22: 23236047-23236147 | GGAAAATCTGTTTTCTCTCTCTGGGGCTTCCTCCCCTCTGTCCTCCCAGCCTTAAGCACTGACCCTTACCTT TCTCCATGGGGCCTGGAGGAGGTGCATT | 1270 |
| IGLJ1_chr22: 23236147-23236247 | AGTCTCCGGGTAACCGGCAGGAAGGGCCTCCACAGTGGGAGCAGCCGGATGCAGCCTGGTCCCGGGGCC TGAGCTGGGATTGGGCAGGGTCAGGGCTCCT | 1271 |
| IGLJ1_chr22: 23236247-23236347 | CCTCTCTTCCAGGGCAGATGTCTGAGTGAGGGACAGAGGCTGGTTCTGATGAGGGGCCCTGCAGTGTCCT TAGGGACATTGCCCAGTGACTCCTGGGGTC | 1272 |
| IGLJI_chr22: 23236277-23236377 | GGACAGAGGCTGGTTCTGATGAGGGGCCCTGCAGTGTCCTTAGGGACATTGCCCAGTGACTCCTGGGGTC AAGGACAGAGGCTGCTGGGGTGGGCCTGGG | 1273 |
| IGLJ1_chr22: 23236377-23236477 | AGCTGCTGAGTCTCATAGTCTAGGGGAGCAGCCCCAAGAACAGCTGAGGGTCTAGGCTGAGGACTGGAT GCCAATCCAGCCTGGGAGGGCCACACGGCCT | 1274 |
| IGLJ1_chr22: 23236387-23236487 | TCTCATAGTCTAGGGGAGCAGCCCCAAGAACAGCTGAGGGTCTAGGCTGAGGACTGGATGCCAATCCAGC CTGGGAGGGCCACACGGCCTGGTGACACAG | 1275 |
| IGLJ1_chr22: 23236487-23236587 | AGGTCACCCCAAGGGGAGACCAATGGAGGGCACAGAGAGGOCTCTOGGTOTAGGCTGCAGCTCTGTGGC CTGTGCTGGGTCATGAGGACATGGGGACACA | 1276 |
| IGLJ1_chr22: 23236557-23236657 | TGTGCTGGGTCATGAGGACATGGGGACACAGAGGGACGGGTGAGACTGGGTGAGGTGCCAGAATCCAAC CCTCCCAGGACAGTCACCAGAAAGGAGACAG | 1277 |
| IGLJ1_chr22: 23236657-23236757 | TCTCTTAGGGCAGAGATGTGTCTGTCCCTGGAGCCCCGTCACCTCTGGGGCCCAGTGTCTCTCTGTTCACG GATCGGCCTCCTGCCTTCCTCAAAGGGCA | 1278 |
| IGLC1_chr22: 23236757-23236857 | TGTTAGACTCAGGAAATGACCAGAGGGGAGTGAATGAGGGGTGCAGAGAACTCCATGGCTACCAGGTGA AGTTTGGGGTCATCACAGGCTGCTGGGGTGG | 1279 |
| IGLC1_chr22: 23236877-23236977 | CATAGTCTGTGGGAGCAGCCCCAGGAACAGCTGAGGTGAAGGGTTCTGTGGTCGGGCTTGTGGAGACAG GAAACATCTCAGAGCCTCAGAGGAGCCCTGA | 1280 |
| IGLC1_chr22: 23236977-23237077 | GGCTTGTCTAGGTGGAGCCCACTCCTTGCCAGGAGAGCCAAGTGGGCTGGGCTGGGGCAGAGCCCGGTGC CTGTGAGGGATAGGAAGCTCCAGTTCAAAG | 1281 |
| IGLC1_chr22: 23237077-23237177 | CAGGCTTGGGTCTCCCCACACACTGCCTGCCAGGACAGTCCTACAGGATGAGCAGGGGACCCACAGTTCA CGGAGGAGGCTCTAGGTCCTGGAAGAATAA | 1282 |
| IGLC1_chr22: 23237177-23237277 | AGTGGGTGATGGAGGGGGGTATAGGGATGGAAATGAGGGATCCAGGGGTCAAGGCCAGATTCTAAACTC AGACTCCAGAGATCAGAGAAGAAGGAACACA | 1283 |
| IGLC1_chr22: 23237277-23237377 | GCCTGCCCTGGGTATATGGAGAAATTGAGGCTGTAGAGGAGAGGGGCTGGGCCAGGACACCTGTGAAAG GTGACTTGGGAGGGCTCCTAGGAAGGCACAG | 1284 |

-continued

| Name | Sequence | SEQ ID NOs. |
|---|---|---|
| IGLC2_chr22: 23242602-23242702 | TGAAAGCCCCACTGCTATGACCAGGTAGCCGGGACGTGGGGTGGATGCCAGAAAAGACTCCACGGAATA AGAGAGAGCCCAGGACAGCAGGCAGGCTCTC | 1285 |
| IGLC2_chr22: 23242702-23242802 | CGATCCCCCCAGGCCCTTGCCCCATACACGGGCTCCAGAACACACATTTGGCTGGAACAGCCTGAGGGAC CAAAAGGCCCCAGTATCCCACAGAGCTGAG | 1286 |
| IGLC2_chr22: 23242802-23242902 | GAGCCAGGCCAGAAAAGTAACCCCAGAGTTCGCTGTGCAGGGGAGACACAGAGCTCTCTTTATCTGTCAG GATGGCAGGAGGGGACAGGGTCAGGGCGCT | 1287 |
| IGLC2_chr22: 23242902-23243002 | GAGGGTCAGATGTCGGTGTTGGGGGCCAAGGCCCCGAGAGATCTCAGGACAGGTGGTCAGGTGTCTAAG GTAAAACAGCTCCCCGTGCAGATCAGGGCAT | 1288 |
| IGLC2_chr22: 23244157-23244257 | ATGCAGGACAGTCCGGAGAGGGAAATCAGGAGAAGTGAAGGGGTCTCTGGGGAGCCCAGATGTGGGCTA GAGGCAGAAGTAAGGGTGAAGAGCACCTATG | 1289 |
| IGLC2_chr22: 23244257-23244357 | AGTCAATGTCATGGTCTCAGCAGGAACACAGTTGAAAATCCCCATTCCACACAAGACCGTTTAGCAGGAA AGGAGTCCATACTTGTGCTGCCACCAGGAT | 1290 |
| IGLC2_chr22: 23244357-23244457 | GTCCTGAGAAGCCTTGGAGAATGAAACATACAGGTGCATTTCCTAGACTTGACAATGCACGTTAGCCAAG TAAAGGCAATGAAAAGTTCTCTACTAGGGA | 1291 |
| IGLJ3_chr22: 23247257-23247357 | TTTGTTTGTTTCTGTATCTTGTCTCAACTTGTGGTCAGCCTTTCTCCCTGCATCCCAGGCCTGAGCAAGGAC CTCTGCCCTCCCTGTTCAGACCCTTGCT | 1292 |
| IGLJ3_chr22: 23247357-23247457 | TGCCTCAGCAGGTCACTACAACCACTTCACCTCTGACCGCAGGGGCAGGGGACTAGATAGAATGACCTAC TGAGCCTCGTCTGTCTGTCTGTCTGTCTGT | 1293 |
| IGLJ3_chr22: 23247467-23247567 | CTGTTTGTCTCTCTGTCTGTCTGACAGGCGCAGGCTGGGTCTCTAAGCCTTGTTCTGTTCTGGCCTCCTCA GTCTGGGTTCTTGTCGGAACAGCTTTGCC | 1294 |
| IGLJ3_chr22: 23247567-23247667 | CTTGGGTTACCTGGGTTCCATOTOCTGGGGAATTGGGAACAAGGGGTCTGAGGGAGGCACCTCCTGGGAG ACTTTAGAAGGACCCAGTGCCCTCGGGGCT | 1295 |
| IGLC3_chr22: 23248182-23248282 | AGAGTTCGCTGTGCAGGGGAGACACAGAGCTCTCTTTATCTGTCAGGATGGCAGGAGGGGACAGGGTCA GGGCGCTGAGGGTCAGATGTCGGTGTTGGGG | 1296 |
| IGLC3_chr22: 23248282-23248382 | GCCAAGGCCCCGAGAGATCTCAGGACAGGTGGTCAGGTGTCTAAGGTAAAACAGCTCCCCGTGCAGATCA GGACATAGTGGAAAACACCCTGACCCCTCT | 1297 |
| IGLC3_chr22: 23248382-23248482 | GCCTGGCATAGACCTTCAGACACAGAGCCCCTGAACAAGGGCACCCCAACACCTCATCATATACTGAGGT CAGGGGCTCCCCAGGTGGACACCAGGACTC | 1298 |
| IGLJ7_chr22: 23263872-23263972 | AGAATATTCCGTGAGAAGGTGGCCCCACAGCGCTGGGTCACACGCCATCCCCCAAGACAGGCAGGACACC ACAGACAGGGTGGTGGGTCTCAGAAAACTC | 1299 |
| IGLJ7_chr22: 23263972-23264072 | AGGCCCTAAACGTGGATGCTTACCAATTCCTCCACTGGAGGAAGACCTCAGAGCAGATGCCCAGGACAGG GACTTCTGGTAGGGACGGTGACTGGGACGG | 1300 |
| IGLJ7_chr22: 23264072-23264172 | GTGCCTGTTTGTCAGGGAAAACCCACTGGAGAGTCAGATCCCCCAGATAACTTCTCACGACATGGAGACT CTTTCGAACAGACAAAGCTCCACGTTCAGC | 1301 |

-continued

| Name | Sequence | SEQ ID NOs. |
|---|---|---|
| IGLC7_chr22: 23264172-23264272 | TCAGGGAGTAAAAAAAAAATGCCTCAAATGGAGGCCTTTGATCTACTGGAATCCAGCCCCCAGGACTGAC ACCCTGTCTCACCAGGCAGCCCAGAGGGGT | 1302 |
| IGLC7_chr22: 23278157-23278257 | CAGGGTCCACCAGAAGGCATCTCAGAACCAGCCAGCAGTGGCCCTGATTGTCAGCAGGACCCCAGGGAG GGGGGTGGCCAGGACAGGGCTCTGAAGCCCC | 1303 |
| IGLC7_chr22: 23278257-23278357 | CACCCCAGGACCTTCCCTGGGCAGAACGAGTTGGTGAGGGAGTGATGAGCAACCACAGGCCTCCTAACTT CCCAAGCTGGCGATTCTGAGAGGCCTCAAG | 1304 |
| IGLC7_chr22: 23278357-23278457 | GCTGAGACACGGTTCAGCCTTTTAGGCCCTCCTGAACGTGTCCCCTGTCTCCACAGCCTGGGAATGCACTC TCTTTTGACCCAGAAATCCTGCTCATAAG | 1305 |
| IGLC7_chr22: 23282767-23282867 | CTGTCATTGTACAACACATCATTTCACTTTGTTTTTCAAACATAGTGAATTCTTTCCTAATTAAAGAAGAA AAGAGTATAAAGAGAAAGTTTCCAGTGCA | 1306 |
| IGLC7_chr22: 23282842-23282942 | GTATAAAGAGAAAGTTTCCAGTGCAGCCTGGAGATCTGTACTGGTTGTATCTGGAATTCCAGACTCAGCC TTGCATTTCACATAGCAGATAGATGATGAT | 1307 |
| IGLC7_chr22: 23282942-23283042 | GATGGAGAAGGAGAAGAAGAAGGAGGAGGAGGAGGAAAGAAGGAAGAAGAAGAAGAGGAGGAGG AAGAAGAAGACGAAGGGAAGAAGAAGAAGGATG | 1308 |
| TBC1D22A_chr22: 47570209-47570309 | TCCAGGTCTGCCAGGTGTAGGGGAGGTGTGACTGGTTCCATCATGGACCGGTTCCTCCATGGACCGGTTC CTCCGTGGACCGGTTCCGCCATGGACCGGT | 1309 |
| TBC1D22A_chr22: 47570309-47570409 | TCCGCCATGGACCACTCCTGCCCTGGACCACTCCTGCCCTGGACCGGTTCTGCCGTGGACTOGTTCCCGCC GTGGACCAGTTCCCGCTGTATACTGGTTC | 1310 |
| TBC1D22A_chr22: 47570409-47570509 | TGCCCTGGACTGGTTCCCGCTGTGGACTGGTTCCTTGGGGCTCTAAGTGCGGAAGGGCCCAGAGCTGGTC CCTGCCCAGCGCCCTGCTAGGGCTGTGTCC | 1311 |
| TMSB4X_chrX: 12993264-12993364 | TCGTACTCGTGCGCCTCGCTTCGGTGAGCCCCAGGGCCCCTGCCTCCTTCCTCCTGCCGTCCTGCCTCCGT CCCCGCCCTTTCATCATCCGCGTCCCTGT | 1312 |
| TMSB4X_chrX: 12993364-12993464 | GAAGGCATTCCCTAAATCCGAGCCCGAGTGGTTCTCCCCGGGAAGGCTACTTTGGGGAGCTGGGGGGATG CGAAACACCCTAGATACTGGATAATGGGGT | 1313 |
| TMSB4X_chrX: 12993464-12993564 | GGGGAAATCGATGATTTAAGAACAAAACCGAAAAACTGGCGTTTTGCCGTGCCGCTCGGAGGGGACATT AAAAAATTTCTTAGTGTTTGCCCGCAAAGGT | 1314 |
| TMSB4X_chrX: 12993544-12993644 | TAGTGTTTGCCCGCAAAGGTATTGTGCGTTGCCTTGGAGGCTGAGATATGGGGGAATAGACAAGTCCTTT GTTCTGAGGTTCATCTTCCGAGCCCCGAGC | 1315 |
| TMSB4X_chrX: 12993644-12993744 | CTCCTCCCAGCCTCGGACGGCTGCGCGGGCTGCATCTGTGCAGCCTGGCGGCGGCGGGGCTGTGCTATGA CATCTTTACAGTCCTTCTTGCAGAGACATG | 1316 |
| TMSB4X_chrX: 12993744-12993844 | TGTGCCAGGGATGCCGAATTGCCGGGAGAGCAGGCAAGACCGGCTTCGGGGCGCGCGGCGGCCGCTTTG TGTGCGGGGCTGCATTGTGACGCGGGCGATG | 1317 |

-continued

| Name | Sequence | SEQ ID NOs. |
|---|---|---|
| TMSB4X_chrX: 12993844-12993944 | AAGCCGGTAGGGCGGTGGTCGGAAGCTCCAGCCGCGGCCGCCGCCTTTGTGAGAGGACTAGAAAGCCGG ATCCGGCCCGCATCCTTGCGGAGAGGCCGCG | 1318 |
| TMSB4X_chrX: 12993944-12994044 | GCTAGGAAATGGAAACGCTTTTCCTACCTGGGCTCCATTTTAGGAATTCTTGCCGATTTTTCCCACTTGAA TTTGGAAGTGGCTTTCCTCTTCTTTCCTT | 1319 |
| TMSB4X_chrX: 12994044-12994144 | GTCCTAGCCAGCCTTTAATTTTAAACGCTGTAATTAACAATTCGCAGTGGTCAATTTCCTTTATTCTGCAA GATTCGGCTTTGAGAGGCATCCGCCCTCT | 1320 |
| TMSB4X_chrX: 12994144-12994244 | TTGGTCCACAGCGTTTTGAAATATGGGGAGGAGGGGCGCGGGGGGTGTCGCCTCTTTTTCTGTAGAAAGA GGAAGCTCGTGAGCGCGGAACGGCAGCAGT | 1321 |
| TMSB4X_chrX: 12994289-12994389 | AAGTGCAGTTCCCAGCCCAGAGACAGCGGGGCGGGTGGCTCTTCCTCACGCTCGCTCTTGGCTTGCTCCCT GCAGCTTTTCCTCCGCAACCATGTCTGAC | 1322 |
| TMSB4X_chrX: 12994389-12994489 | AAACCCGATATGGCTGAGATCGAGAAATTCGATAAGTCGAAACTGAAGAAGACAGAGACC3CAAGAGAAA AATCCACTGCCTTCCAAAGAAAGTGAGCTCC | 1323 |
| TMSB4X_chrX: 12994444-12994544 | AGACGCAAGAGAAAAATCCACTGCCTTCCAAAGAAAGTGAGCTCCGACCCACCCCCATCTTTAGAAAGGC TGGGTGGGAGCGGCCGGTGGGAGGGCGGGA | 1324 |
| DMD_chrX: 33146106-33146206 | TTTATAGAAAGGCATATGGAACAGGAGTCATCCAAATATATCCCAGGGGTTGCAAATTGACCAAAAGAGT CACCTTTAGGGAAGCCTGCTTCTGAATGCT | 1325 |
| DMD_chrX: 33146206-33146306 | TGTGGAATTTATCATTCTTCTGAATGGCTGTTGCATTTATCTGCAGCTTTTACTCACCAGATGAGACCTCA GACATTTCAAATTCTGCGGAGGCTGGCTA | 1326 |
| DMD_chrX: 33146306-33146406 | CACACCTTCATAGGAAAGCTITTTGCTGATTTCCCTGTTGGTACTTTTCTCTTACACATTCTATGGGGTATG GTAAACCTGGAGGTAGAGTCATAGCCAA | 1327 |
| DMD_chrX: 33146406-33146506 | GCACAGATAAAGCAGGCACAGAATCTCTGACCAGCCTCACAAAAGCAGACAAACACACAATCTTTTTGCA CCTGTTTCTTCCACTCCGGTTGCCGTGAAT | 1328 |
| PABPC5_chrX: 90026453-90026553 | TAGAAATGGTTCAACCAGTCCAATATCAATATAGCTGCTTATTACTCTATTCACTTACTTCAAAGTGGCAT TTGTTTTGAGTAAGACTTTATTTAATTCT | 1329 |
| PABPC5_chrX: 90026553-90026653 | TACCGTTAGCTTGAAACCATAGAGATCTTCTCTCTATTTGCCCTACTTCCTTCAAAAGTCAAATGACCTCC TACAAATAAAAGACGTTCTTATTTTCATT | 1330 |

What is claimed is:

1. A method comprising:

(a) obtaining sequencing data for each of at least 150,000 evaluable sequencing fragments, wherein the evaluable sequencing fragments are derived from a plurality of cell-free nucleic acid molecules from a subject;

(b) computer processing the sequencing data for each of the at least 150,000 evaluable sequencing fragments to align the sequencing data for each of the at least 150,000 evaluable sequencing fragments to a human reference genome sequence of at least 10 kb in length;

(c) identifying one or more cell-free nucleic acid molecules of the plurality of cell-free nucleic acid molecules, wherein each of the identified one or more cell-free nucleic acid molecules comprises a plurality of phased variants relative to a sequence from the human reference genome sequence, wherein at least 10% of the one or more cell-free nucleic acid molecules comprises a first phased variant of the plurality of phased variants and a second phased variant of the plurality of phased variants that are separated by at least one nucleotide; and (d) determining (i) the number of evaluable sequencing fragments processed in (b) and (ii) the number of the one or more cell-free nucleic acid molecules that comprise the plurality of phased variants identified in (c);

wherein an evaluable sequencing fragment is a nucleic acid fragment that covers a region of the human reference genome sequence that comprises two or more predefined mutations from a set of phased variants, wherein the predefined mutations occur within 170 bp of each other in genomic space.

2. The method of claim 1, further comprising (e) determining a condition of the subject based at least in part on the number of molecules that comprise the plurality of phased variants as identified in (d).

3. The method of claim 2, wherein the condition is a cancer.

4. The method of claim 3, wherein (e) further comprises determining a cell-of-origin of the cancer of the subject based at least in part on the plurality of phased variants.

5. The method of claim 3, wherein (e) further comprises detecting minimal residual disease of the cancer of the subject based at least in part on the plurality of phased variants.

6. The method of claim 3, wherein (e) further comprises detecting a relapse of cancer.

7. The method of claim 3, wherein the cancer comprises lymphoma.

8. The method of claim 3, wherein the cancer comprises a solid tumor.

9. The method of claim 1, wherein the two or more predefined mutations are single nucleotide variants.

10. The method of claim 1, wherein the set of phased variants is selected based on phased variants identified in a tumor sample of the subject.

11. The method of claim 10, wherein the tumor sample is a solid tumor sample.

12. The method of claim 1, further comprising (1) obtaining the plurality of cell-free nucleic acid molecules from the subject and (2) enriching the plurality of cell-free nucleic acid molecules for regions associated with the set of phased variants to form a sequencing library from which the sequencing data is derived.

13. The method of claim 12, wherein enriching the plurality of cell-free nucleic acid molecules comprises from the subject comprises using a set of nucleic acid probes to selectively capture cell-free nucleic acid molecules from genomic regions associated with the set of phased variants.

14. The method of claim 13, wherein each nucleic acid probe of the set of nucleic acid probes comprises a pull-down tag.

15. The method of claim 14, wherein the pull-down tag comprises biotin.

16. The method of claim 12, wherein the plurality of cell-free nucleic acid molecules is obtained from a plasma sample of the subject.

17. The method of claim 12, wherein the plurality of cell-free nucleic acid molecules is obtained from a blood sample of the subject.

18. The method of claim 12, wherein the plurality of cell-free nucleic acid molecules is obtained from a serum sample of the subject.

19. The method of claim 1, wherein (d) comprises identifying (1) sequencing reads of the sequencing data comprising doublet phased variants having 2 phased variants within individual cell-free nucleic acid molecules and (2) sequencing reads of the sequencing data comprising triplet phased variants having 3 phased variants within individual cell-free nucleic acid molecules, and determining a phased-variant tumor fraction for doublet and triplet phased variants.

20. The method of claim 19, wherein (d) comprises identifying (3) sequencing reads of the sequencing data comprising quadruplet phased variants having 4 phased variants within individual cell-free nucleic acid molecules, and determining a phased-variant tumor fraction for quadruplet phased variants.

21. The method of claim 1, wherein the sequencing data for the at least 150,000 evaluable sequencing fragments is at a molecular depth of at least 5,000×.

22. The method of claim 1, wherein the method does not comprise performing barcode-mediated error suppression of the sequencing data.

23. The method of claim 1, wherein the set of phased variants is selected based on phased variants previously identified in a cell-free DNA sample of the subject.

* * * * *